US012667572B2

(12) United States Patent
Feng et al.

(10) Patent No.: US 12,667,572 B2
(45) Date of Patent: Jun. 30, 2026

(54) TRICYCLIC COMPOUNDS USEFUL IN THE TREATMENT OF CANCER, AUTOIMMUNE AND INFLAMMATORY DISORDERS

(71) Applicant: SCHRÖDINGER, INC., New York, NY (US)

(72) Inventors: Shulu Feng, New York, NY (US); Morgan Lawrenz, New York, NY (US); Jiaye Guo, New York, NY (US); Goran Krilov, New York, NY (US); Andrew Placzek, New York, NY (US); Zhe Nie, New York, NY (US); Lynnie Trzoss, New York, NY (US); Haifeng Tang, New York, NY (US); Pieter Harm Bos, New York, NY (US); Michael Trzoss, New York, NY (US); Shelby Ellery, New York, NY (US)

(73) Assignee: SCHRÖDINGER, INC., New York, NY (US)

( * ) Notice: Subject to any disclaimer, the term of this patent is extended or adjusted under 35 U.S.C. 154(b) by 490 days.

(21) Appl. No.: 18/273,879

(22) PCT Filed: Jan. 25, 2022

(86) PCT No.: PCT/US2022/013671
§ 371 (c)(1),
(2) Date: Jul. 24, 2023

(87) PCT Pub. No.: WO2022/164789
PCT Pub. Date: Aug. 4, 2022

(65) Prior Publication Data

US 2024/0148732 A1 May 9, 2024

Related U.S. Application Data

(60) Provisional application No. 63/276,064, filed on Nov. 5, 2021, provisional application No. 63/145,344, filed on Feb. 3, 2021, provisional application No. 63/141,682, filed on Jan. 26, 2021.

(51) Int. Cl.

| | |
|---|---|
| ***A61K 31/444*** | (2006.01) |
| ***A61K 31/4427*** | (2006.01) |
| ***A61K 31/5025*** | (2006.01) |
| ***A61K 31/519*** | (2006.01) |
| ***A61K 45/06*** | (2006.01) |
| ***C07D 471/04*** | (2006.01) |
| ***C07D 487/04*** | (2006.01) |
| ***C07D 491/12*** | (2006.01) |
| ***C07D 491/20*** | (2006.01) |
| ***G01N 33/573*** | (2006.01) |
| ***G01N 33/68*** | (2006.01) |

(52) U.S. Cl.

CPC ........ *A61K 31/519* (2013.01); *A61K 31/4427* (2013.01); *A61K 31/444* (2013.01); *A61K 31/5025* (2013.01); *A61K 45/06* (2013.01); *C07D 471/04* (2013.01); *C07D 487/04* (2013.01); *C07D 491/12* (2013.01); *C07D 491/20* (2013.01); *G01N 33/573* (2013.01); *G01N 33/6869* (2013.01); *G01N 2333/5428* (2013.01); *G01N 2333/95* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,164,288 | A | 11/1992 | Nelson et al. |
| 5,302,589 | A | 4/1994 | Frye et al. |
| 5,945,441 | A | 8/1999 | Steiner et al. |
| 6,316,429 | B1 | 11/2001 | Tang et al. |
| 7,514,446 | B2 | 4/2009 | Davis-Ward et al. |
| 7,863,289 | B2 | 1/2011 | Spevak et al. |
| 8,026,247 | B2 | 9/2011 | Bold et al. |
| 8,501,756 | B2 | 8/2013 | Artman, III et al. |
| 8,552,002 | B2 | 10/2013 | Ding et al. |
| 8,568,998 | B2 | 10/2013 | Mani et al. |
| 8,815,901 | B2 | 8/2014 | Furet et al. |
| 8,912,204 | B2 | 12/2014 | Ibrahim et al. |
| 9,260,437 | B2 | 2/2016 | Ibrahim et al. |
| 9,273,051 | B2 | 3/2016 | Chen et al. |
| 10,711,036 | B2 | 7/2020 | Gray et al. |

(Continued)

FOREIGN PATENT DOCUMENTS

| | | | |
|---|---|---|---|
| CN | 108623587 | A | 10/2018 |
| CN | 108623588 | A | 10/2018 |

(Continued)

OTHER PUBLICATIONS

Nie Zhe, "Accelerated In Silico Discovery of SGR-1505: A Potent MALT1 Allosteric Inhibitor for the Treatment of Mature B-cell Malignancies." ACS Meeting. Mar. 20, 2024.
Nie, Zilin, et al. "Conversion of the LIMA1 tumour suppressor into an oncogenic LMO-like protein by API2-MALT1 in MALT lymphoma." Nature communications 6.1 (2015): 5908.
Novak, Urban, et al. "The NF-κB negative regulator TNFAIP3 (A20) is inactivated by somatic mutations and genomic deletions in marginal zone lymphomas." Blood, The Journal of the American Society of Hematology 113.20 (2009): 4918-4921.
Ott, Patrick A., et al. "An immunogenic personal neoantigen vaccine for patients with melanoma." Nature 547.7662 (2017): 217-221.

(Continued)

*Primary Examiner* — Jennifer A Berrios
*Assistant Examiner* — Sophia Reilly
(74) *Attorney, Agent, or Firm* — Barnes & Thornburg LLP; Steven M. Sturlis; William Boudreaux

(57) ABSTRACT

The present application relates to compounds of Formula (I), as defined herein, and pharmaceutically acceptable salts thereof. The present application also describes pharmaceutical composition comprising a compound of Formula (I), and pharmaceutically acceptable salts thereof, and methods of using the compounds and compositions for treating diseases, such as cancer, autoimmune disorders, and inflammatory disorders.

33 Claims, No Drawings

Specification includes a Sequence Listing.

(56) References Cited

U.S. PATENT DOCUMENTS

| | | | |
|---|---|---|---|
| 2002/0032262 | A1 | 3/2002 | Zhang et al. |
| 2003/0144292 | A1 | 7/2003 | Natchus et al. |
| 2003/0153788 | A1 | 8/2003 | Kobayashi et al. |
| 2003/0162778 | A1 | 8/2003 | Natchus et al. |
| 2003/0171400 | A1 | 9/2003 | Pikul et al. |
| 2004/0077704 | A1 | 4/2004 | Beight et al. |
| 2005/0065339 | A1 | 3/2005 | Harbeson et al. |
| 2005/0256144 | A1 | 11/2005 | Kath et al. |
| 2006/0084687 | A1 | 4/2006 | Boyce et al. |
| 2006/0116364 | A1 | 6/2006 | Hamaoka et al. |
| 2007/0208001 | A1 | 9/2007 | Zhuo et al. |
| 2011/0206637 | A1 | 8/2011 | Or et al. |
| 2013/0029925 | A1 | 1/2013 | Vandier et al. |
| 2013/0096021 | A1 | 4/2013 | Chinnaiyan et al. |
| 2015/0018336 | A1 | 1/2015 | Chen et al. |
| 2015/0320754 | A1 | 11/2015 | Kutok et al. |
| 2019/0160045 | A1 | 5/2019 | Kukreja et al. |
| 2020/0190155 | A1 | 6/2020 | Arora et al. |
| 2022/0112138 | A1 | 4/2022 | Sun et al. |
| 2023/0056273 | A1 | 2/2023 | Miksztal et al. |
| 2023/0106913 | A1 | 4/2023 | Pardal Filipe et al. |
| 2023/0119316 | A1 | 4/2023 | Kurhade et al. |
| 2023/0219961 | A1 | 7/2023 | Zheng et al. |
| 2023/0354812 | A1 | 11/2023 | Geist et al. |

FOREIGN PATENT DOCUMENTS

| | | | |
|---|---|---|---|
| CN | 111662284 | B | 8/2021 |
| CN | 108456216 | B | 12/2021 |
| CN | 108948019 | B | 7/2022 |
| CN | 114075184 | B | 5/2023 |
| CN | 115181049 | B | 12/2023 |
| DE | 4110487 | A1 | 9/1992 |
| DE | 4208535 | A1 | 9/1992 |
| EP | 0315574 | A2 | 5/1989 |
| EP | 0361341 | A2 | 4/1990 |
| EP | 0507333 | A2 | 10/1992 |
| EP | 0249239 | B1 | 1/1995 |
| EP | 0427225 | B1 | 5/1996 |
| EP | 0423693 | B1 | 4/1997 |
| EP | 0765660 | A2 | 4/1997 |
| EP | 0442323 | B1 | 10/1997 |
| EP | 0529858 | B1 | 10/1997 |
| EP | 0525420 | B1 | 5/1999 |
| EP | 0786690 | B1 | 3/2000 |
| EP | 3583096 | B1 | 3/2024 |
| EP | 3377473 | B1 | 6/2024 |
| JP | S6396652 | A | 4/1988 |
| JP | H05297519 | A | 11/1993 |
| JP | H06192199 | A | 7/1994 |
| JP | 2000221631 | A | 8/2000 |
| JP | 2004245959 | A | 9/2004 |
| JP | 2007256545 | A | 10/2007 |
| JP | 2008033083 | A | 2/2008 |
| JP | 2008122829 | A | 5/2008 |
| JP | 2008224717 | A | 9/2008 |
| JP | 2009053580 | A | 3/2009 |
| JP | 2009069751 | A | 4/2009 |
| JP | 2009075204 | A | 4/2009 |
| JP | 2009103964 | A | 5/2009 |
| JP | 2009163177 | A | 7/2009 |
| JP | 2009276715 | A | 11/2009 |
| JP | 2010020149 | A | 1/2010 |
| JP | 2010072517 | A | 4/2010 |
| JP | 2010085572 | A | 4/2010 |
| JP | 2010097043 | A | 4/2010 |
| JP | 2010117405 | A | 5/2010 |
| JP | 2010117406 | A | 5/2010 |
| JP | 2010117407 | A | 5/2010 |
| JP | 2010117408 | A | 5/2010 |
| JP | 2010117409 | A | 5/2010 |
| JP | 2010164683 | A | 7/2010 |
| JP | 2010164804 | A | 7/2010 |
| JP | 2010164861 | A | 7/2010 |
| JP | 2010204614 | A | 9/2010 |
| JP | 2010256524 | A | 11/2010 |
| JP | 2010256602 | A | 11/2010 |
| JP | 2011008081 | A | 1/2011 |
| JP | 2011048234 | A | 3/2011 |
| JP | 2011053396 | A | 3/2011 |
| WO | 1993013124 | A1 | 7/1993 |
| WO | 1994014833 | A2 | 7/1994 |
| WO | 1996020725 | A2 | 7/1996 |
| WO | 1996020949 | A1 | 7/1996 |
| WO | 1996022966 | A1 | 8/1996 |
| WO | 1997003094 | A1 | 1/1997 |
| WO | 1997007093 | A1 | 2/1997 |
| WO | 1997014695 | A1 | 4/1997 |
| WO | 1998020893 | A1 | 5/1998 |
| WO | 1998028980 | A1 | 7/1998 |
| WO | 1998037882 | A1 | 9/1998 |
| WO | 1998045266 | A1 | 10/1998 |
| WO | 1998047523 | A1 | 10/1998 |
| WO | 1998051688 | A1 | 11/1998 |
| WO | 1998053817 | A1 | 12/1998 |
| WO | 1999026615 | A1 | 6/1999 |
| WO | 1999062484 | A1 | 12/1999 |
| WO | 2000008015 | A2 | 2/2000 |
| WO | 2000013682 | A2 | 3/2000 |
| WO | 2000026186 | A1 | 5/2000 |
| WO | 2000042011 | A1 | 7/2000 |
| WO | 2000046181 | A1 | 8/2000 |
| WO | 2000046193 | A2 | 8/2000 |
| WO | 2000046222 | A1 | 8/2000 |
| WO | 2000051974 | A1 | 9/2000 |
| WO | 2000061789 | A1 | 10/2000 |
| WO | 2000072834 | A2 | 12/2000 |
| WO | 2000078794 | A1 | 12/2000 |
| WO | 2001002376 | A1 | 1/2001 |
| WO | 2001012622 | A1 | 2/2001 |
| WO | 2001055123 | A1 | 8/2001 |
| WO | 2001070682 | A2 | 9/2001 |
| WO | 2001070690 | A1 | 9/2001 |
| WO | 2001070720 | A2 | 9/2001 |
| WO | 2001074784 | A1 | 10/2001 |
| WO | 2002002546 | A1 | 1/2002 |
| WO | 2002051444 | A1 | 7/2002 |
| WO | 2002053565 | A1 | 7/2002 |
| WO | 2002060426 | A2 | 8/2002 |
| WO | 2002094263 | A2 | 11/2002 |
| WO | 2002096892 | A1 | 12/2002 |
| WO | 2003007888 | A2 | 1/2003 |
| WO | 2003032982 | A1 | 4/2003 |
| WO | 2003070706 | A1 | 8/2003 |
| WO | 2003076418 | A1 | 9/2003 |
| WO | 2004020584 | A2 | 3/2004 |
| WO | 2004031145 | A2 | 4/2004 |
| WO | 2004055163 | A2 | 7/2004 |
| WO | 2004058682 | A1 | 7/2004 |
| WO | 2004067008 | A1 | 8/2004 |
| WO | 2005007162 | A1 | 1/2005 |
| WO | 2005009949 | A2 | 2/2005 |
| WO | 2005030774 | A1 | 4/2005 |
| WO | 2005039504 | A2 | 5/2005 |
| WO | 2005046588 | A2 | 5/2005 |
| WO | 2005047899 | A2 | 5/2005 |
| WO | 2005061460 | A1 | 7/2005 |
| WO | 2005077914 | A1 | 8/2005 |
| WO | 2005123748 | A1 | 12/2005 |
| WO | 2006056696 | A2 | 6/2006 |
| WO | 2006089286 | A2 | 8/2006 |
| WO | 2006113875 | A2 | 10/2006 |
| WO | 2006135627 | A2 | 12/2006 |
| WO | 2007002325 | A1 | 1/2007 |
| WO | 2007002433 | A1 | 1/2007 |
| WO | 2007016589 | A2 | 2/2007 |
| WO | 2007062078 | A2 | 5/2007 |
| WO | 2007070556 | A2 | 6/2007 |
| WO | 2007110344 | A1 | 10/2007 |
| WO | 2008046082 | A2 | 4/2008 |
| WO | 2008070039 | A2 | 6/2008 |
| WO | 2008079903 | A1 | 7/2008 |
| WO | 2008079906 | A1 | 7/2008 |
| WO | 2008079909 | A1 | 7/2008 |

(56) References Cited

FOREIGN PATENT DOCUMENTS

| | | | |
|---|---|---|---|
| WO | 2008080001 | A2 | 7/2008 |
| WO | 2008080015 | A2 | 7/2008 |
| WO | 2008101693 | A2 | 8/2008 |
| WO | 2008146674 | A1 | 12/2008 |
| WO | 2009007748 | A2 | 1/2009 |
| WO | 2009012283 | A1 | 1/2009 |
| WO | 2009013976 | A1 | 1/2009 |
| WO | 2009014637 | A2 | 1/2009 |
| WO | 2009019957 | A1 | 2/2009 |
| WO | 2009060694 | A1 | 5/2009 |
| WO | 2009065897 | A2 | 5/2009 |
| WO | 2009071480 | A2 | 6/2009 |
| WO | 2009077844 | A2 | 6/2009 |
| WO | 2009098928 | A1 | 8/2009 |
| WO | 2009108827 | A1 | 9/2009 |
| WO | 2009116352 | A1 | 9/2009 |
| WO | 2009118411 | A2 | 10/2009 |
| WO | 2009119140 | A1 | 10/2009 |
| WO | 2009140464 | A1 | 11/2009 |
| WO | 2009143018 | A2 | 11/2009 |
| WO | 2009143024 | A2 | 11/2009 |
| WO | 2009150947 | A1 | 12/2009 |
| WO | 2009152083 | A1 | 12/2009 |
| WO | 2010007046 | A2 | 1/2010 |
| WO | 2010010793 | A1 | 1/2010 |
| WO | 2010010814 | A1 | 1/2010 |
| WO | 2010011853 | A2 | 1/2010 |
| WO | 2010023307 | A1 | 3/2010 |
| WO | 2010031816 | A1 | 3/2010 |
| WO | 2010056631 | A1 | 5/2010 |
| WO | 2010062821 | A1 | 6/2010 |
| WO | 2010073719 | A1 | 7/2010 |
| WO | 2010074588 | A2 | 7/2010 |
| WO | 2010077680 | A2 | 7/2010 |
| WO | 2010088414 | A2 | 8/2010 |
| WO | 2010093808 | A1 | 8/2010 |
| WO | 2010111527 | A1 | 9/2010 |
| WO | 2010114957 | A1 | 10/2010 |
| WO | 2010145998 | A1 | 12/2010 |
| WO | 2011016576 | A1 | 2/2011 |
| WO | 2011020913 | A2 | 2/2011 |
| WO | 2011035022 | A1 | 3/2011 |
| WO | 2011043994 | A1 | 4/2011 |
| WO | 2011092120 | A1 | 8/2011 |
| WO | 2012021399 | A1 | 2/2012 |
| WO | 2012028578 | A1 | 3/2012 |
| WO | 2012101029 | A1 | 8/2012 |
| WO | 2012101032 | A1 | 8/2012 |
| WO | 2012109075 | A1 | 8/2012 |
| WO | 2012113774 | A1 | 8/2012 |
| WO | 2012139930 | A1 | 10/2012 |
| WO | 2012143248 | A1 | 10/2012 |
| WO | 2012143468 | A1 | 10/2012 |
| WO | 2012152763 | A1 | 11/2012 |
| WO | 2012154888 | A1 | 11/2012 |
| WO | 2012162580 | A2 | 11/2012 |
| WO | 2013014039 | A1 | 1/2013 |
| WO | 2013050446 | A1 | 4/2013 |
| WO | 2013050448 | A1 | 4/2013 |
| WO | 2013085607 | A1 | 6/2013 |
| WO | 2013086322 | A1 | 6/2013 |
| WO | 2013086354 | A1 | 6/2013 |
| WO | 2013086373 | A1 | 6/2013 |
| WO | 2013096642 | A1 | 6/2013 |
| WO | 2013102059 | A1 | 7/2013 |
| WO | 2013173393 | A1 | 11/2013 |
| WO | 2013177241 | A1 | 11/2013 |
| WO | 2014008982 | A1 | 1/2014 |
| WO | 2014011900 | A2 | 1/2014 |
| WO | 2014016314 | A1 | 1/2014 |
| WO | 2014017938 | A2 | 1/2014 |
| WO | 2014019908 | A2 | 2/2014 |
| WO | 2014072220 | A1 | 5/2014 |
| WO | 2014078733 | A1 | 5/2014 |
| WO | 2014083567 | A2 | 6/2014 |
| WO | 2014160521 | A1 | 10/2014 |
| WO | 2014184069 | A1 | 11/2014 |
| WO | 2014194127 | A1 | 12/2014 |
| WO | 2015017528 | A1 | 2/2015 |
| WO | 2015017533 | A1 | 2/2015 |
| WO | 2015023898 | A1 | 2/2015 |
| WO | 2015049624 | A1 | 4/2015 |
| WO | 2015057873 | A1 | 4/2015 |
| WO | 2015058129 | A1 | 4/2015 |
| WO | 2015061572 | A1 | 4/2015 |
| WO | 2015108992 | A1 | 7/2015 |
| WO | 2015112806 | A2 | 7/2015 |
| WO | 2015151490 | A1 | 10/2015 |
| WO | 2015161274 | A1 | 10/2015 |
| WO | 2015161277 | A1 | 10/2015 |
| WO | 2015181747 | A1 | 12/2015 |
| WO | 2015191666 | A2 | 12/2015 |
| WO | 2015191667 | A1 | 12/2015 |
| WO | 2016011141 | A1 | 1/2016 |
| WO | 2016011144 | A1 | 1/2016 |
| WO | 2016011147 | A1 | 1/2016 |
| WO | 2016022569 | A1 | 2/2016 |
| WO | 2016075224 | A1 | 5/2016 |
| WO | 2016081450 | A1 | 5/2016 |
| WO | 2016113668 | A1 | 7/2016 |
| WO | 2016131380 | A1 | 8/2016 |
| WO | 2016140189 | A1 | 9/2016 |
| WO | 2016201319 | A1 | 12/2016 |
| WO | 2016204270 | A1 | 12/2016 |
| WO | 2016210294 | A1 | 12/2016 |
| WO | 2017081641 | A1 | 5/2017 |
| WO | 2017106134 | A1 | 6/2017 |
| WO | 2018020474 | A1 | 2/2018 |
| WO | 2018033135 | A1 | 2/2018 |
| WO | 2018060216 | A1 | 4/2018 |
| WO | 2018129205 | A1 | 7/2018 |
| WO | 2018133845 | A1 | 7/2018 |
| WO | 2018141749 | A1 | 8/2018 |
| WO | 2018165385 | A1 | 9/2018 |
| WO | 2018210658 | A1 | 11/2018 |
| WO | 2018210659 | A1 | 11/2018 |
| WO | 2018215800 | A1 | 11/2018 |
| WO | 2018226150 | A1 | 12/2018 |
| WO | 2018237349 | A1 | 12/2018 |
| WO | 2019013311 | A1 | 1/2019 |
| WO | 2019086009 | A1 | 5/2019 |
| WO | 2019088910 | A1 | 5/2019 |
| WO | 2019195565 | A1 | 10/2019 |
| WO | 2019216322 | A1 | 11/2019 |
| WO | 2019219560 | A1 | 11/2019 |
| WO | 2019219565 | A1 | 11/2019 |
| WO | 2019219570 | A1 | 11/2019 |
| WO | 2019219574 | A1 | 11/2019 |
| WO | 2019219577 | A1 | 11/2019 |
| WO | 2019243037 | A1 | 12/2019 |
| WO | 2020045458 | A1 | 3/2020 |
| WO | 2020051375 | A2 | 3/2020 |
| WO | 2020061470 | A1 | 3/2020 |
| WO | 2020115076 | A2 | 6/2020 |
| WO | 2020182188 | A1 | 9/2020 |
| WO | 2020223133 | A1 | 11/2020 |
| WO | 2021085636 | A1 | 5/2021 |
| WO | 2021110860 | A1 | 6/2021 |
| WO | 2021/134004 | A1 | 7/2021 |
| WO | 2021130731 | A1 | 7/2021 |
| WO | 2021130732 | A1 | 7/2021 |
| WO | 2021133976 | A1 | 7/2021 |
| WO | 2021178362 | A1 | 9/2021 |
| WO | 2021201201 | A1 | 10/2021 |
| WO | 2021243018 | A1 | 12/2021 |
| WO | 2021255071 | A1 | 12/2021 |
| WO | 2022007921 | A1 | 1/2022 |
| WO | 2022010537 | A1 | 1/2022 |
| WO | 2022032073 | A2 | 2/2022 |
| WO | 2022106857 | A1 | 5/2022 |
| WO | 2022240541 | A1 | 11/2022 |
| WO | 2022246118 | A2 | 11/2022 |
| WO | 2023125877 | A1 | 7/2023 |

(56) References Cited

FOREIGN PATENT DOCUMENTS

| | | |
|---|---|---|
| WO | 2023143249 A1 | 8/2023 |
| WO | 2024020534 A2 | 1/2024 |
| WO | 2025059027 A1 | 3/2025 |

OTHER PUBLICATIONS

Pan, Deng, et al. "The CBM Complex Underwrites NF-kB Activation to Promote HER2-Associated Tumor Malignancy." Mol Cancer Res, 2016, vol. 14, pp. 93-102.
Penas, Murga, et al. "The t (14; 18)(q32; q21)/IGH-MALT1 translocation in MALT lymphomas contains templated nucleotide insertions and a major breakpoint region similar to follicular and mantle cell lymphoma." Blood, The Journal of the American Society of Hematology 115.11 (2010): 2214-2219.
Petrelli, Fausto, et al. "Clinical and pathological characterization of HER2 mutations in human breast cancer: a systematic review of the literature." Breast cancer research and treatment 166 (2017): 339-349.
Pétursson, Sigthór. "Protecting groups in carbohydrate chemistry." Journal of chemical education 74.11 (1997): 1297.
Phelan, James D., et al. "A multiprotein supercomplex controlling oncogenic signalling in lymphoma." Nature 560.7718 (2018): 387-391.
Plosker, Greg L. "Sipuleucel-T: in metastatic castration-resistant prostate cancer." Drugs 71 (2011): 101-108.
Quancard et al. "Optimization of the In Vivo Potency of Pyrazolopyrimidine MALT1 Protease Inhibitors by Reducing Metabolism and Increasing Potency in Whole Blood." Journal of Medicinal Chemistry 2020 63 (23), 14594-14608.
Rausch, Steffen, et al. "mRNA vaccine CV9103 and CV9104 for the treatment of prostate cancer." Human vaccines & immunotherapeutics 10.11 (2014): 3146-3152.
Rebeaud, Fabien, et al. "The proteolytic activity of the paracaspase MALT1 is key in T cell activation." Nature immunology 9.3 (2008): 272-281.
Rohr, Joseph, et al. "Recurrent activating mutations of CD28 in peripheral T-cell lymphomas." Leukemia 30.5 (2016): 1062-1070.
Rosebeck, Shaun, et al. "Cleavage of NIK by the API2-MALT1 fusion oncoprotein leads to noncanonical NF-κB activation." science 331.6016 (2011): 468-472.
Sahin, Ugur, et al. "Personalized RNA mutanome vaccines mobilize poly-specific therapeutic immunity against cancer." Nature 547. 7662 (2017): 222-226.
Sau, Andrea, et al. "Persistent activation of NF-κB in BRCA1-deficient mammary progenitors drives aberrant proliferation and accumulation of DNA damage." Cell stem cell 19.1 (2016): 52-65.
Schlauderer, Florian, et al. "Structural analysis of phenothiazine derivatives as allosteric inhibitors of the MALT1 paracaspase." Angewandte Chemie International Edition 52.39 (2013): 10384-10387.
Shi, Jian-hong, et al. "TCR signaling to NF-κB and mTORC1: Expanding roles of the CARMA1 complex." Molecular immunology 68.2 (2015): 546-557.
Staal, Jens, et al. "T-cell receptor-induced JNK activation requires proteolytic inactivation of CYLD by MALT1." The EMBO journal 30.9 (2011): 1742-1752.
Staudt, Louis, "Oncogenic Activation of NF-kB" Cold Spring Harbor Perspectives in Biology 2.6 (2010): a000109.
Streubel, Berthold, et al. "Frequency of chromosomal aberrations involving MALT1 in mucosa-associated lymphoid tissue lymphoma in patients with Sjogren's syndrome." Clinical Cancer Research 10.2 (2004): 476-480.
Uehata, Takuya, et al. "Malt1-induced cleavage of regnase-1 in CD4+ helper T cells regulates immune activation." Cell 153.5 (2013): 1036-1049.
Wang, Y., et al. "MALT1 promotes melanoma progression through JNK/c-Jun signaling." Oncogenesis 6.7 (2017): e365-e365.
Watt, Stephen A., et al. "Novel CARD11 mutations in human cutaneous squamous cell carcinoma lead to aberrant NF-κB regulation." The American Journal of Pathology 185.9 (2015): 2354-2363.
Weisberg, Ellen, et al. "Second generation inhibitors of BCR-ABL for the treatment of imatinib-resistant chronic myeloid leukaemia." Nature Reviews Cancer 7.5 (2007): 345-356.
Williams, Erik A., et al. "CYLD-mutant cylindroma-like basaloid carcinoma of the anus: a genetically and morphologically distinct class of HPV-related anal carcinoma." Modern Pathology 33.12 (2020): 2614-2625.
Willis, Tony G., et al. "Bcl10 is involved in t (1; 14)(p22; q32) of MALT B cell lymphoma and mutated in multiple tumor types." Cell 96.1 (1999): 35-45.
Wu, Chenglin, et al. "Genetic heterogeneity in primary and relapsed mantle cell lymphomas: Impact of recurrent CARD11 mutations." Oncotarget 7.25 (2016): 38180.
Xia, Longzheng, et al. "Role of the NFκB-signaling pathway in cancer." OncoTargets and therapy (2018): 2063-2073.
Xia, Yifeng, et al., "NF-κB, an active player in human cancers." Cancer immunology research 2.9 (2014): 823-830.
Yamamoto, Hiromasa, et al., "Impact of EGFR mutation analysis in non-small cell lung cancer." Lung cancer 63.3 (2009): 315-321.
Yan, Min, et al. "HER2 expression status in diverse cancers: review of results from 37,992 patients." Cancer and Metastasis Reviews 34 (2015): 157-164.
Yang, Ke, et al., "Mechanisms of resistance to BCR-ABL TKIs and the therapeutic strategies: A review." Critical reviews in oncology/hematology 93.3 (2015): 277-292.
Yoo, Hae Yong, et al. "Frequent CTLA4-CD28 gene fusion in diverse types of T-cell lymphoma." Haematologica 101.6 (2016): 757.
Zhang, Quangeng, et al. "Inactivating mutations and overexpression of BCL10, a caspase recruitment domain-containing gene, in MALT lymphoma with t (1; 14)(p22; q32)." nature genetics 22.1 (1999): 63-68.
Zhang, Yue-Lun, et al. "The prevalence of EGFR mutation in patients with non-small cell lung cancer: a systematic review and meta-analysis." Oncotarget 7.48 (2016): 78985.
Zhang, et al. "MALT1 Inhibitors and Degraders: Strategies for NF-κB-Driven Malignancies", J Med Chem. Mar. 13, 2025;68(5):5075-5096.
International Search Report dated Mar. 5, 2021, prepared in International Application No. PCT/US2020/066999.
International Preliminary Report on Patentability dated Jun. 28, 2022, prepared in International Application No. PCT/US2020/066999.
International Search Report dated Apr. 12, 2022, prepared in International Application No. PCT/US2022/013671.
International Preliminary Report on Patentability dated Jul. 31, 2023, prepared in International Application No. PCT/US2022/013671.
International Search Report dated Jan. 12, 2024, prepared in International Application No. PCT/US2023/070683.
International Preliminary Report on Patentability dated Jan. 28, 2025, prepared in International Application No. PCT/US2023/070683.
International Search Report dated Jan. 9, 2025, prepared in International Application No. PCT/US2024/045971.
Afonina, Inna S., et al. "MALT 1—a universal soldier: multiple strategies to ensure NF-κB activation and target gene expression." The FEBS journal 282.17 (2015): 3286-3297.
Alameda, J. P., et al. "An inactivating CYLD mutation promotes skin tumor progression by conferring enhanced proliferative, survival and angiogenic properties to epidermal cancer cells." Oncogene 29.50 (2010): 6522-6532.
Amit, M., et al. "Upregulation of RET induces perineurial invasion of pancreatic adenocarcinoma." Oncogene 36.23 (2017): 3232-3239.
Baens, Mathijs, et al. "MALT1 auto-proteolysis is essential for NF-κB-dependent gene transcription in activated lymphocytes." PloS one 9.8 (2014): e103774.

(56) References Cited

OTHER PUBLICATIONS

Brvara, M. et al., “An updated patent review of MALT1 inhibitors (2021-present)” Expert Opinion On Therapeutic Patents Apr. 11, 2025.
Connell, Claire M., et al., “Activating HER2 mutations as emerging targets in multiple solid cancers.” ESMO open 2.5 (2017): e000279.
Coornaert, Beatrice, et al. “T cell antigen receptor stimulation induces MALT1 paracaspase-mediated cleavage of the NF-κB inhibitor A20.” Nature immunology 9.3 (2008): 263-271.
Courtois, G., et al., “Mutations in the NF-κB signaling pathway: implications for human disease.” Oncogene 25.51 (2006): 6831-6843.
Ding, Keshuo, et al. “Artemin, a member of the glial cell line-derived neurotrophic factor family of ligands, is HER2-regulated and mediates acquired trastuzumab resistance by promoting cancer stem cell-like behavior in mammary carcinoma cells.” Journal of Biological Chemistry 289.23 (2014): 16057-16071.
Ellison, Gillian, et al. “EGFR mutation testing in lung cancer: a review of available methods and their use for analysis of tumour tissue and cytology samples.” Journal of clinical pathology 66.2 (2013): 79-89.
Farinha, Pedro, and Randy D. Gascoyne. “Molecular pathogenesis of mucosa-associated lymphoid tissue lymphoma.” Journal of Clinical Oncology 23.26 (2005): 6370-6378.
Ferch, Uta, et al. “Inhibition of MALT1 protease activity is selectively toxic for activated B cell-like diffuse large B cell lymphoma cells.” Journal of Experimental Medicine 206.11 (2009): 2313-2320.
Finnberg, Niklas et al. “Selective Suppression of Regulatory T-cell Development with Small Molecule Inhibitors of Mucosa-Associated Lymphoid Tissue Lymphoma Translocation Protein 1 (MALT1)”, Poster presented at the Immuno-Oncology Summit (#IOSummit) in Boston, USA, Published Aug. 27, 2018 (Publications (medivir.com); PowerPoint Presentation (medivir.com))).
Forbes, Ian T., et al. “Synthesis, Biological activity, and molecular modeling studies of selective 5-HT2C/2B receptor antagonists.” Journal of medicinal chemistry 39.25 (1996): 4966-4977.
Gao, Li, et al. “Neurotrophic factor artemin promotes invasiveness and neurotrophic function of pancreatic adenocarcinoma in vivo and in vitro.” Pancreas 44.1 (2015): 134.
Hailfinger, Stephan, et al. “Essential role of MALT1 protease activity in activated B cell-like diffuse large B-cell lymphoma.” Proceedings of the National Academy of Sciences 106.47 (2009): 19946-19951.
Hailfinger, Stephan, et al. “Malt1-dependent RelB cleavage promotes canonical NF-κB activation in lymphocytes and lymphoma cell lines.” Proceedings of the National Academy of Sciences 108.35 (2011): 14596-14601.
Hezam, Kamal, et al. “Artemin promotes oncogenicity, metastasis and drug resistance in cancer cells.” Reviews in the Neurosciences 29.1 (2018): 93-98.
Israël, Alain. “The IKK complex, a central regulator of NF-κB activation.” Cold Spring Harbor perspectives in biology 2.3 (2010): a000158.
Jabara, Haifa H., et al. “A homozygous mucosa-associated lymphoid tissue 1 (MALT1) mutation in a family with combined immunodeficiency.” Journal of allergy and clinical immunology 132.1 (2013): 151-158.
Jabbour, Elias, et al. “Practical advice for determining the role of BCR-ABL mutations in guiding tyrosine kinase inhibitor therapy in patients with chronic myeloid leukemia.” Cancer 117.9 (2011): 1800-1811.
Jaworski, et al. “The paracaspase MALT1: biological function and potential for therapeutic inhibition.” Cellular and Molecular Life Sciences 73 (2016): 459-473.
Jaworski, Maike, et al. “Malt1 protease inactivation efficiently dampens immune responses but causes spontaneous autoimmunity.” The EMBO journal 33.23 (2014): 2765-2781.
Jeltsch, Katharina M., et al. “Cleavage of roquin and regnase-1 by the paracaspase MALT1 releases their cooperatively repressed targets to promote TH17 differentiation.” Nature immunology 15.11 (2014): 1079-1089.
Jiang, Tang, et al. “CARMA3 is crucial for EGFR-Induced activation of NF-κB and tumor progression.” Cancer research 71.6 (2011): 2183-2192.
Johansson, Patricia, et al. “Recurrent mutations in NF-κB pathway components, KMT2D, and NOTCH1/2 in ocular adnexal MALT-type marginal zone lymphomas.” Oncotarget 7.38 (2016): 62627.
Juilland, et al. “Holding all the CARDs: how MALT1 controls CARMA/CARD-dependent signaling.” Frontiers in immunology 9 (2018): 1927.
Kasperkiewicz, Paulina, et al. “Determination of extended substrate specificity of the MALT1 as a strategy for the design of potent substrates and activity-based probes.” Scientific reports 8.1 (2018): 1-10.
Kim, Samuel W., et al. “Mammaglobin-A is a target for breast cancer vaccination.” Oncoimmunology 5.2 (2016): e1069940.
Klein, Theo, et al. “The paracaspase MALT1 cleaves HOIL1 reducing linear ubiquitination by LUBAC to dampen lymphocyte NF-κB signalling.” Nature communications 6.1 (2015): 1-17.
Koester, Dennis C. “Schrödinger’s MALT1 Inhibitor Showcases the Potential of Its Computational Platform and Becomes Its First In-House Clinical Compound”, Drug Hunter, May 1, 2024, p. 1-23, https://drughunter.com/molecule/sgr-1505.
Koshkin, Vadim S., et al. “Systematic review: targeting HER2 in bladder cancer.” Bladder Cancer 5.1 (2019): 1-12.
Kübler, Hubert, et al. “Self-adjuvanted mRNA vaccination in advanced prostate cancer patients: a first-in-man phase I/IIa study.” Journal for immunotherapy of cancer 3.1 (2015): 1-14.
Lee, Seung Ho, et al. “A highly recurrent novel missense mutation in CD28 among angioimmunoblastic T-cell lymphoma patients.” Haematologica 100.12 (2015): e505.
Liu, Xiaochun, et al. “Advanced malignancies treated with a combination of the VEGF inhibitor bevacizumab, anti-EGFR antibody cetuximab, and the mTOR inhibitor temsirolimus.” Oncotarget 7.17 (2016): 23227.
Liu, Xuejiao, et al. “MALT1 is a potential therapeutic target in glioblastoma and plays a crucial role in EGFR-induced NF-κB activation.” Journal of cellular and molecular medicine 24.13 (2020): 7550-7562.
Louis, David N., et al. “The 2016 World Health Organization classification of tumors of the central nervous system: a summary.” Acta neuropathologica 131 (2016): 803-820.
Lowes, Michelle A., Mayte Suarez-Farinas, and James G. Krueger. “Immunology of psoriasis.” Annual review of immunology 32 (2014): 227-255.
Lu, Henry Y., et al. “The CBM-opathies—a rapidly expanding spectrum of human inborn errors of immunity caused by mutations in the CARD11-BCL10-MALT1 complex.” Frontiers in Immunology 9 (2018): 2078.
Massoumi, Ramin. “CYLD: a deubiquitination enzyme with multiple roles in cancer.” Future oncology 7.2 (2011): 285-297.
Mcguire, Conor, et al. “Pharmacological inhibition of MALT1 protease activity protects mice in a mouse model of multiple sclerosis.” Journal of neuroinflammation 11.1 (2014): 1-12.
Midha, Anita, et al., “EGFR mutation incidence in non-small-cell lung cancer of adenocarcinoma histology: a systematic review and global map by ethnicity (mutMapll).” American journal of cancer research 5.9 (2015): 2892.

SEQUENCE LISTING

```
<160> NUMBER OF SEQ ID NOS: 36

<210> SEQ ID NO 1
<211> LENGTH: 220
<212> TYPE: PRT
<213> ORGANISM: Homo sapiens

<400> SEQUENCE: 1

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190
```

Asn Met Thr Pro Arg Arg Pro Gly Pro Thr Arg Lys His Tyr Gln Pro
195 200 205

Tyr Ala Pro Pro Arg Asp Phe Ala Ala Tyr Arg Ser
210 215 220

<210> SEQ ID NO 2
<211> LENGTH: 1271
<212> TYPE: PRT
<213> ORGANISM: Homo sapiens

<400> SEQUENCE: 2

Met Val Asp Pro Val Gly Phe Ala Glu Ala Trp Lys Ala Gln Phe Pro
1 5 10 15

Asp Ser Glu Pro Pro Arg Met Glu Leu Arg Ser Val Gly Asp Ile Glu
20 25 30

Gln Glu Leu Glu Arg Cys Lys Ala Ser Ile Arg Arg Leu Glu Gln Glu
35 40 45

Val Asn Gln Glu Arg Phe Arg Met Ile Tyr Leu Gln Thr Leu Leu Ala
50 55 60

Lys Glu Lys Lys Ser Tyr Asp Arg Gln Arg Trp Gly Phe Arg Arg Ala
65 70 75 80

Ala Gln Ala Pro Asp Gly Ala Ser Glu Pro Arg Ala Ser Ala Ser Arg
85 90 95

Pro Gln Pro Ala Pro Ala Asp Gly Ala Asp Pro Pro Pro Ala Glu Glu
100 105 110

Pro Glu Ala Arg Pro Asp Gly Glu Gly Ser Pro Gly Lys Ala Arg Pro
115 120 125

Gly Thr Ala Arg Arg Pro Gly Ala Ala Ala Ser Gly Glu Arg Asp Asp
130 135 140

Arg Gly Pro Pro Ala Ser Val Ala Ala Leu Arg Ser Asn Phe Glu Arg
145 150 155 160

Ile Arg Lys Gly His Gly Gln Pro Gly Ala Asp Ala Glu Lys Pro Phe
165 170 175

Tyr Val Asn Val Glu Phe His His Glu Arg Gly Leu Val Lys Val Asn
180 185 190

Asp Lys Glu Val Ser Asp Arg Ile Ser Ser Leu Gly Ser Gln Ala Met
195 200 205

Gln Met Glu Arg Lys Lys Ser Gln His Gly Ala Gly Ser Ser Val Gly
210 215 220

Asp Ala Ser Arg Pro Pro Tyr Arg Gly Arg Ser Ser Glu Ser Ser Cys
225 230 235 240

Gly Val Asp Gly Asp Tyr Glu Asp Ala Glu Leu Asn Pro Arg Phe Leu
245 250 255

Lys Asp Asn Leu Ile Asp Ala Asn Gly Gly Ser Arg Pro Pro Trp Pro
260 265 270

Pro Leu Glu Tyr Gln Pro Tyr Gln Ser Ile Tyr Val Gly Gly Met Met
275 280 285

Glu Gly Glu Gly Lys Gly Pro Leu Leu Arg Ser Gln Ser Thr Ser Glu
290 295 300

Gln Glu Lys Arg Leu Thr Trp Pro Arg Arg Ser Tyr Ser Pro Arg Ser
305 310 315 320

Phe Glu Asp Cys Gly Gly Gly Tyr Thr Pro Asp Cys Ser Ser Asn Glu
325 330 335

Asn Leu Thr Ser Ser Glu Glu Asp Phe Ser Ser Gly Gln Ser Ser Arg
340 345 350

-continued

```
Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Gly Glu Gly Ala Phe His Gly Asp Ala Asp Gly Ser Phe Gly Thr
            420                 425                 430

Pro Pro Gly Tyr Gly Cys Ala Ala Asp Arg Ala Glu Glu Gln Arg Arg
        435                 440                 445

His Gln Asp Gly Leu Pro Tyr Ile Asp Asp Ser Pro Ser Ser Ser Pro
    450                 455                 460

His Leu Ser Ser Lys Gly Arg Gly Ser Arg Asp Ala Leu Val Ser Gly
465                 470                 475                 480

Ala Leu Glu Ser Thr Lys Ala Ser Glu Leu Asp Leu Glu Lys Gly Leu
                485                 490                 495

Glu Met Arg Lys Trp Val Leu Ser Gly Ile Leu Ala Ser Glu Glu Thr
            500                 505                 510

Tyr Leu Ser His Leu Glu Ala Leu Leu Leu Pro Met Lys Pro Leu Lys
        515                 520                 525

Ala Ala Ala Thr Thr Ser Gln Pro Val Leu Thr Ser Gln Gln Ile Glu
    530                 535                 540

Thr Ile Phe Phe Lys Val Pro Glu Leu Tyr Glu Ile His Lys Glu Phe
545                 550                 555                 560

Tyr Asp Gly Leu Phe Pro Arg Val Gln Gln Trp Ser His Gln Gln Arg
                565                 570                 575

Val Gly Asp Leu Phe Gln Lys Leu Ala Ser Gln Leu Gly Val Tyr Arg
            580                 585                 590

Ala Phe Val Asp Asn Tyr Gly Val Ala Met Glu Met Ala Glu Lys Cys
        595                 600                 605

Cys Gln Ala Asn Ala Gln Phe Ala Glu Ile Ser Glu Asn Leu Arg Ala
    610                 615                 620

Arg Ser Asn Lys Asp Ala Lys Asp Pro Thr Thr Lys Asn Ser Leu Glu
625                 630                 635                 640

Thr Leu Leu Tyr Lys Pro Val Asp Arg Val Thr Arg Ser Thr Leu Val
                645                 650                 655

Leu His Asp Leu Leu Lys His Thr Pro Ala Ser His Pro Asp His Pro
            660                 665                 670

Leu Leu Gln Asp Ala Leu Arg Ile Ser Gln Asn Phe Leu Ser Ser Ile
        675                 680                 685

Asn Glu Glu Ile Thr Pro Arg Arg Gln Ser Met Thr Val Lys Lys Gly
    690                 695                 700

Glu His Arg Gln Leu Leu Lys Asp Ser Phe Met Val Glu Leu Val Glu
705                 710                 715                 720

Gly Ala Arg Lys Leu Arg His Val Phe Leu Phe Thr Asp Leu Leu Leu
                725                 730                 735

Cys Thr Lys Leu Lys Lys Gln Ser Gly Gly Lys Thr Gln Gln Tyr Asp
            740                 745                 750

Cys Lys Trp Tyr Ile Pro Leu Thr Asp Leu Ser Phe Gln Met Val Asp
        755                 760                 765
```

-continued

```
Glu Leu Glu Ala Val Pro Asn Ile Pro Leu Val Pro Asp Glu Glu Leu
    770                 775                 780

Asp Ala Leu Lys Ile Lys Ile Ser Gln Ile Lys Asn Asp Ile Gln Arg
785                 790                 795                 800

Glu Lys Arg Ala Asn Lys Gly Ser Lys Ala Thr Glu Arg Leu Lys Lys
                805                 810                 815

Lys Leu Ser Glu Gln Glu Ser Leu Leu Leu Leu Met Ser Pro Ser Met
            820                 825                 830

Ala Phe Arg Val His Ser Arg Asn Gly Lys Ser Tyr Thr Phe Leu Ile
        835                 840                 845

Ser Ser Asp Tyr Glu Arg Ala Glu Trp Arg Glu Asn Ile Arg Glu Gln
    850                 855                 860

Gln Lys Lys Cys Phe Arg Ser Phe Ser Leu Thr Ser Val Glu Leu Gln
865                 870                 875                 880

Met Leu Thr Asn Ser Cys Val Lys Leu Gln Thr Val His Ser Ile Pro
                885                 890                 895

Leu Thr Ile Asn Lys Glu Asp Asp Glu Ser Pro Gly Leu Tyr Gly Phe
            900                 905                 910

Leu Asn Val Ile Val His Ser Ala Thr Gly Phe Lys Gln Ser Ser Asn
        915                 920                 925

Leu Tyr Cys Thr Leu Glu Val Asp Ser Phe Gly Tyr Phe Val Asn Lys
    930                 935                 940

Ala Lys Thr Arg Val Tyr Arg Asp Thr Ala Glu Pro Asn Trp Asn Glu
945                 950                 955                 960

Glu Phe Glu Ile Glu Leu Glu Gly Ser Gln Thr Leu Arg Ile Leu Cys
                965                 970                 975

Tyr Glu Lys Cys Tyr Asn Lys Thr Lys Ile Pro Lys Glu Asp Gly Glu
            980                 985                 990

Ser Thr Asp Arg Leu Met Gly Lys  Gly Gln Val Gln Leu  Asp Pro Gln
        995                 1000                1005

Ala Leu  Gln Asp Arg Asp Trp  Gln Arg Thr Val Ile  Ala Met Asn
    1010                1015                1020

Gly Ile  Glu Val Lys Leu Ser  Val Lys Phe Asn Ser  Arg Glu Phe
    1025                1030                1035

Ser Leu  Lys Arg Met Pro Ser  Arg Lys Gln Thr Gly  Val Phe Gly
    1040                1045                1050

Val Lys  Ile Ala Val Val Thr  Lys Arg Glu Arg Ser  Lys Val Pro
    1055                1060                1065

Tyr Ile  Val Arg Gln Cys Val  Glu Glu Ile Glu Arg  Arg Gly Met
    1070                1075                1080

Glu Glu  Val Gly Ile Tyr Arg  Val Ser Gly Val Ala  Thr Asp Ile
    1085                1090                1095

Gln Ala  Leu Lys Ala Ala Phe  Asp Val Asn Asn Lys  Asp Val Ser
    1100                1105                1110

Val Met  Met Ser Glu Met Asp  Val Asn Ala Ile Ala  Gly Thr Leu
    1115                1120                1125

Lys Leu  Tyr Phe Arg Glu Leu  Pro Glu Pro Leu Phe  Thr Asp Glu
    1130                1135                1140

Phe Tyr  Pro Asn Phe Ala Glu  Gly Ile Ala Leu Ser  Asp Pro Val
    1145                1150                1155

Ala Lys  Glu Ser Cys Met Leu  Asn Leu Leu Leu Ser  Leu Pro Glu
    1160                1165                1170
```

Ala Asn Leu Leu Thr Phe Leu Phe Leu Leu Asp His Leu Lys Arg
1175 1180 1185

Val Ala Glu Lys Glu Ala Val Asn Lys Met Ser Leu His Asn Leu
1190 1195 1200

Ala Thr Val Phe Gly Pro Thr Leu Leu Arg Pro Ser Glu Lys Glu
1205 1210 1215

Ser Lys Leu Pro Ala Asn Pro Ser Gln Pro Ile Thr Met Thr Asp
1220 1225 1230

Ser Trp Ser Leu Glu Val Met Ser Gln Val Gln Val Leu Leu Tyr
1235 1240 1245

Phe Leu Gln Leu Glu Ala Ile Pro Ala Pro Asp Ser Lys Arg Gln
1250 1255 1260

Ser Ile Leu Phe Ser Thr Glu Val
1265 1270

<210> SEQ ID NO 3
<211> LENGTH: 1210
<212> TYPE: PRT
<213> ORGANISM: Homo sapiens

<400> SEQUENCE: 3

Met Arg Pro Ser Gly Thr Ala Gly Ala Ala Leu Leu Ala Leu Leu Ala
1 5 10 15

Ala Leu Cys Pro Ala Ser Arg Ala Leu Glu Glu Lys Lys Val Cys Gln
20 25 30

Gly Thr Ser Asn Lys Leu Thr Gln Leu Gly Thr Phe Glu Asp His Phe
35 40 45

Leu Ser Leu Gln Arg Met Phe Asn Asn Cys Glu Val Val Leu Gly Asn
50 55 60

Leu Glu Ile Thr Tyr Val Gln Arg Asn Tyr Asp Leu Ser Phe Leu Lys
65 70 75 80

Thr Ile Gln Glu Val Ala Gly Tyr Val Leu Ile Ala Leu Asn Thr Val
85 90 95

Glu Arg Ile Pro Leu Glu Asn Leu Gln Ile Ile Arg Gly Asn Met Tyr
100 105 110

Tyr Glu Asn Ser Tyr Ala Leu Ala Val Leu Ser Asn Tyr Asp Ala Asn
115 120 125

Lys Thr Gly Leu Lys Glu Leu Pro Met Arg Asn Leu Gln Glu Ile Leu
130 135 140

His Gly Ala Val Arg Phe Ser Asn Asn Pro Ala Leu Cys Asn Val Glu
145 150 155 160

Ser Ile Gln Trp Arg Asp Ile Val Ser Ser Asp Phe Leu Ser Asn Met
165 170 175

Ser Met Asp Phe Gln Asn His Leu Gly Ser Cys Gln Lys Cys Asp Pro
180 185 190

Ser Cys Pro Asn Gly Ser Cys Trp Gly Ala Gly Glu Glu Asn Cys Gln
195 200 205

Lys Leu Thr Lys Ile Ile Cys Ala Gln Gln Cys Ser Gly Arg Cys Arg
210 215 220

Gly Lys Ser Pro Ser Asp Cys Cys His Asn Gln Cys Ala Ala Gly Cys
225 230 235 240

Thr Gly Pro Arg Glu Ser Asp Cys Leu Val Cys Arg Lys Phe Arg Asp
245 250 255

-continued

```
Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670
```

-continued

```
Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                 1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080
```

```
Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200

Ser Ser  Glu Phe Ile Gly Ala
    1205                 1210


<210> SEQ ID NO 4
<211> LENGTH: 1255
<212> TYPE: PRT
<213> ORGANISM: Homo sapiens

<400> SEQUENCE: 4

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220
```

-continued

```
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640
```

-continued

```
Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050
```

Ser Gly Gly Gly Asp Leu Thr Leu Gly Leu Glu Pro Ser Glu Glu
1055 1060 1065

Glu Ala Pro Arg Ser Pro Leu Ala Pro Ser Glu Gly Ala Gly Ser
1070 1075 1080

Asp Val Phe Asp Gly Asp Leu Gly Met Gly Ala Ala Lys Gly Leu
1085 1090 1095

Gln Ser Leu Pro Thr His Asp Pro Ser Pro Leu Gln Arg Tyr Ser
1100 1105 1110

Glu Asp Pro Thr Val Pro Leu Pro Ser Glu Thr Asp Gly Tyr Val
1115 1120 1125

Ala Pro Leu Thr Cys Ser Pro Gln Pro Glu Tyr Val Asn Gln Pro
1130 1135 1140

Asp Val Arg Pro Gln Pro Pro Ser Pro Arg Glu Gly Pro Leu Pro
1145 1150 1155

Ala Ala Arg Pro Ala Gly Ala Thr Leu Glu Arg Pro Lys Thr Leu
1160 1165 1170

Ser Pro Gly Lys Asn Gly Val Val Lys Asp Val Phe Ala Phe Gly
1175 1180 1185

Gly Ala Val Glu Asn Pro Glu Tyr Leu Thr Pro Gln Gly Gly Ala
1190 1195 1200

Ala Pro Gln Pro His Pro Pro Pro Ala Phe Ser Pro Ala Phe Asp
1205 1210 1215

Asn Leu Tyr Tyr Trp Asp Gln Asp Pro Pro Glu Arg Gly Ala Pro
1220 1225 1230

Pro Ser Thr Phe Lys Gly Thr Pro Thr Ala Glu Asn Pro Glu Tyr
1235 1240 1245

Leu Gly Leu Asp Val Pro Val
1250 1255

<210> SEQ ID NO 5
<211> LENGTH: 671
<212> TYPE: PRT
<213> ORGANISM: Homo sapiens

<400> SEQUENCE: 5

Met Ala Asp Pro Ala Ala Gly Pro Pro Pro Ser Glu Gly Glu Glu Ser
1 5 10 15

Thr Val Arg Phe Ala Arg Lys Gly Ala Leu Arg Gln Lys Asn Val His
20 25 30

Glu Val Lys Asn His Lys Phe Thr Ala Arg Phe Phe Lys Gln Pro Thr
35 40 45

Phe Cys Ser His Cys Thr Asp Phe Ile Trp Gly Phe Gly Lys Gln Gly
50 55 60

Phe Gln Cys Gln Val Cys Cys Phe Val Val His Lys Arg Cys His Glu
65 70 75 80

Phe Val Thr Phe Ser Cys Pro Gly Ala Asp Lys Gly Pro Ala Ser Asp
85 90 95

Asp Pro Arg Ser Lys His Lys Phe Lys Ile His Thr Tyr Ser Ser Pro
100 105 110

Thr Phe Cys Asp His Cys Gly Ser Leu Leu Tyr Gly Leu Ile His Gln
115 120 125

Gly Met Lys Cys Asp Thr Cys Met Met Asn Val His Lys Arg Cys Val
130 135 140

-continued

```
Met Asn Val Pro Ser Leu Cys Gly Thr Asp His Thr Glu Arg Arg Gly
145                 150                 155                 160

Arg Ile Tyr Ile Gln Ala His Ile Asp Arg Asp Val Leu Ile Val Leu
                165                 170                 175

Val Arg Asp Ala Lys Asn Leu Val Pro Met Asp Pro Asn Gly Leu Ser
            180                 185                 190

Asp Pro Tyr Val Lys Leu Lys Leu Ile Pro Asp Pro Lys Ser Glu Ser
        195                 200                 205

Lys Gln Lys Thr Lys Thr Ile Lys Cys Ser Leu Asn Pro Glu Trp Asn
    210                 215                 220

Glu Thr Phe Arg Phe Gln Leu Lys Glu Ser Asp Lys Asp Arg Arg Leu
225                 230                 235                 240

Ser Val Glu Ile Trp Asp Trp Asp Leu Thr Ser Arg Asn Asp Phe Met
                245                 250                 255

Gly Ser Leu Ser Phe Gly Ile Ser Glu Leu Gln Lys Ala Ser Val Asp
            260                 265                 270

Gly Trp Phe Lys Leu Leu Ser Gln Glu Glu Gly Glu Tyr Phe Asn Val
        275                 280                 285

Pro Val Pro Pro Glu Gly Ser Glu Ala Asn Glu Glu Leu Arg Gln Lys
    290                 295                 300

Phe Glu Arg Ala Lys Ile Ser Gln Gly Thr Lys Val Pro Glu Glu Lys
305                 310                 315                 320

Thr Thr Asn Thr Val Ser Lys Phe Asp Asn Asn Gly Asn Arg Asp Arg
                325                 330                 335

Met Lys Leu Thr Asp Phe Asn Phe Leu Met Val Leu Gly Lys Gly Ser
            340                 345                 350

Phe Gly Lys Val Met Leu Ser Glu Arg Lys Gly Thr Asp Glu Leu Tyr
        355                 360                 365

Ala Val Lys Ile Leu Lys Lys Asp Val Val Ile Gln Asp Asp Asp Val
    370                 375                 380

Glu Cys Thr Met Val Glu Lys Arg Val Leu Ala Leu Pro Gly Lys Pro
385                 390                 395                 400

Pro Phe Leu Thr Gln Leu His Ser Cys Phe Gln Thr Met Asp Arg Leu
                405                 410                 415

Tyr Phe Val Met Glu Tyr Val Asn Gly Gly Asp Leu Met Tyr His Ile
            420                 425                 430

Gln Gln Val Gly Arg Phe Lys Glu Pro His Ala Val Phe Tyr Ala Ala
        435                 440                 445

Glu Ile Ala Ile Gly Leu Phe Phe Leu Gln Ser Lys Gly Ile Ile Tyr
    450                 455                 460

Arg Asp Leu Lys Leu Asp Asn Val Met Leu Asp Ser Glu Gly His Ile
465                 470                 475                 480

Lys Ile Ala Asp Phe Gly Met Cys Lys Glu Asn Ile Trp Asp Gly Val
                485                 490                 495

Thr Thr Lys Thr Phe Cys Gly Thr Pro Asp Tyr Ile Ala Pro Glu Ile
            500                 505                 510

Ile Ala Tyr Gln Pro Tyr Gly Lys Ser Val Asp Trp Trp Ala Phe Gly
        515                 520                 525

Val Leu Leu Tyr Glu Met Leu Ala Gly Gln Ala Pro Phe Glu Gly Glu
    530                 535                 540

Asp Glu Asp Glu Leu Phe Gln Ser Ile Met Glu His Asn Val Ala Tyr
545                 550                 555                 560
```

-continued

```
Pro Lys Ser Met Ser Lys Glu Ala Val Ala Ile Cys Lys Gly Leu Met
                565                 570                 575

Thr Lys His Pro Gly Lys Arg Leu Gly Cys Gly Pro Glu Gly Glu Arg
            580                 585                 590

Asp Ile Lys Glu His Ala Phe Phe Arg Tyr Ile Asp Trp Glu Lys Leu
        595                 600                 605

Glu Arg Lys Glu Ile Gln Pro Pro Tyr Lys Pro Lys Ala Arg Asp Lys
    610                 615                 620

Arg Asp Thr Ser Asn Phe Asp Lys Glu Phe Thr Arg Gln Pro Val Glu
625                 630                 635                 640

Leu Thr Pro Thr Asp Lys Leu Phe Ile Met Asn Leu Asp Gln Asn Glu
                645                 650                 655

Phe Ala Gly Phe Ser Tyr Thr Asn Pro Glu Phe Val Ile Asn Val
            660                 665                 670


<210> SEQ ID NO 6
<211> LENGTH: 706
<212> TYPE: PRT
<213> ORGANISM: Homo sapiens

<400> SEQUENCE: 6

Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175

His Glu Phe Val Trp Gly Leu Asn Lys Gln Gly Tyr Gln Cys Arg Gln
            180                 185                 190

Cys Asn Ala Ala Ile His Lys Lys Cys Ile Asp Lys Val Ile Ala Lys
        195                 200                 205

Cys Thr Gly Ser Ala Ile Asn Ser Arg Glu Thr Met Phe His Lys Glu
    210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270
```

-continued

```
Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Cys Leu
    290                 295                 300

Arg Asp Thr Glu Gln Ile Phe Arg Glu Gly Pro Val Glu Ile Gly Leu
305                 310                 315                 320

Pro Cys Ser Ile Lys Asn Glu Ala Arg Pro Pro Cys Leu Pro Thr Pro
                325                 330                 335

Gly Lys Arg Glu Pro Gln Gly Ile Ser Trp Glu Ser Pro Leu Asp Glu
            340                 345                 350

Val Asp Lys Met Cys His Leu Pro Glu Pro Glu Leu Asn Lys Glu Arg
        355                 360                 365

Pro Ser Leu Gln Ile Lys Leu Lys Ile Glu Asp Phe Ile Leu His Lys
    370                 375                 380

Met Leu Gly Lys Gly Ser Phe Gly Lys Val Phe Leu Ala Glu Phe Lys
385                 390                 395                 400

Lys Thr Asn Gln Phe Phe Ala Ile Lys Ala Leu Lys Lys Asp Val Val
                405                 410                 415

Leu Met Asp Asp Asp Val Glu Cys Thr Met Val Glu Lys Arg Val Leu
            420                 425                 430

Ser Leu Ala Trp Glu His Pro Phe Leu Thr His Met Phe Cys Thr Phe
        435                 440                 445

Gln Thr Lys Glu Asn Leu Phe Phe Val Met Glu Tyr Leu Asn Gly Gly
    450                 455                 460

Asp Leu Met Tyr His Ile Gln Ser Cys His Lys Phe Asp Leu Ser Arg
465                 470                 475                 480

Ala Thr Phe Tyr Ala Ala Glu Ile Ile Leu Gly Leu Gln Phe Leu His
                485                 490                 495

Ser Lys Gly Ile Val Tyr Arg Asp Leu Lys Leu Asp Asn Ile Leu Leu
            500                 505                 510

Asp Lys Asp Gly His Ile Lys Ile Ala Asp Phe Gly Met Cys Lys Glu
        515                 520                 525

Asn Met Leu Gly Asp Ala Lys Thr Asn Thr Phe Cys Gly Thr Pro Asp
    530                 535                 540

Tyr Ile Ala Pro Glu Ile Leu Leu Gly Gln Lys Tyr Asn His Ser Val
545                 550                 555                 560

Asp Trp Trp Ser Phe Gly Val Leu Leu Tyr Glu Met Leu Ile Gly Gln
                565                 570                 575

Ser Pro Phe His Gly Gln Asp Glu Glu Glu Leu Phe His Ser Ile Arg
            580                 585                 590

Met Asp Asn Pro Phe Tyr Pro Arg Trp Leu Glu Lys Glu Ala Lys Asp
        595                 600                 605

Leu Leu Val Lys Leu Phe Val Arg Glu Pro Glu Lys Arg Leu Gly Val
    610                 615                 620

Arg Gly Asp Ile Arg Gln His Pro Leu Phe Arg Glu Ile Asn Trp Glu
625                 630                 635                 640

Glu Leu Glu Arg Lys Glu Ile Asp Pro Pro Phe Arg Pro Lys Val Lys
                645                 650                 655

Ser Pro Phe Asp Cys Ser Asn Phe Asp Lys Glu Phe Leu Asn Glu Lys
            660                 665                 670

Pro Arg Leu Ser Phe Ala Asp Arg Ala Leu Ile Asn Ser Met Asp Gln
        675                 680                 685
```

-continued

Asn Met Phe Arg Asn Phe Ser Phe Met Asn Pro Gly Met Glu Arg Leu
    690                 695                 700

Ile Ser
705

<210> SEQ ID NO 7
<211> LENGTH: 824
<212> TYPE: PRT
<213> ORGANISM: Homo sapiens

<400> SEQUENCE: 7

Met Ser Leu Leu Gly Asp Pro Leu Gln Ala Leu Pro Pro Ser Ala Ala
1               5                   10                  15

Pro Thr Gly Pro Leu Leu Ala Pro Pro Ala Gly Ala Thr Leu Asn Arg
            20                  25                  30

Leu Arg Glu Pro Leu Leu Arg Arg Leu Ser Glu Leu Leu Asp Gln Ala
        35                  40                  45

Pro Glu Gly Arg Gly Trp Arg Arg Leu Ala Glu Leu Ala Gly Ser Arg
    50                  55                  60

Gly Arg Leu Arg Leu Ser Cys Leu Asp Leu Glu Gln Cys Ser Leu Lys
65                  70                  75                  80

Val Leu Glu Pro Glu Gly Ser Pro Ser Leu Cys Leu Leu Lys Leu Met
                85                  90                  95

Gly Glu Lys Gly Cys Thr Val Thr Glu Leu Ser Asp Phe Leu Gln Ala
            100                 105                 110

Met Glu His Thr Glu Val Leu Gln Leu Leu Ser Pro Pro Gly Ile Lys
        115                 120                 125

Ile Thr Val Asn Pro Glu Ser Lys Ala Val Leu Ala Gly Gln Phe Val
    130                 135                 140

Lys Leu Cys Cys Arg Ala Thr Gly His Pro Phe Val Gln Tyr Gln Trp
145                 150                 155                 160

Phe Lys Met Asn Lys Glu Ile Pro Asn Gly Asn Thr Ser Glu Leu Ile
                165                 170                 175

Phe Asn Ala Val His Val Lys Asp Ala Gly Phe Tyr Val Cys Arg Val
            180                 185                 190

Asn Asn Asn Phe Thr Phe Glu Phe Ser Gln Trp Ser Gln Leu Asp Val
        195                 200                 205

Cys Asp Ile Pro Glu Ser Phe Gln Arg Ser Val Asp Gly Val Ser Glu
    210                 215                 220

Ser Lys Leu Gln Ile Cys Val Glu Pro Thr Ser Gln Lys Leu Met Pro
225                 230                 235                 240

Gly Ser Thr Leu Val Leu Gln Cys Val Ala Val Gly Ser Pro Ile Pro
                245                 250                 255

His Tyr Gln Trp Phe Lys Asn Glu Leu Pro Leu Thr His Glu Thr Lys
            260                 265                 270

Lys Leu Tyr Met Val Pro Tyr Val Asp Leu Glu His Gln Gly Thr Tyr
        275                 280                 285

Trp Cys His Val Tyr Asn Asp Arg Asp Ser Gln Asp Ser Lys Lys Val
    290                 295                 300

Glu Ile Ile Ile Gly Arg Thr Asp Glu Ala Val Glu Cys Thr Glu Asp
305                 310                 315                 320

Glu Leu Asn Asn Leu Gly His Pro Asp Asn Lys Glu Gln Thr Thr Asp
                325                 330                 335

Gln Pro Leu Ala Lys Asp Lys Val Ala Leu Leu Ile Gly Asn Met Asn
            340                 345                 350

-continued

```
Tyr Arg Glu His Pro Lys Leu Lys Ala Pro Leu Val Asp Val Tyr Glu
        355                 360                 365

Leu Thr Asn Leu Leu Arg Gln Leu Asp Phe Lys Val Val Ser Leu Leu
    370                 375                 380

Asp Leu Thr Glu Tyr Glu Met Arg Asn Ala Val Asp Glu Phe Leu Leu
385                 390                 395                 400

Leu Leu Asp Lys Gly Val Tyr Gly Leu Leu Tyr Tyr Ala Gly His Gly
                405                 410                 415

Tyr Glu Asn Phe Gly Asn Ser Phe Met Val Pro Val Asp Ala Pro Asn
            420                 425                 430

Pro Tyr Arg Ser Glu Asn Cys Leu Cys Val Gln Asn Ile Leu Lys Leu
        435                 440                 445

Met Gln Glu Lys Glu Thr Gly Leu Asn Val Phe Leu Leu Asp Met Cys
    450                 455                 460

Arg Lys Arg Asn Asp Tyr Asp Asp Thr Ile Pro Ile Leu Asp Ala Leu
465                 470                 475                 480

Lys Val Thr Ala Asn Ile Val Phe Gly Tyr Ala Thr Cys Gln Gly Ala
                485                 490                 495

Glu Ala Phe Glu Ile Gln His Ser Gly Leu Ala Asn Gly Ile Phe Met
            500                 505                 510

Lys Phe Leu Lys Asp Arg Leu Leu Glu Asp Lys Lys Ile Thr Val Leu
        515                 520                 525

Leu Asp Glu Val Ala Glu Asp Met Gly Lys Cys His Leu Thr Lys Gly
    530                 535                 540

Lys Gln Ala Leu Glu Ile Arg Ser Ser Leu Ser Glu Lys Arg Ala Leu
545                 550                 555                 560

Thr Asp Pro Ile Gln Gly Thr Glu Tyr Ser Ala Glu Ser Leu Val Arg
                565                 570                 575

Asn Leu Gln Trp Ala Lys Ala His Glu Leu Pro Glu Ser Met Cys Leu
            580                 585                 590

Lys Phe Asp Cys Gly Val Gln Ile Gln Leu Gly Phe Ala Ala Glu Phe
        595                 600                 605

Ser Asn Val Met Ile Ile Tyr Thr Ser Ile Val Tyr Lys Pro Pro Glu
    610                 615                 620

Ile Ile Met Cys Asp Ala Tyr Val Thr Asp Phe Pro Leu Asp Leu Asp
625                 630                 635                 640

Ile Asp Pro Lys Asp Ala Asn Lys Gly Thr Pro Glu Glu Thr Gly Ser
                645                 650                 655

Tyr Leu Val Ser Lys Asp Leu Pro Lys His Cys Leu Tyr Thr Arg Leu
            660                 665                 670

Ser Ser Leu Gln Lys Leu Lys Glu His Leu Val Phe Thr Val Cys Leu
        675                 680                 685

Ser Tyr Gln Tyr Ser Gly Leu Glu Asp Thr Val Glu Asp Lys Gln Glu
    690                 695                 700

Val Asn Val Gly Lys Pro Leu Ile Ala Lys Leu Asp Met His Arg Gly
705                 710                 715                 720

Leu Gly Arg Lys Thr Cys Phe Gln Thr Cys Leu Met Ser Asn Gly Pro
                725                 730                 735

Tyr Gln Ser Ser Ala Ala Thr Ser Gly Gly Ala Gly His Tyr His Ser
            740                 745                 750

Leu Gln Asp Pro Phe His Gly Val Tyr His Ser His Pro Gly Asn Pro
        755                 760                 765
```

-continued

Ser Asn Val Thr Pro Ala Asp Ser Cys His Cys Ser Arg Thr Pro Asp
770 775 780

Ala Phe Ile Ser Ser Phe Ala His His Ala Ser Cys His Phe Ser Arg
785 790 795 800

Ser Asn Val Pro Val Glu Thr Thr Asp Glu Ile Pro Phe Ser Phe Ser
805 810 815

Asp Arg Leu Arg Ile Ser Glu Lys
820

<210> SEQ ID NO 8
<211> LENGTH: 1154
<212> TYPE: PRT
<213> ORGANISM: Homo sapiens

<400> SEQUENCE: 8

Met Pro Gly Gly Gly Pro Glu Met Asp Asp Tyr Met Glu Thr Leu Lys
1 5 10 15

Asp Glu Glu Asp Ala Leu Trp Glu Asn Val Glu Cys Asn Arg His Met
20 25 30

Leu Ser Arg Tyr Ile Asn Pro Ala Lys Leu Thr Pro Tyr Leu Arg Gln
35 40 45

Cys Lys Val Ile Asp Glu Gln Asp Glu Asp Glu Val Leu Asn Ala Pro
50 55 60

Met Leu Pro Ser Lys Ile Asn Arg Ala Gly Arg Leu Leu Asp Ile Leu
65 70 75 80

His Thr Lys Gly Gln Arg Gly Tyr Val Val Phe Leu Glu Ser Leu Glu
85 90 95

Phe Tyr Tyr Pro Glu Leu Tyr Lys Leu Val Thr Gly Lys Glu Pro Thr
100 105 110

Arg Arg Phe Ser Thr Ile Val Val Glu Glu Gly His Glu Gly Leu Thr
115 120 125

His Phe Leu Met Asn Glu Val Ile Lys Leu Gln Gln Gln Met Lys Ala
130 135 140

Lys Asp Leu Gln Arg Cys Glu Leu Leu Ala Arg Leu Arg Gln Leu Glu
145 150 155 160

Asp Glu Lys Lys Gln Met Thr Leu Thr Arg Val Glu Leu Leu Thr Phe
165 170 175

Gln Glu Arg Tyr Tyr Lys Met Lys Glu Glu Arg Asp Ser Tyr Asn Asp
180 185 190

Glu Leu Val Lys Val Lys Asp Asp Asn Tyr Asn Leu Ala Met Arg Tyr
195 200 205

Ala Gln Leu Ser Glu Glu Lys Asn Met Ala Val Met Arg Ser Arg Asp
210 215 220

Leu Gln Leu Glu Ile Asp Gln Leu Lys His Arg Leu Asn Lys Met Glu
225 230 235 240

Glu Glu Cys Lys Leu Glu Arg Asn Gln Ser Leu Lys Leu Lys Asn Asp
245 250 255

Ile Glu Asn Arg Pro Lys Lys Glu Gln Val Leu Glu Leu Glu Arg Glu
260 265 270

Asn Glu Met Leu Lys Thr Lys Asn Gln Glu Leu Gln Ser Ile Ile Gln
275 280 285

Ala Gly Lys Arg Ser Leu Pro Asp Ser Asp Lys Ala Ile Leu Asp Ile
290 295 300

Leu Glu His Asp Arg Lys Glu Ala Leu Glu Asp Arg Gln Glu Leu Val
305 310 315 320

-continued

```
Asn Arg Ile Tyr Asn Leu Gln Glu Glu Ala Arg Gln Ala Glu Glu Leu
                325                 330                 335

Arg Asp Lys Tyr Leu Glu Glu Lys Glu Asp Leu Glu Leu Lys Cys Ser
            340                 345                 350

Thr Leu Gly Lys Asp Cys Glu Met Tyr Lys His Arg Met Asn Thr Val
        355                 360                 365

Met Leu Gln Leu Glu Glu Val Glu Arg Glu Arg Asp Gln Ala Phe His
    370                 375                 380

Ser Arg Asp Glu Ala Gln Thr Gln Tyr Ser Gln Cys Leu Ile Glu Lys
385                 390                 395                 400

Asp Lys Tyr Arg Lys Gln Ile Arg Glu Leu Glu Glu Lys Asn Asp Glu
                405                 410                 415

Met Arg Ile Glu Met Val Arg Arg Glu Ala Cys Ile Val Asn Leu Glu
            420                 425                 430

Ser Lys Leu Arg Arg Leu Ser Lys Asp Ser Asn Asn Leu Asp Gln Ser
        435                 440                 445

Leu Pro Arg Asn Leu Pro Val Thr Ile Ile Ser Gln Asp Phe Gly Asp
    450                 455                 460

Ala Ser Pro Arg Thr Asn Gly Gln Glu Ala Asp Asp Ser Ser Thr Ser
465                 470                 475                 480

Glu Glu Ser Pro Glu Asp Ser Lys Tyr Phe Leu Pro Tyr His Pro Pro
                485                 490                 495

Gln Arg Arg Met Asn Leu Lys Gly Ile Gln Leu Gln Arg Ala Lys Ser
            500                 505                 510

Pro Ile Ser Leu Lys Arg Thr Ser Asp Phe Gln Ala Lys Gly His Glu
        515                 520                 525

Glu Glu Gly Thr Asp Ala Ser Pro Ser Ser Cys Gly Ser Leu Pro Ile
    530                 535                 540

Thr Asn Ser Phe Thr Lys Met Gln Pro Pro Arg Ser Arg Ser Ser Ile
545                 550                 555                 560

Met Ser Ile Thr Ala Glu Pro Pro Gly Asn Asp Ser Ile Val Arg Arg
                565                 570                 575

Tyr Lys Glu Asp Ala Pro His Arg Ser Thr Val Glu Glu Asp Asn Asp
            580                 585                 590

Ser Gly Gly Phe Asp Ala Leu Asp Leu Asp Asp Asp Ser His Glu Arg
        595                 600                 605

Tyr Ser Phe Gly Pro Ser Ser Ile His Ser Ser Ser Ser Ser His Gln
    610                 615                 620

Ser Glu Gly Leu Asp Ala Tyr Asp Leu Glu Gln Val Asn Leu Met Phe
625                 630                 635                 640

Arg Lys Phe Ser Leu Glu Arg Pro Phe Arg Pro Ser Val Thr Ser Val
                645                 650                 655

Gly His Val Arg Gly Pro Gly Pro Ser Val Gln His Thr Thr Leu Asn
            660                 665                 670

Gly Asp Ser Leu Thr Ser Gln Leu Thr Leu Leu Gly Gly Asn Ala Arg
        675                 680                 685

Gly Ser Phe Val His Ser Val Lys Pro Gly Ser Leu Ala Glu Lys Ala
    690                 695                 700

Gly Leu Arg Glu Gly His Gln Leu Leu Leu Leu Glu Gly Cys Ile Arg
705                 710                 715                 720

Gly Glu Arg Gln Ser Val Pro Leu Asp Thr Cys Thr Lys Glu Glu Ala
                725                 730                 735
```

-continued

His Trp Thr Ile Gln Arg Cys Ser Gly Pro Val Thr Leu His Tyr Lys
740 745 750

Val Asn His Glu Gly Tyr Arg Lys Leu Val Lys Asp Met Glu Asp Gly
755 760 765

Leu Ile Thr Ser Gly Asp Ser Phe Tyr Ile Arg Leu Asn Leu Asn Ile
770 775 780

Ser Ser Gln Leu Asp Ala Cys Thr Met Ser Leu Lys Cys Asp Asp Val
785 790 795 800

Val His Val Arg Asp Thr Met Tyr Gln Asp Arg His Glu Trp Leu Cys
805 810 815

Ala Arg Val Asp Pro Phe Thr Asp His Asp Leu Asp Met Gly Thr Ile
820 825 830

Pro Ser Tyr Ser Arg Ala Gln Gln Leu Leu Leu Val Lys Leu Gln Arg
835 840 845

Leu Met His Arg Gly Ser Arg Glu Glu Val Asp Gly Thr His His Thr
850 855 860

Leu Arg Ala Leu Arg Asn Thr Leu Gln Pro Glu Glu Ala Leu Ser Thr
865 870 875 880

Ser Asp Pro Arg Val Ser Pro Arg Leu Ser Arg Ala Ser Phe Leu Phe
885 890 895

Gly Gln Leu Leu Gln Phe Val Ser Arg Ser Glu Asn Lys Tyr Lys Arg
900 905 910

Met Asn Ser Asn Glu Arg Val Arg Ile Ile Ser Gly Ser Pro Leu Gly
915 920 925

Ser Leu Ala Arg Ser Ser Leu Asp Ala Thr Lys Leu Leu Thr Glu Lys
930 935 940

Gln Glu Glu Leu Asp Pro Glu Ser Glu Leu Gly Lys Asn Leu Ser Leu
945 950 955 960

Ile Pro Tyr Ser Leu Val Arg Ala Phe Tyr Cys Glu Arg Arg Arg Pro
965 970 975

Val Leu Phe Thr Pro Thr Val Leu Ala Lys Thr Leu Val Gln Arg Leu
980 985 990

Leu Asn Ser Gly Gly Ala Met Glu Phe Thr Ile Cys Lys Ser Asp Ile
995 1000 1005

Val Thr Arg Asp Glu Phe Leu Arg Arg Gln Lys Thr Glu Thr Ile
1010 1015 1020

Ile Tyr Ser Arg Glu Lys Asn Pro Asn Ala Phe Glu Cys Ile Ala
1025 1030 1035

Pro Ala Asn Ile Glu Ala Val Ala Ala Lys Asn Lys His Cys Leu
1040 1045 1050

Leu Glu Ala Gly Ile Gly Cys Thr Arg Asp Leu Ile Lys Ser Asn
1055 1060 1065

Ile Tyr Pro Ile Val Leu Phe Ile Arg Val Cys Glu Lys Asn Ile
1070 1075 1080

Lys Arg Phe Arg Lys Leu Leu Pro Arg Pro Glu Thr Glu Glu Glu
1085 1090 1095

Phe Leu Arg Val Cys Arg Leu Lys Glu Lys Glu Leu Glu Ala Leu
1100 1105 1110

Pro Cys Leu Tyr Ala Thr Val Glu Pro Asp Met Trp Gly Ser Val
1115 1120 1125

```
Glu Glu  Leu Leu Arg Val Val  Lys Asp Lys Ile Gly  Glu Glu Gln
    1130                1135                1140

Arg Lys  Thr Ile Trp Val Asp  Glu Asp Gln Leu
    1145                1150


<210> SEQ ID NO 9
<211> LENGTH: 1004
<212> TYPE: PRT
<213> ORGANISM: Homo sapiens

<400> SEQUENCE: 9

Met Gly Glu Leu Cys Arg Arg Asp Ser Ala Leu Thr Ala Leu Asp Glu
1               5                   10                  15

Glu Thr Leu Trp Glu Met Met Glu Ser His Arg His Arg Ile Val Arg
            20                  25                  30

Cys Ile Cys Pro Ser Arg Leu Thr Pro Tyr Leu Arg Gln Ala Lys Val
        35                  40                  45

Leu Cys Gln Leu Asp Glu Glu Glu Val Leu His Ser Pro Arg Leu Thr
    50                  55                  60

Asn Ser Ala Met Arg Ala Gly His Leu Leu Asp Leu Leu Lys Thr Arg
65                  70                  75                  80

Gly Lys Asn Gly Ala Ile Ala Phe Leu Glu Ser Leu Lys Phe His Asn
                85                  90                  95

Pro Asp Val Tyr Thr Leu Val Thr Gly Leu Gln Pro Asp Val Asp Phe
            100                 105                 110

Ser Asn Phe Ser Gly Leu Met Glu Thr Ser Lys Leu Thr Glu Cys Leu
        115                 120                 125

Ala Gly Ala Ile Gly Ser Leu Gln Glu Glu Leu Asn Gln Glu Lys Gly
    130                 135                 140

Gln Lys Glu Val Leu Leu Arg Arg Cys Gln Gln Leu Gln Glu His Leu
145                 150                 155                 160

Gly Leu Ala Glu Thr Arg Ala Glu Gly Leu His Gln Leu Glu Ala Asp
                165                 170                 175

His Ser Arg Met Lys Arg Glu Val Ser Ala His Phe His Glu Val Leu
            180                 185                 190

Arg Leu Lys Asp Glu Met Leu Ser Leu Ser Leu His Tyr Ser Asn Ala
        195                 200                 205

Leu Gln Glu Lys Glu Leu Ala Ala Ser Arg Cys Arg Ser Leu Gln Glu
    210                 215                 220

Glu Leu Tyr Leu Leu Lys Gln Glu Leu Gln Arg Ala Asn Met Val Ser
225                 230                 235                 240

Ser Cys Glu Leu Glu Leu Gln Glu Gln Ser Leu Arg Thr Ala Ser Asp
                245                 250                 255

Gln Glu Ser Gly Asp Glu Glu Leu Asn Arg Leu Lys Glu Glu Asn Glu
            260                 265                 270

Lys Leu Arg Ser Leu Thr Phe Ser Leu Ala Glu Lys Asp Ile Leu Glu
        275                 280                 285

Gln Ser Leu Asp Glu Ala Arg Gly Ser Arg Gln Glu Leu Val Glu Arg
    290                 295                 300

Ile His Ser Leu Arg Glu Arg Ala Val Ala Ala Glu Arg Gln Arg Glu
305                 310                 315                 320

Gln Tyr Trp Glu Glu Lys Glu Gln Thr Leu Leu Gln Phe Gln Lys Ser
                325                 330                 335
```

-continued

```
Lys Met Ala Cys Gln Leu Tyr Arg Glu Lys Val Asn Ala Leu Gln Ala
            340                 345                 350

Gln Val Cys Glu Leu Gln Lys Glu Arg Asp Gln Ala Tyr Ser Ala Arg
        355                 360                 365

Asp Ser Ala Gln Arg Glu Ile Ser Gln Ser Leu Val Glu Lys Asp Ser
    370                 375                 380

Leu Arg Arg Gln Val Phe Glu Leu Thr Asp Gln Val Cys Glu Leu Arg
385                 390                 395                 400

Thr Gln Leu Arg Gln Leu Gln Ala Glu Pro Pro Gly Val Leu Lys Gln
                405                 410                 415

Glu Ala Arg Thr Arg Glu Pro Cys Pro Arg Glu Lys Gln Arg Leu Val
            420                 425                 430

Arg Met His Ala Ile Cys Pro Arg Asp Asp Ser Asp Cys Ser Leu Val
        435                 440                 445

Ser Ser Thr Glu Ser Gln Leu Leu Ser Asp Leu Ser Ala Thr Ser Ser
    450                 455                 460

Arg Glu Leu Val Asp Ser Phe Arg Ser Ser Ser Pro Ala Pro Pro Ser
465                 470                 475                 480

Gln Gln Ser Leu Tyr Lys Arg Val Ala Glu Asp Phe Gly Glu Glu Pro
                485                 490                 495

Trp Ser Phe Ser Ser Cys Leu Glu Ile Pro Glu Gly Asp Pro Gly Ala
            500                 505                 510

Leu Pro Gly Ala Lys Ala Gly Asp Pro His Leu Asp Tyr Glu Leu Leu
        515                 520                 525

Asp Thr Ala Asp Leu Pro Gln Leu Glu Ser Ser Leu Gln Pro Val Ser
    530                 535                 540

Pro Gly Arg Leu Asp Val Ser Glu Ser Gly Val Leu Met Arg Arg Arg
545                 550                 555                 560

Pro Ala Arg Arg Ile Leu Ser Gln Val Thr Met Leu Ala Phe Gln Gly
                565                 570                 575

Asp Ala Leu Leu Glu Gln Ile Ser Val Ile Gly Gly Asn Leu Thr Gly
            580                 585                 590

Ile Phe Ile His Arg Val Thr Pro Gly Ser Ala Ala Asp Gln Met Ala
        595                 600                 605

Leu Arg Pro Gly Thr Gln Ile Val Met Val Asp Tyr Glu Ala Ser Glu
    610                 615                 620

Pro Leu Phe Lys Ala Val Leu Glu Asp Thr Thr Leu Glu Glu Ala Val
625                 630                 635                 640

Gly Leu Leu Arg Arg Val Asp Gly Phe Cys Cys Leu Ser Val Lys Val
                645                 650                 655

Asn Thr Asp Gly Tyr Lys Arg Leu Leu Gln Asp Leu Glu Ala Lys Val
            660                 665                 670

Ala Thr Ser Gly Asp Ser Phe Tyr Ile Arg Val Asn Leu Ala Met Glu
        675                 680                 685

Gly Arg Ala Lys Gly Glu Leu Gln Val His Cys Asn Glu Val Leu His
    690                 695                 700

Val Thr Asp Thr Met Phe Gln Gly Cys Gly Cys Trp His Ala His Arg
705                 710                 715                 720

Val Asn Ser Tyr Thr Met Lys Asp Thr Ala Ala His Gly Thr Ile Pro
                725                 730                 735

Asn Tyr Ser Arg Ala Gln Gln Gln Leu Ile Ala Leu Ile Gln Asp Met
            740                 745                 750
```

-continued

Thr Gln Gln Cys Thr Val Thr Arg Lys Pro Ser Ser Gly Gly Pro Gln
        755                 760                 765

Lys Leu Val Arg Ile Val Ser Met Asp Lys Ala Lys Ala Ser Pro Leu
    770                 775                 780

Arg Leu Ser Phe Asp Arg Gly Gln Leu Asp Pro Ser Arg Met Glu Gly
785                 790                 795                 800

Ser Ser Thr Cys Phe Trp Ala Glu Ser Cys Leu Thr Leu Val Pro Tyr
                805                 810                 815

Thr Leu Val Arg Pro His Arg Pro Ala Arg Pro Arg Pro Val Leu Leu
            820                 825                 830

Val Pro Arg Ala Val Gly Lys Ile Leu Ser Glu Lys Leu Cys Leu Leu
        835                 840                 845

Gln Gly Phe Lys Lys Cys Leu Ala Glu Tyr Leu Ser Gln Glu Glu Tyr
    850                 855                 860

Glu Ala Trp Ser Gln Arg Gly Asp Ile Ile Gln Glu Gly Glu Val Ser
865                 870                 875                 880

Gly Gly Arg Cys Trp Val Thr Arg His Ala Val Glu Ser Leu Met Glu
                885                 890                 895

Lys Asn Thr His Ala Leu Leu Asp Val Gln Leu Asp Ser Val Cys Thr
            900                 905                 910

Leu His Arg Met Asp Ile Phe Pro Ile Val Ile His Val Ser Val Asn
        915                 920                 925

Glu Lys Met Ala Lys Lys Leu Lys Lys Gly Leu Gln Arg Leu Gly Thr
    930                 935                 940

Ser Glu Glu Gln Leu Leu Glu Ala Ala Arg Gln Glu Glu Gly Asp Leu
945                 950                 955                 960

Asp Arg Ala Pro Cys Leu Tyr Ser Ser Leu Ala Pro Asp Gly Trp Ser
                965                 970                 975

Asp Leu Asp Gly Leu Leu Ser Cys Val Arg Gln Ala Ile Ala Asp Glu
            980                 985                 990

Gln Lys Lys Val Val Trp Thr Glu  Gln Ser Pro Arg
        995                 1000

<210> SEQ ID NO 10
<211> LENGTH: 1032
<212> TYPE: PRT
<213> ORGANISM: Homo sapiens

<400> SEQUENCE: 10

Met Pro Gly Arg Ala Glu Ala Gly Glu Ala Glu Glu Glu Ala Gly Ala
1               5                   10                  15

Gly Ser Gly Ser Glu Ala Glu Glu Asp Ala Leu Trp Glu Arg Ile Glu
            20                  25                  30

Gly Val Arg His Arg Leu Ala Arg Ala Leu Asn Pro Ala Lys Leu Thr
        35                  40                  45

Pro Tyr Leu Arg Gln Cys Arg Val Ile Asp Glu Gln Asp Glu Glu Glu
    50                  55                  60

Val Leu Ser Thr Tyr Arg Phe Pro Cys Arg Val Asn Arg Thr Gly Arg
65                  70                  75                  80

Leu Met Asp Ile Leu Arg Cys Arg Gly Lys Arg Gly Tyr Glu Ala Phe
                85                  90                  95

Leu Glu Ala Leu Glu Phe Tyr Tyr Pro Glu His Phe Thr Leu Leu Thr
            100                 105                 110

Gly Gln Glu Pro Ala Gln Arg Cys Ser Met Ile Leu Asp Glu Glu Gly
        115                 120                 125

-continued

```
Pro Glu Gly Leu Thr Gln Phe Leu Met Thr Glu Val Arg Arg Leu Arg
    130                 135                 140

Glu Ala Arg Lys Ser Gln Leu Gln Arg Glu Gln Gln Leu Gln Ala Arg
145                 150                 155                 160

Gly Arg Val Leu Glu Glu Glu Arg Ala Gly Leu Glu Gln Arg Leu Arg
                165                 170                 175

Asp Gln Gln Gln Ala Gln Glu Arg Cys Gln Arg Leu Arg Glu Asp Trp
            180                 185                 190

Glu Ala Gly Ser Leu Glu Leu Leu Arg Leu Lys Asp Glu Asn Tyr Met
        195                 200                 205

Ile Ala Met Arg Leu Ala Gln Leu Ser Glu Glu Lys Asn Ser Ala Val
    210                 215                 220

Leu Arg Ser Arg Asp Leu Gln Leu Ala Val Asp Gln Leu Lys Leu Lys
225                 230                 235                 240

Val Ser Arg Leu Glu Glu Glu Cys Ala Leu Leu Arg Arg Ala Arg Gly
                245                 250                 255

Pro Pro Pro Gly Ala Glu Glu Lys Glu Lys Glu Lys Glu Lys Glu Lys
            260                 265                 270

Glu Pro Asp Asn Val Asp Leu Val Ser Glu Leu Arg Ala Glu Asn Gln
        275                 280                 285

Arg Leu Thr Ala Ser Leu Arg Glu Leu Gln Glu Gly Leu Gln Gln Glu
    290                 295                 300

Ala Ser Arg Pro Gly Ala Pro Gly Ser Glu Arg Ile Leu Leu Asp Ile
305                 310                 315                 320

Leu Glu His Asp Trp Arg Glu Ala Gln Asp Ser Arg Gln Glu Leu Cys
                325                 330                 335

Gln Lys Leu His Ala Val Gln Gly Glu Leu Gln Trp Ala Glu Glu Leu
            340                 345                 350

Arg Asp Gln Tyr Leu Gln Glu Met Glu Asp Leu Arg Leu Lys His Arg
        355                 360                 365

Thr Leu Gln Lys Asp Cys Asp Leu Tyr Lys His Arg Met Ala Thr Val
    370                 375                 380

Leu Ala Gln Leu Glu Glu Ile Glu Lys Glu Arg Asp Gln Ala Ile Gln
385                 390                 395                 400

Ser Arg Asp Arg Ile Gln Leu Gln Tyr Ser Gln Ser Leu Ile Glu Lys
                405                 410                 415

Asp Gln Tyr Arg Lys Gln Val Arg Gly Leu Glu Ala Glu Arg Asp Glu
            420                 425                 430

Leu Leu Thr Thr Leu Thr Ser Leu Glu Gly Thr Lys Ala Leu Leu Glu
        435                 440                 445

Val Gln Leu Gln Arg Ala Gln Gly Gly Thr Cys Leu Lys Ala Cys Ala
    450                 455                 460

Ser Ser His Ser Leu Cys Ser Asn Leu Ser Ser Thr Trp Ser Leu Ser
465                 470                 475                 480

Glu Phe Pro Ser Pro Leu Gly Gly Pro Glu Ala Thr Gly Glu Ala Ala
                485                 490                 495

Val Met Gly Gly Pro Glu Pro His Asn Ser Glu Glu Ala Thr Asp Ser
            500                 505                 510

Glu Lys Glu Ile Asn Arg Leu Ser Ile Leu Pro Phe Pro Pro Ser Ala
        515                 520                 525

Gly Ser Ile Leu Arg Arg Gln Arg Glu Glu Asp Pro Ala Pro Pro Lys
    530                 535                 540
```

-continued

```
Arg Ser Phe Ser Ser Met Ser Asp Ile Thr Gly Ser Val Thr Leu Lys
545                 550                 555                 560

Pro Trp Ser Pro Gly Leu Ser Ser Ser Ser Ser Ser Asp Ser Val Trp
                565                 570                 575

Pro Leu Gly Lys Pro Glu Gly Leu Leu Ala Arg Gly Cys Gly Leu Asp
            580                 585                 590

Phe Leu Asn Arg Ser Leu Ala Ile Arg Val Ser Gly Arg Ser Pro Pro
        595                 600                 605

Gly Gly Pro Glu Pro Gln Asp Lys Gly Pro Asp Gly Leu Ser Phe Tyr
    610                 615                 620

Gly Asp Arg Trp Ser Gly Ala Val Val Arg Arg Val Leu Ser Gly Pro
625                 630                 635                 640

Gly Ser Ala Arg Met Glu Pro Arg Glu Gln Arg Val Glu Ala Ala Gly
                645                 650                 655

Leu Glu Gly Ala Cys Leu Glu Ala Glu Ala Gln Gln Arg Thr Leu Leu
            660                 665                 670

Trp Asn Gln Gly Ser Thr Leu Pro Ser Leu Met Asp Ser Lys Ala Cys
        675                 680                 685

Gln Ser Phe His Glu Ala Leu Glu Ala Trp Ala Lys Gly Pro Gly Ala
    690                 695                 700

Glu Pro Phe Tyr Ile Arg Ala Asn Leu Thr Leu Pro Glu Arg Ala Asp
705                 710                 715                 720

Pro His Ala Leu Cys Val Lys Ala Gln Glu Ile Leu Arg Leu Val Asp
                725                 730                 735

Ser Ala Tyr Lys Arg Arg Gln Glu Trp Phe Cys Thr Arg Val Asp Pro
            740                 745                 750

Leu Thr Leu Arg Asp Leu Asp Arg Gly Thr Val Pro Asn Tyr Gln Arg
        755                 760                 765

Ala Gln Gln Leu Leu Glu Val Gln Glu Lys Cys Leu Pro Ser Ser Arg
    770                 775                 780

His Arg Gly Pro Arg Ser Asn Leu Lys Lys Arg Ala Leu Asp Gln Leu
785                 790                 795                 800

Arg Leu Val Arg Pro Lys Pro Val Gly Ala Pro Ala Gly Asp Ser Pro
                805                 810                 815

Asp Gln Leu Leu Leu Glu Pro Cys Ala Glu Pro Glu Arg Ser Leu Arg
            820                 825                 830

Pro Tyr Ser Leu Val Arg Pro Leu Leu Val Ser Ala Leu Arg Pro Val
        835                 840                 845

Val Leu Leu Pro Glu Cys Leu Ala Pro Arg Leu Ile Arg Asn Leu Leu
    850                 855                 860

Asp Leu Pro Ser Ser Arg Leu Asp Phe Gln Val Cys Pro Ala Glu Ser
865                 870                 875                 880

Leu Ser Gly Glu Glu Leu Cys Pro Ser Ser Ala Pro Gly Ala Pro Lys
                885                 890                 895

Ala Gln Pro Ala Thr Pro Gly Leu Gly Ser Arg Ile Arg Ala Ile Gln
            900                 905                 910

Glu Ser Val Gly Lys Lys His Cys Leu Leu Glu Leu Gly Ala Arg Gly
        915                 920                 925

Val Arg Glu Leu Val Gln Asn Glu Ile Tyr Pro Ile Val Ile His Val
    930                 935                 940

Glu Val Thr Glu Lys Asn Val Arg Glu Val Arg Gly Leu Leu Gly Arg
945                 950                 955                 960
```

Pro Gly Trp Arg Asp Ser Glu Leu Leu Arg Gln Cys Arg Gly Ser Glu
965 970 975

Gln Val Leu Trp Gly Leu Pro Cys Ser Trp Val Gln Val Pro Ala His
980 985 990

Glu Trp Gly His Ala Glu Glu Leu Ala Lys Val Val Arg Gly Arg Ile
995 1000 1005

Leu Gln Glu Gln Ala Arg Leu Val Trp Val Glu Cys Gly Ser Ser
1010 1015 1020

Arg Gly Cys Pro Ser Ser Ser Glu Ala
1025 1030

<210> SEQ ID NO 11
<211> LENGTH: 536
<212> TYPE: PRT
<213> ORGANISM: Homo sapiens

<400> SEQUENCE: 11

Met Ser Asp Tyr Glu Asn Asp Asp Glu Cys Trp Ser Val Leu Glu Gly
1 5 10 15

Phe Arg Val Thr Leu Thr Ser Val Ile Asp Pro Ser Arg Ile Thr Pro
20 25 30

Tyr Leu Arg Gln Cys Lys Val Leu Asn Pro Asp Asp Glu Glu Gln Val
35 40 45

Leu Ser Asp Pro Asn Leu Val Ile Arg Lys Arg Lys Val Gly Val Leu
50 55 60

Leu Asp Ile Leu Gln Arg Thr Gly His Lys Gly Tyr Val Ala Phe Leu
65 70 75 80

Glu Ser Leu Glu Leu Tyr Tyr Pro Gln Leu Tyr Lys Lys Val Thr Gly
85 90 95

Lys Glu Pro Ala Arg Val Phe Ser Met Ile Ile Asp Ala Ser Gly Glu
100 105 110

Ser Gly Leu Thr Gln Leu Leu Met Thr Glu Val Met Lys Leu Gln Lys
115 120 125

Lys Val Gln Asp Leu Thr Ala Leu Leu Ser Ser Lys Asp Asp Phe Ile
130 135 140

Lys Glu Leu Arg Val Lys Asp Ser Leu Leu Arg Lys His Gln Glu Arg
145 150 155 160

Val Gln Arg Leu Lys Glu Glu Cys Glu Ala Gly Ser Arg Glu Leu Lys
165 170 175

Arg Cys Lys Glu Glu Asn Tyr Asp Leu Ala Met Arg Leu Ala His Gln
180 185 190

Ser Glu Glu Lys Gly Ala Ala Leu Met Arg Asn Arg Asp Leu Gln Leu
195 200 205

Glu Ile Asp Gln Leu Lys His Ser Leu Met Lys Ala Glu Asp Asp Cys
210 215 220

Lys Val Glu Arg Lys His Thr Leu Lys Leu Arg His Ala Met Glu Gln
225 230 235 240

Arg Pro Ser Gln Glu Leu Leu Trp Glu Leu Gln Gln Glu Lys Ala Leu
245 250 255

Leu Gln Ala Arg Val Gln Glu Leu Glu Ala Ser Val Gln Glu Gly Lys
260 265 270

Leu Asp Arg Ser Ser Pro Tyr Ile Gln Val Leu Glu Glu Asp Trp Arg
275 280 285

```
Gln Ala Leu Arg Asp His Gln Glu Gln Ala Asn Thr Ile Phe Ser Leu
    290                 295                 300

Arg Lys Asp Leu Arg Gln Gly Glu Ala Arg Arg Leu Arg Cys Met Glu
305                 310                 315                 320

Glu Lys Glu Met Phe Glu Leu Gln Cys Leu Ala Leu Arg Lys Asp Ser
                325                 330                 335

Lys Met Tyr Lys Asp Arg Ile Glu Ala Ile Leu Leu Gln Met Glu Glu
            340                 345                 350

Val Ala Ile Glu Arg Asp Gln Ala Ile Ala Thr Arg Glu Glu Leu His
        355                 360                 365

Ala Gln His Ala Arg Gly Leu Gln Glu Lys Asp Ala Leu Arg Lys Gln
    370                 375                 380

Val Arg Glu Leu Gly Glu Lys Ala Asp Glu Leu Gln Leu Gln Val Phe
385                 390                 395                 400

Gln Cys Glu Ala Gln Leu Leu Ala Val Glu Gly Arg Leu Arg Arg Gln
                405                 410                 415

Gln Leu Glu Thr Leu Val Leu Ser Ser Asp Leu Glu Asp Gly Ser Pro
            420                 425                 430

Arg Arg Ser Gln Glu Leu Ser Leu Pro Gln Asp Leu Glu Asp Thr Gln
        435                 440                 445

Leu Ser Asp Lys Gly Cys Leu Ala Gly Gly Gly Ser Pro Lys Gln Pro
    450                 455                 460

Phe Ala Ala Leu His Gln Glu Gln Val Leu Arg Asn Pro His Asp Ala
465                 470                 475                 480

Gly Leu Ser Ser Gly Glu Pro Pro Glu Lys Glu Arg Arg Arg Leu Lys
                485                 490                 495

Glu Ser Phe Glu Asn Tyr Arg Arg Lys Arg Ala Leu Arg Lys Met Gln
            500                 505                 510

Lys Gly Trp Arg Gln Gly Glu Glu Asp Arg Glu Asn Thr Thr Gly Ser
        515                 520                 525

Asp Asn Thr Asp Thr Glu Gly Ser
    530                 535
```

<210> SEQ ID NO 12
<211> LENGTH: 233
<212> TYPE: PRT
<213> ORGANISM: Homo sapiens

<400> SEQUENCE: 12

```
Met Glu Pro Thr Ala Pro Ser Leu Thr Glu Glu Asp Leu Thr Glu Val
1               5                   10                  15

Lys Lys Asp Ala Leu Glu Asn Leu Arg Val Tyr Leu Cys Glu Lys Ile
            20                  25                  30

Ile Ala Glu Arg His Phe Asp His Leu Arg Ala Lys Lys Ile Leu Ser
        35                  40                  45

Arg Glu Asp Thr Glu Glu Ile Ser Cys Arg Thr Ser Ser Arg Lys Arg
    50                  55                  60

Ala Gly Lys Leu Leu Asp Tyr Leu Gln Glu Asn Pro Lys Gly Leu Asp
65                  70                  75                  80

Thr Leu Val Glu Ser Ile Arg Arg Glu Lys Thr Gln Asn Phe Leu Ile
                85                  90                  95

Gln Lys Ile Thr Asp Glu Val Leu Lys Leu Arg Asn Ile Lys Leu Glu
            100                 105                 110
```

His Leu Lys Gly Leu Lys Cys Ser Ser Cys Glu Pro Phe Pro Asp Gly
115 120 125

Ala Thr Asn Asn Leu Ser Arg Ser Asn Ser Asp Glu Ser Asn Phe Ser
130 135 140

Glu Lys Leu Arg Ala Ser Thr Val Met Tyr His Pro Glu Gly Glu Ser
145 150 155 160

Ser Thr Thr Pro Phe Phe Ser Thr Asn Ser Ser Leu Asn Leu Pro Val
165 170 175

Leu Glu Val Gly Arg Thr Glu Asn Thr Ile Phe Ser Ser Thr Thr Leu
180 185 190

Pro Arg Pro Gly Asp Pro Gly Ala Pro Pro Leu Pro Pro Asp Leu Gln
195 200 205

Leu Glu Glu Glu Gly Thr Cys Ala Asn Ser Ser Glu Met Phe Leu Pro
210 215 220

Leu Arg Ser Arg Thr Val Ser Arg Gln
225 230

<210> SEQ ID NO 13
<211> LENGTH: 790
<212> TYPE: PRT
<213> ORGANISM: Homo sapiens

<400> SEQUENCE: 13

Met Ala Glu Gln Val Leu Pro Gln Ala Leu Tyr Leu Ser Asn Met Arg
1 5 10 15

Lys Ala Val Lys Ile Arg Glu Arg Thr Pro Glu Asp Ile Phe Lys Pro
20 25 30

Thr Asn Gly Ile Ile His His Phe Lys Thr Met His Arg Tyr Thr Leu
35 40 45

Glu Met Phe Arg Thr Cys Gln Phe Cys Pro Gln Phe Arg Glu Ile Ile
50 55 60

His Lys Ala Leu Ile Asp Arg Asn Ile Gln Ala Thr Leu Glu Ser Gln
65 70 75 80

Lys Lys Leu Asn Trp Cys Arg Glu Val Arg Lys Leu Val Ala Leu Lys
85 90 95

Thr Asn Gly Asp Gly Asn Cys Leu Met His Ala Thr Ser Gln Tyr Met
100 105 110

Trp Gly Val Gln Asp Thr Asp Leu Val Leu Arg Lys Ala Leu Phe Ser
115 120 125

Thr Leu Lys Glu Thr Asp Thr Arg Asn Phe Lys Phe Arg Trp Gln Leu
130 135 140

Glu Ser Leu Lys Ser Gln Glu Phe Val Glu Thr Gly Leu Cys Tyr Asp
145 150 155 160

Thr Arg Asn Trp Asn Asp Glu Trp Asp Asn Leu Ile Lys Met Ala Ser
165 170 175

Thr Asp Thr Pro Met Ala Arg Ser Gly Leu Gln Tyr Asn Ser Leu Glu
180 185 190

Glu Ile His Ile Phe Val Leu Cys Asn Ile Leu Arg Arg Pro Ile Ile
195 200 205

Val Ile Ser Asp Lys Met Leu Arg Ser Leu Glu Ser Gly Ser Asn Phe
210 215 220

Ala Pro Leu Lys Val Gly Gly Ile Tyr Leu Pro Leu His Trp Pro Ala
225 230 235 240

-continued

```
Gln Glu Cys Tyr Arg Tyr Pro Ile Val Leu Gly Tyr Asp Ser His His
                245                 250                 255

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
        275                 280                 285

His Phe Leu Thr Asp Pro Glu Asn Glu Met Lys Glu Lys Leu Leu Lys
    290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
                325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
        355                 360                 365

Ala Gln Asn Pro Met Glu Pro Ser Val Pro Gln Leu Ser Leu Met Asp
    370                 375                 380

Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
                405                 410                 415

Lys Leu Pro Lys Leu Asn Ser Lys Pro Gly Pro Glu Gly Leu Pro Gly
            420                 425                 430

Met Ala Leu Gly Ala Ser Arg Gly Glu Ala Tyr Glu Pro Leu Ala Trp
        435                 440                 445

Asn Pro Glu Glu Ser Thr Gly Gly Pro His Ser Ala Pro Pro Thr Ala
    450                 455                 460

Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
                485                 490                 495

Arg Cys His Asn Ala Arg Gln Leu His Ala Ser His Ala Pro Asp His
            500                 505                 510

Thr Arg His Leu Asp Pro Gly Lys Cys Gln Ala Cys Leu Gln Asp Val
        515                 520                 525

Thr Arg Thr Phe Asn Gly Ile Cys Ser Thr Cys Phe Lys Arg Thr Thr
    530                 535                 540

Ala Glu Ala Ser Ser Ser Leu Ser Thr Ser Leu Pro Pro Ser Cys His
545                 550                 555                 560

Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
            580                 585                 590

Gln Ala Ala Arg Thr Pro Gly Asp Arg Thr Gly Thr Ser Lys Cys Arg
        595                 600                 605

Lys Ala Gly Cys Val Tyr Phe Gly Thr Pro Glu Asn Lys Gly Phe Cys
    610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655
```

```
Cys Leu Gly Arg Glu Cys Gly Thr Leu Gly Ser Thr Met Phe Glu Gly
            660                 665                 670

Tyr Cys Gln Lys Cys Phe Ile Glu Ala Gln Asn Gln Arg Phe His Glu
        675                 680                 685

Ala Lys Arg Thr Glu Glu Gln Leu Arg Ser Ser Gln Arg Arg Asp Val
    690                 695                 700

Pro Arg Thr Thr Gln Ser Thr Ser Arg Pro Lys Cys Ala Arg Ala Ser
705                 710                 715                 720

Cys Lys Asn Ile Leu Ala Cys Arg Ser Glu Glu Leu Cys Met Glu Cys
                725                 730                 735

Gln His Pro Asn Gln Arg Met Gly Pro Gly Ala His Arg Gly Glu Pro
            740                 745                 750

Ala Pro Glu Asp Pro Pro Lys Gln Arg Cys Arg Ala Pro Ala Cys Asp
        755                 760                 765

His Phe Gly Asn Ala Lys Cys Asn Gly Tyr Cys Asn Glu Cys Phe Gln
    770                 775                 780

Phe Lys Gln Met Tyr Gly
785                 790


<210> SEQ ID NO 14
<211> LENGTH: 956
<212> TYPE: PRT
<213> ORGANISM: Homo sapiens

<400> SEQUENCE: 14

Met Ser Ser Gly Leu Trp Ser Gln Glu Lys Val Thr Ser Pro Tyr Trp
1               5                   10                  15

Glu Glu Arg Ile Phe Tyr Leu Leu Leu Gln Glu Cys Ser Val Thr Asp
            20                  25                  30

Lys Gln Thr Gln Lys Leu Leu Lys Val Pro Lys Gly Ser Ile Gly Gln
        35                  40                  45

Tyr Ile Gln Asp Arg Ser Val Gly His Ser Arg Ile Pro Ser Ala Lys
    50                  55                  60

Gly Lys Lys Asn Gln Ile Gly Leu Lys Ile Leu Glu Gln Pro His Ala
65                  70                  75                  80

Val Leu Phe Val Asp Glu Lys Asp Val Val Glu Ile Asn Glu Lys Phe
                85                  90                  95

Thr Glu Leu Leu Leu Ala Ile Thr Asn Cys Glu Glu Arg Phe Ser Leu
            100                 105                 110

Phe Lys Asn Arg Asn Arg Leu Ser Lys Gly Leu Gln Ile Asp Val Gly
        115                 120                 125

Cys Pro Val Lys Val Gln Leu Arg Ser Gly Glu Glu Lys Phe Pro Gly
    130                 135                 140

Val Val Arg Phe Arg Gly Pro Leu Leu Ala Glu Arg Thr Val Ser Gly
145                 150                 155                 160

Ile Phe Phe Gly Val Glu Leu Leu Glu Glu Gly Arg Gly Gln Gly Phe
                165                 170                 175

Thr Asp Gly Val Tyr Gln Gly Lys Gln Leu Phe Gln Cys Asp Glu Asp
            180                 185                 190

Cys Gly Val Phe Val Ala Leu Asp Lys Leu Glu Leu Ile Glu Asp Asp
        195                 200                 205

Asp Thr Ala Leu Glu Ser Asp Tyr Ala Gly Pro Gly Asp Thr Met Gln
    210                 215                 220

Val Glu Leu Pro Pro Leu Glu Ile Asn Ser Arg Val Ser Leu Lys Val
225                 230                 235                 240
```

-continued

```
Gly Glu Thr Ile Glu Ser Gly Thr Val Ile Phe Cys Asp Val Leu Pro
                245                 250                 255

Gly Lys Glu Ser Leu Gly Tyr Phe Val Gly Val Asp Met Asp Asn Pro
            260                 265                 270

Ile Gly Asn Trp Asp Gly Arg Phe Asp Gly Val Gln Leu Cys Ser Phe
        275                 280                 285

Ala Cys Val Glu Ser Thr Ile Leu Leu His Ile Asn Asp Ile Ile Pro
    290                 295                 300

Ala Leu Ser Glu Ser Val Thr Gln Glu Arg Arg Pro Pro Lys Leu Ala
305                 310                 315                 320

Phe Met Ser Arg Gly Val Gly Asp Lys Gly Ser Ser Ser His Asn Lys
                325                 330                 335

Pro Lys Ala Thr Gly Ser Thr Ser Asp Pro Gly Asn Arg Asn Arg Ser
            340                 345                 350

Glu Leu Phe Tyr Thr Leu Asn Gly Ser Ser Val Asp Ser Gln Pro Gln
        355                 360                 365

Ser Lys Ser Lys Asn Thr Trp Tyr Ile Asp Glu Val Ala Glu Asp Pro
    370                 375                 380

Ala Lys Ser Leu Thr Glu Ile Ser Thr Asp Phe Asp Arg Ser Ser Pro
385                 390                 395                 400

Pro Leu Gln Pro Pro Pro Val Asn Ser Leu Thr Thr Glu Asn Arg Phe
                405                 410                 415

His Ser Leu Pro Phe Ser Leu Thr Lys Met Pro Asn Thr Asn Gly Ser
            420                 425                 430

Ile Gly His Ser Pro Leu Ser Leu Ser Ala Gln Ser Val Met Glu Glu
        435                 440                 445

Leu Asn Thr Ala Pro Val Gln Glu Ser Pro Pro Leu Ala Met Pro Pro
    450                 455                 460

Gly Asn Ser His Gly Leu Glu Val Gly Ser Leu Ala Glu Val Lys Glu
465                 470                 475                 480

Asn Pro Pro Phe Tyr Gly Val Ile Arg Trp Ile Gly Gln Pro Pro Gly
                485                 490                 495

Leu Asn Glu Val Leu Ala Gly Leu Glu Leu Glu Asp Glu Cys Ala Gly
            500                 505                 510

Cys Thr Asp Gly Thr Phe Arg Gly Thr Arg Tyr Phe Thr Cys Ala Leu
        515                 520                 525

Lys Lys Ala Leu Phe Val Lys Leu Lys Ser Cys Arg Pro Asp Ser Arg
    530                 535                 540

Phe Ala Ser Leu Gln Pro Val Ser Asn Gln Ile Glu Arg Cys Asn Ser
545                 550                 555                 560

Leu Ala Phe Gly Gly Tyr Leu Ser Glu Val Val Glu Glu Asn Thr Pro
                565                 570                 575

Pro Lys Met Glu Lys Glu Gly Leu Glu Ile Met Ile Gly Lys Lys Lys
            580                 585                 590

Gly Ile Gln Gly His Tyr Asn Ser Cys Tyr Leu Asp Ser Thr Leu Phe
        595                 600                 605

Cys Leu Phe Ala Phe Ser Ser Val Leu Asp Thr Val Leu Leu Arg Pro
    610                 615                 620

Lys Glu Lys Asn Asp Val Glu Tyr Tyr Ser Glu Thr Gln Glu Leu Leu
625                 630                 635                 640

Arg Thr Glu Ile Val Asn Pro Leu Arg Ile Tyr Gly Tyr Val Cys Ala
                645                 650                 655
```

-continued

```
Thr Lys Ile Met Lys Leu Arg Lys Ile Leu Glu Lys Val Glu Ala Ala
            660                 665                 670

Ser Gly Phe Thr Ser Glu Glu Lys Asp Pro Glu Glu Phe Leu Asn Ile
        675                 680                 685

Leu Phe His His Ile Leu Arg Val Glu Pro Leu Leu Lys Ile Arg Ser
    690                 695                 700

Ala Gly Gln Lys Val Gln Asp Cys Tyr Phe Tyr Gln Ile Phe Met Glu
705                 710                 715                 720

Lys Asn Glu Lys Val Gly Val Pro Thr Ile Gln Gln Leu Leu Glu Trp
                725                 730                 735

Ser Phe Ile Asn Ser Asn Leu Lys Phe Ala Glu Ala Pro Ser Cys Leu
            740                 745                 750

Ile Ile Gln Met Pro Arg Phe Gly Lys Asp Phe Lys Leu Phe Lys Lys
        755                 760                 765

Ile Phe Pro Ser Leu Glu Leu Asn Ile Thr Asp Leu Leu Glu Asp Thr
    770                 775                 780

Pro Arg Gln Cys Arg Ile Cys Gly Gly Leu Ala Met Tyr Glu Cys Arg
785                 790                 795                 800

Glu Cys Tyr Asp Asp Pro Asp Ile Ser Ala Gly Lys Ile Lys Gln Phe
                805                 810                 815

Cys Lys Thr Cys Asn Thr Gln Val His Leu His Pro Lys Arg Leu Asn
            820                 825                 830

His Lys Tyr Asn Pro Val Ser Leu Pro Lys Asp Leu Pro Asp Trp Asp
        835                 840                 845

Trp Arg His Gly Cys Ile Pro Cys Gln Asn Met Glu Leu Phe Ala Val
    850                 855                 860

Leu Cys Ile Glu Thr Ser His Tyr Val Ala Phe Val Lys Tyr Gly Lys
865                 870                 875                 880

Asp Asp Ser Ala Trp Leu Phe Phe Asp Ser Met Ala Asp Arg Asp Gly
                885                 890                 895

Gly Gln Asn Gly Phe Asn Ile Pro Gln Val Thr Pro Cys Pro Glu Val
            900                 905                 910

Gly Glu Tyr Leu Lys Met Ser Leu Glu Asp Leu His Ser Leu Asp Ser
        915                 920                 925

Arg Arg Ile Gln Gly Cys Ala Arg Arg Leu Leu Cys Asp Ala Tyr Met
    930                 935                 940

Cys Met Tyr Gln Ser Pro Thr Met Ser Leu Tyr Lys
945                 950                 955


<210> SEQ ID NO 15
<211> LENGTH: 579
<212> TYPE: PRT
<213> ORGANISM: Homo sapiens

<400> SEQUENCE: 15

Met Leu Arg Ser Gly Pro Ala Ser Gly Pro Ser Val Pro Thr Gly Arg
1               5                   10                  15

Ala Met Pro Ser Arg Arg Val Ala Arg Pro Pro Ala Ala Pro Glu Leu
            20                  25                  30

Gly Ala Leu Gly Ser Pro Asp Leu Ser Ser Leu Ser Leu Ala Val Ser
        35                  40                  45

Arg Ser Thr Asp Glu Leu Glu Ile Ile Asp Glu Tyr Ile Lys Glu Asn
    50                  55                  60

Gly Phe Gly Leu Asp Gly Gly Gln Pro Gly Pro Gly Glu Gly Leu Pro
65                  70                  75                  80
```

-continued

```
Arg Leu Val Ser Arg Gly Ala Ala Ser Leu Ser Thr Val Thr Leu Gly
                85                  90                  95

Pro Val Ala Pro Pro Ala Thr Pro Pro Pro Trp Gly Cys Pro Leu Gly
            100                 105                 110

Arg Leu Val Ser Pro Ala Pro Gly Pro Gly Pro Gln Pro His Leu Val
        115                 120                 125

Ile Thr Glu Gln Pro Lys Gln Arg Gly Met Arg Phe Arg Tyr Glu Cys
    130                 135                 140

Glu Gly Arg Ser Ala Gly Ser Ile Leu Gly Glu Ser Ser Thr Glu Ala
145                 150                 155                 160

Ser Lys Thr Leu Pro Ala Ile Glu Leu Arg Asp Cys Gly Gly Leu Arg
                165                 170                 175

Glu Val Glu Val Thr Ala Cys Leu Val Trp Lys Asp Trp Pro His Arg
            180                 185                 190

Val His Pro His Ser Leu Val Gly Lys Asp Cys Thr Asp Gly Ile Cys
        195                 200                 205

Arg Val Arg Leu Arg Pro His Val Ser Pro Arg His Ser Phe Asn Asn
    210                 215                 220

Leu Gly Ile Gln Cys Val Arg Lys Lys Glu Ile Glu Ala Ala Ile Glu
225                 230                 235                 240

Arg Lys Ile Gln Leu Gly Ile Asp Pro Tyr Asn Ala Gly Ser Leu Lys
                245                 250                 255

Asn His Gln Glu Val Asp Met Asn Val Val Arg Ile Cys Phe Gln Ala
            260                 265                 270

Ser Tyr Arg Asp Gln Gln Gly Gln Met Arg Arg Met Asp Pro Val Leu
        275                 280                 285

Ser Glu Pro Val Tyr Asp Lys Lys Ser Thr Asn Thr Ser Glu Leu Arg
    290                 295                 300

Ile Cys Arg Ile Asn Lys Glu Ser Gly Pro Cys Thr Gly Gly Glu Glu
305                 310                 315                 320

Leu Tyr Leu Leu Cys Asp Lys Val Gln Lys Glu Asp Ile Ser Val Val
                325                 330                 335

Phe Ser Arg Ala Ser Trp Glu Gly Arg Ala Asp Phe Ser Gln Ala Asp
            340                 345                 350

Val His Arg Gln Ile Ala Ile Val Phe Lys Thr Pro Pro Tyr Glu Asp
        355                 360                 365

Leu Glu Ile Val Glu Pro Val Thr Val Asn Val Phe Leu Gln Arg Leu
    370                 375                 380

Thr Asp Gly Val Cys Ser Glu Pro Leu Pro Phe Thr Tyr Leu Pro Arg
385                 390                 395                 400

Asp His Asp Ser Tyr Gly Val Asp Lys Lys Arg Lys Arg Gly Met Pro
                405                 410                 415

Asp Val Leu Gly Glu Leu Asn Ser Ser Asp Pro His Gly Ile Glu Ser
            420                 425                 430

Lys Arg Arg Lys Lys Lys Pro Ala Ile Leu Asp His Phe Leu Pro Asn
        435                 440                 445

His Gly Ser Gly Pro Phe Leu Pro Pro Ser Ala Leu Leu Pro Asp Pro
    450                 455                 460

Asp Phe Phe Ser Gly Thr Val Ser Leu Pro Gly Leu Glu Pro Pro Gly
465                 470                 475                 480

Gly Pro Asp Leu Leu Asp Asp Gly Phe Ala Tyr Asp Pro Thr Ala Pro
                485                 490                 495
```

-continued

```
Thr Leu Phe Thr Met Leu Asp Leu Leu Pro Pro Ala Pro Pro His Ala
            500                 505                 510

Ser Ala Val Val Cys Ser Gly Gly Ala Gly Ala Val Val Gly Glu Thr
        515                 520                 525

Pro Gly Pro Glu Pro Leu Thr Leu Asp Ser Tyr Gln Ala Pro Gly Pro
    530                 535                 540

Gly Asp Gly Gly Thr Ala Ser Leu Val Gly Ser Asn Met Phe Pro Asn
545                 550                 555                 560

His Tyr Arg Glu Ala Ala Phe Gly Gly Gly Leu Leu Ser Pro Gly Pro
                565                 570                 575

Glu Ala Thr


<210> SEQ ID NO 16
<211> LENGTH: 599
<212> TYPE: PRT
<213> ORGANISM: Homo sapiens

<400> SEQUENCE: 16

Met Ser Gly Pro Cys Gly Glu Lys Pro Val Leu Glu Ala Ser Pro Thr
1               5                   10                  15

Met Ser Leu Trp Glu Phe Glu Asp Ser His Ser Arg Gln Gly Thr Pro
            20                  25                  30

Arg Pro Gly Gln Glu Leu Ala Ala Glu Glu Ala Ser Ala Leu Glu Leu
        35                  40                  45

Gln Met Lys Val Asp Phe Phe Arg Lys Leu Gly Tyr Ser Ser Thr Glu
    50                  55                  60

Ile His Ser Val Leu Gln Lys Leu Gly Val Gln Ala Asp Thr Asn Thr
65                  70                  75                  80

Val Leu Gly Glu Leu Val Lys His Gly Thr Ala Thr Glu Arg Glu Arg
                85                  90                  95

Gln Thr Ser Pro Asp Pro Cys Pro Gln Leu Pro Leu Val Pro Arg Gly
            100                 105                 110

Gly Gly Thr Pro Lys Ala Pro Asn Leu Glu Pro Pro Leu Pro Glu Glu
        115                 120                 125

Glu Lys Glu Gly Ser Asp Leu Arg Pro Val Val Ile Asp Gly Ser Asn
    130                 135                 140

Val Ala Met Ser His Gly Asn Lys Glu Val Phe Ser Cys Arg Gly Ile
145                 150                 155                 160

Leu Leu Ala Val Asn Trp Phe Leu Glu Arg Gly His Thr Asp Ile Thr
                165                 170                 175

Val Phe Val Pro Ser Trp Arg Lys Glu Gln Pro Arg Pro Asp Val Pro
            180                 185                 190

Ile Thr Asp Gln His Ile Leu Arg Glu Leu Glu Lys Lys Lys Ile Leu
        195                 200                 205

Val Phe Thr Pro Ser Arg Arg Val Gly Gly Lys Arg Val Val Cys Tyr
    210                 215                 220

Asp Asp Arg Phe Ile Val Lys Leu Ala Tyr Glu Ser Asp Gly Ile Val
225                 230                 235                 240

Val Ser Asn Asp Thr Tyr Arg Asp Leu Gln Gly Glu Arg Gln Glu Trp
                245                 250                 255

Lys Arg Phe Ile Glu Glu Arg Leu Leu Met Tyr Ser Phe Val Asn Asp
            260                 265                 270

Lys Phe Met Pro Pro Asp Asp Pro Leu Gly Arg His Gly Pro Ser Leu
        275                 280                 285
```

-continued

Asp Asn Phe Leu Arg Lys Lys Pro Leu Thr Leu Glu His Arg Lys Gln
290 295 300

Pro Cys Pro Tyr Gly Arg Lys Cys Thr Tyr Gly Ile Lys Cys Arg Phe
305 310 315 320

Phe His Pro Glu Arg Pro Ser Cys Pro Gln Arg Ser Val Ala Asp Glu
325 330 335

Leu Arg Ala Asn Ala Leu Leu Ser Pro Pro Arg Ala Pro Ser Lys Asp
340 345 350

Lys Asn Gly Arg Arg Pro Ser Pro Ser Ser Gln Ser Ser Ser Leu Leu
355 360 365

Thr Glu Ser Glu Gln Cys Ser Leu Asp Gly Lys Lys Leu Gly Ala Gln
370 375 380

Ala Ser Pro Gly Ser Arg Gln Glu Gly Leu Thr Gln Thr Tyr Ala Pro
385 390 395 400

Ser Gly Arg Ser Leu Ala Pro Ser Gly Gly Ser Gly Ser Ser Phe Gly
405 410 415

Pro Thr Asp Trp Leu Pro Gln Thr Leu Asp Ser Leu Pro Tyr Val Ser
420 425 430

Gln Asp Cys Leu Asp Ser Gly Ile Gly Ser Leu Glu Ser Gln Met Ser
435 440 445

Glu Leu Trp Gly Val Arg Gly Gly Gly Pro Gly Glu Pro Gly Pro Pro
450 455 460

Arg Ala Pro Tyr Thr Gly Tyr Ser Pro Tyr Gly Ser Glu Leu Pro Ala
465 470 475 480

Thr Ala Ala Phe Ser Ala Phe Gly Arg Ala Met Gly Ala Gly His Phe
485 490 495

Ser Val Pro Ala Asp Tyr Pro Pro Ala Pro Pro Ala Phe Pro Pro Arg
500 505 510

Glu Tyr Trp Ser Glu Pro Tyr Pro Leu Pro Pro Pro Thr Ser Val Leu
515 520 525

Gln Glu Pro Pro Val Gln Ser Pro Gly Ala Gly Arg Ser Pro Trp Gly
530 535 540

Arg Ala Gly Ser Leu Ala Lys Glu Gln Ala Ser Val Tyr Thr Lys Leu
545 550 555 560

Cys Gly Val Phe Pro Pro His Leu Val Glu Ala Val Met Gly Arg Phe
565 570 575

Pro Gln Leu Leu Asp Pro Gln Gln Leu Ala Ala Glu Ile Leu Ser Tyr
580 585 590

Lys Ser Gln His Pro Ser Glu
595

<210> SEQ ID NO 17
<211> LENGTH: 1133
<212> TYPE: PRT
<213> ORGANISM: Homo sapiens

<400> SEQUENCE: 17

Met Pro Val Gln Ala Pro Gln Trp Thr Asp Phe Leu Ser Cys Pro Ile
1 5 10 15

Cys Thr Gln Thr Phe Asp Glu Thr Ile Arg Lys Pro Ile Ser Leu Gly
20 25 30

Cys Gly His Thr Val Cys Lys Met Cys Leu Asn Lys Leu His Arg Lys
35 40 45

Ala Cys Pro Phe Asp Gln Thr Thr Ile Asn Thr Asp Ile Glu Leu Leu
50 55 60

```
Pro Val Asn Ser Ala Leu Leu Gln Leu Val Gly Ala Gln Val Pro Glu
65                  70                  75                  80

Gln Gln Pro Ile Thr Leu Cys Ser Gly Val Glu Asp Thr Lys His Tyr
                85                  90                  95

Glu Glu Ala Lys Lys Cys Val Glu Glu Leu Ala Leu Tyr Leu Lys Pro
            100                 105                 110

Leu Ser Ser Ala Arg Gly Val Gly Leu Asn Ser Thr Thr Gln Ser Val
        115                 120                 125

Leu Ser Arg Pro Met Gln Arg Lys Leu Val Thr Leu Val His Cys Gln
    130                 135                 140

Leu Val Glu Glu Glu Gly Arg Ile Arg Ala Met Arg Ala Ala Arg Ser
145                 150                 155                 160

Leu Gly Glu Arg Thr Val Thr Glu Leu Ile Leu Gln His Gln Asn Pro
                165                 170                 175

Gln Gln Leu Ser Ser Asn Leu Trp Ala Ala Val Arg Ala Arg Gly Cys
            180                 185                 190

Gln Phe Leu Gly Pro Ala Met Gln Glu Glu Ala Leu Lys Leu Val Leu
        195                 200                 205

Leu Ala Leu Glu Asp Gly Ser Ala Leu Ser Arg Lys Val Leu Val Leu
    210                 215                 220

Phe Val Val Gln Arg Leu Glu Pro Arg Phe Pro Gln Ala Ser Lys Thr
225                 230                 235                 240

Ser Ile Gly His Val Val Gln Leu Leu Tyr Arg Ala Ser Cys Phe Lys
                245                 250                 255

Val Thr Lys Arg Asp Glu Asp Ser Ser Leu Met Gln Leu Lys Glu Glu
            260                 265                 270

Phe Arg Thr Tyr Glu Ala Leu Arg Arg Glu His Asp Ser Gln Ile Val
        275                 280                 285

Gln Ile Ala Met Glu Ala Gly Leu Arg Ile Ala Pro Asp Gln Trp Ser
    290                 295                 300

Ser Leu Leu Tyr Gly Asp Gln Ser His Lys Ser His Met Gln Ser Ile
305                 310                 315                 320

Ile Asp Lys Leu Gln Thr Pro Ala Ser Phe Ala Gln Ser Val Gln Glu
                325                 330                 335

Leu Thr Ile Ala Leu Gln Arg Thr Gly Asp Pro Ala Asn Leu Asn Arg
            340                 345                 350

Leu Arg Pro His Leu Glu Leu Leu Ala Asn Ile Asp Pro Ser Pro Asp
        355                 360                 365

Ala Pro Pro Pro Thr Trp Glu Gln Leu Glu Asn Gly Leu Val Ala Val
    370                 375                 380

Arg Thr Val Val His Gly Leu Val Asp Tyr Ile Gln Asn His Ser Lys
385                 390                 395                 400

Lys Gly Ala Asp Gln Gln Gln Pro Pro Gln His Ser Lys Tyr Lys Thr
                405                 410                 415

Tyr Met Cys Arg Asp Met Lys Gln Arg Gly Gly Cys Pro Arg Gly Ala
            420                 425                 430

Ser Cys Thr Phe Ala His Ser Gln Glu Glu Leu Glu Lys Phe Arg Lys
        435                 440                 445

Met Asn Lys Arg Leu Val Pro Arg Arg Pro Leu Ser Ala Ser Leu Gly
    450                 455                 460

Gln Leu Asn Glu Val Gly Leu Pro Ser Ala Ala Ile Leu Pro Asp Glu
465                 470                 475                 480
```

-continued

```
Gly Ala Val Asp Leu Pro Ser Arg Lys Pro Pro Ala Leu Pro Asn Gly
                485                 490                 495

Ile Val Ser Thr Gly Asn Thr Val Thr Gln Leu Ile Pro Arg Gly Thr
            500                 505                 510

Asp Pro Ser Tyr Asp Ser Ser Leu Lys Pro Gly Lys Ile Asp His Leu
        515                 520                 525

Ser Ser Ser Ala Pro Gly Ser Pro Pro Asp Leu Leu Glu Ser Val Pro
    530                 535                 540

Lys Ser Ile Ser Ala Leu Pro Val Asn Pro His Ser Ile Pro Pro Arg
545                 550                 555                 560

Gly Pro Ala Asp Leu Pro Pro Met Pro Val Thr Lys Pro Leu Gln Met
                565                 570                 575

Val Pro Arg Gly Ser Gln Leu Tyr Pro Ala Gln Gln Thr Asp Val Tyr
            580                 585                 590

Tyr Gln Asp Pro Arg Gly Ala Ala Pro Pro Phe Glu Pro Ala Pro Tyr
        595                 600                 605

Gln Gln Gly Met Tyr Tyr Thr Pro Pro Pro Gln Cys Val Ser Arg Phe
    610                 615                 620

Val Arg Pro Pro Pro Ser Ala Pro Glu Pro Ala Pro Pro Tyr Leu Asp
625                 630                 635                 640

His Tyr Pro Pro Tyr Leu Gln Glu Arg Val Val Asn Ser Gln Tyr Gly
                645                 650                 655

Thr Gln Pro Gln Gln Tyr Pro Pro Ile Tyr Pro Ser His Tyr Asp Gly
            660                 665                 670

Arg Arg Val Tyr Pro Ala Pro Ser Tyr Thr Arg Glu Glu Ile Phe Arg
        675                 680                 685

Glu Ser Pro Ile Pro Ile Glu Ile Pro Pro Ala Ala Val Pro Ser Tyr
    690                 695                 700

Val Pro Glu Ser Arg Glu Arg Tyr Gln Gln Ile Glu Ser Tyr Tyr Pro
705                 710                 715                 720

Val Ala Pro His Pro Thr Gln Ile Arg Pro Ser Tyr Leu Arg Glu Pro
                725                 730                 735

Pro Tyr Ser Arg Leu Pro Pro Pro Pro Gln Pro His Pro Ser Leu Asp
            740                 745                 750

Glu Leu His Arg Arg Arg Lys Glu Ile Met Ala Gln Leu Glu Glu Arg
        755                 760                 765

Lys Val Ile Ser Pro Pro Pro Phe Ala Pro Ser Pro Thr Leu Pro Pro
    770                 775                 780

Thr Phe His Pro Glu Glu Phe Leu Asp Glu Asp Leu Lys Val Ala Gly
785                 790                 795                 800

Lys Tyr Lys Gly Asn Asp Tyr Ser Gln Tyr Ser Pro Trp Ser Cys Asp
                805                 810                 815

Thr Ile Gly Ser Tyr Ile Gly Thr Lys Asp Ala Lys Pro Lys Asp Val
            820                 825                 830

Val Ala Ala Gly Ser Val Glu Met Met Asn Val Glu Ser Lys Gly Met
        835                 840                 845

Arg Asp Gln Arg Leu Asp Leu Gln Arg Arg Ala Ala Glu Thr Ser Asp
    850                 855                 860

Asp Asp Leu Ile Pro Phe Gly Asp Arg Pro Thr Val Ser Arg Phe Gly
865                 870                 875                 880

Ala Ile Ser Arg Thr Ser Lys Thr Ile Tyr Gln Gly Ala Gly Pro Met
                885                 890                 895
```

```
Gln Ala Met Ala Pro Gln Gly Ala Pro Thr Lys Ser Ile Asn Ile Ser
            900                 905                 910

Asp Tyr Ser Pro Tyr Gly Thr His Gly Gly Trp Gly Ala Ser Pro Tyr
        915                 920                 925

Ser Pro His Gln Asn Ile Pro Ser Gln Gly His Phe Ser Glu Arg Glu
    930                 935                 940

Arg Ile Ser Met Ser Glu Val Ala Ser His Gly Lys Pro Leu Pro Ser
945                 950                 955                 960

Ala Glu Arg Glu Gln Leu Arg Leu Glu Leu Gln Gln Leu Asn His Gln
                965                 970                 975

Ile Ser Gln Gln Thr Gln Leu Arg Gly Leu Glu Ala Val Ser Asn Arg
            980                 985                 990

Leu Val Leu Gln Arg Glu Ala Asn  Thr Leu Ala Gly Gln  Ser Gln Pro
        995                 1000                1005

Pro Pro  Pro Pro Pro Pro Lys  Trp Pro Gly Met Ile  Ser Ser Glu
    1010                1015                1020

Gln Leu  Ser Leu Glu Leu His  Gln Val Glu Arg Glu  Ile Gly Lys
    1025                1030                1035

Arg Thr  Arg Glu Leu Ser Met  Glu Asn Gln Cys Ser  Leu Asp Met
    1040                1045                1050

Lys Ser  Lys Leu Asn Thr Ser  Lys Gln Ala Glu Asn  Gly Gln Pro
    1055                1060                1065

Glu Pro  Gln Asn Lys Val Pro  Ala Glu Asp Leu Thr  Leu Thr Phe
    1070                1075                1080

Ser Asp  Val Pro Asn Gly Ser  Ala Leu Thr Gln Glu  Asn Ile Ser
    1085                1090                1095

Leu Leu  Ser Asn Lys Thr Ser  Ser Leu Asn Leu Ser  Glu Asp Pro
    1100                1105                1110

Glu Gly  Gly Gly Asp Asn Asn  Asp Ser Gln Arg Ser  Gly Val Thr
    1115                1120                1125

Pro Ser  Ser Ala Pro
    1130
```

<210> SEQ ID NO 18
<211> LENGTH: 510
<212> TYPE: PRT
<213> ORGANISM: Homo sapiens

<400> SEQUENCE: 18

```
Met Asp Glu Lys Thr Lys Lys Ala Glu Glu Met Ala Leu Ser Leu Thr
1               5                   10                  15

Arg Ala Val Ala Gly Gly Asp Glu Gln Val Ala Met Lys Cys Ala Ile
            20                  25                  30

Trp Leu Ala Glu Gln Arg Val Pro Leu Ser Val Gln Leu Lys Pro Glu
        35                  40                  45

Val Ser Pro Thr Gln Asp Ile Arg Leu Trp Val Ser Val Glu Asp Ala
    50                  55                  60

Gln Met His Thr Val Thr Ile Trp Leu Thr Val Arg Pro Asp Met Thr
65                  70                  75                  80

Val Ala Ser Leu Lys Asp Met Val Phe Leu Asp Tyr Gly Phe Pro Pro
                85                  90                  95

Val Leu Gln Gln Trp Val Ile Gly Gln Arg Leu Ala Arg Asp Gln Glu
            100                 105                 110
```

```
Thr Leu His Ser His Gly Val Arg Gln Asn Gly Asp Ser Ala Tyr Leu
        115                 120                 125

Tyr Leu Leu Ser Ala Arg Asn Thr Ser Leu Asn Pro Gln Glu Leu Gln
    130                 135                 140

Arg Glu Arg Gln Leu Arg Met Leu Glu Asp Leu Gly Phe Lys Asp Leu
145                 150                 155                 160

Thr Leu Gln Pro Arg Gly Pro Leu Glu Pro Gly Pro Pro Lys Pro Gly
                165                 170                 175

Val Pro Gln Glu Pro Gly Arg Gly Gln Pro Asp Ala Val Pro Glu Pro
            180                 185                 190

Pro Pro Val Gly Trp Gln Cys Pro Gly Cys Thr Phe Ile Asn Lys Pro
        195                 200                 205

Thr Arg Pro Gly Cys Glu Met Cys Cys Arg Ala Arg Pro Glu Ala Tyr
    210                 215                 220

Gln Val Pro Ala Ser Tyr Gln Pro Asp Glu Glu Glu Arg Ala Arg Leu
225                 230                 235                 240

Ala Gly Glu Glu Glu Ala Leu Arg Gln Tyr Gln Gln Arg Lys Gln Gln
                245                 250                 255

Gln Gln Glu Gly Asn Tyr Leu Gln His Val Gln Leu Asp Gln Arg Ser
            260                 265                 270

Leu Val Leu Asn Thr Glu Pro Ala Glu Cys Pro Val Cys Tyr Ser Val
        275                 280                 285

Leu Ala Pro Gly Glu Ala Val Val Leu Arg Glu Cys Leu His Thr Phe
    290                 295                 300

Cys Arg Glu Cys Leu Gln Gly Thr Ile Arg Asn Ser Gln Glu Ala Glu
305                 310                 315                 320

Val Ser Cys Pro Phe Ile Asp Asn Thr Tyr Ser Cys Ser Gly Lys Leu
                325                 330                 335

Leu Glu Arg Glu Ile Lys Ala Leu Leu Thr Pro Glu Asp Tyr Gln Arg
            340                 345                 350

Phe Leu Asp Leu Gly Ile Ser Ile Ala Glu Asn Arg Ser Ala Phe Ser
        355                 360                 365

Tyr His Cys Lys Thr Pro Asp Cys Lys Gly Trp Cys Phe Phe Glu Asp
    370                 375                 380

Asp Val Asn Glu Phe Thr Cys Pro Val Cys Phe His Val Asn Cys Leu
385                 390                 395                 400

Leu Cys Lys Ala Ile His Glu Gln Met Asn Cys Lys Glu Tyr Gln Glu
                405                 410                 415

Asp Leu Ala Leu Arg Ala Gln Asn Asp Val Ala Ala Arg Gln Thr Thr
            420                 425                 430

Glu Met Leu Lys Val Met Leu Gln Gln Gly Glu Ala Met Arg Cys Pro
        435                 440                 445

Gln Cys Gln Ile Val Val Gln Lys Lys Asp Gly Cys Asp Trp Ile Arg
    450                 455                 460

Cys Thr Val Cys His Thr Glu Ile Cys Trp Val Thr Lys Gly Pro Arg
465                 470                 475                 480

Trp Gly Pro Gly Gly Pro Gly Asp Thr Ser Gly Gly Cys Arg Cys Arg
                485                 490                 495

Val Asn Gly Ile Pro Cys His Pro Ser Cys Gln Asn Cys His
            500                 505                 510
```

<210> SEQ ID NO 19
<211> LENGTH: 947

<212> TYPE: PRT
<213> ORGANISM: Homo sapiens

<400> SEQUENCE: 19

```
Met Ala Val Met Glu Met Ala Cys Pro Gly Ala Pro Gly Ser Ala Val
1               5                   10                  15

Gly Gln Gln Lys Glu Leu Pro Lys Ala Lys Glu Lys Thr Pro Pro Leu
            20                  25                  30

Gly Lys Lys Gln Ser Ser Val Tyr Lys Leu Glu Ala Val Glu Lys Ser
        35                  40                  45

Pro Val Phe Cys Gly Lys Trp Glu Ile Leu Asn Asp Val Ile Thr Lys
    50                  55                  60

Gly Thr Ala Lys Glu Gly Ser Glu Ala Gly Pro Ala Ala Ile Ser Ile
65                  70                  75                  80

Ile Ala Gln Ala Glu Cys Glu Asn Ser Gln Glu Phe Ser Pro Thr Phe
                85                  90                  95

Ser Glu Arg Ile Phe Ile Ala Gly Ser Lys Gln Tyr Ser Gln Ser Glu
            100                 105                 110

Ser Leu Asp Gln Ile Pro Asn Asn Val Ala His Ala Thr Glu Gly Lys
        115                 120                 125

Met Ala Arg Val Cys Trp Lys Gly Lys Arg Arg Ser Lys Ala Arg Lys
    130                 135                 140

Lys Arg Lys Lys Lys Ser Ser Lys Ser Leu Ala His Ala Gly Val Ala
145                 150                 155                 160

Leu Ala Lys Pro Leu Pro Arg Thr Pro Glu Gln Glu Ser Cys Thr Ile
                165                 170                 175

Pro Val Gln Glu Asp Glu Ser Pro Leu Gly Ala Pro Tyr Val Arg Asn
            180                 185                 190

Thr Pro Gln Phe Thr Lys Pro Leu Lys Glu Pro Gly Leu Gly Gln Leu
        195                 200                 205

Cys Phe Lys Gln Leu Gly Glu Gly Leu Arg Pro Ala Leu Pro Arg Ser
    210                 215                 220

Glu Leu His Lys Leu Ile Ser Pro Leu Gln Cys Leu Asn His Val Trp
225                 230                 235                 240

Lys Leu His His Pro Gln Asp Gly Gly Pro Leu Pro Leu Pro Thr His
                245                 250                 255

Pro Phe Pro Tyr Ser Arg Leu Pro His Pro Phe Pro Phe His Pro Leu
            260                 265                 270

Gln Pro Trp Lys Pro His Pro Leu Glu Ser Phe Leu Gly Lys Leu Ala
        275                 280                 285

Cys Val Asp Ser Gln Lys Pro Leu Pro Asp Pro His Leu Ser Lys Leu
    290                 295                 300

Ala Cys Val Asp Ser Pro Lys Pro Leu Pro Gly Pro His Leu Glu Pro
305                 310                 315                 320

Ser Cys Leu Ser Arg Gly Ala His Glu Lys Phe Ser Val Glu Glu Tyr
                325                 330                 335

Leu Val His Ala Leu Gln Gly Ser Val Ser Ser Gly Gln Ala His Ser
            340                 345                 350

Leu Thr Ser Leu Ala Lys Thr Trp Ala Ala Arg Gly Ser Arg Ser Arg
        355                 360                 365

Glu Pro Ser Pro Lys Thr Glu Asp Asn Glu Gly Val Leu Leu Thr Glu
    370                 375                 380

Lys Leu Lys Pro Val Asp Tyr Glu Tyr Arg Glu Glu Val His Trp Ala
385                 390                 395                 400
```

-continued

```
Thr His Gln Leu Arg Leu Gly Arg Gly Ser Phe Gly Glu Val His Arg
                405                 410                 415

Met Glu Asp Lys Gln Thr Gly Phe Gln Cys Ala Val Lys Lys Val Arg
            420                 425                 430

Leu Glu Val Phe Arg Ala Glu Glu Leu Met Ala Cys Ala Gly Leu Thr
        435                 440                 445

Ser Pro Arg Ile Val Pro Leu Tyr Gly Ala Val Arg Glu Gly Pro Trp
    450                 455                 460

Val Asn Ile Phe Met Glu Leu Leu Glu Gly Gly Ser Leu Gly Gln Leu
465                 470                 475                 480

Val Lys Glu Gln Gly Cys Leu Pro Glu Asp Arg Ala Leu Tyr Tyr Leu
                485                 490                 495

Gly Gln Ala Leu Glu Gly Leu Glu Tyr Leu His Ser Arg Arg Ile Leu
            500                 505                 510

His Gly Asp Val Lys Ala Asp Asn Val Leu Leu Ser Ser Asp Gly Ser
        515                 520                 525

His Ala Ala Leu Cys Asp Phe Gly His Ala Val Cys Leu Gln Pro Asp
    530                 535                 540

Gly Leu Gly Lys Ser Leu Leu Thr Gly Asp Tyr Ile Pro Gly Thr Glu
545                 550                 555                 560

Thr His Met Ala Pro Glu Val Val Leu Gly Arg Ser Cys Asp Ala Lys
                565                 570                 575

Val Asp Val Trp Ser Ser Cys Cys Met Met Leu His Met Leu Asn Gly
            580                 585                 590

Cys His Pro Trp Thr Gln Phe Phe Arg Gly Pro Leu Cys Leu Lys Ile
        595                 600                 605

Ala Ser Glu Pro Pro Pro Val Arg Glu Ile Pro Pro Ser Cys Ala Pro
    610                 615                 620

Leu Thr Ala Gln Ala Ile Gln Glu Gly Leu Arg Lys Glu Pro Ile His
625                 630                 635                 640

Arg Val Ser Ala Ala Glu Leu Gly Gly Lys Val Asn Arg Ala Leu Gln
                645                 650                 655

Gln Val Gly Gly Leu Lys Ser Pro Trp Arg Gly Glu Tyr Lys Glu Pro
            660                 665                 670

Arg His Pro Pro Pro Asn Gln Ala Asn Tyr His Gln Thr Leu His Ala
        675                 680                 685

Gln Pro Arg Glu Leu Ser Pro Arg Ala Pro Gly Pro Arg Pro Ala Glu
    690                 695                 700

Glu Thr Thr Gly Arg Ala Pro Lys Leu Gln Pro Pro Leu Pro Pro Glu
705                 710                 715                 720

Pro Pro Glu Pro Asn Lys Ser Pro Pro Leu Thr Leu Ser Lys Glu Glu
                725                 730                 735

Ser Gly Met Trp Glu Pro Leu Pro Leu Ser Ser Leu Glu Pro Ala Pro
            740                 745                 750

Ala Arg Asn Pro Ser Ser Pro Glu Arg Lys Ala Thr Val Pro Glu Gln
        755                 760                 765

Glu Leu Gln Gln Leu Glu Ile Glu Leu Phe Leu Asn Ser Leu Ser Gln
    770                 775                 780

Pro Phe Ser Leu Glu Glu Gln Glu Gln Ile Leu Ser Cys Leu Ser Ile
785                 790                 795                 800

Asp Ser Leu Ser Leu Ser Asp Asp Ser Glu Lys Asn Pro Ser Lys Ala
                805                 810                 815
```

-continued

Ser Gln Ser Ser Arg Asp Thr Leu Ser Ser Gly Val His Ser Trp Ser
820 825 830

Ser Gln Ala Glu Ala Arg Ser Ser Ser Trp Asn Met Val Leu Ala Arg
835 840 845

Gly Arg Pro Thr Asp Thr Pro Ser Tyr Phe Asn Gly Val Lys Val Gln
850 855 860

Ile Gln Ser Leu Asn Gly Glu His Leu His Ile Arg Glu Phe His Arg
865 870 875 880

Val Lys Val Gly Asp Ile Ala Thr Gly Ile Ser Ser Gln Ile Pro Ala
885 890 895

Ala Ala Phe Ser Leu Val Thr Lys Asp Gly Gln Pro Val Arg Tyr Asp
900 905 910

Met Glu Val Pro Asp Ser Gly Ile Asp Leu Gln Cys Thr Leu Ala Pro
915 920 925

Asp Gly Ser Phe Ala Trp Ser Trp Arg Val Lys His Gly Gln Leu Glu
930 935 940

Asn Arg Pro
945

<210> SEQ ID NO 20
<211> LENGTH: 599
<212> TYPE: PRT
<213> ORGANISM: Homo sapiens

<400> SEQUENCE: 20

Met Glu Asn Cys Leu Gly Glu Ser Arg His Glu Val Glu Lys Ser Glu
1 5 10 15

Ile Ser Glu Asn Thr Asp Ala Ser Gly Lys Ile Glu Lys Tyr Asn Val
20 25 30

Pro Leu Asn Arg Leu Lys Met Met Phe Glu Lys Gly Glu Pro Thr Gln
35 40 45

Thr Lys Ile Leu Arg Ala Gln Ser Arg Ser Ala Ser Gly Arg Lys Ile
50 55 60

Ser Glu Asn Ser Tyr Ser Leu Asp Asp Leu Glu Ile Gly Pro Gly Gln
65 70 75 80

Leu Ser Ser Ser Thr Phe Asp Ser Glu Lys Asn Glu Ser Arg Arg Asn
85 90 95

Leu Glu Leu Pro Arg Leu Ser Glu Thr Ser Ile Lys Asp Arg Met Ala
100 105 110

Lys Tyr Gln Ala Ala Val Ser Lys Gln Ser Ser Ser Thr Asn Tyr Thr
115 120 125

Asn Glu Leu Lys Ala Ser Gly Gly Glu Ile Lys Ile His Lys Met Glu
130 135 140

Gln Lys Glu Asn Val Pro Pro Gly Pro Glu Val Cys Ile Thr His Gln
145 150 155 160

Glu Gly Glu Lys Ile Ser Ala Asn Glu Asn Ser Leu Ala Val Arg Ser
165 170 175

Thr Pro Ala Glu Asp Asp Ser Arg Asp Ser Gln Val Lys Ser Glu Val
180 185 190

Gln Gln Pro Val His Pro Lys Pro Leu Ser Pro Asp Ser Arg Ala Ser
195 200 205

Ser Leu Ser Glu Ser Ser Pro Pro Lys Ala Met Lys Lys Phe Gln Ala
210 215 220

Pro Ala Arg Glu Thr Cys Val Glu Cys Gln Lys Thr Val Tyr Pro Met
225 230 235 240

```
Glu Arg Leu Leu Ala Asn Gln Gln Val Phe His Ile Ser Cys Phe Arg
                245                 250                 255

Cys Ser Tyr Cys Asn Asn Lys Leu Ser Leu Gly Thr Tyr Ala Ser Leu
            260                 265                 270

His Gly Arg Ile Tyr Cys Lys Pro His Phe Asn Gln Leu Phe Lys Ser
        275                 280                 285

Lys Gly Asn Tyr Asp Glu Gly Phe Gly His Arg Pro His Lys Asp Leu
    290                 295                 300

Trp Ala Ser Lys Asn Glu Asn Glu Glu Ile Leu Glu Arg Pro Ala Gln
305                 310                 315                 320

Leu Ala Asn Ala Arg Glu Thr Pro His Ser Pro Gly Val Glu Asp Ala
                325                 330                 335

Pro Ile Ala Lys Val Gly Val Leu Ala Ala Ser Met Glu Ala Lys Ala
            340                 345                 350

Ser Ser Gln Gln Glu Lys Glu Asp Lys Pro Ala Glu Thr Lys Lys Leu
        355                 360                 365

Arg Ile Ala Trp Pro Pro Pro Thr Glu Leu Gly Ser Ser Gly Ser Ala
    370                 375                 380

Leu Glu Glu Gly Ile Lys Met Ser Lys Pro Lys Trp Pro Pro Glu Asp
385                 390                 395                 400

Glu Ile Ser Lys Pro Glu Val Pro Glu Asp Val Asp Leu Asp Leu Lys
                405                 410                 415

Lys Leu Arg Arg Ser Ser Ser Leu Lys Glu Arg Ser Arg Pro Phe Thr
            420                 425                 430

Val Ala Ala Ser Phe Gln Ser Thr Ser Val Lys Ser Pro Lys Thr Val
        435                 440                 445

Ser Pro Pro Ile Arg Lys Gly Trp Ser Met Ser Glu Gln Ser Glu Glu
    450                 455                 460

Ser Val Gly Gly Arg Val Ala Glu Arg Lys Gln Val Glu Asn Ala Lys
465                 470                 475                 480

Ala Ser Lys Lys Asn Gly Asn Val Gly Lys Thr Thr Trp Gln Asn Lys
                485                 490                 495

Glu Ser Lys Gly Glu Thr Gly Lys Arg Ser Lys Glu Gly His Ser Leu
            500                 505                 510

Glu Met Glu Asn Glu Asn Leu Val Glu Asn Gly Ala Asp Ser Asp Glu
        515                 520                 525

Asp Asp Asn Ser Phe Leu Lys Gln Gln Ser Pro Gln Glu Pro Lys Ser
    530                 535                 540

Leu Asn Trp Ser Ser Phe Val Asp Asn Thr Phe Ala Glu Glu Phe Thr
545                 550                 555                 560

Thr Gln Asn Gln Lys Ser Gln Asp Val Glu Leu Trp Glu Gly Glu Val
                565                 570                 575

Val Lys Glu Leu Ser Val Glu Glu Gln Ile Lys Arg Asn Arg Tyr Tyr
            580                 585                 590

Asp Glu Asp Glu Asp Glu Glu
        595
```

<210> SEQ ID NO 21
<211> LENGTH: 606
<212> TYPE: PRT
<213> ORGANISM: Homo sapiens

<400> SEQUENCE: 21

Met Ser Thr Ala Ser Ala Ala Ser Ser Ser Ser Ser Ser Ser Ala Gly
1 5 10 15

Glu Met Ile Glu Ala Pro Ser Gln Val Leu Asn Phe Glu Glu Ile Asp
20 25 30

Tyr Lys Glu Ile Glu Val Glu Glu Val Val Gly Arg Gly Ala Phe Gly
35 40 45

Val Val Cys Lys Ala Lys Trp Arg Ala Lys Asp Val Ala Ile Lys Gln
50 55 60

Ile Glu Ser Glu Ser Glu Arg Lys Ala Phe Ile Val Glu Leu Arg Gln
65 70 75 80

Leu Ser Arg Val Asn His Pro Asn Ile Val Lys Leu Tyr Gly Ala Cys
85 90 95

Leu Asn Pro Val Cys Leu Val Met Glu Tyr Ala Glu Gly Gly Ser Leu
100 105 110

Tyr Asn Val Leu His Gly Ala Glu Pro Leu Pro Tyr Tyr Thr Ala Ala
115 120 125

His Ala Met Ser Trp Cys Leu Gln Cys Ser Gln Gly Val Ala Tyr Leu
130 135 140

His Ser Met Gln Pro Lys Ala Leu Ile His Arg Asp Leu Lys Pro Pro
145 150 155 160

Asn Leu Leu Leu Val Ala Gly Gly Thr Val Leu Lys Ile Cys Asp Phe
165 170 175

Gly Thr Ala Cys Asp Ile Gln Thr His Met Thr Asn Asn Lys Gly Ser
180 185 190

Ala Ala Trp Met Ala Pro Glu Val Phe Glu Gly Ser Asn Tyr Ser Glu
195 200 205

Lys Cys Asp Val Phe Ser Trp Gly Ile Ile Leu Trp Glu Val Ile Thr
210 215 220

Arg Arg Lys Pro Phe Asp Glu Ile Gly Gly Pro Ala Phe Arg Ile Met
225 230 235 240

Trp Ala Val His Asn Gly Thr Arg Pro Pro Leu Ile Lys Asn Leu Pro
245 250 255

Lys Pro Ile Glu Ser Leu Met Thr Arg Cys Trp Ser Lys Asp Pro Ser
260 265 270

Gln Arg Pro Ser Met Glu Glu Ile Val Lys Ile Met Thr His Leu Met
275 280 285

Arg Tyr Phe Pro Gly Ala Asp Glu Pro Leu Gln Tyr Pro Cys Gln Tyr
290 295 300

Ser Asp Glu Gly Gln Ser Asn Ser Ala Thr Ser Thr Gly Ser Phe Met
305 310 315 320

Asp Ile Ala Ser Thr Asn Thr Ser Asn Lys Ser Asp Thr Asn Met Glu
325 330 335

Gln Val Pro Ala Thr Asn Asp Thr Ile Lys Arg Leu Glu Ser Lys Leu
340 345 350

Leu Lys Asn Gln Ala Lys Gln Gln Ser Glu Ser Gly Arg Leu Ser Leu
355 360 365

Gly Ala Ser Arg Gly Ser Ser Val Glu Ser Leu Pro Pro Thr Ser Glu
370 375 380

Gly Lys Arg Met Ser Ala Asp Met Ser Glu Ile Glu Ala Arg Ile Ala
385 390 395 400

Ala Thr Thr Ala Tyr Ser Lys Pro Lys Arg Gly His Arg Lys Thr Ala
405 410 415

Ser Phe Gly Asn Ile Leu Asp Val Pro Glu Ile Val Ile Ser Gly Asn
420 425 430

Gly Gln Pro Arg Arg Arg Ser Ile Gln Asp Leu Thr Val Thr Gly Thr
435 440 445

Glu Pro Gly Gln Val Ser Ser Arg Ser Ser Ser Pro Ser Val Arg Met
450 455 460

Ile Thr Thr Ser Gly Pro Thr Ser Glu Lys Pro Thr Arg Ser His Pro
465 470 475 480

Trp Thr Pro Asp Asp Ser Thr Asp Thr Asn Gly Ser Asp Asn Ser Ile
485 490 495

Pro Met Ala Tyr Leu Thr Leu Asp His Gln Leu Gln Pro Leu Ala Pro
500 505 510

Cys Pro Asn Ser Lys Glu Ser Met Ala Val Phe Glu Gln His Cys Lys
515 520 525

Met Ala Gln Glu Tyr Met Lys Val Gln Thr Glu Ile Ala Leu Leu Leu
530 535 540

Gln Arg Lys Gln Glu Leu Val Ala Glu Leu Asp Gln Asp Glu Lys Asp
545 550 555 560

Gln Gln Asn Thr Ser Arg Leu Val Gln Glu His Lys Lys Leu Leu Asp
565 570 575

Glu Asn Lys Ser Leu Ser Thr Tyr Tyr Gln Gln Cys Lys Lys Gln Leu
580 585 590

Glu Val Ile Arg Ser Gln Gln Gln Lys Arg Gln Gly Thr Ser
595 600 605

<210> SEQ ID NO 22
<211> LENGTH: 522
<212> TYPE: PRT
<213> ORGANISM: Homo sapiens

<400> SEQUENCE: 22

Met Ser Leu Leu Asn Cys Glu Asn Ser Cys Gly Ser Ser Gln Ser Glu
1 5 10 15

Ser Asp Cys Cys Val Ala Met Ala Ser Ser Cys Ser Ala Val Thr Lys
20 25 30

Asp Asp Ser Val Gly Gly Thr Ala Ser Thr Gly Asn Leu Ser Ser Ser
35 40 45

Phe Met Glu Glu Ile Gln Gly Tyr Asp Val Glu Phe Asp Pro Pro Leu
50 55 60

Glu Ser Lys Tyr Glu Cys Pro Ile Cys Leu Met Ala Leu Arg Glu Ala
65 70 75 80

Val Gln Thr Pro Cys Gly His Arg Phe Cys Lys Ala Cys Ile Ile Lys
85 90 95

Ser Ile Arg Asp Ala Gly His Lys Cys Pro Val Asp Asn Glu Ile Leu
100 105 110

Leu Glu Asn Gln Leu Phe Pro Asp Asn Phe Ala Lys Arg Glu Ile Leu
115 120 125

Ser Leu Met Val Lys Cys Pro Asn Glu Gly Cys Leu His Lys Met Glu
130 135 140

Leu Arg His Leu Glu Asp His Gln Ala His Cys Glu Phe Ala Leu Met
145 150 155 160

-continued

Asp Cys Pro Gln Cys Gln Arg Pro Phe Gln Lys Phe His Ile Asn Ile
165 170 175

His Ile Leu Lys Asp Cys Pro Arg Arg Gln Val Ser Cys Asp Asn Cys
180 185 190

Ala Ala Ser Met Ala Phe Glu Asp Lys Glu Ile His Asp Gln Asn Cys
195 200 205

Pro Leu Ala Asn Val Ile Cys Glu Tyr Cys Asn Thr Ile Leu Ile Arg
210 215 220

Glu Gln Met Pro Asn His Tyr Asp Leu Asp Cys Pro Thr Ala Pro Ile
225 230 235 240

Pro Cys Thr Phe Ser Thr Phe Gly Cys His Glu Lys Met Gln Arg Asn
245 250 255

His Leu Ala Arg His Leu Gln Glu Asn Thr Gln Ser His Met Arg Met
260 265 270

Leu Ala Gln Ala Val His Ser Leu Ser Val Ile Pro Asp Ser Gly Tyr
275 280 285

Ile Ser Glu Val Arg Asn Phe Gln Glu Thr Ile His Gln Leu Glu Gly
290 295 300

Arg Leu Val Arg Gln Asp His Gln Ile Arg Glu Leu Thr Ala Lys Met
305 310 315 320

Glu Thr Gln Ser Met Tyr Val Ser Glu Leu Lys Arg Thr Ile Arg Thr
325 330 335

Leu Glu Asp Lys Val Ala Glu Ile Glu Ala Gln Gln Cys Asn Gly Ile
340 345 350

Tyr Ile Trp Lys Ile Gly Asn Phe Gly Met His Leu Lys Cys Gln Glu
355 360 365

Glu Glu Lys Pro Val Val Ile His Ser Pro Gly Phe Tyr Thr Gly Lys
370 375 380

Pro Gly Tyr Lys Leu Cys Met Arg Leu His Leu Gln Leu Pro Thr Ala
385 390 395 400

Gln Arg Cys Ala Asn Tyr Ile Ser Leu Phe Val His Thr Met Gln Gly
405 410 415

Glu Tyr Asp Ser His Leu Pro Trp Pro Phe Gln Gly Thr Ile Arg Leu
420 425 430

Thr Ile Leu Asp Gln Ser Glu Ala Pro Val Arg Gln Asn His Glu Glu
435 440 445

Ile Met Asp Ala Lys Pro Glu Leu Leu Ala Phe Gln Arg Pro Thr Ile
450 455 460

Pro Arg Asn Pro Lys Gly Phe Gly Tyr Val Thr Phe Met His Leu Glu
465 470 475 480

Ala Leu Arg Gln Arg Thr Phe Ile Lys Asp Asp Thr Leu Leu Val Arg
485 490 495

Cys Glu Val Ser Thr Arg Phe Asp Met Gly Ser Leu Arg Arg Glu Gly
500 505 510

Phe Gln Pro Arg Ser Thr Asp Ala Gly Val
515 520

<210> SEQ ID NO 23
<211> LENGTH: 504
<212> TYPE: PRT
<213> ORGANISM: Homo sapiens

<400> SEQUENCE: 23

Met Ala Ala Gln Arg Arg Ser Leu Leu Gln Ser Glu Gln Gln Pro Ser
1               5                   10                  15

Trp Thr Asp Asp Leu Pro Leu Cys His Leu Ser Gly Val Gly Ser Ala
            20                  25                  30

Ser Asn Arg Ser Tyr Ser Ala Asp Gly Lys Gly Thr Glu Ser His Pro
        35                  40                  45

Pro Glu Asp Ser Trp Leu Lys Phe Arg Ser Glu Asn Asn Cys Phe Leu
    50                  55                  60

Tyr Gly Val Phe Asn Gly Tyr Asp Gly Asn Arg Val Thr Asn Phe Val
65                  70                  75                  80

Ala Gln Arg Leu Ser Ala Glu Leu Leu Leu Gly Gln Leu Asn Ala Glu
                85                  90                  95

His Ala Glu Ala Asp Val Arg Arg Val Leu Leu Gln Ala Phe Asp Val
            100                 105                 110

Val Glu Arg Ser Phe Leu Glu Ser Ile Asp Asp Ala Leu Ala Glu Lys
        115                 120                 125

Ala Ser Leu Gln Ser Gln Leu Pro Glu Gly Val Pro Gln His Gln Leu
    130                 135                 140

Pro Pro Gln Tyr Gln Lys Ile Leu Glu Arg Leu Lys Thr Leu Glu Arg
145                 150                 155                 160

Glu Ile Ser Gly Gly Ala Met Ala Val Val Ala Val Leu Leu Asn Asn
                165                 170                 175

Lys Leu Tyr Val Ala Asn Val Gly Thr Asn Arg Ala Leu Leu Cys Lys
            180                 185                 190

Ser Thr Val Asp Gly Leu Gln Val Thr Gln Leu Asn Val Asp His Thr
        195                 200                 205

Thr Glu Asn Glu Asp Glu Leu Phe Arg Leu Ser Gln Leu Gly Leu Asp
    210                 215                 220

Ala Gly Lys Ile Lys Gln Val Gly Ile Ile Cys Gly Gln Glu Ser Thr
225                 230                 235                 240

Arg Arg Ile Gly Asp Tyr Lys Val Lys Tyr Gly Tyr Thr Asp Ile Asp
                245                 250                 255

Leu Leu Ser Ala Ala Lys Ser Lys Pro Ile Ile Ala Glu Pro Glu Ile
            260                 265                 270

His Gly Ala Gln Pro Leu Asp Gly Val Thr Gly Phe Leu Val Leu Met
        275                 280                 285

Ser Glu Gly Leu Tyr Lys Ala Leu Glu Ala Ala His Gly Pro Gly Gln
    290                 295                 300

Ala Asn Gln Glu Ile Ala Ala Met Ile Asp Thr Glu Phe Ala Lys Gln
305                 310                 315                 320

Thr Ser Leu Asp Ala Val Ala Gln Ala Val Val Asp Arg Val Lys Arg
                325                 330                 335

Ile His Ser Asp Thr Phe Ala Ser Gly Gly Glu Arg Ala Arg Phe Cys
            340                 345                 350

Pro Arg His Glu Asp Met Thr Leu Leu Val Arg Asn Phe Gly Tyr Pro
        355                 360                 365

Leu Gly Glu Met Ser Gln Pro Thr Pro Ser Pro Ala Pro Ala Ala Gly
    370                 375                 380

Gly Arg Val Tyr Pro Val Ser Val Pro Tyr Ser Ser Ala Gln Ser Thr
385                 390                 395                 400

Ser Lys Thr Ser Val Thr Leu Ser Leu Val Met Pro Ser Gln Gly Gln
405 410 415

Met Val Asn Gly Ala His Ser Ala Ser Thr Leu Asp Glu Ala Thr Pro
420 425 430

Thr Leu Thr Asn Gln Ser Pro Thr Leu Thr Leu Gln Ser Thr Asn Thr
435 440 445

His Thr Gln Ser Ser Ser Ser Ser Ser Asp Gly Gly Leu Phe Arg Ser
450 455 460

Arg Pro Ala His Ser Leu Pro Pro Gly Glu Asp Gly Arg Val Glu Pro
465 470 475 480

Tyr Val Asp Phe Ala Glu Phe Tyr Arg Leu Trp Ser Val Asp His Gly
485 490 495

Glu Gln Ser Val Val Thr Ala Pro
500

<210> SEQ ID NO 24
<211> LENGTH: 693
<212> TYPE: PRT
<213> ORGANISM: Homo sapiens

<400> SEQUENCE: 24

Met Ala Gln Gly Ser His Gln Ile Asp Phe Gln Val Leu His Asp Leu
1 5 10 15

Arg Gln Lys Phe Pro Glu Val Pro Glu Val Val Val Ser Arg Cys Met
20 25 30

Leu Gln Asn Asn Asn Asn Leu Asp Ala Cys Cys Ala Val Leu Ser Gln
35 40 45

Glu Ser Thr Arg Tyr Leu Tyr Gly Glu Gly Asp Leu Asn Phe Ser Asp
50 55 60

Asp Ser Gly Ile Ser Gly Leu Arg Asn His Met Thr Ser Leu Asn Leu
65 70 75 80

Asp Leu Gln Ser Gln Asn Ile Tyr His His Gly Arg Glu Gly Ser Arg
85 90 95

Met Asn Gly Ser Arg Thr Leu Thr His Ser Ile Ser Asp Gly Gln Leu
100 105 110

Gln Gly Gly Gln Ser Asn Ser Glu Leu Phe Gln Gln Glu Pro Gln Thr
115 120 125

Ala Pro Ala Gln Val Pro Gln Gly Phe Asn Val Phe Gly Met Ser Ser
130 135 140

Ser Ser Gly Ala Ser Asn Ser Ala Pro His Leu Gly Phe His Leu Gly
145 150 155 160

Ser Lys Gly Thr Ser Ser Leu Ser Gln Gln Thr Pro Arg Phe Asn Pro
165 170 175

Ile Met Val Thr Leu Ala Pro Asn Ile Gln Thr Gly Arg Asn Thr Pro
180 185 190

Thr Ser Leu His Ile His Gly Val Pro Pro Pro Val Leu Asn Ser Pro
195 200 205

Gln Gly Asn Ser Ile Tyr Ile Arg Pro Tyr Ile Thr Thr Pro Gly Gly
210 215 220

Thr Thr Arg Gln Thr Gln Gln His Ser Gly Trp Val Ser Gln Phe Asn
225 230 235 240

Pro Met Asn Pro Gln Gln Val Tyr Gln Pro Ser Gln Pro Gly Pro Trp
245 250 255

```
Thr Thr Cys Pro Ala Ser Asn Pro Leu Ser His Thr Ser Ser Gln Gln
            260                 265                 270

Pro Asn Gln Gln Gly His Gln Thr Ser His Val Tyr Met Pro Ile Ser
        275                 280                 285

Ser Pro Thr Thr Ser Gln Pro Pro Thr Ile His Ser Ser Gly Ser Ser
    290                 295                 300

Gln Ser Ser Ala His Ser Gln Tyr Asn Ile Gln Asn Ile Ser Thr Gly
305                 310                 315                 320

Pro Arg Lys Asn Gln Ile Glu Ile Lys Leu Glu Pro Pro Gln Arg Asn
                325                 330                 335

Asn Ser Ser Lys Leu Arg Ser Ser Gly Pro Arg Thr Ser Ser Thr Ser
            340                 345                 350

Ser Ser Val Asn Ser Gln Thr Leu Asn Arg Asn Gln Pro Thr Val Tyr
        355                 360                 365

Ile Ala Ala Ser Pro Pro Asn Thr Asp Glu Leu Met Ser Arg Ser Gln
    370                 375                 380

Pro Lys Val Tyr Ile Ser Ala Asn Ala Ala Thr Gly Asp Glu Gln Val
385                 390                 395                 400

Met Arg Asn Gln Pro Thr Leu Phe Ile Ser Thr Asn Ser Gly Ala Ser
                405                 410                 415

Ala Ala Ser Arg Asn Met Ser Gly Gln Val Ser Met Gly Pro Ala Phe
            420                 425                 430

Ile His His His Pro Pro Lys Ser Arg Ala Ile Gly Asn Asn Ser Ala
        435                 440                 445

Thr Ser Pro Arg Val Val Val Thr Gln Pro Asn Thr Lys Tyr Thr Phe
    450                 455                 460

Lys Ile Thr Val Ser Pro Asn Lys Pro Pro Ala Val Ser Pro Gly Val
465                 470                 475                 480

Val Ser Pro Thr Phe Glu Leu Thr Asn Leu Leu Asn His Pro Asp His
                485                 490                 495

Tyr Val Glu Thr Glu Asn Ile Gln His Leu Thr Asp Pro Thr Leu Ala
            500                 505                 510

His Val Asp Arg Ile Ser Glu Thr Arg Lys Leu Ser Met Gly Ser Asp
        515                 520                 525

Asp Ala Ala Tyr Thr Gln Ala Leu Leu Val His Gln Lys Ala Arg Met
    530                 535                 540

Glu Arg Leu Gln Arg Glu Leu Glu Ile Gln Lys Lys Lys Leu Asp Lys
545                 550                 555                 560

Leu Lys Ser Glu Val Asn Glu Met Glu Asn Asn Leu Thr Arg Arg Arg
                565                 570                 575

Leu Lys Arg Ser Asn Ser Ile Ser Gln Ile Pro Ser Leu Glu Glu Met
            580                 585                 590

Gln Gln Leu Arg Ser Cys Asn Arg Gln Leu Gln Ile Asp Ile Asp Cys
        595                 600                 605

Leu Thr Lys Glu Ile Asp Leu Phe Gln Ala Arg Gly Pro His Phe Asn
    610                 615                 620

Pro Ser Ala Ile His Asn Phe Tyr Asp Asn Ile Gly Phe Val Gly Pro
625                 630                 635                 640

Val Pro Pro Lys Pro Lys Asp Gln Arg Ser Ile Ile Lys Thr Pro Lys
                645                 650                 655

Thr Gln Asp Thr Glu Asp Asp Glu Gly Ala Gln Trp Asn Cys Thr Ala
            660                 665                 670
```

Cys Thr Phe Leu Asn His Pro Ala Leu Ile Arg Cys Glu Gln Cys Glu
675 680 685

Met Pro Arg His Phe
690

<210> SEQ ID NO 25
<211> LENGTH: 712
<212> TYPE: PRT
<213> ORGANISM: Homo sapiens

<400> SEQUENCE: 25

Met Ala Gln Ser Ser Pro Gln Leu Asp Ile Gln Val Leu His Asp Leu
1 5 10 15

Arg Gln Arg Phe Pro Glu Ile Pro Glu Gly Val Val Ser Gln Cys Met
20 25 30

Leu Gln Asn Asn Asn Asn Leu Glu Ala Cys Cys Arg Ala Leu Ser Gln
35 40 45

Glu Ser Ser Lys Tyr Leu Tyr Met Glu Tyr His Ser Pro Asp Asp Asn
50 55 60

Arg Met Asn Arg Asn Arg Leu Leu His Ile Asn Leu Gly Ile His Ser
65 70 75 80

Pro Ser Ser Tyr His Pro Gly Asp Gly Ala Gln Leu Asn Gly Gly Arg
85 90 95

Thr Leu Val His Ser Ser Ser Asp Gly His Ile Asp Pro Gln His Ala
100 105 110

Ala Gly Lys Gln Leu Ile Cys Leu Val Gln Glu Pro His Ser Ala Pro
115 120 125

Ala Val Val Ala Ala Thr Pro Asn Tyr Asn Pro Phe Phe Met Asn Glu
130 135 140

Gln Asn Arg Ser Ala Ala Thr Pro Pro Ser Gln Pro Pro Gln Gln Pro
145 150 155 160

Ser Ser Met Gln Thr Gly Met Asn Pro Ser Ala Met Gln Gly Pro Ser
165 170 175

Pro Pro Pro Pro Pro Pro Ser Tyr Met His Ile Pro Arg Tyr Ser Thr
180 185 190

Asn Pro Ile Thr Val Thr Val Ser Gln Asn Leu Pro Ser Gly Gln Thr
195 200 205

Val Pro Arg Ala Leu Gln Ile Leu Pro Gln Ile Pro Ser Asn Leu Tyr
210 215 220

Gly Ser Pro Gly Ser Ile Tyr Ile Arg Gln Thr Ser Gln Ser Ser Ser
225 230 235 240

Gly Arg Gln Thr Pro Gln Ser Thr Pro Trp Gln Ser Ser Pro Gln Gly
245 250 255

Pro Val Pro His Tyr Ser Gln Arg Pro Leu Pro Val Tyr Pro His Gln
260 265 270

Gln Asn Tyr Gln Pro Ser Gln Tyr Ser Pro Lys Gln Gln Gln Ile Pro
275 280 285

Gln Ser Ala Tyr His Ser Pro Pro Pro Ser Gln Cys Pro Ser Pro Phe
290 295 300

Ser Ser Pro Gln His Gln Val Gln Pro Ser Gln Leu Gly His Ile Phe
305 310 315 320

Met Pro Pro Ser Pro Ser Thr Thr Pro Pro His Pro Tyr Gln Gln Gly
325 330 335

Pro Pro Ser Tyr Gln Lys Gln Gly Ser His Ser Val Ala Tyr Leu Pro
340 345 350

-continued

Tyr Thr Ala Ser Ser Leu Ser Lys Gly Ser Met Lys Lys Ile Glu Ile
355 360 365

Thr Val Glu Pro Ser Gln Arg Pro Gly Thr Ala Ile Asn Arg Ser Pro
370 375 380

Ser Pro Ile Ser Asn Gln Pro Ser Pro Arg Asn Gln His Ser Leu Tyr
385 390 395 400

Thr Ala Thr Thr Pro Pro Ser Ser Ser Pro Ser Arg Gly Ile Ser Ser
405 410 415

Gln Pro Lys Pro Pro Phe Ser Val Asn Pro Val Tyr Ile Thr Tyr Thr
420 425 430

Gln Pro Thr Gly Pro Ser Cys Thr Pro Ser Pro Ser Pro Arg Val Ile
435 440 445

Pro Asn Pro Thr Thr Val Phe Lys Ile Thr Val Gly Arg Ala Thr Thr
450 455 460

Glu Asn Leu Leu Asn Leu Val Asp Gln Glu Glu Arg Ser Ala Ala Pro
465 470 475 480

Glu Pro Ile Gln Pro Ile Ser Val Ile Pro Gly Ser Gly Gly Glu Lys
485 490 495

Gly Ser His Lys Tyr Gln Arg Ser Ser Ser Ser Gly Ser Asp Asp Tyr
500 505 510

Ala Tyr Thr Gln Ala Leu Leu Leu His Gln Arg Ala Arg Met Glu Arg
515 520 525

Leu Ala Lys Gln Leu Lys Leu Glu Lys Glu Glu Leu Glu Arg Leu Lys
530 535 540

Ser Glu Val Asn Gly Met Glu His Asp Leu Met Gln Arg Arg Leu Arg
545 550 555 560

Arg Val Ser Cys Thr Thr Ala Ile Pro Thr Pro Glu Glu Met Thr Arg
565 570 575

Leu Arg Ser Met Asn Arg Gln Leu Gln Ile Asn Val Asp Cys Thr Leu
580 585 590

Lys Glu Val Asp Leu Leu Gln Ser Arg Gly Asn Phe Asp Pro Lys Ala
595 600 605

Met Asn Asn Phe Tyr Asp Asn Ile Glu Pro Gly Pro Val Val Pro Pro
610 615 620

Lys Pro Ser Lys Lys Asp Ser Ser Asp Pro Cys Thr Ile Glu Arg Lys
625 630 635 640

Ala Arg Arg Ile Ser Val Thr Ser Lys Val Gln Ala Asp Ile His Asp
645 650 655

Thr Gln Ala Ala Ala Ala Asp Glu His Arg Thr Gly Ser Thr Gln Ser
660 665 670

Pro Arg Thr Gln Pro Arg Asp Glu Asp Tyr Glu Gly Ala Pro Trp Asn
675 680 685

Cys Asp Ser Cys Thr Phe Leu Asn His Pro Ala Leu Asn Arg Cys Glu
690 695 700

Gln Cys Glu Met Pro Arg Tyr Thr
705 710

<210> SEQ ID NO 26
<211> LENGTH: 419
<212> TYPE: PRT
<213> ORGANISM: Homo sapiens -continued

<400> SEQUENCE: 26

Met Ala Ala Ser Ser Leu Glu Gln Lys Leu Ser Arg Leu Glu Ala Lys
1               5                   10                  15

Leu Lys Gln Glu Asn Arg Glu Ala Arg Arg Arg Ile Asp Leu Asn Leu
            20                  25                  30

Asp Ile Ser Pro Gln Arg Pro Arg Pro Thr Leu Gln Leu Pro Leu Ala
        35                  40                  45

Asn Asp Gly Gly Ser Arg Ser Pro Ser Ser Glu Ser Ser Pro Gln His
    50                  55                  60

Pro Thr Pro Pro Ala Arg Pro Arg His Met Leu Gly Leu Pro Ser Thr
65                  70                  75                  80

Leu Phe Thr Pro Arg Ser Met Glu Ser Ile Glu Ile Asp Gln Lys Leu
                85                  90                  95

Gln Glu Ile Met Lys Gln Thr Gly Tyr Leu Thr Ile Gly Gly Gln Arg
            100                 105                 110

Tyr Gln Ala Glu Ile Asn Asp Leu Glu Asn Leu Gly Glu Met Gly Ser
        115                 120                 125

Gly Thr Cys Gly Gln Val Trp Lys Met Arg Phe Arg Lys Thr Gly His
    130                 135                 140

Val Ile Ala Val Lys Gln Met Arg Arg Ser Gly Asn Lys Glu Glu Asn
145                 150                 155                 160

Lys Arg Ile Leu Met Asp Leu Asp Val Val Leu Lys Ser His Asp Cys
                165                 170                 175

Pro Tyr Ile Val Gln Cys Phe Gly Thr Phe Ile Thr Asn Thr Asp Val
            180                 185                 190

Phe Ile Ala Met Glu Leu Met Gly Thr Cys Ala Glu Lys Leu Lys Lys
        195                 200                 205

Arg Met Gln Gly Pro Ile Pro Glu Arg Ile Leu Gly Lys Met Thr Val
    210                 215                 220

Ala Ile Val Lys Ala Leu Tyr Tyr Leu Lys Glu Lys His Gly Val Ile
225                 230                 235                 240

His Arg Asp Val Lys Pro Ser Asn Ile Leu Leu Asp Glu Arg Gly Gln
                245                 250                 255

Ile Lys Leu Cys Asp Phe Gly Ile Ser Gly Arg Leu Val Asp Ser Lys
            260                 265                 270

Ala Lys Thr Arg Ser Ala Gly Cys Ala Ala Tyr Met Ala Pro Glu Arg
        275                 280                 285

Ile Asp Pro Pro Asp Pro Thr Lys Pro Asp Tyr Asp Ile Arg Ala Asp
    290                 295                 300

Val Trp Ser Leu Gly Ile Ser Leu Val Glu Leu Ala Thr Gly Gln Phe
305                 310                 315                 320

Pro Tyr Lys Asn Cys Lys Thr Asp Phe Glu Val Leu Thr Lys Val Leu
                325                 330                 335

Gln Glu Glu Pro Pro Leu Leu Pro Gly His Met Gly Phe Ser Gly Asp
            340                 345                 350

Phe Gln Ser Phe Val Lys Asp Cys Leu Thr Lys Asp His Arg Lys Arg
        355                 360                 365

Pro Lys Tyr Asn Lys Leu Leu Glu His Ser Phe Ile Lys Arg Tyr Glu
    370                 375                 380

Thr Leu Glu Val Asp Val Ala Ser Trp Phe Lys Asp Val Met Ala Lys
385                 390                 395                 400

Thr Glu Ser Pro Arg Thr Ser Gly Val Leu Ser Gln Pro His Leu Pro
405 410 415

Phe Phe Arg

<210> SEQ ID NO 27
<211> LENGTH: 745
<212> TYPE: PRT
<213> ORGANISM: Homo sapiens

<400> SEQUENCE: 27

Met Glu Arg Pro Pro Gly Leu Arg Pro Gly Ala Gly Gly Pro Trp Glu
1 5 10 15

Met Arg Glu Arg Leu Gly Thr Gly Gly Phe Gly Asn Val Cys Leu Tyr
20 25 30

Gln His Arg Glu Leu Asp Leu Lys Ile Ala Ile Lys Ser Cys Arg Leu
35 40 45

Glu Leu Ser Thr Lys Asn Arg Glu Arg Trp Cys His Glu Ile Gln Ile
50 55 60

Met Lys Lys Leu Asn His Ala Asn Val Val Lys Ala Cys Asp Val Pro
65 70 75 80

Glu Glu Leu Asn Ile Leu Ile His Asp Val Pro Leu Leu Ala Met Glu
85 90 95

Tyr Cys Ser Gly Gly Asp Leu Arg Lys Leu Leu Asn Lys Pro Glu Asn
100 105 110

Cys Cys Gly Leu Lys Glu Ser Gln Ile Leu Ser Leu Leu Ser Asp Ile
115 120 125

Gly Ser Gly Ile Arg Tyr Leu His Glu Asn Lys Ile Ile His Arg Asp
130 135 140

Leu Lys Pro Glu Asn Ile Val Leu Gln Asp Val Gly Gly Lys Ile Ile
145 150 155 160

His Lys Ile Ile Asp Leu Gly Tyr Ala Lys Asp Val Asp Gln Gly Ser
165 170 175

Leu Cys Thr Ser Phe Val Gly Thr Leu Gln Tyr Leu Ala Pro Glu Leu
180 185 190

Phe Glu Asn Lys Pro Tyr Thr Ala Thr Val Asp Tyr Trp Ser Phe Gly
195 200 205

Thr Met Val Phe Glu Cys Ile Ala Gly Tyr Arg Pro Phe Leu His His
210 215 220

Leu Gln Pro Phe Thr Trp His Glu Lys Ile Lys Lys Lys Asp Pro Lys
225 230 235 240

Cys Ile Phe Ala Cys Glu Glu Met Ser Gly Glu Val Arg Phe Ser Ser
245 250 255

His Leu Pro Gln Pro Asn Ser Leu Cys Ser Leu Val Val Glu Pro Met
260 265 270

Glu Asn Trp Leu Gln Leu Met Leu Asn Trp Asp Pro Gln Gln Arg Gly
275 280 285

Gly Pro Val Asp Leu Thr Leu Lys Gln Pro Arg Cys Phe Val Leu Met
290 295 300

Asp His Ile Leu Asn Leu Lys Ile Val His Ile Leu Asn Met Thr Ser
305 310 315 320

Ala Lys Ile Ile Ser Phe Leu Leu Pro Pro Asp Glu Ser Leu His Ser
325 330 335

Leu Gln Ser Arg Ile Glu Arg Glu Thr Gly Ile Asn Thr Gly Ser Gln
340 345 350

```
Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Ala Val Thr Pro Gln Thr Ser Ala Trp Leu Pro Pro Thr Ser Ala
        675                 680                 685

Glu His Asp His Ser Leu Ser Cys Val Val Thr Pro Gln Asp Gly Glu
    690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
            740                 745
```

<210> SEQ ID NO 28
<211> LENGTH: 756

<212> TYPE: PRT
<213> ORGANISM: Homo sapiens

<400> SEQUENCE: 28

```
Met Ser Trp Ser Pro Ser Leu Thr Thr Gln Thr Cys Gly Ala Trp Glu
1               5                   10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

Ile Ala Ser Ala Leu Arg Tyr Leu His Glu Asn Arg Ile Ile His Arg
    130                 135                 140

Asp Leu Lys Pro Glu Asn Ile Val Leu Gln Gln Gly Glu Gln Arg Leu
145                 150                 155                 160

Ile His Lys Ile Ile Asp Leu Gly Tyr Ala Lys Glu Leu Asp Gln Gly
                165                 170                 175

Ser Leu Cys Thr Ser Phe Val Gly Thr Leu Gln Tyr Leu Ala Pro Glu
            180                 185                 190

Leu Leu Glu Gln Gln Lys Tyr Thr Val Thr Val Asp Tyr Trp Ser Phe
        195                 200                 205

Gly Thr Leu Ala Phe Glu Cys Ile Thr Gly Phe Arg Pro Phe Leu Pro
    210                 215                 220

Asn Trp Gln Pro Val Gln Trp His Ser Lys Val Arg Gln Lys Ser Glu
225                 230                 235                 240

Val Asp Ile Val Val Ser Glu Asp Leu Asn Gly Thr Val Lys Phe Ser
                245                 250                 255

Ser Ser Leu Pro Tyr Pro Asn Asn Leu Asn Ser Val Leu Ala Glu Arg
            260                 265                 270

Leu Glu Lys Trp Leu Gln Leu Met Leu Met Trp His Pro Arg Gln Arg
        275                 280                 285

Gly Thr Asp Pro Thr Tyr Gly Pro Asn Gly Cys Phe Lys Ala Leu Asp
    290                 295                 300

Asp Ile Leu Asn Leu Lys Leu Val His Ile Leu Asn Met Val Thr Gly
305                 310                 315                 320

Thr Ile His Thr Tyr Pro Val Thr Glu Asp Glu Ser Leu Gln Ser Leu
                325                 330                 335

Lys Ala Arg Ile Gln Gln Asp Thr Gly Ile Pro Glu Glu Asp Gln Glu
            340                 345                 350

Leu Leu Gln Glu Ala Gly Leu Ala Leu Ile Pro Asp Lys Pro Ala Thr
        355                 360                 365

Gln Cys Ile Ser Asp Gly Lys Leu Asn Glu Gly His Thr Leu Asp Met
    370                 375                 380

Asp Leu Val Phe Leu Phe Asp Asn Ser Lys Ile Thr Tyr Glu Thr Gln
385                 390                 395                 400
```

```
Ile Ser Pro Arg Pro Gln Pro Glu Ser Val Ser Cys Ile Leu Gln Glu
                405                 410                 415

Pro Lys Arg Asn Leu Ala Phe Phe Gln Leu Arg Lys Val Trp Gly Gln
            420                 425                 430

Val Trp His Ser Ile Gln Thr Leu Lys Glu Asp Cys Asn Arg Leu Gln
        435                 440                 445

Gln Gly Gln Arg Ala Ala Met Met Asn Leu Leu Arg Asn Asn Ser Cys
    450                 455                 460

Leu Ser Lys Met Lys Asn Ser Met Ala Ser Met Ser Gln Gln Leu Lys
465                 470                 475                 480

Ala Lys Leu Asp Phe Phe Lys Thr Ser Ile Gln Ile Asp Leu Glu Lys
                485                 490                 495

Tyr Ser Glu Gln Thr Glu Phe Gly Ile Thr Ser Asp Lys Leu Leu Leu
            500                 505                 510

Ala Trp Arg Glu Met Glu Gln Ala Val Glu Leu Cys Gly Arg Glu Asn
        515                 520                 525

Glu Val Lys Leu Leu Val Glu Arg Met Met Ala Leu Gln Thr Asp Ile
    530                 535                 540

Val Asp Leu Gln Arg Ser Pro Met Gly Arg Lys Gln Gly Gly Thr Leu
545                 550                 555                 560

Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Val Cys Lys Gln Lys Ala Leu Glu
    610                 615                 620

Leu Leu Pro Lys Val Glu Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
        675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu Glu His Ser Cys Leu
            740                 745                 750

Glu Gln Ala Ser
        755
```

<210> SEQ ID NO 29
<211> LENGTH: 419
<212> TYPE: PRT
<213> ORGANISM: Homo sapiens

<400> SEQUENCE: 29

Met Asn Arg His Leu Trp Lys Ser Gln Leu Cys Glu Met Val Gln Pro
1               5                   10                  15

Ser Gly Gly Pro Ala Ala Asp Gln Asp Val Leu Gly Glu Glu Ser Pro
            20                  25                  30

Leu Gly Lys Pro Ala Met Leu His Leu Pro Ser Glu Gln Gly Ala Pro
        35                  40                  45

Glu Thr Leu Gln Arg Cys Leu Glu Glu Asn Gln Glu Leu Arg Asp Ala
    50                  55                  60

Ile Arg Gln Ser Asn Gln Ile Leu Arg Glu Arg Cys Glu Glu Leu Leu
65                  70                  75                  80

His Phe Gln Ala Ser Gln Arg Glu Glu Lys Glu Phe Leu Met Cys Lys
                85                  90                  95

Phe Gln Glu Ala Arg Lys Leu Val Glu Arg Leu Gly Leu Glu Lys Leu
            100                 105                 110

Asp Leu Lys Arg Gln Lys Glu Gln Ala Leu Arg Glu Val Glu His Leu
        115                 120                 125

Lys Arg Cys Gln Gln Gln Met Ala Glu Asp Lys Ala Ser Val Lys Ala
    130                 135                 140

Gln Val Thr Ser Leu Leu Gly Glu Leu Gln Glu Ser Gln Ser Arg Leu
145                 150                 155                 160

Glu Ala Ala Thr Lys Glu Cys Gln Ala Leu Glu Gly Arg Ala Arg Ala
                165                 170                 175

Ala Ser Glu Gln Ala Arg Gln Leu Glu Ser Glu Arg Glu Ala Leu Gln
            180                 185                 190

Gln Gln His Ser Val Gln Val Asp Gln Leu Arg Met Gln Gly Gln Ser
        195                 200                 205

Val Glu Ala Ala Leu Arg Met Glu Arg Gln Ala Ala Ser Glu Glu Lys
    210                 215                 220

Arg Lys Leu Ala Gln Leu Gln Val Ala Tyr His Gln Leu Phe Gln Glu
225                 230                 235                 240

Tyr Asp Asn His Ile Lys Ser Ser Val Val Gly Ser Glu Arg Lys Arg
                245                 250                 255

Gly Met Gln Leu Glu Asp Leu Lys Gln Gln Leu Gln Gln Ala Glu Glu
            260                 265                 270

Ala Leu Val Ala Lys Gln Glu Val Ile Asp Lys Leu Lys Glu Glu Ala
        275                 280                 285

Glu Gln His Lys Ile Val Met Glu Thr Val Pro Val Leu Lys Ala Gln
    290                 295                 300

Ala Asp Ile Tyr Lys Ala Asp Phe Gln Ala Glu Arg Gln Ala Arg Glu
305                 310                 315                 320

Lys Leu Ala Glu Lys Lys Glu Leu Leu Gln Glu Gln Leu Glu Gln Leu
                325                 330                 335

Gln Arg Glu Tyr Ser Lys Leu Lys Ala Ser Cys Gln Glu Ser Ala Arg
            340                 345                 350

Ile Glu Asp Met Arg Lys Arg His Val Glu Val Ser Gln Ala Pro Leu
        355                 360                 365

Pro Pro Ala Pro Ala Tyr Leu Ser Ser Pro Leu Ala Leu Pro Ser Gln
    370                 375                 380

Arg Arg Ser Pro Pro Glu Glu Pro Pro Asp Phe Cys Cys Pro Lys Cys
385                 390                 395                 400

Gln Tyr Gln Ala Pro Asp Met Asp Thr Leu Gln Ile His Val Met Glu
405 410 415

Cys Ile Glu

<210> SEQ ID NO 30
<211> LENGTH: 317
<212> TYPE: PRT
<213> ORGANISM: Homo sapiens

<400> SEQUENCE: 30

Met Phe Gln Ala Ala Glu Arg Pro Gln Glu Trp Ala Met Glu Gly Pro
1 5 10 15

Arg Asp Gly Leu Lys Lys Glu Arg Leu Leu Asp Asp Arg His Asp Ser
20 25 30

Gly Leu Asp Ser Met Lys Asp Glu Glu Tyr Glu Gln Met Val Lys Glu
35 40 45

Leu Gln Glu Ile Arg Leu Glu Pro Gln Glu Val Pro Arg Gly Ser Glu
50 55 60

Pro Trp Lys Gln Gln Leu Thr Glu Asp Gly Asp Ser Phe Leu His Leu
65 70 75 80

Ala Ile Ile His Glu Glu Lys Ala Leu Thr Met Glu Val Ile Arg Gln
85 90 95

Val Lys Gly Asp Leu Ala Phe Leu Asn Phe Gln Asn Asn Leu Gln Gln
100 105 110

Thr Pro Leu His Leu Ala Val Ile Thr Asn Gln Pro Glu Ile Ala Glu
115 120 125

Ala Leu Leu Gly Ala Gly Cys Asp Pro Glu Leu Arg Asp Phe Arg Gly
130 135 140

Asn Thr Pro Leu His Leu Ala Cys Glu Gln Gly Cys Leu Ala Ser Val
145 150 155 160

Gly Val Leu Thr Gln Ser Cys Thr Thr Pro His Leu His Ser Ile Leu
165 170 175

Lys Ala Thr Asn Tyr Asn Gly His Thr Cys Leu His Leu Ala Ser Ile
180 185 190

His Gly Tyr Leu Gly Ile Val Glu Leu Leu Val Ser Leu Gly Ala Asp
195 200 205

Val Asn Ala Gln Glu Pro Cys Asn Gly Arg Thr Ala Leu His Leu Ala
210 215 220

Val Asp Leu Gln Asn Pro Asp Leu Val Ser Leu Leu Leu Lys Cys Gly
225 230 235 240

Ala Asp Val Asn Arg Val Thr Tyr Gln Gly Tyr Ser Pro Tyr Gln Leu
245 250 255

Thr Trp Gly Arg Pro Ser Thr Arg Ile Gln Gln Gln Leu Gly Gln Leu
260 265 270

Thr Leu Glu Asn Leu Gln Met Leu Pro Glu Ser Glu Asp Glu Glu Ser
275 280 285

Tyr Asp Thr Glu Ser Glu Phe Thr Glu Phe Thr Glu Asp Glu Leu Pro
290 295 300

Tyr Asp Asp Cys Val Phe Gly Gly Gln Arg Leu Thr Leu
305 310 315

<210> SEQ ID NO 31
<211> LENGTH: 968
<212> TYPE: PRT
<213> ORGANISM: Homo sapiens

<400> SEQUENCE: 31

Met Ala Glu Asp Asp Pro Tyr Leu Gly Arg Pro Glu Gln Met Phe His
1 5 10 15

Leu Asp Pro Ser Leu Thr His Thr Ile Phe Asn Pro Glu Val Phe Gln
20 25 30

Pro Gln Met Ala Leu Pro Thr Asp Gly Pro Tyr Leu Gln Ile Leu Glu
35 40 45

Gln Pro Lys Gln Arg Gly Phe Arg Phe Arg Tyr Val Cys Glu Gly Pro
50 55 60

Ser His Gly Gly Leu Pro Gly Ala Ser Ser Glu Lys Asn Lys Lys Ser
65 70 75 80

Tyr Pro Gln Val Lys Ile Cys Asn Tyr Val Gly Pro Ala Lys Val Ile
85 90 95

Val Gln Leu Val Thr Asn Gly Lys Asn Ile His Leu His Ala His Ser
100 105 110

Leu Val Gly Lys His Cys Glu Asp Gly Ile Cys Thr Val Thr Ala Gly
115 120 125

Pro Lys Asp Met Val Val Gly Phe Ala Asn Leu Gly Ile Leu His Val
130 135 140

Thr Lys Lys Lys Val Phe Glu Thr Leu Glu Ala Arg Met Thr Glu Ala
145 150 155 160

Cys Ile Arg Gly Tyr Asn Pro Gly Leu Leu Val His Pro Asp Leu Ala
165 170 175

Tyr Leu Gln Ala Glu Gly Gly Gly Asp Arg Gln Leu Gly Asp Arg Glu
180 185 190

Lys Glu Leu Ile Arg Gln Ala Ala Leu Gln Gln Thr Lys Glu Met Asp
195 200 205

Leu Ser Val Val Arg Leu Met Phe Thr Ala Phe Leu Pro Asp Ser Thr
210 215 220

Gly Ser Phe Thr Arg Arg Leu Glu Pro Val Val Ser Asp Ala Ile Tyr
225 230 235 240

Asp Ser Lys Ala Pro Asn Ala Ser Asn Leu Lys Ile Val Arg Met Asp
245 250 255

Arg Thr Ala Gly Cys Val Thr Gly Gly Glu Glu Ile Tyr Leu Leu Cys
260 265 270

Asp Lys Val Gln Lys Asp Asp Ile Gln Ile Arg Phe Tyr Glu Glu Glu
275 280 285

Glu Asn Gly Gly Val Trp Glu Gly Phe Gly Asp Phe Ser Pro Thr Asp
290 295 300

Val His Arg Gln Phe Ala Ile Val Phe Lys Thr Pro Lys Tyr Lys Asp
305 310 315 320

Ile Asn Ile Thr Lys Pro Ala Ser Val Phe Val Gln Leu Arg Arg Lys
325 330 335

Ser Asp Leu Glu Thr Ser Glu Pro Lys Pro Phe Leu Tyr Tyr Pro Glu
340 345 350

Ile Lys Asp Lys Glu Glu Val Gln Arg Lys Arg Gln Lys Leu Met Pro
355 360 365

Asn Phe Ser Asp Ser Phe Gly Gly Gly Ser Gly Ala Gly Ala Gly Gly
370 375 380

Gly Gly Met Phe Gly Ser Gly Gly Gly Gly Gly Gly Thr Gly Ser Thr
385 390 395 400

-continued

Gly Pro Gly Tyr Ser Phe Pro His Tyr Gly Phe Pro Thr Tyr Gly Gly
405 410 415

Ile Thr Phe His Pro Gly Thr Thr Lys Ser Asn Ala Gly Met Lys His
420 425 430

Gly Thr Met Asp Thr Glu Ser Lys Lys Asp Pro Glu Gly Cys Asp Lys
435 440 445

Ser Asp Asp Lys Asn Thr Val Asn Leu Phe Gly Lys Val Ile Glu Thr
450 455 460

Thr Glu Gln Asp Gln Glu Pro Ser Glu Ala Thr Val Gly Asn Gly Glu
465 470 475 480

Val Thr Leu Thr Tyr Ala Thr Gly Thr Lys Glu Glu Ser Ala Gly Val
485 490 495

Gln Asp Asn Leu Phe Leu Glu Lys Ala Met Gln Leu Ala Lys Arg His
500 505 510

Ala Asn Ala Leu Phe Asp Tyr Ala Val Thr Gly Asp Val Lys Met Leu
515 520 525

Leu Ala Val Gln Arg His Leu Thr Ala Val Gln Asp Glu Asn Gly Asp
530 535 540

Ser Val Leu His Leu Ala Ile Ile His Leu His Ser Gln Leu Val Arg
545 550 555 560

Asp Leu Leu Glu Val Thr Ser Gly Leu Ile Ser Asp Asp Ile Ile Asn
565 570 575

Met Arg Asn Asp Leu Tyr Gln Thr Pro Leu His Leu Ala Val Ile Thr
580 585 590

Lys Gln Glu Asp Val Val Glu Asp Leu Leu Arg Ala Gly Ala Asp Leu
595 600 605

Ser Leu Leu Asp Arg Leu Gly Asn Ser Val Leu His Leu Ala Ala Lys
610 615 620

Glu Gly His Asp Lys Val Leu Ser Ile Leu Leu Lys His Lys Lys Ala
625 630 635 640

Ala Leu Leu Leu Asp His Pro Asn Gly Asp Gly Leu Asn Ala Ile His
645 650 655

Leu Ala Met Met Ser Asn Ser Leu Pro Cys Leu Leu Leu Leu Val Ala
660 665 670

Ala Gly Ala Asp Val Asn Ala Gln Glu Gln Lys Ser Gly Arg Thr Ala
675 680 685

Leu His Leu Ala Val Glu His Asp Asn Ile Ser Leu Ala Gly Cys Leu
690 695 700

Leu Leu Glu Gly Asp Ala His Val Asp Ser Thr Thr Tyr Asp Gly Thr
705 710 715 720

Thr Pro Leu His Ile Ala Ala Gly Arg Gly Ser Thr Arg Leu Ala Ala
725 730 735

Leu Leu Lys Ala Ala Gly Ala Asp Pro Leu Val Glu Asn Phe Glu Pro
740 745 750

Leu Tyr Asp Leu Asp Asp Ser Trp Glu Asn Ala Gly Glu Asp Glu Gly
755 760 765

Val Val Pro Gly Thr Thr Pro Leu Asp Met Ala Thr Ser Trp Gln Val
770 775 780

Phe Asp Ile Leu Asn Gly Lys Pro Tyr Glu Pro Glu Phe Thr Ser Asp
785 790 795 800

Asp Leu Leu Ala Gln Gly Asp Met Lys Gln Leu Ala Glu Asp Val Lys
805 810 815

-continued

```
Leu Gln Leu Tyr Lys Leu Leu Glu Ile Pro Asp Pro Asp Lys Asn Trp
            820                 825                 830

Ala Thr Leu Ala Gln Lys Leu Gly Leu Gly Ile Leu Asn Asn Ala Phe
        835                 840                 845

Arg Leu Ser Pro Ala Pro Ser Lys Thr Leu Met Asp Asn Tyr Glu Val
    850                 855                 860

Ser Gly Gly Thr Val Arg Glu Leu Val Glu Ala Leu Arg Gln Met Gly
865                 870                 875                 880

Tyr Thr Glu Ala Ile Glu Val Ile Gln Ala Ala Ser Ser Pro Val Lys
                885                 890                 895

Thr Thr Ser Gln Ala His Ser Leu Pro Leu Ser Pro Ala Ser Thr Arg
            900                 905                 910

Gln Gln Ile Asp Glu Leu Arg Asp Ser Asp Ser Val Cys Asp Ser Gly
        915                 920                 925

Val Glu Thr Ser Phe Arg Lys Leu Ser Phe Thr Glu Ser Leu Thr Ser
    930                 935                 940

Gly Ala Ser Leu Leu Thr Leu Asn Lys Met Pro His Asp Tyr Gly Gln
945                 950                 955                 960

Glu Gly Pro Leu Glu Gly Lys Ile
                965


<210> SEQ ID NO 32
<211> LENGTH: 551
<212> TYPE: PRT
<213> ORGANISM: Homo sapiens

<400> SEQUENCE: 32

Met Asp Glu Leu Phe Pro Leu Ile Phe Pro Ala Glu Pro Ala Gln Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ser Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220
```

```
Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Ser Gly
305                 310                 315                 320

Pro Thr Asp Pro Arg Pro Pro Pro Arg Arg Ile Ala Val Pro Ser Arg
                325                 330                 335

Ser Ser Ala Ser Val Pro Lys Pro Ala Pro Gln Pro Tyr Pro Phe Thr
            340                 345                 350

Ser Ser Leu Ser Thr Ile Asn Tyr Asp Glu Phe Pro Thr Met Val Phe
        355                 360                 365

Pro Ser Gly Gln Ile Ser Gln Ala Ser Ala Leu Ala Pro Ala Pro Pro
    370                 375                 380

Gln Val Leu Pro Gln Ala Pro Ala Pro Ala Pro Ala Pro Ala Met Val
385                 390                 395                 400

Ser Ala Leu Ala Gln Ala Pro Ala Pro Val Pro Val Leu Ala Pro Gly
                405                 410                 415

Pro Pro Gln Ala Val Ala Pro Pro Ala Pro Lys Pro Thr Gln Ala Gly
            420                 425                 430

Glu Gly Thr Leu Ser Glu Ala Leu Leu Gln Leu Gln Phe Asp Asp Glu
        435                 440                 445

Asp Leu Gly Ala Leu Leu Gly Asn Ser Thr Asp Pro Ala Val Phe Thr
    450                 455                 460

Asp Leu Ala Ser Val Asp Asn Ser Glu Phe Gln Gln Leu Leu Asn Gln
465                 470                 475                 480

Gly Ile Pro Val Ala Pro His Thr Thr Glu Pro Met Leu Met Glu Tyr
                485                 490                 495

Pro Glu Ala Ile Thr Arg Leu Val Thr Gly Ala Gln Arg Pro Pro Asp
            500                 505                 510

Pro Ala Pro Ala Pro Leu Gly Ala Pro Gly Leu Pro Asn Gly Leu Leu
        515                 520                 525

Ser Gly Asp Glu Asp Phe Ser Ser Ile Ala Asp Met Asp Phe Ser Ala
    530                 535                 540

Leu Leu Ser Gln Ile Ser Ser
545                 550


<210> SEQ ID NO 33
<211> LENGTH: 619
<212> TYPE: PRT
<213> ORGANISM: Homo sapiens

<400> SEQUENCE: 33

Met Ala Ser Gly Ala Tyr Asn Pro Tyr Ile Glu Ile Ile Glu Gln Pro
1               5                   10                  15

Arg Gln Arg Gly Met Arg Phe Arg Tyr Lys Cys Glu Gly Arg Ser Ala
            20                  25                  30
```

-continued

```
Gly Ser Ile Pro Gly Glu His Ser Thr Asp Asn Asn Arg Thr Tyr Pro
        35                  40                  45

Ser Ile Gln Ile Met Asn Tyr Tyr Gly Lys Gly Lys Val Arg Ile Thr
    50                  55                  60

Leu Val Thr Lys Asn Asp Pro Tyr Lys Pro His Pro His Asp Leu Val
65                  70                  75                  80

Gly Lys Asp Cys Arg Asp Gly Tyr Tyr Glu Ala Glu Phe Gly Gln Glu
                85                  90                  95

Arg Arg Pro Leu Phe Phe Gln Asn Leu Gly Ile Arg Cys Val Lys Lys
            100                 105                 110

Lys Glu Val Lys Glu Ala Ile Ile Thr Arg Ile Lys Ala Gly Ile Asn
        115                 120                 125

Pro Phe Asn Val Pro Glu Lys Gln Leu Asn Asp Ile Glu Asp Cys Asp
    130                 135                 140

Leu Asn Val Val Arg Leu Cys Phe Gln Val Phe Leu Pro Asp Glu His
145                 150                 155                 160

Gly Asn Leu Thr Thr Ala Leu Pro Pro Val Val Ser Asn Pro Ile Tyr
                165                 170                 175

Asp Asn Arg Ala Pro Asn Thr Ala Glu Leu Arg Ile Cys Arg Val Asn
            180                 185                 190

Lys Asn Cys Gly Ser Val Arg Gly Gly Asp Glu Ile Phe Leu Leu Cys
        195                 200                 205

Asp Lys Val Gln Lys Asp Asp Ile Glu Val Arg Phe Val Leu Asn Asp
    210                 215                 220

Trp Glu Ala Lys Gly Ile Phe Ser Gln Ala Asp Val His Arg Gln Val
225                 230                 235                 240

Ala Ile Val Phe Lys Thr Pro Pro Tyr Cys Lys Ala Ile Thr Glu Pro
                245                 250                 255

Val Thr Val Lys Met Gln Leu Arg Arg Pro Ser Asp Gln Glu Val Ser
            260                 265                 270

Glu Ser Met Asp Phe Arg Tyr Leu Pro Asp Glu Lys Asp Thr Tyr Gly
        275                 280                 285

Asn Lys Ala Lys Lys Gln Lys Thr Thr Leu Leu Phe Gln Lys Leu Cys
    290                 295                 300

Gln Asp His Val Glu Thr Gly Phe Arg His Val Asp Gln Asp Gly Leu
305                 310                 315                 320

Glu Leu Leu Thr Ser Gly Asp Pro Pro Thr Leu Ala Ser Gln Ser Ala
                325                 330                 335

Gly Ile Thr Val Asn Phe Pro Glu Arg Pro Arg Pro Gly Leu Leu Gly
            340                 345                 350

Ser Ile Gly Glu Gly Arg Tyr Phe Lys Lys Glu Pro Asn Leu Phe Ser
        355                 360                 365

His Asp Ala Val Val Arg Glu Met Pro Thr Gly Val Ser Ser Gln Ala
    370                 375                 380

Glu Ser Tyr Tyr Pro Ser Pro Gly Pro Ile Ser Ser Gly Leu Ser His
385                 390                 395                 400

His Ala Ser Met Ala Pro Leu Pro Ser Ser Ser Trp Ser Ser Val Ala
                405                 410                 415

His Pro Thr Pro Arg Ser Gly Asn Thr Asn Pro Leu Ser Ser Phe Ser
            420                 425                 430

Thr Arg Thr Leu Pro Ser Asn Ser Gln Gly Ile Pro Pro Phe Leu Arg
        435                 440                 445
```

```
Ile Pro Val Gly Asn Asp Leu Asn Ala Ser Asn Ala Cys Ile Tyr Asn
    450                 455                 460

Asn Ala Asp Asp Ile Val Gly Met Glu Ala Ser Ser Met Pro Ser Ala
465                 470                 475                 480

Asp Leu Tyr Gly Ile Ser Asp Pro Asn Met Leu Ser Asn Cys Ser Val
                485                 490                 495

Asn Met Met Thr Thr Ser Ser Asp Ser Met Gly Glu Thr Asp Asn Pro
            500                 505                 510

Arg Leu Leu Ser Met Asn Leu Glu Asn Pro Ser Cys Asn Ser Val Leu
        515                 520                 525

Asp Pro Arg Asp Leu Arg Gln Leu His Gln Met Ser Ser Ser Ser Met
    530                 535                 540

Ser Ala Gly Ala Asn Ser Asn Thr Thr Val Phe Val Ser Gln Ser Asp
545                 550                 555                 560

Ala Phe Glu Gly Ser Asp Phe Ser Cys Ala Asp Asn Ser Met Ile Asn
                565                 570                 575

Glu Ser Gly Pro Ser Asn Ser Thr Asn Pro Asn Ser His Gly Phe Val
            580                 585                 590

Gln Asp Ser Gln Tyr Ser Gly Ile Gly Ser Met Gln Asn Glu Gln Leu
        595                 600                 605

Ser Asp Ser Phe Pro Tyr Glu Phe Phe Gln Val
    610                 615
```

<210> SEQ ID NO 34
<211> LENGTH: 427
<212> TYPE: PRT
<213> ORGANISM: Homo sapiens

<400> SEQUENCE: 34

```
Met Ser Arg Ser Lys Arg Asp Asn Asn Phe Tyr Ser Val Glu Ile Gly
1               5                   10                  15

Asp Ser Thr Phe Thr Val Leu Lys Arg Tyr Gln Asn Leu Lys Pro Ile
            20                  25                  30

Gly Ser Gly Ala Gln Gly Ile Val Cys Ala Ala Tyr Asp Ala Ile Leu
        35                  40                  45

Glu Arg Asn Val Ala Ile Lys Lys Leu Ser Arg Pro Phe Gln Asn Gln
    50                  55                  60

Thr His Ala Lys Arg Ala Tyr Arg Glu Leu Val Leu Met Lys Cys Val
65                  70                  75                  80

Asn His Lys Asn Ile Ile Gly Leu Leu Asn Val Phe Thr Pro Gln Lys
                85                  90                  95

Ser Leu Glu Glu Phe Gln Asp Val Tyr Ile Val Met Glu Leu Met Asp
            100                 105                 110

Ala Asn Leu Cys Gln Val Ile Gln Met Glu Leu Asp His Glu Arg Met
        115                 120                 125

Ser Tyr Leu Leu Tyr Gln Met Leu Cys Gly Ile Lys His Leu His Ser
    130                 135                 140

Ala Gly Ile Ile His Arg Asp Leu Lys Pro Ser Asn Ile Val Val Lys
145                 150                 155                 160

Ser Asp Cys Thr Leu Lys Ile Leu Asp Phe Gly Leu Ala Arg Thr Ala
                165                 170                 175

Gly Thr Ser Phe Met Met Thr Pro Tyr Val Val Thr Arg Tyr Tyr Arg
            180                 185                 190

Ala Pro Glu Val Ile Leu Gly Met Gly Tyr Lys Glu Asn Val Asp Leu
        195                 200                 205
```

```
Trp Ser Val Gly Cys Ile Met Gly Glu Met Val Cys His Lys Ile Leu
    210                 215                 220

Phe Pro Gly Arg Asp Tyr Ile Asp Gln Trp Asn Lys Val Ile Glu Gln
225                 230                 235                 240

Leu Gly Thr Pro Cys Pro Glu Phe Met Lys Lys Leu Gln Pro Thr Val
                245                 250                 255

Arg Thr Tyr Val Glu Asn Arg Pro Lys Tyr Ala Gly Tyr Ser Phe Glu
            260                 265                 270

Lys Leu Phe Pro Asp Val Leu Phe Pro Ala Asp Ser Glu His Asn Lys
        275                 280                 285

Leu Lys Ala Ser Gln Ala Arg Asp Leu Leu Ser Lys Met Leu Val Ile
    290                 295                 300

Asp Ala Ser Lys Arg Ile Ser Val Asp Glu Ala Leu Gln His Pro Tyr
305                 310                 315                 320

Ile Asn Val Trp Tyr Asp Pro Ser Glu Ala Glu Ala Pro Pro Pro Lys
                325                 330                 335

Ile Pro Asp Lys Gln Leu Asp Glu Arg Glu His Thr Ile Glu Glu Trp
            340                 345                 350

Lys Glu Leu Ile Tyr Lys Glu Val Met Asp Leu Glu Glu Arg Thr Lys
        355                 360                 365

Asn Gly Val Ile Arg Gly Gln Pro Ser Pro Leu Gly Ala Ala Val Ile
    370                 375                 380

Asn Gly Ser Gln His Pro Ser Ser Ser Ser Ser Val Asn Asp Val Ser
385                 390                 395                 400

Ser Met Ser Thr Asp Pro Thr Leu Ala Ser Asp Thr Asp Ser Ser Leu
                405                 410                 415

Glu Ala Ala Ala Gly Pro Leu Gly Cys Cys Arg
            420                 425
```

<210> SEQ ID NO 35
<211> LENGTH: 424
<212> TYPE: PRT
<213> ORGANISM: Homo sapiens

<400> SEQUENCE: 35

```
Met Ser Asp Ser Lys Cys Asp Ser Gln Phe Tyr Ser Val Gln Val Ala
1               5                   10                  15

Asp Ser Thr Phe Thr Val Leu Lys Arg Tyr Gln Gln Leu Lys Pro Ile
            20                  25                  30

Gly Ser Gly Ala Gln Gly Ile Val Cys Ala Ala Phe Asp Thr Val Leu
        35                  40                  45

Gly Ile Asn Val Ala Val Lys Lys Leu Ser Arg Pro Phe Gln Asn Gln
    50                  55                  60

Thr His Ala Lys Arg Ala Tyr Arg Glu Leu Val Leu Leu Lys Cys Val
65                  70                  75                  80

Asn His Lys Asn Ile Ile Ser Leu Leu Asn Val Phe Thr Pro Gln Lys
                85                  90                  95

Thr Leu Glu Glu Phe Gln Asp Val Tyr Leu Val Met Glu Leu Met Asp
            100                 105                 110

Ala Asn Leu Cys Gln Val Ile His Met Glu Leu Asp His Glu Arg Met
        115                 120                 125

Ser Tyr Leu Leu Tyr Gln Met Leu Cys Gly Ile Lys His Leu His Ser
    130                 135                 140
```

Ala Gly Ile Ile His Arg Asp Leu Lys Pro Ser Asn Ile Val Val Lys
145 150 155 160

Ser Asp Cys Thr Leu Lys Ile Leu Asp Phe Gly Leu Ala Arg Thr Ala
165 170 175

Cys Thr Asn Phe Met Met Thr Pro Tyr Val Val Thr Arg Tyr Tyr Arg
180 185 190

Ala Pro Glu Val Ile Leu Gly Met Gly Tyr Lys Glu Asn Val Asp Ile
195 200 205

Trp Ser Val Gly Cys Ile Met Gly Glu Leu Val Lys Gly Cys Val Ile
210 215 220

Phe Gln Gly Thr Asp His Ile Asp Gln Trp Asn Lys Val Ile Glu Gln
225 230 235 240

Leu Gly Thr Pro Ser Ala Glu Phe Met Lys Lys Leu Gln Pro Thr Val
245 250 255

Arg Asn Tyr Val Glu Asn Arg Pro Lys Tyr Pro Gly Ile Lys Phe Glu
260 265 270

Glu Leu Phe Pro Asp Trp Ile Phe Pro Ser Glu Ser Glu Arg Asp Lys
275 280 285

Ile Lys Thr Ser Gln Ala Arg Asp Leu Leu Ser Lys Met Leu Val Ile
290 295 300

Asp Pro Asp Lys Arg Ile Ser Val Asp Glu Ala Leu Arg His Pro Tyr
305 310 315 320

Ile Thr Val Trp Tyr Asp Pro Ala Glu Ala Glu Ala Pro Pro Pro Gln
325 330 335

Ile Tyr Asp Ala Gln Leu Glu Glu Arg Glu His Ala Ile Glu Glu Trp
340 345 350

Lys Glu Leu Ile Tyr Lys Glu Val Met Asp Trp Glu Glu Arg Ser Lys
355 360 365

Asn Gly Val Val Lys Asp Gln Pro Ser Asp Ala Ala Val Ser Ser Asn
370 375 380

Ala Thr Pro Ser Gln Ser Ser Ser Ile Asn Asp Ile Ser Ser Met Ser
385 390 395 400

Thr Glu Gln Thr Leu Ala Ser Asp Thr Asp Ser Ser Leu Asp Ala Ser
405 410 415

Thr Gly Pro Leu Glu Gly Cys Arg
420

<210> SEQ ID NO 36
<211> LENGTH: 464
<212> TYPE: PRT
<213> ORGANISM: Homo sapiens

<400> SEQUENCE: 36

Met Ser Leu His Phe Leu Tyr Tyr Cys Ser Glu Pro Thr Leu Asp Val
1 5 10 15

Lys Ile Ala Phe Cys Gln Gly Phe Asp Lys Gln Val Asp Val Ser Tyr
20 25 30

Ile Ala Lys His Tyr Asn Met Ser Lys Ser Lys Val Asp Asn Gln Phe
35 40 45

Tyr Ser Val Glu Val Gly Asp Ser Thr Phe Thr Val Leu Lys Arg Tyr
50 55 60

Gln Asn Leu Lys Pro Ile Gly Ser Gly Ala Gln Gly Ile Val Cys Ala
65 70 75 80

-continued

```
Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe Gln Asp Val Tyr Leu
    130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
    210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
        275                 280                 285

Lys Leu Gln Pro Thr Val Arg Asn Tyr Val Glu Asn Arg Pro Lys Tyr
    290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
        355                 360                 365

Glu Ala Pro Pro Pro Gln Ile Tyr Asp Lys Gln Leu Asp Glu Arg Glu
    370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415

Ser Gly Ala Ala Val Asn Ser Ser Glu Ser Leu Pro Pro Ser Ser Ser
            420                 425                 430

Val Asn Asp Ile Ser Ser Met Ser Thr Asp Gln Thr Leu Ala Ser Asp
        435                 440                 445

Thr Asp Ser Ser Leu Glu Ala Ser Ala Gly Pro Leu Gly Cys Cys Arg
    450                 455                 460
```

TRICYCLIC COMPOUNDS USEFUL IN THE TREATMENT OF CANCER, AUTOIMMUNE AND INFLAMMATORY DISORDERS

This application is a National Stage application of International Application No. PCT/US2022/013671, filed Jan. 25, 2022, which claims the benefit of U.S. Provisional Application No. 63/141,682, filed Jan. 26, 2021; U.S. Provisional Application No. 63/145,344, filed Feb. 3, 2021; and U.S. Provisional Application No. 63/276,064, filed Nov. 5, 2021.

TECHNICAL FIELD

This present application relates to tricyclic, and other multi-cyclic compounds, that are useful for treating proliferative disorders such as cancer, as well as autoimmune and inflammatory disorders.

BACKGROUND

MALT1 (mucosa-associated lymphoid tissue lymphoma translocation protein 1) is an intracellular protein involved in lymphocyte proliferation via upstream signaling of NF-κB to control lymphocyte activation, survival, proliferation, and differentiation. Together with a CARMA or CARD scaffold protein, (e.g., CARD11 (caspase recruitment domain family member 11, also known as CARMA1), CARD14 (caspase recruitment domain family member 14, also known as CARMA2), CARD10 (caspase recruitment domain family member 10, also known as CARMA3), or CARD9 (caspase recruitment domain family member 9)) and BCL10 (B-cell CLL/Lymphoma 10), MALT1 is one of the three subunits of the CBM complex which is formed upon cell-surface antigen receptor activation. See Jaworski et al., Cell Mol Life Science 2016, 73, 459-473, and Juilland and Thome. Frontiers in Immunology 2018, 9, 1927. MALT1 is known to mediate NF-κB signaling by at least two mechanisms: firstly, MALT1 functions as a scaffold protein, recruiting NF-κB signaling proteins such as TRAF6, TABs (e.g., TAB1, TAB2, TAB3), TAK1 and NEMO-IKK α/β; and secondly, as a cysteine protease, it cleaves and deactivates negative regulators of NF-κB signaling, such as RelB, A20, or CYLD. See Rosebeck et al., Science, 2011, 331, 468-472.

The protease activity of MALT1 has emerged as a potential therapeutic target, particularly where NF-κB and related pathways are believed to play a significant role. Activated B cell-like diffuse large B cell lymphomas (ABC-DLBCLs) are aggressive lymphomas that are often characterized by NF-κB hyperactivation, and it has been shown that MALT1 protease inhibition can dramatically inhibit growth and promote apoptosis of the highly aggressive ABC type DLBCLs. See Ferch U, et al., J Exp Med 2009, 206, 2313-2320; see also, Hailfinger S, et al., Proc Natl Acad Sci USA 2009, 106, 19946-19951. Known peptide substrates of MALT1, or fusion protein API2-MALT1, include A20, CYLD, BCL10, RelB, regnase-1, roquin-1, NIK, and LIMA 1a. See Rebeaud et al., Nat Immunol 2008, 9, 272-281; see also, Coornaert et al., Nat Immunol 20008, 9, 263-271; Staal et al., EMBO J 2011, 30, 1742-1752; Hailfinger et al., PNAS 2011, 108, 14596-14601; Jeltsch et al., Nat Immunol 2014, 15, 1079-1089; Uehata et al., Cell 2013, 153, 1036-1049; Nie et al., Nat Commun 2015, 6, 5908; and Baens et al., PLoS ONE 2014, 9, e103774. One general profile of MALT1 substrates is described in Kasperkiewicz, et al. Scientific Reports 8.1 (2018): 1-10.

Additionally, several chromosomal translocations that lead to the generation of constitutively active MALT1 have been identified in ABC-DLBCLs and the identification of the MALT1 fusion protein API2-MALT1/IgH-MALT1 that leads to NF-κB activation independent of upstream stimulation further highlights the importance of this protein in cancer and various diseases. See Farinha et al., J Clinical Oncology 2005, 23, 6370-6378. Further, MALT1 has been shown to be involved in several different types of cancers, for example hematological malignancies such as mantle cell lymphoma, chronic lymphocytic leukemia (CLL) and solid tumors such as lung adenocarcinoma, breast cancer, pancreatic cancer, and glioblastoma. See Jiang et al., Cancer Research 2011, 71, 2183-2192; see also, Pan et al., Mol Cancer Res 2016, 14, 93-102, Penas et al., Blood 2010, 115, 2214-2219, and J Cell Mol Med. 2020 July; 24(13):7550-7562. MALT1, as an immunomodulatory protein, is also involved in innate and adaptive immunity and may have effects on several inflammatory disorders, e.g., psoriasis, multiple sclerosis, rheumatoid arthritis, Sjogren's syndrome, ulcerative colitis, and different types of allergic disorders resulting from chronic inflammation. See Afofina et al., FEBS Journal 2015, DOI: 10.1 111/febs. 13325; see also Lowes et al., Ann Review Immunology 2014, 32, 227-255; Jabara et al., J Allergy Clin Immunology 2013, 132, 151-158; Streubel et al., Clin Cancer Research 2004, 10, 476-480; and Liu et al., Oncotarget 2016, 1-14. Recently, findings also suggest the importance of MALT1 in the control of regulatory T cell (Treg) function and homeostasis. Studies are ongoing to confirm the potential of MALT1 inhibitors for the treatment of patients with solid tumors alone or in combination with immune-checkpoint mechanisms. However, no MALT1 inhibitors are currently approved for therapeutic use.

SUMMARY

Accordingly, provided herein is a compound of the Formula (I):

(I)

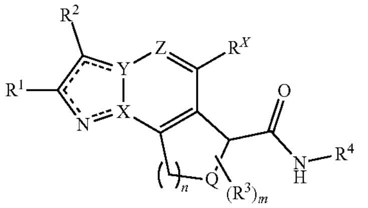

or a pharmaceutically acceptable salt thereof, wherein X, Y, Z, Q, n, $R^X$, $R^1$, $R^2$, $R^3$, m, and $R^4$ are as defined herein.

In some embodiments, the compound of Formula (I) has the structure:

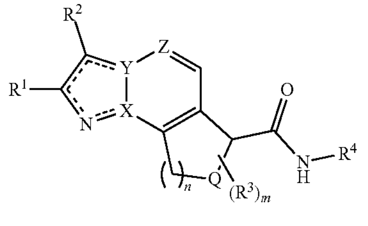

or a pharmaceutically acceptable salt thereof, wherein X, Y, Z, Q, n, $R^1$, $R^2$, $R^3$, m, and $R^4$ are as defined herein.

Also provided herein is a pharmaceutical composition comprising a compound of Formula (I), or a pharmaceutically acceptable salt thereof, and at least one pharmaceutically acceptable excipient.

Also provided are methods for treating a CBM complex pathway-associated cancer in a subject in need thereof, comprising administering to the subject an effective amount of a compound of Formula (I), or a pharmaceutically acceptable salt thereof, or a pharmaceutical composition as described herein.

Also provided are methods for treating a cancer in a subject in need thereof, comprising:

(a) identifying the cancer as being a CBM complex pathway-associated cancer; and (b) administering to the subject an effective amount of a compound of Formula (I), or a pharmaceutically acceptable salt thereof, or a pharmaceutical composition as described herein.

Also provided are methods for treating a cancer in a subject in need thereof, comprising:

administering an effective amount of a compound of Formula (I), or a pharmaceutically acceptable salt thereof, or a pharmaceutical composition as described herein, to a subject identified as having a CBM complex pathway-associated cancer Also provided are methods for treating a MALT1-associated cancer in a subject, comprising administering to a subject identified or diagnosed as having a MALT1-associated cancer an effective amount of a compound of Formula (I), or a pharmaceutically acceptable salt thereof, or a pharmaceutical composition as described herein.

Also provided are methods for treating cancer in a subject in need thereof, comprising:

(a) determining that the cancer is associated with a dysregulation of a MALT1 gene, a MALT1 protease, or expression or activity or level of any of the same; and (b) administering to the subject an effective amount of a compound of Formula (I), or a pharmaceutically acceptable salt thereof, or a pharmaceutical composition as described herein.

Also provided are methods for inhibiting metastasis in a subject having a cancer in need of such treatment, comprising administering to the subject an effective amount of a compound of Formula (I), or a pharmaceutically acceptable salt thereof, or a pharmaceutical composition as described herein.

Also provided are methods for treating an autoimmune disorder in a subject in need thereof, comprising administering to the subject an effective amount of a compound of Formula (I), or a pharmaceutically acceptable salt thereof, or a pharmaceutical composition as described herein.

Also provided are methods for treating a CBM complex pathway-associated disease or disorder in a subject in need thereof, comprising administering to the subject an effective amount of a compound of Formula (I), or a pharmaceutically acceptable salt thereof, or a pharmaceutical composition as described herein.

Also provided are methods for treating a disease or disorder in a subject in need thereof, comprising:

(a) identifying the disease or disorder as being a CBM complex pathway-associated disease or disorder; and (b) administering to the subject an effective amount of a compound of Formula (I), or a pharmaceutically acceptable salt thereof, or a pharmaceutical composition as described herein.

Also provided are methods for treating a disease or disorder in a subject in need thereof, comprising:

administering to the subject an effective amount of a compound of Formula (I), or a pharmaceutically acceptable salt thereof, or a pharmaceutical composition as described herein, to a subject identified as having a CBM complex pathway-associated disease or disorder.

Also provided are methods for treating a MALT1-associated autoimmune disorder in a subject, comprising administering to a subject identified or diagnosed as having a MALT1-associated autoimmune disorder an effective amount of a compound of Formula (I), or a pharmaceutically acceptable salt thereof, or a pharmaceutical composition as described herein.

Also provided are methods for treating a MALT1-associated autoimmune disorder in a subject, comprising administering to a subject identified or diagnosed as having a MALT1-associated autoimmune disorder an effective amount of a compound of Formula (I), or a pharmaceutically acceptable salt thereof, or a pharmaceutical composition as described herein.

Also provided are methods for treating an autoimmune disorder in a subject in need thereof, comprising:

(a) determining that the autoimmune disorder is associated with a dysregulation of a MALT1 gene, a MALT1 protease, or expression or activity or level of any of the same; and (b) administering to the subject an effective amount of a compound of Formula (I), or a pharmaceutically acceptable salt thereof, or a pharmaceutical composition as described herein.

Also provided are methods for treating a MALT1-associated autoimmune disorder in a subject, comprising administering an effective amount of a compound of Formula (I), or a pharmaceutically acceptable salt thereof, or a pharmaceutical composition as described herein, to a subject determined to have a MALT1-associated autoimmune disorder.

Also provided are methods for treating an inflammatory disorder in a subject in need thereof, comprising administering to the subject an effective amount of a compound of Formula (I), or a pharmaceutically acceptable salt thereof, or a pharmaceutical composition as described herein.

Also provided are methods for treating a MALT1-associated inflammatory disorder in a subject, comprising administering to a subject identified or diagnosed as having a MALT1-associated inflammatory disorder an effective amount of a compound of Formula (I), or a pharmaceutically acceptable salt thereof, or a pharmaceutical composition as described herein.

Also provided are methods for treating a MALT1-associated inflammatory disorder in a subject, comprising administering to a subject identified or diagnosed as having a MALT1-associated inflammatory disorder an effective amount of a compound of Formula (I), or a pharmaceutically acceptable salt thereof, or a pharmaceutical composition as described herein.

Also provided are methods for treating an inflammatory disorder in a subject in need thereof, comprising:

(a) determining that the inflammatory disorder is associated with a dysregulation of a MALT1 gene, a MALT1 protease, or expression or activity or level of any of the same; and (b) administering to the subject an effective amount of a compound of Formula (I), or a pharmaceutically acceptable salt thereof, or a pharmaceutical composition as described herein.

Also provided are methods for treating a MALT1-associated inflammatory disorder in a subject, comprising administering an effective amount of a compound of Formula (I), or a pharmaceutically acceptable salt thereof, or a pharmaceutical composition as described herein, to a subject determined to have a MALT1-associated inflammatory disorder.

Also provided are methods for inhibiting CBM complex pathway activity in a mammalian cell, comprising contacting the mammalian cell with a compound of Formula (I), or a pharmaceutically acceptable salt thereof.

Also provided are methods for inhibiting MALT1 protease activity in a mammalian cell, comprising contacting the mammalian cell with a compound of Formula (I), or a pharmaceutically acceptable salt thereof.

Also provided are the use of compounds of Formula (I), or pharmaceutically acceptable salts thereof, for treating a CBM complex pathway-associated disease or disorder.

Also provided are compounds of Formula (I), or pharmaceutically acceptable salts thereof, for use in the manufacture of a medicament for the treatment of a CBM complex pathway-associated disease or disorder.

Also provided are methods of treating an individual with a MALT1-associated cancer that include administering a compound of Formula (I), or a pharmaceutically acceptable salt thereof, before, during, or after administration of other anticancer drug(s) (e.g., a first MALT1 inhibitor or another MALT1 inhibitor).

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entireties. In case of conflict, the present specification, including definitions, will control.

Other features and advantages of the disclosure will be apparent from the following detailed description and from the claims.

DETAILED DESCRIPTION

The term "compound," as used herein is meant to include all stereoisomers, geometric isomers, tautomers, and isotopically enriched variants of the structures depicted. Compounds herein identified by name or structure as one particular tautomeric form are intended to include other tautomeric forms unless otherwise specified.

The term "tautomer," as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the disclosure, and the naming of the compounds does not exclude any tautomer. The following is an example of included tautomeric forms:

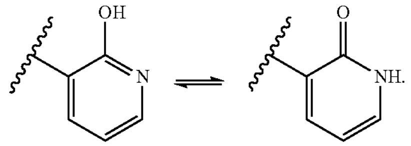 [SMILES: *c1cccnc1O ; *c1ccc[nH]c1=O]

It will be appreciated that certain compounds provided herein may contain one or more centers of asymmetry and may therefore be prepared and isolated in a mixture of isomers such as a racemic mixture, or in an enantiomerically pure form.

The term "halo" refers to one of the halogens, group 17 of the periodic table. In particular, the term refers to fluorine, chlorine, bromine and iodine. Preferably, the term refers to fluorine or chlorine.

The term "C1-C6 alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. Similarly, a C1-C3 alkyl group is linear or branched hydrocarbon chain containing 1, 2, or 3 carbon atoms.

The term "C1-C6 haloalkyl" refers to a hydrocarbon chain substituted with at least one halogen atom independently chosen at each occurrence, for example fluorine, chlorine, bromine and iodine. The halogen atom may be present at any position on the hydrocarbon chain. Similarly, a C1-C3 haloalkyl group is linear or branched hydrocarbon chain containing 1, 2, or 3 carbon atoms substituted with at least one halogen atom. For example, C1-C3 haloalkyl may refer to chloromethyl, fluoromethyl, trifluoromethyl, chloroethyl e.g. 1-chloroethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "C1-C6 alkoxy" refers to a C1-C6 alkyl group which is attached to a molecule via oxygen. This includes moieties where the alkyl part may be linear or branched, such as methoxy, ethoxy, n-propoxy, iso-propoxy, n-butoxy, sec-butoxy, tert-butoxy, n-pentoxy and n-hexoxy.

The term "C1-C6 haloalkoxy" refers to a C1-C6 alkyl group which is attached to a molecule via oxygen and where at least one hydrogen atom of the alkyl group is replaced with a halogen. This includes moieties where the alkyl part may be linear or branched, such as fluoromethoxy, difluoromethoxy, trifluoromethoxy, 2,2,2-trifluoroethoxy, or trifluoropropoxy.

A  represents a single or double bond, valence permitting. For example,

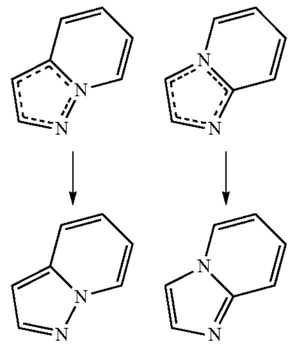

As used herein, the term "cyano" refers to a —CN radical.

As used herein, the term "hydroxyl" refers to an —OH radical.

As used herein, the term "amino" refers to an $—NH_2$ group.

As used herein, the term "aryl" refers to a 6-10 all carbon mono- or bicyclic group wherein at least one ring in the system is aromatic. Non-limiting examples of aryl groups include phenyl, naphthyl, tetrahydronaphthyl. In bicyclic ring systems where only one ring is aromatic, the non-aromatic ring can be a cycloalkyl group, as defined herein.

As used herein, the term "heteroaryl" refers to a 5-10 membered mono- or bicyclic group wherein at least one ring in the system is aromatic; wherein one or more carbon atoms in at least one ring in the system is/are replaced with an heteroatom independently selected from N, O, and S. Heteroaryl groups include rings where one or more atoms are oxidized (e.g., carbon, nitrogen, and sulfur), such as a pyridone moiety. Non-limiting examples of heteroaryl groups include pyridine, pyrimidine, pyrrole, imidazole, and indole. In bicyclic ring systems where only one ring is aromatic, the non-aromatic ring can be a cycloalkyl or heterocyclyl group, as defined herein.

As used herein, the term "cycloalkoxy" refers to a saturated or partially unsaturated 3-10 mono- or bicyclic hydrocarbon group connected through an oxy (i.e., —O—); wherein bicyclic systems include fused, spiro (optionally referred to as "spirocycloalkyl" groups), and bridged ring systems. Non-limiting examples of cycloalkoxy groups include cyclopropoxy, cyclohexoxy, spiro[2.3]hexoxy, and bicyclo[1.1.1]pentoxy.

As used herein, the term "cycloalkyl" refers to a saturated or partially unsaturated 3-10 mono- or bicyclic hydrocarbon group; wherein bicyclic systems include fused, spiro (optionally referred to as "spirocycloalkyl" groups), and bridged ring systems. Non-limiting examples of cycloalkyl groups include cyclopropyl, cyclohexyl, spiro[2.3]hexyl, and bicyclo[1.1.1]pentyl.

The term "heterocyclyl" refers to a saturated or partially unsaturated 3-12 membered hydrocarbon monocyclic or bicyclic ring system, that is not aromatic, having at least one heteroatom within the ring selected from N, O and S. Bicyclic heterocyclyl groups include fused, spiro (optionally referred to as "spiroheterocyclyl" groups), and bridged ring systems. The heterocyclyl ring system may include oxo substitution at one or more C, N, or S ring members. The heterocyclyl group may be denoted as, for example, a "5-10 membered heterocyclyl group," which is a ring system containing 5, 6, 7, 8, 9 or 10 atoms at least one being a heteroatom. For example, there may be 1, 2 or 3 heteroatoms, optionally 1 or 2. The heterocyclyl group may be bonded to the rest of the molecule through any carbon atom or through a heteroatom such as nitrogen. Exemplary heterocyclyl groups include, but are not limited to, piperidinyl, piperazinyl, morpholino, tetrahydropyranyl, azetidinyl, oxetanyl, 2-azaspiro[3.3]heptanyl, pyrrolidin-2-one, sulfolane, isothiazoline S,S-dioxide, and decahydronaphthalenyl.

As used herein, the term "geminal" refers to substituent atoms or groups attached to the same atom in a molecule.

As used herein, the term "vicinal" refers to substituent atoms or groups attached to adjacent atoms in a molecule. The stereochemical relationship between the substituent atoms or groups can be cis, trans, undefined, or unresolved.

As used herein, the term "oxo" refers to an "═O" group attached to a carbon atom.

As used herein, the symbol  depicts the point of attachment of an atom or moiety to the indicated atom or group in the remainder of the molecule.

It is to be understood that the ring in compounds of Formula (I) comprising atoms X, Y and Z does not contain more than two adjacent nitrogen atoms.

The compounds of Formula (I) include pharmaceutically acceptable salts thereof. In addition, the compounds of Formula (I) also include other salts of such compounds which are not necessarily pharmaceutically acceptable salts, and which may be useful as intermediates for preparing and/or purifying compounds of Formula (I) and/or for separating enantiomers of compounds of Formula (I). Non-limiting examples of pharmaceutically acceptable salts of compounds of Formula (I) include trifluoroacetic acid and hydrochloride salts.

It will further be appreciated that the compounds of Formula (I) or their salts may be isolated in the form of solvates, and accordingly that any such solvate is included within the scope of the present disclosure. For example, compounds of Formula (I) and salts thereof can exist in unsolvated as well as solvated forms with pharmaceutically acceptable solvents such as water, ethanol, and the like.

In some embodiments, the compounds of Formula (I) include the compounds of Examples 1-203 and stereoisomers and pharmaceutically acceptable salts thereof. In some embodiments, the compounds of Formula (I) include the compounds of Examples 1-203 and pharmaceutically acceptable salts thereof. In some embodiments, the compounds of Examples 1-203 are in the free base form. In some embodiments, the compounds of Examples 1-203 are in the form of pharmaceutically acceptable salts.

The term "pharmaceutically acceptable" indicates that the compound, or salt or composition thereof is compatible chemically and/or toxicologically with the other ingredients comprising a formulation and/or the subject being treated therewith.

Protecting groups can be a temporary substituent which protects a potentially reactive functional group from undesired chemical transformations. The choice of the particular protecting group employed is well within the skill of one of ordinary skill in the art. A number of considerations can determine the choice of protecting group including, but not limited to, the functional group being protected, other functionality present in the molecule, reaction conditions at each step of the synthetic sequence, other protecting groups present in the molecule, functional group tolerance to conditions required to remove the protecting group, and reaction conditions for the thermal decomposition of the compounds provided herein. The field of protecting group chemistry has been reviewed (Greene, T. W. and Wuts, P. G. M. *Protective Groups in Organic Synthesis,* 2.sup. ed. Wiley: New York, 1991).

A nitrogen protecting group can be any temporary substituent which protects an amine moiety from undesired chemical transformations. Examples of moieties formed when such protecting groups are bonded to an amine include, but are not limited to allylamine, benzylamines (e.g., bezylamine, p-methoxybenzylamine, 2,4-dimethoxybenzylamine, and tritylamine), acetylamide, trichloroacetammide, trifluoroacetamide, pent-4-enamide, phthalimides, carbamates (e.g., methyl carbamate, t-butyl carbamate, benzyl carbamate, allyl carbamates, 2,2,2-trichloroethyl carbamate, and 9-fluorenylmethyl carbamate), imines, and sulfonamides (e.g., benzene sulfonamide, p-toluenesulfonamide, and p-nitrobenzenesulfonamide).

An oxygen protecting group can be any temporary substituent which protects a hydroxyl moiety from undesired chemical transformations. Examples of moieties formed when such protecting groups are bonded to a hydroxyl include, but are not limited to esters (e.g., acetyl, t-butyl carbonyl, and benzoyl), benzyl (e.g., benzyl, p-methoxybenzyl, and 2,4-dimethoxybenzyl, and trityl), carbonates (e.g., methyl carbonate, allyl carbonate, 2,2,2-trichloroethyl carbonate and benzyl carbonate) ketals, and acetals, and ethers.

Compounds provided herein may also contain unnatural proportions of atomic isotopes at one or more of the atoms that constitute such compounds. That is, an atom, in particular when mentioned in relation to a compound according to Formula (I), comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof; unless expressly noted otherwise. For example, in deuteroalkyl and deuteroalkoxy groups, where one or more hydrogen atoms are specifically replaced with deuterium ($^{2}H$). As some of the aforementioned isotopes are radioactive, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present disclosure.

For illustrative purposes, general methods for preparing the compounds are provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

The ability of selected compounds to act as MALT1 inhibitors may be demonstrated by the biological assays described herein. $IC_{50}$ values are shown in Tables A and B.

Compounds of Formula (I), or a pharmaceutically acceptable salt thereof, are useful for treating diseases and disorders which can be treated with a MALT1 inhibitor, such as MALT1-associated cancers, including hematological cancers and solid tumors, MALT1-associated autoimmune disorders, and MALT1-associated inflammatory disorders.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the term "subject" refers to any animal, including mammals such as humans. In some embodiments, the subject is a human. In some embodiments, the subject has experienced and/or exhibited at least one symptom of the disease or disorder to be treated and/or prevented.

The term "pediatric subject" as used herein refers to a subject under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W. B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula (I), or a pharmaceutically acceptable salt thereof are useful for preventing diseases and disorders as defined herein (for example, autoimmune disorders, inflammatory disorders, and cancer). The term "preventing" as used herein means the prevention of the onset, recurrence or spread, in whole or in part, of the disease or condition as described herein, or a symptom thereof.

The term "regulatory agency" refers to a country's agency for the approval of the medical use of pharmaceutical agents with the country. For example, a non-limiting example of a regulatory agency is the U.S. Food and Drug Administration (FDA).

Signaling through the NF-κB pathway has been implicated in many cancers. See, e.g., Staudt, Cold Spring Harbor Perspectives in Biology 2.6 (2010): a000109, Xia, et al. Cancer Immunol. Res. 2.9 (2014): 823-830, Xia, et al. OncoTargets and Therapy 11 (2018): 2063. NF-κB is a family of transcription factors, including p50, p52, p65 (RelA), RelB, and c-Rel, which can bind to the kB enhancer element as various homo- and heterodimers to induce transcription of a number of genes. Following activation of certain cell-surface receptors (e.g., CD28, BCR, HER1 (also known as EGFR (Epidermal Growth Factor Receptor) and ERBB1), or HER2 (also known as HER2/neu or ERBB2)), a CBM complex is formed via phosphorylation of a CARD or CARMA protein, likely by a protein kinase C (e.g., protein kinase C beta or protein kinase C theta) and recruitment of the BCL10-MALT1 complex. See, e.g., Xia, et al. OncoTargets and Therapy 11 (2018): 2063, Shi, and Sun. Mol. Immunol. 68.2 (2015): 546-557, Xia, et al. Cancer Immunol. Res. 2.9 (2014): 823-830, and Pan, Mol. Cancer Res. 14.1 (2016): 93-102.

As noted hereinabove, the CBM complex can function as a scaffold protein in the activation of the NF-κB pathway. When formed, the CBM complex can activate the IKK complex (e.g., IKKγ (also called NEMO), IKKα, and IKKβ), likely by ubiquintination (e.g., K63-linked ubiquitination) of MALT1, which results in the recruitment, ubiquitination (e.g., K63-linked ubiquitination), and degredation of IKKγ, thereby releasing IKKα and IKKβ to phosphorylate IκB, resulting in the ubiquitination (e.g., K48-linked ubiquitination) and degradation of IκB, releasing the NF-κB transcription factors (typically of the NF-κB 1 subtype: p50-ReA and p50-cRel) to the nucleus. This cascade is likely mediated by the ubiquitin ligase TRAF6 (Tumor necrosis factor receptor (TNFR)-associated factor 6). The CBM complex may also affect NF-κB signaling through additional protein complexes, such as TAB1/2-TAK and the linear ubiquitin chain assembly complex (LUBAC). See, e.g., Israël, Cold Spring Harbor Perspectives in Biology 2.3 (2010): a000158, Xia, et al. OncoTargets and Therapy 11 (2018): 2063, Juilland, Front. Immunol. 9 (2018): 1927. MALT1 can also activate the JNK pathway (also called the JNK/AP-1 pathway), though less work has been done to study this area. See, e.g., Juilland, Front. Immunol. 9 (2018): 1927, and Wang, et al., Oncogenesis 6.7 (2017): e365-e365.

In addition, MALT1 has cysteine protease activity. Non-limiting examples of substrates of wild-type MALT1 include BCL10, A20, CYLD, RelB, Regnase 1, roquin-1, and HOIL1. In addition, the API2-MALT1 (also called cIAP2; amino terminus of inhibitor of apoptosis 2) fusion protein has also been shown to cleave NIK and LIMA1α. BCL10 cleavage by MALT1 is believed to result in BCL10-independent NF-κB activation. By cleaving A20 (TNF Alpha Induced Protein 3), MALT1 can reduce negative regulation of the NF-κB pathway, as A20 is a deubiquitinating enzyme that has been suggested to reduce the ubiquitination of MALT1 and thus recruitment and activation of the IKK complex. CYLD (CYLD Lysine 63 Deubiquitinase) is a deubiquitinating enzyme, and by cleavage of this enzyme, it is believed that MALT1 increases signaling through the NF-κB pathway and/or JNK pathway. Cleavage of RelB typically results in relief of negative regulation of the NF-κB pathway, as RelB forms transcriptionally inactive complexes with RelA and c-Rel. By cleaving HOIL1 (also known as RBCK1), it is believed that negative regulation of the NF-κB is relieved, as HOIL1 is thought to decrease linear ubiquitination. MALT1 can also autoprocess, which promotes signaling through the NF-κB pathway through a mechanism that is not fully understood. By cleaving NIK (NF-κB inducing kinase), the API2-MALT1 protease generates a c-terminal fragment of NIK that is resistant to proteasomal degradation and thereby increases noncanonical NF-κB signaling. By cleaving LIMA1a (LIM domain and actin-binding protein 1), the tumor-suppressing properties of this protein are diminished, and it believed that the remaining fragment has oncogenic properties and enhances cell proliferation, colony formation, and cell adhesion. Cleavage of Regnase 1 (Regulatory RNase 1, also known as MCPIP-1 or Zc3h12a), and roquin-1 (also known as RC3H1) is believed to result in the stabilization of mRNAs, including those of cytokines, chemokines, and costimulatory proteins such as ICOS, OX40, and TNF. This activity may be independent of MALT1 activity in the NF-κB and JNK pathways. See, e.g., Afonina, et al. FEBS J. 282.17 (2015): 3286-3297 Klein et al. Nat. Comm. 6.1 (2015): 1-17, Baens, et al. PloS one 9.8 (2014): e103774, and Juilland, Front. Immunol. 9 (2018): 1927. MALT1 is also involved in oncogenic BCR signalling in ibrutinib-responsive cell lines and biopsie samples, coordinated by a multiprotein supercomplex formed by MYD88, TLR9 and the BCR (hereafter termed the My-T-BCR supercomplex). The My-T-BCR supercomplex co-localizes with mTOR on endolysosomes, where it drives pro-survival NF-κB and mTOR signalling. See Phelan et al., Nature 2018 August; 560(7718):387-391.

Accordingly, inhibition of MALT1 can provide beneficial effects to many types of disorders associated with aberrant signaling in the NF-κB pathway or JNK pathway. For example, inhibition of MALT1 can decrease flux through the NF-κB or INK pathways resulting from one or more of:

(1) An inactivated tumor suppressor gene. Non-limiting examples of tumor suppressor genes that can be inactivated include BRCA1 and p53 (e.g., p53H61L or I123T). See, e.g., Sau, et al. Cell Stem Cell 19.1 (2016): 52-65, Xia, et al. Cancer Immunol. Res. 2.9 (2014): 823-830, Johansson, et al. Oncotarget 7.38 (2016): 62627.

(2) A dysregulated cell surface receptor. Non-limiting examples of cell surface receptors include HER1 and HER2. See, e.g., Xia, et al. Cancer Immunol. Res. 2.9 (2014): 823-830 and Pan, Mol. Cancer Res. 14.1 (2016): 93-102.

(3) Dysregulation of one or more components of a CBM complex. Non-limiting examples of components of a CBM complex include MALT1, CARD11, CARD14, CARD10, CARD9, and BCL10.

(4) Dysregulation of one or more substrates of a MALT1 protease (e.g., a wild-type MALT1 protease or a dysregulated MALT1 protease). Non-limiting examples of substrates of a MALT1 protease include BCL10, A20, CYLD, RelB, Regnase 1, roquin-1, HOIL1, NIK, and LIMA1α.

(5) Dysregulation of one or more components of the NF-κB pathway downstream of a CBM complex. Non-limiting examples of a component of the NF-κB pathway downstream of a CBM complex include TRAF6, IKKα, IKKβ, IKKγ (also called NEMO), IkBα, p50, p52, p65 (RelA), RelB, and c-Rel.

(6) Dysregulation of one or more components of the JNK pathway downstream of a CBM complex. Non-limiting examples of a component of the JNK pathway downstream of a CBM complex include JNK1 (Mitogen-Activated Protein Kinase 8), JNK2 (Mitogen-Activated Protein Kinase 9), JNK3 (Mitogen-Activated Protein Kinase 10), or an AP-1 transcription factor (e.g., a heterodimer of any of the c-Fos, c-Jun, ATF, or JDP families).

(7) Dysregulation of one or more fusion proteins caused by chromosome translocation of MALT1 gene. Non-limiting example includes the cIAP-MALT1 fusion protein.

(8) Dysregulation of one or more components of the My-T-BCR supercomplex. Non-limiting examples of a component of the My-T-BCR supercomplex include MYD88, TLR9, and mTOR.

The term "CBM complex pathway" as associated herein includes genes, transcripts, and proteins in a signaling pathway that includes a CBM. For example, many aspects of the NF-κB pathway are part of a CBM complex pathway. A CBM complex pathway can include, for example, cell surface receptors (e.g., CD28, BCR, HER1, and HER2), a signal transducer between a cell surface receptor and a CBM complex (e.g., a protein kinase C beta or protein kinase C theta), a component of a CBM complex (e.g., MALT1, CARD11, CARD14, CARD10, CARD9, or BCL10), substrates of a MALT1 protease (e.g., BCL10, A20, CYLD, RelB, Regnase 1, roquin-1, HOIL1, NIK, and LIMA1α), a component of the NF-κB pathway downstream of a CBM complex (e.g., TAK1, TRAF6, TAB1, TAB2, TAB3, MKK7, IKKα, IKKβ, IKKγ, IkBα, p50, p65 (RelA), or c-Rel), a component of the JNK pathway downstream of a CBM complex (e.g., JNK1, JNK2, JNK3, or an AP-1 transcription factor), or a components of the My-T-BCR supercomplex (e.g., MYD88, TLR9, or mTOR).

As used herein, the term "CBM complex pathway-associated disease or disorder" refers to diseases or disorders associated with or having a dysregulation of a gene in a CBM complex pathway, a protein in a CBM complex pathway, or the expression or activity or level of any (e.g., one or more) of the same (e.g., any of the types of dysregulation of a gene in a CBM complex pathway, a protein in a CBM complex pathway, or the expression or activity or level of any of the same, as described herein). Non-limiting examples of a CBM complex pathway-associated diseases or disorders include, for example, CBM-related primary immunodeficiency diseases, autoimmune disorders, multiple sclerosis, colitis, psoriasis, and cancer. See, e.g., McGuire, et al. J. Neuroinflamm. 11.1 (2014): 1-12, Lu, et al., Front. Immunol. 9 (2018): 2078, Jaworski, et al., EMBO J. 33.23 (2014): 2765-2781. Non-limiting examples of a CBM complex pathway-associated disease or disorder include MALT1-associated diseases or disorders such as MALT1-associated cancers, MALT1-associated autoimmune disorders, and MALT1-associated inflammatory disorders.

The term "CBM complex pathway-associated autoimmune disorder" as used herein refers to autoimmune disorders associated with or having a dysregulation of a CBM complex pathway gene, a CBM complex pathway protein, or the expression or activity or level of any (e.g., one or more) of the same (e.g., any of the types of dysregulation of a CBM complex pathway gene, a CBM complex pathway protein, or the expression or activity or level of any of the same described herein). Non-limiting examples of a CBM complex pathway-associated autoimmune disorders are described herein.

The term "CBM complex pathway-associated inflammatory disorder" as used herein refers to inflammatory disorders associated with or having a dysregulation of a CBM complex pathway gene, a CBM complex pathway protein, or the expression or activity or level of any (e.g., one or more) of the same (e.g., any of the types of dysregulation of a CBM complex pathway gene, a CBM complex pathway protein, or the expression or activity or level of any of the same described herein). Non-limiting examples of a CBM complex pathway-associated inflammatory disorders are described herein.

In some embodiments, a CBM complex pathway-associated disease or disorder is a CBM complex pathway-associated cancer, such as a CBM complex pathway cell surface receptor-associated cancer (e.g., a CD28-associated cancer, a BCR-associated cancer, a HER1-associated cancer, or a HER2-associated cancer), a cancer associated with a signal transducer between a cell surface receptor and a CBM complex (e.g, a protein kinase C beta (PKCβ)-associated cancer or a protein kinase C theta (PCKθ)-associated cancer), a component of a CBM complex-associated cancer (e.g., a MALT1-associated cancer, a CARD11-associated cancer, a CARD14-associated cancer, a CARD10-associated cancer, a CARDS-associated cancer, or a BCL10-associated cancer), a MALT1 protease substrate-associated cancer (e.g., a BCL10-associated cancer, an A20-associated cancer, a CYLD-associated cancer, a RelB-associated cancer, a Regnase 1-associated cancer, a roquin-1-associated cancer, a HOIL1-associated cancer, a NIK associated cancer, or a LIMA1α-associated cancer), a cancer associated with a component of the NF-κB pathway downstream of a CBM complex (e.g., TAK1-associated cancer, a TRAF6-associated cancer, a TAB1-associated cancer, a TAB2-associated cancer, a TABS-associated cancer, a MKK7-associated cancer, an IKKα-associated cancer, an IKKβ-associated cancer, an IKKγ-associated cancer, an IkBα-associated cancer, a p50-associated cancer, a p65 (RelA)-associated cancer, or a c-Rel-associated cancer), a cancer associated with a component of the JNK pathway downstream of a CBM complex (e.g., a JNK1-associated cancer, a JNK2-associated cancer, a JNK3-associated cancer, or an AP-1 transcription factor-associated cancer), a MYD88-associated cancer, or a combination thereof.

The term "CBM complex pathway-associated cancer" as used herein refers to cancers associated with or having a dysregulation of a gene in a CBM complex pathway, a protein in a CBM complex pathway, or the expression or activity or level of any (e.g., one or more) of the same (e.g., any of the types of dysregulation of a gene in a CBM complex pathway, a protein in a CBM complex pathway, or the expression or activity or level of any of the same, as described herein) (e.g., upon diagnosis or after developing resistance to previous therapies. Non-limiting examples of a CBM complex pathway-associated cancer are described herein. In some embodiments, a CBM pathway-associated cancer can be a CBM complex pathway cell surface receptor-associated cancer (e.g., a CD28-associated cancer, a BCR-associated cancer, a HER1-associated cancer, or a HER2-associated cancer), a cancer associated with a signal transducer between a cell surface receptor and a CBM complex (e.g, a protein kinase C beta (PKCβ)-associated cancer or a protein kinase C theta (PCKθ)-associated cancer, a component of a CBM complex-associated cancer (e.g., a MALT1-associated cancer, a CARD11-associated cancer, a CARD14-associated cancer, a CARD10-associated cancer, a CARDS-associated cancer, or a BCL10-associated cancer), a MALT1 protease substrate-associated cancer (e.g., a BCL10-associated cancer, an A20-associated cancer, a CYLD-associated cancer, a RelB-associated cancer, a Regnase 1-associated cancer, a roquin-1-associated cancer, a HOIL1-associated cancer, a NIK associated cancer, or a LIMA1α-associated cancer), a cancer associated with a component of the NF-κB pathway downstream of a CBM complex (e.g., TAK1-associated cancer, a TRAF6-associated cancer, a TAB1-associated cancer, a TAB2-associated cancer, a TABS-associated cancer, a MKK7-associated cancer, an IKKα-associated cancer, an IKKβ-associated cancer, an IKKγ-associated cancer, an IkBα-associated cancer, a p50-associated cancer, a p65 (RelA)-associated cancer, or a c-Rel-associated cancer), a cancer associated with a component of the JNK pathway downstream of a CBM complex (e.g., a JNK1-associated cancer, a JNK2-associated cancer, a JNK3-associated cancer, or an AP-1 transcription factor-associated cancer), or a combination thereof.

In some embodiments, a dysregulation can be a dysregulation that results in aberrant activation of a gene, protein, or expression or activity or level of any of the same. Activation can be through any appropriate mechanism, including, but not limited to, gene amplification, activating mutation, activating translocation, transcriptional activation, epigenetic alteration, and/or overexpression of the protein product of the oncogene. In some embodiments, a dysregulation can be a dysregulation that results in aberrant inactivation of a gene, protein, or expression or activity or level of any of the same. Inactivation can be through any appropriate mechanism, including, but not limited to, gene deletion, inactivating mutation, inactivating translocation, transcriptional silencing, epigenetic alteration, and degradation of mRNA and/or protein products of the gene. Typically, as used herein, a dysregulation, whether it be activation or inactivation, is a dysregulation that results in increased signaling through the NF-κB or JNK signaling pathways.

The term "wild-type" describes a nucleic acid (e.g., a MALT1 gene or a MALT1 mRNA) or protein (e.g., a MALT1 protein) that is found in a subject that does not have a disease or disorder associated with the nucleic acid or the protein (e.g., the MALT1 gene, MALT1 mRNA, or MALT1 protein) (and optionally also does not have an increased risk of developing a disease or disorder associated with the nucleic acid or the protein and/or is not suspected of having a disease or disorder associated with the gene or the protein), or is found in a cell or tissue from a subject that does not have a disease or disorder associated with the gene or the protein (e.g., a MALT1-associated cancer, autoimmune disorder, or inflammatory disorder) (and optionally also does not have an increased risk of developing a disease or disorder associated with the nucleic acid or the protein and/or is not suspected of having a disease or disorder associated with the nucleic acid or the protein.

In some embodiments, the subject has been identified or diagnosed as having a cancer with a dysregulation of a CBM complex pathway-associated gene (e.g., a MALT1 gene), a CBM complex pathway-associated protein (e.g., a MALT1 protein), or expression or activity, or level of any of the same (a CBM complex pathway-associated-associated cancer) (e.g., as determined using a regulatory agency-approved, e.g., FDA-approved, assay or kit). In some embodiments, the subject has a cancer resistant to one or more previous therapies. In some embodiments, the subject has a tumor that is positive for a dysregulation of a CBM complex pathway-associated gene (e.g., a MALT1 gene), a CBM complex pathway-associated protein (e.g., a MALT1 protein), or expression or activity, or level of any of the same (e.g., as determined using a regulatory agency-approved, e.g., FDA-approved, assay or kit). The subject can be a subject with a tumor(s) that is positive for a dysregulation of a CBM complex pathway-associated gene (e.g., a MALT1 gene), a CBM complex pathway-associated protein (e.g., a MALT1 protein), or expression or activity, or level of any of the same (e.g., identified as positive using a regulatory agency-approved, e.g., FDA-approved, assay or kit). The subject can be a subject whose tumors have a dysregulation of a CBM complex pathway-associated gene (e.g., a MALT1 gene), a CBM complex pathway-associated protein (e.g., a MALT1 protein), or expression or activity, or a level of the same (e.g., where the tumor is identified as such using a regulatory agency-approved, e.g., FDA-approved, kit or assay). In some embodiments, the subject has a tumor resistant to one or more previous therapies. In some embodiments, the subject is suspected of having a CBM complex pathway-associated-associated cancer. In some embodiments, the subject has a tumor that is suspected of being resistant to one or more previous therapies. In some embodiments, the subject has a clinical record indicating that the subject has a tumor that has a dysregulation of a CBM complex pathway-associated gene (e.g., a MALT1 gene), a CBM complex pathway-associated protein (e.g., a MALT1 protein), or expression or activity, or level of any of the same (and optionally the clinical record indicates that the subject should be treated with any of the compositions provided herein). In some embodiments, the subject is a pediatric subject. In some embodiments, the subject has a clinical record indicating that the subject has a tumor resistant to one or more previous therapies. In some embodiments, the subject has been identified or diagnosed as having a cancer that, based on histological examination, is determined to be associated with a dysregulation of a CBM complex pathway-associated gene (e.g., a MALT1 gene), a CBM complex pathway-associated protein (e.g., a MALT1 protein), or expression or activity, or level of any of the same (a CBM complex pathway-associated-associated cancer).

In some embodiments, the subject has been identified or diagnosed as having an autoimmune disorder with a dysregulation of a CBM complex pathway-associated gene (e.g., a MALT1 gene), a CBM complex pathway-associated protein (e.g., a MALT1 protein), or expression or activity, or level of any of the same (a CBM complex pathway-associated-associated autoimmune disorder) (e.g., as determined using a regulatory agency-approved, e.g., FDA-approved, assay or kit). In some embodiments, the subject has a tumor that is positive for a dysregulation of a CBM complex pathway-associated gene (e.g., a MALT1 gene), a CBM complex pathway-associated protein (e.g., a MALT1 protein), or expression or activity, or level of any of the same (e.g., as determined using a regulatory agency-approved, e.g., FDA-approved, assay or kit). In some embodiments, the subject is suspected of having a CBM complex pathway-associated-associated autoimmune disorder. In some embodiments, the subject has a clinical record indicating that the subject has a tumor that has a dysregulation of a CBM complex pathway-associated gene (e.g., a MALT1 gene), a CBM complex pathway-associated protein (e.g., a MALT1 protein), or expression or activity, or level of any of the same (and optionally the clinical record indicates that the subject should be treated with any of the compositions provided herein). In some embodiments, the subject is a pediatric subject. In some embodiments, the subject has been identified or diagnosed as having an autoimmune disorder that, based on histological examination, is determined to be associated with a dysregulation of a CBM complex pathway-associated gene (e.g., a MALT1 gene), a CBM complex pathway-associated protein (e.g., a MALT1 protein), or expression or activity, or level of any of the same (a CBM complex pathway-associated-associated autoimmune disorder).

In some embodiments, the subject has been identified or diagnosed as having an inflammatory disorder with a dysregulation of a CBM complex pathway-associated gene (e.g., a MALT1 gene), a CBM complex pathway-associated protein (e.g., a MALT1 protein), or expression or activity, or level of any of the same (a CBM complex pathway-associated-associated inflammatory disorder) (e.g., as determined using a regulatory agency-approved, e.g., FDA-approved, assay or kit). In some embodiments, the subject has a tumor that is positive for a dysregulation of a CBM complex pathway-associated gene (e.g., a MALT1 gene), a CBM complex pathway-associated protein (e.g., a MALT1 protein), or expression or activity, or level of any of the same (e.g., as determined using a regulatory agency-approved, e.g., FDA-approved, assay or kit). In some embodiments, the subject is suspected of having a CBM complex pathway-associated-associated inflammatory disorder. In some embodiments, the subject has a clinical record indicating that the subject has a tumor that has a dysregulation of a CBM complex pathway-associated gene (e.g., a MALT1 gene), a CBM complex pathway-associated protein (e.g., a MALT1 protein), or expression or activity, or level of any of the same (and optionally the clinical record indicates that the subject should be treated with any of the compositions provided herein). In some embodiments, the subject is a pediatric subject. In some embodiments, the subject has been identified or diagnosed as having an inflammatory disorder that, based on histological examination, is determined to be associated with a dysregulation of a CBM complex pathway-associated gene (e.g., a MALT1 gene), a CBM complex pathway-associated protein (e.g., a MALT1 protein), or expression or activity, or level of any of the same (a CBM complex pathway-associated-associated inflammatory disorder).

The term "CBM complex pathway cell surface receptor-associated cancer" as used herein refers to cancers associated with or having a dysregulation of a gene, a protein, or the expression or activity or level of any (e.g., one or more) of the same associated with a CBM complex pathway cell surface receptor. In some embodiments, a CBM complex pathway cell surface receptor-associated cancer is selected from the group consisting of a CD28-associated cancer, a BCR-associated cancer, a HER1-associated cancer, a HER2-associated cancer, and combinations thereof.

The term "*-associated cancer" as used herein refers to cancers associated with or having a dysregulation of a * gene, a * protein, or the expression or activity or level of any (e.g., one or more) of the same (e.g., any of the types of dysregulation of a * gene, a * protein, or the expression or activity or level of any of the same described herein), where "*" refers to a particular CBM complex pathway gene or protein, described herein. In some embodiments, the *-associated cancer is selected from the group consisting of: CD28-associated cancer, BCR-associated cancer, HER1-associated cancer, HER2-associated cancer, PKCβ-associated cancer, PKCθ-associated cancer, MALT1-associated cancer, CARD11-associated cancer, CARD14-associated cancer, A20-associated cancer, CYLD-associated cancer, RelB-associated cancer, HOIL1-associated cancer, NIK-associated cancer, Regnase 1-associated cancer, LIMA1α-associated cancer, roquin-1-associated cancer, TRAF6-associated cancer, TAK1-associated cancer, TAB1-associated cancer, TAB2-associated cancer, TAB3-associated cancer, MKK7-associated cancer, IKKα-associated cancer, IKKβ-associated cancer, IKKγ-associated cancer, IkBα-associated cancer, p50-associated cancer, p65-associated cancer, c-Rel-associated cancer, JNK1-associated cancer, JNK2-associated cancer, JNK3-associated cancer, MYD88 transcription factor-associated cancer, and an AP-1 transcription factor-associated cancer. In some embodiments, the *-associated cancer is a CD28-associated cancer. In some embodiments, the *-associated cancer is a BCR-associated cancer. In some embodiments, the *-associated cancer is a HER1-associated cancer. In some embodiments, the *-associated cancer is a HER2-associated cancer. In some embodiments, the *-associated cancer is a PKCβ-associated cancer. In some embodiments, the *-associated cancer is a PKCθ-associated cancer. In some embodiments, the *-associated cancer is a MALT1-associated cancer. In some embodiments, the *-associated cancer is a CARD11-associated cancer. In some embodiments, the *-associated cancer is a CARD14-associated cancer. In some embodiments, the *-associated cancer is an A20-associated cancer. In some embodiments, the *-associated cancer is a CYLD-associated cancer. In some embodiments, the *-associated cancer is a RelB-associated cancer. In some embodiments, the *-associated cancer is a HOIL1-associated cancer. In some embodiments, the *-associated cancer is a NIK-associated cancer. In some embodiments, the * associated cancer is a Regnase 1-associated cancer. In some embodiments, the *-associated cancer is a LIMA1α-associated cancer. In some embodiments, the *-associated cancer is a roquin-1-associated cancer. In some embodiments, the *-associated cancer is a TRAF6-associated cancer. In some embodiments, the *-associated cancer is a TAK1-associated cancer. In some embodiments, the *-associated cancer is a TAB1-associated cancer. In some embodiments, the * associated cancer is a TAB2-associated cancer. In some embodiments, the *-associated cancer is a TAB3-associated cancer. In some embodiments, the *-associated cancer is a MKK7-associated cancer, and an IKKα-associated cancer. In some embodiments, the *-associated cancer is an IKKβ-associated cancer. In some embodiments, the *-associated cancer is an IKKγ-associated cancer. In some embodiments, the *-associated cancer is an IkBα-associated cancer. In some embodiments, the *-associated cancer is a p50-associated cancer. In some embodiments, the *-associated cancer is a p65-associated cancer. In some embodiments, the *-associated cancer is a c-Rel-associated cancer. In some embodiments, the *-associated cancer is a JNK1-associated cancer. In some embodiments, the *-associated cancer is a JNK2-associated cancer. In some embodiments, the * associated cancer is a JNK3-associated cancer. In some embodiments, the *-associated cancer is a AP-1 transcription factor-associated cancer. In some embodiments, the *-associated cancer is a MYD88 transcription factor-associated cancer.

The phrase "dysregulation of a * gene, a * protein, or the expression or activity or level of any of the same" (where * is a particular CBM complex pathway gene or protein, described herein) refers to a genetic mutation (e.g., a chromosomal translocation that results in the expression of a fusion protein including a * domain and a fusion partner, a mutation in a * gene that results in the expression of a * protein that includes a deletion of at least one amino acid as compared to a wild-type * protein, a mutation in a * gene that results in the expression of a * protein with one or more point mutations as compared to a wild-type * protein, a mutation in a * gene that results in the expression of a * protein with at least one inserted amino acid as compared to a wild-type * protein, a gene duplication that results in an increased level of * protein in a cell, or a mutation in a regulatory sequence (e.g., a promoter and/or enhancer) that results in an increased level of * protein in a cell), an alternative spliced version of a * mRNA that results in a * protein having a deletion of at least one amino acid in the * protein as compared to the wild-type * protein, or increased expression (e.g., increased levels) of a wild-type * protein in a mammalian cell due to aberrant cell signaling and/or dysregulated autocrine/paracrine signaling (e.g., as compared to a control non cancerous cell). As a further example, an increased copy number of the * gene can result in overexpression of the * protein. For example, a dysregulation of a * gene, a * protein, or expression or activity, or level of any of the same, can be the result of a gene or chromosome translocation which results in the expression of a fusion protein that contains a first portion of *, and a second portion of a partner protein (i.e., that is not *). In some examples, dysregulation of a * gene, a * protein, or expression or activity or level of any of the same can be a result of a gene translocation of one * gene with another non-*gene. In some embodiments, the * gene, a * protein, or the expression or activity or level of any of the same is selected from the group consisting of: CD28, BCR, HER1, HER2, PKCθ, PKCθ, MALT1, CARD11, CARD14, A20, CYLD, RelB, HOIL1, NIK, Regnase 1, LIMA1α, roquin-1, TRAF6, TAK1, TAB1, TAB2, TAB3, MKK7, IKKα, IKKβ, IKKγ, IkBα, p50, p65, c-Rel, JNK1, JNK2, JNK3, MYD88, and an AP-1 transcription factor. In some embodiments, the * gene or * protein is CD28. In some embodiments, the * gene or * protein is BCR. In some embodiments, the * gene or * protein is HER1. In some embodiments, the * gene or * protein is HER2. In some embodiments, the * gene or * protein is PKCβ. In some embodiments, the * gene or * protein is PKCθ. In some embodiments, the * gene or * protein is MALT1. In some embodiments, the * gene or * protein is CARD11. In some embodiments, the * gene or * protein is CARD14. In some embodiments, the * gene or * protein is A20. In some embodiments, the * gene or * protein is CYLD. In some embodiments, the * gene or * protein is RelB. In some embodiments, the * gene or * protein is HOIL1. In some embodiments, the * gene or * protein is NIK. In some embodiments, the * gene or * protein is Regnase 1. In some embodiments, the * gene or * protein is LIMA1α. In some embodiments, the * gene or * protein is roquin-1. In some embodiments, the * gene or * protein is TRAF6. In some embodiments, the * gene or * protein is TAK1. In some embodiments, the * gene or * protein is TAB1. In some embodiments, the * gene or * protein is TAB2. In some embodiments, the * gene or * protein is TAB3. In some embodiments, the * gene or * protein is MKK7. In some embodiments, the * gene or * protein is IKKα. In some embodiments, the * gene or * protein is IKKβ. In some embodiments, the * gene or * protein is IKKγ. In some embodiments, the * gene or * protein is IkBα. In some embodiments, the * gene or * protein is p50. In some embodiments, the * gene or * protein is p65.

In some embodiments, the * gene or * protein is c-Rel. In some embodiments, the * gene or * protein is JNK1. In some embodiments, the * gene or * protein is JNK2. In some embodiments, the * gene or * protein is JNK3. In some embodiments, the * gene or * protein is MYD88 transcription factor. In some embodiments, the * gene or * protein is AP-1 transcription factor.

In some embodiments, dysregulation of a * gene, a * protein, or expression or activity, or level of any of the same, can be a mutation in a * gene that encodes a * protein that is constitutively active or has increased activity as compared to a protein encoded by a * gene that does not include the mutation. In some embodiments, an increased copy number of the * gene can result in overexpression of * protein. In some embodiments, the * gene, * protein, or expression or activity, or level of any of the same, is CD28. In some embodiments, the * gene, * protein, or expression or activity, or level of any of the same, is BCR. In some embodiments, the * gene, * protein, or expression or activity, or level of any of the same, is HER1. In some embodiments, the * gene, * protein, or expression or activity, or level of any of the same, is HER2. In some embodiments, the * gene, * protein, or expression or activity, or level of any of the same, is PKCβ. In some embodiments, the * gene, * protein, or expression or activity, or level of any of the same, is PKCθ. In some embodiments, the * gene, * protein, or expression or activity, or level of any of the same, is CARD14. In some embodiments, the * gene, * protein, or expression or activity, or level of any of the same, is CARDS. In some embodiments, the * gene, * protein, or expression or activity, or level of any of the same, is CARD10. In some embodiments, the * gene, * protein, or expression or activity, or level of any of the same, is CARD11. In some embodiments, the * gene, * protein, or expression or activity, or level of any of the same, is MALT1.

As another example, a dysregulation of an * gene, an * protein, or expression or activity, or level of any of the same, can be a mutation in an * gene that encodes an * protein that is constitutively inactive or has decreased activity as compared to a protein encoded by an * gene that does not include the mutation. In some embodiments, the * gene, * protein, or expression or activity, or level of any of the same, is A20. In some embodiments, the * gene, * protein, or expression or activity, or level of any of the same, is CYLD. In some embodiments, the * gene, * protein, or expression or activity, or level of any of the same, is RelB. In some embodiments, the * gene, * protein, or expression or activity, or level of any of the same, is HOIL1. In some embodiments, the * gene, * protein, or expression or activity, or level of any of the same, is NIK.

Diseases or disorders "associated" with a particular gene or protein described herein refer to diseases or disorder associated with or having a dysregulation of the particular gene, the particular protein, or the expression or activity or level of any (e.g., one or more) of the same (e.g., any of the types of dysregulation of the particular gene, the particular protein, or the expression or activity or level of any of the same described herein). Non-limiting examples of such diseases or disorders are described herein. Likewise, cancers "associated" with a particular gene or protein described herein refer to cancers associated with or having a dysregulation of the particular gene, the particular protein, or the expression or activity or level of any (e.g., one or more) of the same (e.g., any of the types of dysregulation of the particular gene, the particular protein, or the expression or activity or level of any of the same described herein). Non-limiting examples of such cancers are described herein.

Exemplary sequences of the proteins described herein are shown below.

An exemplary sequence of human CD28 is shown below:

```
(UniParc Accession No. UPI0000043F4D)
                                             SEQ ID NO: 1
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYL

QNLYVNQTDIYFCKIEVMYPPPYLDNEKSNGTIIHVKGKHLCPSPLFPGP

SKPFWVLVVVGGVLACYSLLVTVAFIIFWVRSKRSRLLHSDYMNMTPRRP

GPTRKHYQPYAPPRDFAAYRS
```

Non-limiting examples of dysregulation of a CD28 gene or a CD28 protein can be found in, for example, Rohr, et al., Leukemia 30.5 (2016): 1062-1070, Yoo, et al., Haematologica 101.6 (2016): 757-763, and Lee, et al., Haematologica 100.12 (2015): e505.

An exemplary sequence of human BCR is shown below:

```
(UniParc Accession No. UPI000016A088)
                                             SEQ ID NO: 2
MVDPVGFAEAWKAQFPDSEPPRMELRSVGDIEQELERCKASIRRLEQEV

QERFRMIYLQTLLAKEKKSYDRQRWGFRRAAQAPDGASEPRASASRPQP

APADGADPPPAEEPEARPDGEGSPGKARPGTARRPGAAASGERDDRGPP

ASVAALRSNFERIRKGHGQPGADAEKPFYVNVEFHHERGLVKVNDKEVS

DRISSLGSQAMQMERKKSQHGAGSSVGDASRPPYRGRSSESSCGVDGDY

EDAELNPRFLKDNLIDANGGSRPPWPPLEYQPYQSIYVGGMMEGEGKGP
```

-continued

```
LLRSQSTSEQEKRLTWPRRSYSPRSFEDCGGGYTPDCSSNENLTSSEED

FSSGQSSRVSPSPTTYRMFRDKSRSPSQNSQQSFDSSSPPTPQCHKRHR

HCPVVVSEATIVGVRKTGQIWPNDGEGAFHGDADGSFGTPPGYGCAADR

AEEQRRHQDGLPYIDDSPSSSPHLSSKGRGSRDALVSGALESTKASELD

LEKGLEMRKWVLSGILASEETYLSHLEALLLPMKPLKAATTSQPVLTS

QQIETIFFKVPELYEIHKEFYDGLFPRVQQWSHQQRVGDLFQKLASQLG

VYRAFVDNYGVAMEMAEKCCQANAQFAEISENLRARSNKDAKDPTTKNS

LETLLYKPVDRVTRSTLVLHDLLKHTPASHPDHPLLQDALRISQNFLSS

INEEITPRRQSMTVKKGEHRQLLKDSFMVELVEGARKLRHVFLFTDLLL

CTKLKKQSGGKTQQYDCKWYIPLTDLSFQMVDELEAVPNIPLVPDEELD

ALKIKISQIKNDIQREKRANKGSKATERLKKKLSEQESLLLLMSPSMAF

RVHSRNGKSYTFLISSDYERAEWRENIREQQKKCFRSFSLTSVELQMLT

NSCVKLQTVHSIPLTINKEDDESPGLYGFLNVIVHSATGFKQSSNLYCT

LEVDSFGYFVNKAKTRVYRDTAEPNWNEEFEIELEGSQTLRILCYEKCY

NKTKIPKEDGESTDRLMGKGQVQLDPQALQDRDWQRTVIAMNGIEVKLS

VKFNSREFSLKRMPSRKQTGVFGVKIAVVTKRERSKVPYIVRQCVEEIE

RRGMEEVGIYRVSGVATDIQALKAAFDVNNKDVSVMMSEMDVNAIAGTL

KLYFRELPEPLFTDEFYPNFAEGIALSDPVAKESCMLNLLLSLPEANLL

TFLFLLDHLKRVAEKEAVNKMSLHNLATVFGPTLLRPSEKESKLPANPS

QPITMTDSWSLEVMSQVQVLLYFLQLEAIPAPDSKRQSILFSTEV
```

Non-limiting examples of dysregulation of a BCR gene or a BCR protein (e.g., a BCR-ABL fusion) can be found in, for example, Yang and Fu, Crit. Rev. Oncol./Hematol. 93.3 (2015): 277-292, Weisberg, et al. Nat. Rev. Cancer 7.5 (2007): 345-356, and Jabbour, et al. Cancer 117.9 (2011): 1800-1811.

An exemplary sequence of human HER1 is shown below:

```
(UniParc Accession No. UPI000003E750)
                                         SEQ ID NO: 3
MRPSGTAGAALLALLAALCPASRALEEKKVCQGTSNKLTQLGTFEDHFL

SLQRMFNNCEVVLGNLEITYVQRNYDLSFLKTIQEVAGYVLIALNTVER

IPLENLQIIRGNMYYENSYALAVLSNYDANKTGLKELPMRNLQEILHGA

VRFSNNPALCNVESIQWRDIVSSDFLSNMSMDFQNHLGSCQKCDPSCPN

GSCWGAGEENCQKLTKIICAQQCSGRCRGKSPSDCCHNQCAAGCTGPRE

SDCLVCRKFRDEATCKDTCPPLMLYNPTTYQMDVNPEGKYSFGATCVKK

CPRNYVVTDHGSCVRACGADSYEMEEDGVRKCKKCEGPCRKVCNGIGIG

EFKDSLSINATNIKHFKNCTSISGDLHILPVAFRGDSFTHTPPLDPQEL

DILKTVKEITGFLLIQAWPENRTDLHAFENLEIIRGRTKQHGQFSLAVV

SLNITSLGLRSLKEISDGDVIISGNKNLCYANTINWKKLFGTSGQKTKI

ISNRGENSCKATGQVCHALCSPEGCWGPEPRDCVSCRNVSRGRECVDKC

NLLEGEPREFVENSECIQCHPECLPQAMNITCTGRGPDNCIQCAHYIDG

PHCVKTCPAGVMGENNTLVWKYADAGHVCHLCHPNCTYGCTGPGLEGCP

TNGPKIPSIATGMVGALLLLLVVALGIGLFMRRRHIVRKRTLRRLLQER
```

-continued

```
ELVEPLTPSGEAPNQALLRILKETEFKKIKVLGSGAFGTVYKGLWIPEG

EKVKIPVAIKELREATSPKANKEILDEAYVMASVDNPHVCRLLGICLTS

TVQLITQLMPFGCLLDYVREHKDNIGSQYLLNWCVQIAKGMNYLEDRRL

VHRDLAARNVLVKTPQHVKITDFGLAKLLGAEEKEYHAEGGKVPIKWMA

LESILHRIYTHQSDVWSYGVTVWELMTFGSKPYDGIPASEISSILEKGE

RLPQPPICTIDVYMIMVKCWMIDADSRPKFRELIIEFSKMARDPQRYLV

IQGDERMHLPSPTDSNFYRALMDEEDMDDVVDADEYLIPQQGFFSSPST

SRTPLLSSLSATSNNSTVACIDRNGLQSCPIKEDSFLQRYSSDPTGALT

EDSIDDTFLPVPEYINQSVPKRPAGSVQNPVYHNQPLNPAPSRDPHYQD

PHSTAVGNPEYLNTVQPTCVNSTFDSPAHWAQKGSHQISLDNPDYQQDF

FPKEAKPNGIFKGSTAENAEYLRVAPQSSEFIGA
```

Non-limiting examples of dysregulation of a HER1 gene or a HER1 protein can be found in, for example, Zhang, et al., Oncotarget 7.48 (2016): 78985, Ellison, et al., Journal of Clinical Pathology 66.2 (2013): 79-89, Midha, et al., American Journal of Cancer Research 5.9 (2015): 2892, and Yamamoto, et al., Lung Cancer 63.3 (2009): 315-321.

An exemplary sequence of human HER2 is shown below:

```
(UniParc Accession No. UPI000003F55F)
                                         SEQ ID NO: 4
MELAALCRWGLLLALLPPGAASTQVCTGTDMKLRLPASPETHLDMLRHL

YQGCQVVQGNLELTYLPTNASLSFLQDIQEVQGYVLIAHNQVRQVPLQR

LRIVRGTQLFEDNYALAVLDNGDPLNNTTPVTGASPGGLRELQLRSLTE

ILKGGVLIQRNPQLCYQDTILWKDIFHKNNQLALTLIDTNRSRACHPCS

PMCKGSRCWGESSEDCQSLTRTVCAGGCARCKGPLPTDCCHEQCAAGCT

GPKHSDCLACLHFNHSGICELHCPALVTYNTDTFESMPNPEGRYTFGAS

CVTACPYNYLSTDVGSCTLVCPLHNQEVTAEDGTQRCEKCSKPCARVCY

GLGMEHLREVRAVTSANIQEFAGCKKIFGSLAFLPESFDGDPASNTAPL

QPEQLQVFETLEEITGYLYISAWPDSLPDLSVFQNLQVIRGRILHNGAY

SLTLQGLGISWLGLRSLRELGSGLALIHHNTHLCFVHTVPWDQLFRNPH

QALLHTANRPEDECVGEGLACHQLCARGHCWGPGPTQCVNCSQFLRGQE

CVEECRVLQGLPREYVNARHCLPCHPECQPQNGSVTCFGPEADQCVACA

HYKDPPFCVARCPSGVKPDLSYMPIWKFPDEEGACQPCPINCTHSCVDL

DDKGCPAEQRASPLTSIISAVVGILLVVVLGVVFGILIKRRQQKIRKYT

MRRLLQETELVEPLTPSGAMPNQAQMRILKETELRKVKVLGSGAFGTVY

KGIWIPDGENVKIPVAIKVLRENTSPKANKEILDEAYVMAGVGSPYVSR

LLGICLTSTVQLVTQLMPYGCLLDHVRENRGRLGSQDLLNWCMQIAKGM

SYLEDVRLVHRDLAARNVLVKSPNHVKITDFGLARLLDIDETEYHADGG

KVPIKWMALESILRRRFTHQSDVWSYGVTVWELMTFGAKPYDGIPAREI

PDLLEKGERLPQPPICTIDVYMIMVKCWMIDSECRPRFRELVSEFSRMA

RDPQRFVVIQNEDLGPASPLDSTFYRSLLEDDDMGDLVDAEEYLVPQQG

FFCPDDPAPGAGGMVHHRHRSSSTRSGGGDLTLGLEPSEEEAPRSPLAPS

EGAGSDVFDGDLGMGAAKGLQSLPTHDPSPLQRYSEDPTVPLPSETDGY
```

-continued

VAPLTCSPQPEYVNQPDVRPQPPSPREGPLPAARPAGATLERPKTLSPG

KNGVVKDVFAFGGAVENPEYLTPQGGAAPQPHPPPAFSPAFDNLYYWDQ

DPPERGAPPSTFKGTPTAENPEYLGLDVPV

Non-limiting examples of dysregulation of a HER2 gene or a HER2 protein can be found, for example, Petrelli, Fausto, et al., Breast Cancer Research and Treatment 166.2 (2017): 339-349, Yan, et al., Cancer and Metastasis Reviews 34.1 (2015): 157-164, Koshkin, et al., Bladder Cancer 5.1 (2019): 1-12, and Connell, et al., ESMO Open 2.5 (2017).

The term "cancer associated with a signal transducer between a cell surface receptor and a CBM complex" as used herein refers to cancers associated with or having a dysregulation of a gene, a protein, or the expression or activity or level of any (e.g., one or more) of the same associated with a signal transducer between a cell surface receptor and a CBM complex. In some embodiments, a cancer associated with a signal transducer between a cell surface receptor and a CBM complex is selected from the group consisting of a PKCβ-associated cancer, PCKθ-associated cancer, and a combination thereof. The cancers "associated" with a particular gene or protein described in this paragraph refer to cancers associated with or having a dysregulation of the particular gene, the particular protein, or the expression or activity or level of any (e.g., one or more) of the same (e.g., any of the types of dysregulation of the particular gene, the particular protein, or the expression or activity or level of any of the same described herein). Non-limiting examples of such cancers are described herein.

An exemplary sequence of human PKCβ is shown below:

(UniParc Accession No. UPI000012DF67)

SEQ ID NO: 5

MADPAAGPPPSEGEESTVRFARKGALRQKNVHEVKNHKFTARFFKQPTF

CSHCTDFIWGFGKQGFQCQVCCFVVHKRCHEFVTFSCPGADKGPASDDP

RSKHKFKIHTYSSPTFCDHCGSLLYGLIHQGMKCDTCMMNVHKRCVMN

VPSLCGTDHTERRGRIYIQAHIDRDVLIVLVRDAKNLVPMDPNGLSDPY

VKLKLIPDPKSESKQKTKTIKCSLNPEWNETFRFQLKESDKDRRLSVEI

WDWDLTSRNDFMGSLSFGISELQKASVDGWFKLLSQEEGEYFNVPVPPE

GSEANEELRQKFERAKISQGTKVPEEKTTNTVSKFDNNGNRDRMKLTDF

NFLMVLGKGSFGKVMLSERKGTDELYAVKILKKDVVIQDDDVECTMVEK

RVLALPGKPPFLTQLHSCFQTMDRLYFVMEYVNGGDLMYHIQQVGRFKE

PHAVFYAAEIAIGLFFLQSKGIIYRDLKLDNVMLDSEGHIKIADFGMCK

ENIWDGVTTKTFCGTPDYIAPEIIAYQPYGKSVDWWAFGVLLYEMLAGQ

APFEGEDEDELFQSIMEHNVAYPKSMSKEAVAICKGLMTKHPGKRLGCG

PEGERDIKEHAFFRYIDWEKLERKEIQPPYKPKARDKRDTSNFDKEFTR

QPVELTPTDKLFIMNLDQNEFAGFSYTNPEFVINV

An exemplary sequence of human PKCθ is shown below:

(UniParc Accession No. UPI000012DF74)

SEQ ID NO: 6

MSPFLRIGLSNFDCGSCQSCQGEAVNPYCAVLVKEYVESENGQMYIQKKP

TMYPPWDSTFDAHINKGRVMQIIVKGKNVDLISETTVELYSLAERCRKNN

-continued

GKTEIWLELKPQGRMLMNARYFLEMSDTKDMNEFETEGFFALHQRRGAI

KQAKVHHVKCHEFTATFFPQPTFCSVCHEFVWGLNKQGYQCRQCNAAIH

KKCIDKVIAKCTGSAINSRETMFHKERFKIDMPHRFKVYNYKSPTFCEHC

GTLLWGLARQGLKCDACGMNVHHRCQTKVANLCGINQKLMAEALAMI

ESTQQARCLRDTEQIFREGPVEIGLPCSIKNEARPPCLPTPGKREPQGISW

ESPLDEVDKMCHLPEPELNKERPSLQIKLKIEDFILHKMLGKGSFGKVFLA

EFKKTNQFFAIKALKKDVVLMDDDVECTMVEKRVLSLAWEHPFLTHMFC

TFQTKENLFFVMEYLNGGDLMYHIQSCHKFDLSRATFYAAEIILGLQFLHS

KGIVYRDLKLDNILLDKDGHIKIADFGMCKENMLGDAKTNTFCGTPDYIA

PEILLGQKYNHSVDWWSFGVLLYEMLIGQSPFHGQDEEELFHSIRMDNPF

YPRWLEKEAKDLLVKLFVREPEKRLGVRGDIRQHPLFREINWEELERKEI

DPPFRPKVKSPFDCSNFDKEFLNEKPRLSFADRALINSMDQNMFRNFSFM

NPGMERLIS

The term "component of a CBM complex-associated cancer" as used herein refers to cancers associated with or having a dysregulation of a gene, a protein, or the expression or activity or level of any (e.g., one or more) of the same associated with a component of a CBM complex. In some embodiments, a component of a CBM complex-associated cancer is selected from the group consisting of a MALT1-associated cancer, a CARD11-associated cancer, a CARD14-associated cancer, a CARD10-associated cancer, a CARD9-associated cancer, a BCL10-associated cancer, and combinations thereof. In some embodiments, a CBM complex-associated cancer is selected from the group consisting of a MALT1-associated cancer, a CARD11-associated cancer, a BCL10-associated cancer, and combinations thereof. The cancers "associated" with a particular gene or protein described in this paragraph refer to cancers associated with or having a dysregulation of the particular gene, the particular protein, or the expression or activity or level of any (e.g., one or more) of the same (e.g., any of the types of dysregulation of the particular gene, the particular protein, or the expression or activity or level of any of the same described herein). Non-limiting examples of such cancers are described herein.

The term "MALT1-associated autoimmune disorder" as used herein refers to autoimmune disorders associated with or having a dysregulation of a MALT1 gene, a MALT1 protein (also called herein MALT1 protease protein or MALT1 protease), or the expression or activity or level of any (e.g., one or more) of the same (e.g., any of the types of dysregulation of a MALT1 gene, a MALT1 protease, a MALT1 protease domain, or the expression or activity or level of any of the same described herein). Non-limiting examples of a MALT1-associated autoimmune disorders are described herein.

The term "MALT1-associated inflammatory disorder" as used herein refers to inflammatory disorders associated with or having a dysregulation of a MALT1 gene, a MALT1 protein (also called herein MALT1 protease protein or MALT1 protease), or the expression or activity or level of any (e.g., one or more) of the same (e.g., any of the types of dysregulation of a MALT1 gene, a MALT1 protease, a MALT1 protease domain, or the expression or activity or level of any of the same described herein). Non-limiting examples of a MALT1-associated inflammatory disorders are described herein.

The term "MALT1-associated cancer" as used herein refers to cancers associated with or having a dysregulation of a MALT1 gene, a MALT1 protein (also called herein MALT1 protease protein or MALT1 protease), or the expression or activity or level of any (e.g., one or more) of the same (e.g., any of the types of dysregulation of a MALT1 gene, a MALT1 protein, a MALT1 protease domain, or the expression or activity or level of any of the same described herein). Non-limiting examples of a MALT1-associated cancer are described herein.

The phrase "dysregulation of a MALT1 gene, a MALT1 protein, or the expression or activity or level of any of the same" refers to a genetic mutation (e.g., a chromosomal translocation that results in the expression of a fusion protein including a MALT1 protease domain and a fusion partner, a mutation in a MALT1 gene that results in the expression of a MALT1 protein that includes a deletion of at least one amino acid as compared to a wild-type MALT1 protein, a mutation in a MALT1 gene that results in the expression of a MALT1 protein with one or more point mutations as compared to a wild-type MALT1 protein, a mutation in a MALT1 gene that results in the expression of a MALT1 protein with at least one inserted amino acid as compared to a wild-type MALT1 protein, a gene duplication that results in an increased level of MALT1 protein in a cell, or a mutation in a regulatory sequence (e.g., a promoter and/or enhancer) that results in an increased level of MALT1 protein in a cell), an alternative spliced version of a MALT1 mRNA that results in a MALT1 protein having a deletion of at least one amino acid in the MALT1 protein as compared to the wild-type MALT1 protein, or increased expression (e.g., increased levels) of a wild-type MALT1 protein in a mammalian cell due to aberrant cell signaling and/or dysregulated autocrine/paracrine signaling (e.g., as compared to a control non-cancerous cell). As another example, a dysregulation of a MALT1 gene, a MALT1 protein, or expression or activity, or level of any of the same, can be a mutation in a MALT1 gene that encodes a MALT1 protein that is constitutively active or has increased activity as compared to a protein encoded by a MALT1 gene that does not include the mutation. As a further example, an increased copy number of the MALT1 gene can result in overexpression of MALT1 protease. For example, a dysregulation of a MALT1 gene, a MALT1 protein, or expression or activity, or level of any of the same, can be the result of a gene or chromosome translocation which results in the expression of a fusion protein that contains a first portion of MALT1 that includes a functional protease domain, and a second portion of a partner protein (i.e., that is not MALT1). In some examples, dysregulation of a MALT1 gene, a MALT1 protein, or expression or activity or level of any of the same can be a result of a gene translocation of one MALT1 gene with another non-MALT1 gene.

An exemplary sequence of human MALT1 is shown below:

```
(UniParc Accession No. UPI000004D05E)
                                          SEQ ID NO: 7
MSLLGDPLQALPPSAAPTGPLLAPPAGATLNRLREPLLRRLSELLDQAPEG

RGWRRLAELAGSRGRLRLSCLDLEQCSLKVLEPEGSPSLCLLKLMGEKGC

TVTELSDFLQAMEHTEVLQLLSPPGIKITVNPESKAVLAGQFVKLCCRATG

HPFVQYQWFKMNKEIPNGNTSELIFNAVHVKDAGFYVCRVNNNFTFEFS

QWSQLDVCDIPESFQRSVDGVSESKLQICVEPTSQKLMPGSTLVLQCVAV
```

-continued

```
GSPIPHYQWFKNELPLTHETKKLYMVPYVDLEHQGTYWCHVYNDRDSQ

DSKKVEIIIGRTDEAVECTEDELNNLGHPDNKEQTTDQPLAKDKVALLIGN

MNYREHPKLKAPLVDVYELTNLLRQLDFKVVSLLDLTEYEMRNAVDEFL

LLLDKGVYGLLYYAGHGYENFGNSFMVPVDAPNPYRSENCLCVQNILKL

MQEKETGLNVFLLDMCRKRNDYDDTIPILDALKVTANIVFGYATCQGAE

AFEIQHSGLANGIFMKFLKDRLLEDKKITVLLDEVAEDMGKCHLTKGKQ

ALEIRSSLSEKRALTDPIQGTEYSAESLVRNLQWAKAHELPESMCLKFDC

GVQIQLGFAAEFSNVMIIYTSIVYKPPEIIMCDAYVTDFPLDLDIDPKDAN

KGTPEETGSYLVSKDLPKHCLYTRLSSLQKLKEHLVFTVCLSYQYSGLEDT

VEDKQEVNVGKPLIAKLDMHRGLGRKTCFQTCLMSNGPYQSSAATSGGA

GHYHSLQDPFHGVYHSHPGNPSNVTPADSCHCSRTPDAFISSFAHHASCH

FSRSNVPVETTDEIPFSFSDRLRISEK
```

Non-limiting examples of dysregulation of a MALT1 gene or a MALT1 protein are shown in Table B1 below.

TABLE B1

| MALT1 Protein Amino Acid Substitutions/Insertions/Deletions | | |
|---|---|---|
| Amino Acid Position(s) | Non-limiting Exemplary Mutations | Non-Limiting Exemplary MALT1-associated Cancers |
| 717 | M717I[4] | |

| MALT Fusion Partners | |
|---|---|
| Fusion Partner | Non-limiting Exemplary MALT1-Associated Cancer(s) |
| BIRC3 (Also called IAP2; CIAP2; and API2)[1] | Diffuse Large B-cell Lymphoma (DLBCL)[1]; Extra nodal low-grade MALT lymphoma[2] |
| IGH | ABC-DLBCL[2] |
| SEC11C | Breast Cancer[3] |

[1]United States Patent U.S. Pat. No. 10,711,036
[2]United States Patent Application Publication US20190160045A1
[3]United States Patent Application Publication US20130096021A1
[4]United States Patent Application Publication US20150320754A1

The term "CARD11-associated autoimmune disorder" as used herein refers to autoimmune disorders associated with or having a dysregulation of a CARD11 gene, a CARD11 protein, or the expression or activity or level of any (e.g., one or more) of the same (e.g., any of the types of dysregulation of a CARD11 gene, a CARD11 protein, or the expression or activity or level of any of the same described herein).

The term "CARD11-associated inflammatory disorder" as used herein refers to inflammatory disorders associated with or having a dysregulation of a CARD11 gene, a CARD11 protein, or the expression or activity or level of any (e.g., one or more) of the same (e.g., any of the types of dysregulation of a CARD11 gene, a CARD11 protein, or the expression or activity or level of any of the same described herein).

The term "CARD11-associated cancer" as used herein refers to cancers associated with or having a dysregulation of a CARD11 gene, a CARD11 protein, or the expression or activity or level of any (e.g., one or more) of the same (e.g., any of the types of dysregulation of a CARD11 gene, a CARD11 protein, or the expression or activity or level of any of the same described herein). Non-limiting examples of a CARD11-associated cancer are described herein.

The phrase "dysregulation of a CARD11 gene, a CARD11 protein, or the expression or activity or level of any of the same" refers to a genetic mutation (e.g., a chromosomal translocation that results in the expression of a fusion protein including a CARD11 domain and a fusion partner, a mutation in a CARD11 gene that results in the expression of a CARD11 protein that includes a deletion of at least one amino acid as compared to a wild-type CARD11 protein, a mutation in a CARD11 gene that results in the expression of a CARD11 protein with one or more point mutations as compared to a wild-type CARD11 protein, a mutation in a CARD11 gene that results in the expression of a CARD11 protein with at least one inserted amino acid as compared to a wild-type CARD11 protein, a gene duplication that results in an increased level of CARD11 protein in a cell, or a mutation in a regulatory sequence (e.g., a promoter and/or enhancer) that results in an increased level of CARD11 protein in a cell), an alternative spliced version of a CARD11 mRNA that results in a CARD11 protein having a deletion of at least one amino acid in the CARD11 protein as compared to the wild-type CARD11 protein, or increased expression (e.g., increased levels) of a wild-type CARD11 protein in a mammalian cell due to aberrant cell signaling and/or dysregulated autocrine/paracrine signaling (e.g., as compared to a control non-cancerous cell). As another example, a dysregulation of a CARD11 gene, a CARD11 protein, or expression or activity, or level of any of the same, can be a mutation in a CARD11 gene that encodes a CARD11 protein that is constitutively active or has increased activity as compared to a protein encoded by a CARD11 gene that does not include the mutation. As a further example, an increased copy number of the CARD11 gene can result in overexpression of CARD11 protein. For example, a dysregulation of a CARD11 gene, a CARD11 protein, or expression or activity, or level of any of the same, can be the result of a gene or chromosome translocation which results in the expression of a fusion protein that contains a first portion of CARD11, and a second portion of a partner protein (i.e., that is not CARD11). In some examples, dysregulation of a CARD11 gene, a CARD11 protein, or expression or activity or level of any of the same can be a result of a gene translocation of one CARD11 gene with another non-CARD11 gene.

An exemplary sequence of human CARD11 is shown below:

```
(UniParc Accession No. UPI00003FED38)
                                          SEQ ID NO: 8
MPGGGPEMDDYMETLKDEEDALWENVECNRHMLSRYINPAKLTPYLRQ

CKVIDEQDEDEVLNAPMLPSKINRAGRLLDILHTKGQRGYVVFLESLEFY

YPELYKLVTGKEPTRRFSTIVVEEGHEGLTHFLMNEVIKLQQQMKAKDLQ

RCELLARLRQLEDEKKQMTLTRVELLTFQERYYKMKEERDSYNDELVKV

KDDNYNLAMRYAQLSEEKNMAVMRSRDLQLEIDQLKHRLNKMEEECKL

ERNQSLKLKNDIENRPKKEQVLELERENEMLKTKNQELQSIIQAGKRSLPD

SDKAILDILEHDRKEALEDRQELVNRIYNLQEEARQAEELRDKYLEEKED

LELKCSTLGKDCEMYKHRMNTVMLQLEEVERERDQAFHSRDEAQTQYS

QCLIEKDKYRKQIRELEEKNDEMRIEMVRREACIVNLESKLRRLSKDSNN

LDQSLPRNLPVTIISQDFGDASPRINGQEADDSSTSEESPEDSKYFLPYHP

PQRRMNLKGIQLQRAKSPISLKRTSDFQAKGHEEEGTDASPSSCGSLPITN
```

-continued

```
SFTKMQPPRSRSSIMSITAEPPGNDSIVRRYKEDAPHRSTVEEDNDSGGFD

ALDLDDDSHERYSFGPSSIHSSSSSHQSEGLDAYDLEQVNLMFRKFSLERP

FRPSVTSVGHVRGPGPSVQHTTLNGDSLTSQLTLLGGNARGSFVHSVKPGS

LAEKAGLREGHQLLLLEGCIRGERQSVPLDTCTKEEAHWTIQRCSGPVTL

HYKVNHEGYRKLVKDMEDGLITSGDSFYIRLNLNISSQLDACTMSLKCDD

VVHVRDTMYQDRHEWLCARVDPFTDHDLDMGTIPSYSRAQQLLLVKLQ

RLMHRGSREEVDGTHHTLRALRNTLQPEEALSTSDPRVSPRLSRASFLFG

QLLQFVSRSENKYKRMNSNERVRIISGSPLGSLARSSLDATKLLTEKQEEL

DPESELGKNLSLIPYSLVRAFYCERRRPVLFTPTVLAKTLVQRLLNSGGAM

EFTICKSDIVTRDEFLRRQKTETIIYSREKNPNAFECIAPANIEAVAAKNK

HCLLEAGIGCTRDLIKSNIYPIVLFIRVCEKNIKRFRKLLPRPETEEEFLR

VCRLKEKELEALPCLYATVEPDMWGSVEELLRVVKDKIGEEQRKTIWVDED

QL
```

Non-limiting examples of dysregulation of a CARD11 gene or a CARD11 protein are shown in Table B2 below.

TABLE B2

CARD11 Protein Amino Acid Substitutions/Insertions/Deletions

| Amino Acid Position(s) | Non-limiting Exemplary Mutations | Non-Limiting Exemplary CARD11-associated Cancers |
|---|---|---|
| 47 | R47C[2] | Cutaneous squamous cell carcinoma[2] |
| 123 | G123S[1] | Lymphoma[1] |
| 126 | G126D[1] | Lymphoma[1] |
| 130 | F130V[2] | Cutaneous squamous cell carcinoma[2] |
| 167 | T167M[2] | Cutaneous squamous cell carcinoma[2] |
| 215 | K215M, K215N[1] | Lymphoma[1] |
| 230 | D230N[1] | Lymphoma[1] |
| 357 | D357E[1] | Lymphoma[1] |
| 360 | M360V[1] | Lymphoma[1] |
| 361 | Y361C[1] | Lymphoma[1] |
| 368 | V368I[2] | Cutaneous squamous cell carcinoma[2] |
| 737 | H737L[2] | Cutaneous squamous cell carcinoma[2] |
| 750 | H750R[2] | Cutaneous squamous cell carcinoma[2] |
| 833 | P833L[2] | Cutaneous squamous cell carcinoma[2] |
| 900 | L900F[2] | Cutaneous squamous cell carcinoma[2] |
| 1015 | L1015F[2] | Cutaneous squamous cell carcinoma[2] |
| 1016 | R1016L[2] | Cutaneous squamous cell carcinoma[2] |
| 1085 | R1085S[2] | Cutaneous squamous cell carcinoma[2] |
| 1086 | F1086S[2] | Cutaneous squamous cell carcinoma[2] |

[1]Wu, et al., Oncotarget 7.25 (2016): 38180.

[2]Watt, et al. The American Journal of Pathology 185.9 (2015): 2354-2363.

The term "CARD14-associated autoimmune disorder" as used herein refers to autoimmune disorders associated with or having a dysregulation of a CARD14 gene, a CARD14 protein, or the expression or activity or level of any (e.g., one or more) of the same (e.g., any of the types of dysregulation of a CARD14 gene, a CARD14 protein, or the expression or activity or level of any of the same described herein).

The term "CARD14-associated inflammatory disorder" as used herein refers to inflammatory disorders associated with or having a dysregulation of a CARD14 gene, a CARD14 protein, or the expression or activity or level of any (e.g., one or more) of the same (e.g., any of the types of dysregulation of a CARD14 gene, a CARD14 protein, or the expression or activity or level of any of the same described herein).

The term "CARD14-associated cancer" as used herein refers to cancers associated with or having a dysregulation of a CARD14 gene, a CARD14 protein, or the expression or activity or level of any (e.g., one or more) of the same (e.g., any of the types of dysregulation of a CARD14 gene, a CARD14 protein, or the expression or activity or level of any of the same described herein).

An exemplary sequence of human CARD14 is shown below:

(UniParc Accession No. UPI000013D81B)

SEQ ID NO: 9

MGELCRRDSALTALDEETLWEMMESHRHRIVRCICPSRLTPYLRQAKVLC

QLDEEEVLHSPRLTNSAMRAGHLLDLLKTRGKNGAIAFLESLKFHNPDVY

TLVTGLQPDVDFSNFSGLMETSKLTECLAGAIGSLQEELNQEKGQKEVLL

RRCQQLQEHLGLAETRAEGLHQLEADHSRMKREVSAHFHEVLRLKDEM

LSLSLHYSNALQEKELAASRCRSLQEELYLLKQELQRANMVSSCELELQE

QSLRTASDQESGDEELNRLKEENEKLRSLTFSLAEKDILEQSLDEARGSRQ

ELVERIHSLRERAVAAERQREQYWEEKEQTLLQFQKSKMACQLYREKVN

ALQAQVCELQKERDQAYSARDSAQREISQSLVEKDSLRRQVFELTDQVC

ELRTQLRQLQAEPPGVLKQEARTREPCPREKQRLVRMHAICPRDDSDCSL

VSSTESQLLSDLSATSSRELVDSFRSSSPAPPSQQSLYKRVAEDFGEEPWS

FSSCLEIPEGDPGALPGAKAGDPHLDYELLDTADLPQLESSLQPVSPGRLD

VSESGVLMRRRPARRILSQVTMLAFQGDALLEQISVIGGNLTGIFIHRVTP

GSAADQMALRPGTQIVMVDYEASEPLFKAVLEDTTLEEAVGLLRRVDGFCC

LSVKVNTDGYKRLLQDLEAKVATSGDSFYIRVNLAMEGRAKGELQVHC

NEVLHVTDTMFQGCGCWHAHRVNSYTMKDTAAHGTIPNYSRAQQQLIA

LIQDMTQQCTVTRKPSSGGPQKLVRIVSMDKAKASPLRLSFDRGQLDPSR

MEGSSTCFWAESCLTLVPYTLVRPHRPARPRPVLLVPRAVGKILSEKLCLL

QGFKKCLAEYLSQEEYEAWSQRGDIIQEGEVSGGRCWVTRHAVESLMEK

NTHALLDVQLDSVCTLHRMDIFPIVIHVSVNEKMAKKLKKGLQRLGTSEE

QLLEAARQEEGDLDRAPCLYSSLAPDGWSDLDGLLSCVRQAIADEQKKV

VWTEQSPR

The term "CARD10-associated autoimmune disorder" as used herein refers to autoimmune disorders associated with or having a dysregulation of a CARD10 gene, a CARD10 protein, or the expression or activity or level of any (e.g., one or more) of the same (e.g., any of the types of dysregulation of a CARD10 gene, a CARD10 protein, or the expression or activity or level of any of the same described herein).

The term "CARD10-associated inflammatory disorder" as used herein refers to inflammatory disorders associated with or having a dysregulation of a CARD10 gene, a CARD10 protein, or the expression or activity or level of any (e.g., one or more) of the same (e.g., any of the types of dysregulation of a CARD10 gene, a CARD10 protein, or the expression or activity or level of any of the same described herein).

The term "CARD10-associated cancer" as used herein refers to cancers associated with or having a dysregulation of a CARD10 gene, a CARD10 protein, or the expression or activity or level of any (e.g., one or more) of the same (e.g., any of the types of dysregulation of a CARD10 gene, a CARD10 protein, or the expression or activity or level of any of the same described herein).

The phrase "dysregulation of a CARD10 gene, a CARD10 protein, or the expression or activity or level of any of the same" refers to a genetic mutation (e.g., a chromosomal translocation that results in the expression of a fusion protein including a CARD10 domain and a fusion partner, a mutation in a CARD10 gene that results in the expression of a CARD10 protein that includes a deletion of at least one amino acid as compared to a wild-type CARD10 protein, a mutation in a CARD10 gene that results in the expression of a CARD10 protein with one or more point mutations as compared to a wild-type CARD10 protein, a mutation in a CARD10 gene that results in the expression of a CARD10 protein with at least one inserted amino acid as compared to a wild-type CARD10 protein, a gene duplication that results in an increased level of CARD10 protein in a cell, or a mutation in a regulatory sequence (e.g., a promoter and/or enhancer) that results in an increased level of CARD10 protein in a cell), an alternative spliced version of a CARD10 mRNA that results in a CARD10 protein having a deletion of at least one amino acid in the CARD10 protein as compared to the wild-type CARD10 protein, or increased expression (e.g., increased levels) of a wild-type CARD10 protein in a mammalian cell due to aberrant cell signaling and/or dysregulated autocrine/paracrine signaling (e.g., as compared to a control non-cancerous cell). As another example, a dysregulation of a CARD10 gene, a CARD10 protein, or expression or activity, or level of any of the same, can be a mutation in a CARD10 gene that encodes a CARD10 protein that is constitutively active or has increased activity as compared to a protein encoded by a CARD10 gene that does not include the mutation. As a further example, an increased copy number of the CARD10 gene can result in overexpression of CARD10 protein. For example, a dysregulation of a CARD10 gene, a CARD10 protein, or expression or activity, or level of any of the same, can be the result of a gene or chromosome translocation which results in the expression of a fusion protein that contains a first portion of CARD10, and a second portion of a partner protein (i.e., that is not CARD10). In some examples, dysregulation of a CARD10 gene, a CARD10 protein, or expression or activity or level of any of the same can be a result of a gene translocation of one CARD10 gene with another non-CARD10 gene.

An exemplary sequence of human CARD10 is shown below:

(UniParc Accession No. UPI0000044645)

SEQ ID NO: 10

MPGRAEAGEAEEEAGAGSGSEAEEDALWERIEGVRHRLARALNPAKLTP

YLRQCRVIDEQDEEEVLSTYRFPCRVNRTGRLMDILRCRGKRGYEAFLEA

LEFYYPEHFTLLTGQEPAQRCSMILDEEGPEGLTQFLMTEVRRLREARKS

QLQREQQLQARGRVLEEERAGLEQRLRDQQQAQERCQRLREDWEAGSL

ELLRLKDENYMIAMRLAQLSEEKNSAVLRSRDLQLAVDQLKLKVSRLEE

ECALLRRARGPPPGAEEKEKEKEKEKEPDNVDLVSELRAENQRLTASLRE

LQEGLQQEASRPGAPGSERILLDILEHDWREAQDSRQELCQKLHAVQGEL

-continued

QWAEELRDQYLQEMEDLRLKHRTLQKDCDLYKHRMATVLAQLEEIEKE

RDQAIQSRDRIQLQYSQSLIEKDQYRKQVRGLEAERDELLTTLTSLEGTKA

LLEVQLQRAQGGTCLKACASSHSLCSNLSSTWSLSEFPSPLGGPEATGEA

AVMGGPEPHNSEEATDSEKEINRLSILPFPPSAGSILRRQREEDPAPPKRS

FSSMSDITGSVTLKPWSPGLSSSSSSDSVWPLGKPEGLLARGCGLDFLNRS

LAIRVSGRSPPGGPEPQDKGPDGLSFYGDRWSGAVVRRVLSGPGSARMEPR

EQRVEAAGLEGACLEAEAQQRTLLWNQGSTLPSLMDSKACQSFHEALEA

WAKGPGAEPFYIRANLTLPERADPHALCVKAQEILRLVDSAYKRRQEWF

CTRVDPLTLRDLDRGTVPNYQRAQQLLEVQEKCLPSSRHRGPRSNLKKR

ALDQLRLVRPKPVGAPAGDSPDQLLLEPCAEPERSLRPYSLVRPLLVSALR

PVVLLPECLAPRLIRNLLDLPSSRLDFQVCPAESLSGEELCPSSAPGAPKA

QPATPGLGSRIRAIQESVGKKHCLLELGARGVRELVQNEIYPIVIHVEVTE

KNVREVRGLLGRPGWRDSELLRQCRGSEQVLWGLPCSWVQVPAHEWGHA

EELAKVVRGRILQEQARLVWVECGSSRGCPSSSEA

The term “CARD9-associated autoimmune disorder” as used herein refers to autoimmune disorders associated with or having a dysregulation of a CARD9 gene, a CARD9 protein, or the expression or activity or level of any (e.g., one or more) of the same (e.g., any of the types of dysregulation of a CARD9 gene, a CARD9 protein, or the expression or activity or level of any of the same described herein).

The term “CARD9-associated inflammatory disorder” as used herein refers to inflammatory disorders associated with or having a dysregulation of a CARD9 gene, a CARD9 protein, or the expression or activity or level of any (e.g., one or more) of the same (e.g., any of the types of dysregulation of a CARD9 gene, a CARD9 protein, or the expression or activity or level of any of the same described herein).

The term “CARD9-associated cancer” as used herein refers to cancers associated with or having a dysregulation of a CARD9 gene, a CARD9 protein, or the expression or activity or level of any (e.g., one or more) of the same (e.g., any of the types of dysregulation of a CARD9 gene, a CARD9 protein, or the expression or activity or level of any of the same described herein).

The phrase “dysregulation of a CARD9 gene, a CARD9 protein, or the expression or activity or level of any of the same” refers to a genetic mutation (e.g., a chromosomal translocation that results in the expression of a fusion protein including a CARD9 domain and a fusion partner, a mutation in a CARD9 gene that results in the expression of a CARD9 protein that includes a deletion of at least one amino acid as compared to a wild-type CARD9 protein, a mutation in a CARD9 gene that results in the expression of a CARD9 protein with one or more point mutations as compared to a wild-type CARD9 protein, a mutation in a CARD9 gene that results in the expression of a CARD9 protein with at least one inserted amino acid as compared to a wild-type CARD9 protein, a gene duplication that results in an increased level of CARD9 protein in a cell, or a mutation in a regulatory sequence (e.g., a promoter and/or enhancer) that results in an increased level of CARD9 protein in a cell), an alternative spliced version of a CARD9 mRNA that results in a CARD9 protein having a deletion of at least one amino acid in the CARD9 protein as compared to the wild-type CARD9 protein, or increased expression (e.g., increased levels) of a wild-type CARD9 protein in a mammalian cell due to aberrant cell signaling and/or dysregulated autocrine/paracrine signaling (e.g., as compared to a control non-cancerous cell). As another example, a dysregulation of a CARD9 gene, a CARD9 protein, or expression or activity, or level of any of the same, can be a mutation in a CARD9 gene that encodes a CARD9 protein that is constitutively active or has increased activity as compared to a protein encoded by a CARD9 gene that does not include the mutation. As a further example, an increased copy number of the CARD9 gene can result in overexpression of CARD9 protein. For example, a dysregulation of a CARD9 gene, a CARD9 protein, or expression or activity, or level of any of the same, can be the result of a gene or chromosome translocation which results in the expression of a fusion protein that contains a first portion of CARD9, and a second portion of a partner protein (i.e., that is not CARD9). In some examples, dysregulation of a CARD9 gene, a CARD9 protein, or expression or activity or level of any of the same can be a result of a gene translocation of one CARD9 gene with another non-CARD9 gene.

An exemplary sequence of human CARD9 is shown below:

(UniParc Accession No. UPI000013E4EB)

SEQ ID NO: 11

MSDYENDDECWSVLEGFRVTLTSVIDPSRITPYLRQCKVLNPDDEEQVLS

DPNLVIRKRKVGVLLDILQRTGHKGYVAFLESLELYYPQLYKKVTGKEPA

RVFSMIIDASGESGLTQLLMTEVMKLQKKVQDLTALLSSKDDFIKELRVK

DSLLRKHQERVQRLKEECEAGSRELKRCKEENYDLAMRLAHQSEEKGAA

LMRNRDLQLEIDQLKHSLMKAEDDCKVERKHTLKLRHAMEQRPSQELL

WELQQEKALLQARVQELEASVQEGKLDRSSPYIQVLEEDWRQALRDHQE

QANTIFSLRKDLRQGEARRLRCMEEKEMFELQCLALRKDSKMYKDRIEAI

LLQMEEVAIERDQAIATREELHAQHARGLQEKDALRKQVRELGEKADEL

QLQVFQCEAQLLAVEGRLRRQQLETLVLSSDLEDGSPRRSQELSLPQDLE

DTQLSDKGCLAGGGSPKQPFAALHQEQVLRNPHDAGLSSGEPPEKERRRL

KESFENYRRKRALRKMQKGWRQGEEDRENTTGSDNTDTEGS

The term “BCL10-associated autoimmune disorder” as used herein refers to autoimmune disorders associated with or having a dysregulation of a BCL10 gene, a BCL10 protein, or the expression or activity or level of any (e.g., one or more) of the same (e.g., any of the types of dysregulation of a BCL10 gene, a BCL10 protein, or the expression or activity or level of any of the same described herein).

The term “BCL10-associated inflammatory disorder” as used herein refers to inflammatory disorders associated with or having a dysregulation of a BCL10 gene, a BCL10 protein, or the expression or activity or level of any (e.g., one or more) of the same (e.g., any of the types of dysregulation of a BCL10 gene, a BCL10 protein, or the expression or activity or level of any of the same described herein).

The term “BCL10-associated cancer” as used herein refers to cancers associated with or having a dysregulation of a BCL10 gene, a BCL10 protein, or the expression or activity or level of any (e.g., one or more) of the same (e.g., any of the types of dysregulation of a BCL10 gene, a BCL10 protein, or the expression or activity or level of any of the same described herein).

The phrase “dysregulation of a BCL10 gene, a BCL10 protein, or the expression or activity or level of any of the same" refers to a genetic mutation (e.g., a chromosomal translocation that results in the expression of a fusion protein including a BCL10 domain and a fusion partner, a mutation in a BCL10 gene that results in the expression of a BCL10 protein that includes a deletion of at least one amino acid as compared to a wild-type BCL10 protein, a mutation in a BCL10 gene that results in the expression of a BCL10 protein with one or more point mutations as compared to a wild-type BCL10 protein, a mutation in a BCL10 gene that results in the expression of a BCL10 protein with at least one inserted amino acid as compared to a wild-type BCL10 protein, a gene duplication that results in an increased level of BCL10 protein in a cell, or a mutation in a regulatory sequence (e.g., a promoter and/or enhancer) that results in an increased level of BCL10 protein in a cell), an alternative spliced version of a BCL10 mRNA that results in a BCL10 protein having a deletion of at least one amino acid in the BCL10 protein as compared to the wild-type BCL10 protein, or increased expression (e.g., increased levels) of a wild-type BCL10 protein in a mammalian cell due to aberrant cell signaling and/or dysregulated autocrine/paracrine signaling (e.g., as compared to a control non-cancerous cell). For example, a dysregulation of a BCL10 gene, a BCL10 protein, or expression or activity, or level of any of the same, can be the result of a gene or chromosome translocation which results in the expression of a fusion protein that contains a first portion of BCL10, and a second portion of a partner protein (i.e., that is not BCL10). In some examples, dysregulation of a BCL10 gene, a BCL10 protein, or expression or activity or level of any of the same can be a result of a gene translocation of one BCL10 gene with another non-BCL10 gene.

An exemplary sequence of human BCL10 is shown below:

(UniParc Accession No. UPI000012682F)

SEQ ID NO: 12

MEPTAPSLTEEDLTEVKKDALENLRVYLCEKIIAERHFDHLRAKKILSRED

TEEISCRTSSRKRAGKLLDYLQENPKGLDTLVESIRREKTQNFLIQKITDE

VLKLRNIKLEHLKGLKCSSCEPFPDGATNNLSRSNSDESNFSEKLRASTVM

YHPEGESSTTPFFSTNSSLNLPVLEVGRTENTIFSSTTLPRPGDPGAPPLP

PDLQLEEEGTCANSSEMFLPLRSRTVSRQ

Non-limiting examples of dysregulation of a BCL10 gene or a BCL10 protein are shown in Table B3 below.

TABLE B3

BCL10 Protein Amino Acid Substitutions/Insertions/Deletions

| Amino Acid Position(s) | Non-limiting Exemplary Mutations | Non-Limiting Exemplary BCL10-associated Cancers |
|---|---|---|
| 5 | A5S[2] | Lymphoma[2] |
| 16 | V16E[2] | Lymphoma[2] |
| 20 | A20T[1] | Germ cell tumor[1] |
| 31 | K31E | Lymphoma[2] |
| 32 | I32V[1] | Lymphoma[1] |
| 43 | A43*[2] | Lymphoma[2] |
| 46 | I46*[1] | T-ALL[1], colonic carcinoma[1] |
| 49 | R49G[1] | Lymphoma[1] |
| 52 | T52I[1] | Mesothelioma[1] |
| 55 | I55*[1] | Lymphoma[1] |
| 57 | C57R[2] | Lymphoma[2] |
| 58 | R58G[1], R58*[1] | Germ cell tumor[1] |
| 64 | R64K[2] | Lymphoma[2] |
| 77 | K77*[1] | Lymphoma[1] |
| 80 | D80N | Lymphoma[1] |
| 91 | T91*[1] | Germ cell tumor[1] |
| 100 | T100S[1] | Lymphoma[1] |
| 101 | D101E[2] | Lymphoma[2] |
| 115 | K115*[1] | Lymphoma[1] |
| 116-126 | Splice mutation[1] | Lymphoma[1] |
| 116-121 | Splice mutation[2] | Lymphoma[2] |
| 116-120 | Splice mutation[1] | Mesothelioma[1] |
| 133 | L133*[1] | Lymphoma[1] |
| 134 | S134P[2] | Lymphoma[2] |
| 137 | N137*[1] | Lymphoma[1] |
| 143 | F143*[1] | Lymphoma[1] |
| 152 | V152*[2] | Lymphoma[2] |
| 165 | F165*[2] | Lymphoma[2] |
| 167 | S167*[1] | Lymphoma[1] |
| 168 | T168A[2] | Lymphoma[2] |
| 170-180 | del S170-G180[1] | Lymphoma[1] |
| 175-181 | del P175-G180[1] | Lymphoma[1] |
| 210 | del 210[1] | Lymphoma[1] |
| 213 | G213E | Lymphoma[2] |
| 218 | S218F[1] | Germ cell tumor[1] |
| 230 | V230I[2] | Lymphoma[2] |
| Stop | Stop -> R | Lymphoma[2] |

[1]Willis, et al. Cell 96.1 (1999): 35-45.
[2]Zhang, et al. Nature Genetics 22.1 (1999): 63-68.

The term "MALT1 protease substrate-associated cancer" as used herein refers to cancers associated with or having a dysregulation of a gene, a protein, or the expression or activity or level of any (e.g., one or more) of the same associated with a MALT1 protease substrate. In some embodiments, a MALT1 protease substrate-associated cancer is selected from the group consisting of a BCL10-associated cancer, an A20-associated cancer, a CYLD-associated cancer, a RelB-associated cancer, a Regnase 1-associated cancer, a roquin-1-associated cancer, a HOIL1-associated cancer, a NIK associated cancer, a LIMA1α-associated cancer, and combinations thereof. In some embodiments, a MALT1 protease substrate-associated cancer is selected from the group consisting of a BCL10-associated cancer, an A20-associated cancer, a CYLD-associated cancer, and combinations thereof. The cancers "associated" with a particular gene or protein described in this paragraph refer to cancers associated with or having a dysregulation of the particular gene, the particular protein, or the expression or activity or level of any (e.g., one or more) of the same (e.g., any of the types of dysregulation of the particular gene, the particular protein, or the expression or activity or level of any of the same described herein). Non-limiting examples of such cancers are described herein.

An exemplary sequence of human A20 is shown below:

(UniParc Accession No. UPI000000D92D)

SEQ ID NO: 13

MAEQVLPQALYLSNMRKAVKIRERTPEDIFKPTNGIIHHFKTMHRYTLEM

FRTCQFCPQFREIIHKALIDRNIQATLESQKKLNWCREVRKLVALKTNGDG

NCLMHATSQYMWGVQDTDLVLRKALFSTLKETDTRNFKFRWQLESLKS

QEFVETGLCYDTRNWNDEWDNLIKMASTDTPMARSGLQYNSLEEIHIFVL

CNILRRPIIVISDKMLRSLESGSNFAPLKVGGIYLPLHWPAQECYRYPIVL

GYDSHHFVPLVTLKDSGPEIRAVPLVNRDRGRFEDLKVHFLTDPENEMKEK

-continued

LLKEYLMVIEIPVQGWDHGTTHLINAAKLDEANLPKEINLVDDYFELVQH

EYKKWQENSEQGRREGHAQNPMEPSVPQLSLMDVKCETPNCPFFMSVNT

QPLCHECSERRQKNQNKLPKLNSKPGPEGLPGMALGASRGEAYEPLAWN

PEESTGGPHSAPPTAPSPFLFSETTAMKCRSPGCPFTLNVQHNGFCERCHN

ARQLHASHAPDHTRHLDPGKCQACLQDVTRTFNGICSTCFKRTTAEASS

LSTSLPPSCHQRSKSDPSRLVRSPSPHSCHRAGNDAPAGCLSQAARTPGDR

TGTSKCRKAGCVYFGTPENKGFCTLCFIEYRENKHFAAASGKVSPTASRF

QNTIPCLGRECGTLGSTMFEGYCQKCFIEAQNQRFHEAKRTEEQLRSSQR

RDVPRTTQSTSRPKCARASCKNILACRSEELCMECQHPNQRMGPGAHRG

EPAPEDPPKQRCRAPACDHFGNAKCNGYCNECFQFKQMYG

Non-limiting examples of dysregulation of an A20 gene or an A20 protein are shown in Table B4 below.

TABLE B4

| A20 Protein Amino Acid Substitutions/Insertions/Deletions | | |
|---|---|---|
| Amino Acid Position(s) | Non-limiting Exemplary Mutations | Non-Limiting Exemplary A20-associated Cancers |
| 100 | D100*[2] | Extranodal marginal zone lymphoma[2] |
| 162 | R162*[2] | Nodal marginal zone lymphoma[2] |
| 183 | R183X[1] | Lymphoma[1] |
| 271 | R271X[1] | Lymphoma[1] |
| 278 | R278*[2] | Nodal marginal zone lymphoma[2] |
| 288 | V288*[2] | Splenic marginal zone lymphoma[2] |
| 491 | H491*[2] | Nodal marginal zone lymphoma[2] |
| 633 | E633*[2] | Extranodal marginal zone lymphoma[2] |

[1]Johansson et al. Oncotarget 7.38 (2016): 62627.
[2]Novak, et al. Blood 113.20 (2009): 4918-4921.

An exemplary sequence of human CYLD is shown below:

(UniParc Accession No. UPI0000073A15)
SEQ ID NO: 14

MSSGLWSQEKVTSPYWEERIFYLLLQECSVTDKQTQKLLKVPKGSIGQYI

QDRSVGHSRIPSAKGKKNQIGLKILEQPHAVLFVDEKDVVEINEKFTELLL

AITNCEERFSLFKNRNRLSKGLQIDVGCPVKVQLRSGEEKFPGVVRFRGPL

LAERTVSGIFFGVELLEEGRGQGFTDGVYQGKQLFQCDEDCGVFVALDK

LELIEDDDTALESDYAGPGDTMQVELPPLEINSRVSLKVGETIESGTVIFC

DVLPGKESLGYFVGVDMDNPIGNWDGRFDGVQLCSFACVESTILLHINDII

PALSESVTQERRPPKLAFMSRGVGDKGSSSHNKPKATGSTSDPGNRNRSEL

FYTLNGSSVDSQPQSKSKNTWYIDEVAEDPAKSLTEISTDFDRSSPPLQPP

PVNSLTTENRFHSLPFSLTKMPNINGSIGHSPLSLSAQSVMEELNTAPVQE

SPPLAMPPGNSHGLEVGSLAEVKENPPFYGVIRWIGQPPGLNEVLAGLELE

DECAGCTDGTFRGTRYFTCALKKALFVKLKSCRPDSRFASLQPVSNQIER

CNSLAFGGYLSEVVEENTPPKMEKEGLEIMIGKKKGIQGHYNSCYLDSTL

FCLFAFSSVLDTVLLRPKEKNDVEYYSETQELLRTEIVNPLRIYGYVCATK

IMKLRKILEKVEAASGFTSEEKDPEEFLNILFHHILRVEPLLKIRSAGQKV

-continued

QDCYFYQIFMEKNEKVGVPTIQQLLEWSFINSNLKFAEAPSCLIIQMPRFG

KDFKLFKKIFPSLELNITDLLEDTPRQCRICGGLAMYECRECYDDPDISAG

KIKQFCKTCNTQVHLHPKRLNHKYNPVSLPKDLPDWDWRHGCIPCQNMELF

AVLCIETSHYVAFVKYGKDDSAWLFFDSMADRDGGQNGFNIPQVTPCPE

VGEYLKMSLEDLHSLDSRRIQGCARRLLCDAYMCMYQSPTMSLYK

Non-limiting examples of dysregulation of a CYLD gene or a CYLD protein can be found, for example, in Massoumi, Future Oncology 7.2 (2011): 285-297, Alameda, J. P., et al., Oncogene 29.50 (2010): 6522-6532, Williams, et al., Modern Pathology (2020): 1-13, and Courtois and Gilmore. Oncogene 25.51 (2006): 6831-6843.

An exemplary sequence of human RelB is shown below:

(UniParc Accession No. UPI00000012B7)
SEQ ID NO: 15

MLRSGPASGPSVPTGRAMPSRRVARPPAAPELGALGSPDLSSLSLAVSRST

DELEIIDEYIKENGFGLDGGQPGPGEGLPRLVSRGAASLSTVTLGPVAPPA

TPPPWGCPLGRLVSPAPGPGPQPHLVITEQPKQRGMRFRYECEGRSAGSIL

GESSTEASKTLPAIELRDCGGLREVEVTACLVWKDWPHRVHPHSLVGKD

CTDGICRVRLRPHVSPRHSFNNLGIQCVRKKEIEAAIERKIQLGIDPYNAG

SLKNHQEVDMNVVRICFQASYRDQQGQMRRMDPVLSEPVYDKKSTNTSE

LRICRINKESGPCTGGEELYLLCDKVQKEDISVVFSRASWEGRADFSQAD

VHRQIAIVFKTPPYEDLEIVEPVTVNVFLQRLTDGVCSEPLPFTYLPRDHD

SYGVDKKRKRGMPDVLGELNSSDPHGIESKRRKKKPAILDHFLPNHGSGPF

LPPSALLPDPDFFSGTVSLPGLEPPGGPDLLDDGFAYDPTAPTLFTMLDLL

PPAPPHASAVVCSGGAGAVVGETPGPEPLTLDSYQAPGPGDGGTASLVGS

NMFPNHYREAAFGGGLLSPGPEAT

An exemplary sequence of human Regnase 1 is shown below:

(UniParc Accession No. UPI000004D30E)
SEQ ID NO: 16

MSGPCGEKPVLEASPTMSLWEFEDSHSRQGTPRPGQELAAEEASALELQ

MKVDFFRKLGYSSTEIHSVLQKLGVQADTNTVLGELVKHGTATERERQT

SPDPCPQLPLVPRGGGTPKAPNLEPPLPEEEKEGSDLRPVVIDGSNVAMSH

GNKEVFSCRGILLAVNWFLERGHTDITVFVPSWRKEQPRPDVPITDQHILR

ELEKKKILVFTPSRRVGGKRVVCYDDRFIVKLAYESDGIVVSNDTYRDLQ

GERQEWKRFIEERLLMYSFVNDKFMPPDDPLGRHGPSLDNFLRKKPLTLE

HRKQPCPYGRKCTYGIKCRFFHPERPSCPQRSVADELRANALLSPPRAPSK

DKNGRRPSPSSQSSSLLTESEQCSLDGKKLGAQASPGSRQEGLTQTYAPSG

RSLAPSGGSGSSFGPTDWLPQTLDSLPYVSQDCLDSGIGSLESQMSELWG

VRGGGPGEPGPPRAPYTGYSPYGSELPATAAFSAFGRAMGAGHFSVPAD

YPPAPPAFPPREYWSEPYPLPPPTSVLQEPPVQSPGAGRSPWGRAGSLAKE

QASVYTKLCGVFPPHLVEAVMGRFPQLLDPQQLAAEILSYKSQHPSE

An exemplary sequence of human roquin-1 is shown below:

(UniParc Accession No. UPI00001D7DA8)

SEQ ID NO: 17

MPVQAPQWTDFLSCPICTQTFDETIRKPISLGCGHTVCKMCLNKLHRKAC

PFDQTTINTDIELLPVNSALLQLVGAQVPEQQPITLCSGVEDTKHYEEAK

KCVEELALYLKPLSSARGVGLNSTTQSVLSRPMQRKLVTLVHCQLVEEEG

RIRAMRAARSLGERTVTELILQHQNPQQLSSNLWAAVRARGCQFLGPAMQ

EEALKLVLLALEDGSALSRKVLVLFVVQRLEPRFPQASKTSIGHVVQLLY

RASCFKVTKRDEDSSLMQLKEEFRTYEALRREHDSQIVQIAMEAGLRIAP

DQWSSLLYGDQSHKSHMQSIIDKLQTPASFAQSVQELTIALQRTGDPANL

NRLRPHLELLANIDPSPDAPPPTWEQLENGLVAVRTVVHGLVDYIQNHSK

KGADQQQPPQHSKYKTYMCRDMKQRGGCPRGASCTFAHSQEELEKFRK

MNKRLVPRRPLSASLGQLNEVGLPSAAILPDEGAVDLPSRKPPALPNGIV

STGNTVTQLIPRGTDPSYDSSLKPGKIDHLSSSAPGSPPDLLESVPKSIS

ALPVNPHSIPPRGPADLPPMPVTKPLQMVPRGSQLYPAQQTDVYYQDPRG

AAPPFEPAPYQQGMYYTPPPQCVSRFVRPPPSAPEPAPPYLDHYPPYLQE

RVVNSQYGTQPQQYPPIYPSHYDGRRVYPAPSYTREEIFRESPIPIEIPP

AAVPSYVPESRERYQQIESYYPVAPHPTQIRPSYLREPPYSRLPPPPQPH

PSLDELHRRRKEIMAQLEERKVISPPPFAPSPTLPPTFHPEEFLDEDLKV

AGKYKGNDYSQYSPWSCDTIGSYIGTKDAKPKDVVAAGSVEMMNVESKGM

RDQRLDLQRRAAETSDDDLIPFGDRPTVSRFGAISRTSKTIYQGAGPMQA

MAPQGAPTKSINISDYSPYGTHGGWGASPYSPHQNIPSQGHFSERERISM

SEVASHGKPLPSAEREQLRLELQQLNHQISQQTQLRGLEAVSNRLVLQRE

ANTLAGQSQPPPPPPPKWPGMISSEQLSLELHQVEREIGKRTRELSMENQ

CSLDMKSKLNTSKQAENGQPEPQNKVPAEDLTLTFSDVPNGSALTQENIS

LLSNKTSSLNLSEDPEGGGDNNDSQRSGVTPSSAP

An exemplary sequence of human HOIL1 is shown below:

(UniParc Accession No. UPI000006F045)

SEQ ID NO: 17

MDEKTKKAEEMALSLTRAVAGGDEQVAMKCAIWLAEQRVPLSVQLKPE

VSPTQDIRLWVSVEDAQMHTVTIWLTVRPDMTVASLKDMVFLDYGFPPV

LQQWVIGQRLARDQETLHSHGVRQNGDSAYLYLLSARNTSLNPQELQRE

RQLRMLEDLGFKDLTLQPRGPLEPGPPKPGVPQEPGRGQPDAVPEPPPVG

WQCPGCTFINKPTRPGCEMCCRARPEAYQVPASYQPDEEERARLAGEEE

ALRQYQQRKQQQQEGNYLQHVQLDQRSLVLNTEPAECPVCYSVLAPGE

AVVLRECLHTFCRECLQGTIRNSQEAEVSCPFIDNTYSCSGKLLEREIKA

LLTPEDYQRFLDLGISIAENRSAFSYHCKTPDCKGWCFFEDDVNEFTCPV

CFHVNCLLCKAIHEQMNCKEYQEDLALRAQNDVAARQTTEMLKVMLQQGE

AMRCPQCQIVVQKKDGCDWIRCTVCHTEICWVTKGPRWGPGGPGDTSG

GCRCRVNGIPCHPSCQNCH

An exemplary sequence of human NIK is shown below:

(UniParc Accession No. UPI0000074220)

SEQ ID NO: 18

MAVMEMACPGAPGSAVGQQKELPKAKEKTPPLGKKQSSVYKLEAVEKS

PVFCGKWEILNDVITKGTAKEGSEAGPAAISIIAQAECENSQEFSPTFSE

RIFIAGSKQYSQSESLDQIPNNVAHATEGKMARVCWKGKRRSKARKKRKKK

SSKSLAHAGVALAKPLPRTPEQESCTIPVQEDESPLGAPYVRNTPQFTKPL

KEPGLGQLCFKQLGEGLRPALPRSELHKLISPLQCLNHVWKLHHPQDGGP

LPLPTHPFPYSRLPHPFPFHPLQPWKPHPLESFLGKLACVDSQKPLPDPHL

SKLACVDSPKPLPGPHLEPSCLSRGAHEKFSVEEYLVHALQGSVSSGQAHS

LTSLAKTWAARGSRSREPSPKTEDNEGVLLTEKLKPVDYEYREEVHWAT

HQLRLGRGSFGEVHRMEDKQTGFQCAVKKVRLEVFRAEELMACAGLTS

PRIVPLYGAVREGPWVNIFMELLEGGSLGQLVKEQGCLPEDRALYYLGQ

ALEGLEYLHSRRILHGDVKADNVLLSSDGSHAALCDFGHAVCLQPDGLG

KSLLTGDYIPGTETHMAPEVVLGRSCDAKVDVWSSCCMMLHMLNGCHP

WTQFFRGPLCLKIASEPPPVREIPPSCAPLTAQAIQEGLRKEPIHRVSAAE

LGGKVNRALQQVGGLKSPWRGEYKEPRHPPPNQANYHQTLHAQPRELSPR

APGPRPAEETTGRAPKLQPPLPPEPPEPNKSPPLTLSKEESGMWEPLPLSS

LEPAPARNPSSPERKATVPEQELQQLEIELFLNSLSQPFSLEEQEQILSCL

SIDSLSLSDDSEKNPSKASQSSRDTLSSGVHSWSSQAEARSSSWNMVLARG

RPTDTPSYFNGVKVQIQSLNGEHLHIREFHRVKVGDIATGISSQIPAAAFS

LVTKDGQPVRYDMEVPDSGIDLQCTLAPDGSFAWSWRVKHGQLENRP

An exemplary sequence of human LIMA1a is shown below:

(UniParc Accession No. UPI000002A906)

SEQ ID NO: 19

MENCLGESRHEVEKSEISENTDASGKIEKYNVPLNRLKMMFEKGEPTQTK

ILRAQSRSASGRKISENSYSLDDLEIGPGQLSSSTFDSEKNESRRNLELPR

LSETSIKDRMAKYQAAVSKQSSSTNYTNELKASGGEIKIHKMEQKENVPPG

PEVCITHQEGEKISANENSLAVRSTPAEDDSRDSQVKSEVQQPVHPKPLSP

DSRASSLSESSPPKAMKKFQAPARETCVECQKTVYPMERLLANQQVFHISC

FRCSYCNNKLSLGTYASLHGRIYCKPHFNQLFKSKGNYDEGFGHRPHKDL

WASKNENEEILERPAQLANARETPHSPGVEDAPIAKVGVLAASMEAKASS

QQEKEDKPAETKKLRIAWPPPTELGSSGSALEEGIKMSKPKWPPEDEISKP

EVPEDVDLDLKKLRRSSSLKERSRPFTVAASFQSTSVKSPKTVSPPIRKGW

SMSEQSEESVGGRVAERKQVENAKASKKNGNVGKTTWQNKESKGETGK

RSKEGHSLEMENENLVENGADSDEDDNSFLKQQSPQEPKSLNWSSFVDN

TFAEEFTTQNQKSQDVELWEGEVVKELSVEEQIKRNRYYDEDEDEE

The term “cancer associated with a component of the NF-κB pathway downstream of a CBM complex” as used herein refers to cancers associated with or having a dysregulation of a gene, a protein, or the expression or activity or level of any (e.g., one or more) of the same associated with a component of the NF-κB pathway downstream of a CBM complex. In some embodiments, a cancer associated with a component of the NF-κB pathway downstream of a CBM complex is selected from the group consisting of a TAK1-associated cancer, a TRAF6-associated cancer, a TAB1-associated cancer, a TAB2-associated cancer, a TABS-associated cancer, a MKK7-associated cancer, an IKKα-associated cancer, an IKKβ-associated cancer, an IKKγ-associated cancer, an IkBα-associated cancer, a p50-associated cancer, a p65 (RelA)-associated cancer, a c-Rel-associated cancer, and combinations thereof. In some embodiments, a cancer associated with a component of the NF-κB pathway downstream of a CBM complex is an IKKγ-associated cancer. The cancers "associated" with a particular gene or protein described in this paragraph refer to cancers associated with or having a dysregulation of the particular gene, the particular protein, or the expression or activity or level of any (e.g., one or more) of the same (e.g., any of the types of dysregulation of the particular gene, the particular protein, or the expression or activity or level of any of the same described herein). Non-limiting examples of such cancers are described herein.

An exemplary sequence of human TAK1 is shown below:

```
(UniParc Accession No. UPI000012EAD6)
                                            SEQ ID NO: 20
MSTASAASSSSSSSAGEMIEAPSQVLNFEEIDYKEIEVEEVVGRGAFGVVC

KAKWRAKDVAIKQIESESERKAFIVELRQLSRVNHPNIVKLYGACLNPVC

LVMEYAEGGSLYNVLHGAEPLPYYTAAHAMSWCLQCSQGVAYLHSMQ

PKALIHRDLKPPNLLLVAGGTVLKICDFGTACDIQTHMTNNKGSAAWMA

PEVFEGSNYSEKCDVFSWGIILWEVITRRKPFDEIGGPAFRIMWAVHNGTR

PPLIKNLPKPIESLMTRCWSKDPSQRPSMEEIVKIMTHLMRYFPGADEPLQ

YPCQYSDEGQSNSATSTGSFMDIASTNTSNKSDTNMEQVPATNDTIKRLE

SKLLKNQAKQQSESGRLSLGASRGSSVESLPPTSEGKRMSADMSEIEARIA

ATTAYSKPKRGHRKTASFGNILDVPEIVISGNGQPRRRSIQDLTVTGTEPG

QVSSRSSSPSVRMITTSGPTSEKPTRSHPWTPDDSTDTNGSDNSIPMAYLT

LDHQLQPLAPCPNSKESMAVFEQHCKMAQEYMKVQTEIALLLQRKQELV

AELDQDEKDQQNTSRLVQEHKKLLDENKSLSTYYQQCKKQLEVIRSQQQ

KRQGTS
```

An exemplary sequence of human TRAF6 is shown below:

```
(UniParc Accession No. UPI000000D924)
                                            SEQ ID NO: 21
MSLLNCENSCGSSQSESDCCVAMASSCSAVTKDDSVGGTASTGNLSSSF

MEEIQGYDVEFDPPLESKYECPICLMALREAVQTPCGHRFCKACIIKSI

RDAGHKCPVDNEILLENQLFPDNFAKREILSLMVKCPNEGCLHKMELRH

LEDHQAHCEFALMDCPQCQRPFQKFHINIHILKDCPRRQVSCDNCAASM

AFEDKEIHDQNCPLANVICEYCNTILIREQMPNHYDLDCPTAPIPCTFS

TFGCHEKMQRNHLARHLQENTQSHMRMLAQAVHSLSVIPDSGYISEVRN

FQETIHQLEGRLVRQDHQIRELTAKMETQSMYVSELKRTIRTLEDKVAE

IEAQQCNGIYIWKIGNFGMHLKCQEEEKPVVIHSPGFYTGKPGYKLCMR

LHLQLPTAQRCANYISLFVHTMQGEYDSHLPWPFQGTIRLTILDQSEAP
```

-continued

```
VRQNHEEIMDAKPELLAFQRPTIPRNPKGFGYVTFMHLEALRQRTFIKD

DTLLVRCEVSTRFDMGSLRREGFQPRSTDAGV
```

An exemplary sequence of human TAB1 is shown below:

```
(UniParc Accession No. UPI0000136861)
                                            SEQ ID NO: 22
MAAQRRSLLQSEQQPSWTDDLPLCHLSGVGSASNRSYSADGKGTESHPP

EDSWLKFRSENNCFLYGVFNGYDGNRVTNFVAQRLSAELLLGQLNAEHA

EADVRRVLLQAFDVVERSFLESIDDALAEKASLQSQLPEGVPQHQLPPQ

YQKILERLKTLEREISGGAMAVVAVLLNNKLYVANVGTNRALLCKSTVD

GLQVTQLNVDHTTENEDELFRLSQLGLDAGKIKQVGIICGQESTRRIGD

YKVKYGYTDIDLLSAAKSKPIIAEPEIHGAQPLDGVTGFLVLMSEGLYK

ALEAAHGPGQANQEIAAMIDTEFAKQTSLDAVAQAVVDRVKRIHSDTFA

SGGERARFCPRHEDMTLLVRNFGYPLGEMSQPTPSPAPAAGGRVYPVSV

PYSSAQSTSKTSVTLSLVMPSQGQMVNGAHSASTLDEATPTLTNQSPTL

TLQSTNTHTQSSSSSSDGGLFRSRPAHSLPPGEDGRVEPYVDFAEFYRL

WSVDHGEQSVVTAP
```

An exemplary sequence of human TAB2 is shown below:

```
(UniParc Accession No. UPI0000073C75)
                                            SEQ ID NO: 23
MAQGSHQIDFQVLHDLRQKFPEVPEVVVSRCMLQNNNNLDACCAVLSQ

ESTRYLYGEGDLNFSDDSGISGLRNHMTSLNLDLQSQNIYHHGREGSRM

NGSRTLTHSISDGQLQGGQSNSELFQQEPQTAPAQVPQGFNVFGMSSSS

GASNSAPHLGFHLGSKGTSSLSQQTPRFNPIMVTLAPNIQTGRNTPTSL

HIHGVPPPVLNSPQGNSIYIRPYITTPGGTTRQTQQHSGWVSQFNPMNP

QQVYQPSQPGPWTTCPASNPLSHTSSQQPNQQGHQTSHVYMPISSPTTS

QPPTIHSSGSSQSSAHSQYNIQNISTGPRKNQIEIKLEPPQRNNSSKLR

SSGPRTSSTSSSVNSQTLNRNQPTVYIAASPPNTDELMSRSQPKVYISA

NAATGDEQVMRNQPTLFISTNSGASAASRNMSGQVSMGPAFIHHHPPKS

RAIGNNSATSPRVVVTQPNTKYTFKITVSPNKPPAVSPGVVSPTFELTN

LLNHPDHYVETENIQHLTDPTLAHVDRISETRKLSMGSDDAAYTQALLV

HQKARMERLQRELEIQKKKLDKLKSEVNEMENNLTRRRLKRSNSISQIP

SLEEMQQLRSCNRQLQIDIDCLTKEIDLFQARGPHFNPSAIHNFYDNIG

FVGPVPPKPKDQRSIIKTPKTQDTEDDEGAQWNCTACTFLNHPALIRCE

QCEMPRHF
```

An exemplary sequence of human TAB3 is shown below:

```
(UniParc Accession No. UPI0000071648)
                                            SEQ ID NO: 24
MAQSSPQLDIQVLHDLRQRFPEIPEGVVSQCMLQNNNNLEACCRALSQE

SSKYLYMEYHSPDDNRMNRNRLLHINLGIHSPSSYHPGDGAQLNGGRTL

VHSSSDGHIDPQHAAGKQLICLVQEPHSAPAVVAATPNYNPFFMNEQNR

SAATPPSQPPQQPSSMQTGMNPSAMQGPSPPPPPPSYMHIPRYSTNPIT
```

-continued

VTVSQNLPSGQTVPRALQILPQIPSNLYGSPGSIYIRQTSQSSSGRQTP
QSTPWQSSPQGPVPHYSQRPLPVYPHQQNYQPSQYSPKQQQIPQSAYHS
PPPSQCPSPFSSPQHQVQPSQLGHIFMPPSPSTTPPHPYQQGPPSYQKQ
GSHSVAYLPYTASSLSKGSMKKIEITVEPSQRPGTAINRSPSPISNQPS
PRNQHSLYTATTPPSSSPSRGISSQPKPPFSVNPVYITYTQPTGPSCTP
SPSPRVIPNPTTVFKITVGRATTENLLNLVDQEERSAAPEPIQPISVIP
GSGGEKGSHKYQRSSSSGSDDYAYTQALLLHQRARMERLAKQLKLEKEE
LERLKSEVNGMEHDLMQRRLRRVSCTTAIPTPEEMTRLRSMNRQLQINV
DCTLKEVDLLQSRGNFDPKAMNNFYDNIEPGPVVPPKPSKKDSSDPCTI
ERKARRISVTSKVQADIHDTQAAAADEHRTGSTQSPRTQPRDEDYEGAP
WNCDSCTFLNHPALNRCEQCEMPRYT

An exemplary sequence of human MKK7 is shown below:

(UniParc Accession No. UPI000012F494)
SEQ ID NO: 25
MAASSLEQKLSRLEAKLKQENREARRRIDLNLDISPQRPRPTLQLPLAN
DGGSRSPSSESSPQHPTPPARPRHMLGLPSTLFTPRSMESIEIDQKLQE
IMKQTGYLTIGGQRYQAEINDLENLGEMGSGTCGQVWKMRFRKTGHVIA
VKQMRRSGNKEENKRILMDLDVVLKSHDCPYIVQCFGTFITNTDVFIAM
ELMGTCAEKLKKRMQGPIPERILGKMTVAIVKALYYLKEKHGVIHRDVK
PSNILLDERGQIKLCDFGISGRLVDSKAKTRSAGCAAYMAPERIDPPDP
TKPDYDIRADVWSLGISLVELATGQFPYKNCKTDFEVLTKVLQEEPPLL
PGHMGFSGDFQSFVKDCLTKDHRKRPKYNKLLEHSFIKRYETLEVDVAS
WFKDVMAKTESPRTSGVLSQPHLPFFR An exemplary sequence of human IKKα is shown below:

(UniParc Accession No. UPI000013D6C7)
SEQ ID NO: 26
MERPPGLRPGAGGPWEMRERLGTGGFGNVCLYQHRELDLKIAIKSCRLE
LSTKNRERWCHEIQIMKKLNHANVVKACDVPEELNILIHDVPLLAMEYC
SGGDLRKLLNKPENCCGLKESQILSLLSDIGSGIRYLHENKIIHRDLKP
ENIVLQDVGGKIIHKIIDLGYAKDVDQGSLCTSFVGTLQYLAPELFENK
PYTATVDYWSFGTMVFECIAGYRPFLHHLQPFTWHEKIKKKDPKCIFAC
EEMSGEVRFSSHLPQPNSLCSLVVEPMENWLQLMLNWDPQQRGGPVDLT
LKQPRCFVLMDHILNLKIVHILNMTSAKIISFLLPPDESLHSLQSRIER
ETGINTGSQELLSETGISLDPRKPASQCVLDGVRGCDSYMVYLFDKSKT
VYEGPFASRSLSDCVNYIVQDSKIQLPIIQLRKVWAEAVHYVSGLKEDY
SRLFQGQRAAMLSLLRYNANLTKMKNTLISASQQLKAKLEFFHKSIQLD
LERYSEQMTYGISSEKMLKAWKEMEEKAIHYAEVGVIGYLEDQIMSLHA
EIMELQKSPYGRRQGDLMESLEQRAIDLYKQLKHRPSDHSYSDSTEMVK
IIVHTVQSQDRVLKELFGHLSKLLGCKQKIIDLLPKVEVALSNIKEADN
TVMFMQGKRQKEIWHLLKIACTQSSARSLVGSSLEGAVTPQTSAWLPPT -continued

SAEHDHSLSCVVTPQDGETSAQMIEENLNCLGHLSTIIHEANEEQGNSM
MNLDWSWLTE

An exemplary sequence of human IKKβ is shown below:

(UniParc Accession No. UPI0000033729)
SEQ ID NO: 27
MSWSPSLTTQTCGAWEMKERLGTGGFGNVIRWHNQETGEQIAIKQCRQE
LSPRNRERWCLEIQIMRRLTHPNVVAARDVPEGMQNLAPNDLPLLAMEY
CQGGDLRKYLNQFENCCGLREGAILTLLSDIASALRYLHENRIIHRDLK
PENIVLQQGEQRLIHKIIDLGYAKELDQGSLCTSFVGTLQYLAPELLEQ
QKYTVTVDYWSFGTLAFECITGFRPFLPNWQPVQWHSKVRQKSEVDIVV
SEDLNGTVKFSSSLPYPNNLNSVLAERLEKWLQLMLMWHPRQRGTDPTY
GPNGCFKALDDILNLKLVHILNMVTGTIHTYPVTEDESLQSLKARIQQD
TGIPEEDQELLQEAGLALIPDKPATQCISDGKLNEGHTLDMDLVFLFDN
SKITYETQISPRPQPESVSCILQEPKRNLAFFQLRKVWGQVWHSIQTLK
EDCNRLQQGQRAAMMNLLRNNSCLSKMKNSMASMSQQLKAKLDFFKTSI
QIDLEKYSEQTEFGITSDKLLLAWREMEQAVELCGRENEVKLLVERMMA
LQTDIVDLQRSPMGRKQGGTLDDLEEQARELYRRLREKPRDQRTEGDSQ
EMVRLLLQAIQSFEKKVRVIYTQLSKTVVCKQKALELLPKVEEVVSLMN
EDEKTVVRLQEKRQKELWNLLKIACSKVRGPVSGSPDSMNASRLSQPGQ
LMSQPSTASNSLPEPAKKSEELVAEAHNLCTLLENAIQDTVREQDQSFT
ALDWSWLQTEEEEHSCLEQAS An exemplary sequence of human IKKγ is shown below:

(UniParc Accession No. UPI0000000CC4)
SEQ ID NO: 28
MNRHLWKSQLCEMVQPSGGPAADQDVLGEESPLGKPAMLHLPSEQGAP
ETLQRCLEENQELRDAIRQSNQILRERCEELLHFQASQREEKEFLMCKF
QEARKLVERLGLEKLDLKRQKEQALREVEHLKRCQQQMAEDKASVKAQV
TSLLGELQESQSRLEAATKECQALEGRARAASEQARQLESEREALQQQH
SVQVDQLRMQGQSVEAALRMERQAASEEKRKLAQLQVAYHQLFQEYDNH
IKSSVVGSERKRGMQLEDLKQQLQQAEEALVAKQEVIDKLKEEAEQHKI
VMETVPVLKAQADIYKADFQAERQAREKLAEKKELLQEQLEQLQREYSK
LKASCQESARIEDMRKRHVEVSQAPLPPAPAYLSSPLALPSQRRSPPEE
PPDFCCPKCQYQAPDMDTLQIHVMECIE Non-limiting examples of dysregulation of an IKKγ gene or an IKKγ protein are described in, for example, Courtois and Gilmore, Oncogene 25.51 (2006): 6831-6843.

An exemplary sequence of human IkBα is shown below:

(UniParc Accession No. UPI000004F0A9)
SEQ ID NO: 29
MFQAAERPQEWAMEGPRDGLKKERLLDDRHDSGLDSMKDEEYEQMVK
ELQEIRLEPQEVPRGSEPWKQQLTEDGDSFLHLAIIHEEKALTMEVIRQ
VKGDLAFLNFQNNLQQTPLHLAVITNQPEIAEALLGAGCDPELRDFRGN
TPLHLACEQGCLASVGVLTQSCTTPHLHSILKATNYNGHTCLHLASIHG -continued

YLGIVELLVSLGADVNAQEPCNGRTALHLAVDLQNPDLVSLLLKCGADV

NRVTYQGYSPYQLTWGRPSTRIQQQLGQLTLENLQMLPESEDEESYDTE

SEFTEFTEDELPYDDCVFGGQRLTL

An exemplary sequence of human p105, which is processed into p50, is shown below:

(UniParc Accession No. UPI000000D917)

SEQ ID NO: 30

MAEDDPYLGRPEQMFHLDPSLTHTIFNPEVFQPQMALPTDGPYLQILEQP

KQRGFRFRYVCEGPSHGGLPGASSEKNKKSYPQVKICNYVGPAKVIVQLV

TNGKNIHLHAHSLVGKHCEDGICTVTAGPKDMVVGFANLGILHVTKKKV

FETLEARMTEACIRGYNPGLLVHPDLAYLQAEGGGDRQLGDREKELIRQA

ALQQTKEMDLSVVRLMFTAFLPDSTGSFTRRLEPVVSDAIYDSKAPNASN

LKIVRMDRTAGCVTGGEEIYLLCDKVQKDDIQIRFYEEEENGGVWEGFGD

FSPTDVHRQFAIVFKTPKYKDINITKPASVFVQLRRKSDLETSEPKPFLY

YPEIKDKEEVQRKRQKLMPNFSDSFGGGSGAGAGGGGMFGSGGGGGGTGS

TGPGYSFPHYGFPTYGGITFHPGTTKSNAGMKHGTMDTESKKDPEGCDK

SDDKNTVNLFGKVIETTEQDQEPSEATVGNGEVTLTYATGTKEESAGVQD

NLFLEKAMQLAKRHANALFDYAVTGDVKMLLAVQRHLTAVQDENGDS

VLHLAIIHLHSQLVRDLLEVTSGLISDDIINMRNDLYQTPLHLAVITKQE

DVVEDLLRAGADLSLLDRLGNSVLHLAAKEGHDKVLSILLKHKKAALLLD

HPNGDGLNAIHLAMMSNSLPCLLLLVAAGADVNAQEQKSGRTALHLAVE

HDNISLAGCLLLEGDAHVDSTTYDGTTPLHIAAGRGSTRLAALLKAAGAD

PLVENFEPLYDLDDSWENAGEDEGVVPGTTPLDMATSWQVFDILNGKPY

EPEFTSDDLLAQGDMKQLAEDVKLQLYKLLEIPDPDKNWATLAQKLGLG

ILNNAFRLSPAPSKTLMDNYEVSGGTVRELVEALRQMGYTEAIEVIQAAS

SPVKTTSQAHSLPLSPASTRQQIDELRDSDSVCDSGVETSFRKLSFTESL

TSGASLLTLNKMPHDYGQEGPLEGKI

An exemplary sequence of human p65 is shown below:

(UniParc Accession No. UPI000013ED68)

SEQ ID NO: 31

MDELFPLIFPAEPAQASGPYVEIIEQPKQRGMRFRYKCEGRSAGSIPGER

STDTTKTHPTIKINGYTGPGTVRISLVTKDPPHRPHPHELVGKDCRDGFY

EAELCPDRCIHSFQNLGIQCVKKRDLEQAISQRIQTNNNPFQVPIEEQRG

DYDLNAVRLCFQVTVRDPSGRPLRLPPVLSHPIFDNRAPNTAELKICRVN

RNSGSCLGGDEIFLLCDKVQKEDIEVYFTGPGWEARGSFSQADVHRQVAI

VFRTPPYADPSLQAPVRVSMQLRRPSDRELSEPMEFQYLPDTDDRHRIEE

KRKRTYETFKSIMKKSPFSGPTDPRPPPRRIAVPSRSSASVPKPAPQPYP

FTSSLSTINYDEFPTMVFPSGQISQASALAPAPPQVLPQAPAPAPAPAMV

SALAQAPAPVPVLAPGPPQAVAPPAPKPTQAGEGTLSEALLQLQFDDEDL

-continued

GALLGNSTDPAVFTDLASVDNSEFQQLLNQGIPVAPHTTEPMLMEYPEAI

TRLVTGAQRPPDPAPAPLGAPGLPNGLLSGDEDFSSIADMDFSALLSQIS

S

An exemplary sequence of human c-Rel is shown below:

(UniParc Accession No. UPI000013367B)

SEQ ID NO: 32

MASGAYNPYIEIIEQPRQRGMRFRYKCEGRSAGSIPGEHSTDNNRTYPSI

QIMNYYGKGKVRITLVTKNDPYKPHPHDLVGKDCRDGYYEAEFGQERRPL

FFQNLGIRCVKKKEVKEAIITRIKAGINPFNVPEKQLNDIEDCDLNVVRL

CFQVFLPDEHGNLTTALPPVVSNPIYDNRAPNTAELRICRVNKNCGSVRG

GDEIFLLCDKVQKDDIEVRFVLNDWEAKGIFSQADVHRQVAIVEKTPPYC

KAITEPVTVKMQLRRPSDQEVSESMDFRYLPDEKDTYGNKAKKQKTTLLF

QKLCQDHVETGFRHVDQDGLELLTSGDPPTLASQSAGITVNFPERPRPGL

LGSIGEGRYFKKEPNLFSHDAVVREMPTGVSSQAESYYPSPGPISSGLSH

HASMAPLPSSSWSSVAHPTPRSGNTNPLSSFSTRTLPSNSQGIPPFLRIP

VGNDLNASNACIYNNADDIVGMEASSMPSADLYGISDPNMLSNCSVNMMT

TSSDSMGETDNPRLLSMNLENPSCNSVLDPRDLRQLHQMSSSSMSAGANS

NTTVFVSQSDAFEGSDFSCADNSMINESGPSNSTNPNSHGFVQDSQYSGI

GSMQNEQLSDSFPYEFFQV

The term "cancer associated with a component of the JNK pathway downstream of a CBM complex" as used herein refers to cancers associated with or having a dysregulation of a gene, a protein, or the expression or activity or level of any (e.g., one or more) of the same associated with a component of the JNK pathway downstream of a CBM complex. In some embodiments, a cancer associated with a component of the JNK pathway downstream of a CBM complex is selected from the group consisting of a JNK1-associated cancer, a JNK2-associated cancer, a JNK3-associated cancer, a MYD88 transcription factor-associated cancer, an AP-1 transcription factor-associated cancer, and combinations thereof. The cancers "associated" with a particular gene or protein described in this paragraph refer to cancers associated with or having a dysregulation of the particular gene, the particular protein, or the expression or activity or level of any (e.g., one or more) of the same (e.g., any of the types of dysregulation of the particular gene, the particular protein, or the expression or activity or level of any of the same described herein). Non-limiting examples of such cancers are described herein.

An exemplary sequence of human JNK1 is shown below:

(UniParc Accession No. UPI000012F17A)

SEQ ID NO: 33

MSRSKRDNNFYSVEIGDSTFTVLKRYQNLKPIGSGAQGIVCAAYDAILER

NVAIKKLSRPFQNQTHAKRAYRELVLMKCVNHKNIIGLLNVFTPQKSLEE

FQDVYIVMELMDANLCQVIQMELDHERMSYLLYQMLCGIKHLHSAGIIH

RDLKPSNIVVKSDCTLKILDFGLARTAGTSFMMTPYVVTRYYRAPEVILG

MGYKENVDLWSVGCIMGEMVCHKILFPGRDYIDQWNKVIEQLGTPCPEF

-continued

MKKLQPTVRTYVENRPKYAGYSFEKLFPDVLFPADSEHNKLKASQARDL

LSKMLVIDASKRISVDEALQHPYINVWYDPSEAEAPPPKIPDKQLDEREHT

IEEWKELIYKEVMDLEERTKNGVIRGQPSPLGAAVINGSQHPSSSSSVNDV

SSMSTDPTLASDTDSSLEAAAGPLGCCR

An exemplary sequence of human JNK2 is shown below:

(UniParc Accession No. UPI000006E3AD)

SEQ ID NO: 34

MSDSKCDSQFYSVQVADSTFTVLKRYQQLKPIGSGAQGIVCAAFDTVLGI

NVAVKKLSRPFQNQTHAKRAYRELVLLKCVNHKNIISLLNVFTPQKTLEE

FQDVYLVMELMDANLCQVIHMELDHERMSYLLYQMLCGIKHLHSAGIIH

RDLKPSNIVVKSDCTLKILDFGLARTACTNFMMTPYVVTRYYRAPEVILG

MGYKENVDIWSVGCIMGELVKGCVIFQGTDHIDQWNKVIEQLGTPSAEF

MKKLQPTVRNYVENRPKYPGIKFEELFPDWIFPSESERDKIKTSQARDLLS

KMLVIDPDKRISVDEALRHPYITVWYDPAEAEAPPPQIYDAQLEEREHAIE

EWKELIYKEVMDWEERSKNGVVKDQPSDAAVSSNATPSQSSSINDISSMS

TEQTLASDTDSSLDASTGPLEGCR

An exemplary sequence of human JNK3 is shown below:

(UniParc Accession No. UPI0000049042)

SEQ ID NO: 35

MSLHFLYYCSEPTLDVKIAFCQGFDKQVDVSYIAKHYNMSKSKVDNQFY

SVEVGDSTFTVLKRYQNLKPIGSGAQGIVCAAYDAVLDRNVAIKKLSRPF

QNQTHAKRAYRELVLMKCVNHKNIISLLNVFTPQKTLEEFQDVYLVMEL

MDANLCQVIQMELDHERMSYLLYQMLCGIKHLHSAGIIHRDLKPSNIVVK

SDCTLKILDFGLARTAGTSFMMTPYVVTRYYRAPEVILGMGYKENVDIW

SVGCIMGEMVRHKILFPGRDYIDQWNKVIEQLGTPCPEFMKKLQPTVRNY

VENRPKYAGLTFPKLFPDSLFPADSEHNKLKASQARDLLSKMLVIDPAKRI

SVDDALQHPYINVWYDPAEVEAPPPQIYDKQLDEREHTIEEWKELIYKEV

MNSEEKTKNGVVKGQPSPSGAAVNSSESLPPSSSVNDISSMSTDQTLASDT

DSSLEASAGPLGCCR

Compounds of Formula (I)

Provided herein are compounds of Formula (I), or a pharmaceutically acceptable salt thereof:

(I)

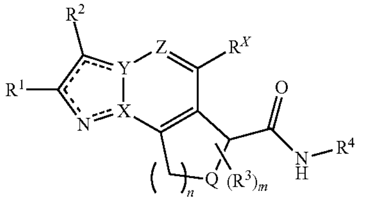

wherein:

each ═ is a single or double bond;

Q is —$CH_2$—, 0, or NH;

X is N or C;

Y is N or C;

Z is N or $CR^5$, wherein when one of X and Y is N, the other of X and Y is C;

n is 1, 2, or 3;

$R^X$ is hydrogen or halogen;

$R^1$ is hydrogen, halogen, cyano, hydroxyl, C1-C3 alkoxy, C1-C3 haloalkoxy, C1-C3 haloalkyl, —$NR^AR^B$, or C1-C3 alkyl optionally substituted with 1-3 substituents selected from hydroxyl and C1-C3 alkoxy;

Z is N or $CR^5$;

wherein when one of X and Y is N, the other of X and Y is C;

n is 1, 2, or 3;

$R^X$ is hydrogen or halogen;

$R^1$ is hydrogen, halogen, cyano, hydroxyl, C1-C3 alkoxy, C1-C3 haloalkoxy, C1-C3 haloalkyl, —$NR^AR^B$, or C1-C3 alkyl optionally substituted with 1-3 substituents selected from hydroxyl and C1-C3 alkoxy;

$R^2$ is hydrogen, halogen, amino, or C1-C3 alkyl;

each $R^3$ is independently deuterium, halogen, hydroxyl, C3-C6 cycloalkyl, C1-C3 alkyl, C1-C3 alkoxy, C1-C3 haloalkoxy, or C1-C3 haloalkyl; or two $R^3$ together with the carbon atom to which they are attached come together to form an oxo group, a 4-8 membered heterocyclyl, or a C3-C8 cycloalkyl;

m is 0, 1, 2, or 3;

$R^4$ is phenyl or 5-9 membered heteroaryl; wherein each $R^4$ group is optionally substituted with 1-3 substituents independently selected from $R^6$;

$R^5$ is hydrogen, halogen, cyano, hydroxyl, C1-C3 alkoxy, C1-C3 haloalkoxy, C1-C3 haloalkyl, —$NR^CR^D$, or C1-C3 alkyl; and each $R^6$ is independently selected from halogen; cyano; amino; —N═(S═O)(C1-C3 alkyl)$_2$; —S(═O)$_p$(C1-C3 alkyl); —(C═O)$NR^ER^F$; C1-C3 alkoxy; C1-C3 haloalkyl optionally substituted with hydroxyl; C1-C3 haloalkoxy; 5-6 membered heteroaryl optionally substituted with halogen, cyano, hydroxyl, C1-C3 alkoxy, C1-C3 haloalkoxy, amino, C1-C3 haloalkyl, 4-6 membered heterocyclyl, or C1-C3 alkyl optionally substituted with hydroxyl or —$NR^ER^F$; C1-C4 alkyl optionally substituted with hydroxyl, —$NR^ER^F$, or C1-C3 alkoxy; 3-8 membered heterocyclyl; and C3-C6 cycloalkoxy;

p is 1 or 2; and $R^A$, $R^B$, $R^C$, $R^D$, $R^E$ and $R^F$ are independently hydrogen, C1-C3 alkyl, C3-C6 cycloalkyl, or $R^A$ and $R^B$, or $R^C$ and $R^D$, or $R^E$ and $R^F$, together with the nitrogen atom to which they are attached come together to form a 4-6 membered heterocyclyl optionally substituted with 1-2 halogens.

In some embodiments, the compound of Formula (I), or a pharmaceutically acceptable salt thereof, has the structure:

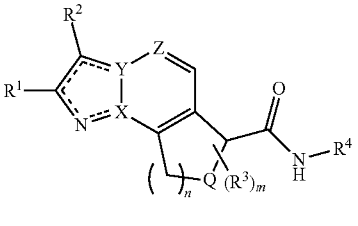

wherein:

each ═ is a single or double bond;

Q is —$CH_2$—, 0, or NH;

X is N or C;

Y is N or C;

Z is N or $CR^5$;

wherein when one of X and Y is N, the other of X and Y is C;

n is 1, 2, or 3;

$R^1$ is hydrogen, halogen, cyano, hydroxyl, C1-C3 alkoxy, C1-C3 haloalkoxy, C1-C3 haloalkyl, —$NR^AR^B$, or C1-C3 alkyl optionally substituted with 1-3 substituents selected from hydroxyl and C1-C3 alkoxy;

$R^2$ is hydrogen, halogen, amino, or C1-C3 alkyl;

each $R^3$ is independently deuterium, halogen, hydroxyl, C3-C6 cycloalkyl, C1-C3 alkyl, C1-C3 alkoxy, C1-C3 haloalkoxy, or C1-C3 haloalkyl; or two $R^3$ together with the carbon atom to which they are attached come together to form an oxo group, a 4-8 membered heterocyclyl, or a C3-C8 cycloalkyl;

m is 0, 1, 2, or 3;

$R^4$ is phenyl or 5-9 membered heteroaryl; wherein each $R^4$ group is optionally substituted with 1-3 substituents independently selected from $R^6$;

$R^5$ is hydrogen, halogen, cyano, hydroxyl, C1-C3 alkoxy, C1-C3 haloalkoxy, C1-C3 haloalkyl, —$NR^CR^D$, or C1-C3 alkyl; and each $R^6$ is independently selected from halogen; cyano; amino; —N═(S═O)(C1-C3 alkyl)$_2$; —S(═O)$_p$(C1-C3 alkyl); —(C═O)$NR^ER^F$; C1-C3 alkoxy; C1-C3 haloalkyl optionally substituted with hydroxyl; C1-C3 haloalkoxy; 5-6 membered heteroaryl optionally substituted with halogen, cyano, hydroxyl, C1-C3 alkoxy, C1-C3 haloalkoxy, amino, C1-C3 haloalkyl, 4-6 membered heterocyclyl, or C1-C3 alkyl optionally substituted with hydroxyl or —$NR^ER^F$; C1-C4 alkyl optionally substituted with hydroxyl, —$NR^ER^F$, or C1-C3 alkoxy; 3-8 membered heterocyclyl; and C3-C6 cycloalkoxy;

p is 1 or 2; and $R^A$, $R^B$, $R^C$, $R^D$, $R^E$ and $R^F$ are independently hydrogen, C1-C3 alkyl, C3-C6 cycloalkyl, or $R^A$ and $R^B$, or $R^C$ and $R^D$, or $R^E$ and $R^F$, together with the nitrogen atom to which they are attached come together to form a 4-6 membered heterocyclyl optionally substituted with 1-2 halogens.

In some embodiments, Q is —$CH_2$—. In some embodiments, Q is O. In some embodiments, Q is NH.

In some embodiments, the five-membered nitrogen-containing ring, formed in part by X and Y, is a heteroaromatic ring.

In some embodiments, X is C and Y is C.

In some embodiments, X is N and Y is C.

In some embodiments, X is C and Y is N.

In some embodiments, Z is N. In some embodiments, Z is $CR^5$.

In some embodiments, X is C; Y is C; and Z is $CR^5$. In some embodiments, X is N; Y is C; and Z is $CR^5$. In some embodiments, X is C; Y is N; and Z is $CR^5$. In some embodiments, X is C; Y is C; and Z is N. In some embodiments, X is N; Y is C; and Z is N. In some embodiments, X is C; Y is N; and Z is N.

In some embodiments, $R^1$ is halogen, cyano, hydroxyl, C1-C3 alkoxy, C1-C3 haloalkyl, —$NR^AR^B$, or C1-C3 alkyl optionally substituted with 1-3 substituents selected from hydroxyl and C1-C3 alkoxy.

In some embodiments, $R^1$ is halogen or cyano. In some embodiments, $R^1$ is chloro or cyano. In some embodiments, $R^1$ is hydrogen. In some embodiments, $R^1$ is halogen. In some embodiments, $R^1$ is fluoro. In some embodiments, $R^1$ is chloro. In some embodiments, $R^1$ is cyano. In some embodiments, $R^1$ is hydroxyl.

In some embodiments, $R^1$ is C1-C3 alkoxy. In some embodiments, $R^1$ is methoxy or ethoxy.

In some embodiments, $R^1$ is C1-C3 haloalkoxy. In some embodiments, $R^1$ is trifluoromethoxy, difluoromethoxy, or fluoromethoxy.

In some embodiments, $R^1$ is C1-C3 haloalkyl. In some embodiments, $R^1$ is difluoromethyl, trifluoromethyl or 2,2,2-trifluoroethyl.

In some embodiments, $R^1$ is —$NR^AR^B$. In some embodiments, $R^A$ and $R^B$ are independently hydrogen or C1-C3 alkyl. In certain embodiments, one of $R^A$ and $R^B$ is hydrogen and the other of $R^A$ and $R^B$ is C1-C3 alkyl. In some embodiments, one of $R^A$ and $R^B$ is hydrogen and the other of $R^A$ and $R^B$ is methyl. In some embodiments, one of $R^A$ and $R^B$ is hydrogen and the other of $R^A$ and $R^B$ is ethyl. In certain embodiments, $R^A$ and $R^B$ are both hydrogens. In certain embodiments, $R^A$ and $R^B$ are both C1-C3 alkyl. In some embodiments, $R^A$ and $R^B$ are both methyl. In some embodiments, one of $R^A$ and $R^B$ is methyl and the other of $R^A$ and $R^B$ is ethyl. In some embodiments, $R^A$ and $R^B$ are both ethyl.

In some embodiments, $R^A$ and $R^B$ together with the nitrogen atom to which they are attached come together to form a 4-6 membered heterocyclyl. In certain embodiments, $R^A$ and $R^B$ together with the nitrogen atom to which they are attached come together to form a 4 membered heterocyclyl. In some embodiments, $R^A$ and $R^B$ together with the nitrogen atom to which they are attached come together to form a 5 membered heterocyclyl. In some embodiments, $R^A$ and $R^B$ together with the nitrogen atom to which they are attached come together to form a 6 membered heterocyclyl.

In some embodiments, $R^1$ is C1-C3 alkyl optionally substituted with 1-3 substituents selected from hydroxyl and C1-C3 alkoxy. In certain embodiments, $R^1$ is C1-C3 alkyl optionally substituted with 1 substituent selected from hydroxyl and C1-C3 alkoxy. In certain of these embodiments, $R^1$ is methyl optionally substituted with 1 substituent selected from hydroxyl and C1-C3 alkoxy. In certain embodiments, $R^1$ is ethyl optionally substituted with 1 substituent selected from hydroxyl and C1-C3 alkoxy. In certain embodiments, $R^1$ is C1-C3 alkyl optionally substituted with hydroxyl. In certain embodiments, $R^1$ is C1-C3 alkyl optionally substituted with C1-C3 alkoxy (e.g., methoxy). In some embodiments, $R^1$ is hydroxymethyl or methoxyethyl.

In some embodiments, $R^1$ is unsubstituted C1-C3 alkyl (e.g., methyl or ethyl).

In some embodiments, $R^2$ is hydrogen. In some embodiments, $R^2$ is halogen. In some embodiments, $R^2$ is fluoro. In some embodiments, $R^2$ is chloro. In some embodiments, $R^2$ is amino. In some embodiments, $R^2$ is C1-C3 alkyl, such as methyl.

In some embodiments, n is 1, 2, or 3. In some embodiments, n is 1 or 2. In some embodiments, n is 2 or 3. In some embodiments, n is 1 or 3. In some embodiments, n is 1. In some embodiments, n is 2. In some embodiments, n is 3.

In some embodiments, m is 0, 1, 2, or 3. In some embodiments, m is 0, 1, or 2. In some embodiments, m is 1, 2, or 3. In some embodiments, m is 0, 2, or 3. In some embodiments, m is 0, 1, or 3. In some embodiments, m is 0 or 1. In some embodiments, m is 0 or 2. In some embodiments, m is 0 or 3. In some embodiments, m is 1 or 2. In some embodiments, m is 1 or 3. In some embodiments, m is 2 or 3. In some embodiments, m is 0. In some embodiments, m is 1. In some embodiments, m is 2. In some embodiments, m is 3.

In some embodiments, each $R^3$ is independently deuterium, halogen, hydroxyl, C3-C6 cycloalkyl, C1-C3 alkyl, C1-C3 haloalkyl, C1-C3 alkoxy, or C1-C3 haloalkoxy.

In some embodiments, each $R^3$ is deuterium.

In some embodiments, each $R^3$ is independently halogen. In some embodiments, $R^3$ is fluoro. In some embodiments, $R^3$ is chloro. In some embodiments, each $R^3$ is independently hydroxyl.

In some embodiments, each $R^3$ is independently C3-C6 cycloalkyl, C1-C3 alkyl, C1-C3 alkoxy, C1-C3 haloalkoxy, or C1-C3 haloalkyl.

In some embodiments, each $R^3$ is independently C1-C3 alkyl. For example, $R^3$ is methyl or ethyl. In some embodiments, each $R^3$ is independently C1-C3 alkoxy. For example, $R^3$ is methoxy or ethoxy. In some embodiments, each $R^3$ is independently C1-C3 haloalkoxy. For example, $R^3$ is trifluoromethoxy, difluoromethoxy, or fluoromethoxy. In some embodiments, each $R^3$ is independently C1-C3 haloalkyl. For example, each $R^3$ is trifluoromethyl or 2,2,2-trifluoroethyl.

In some embodiments, Q is —$CH_2$—, m is 1, and each $R^3$ is C1-C3 alkyl. In some embodiments, Q is —$CH_2$—, m is 2, and each $R^3$ is C1-C3 alkyl. In some embodiments, Q is —$CH_2$—, m is 2, and $R^3$ is C1-C3 alkyl, the $R^3$ groups are geminal C1-C3 alkyl groups. In some embodiments, Q is —$CH_2$— and each $R^3$ is independently C1-C3 alkyl. In some embodiments, Q is —$CH_2$—, m is 2, and the $R^3$ groups are geminal. In some embodiments, Q is —$CH_2$—, m is 2, and each $R^3$ is C1-C3 haloalkyl. In some embodiments, Q is —$CH_2$— and the $R^3$ groups are geminal C1-C3 haloalkyl groups In some embodiments, Q is —$CH_2$—, m is 2, one $R^3$ is C1-C3 alkyl, and the other $R^3$ is C1-C3 haloalkyl. In some embodiments, Q is —$CH_2$—, m is 2, one $R^3$ is C1-C3 alkoxy, and the other $R^3$ is C1-C3 haloalkyl. In some embodiments, Q is —$CH_2$—, the $R^3$ groups are geminal C1-C3 alkyl and C1-C3 haloalkyl groups In some embodiments, Q is —$CH_2$—, m is 2, one $R^3$ is C1-C3 alkyl and the other $R^3$ is C3-C6 cycloalkyl. In some embodiments, m is 2 and one $R^3$ is trifluoromethyl and the other $R^3$ is ethoxy. In some embodiments, Q is —$CH_2$— and the $R^3$ groups are geminal C1-C3 alkyl and C3-C6 cycloalkyl groups. In some embodiments, Q is —$CH_2$—, m is 2, and one $R^3$ is C1-C3 haloalkyl and the other $R^3$ is C3-C6 cycloalkyl. In some embodiments, Q is —$CH_2$— and the $R^3$ groups are geminal C1-C3 haloalkyl and C3-C6 cycloalkyl groups.

In some embodiments, Q is —$CH_2$—, m is 1, and each $R^3$ is methyl. In some embodiments, Q is —$CH_2$—, m is 2, and each $R^3$ is methyl. In some embodiments, Q is —$CH_2$—, m is 2, each $R^3$ is methyl, and the two $R^3$ groups are geminal methyl groups. In some embodiments, Q is —$CH_2$—, each $R^3$ is independently methyl. In some embodiments, Q is —$CH_2$—, m is 2, and the $R^3$ groups are geminal. In some embodiments, Q is —$CH_2$—, m is 2, and each $R^3$ is trifluoromethyl. In some embodiments, Q is —$CH_2$— and the $R^3$ groups are geminal trifluoromethyl groups. In some embodiments, Q is —$CH_2$—, m is 2, and one $R^3$ is methyl and the other $R^3$ is trifluoromethyl. In some embodiments, Q is —$CH_2$— and the $R^3$ groups are geminal methyl and trifluoromethyl groups. In some embodiments, Q is —$CH_2$—, m is 2, and one $R^3$ is methyl and the other $R^3$ is cyclopropyl. In some embodiments, Q is —$CH_2$— and the $R^3$ groups are geminal methyl and cyclopropyl groups. In some embodiments, Q is —$CH_2$—, m is 2, and one $R^3$ is trifluoromethyl and the other $R^3$ is cyclopropyl. In some embodiments, Q is —$CH_2$— and the $R^3$ groups are geminal trifluoromethyl and cyclopropyl groups.

In some embodiments, Q is —$CH_2$—, m is 2, and the two $R^3$ together with the carbon atom to which they are attached come together to form an oxo group. In some embodiments, m is 2 and the two $R^3$ together with the carbon atom to which they are attached come together to form a C3-C8 cycloalkyl (e.g., a cyclopropyl, cyclobutyl, cyclopentyl, cyclohexyl, cycloheptyl, or cyclooctyl). In some embodiments, m is 2 and the two $R^3$ together with the carbon atom to which they are attached form cyclopropyl or cyclobutyl.

In some embodiments, two $R^3$ together with the carbon atom to which they are attached come together to form a 4-8 membered heterocyclyl. In some embodiments, m is 2 and the two $R^3$ together with the carbon atom to which they are attached come together to form a 4-8 membered heterocyclyl. In some embodiments, two $R^3$ together with the carbon atom to which they are attached come together to form a 4-6 membered heterocyclyl. In some embodiments, two $R^3$ together with the carbon atom to which they are attached come together to form a 4 membered heterocyclyl such as oxetanyl or azetidinyl. In some embodiments, two $R^3$ together with the carbon atom to which they are attached come together to form a 5 membered heterocyclyl. In some embodiments, two $R^3$ together with the carbon atom to which they are attached come together to form a 6 membered heterocyclyl such tetrahydropyranyl. In some embodiments, m is 2 and the two $R^3$ together with the carbon atom to which they are attached form oxetanyl or tetrahydropyranyl.

In some embodiments, m is 3; two $R^3$ groups are methyl, and one $R^3$ is selected from the group consisting of methyl and hydroxyl.

In some embodiments, Q is O, m is 1, and each $R^3$ is C1-C3 alkyl. In some embodiments, Q is O, m is 2, and each $R^3$ is C1-C3 alkyl. In some embodiments, Q is O, m is 2, and $R^3$ is C1-C3 alkyl, the $R^3$ groups are geminal C1-C3 alkyl groups. In some embodiments, Q is O and each $R^3$ is independently C1-C3 alkyl. In some embodiments, Q is O, m is 2, and the $R^3$ groups are geminal. In some embodiments, Q is O, m is 2, and each $R^3$ is C1-C3 haloalkyl. In some embodiments, Q is 0 and the $R^3$ groups are geminal C1-C3 haloalkyl groups. In some embodiments, Q is O, m is 2, one $R^3$ is C1-C3 alkyl, and the other $R^3$ is C1-C3 haloalkyl. In some embodiments, Q is O, the $R^3$ groups are geminal C1-C3 alkyl and C1-C3 haloalkyl groups. In some embodiments, Q is O, m is 2, one $R^3$ is C1-C3 alkyl and the other $R^3$ is C3-C6 cycloalkyl. In some embodiments, Q is 0 and the $R^3$ groups are geminal C1-C3 alkyl and C3-C6 cycloalkyl groups. In some embodiments, Q is O, m is 2, and one $R^3$ is C1-C3 haloalkyl and the other $R^3$ is C3-C6 cycloalkyl. In some embodiments, Q is 0 and the $R^3$ groups are geminal C1-C3 haloalkyl and C3-C6 cycloalkyl groups.

In some embodiments, Q is O, m is 1, and each $R^3$ is methyl. In some embodiments, Q is O, m is 2, and each $R^3$ is methyl. In some embodiments, Q is O, m is 2, each $R^3$ is methyl, and the two $R^3$ groups are geminal methyl groups. In some embodiments, Q is O, each $R^3$ is independently methyl. In some embodiments, Q is O, m is 2, and the $R^3$ groups are geminal. In some embodiments, Q is O, m is 2, and each $R^3$ is trifluoromethyl. In some embodiments, Q is 0 and the $R^3$ groups are geminal trifluoromethyl groups. In some embodiments, Q is O, m is 2, and one $R^3$ is methyl and the other $R^3$ is trifluoromethyl. In some embodiments, Q is 0 and the $R^3$ groups are geminal methyl and trifluoromethyl groups. In some embodiments, Q is O, m is 2, and one $R^3$ is methyl and the other $R^3$ is cyclopropyl. In some embodiments, Q is 0 and the $R^3$ groups are geminal methyl and cyclopropyl groups. In some embodiments, Q is O, m is 2, and one $R^3$ is trifluoromethyl and the other $R^3$ is cyclopropyl. In some embodiments, Q is 0 and the $R^3$ groups are geminal trifluoromethyl and cyclopropyl groups.

In some embodiments, Q is O, m is 2, and the two $R^3$ together with the carbon atom to which they are attached come together with the carbon atom to which they are attached come together to form an oxo group. In some embodiments, m is 2 and the two $R^3$ together with the carbon atom to which they are attached come together to form a C3-C8 cycloalkyl (e.g., a cyclopropyl, cyclobutyl, cyclopentyl, cyclohexyl, cycloheptyl, or cyclooctyl).

In some embodiments, Q is NH, m is 1, and each $R^3$ is C1-C3 alkyl. In some embodiments, Q is NH, m is 2, and each $R^3$ is C1-C3 alkyl. In some embodiments, Q is NH, m is 2, and $R^3$ is C1-C3 alkyl, the $R^3$ groups are geminal C1-C3 alkyl groups. In some embodiments, Q is NH and each $R^3$ is independently C1-C3 alkyl. In some embodiments, Q is NH, m is 2, and the $R^3$ groups are geminal. In some embodiments, Q is NH, m is 2, and each $R^3$ is C1-C3 haloalkyl. In some embodiments, Q is NH and the $R^3$ groups are geminal C1-C3 haloalkyl groups. In some embodiments, Q is NH, m is 2, one $R^3$ is C1-C3 alkyl, and the other $R^3$ is C1-C3 haloalkyl. In some embodiments, Q is NH, the $R^3$ groups are geminal C1-C3 alkyl and C1-C3 haloalkyl groups. In some embodiments, Q is NH, m is 2, one $R^3$ is C1-C3 alkyl and the other $R^3$ is C3-C6 cycloalkyl. In some embodiments, Q is NH and the $R^3$ groups are geminal C1-C3 alkyl and C3-C6 cycloalkyl groups. In some embodiments, Q is NH, m is 2, and one $R^3$ is C1-C3 haloalkyl and the other $R^3$ is C3-C6 cycloalkyl. In some embodiments, Q is NH and the $R^3$ groups are geminal C1-C3 haloalkyl and C3-C6 cycloalkyl groups.

In some embodiments, Q is NH, m is 1, and each $R^3$ is methyl. In some embodiments, Q is NH, m is 2, and each $R^3$ is methyl. In some embodiments, Q is NH, m is 2, each $R^3$ is methyl, and the two $R^3$ groups are geminal methyl groups. In some embodiments, Q is NH, each $R^3$ is independently methyl. In some embodiments, Q is NH, m is 2, and the $R^3$ groups are geminal. In some embodiments, Q is NH, m is 2, and each $R^3$ is trifluoromethyl. In some embodiments, Q is NH and the $R^3$ groups are geminal trifluoromethyl groups. In some embodiments, Q is NH, m is 2, and one $R^3$ is methyl and the other $R^3$ is trifluoromethyl. In some embodiments, Q is NH and the $R^3$ groups are geminal methyl and trifluoromethyl groups. In some embodiments, Q is NH, m is 2, and one $R^3$ is methyl and the other $R^3$ is cyclopropyl. In some embodiments, Q is NH and the $R^3$ groups are geminal methyl and cyclopropyl groups. In some embodiments, Q is NH, m is 2, and one $R^3$ is trifluoromethyl and the other $R^3$ is cyclopropyl. In some embodiments, Q is NH and the $R^3$ groups are geminal trifluoromethyl and cyclopropyl groups.

In some embodiments, Q is NH, m is 2, and the two $R^3$ together with the carbon atom to which they are attached come together with the carbon atom to which they are attached come together to form an oxo group. In some embodiments, m is 2 and the two $R^3$ together with the carbon atom to which they are attached come together to form a C3-C8 cycloalkyl (e.g., a cyclopropyl, cyclobutyl, cyclopentyl, cyclohexyl, cycloheptyl, or cyclooctyl).

In some embodiments, $R^4$ is phenyl or 5-6 membered heteroaryl; wherein each $R^4$ group is optionally substituted with 1-2 independently selected $R^6$. In some embodiments, $R^4$ is phenyl or 5-6 membered heteroaryl; wherein each $R^4$ group is optionally substituted with 2-3 independently selected $R^6$. In some embodiments, $R^4$ is phenyl or 5-6 membered heteroaryl; wherein each $R^4$ group is optionally substituted with 1 or 3 independently selected $R^6$. In some embodiments, $R^4$ is phenyl or 5-6 membered heteroaryl; wherein each $R^4$ group is optionally substituted with 1 independently selected $R^6$. In some embodiments, $R^4$ is phenyl or 5-6 membered heteroaryl; wherein each $R^4$ group is optionally substituted with 2 independently selected $R^6$. In some embodiments, $R^4$ is phenyl or 5-6 membered heteroaryl; wherein each $R^4$ group is optionally substituted with 3 independently selected $R^6$.

In some embodiments, $R^4$ is phenyl or 5 membered heteroaryl; wherein each $R^4$ group is optionally substituted with 1-3 substituents independently selected from $R^6$. In some embodiments, $R^4$ is phenyl or 6 membered heteroaryl; wherein each $R^4$ group is optionally substituted with 1-3 substituents independently selected from $R^6$.

In some embodiments, $R^4$ is phenyl optionally substituted with 1-3 independently selected $R^6$. In certain embodiments, $R^4$ is phenyl optionally substituted with 1 $R^6$. In certain embodiments, $R^4$ is phenyl optionally substituted with 2 independently selected $R^6$. In certain embodiments, $R^4$ is phenyl optionally substituted with 3 independently selected $R^6$.

In some embodiments, $R^4$ is unsubstituted phenyl.

In some embodiments, $R^4$ is phenyl substituted with 1-3 substituents independently selected from $R^6$. In certain embodiments, $R^4$ is phenyl substituted with $R^6$. In certain embodiments, $R^4$ is phenyl substituted with 2 independently selected $R^6$. In some embodiments, $R^4$ is phenyl substituted with 3 independently selected $R^6$.

In some embodiments, $R^4$ is 5-6 membered heteroaryl optionally substituted with 1-3 (e.g., 2) substituents independently selected from $R^6$. In some embodiments, $R^4$ is 6 membered heteroaryl optionally substituted with 1-3 (e.g., 2) substituents independently selected from $R^6$.

In some embodiments, $R^4$ is unsubstituted 5-6 membered heteroaryl.

In some embodiments, $R^4$ is 5-6 membered heteroaryl substituted with 1-3 substituents independently selected from $R^6$.

In some embodiments, $R^4$ is 5-9 membered heteroaryl optionally substituted with 1-3 (e.g., 1 or 2) independently selected $R^6$. In some embodiments, $R^4$ is 5-9 membered heteroaryl substituted with 1-3 (e.g., 2) substituents independently selected from $R^6$. In some embodiments, $R^4$ is 9 membered heteroaryl optionally substituted with 1-3 (e.g., 2) substituents independently selected from $R^6$. In some embodiments, $R^4$ is 9 membered heteroaryl substituted with one substituent selected from $R^6$. In some embodiments, $R^4$ is 9 membered heteroaryl containing pyridyl. In some embodiments, $R^4$ is

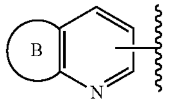, wherein ring B is a 4-5 membered heterocyclyl optionally substituted with 1-2 (e.g., 1) substituents selected from $R^6$. In some embodiments, $R^4$ is

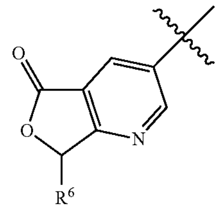

.

In some embodiments, $R^4$ is unsubstituted 5-6 membered heteroaryl. In some embodiments, at least one of $R^6$ is halogen. In some embodiments, at least one of $R^6$ is fluoro. In some embodiments, at least one of $R^6$ is chloro. In some embodiments, one of $R^6$ is halogen. In some embodiments, one of $R^6$ is fluoro. In some embodiments, one of $R^6$ is chloro. In some embodiments, two of $R^6$ is halogen. In some embodiments, two of $R^6$ is fluoro. In some embodiments, two of $R^6$ is chloro. In some embodiments, three of $R^6$ is halogen. In some embodiments, three of $R^6$ is fluoro. In some embodiments, three of $R^6$ is chloro. In some embodiments, at least one of $R^6$ is cyano. In some embodiments, at least one of $R^6$ is amino.

In some embodiments, at least one of $R^6$ is —(C═O)$NR^ER^F$. In some embodiments, $R^E$ and $R^F$ are independently hydrogen or C1-C3 alkyl. In some embodiments, one of $R^E$ and $R^F$ is hydrogen and the other of $R^E$ and $R^F$ is C1-C3 alkyl. In some embodiments, one of $R^E$ and $R^F$ is hydrogen and the other of $R^E$ and $R^F$ is C3-C6 cycloalkyl. In some embodiments, one of $R^E$ and $R^F$ is C1-C3 alkyl and the other of $R^E$ and $R^F$ is C3-C6 cycloalkyl. In some embodiments, one of $R^E$ and $R^F$ is hydrogen and the other of $R^E$ and $R^F$ is methyl. In some embodiments, one of $R^E$ and $R^F$ is hydrogen and the other of $R^E$ and $R^F$ is ethyl. In some embodiments, one of $R^E$ and $R^F$ is hydrogen and the other of $R^E$ and $R^F$ is cyclopropyl. In some embodiments, one of $R^E$ and $R^F$ is methyl and the other of $R^E$ and $R^F$ is cyclopropyl. In certain embodiments, $R^E$ and $R^F$ are both hydrogens. In certain embodiments, $R^E$ and $R^F$ are both C1-C3 alkyl. In some embodiments, $R^E$ and $R^F$ are both methyl. In some embodiments, one of $R^E$ and $R^F$ is methyl and the other of $R^E$ and $R^F$ is ethyl. In some embodiments, $R^E$ and $R^F$ are both ethyl.

In some embodiments, $R^E$ and $R^F$ together with the nitrogen atom to which they are attached come together to form a 4-6 membered heterocyclyl. In some embodiments, $R^E$ and $R^F$ together with the nitrogen atom to which they are attached come together to form a 4-6 membered heterocyclyl optionally substituted with 1-2 halogens. In certain embodiments, $R^E$ and $R^F$ together with the nitrogen atom to which they are attached come together to form a 4 membered heterocyclyl. In certain embodiments, $R^E$ and $R^F$ together with the nitrogen atom to which they are attached come together to form azetidine-1-yl or 3,3-difluoro-azetidine-1-yl. In some embodiments, $R^E$ and $R^F$ together with the nitrogen atom to which they are attached come together to form a 5 membered heterocyclyl. In some embodiments, $R^E$ and $R^F$ together with the nitrogen atom to which they are attached come together to form a 6 membered heterocyclyl.

In some embodiments, at least one of $R^6$ is —N═(S═O)(C1-C3 alkyl)$_2$. In some embodiments, each (C1-C3 alkyl) is the same. In some embodiments, each (C1-C3 alkyl) is different. In some embodiments, each (C1-C3 alkyl) is methyl.

In some embodiments, at least one of $R^6$ is —S(═O)$_p$(C1-C3 alkyl). In some embodiments, each (C1-C3 alkyl) is the same. In some embodiments, each (C1-C3 alkyl) is different. In some embodiments, each (C1-C3 alkyl) is methyl.

In some embodiments, p is 1. In some embodiments, p is 2.

In some embodiments, at least one of $R^6$ is C1-C3 alkoxy. In some embodiments, at least one of $R^6$ is methoxy or ethoxy.

In some embodiments, at least one of $R^6$ is C1-C3 haloalkyl optionally substituted with hydroxyl. In some embodiments, at least one of $R^6$ is unsubstituted C1-C3 haloalkyl. In some embodiments, at least one of $R^6$ is C1-C3 haloalkyl substituted with hydroxyl. In some embodiments, at least one of $R^6$ is trifluoromethyl, 2,2-difluoroethyl, or 2,2,2-trifluoroethyl. In some embodiments, at least one of $R^6$ is 1-hydroxy-2,2-difluoroethyl.

In some embodiments, at least one of $R^6$ is C1-C3 haloalkoxy. In some embodiments, at least one of $R^6$ is trifluoromethoxy.

In some embodiments, at least one of $R^6$ is 5-6 membered heteroaryl optionally substituted with halogen, cyano, hydroxyl, C1-C3 alkoxy, C1-C3 haloalkoxy, amino, C1-C3 haloalkyl, 4-6 membered heterocyclyl, or C1-C3 alkyl optionally substituted with hydroxyl or —$NR^ER^F$. In some embodiments, at least one of $R^6$ is 5-6 membered heteroaryl optionally substituted with halogen, cyano, hydroxyl, C1-C3 alkoxy, C1-C3 haloalkoxy, C1-C3 alkyl optionally substituted with hydroxyl or —$NR^ER^F$, amino, or C1-C3 haloalkyl. In some embodiments, $R^6$ is 5-6 membered heteroaryl optionally substituted with C1-C3 alkyl optionally substituted with hydroxyl or —$NR^ER^F$. In some embodiments, at least one of $R^6$ is 5-6 membered heteroaryl optionally substituted with halogen, C1-C3 haloalkyl, or C1-C3 alkyl optionally substituted with hydroxyl or —$NR^ER^F$. In some embodiments, $R^6$ is 5-6 membered heteroaryl substituted with C1-C3 alkyl substituted with hydroxyl or —$NR^ER^F$. In some embodiments, $R^6$ is 5-6 membered heteroaryl substituted with hydroxymethyl, aminomethyl, hydroxyethyl, aminoethyl, propan-2-ol, or propan-2-amine. In some embodiments, at least one of $R^6$ is 5-6 membered heteroaryl optionally substituted with a 4-6 membered heterocyclyl.

In certain embodiments, at least one of $R^6$ is 5 membered heteroaryl optionally substituted with halogen, cyano, hydroxyl, C1-C3 alkoxy, C1-C3 haloalkoxy, C1-C3 alkyl, amino, or C1-C3 haloalkyl. In some embodiments, at least one of $R^6$ is 6 membered heteroaryl optionally substituted with halogen, cyano, hydroxyl, C1-C3 alkoxy, C1-C3 haloalkoxy, amino, C1-C3 haloalkyl, or C1-C3 alkyl optionally substituted with hydroxyl or —$NR^ER^F$. In some embodiments, $R^6$ is 5 membered heteroaryl substituted with hydroxymethyl, aminomethyl, hydroxyethyl, aminoethyl, propan-2-ol, or propan-2-amine. In some embodiments, $R^6$ is 6 membered heteroaryl substituted with hydroxymethyl, aminomethyl, hydroxyethyl, aminoethyl, propan-2-ol, or propan-2-amine.

In some embodiments, at least one of $R^6$ is C1-C3 alkyl optionally substituted with hydroxyl, —$NR^ER^F$, or C1-C3 alkoxy. In some embodiments, at least one of $R^6$ is C1-C4 alkyl optionally substituted with hydroxyl, —$NR^ER^F$, or C1-C3 alkoxy. In certain embodiments, at least one of $R^6$ is methyl optionally substituted with hydroxyl, —$NR^ER^F$, or C1-C3 alkoxy. In some embodiments, at least one of $R^6$ is hydroxymethyl, 2-aminoethyl, or methoxyethyl. In some embodiments, at least one of $R^6$ is ethyl optionally substituted with hydroxyl, —$NR^ER^F$, or C1-C3 alkoxy. In some embodiments, at least one of $R^6$ is 1-hydroxyethyl or 2-hydroxypropan-2-yl.

In some embodiments, $R^E$ and $R^F$ are independently hydrogen or C1-C3 alkyl. In some embodiments, one of $R^E$ and $R^F$ is hydrogen and the other of $R^E$ and $R^F$ is C1-C3 alkyl. In some embodiments, one of $R^E$ and $R^F$ is hydrogen and the other of $R^E$ and $R^F$ is C3-C6 cycloalkyl. In some embodiments, one of $R^E$ and $R^F$ is C1-C3 alkyl and the other of $R^E$ and $R^F$ is C3-C6 cycloalkyl. In some embodiments, one of $R^E$ and $R^F$ is hydrogen and the other of $R^E$ and $R^F$ is methyl. In some embodiments, one of $R^E$ and $R^F$ is hydrogen and the other of $R^E$ and $R^F$ is ethyl. In some embodiments, one of $R^E$ and $R^F$ is hydrogen and the other of $R^E$ and $R^F$ is cyclopropyl. In some embodiments, one of $R^E$ and $R^F$ is methyl and the other of $R^E$ and $R^F$ is cyclopropyl. In certain embodiments, $R^E$ and $R^F$ are both hydrogens. In certain embodiments, $R^E$ and $R^F$ are both C1-C3 alkyl. In some embodiments, $R^E$ and $R^F$ are both methyl. In some embodiments, one of $R^E$ and $R^F$ is methyl and the other of $R^E$ and $R^F$ is ethyl. In some embodiments, $R^E$ and $R^F$ are both ethyl.

In some embodiments, $R^E$ and $R^F$ together with the nitrogen atom to which they are attached come together to form a 4-6 membered heterocyclyl. In certain embodiments, $R^E$ and $R^F$ together with the nitrogen atom to which they are attached come together to form a 4 membered heterocyclyl. In certain embodiments, $R^E$ and $R^F$ together with the nitrogen atom to which they are attached come together to form azetidinyl or 2-oxoazetidin-1-yl. In some embodiments, $R^E$ and $R^F$ together with the nitrogen atom to which they are attached come together to form a 5 membered heterocyclyl. In certain embodiments, $R^E$ and $R^F$ together with the nitrogen atom to which they are attached come together to form 2-oxopyrrolidin-1-yl. In some embodiments, $R^E$ and $R^F$ together with the nitrogen atom to which they are attached come together to form a 6 membered heterocyclyl.

In some embodiments, at least one of $R^6$ is 3-8 membered heterocyclyl. In certain embodiments, at least one of $R^6$ is 3 membered heterocyclyl. In certain embodiments, at least one of $R^6$ is 4 membered heterocyclyl. In certain embodiments, at least one of $R^6$ is 5 membered heterocyclyl. In certain embodiments, at least one of $R^6$ is 6 membered heterocyclyl. In certain embodiments, at least one of $R^6$ is 7 membered heterocyclyl. In certain embodiments, at least one of $R^6$ is 8 membered heterocyclyl.

In some embodiments, at least one of $R^6$ is C3-C6 cycloalkoxy. In some embodiments, at least one of $R^6$ is cyclopropoxy or cyclobutoxy.

In some embodiments, $R^4$ is pyridyl, pyrimidinyl, pyrazinyl, pyrrolyl, or imidazolyl; each of which is substituted with 2 $R^6$: one $R^6$ is triazolyl, imidazolyl, oxazolyl, pyrazolyl, or pyrrolidinyl; and the other $R^6$ is methyl, methoxy, trifluoromethyl, trifluoromethoxy, chloro, or cyano. In some embodiments, $R^4$ is pyridyl, pyrimidinyl, or pyrazinyl; each of which is substituted with 2 $R^6$: one $R^6$ is triazolyl, imidazolyl, oxazolyl, pyrazolyl, or pyrrolidinyl; and the other $R^6$ is methyl, methoxy, trifluoromethyl, trifluoromethoxy, chloro, or cyano. In some embodiments, $R^4$ is pyridyl substituted with 2 $R^6$: one $R^6$ is triazolyl, imidazolyl, or oxazolyl; and the other $R^6$ is methyl, methoxy, trifluoromethyl, trifluoromethoxy, chloro, or cyano.

In some embodiments, each $R^6$ is independently selected from halogen; cyano; amino; C1-C3 alkoxy; C1-C3 haloalkyl; C1-C3 haloalkoxy; C1-C3 alkyl; and C3-C6 cycloalkoxy.

In some embodiments, $R^4$ is 3-pyridyl or 4-pyridyl substituted with 1-3 independently selected $R^6$.

In some embodiments, $R^4$ is

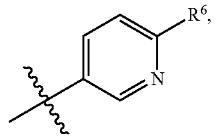

wherein the wavy line crosses the bond that connects to the —C(=O)NH— moiety of Formula (I).

In some embodiments, $R^4$ is

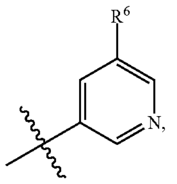

wherein the wavy line crosses the bond that connects to the —C(=O)NH— moiety of Formula (I).

In some embodiments, $R^4$ is

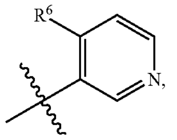

wherein the wavy line crosses the bond that connects to the —C(=O)NH— moiety of Formula (I).

In some embodiments, $R^4$ is

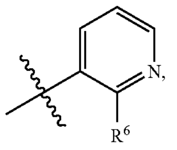

wherein the wavy line crosses the bond that connects to the —C(=O)NH— moiety of Formula (I).

In some embodiments, $R^4$ is

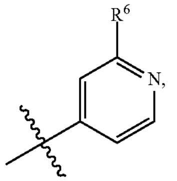

wherein the wavy line crosses the bond that connects to the —C(=O)NH— moiety of Formula (I).

In some embodiments, $R^4$ is

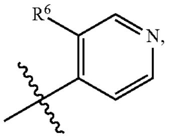

wherein the wavy line crosses the bond that connects to the —C(═O)NH— moiety of Formula (I).

In some embodiments, when $R^4$ is

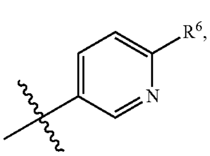
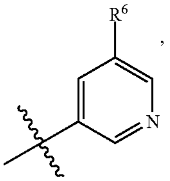
, or
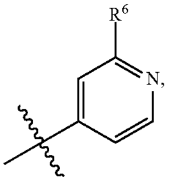

$R^6$ is selected from the group consisting of cyano, halogen, C1-C3 haloalkyl, and C1-C3 alkoxy.

In some embodiments, when $R^4$ is

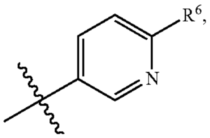
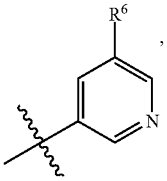
,
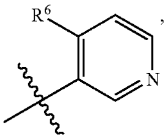
,
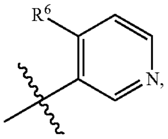
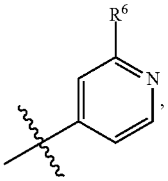
, or
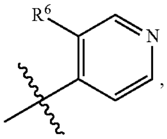
, $R^6$ is selected from the group consisting of cyano, halogen, C1-C3 haloalkyl optionally substituted with hydroxyl, C1-C3 haloalkoxy, and C1-C3 alkoxy.

In some embodiments, when $R^4$ is

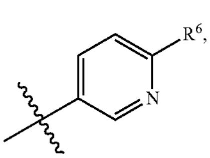
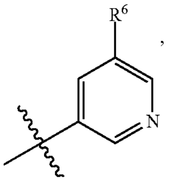
, or

-continued

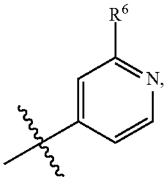

$R^6$ is selected from the group consisting of cyano, chloro, difluoromethyl, trifluoromethyl, difluoromethoxy, and methoxy. For example, when $R^4$ is

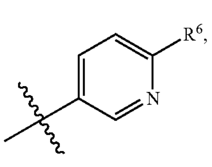
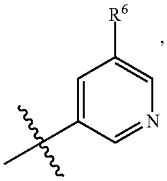
, or
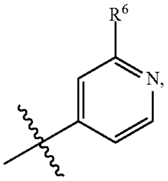

$R^6$ is chloro or trifluoromethyl (e.g., chloro).

In some embodiments, $R^4$ is

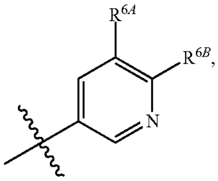

wherein $R^{6A}$ and $R^{6B}$ are independently selected from $R^6$ and the wavy line crosses the bond that connects to the —C(═O)NH— moiety of Formula (I).

In some embodiments, $R^4$ is

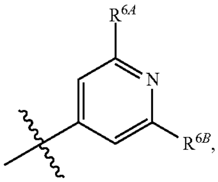

wherein $R^{6A}$ and $R^{6B}$ are independently selected from $R^6$ and the wavy line crosses the bond that connects to the —C(═O)NH— moiety of Formula (I).

In some embodiments, $R^4$ is

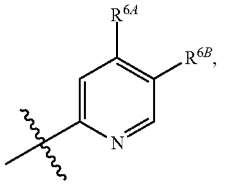

wherein $R^{6A}$ and $R^{6B}$ are independently selected from $R^6$ and the wavy line crosses the bond that connects to the —C(═O)NH— moiety of Formula (I).

In some embodiments, $R^4$ is

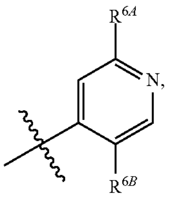

wherein $R^{6A}$ and $R^{6B}$ are independently selected from $R^6$ and the wavy line crosses the bond that connects to the —C(═O)NH— moiety of Formula (I).

In some embodiments, when $R^4$ is

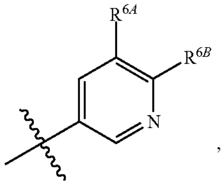
,
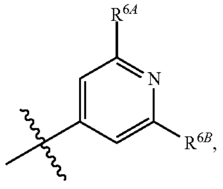

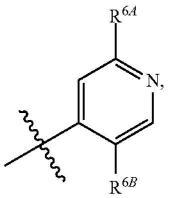
or
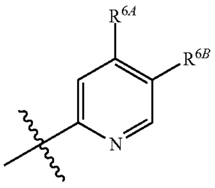
.

$R^{6A}$ is selected from the group consisting of: cyano, halogen, C1-C3 alkyl, C1-C3 alkoxy, and C1-C3 haloalkyl; and $R^{6B}$ is selected from the group consisting of: 5-6 membered heteroaryl optionally substituted with cyano, C1-C3 alkyl optionally substituted with hydroxyl, 4-6 membered heterocyclyl, or amino; —N═(S═O)(C1-C3 alkyl)$_2$; —(C═O)NR$^E$R$^F$; C1-C3 alkoxy; C1-C3 haloalkyl optionally substituted with hydroxyl; C1-C3 haloalkoxy; cyano; C3-C6 cycloalkoxy; and C1-C3 alkyl optionally substituted with hydroxyl.

In some embodiments, when $R^4$ is

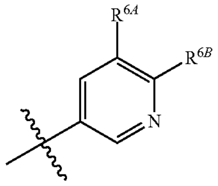
or
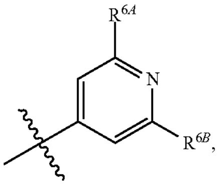

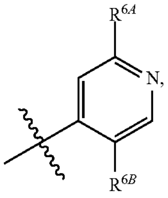
or
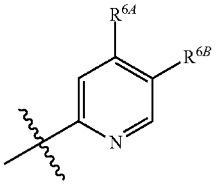

$R^{6A}$ is selected from the group consisting of: cyano, fluoro, chloro, methyl, ethyl, methoxy, trifluoromethyl; and $R^{6B}$ is selected from the group consisting of: 1,2,3-triazol-2-yl, 4-methyl-1,2,3-triazol-2-yl, 4-methyl-1,2,3-triazol-1-yl, 4-amino-1,2,3-triazol-2-yl, 5-cyano-1,2,3-triazol-1-yl, 1,2,3-triazol-1-yl, 3-methyl-1,2,4-triazol-1-yl, 5-methyl-1,2,4-triazol-1-yl, 5-amino-1,2,4-triazol-1-yl, 1-methyl-5-amino-1,2,4-triazol-3-yl, 1,2,4-triazol-4-on-2-yl, tetrazol-5-yl, 2-methyl-tetrazol-5-yl, 1-methyl-tetrazol-5-yl, imidazol-1-yl, 1-methyl-imidazol-3-yl, 1-methyl-5-amino-imidazol-3-yl, 3-methylimidazol-2-on-1-yl, 1-methyl-pyrazol-3-yl, 1-methyl-pyrazol-4-yl, 1-methyl-pyrazol-5-yl, pyrrol-1-yl, triazol-2-yl, isothiazolidin-2-yl-1,1-dioxide, pyrrolidin-2-on-1-yl, oxazol-2-yl, oxadiazol-2-yl, 2-amino-pyrimidin-4-yl, —(C═O)$_4$-methylpiperazin-1-yl, 2-oxoazetidin-1-yl, azetidin-1-yl, —(C═O)N(CH$_3$)$_2$, —(C═O)NHCH$_3$, —(C═O)NHCH$_2$CH$_3$, —(C═O)NHCyclopropyl, —(C═O)(3,3-difluoroazetidin-1-y), 2-hydroxypropan-2-yl, 1-hydroxyethy, dimethyl(oxo)-$\lambda^6$-sulfaneylidene, methoxy, ethoxy, difluoromethoxy, methyl, cyano.

In some embodiments, when $R^4$ is

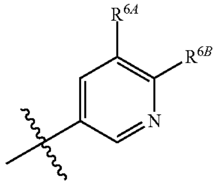
or
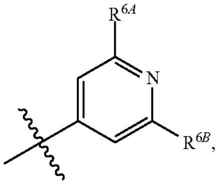

$R^{6A}$ is selected from the group consisting of: cyano, chloro, methyl, and trifluoromethyl; and $R^{6B}$ is selected from the group consisting of: 1,2,3-triazol-2-yl, 4-methyl-1,2,3-triazol-2-yl, 4-methyl-1,2,3-triazol-1-yl, 4-amino-1,2,3-triazol-2-yl, 5-cyano-1,2,3-triazol-1-yl, 1,2,3-triazol-1-yl, 3-methyl-1,2,4-triazol-1-yl, 5-methyl-1,2,4-triazol-1-yl, 5-amino-1,2,4-triazol-1-yl, 1-methyl-5-amino-1,2,4-triazol-3-yl, and 1,2,4-triazol-4-on-2-yl.

In some embodiments, when $R^4$ is

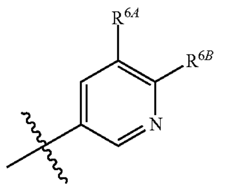
or
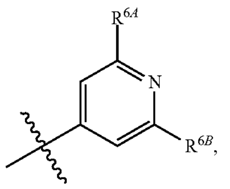

$R^{6A}$ is chloro; and $R^{6B}$ is selected from the group consisting of: 1,2,3-triazol-2-yl, 1,2,3-triazol-1-yl, and 1,2,4-triazol-4-on-2-yl.

In some embodiments, $R^4$ is

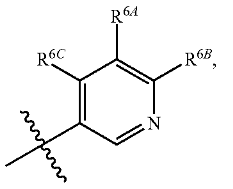

wherein $R^{6A}$, $R^{6B}$, and $R^{6C}$ are independently selected from $R^6$ and the wavy line crosses the bond that connects to the —C(═O)NH— moiety of Formula (I).

In some embodiments, $R^4$ is

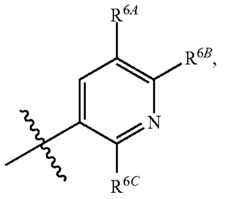

wherein $R^{6A}$, $R^{6B}$, and $R^{6C}$ are independently selected from $R^6$ and the wavy line crosses the bond that connects to the —C(═O)NH— moiety of Formula (I).

In some embodiments, when $R^4$ is

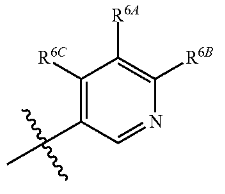
or
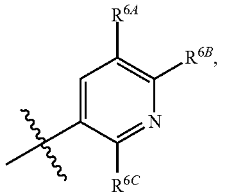

$R^{6A}$ is selected from the group consisting of: cyano, halogen, C1-C3 alkyl, C1-C3 alkoxy, and C1-C3 haloalkyl;

$R^{6B}$ is selected from the group consisting of: 5-6 membered heteroaryl optionally substituted with cyano, C1-C3 alkyl, or amino; —(C═O)NR$^E$R$^F$; C1-C3 alkoxy; C1-C3 haloalkyl; C1-C3 haloalkoxy; cyano; and C1-C3 alkyl; and $R^{6C}$ is selected from the group consisting of: cyano, halogen, C1-C3 alkyl, C1-C3 alkoxy, and C1-C3 haloalkyl.

In some embodiments, when $R^4$ is

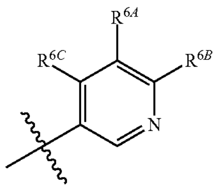
or
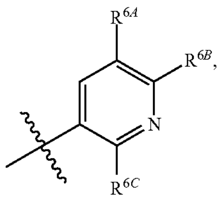

$R^{6A}$ is selected from the group consisting of: cyano, fluoro, chloro, methyl, ethyl, methoxy, trifluoromethyl;

$R^{6B}$ is selected from the group consisting of: 1,2,3-triazol-2-yl, 4-methyl-1,2,3-triazol-2-yl, 4-methyl-1,2,3-triazol-1-yl, 4-amino-1,2,3-triazol-2-yl, 5-cyano-1,2,3-triazol-1-yl, 1,2,3-triazol-1-yl, 3-methyl-1,2,4-triazol-1-yl, 5-methyl-1,2,4-triazol-1-yl, 5-amino-1,2,4-triazol-1-yl, 1-methyl-5-amino-1,2,4-triazol-3-yl, 1,2,4-triazol-4-on-2-yl, tetrazol-5-yl, 2-methyl-tetrazol-5-yl, 1-methyl-tetrazol-5-yl, imidazol-1-yl, 1-methyl-imidazol-3-yl, 1-methyl-5-amino-imidazol-3-yl, 3-methyl imidazol-2-on-1-yl, 1-methyl-pyrazol-3-yl, 1-methyl-pyrazol-5-yl, pyrrol-1-yl, thiazol-2-yl, isothiazolidin-2-yl-1,1-dioxide, pyrrolidin-2-on-1-yl, oxazol-2-yl, oxadiazol-2-yl, 2-amino-pyrimidin-4-yl, —(C═O)$_4$-methylpiperazin-1-yl, —(C═O)N$(CH_3)_2$, —(C═O)NH$CH_3$, methoxy, ethoxy, difluoromethoxy, methyl, cyano; and $R^{6C}$ is selected from the group consisting of: cyano, fluoro, chloro, methyl, ethyl, methoxy, methyl, and trifluoromethyl.

In some embodiments, when $R^4$ is

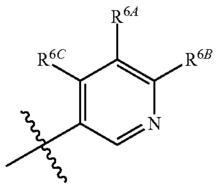
or
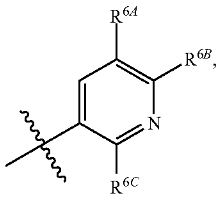

$R^{6A}$ is selected from the group consisting of: cyano, chloro, and trifluoromethyl;

$R^{6B}$ is selected from the group consisting of: 1,2,3-triazol-2-yl, 4-methyl-1,2,3-triazol-2-yl, 4-methyl-1,2,3-triazol-1-yl, 4-amino-1,2,3-triazol-2-yl, 5-cyano-1,2,3-triazol-1-yl, 1,2,3-triazol-1-yl, 3-methyl-1,2,4-triazol-1-yl, 5-methyl-1,2,4-triazol-1-yl, 5-amino-1,2,4-triazol-1-yl, 1-methyl-5-amino-1,2,4-triazol-3-yl, and 1,2,4-triazol-4-on-2-yl; and $R^{6C}$ is selected from the group consisting of: cyano, chloro, methyl, and trifluoromethyl.

In some embodiments, when $R^4$ is or

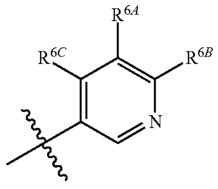
or
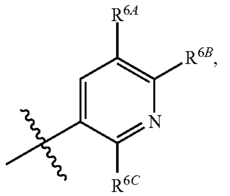

$R^{6A}$ is chloro;

$R^{6B}$ is selected from the group consisting of: 1,2,3-triazol-2-yl and 1,2,4-triazol-4-on-2-yl; and $R^{6C}$ is selected from the group consisting of: cyano, chloro, methyl, and trifluoromethyl.

In some embodiments, $R^5$ is hydrogen.

In some embodiments, $R^5$ is halogen. For example, $R^5$ is fluoro. For example, $R^5$ is chloro. In some embodiments, $R^5$ is cyano. In some embodiments, $R^5$ is hydroxyl.

In some embodiments, $R^5$ is C1-C3 alkoxy. In some embodiments, $R^5$ is methoxy or ethoxy.

In some embodiments, $R^5$ is C1-C3 haloalkoxy. In some embodiments, $R^5$ is trifluoromethoxy, difluoromethoxy, or fluoromethoxy.

In some embodiments, $R^5$ is C1-C3 haloalkyl. In some embodiments, $R^5$ is trifluoromethyl or 2,2,2-trifluoroethyl.

In some embodiments, $R^5$ is —$NR^CR^D$. In some embodiments, $R^C$ and $R^D$ are independently hydrogen or C1-C3 alkyl. In certain embodiments, one of $R^C$ and $R^D$ is hydrogen and the other of $R^C$ and $R^D$ is C1-C3 alkyl. In some embodiments, one of $R^C$ and $R^D$ is hydrogen and the other of $R^C$ and $R^D$ is methyl. In some embodiments, one of $R^C$ and $R^D$ is hydrogen and the other of $R^C$ and $R^D$ is ethyl. In certain embodiments, $R^C$ and $R^D$ are both hydrogens. In certain embodiments, $R^C$ and $R^D$ are both C1-C3 alkyl. In some embodiments, $R^C$ and $R^D$ are both methyl. In some embodiments, one of $R^C$ and $R^D$ is methyl and the other of $R^C$ and $R^D$ is ethyl. In some embodiments, $R^C$ and $R^D$ are both ethyl.

In some embodiments, $R^C$ and $R^D$ together with the nitrogen atom to which they are attached come together to form a 4-6 membered heterocyclyl. In certain embodiments, $R^C$ and $R^D$ together with the nitrogen atom to which they are attached come together to form a 4 membered heterocyclyl. In some embodiments, $R^C$ and $R^D$ together with the nitrogen atom to which they are attached come together to form a 5 membered heterocyclyl. In some embodiments, $R^C$ and $R^D$ together with the nitrogen atom to which they are attached come together to form a 6 membered heterocyclyl.

In some embodiments, $R^5$ is C1-C3 alkyl. In some embodiments, $R^5$ is methyl or ethyl.

In some embodiments, $R^X$ is hydrogen. In some embodiments, $R^X$ is halogen. In some embodiments, $R^X$ is fluoro. In some embodiments, $R^X$ is chloro.

In some embodiments, the compound is a compound selected from Table 1, or a pharmaceutically acceptable salt thereof.

TABLE 1

| Example Number | Structure |
| --- | --- |
| 1 (first eluting isomer)* 2 (second eluting isomer)* | 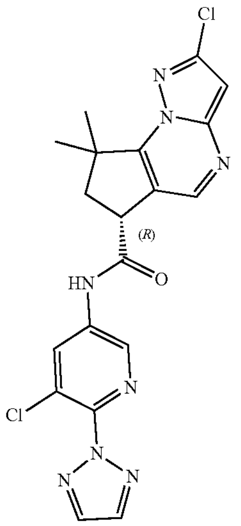 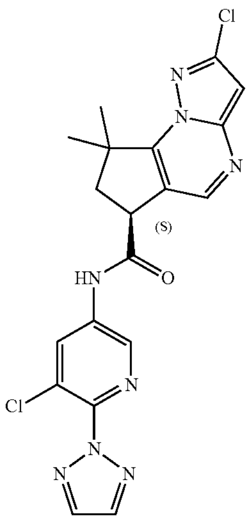 |

TABLE 1-continued
| Example Number | Structure |
| --- | --- |
| 3 (first eluting isomer)* 4 (second eluting isomer)* | 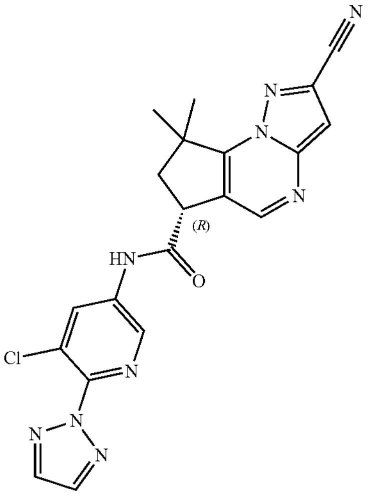 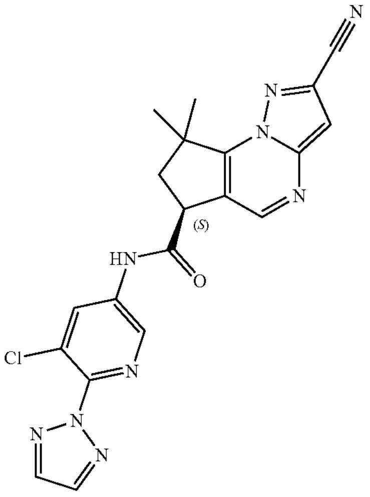 |
| 5 (first eluting isomer)* 6 (second eluting isomer)* | 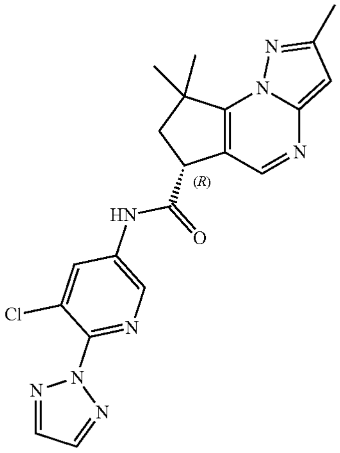 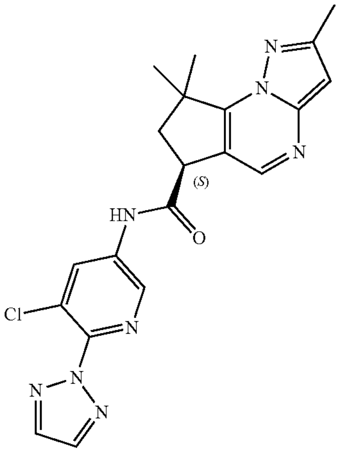 |
| 7 | 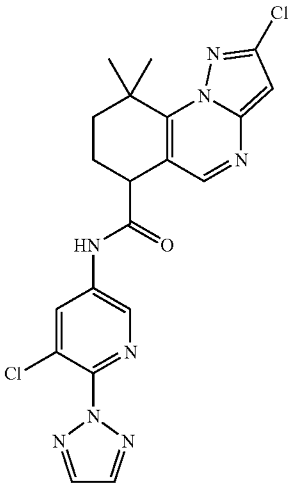 [SMILES: CC1(C)CCC(C(=O)Nc2cnc(-n3nccn3)c(Cl)c2)c2cnc3cc(Cl)nn3c21] |

TABLE 1-continued
| Example Number | Structure | |
|---|---|---|
| 8 (first eluting isomer)* 9 (second eluting isomer)* | 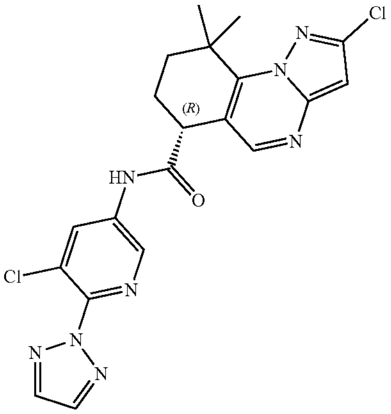 | 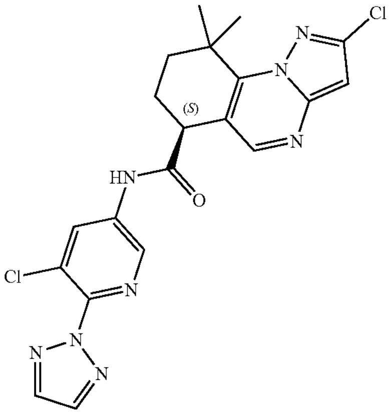 |
| 10 (first eluting isomer)* 11 (second eluting isomer)* | 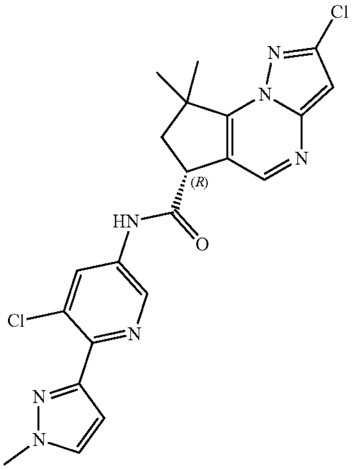 | 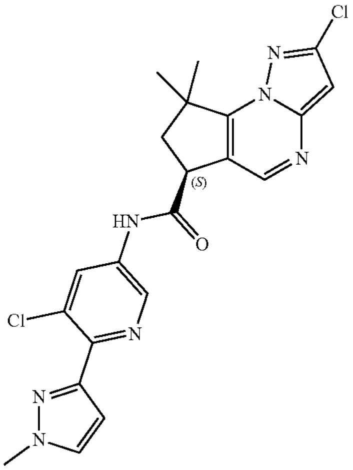 |
| 12 (first eluting isomer)* 13 (second eluting isomer)* | 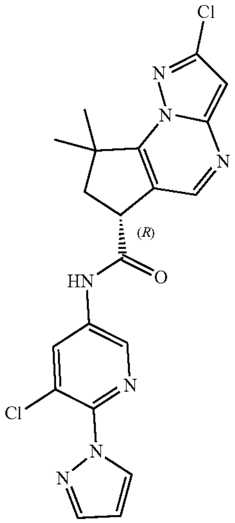 | 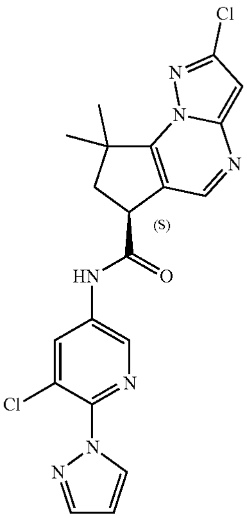 |

TABLE 1-continued
| Example Number | Structure | |
|---|---|---|
| 14 (first eluting isomer)* 15 (second eluting isomer)* | 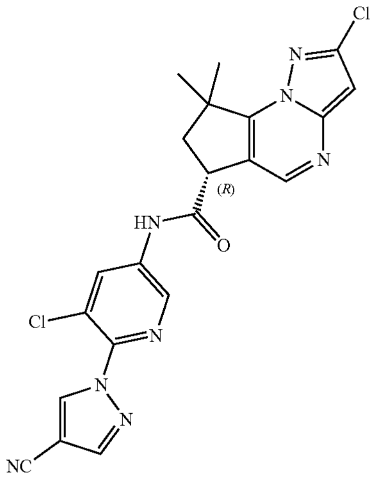 | 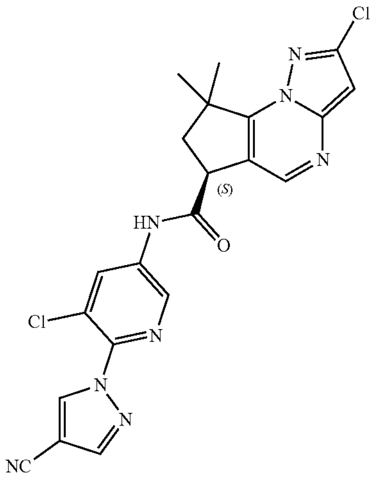 |
| 16 (first eluting isomer)* 17 (second eluting isomer)* | 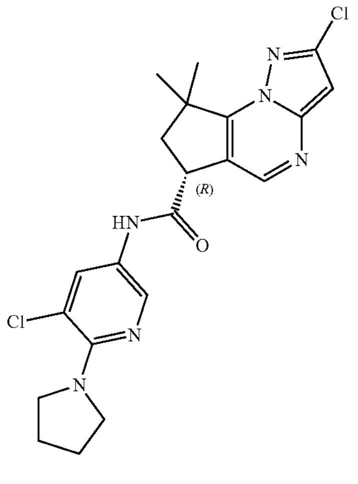 | 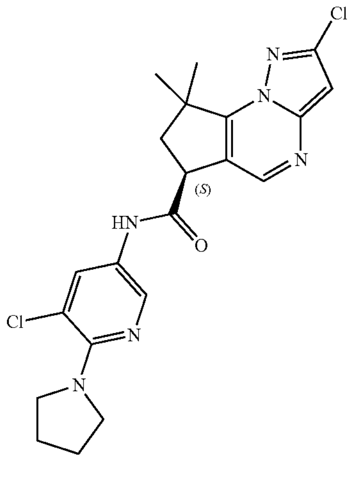 |
| 18 | 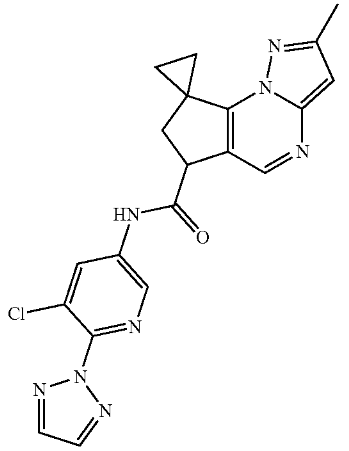 [SMILES: Cc1cc2ncc3c(n2n1)C1(CC1)CC3C(=O)Nc1cnc(-n2nccn2)c(Cl)c1] | |

TABLE 1-continued
| Example Number | Structure | |
|---|---|---|
| 19 | 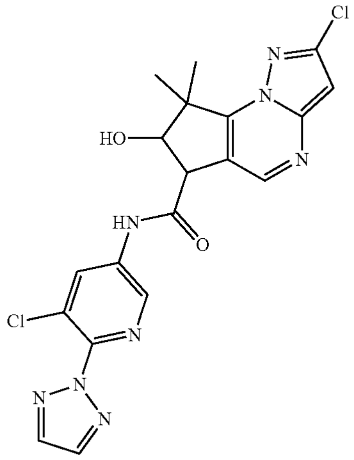 [SMILES: CC1(C)c2c(cnc3cc(Cl)nn23)C(C(=O)Nc2cnc(-n3nccn3)c(Cl)c2)C1O] | |
| 20 (first eluting isomer)* 21 (second eluting isomer)* | 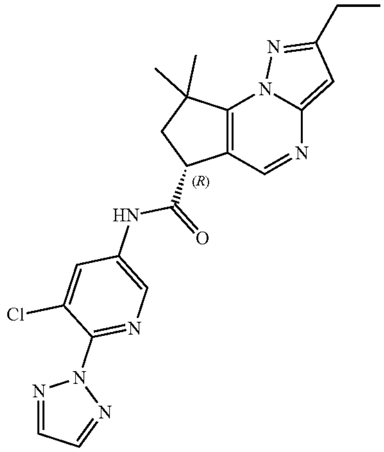 | 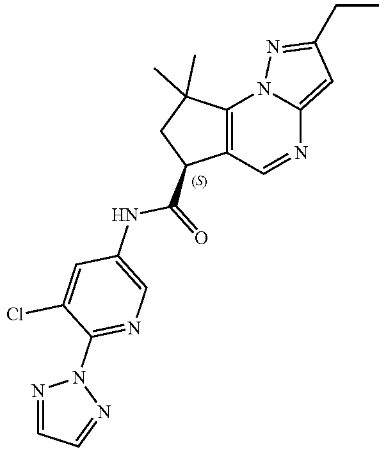 |
| 22 (first eluting isomer)* 23 (second eluting isomer)* | 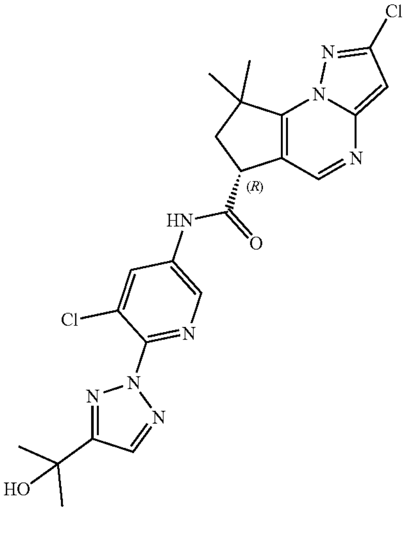 | 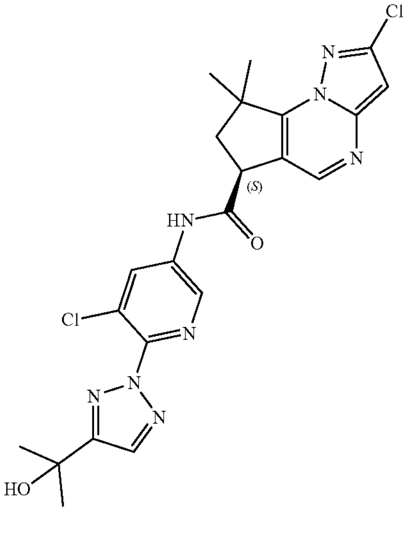 |

TABLE 1-continued
| Example Number | Structure | |
|---|---|---|
| 24 (first eluting isomer)* 25 (second eluting isomer)* | 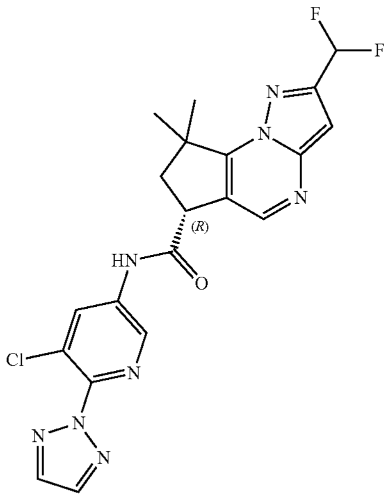 | 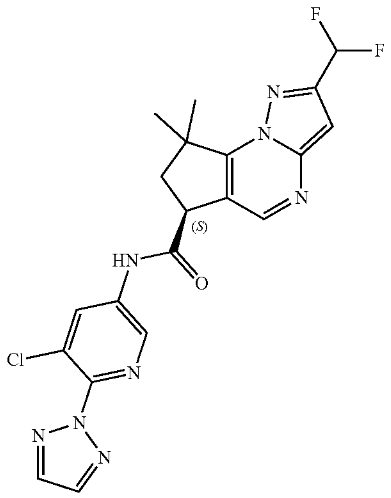 |
| 26, 27, 28 and 29* | 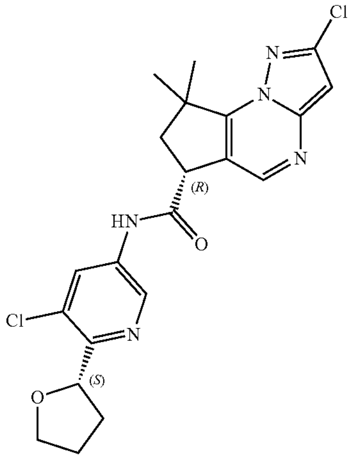 | 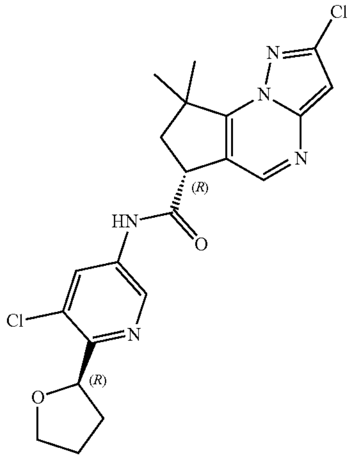 |
| | 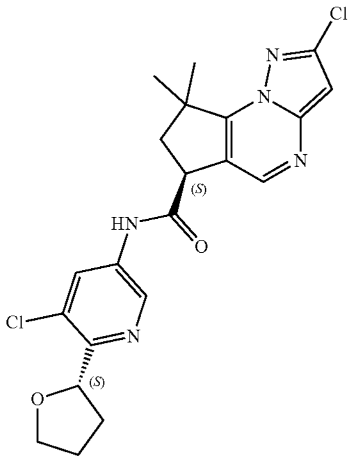 | 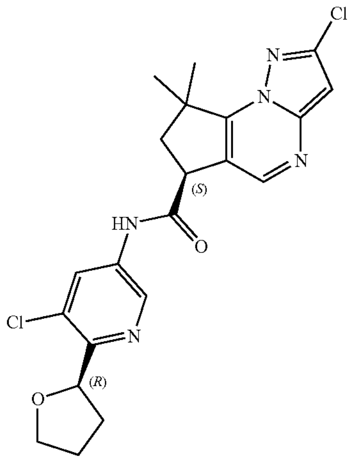 |

TABLE 1-continued
| Example Number | Structure |
|---|---|
| 30 (first eluting isomer)* 31 (second eluting isomer)* | 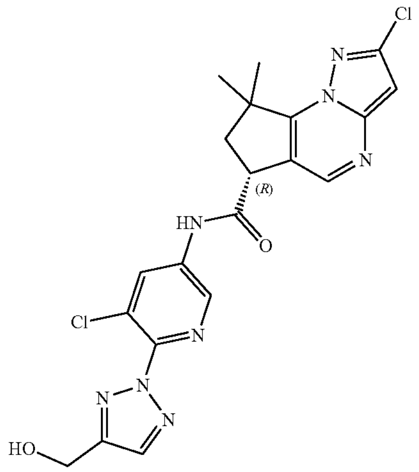 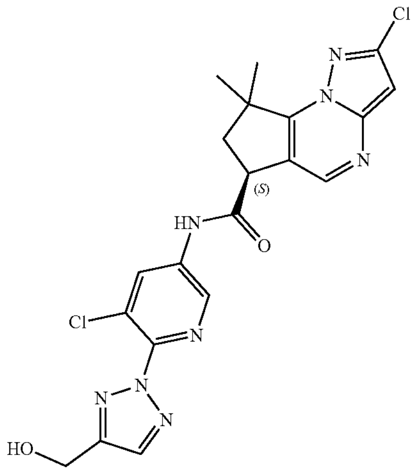 |
| 32 (first eluting isomer)* 33 (second eluting isomer)* | 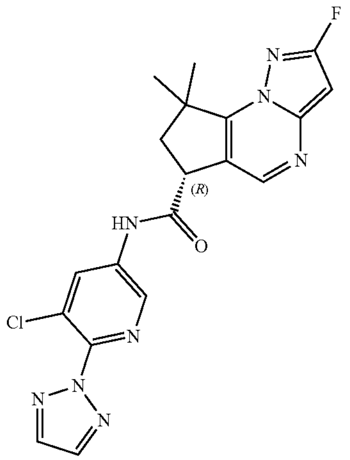 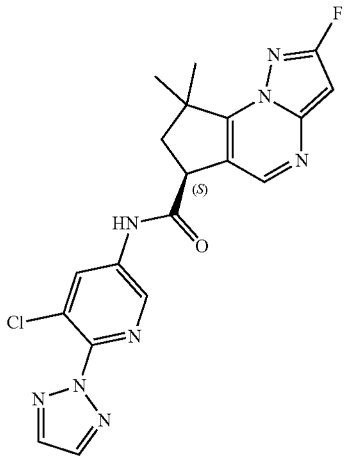 |
| 34 (first eluting isomer)* 35 (second eluting isomer)* | 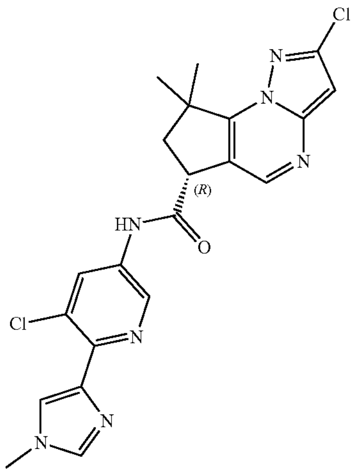 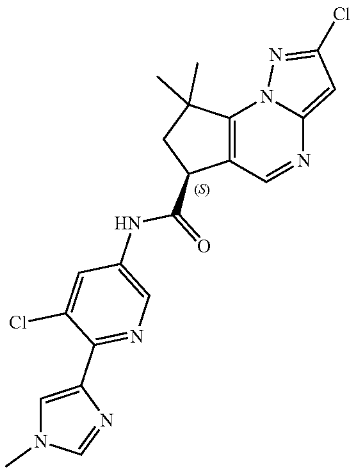 |

TABLE 1-continued
| Example Number | Structure |
| --- | --- |
| 36, 37, 38 and 39* | 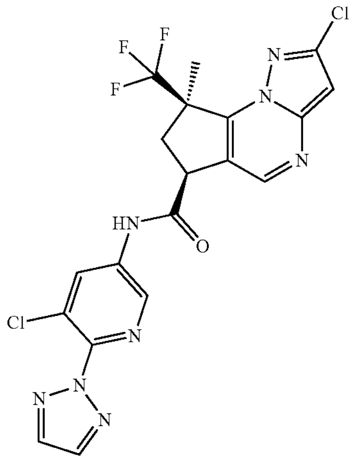 [SMILES: C[C@@]1(C(F)(F)F)C[C@H](C(=O)Nc2cnc(-n3nccn3)c(Cl)c2)c2cnc3cc(Cl)nn3c21] 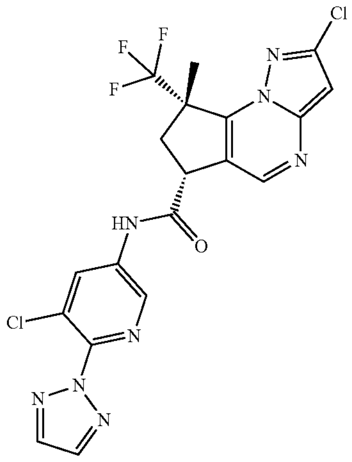 [SMILES: C[C@]1(C(F)(F)F)C[C@@H](C(=O)Nc2cnc(-n3nccn3)c(Cl)c2)c2cnc3cc(Cl)nn3c21] 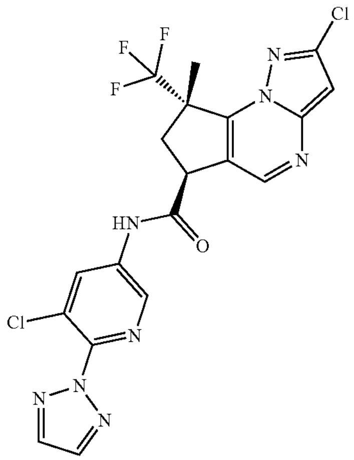 [SMILES: C[C@]1(C(F)(F)F)C[C@H](C(=O)Nc2cnc(-n3nccn3)c(Cl)c2)c2cnc3cc(Cl)nn3c21] 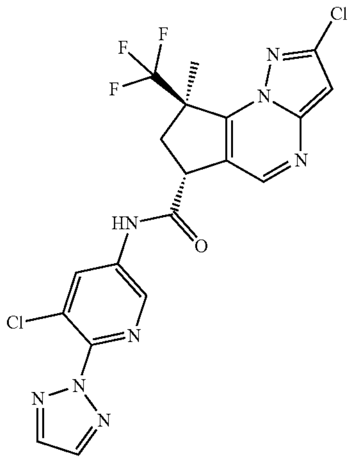 [SMILES: C[C@@]1(C(F)(F)F)C[C@@H](C(=O)Nc2cnc(-n3nccn3)c(Cl)c2)c2cnc3cc(Cl)nn3c21] |
| 40 | 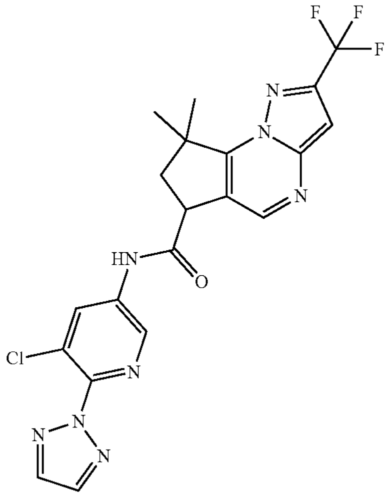 [SMILES: CC1(C)CC(C(=O)Nc2cnc(-n3nccn3)c(Cl)c2)c2cnc3cc(C(F)(F)F)nn3c21] |

TABLE 1-continued
| Example Number | Structure |
|---|---|
| 41 | 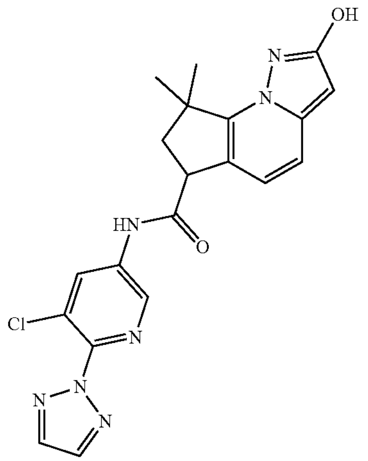 [SMILES: CC1(C)CC(C(=O)Nc2cnc(-n3nccn3)c(Cl)c2)c2ccc3cc(O)nn3c21] |
| 42 | 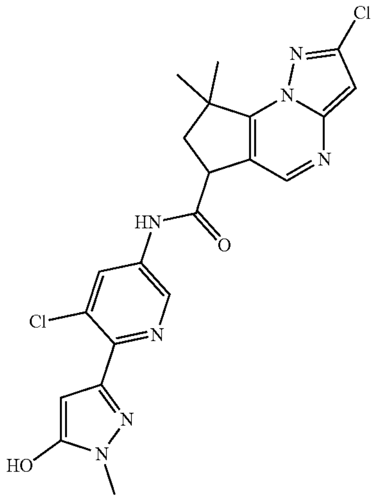 [SMILES: Cn1nc(-c2ncc(NC(=O)C3CC(C)(C)c4c3cnc3cc(Cl)nn43)cc2Cl)cc1O] |
| 43 | 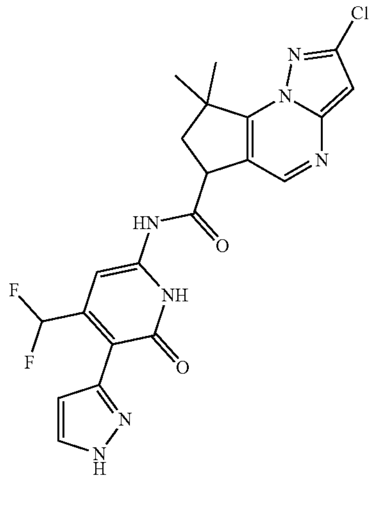 [SMILES: CC1(C)CC(C(=O)Nc2cc(C(F)F)c(-c3cc[nH]n3)c(=O)[nH]2)c2cnc3cc(Cl)nn3c21] |

TABLE 1-continued
| Example Number | Structure | |
|---|---|---|
| 44 (first eluting isomer)* 45 (second eluting isomer)* | 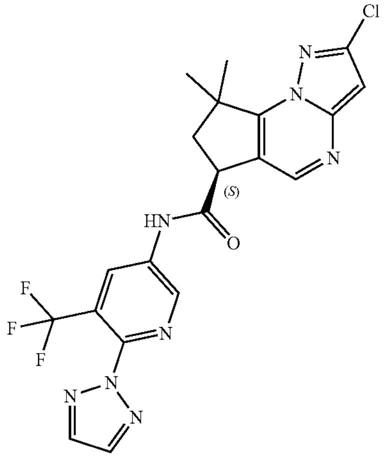 | 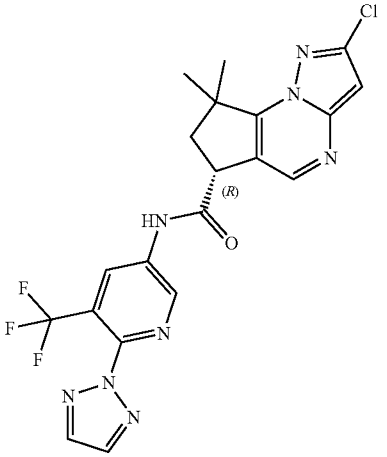 |
| 46 (first eluting isomer)* 47 (second eluting isomer)* | 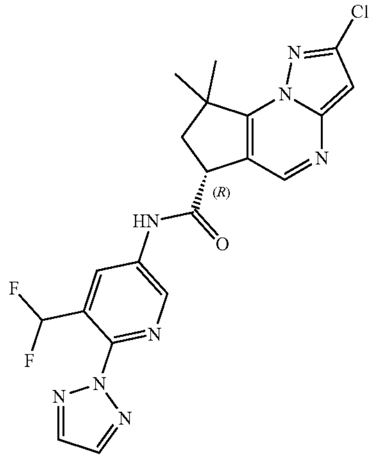 | 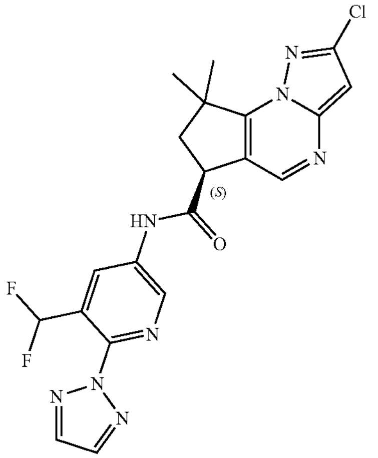 |
| 48 | 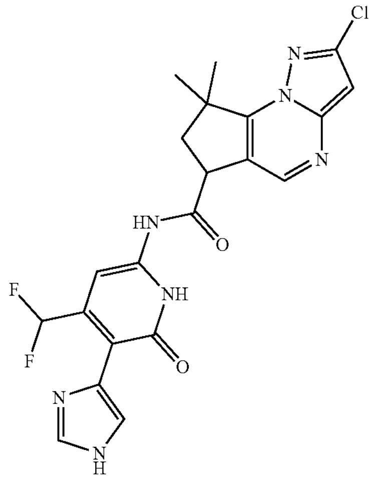 [SMILES: CC1(C)CC(C(=O)Nc2cc(C(F)F)c(-c3c[nH]cn3)c(=O)[nH]2)c2cnc3cc(Cl)nn3c21] | |

TABLE 1-continued
| Example Number | Structure | |
|---|---|---|
| 49, 50, 51 and 52* | 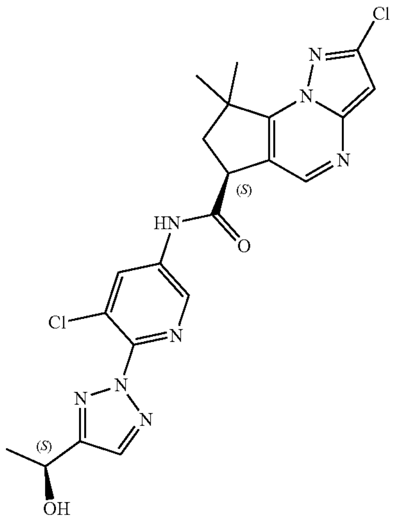 | 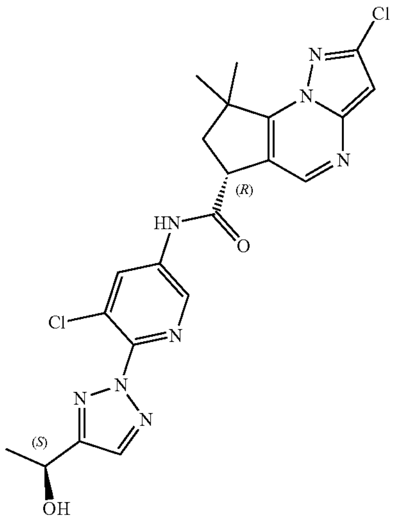 |
| | 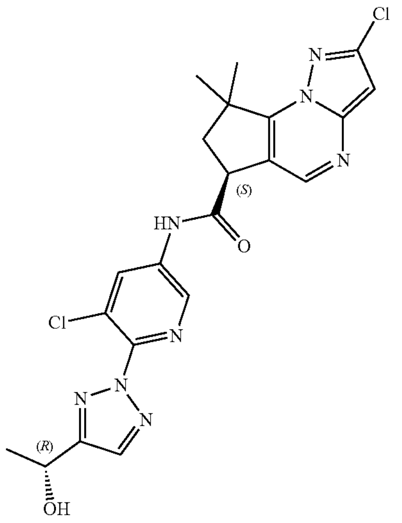 | 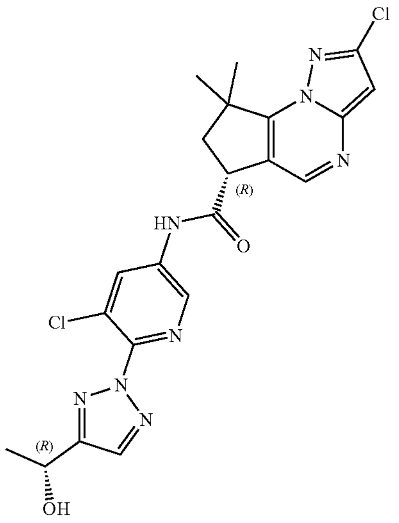 |
| 53, 54, 55 and 56* | 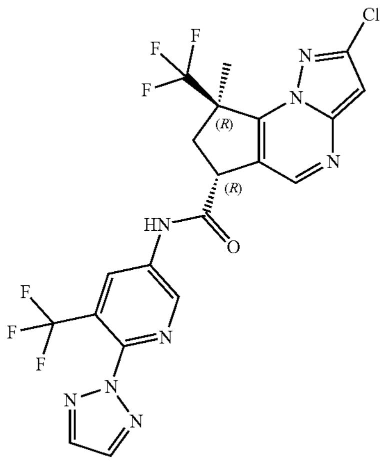 | 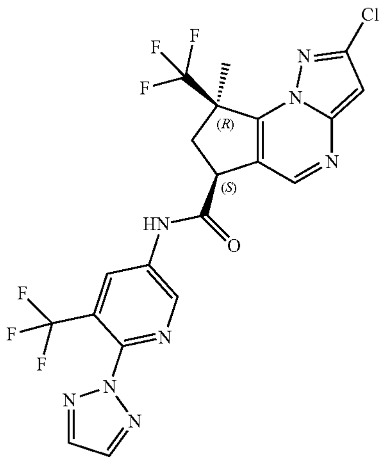 |

TABLE 1-continued
| Example Number | Structure |
| --- | --- |
| | 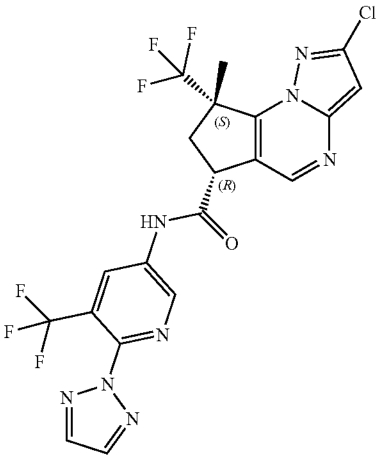 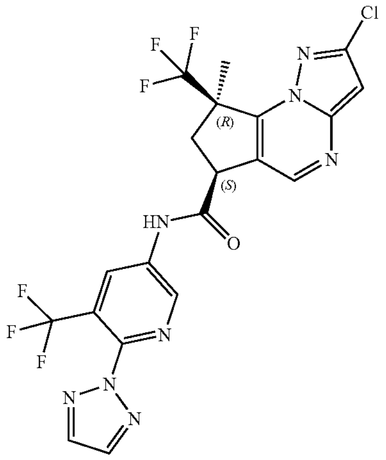 |
| 57<br>(first eluting isomer)*<br>58<br>(second eluting isomer)* | 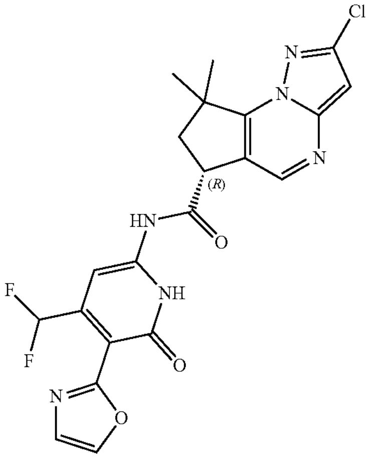 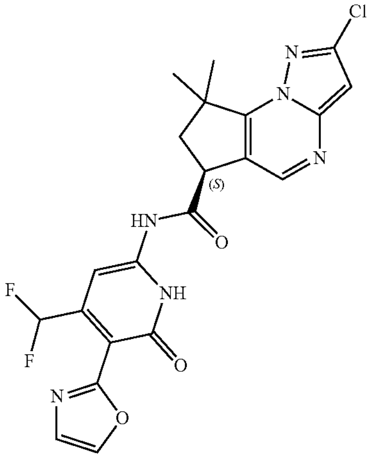 |
| 59 | 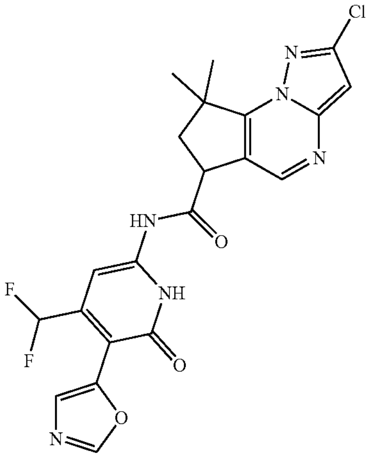 [SMILES: CC1(C)CC(C(=O)Nc2cc(C(F)F)c(-c3cnco3)c(=O)[nH]2)c2cnc3cc(Cl)nn3c21] |

TABLE 1-continued
| Example Number | Structure |
|---|---|
| 60 | 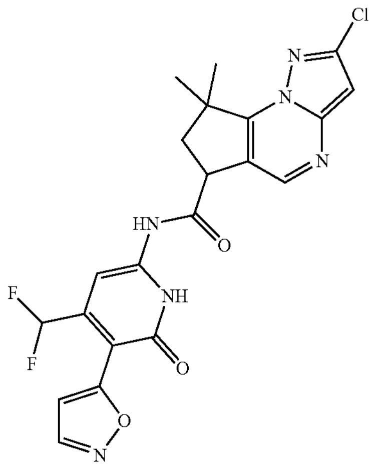 [SMILES: CC1(C)CC(C(=O)Nc2cc(C(F)F)c(-c3ccno3)c(=O)[nH]2)c2cnc3cc(Cl)nn3c21] |
| 61 | 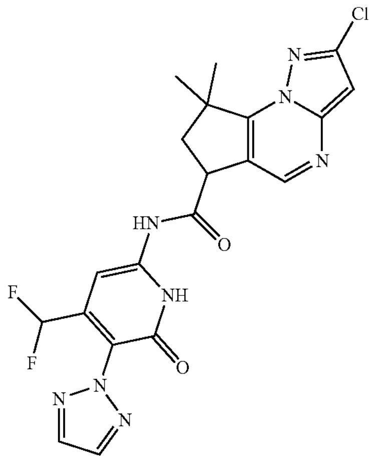 [SMILES: CC1(C)CC(C(=O)Nc2cc(C(F)F)c(-n3nccn3)c(=O)[nH]2)c2cnc3cc(Cl)nn3c21] |
| 62 | 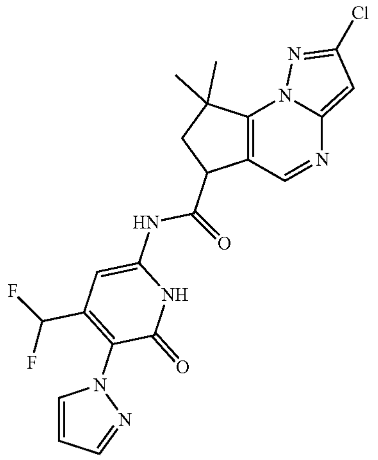 [SMILES: CC1(C)CC(C(=O)Nc2cc(C(F)F)c(-n3cccn3)c(=O)[nH]2)c2cnc3cc(Cl)nn3c21] |

TABLE 1-continued
| Example Number | Structure |
| --- | --- |
| 63, 64, 65 and 66* | 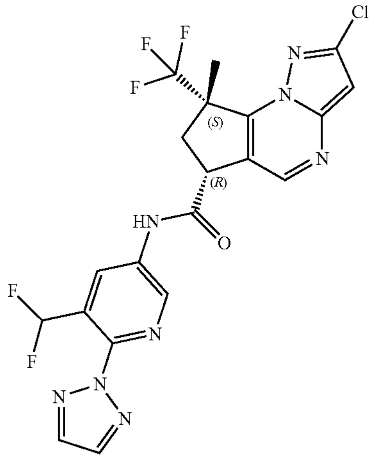 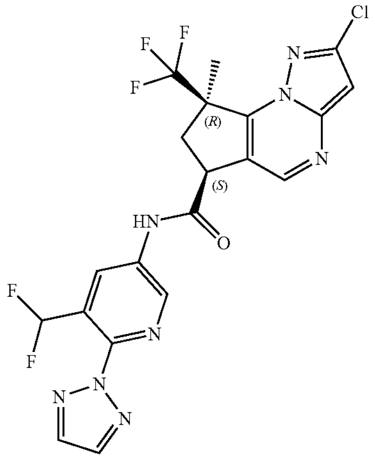 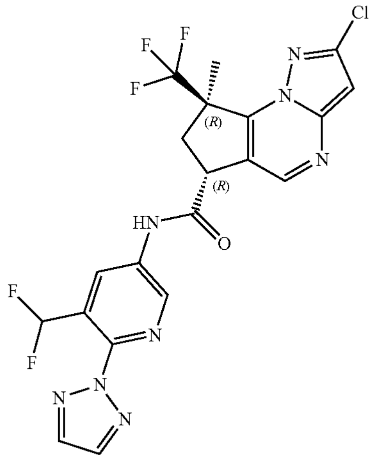 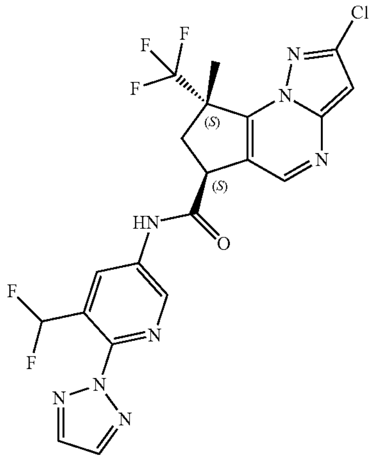 |
| 67 (first eluting isomer)* 68 (second eluting isomer)* | 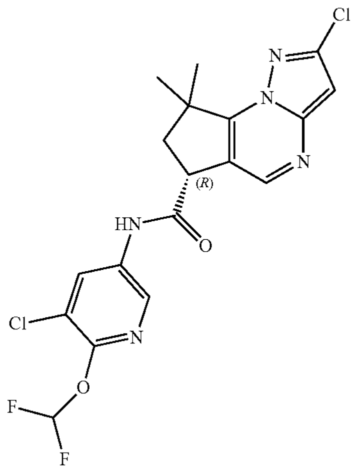 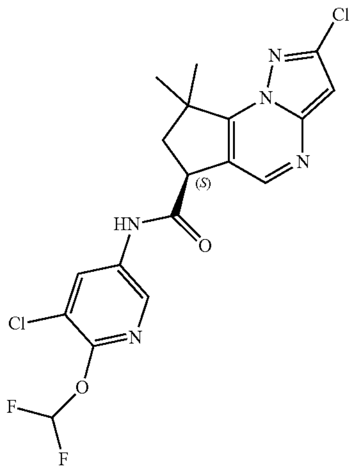 |

TABLE 1-continued
| Example Number | Structure |
| --- | --- |
| 69 | 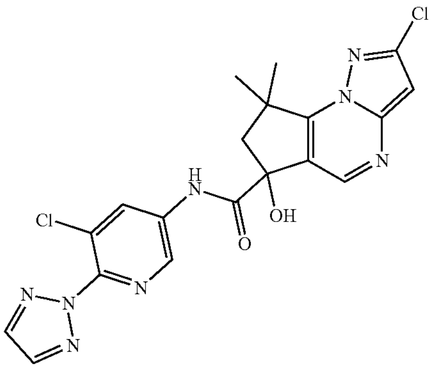 [SMILES: CC1(C)CC(O)(C(=O)Nc2cnc(-n3nccn3)c(Cl)c2)c2cnc3cc(Cl)nn3c21] |
| 70 (first eluting isomer)* 71 (second eluting isomer)* | 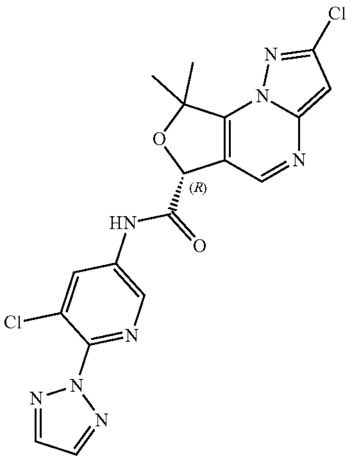 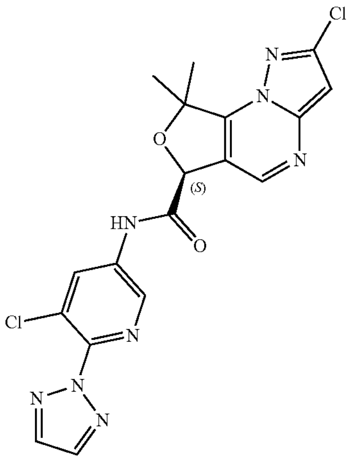 |
| 72 (first eluting isomer)* 73 (second eluting isomer)* | 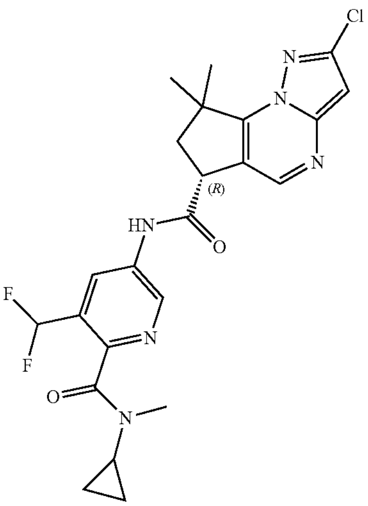 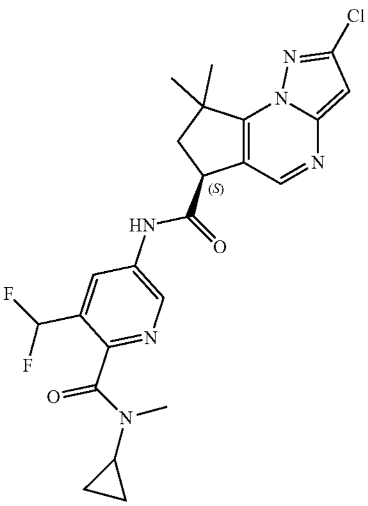 |

TABLE 1-continued
| Example Number | Structure | |
|---|---|---|
| 74 (first eluting isomer)* 75 (second eluting isomer)* | 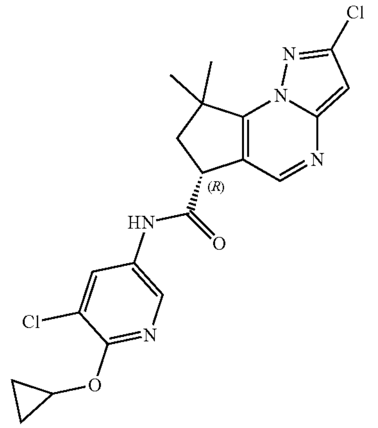 | 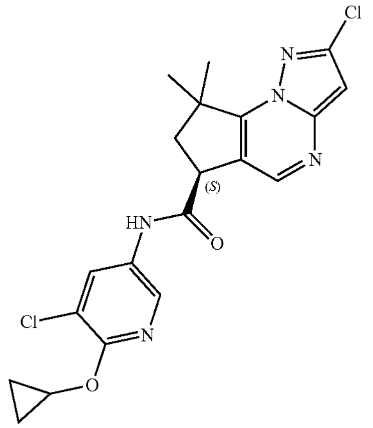 |
| 76 (first eluting isomer)* 77 (second eluting isomer)* | 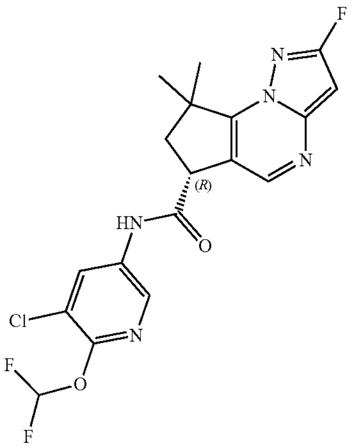 | 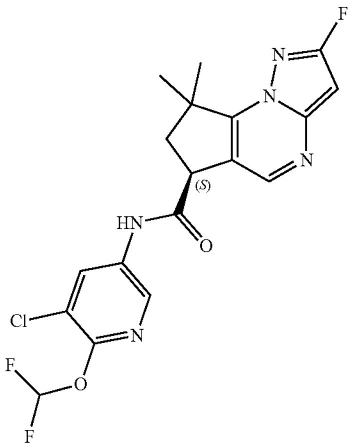 |
| 78 (first eluting isomer)* 79 (second eluting isomer)* | 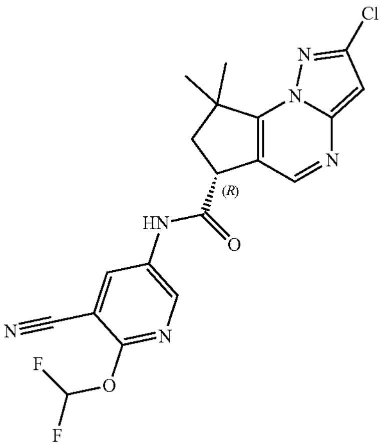 | 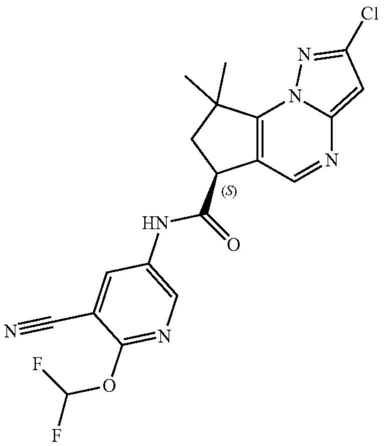 |

TABLE 1-continued
| Example Number | Structure |
|---|---|
| 80 (first eluting isomer)* 81 (second eluting isomer)* | 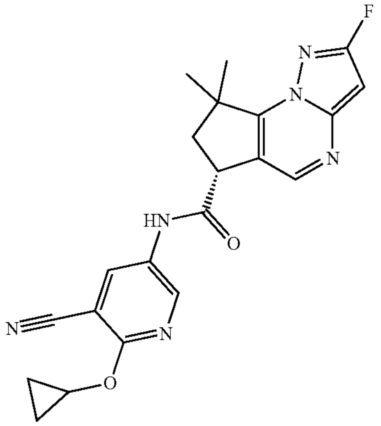 [SMILES: CC1(C)C[C@@H](C(=O)Nc2cnc(OC3CC3)c(C#N)c2)c2cnc3cc(F)nn3c21] 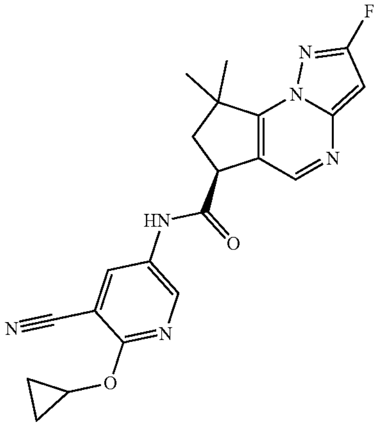 [SMILES: CC1(C)C[C@H](C(=O)Nc2cnc(OC3CC3)c(C#N)c2)c2cnc3cc(F)nn3c21] |
| 82 | 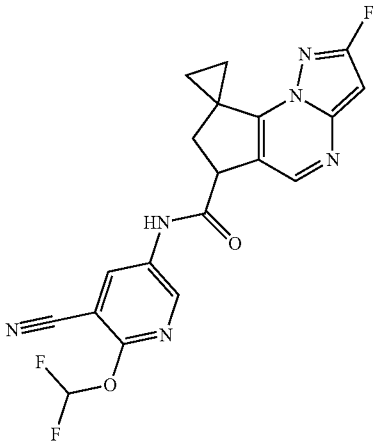 [SMILES: N#Cc1cc(NC(=O)C2CC3(CC3)c3c2cnc2cc(F)nn32)cnc1OC(F)F] |
| 83 (first eluting isomer)* 84 (second eluting isomer)* | 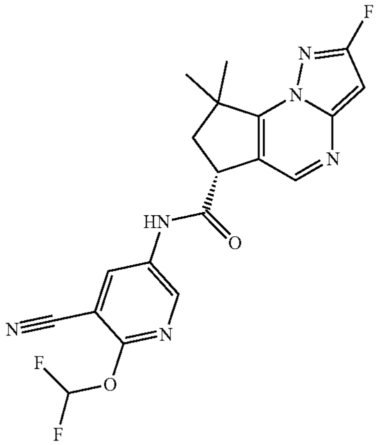 [SMILES: CC1(C)C[C@@H](C(=O)Nc2cnc(OC(F)F)c(C#N)c2)c2cnc3cc(F)nn3c21] 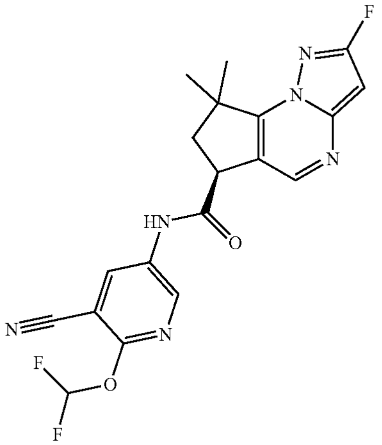 [SMILES: CC1(C)C[C@H](C(=O)Nc2cnc(OC(F)F)c(C#N)c2)c2cnc3cc(F)nn3c21] |

TABLE 1-continued
| Example Number | Structure |
| --- | --- |
| 85 | 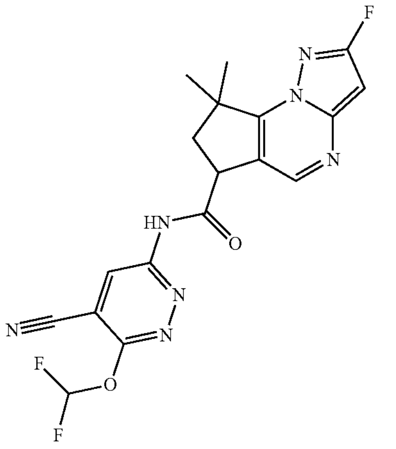 [SMILES: CC1(C)CC(C(=O)Nc2cc(C#N)c(OC(F)F)nn2)c2cnc3cc(F)nn3c21] |
| 86 (first eluting isomer)* 87 (second eluting isomer)* | 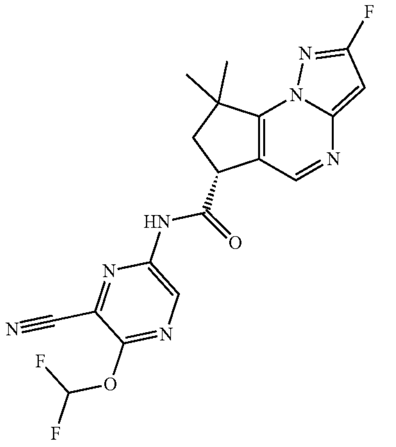 [SMILES: CC1(C)C[C@@H](C(=O)Nc2cnc(OC(F)F)c(C#N)n2)c2cnc3cc(F)nn3c21] 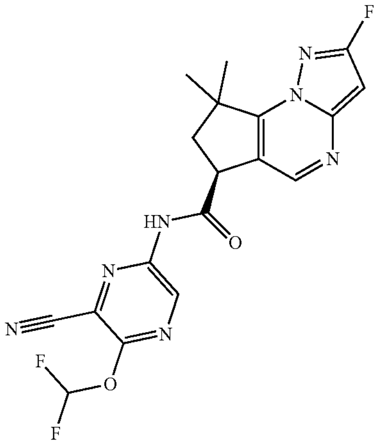 [SMILES: CC1(C)C[C@H](C(=O)Nc2cnc(OC(F)F)c(C#N)n2)c2cnc3cc(F)nn3c21] |
| 88 (first eluting isomer)* 89 (second eluting isomer)* | 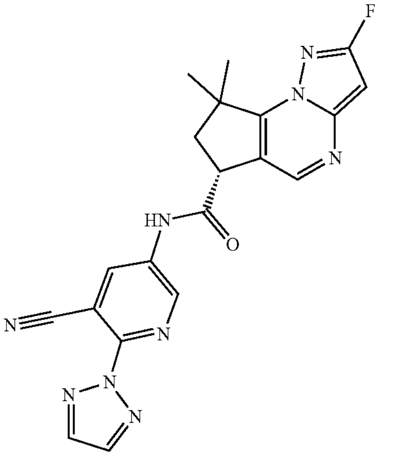 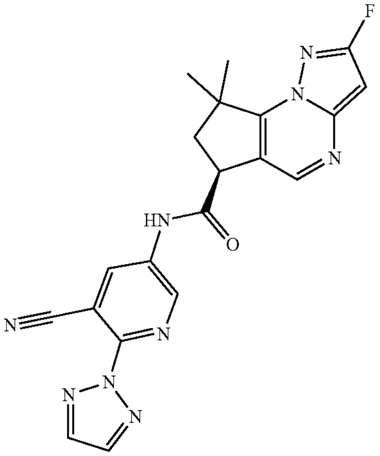 |

TABLE 1-continued
| Example Number | Structure |
| --- | --- |
| 90 (first eluting isomer)* 91 (second eluting isomer)* | 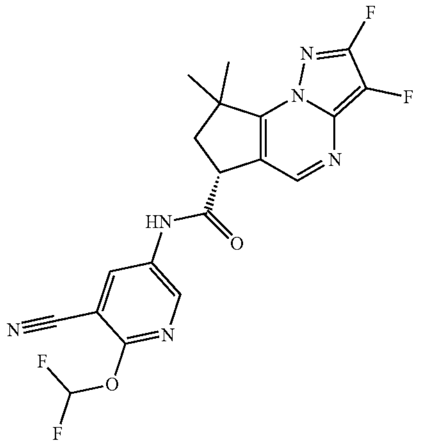 [SMILES: CC1(C)C[C@@H](C(=O)Nc2cnc(OC(F)F)c(C#N)c2)c2cnc3c(F)c(F)nn3c21] 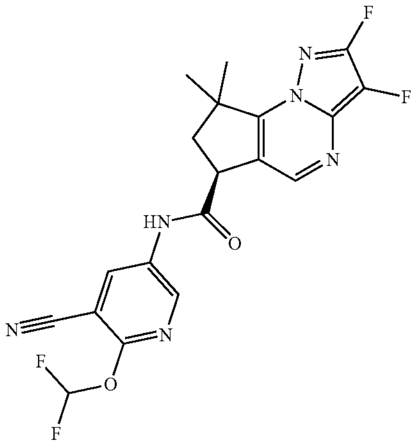 [SMILES: CC1(C)C[C@H](C(=O)Nc2cnc(OC(F)F)c(C#N)c2)c2cnc3c(F)c(F)nn3c21] |
| 92 (second eluting isomer)* 93 (first eluting isomer)* | 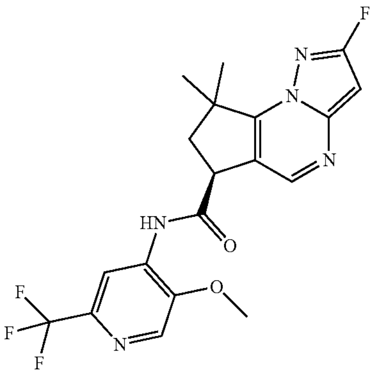 [SMILES: COc1cnc(C(F)(F)F)cc1NC(=O)[C@H]1CC(C)(C)c2c1cnc1cc(F)nn21] 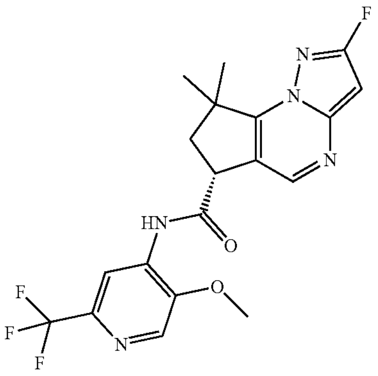 [SMILES: COc1cnc(C(F)(F)F)cc1NC(=O)[C@@H]1CC(C)(C)c2c1cnc1cc(F)nn21] |
| 94 (first eluting isomer)* 95 (second eluting isomer)* | 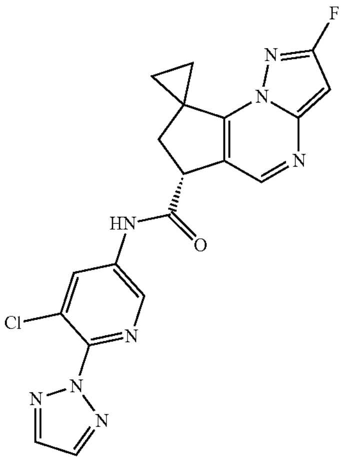 [SMILES: O=C(Nc1cnc(-n2nccn2)c(Cl)c1)[C@@H]1CC2(CC2)c2c1cnc1cc(F)nn21] 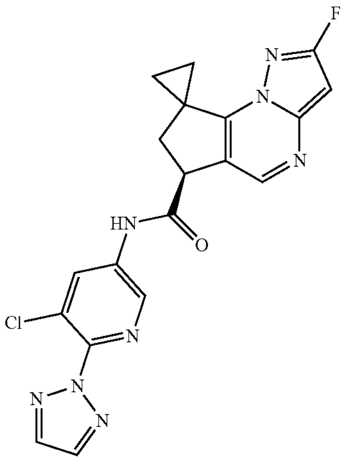 [SMILES: O=C(Nc1cnc(-n2nccn2)c(Cl)c1)[C@H]1CC2(CC2)c2c1cnc1cc(F)nn21] |

TABLE 1-continued
| Example Number | Structure | |
|---|---|---|
| 96 (first eluting isomer)* 97 (second eluting isomer)* | 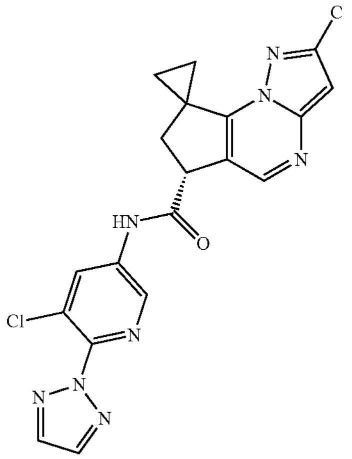 | 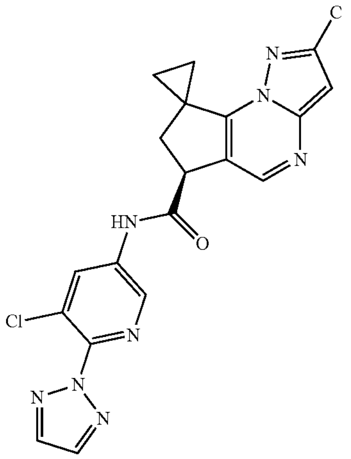 |
| 98 (first eluting isomer)* 99 (second eluting isomer)* | 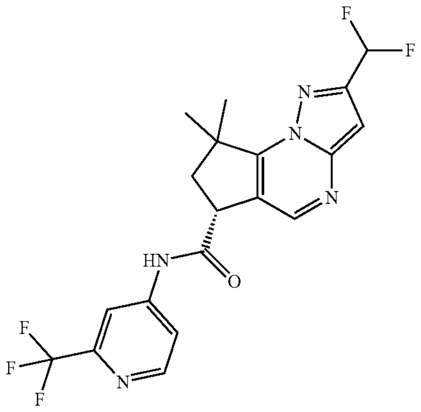 [SMILES: CC1(C)C[C@@H](C(=O)Nc2ccnc(C(F)(F)F)c2)c2cnc3cc(C(F)F)nn3c21] | 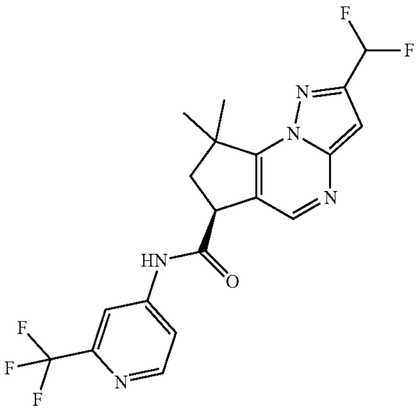 [SMILES: CC1(C)C[C@H](C(=O)Nc2ccnc(C(F)(F)F)c2)c2cnc3cc(C(F)F)nn3c21] |
| 100 (first eluting isomer)* 101 (second eluting isomer)* | 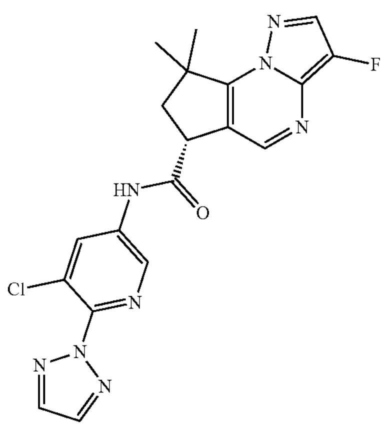 | 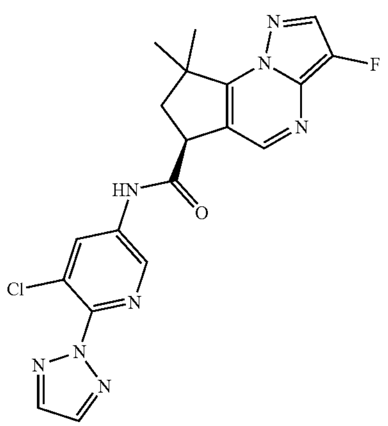 [SMILES: CC1(C)C[C@H](C(=O)Nc2cnc(-n3nccn3)c(Cl)c2)c2cnc3c(F)cnn3c21] |

TABLE 1-continued
| Example Number | Structure | |
|---|---|---|
| 102 (first eluting isomer)* 103 (second eluting isomer)* | 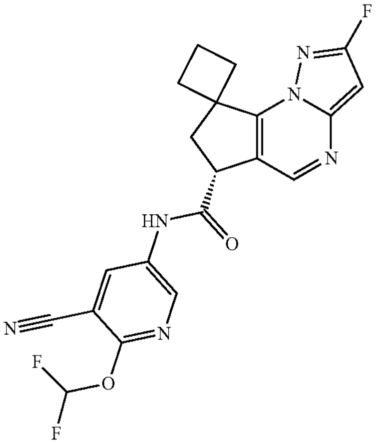 | 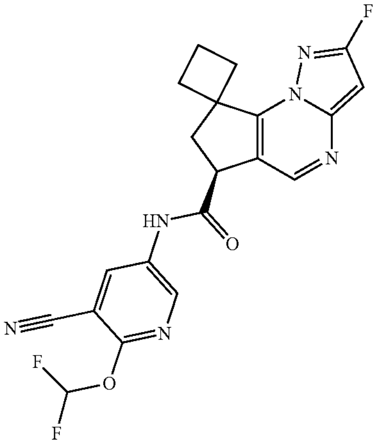 [SMILES: N#Cc1cc(NC(=O)[C@H]2CC3(CCC3)c3c2cnc2cc(F)nn32)cnc1OC(F)F] |
| 104 (first eluting isomer)* 105 (second eluting isomer)* | 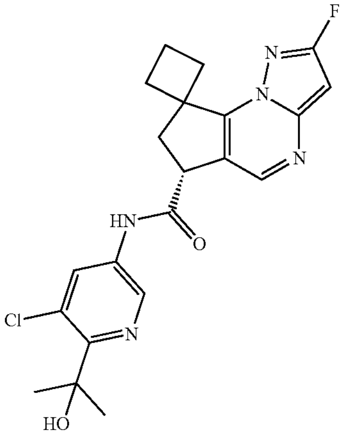 [SMILES: CC(C)(O)c1ncc(NC(=O)[C@@H]2CC3(CCC3)c3c2cnc2cc(F)nn32)cc1Cl] | 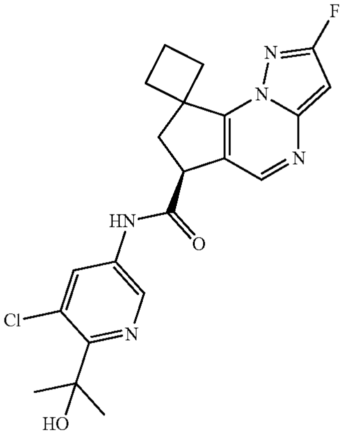 [SMILES: CC(C)(O)c1ncc(NC(=O)[C@H]2CC3(CCC3)c3c2cnc2cc(F)nn32)cc1Cl] |
| 106 (first eluting isomer)* 107 (second eluting isomer)* | 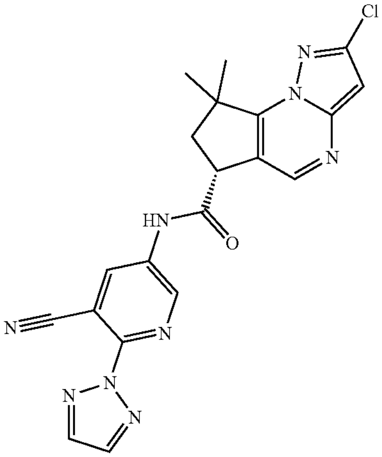 [SMILES: CC1(C)C[C@@H](C(=O)Nc2cnc(-n3nccn3)c(C#N)c2)c2cnc3cc(Cl)nn3c21] | 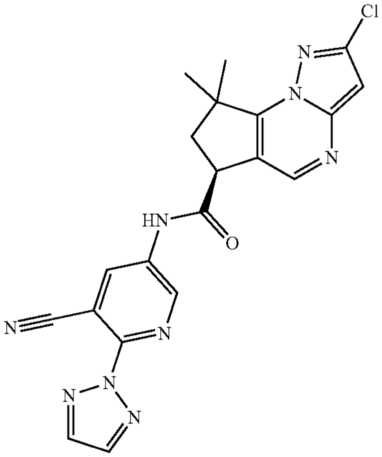 [SMILES: CC1(C)C[C@H](C(=O)Nc2cnc(-n3nccn3)c(C#N)c2)c2cnc3cc(Cl)nn3c21] |

TABLE 1-continued
| Example Number | Structure | |
|---|---|---|
| 108 (first eluting isomer)* 109 (second eluting isomer)* | 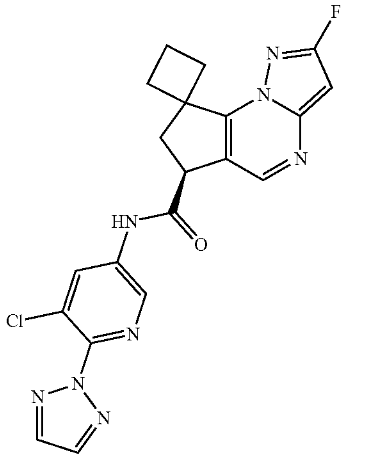 [SMILES: O=C(Nc1cnc(-n2nccn2)c(Cl)c1)[C@H]1CC2(CCC2)c2c1cnc1cc(F)nn21] | 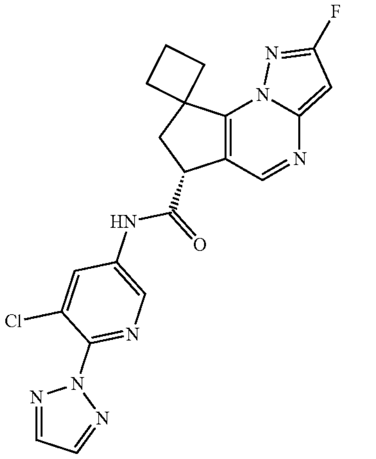 [SMILES: O=C(Nc1cnc(-n2nccn2)c(Cl)c1)[C@@H]1CC2(CCC2)c2c1cnc1cc(F)nn21] |
| 110 (first eluting isomer)* 111 (second eluting isomer)* | 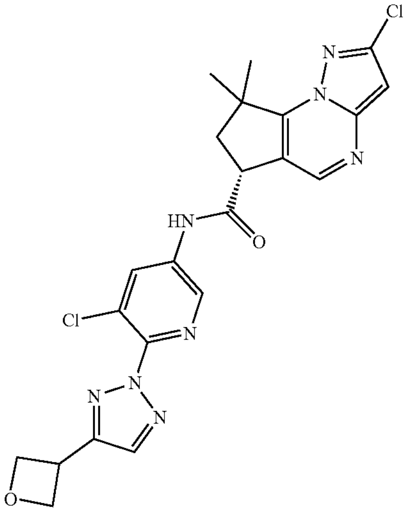 [SMILES: CC1(C)C[C@@H](C(=O)Nc2cnc(-n3ncc(C4COC4)n3)c(Cl)c2)c2cnc3cc(Cl)nn3c21] | 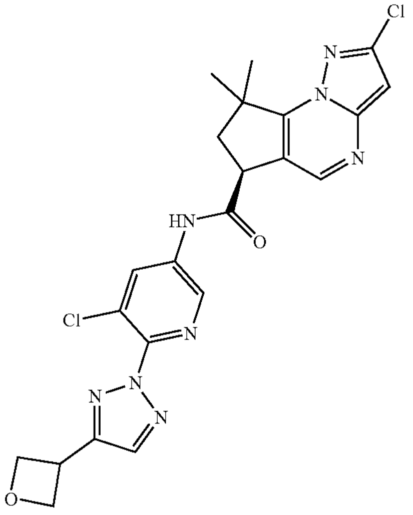 [SMILES: CC1(C)C[C@H](C(=O)Nc2cnc(-n3ncc(C4COC4)n3)c(Cl)c2)c2cnc3cc(Cl)nn3c21] |
| 112 | 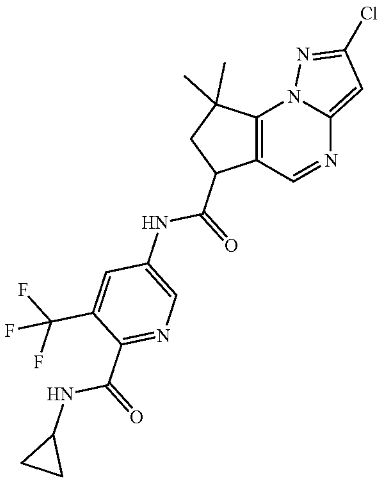 [SMILES: CC1(C)CC(C(=O)Nc2cnc(C(=O)NC3CC3)c(C(F)(F)F)c2)c2cnc3cc(Cl)nn3c21] | |

TABLE 1-continued
| Example Number | Structure |
|---|---|
| 113 (first eluting isomer)* 114 (second eluting isomer)* | 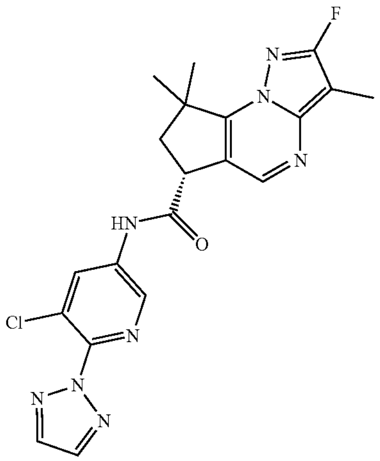 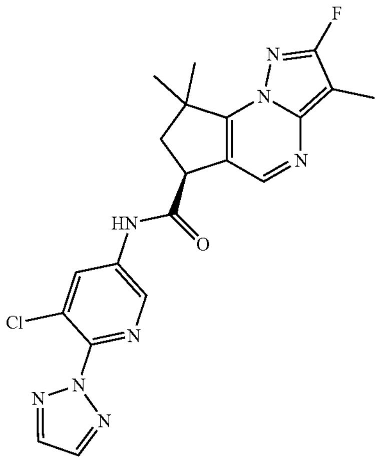 |
| 115 | 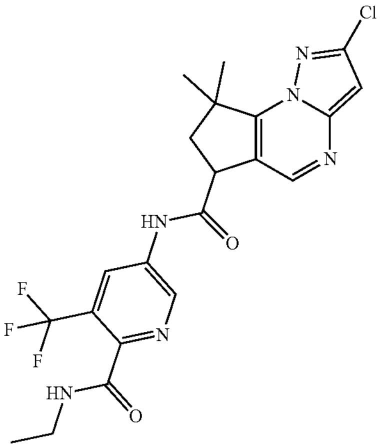 [SMILES: CCNC(=O)c1ncc(NC(=O)C2CC(C)(C)c3c2cnc2cc(Cl)nn32)cc1C(F)(F)F] |
| 116 racemic and trans (O and amide on 5-mem ring) | 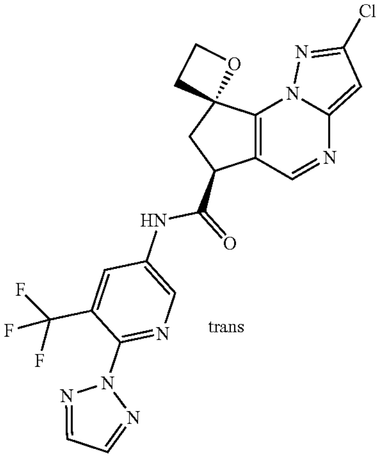 trans |

TABLE 1-continued
| Example Number | Structure |
|---|---|
| 117 racemic and cis (O and amide on 5-mem ring) | 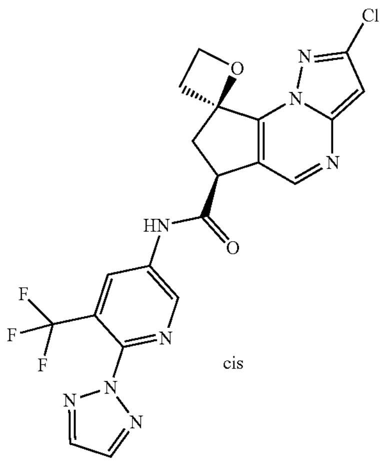 cis |
| 118 | 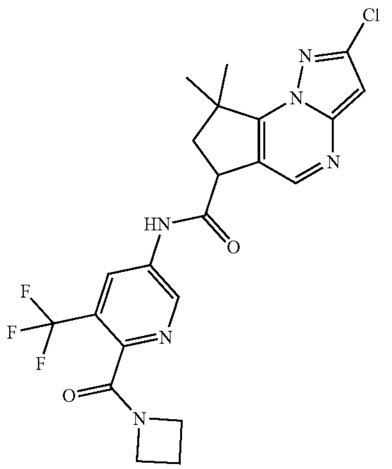 [SMILES: CC1(C)CC(C(=O)Nc2cnc(C(=O)N3CCC3)c(C(F)(F)F)c2)c2cnc3cc(Cl)nn3c21] |
| 119 | 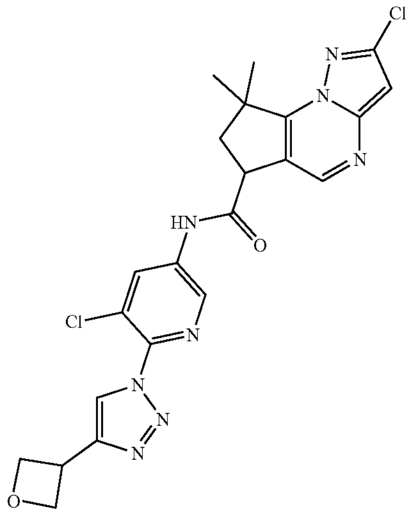 [SMILES: CC1(C)CC(C(=O)Nc2cnc(-n3cc(C4COC4)nn3)c(Cl)c2)c2cnc3cc(Cl)nn3c21] |

TABLE 1-continued
| Example Number | Structure | |
|---|---|---|
| 120 | 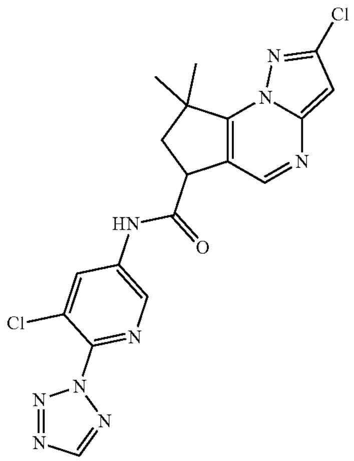 [SMILES: CC1(C)CC(C(=O)Nc2cnc(-n3ncnn3)c(Cl)c2)c2cnc3cc(Cl)nn3c21] | |
| 121 (first eluting isomer)* 122 (second eluting isomer)* | 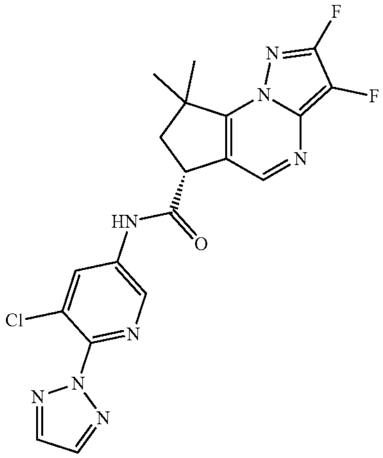 | 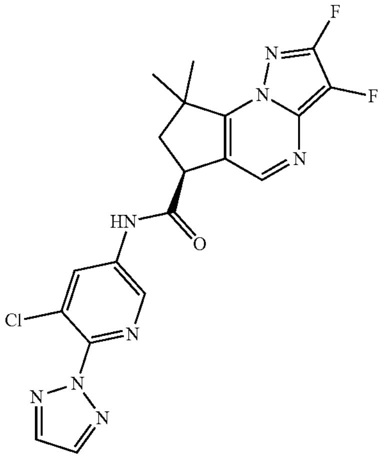 [SMILES: CC1(C)C[C@H](C(=O)Nc2cnc(-n3nccn3)c(Cl)c2)c2cnc3c(F)c(F)nn3c21] |
| 123 and 124 | 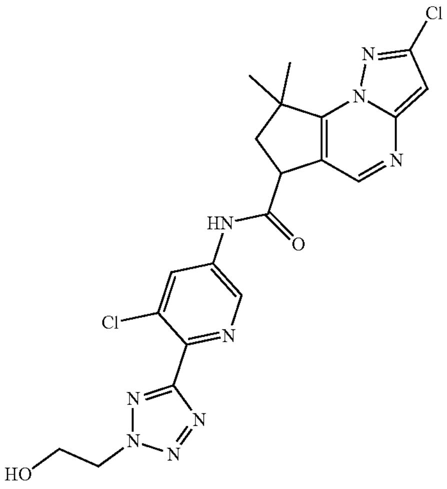 [SMILES: CC1(C)CC(C(=O)Nc2cnc(-c3nnn(CCO)n3)c(Cl)c2)c2cnc3cc(Cl)nn3c21] | 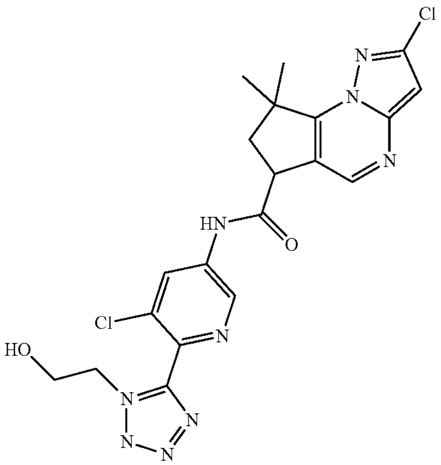 |

TABLE 1-continued
| Example Number | Structure | |
|---|---|---|
| 125 (first eluting isomer)* 126 (second eluting isomer)* | 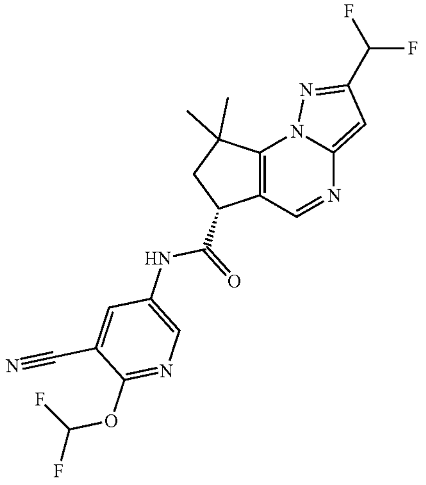 [SMILES: CC1(C)C[C@@H](C(=O)Nc2cnc(OC(F)F)c(C#N)c2)c2cnc3cc(C(F)F)nn3c21] | 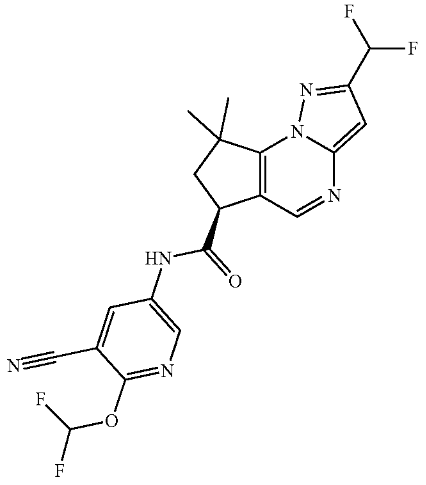 [SMILES: CC1(C)C[C@H](C(=O)Nc2cnc(OC(F)F)c(C#N)c2)c2cnc3cc(C(F)F)nn3c21] |
| 127 (first eluting isomer)* 128 (second eluting isomer)* | 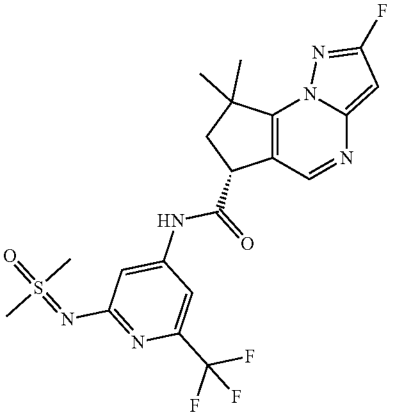 [SMILES: CC1(C)C[C@@H](C(=O)Nc2cc(N=S(C)(C)=O)nc(C(F)(F)F)c2)c2cnc3cc(F)nn3c21] | 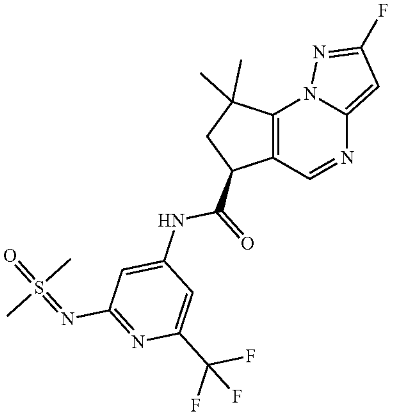 [SMILES: CC1(C)C[C@H](C(=O)Nc2cc(N=S(C)(C)=O)nc(C(F)(F)F)c2)c2cnc3cc(F)nn3c21] |
| 129 (first eluting isomer)* 130 (second eluting isomer)* | 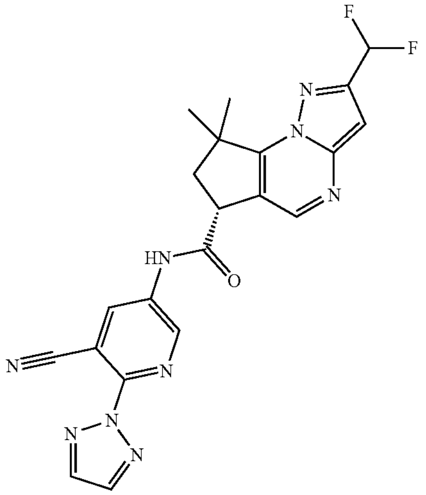 [SMILES: CC1(C)C[C@@H](C(=O)Nc2cnc(-n3nccn3)c(C#N)c2)c2cnc3cc(C(F)F)nn3c21] | 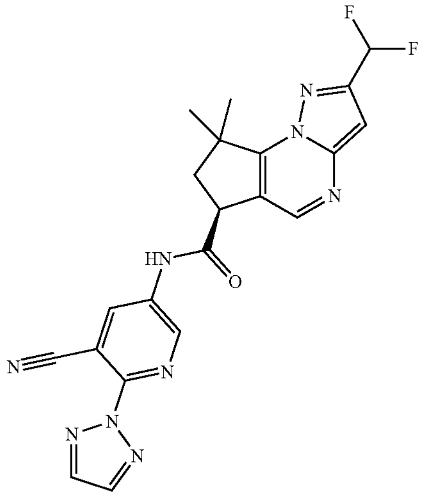 [SMILES: CC1(C)C[C@H](C(=O)Nc2cnc(-n3nccn3)c(C#N)c2)c2cnc3cc(C(F)F)nn3c21] |

TABLE 1-continued
| Example Number | Structure |
|---|---|
| 131 (first eluting isomer)* 132 (second eluting isomer)* | 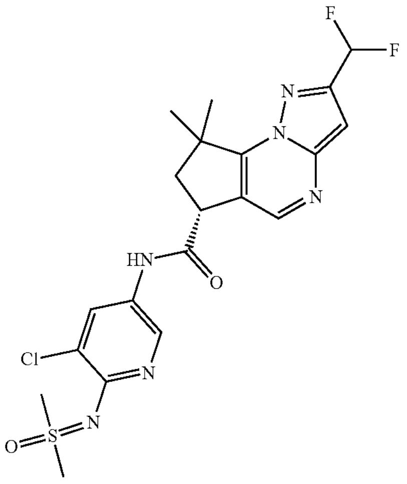 [SMILES: CC1(C)C[C@@H](C(=O)Nc2cnc(N=S(C)(C)=O)c(Cl)c2)c2cnc3cc(C(F)F)nn3c21] 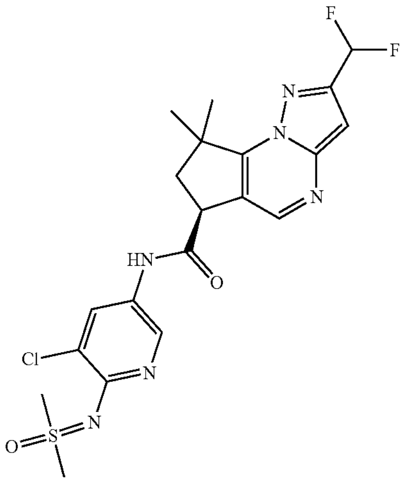 [SMILES: CC1(C)C[C@H](C(=O)Nc2cnc(N=S(C)(C)=O)c(Cl)c2)c2cnc3cc(C(F)F)nn3c21] |
| 133, 134, 135 and 136 | 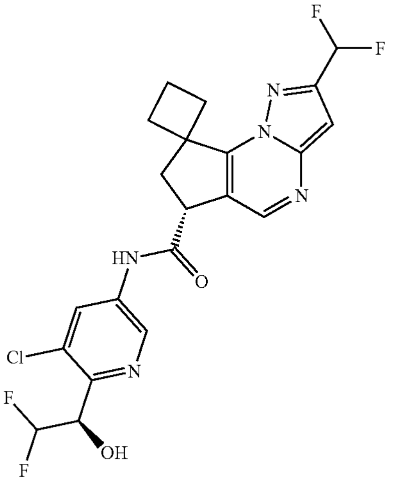 [SMILES: O=C(Nc1cnc([C@@H](O)C(F)F)c(Cl)c1)[C@@H]1CC2(CCC2)c2c1cnc1cc(C(F)F)nn21] 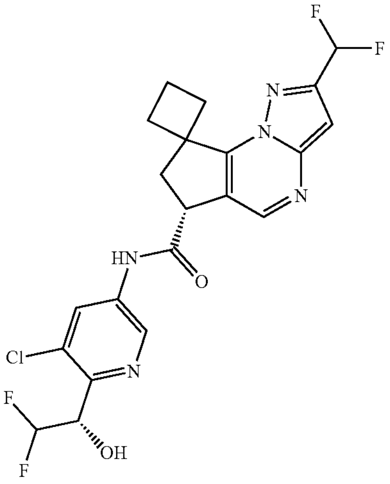 [SMILES: O=C(Nc1cnc([C@H](O)C(F)F)c(Cl)c1)[C@@H]1CC2(CCC2)c2c1cnc1cc(C(F)F)nn21] 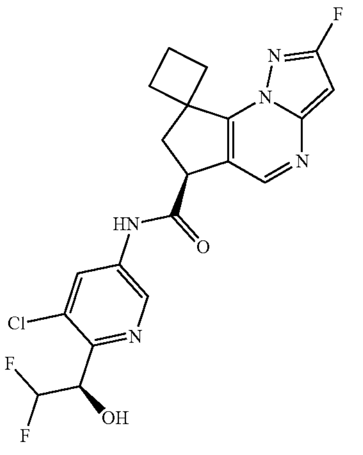 [SMILES: O=C(Nc1cnc([C@@H](O)C(F)F)c(Cl)c1)[C@H]1CC2(CCC2)c2c1cnc1cc(F)nn21] 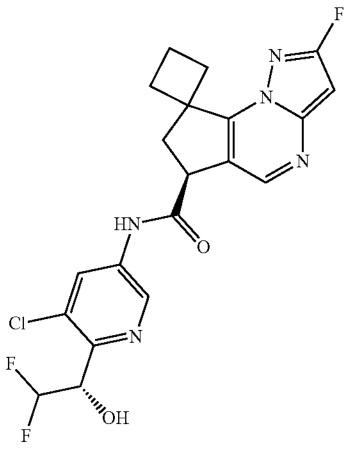 [SMILES: O=C(Nc1cnc([C@H](O)C(F)F)c(Cl)c1)[C@H]1CC2(CCC2)c2c1cnc1cc(F)nn21] |

TABLE 1-continued
| Example Number | Structure | |
|---|---|---|
| 137 | 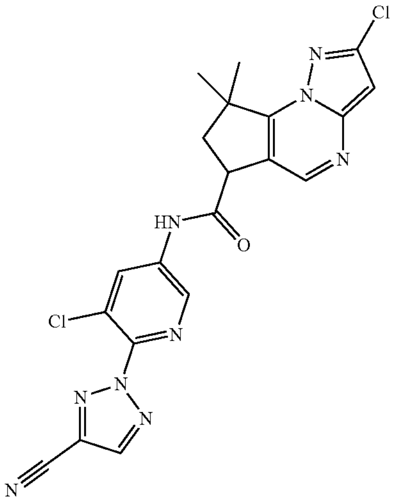 [SMILES: CC1(C)CC(C(=O)Nc2cnc(-n3ncc(C#N)n3)c(Cl)c2)c2cnc3cc(Cl)nn3c21] | |
| 138 (first eluting isomer)* 139 (second eluting isomer)* | 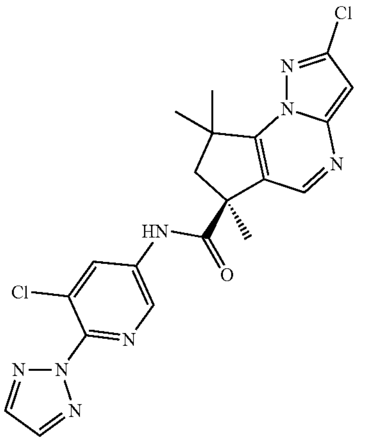 [SMILES: CC1(C)C[C@](C)(C(=O)Nc2cnc(-n3nccn3)c(Cl)c2)c2cnc3cc(Cl)nn3c21] | 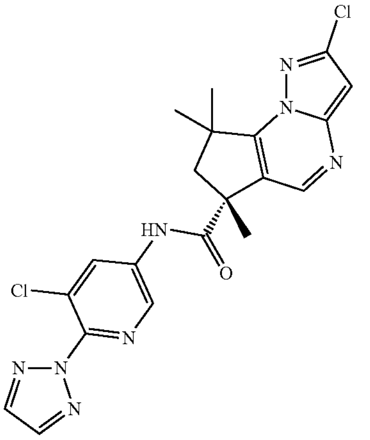 [SMILES: CC1(C)C[C@@](C)(C(=O)Nc2cnc(-n3nccn3)c(Cl)c2)c2cnc3cc(Cl)nn3c21] |
| 140 (first eluting isomer)* 141 (second eluting isomer)* | 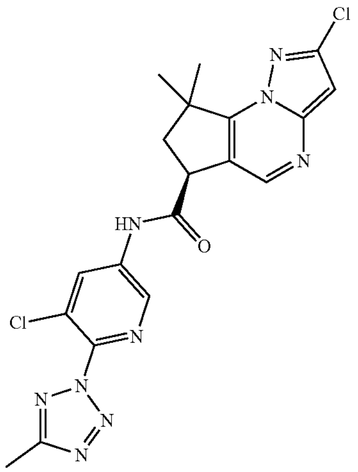 [SMILES: Cc1nnn(-c2ncc(NC(=O)[C@H]3CC(C)(C)c4c3cnc3cc(Cl)nn43)cc2Cl)n1] | 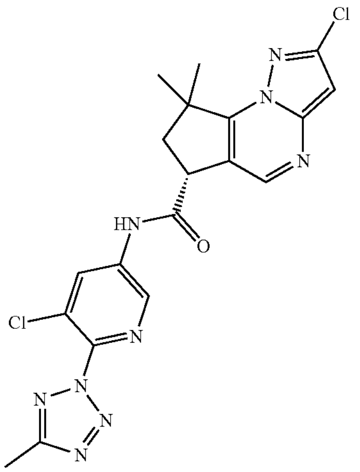 [SMILES: Cc1nnn(-c2ncc(NC(=O)[C@@H]3CC(C)(C)c4c3cnc3cc(Cl)nn43)cc2Cl)n1] |

TABLE 1-continued
| Example Number | Structure |
|---|---|
| 142 (first eluting isomer)* 143 (second eluting isomer)* | 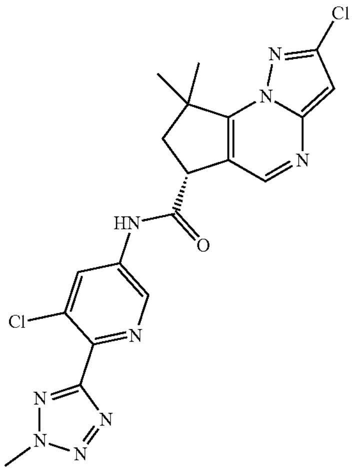 [SMILES: Cn1nnc(-c2ncc(NC(=O)[C@@H]3CC(C)(C)c4c3cnc3cc(Cl)nn43)cc2Cl)n1] 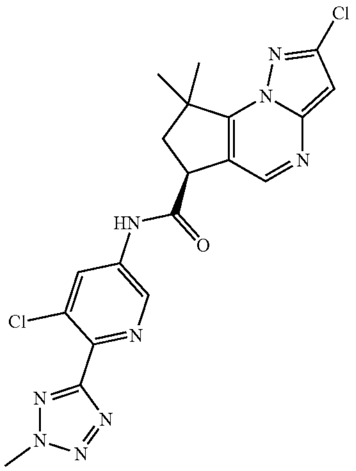 [SMILES: Cn1nnc(-c2ncc(NC(=O)[C@H]3CC(C)(C)c4c3cnc3cc(Cl)nn43)cc2Cl)n1] |
| 144 (first eluting isomer)* 145 (second eluting isomer)* | 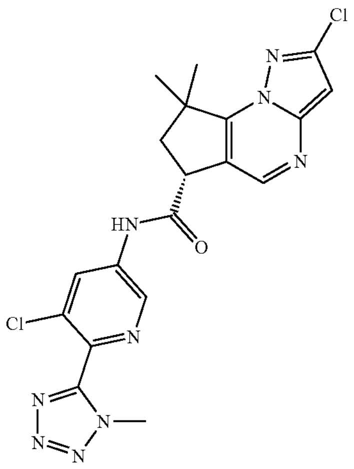 [SMILES: Cn1nnnc1-c1ncc(NC(=O)[C@@H]2CC(C)(C)c3c2cnc2cc(Cl)nn32)cc1Cl] 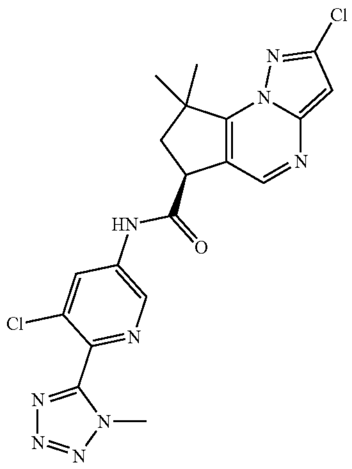 [SMILES: Cn1nnnc1-c1ncc(NC(=O)[C@H]2CC(C)(C)c3c2cnc2cc(Cl)nn32)cc1Cl] |
| 146 (first eluting isomer)* 147 (second eluting isomer)* | 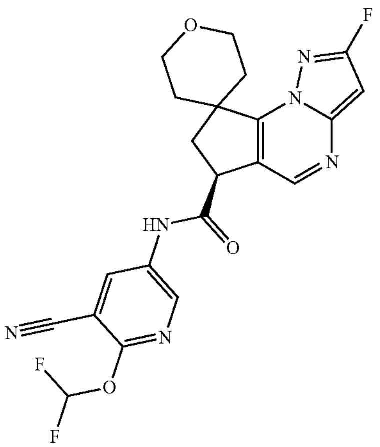 [SMILES: N#Cc1cc(NC(=O)[C@H]2CC3(CCOCC3)c3c2cnc2cc(F)nn32)cnc1OC(F)F] 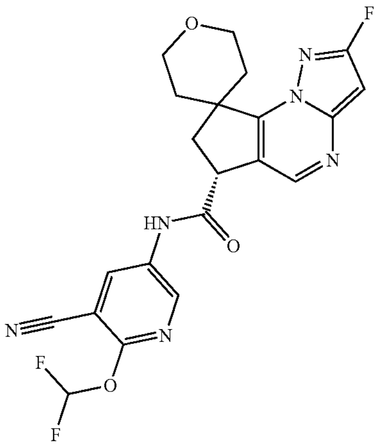 |

TABLE 1-continued
| Example Number | Structure |
| --- | --- |
| 148 (first eluting isomer)* 149 (second eluting isomer)* | 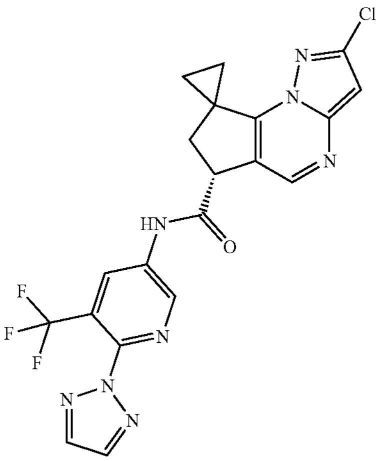 [SMILES: O=C(Nc1cnc(-n2nccn2)c(C(F)(F)F)c1)[C@@H]1CC2(CC2)c2c1cnc1cc(Cl)nn21] 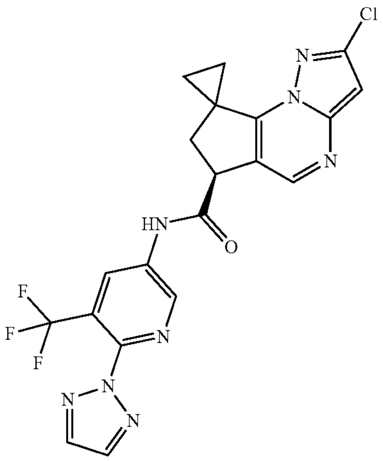 [SMILES: O=C(Nc1cnc(-n2nccn2)c(C(F)(F)F)c1)[C@H]1CC2(CC2)c2c1cnc1cc(Cl)nn21] |
| 150 (first eluting isomer)* 151 (second eluting isomer)* | 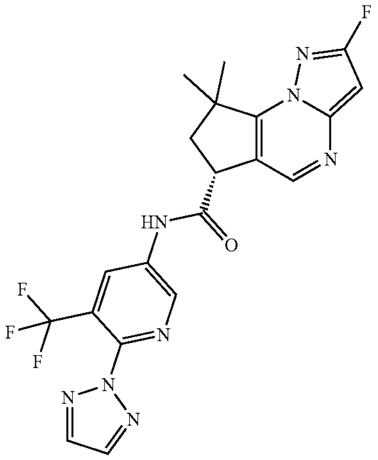 [SMILES: CC1(C)C[C@@H](C(=O)Nc2cnc(-n3nccn3)c(C(F)(F)F)c2)c2cnc3cc(F)nn3c21] 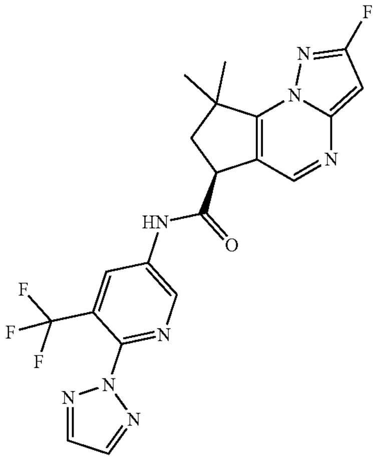 [SMILES: CC1(C)C[C@H](C(=O)Nc2cnc(-n3nccn3)c(C(F)(F)F)c2)c2cnc3cc(F)nn3c21] |
| 152 (second eluting isomer)* 153 (first eluting isomer)* | 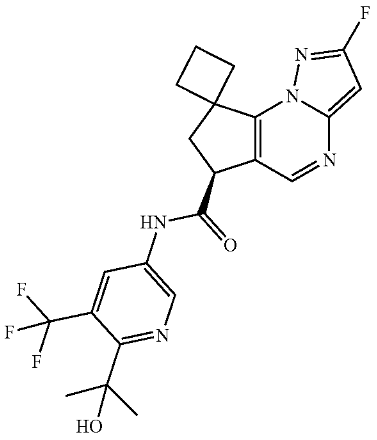 [SMILES: CC(C)(O)c1ncc(NC(=O)[C@H]2CC3(CCC3)c3c2cnc2cc(F)nn32)cc1C(F)(F)F] 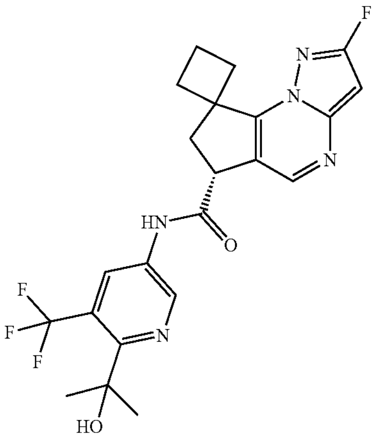 [SMILES: CC(C)(O)c1ncc(NC(=O)[C@@H]2CC3(CCC3)c3c2cnc2cc(F)nn32)cc1C(F)(F)F] |

TABLE 1-continued
| Example Number | Structure |
|---|---|
| 154 (first eluting isomer)* 155 (second eluting isomer)* | 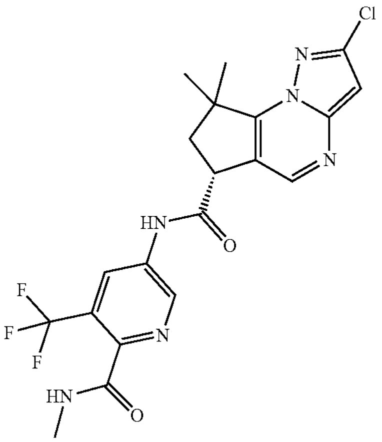 [SMILES: CNC(=O)c1ncc(NC(=O)[C@@H]2CC(C)(C)c3c2cnc2cc(Cl)nn32)cc1C(F)(F)F] 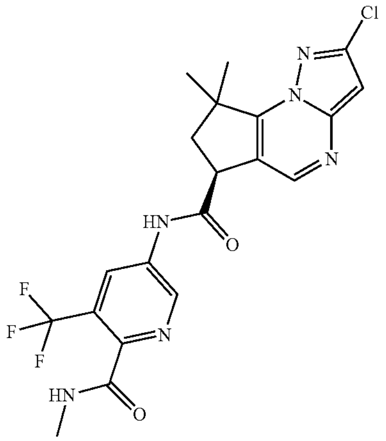 [SMILES: CNC(=O)c1ncc(NC(=O)[C@H]2CC(C)(C)c3c2cnc2cc(Cl)nn32)cc1C(F)(F)F] |
| 156 (first eluting isomer)* 157 (second eluting isomer)* | 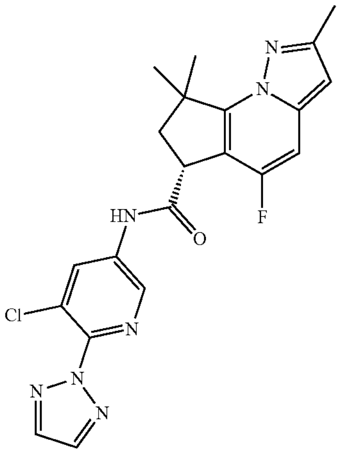 [SMILES: Cc1cc2cc(F)c3c(n2n1)C(C)(C)C[C@H]3C(=O)Nc1cnc(-n2nccn2)c(Cl)c1] 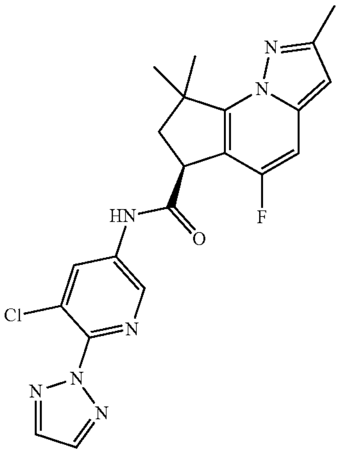 [SMILES: Cc1cc2cc(F)c3c(n2n1)C(C)(C)C[C@@H]3C(=O)Nc1cnc(-n2nccn2)c(Cl)c1] |
| 158 (first eluting isomer)* 159 (second eluting isomer)* | 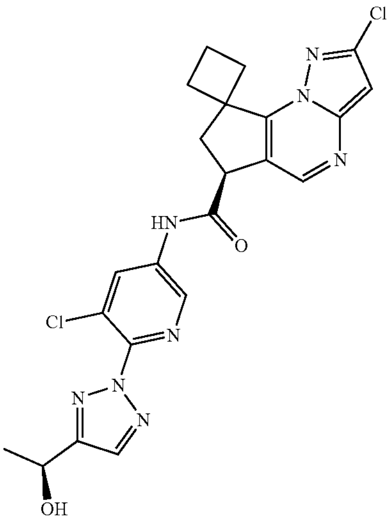 [SMILES: C[C@H](O)c1cnn(-c2ncc(NC(=O)[C@H]3CC4(CCC4)c4c3cnc3cc(Cl)nn43)cc2Cl)n1] 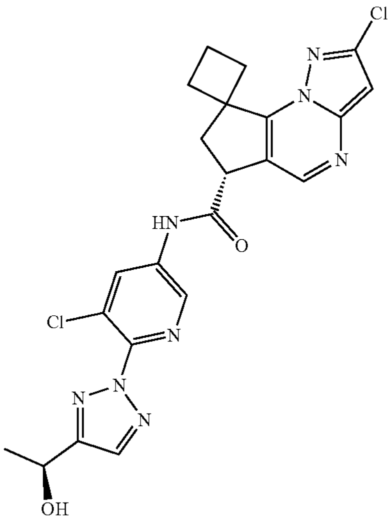 |

TABLE 1-continued
| Example Number | Structure |
| --- | --- |
| 160 (first eluting isomer)* 161 (second eluting isomer)* | 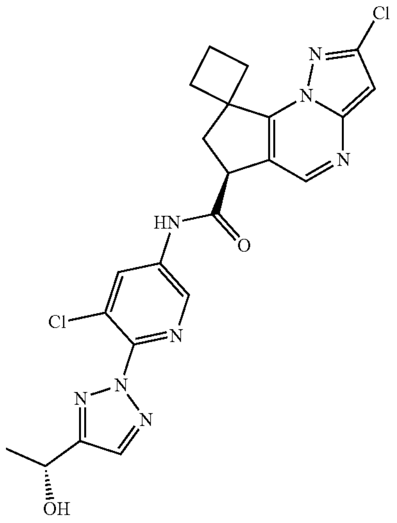 [SMILES: C[C@@H](O)c1cnn(-c2ncc(NC(=O)[C@H]3CC4(CCC4)c4c3cnc3cc(Cl)nn43)cc2Cl)n1] 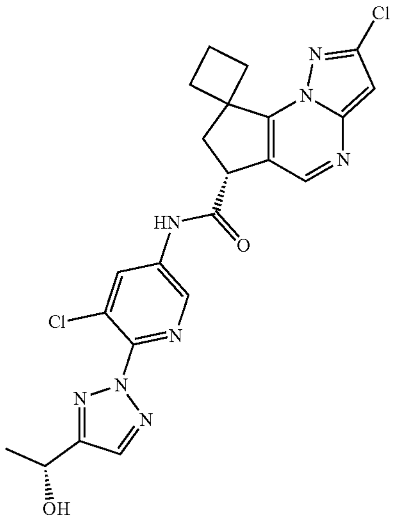 [SMILES: C[C@@H](O)c1cnn(-c2ncc(NC(=O)[C@@H]3CC4(CCC4)c4c3cnc3cc(Cl)nn43)cc2Cl)n1] |
| 162 | 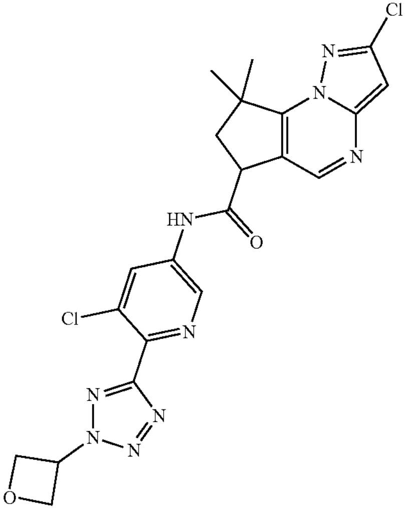 [SMILES: CC1(C)CC(C(=O)Nc2cnc(-c3nnn(C4COC4)n3)c(Cl)c2)c2cnc3cc(Cl)nn3c21] |
| 163 | 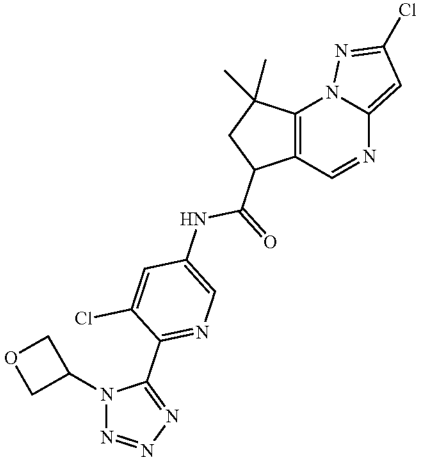 [SMILES: CC1(C)CC(C(=O)Nc2cnc(-c3nnnn3C3COC3)c(Cl)c2)c2cnc3cc(Cl)nn3c21] |

TABLE 1-continued
| Example Number | Structure |
| --- | --- |
| 164 | 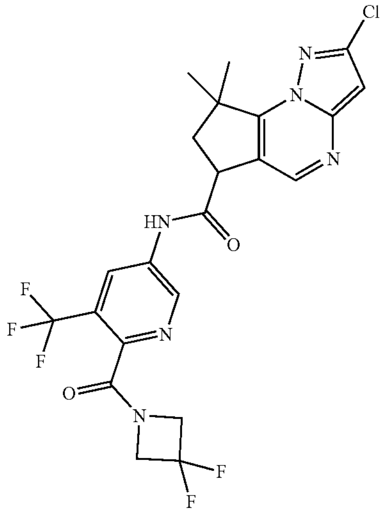 [SMILES: CC1(C)CC(C(=O)Nc2cnc(C(=O)N3CC(F)(F)C3)c(C(F)(F)F)c2)c2cnc3cc(Cl)nn3c21] |
| 165 | 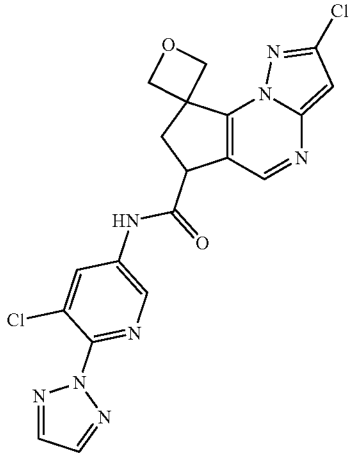 [SMILES: O=C(Nc1cnc(-n2nccn2)c(Cl)c1)C1CC2(COC2)c2c1cnc1cc(Cl)nn21] |
| 166 | 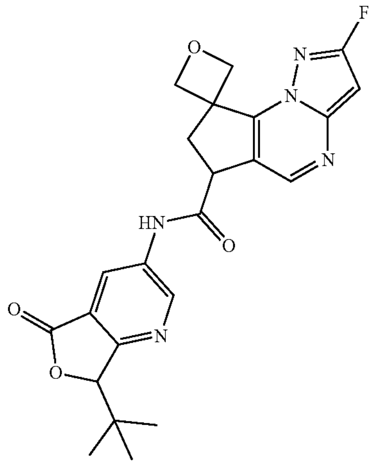 [SMILES: CC(C)(C)C1OC(=O)c2cc(NC(=O)C3CC4(COC4)c4c3cnc3cc(F)nn43)cnc21] |

TABLE 1-continued
| Example Number | Structure | |
|---|---|---|
| 167 (first eluting isomer)* 168 (second eluting isomer)* | 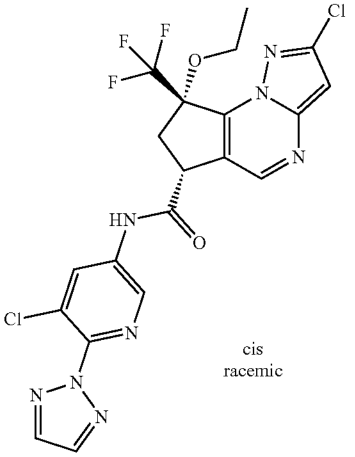 [SMILES: CCO[C@@]1(C(F)(F)F)C[C@@H](C(=O)Nc2cnc(-n3nccn3)c(Cl)c2)c2cnc3cc(Cl)nn3c21] cis racemic | 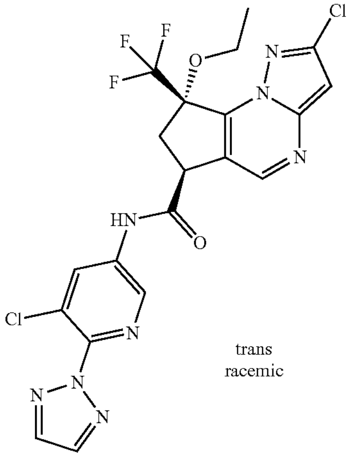 [SMILES: CCO[C@@]1(C(F)(F)F)C[C@H](C(=O)Nc2cnc(-n3nccn3)c(Cl)c2)c2cnc3cc(Cl)nn3c21] trans racemic |
| 169 (first eluting isomer)* 170 (second eluting isomer)* | 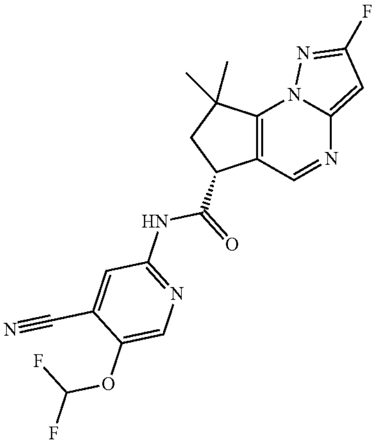 [SMILES: CC1(C)C[C@@H](C(=O)Nc2cc(C#N)c(OC(F)F)cn2)c2cnc3cc(F)nn3c21] | 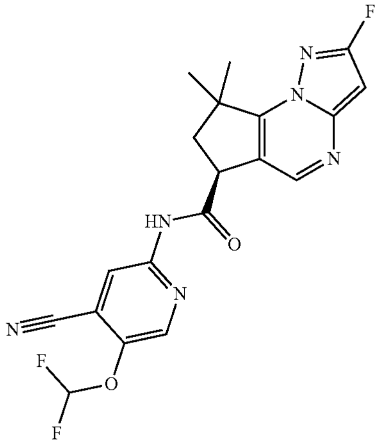 [SMILES: CC1(C)C[C@H](C(=O)Nc2cc(C#N)c(OC(F)F)cn2)c2cnc3cc(F)nn3c21] |
| 171 | 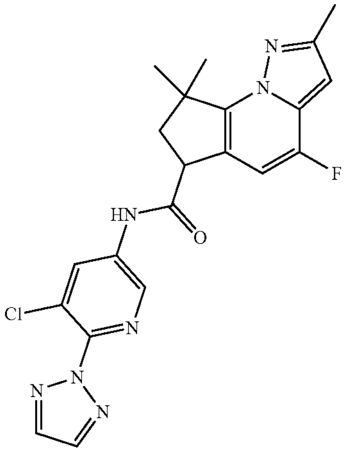 [SMILES: Cc1cc2c(F)cc3c(n2n1)C(C)(C)CC3C(=O)Nc1cnc(-n2nccn2)c(Cl)c1] | |

TABLE 1-continued
| Example Number | Structure |
|---|---|
| 172 (first eluting isomer)* 173 (second eluting isomer)* | 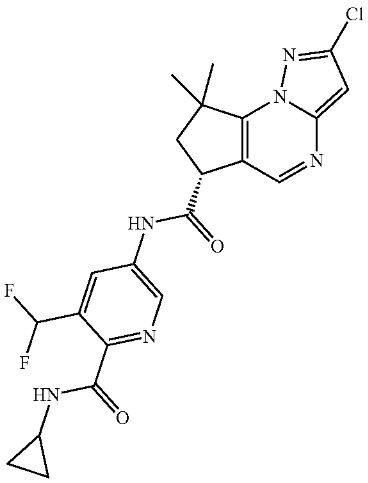 [SMILES: CC1(C)C[C@@H](C(=O)Nc2cnc(C(=O)NC3CC3)c(C(F)F)c2)c2cnc3cc(Cl)nn3c21] 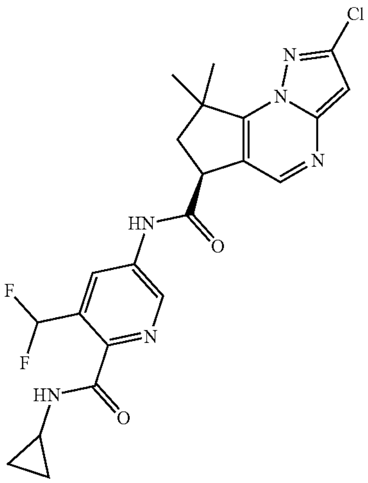 [SMILES: CC1(C)C[C@H](C(=O)Nc2cnc(C(=O)NC3CC3)c(C(F)F)c2)c2cnc3cc(Cl)nn3c21] |
| 174 | 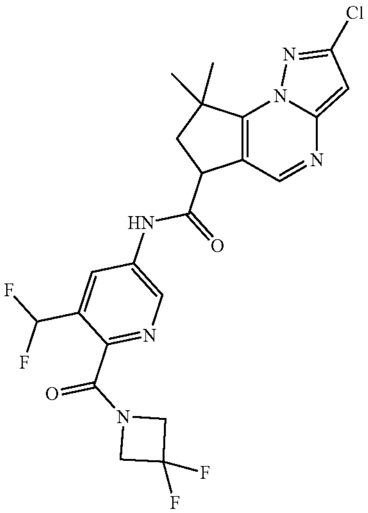 [SMILES: CC1(C)CC(C(=O)Nc2cnc(C(=O)N3CC(F)(F)C3)c(C(F)F)c2)c2cnc3cc(Cl)nn3c21] |
| 175 | 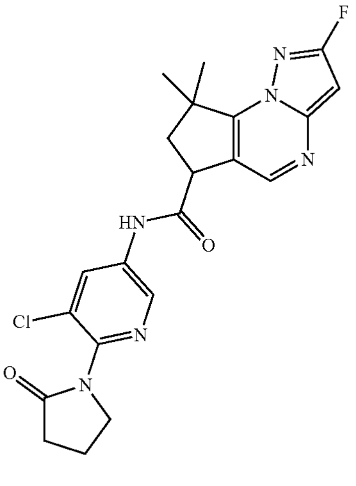 [SMILES: CC1(C)CC(C(=O)Nc2cnc(N3CCCC3=O)c(Cl)c2)c2cnc3cc(F)nn3c21] |

TABLE 1-continued
| Example Number | Structure |
| --- | --- |
| 176 | 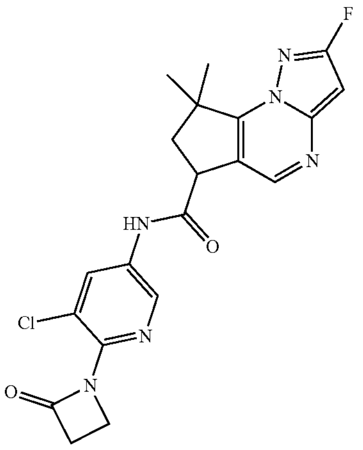 [SMILES: CC1(C)CC(C(=O)Nc2cnc(N3CCC3=O)c(Cl)c2)c2cnc3cc(F)nn3c21] |
| 177 | 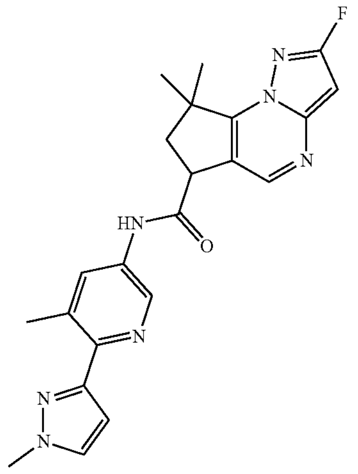 [SMILES: Cc1cc(NC(=O)C2CC(C)(C)c3c2cnc2cc(F)nn32)cnc1-c1ccn(C)n1] |
| 178 | 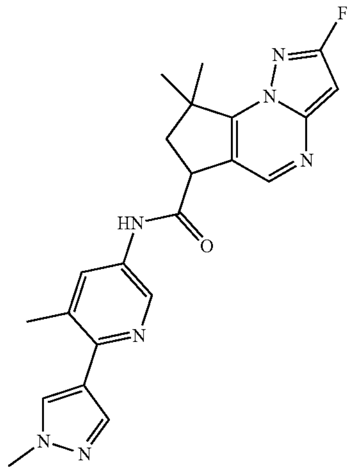 [SMILES: Cc1cc(NC(=O)C2CC(C)(C)c3c2cnc2cc(F)nn32)cnc1-c1cnn(C)c1] |

TABLE 1-continued
| Example Number | Structure |
|---|---|
| 179 | 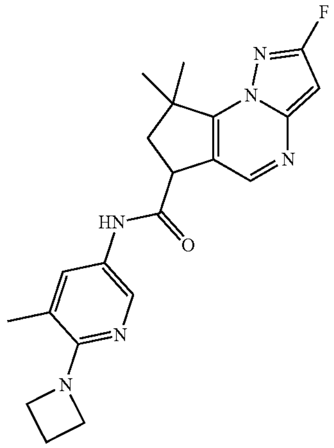 [SMILES: Cc1cc(NC(=O)C2CC(C)(C)c3c2cnc2cc(F)nn32)cnc1N1CCC1] |
| 180 (first eluting isomer)* 181 (second eluting isomer)* | 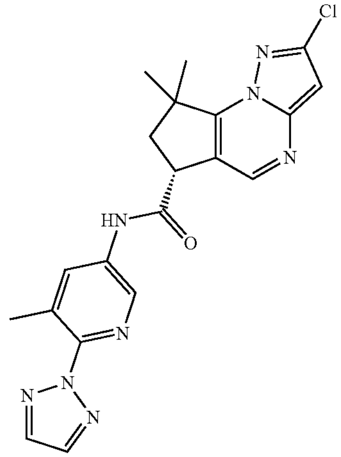 [SMILES: Cc1cc(NC(=O)[C@@H]2CC(C)(C)c3c2cnc2cc(Cl)nn32)cnc1-n1nccn1] |
| 182 (first eluting isomer)* 183 (second eluting isomer)* | 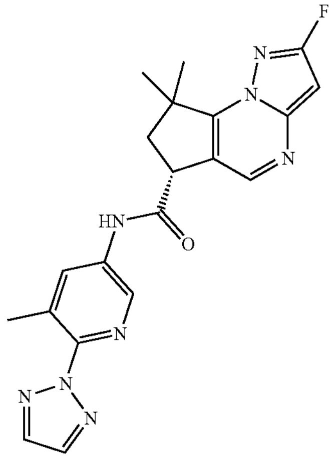 [SMILES: Cc1cc(NC(=O)[C@@H]2CC(C)(C)c3c2cnc2cc(F)nn32)cnc1-n1nccn1] 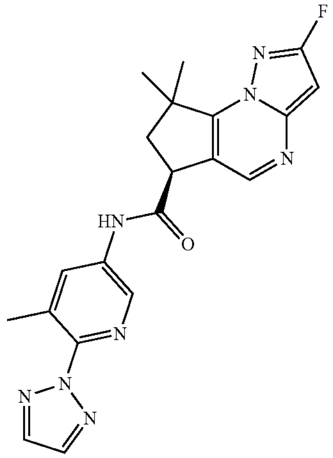 [SMILES: Cc1cc(NC(=O)[C@H]2CC(C)(C)c3c2cnc2cc(F)nn32)cnc1-n1nccn1] |

TABLE 1-continued
| Example Number | Structure |
|---|---|
| 184, 185, 186 and 187* | 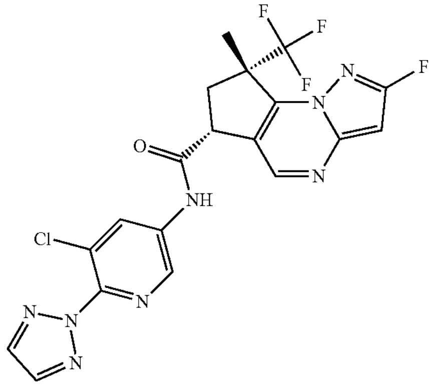 [SMILES: C[C@]1(C(F)(F)F)C[C@@H](C(=O)Nc2cnc(-n3nccn3)c(Cl)c2)c2cnc3cc(F)nn3c21] 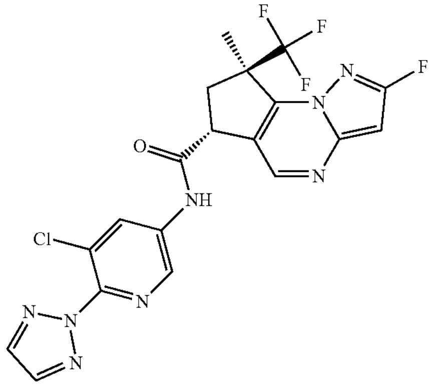 [SMILES: C[C@@]1(C(F)(F)F)C[C@@H](C(=O)Nc2cnc(-n3nccn3)c(Cl)c2)c2cnc3cc(F)nn3c21] 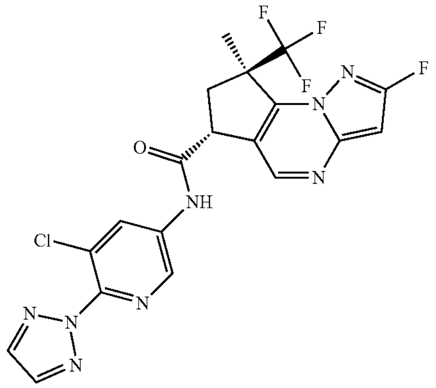 [SMILES: C[C@@]1(C(F)(F)F)C[C@@H](C(=O)Nc2cnc(-n3nccn3)c(Cl)c2)c2cnc3cc(F)nn3c21] 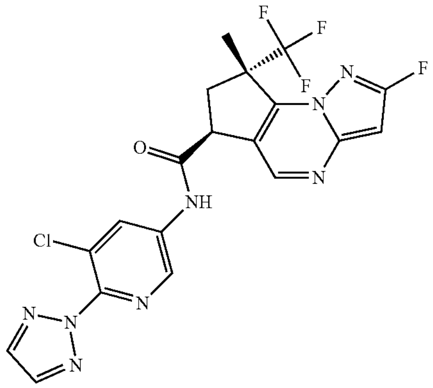 [SMILES: C[C@]1(C(F)(F)F)C[C@H](C(=O)Nc2cnc(-n3nccn3)c(Cl)c2)c2cnc3cc(F)nn3c21] |
| 188 (first eluting isomer)* 189 (second eluting isomer)* | 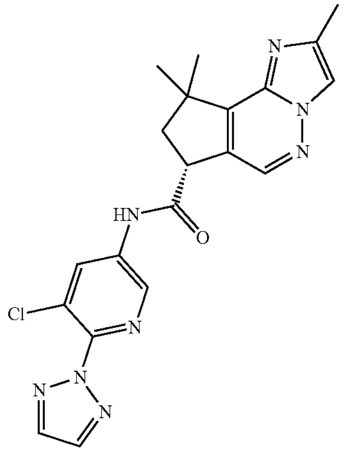 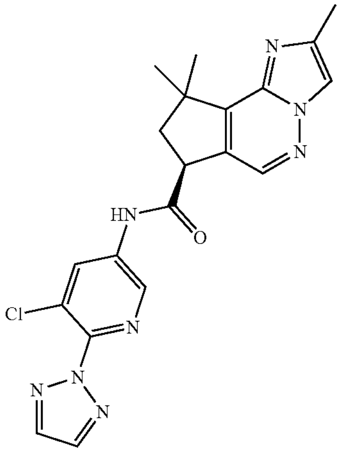 [SMILES: Cc1cn2ncc3c(c2n1)C(C)(C)C[C@@H]3C(=O)Nc1cnc(-n2nccn2)c(Cl)c1] |

TABLE 1-continued
| Example Number | Structure | |
|---|---|---|
| 190 (first eluting isomer)* 191 (second eluting isomer)* | 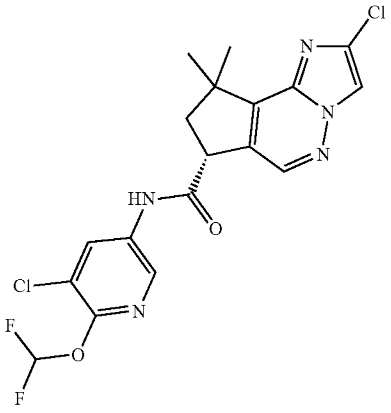 | 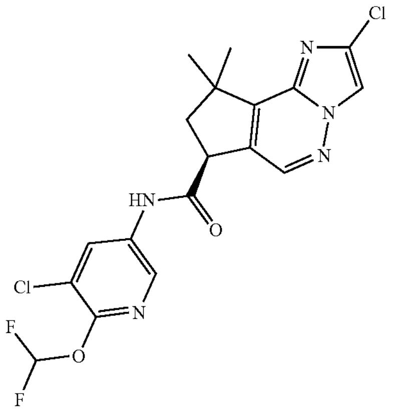 [SMILES: CC1(C)C[C@H](C(=O)Nc2cnc(OC(F)F)c(Cl)c2)c2cnn3cc(Cl)nc3c21] |
| 192 (first eluting isomer)* 193 (second eluting isomer)* | 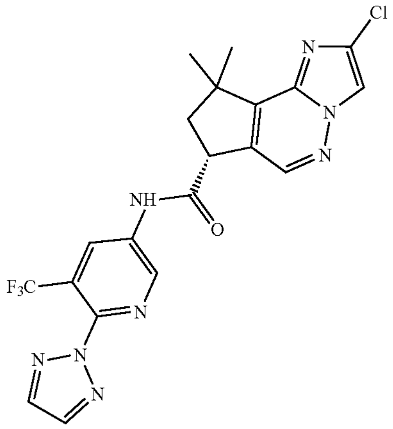 [SMILES: CC1(C)C[C@@H](C(=O)Nc2cnc(-n3nccn3)c(C(F)(F)F)c2)c2cnn3cc(Cl)nc3c21] | 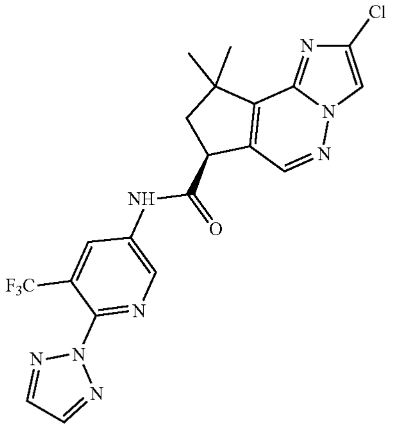 [SMILES: CC1(C)C[C@H](C(=O)Nc2cnc(-n3nccn3)c(C(F)(F)F)c2)c2cnn3cc(Cl)nc3c21] |
| 194 (first eluting isomer)* 195 (second eluting isomer)* | 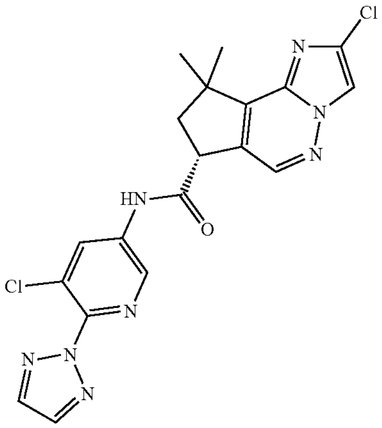 [SMILES: CC1(C)C[C@@H](C(=O)Nc2cnc(-n3nccn3)c(Cl)c2)c2cnn3cc(Cl)nc3c21] | 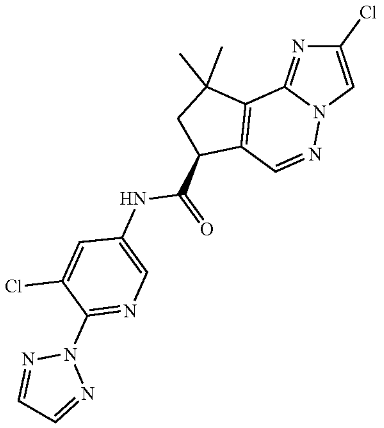 [SMILES: CC1(C)C[C@H](C(=O)Nc2cnc(-n3nccn3)c(Cl)c2)c2cnn3cc(Cl)nc3c21] |

TABLE 1-continued
| Example Number | Structure |
|---|---|
| 196 (first eluting isomer)* 197 (second eluting isomer)* | 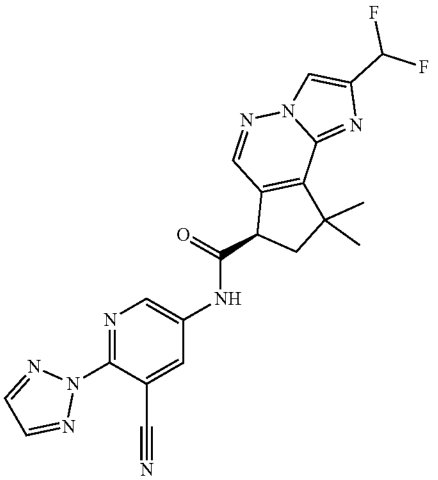 [SMILES: CC1(C)C[C@@H](C(=O)Nc2cnc(-n3nccn3)c(C#N)c2)c2cnn3cc(C(F)F)nc3c21] 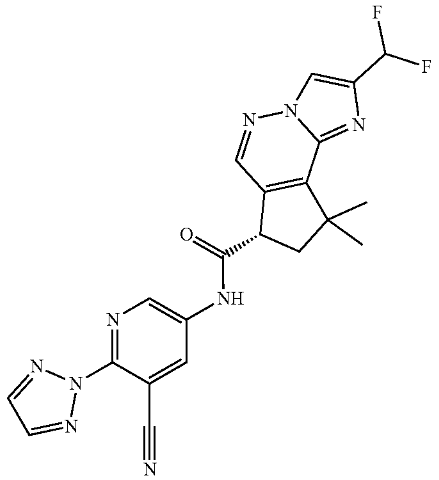 [SMILES: CC1(C)C[C@H](C(=O)Nc2cnc(-n3nccn3)c(C#N)c2)c2cnn3cc(C(F)F)nc3c21] |
| 198 (first eluting isomer)* 199 (second eluting isomer)* | 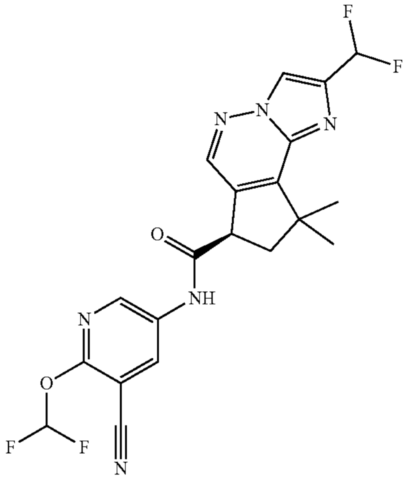 [SMILES: CC1(C)C[C@@H](C(=O)Nc2cnc(OC(F)F)c(C#N)c2)c2cnn3cc(C(F)F)nc3c21] 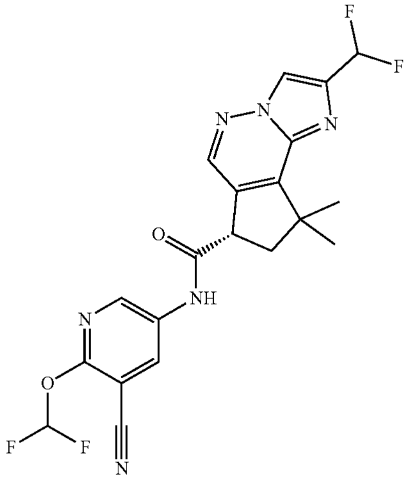 [SMILES: CC1(C)C[C@H](C(=O)Nc2cnc(OC(F)F)c(C#N)c2)c2cnn3cc(C(F)F)nc3c21] |
| 200 (first eluting isomer)* 201 (second eluting isomer)* | 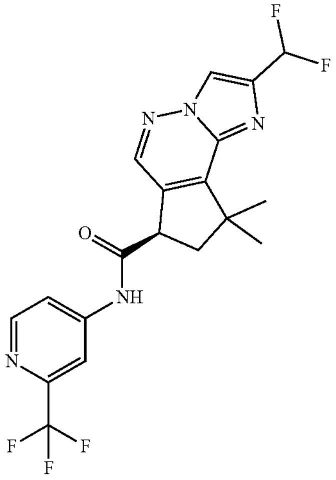 [SMILES: CC1(C)C[C@@H](C(=O)Nc2ccnc(C(F)(F)F)c2)c2cnn3cc(C(F)F)nc3c21] 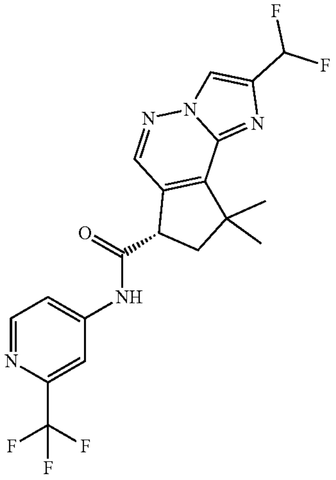 [SMILES: CC1(C)C[C@H](C(=O)Nc2ccnc(C(F)(F)F)c2)c2cnn3cc(C(F)F)nc3c21] |

TABLE 1-continued

| Example Number | Structure |
|---|---|
| 202 (first eluting isomer)* 203 (second eluting isomer)* | 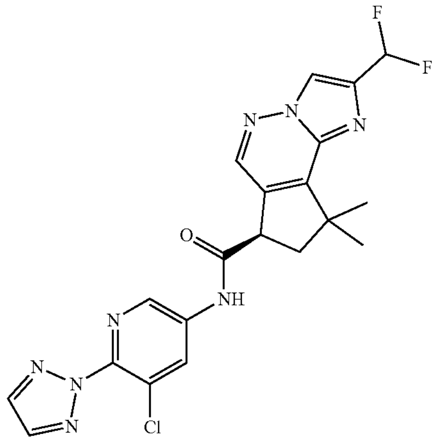 [SMILES: CC1(C)C[C@@H](C(=O)Nc2cnc(-n3nccn3)c(Cl)c2)c2cnn3cc(C(F)F)nc3c21] 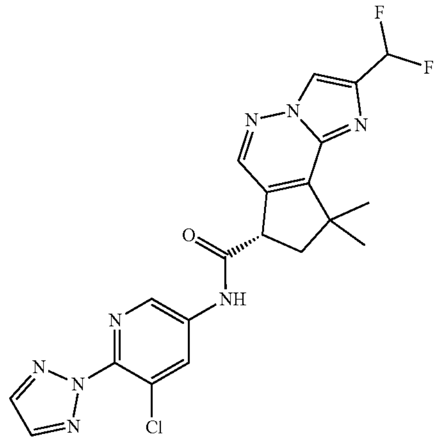 [SMILES: CC1(C)C[C@H](C(=O)Nc2cnc(-n3nccn3)c(Cl)c2)c2cnn3cc(C(F)F)nc3c21] |

*See experimental procedures on details for separation of isomers.

Processes of Preparation

Provided herein is a process of preparing a compound of Formula (I) (e.g., any compound described herein), comprising:

reacting a compound of Formula (I-A)

(I-A)

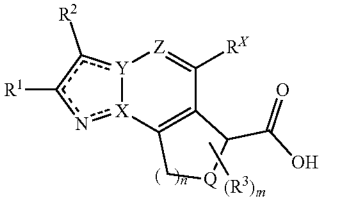

with $R^4$—$NH_2$, to form the compound of Formula (I).

In some embodiments, reacting the compound of Formula (I-A) with $R^4$—$NH_2$ (e.g., 5-chloro-6-(triazolyl)pyridin-3-amine) is performed in the presence of $POCl_3$ and pyridine.

In some embodiments, reacting the compound of Formula (I-A) with $R^4$—$NH_2$ is performed in the presence of N,N,N',N'-tetramethylchloroformamidinium hexafluorophosphate (TCFH).

In some embodiments, reacting the compound of Formula (I-A) with $R^4$—$NH_2$ is performed in the presence of N-methylimidazole (NMI).

In some embodiments, the compound of Formula (I-A) is prepared from a compound of Formula (I-A-N):

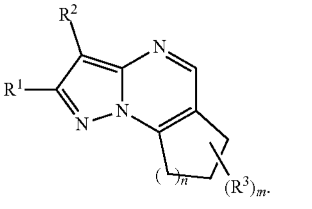

In some embodiments (when the compound of Formula (I-A) is prepared from a compound of Formula (I-A-N)), the process comprises reacting a compound of Formula (I-A-N-i)

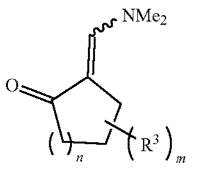

with a compound of Formula (I-A-N-ii)

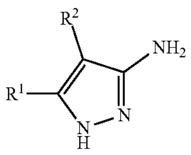

to form the compound of Formula (I-A-N).

In certain embodiments, reacting the compound of Formula (I-A-N-i) with the compound of Formula (I-A-N-ii) is performed in the presence of acid.

In certain of these embodiments, the acid is selected from the group consisting of hydrochloric acid and acetic acid.

Provided herein is a process of preparing a compound of Formula (I) (e.g., any compound described herein), comprising:

reacting a compound of Formula (I-B)

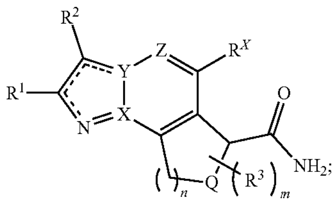

with $R^4$-Hal, where Hal is selected from the group consisting of C1, Br, I, and $OSO_2CF_3$;

to form the compound of Formula (I).

In some embodiments, reacting the compound of Formula (I-B) with $R^4$-Hal is performed in the presence of a catalyst and a ligand.

In some embodiments (when reacting the compound of Formula (I-B) with $R^4$-Hal is performed in the presence of a catalyst and a ligand), the catalyst is tris(dibenzylideneacetone)dipalladium(O).

In some embodiments (when reacting the compound of Formula (I-B) with $R^4$-Hal is performed in the presence of a catalyst and a ligand), the ligand is 4,5-bis(diphenylphosphino)-9,9-dimethylxanthene.

In some embodiments, the compound of Formula (I-B) is prepared from a compound of

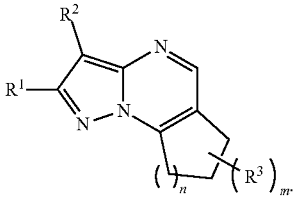

In some embodiments, the process comprises reacting a compound of Formula (I-A-N-i)

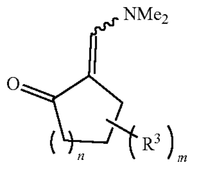

with a compound of Formula (I-A-N-ii)

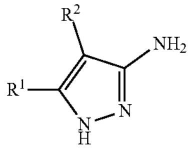

to form the compound of Formula (I-A-N).

In some embodiments, reacting the compound of Formula (I-A-N-i) with the compound of Formula (I-A-N-ii) is performed in the presence of acid.

In some embodiments (when reacting the compound of Formula (I-A-N-i) with the compound of Formula (I-A-N-ii) is performed in the presence of acid), the acid is selected from the group consisting of hydrochloric acid and acetic acid.

Methods of Treatment

Some embodiments provide a method of treating an autoimmune disorder (e.g., a MALT1-associated autoimmune disorder) in a subject in need of such treatment, the method comprising administering to the subject an effective amount of a compound of Formula (I), or a pharmaceutically acceptable salt thereof or a pharmaceutical composition thereof. In some embodiments, the autoimmune disorder is rheumatoid arthritis, multiple sclerosis, or systemic lupus erythematosus (SLE).

Some embodiments provide a method of treating an inflammatory disorder (e.g., a MALT1-associated inflammatory disorder) in a subject in need of such treatment, the method comprising administering to the subject an effective amount of a compound of Formula (I), or a pharmaceutically acceptable salt thereof or a pharmaceutical composition thereof. In some embodiments, the inflammatory disorder is chronic graft versus host disease (cGVHD).

Some embodiments provide a method of treating cancer (e.g., a MALT1-associated cancer) in a subject in need of such treatment, the method comprising administering to the subject an effective amount of a compound of Formula (I), or a pharmaceutically acceptable salt thereof or a pharmaceutical composition thereof. For example, provided herein are methods for treating a MALT1-associated cancer in a subject in need of such treatment, the method comprising a) detecting a dysregulation of a MALT1 gene, a MALT1 protease, or the expression or activity or level of any of the same in a sample from the subject; and b) administering an effective amount of a compound of Formula (I), or a pharmaceutically acceptable salt thereof. In some embodiments, the dysregulation of a MALT1 gene, a MALT1 protease, or the expression or activity or level of any of the same includes one or more fusion proteins.

In some embodiments of any of the methods or uses described herein, the cancer (e.g., MALT1-associated cancer) is a hematological cancer. In some embodiments of any of the methods or uses described herein, the cancer (e.g., MALT1-associated cancer) is a solid tumor. In some embodiments of any of the methods or uses described herein, the cancer (e.g., MALT1-associated cancer) is a lung cancer (e.g., small cell lung carcinoma or non-small cell lung carcinoma), thyroid cancer (e.g., papillary thyroid cancer, medullary thyroid cancer (e.g., sporadic medullary thyroid cancer or hereditary medullary thyroid cancer), differentiated thyroid cancer, recurrent thyroid cancer, or refractory differentiated thyroid cancer), thyroid adenoma, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., MALT1-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis, unknown primary carcinoma, urethral cancer, uterine cancer, uterine sarcoma, vaginal cancer, vulvar cancer, and Wilms' tumor.

In some embodiments, the cancer is a hematological cancer, such as a leukemia or a lymphoma. In some embodiments, a hematological cancer (e.g., hematological cancers that are MALT1-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CIVIL), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a MALT1-associated cancer) is AML or CMML.

In some embodiments, the cancer is glioblastoma, chronic myelogenous leukemia, myeloid leukemia, or non-Hodgkin's lymphoma.

In some embodiments, the cancer (e.g., the MALT1-associated cancer) is a solid tumor. Examples of solid tumors (e.g., solid tumors that are MALT1-associated cancers) include, for example, lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, neuroblastoma, and melanoma. See, e.g., Jiang et al., Cancer Research 2011, 71, 2183-2192; see also, Pan et al., Mol Cancer Res 2016, 14, 93-102 and Penas et al., Blood 2010, 115, 2214-2219.

In some embodiments, the subject is a human.

Compounds of Formula (I) and pharmaceutically acceptable salts thereof are also useful for treating a MALT1-associated cancer. Compounds of Formula (I) and pharmaceutically acceptable salts thereof are also useful for treating a MALT1-associated autoimmune disorder. Compounds of Formula (I) and pharmaceutically acceptable salts thereof are also useful for treating a MALT1-associated inflammatory disease.

Accordingly, also provided herein is a method for treating a subject diagnosed with or identified as having a MALT1-associated cancer, e.g., any of the exemplary MALT1-associated cancers disclosed herein, comprising administering to the subject an effective amount of a compound of Formula (I), or a pharmaceutically acceptable salt thereof, or a pharmaceutical composition thereof as defined herein.

In some embodiments of any of the methods provided herein, a compound of Formula (I) is selected from Examples 1-168.

Dysregulation of a MALT1 protease, a MALT1 gene, or the expression or activity or level of any (e.g., one or more) of the same can contribute to tumorigenesis. For example, a fusion protein can have increased protease activity as compared to a wild-type MALT1 protein, increased expression (e.g., increased levels) of a wild-type MALT1 protease in a mammalian cell can occur due to aberrant cell signaling and/or dysregulated autocrine/paracrine signaling (e.g., as compared to a control non-cancerous cell), MALT1 mRNA splice variants may also result in dysregulation of MALT1.

In some aspects, provided herein is a method for treating cancer in a subject in need thereof, including administering to the subject an effective amount of a compound of Formula (I), or a pharmaceutically acceptable salt thereof. Also provided herein is a method for treating a CBM complex pathway-associated cancer (such as any of those disclosed herein) in a subject in need thereof, including administering to the subject an effective amount of a compound of Formula (I), or a pharmaceutically acceptable salt thereof. Also provided is a method for treating a cancer in a subject in need thereof, including (a) identifying the cancer as being a CBM complex pathway-associated cancer; and (b) administering to the subject an effective amount of a compound of Formula (I), or a pharmaceutically acceptable salt thereof.

Identifying the cancer identifying the cancer in the subject as a CBM complex pathway-associated cancer can be performed by any appropriate method. In some embodiments, the step of identifying the cancer in the subject as a CBM complex pathway-associated cancer includes performing an assay to detect dysregulation in a CBM complex pathway-associated gene, a CBM complex pathway-associated protease protein, or expression or activity or level of any of the same in a sample from the subject. In some embodiments, the method further includes obtaining a sample from the subject (e.g., a biopsy sample). An assay can be any appropriate assay. In some embodiments, the assay is selected from the group consisting of sequencing (e.g., pyrosequencing or next generation sequencing), immunohistochemistry, enzyme-linked immunosorbent assay, and fluorescence in situ hybridization (FISH).

Also provided herein is a method for treating a cancer in a subject in need thereof, including administering to the subject an effective amount of a compound of Formula (I), or a pharmaceutically acceptable salt thereof to a subject identified as having a CBM complex pathway-associated cancer.

Also provided herein is a method of treating a MALT1-associated cancer in a subject, including administering to a subject identified or diagnosed as having a MALT1-associated cancer an effective amount of a compound of Formula (I), or a pharmaceutically acceptable salt thereof. Provided herein is also a method for treating cancer in a subject in need thereof, including: (a) determining that the cancer is associated with a dysregulation of a MALT1 gene, a MALT1 protease, or expression or activity or level of any of the same; and (b) administering to the subject an effective amount of a compound of Formula (I), or a pharmaceutically acceptable salt thereof.

Determining that the cancer is associated with a dysregulation of a MALT1 gene, a MALT1 protease, or expression or activity or level of any of the same can be performed using any appropriate method. In some embodiments, the step of determining that the cancer in the subject is a MALT1-associated cancer includes performing an assay to detect dysregulation in a MALT1 gene, a MALT1 protease protein, or expression or activity or level of any of the same in a sample from the subject. In some embodiments, the method further includes obtaining a sample from the subject (e.g., a biopsy sample). An assay can be any appropriate assay. In some embodiments, the assay is selected from the group consisting of sequencing (e.g., pyrosequencing or next generation sequencing), immunohistochemistry, enzyme-linked immunosorbent assay, and fluorescence in situ hybridization (FISH).

As described herein, a CBM complex pathway-associated cancer can be any appropriate CBM complex pathway-associated cancer (such as any of those described herein). In some embodiments, a CBM complex pathway-associated cancer is selected from the group consisting of a CBM complex pathway cell surface receptor-associated cancer, a cancer associated with a signal transducer between a cell surface receptor and a CBM complex, a component of a CBM complex-associated cancer, a MALT1 protease substrate-associated cancer, a cancer associated with a component of the NF-κB pathway downstream of a CBM complex, a cancer associated with a component of the JNK pathway downstream of a CBM complex, and a combination thereof. In some embodiments, the CBM complex pathway cell surface receptor-associated cancer is selected from the group consisting of a CD28-associated cancer, a BCR-associated cancer, a HER1-associated cancer, a HER2-associated cancer, and combinations thereof. In some embodiments, the cancer associated with a signal transducer between a cell surface receptor and a CBM complex is a protein kinase C beta (PKCβ)-associated cancer, a protein kinase C theta (PCKθ)-associated cancer, or a combination thereof. In some embodiments, the component of a CBM complex-associated cancer is selected from the group consisting of a MALT1-associated cancer, a CARD11-associated cancer, a CARD14-associated cancer, a CARD10-associated cancer, a CARDS-associated cancer, a BCL10-associated cancer, and combinations thereof. In some embodiments, the component of a CBM complex-associated cancer is selected from the group consisting of a MALT1-associated cancer, a CARD11-associated cancer, a BCL10-associated cancer, and combinations thereof. See, e.g., Tables B1, B2, and B3 for exemplary dysregulations in MALT1, CARD11, and BCL10. In some embodiments, the MALT1 protease substrate-associated cancer is selected from the group consisting of a BCL10-associated cancer, an A20-associated cancer, a CYLD-associated cancer, a RelB-associated cancer, a Regnase 1-associated cancer, a roquin-1-associated cancer, a HOIL1-associated cancer, a NIK associated cancer, a LIMA1α-associated cancer, and a combination thereof. In some embodiments, the MALT1 protease substrate-associated cancer is selected from the group consisting of a BCL10-associated cancer, an A20-associated cancer, a CYLD-associated cancer, and combinations thereof. See, e.g., Tables B3 and B4 for exemplary dysregulations in BCL10 and A20. In some embodiments, the cancer associated with a component of the NF-κB pathway downstream of a CBM complex is selected from the group consisting of a TAK1-associated cancer, a TRAF6-associated cancer, a TAB1-associated cancer, a TAB2-associated cancer, a TAB3-associated cancer, a MKK7-associated cancer, an IKKα-associated cancer, an IKKβ-associated cancer, an IKKγ-associated cancer, an IkBα-associated cancer, a p50-associated cancer, a p65 (RelA)-associated cancer, a c-Rel-associated cancer, and combinations thereof. In some embodiments, the cancer associated with a component of the NF-κB pathway downstream of a CBM complex is an IKKγ-associated cancer. In some embodiments, the cancer associated with a component of the JNK pathway downstream of a CBM complex is selected from the group consisting of a JNK1-associated cancer, a JNK2-associated cancer, a JNK3-associated cancer, a MYD88 transcription factor-associated cancer, an AP-1 transcription factor-associated cancer, and combinations thereof.

In some embodiments, the CBM complex pathway-associated cancer is a MALT1-associated cancer. A MALT1-associated cancer can have any appropriate dysregulation, such as any of those described herein. In some embodiments, the MALT1-associated cancer comprises an IAP2-MALT1 fusion. In some embodiments, the MALT1-associated cancer comprises an IGH-MALT1 fusion.

Also provided herein are methods of treating CBM complex pathway-associated diseases or disorders, autoimmune disorders, and inflammatory disorders. Accordingly, provided herein is a method for treating an autoimmune disorder in a subject in need thereof, including administering to the subject an effective amount of a compound of Formula (I), or a pharmaceutically acceptable salt thereof. Also provided herein is a method of treating a MALT1-associated autoimmune disorder in a subject, including administering to a subject identified or diagnosed as having a MALT1-associated autoimmune disorder an effective amount of a compound of Formula (I), or a pharmaceutically acceptable salt thereof. In some cases, provided herein is a method for treating an autoimmune disorder in a subject in need thereof, including: (a) determining that the autoimmune disorder is associated with a dysregulation of a MALT1 gene, a MALT1 protease, or expression or activity or level of any of the same; and (b) administering to the subject an effective amount of a compound of Formula (I), or a pharmaceutically acceptable salt thereof. Provided also herein is a method of treating a MALT1-associated autoimmune disorder in a subject, including administering an effective amount of a compound of Formula (I), or a pharmaceutically acceptable salt thereof to a subject determined to have a MALT1-associated autoimmune disorder. In addition, provided herein is a method for treating an inflammatory disorder in a subject in need thereof, including administering to the subject an effective amount of a compound of Formula (I), or a pharmaceutically acceptable salt thereof. In some cases, provided herein is a method of treating a MALT1-associated inflammatory disorder in a subject, including administering to a subject identified or diagnosed as having a MALT1-associated inflammatory disorder an effective amount of a compound of Formula (I), or a pharmaceutically acceptable salt thereof. Also provided herein is a method for treating an inflammatory disorder in a subject in need thereof, including: (a) determining that the inflammatory disorder is associated with a dysregulation of a MALT1 gene, a MALT1 protease, or expression or activity or level of any of the same; and (b) administering to the subject an effective amount of a compound of Formula (I), or a pharmaceutically acceptable salt thereof. Provided also herein is a method of treating a MALT1-associated inflammatory disorder in a subject, including administering an effective amount of a compound of Formula (I), or a pharmaceutically acceptable salt thereof to a subject determined to have a MALT1-associated inflammatory disorder Additionally provided herein is a method for treating a CBM complex pathway-associated disease or disorder in a subject in need thereof, including administering to the subject an effective amount of a compound of Formula (I), or a pharmaceutically acceptable salt thereof. Also provided is a method for treating a disease or disorder in a subject in need thereof, including: (a) identifying the cancer as being a CBM complex pathway-associated disease or disorder; and (b) administering to the subject an effective amount of a compound of Formula (I), or a pharmaceutically acceptable salt thereof. In addition, provided herein is a method for treating a disease or disorder in a subject in need thereof, including: administering to the subject an effective amount of a compound of Formula (I), or a pharmaceutically acceptable salt thereof to a subject identified as having a CBM complex pathway-associated disease or disorder.

A CBM complex pathway-associated disease or disorder can be any appropriate CBM complex pathway-associated disease or disorder, such as any of those described herein. In some embodiments, the CBM complex pathway-associated disease or disorder is an autoimmune disease. In some embodiments, the CBM complex pathway-associated disease or disorder is an inflammatory disease. In some embodiments, the CBM complex pathway-associated cancer is selected from the group consisting of a CBM complex pathway cell surface receptor-associated cancer, a disease or disorder associated with a signal transducer between a cell surface receptor and a CBM complex, a component of a CBM complex-associated cancer, a MALT1 protease substrate-associated cancer, a disease or disorder associated with a component of the NF-κB pathway downstream of a CBM complex, a disease or disorder associated with a component of the JNK pathway downstream of a CBM complex, and a combination thereof. In some embodiments, the CBM complex pathway-associated disease or disorder is a MALT1-associated disease or disorder.

In some cases, compounds of Formula (I), or a pharmaceutically acceptable salt thereof can be useful for inhibiting the processes of cells, such as inhibiting the proliferation of cells. Accordingly, provided herein is a method for inhibiting mammalian cell proliferation, including contacting the mammalian cell with a compound of Formula (I), or a pharmaceutically acceptable salt thereof. Also provided herein is a method for inhibiting CBM complex pathway activity in a mammalian cell, including contacting the mammalian cell with a compound of Formula (I), or a pharmaceutically acceptable salt thereof. Provided also herein is a method for inhibiting MALT1 protease activity in a mammalian cell, including contacting the mammalian cell with a compound of Formula (I), or a pharmaceutically acceptable salt thereof. In some embodiments, the contacting occurs in vivo. In some embodiments, the contacting occurs in vitro. A mammalian cell can be any appropriate cell. In some embodiments, the mammalian cell is a mammalian immune cell. In some embodiments, the mammalian cell is a mammalian cancer cell. In some embodiments, the mammalian cancer cell is a mammalian CBM complex pathway-associated cancer cell. In some embodiments, the mammalian cancer cell is a mammalian MALT1-associated cancer cell. In some embodiments, the mammalian cell has dysregulation of a MALT1 gene, a MALT1 protease protein, or expression or activity or level of any of the same. In some embodiments, the dysregulation of a MALT1 gene, a MALT1 protease protein, or expression or activity or level of any of the same is an IAP2-MALT1 fusion, an IGH-MALT1 fusion, or a combination thereof.

Compounds of Formula (I), or a pharmaceutically acceptable salt thereof can also be useful in the manufacture of medicaments. Accordingly, provided herein is a use of a compound of Formula (I), or a pharmaceutically acceptable salt thereof in the manufacture of a medicament for the treatment of a CBM complex pathway-associated disease or disorder. A CBM complex pathway-associated disease or disorder can be any appropriate CBM complex pathway-associated disease or disorder, such as those described herein. In some embodiments, the CBM complex pathway-associated disease or disorder is selected from the group consisting of a CBM complex pathway cell surface receptor-associated cancer, a disease or disorder associated with a signal transducer between a cell surface receptor and a CBM complex, a component of a CBM complex-associated cancer, a MALT1 protease substrate-associated cancer, a disease or disorder associated with a component of the NF-κB pathway downstream of a CBM complex, a disease or disorder associated with a component of the JNK pathway downstream of a CBM complex, and a combination thereof. In some embodiments, the CBM complex pathway-associated disease or disorder is a CBM complex pathway-associated autoimmune disorder. In some embodiments, the CBM complex pathway-associated disease or disorder is a CBM complex pathway-associated inflammatory disorder. In some embodiments, the CBM complex pathway-associated disease or disorder is a CBM complex pathway-associated cancer. In some embodiments, the CBM complex pathway-associated disease or disorder is a MALT1-associated disease or disorder. In some embodiments, the MALT1-associated disease or disorder comprises a dysregulation of a MALT1 gene, a MALT1 protease protein, or expression or activity or level of any of the same. In some embodiments, the dysregulation of a MALT1 gene, a MALT1 protease protein, or expression or activity or level of any of the same is an IAP2-MALT1 fusion, an IGH-MALT1 fusion, or a combination thereof.

In some embodiments, the compounds provided herein exhibit brain and/or central nervous system (CNS) penetrance. Such compounds are capable of crossing the blood brain barrier and inhibiting a MALT1 protease in the brain and/or other CNS structures. In some embodiments, the compounds provided herein are capable of crossing the blood brain barrier in an effective amount. For example, treatment of a subject with cancer (e.g., a MALT1-associated cancer such as a MALT1-associated brain or CNS cancer) can include administration (e.g., oral administration) of the compound to the subject. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the subject has previously been treated with another anticancer agent, e.g., another protease inhibitor (e.g., a compound that is not a compound of Formula (I)). In some embodiments, the brain tumor is a metastatic brain tumor. In some embodiments, the subject has previously been treated with another anticancer agent, e.g., another protease inhibitor (e.g., a compound that is not a compound of Formula (I)).

In some embodiments of any of the methods or uses described herein, an assay used to determine whether the subject has a dysregulation of a gene (e.g., a MALT1 gene), or a protein (e.g., a MALT1 protein), or expression or activity or level of any of the same, using a sample from a subject can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a gene (e.g., a MALT1 gene), a protein (e.g., a MALT1 protein), or expression or activity or levels of any of the same. In some embodiments, the sample is a biological sample or a biopsy sample (e.g., a paraffin-embedded biopsy sample) from the subject. In some embodiments, the subject is a subject suspected of having a MALT1-associated cancer, a subject having one or more symptoms of a MALT1-associated cancer, and/or a subject that has an increased risk of developing a MALT1-associated cancer).

In some embodiments, dysregulation of a gene (e.g., a MALT1 gene), a MALT1 protein (e.g., a MALT1 protein), or the expression or activity or level of any of the same can be identified using a liquid biopsy (variously referred to as a fluid biopsy or fluid phase biopsy). Liquid biopsy methods can be used to detect total tumor burden and/or the dysregulation of a gene (e.g., a MALT1 protein), a MALT1 protein (e.g., a MALT1 protein), or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a gene (e.g., a MALT1 gene), a protein (e.g., a MALT1 protein), or the expression or activity or level of any of the same. In some embodiments, liquid biopsies can be used to detect the presence of dysregulation of a gene (e.g., a MALT1 gene), a protein (e.g., a MALT1 protein), or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a gene (e.g., a MALT1 gene), a protein (e.g., a MALT1 protein), or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially available testing panels designed to detect dysregulation of a gene (e.g., a MALT1 gene), a protein (e.g., a MALT1 protein), or the expression or activity or level of any of the same). Liquid biopsies can be used to detect dysregulation of a gene (e.g., a MALT1 gene), a protein (e.g., a MALT1 protein), or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a dysregulation of a gene (e.g., a MALT1 gene), a protein (e.g., a MALT1 protein), or the expression or activity or level of any of the same identified using a liquid biopsy is also present in a cancer cell that is present in the subject (e.g., in a tumor). In some embodiments, any of the types of dysregulation of a gene (e.g., a MALT1 gene), a protein (e.g., a MALT1 protein), or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a gene (e.g., a MALT1 gene), a protein (e.g., a MALT1 protein), or the expression or activity or level of any of the same in the subject can indicate that the subject will be responsive to a treatment that includes administration of a compound of Formula (I), or a pharmaceutically acceptable salt thereof.

Liquid biopsies can be performed at multiple times during a course of diagnosis, a course of monitoring, and/or a course of treatment to determine one or more clinically relevant parameters including, without limitation, progression of the disease and/or efficacy of a treatment. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable). In some embodiments, a treatment to be administered to a subject can include a compound of Formula (I), or a pharmaceutically acceptable salt thereof.

In some embodiments, the efficacy of a compound of Formula (I), or a pharmaceutically acceptable salt thereof, can be determined by assessing the allele frequency of a dysregulation of a gene (e.g., a MALT1 gene) in cfDNA obtained from a subject at different time points, e.g., cfDNA obtained from the subject at a first time point and cfDNA obtained from the subject at a second time point, where at least one dose of a compound of Formula (I), or a pharmaceutically acceptable salt thereof, is administered to the subject between the first and second time points. Some embodiments of these methods can further include administering to the subject at least one dose of the compound of Formula (I), or a pharmaceutically acceptable salt thereof, between the first and second time points. For example, a reduction (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction) in the allele frequency (AF) of the dysregulation of a gene (e.g., MALT1 gene) in the cfDNA obtained from the subject at the second time point as compared to the allele frequency (AF) of the dysregulation of a gene (e.g., MALT1 gene) in the cfDNA obtained from the subject at the first time point indicates that the compound of Formula (I), or a pharmaceutically acceptable salt thereof, was effective in the subject. In some embodiments, the AF is reduced such that the level is below the detection limit of the instrument. Alternatively, an increase in the allele frequency (AF) of the dysregulation of a gene (e.g., MALT1 gene) in the cfDNA obtained from the subject at the second time point as compared to the allele frequency (AF) of the dysregulation of a gene (e.g., MALT1 gene) in the cfDNA obtained from the subject at the first time point indicates that the compound of Formula (I), or a pharmaceutically acceptable salt thereof, was not effective in the subject. Some embodiments of these methods can further include, administering additional doses of a compound of Formula (I), or a pharmaceutically acceptable salt thereof, to a subject in which a compound of Formula (I), or a pharmaceutically acceptable salt thereof, was determined to be effective. Some embodiments of these methods can further include, administering a different treatment (e.g., a treatment that does not include the administration of a compound of Formula (I), or a pharmaceutically acceptable salt thereof, as a monotherapy) to a subject in which a compound of Formula (I), or a pharmaceutically acceptable salt thereof, was determined not to be effective.

In some examples of these methods, the time difference between the first and second time points can be about 1 day to about 1 year, about 1 day to about 11 months, about 1 day to about 10 months, about 1 day to about 9 months, about 1 day to about 8 months, about 1 day to about 7 months, about 1 day to about 6 months, about 1 day to about 5 months, about 1 day to about 4 months, about 1 day to about 3 months, about 1 day to about 10 weeks, about 1 day to about 2 months, about 1 day to about 6 weeks, about 1 day to about 1 month, about 1 day to about 25 days, about 1 day to about 20 days, about 1 day to about 15 days, about 1 day to about 10 days, about 1 day to about 5 days, about 2 days to about 1 year, about 5 days to about 1 year, about 10 days to about 1 year, about 15 days to about 1 year, about 20 days to about 1 year, about 25 days to about 1 year, about 1 month to about 1 year, about 6 weeks to about 1 year, about 2 months to about 1 year, about 3 months to about 1 year, about 4 months to about 1 year, about 5 months to about 1 year, about 6 months to about 1 year, about 7 months to about 1 year, about 8 months to about 1 year, about 9 months to about 1 year, about 10 months to about 1 year, about 11 months to about 1 year, about 1 day to about 7 days, about 1 day to about 14 days, about 5 days to about 10 days, about 5 day to about 20 days, about 10 days to about 20 days, about 15 days to about 1 month, about 15 days to about 2 months, about 1 week to about 1 month, about 2 weeks to about 1 month, about 1 month to about 3 months, about 3 months to about 6 months, about 4 months to about 6 months, about 5 months to about 8 months, or about 7 months to about 9 months. In some embodiments of these methods, the subject can be previously identified as having a cancer having a dysregulated gene (e.g., any of the examples of a dysregulated gene described herein) (e.g., a MALT1 gene). In some embodiments of these methods, a subject can have been previously diagnosed as having any of the types of cancer described herein. In some embodiments of these methods, the subject can have one or more metastases (e.g., one or more brain metastases).

In some of the above embodiments, the cfDNA comprises ctDNA such as MALT1-associated ctDNA. For example, the cfDNA is ctDNA such as MALT1-associated ctDNA. In some embodiments, at least some portion of cfDNA is determined to be MALT1-associated ctDNA, for example, a sequenced and/or quantified amount of the total cfDNA is determined to have a MALT1 fusion and/or overexpression of MALT1.

In the field of medical oncology, it is normal practice to use a combination of different forms of treatment to treat each subject with cancer. In medical oncology the other component(s) of such conjoint treatment or therapy in addition to compositions provided herein may be, for example, surgery, radiotherapy, and chemotherapeutic agents, such as other protease inhibitors, kinase inhibitors, signal transduction inhibitors, and/or monoclonal antibodies.

For example, a surgery may be open surgery or minimally invasive surgery. Compounds of Formula (I), or a pharmaceutically acceptable salt thereof therefore may also be useful as adjuvants to cancer treatment, that is, they can be used in combination with one or more additional therapies or therapeutic agents, for example, a chemotherapeutic agent that works by the same or by a different mechanism of action. In some embodiments, a compound of Formula (I), or a pharmaceutically acceptable salt thereof, can be used prior to administration of an additional therapeutic agent or additional therapy. For example, a subject in need thereof can be administered one or more doses of a compound of Formula (I), or a pharmaceutically acceptable salt thereof for a period of time and then undergo at least partial resection of the tumor. In some embodiments, the treatment with one or more doses of a compound of Formula (I), or a pharmaceutically acceptable salt thereof reduces the size of the tumor (e.g., the tumor burden) prior to the at least partial resection of the tumor. In some embodiments, a subject in need thereof can be administered one or more doses of a compound of Formula (I), or a pharmaceutically acceptable salt thereof for a period of time and under one or more rounds of radiation therapy. In some embodiments, the treatment with one or more doses of a compound of Formula (I), or a pharmaceutically acceptable salt thereof reduces the size of the tumor (e.g., the tumor burden) prior to the one or more rounds of radiation therapy.

In some embodiments, a subject has a cancer (e.g., a locally advanced or metastatic tumor) that is refractory or intolerant to standard therapy (e.g., administration of a chemotherapeutic agent), such as a first MALT1 inhibitor, a kinase inhibitor, immunotherapy, cell or gene therapy, or radiation (e.g., radioactive iodine). In some embodiments, a subject has a cancer (e.g., a locally advanced or metastatic tumor) that is refractory or intolerant to prior therapy (e.g., administration of a chemotherapeutic agent, such as a first MALT1 inhibitor or another protease inhibitor, immunotherapy, cell or gene therapy, or radiation (e.g., radioactive iodine). In some embodiments, a subject has a cancer (e.g., a locally advanced or metastatic tumor) that has no standard therapy. In some embodiments, a subject is MALT1-protease inhibitor naïve. For example, the subject is naïve to treatment with a selective MALT1-protease inhibitor. In some embodiments, a subject is not MALT1-protease inhibitor naïve.

In some embodiments of any of the methods described herein, the compound of Formula (I), or a pharmaceutically acceptable salt thereof, is administered in combination with an effective amount of at least one additional therapeutic agent selected from one or more additional therapies or therapeutic (e.g., chemotherapeutic or immunomodulatory) agents. An additional therapy or therapeutic agent can be any appropriate additional therapy or therapeutic agent, such as any of those described herein.

Non-limiting examples of additional therapeutic agents include: other MALT1-targeted therapeutic agents (i.e. a first or second MALT1 protease inhibitor, e.g., JNJ-67856633 or CTX-177), other protease inhibitors, kinase inhibitors (e.g., receptor tyrosine kinase-targeted therapeutic agents such as BTK or EGFR inhibitors), signal transduction pathway inhibitors, checkpoint inhibitors, modulators of the apoptosis pathway (e.g., venetoclax or obataclax); cytotoxic chemotherapeutics, angiogenesis-targeted therapies, immune-targeted agents (including antibody and cell-based immunotherapies, and antibody-drug conjugates) and radiotherapy.

In some embodiments, the compound of Formula (I), or a pharmaceutically acceptable salt thereof, and the additional therapeutic agent are administered simultaneously as separate dosages. In some embodiments, the compound of Formula (I), or a pharmaceutically acceptable salt thereof, and the additional therapeutic agent are administered as separate dosages sequentially in any order.

In some embodiments, the other MALT1-targeted therapeutic is another protease inhibitor exhibiting MALT1 inhibition activity. In some embodiments, the other MALT1-targeted therapeutic inhibitor is selective for a MALT1 protease. Exemplary MALT1 protease inhibitors can exhibit inhibition activity ($IC_{50}$) against a MALT1 protease of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a MALT1 protease inhibitors can exhibit inhibition activity ($IC_{50}$) against a MALT1 protease of less than about 25 nM, less than about 10 nM, less than about 5 nM, or less than about 1 nM as measured in an assay as provided herein.

Non-limiting examples of protease-targeted therapeutic agents (e.g., a first MALT1 inhibitor or a second MALT1 inhibitor) include JNJ-67856633 and CTX-177.

Non-limiting examples of multi-kinase inhibitors include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl) piperazine-1-carbothioamide); apatinib (YN968D1) (N-[4-(1-cyanocyclopentyl) phenyl-2-(4-picolyl)amino-3-Nicotinamide methanesulphonate); cabozantinib (Cometriq XL-184) (N-(4-((6,7-Dimethoxyquinolin-4-yl)oxy)phenyl)-N'-(4-fluorophenyl)cyclopropane-1,1-dicarboxamide); dovitinib (TKI258; GFKI-258; CHIR-258) ((3Z)-4-amino-5-fluoro-3-[5-(4-methylpiperazin-1-yl)-1,3-dihydrobenzimidazol-2-ylidene]quinolin-2-one); famitinib (5-[2-(diethylamino)ethyl]-2-[(Z)-(5-fluoro-2-oxo-1H-indol-3-ylidene) methyl]-3-methyl-6,7-dihydro-1H-pyrrolo[3,2-c]pyridin-4-one); fedratinib (SAR302503, TG101348) (N-(2-Methyl-2-propanyl)-3-{[5-methyl-2-({4-[2-(1-pyrrolidinyl)ethoxy] phenyl}amino)-4-pyrimidinyl] amino}benzenesulfonamide); foretinib (XL880, EXEL-2880, GSK1363089, GSK089) (N1'-[3-fluoro-4-[[6-methoxy-7-(3-morpholinopropoxy)-4-quinolyl]oxy]

phenyl]-N1-(4-fluorophenyl)cyclopropane-1,1-dicarboxamide); fostamantinib (R788) (2H-Pyrido[3,2-b]-1,4-oxazin-3(4H)-one, 6-[[5-fluoro-2-[(3,4,5-trimethoxyphenyl)amino]-4-pyrimidinyl]amino]-2,2-dimethyl-4-[(phosphonooxy)methyl]-, sodium salt (1:2)); ilorasertib (ABT-348) (1-(4-(4-amino-7-(1-(2-hydroxyethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methyl-amino)-anilino)-1-phenyl-methylene]-6-methyoxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl)phenyl]benzamide); PP242 (torkinib) (2-[4-Amino-1-(1-methylethyl)-1H-pyrazolo[3,4-d]pyrimidin-3-yl]-1H-indol-5-01); quizartinib (1-(5-(tert-Butyl)isoxazol-3-yl)-3-(4-(7-(2-morpholinoethoxy)benzo[d]imidazo[2,1-b]thiazol-2-yl)phenyl)urea); regorafenib (BAY 73-4506, stivarga) (4-[4-({[4-Chloro-3-(trifluoromethyl)phenyl]carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCDS 16, MG516) (N-(3-Fluoro-4-{[2-(5-{[(2-methoxyethyl)amino]methyl}-2-pyridinyl)thieno[3,2-b]pyridin-7-yl]oxy}phenyl)-N'-(4-fluorophenyl)-1,1-cyclopropanedicarboxamide); sorafenib (BAY 43-9006) (4-[4-[[[[4-chloro-3-(trifluoromethyl)phenyl]amino]carbonyl]amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl)methyl)-3-(trifluoromethyl)phenyl)carbamoyl)-2-methylphenyl)-5-(thiophen-2-yl)nicotinamide); BPR 1K871 (1-(3-chlorophenyl)-3-(5-(2-((7-(3-(dimethylamino)propoxy)quinazolin-4-yl)amino)ethyl)thiazol-2-yl)urea); CLM3 (1-phenethyl-N-(1-phenylethyl)-1H-pyrazolo[3,4-d]pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl)phenyl]-N'-[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methyl sulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl)phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl)phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinb (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-dione); XL-999 ((Z)-5-((1-ethylpiperidin-4-yl)amino)-3-((3-fluorophenyl)(5-methyl-1H-imidazol-2-yl)methylene)indolin-2-one); BPR1J373 (a 5-phenylthiazol-2-ylamine-pyriminide derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD15-44 (N-(4-((4-ethylpiperazin-1-yl)methyl)-3-(trifluoromethyl)phenyl)-4-methyl-3-(pyridin-3-ylethynyl)benzamide (generated from structure)); ITRI-305 (DONS TB, DIB003599); BLU-667 ((1S,4R)—N—((S)-1-(6-(4-fluoro-1H-pyrazol-1-yl)pyridin-3-yl)ethyl)-1-methoxy-4-(4-methyl-6-((5-methyl-1H-pyrazol-3-yl)amino)pyrimidin-2-yl)cyclohexane-1-carboxamide); BLU6864; DS-5010; GSK3179106; GSK3352589; NMS-E668; TAS0286/HM05; TPX0046; and N-(3-(2-(dimethyl amino)ethoxy)-5-(trifluoromethyl)phenyl)-2-(4-(4-ethoxy-6-oxo-1,6-dihydropyridin-3-yl)-2-fluorophenyl)acetamide.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3 S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Gö 6976, GNF-5837, GTx-186, GW 441756, LOXO-101, MGCD516, PLX7486, RXDX101, VM-902A, TPX-0005, TSR-011, GNF-4256, N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea, AZ623, AZ64, (S)-5-Chloro-N2-(1-(5-fluoropyridin-2-yl)ethyl)-N4-(5-isopropoxy-1H-pyrazol-3-yl)pyrimidine-2,4-diamine, AZD7451, CEP-751, CT327, sunitinib, GNF-8625, and (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol.

In some embodiments, the additional therapeutic agent is a BRAF inhibitor. Non-limiting examples of a BRAF inhibitor include dabrafenib, vemurafenib (also called RG7204 or PLX4032), sorafenib tosylate, PLX-4720, GDC-0879, BMS-908662 (Bristol-Meyers Squibb), LGX818 (Novartis), PLX3603 (Hofmann-LaRoche), RAF265 (Novartis), RO5185426 (Hofmann-LaRoche), and GSK2118436 (GlaxoSmithKline). Additional examples of a BRAF inhibitor are known in the art.

In some embodiments, the additional therapeutic agent is an epidermal growth factor receptor typrosine kinase inhibitor (EGFR). For example, EGFR inhibitors can include osimertinib (merelectinib, Tagrisso), erlotinib (Tarceva), gefitinib (Iressa), cetuximab (Erbitux), necitumumab (Portrazza), neratinib (Nerlynx), lapatinib (Tykerb), panitumumab (Vectibix), and vandetanib (Caprelsa).

In some embodiments, the additional therapeutic agent is a Ras-Raf-MEK-ERK pathway inhibitors (e.g., binimetinib, selumetinib, encorafenib, sorafenib, trametinib, and vemurafenib), PI3K-Akt-mTOR-S6K pathway inhibitors (e.g., everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

In some embodiments, the additional therapeutic agent is a BTK inhibitor. Non-limiting examples of BTK inhibitors include ibrutinib, acalabrutinib, and zanubrutinib.

In some embodiments, the additional therapeutic agent is a Bcl-2 inhibitor. Non-limiting examples of Bcl-2 inhibitors include venetoclax, navitoclax, oblimersen, obatoclax, and AT-101.

In some embodiments, the additional therapeutic agent is a PI3K inhibitor. Non-limiting examples of PI3K inhibitors include idelalisib, copanlisib, duvelisib, alpelisib, taselisib, buparlisib, umbralisib, and copanlisib.

In some embodiments, the additional therapeutic agent is a mTOR inhibitor. Non-limiting examples of mTOR inhibitors include everolimus, temsirolimus, and ridaforolimus.

In some embodiments, the additional therapeutic agent is a HDAC inhibitor. Non-limiting examples of HDAC inhibitors include vorinostat, romidepsin, belinostat, chidamide, panobinostat, CXD101, and abexinostat.

In some embodiments, the additional therapeutic agent is a checkpoint inhibitor. Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, the additional therapeutic agent is a cytotoxic chemotherapeutic. Non-limiting example of cytotoxic chemotherapeutics include arsenic trioxide, bleomycin, bendamustine, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In some embodiments, the additional therapeutic agent is an angiogenesis-targeted therapeutic. Non-limiting examples of angiogenesis-targeted therapies include lenalidomide, enzastaurine, aflibercept, and bevacizumab.

In some embodiments, an additional therapy or therapeutic agent can include a histidyl-tRNA synthetase (HRS) polypeptide or an expressible nucleotide that encodes the HRS polypeptide.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymria). In some embodiments, the CAR-T cell therapy is axicabtagene ciloleucel (Yescarta). In some embodiments, the CAR-T cell therapy is brexucabtagene autoleucel (Tecartus). In some embodiments, the CAR-T cell therapy is relmacabtagene autoleucel. In some embodiments, the CAR-T cell therapy is ALLO-501.

In some embodiments, the immunotherapy is an antibody therapy (e.g., a monoclonal antibody, a conjugated antibody, or a bispecific antibody). In some embodiments, the antibody therapy is bevacizumab (Mvasti™, Avastin®), trastuzumab (Herceptin®), avelumab (Bavencio®), rituximab (MabThera™, Rituxan®), rituximab with human hyaluronidase (Rituxan Hycela™), edrecolomab (Panorex), daratumuab (Darzalex®), olaratumab (Lartruvo™) ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™) cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), lenzilumab, avelumab, spartalizumab, pembrolizumab, utomilumab, ublituximab, blinatumomab ganitumab, urelumab, pidilizumab, amatuximab, mosunetuzumab (BTCT4465A), CD20-TCB, RO7082859, XmAb13676, glofitamab, CD20-TDB, odronextamab (REGN1979), IGM-2323, BTCT4465A, AMG-562, or TTI-621.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853), anetumab ravtansine, polatuzumab vedotine, loncastuximab tesirine (ADCT-402), camidanlumab tesirine (ADCT-301), or naratuximab emtansine (Debio 1562).

In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors. In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is bacillus Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S(E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) Oncotmmunology 5(2): e1069940).

In some embodiments, immune-targeted agents are selected from aldesleukin, interferon alfa-2b, ipilimumab, lambrolizumab, nivolumab, prednisone, and sipuleucel-T.

In some embodiments, the additional therapy is radiotherapy. Non-limiting examples of radiotherapy include radioiodide therapy, external-beam radiation, and radium 223 therapy.

In some embodiments, the additional therapeutic agent is GSK-3368715, PF-06821497, ceralasertib; AZD6738, B1-894999, MAK-683, AZD-6738, taminadenant, TAK-981, MIK-665, or danvatirsen.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; WO 2016/075224; WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

In some embodiments, the subject was previously administered one or more standard of care therapies for a lymphoma. In some embodiments, the previously administered standard of care therapy is polatuzumab vedotine, selinexor, axicabtagene ciloleucel (Yescarta), tisagenlecleucel (Kymriah), bendamustine in combination with rituximab and polatuzumab vedotin, tafasitamab in combination with lenalidomide, or rituximab with human hyaluronidase (Rituxan Hycela).

In some embodiments, the subject is concomitantly receiving standard of care therapy for a lymphoma. In some embodiments, the standard of care therapy is polatuzumab vedotine, selinexor, axicabtagene ciloleucel (Yescarta), tisagenlecleucel (Kymriah), bendamustine in combination with rituximab and polatuzumab vedotin, tafasitamab in combination with lenalidomide, or rituximab with human hyaluronidase (Rituxan Hycela).

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies.

Accordingly, also provided herein are methods for inhibiting, preventing, aiding in the prevention, or decreasing the symptoms of metastasis of a cancer in a subject in need thereof, the method comprising administering to the subject an effective amount of a compound of Formula (I), or a pharmaceutically acceptable salt thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., *Rev Neurosci* 2018 Jan. 26; 29:93-98; Gao L, et al., Pancreas 2015 January; 44:134-143; Ding K et al., *J Biol Chem* 2014 Jun. 6; 289:16057-71; and Amit M et al., Oncogene 2017 Jun. 8; 36:3232-3239. In some embodiments, the cancer is a MALT1-associated cancer. In some embodiments, the compound of Formula (I), or a pharmaceutically acceptable salt thereof is used in combination with an additional therapy or another therapeutic agent, as described herein. For example, a first or second MALT1 protease inhibitor.

The term "metastasis" is an art known term and means the formation of an additional tumor (e.g., a solid tumor) at a site distant from a primary tumor in a subject, where the additional tumor includes the same or similar cancer cells as the primary tumor.

Also provided are methods of decreasing the risk of developing a metastasis or an additional metastasis in a subject having a MALT1-associated cancer that include: selecting, identifying, or diagnosing a subject as having a MALT1-associated cancer, and administering an effective amount of a compound of Formula (I), or a pharmaceutically acceptable salt thereof to the subject selected, identified, or diagnosed as having a MALT1-associated cancer. Also provided are methods of decreasing the risk of developing a metastasis or an additional metastasis in a subject having a MALT1-associated cancer that includes administering an effective amount of a compound of Formula (I), or a pharmaceutically acceptable salt thereof to a subject having a MALT1-associated cancer. The decrease in the risk of developing a metastasis or an additional metastasis in a subject having a MALT1-associated cancer can be compared to the risk of developing a metastasis or an additional metastasis in the subject prior to treatment, or as compared to a subject or a population of subjects having a similar or the same MALT1-associated cancer that has received no treatment or a different treatment.

The phrase "risk of developing a metastasis" means the risk that a subject having a primary tumor will develop an additional tumor (e.g., a solid tumor) at a site distant from a primary tumor in a subject over a set period of time, where the additional tumor includes the same or similar cancer cells as the primary tumor. Methods for reducing the risk of developing a metastasis in a subject having a cancer are described herein.

The phrase "risk of developing additional metastases" means the risk that a subject having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

Some embodiments described herein provide methods of treating an autoimmune disorder (e.g., a MALT1-associated autoimmune disorder), such as rheumatoid arthritis, multiple sclerosis, and SLE, the method comprising administering an effective amount of a compound of Formula (I), or a pharmaceutically acceptable salt thereof, to a subject in need thereof.

Some embodiments described herein provide methods of treating an inflammatory disorder (e.g., a MALT1-associated autoimmune disorder), such as chronic graft versus host disease, the method comprising administering an effective amount of a compound of Formula (I), or a pharmaceutically acceptable salt thereof, to a subject in need thereof.

Also provided is a method for inhibiting MALT1 protease activity in a mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a subject having a mammalian cell having MALT1 protease activity. In some embodiments, the mammalian cell is a mammalian immune cell. In some embodiments, the mammalian cell is a mammalian cancer cell. In some embodiments, the mammalian cancer cell is any cancer as described herein. In some embodiments, the mammalian cancer cell is a MALT1-associated mammalian cancer cell.

Also provided is a method for inhibiting MALT1 protease activity in a mammalian mammalian cell, comprising contacting the mammalian cell with a compound of Formula (I). In some embodiments, the contacting is in vitro. In some embodiments, the contacting is in vivo. In some embodiments, the contacting is in vivo, wherein the method comprises administering an effective amount of a compound of Formula (I), or a pharmaceutically acceptable salt thereof to a mammal having a mammalian cell having MALT1 protease activity. In some embodiments, the mammalian cell is a mammalian immune cell. In some embodiments, the mammalian cell is a mammalian cancer cell. In some embodiments, the mammalian cancer cell is any cancer as described herein. In some embodiments, the mammalian cancer cell is a MALT1-associated mammalian cancer cell. In some embodiments, the mammalian cell is a gastrointestinal mammalian cell.

As used herein, the term "contacting" refers to the bringing together of indicated moieties in an in vitro system or an in vivo system. For example, "contacting" a MALT1 protease with a compound provided herein includes the administration of a compound provided herein to a subject, such as a human, having a MALT1 protease, as well as, for example, introducing a compound provided herein into a sample containing a mammalian cellular or purified preparation containing the MALT1 protease.

Also provided herein is a method of inhibiting mammalian cell proliferation, in vitro or in vivo, the method comprising contacting a mammalian cell with an effective amount of a compound of Formula (I), or a pharmaceutically acceptable salt thereof, or a pharmaceutical composition thereof as defined herein.

A "MALT1 protease inhibitor" as defined herein includes any compound exhibiting MALT1 inhibition activity. In some embodiments, a MALT1 protease inhibitor is selective for a MALT1 protease. Exemplary MALT1 protease inhibitors can exhibit inhibition activity ($IC_{50}$) against a MALT1 protease of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a MALT1 protease inhibitor can exhibit inhibition activity ($IC_{50}$) against a MALT1 protease of less than about 25 nM, less than about 10 nM, less than about 5 nM, or less than about 1 nM as measured in an assay as provided herein.

As used herein, a "first MALT1 protease inhibitor" or "first MALT1 inhibitor" is a MALT1 protease inhibitor as defined herein, but which does not include a compound of Formula (I), or a pharmaceutically acceptable salt thereof as defined herein. As used herein, a "second MALT1 protease inhibitor" or a "second MALT1 inhibitor" is a MALT1 protease inhibitor as defined herein, but which does not include a compound of Formula (I), or a pharmaceutically acceptable salt thereof as defined herein. When both a first and a second MALT1 inhibitor are present in a method provided herein, the first and second MALT1 protease inhibitor are different.

Exemplary first and second MALT1 protease inhibitors are described herein. In some embodiments, a first or second MALT1 protease inhibitor can be, for example, JNJ-67856633 or CTX-177.

The phrase "effective amount" means an amount of compound that, when administered to a subject in need of such treatment, is sufficient to (i) treat a MALT1-associated disease or disorder (such as a MALT1-associated cancer), (ii) attenuate, ameliorate, or eliminate one or more symptoms of the particular disease, condition, or disorder, or (iii) delay the onset of one or more symptoms of the particular disease, condition, or disorder described herein. The amount of a compound of Formula (I), or a pharmaceutically acceptable salt thereof that will correspond to such an amount will vary depending upon factors such as the particular compound, disease condition and its severity, the identity (e.g., weight) of the subject in need of treatment, but can nevertheless be routinely determined by one skilled in the art.

Pharmaceutical Compositions

When employed as pharmaceuticals, compounds of Formula (I), including pharmaceutically acceptable salts thereof, can be administered in the form of pharmaceutical compositions. These compositions can be prepared in a manner well known in the pharmaceutical art, and can be administered by a variety of routes, depending upon whether local or systemic treatment is desired and upon the area to be treated. Administration can be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula (I) or pharmaceutically acceptable salt thereof, in combination with one or more pharmaceutically acceptable excipients. For example, a pharmaceutical composition prepared using a compound of Formula (I) or a pharmaceutically acceptable salt thereof. In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is a solid oral formulation. In some embodiments, the composition is formulated as a tablet or capsule.

Further provided herein are pharmaceutical compositions containing a compound of Formula (I) or a pharmaceutically acceptable salt thereof with a pharmaceutically acceptable carrier. Pharmaceutical compositions containing a compound of Formula (I) or a pharmaceutically acceptable salt thereof as the active ingredient can be prepared by intimately mixing the compound of Formula (I), or a pharmaceutically acceptable salt thereof with a pharmaceutical carrier according to conventional pharmaceutical compounding techniques. The carrier can take a wide variety of forms depending upon the desired route of administration (e.g., oral, parenteral). In some embodiments, the composition is a solid oral composition.

Suitable pharmaceutically acceptable carriers are well known in the art. Descriptions of some of these pharmaceutically acceptable carriers can be found in *The Handbook of Pharmaceutical Excipients*, published by the American Pharmaceutical Association and the Pharmaceutical Society of Great Britain.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

In preparing the compositions in oral dosage form, any of the usual pharmaceutical media can be employed. Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Solid oral preparations can also be coated with substances such as sugars or be enteric-coated so as to modulate major site of absorption. For parenteral administration, the carrier will usually consist of sterile water and other ingredients can be added to increase solubility or preservation. Injectable suspensions or solutions can also be prepared utilizing aqueous carriers along with appropriate additives. The pharmaceutical compositions herein will contain, per dosage unit, e.g., tablet, capsule, powder, injection, teaspoonful and the like, an amount of the active ingredient necessary to deliver an effective dose as described herein.

The compositions comprising a compound of Formula (I) or a pharmaceutically acceptable salt thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other subjects, each unit containing a predetermined quantity of active material (i.e., a compound of Formula (I) or a pharmaceutically acceptable salt thereof) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain about 10 mg, about 20 mg, about 80 mg, or about 160 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The daily dosage of the compound of Formula (I) or a pharmaceutically acceptable salt thereof can be varied over a wide range from 1.0 to 10,000 mg per adult human per day, or higher, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 160, 200, 250 and 500 milligrams of the active ingredient for the symptomatic adjustment of the dosage to the subject to be treated. An effective amount of the drug is ordinarily supplied at a dosage level of from about 0.1 mg/kg to about 1000 mg/kg of body weight per day, or any range therein. Preferably, the range is from about 0.5 to about 500 mg/kg of body weight per day, or any range therein. More preferably, from about 1.0 to about 250 mg/kg of body weight per day, or any range therein. More preferably, from about 0.1 to about 100 mg/kg of body weight per day, or any range therein. In an example, the range can be from about 0.1 to about 50.0 mg/kg of body weight per day, or any amount or range therein. In another example, the range can be from about 0.1 to about 15.0 mg/kg of body weight per day, or any range therein. In yet another example, the range can be from about 0.5 to about 7.5 mg/kg of body weight per day, or any amount to range therein. Pharmaceutical compositions containing a compound of Formula (I) or a pharmaceutically acceptable salt thereof can be administered on a regimen of 1 to 4 times per day or in a single daily dose.

The active compound may be effective over a wide dosage range and is generally administered in a pharmaceutically effective amount. Optimal dosages to be administered can be readily determined by those skilled in the art. It will be understood, therefore, that the amount of the compound actually administered will usually be determined by a physician, and will vary according to the relevant circumstances, including the mode of administration, the actual compound administered, the strength of the preparation, the condition to be treated, and the advancement of the disease condition. In addition, factors associated with the particular subject being treated, including subject response, age, weight, diet, time of administration and severity of the subject's symptoms, will result in the need to adjust dosages.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

One skilled in the art will recognize that both in vivo and in vitro trials using suitable, known and generally accepted cell and/or animal models are predictive of the ability of a test compound to treat or prevent a given disorder.

One skilled in the art will further recognize that human clinical trials including first-in human, dose ranging and efficacy trials, in healthy subjects and/or those suffering from a given disorder, can be completed according to methods well known in the clinical and medical arts.

Provided herein are pharmaceutical kits useful, for example, in the treatment of MALT1-associated diseases or disorders, such as cancer, which include one or more containers containing a pharmaceutical composition comprising an effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

Materials and Methods

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, $1^{st}$ Ed., Oxford University Press, 2000; *March's Advanced Organic Chemistry: Reactions, Mechanisms, and Structure*, $5^{th}$ Ed., Wiley-Interscience Publication, 2001; and Petursson, S. et al., "*Protecting Groups in Carbohydrate Chemistry,*" *J. Chem. Educ.,* 74(11), 1297 (1997).

Reactions sensitive to moisture or air were performed under nitrogen or argon using anhydrous solvents and reagents. The progress of reactions was determined by either analytical thin layer chromatography (TLC) usually performed with Sanpont precoated TLC plates, silica gel GF-254, layer thickness 0.25 mm or liquid chromatography-mass spectrometry (LC-MS).

Typically, the analytical LC-MS system used consisted of Shimadzu LCMS-2020 with electrospray ionization in positive ion detection mode with 20ADXR pump, SIL-20ACXR autosampler, CTO-20AC column oven, M20A PDA Detector and LCMS 2020 MS detector. The column was usually HALO a C18 30*5.0 mm, 2.7 μm. The mobile phase A is water containing 0.05% TFA and mobile phase B is acetonitrile containing 0.05% TFA. The gradient is from 5% mobile phase B to 100% in 2.0 min, hold 0.7 min, then reverting to 5% mobile phase B over 0.05 min and maintained for 0.25 min. The Column Oven (CTO-20AC) was operated at a temperature of 40.0° C. The flow rate was 1.5 mL/min, and the injection volume was 1 PDA (SPD-M20A) detection was in the range 190-400 nm. The MS detector, which was configured with electrospray ionization as ionizable source; Acquisition mode: Scan; Nebulizing Gas Flow: 1.5 L/min; Drying Gas Flow: 15 L/min; Detector Voltage: Tuning Voltage±0.2 kv; DL Temperature: 250° C.; Heat Block Temperature: 250° C.; Scan Range: 90.00-900.00 m/z. ELSD (Alltech 3300) detector Parameters: Drift Tube Temperature: 60±5° C.; N2 Flow-Rate: 1.8±0.2 L/min. Mobile phase gradients were optimized for the individual compounds.

The GC-MS system was usually performed with Shimadzu GCMS-QP2010 Ultra with FID and MS Detector. The MS detector of acquisition mode: Start Time: 2.00 min; End Time: 9.00 min; ACQ Mode: Scan; Event Time: 0.30 sec; Scan Speed: 2000; Start m/z: 50.00; End m/z: 550.00; Ion Source temperature: 200.00° C.; Interface temperature: 250.00° C.; Solvent Cut Time: 2.00 min.

Preparative HPLC purifications were usually performed with Waters Auto purification system (2545-2767) with a 2489 UV detector. The column was Waters C18,19×150 mm, 5 μm. The mobile phases consisted of mixtures of acetonitrile (5-95%) in water containing 0.1% FA. Flow rates were maintained at 25 mL/min, the injection volume was 1200 μL, and the UV detector used two channels 254 nm and 220 nm. Mobile phase gradients were optimized for the individual compounds.

Chiral analytical chromatography was performed on one of Chiralpak AS, AD, Chiralcel OD, OJ Chiralpak IA, IB, IC, ID, IE, IF, IG, IH columns (Daicel Chemical Industries, Ltd.); (R,R)-Whelk-01, (S,S)-Whelk-01 columns (Regis technologies, Inc.); CHIRAL Cellulose-SB, SC, SA columns (YMC Co., Ltd.) at different column sizes (50×4.6 mm, 100×4.6 mm, 150×4.6 mm, 250×4.6 mm, 50×3.0 mm, 100×3.0 mm) with noted percentage of either ethanol in hexane (% Et/Hex) or isopropanol in hexane (% IPA/Hex) as isocratic solvent systems.

Reactions performed using microwave irradiation were normally carried out using an Initiator manufactured by Biotage. Concentration of solutions was carried out on a rotary evaporator under reduced pressure. Flash column chromatography was usually performed using a Biotage Flash Chromatography apparatus (Dyax Corp.) on silica gel (40-60 μM, 60 Å pore size) in pre-packed cartridges of the size noted. $^1$H NMR spectra were acquired at 400 MHz spectrometers in DMSO-$d_6$ solutions unless otherwise noted. Chemical shifts were reported in parts per million (ppm). Tetramethylsilane (TMS) was used as internal reference in DMSO-$d_6$ solutions, and residual $CH_3OH$ peak or TMS was used as internal reference in $CD_3OD$ solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, AD, Chiralcel OD, OJ, Chiralpak IA, IB, IC, ID, IE, IF, IG, IH columns (Daicel Chemical Industries, Ltd.); (R,R)-Whelk-O1, (S,S)-Whelk-O1 columns (Regis technologies, Inc.); CHIRAL Cellulose-SB, SC, SA columns (YMC Co., Ltd.) at different column size (250×20 mm, 250×30 mm, 250×50 mm) with desired isocratic solvent systems identified on chiral analytical chromatography.

Abbreviations used herein include: —$C(O)CH_3$ (Ac); acetic acid (AcOH); —$OC(O)CH_3$ (OAc); aqueous (aq); Cbz (benzyloxycarbonyl); N,N-diisopropylethylamine (DIEA); N;N-dimethylformamide (DMF); 1-Ethyl-3-(3-dimethylaminopropyl)carbodiimide (EDCI); EtOAc (EtOAc); diethyl ether (ether or $Et_2O$); PE (PE); gram(s) (g); hour(s) (h or hr); 2-propanol (IPA); mass spectrum (ms or MS); microliter(s) (μL); milligram(s) (mg); milliliter(s) (mL); millimole (mmol); minute(s) (min); methyl t-butylether (MTBE); (benzotriazol-1-yloxy)tripyrrolidino-phosphonium hexafluorophosphate (PyBOP); retention time ($R_t$); rt (rt or RT); saturated aq sodium chloride solution (brine); trifluoroacetic acid (TFA); tetrahydrofuran (THF); flash chromatography (FC); liquid chromatography (LC); liquid chromatography-mass spectrometry (LCMS or LC-MS); supercritical fluid chromatography (SFC); t-butyloxycarbonyl (Boc or BOC); Diethylaminosulfur trifluoride (DAST); DCM (DCM); dimethylacetamide (DMA; DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N,N,N',N'-tetramethylchloroformamidinium hexafluorophosphate (TCFH); N-methylimidazole (NMI); N-bromosuccinamide (NB S); thin layer chromatography (TLC).

The following are representative procedures for the preparation of the compounds used in the following Examples, or which can be substituted for the compounds used in the following Examples which may not be commercially available.

Method A1

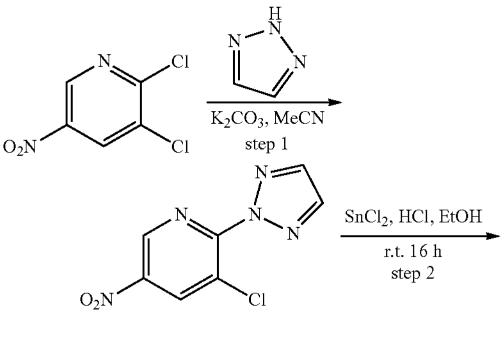

-continued

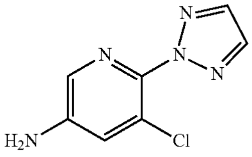

Method A1 Step 2

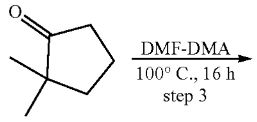

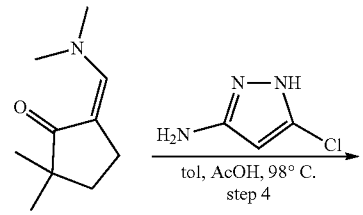

Method A1 Step 3

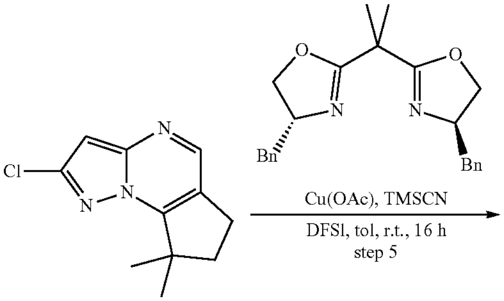

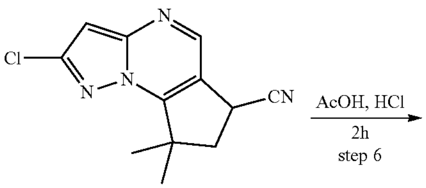

Method A1 Step 5

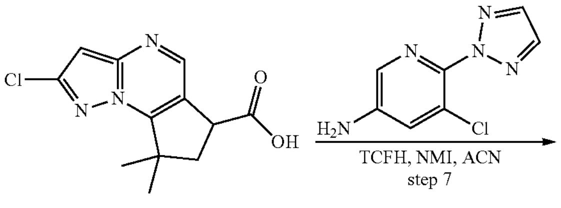

Method A1 Step 6

-continued

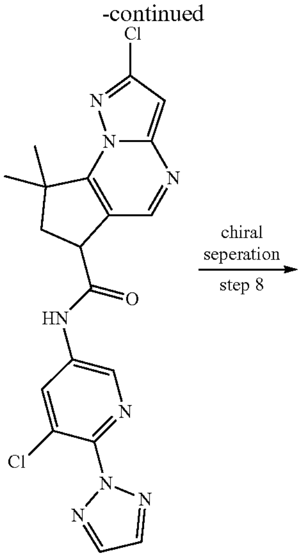

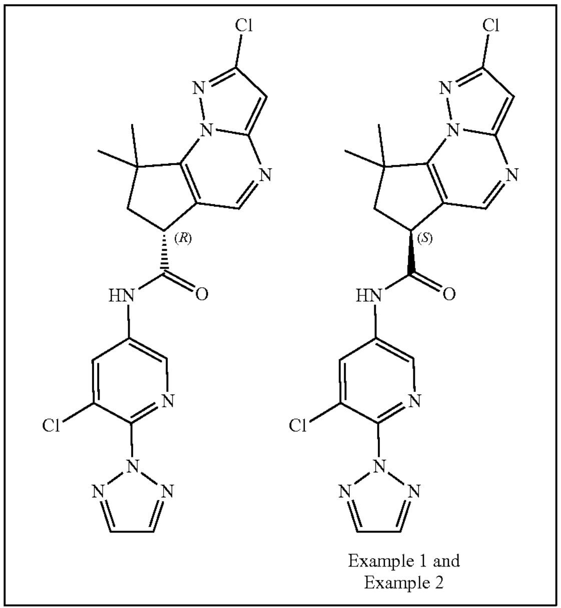

Example 1 and
Example 2

Examples 1 and 2: Single Enantiomers Obtained from a Racemic Mixture Containing (R)-2-chloro-N-(5-chloro-6-(2H-1,2,3-triazol-2-yl)pyridin-3-yl)-8,8-dimethyl-7,8-dihydro-6H cyclopenta[e]pyrazolo[1,5-a]pyrimidine-6-carboxamide and (S)-2-chloro-N-(5-chloro-6-(2H-1,2,3-triazol-2-yl)pyridin-3-yl)-8,8-dimethyl-7,8-dihydro-6Hcyclopenta[e]pyrazolo[1,5a]pyrimidine-6-carboxamide Step 1: 3-chloro-5-nitro-2-(2H-1,2,3-triazol-2-yl) pyridine

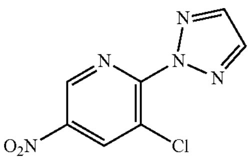 [SMILES: O=[N+]([O-])c1cnc(-n2nccn2)c(Cl)c1]

Into a 500 mL flask were placed 2,3-dichloro-5-nitropyridine (22.8 g, 118.2 mmol, 1.0 equiv.), $CH_3CN$ (250 mL), 2H-1,2,3-triazole (9.0 g, 130.0 mmol, 1.1 equiv.), and $K_2CO_3$ (21.2 g, 153.6 mmol, 1.3 equiv.). The resulting mixture was stirred for 15 h at 40° C. The mixture was allowed to cool down to 25° C. The mixture was poured into EtOAc (300 mL). The organic layer was washed with water (2×300 mL), brine (lx 300 mL) and dried over anhydrous $Na_2SO_4$. After filtration, the filtrate was concentrated under reduced pressure. To the residue was added DCM (50 mL). The resulting mixture was filtered. The filter cake was washed with $CH_2C12$ (2×10 mL) and dried to give 3-chloro-5-nitro-2-(1,2,3-triazol-2-yl)pyridine (6.8 g, 26% yield) as an off-white solid. $^1H$ NMR (400 MHz, DMSO-$d_6$) δ: 8.39 (d, J=2.4 Hz, 1H), 8.14 (d, J=2.4 Hz, 1H), 8.33 (s, 2H). LC-MS: m/z 226 $[M+H]^+$.

Step 2: 5-chloro-6-(2H-1,2,3-triazol-2-yl)pyridin-3-amine

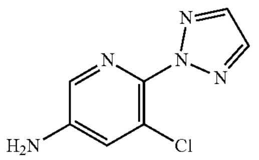

Into a 1.0 L flask were placed 3-chloro-5-nitro-2-(1,2,3-triazol-2-yl)pyridine (6.6 g, 29.3 mmol, 1.0 equiv.) and EtOH (200 mL). HCl (50 mL) was added at 0° C., followed by $SnCl_2 \cdot 2H_2O$ (33.0 g, 146.3 mmol, 5.0 equiv.) which was added at 0° C. in small portions. The resulting mixture was stirred for 16 h at room temperature. The resulting mixture was concentrated under reduced pressure. The residue was dissolved in water (300 mL) and the pH was adjusted to 9 using 3N NaOH solution in water. The resulting mixture was extracted with EtOAc (2×400 mL). The combined organic layers were washed with brine (500 mL), dried over anhydrous sodium sulfate and concentrated under reduced pressure to afford 5-chloro-6-(1,2,3-triazol-2-yl)pyridin-3-amine (Method A1 step 2; 5.4 g, 94% yield) as an off-white solid. $^1H$ NMR (300 MHz, DMSO-$d_6$) δ: 8.05 (s, 2H), 7.83 (d, J=2.5 Hz, 1H), 7.21 (d, J=2.5 Hz, 1H), 6.19 (s, 2H). LC-MS: m/z 196 $[M+H]^+$.

Step 3: 5-((dimethylamino)methyl ene)-2,2-dimethyl cyclopentan-1-one

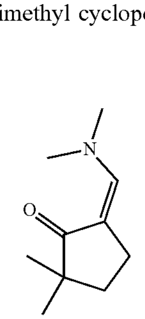

A solution of 2,2-dimethylcyclopentanone (2 g, 17.8 mmol) in DMF-DMA (20 mL) was stirred for 16 h at 100° C. The mixture was allowed to cool down to room temperature. The resulting mixture was concentrated under reduced pressure. This resulted in 5-((dimethylamino) methylene)-2,2-dimethylcyclopentan-1-one (Method A1 step 3; 2 g, crude) as a yellow oil which was used directly and without further purification in next step. LCMS (ES, m/z): 168$[M+H]^+$.

Step 4: 2-chloro-8,8-dimethyl-7,8-dihydro-6H-cyclopenta[e]pyrazolo[1,5-a]pyrimidine

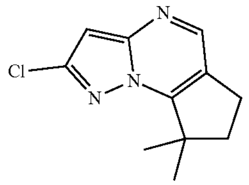

To a stirred solution of 5-((dimethylamino)methylene)-2,2-dimethylcyclopentan-1-one (1.5 g, 8.9 mmol) in toluene (20 mL) added 5-chloro-1H-pyrazol-3-amine (1.5 g, 12.7 mmol) and AcOH (2 mL) at room temperature. The resulting mixture was stirred for 16 h at 95° C. The mixture was allowed to cool down to room temperature. The reaction mixture was concentrated under reduced pressure. The residue was diluted with water (100 mL). The pH was adjusted to 6-7 with sat. aq. sodium bicarbonate solution. The resulting mixture was extracted with ethyl acetate (100 mL×2). The combined organic layers were dried over anhydrous sodium sulfate and concentrated under vacuum. The residue was applied on a silica gel column and eluted with ethyl acetate/petroleum ether (1:5) to give 2-chloro-8,8-dimethyl-7,8-dihydro-6H-cyclopenta[e]pyrazolo[1,5-a]pyrimidine (1.4 g, 63.3% yield). $^1$HNMR (300 MHz, DMSO-$d_6$) δ: 8.56 (s, 1H), 6.86 (s, 1H), 2.88-3.03 (m, 2H), 2.01-2.12 (m, 1H), 1.27 (s, 3H). LC-MS (ES, m/z): 222 $[M+H]^+$.

Step 5: 2-chloro-8,8-dimethyl-7,8-dihydro-6H-cyclopenta[e]pyrazolo[1,5-a]pyrimidine-6-carbonitrile

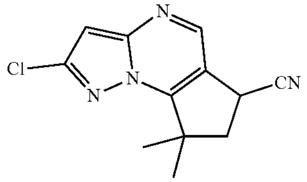 [SMILES: CC1(C)CC(C#N)c2cnc3cc(Cl)nn3c21]

To a stirred solution of 2-chloro-8,8-dimethyl-7,8-dihydro-6H-cyclopenta[e]pyrazolo[1,5-a]pyrimidine (1.4 g, 6.3 mmol) in toluene (30 mL) were added (4R)-4-benzyl-2-[1-[(4R)-4-benzyl-4,5-dihydrooxazol-2-yl]-1-methyl-ethyl]-4,5-dihydrooxazole (274 mg, 0.8 mmol), acetoxycopper (154 mg, 1.2 mmol), N-FluorobenzenesulfoniMide (3 g, 9.4 mmol) and TMSCN (3.1 g, 31.5 mmol). The reaction was stirred at room temperature for 16 h under nitrogen. The solvent was removed under vacuum and the residue was applied on a silica gel column and eluted with ethyl acetate/petroleum ether (1:5) to give 2-chloro-8,8-dimethyl-7,8-dihydro-6H-cyclopenta[e]pyrazolo[1,5-a]pyrimidine-6-carbonitrile (Method A1 step 5; 690 mg, 17.7% yield). $^1$HNMR (300 MHz, DMSO-$d_6$) δ: 8.74 (s, 1H), 7.00 (s, 1H), 4.71-4.76 (m, 1H), 2.54-2.67 (m, H), 2.32-2.45 (m, 1H), 1.63 (s, 3H), 1.51 (s, 3H). LC-MS (ES, m/z): 247$[M+H]^+$.

Step 6: 2-chloro-8,8-dimethyl-7,8-dihydro-6H-cyclopenta[e]pyrazolo[1,5-a]pyrimidine-6-carboxylic acid

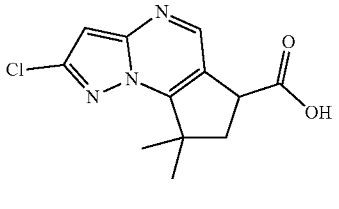 [SMILES: CC1(C)CC(C(=O)O)c2cnc3cc(Cl)nn3c21]

Into a 30 mL vial was added 2-chloro-8,8-dimethyl-7,8-dihydro-6H-cyclopenta[e]pyrazolo[1,5-a]pyrimidine-6-carbonitrile (690 mg, 2.8 mmol) in AcOH (6 mL) and HCl (6 mL). The resulting mixture was stirred for 2 h at 100° C. The mixture was allowed to cool down to room temperature. The solvent was concentrated under vacuum and the residue was diluted with water (100 mL) and the pH was adjusted to 5~6 with $NaHCO_3$. The resulting solution was extracted with ethyl acetate (100 mL×3). The combined organic layers were dried over anhydrous sodium sulfate and concentrated under vacuum. The residue was applied on a silica gel column and eluted with MeOH/DCM (1:10) to give 2-chloro-8,8-dimethyl-7,8-dihydro-6H-cyclopenta[e]pyrazolo[1,5-a]pyrimidine-6-carboxylic acid (Method A1 step 6; 300 mg, 32.3% yield). $^1$HNMR (400 MHz, DMSO-$d_6$) δ: 12.75 (s, 1H), 8.63 (s, 1H), 6.92 (s, 1H), 4.26-4.29 (m, 1H), 2.40-2.45 (m, 1H), 2.28-2.33 (m, 1H), 1.56 (s, 3H), 1.52 (s, 3H). LC-MS (ES, m/z): 266[M+H]$^+$.

Step 7: 2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

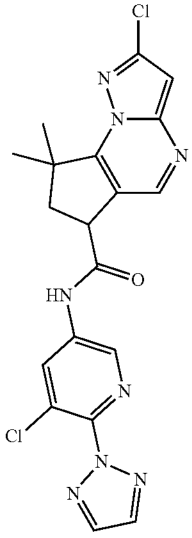 [SMILES: CC1(C)CC(C(=O)Nc2cnc(-n3nccn3)c(Cl)c2)c2cnc3cc(Cl)nn3c21]

To a stirred solution of 2-chloro-8,8-dimethyl-7,8-dihydro-6H-cyclopenta[e]pyrazolo[1,5-a]pyrimidine-6-carboxylic acid (390 mg, 1.4 mmol) in ACN (20 mL) was added 5-chloro-6-(triazol-2-yl)pyridin-3-amine (430.69 mg, 2.2 mmol), TCFH (1.65 g, 5.8 mmol) and NMI (482.06 mg, 5.87 mmol). The resulting mixture was stirred for 16 h at room temperature. The reaction mixture was quenched with water (100 mL). The resulting solution was extracted with ethyl acetate (100 mL×3). The combined organic layers were dried over anhydrous sodium sulfate and concentrated under vacuum. The residue was submitted to Prep-HPLC and the collected fraction was lyophilized to give a racemic mixture of 2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide (200 mg, 60% yield) as a white solid. LC-MS (ES, m/z): 443 [M+H].

Step 8: Separation of Enantiomers to Obtain (R)-2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6 carboxamide and (S)-2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

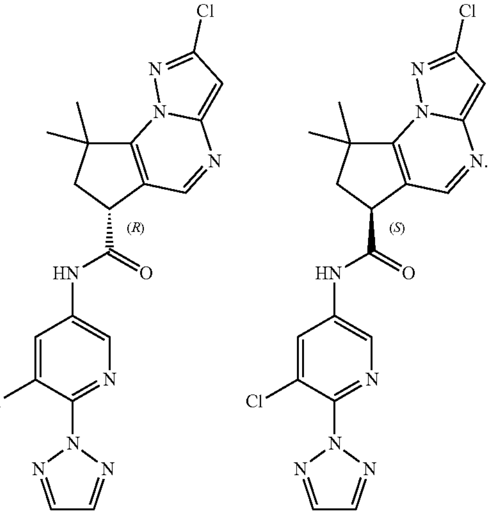

Example 1 and Example 2

200 mg of racemic 2-chloro-N-(5-chloro-6-(2H-1,2,3-triazol-2-yl) pyridin-3-yl)-8,8-dimethyl-7,8-dihydro-6H-cyclopenta[e]pyrazolo[1,5-a]pyrimidine-6-carboxamide were submitted to chiral HPLC purification (CHIRALPAK IE, 2×25 cm, 5 um; Mobile Phase A: Hex (8 mmol/L $NH_3$·MeOH), Mobile Phase B: EtOH; Flow rate: 17 mL/min; isocratic: 50 B; 220/254 nm; RT1: 8.332; RT2: 12.438; Injection Volume: 1 ml; Number of Runs: 5). The first eluting isomer was concentrated and lyophilized to afford Example 1 (74.3 mg, 11.4% yield) as a white solid. The second eluting isomer was concentrated and lyophilized to afford Example 2 (69.6 mg, 10.6% yield) as a white solid.

Example 1: $^1$H NMR (300 MHz, Methanol-$d_4$) δ: 8.71 (d, J=2.4 Hz, 1H), 8.66 (d, J=2.4 Hz, 1H), 8.55 (s, 1H), 8.04 (s, 2H), 6.72 (s, 1H), 4.42-4.47 (m, 1H), 2.62-2.70 (m, 1H), 2.45-2.48 (m, 1H), 1.76 (s, 3H), 1.65 (s, 3H). LCMS (ES, m/z): 443[M+H]$^+$.

Example 2: $^1$H NMR (300 MHz, Methanol-$d_4$) δ: 8.71 (d, J=2.4 Hz, 1H), 8.66 (d, J=2.4 Hz, 1H), 8.55 (s, 1H), 8.04 (s, 2H), 6.73 (s, 1H), 4.42-4.47 (m, 1H), 2.62-2.66 (m, 1H), 2.45-2.48 (m, 1H), 1.76 (s, 3H), 1.65 (s, 3H). LC-MS (ES, m/z): 443 [M+H]$^+$.

The absolute stereochemistry for each separated isomer was not determined.
Method B1
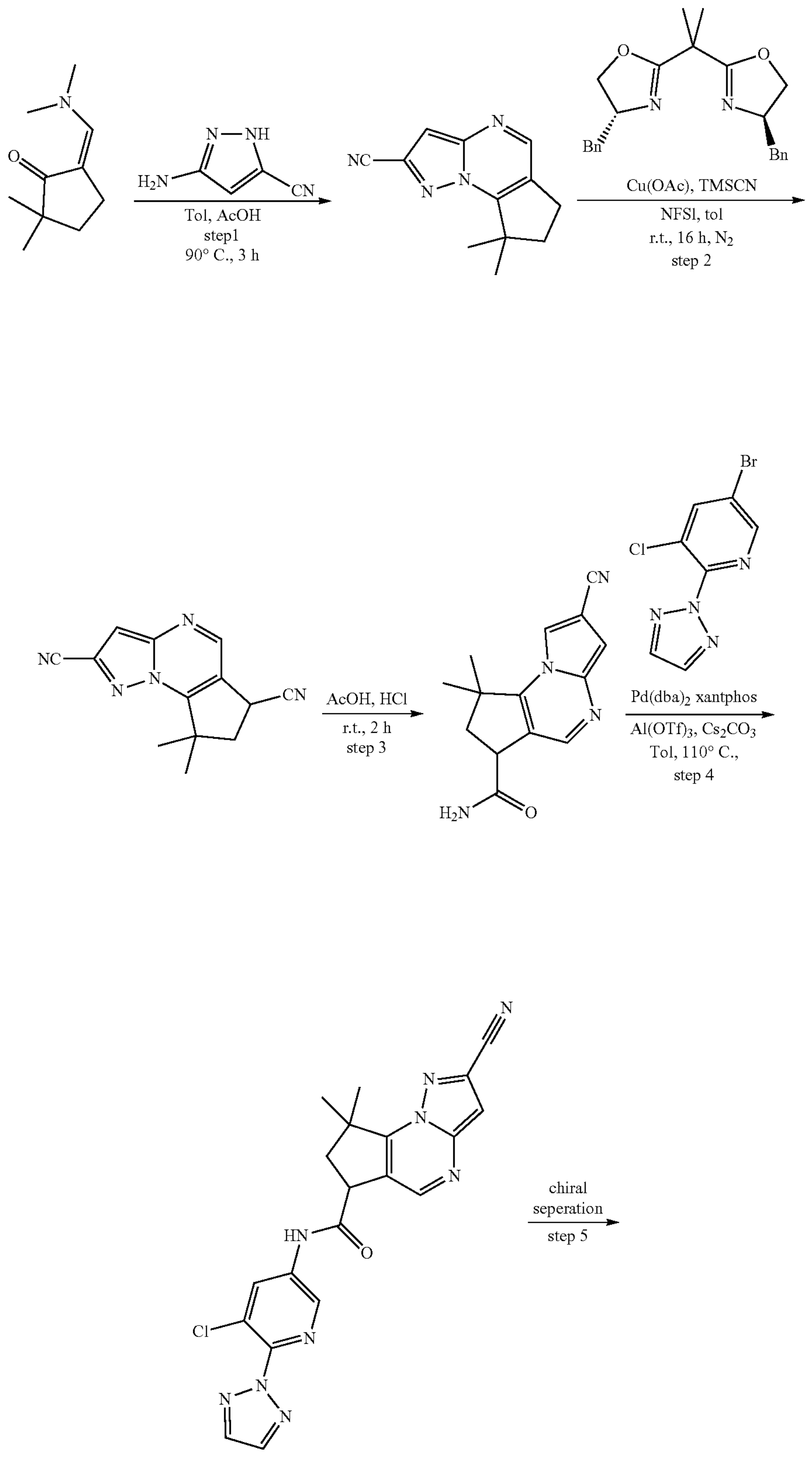

-continued

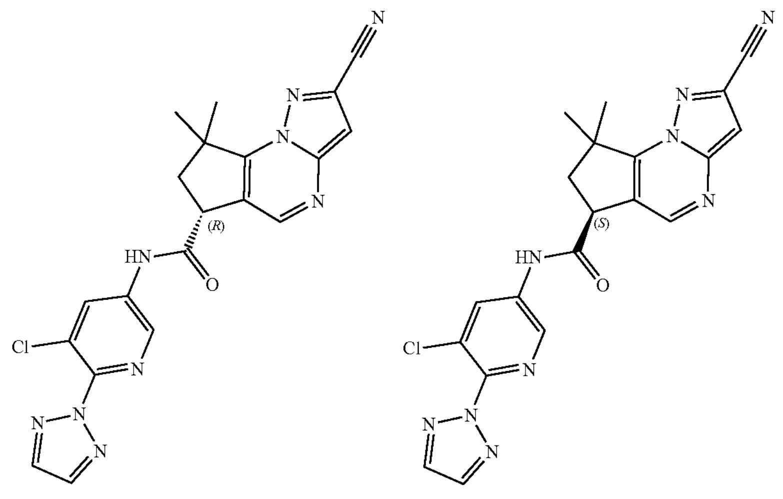

Example 3 and
Example 4

Examples 3 and 4: Single Enantiomers Obtained from a Racemic Mixture Containing (R)—N-(5-chloro-6-(2H-1,2,3-triazol-2-yl)pyridin-3-yl)-2-cyano-8,8-dimethyl-7,8-dihydro-611-cyclopenta[e]pyrazolo[1,5-a]pyrimidine-6-carboxamide and (S)—N-(5-chloro-6-(2H-1,2,3-triazol-2-yl)pyridin-3-yl)-2-cyano-8,8-dimethyl-7,8-dihydro-6H-cyclopenta[e]pyrazolo[1,5-a]pyrimidine-6-carboxamide Step 1: 8,8-dimethyl-7,8-dihydro-6H-cyclopenta[e]pyrazolo[1,5-a]pyrimidine-2-carbonitrile

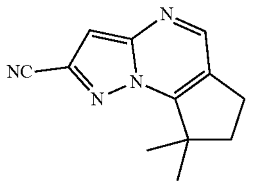 [SMILES: CC1(C)CCc2cnc3cc(C#N)nn3c21]

A solution of 3-amino-1H-pyrazole-5-carbonitrile (258 mg, 2.4 mmol) and (Z)-5-((dimethylamino)methylene)-2,2-dimethylcyclopentan-1-one (Method A1 Step 3; 400 mg, 2.4 mmol) in AcOH (1 mL) and toluene (10 mL) was stirred for 3 h at 90° C. under nitrogen. The mixture was allowed to cool down to room temperature and concentrated under vacuum. The residue was applied on a silica gel column and eluted with 0-50% EtOAc in PE to afford 8,8-dimethyl-7,8-dihydro-6H-cyclopenta[e]pyrazolo[1,5-a]pyrimidine-2-carbonitrile (220 mg, 43% yield) as a brown solid. $^1$H NMR (300 MHz, DMSO-$d_6$) δ 8.71 (s, 1H), 7.53 (s, 1H), 3.09-2.98 (m, 2H), 2.09-2.14 (m, 2H), 1.52 (s, 6H). LC-MS: m/z 213 $[M+H]^+$.

Step 2: 8,8-dimethyl-7,8-dihydro-6H-cyclopenta[e]pyrazolo[1,5-a]pyrimidine-2,6-dicarbonitrile

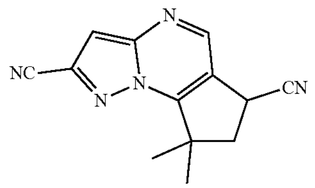 [SMILES: CC1(C)CC(C#N)c2cnc3cc(C#N)nn3c21]

To a stirred solution of 8,8-dimethyl-7,8-dihydro-6H-cyclopenta[e]pyrazolo[1,5-a]pyrimidine-2-carbonitrile (220 mg, 1 mmol), N-(benzenesulfonyl)-N-fluoro-benzenesulfonamide (490 mg, 1.6 mmol), (4R)-4-benzyl-2-[1-[(4R)-4-benzyl-4,5-dihydrooxazol-2-yl]-1-methyl-ethyl]-4,5-dihydrooxazole (45.1 mg, 124.4 μmol) and acetoxycopper (25 mg, 207.3 μmol) in toluene (10 mL) was added trimethylsilylcyanide (514 mg, 5.2 mmol) in portions at room temperature and the resulting mixture was stirred overnight. The mixture was concentrated under vacuum, diluted with water (100 mL) and then extracted with DCM (3×100 mL). The organic layers were combined, washed with brine, dried and concentrated under vacuum. The residue was applied on a silica gel column and eluted with 0-30% EtOAc in PE to afford 8,8-dimethyl-7,8-dihydro-6H-cyclopenta[e]pyrazolo[1,5-a]pyrimidine-2,6-dicarbonitrile (130 mg, 53% yield) as an off-white solid. LC-MS: m/z 238 $[M+H]^+$.

Step 3: 2-cyano-8,8-dimethyl-7,8-dihydro-6H-cyclopenta[e]pyrazolo[1,5-a]pyrimidine-6-carboxamide

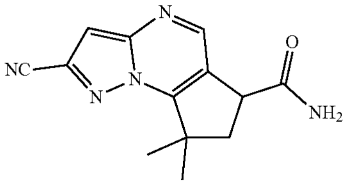 [SMILES: CC1(C)CC(C(N)=O)c2cnc3cc(C#N)nn3c21]

A solution of 8,8-dimethyl-7,8-dihydro-6H-cyclopenta[e]pyrazolo[1,5-a]pyrimidine-2,6-dicarbonitrile (130 mg, 547.9 μmol) in HCl (1 mL) and AcOH (3 mL) was stirred for 6 h at room temperature. The resulting mixture was concentrated under vacuum. The residue was diluted with water (2 mL) and the pH was adjusted to 8-9 with $NaHCO_3$. The resulting mixture was concentrated under vacuum and purified by HPLC to afford 2-cyano-8,8-dimethyl-7,8-dihydro-6H-cyclopenta[e]pyrazolo[1,5-a]pyrimidine-6-carboxamide (60 mg, 43% yield) as a white solid. $^1H$ NMR (300 MHz, DMSO-$d_6$) δ 8.67 (s, 1H), 7.70 (s, 1H), 7.55 (s, 1H), 7.21 (s, 1H), 4.20-4.03 (m, 1H), 2.41 (dd, J=13.2, 9.1 Hz, 1H), 2.22 (dd, J=13.2, 6.3 Hz, 1H), 1.59 (s, 3H), 1.49 (s, 3H). LC-MS: m/z 256 $[M+H]^+$.

Step 4: N-(5-chloro-6-(2H-1,2,3-triazol-2-yl)pyridin-3-yl)-2-cyano-8,8-dimethyl-7,8-dihydro-6H-cyclopenta[e]pyrazolo[1,5-a]pyrimidine-6-carboxamide

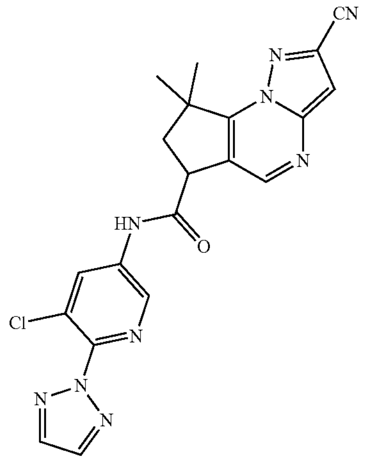 [SMILES: CC1(C)CC(C(=O)Nc2cnc(-n3nccn3)c(Cl)c2)c2cnc3cc(C#N)nn3c21]

To a stirred mixture of 5-bromo-3-chloro-2-(triazol-2-yl)pyridine (60 mg, 235.0 μmol) and 2-cyano-8,8-dimethyl-7,8-dihydro-6H-cyclopenta[e]pyrazolo[1,5-a]pyrimidine-6-carboxamide (60 mg, 235.0 μmol) in toluene (1 mL) were added (5-diphenylphosphanyl-9,9-dimethyl-xanthen-4-yl)-diphenyl-phosphane (13 mg, 23.5 μmol), tris(dibenzylideneacetone)dipalladium-chloroform adduct (13 mg, 23.5 μmol) and cesium carbonate (114 mg, 352.6 μmol). Aluminum trifluoromethanesulfonate (11 mg, 23.5 μmol) was added in portions at room temperature under nitrogen. The resulting mixture was stirred for 16 hours at 110° C. under nitrogen. The mixture was allowed to cool down to room temperature, diluted with water (50 mL) and then extracted with DCM (3×50 mL). The organic layers were combined, washed with brine, dried and concentrated under vacuum. The crude product (70 mg) was purified by Prep-HPLC (Column: XBridge Prep OBD C18 Column, 19×250 mm, 5 um; Mobile Phase A:Water(0.05% TFA), Mobile Phase B:ACN; Flow rate: 25 mL/min; Gradient: 46 B to 66 B in 7 min; 220 nm; RT 1:6.12; Injection Volume: 1.5 ml; Number of Runs: 2) to afford N-(5-chloro-6-(2H-1,2,3-triazol-2-yl)pyridin-3-yl)-2-cyano-8,8-dimethyl-7,8-dihydro-6H-cyclopenta[e]pyrazolo[1,5-a]pyrimidine-6-carboxamide (22 mg, 22% yield) as a white solid. LC-MS: m/z 434 $[M+H]^+$.

Step 5: Separation of Enantiomers to Obtain (R)—N-(5-chloro-6-(2H-1,2,3-triazol-2-yl)pyridin-3-yl)-2-cyano-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-cyano-8,8-dimethyl-7,8-dihydro-6H-cyclopenta[e]pyrazolo[1,5-a]pyrimidine-6-carboxamide

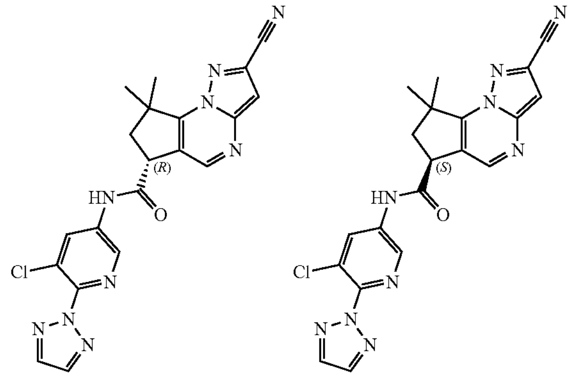

Example 3
and Example 4

N-(5-chloro-6-(2H-1,2,3-triazol-2-yl)pyridin-3-yl)-2-cyano-8,8-dimethyl-7,8-dihydro-6H-cyclopenta[e]pyrazolo[1,5-a]pyrimidine-6-carboxamide (22 mg, 50.4 μcool) was submitted to chiral HPLC purification (Column: Chiralpak ID-2, 2*25 cm, Sum; Mobile Phase A:MTBE (2 mM NH3-MEOH), Mobile Phase B:EtOH; Flow rate: 17 mL/min; isocratic: 30 B; 254/220 nm; RT1:6.593; RT2:8.779; Injection Volume: 1 ml; Number of Runs: 2). The first eluting isomer was concentrated and lyophilized to afford Example 3 as a white solid (7.3 mg, 33% yield). The second eluting isomer was concentrated and lyophilized to afford Example 4 as a white solid (6.2 mg, 28% yield).

Example 3: $^1H$ NMR (400 MHz, Methanol-$d_4$) δ 8.69 (s, 1H), 8.63 (d, J=2.4 Hz, 1H), 8.02 (s, 2H), 7.29 (s, 1H), 4.48 (dd, J=9.2, 6.8 Hz, 1H), 2.71 (dd, J=13.2, 9.2 Hz, 1H), 2.48 (dd, J=13.2, 6.8 Hz, 1H), 1.75 (s, 3H), 1.65 (s, 3H). LC-MS: m/z 434 $[M+H]^+$.

Example 4: $^1H$ NMR (400 MHz, Methanol-$d_4$) δ 8.69 (s, 1H), 8.63 (d, J=2.4 Hz, 1H), 8.02 (s, 2H), 7.28 (s, 1H), 4.48 (dd, J=9.2, 6.8 Hz, 1H), 2.71 (dd, J=13.2, 9.2 Hz, 1H), 2.47 (dd, J=13.2, 6.8 Hz, 1H), 1.75 (s, 3H), 1.65 (s, 3H). LC-MS: m/z 434 $[M+H]^+$.

The absolute stereochemistry for each separated isomer was not determined.

Method C1
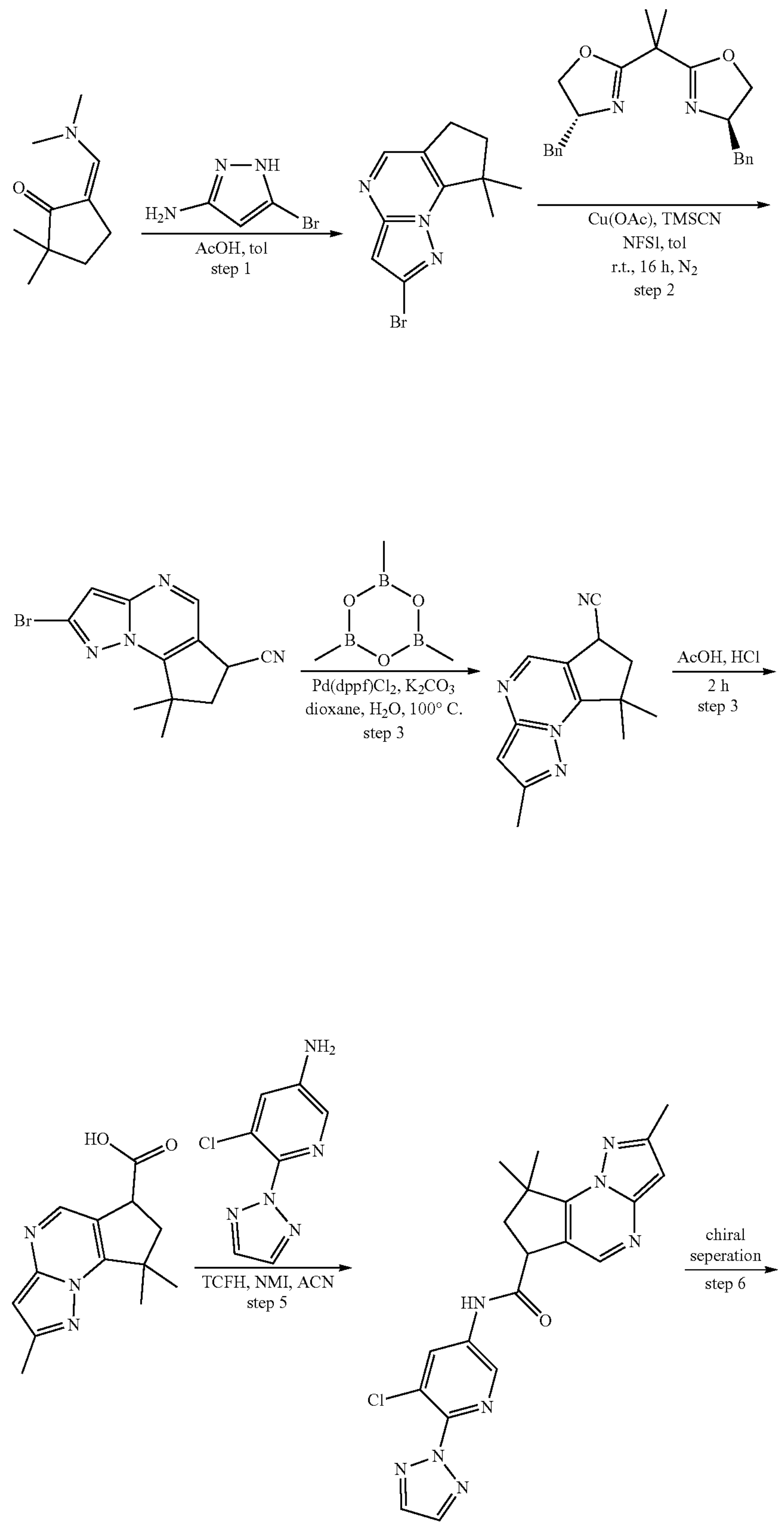

-continued

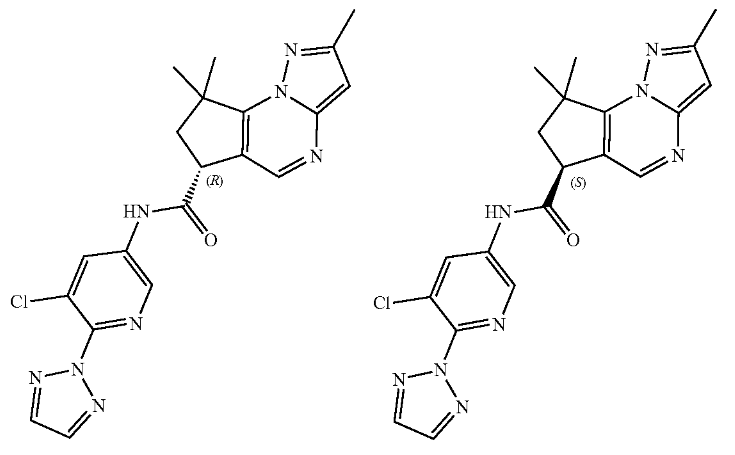

Example 5
and Example 6

Examples 5 and 6: Single Enantiomers Obtained from a Racemic Mixture Containing (R)—N-(5-chloro-6-(2H-1,2,3-triazol-2-yl)pyridin-3-yl)-2,8,8-trimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2,8,8-trimethyl-7,8-dihydro-6H-cyclopenta[e]pyrazolo[1,5-a]pyrimidine-6-carboxamide Step 1: 2-bromo-8,8-dimethyl-7,8-dihydro-6H-cyclopenta[e]pyrazolo[1,5-a]pyrimidine

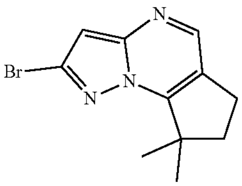

To a stirred solution of 5-(dimethylaminomethylene)-2,2-dimethyl-cyclopentan-1-one (Method A1 Step 3; 10 g, 59.8 mmol) in toluene (150 mL) were added 5-bromo-1H-pyrazol-3-amine (11.6 g, 71.8 mmol) and AcOH (15 mL) at room temperature. The resulting mixture was stirred for 16 h at 90° C. The mixture was allowed to cool down to room temperature. The reaction mixture was concentrated under reduced pressure. The residue was diluted with water (200 mL). The pH was adjusted to 6-7 with sodium bicarbonate (sat., aq.). The resulting solution was extracted with EtOAc (3×200 mL), dried over anhydrous sodium sulfate and concentrated under vacuum. The residue was applied onto a silica gel column and eluted with EtOAc/PE (1:2) to give 2-bromo-8,8-dimethyl-7,8-dihydro-6H-cyclopenta[e]pyrazolo[1,5-a]pyrimidine (4 g, 20% yield). $^1$H NMR (300 MHz, DMSO-$d_6$) δ: 8.54 (s, 1H), 6.93 (s, 1H), 2.94-3.05 (m, 2H), 2.07-2.12 (m, 2H), 1.52 (s, 6H). LC-MS: m/z 266 $[M+H]^+$.

Step 2: 2-bromo-8,8-dimethyl-7,8-dihydro-6H-cyclopenta[e]pyrazolo[1,5-a]pyrimidine-6-carbonitrile

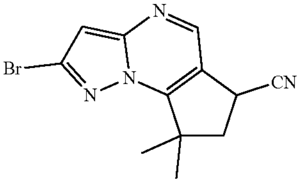 [SMILES: CC1(C)CC(C#N)c2cnc3cc(Br)nn3c21]

To a stirred solution of 2-bromo-8,8-dimethyl-7,8-dihydro-6H-cyclopenta[e]pyrazolo[1,5-a]pyrimidine (440 mg, 1.65 mmol) in toluene (10 mL) were added (4R)-4-benzyl-2-[1-[(4R)-4-benzyl-4,5-dihydrooxazol-2-yl]-1-methyl-ethyl]-4,5-dihydrooxazole (72 mg, 198.4 μmol), acetoxycopper (40 mg, 330.7 μmol), N-fluorobenzenesulfonimide (782 mg, 2.5 mmol) and TMSCN (820 mg, 8.3 mmol). The reaction mixture was stirred at room temperature for 16 h under nitrogen. The solvent was removed under vacuum and the residue was applied on a silica gel column and eluted with EtOAc/PE (1:2) to give 2-bromo-8,8-dimethyl-7,8-dihydro-6H-cyclopenta[e]pyrazolo[1,5-a]pyrimidine-6-carbonitrile (390 mg, 41% yield). $^1$H NMR (300 MHz, DMSO-$d_6$) δ: 8.72 (s, 1H), 7.06 (s, 1H), 4.71-4.76 (m, 1H), 2.54-2.64 (m, H), 2.35-2.47 (m, 1H), 1.64 (s, 3H), 1.51 (s, 3H). LC-MS: m/z 291 $[M+H]^+$.

Step 3: 2,8,8-timethyl-7,8-dihydro-6H-cyclopenta[e]pyrazolo[1,5-a]pyrimidine-6-carbonitrile

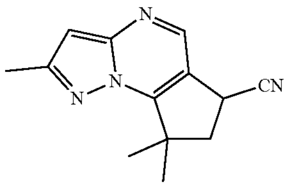 [SMILES: Cc1cc2ncc3c(n2n1)C(C)(C)CC3C#N]

To a mixture of 2-bromo-8,8-dimethyl-7,8-dihydro-6H-cyclopenta[e]pyrazolo[1,5-a]pyrimidine-6-carbonitrile (370 mg, 1.3 mmol) in dioxane (4 mL) were added 2,4,6-trimethyl-1,3,5,2,4,6-trioxatriborinane (638 mg, 2.5 mmol), Pd(dppf)C12 (93 mg, 127.1 μmol), $K_2CO_3$ (351 mg, 2.5 mmol, 153.4 μL) and $H_2O$ (1 mL). The mixture was stirred at 100° C. for 2 h under nitrogen. The mixture was allowed to cool down to room temperature and concentrated under reduced pressure. The residue was diluted with water (50 mL), extracted with EtOAc (3×50 mL), dried over anhydrous sodium sulfate and concentrated under vacuum. The residue was applied on a silica gel column and eluted with EtOAc/PE (1:2) to give 2,8,8-trimethyl-7,8-dihydro-6H-cyclopenta[e]pyrazolo[1,5-a]pyrimidine-6-carbonitrile (105 mg, 36% yield). $^1H$ NMR (300 MHz, DMSO-$d_6$) δ: 8.58 (s, 1H), 6.63 (s, 1H), 4.66-4.73 (m, 1H), 2.55-2.62 (m, 1H), 2.33-2.43 (m, 1H), 1.65 (s, 3H), 1.53 (s, 3H). LC-MS: m/z 227 $[M+H]^+$.

Step 4: 2,8,8-trimethyl-7,8-dihydro-6H-cyclopenta[e]pyrazolo[1,5-a]pyrimidine-6-carboxylic acid

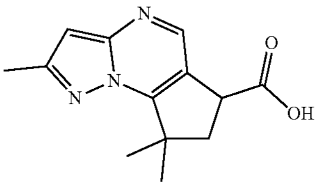 [SMILES: Cc1cc2ncc3c(n2n1)C(C)(C)CC3C(=O)O]

A solution of 2,8,8-trimethyl-7,8-dihydro-6H-cyclopenta[e]pyrazolo[1,5-a]pyrimidine-6-carbonitrile (97 mg, 428.7 μmol) in AcOH (2 mL) and HCl (2 mL) was stirred for 2 h at 100° C.

The mixture was allowed to cool down to room temperature. The mixture was concentrated under vacuum and the residue was diluted with water (50 mL) and the pH adjusted to 5-6 with $NaHCO_3$. The resulting solution was extracted with EtOAc (3×50 mL), dried over anhydrous sodium sulfate and concentrated under vacuum. The residue was applied onto a silica gel column and eluted with DCM/MeOH (10:1) to give 2,8,8-trimethyl-7,8-dihydro-6H-cyclopenta[e]pyrazolo[1,5-a]pyrimidine-6-carboxylic acid (56 mg, 182.6 μmol, 43% yield). LC-MS: m/z 246 $[M+H]^+$.

Step 5. N-(5-chloro-6-(2H-1,2,3-triazol-2-yl)pyridin-3-yl)-2,8,8-trimethyl-7,8-dihydro-6H-cyclopenta[e]pyrazolo[1,5-a]pyrimidine-6-carboxamide

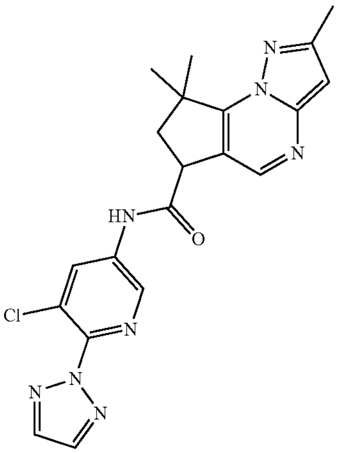 [SMILES: Cc1cc2ncc3c(n2n1)C(C)(C)CC3C(=O)Nc1cnc(-n2nccn2)c(Cl)c1]

To a solution of 2,8,8-trimethyl-7,8-dihydro-6H-cyclopenta[e]pyrazolo[1,5-a]pyrimidine-6-carboxylic acid (56 mg, 228.3 μmol) in ACN (3 mL) was added 5-chloro-6-(triazol-2-yl)pyridin-3-amine (67 mg, 342.5 μmol), TCFH (320 mg, 1.1 mmol), NMI (94 mg, 1.1 mmol).

The resulting mixture was stirred for 16 h at room temperature. The reaction mixture was quenched with water (100 mL). The resulting solution was extracted with EtOAc (3×100 mL), dried over anhydrous sodium sulfate and concentrated under vacuum. The residue was applied onto a silica gel column and eluted with EA/PE (1:1) to get crude product. The crude product was submitted to HPLC purification and the collected fractions were lyophilized to give N-(5-chloro-6-(2H-1,2,3-triazol-2-yl)pyridin-3-yl)-2,8,8-trimethyl-7,8-dihydro-6H-cyclopenta[e]pyrazolo[1,5-a]pyrimidine-6-carboxamide (30 mg, 31%) as a white solid. LC-MS: m/z 423 $[M+H]^+$.

Step 6: Separation of Enantiomers to Obtain (S)—N-(5-chloro-6-(2H-1,2,3-triazol-2-yl)pyridin-3-yl)-2,8,8-trimethyl-7,8-dihydro-6H-cyclopenta[e]pyrazolo[1,5-a]pyrimidine-6-carboxamide and (R)—N-(5-chloro-6-(2H-1,2,3-triazol-2-yl)pyridin-3-yl)-2,8,8-trimethyl-7,8-dihydro-6H-cyclopenta[e]pyrazolo[1,5-a]pyrimidine-6-carboxamide

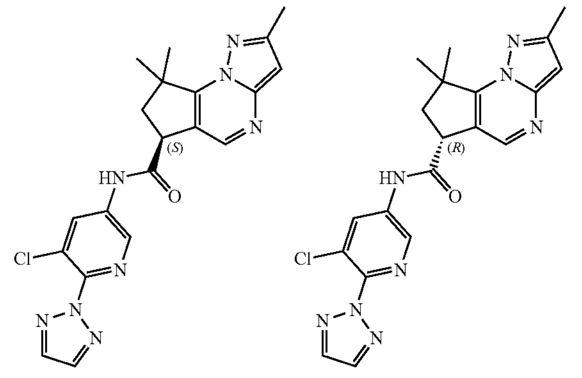

Example 5
and Example 6

30 mg of N-(5-chloro-6-(2H-1,2,3-triazol-2-yl)pyridin-3-yl)-2,8,8-trimethyl-7,8-dihydro-6H-cyclopenta[e]pyrazolo[1,5-a]pyrimidine-6-carboxamide were submitted to chiral HPLC purification (Column: Chiralpak ID-2, 2*25 cm, Sum; Mobile Phase A:MTBE (2 mM $NH_3$-MEOH), Mobile Phase B:EtOH; Flow rate: 14 mL/min; isocratic 50 B; 254/220 nm; RT1:11.394; RT2:17.177; Injection Volume: 2 ml; Number of Runs: 2). The first eluting isomer was concentrated and lyophilized to afford Example 5 (6 mg, 6.2% yield) as a white solid. The second eluting isomer was concentrated and lyophilized to afford Example 6 (8.6 mg, 8.9% yield) as a white solid.

Example 5: $^1$H NMR (300 MHz, Methanol-$d_4$): 8.71 (d, J=2.4 Hz, 1H), 8.66 (d, J=2.4 Hz, 1H), 8.42 (s, 1H), 8.04 (s, 2H), 6.53 (s, 1H), 4.41-4.87 (m, 1H), 2.60-2.67 (m, 1H), 2.54 (s, 3H), 2.40-2.47 (m, 1H), 1.80 (s, 3H), 1.66 (s, 3H). LC-MS: m/z 423 $[M+H]^+$.

Example 6: $^1$H NMR (300 MHz, Methanol-$d_4$): 8.71 (d, J=2.4 Hz, 1H), 8.66 (d, J=2.4 Hz, 1H), 8.42 (s, 1H), 8.04 (s, 2H), 6.53 (s, 1H), 4.41-4.87 (m, 1H), 2.60-2.67 (m, 1H), 2.54 (s, 3H), 2.40-2.47 (m, 1H), 1.80 (s, 3H), 1.66 (s, 3H). LC-MS: m/z 423 $[M+H]^+$.

Example 7: 2-chloro-N-(5-chloro-6-(2H-1,2,3-triazol-2-yl)pyridin-3-yl)-9,9-dimethyl-6,7,8,9-tetrahydropyrazolo[1,5-a]quinazoline-6-carboxamide Example 7

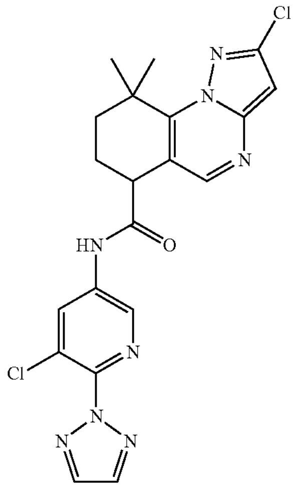

The title compound was prepared similarly to Example 1 using Method A1, starting from 2,2-dimethylcyclohexanone. $^1$H NMR (400 MHz, DMSO-$d_6$) δ: 10.98 (s, 1H), 8.71 (d, J=2.4 Hz, 1H), 8.56 (d, J=2.4 Hz, 1H), 8.45 (s, 1H), 8.16 (s, 2H), 6.88 (s, 1H), 4.11-4.16 (m, 1H), 2.05-2.27 (m, 2H), 1.87-1.99 (m, 1H), 1.75-1.85 (m, 1H), 1.64 (s, 3H), 1.59 (s, 3H). LC-MS: m/z 457 $[M+H]^+$.

Examples 8 and 9: Single Enantiomers Obtained from a Racemic Mixture Containing (R)-2-chloro-N-(5-chloro-6-(2H-1,2,3-triazol-2-yl)pyridin-3-yl)-9,9-dimethyl-6,7,8,9-tetrahydropyrazolo[1,5-a]quinazoline-6-carboxamide and (S)-2-chloro-N-(5-chloro-6-(2H-1,2,3-triazol-2-yl)pyridin-3-yl)-9,9-dimethyl-6,7,8,9-tetrahydropyrazolo[1,5-a]quinazoline-6-carboxamide

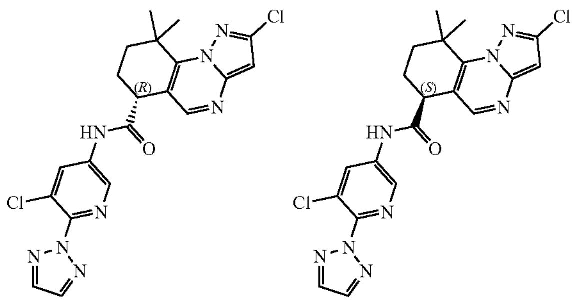

Example 8
and Example 9

2-chloro-N-(5-chloro-6-(2H-1,2,3-triazol-2-yl)pyridin-3-yl)-9,9-dimethyl-6,7,8,9-tetrahydropyrazolo[1,5-a]quinazoline-6-carboxamide were submitted to chiral-HPLC purification (CHIRALPAK IE, 2×25 cm, 5 um; Mobile Phase A: Hex (8 mmol/L $NH_3$·MeOH), Mobile Phase B: EtOH; Flow rate: 17 mL/min; isocratic: 50 B; 220/254 nm; RT1: 8.332; RT2: 12.438; Injection Volume: 1 ml; Number of Runs: 5).

The first eluting isomer was concentrated and lyophilized to afford Example 8 as a white solid (34.6 mg, 35% yield). The second eluting isomer was concentrated and lyophilized to afford Example 9 as a white solid (31.1 mg, 31% yield).

Example 8: $^{1}H$ NMR (300 MHz, DMSO-$d_6$) δ 11.00 (s, 1H), 8.71 (d, J=2.1 Hz, 1H), 8.57 (d, J=2.1 Hz, 1H), 8.46 (s, 1H), 8.17 (s, 2H), 6.89 (s, 1H), 4.10-4.18 (m, 1H), 2.04-2.32 (m, 2H), 1.74-2.03 (m, 2H), 1.65 (s, 3H), 1.59 (s, 3H). LC-MS: m/z 457 $[M+H]^+$.

Example 9: $^{1}H$NMR (300 MHz, DMSO-$d_6$) δ 11.00 (s, 1H), 8.71 (d, J=2.1 Hz, 1H), 8.57 (d, J=2.1 Hz, 1H), 8.45 (s, 1H), 8.17 (s, 2H), 6.89 (s, 1H), 4.10-4.18 (m, 1H), 2.04-2.32 (m, 2H), 1.74-2.03 (m, 2H), 1.65 (s, 3H), 1.59 (s, 3H). LC-MS: m/z 457 $[M+H]^+$.

The absolute stereochemistry for each separated isomer was not determined.

Method D1

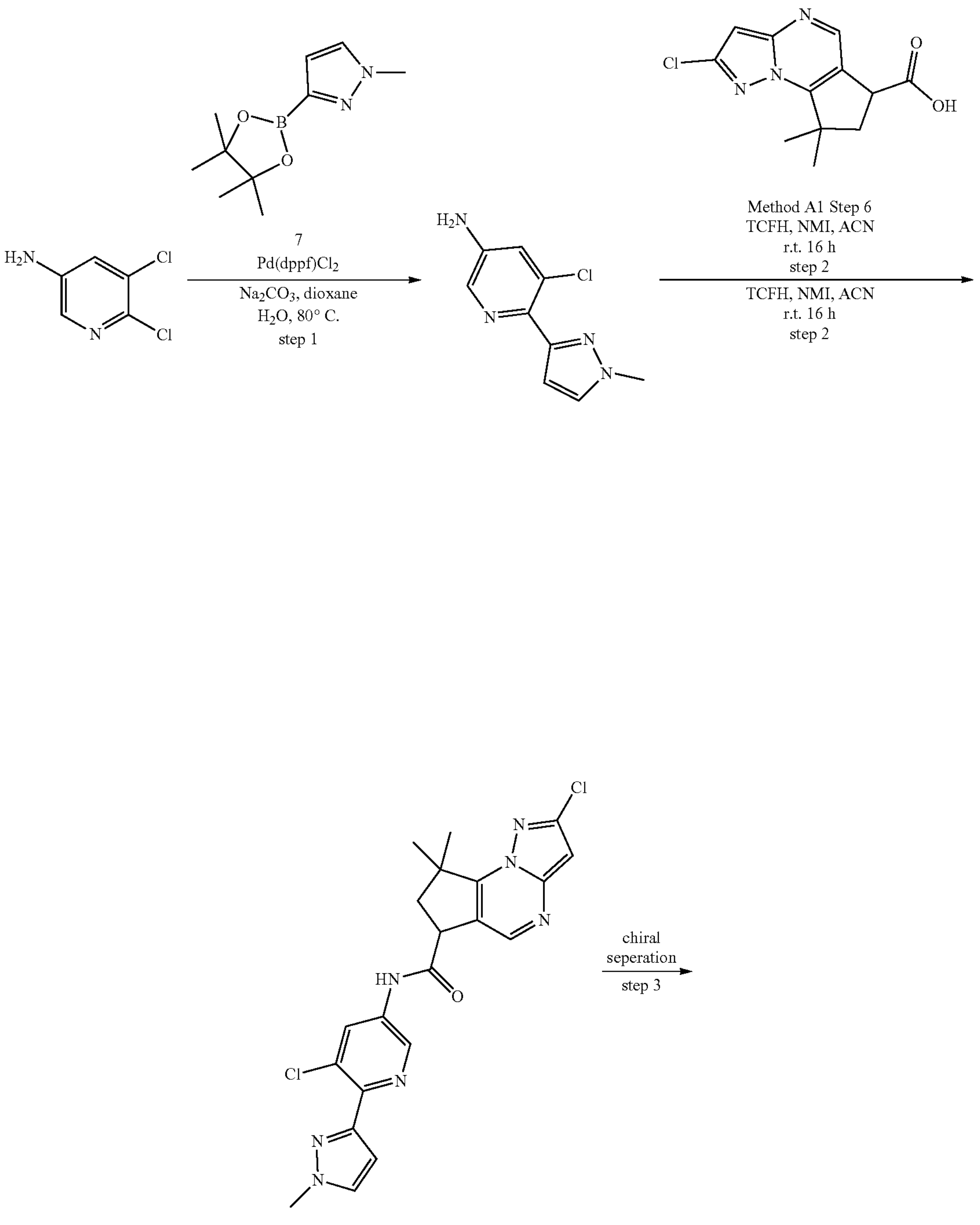

-continued

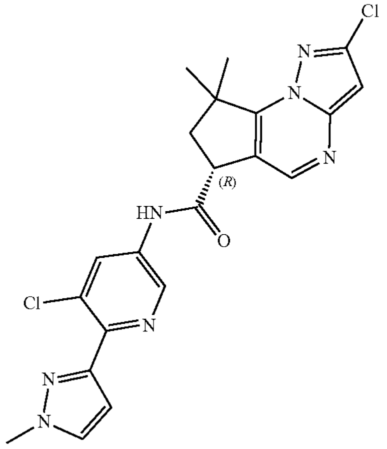

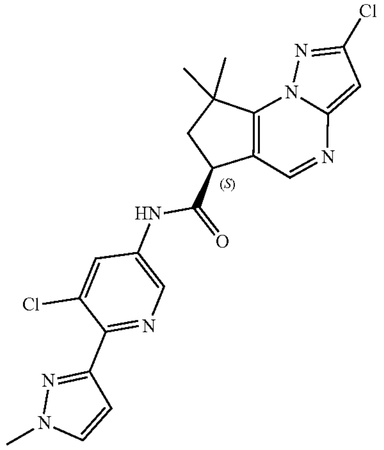

Example 10 and
Example 11

Examples 10 and 11: Single Enantiomers Obtained from a Racemic Mixture Containing (R)-2-chloro-N-(5-chloro-6-(1-methyl-1H-pyrazol-3-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(1-methyl-1H-pyrazol-3-yl)pyridin-3-yl)-8,8-dimethyl-7,8-dihydro-6H-cyclopenta[e]pyrazolo[1,5-a]pyrimidine-6-carboxamide Step 1: 5-chloro-6-(1-methyl-1H-pyrazol-3-yl)pyridin-3-amine

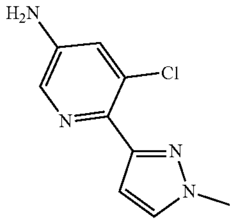

To a solution of 5,6-dichloropyridin-3-amine (1 g, 6.1 mmol) in dioxane (16 mL) and $H_2O$ (4 mL) were added 1-methyl-3-(4,4,5,5-tetramethyl-1,3,2-dioxaborolan-2-yl)-1H-pyrazole (1.2 g, 6.1 mmol), Pd(dppf)C12 (513 mg, 610 μmol), $Na_2CO_3$ (2.6 g, 4 mmol) under N2. The resulting mixture was stirred for 16 h at 80° C. The reaction mixture was quenched with water (150 mL). The resulting solution was extracted with EtOAc (3×150 mL), dried over anhydrous $Na_2$ $SO_4$ and concentrated under vacuum. The residue was applied onto a silica gel column and eluted with EtOAc/PE (1:3) to 5-chloro-6-(1-methyl-1H-pyrazol-3-yl)pyridine-3-amine (1.2 g, crude) as a yellow oil. LC-MS: m/z 209 $[M+H]^+$.

Step 2: 2-chloro-N-(5-chloro-6-(1-methyl-1H-pyrazol-3-yl)pyridin-3-yl)-8,8-dimethyl-7,8-dihydro-6H-cyclopenta[e]pyrazolo[1,5-a]pyrimidine-6-carboxamide

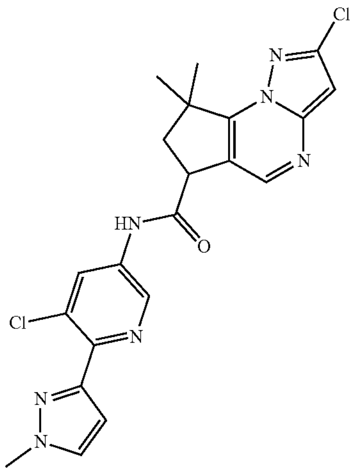

To a solution of 2-chloro-8,8-dimethyl-7,8-dihydro-6H-cyclopenta[e]pyrazolo[1,5-a]pyrimidine-6-carboxylic acid (Method A1 Step 6; 100 mg, 376.3 μmol) in ACN (6 mL) were added 5-chloro-6-(1-methyl-1H-pyrazol-3-yl)pyridin-3-amine (117 mg, 564.5 μmol), TCFH (422 mg, 1.5 mmol) and NMI (123 mg, 1.5 mmol). The resulting mixture was stirred for 3 h at room temperature. The reaction mixture was quenched with water (100 mL). The resulting solution was extracted with EtOAc (3×100 mL), dried over anhydrous $Na_2SO_4$ and concentrated under vacuum. The residue was applied onto a silica gel column and eluted with DCM/MeOH (10:1). The obtained product was further purified by Prep-HPLC to give 2-chloro-N-(5-chloro-6-(1-methyl-1H- pyrazol-3-yl)pyridin-3-yl)-8,8-dimethyl-7,8-dihydro-6H-cyclopenta[e]pyrazolo[1,5-a]pyrimidine-6-carboxamide (28.6 mg, 17% yield) as a white solid. LC-MS: m/z 456 $[M+H]^+$.

Step 3: Separation of Enantiomers to Obtain (R)-2-chloro-N-(5-chloro-6-(1-methyl-1H-pyrazol-3-yl) pyridin-3-yl)-8,8-dimethyl-7,8-dihydro-6H-cyclopenta[e]pyrazolo[1,5-a]pyrimidine-6-carboxamide and (5)-2-chloro-N-(5-chloro-6-(1-methyl-1H-pyrazol-3-yl)pyridin-3-yl)-8,8-dimethyl-7,8-dihydro-6H-cyclopenta[e]pyrazolo[1,5-a]pyrimidine-6-carboxamide

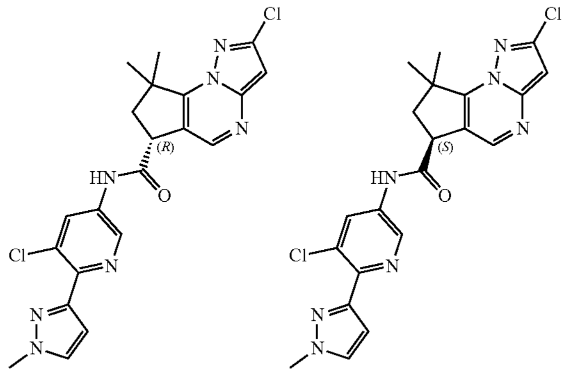

Example 10
and Example 11

28.6 mg of 2-chloro-N-(5-chloro-6-(1-methyl-1H-pyrazol-3-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: Chiralpak ID-2, 2*25 cm, Sum; Mobile Phase A:MTBE (0.5% 2M $NH_3$-MeOH), Mobile Phase B:EtOH; Flow rate: 15 mL/min; isocratic: 50 B; 254/220 nm; RT1:12.336; RT2: 26.017; Injection Volume: 1.5 ml; Number of Runs: 1). The first eluting isomer was concentrated and lyophilized to afford Example 10 as a white solid (7.8 mg, 27% yield). The second eluting isomer was concentrated and lyophilized to afford Example 11 as a white solid (7.2 mg, 27% yield).

Example 10: $^1H$ NMR (400 MHz, DMSO-$d_6$) δ: 10.79 (s, 1H), 8.72 (d, J=2.0 Hz, 1H), 8.63 (s, 1H), 8.34 (d, J=2.0 Hz, 1H), 7.77 (d, J=2.0 Hz, 1H), 6.94 (s, 1H), 6.72 (d, J=2.0 Hz, 1H), 4.39-4.44 (m, 1H), 3.92 (s, 3H), 2.50-2.52 (m, 1H), 2.27-2.33 (m, 1H), 1.64 (s, 3H), 1.56 (s, 3H). LC-MS: m/z 456 $[M+H]^+$.

Example 11: $^1H$ NMR (400 MHz, DMSO-$d_6$) δ: 10.79 (s, 1H), 8.72 (d, J=2.0 Hz, 1H), 8.64 (s, 1H), 8.34 (d, J=2.0 Hz, 1H), 7.77 (d, J=2.0 Hz, 1H), 6.94 (s, 1H), 6.72 (d, J=2.0 Hz, 1H), 4.39-4.45 (m, 1H), 3.92 (s, 3H), 2.50-2.51 (m, 1H), 2.28-2.35 (m, 1H), 1.64 (s, 3H), 1.56 (s, 3H). LC-MS: m/z 456 $[M+H]^+$.

The absolute stereochemistry for each separated isomer was not determined.

Method E1

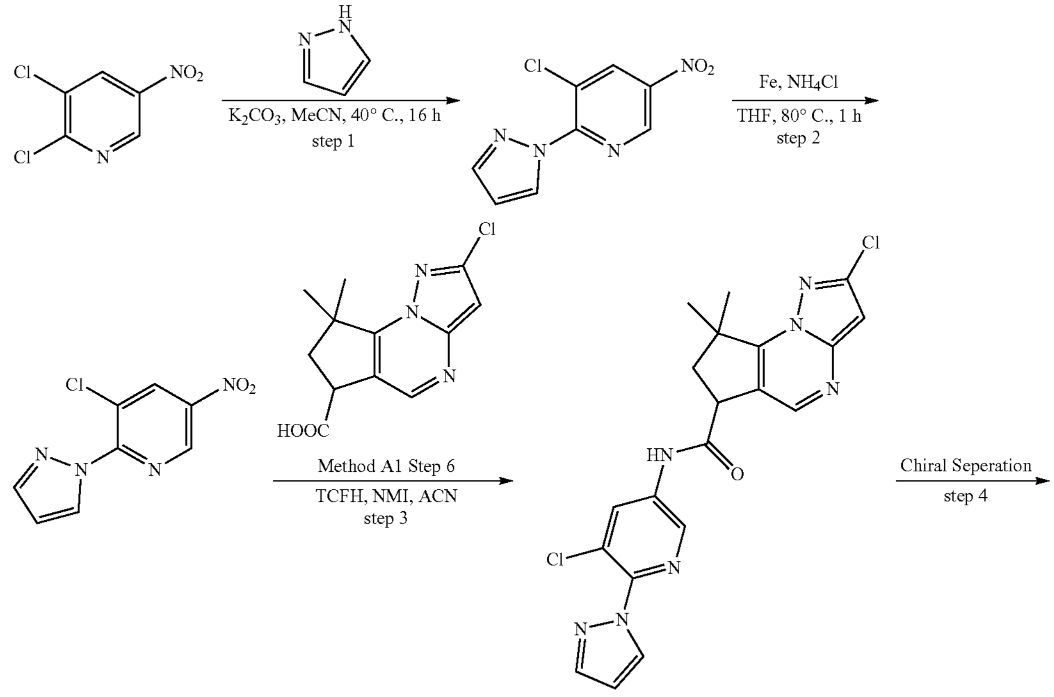

-continued

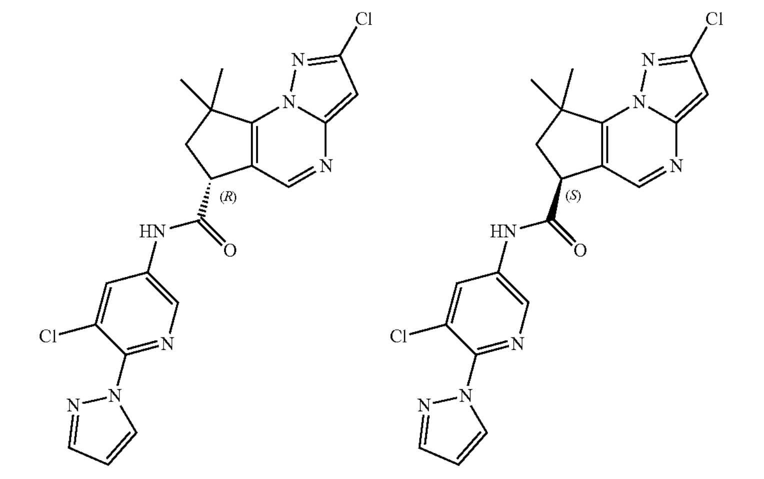

Example 12 and
Example 13

Examples 12 and 13: Single Enantiomers Obtained from a Racemic Mixture Containing (R)-2-chloro-N-(5-chloro-6-(1H-pyrazol-1-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(1H-pyrazol-1-yl)pyridin-3-yl)-8,8-dimethyl-7,8-dihydro-6H-cyclopenta[e]pyrazolo[1,5-a]pyrimidine-6-carboxamide Step 1: 3-chloro-5-nitro-2-(1H-pyrazol-1-yl)pyridine

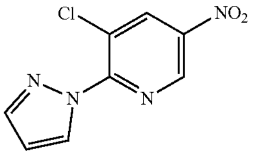 [SMILES: O=[N+]([O-])c1cnc(-n2cccn2)c(Cl)c1]

To a stirred solution of 2,3-dichloro-5-nitro-pyridine (5 g, 25.9 mmol) in MeCN (100 mL) was added 1H-pyrazole (7 g, 28.5 mmol) and $K_2CO_3$ (2 g, 51.8 mmol). The resulting mixture was stirred for 16 h at 40° C. The mixture was allowed to cool down to room temperature. The reaction mixture was filtered and the collected solid was washed with EtOAc (3×50 mL). The resulting solution was concentrated under reduced pressure. The residue was applied on a silica gel column and eluted with EtOAc/PE (1:10) to give 3-chloro-5-nitro-2-(1H-pyrazol-1-yl)pyridine (4 g, 68% yield) as a white solid. $^1H$ NMR (300 MHz, DMSO-$d_6$) δ: 9.30 (d, J=2.4 Hz, 1H), 9.00 (d, J=2.4 Hz, 1H), 8.50-8.51 (m, 1H), 7.67-7.68 (m, 1H), 6.67-6.68 (m, 1H). LC-MS: m/z 225 $[M+H]^+$.

Step 2: 5-chloro-6-(1H-pyrazol-1-yl)pyridin-3-amine

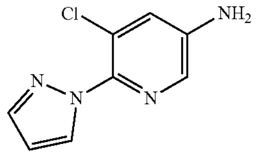 [SMILES: Nc1cnc(-n2cccn2)c(Cl)c1]

To a stirred solution of 3-chloro-5-nitro-2-(1H-pyrazol-1-yl)pyridine (2 g, 8.9 mmol) in THE (33 mL) and $H_2O$ (33 mL) was added Ammonium chloride (3.8 g, 71.2 mmol). Then Fe (4.0 g, 71.2 mmol) was added to the mixture at 80° C. for 1 h. The mixture was allowed to cool down to room temperature and filtered through a pad of diatomaceous earth and the pad was washed with EtOAc (3×10 mL). The resulting solution was extracted with EtOAc (3×100 mL). The combined organic layers were dried over anhydrous $Na_2SO_4$ and concentrated under vacuum. The residue was applied on a silica gel column and eluted with EtOAc/PE (1:1) to afford 5-chloro-6-(1H-pyrazol-1-yl)pyridin-3-amine (0.38 g, 22% yield) as a yellow solid. $^1H$ NMR (300 MHz, Chloroform-d) δ: 7.87-7.90 (m, 2H), 7.78 (d, J=1.8 Hz, 1H), 7.15 (d, J=2.6 Hz, 1H), 6.45-6.47 (m, 1H) 4.50 (s, 2H). LC-MS: m/z 195 $[M+H]^+$.

Step 3: 2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

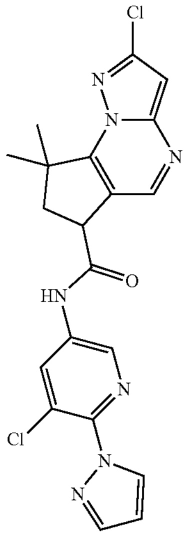

To a stirred solution of 2-chloro-8,8-dimethyl-7,8-dihydro-6H-cyclopenta[e]pyrazolo[1,5-a]pyrimidine-6-carboxylic acid (Method A1 Step 6; 50 mg, 188.2 μmol) in ACN (5 mL) were added 3-chloro-5-nitro-2-(1H-pyrazol-1-yl)pyridine (55 mg, 282.3 μmol), TCFH (211 mg, 752.7 μmol) and NMI (62 mg, 752.7 μmol). The resulting mixture was stirred for 16 h at room temperature. The reaction mixture was quenched with water (20 mL). The resulting solution was extracted with EtOAc (3×20 mL). The combined organic layers were dried over anhydrous $Na_2SO_4$ and concentrated under vacuum. The residue was submitted to Prep-HPLC purification and the collected fractions were lyophilized to give 2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide (60 mg, 84% yield) as a white solid. LC-MS: m/z $442[M+H]^+$.

Step 4: Separation of Enantiomers to Obtain (R)-2-chloro-N-(5-chloro-6-(1H-pyrazol-1-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(1H-pyrazol-1-yl)pyridin-3-yl)-8,8-dimethyl-7,8-dihydro-6H-cyclopenta[e]pyrazolo[1,5-a]pyrimidine-6-carboxamide

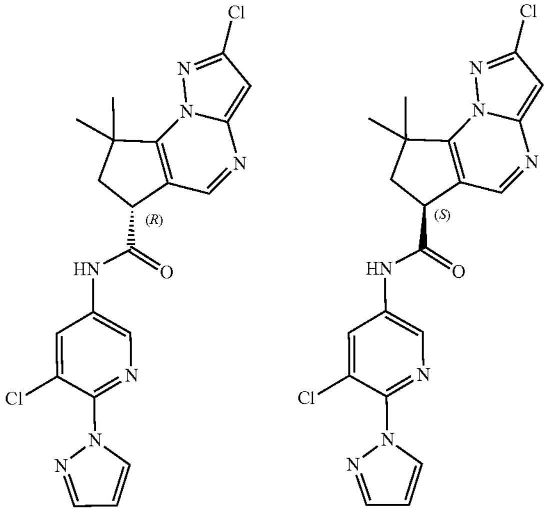

Example 12
and Example 13

60 mg of 2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: Chiralpak IA, 2*25 cm, 5um; Mobile Phase A:Hex(0.5% 2M $NH_3$-MeOH), Mobile Phase B:EtOH; Flow rate: 18 mL/min; isocratic: 50 B; 220/254 nm; RT1:7.267; RT2:12.331; Injection Volume: 2 ml; Number of Runs: 4). Fractions containing the first eluting isomer were concentrated and lyophilized to afford Example 12 as a white solid (25.8 mg, 31% yield). Fractions containing the second eluting isomer were concentrated and lyophilized to afford Example 13 as a white solid (32.1 mg, 38% yield).

Example 12: $^1H$ NMR (400 MHz, Methanol-$d_4$) δ: 8.65 (d, J=2.4 Hz, 1H), 8.56 (d, J=2.0 Hz, 1H), 8.51 (s, 1H), 8.13 (d, J=2.4 Hz, 1H), 7.78 (d, J=1.2 Hz, 1H), 6.70 (s, 1H), 6.55-6.56 (m, 1H), 4.38-4.41 (m, 1H), 2.60-2.65 (m, 1H), 2.40-2.43 (m, 1H), 1.73 (s, 3H), 1.62 (s, 3H). LC-MS: m/z $442[M+H]^+$.

Example 13: $^1H$ NMR (400 MHz, Methanol-$d_4$) δ: 8.65 (d, J=2.4 Hz, 1H), 8.56 (d, J=2.0 Hz, 1H), 8.51 (s, 1H), 8.13 (d, J=2.4 Hz, 1H), 7.78 (d, J=1.2 Hz, 1H), 6.70 (s, 1H), 6.55-6.56 (m, 1H), 4.38-4.41 (m, 1H), 2.60-2.65 (m, 1H), 2.40-2.43 (m, 1H), 1.73 (s, 3H), 1.62 (s, 3H). LC-MS: m/z $442[M+H]^+$.

The absolute stereochemistry for each separated isomer was not determined.

Method F1

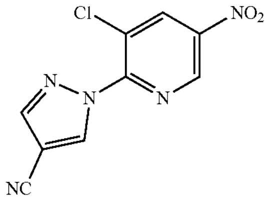 [SMILES: N#Cc1cnn(-c2ncc([N+](=O)[O-])cc2Cl)c1]

Examples 14 and 15: Single Enantiomers Obtained from a Racemic Mixture Containing (R)-2-chloro-N-(5-chloro-6-(4-cyano-1H-pyrazol-1-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(4-cyano-1H-pyrazol-1-yl)pyridin-3-yl)-8,8-dimethyl-7,8-dihydro-6H-cyclopenta[e]pyrazolo[1,5-a]pyrimidine-6-carboxamide Step 1: 1-(3-chloro-5-nitropyridin-2-yl)-1H-pyrazole-4-carbonitrile

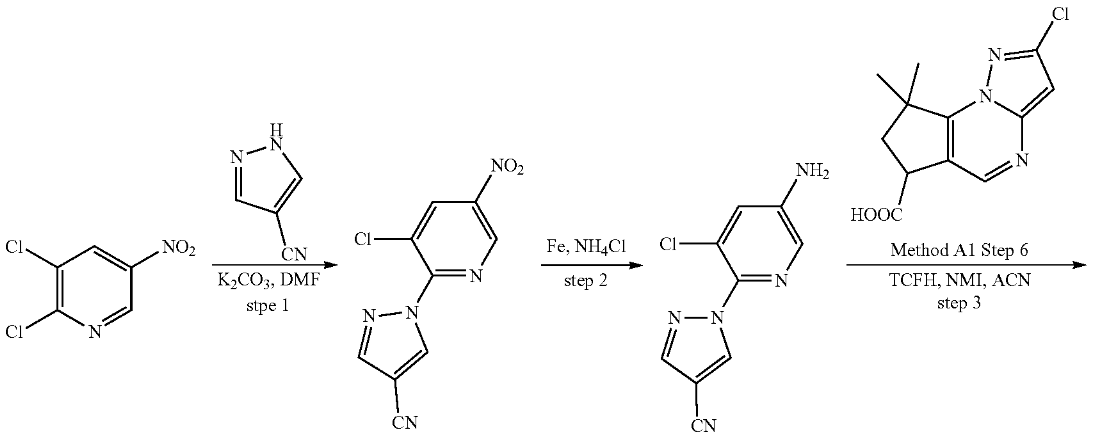

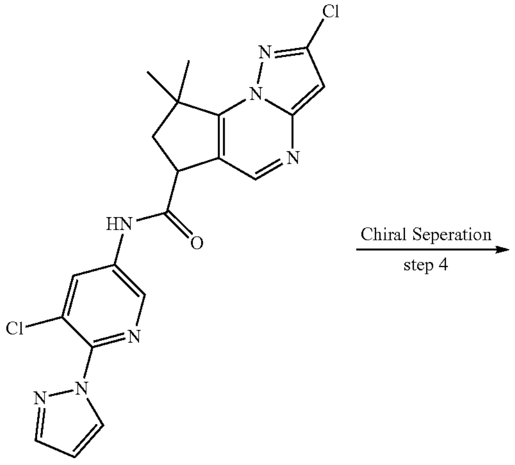

-continued

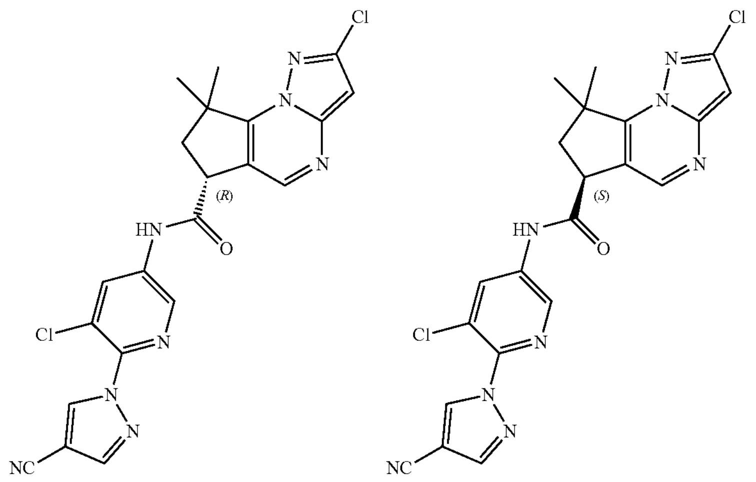

Example 14 and Example 15

A mixture of 2,3-dichloro-5-nitro-pyridine (3 g, 15.6 mmol), 1H-pyrazole-4-carbonitrile (1.59 g, 17.1 mmol) and potassium carbonate (6.45 g, 46.6 mmol) in DMF (40 mL) was stirred for 4 h at 25° C. The resulting mixture was poured into ice/water (100 mL). The precipitated solids were collected by filtration and washed with water (5×20 mL). The resulting solid was dried under infrared light. This resulted in 1-(3-chloro-5-nitro-2-pyridyl)pyrazole-4-carbonitrile (3.4 g, 88% yield) as a yellow solid. $^1$H NMR (400 MHz, DMSO-$d_6$) δ: 9.34 (d, J=2.4 Hz, 1H), 9.30 (s, 1H), 9.10 (d, J=2.4 Hz, 1H), 8.51 (s, 1H).

Step 2:1-(5-amino-3-chloropyridin-2-yl)-1H-pyrazole-4-carbonitrile

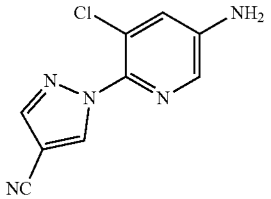 [SMILES: N#Cc1cnn(-c2ncc(N)cc2Cl)c1]

To a stirred mixture of 1-(3-chloro-5-nitro-2-pyridyl) pyrazole-4-carbonitrile (1 g, 4.0 mmol) in EtOH (15 mL) and $H_2O$ (15 mL) were added iron (940 mg, 16.8 mmol) and ammonium chloride (900 mg, 16.8 mmol). The resulting mixture was stirred for 1 h at 95° C. The mixture was cooled down to room temperature, filtered and concentrated under reduced pressure to remove EtOH. The aqueous layer was extracted with EtOAc (3×100 mL). The combined organic layers were dried over anhydrous $Na_2SO_4$, filtered and concentrated under reduced pressure. The residue was purified by silica gel column chromatography and eluted with DCM/MeOH (92:8) to give 1-(5-amino-3-chloro-2-pyridyl) pyrazole-4-carbonitrile (630 mg, 72% yield) as a yellow solid. $^1$H NMR (400 MHz, DMSO-$d_6$) δ 8.89 (s, 1H), 8.26 (s, 1H), 7.79 (d, J=2.4 Hz, 1H), 7.18 (d, J=2.4 Hz, 1H), 6.14 (s, 2H). LC-MS: m/z 220 [M+H]$^+$.

Step 3: 2-chloro-N-(5-chloro-6-(4-cyano-1H-pyrazol-1-yl)pyridin-3-yl)-8,8-dimethyl-7,8-dihydro-6H-cyclopenta[e]pyrazolo[1,5-a]pyrimidine-6-carboxamide

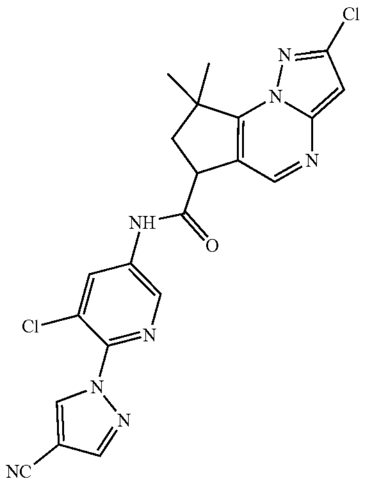

To a stirred mixture of 1-(5-amino-3-chloro-2-pyridyl) pyrazole-4-carbonitrile (100 mg, 0.46 mmol) and 2-chloro-8,8-dimethyl-7,8-dihydro-6H-cyclopenta[e]pyrazolo[1,5-a] pyrimidine-6-carboxylic acid (Method A1 Step 6; 121 mg, 0.46 mmol) in ACN (10 mL) were added TCFH (383 mg, 1.37 mmol) and NMI (187 mg, 2.28 mmol). The resulting mixture was stirred for 3 h at 25° C. The resulting mixture was concentrated under reduced pressure. The residue was purified by silica gel column chromatography and eluted with EtOAc/PE (7:3) to give the crude product which was submitted to HPLC purification. The collected fractions were lyophilized to give 2-chloro-N-(5-chloro-6-(4-cyano-1H-pyrazol-1-yl)pyridin-3-yl)-8,8-dimethyl-7,8-dihydro- 6H-cyclopenta[e]pyrazolo[1,5-a]pyrimidine-6-carboxamide (34.3 mg, 16% yield) as a white solid. LC-MS: m/z 467 $[M+H]^+$.

Step 4: Separation of Enantiomers to Obtain (R)-2-chloro-N-(5-chloro-6-(4-cyano-1H-pyrazol-1-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(4-cyano-1H-pyrazol-1-yl)pyridin-3-yl)-8,8-dimethyl-7,8-dihydro-6H-cyclopenta[e]pyrazolo[1,5-a]pyrimidine-6-carboxamide

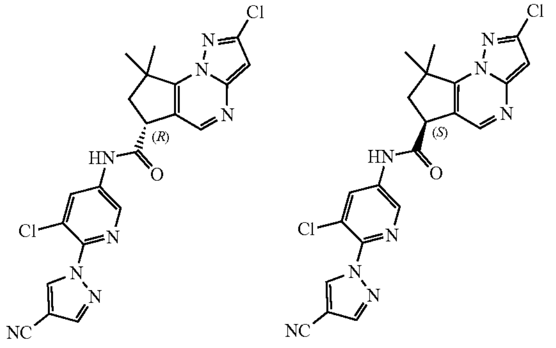

Example 14
and Example 15

30 mg of 2-chloro-N-(5-chloro-6-(4-cyano-1H-pyrazol-1-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: Chiralpak ID-2, 2×25 cm, 5 um; Mobile Phase A: Hex (0.5% 2M $NH_3$-MeOH), Mobile Phase B: EtOH; Flow rate: 18 mL/min; isocratic: 50 B; 254/220 nm; RT1: 15.609; RT2: 19.773; Injection Volume: 0.7 ml; Number of Runs: 4). Fractions containing the first eluting isomer were concentrated and lyophilized to afford Example 14 as a white solid (5.7 mg, 19% yield). Fractions containing the second eluting isomer were concentrated and lyophilized to Example 15 as a white solid (5.6 mg, 19% yield).

Example 14: $^1H$ NMR (400 MHz, DMSO-$d_6$) δ 11.04 (s, 1H), 9.10 (s, 1H), 8.70 (d, J=2.4 Hz, 1H), 8.65 (s, 1H), 8.54 (d, J=2.4 Hz, 1H), 8.40 (s, 1H), 6.95 (s, 1H), 4.42-4.48 (m, 1H), 2.53-2.60 (m, 1H), 2.29-2.37 (m, 1H), 1.64 (s, 3H), 1.56 (s, 3H). LC-MS: m/z 467 $[M+H]^+$.

Example 15: $^1H$ NMR (400 MHz, DMSO-$d_6$) δ 11.04 (s, 1H), 9.10 (s, 1H), 8.70 (d, J=2.4 Hz, 1H), 8.65 (s, 1H), 8.54 (d, J=2.4 Hz, 1H), 8.40 (s, 1H), 6.95 (s, 1H), 4.42-4.48 (m, 1H), 2.53-2.60 (m, 1H), 2.29-2.37 (m, 1H), 1.64 (s, 3H), 1.56 (s, 3H). LC-MS: m/z 467 $[M+H]^+$.

The absolute stereochemistry for each separated isomer was not determined.

Method G1

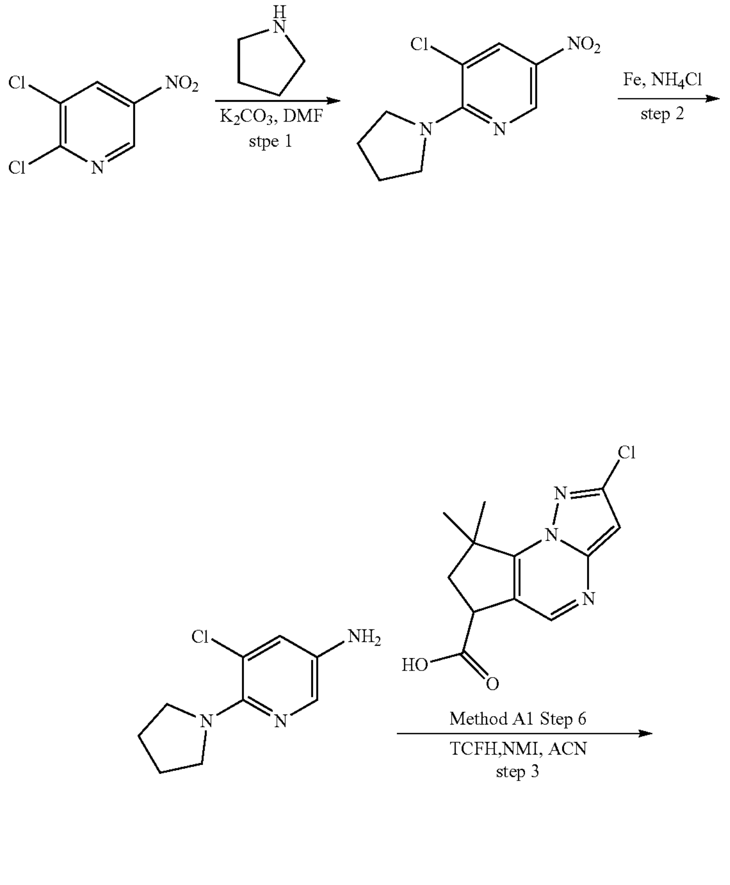

-continued

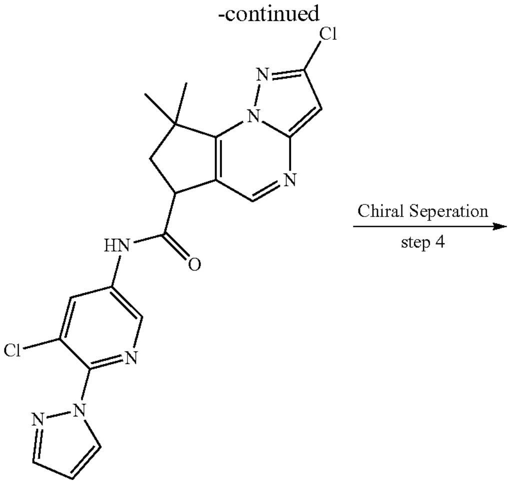

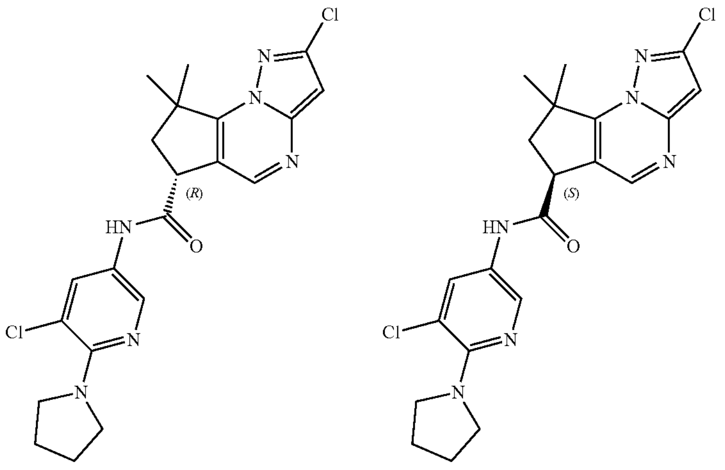

Example 16 and
Example 17

Examples 16 and 17: Single Enantiomers Obtained from a Racemic Mixture Containing (R)-2-chloro-N-(5-chloro-6-(pyrrolidin-1-yl)pyridin-3-yl)-8,8-dimethyl-7,8-dihydro-6H-cyclopenta[e]pyrazolo[1,5-a]pyrimidine-6-carboxamid and (S)-2-chloro-N-(5-chloro-6-(pyrrolidin-1-yl)pyridin-3-yl)-8,8-dimethyl-7,8-dihydro-6H-cyclopenta[e]pyrazolo[1,5-a] pyrimidine-6-carboxamide Step 1: 3-chloro-5-nitro-2-(pyrrolidin-1-yl)pyridine

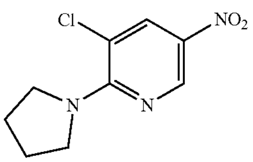 [SMILES: O=[N+]([O-])c1cnc(N2CCCC2)c(Cl)c1]

To a stirred solution of 2,3-dichloro-5-nitro-pyridine (2.00 g, 10.4 mmol) in DMF (20 mL) were added pyrrolidine (884 mg, 12.4 mmol) and $K_2CO_3$ (1.43 g, 10.4 mmol). The mixture was stirred at 25° C. for 16 h. The resulting mixture was poured into water (50 mL) and extracted with EtOAc (3×100 mL). The combined organic layers were washed with water (3×100 mL), dried over anhydrous $Na_2SO_4$, filtered and concentrated under reduced pressure. The residue was purified by silica gel column chromatography and eluted with EtOAc/PE (1:1) to afford 3-chloro-5-nitro-2-(pyrrolidin-1-yl)pyridine (2.00 g, 85% yield) as a yellow solid. $^1H$ NMR (400 MHz, $CDCl_3$) δ 8.90 (d, J=2.4 Hz, 1H), 8.23 (d, J=2.4 Hz, 1H), 3.85-3.91 (m, 4H), 1.95-2.05 (m, 4H).

LC-MS: m/z 228 $[M+H]^+$.

Step 2: 5-chloro-6-(pyrrolidin-1-yl)pyridin-3-amine

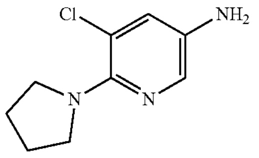 [SMILES: Nc1cnc(N2CCCC2)c(Cl)c1]

To a stirred solution of 5-chloro-6-(pyrrolidin-1-yl)pyridin-3-amine (500 mg, 2.2 mmol) in $H_2O$ (5 mL) and EtOH (15 mL) were added $NH_4Cl$ (352 mg, 6.6 mmol) and iron (613 mg, 11.0 mmol). The mixture was stirred at 80° C. for 3 h. The resulting mixture was filtered and the filtrate was concentrated under reduced pressure to remove EtOH. The resulting mixture was extracted with EtOAc (3×20 mL). The combined organic layers were dried over anhydrous $Na_2SO_4$, filtered and concentrated under reduced pressure. The residue was purified by silica gel column chromatography and eluted with EtOAc/PE (1:1) to afford 5-chloro-6-(pyrrolidin-1-yl)pyridin-3-amine (300 mg, 69% yield) as a yellow solid. $^1H$ NMR (400 MHz, $CDCl_3$) δ 7.66 (d, J=2.4 Hz, 1H), 7.03 (d, J=2.4 Hz, 1H), 3.46-3.56 (m, 4H), 3.31 (br s, 2H), 1.84-1.95 (m, 4H). LC-MS: m/z 198 $[M+H]^+$.

Step 3: 2-chloro-N-(5-chloro-6-(pyrrolidin-1-yl)pyridin-3-yl)-8,8-dimethyl-7,8-dihydro-6H-cyclopenta[e]pyrazolo[1,5-a]pyrimidine-6-carboxamide

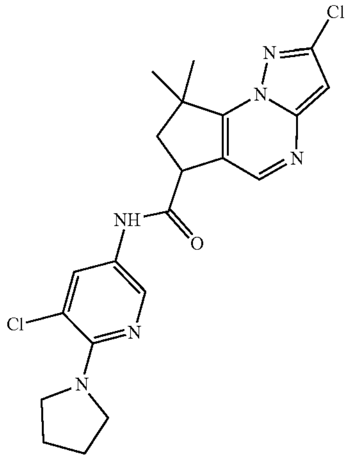

To a stirred solution of 5-chloro-6-(pyrrolidin-1-yl)pyridin-3-amine (100 mg, 505.9 μmol) and 2-chloro-8,8-dimethyl-7,8-dihydro-6H-cyclopenta[e]pyrazolo[1,5-a]pyrimidine-6-carboxylic acid (Method A1 Step 6; 134 mg, 505.9 μmol) in ACN (10 mL) were added TCFH (426 mg, 1.5 mmol) and NMI (208 mg, 2.53 mmol). The mixture was stirred at 25° C. for 16 h. The resulting mixture was concentrated under reduced pressure. The residue was submitted to Prep-HPLC purification and the collected fractions were lyophilized to give 2-chloro-N-(5-chloro-6-(pyrrolidin-1-yl)pyridin-3-yl)-8,8-dimethyl-7,8-dihydro-6H-cyclopenta[e]pyrazolo[1,5-a]pyrimidine-6-carboxamide (63.6 mg, 28% yield) as a white solid. LC-MS: m/z 445 $[M+H]^+$.

Step 4: Separation of Enantiomers to Obtain (R)-2-chloro-N-(5-chloro-6-(pyrrolidin-1-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(pyrrolidin-1-yl)pyridin-3-yl)-8,8-dimethyl-7,8-dihydro-6H-cyclopenta[e]pyrazolo[1,5-a]pyrimidine-6-carboxamide

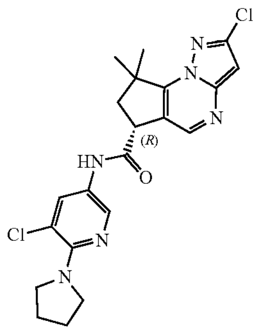
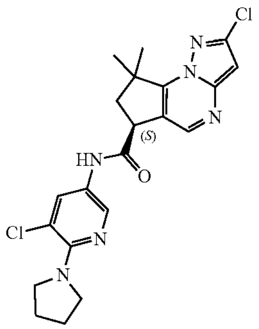

Example 16
and Example 17

63.6 mg of 2-chloro-N-(5-chloro-6-(pyrrolidin-1-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: Chiralpak ID-2, 2×25 cm, 5 um; Mobile Phase A: Hex:DCM=3:1 (0.5% 2 M $NH_3$-MeOH), Mobile Phase B: EtOH; Flow rate: 20 mL/min; isocratic: 10 B; 254/220 nm; RT1: 11.691; RT2: 21.128; Injection Volume: 2 ml; Number of Runs: 2). The first eluting isomer was concentrated and lyophilized to afford Example 16 as a white solid (11.3 mg, 17% yield). The second eluting isomer was concentrated and lyophilized to afford Example 17 as a white solid (14.3 mg, 22% yield).

Example 16: $^1H$ NMR (400 MHz, DMSO-$d_6$) δ 10.33 (s, 1H), 8.59 (s, 1H), 8.23 (d, J=2.4 Hz, 1H), 8.00 (d, J=2.4 Hz, 1H), 6.93 (s, 1H), 4.28-4.56 (m, 1H), 3.49-3.57 (m, 4H), 2.45-2.48 (m, 1H), 2.25-2.52 (m, 1H), 1.80-1.91 (m, 4H), 1.63 (s, 3H), 1.54 (s, 3H). LC-MS: m/z 445 $[M+H]^+$.

Example 17: $^1H$ NMR (400 MHz, DMSO-$d_6$) δ 10.33 (s, 1H), 8.59 (s, 1H), 8.23 (d, J=2.4 Hz, 1H), 8.00 (d, J=2.4 Hz, 1H), 6.93 (s, 1H), 4.28-4.56 (m, 1H), 3.49-3.57 (m, 4H), 2.45-2.48 (m, 1H), 2.25-2.52 (m, 1H), 1.80-1.91 (m, 4H), 1.63 (s, 3H), 1.54 (s, 3H). LC-MS: m/z 445 $[M+H]^+$.

Method H1

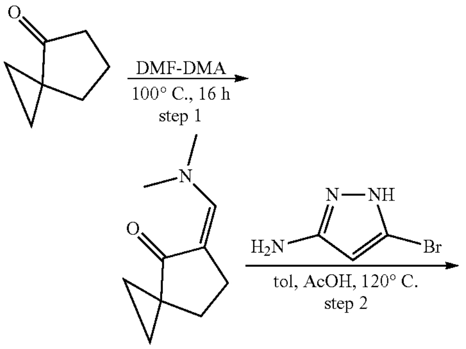

-continued

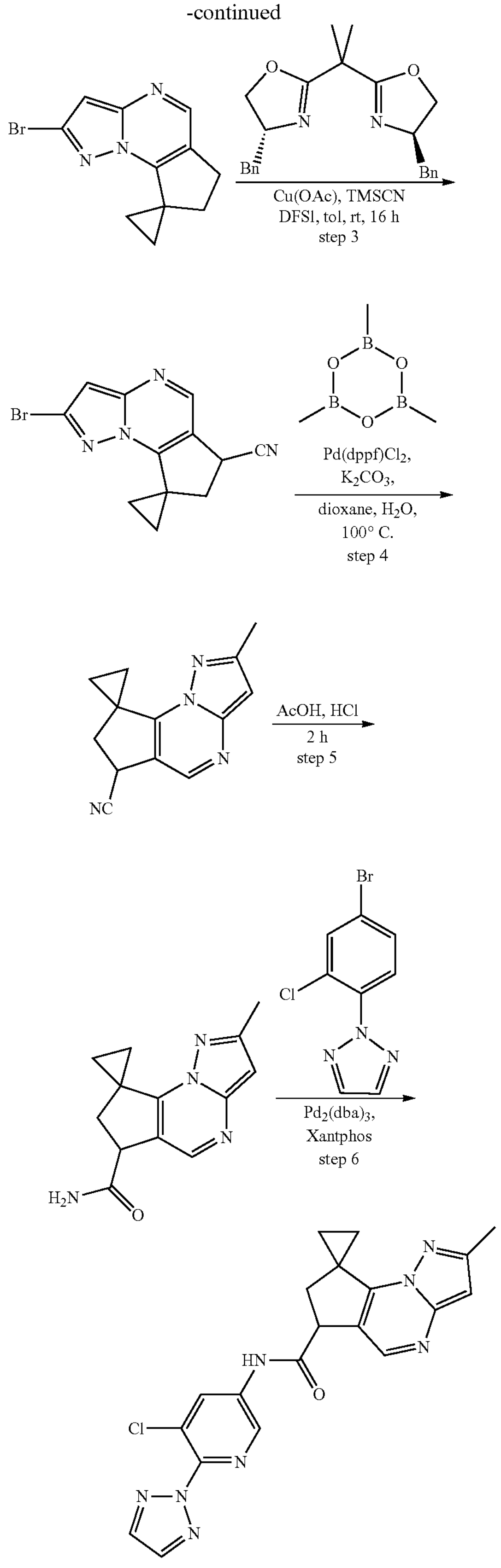

Example 18

Example 18: N-(5-chloro-6-(2H-1,2,3-triazol-2-yl)pyridin-3-yl)-2-methyl-6,7-dihydrospiro[cyclopenta[e]pyrazolo[1,5-a]pyrimidine-8,1'-cyclopropane]-6-carboxamide Step 1: (Z)-5-((dimethylamino)methylene)spiro[2.4]heptan-4-one-N

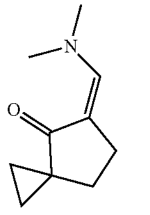

To a mixture of DMF-DMA (20 mL) was added spiro[2.4]heptan-4-one (2 g, 90.9 mmol) at room temperature and the reaction mixture was stirred for 16 h at 100° C. The mixture was allowed to cool down to room temperature. The mixture was concentrated under reduced pressure to afford (Z)-5((dimethylamino)methylene)spiro[2.4]heptan-4-one (10 g, crude) as a yellow oil, which was used directly in the next step. LC-MS: m/z 166 $[M+H]^+$.

Step 2: 2-bromo-6,7-dihydrospiro[cyclopenta[e]pyrazolo[1,5-a]pyrimidine-8,1'-cyclopropane]

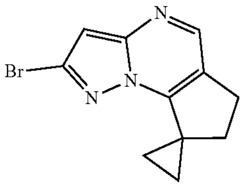 [SMILES: Brc1cc2ncc3c(n2n1)C1(CC3)CC1]

To a stirred solution of (Z)-5-((dimethylamino)methylene)spiro[2.4]heptan-4-one (5 g, 30.3 mmol) in toluene (50 mL) was added 5-bromo-1H-pyrazol-3-amine (4.9 g, 30.3 mmol) and AcOH (5 mL) at room temperature. The resulting mixture was stirred for 16 h at 120° C. The mixture was allowed to cool down to room temperature and concentrated under reduced pressure. The residue was diluted with water (300 mL). The pH was adjusted to 6-7 with sodium bicarbonate (sat., aq.). The resulting solution was extracted with EtOAc (2×300 mL). The combined organic layers were dried over anhydrous $Na_2SO_4$ and concentrated under vacuum. The residue was applied on a silica gel column and eluted with EtOAc/PE (1:3) to give 2-bromo-6,7-dihydrospiro[cyclopenta[e]pyrazolo[1,5-a]pyrimidine-8,1'-cyclopropane](2.0 g, 25% yield of two steps) as a brown solid. $^1H$ NMR (400 MHz, DMSO-$d_6$) δ: 8.41 (s, 1H), 6.80 (s, 1H), 2.96-3.16 (m, 2H), 2.14-3.23 (m, 2H), 1.89-2.08 (m, 2H), 1.05-1.07 (m, 2H). LC-MS: m/z 264 $[M+H]^+$.

Step 3: 2-bromo-6,7-dihydrospiro[cyclopenta[e]pyrazolo[1,5-a]pyrimidine-8,1'-cyclopropane]-6-carbonitrile

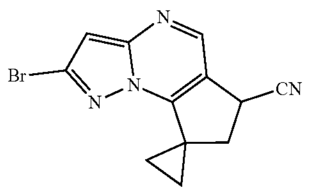

To a stirred solution of 2-bromo-6,7-dihydrospiro[cyclopenta[e]pyrazolo[1,5-a]pyrimidine-8,1'-cyclopropane](2 g, 7.6 mmol) in toluene (30 mL) was added (4R)-4-benzyl-2-[-[(4R)-4-benzyl-4,5-dihydrooxazol-2-yl]-1-methyl-ethyl]-4,5-dihydrooxazole (297 mg, 912 μmol), acetoxycopper (154 mg, 1.3 mmol), N-fluorobenzenesulfonimide (3.6 g, 11.4 mmol) and TMSCN (3.8 g, 38 mmol). The reaction was stirred at room temperature for 16 h under nitrogen. The solvent was removed under vacuum and the residue was applied onto a silica gel column and eluted with EtOAc/PE (1:2) to give 2-bromo-6,7-dihydrospiro[cyclopenta[e]pyrazolo[1,5-a]pyrimidine-8,1'-cyclopropane]-6-carbonitrile (150 mg, 7% yield) as an off white solid. LC-MS: m/z 289 $[M+H]^+$.

Step 4: 2-methyl-6,7-dihydrospiro[cyclopenta[e]pyrazolo[1,5-a]pyrimidine-8,1'-cyclopropane]-6-carbonitrile

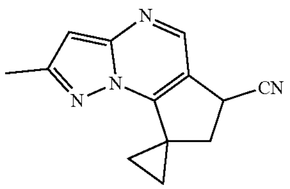 [SMILES: Cc1cc2ncc3c(n2n1)C1(CC1)CC3C#N]

To a mixture of 2-bromo-6,7-dihydrospiro[cyclopenta[e]pyrazolo[1,5-a]pyrimidine-8,1'-cyclopropane]-6-carbonitrile (150 mg, 259.4 μmol) in dioxane (4 mL) were added 2,4,6-trimethyl-1,3,5,2,4,6-trioxatriborinane (130 mg, 518.8 μmol), Pd(dppf)C12 (19 mg, 25.9 μmol), $K_2CO_3$ (71 mg, 518.8 μmol) and $H_2O$ (1 mL). The mixture was stirred at 100° C. for 2 h under nitrogen. The mixture was allowed to cool down to room temperature and concentrated under reduced pressure. The residue was diluted with water (50 mL), extracted with EtOAc (3×50 mL). The combined organic layers were dried over anhydrous $Na_2SO_4$ and concentrated under vacuum. The residue was applied onto a silica gel column and eluted with EtOAc/PE (1:2) to give 2-methyl-6,7-dihydrospiro[cyclopenta[e]pyrazolo[1,5-a]pyrimidine-8,1'-cyclopropane]-6-carbonitrile (25 mg, 42% yield) as a yellow oil. LC-MS: m/z 225 $[M+H]^+$.

Step 5: 2-methyl-6,7-dihydrospiro[cyclopenta[e]pyrazolo[1,5-a]pyrimidine-8,1'-cyclopropane]-6-carboxamide

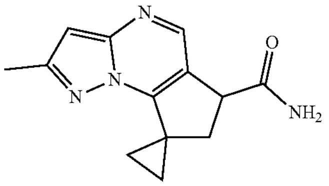 [SMILES: Cc1cc2ncc3c(n2n1)C1(CC1)CC3C(N)=O]

2-methyl-6,7-dihydrospiro[cyclopenta[e]pyrazolo[1,5-a]pyrimidine-8,1'-cyclopropane]-6-carbonitrile (25 mg, 111.6 μmol) was added to a solution of HCl (1 mL) and AcOH (3 mL). The reaction solution was stirred at room temperature for 6 h. The resulting mixture was concentrated under vacuum. The residue was diluted with water (2 mL). The pH was adjusted to 8-9 with $NaHCO_3$(aq., sat.). The resulting mixture was concentrated under vacuum. The residue was submitted to Prep-HPLC and the collected fractions were lyophilized to give 2-methyl-6,7-dihydrospiro[cyclopsenta[e]pyrazolo[1,5-a]pyrimidine-8,1'-cyclopropane]-6-carboxamide (10 mg, 24% yield) as a white solid. LC-MS: m/z 243 $[M+H]^+$.

Step 6: N-(5-chloro-6-(2H-1,2,3-triazol-2-yl)pyridin-3-yl)-2-methyl-6,7-dihydrospiro[cyclopenta[e]pyrazolo[1,5-a]pyrimidine-8,1'-cyclopropane]-6-carboxamide Example 18

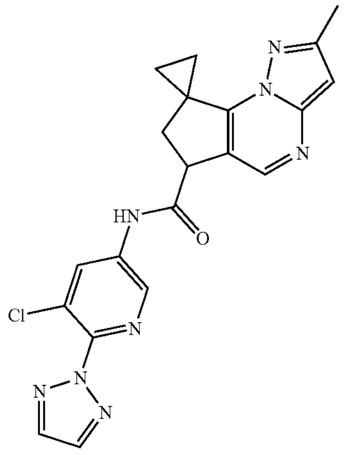

To a stirred mixture of 5-bromo-3-chloro-2-(triazol-2-yl)pyridine (11 mg, 41.3 μmol) and 2-methyl-6,7-dihydrospiro[cyclopenta[e]pyrazolo[1,5-a]pyrimidine-8,1'-cyclopropane]-6-carboxamide (10 mg, 41.3 μmol) in toluene (1 mL) were added (5-diphenylphosphanyl-9,9-dimethyl-xanthen-4-yl)-diphenyl-phosphane (XantPhos) (3 mg, 4.1 μmol), $Pd_2(dba)_3$ (3 mg, 4.1 μmol), cesium carbonate (20 mg, 61.9 μmol) and aluminum trifluoromethanesulfonate (2 mg, 4.1 μmol) at room temperature under nitrogen. The resulting mixture was stirred overnight at 110° C. under nitrogen. The mixture was allowed to cool down to room temperature. The resulting solution was diluted with water (50 mL) and extracted with DCM (3×50 mL). The combined organic layers were dried over anhydrous $Na_2SO_4$ and concentrated under vacuum. The residue was submitted to Prep-HPLC purification and the collected fractions were lyophilized to give N-(5-chloro-6-(2H-1,2,3-triazol-2-yl)pyridin-3-yl)-2-cyano-8,8-dimethyl-7,8-dihydro-6H-cyclopenta[e]pyrazolo[1,5-a]pyrimidine-6-carboxamide (1 mg, 5% yield) as a white solid.

Example 18: $^1H$ NMR (400 MHz, Methanol-$d_4$) δ: 8.69 (d, J=2.0 Hz, 1H), 8.64 (d, J=2.0 Hz, 1H), 8.35 (s, 1H), 8.02 (s, 2H), 6.42 (s, 1H), 4.51 (dd, J=9.6, 5.6 Hz, 1H), 2.75 (dd, J=13.2, 9.6 Hz, 1H), 2.64 (dd, J=13.2, 5.6 Hz, 1H), 2.46-2.49 (m, 3H), 2.39-2.45 (m, 1H), 2.28-2.32 (m, 1H), 1.10-1.25 (m, 2H). LC-MS: m/z 421 $[M+H]^+$.

Method I1

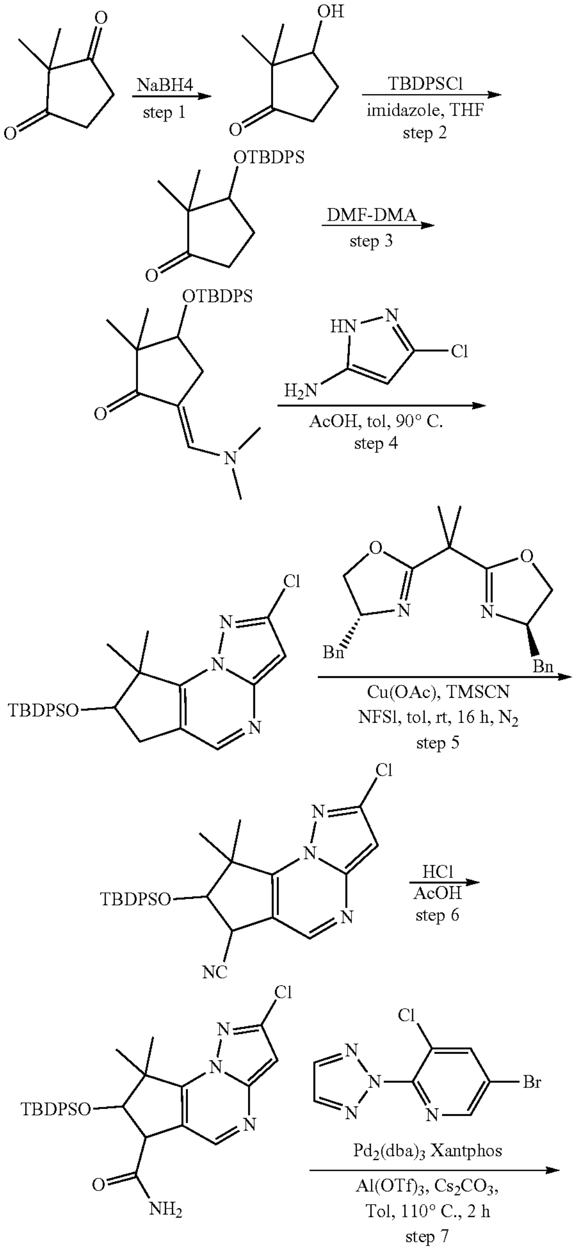

-continued

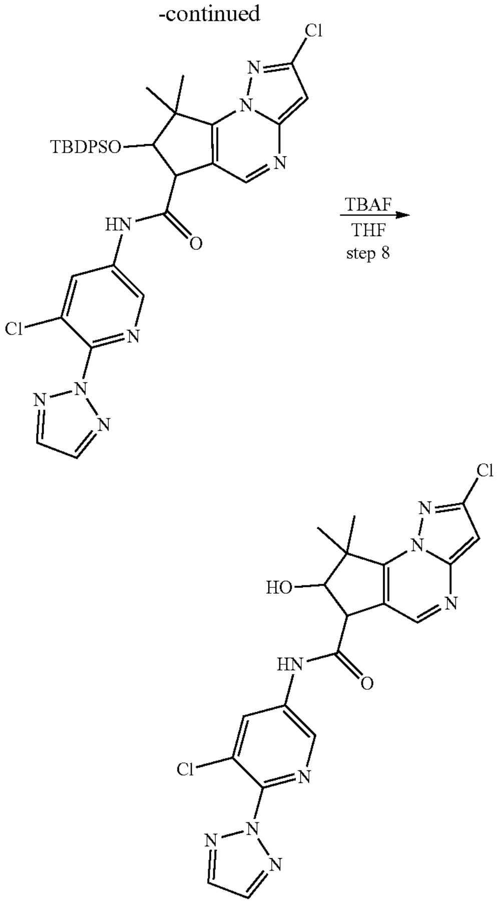

Example 19

Example 19: 2-chloro-N-(5-chloro-6-(2H-1,2,3-triazol-2-yl)pyridin-3-yl)-7-hydroxy-8,8-dimethyl-7,8-dihydro-6H-cyclopenta[e]pyrazolo[1,5-a]pyrimidine-6-carboxamide Step 1: 3-hydroxy-2,2-dimethylcyclopentan-1-one

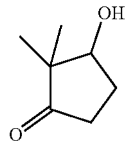

To a solution of 2,2-dimethylcyclopentane-1,3-dione (7 g, 55.5 mmol) in MeOH (150 mL) was added sodium borohydride (525 mg, 13.9 mmol) in small portions at 0° C. The reaction was stirred at 0° C. for 2 h. The reaction solution was quenched with saturated aq. ammonium chloride (100 mL). After removal of methanol in vacuo, the residue was extracted with EtOAc (3×200 mL). The combined organic layers were washed with brine (100 mL), dried over anhydrous $Na_2SO_4$, filtered and concentrated. The residue was applied onto a silica gel column and eluted with ethyl acetate/petroleum ether (1:2) to get 3-hydroxy-2,2-dimethylcyclopentan-1-one (6 g, 75% yield) as a yellow oil. $^1H$ NMR (400 MHz, DMSO-$d_6$) δ: 4.92-4.97 (m, 1H), 3.83 (t, J=5.6 Hz, 1H), 1.96-2.30 (m, 3H), 1.68-1.79 (m, 1H), 0.90 (s, 3H), 0.84 (s, 3H). LC-MS: m/z 129 $[M+H]^+$.

Step 2: 3-((tert-butyldiphenyl silyl)oxy)-2,2-dimethyl cyclopentan-1-one

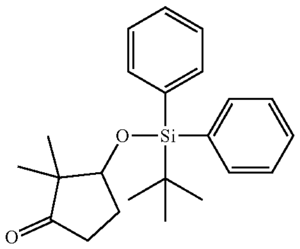 [SMILES: CC1(C)C(=O)CCC1O[Si](c1ccccc1)(c1ccccc1)C(C)(C)C]

To a solution of 3-hydroxy-2,2-dimethylcyclopentan-1-one (12 g, 93.6 mmol) in DCM (300 mL) were added imidazole (12.7 g, 187.2 mmol), N,N-dimethylpyridin-4-amine (1.1 g, 9.4 mmol) and tert-butyl-chloro-diphenyl-silane (51.5 g, 187.2 mmol). The reaction mixture was stirred at room temperature for 16 h. The resulting solution was added to water (300 mL), extracted with DCM (3×300 mL). The combined organic layers were dried over anhydrous $Na_2SO_4$ and concentrated under vacuum. The residue was applied onto a silica gel column and eluted with EtOAc/PE (1:3) to give 3-((tert-butyldiphenylsilyl)oxy)-2,2-dimethylcyclopentan-1-one (20 g, 23% yield) as a yellow oil. $^1$H NMR (400 MHz, $CDCl_3$) δ: 7.41-7.64 (m, 10H), 4.06 (t, J=6.0 Hz, 1H), 2.01-2.10 (m, 2H), 1.77-1.91 (m, 2H), 1.10 (s, 6H), 0.96 (s, 9H). LC-MS: m/z 367 $[M+H]^+$.

Step 3: 3-((tert-butyldiphenylsilyl)oxy)-5-((dimethylamino)methylene)-2,2-dimethylcyclopentan-1-one

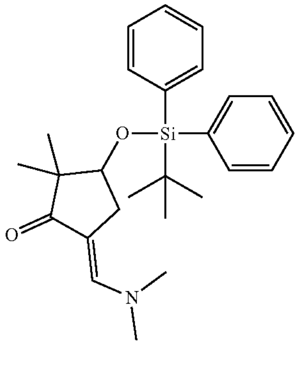 [SMILES: CN(C)/C=C1\CC(O[Si](c2ccccc2)(c2ccccc2)C(C)(C)C)C(C)(C)C1=O]

A solution of 3-((tert-butyldiphenylsilyl)oxy)-2,2-dimethylcyclopentan-1-one (20 g, 54.5 mmol) in DMF-DMA (200 mL) was stirred for 16 h at 100° C. under an atmosphere of nitrogen. The mixture was cooled down to room temperature. The resulting mixture was concentrated under vacuum to afford 3-((tert-butyldiphenylsilyl)oxy)-5-((dimethylamino)methylene)-2,2-dimethylcyclopentan-1-one (20 g, crude) as a yellow oil. The crude product was used directly in the next step. LC-MS: m/z 422 $[M+H]^+$.

Step 4: 7-((tert-butyldiphenyl silyl)oxy)-2-chloro-8,8-dimethyl-7,8-dihydro-6H-cyclopenta[e]pyrazolo[1,5-a]pyrimidine

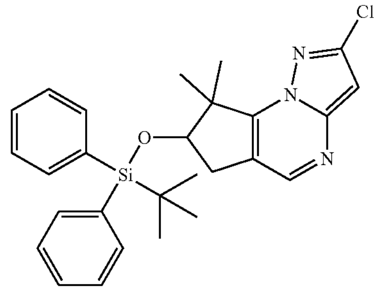 [SMILES: CC1(C)c2c(cnc3cc(Cl)nn23)CC1O[Si](c1ccccc1)(c1ccccc1)C(C)(C)C]

To a solution of 3-((tert-butyl diphenyl silyl)oxy)-5-((dimethylamino)methylene)-2,2-dimethylcyclopentan-1-one (7 g, 16.6 mmol) in toluene (100 mL) were added 3-chloro-1H-pyrazol-5-amine (1.9 g, 16.6 mmol) and AcOH (10 mL). The reaction was stirred for 16 h at 90° C. The mixture was allowed to cool down to room temperature and was concentrated under reduced pressure. The residue was diluted with water (200 mL). The pH was adjusted to 6-7 with sodium bicarbonate (sat., aq.). The resulting solution was extracted with EtOAc (3×200 mL). The combined organic layers were dried over anhydrous $Na_2SO_4$ and concentrated under vacuum. The residue was applied on a silica gel column and eluted with EtOAc/PE (1:5) to give 7-((tert-butyldiphenyl silyl)oxy)-2-chloro-8,8-dimethyl-7,8-dihydro-6H-cyclopenta[e]pyrazolo[1,5-a]pyrimidine (5 g, 37% yield) as a yellow solid. $^1$H NMR (300 MHz, DMSO-$d_6$) δ: 8.41 (s, 1H), 7.58-7.74 (m, 5H), 7.35-7.57 (m, 5H), 6.84 (s, 1H), 4.34-4.40 (m, 1H), 2.87-3.18 (m, 2H), 1.46 (s, 3H), 1.42 (s, 3H), 0.89 (s, 9H). LC-MS: m/z 476 $[M+H]^+$.

Step 5: 7-((tert-butyldiphenylsilyl)oxy)-2-chloro-8,8-dimethyl-7,8-dihydro-6H-cyclopenta[e]pyrazolo[1,5-a]pyrimidine-6-carbonitrile

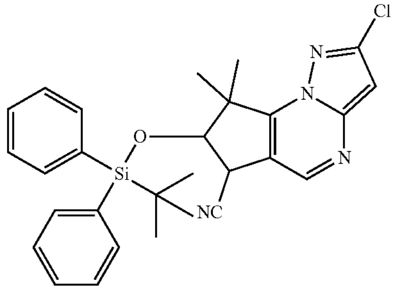 [SMILES: CC1(C)c2c(cnc3cc(Cl)nn23)C(C#N)C1O[Si](c1ccccc1)(c1ccccc1)C(C)(C)C]

To a solution of 7-((tert-butyldiphenylsilyl)oxy)-2-chloro-8,8-dimethyl-7,8-dihydro-6H-cyclopenta[e]pyrazolo[1,5-a]pyrimidine (2 g, 4.2 mmol) in toluene (50 mL) were added (4R)-4-benzyl-2-[1-[(4R)-4-benzyl-4,5-dihydrooxazol-2-yl]-1-methyl-ethyl]-4,5-dihydrooxazole (183 mg, 504 umol), acetoxycopper (103 mg, 840.2 umol), N-(benzenesulfonyl)-N-fluoro-benzenesulfonamide (2 g, 6.3 mmol) and TMSCN (2.1 g, 21 mmol). The reaction mixture was stirred at room temperature for 16 h under nitrogen. The solvent was removed under vacuum and the residue was applied onto a silica gel column and eluted with EtOAc/PE (1:2) to get 7-((tert-butyl diphenylsilyl)oxy)-2-chloro-8,8-dimethyl-7,8-dihydro-6H-cyclopenta[e]pyrazolo[1,5-a]pyrimidine-6-carbonitrile (300 mg, 5% yield) as a yellow solid. LC-MS: m/z 501 $[M+H]^+$.

Step 6: 7-((tert-butyldiphenylsilyl)oxy)-2-chloro-8,8-dimethyl-7,8-dihydro-6H-cyclopenta[e]pyrazolo[1,5-a]pyrimidine-6-carboxamide

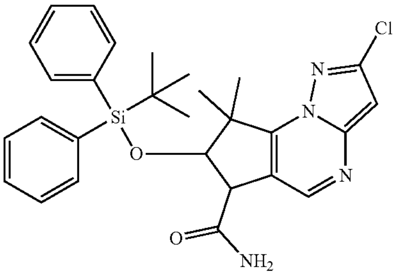 [SMILES: CC1(C)c2c(cnc3cc(Cl)nn23)C(C(N)=O)C1O[Si](c1ccccc1)(c1ccccc1)C(C)(C)C]

To a solution of 4-[tert-butyl(diphenyl)silyl]oxy-11-chloro-3,3-dimethyl-1,8,12-triazatricyclo[7.3.0.0.02,6]dodeca-2(6),7,9,11-tetraene-5-carbonitrile (500 mg, 997.8 umol) in AcOH (5 mL) was added concentrated hydrochloric acid (5 mL) at room temperature. The resulting mixture was stirred for 16 h. The reaction mixture was concentrated under reduced pressure. The residue was diluted with water (20 mL). The pH was adjusted to 6-7 with sodium bicarbonate (sat., aq.). The resulting solution was extracted with EtOAc (3×20 mL). The combined organic layers were dried over anhydrous $Na_2SO_4$ and concentrated under vacuum. The residue was applied on a silica gel column and eluted with EtOAc/PE (1:1) to give 7-((tert-butyldiphenylsilyl)oxy)-2-chloro-8,8-dimethyl-7,8-dihydro-6H-cyclopenta[e]pyrazolo[1,5-a]pyrimidine-6-carboxamide (120 mg, 22% yield) as a yellow solid. $^1H$ NMR (300 MHz, DMSO-$d_6$) δ: 8.38 (s, 1H), 7.78 (s, 1H), 7.60-7.78 (m, 5H), 7.56-7.65 (m, 5H), 6.89 (s, 1H), 4.71 (d, J=5.6 Hz, 1H), 4.10 (d, J=5.6 Hz, 1H), 3.17 (s, 1H), 1.38 (s, 3H), 1.19 (s, 3H), 1.07 (s, 9H). LC-MS: m/z 519$[M+H]^+$.

Step 7: 7-((tert-butyldiphenylsilyl)oxy)-2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

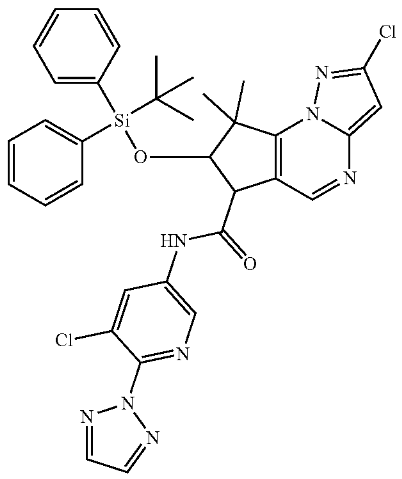 [SMILES: CC1(C)c2c(cnc3cc(Cl)nn23)C(C(=O)Nc2cnc(-n3nccn3)c(Cl)c2)C1O[Si](c1ccccc1)(c1ccccc1)C(C)(C)C]

To a solution of 7-((tert-butyldiphenyl silyl)oxy)-2-chloro-8,8-dimethyl-7,8-dihydro-6H-cyclopenta[e]pyrazolo[1,5-a]pyrimidine-6-carboxamide (20 mg, 38.5 μmol) in toluene (1 mL) was added 5-bromo-3-chloro-2-(triazol-2-yl)pyridine (20 mg, 77.1 μmol) at room temperature. The resulting mixture was stirred for 16 h at 110° C. under nitrogen. The reaction mixture was concentrated under reduced pressure. The residue was purified by Prep-TLC with EtOAc/PE (1:1) to give 7-((tert-butyldiphenylsilyl)oxy)-2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide (10 mg, 29% yield) as a yellow solid. LC-MS: m/z 697$[M+H]^+$.

Step 8: 2-chloro-N-(5-chloro-6-(2H-1,2,3-triazol-2-yl)pyridin-3-yl)-7-hydroxy-8,8-dimethyl-7,8-dihydro-6H-cyclopenta[e]pyrazolo[1,5-a]pyrimidine-6-carboxamide (Example 19)

Example 19

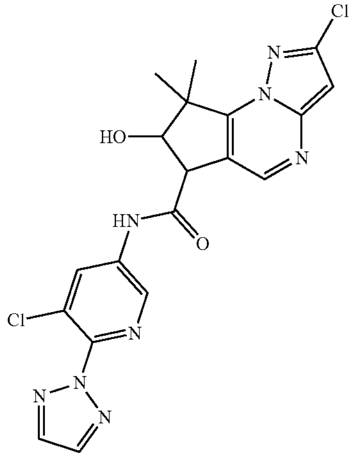

To a solution of 7-((tert-butyldiphenylsilyl)oxy)-2-chloro-N-(5-chloro-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide(10 mg, 14.3 μmol) in THE (1 mL) was added tetrabutylammonium fluoride (1 M, 143.3 μL) at room temperature. The resulting mixture was stirred for 2 h at 25° C. The reaction mixture was concentrated under reduced pressure. The residue was diluted with water (10 mL), extracted with EtOAc (3x10 mL). The combined organic layers were washed with saturated aqueous $NH_4C1$ solution (3x10 mL), dried over anhydrous $Na_2SO_4$ and concentrated under vacuum. The residue was purified by Prep-TLC with MeOH/DCM (1:10) to give the crude product (5 mg). The residue was submitted to Prep-HPLC purification and the collected fractions were lyophilized to give 2-chloro-N-(5-chloro-6-(2H-1,2,3-triazol-2-yl)pyridin-3-yl)-7-hydroxy-8,8-dimethyl-7,8-dihydro-6H-cyclopenta[e]pyrazolo[1,5-a]pyrimidine-6-carboxamide (2 mg, 29% yield) as a white solid.

Example 19: $^1$H NMR (~1:1 mixture of both racemic diastereomers, 400 MHz, Methanol-$d_4$) δ: 8.71-8.75 (m, 1H), 8.66-8.67 (m, 1H), 8.53-8.55 (m, 1H), 8.03 (s, 2H), 6.69 (s, 1H), 4.59-4.60 (m, 1H), 4.11-4.13 (m, 1H), 1.64 (s, 3H), 1.58 (s, 3H). LC-MS: m/z 459[M+H]$^+$.

Method J1

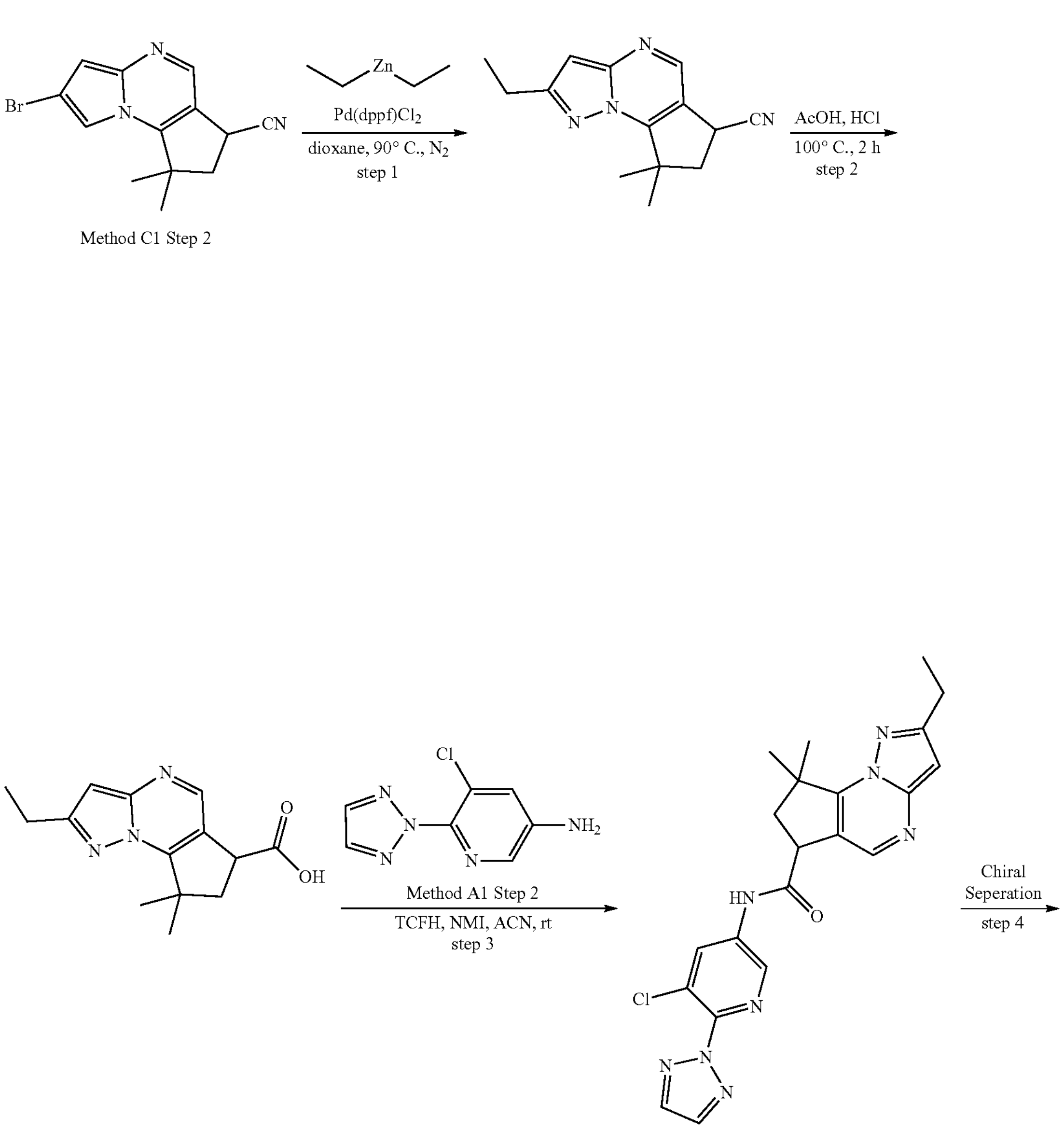

-continued

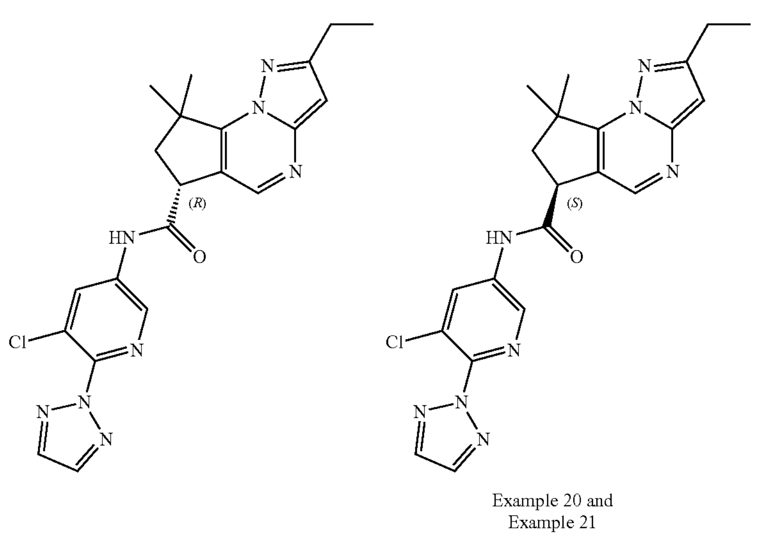

Example 20 and Example 21

Examples 20 and 21: Single Enantiomers Obtained from a Racemic Mixture Containing (R)—N-(5-chloro-6-(2H-1,2,3-triazol-2-yl)pyridin-3-yl)-2-ethyl-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-ethyl-8,8-dimethyl-7,8-dihydro-6H-cyclopenta[e]pyrazolo[1,5a]pyrimidine-6-carboxamide Step 1: 2-ethyl-8,8-dimethyl-7,8-dihydro-6H-cyclopenta[e]pyrazolo[1,5-a]pyrimidine-6-carbonitrile

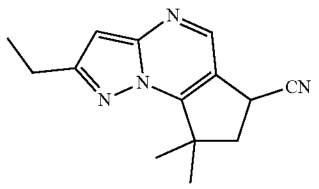 [SMILES: CCc1cc2ncc3c(n2n1)C(C)(C)CC3C#N]

To a solution of 2-bromo-8,8-dimethyl-7,8-dihydro-6H-cyclopenta[e]pyrazolo[1,5-a]pyrimidine-6-carbonitrile (Method C1 Step 2; 800 mg, 2.8 mmol) in dioxane (20 mL) were added diethylzinc (509 mg, 4.1 mmol) and Pd(dppf) C12 (178 mg, 0.3 mmol).

The resulting mixture was stirred for 3 h at 90° C. The mixture was allowed to cool down to room temperature and concentrated under vacuum. The residue was diluted with 100 ml water. The pH was adjusted to 5-6 with $NaHCO_3$(aq., sat.). The resulting solution was extracted with EtOAc (3×100 mL). The combined organic layers were dried over anhydrous $Na_2SO_4$ and concentrated under vacuum. The residue was applied onto a silica gel column and eluted with EtOAc/PE (1:3) to give 2-ethyl-8,8-dimethyl-7,8-dihydro-6H-cyclopenta[e]pyrazolo[1,5-a]pyrimidine-6-carbonitrile (350 mg, 43% yield) as a yellow solid. $^1H$ NMR (400 MHz, DMSO-$d_6$) δ: 8.56 (s, 1H), 6.64 (s, 1H), 4.66 (m, J=8.9, 5.9 Hz, 1H), 2.81 (m, J=7.6 Hz, 2H), 2.56 (m, J=13.2, 8.8 Hz, 1H), 2.34 (m, J=13.1, 5.9 Hz, 1H), 1.63 (s, 3H), 1.51 (s, 3H), 1.28 (m, J=7.6 Hz, 3H). LC-MS: m/z 241 $[M+H]^+$.

Step 2: 2-ethyl-8,8-dimethyl-7,8-dihydro-6H-cyclopenta[e]pyrazolo[1,5-a]pyrimidine-6-carboxylic acid

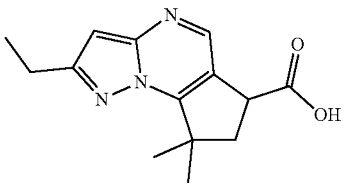 [SMILES: CCc1cc2ncc3c(n2n1)C(C)(C)CC3C(=O)O]

To a 20 mL vial were added 2-ethyl-8,8-dimethyl-7,8-dihydro-6H-cyclopenta[e]pyrazolo[1,5-a]pyrimidine-6-carbonitrile (350 mg, 1.4 mmol), AcOH (6 mL) and HCl (6 mL). The resulting mixture was stirred for 2 h at 100° C. The mixture was allowed to cool down to room temperature and concentrated under vacuum. The residue was diluted with water (100 mL) and pH was adjusted to 5-6 with $NaHCO_3$ (aq., sat.). The resulting solution was extracted with EtOAc (3×100 mL). The combined organic layers were dried over anhydrous $Na_2SO_4$ and concentrated under vacuum. The residue was applied onto a silica gel column and eluted with DCM/MeOH (10:1) to give 2-ethyl-8,8-dimethyl-7,8-dihydro-6H-cyclopenta[e]pyrazolo[1,5-a]pyrimidine-6-carboxylic acid (150 mg, 39% yield) as a yellow solid. LC-MS: m/z 260 $[M+H]^+$.

Step 3: N-(5-chloro-6-(2H-1,2,3-triazol-2-yl)pyridin-3-yl)-2-ethyl-8,8-dimethyl-7,8-dihydro-6H-cyclopenta[e]pyrazolo[1,5-a]pyrimidine-6-carboxamide

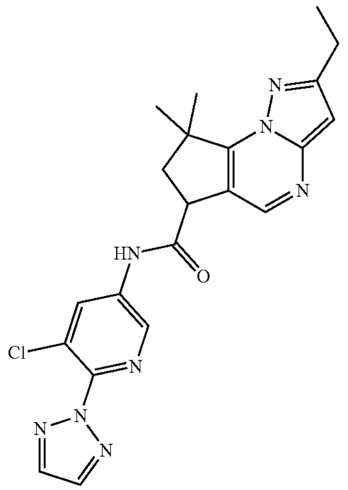 [SMILES: CCc1cc2ncc3c(n2n1)C(C)(C)CC3C(=O)Nc1cnc(-n2nccn2)c(Cl)c1]

To a solution of 2-ethyl-8,8-dimethyl-7,8-dihydro-6H-cyclopenta[e]pyrazolo[1,5-a]pyrimidine-6-carboxylic acid (150 mg, 578.4 μmol) in ACN (10 mL) were added 5-chloro-6-(1-methyl-1H-pyrazol-3-yl)pyridin-3-amine (Method A1 Step 2; 113 mg, 578.4 μcool), TCFH (649 mg, 2.3 mmol) and NMI (189 mg, 2.3 mmol). The resulting mixture was stirred for 3 h at room temperature. The reaction mixture was quenched with water (100 mL). The resulting solution was extracted with EtOAc (3×100 mL). The combined organic layers were dried over anhydrous $Na_2SO_4$ and concentrated under vacuum. The residue was applied onto a silica gel column and eluted with DCM/MeOH (10:1) to give 90 mg (85% purity) product. The product was submitted to Prep-HPLC purification and the collected fractions were lyophilized to give N-(5-chloro-6-(2H-1,2,3-triazol-2-yl)pyridin-3-yl)-2-ethyl-8,8-dimethyl-7,8-dihydro-6H-cyclopenta[e]pyrazolo[1,5-a]pyrimidine-6-carboxamide (20 mg, 11% yield) as a white solid. LC-MS: m/z 437 $[M+H]^+$.

Step 4: Separation of Enantiomers to Obtain (R)—N-(5-chloro-6-(2H-1,2,3-triazol-2-yl)pyridin-3-yl)-2-ethyl-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-ethyl-8,8-dimethyl-7,8-dihydro-6H-cyclopenta[e]pyrazolo[1,5-a]pyrimidine-6-carboxamide Example 20

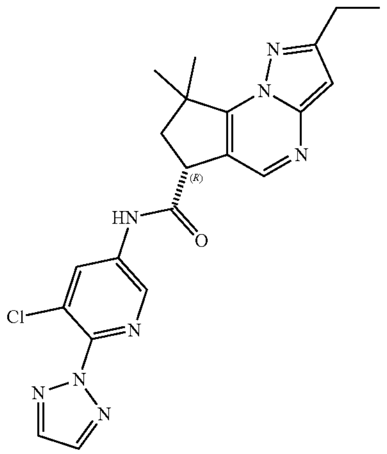

and

Example 21

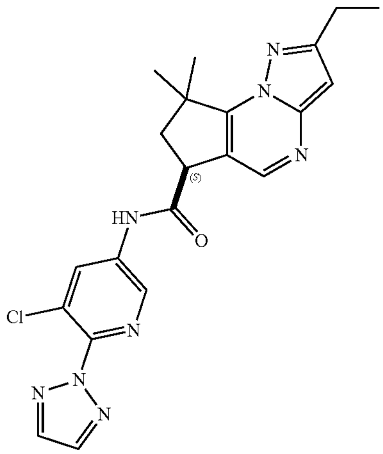

20 mg of N-(5-chloro-6-(2H-1,2,3-triazol-2-yl)pyridin-3-yl)-2-ethyl-8,8-dimethyl-7,8-dihydro-6H-cyclopenta[e]pyrazolo[1,5-a]pyrimidine-6-carboxamide were submitted to chiral HPLC purification (Column: Chiralpak ID-2, 2*25 cm, Sum; Mobile Phase A:MTBE (0.5% 2M $NH_3$-MeOH), Mobile Phase B:EtOH; Flow rate: 15 mL/min; isocratic: 50 B; 254/220 nm; RT1:12.604; RT2:17.755; Injection Volume: 1.5 ml; Number of Runs: 1). The first eluting isomer was concentrated and lyophilized to afford Example 20 as a white solid (5.3 mg, 12% yield). The second eluting isomer was concentrated and lyophilized to afford Example 21 as a white solid (4.5 mg, 11% yield).

Example 20: $^1H$ NMR (300 MHz, Methanol-$d_4$) δ: 8.68 (d, J=2.1 Hz, 1H), 8.64 (d, J=2.1 Hz, 1H), 8.40 (s, 1H), 8.02 (s, 2H), 6.53 (s, 1H), 4.36-4.42 (m, 1H), 2.85-2.93 (m, 2H), 2.57-2.64 (m, 1H), 2.38-2.44 (m, 1H), 1.76 (s, 3H), 1.64 (s, 3H), 1.28-1.42 (m, 3H). LC-MS: m/z 437 $[M+H]^+$.

Example 21: $^1H$ NMR (300 MHz, Methanol-$d_4$) δ: 8.68 (d, J=2.1 Hz, 1H), 8.64 (d, J=2.1 Hz, 1H), 8.40 (s, 1H), 8.02

(s, 2H), 6.53 (s, 1H), 4.36-4.42 (m, 1H), 2.85-2.93 (m, 2H), 2.57-2.64 (m, 1H), 2.38-2.44 (m, 1H), 1.76 (s, 3H), 1.64 (s, 3H), 1.28-1.42 (m, 3H). LC-MS: m/z 437 $[M+H]^+$.
The absolute stereochemistry for each separated isomer was not determined.
Method K1
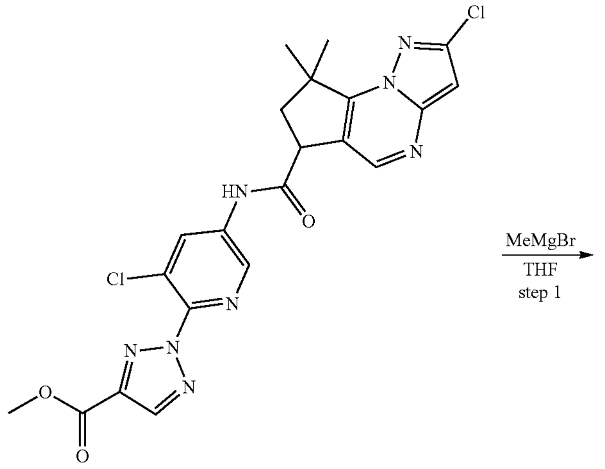
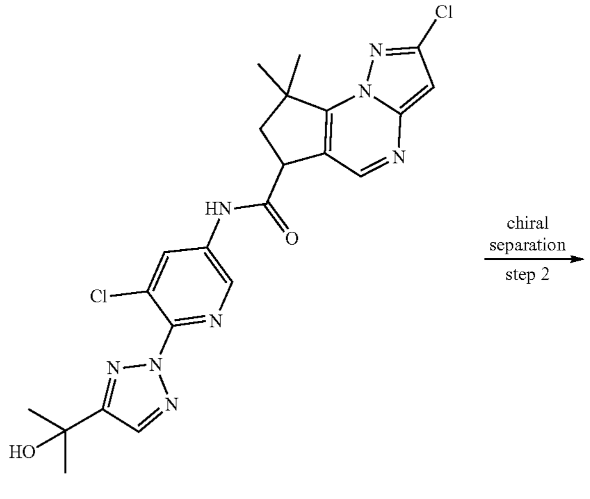

-continued

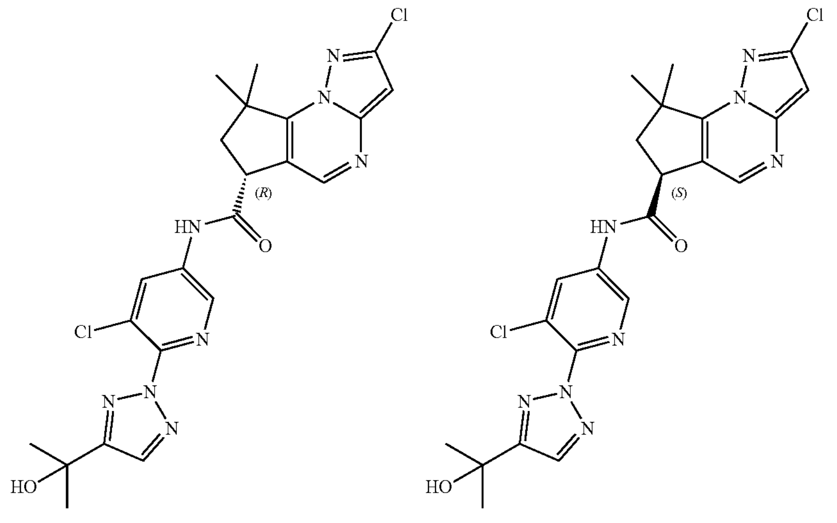

Example 22 and
Example 23

Examples 22 and 23: Single Enantiomers Obtained from a Racemic Mixture Containing (R)-2-chloro-N-(5-chloro-6-(4-(2-hydroxypropan-2-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(4-(2-hydroxypropan-2-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide Step 1: 2-chloro-N-(5-chloro-6-(4-(2-hydroxypropan-2-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide

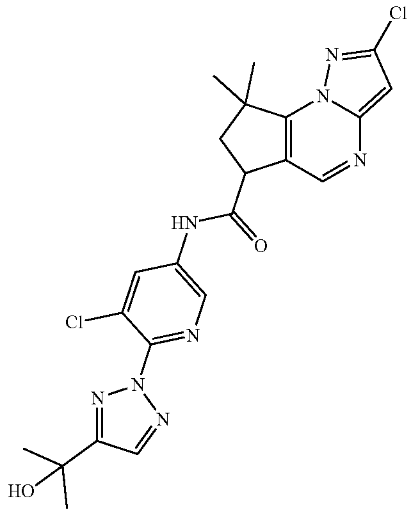

To a solution of methyl 2-(3-chloro-5-(2-chloro-8,8-dimethyl-7,8-dihydro-6H-cyclopenta[e]pyrazolo[1,5-a]pyrimidine-6-carboxamido)pyridin-2-yl)-2H-1,2,3-triazole-4-carboxylate (Method N1 Step 3; 50.0 mg, 95.7 μmol) in anhydrous THE (5 mL) was added MeMgBr (4 M, 47.8 μL) over a period of 5 min at 0° C. under an atmosphere of nitrogen. The reaction mixture was stirred for 2 h and quenched with a saturated aqueous solution of $NH_4C1$(5 ml). The resulting mixture was extracted with EtOAc (3×10 mL). The combined organic layers were dried over anhydrous sodium sulfate and concentrated under vacuum. The residue was submitted to Prep-HPLC purification and the collected fractions were lyophilized to give 2-chloro-N-(5-chloro-6-(4 (2-hydroxypropan-2-yl)-2H-1,2,3-triazol-2-yl) pyridin-3-yl)-8,8-dimethyl-7,8-dihydro-6H-cyclopenta[e] pyrazolo[1,5-a]pyrimidine-6-carboxamide (7.7 mg, 16% yield) as a white solid. LC-MS: m/z 501 $[M+H]^+$.

Step 2: Separation of Enantiomers to Obtain (R)-2-chloro-N-(5-chloro-6-(4-(2-hydroxypropan-2-yl)-2H-1,2,3-triazol-2-yl)pyridin-3-yl)-8,8-dimethyl-7,8-dihydro-6H-cyclopenta[e]pyrazolo[1,5-a] pyrimidine-6-carboxamide and (S)-2-chloro-N-(5-chloro-6-(4-(2-hydroxypropan-2-yl)-2H-1,2,3-triazol-2-yl) pyridin-3-yl)-8,8-dimethyl-7,8-dihydro-6H-cyclopenta[e]pyrazolo[1,5-a]pyrimidine-6-carboxamide Example 22

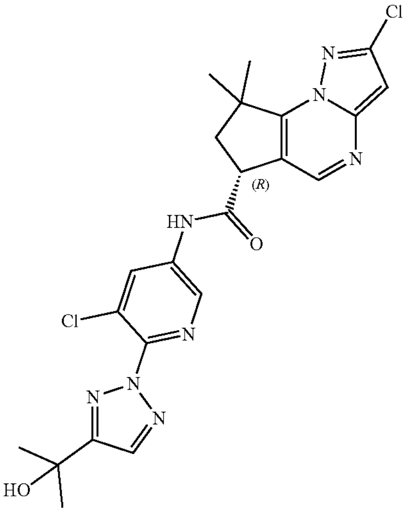

and

-continued

Example 23

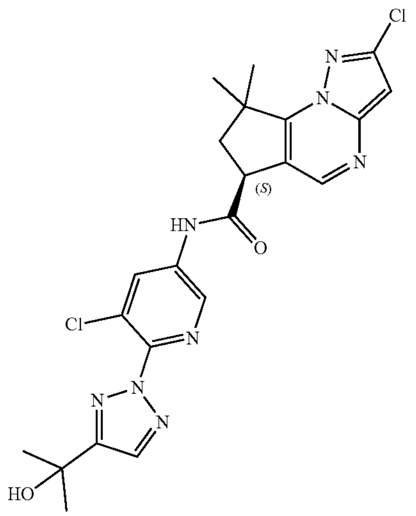

50 mg of 2-chloro-N-(5-chloro-6-(4-(2-hydroxypropan-2-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: Chiralpak ID-2, 2*25 cm, Sum; Mobile Phase A:Hex(0.5% 2M $NH_3$-MeOH), Mobile Phase B:EtOH; Flow rate: 20 mL/min; isocratic: 50 B; 254/220 nm; RT1: 7.8; RT2:13.072; Injection Volume: 3 ml; Number of Runs: 1). The first eluting isomer was concentrated and lyophilized to afford Example 22 (19.6 mg, 79% yield) as a white solid. The second eluting isomer was concentrated and lyophilized to afford Example 23 (19.1 mg, 77% yield) as a white solid.

Example 22: $^1H$ NMR (300 MHz, Chloroform-d) δ: 8.63 (s, 1H), 8.49 (br, 2H), 7.88 (s, 2H), 6.70 (s, 1H), 4.27 (t, J=7.9 Hz, 1H), 2.58 (dd, J=13.2, 8.8 Hz, 1H), 2.44 (dd, J=13.1, 6.8 Hz, 1H), 1.78 (s, 3H), 1.71 (s, 6H), 1.62 (s, 3H). LC-MS: m/z 501 $[M+H]^+$.

Example 23: $^1H$ NMR (300 MHz, Chloroform-d) δ 9.10 (s, 1H), 8.53 (d, J=2.3 Hz, 1H), 8.41 (d, J=2.3 Hz, 1H), 8.35 (s, 1H), 7.83 (s, 1H), 6.65 (s, 1H), 4.26 (t, J=7.8 Hz, 1H), 3.52 (s, 1H), 2.53-2.29 (m, 2H), 1.73 (s, 3H), 1.71-1.65 (m, 6H), 1.54 (s, 3H). LC-MS: m/z 501 $[M+H]^+$.

The absolute stereochemistry for each separated isomer was not determined.

Method L1
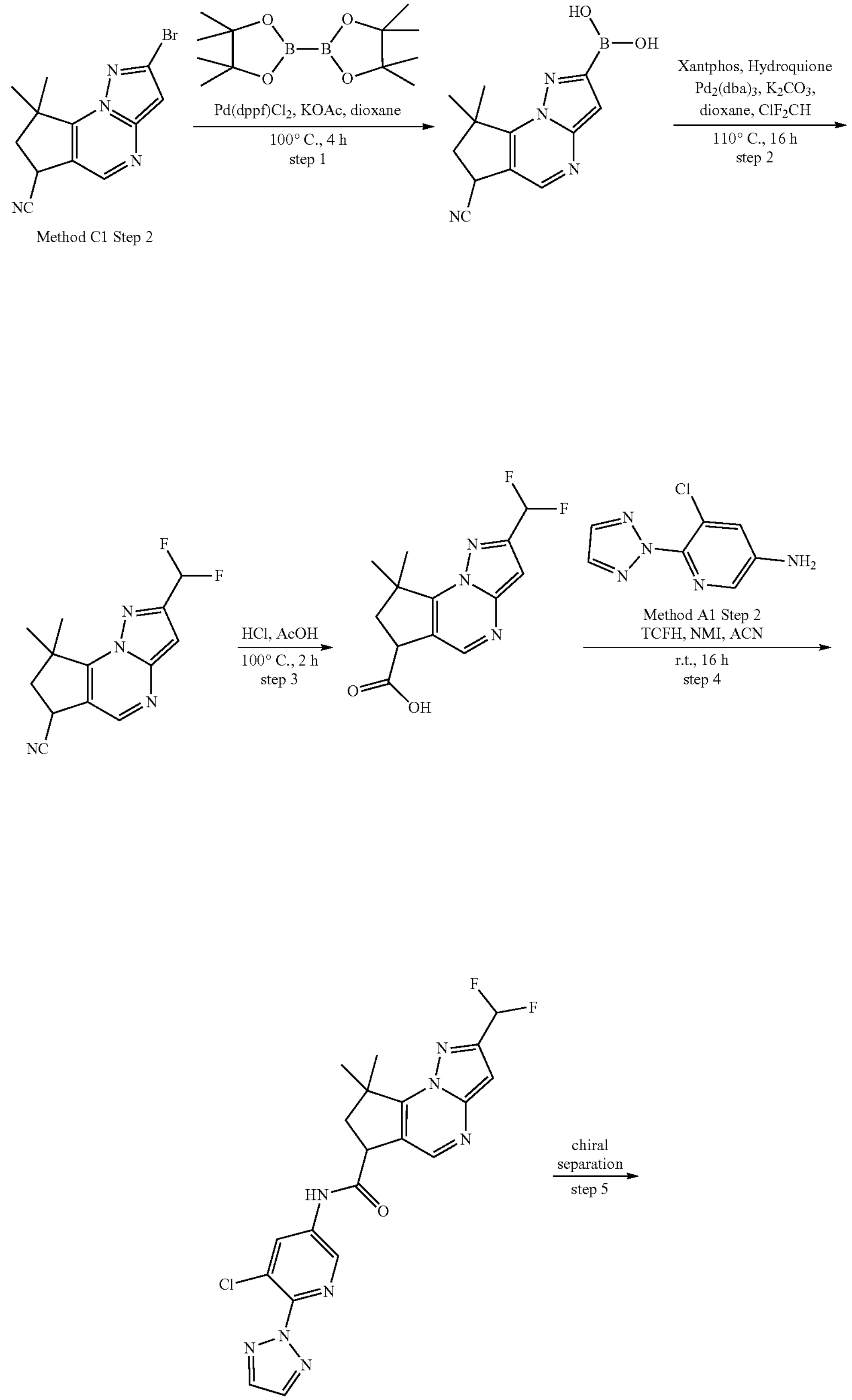

-continued

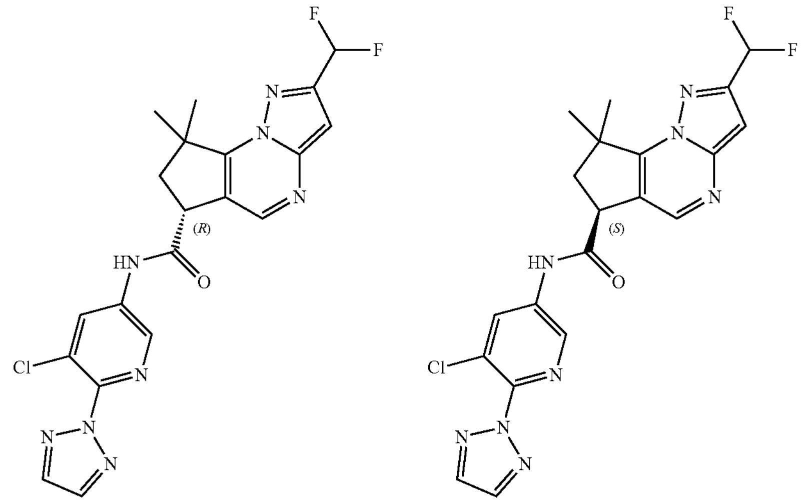

Example 24 and
Example 25

Examples 24 and 25: Single Enantiomers Obtained from a Racemic Mixture Containing (R)—N-(5-chloro-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide Step 1: (6-cyano-8,8-dimethyl-7,8-dihydro-6H-cyclopenta[e]pyrazolo[1,5-a]pyrimidin-2-yl)boronic acid

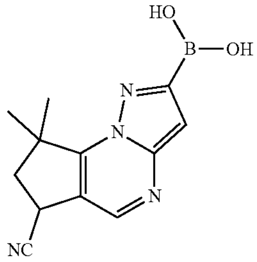 [SMILES: CC1(C)CC(C#N)c2cnc3cc(B(O)O)nn3c21]

To a stirred solution of 2-bromo-8,8-dimethyl-7,8-dihydro-6H-cyclopenta[e]pyrazolo[1,5-a]pyrimidine-6-carbonitrile (Method C1 Step 2; 800 mg, 2.7 mmol) and 4,4,4',4',5,5,5',5'-octamethyl-2,2'-bi(1,3,2-dioxaborolane) (837 mg, 3.3 mmol) in dioxane (32 mL) were added KOAc (809 mg, 8.2 mmol) and Pd(dppf)C12 (448 mg, 549 μmol). The mixture was stirred at 100° C. for 4 h. The mixture was allowed to cool down to room temperature. The resulting mixture was diluted with MeOH (80 mL). The resulting mixture was filtered, and the filter cake was washed with MeOH (3x20 mL). The filtrate was concentrated under vacuum. The residue was submitted to Prep-HPLC purification and the collected fractions were lyophilized to give (6-cyano-8,8-dimethyl-7,8-dihydro-6H-cyclopenta[e]pyrazolo[1,5-a]pyrimidin-2-yl)boronic acid (600 mg, 85% yield) as a white solid. $^1$H NMR (300 MHz, DMSO-$d_6$) δ 8.62 (s, 1H), 7.10 (s, 1H), 4.66-4.75 (m, 1H), 2.54-2.66 (m, 1H), 2.30-2.42 (m, 1H), 1.70 (s, 3H), 1.57 (s, 3H). LC-MS: m/z 257 $[M+H]^+$.

Step 2: 2-(difluoromethyl)-8,8-dimethyl-7,8-dihydro-6H-cyclopenta[e]pyrazolo[1,5-a]pyrimidine-6-carbonitrile

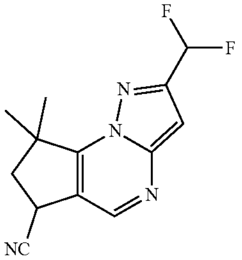 [SMILES: CC1(C)CC(C#N)c2cnc3cc(C(F)F)nn3c21]

A mixture of (6-cyano-8,8-dimethyl-7,8-dihydro-6H-cyclopenta[e]pyrazolo[1,5-a]pyrimidin-2-yl)boronic acid (600 mg, 2.3 mmol), Xantphos (406 mg, 702 μmol), hydroquinone (516 mg, 4.7 mmol), $Pd_2(dba)_3$ (134 mg, 234 μcool) and $K_2CO_3$ (1.3 g, 9.4 mmol) in C1F2CH (50 mL, 2 M in dioxane) was stirred for 15 h at 110° C. under an atmosphere of nitrogen. After cooled to room temperature, the reaction was quenched by the addition of water (50 mL). The resulting solution was extracted with ethyl acetate (3x50 mL). The organic layers were combined and dried over anhydrous $Na_2SO_4$, filtered, and concentrated under vacuum. The residue was submitted to Prep-HPLC purification and the collected fractions were lyophilized to give 2-(difluoromethyl)-8,8-dimethyl-7,8-dihydro-6H-cyclopenta[e]pyrazolo[1,5-a]pyrimidine-6-carbonitrile (500 mg, 75% yield) as a yellow solid. $^1$H NMR (400 MHz, Methanol-$d_4$) δ 8.67 (s, 1H), 6.84-7.15 (m, 2H), 4.53-4.63 (m, 1H), 2.59-2.78 (m, 1H), 2.38-2.53 (m, 1H), 1.74 (s, 3H), 1.62 (s, 3H). LC-MS: m/z 263 $[M+H]^+$.

Step 3: 2-(difluoromethyl)-8,8-dimethyl-7,8-dihydro-6H-cyclopenta[e]pyrazolo[1,5-a]pyrimidine-6-carboxylic acid

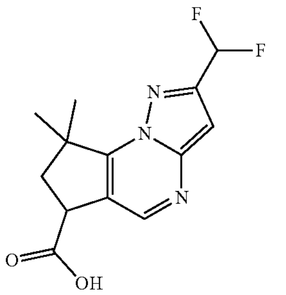 [SMILES: CC1(C)CC(C(=O)O)c2cnc3cc(C(F)F)nn3c21]

Into a 30 mL vial was added 2-(difluoromethyl)-8,8-dimethyl-7,8-dihydro-6H-cyclopenta[e]pyrazolo[1,5-a]pyrimidine-6-carbonitrile (280 mg, 1.0 mmol) in AcOH (2 mL) and conc. HCl (2 mL). The resulting mixture was stirred for 2 h at 100° C. The mixture was allowed to cool down to room temperature. The solvent was concentrated under vacuum. The residue was submitted to Prep-HPLC purification and the collected fractions were lyophilized to give 2-(difluoromethyl)-8,8-dimethyl-7,8-dihydro-6H-cyclopenta[e]pyrazolo[1,5-a]pyrimidine-6-carboxylic acid (140 mg, 46% yield) as a white solid. $^1H$ NMR (400 MHz, Methanol-$d_4$) δ 8.66 (s, 1H), 6.86-7.17 (m, 2H), 4.41-4.51 (m, 1H), 2.49-2.68 (m, 1H), 2.28-2.43 (m, 1H), 1.74 (s, 3H), 1.62 (s, 3H). LC-MS: m/z 282 $[M+H]^+$.

Step 4: N-(5-chloro-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide

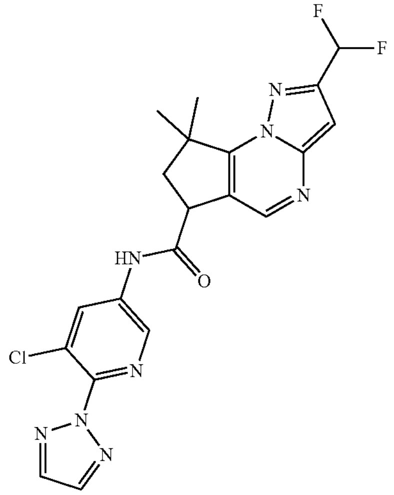 [SMILES: CC1(C)CC(C(=O)Nc2cnc(-n3nccn3)c(Cl)c2)c2cnc3cc(C(F)F)nn3c21]

To a stirred solution of 2-(difluoromethyl)-8,8-dimethyl-7,8-dihydro-6H-cyclopenta[e]pyrazolo[1,5-a]pyrimidine-6-carboxylic acid (30 mg, 106 μmol) in ACN (3 mL) were added 5-chloro-6-(2H-1,2,3-triazol-2-yl)pyridin-3-amine (Method A1 Step 2; 20 mg, 106 μmol) TCFH (89 mg, 319 μmol) and NMI (43 mg, 533 μmol). The resulting mixture was stirred for 16 h at room temperature. The reaction mixture was quenched by water (20 mL). The resulting solution was extracted with ethyl acetate (3×20 mL). The combined organic layers were dried over anhydrous $Na_2SO_4$ and concentrated under vacuum. The residue was submitted to Prep-HPLC purification and the collected fractions were lyophilized to give N-(5-chloro-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide (25 mg, 51% yield) as a white solid. LC-MS: m/z 459 $[M+H]^+$.

Step 5: Separation of Enantiomers to Obtain (R)—N-(5-chloro-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide Example 24

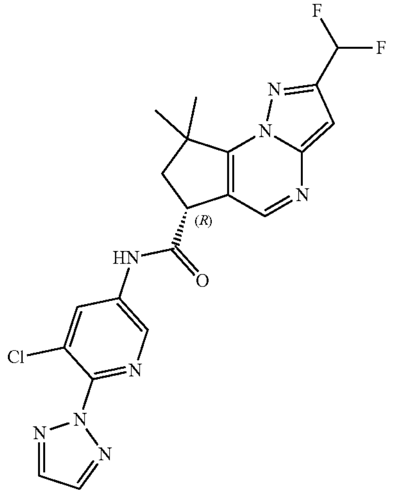

and

Example 25

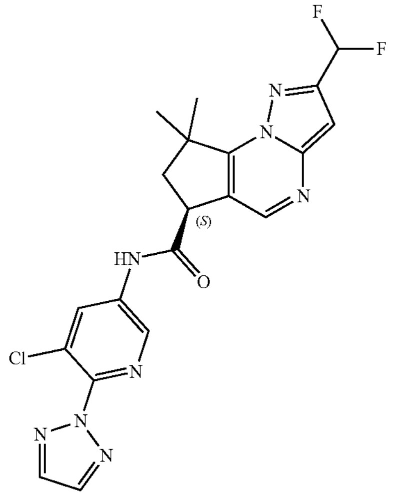

25 mg of N-(5-chloro-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide were submitted to chiral HPLC purification (Column: Chiralpak ID-2, 2×25 cm, 5 um; Mobile Phase A: MTBE (0.5% 2M $NH_3$-MeOH), Mobile Phase B:EtOH; Flow rate: 14 mL/min; isocratic: 50 B; 220/254 nm; RT1: 6.349; RT2: 9.554; Injection Volume: 3 ml; Number of Runs: 1). The first eluting isomer was concentrated and lyophilized to afford Example 24 (6.4 mg, 25% yield). The second eluting isomer was concentrated and lyophilized to afford Example 25 (6.5 mg, 26% yield).

Example 24: $^1H$ NMR (300 MHz, DMSO-$d_6$) δ: 11.10 (s, 1H), 8.70-8.76 (m, 2H), 8.59 (d, J=2.4 Hz, 1H), 8.18 (s, 2H), 7.31 (t, J=54.3 Hz, 1H), 7.09 (s, 1H), 4.40-4.57 (m, 1H), 2.53-2.66 (m, 1H), 2.28-2.42 (m, 1H), 1.67 (s, 3H), 1.59 (s, 3H). LC-MS: m/z 459 $[M+H]^+$.

Example 25: $^1H$ NMR (300 MHz, DMSO-$d_6$) δ: 11.10 (s, 1H), 8.70-8.76 (m, 2H), 8.59 (d, J=2.4 Hz, 1H), 8.18 (s, 2H), 7.31 (t, J=54.3 Hz, 1H), 7.09 (s, 1H), 4.40-4.57 (m, 1H), 2.53-2.66 (m, 1H), 2.28-2.42 (m, 1H), 1.67 (s, 3H), 1.59 (s, 3H). LC-MS: m/z 459 $[M+H]^+$.

The absolute stereochemistry for each separated isomer was not determined.

Method M1

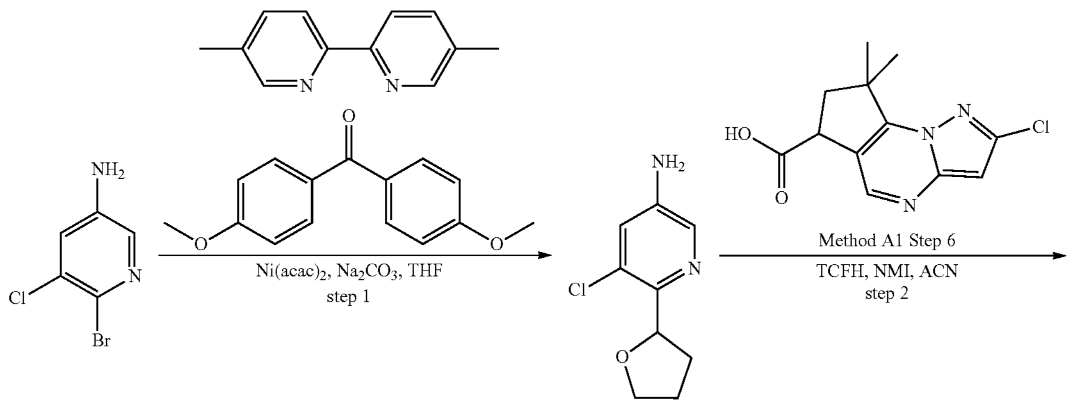

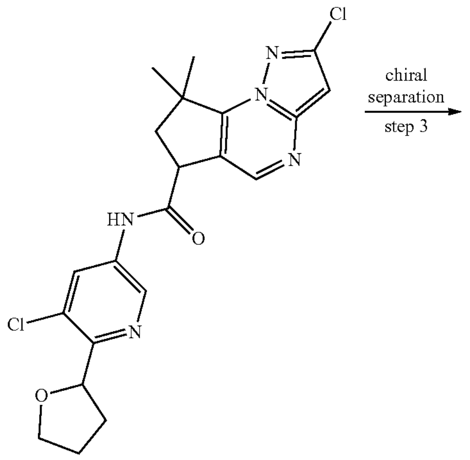

-continued

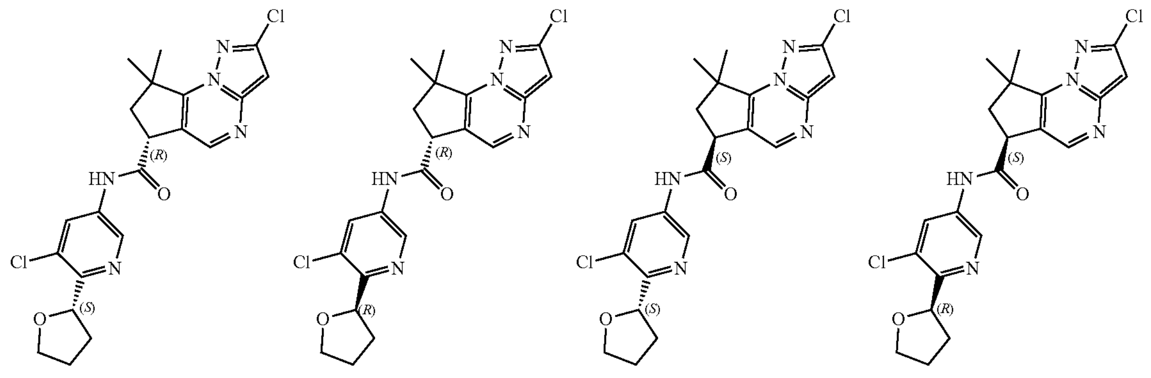

Example 26,
Example 27,
Example 28 and,
Example 29

Examples 26, 27, 28 and 29: Single enantiomers obtained from racemic mixtures containing (R)-2-chloro-N-(5-chloro-6-((S)-tetrahydrofuran-2-yl)pyridin-3-yl)-8,8-dimethyl-7,8-dihydro-6H-cyclopenta[e]pyrazolo[1,5-a]pyrimidine-6-carboxamide, (R)-2-chloro-N-(5-chloro-6-((R)-tetrahydrofuran-2-yl)pyridin-3-yl)-8,8-dimethyl-7,8-dihydro-6H-cyclopenta[e]pyrazolo[1,5-a]pyrimidine-6-carboxamide, (S)-2-chloro-N-(5-chloro-6-((S)-tetrahydrofuran-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-((R)-tetrahydrofuran-2-yl)pyridin-3-yl)-8,8-dimethyl-7,8-dihydro-6H-cyclopenta[e]pyrazolo[1,5-a]pyrimidine-6-carboxamide Step 1: 5-chloro-6-(tetrahydrofuran-2-yl)pyridin-3-amine

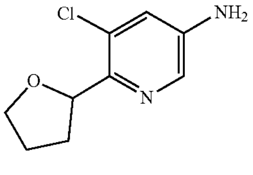 [SMILES: Nc1cnc(C2CCCO2)c(Cl)c1]

To a solution of 6-bromo-5-chloropyridin-3-amine (400 mg, 1.9 mmol) in anhydrous THE (60 mL) were added 5,5'-dimethyl-2,2'-bipyridine (71 mg, 385.6 μmol), bis(4-methoxyphenyl)methanone (93 mg, 385.6 μmol), sodium carbonate (204 mg, 1.9 mmol) and Bis(2,4-pentanediono) nickel (99 mg, 385.6 μmol) under nitrogen. The reaction mixture was irradiated using an Integrated Photoreactor with a blue LED (365 nm) for 24 h under nitrogen. The reaction mixture was quenched with water (50 mL). The resulting solution was extracted with EtOAc (3×50 mL). The combined organic layers were dried over anhydrous $Na_2SO_4$ and concentrated under vacuum. The residue was applied onto a silica gel column and eluted with EtOAc/PE (2:1) to give 5-chloro-6-(tetrahydrofuran-2-yl)pyridin-3-amine (15 mg, 4% yield) as a yellow solid. $^1$H NMR (300 MHz, Chloroform-d) δ: 7.99 (d, J=2.4 Hz, 1H), 6.96 (d, J=2.4 Hz, 1H), 5.27-5.29 (m, 1H), 4.09-4.17 (m, 1H), 3.87-3.96 (m, 1H), 3.77 (br, 2H), 1.98-2.28 (m, 4H). LC-MS: m/z 199 [M+H]$^+$.

Step 2: 2-chloro-N-(5-chloro-6-(tetrahydrofuran-2-yl)pyridin-3-yl)-8,8-dimethyl-7,8-dihydro-6H-cyclopenta[e]pyrazolo[1,5-a]pyrimidine-6-carboxamide

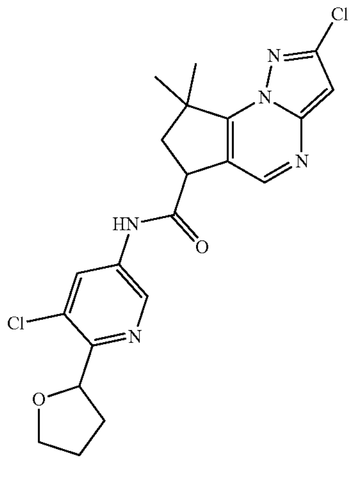 [SMILES: CC1(C)CC(C(=O)Nc2cnc(C3CCCO3)c(Cl)c2)c2cnc3cc(Cl)nn3c21]

To a stirred solution of 2-chloro-8,8-dimethyl-7,8-dihydro-6H-cyclopenta[e]pyrazolo[1,5-a]pyrimidine-6-carboxylic acid (20 mg, 75.1 μmol) in ACN (3 mL) were added 5-chloro-6-(tetrahydrofuran-2-yl)pyridin-3-amine (15 mg, 75.1 μmol), TCFH (85 mg, 302.0 μmol) and NMI (25 mg, 302.0 μmol). The resulting mixture was stirred for 16 h at room temperature. The reaction mixture was quenched with water (10 mL). The resulting solution was extracted with EtOAc (3×10 mL). The combined organic layers were dried over anhydrous $Na_2SO_4$ and concentrated under vacuum. The residue was submitted to Prep-HPLC purification and the collected fractions were lyophilized to give 2-chloro-N-(5-chloro-6-(tetrahydrofuran-2-yl)pyridin-3-yl)-8,8-dimethyl-7,8-dihydro-6H-cyclopenta[e]pyrazolo[1,5-a]pyrimidine-6-carboxamide (4.7 mg, 14% yield) as a white solid. $^1$H NMR (300 MHz, Chloroform-d) δ: 8.46-8.49 (m, 2H), 8.37 (s, 1H), 7.59 (s, 1H), 6.71 (s, 1H), 5.35-5.40 (m, 1H) 4.17-4.26 (m, 2H), 3.95-4.00 (m, 1H), 2.52-2.65 (m, 1H), 2.35-2.48 (m, 2H), 1.96-2.20 (m, 3H), 1.77 (s, 3H), 1.63 (s, 3H). LC-MS: m/z 446 [M+H].

Step 3: Separation of Enantiomers to Obtain (R)-2-chloro-N-(5-chloro-6-((S)-tetrahydrofuran-2-yl)pyridin-3-yl)-8,8-dimethyl-7,8-dihydro-6H-cyclopenta[e]pyrazolo[1,5-a]pyrimidine-6-carboxamide, (R)-2-chloro-N-(5-chloro-6-((R)-tetrahydrofuran-2-yl)pyridin-3-yl)-8,8-dimethyl-7,8-dihydro-6H-cyclopenta[e]pyrazolo[1,5-a]pyrimidine-6-carboxamide, (S)-2-chloro-N-(5-chloro-6-((S)-tetrahydrofuran-2-yl)pyridin-3-yl)-8,8-dimethyl-7,8-dihydro-6H-cyclopenta[e]pyrazolo[1,5-a]pyrimidine-6-carboxamide, and (S)-2-chloro-N-(5-chloro-6-((R)-tetrahydrofuran-2-yl)pyridin-3-yl)-8,8-dimethyl-7,8-dihydro-6H-cyclopenta[e]pyrazolo[1,5-a]pyrimidine-6-carboxamide Example 26

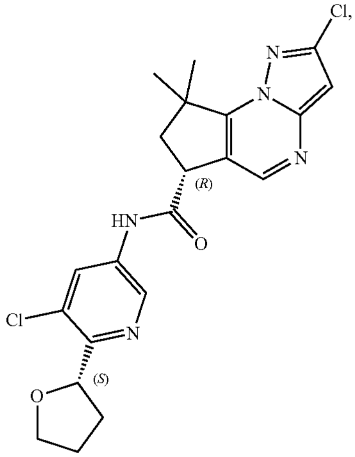

Example 27

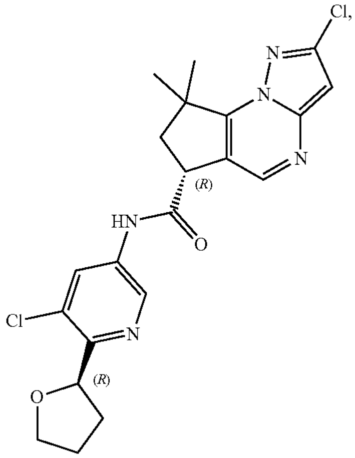

-continued

Example 28

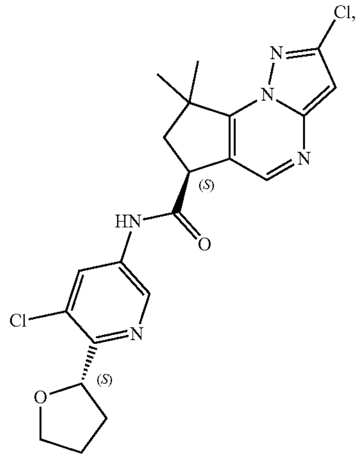

and

Example 29

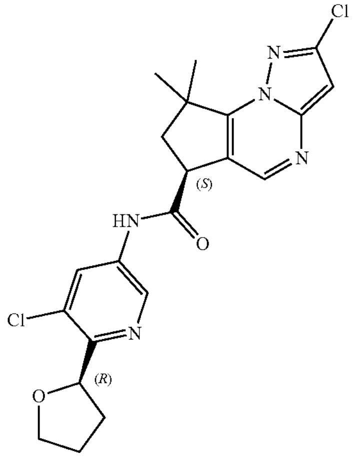

50 mg of 2-chloro-N-(5-chloro-6-(tetrahydrofuran-2-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: Chiralpak ID-2, 2*25 cm, Sum; Mobile Phase A:Hex(0.5% 2M $NH_3$-MeOH), Mobile Phase B:EtOH; Flow rate: 35 mL/min; isocratic: 50 B; 220/254 nm; RT1:7.3; RT2:16.2; Injection Volume: 1 ml; Number of Runs: 5). The first eluting isomer was concentrated and lyophilized, then submitted to Prep-HPLC purification and the collected fractions were lyophilized to afford Example 29 as a white solid (2.3 mg, 18% yield). The second eluting isomer was concentrated and lyophilized, then submitted to Prep-HPLC purification and the collected fractions were lyophilized to afford Example 28 as a white solid (2.8 mg, 22% yield). Fractions containing a mixture of the two other isomers were concentrated and submitted to chiral HPLC purification (CHIRALPAK IC, 2*25 cm, 5 um; Mobile Phase A:Hex(0.5% 2M $NH_3$-MeOH), Mobile Phase B:EtOH; Flow rate: 20 mL/min; isocratic: 30 B; 220/254 nm; RT1:9.805; RT2:12.846; Injection Volume: 3 ml; Number of Runs: 1). The first eluting isomer was concentrated and lyophilized to afford Example 27 as a white solid (2.5 mg, 20% yield). The second eluting isomer was concentrated and lyophilized to afford Example 26 as a white solid (2.4 mg, 19% yield).

Example 26: $^1$H NMR (400 MHz, Chloroform-d) δ: 8.63 (br, 1H), 8.48 (s, 1H), 8.44 (s, 1H), 8.41 (s, 1H), 6.66 (s, 1H), 5.33-5.37 (m, 1H), 4.17-4.29 (m, 2H), 3.95-4.01 (m, 1H), 2.35-2.51 (m, 3H), 1.99-2.19 (m, 3H), 1.75 (s, 3H), 1.58 (s, 3H). LC-MS: m/z 446 $[M+H]^+$.

Example 27: $^1H$ NMR (400 MHz, Chloroform-d) δ: 8.46 (s, 2H), 8.36 (s, 1H), 8.34 (s, 1H), 6.67 (s, 1H), 5.34-5.38 (m, 1H), 4.17-4.26 (m, 2H), 3.95-4.00 (m, 1H), 2.49-2.55 (m, 1H), 2.33-2.43 (m, 2H), 2.01-2.15 (m, 3H), 1.75 (s, 3H), 1.59 (s, 3H). LC-MS: m/z 446 $[M+H]^+$.

Example 28: $^1H$ NMR (300 MHz, Chloroform-d) δ: 10.66 (s, 1H), 9.26 (s, 1H), 9.18 (s, 1H), 8.49 (s, 1H), 6.67 (s, 1H), 5.34 (dd, J=6.6, 7.8 Hz, 1H), 4.30-4.43 (m, 2H), 3.96-4.04 (m, 1H), 2.54-2.65 (m, 2H), 2.41 (dd, J=6.6, 13.2 Hz, 1H), 1.89-2.11 (m, 3H), 1.75 (s, 3H), 1.61 (s, 3H). LC-MS: m/z 446 $[M+H]^+$.

Example 29: $^1H$ NMR (300 MHz, Chloroform-d) δ: 10.38 (s, 1H), 9.12 (s, 1H), 8.97 (s, 1H), 8.51 (s, 1H), 6.68 (s, 1H), 5.35 (dd, J=6.9, 8.1 Hz, 1H), 4.25-4.40 (m, 2H), 3.96-4.04 (m, 1H), 2.51-2.61 (m, 2H), 2.43 (dd, J=6.9, 13.2 Hz, 1H), 1.92-2.10 (m, 3H), 1.76 (s, 3H), 1.60 (s, 3H). LC-MS: m/z 446 $[M+H]^+$.

The absolute stereochemistry for each separated isomer was not determined.

Method N1

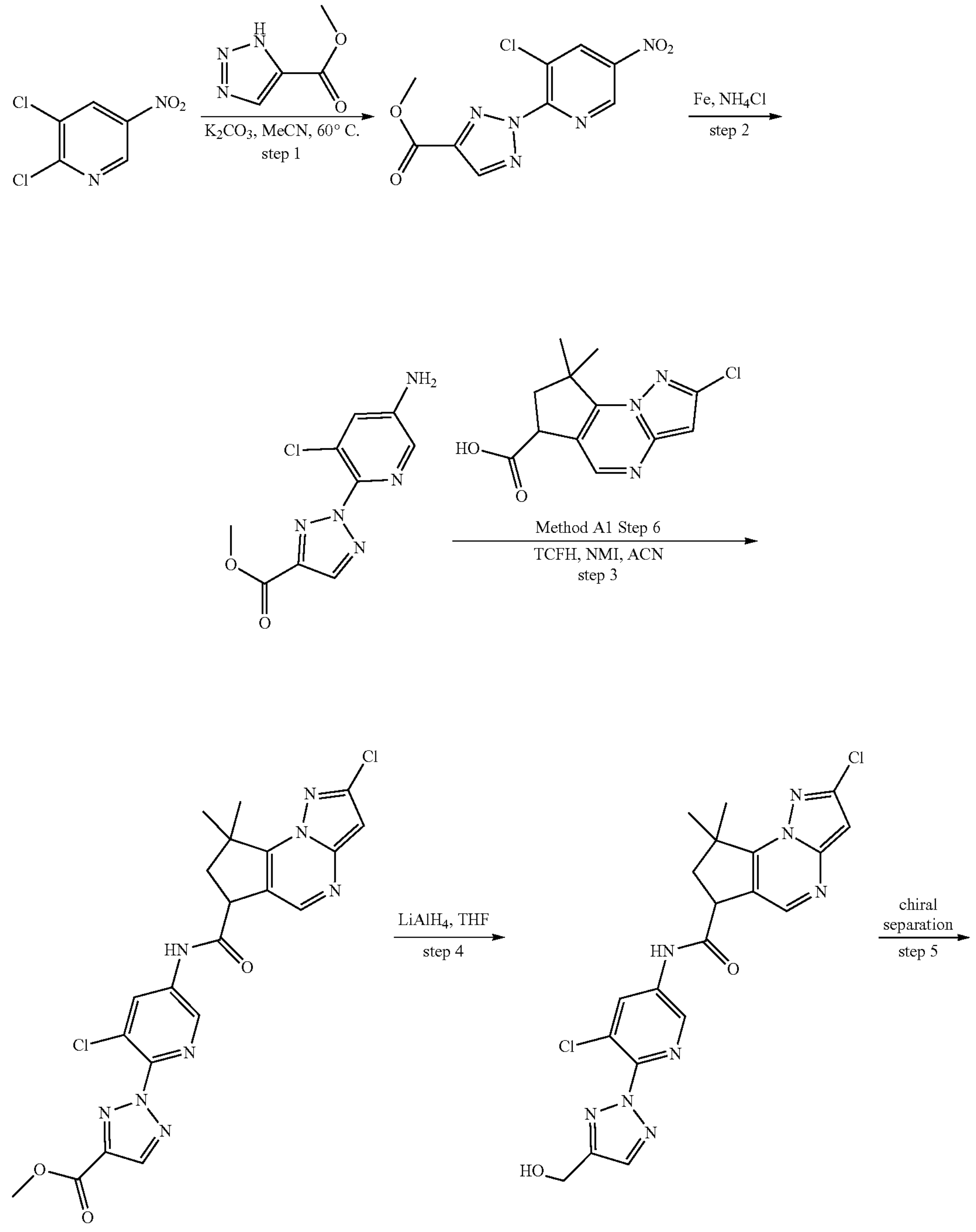

-continued

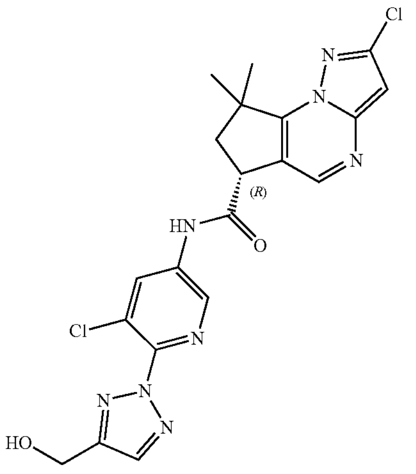

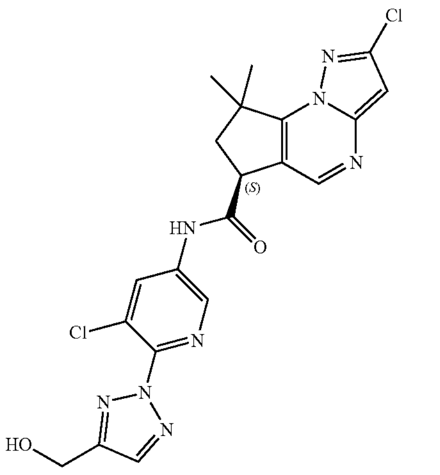

Example 30 and Example 31

Example 30 and 31: Single Enantiomers Obtained from a Racemic Mixture Containing (R)-2-chloro-N-(5-chloro-6-(4-(hydroxymethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(4-(hydroxymethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide Step 1: methyl 2-(3-chloro-5-nitropyridin-2-yl)-2H-1,2,3-triazole-4-carboxylate

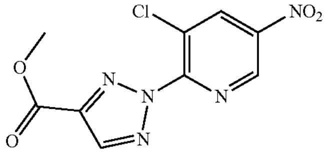 [SMILES: COC(=O)c1cnn(-c2ncc([N+](=O)[O-])cc2Cl)n1]

To a stirred solution of 2,3-dichloro-5-nitropyridine (5 g, 25.9 mmol), methyl 1H-1,2,3-triazole-5-carboxylate (3 g, 23.6 mmol) in MeCN (60 mL) was added $K_2CO_3$ (9.8 g, 70.7 mmol). The reaction mixture was stirred at 60° C. for 16 h. The resulting mixture was filtrated, and the filtrate was concentrated under reduced pressure to give crude product methyl 2-(3-chloro-5-nitropyridin-2-yl)-2H-1,2,3-triazole-4-carboxylate (4.8 g, 66% yield) as a white solid which was used directly in next step. LC-MS: m/z 284 $[M+H]^+$.

Step 2: methyl 2-(5-amino-3-chloropyridin-2-yl)-2H-1,2,3-triazole-4-carboxylate

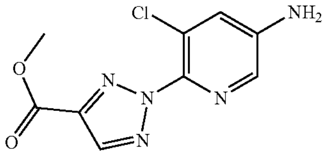

To a stirred solution of methyl 2-(3-chloro-5-nitropyridin-2-yl)-2H-1,2,3-triazole-4-carboxylate (1 g, 3.5 mmol) and iron powder (984 mg, 17.6 mmol) in THE (20 mL) were added $NH_4Cl$ (943 mg, 17.6 mmol) and water (10 mL). The reaction mixture was stirred at 60° C. for 2 h. The mixture was filtered through a pad of diatomaceous earth and the pad was washed with EtOAc (2×5 mL). The combined filtrates were concentrated under reduced pressure. The residue was applied on silica gel column and eluted with PE/EtOAc (1:1) to afford methyl 2-(5-amino-3-chloropyridin-2-yl)-2H-1,2,3-triazole-4-carboxylate (330 mg, 35% yield) as a yellow solid. $^1H$ NMR (300 MHz, Chloroform-d) 6:8.30 (s, 1H), 7.92 (d, J=2.5 Hz, 1H), 7.17 (d, J=2.5 Hz, 1H), 3.99 (s, 3H). LC-MS: m/z 254$[M+H]^+$.

Step 3: methyl 2-(3-chloro-5-(2-chloro-8,8-dimethyl-7,8-dihydro-6H-cyclopenta[e]pyrazolo[1,5-a]pyrimidine-6-carboxamido) pyridin-2-yl)-2H-1,2,3-triazole-4-carboxylate

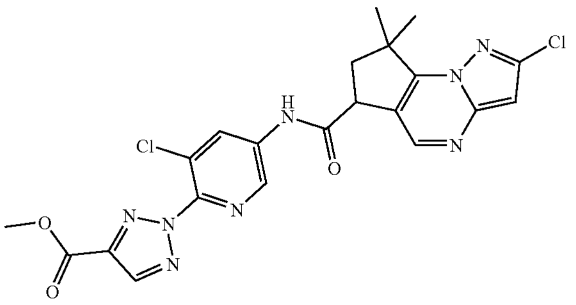 [SMILES: COC(=O)c1cnn(-c2ncc(NC(=O)C3CC(C)(C)c4c3cnc3cc(Cl)nn43)cc2Cl)n1]

A solution of methyl 2-(5-amino-3-chloropyridin-2-yl)-2H-1,2,3-triazole-4-carboxylate (301 mg, 1.1 mmol), 2-chloro-8,8-dimethyl-7,8-dihydro-6H-cyclopenta[e]pyrazolo[1,5-a]pyrimidine-6-carboxylic acid (Method A1 Step 6; 200 mg, 752.7 umol), N,N,N',N'-Tetramethylchloroformamidinium hexafluorophosphate (TCFH) (844.81 mg, 3.0 mmol) and N-methylimidazole (NMI) (247 mg, 3.0 mmol) was stirred in ACN (2 mL) at 25° C. for 1 h. The reaction mixture was quenched with water (10 mL). The resulting solution was extracted with EtOAc (3×10 mL). The combined organic layers were dried over anhydrous $Na_2SO_4$ and concentrated under vacuum. The residue was applied on silica gel column and eluted with PE/EtOAc (1:1) to afford methyl 2-(3-chloro-5-(2-chloro-8,8-dimethyl-7,8-dihydro-6H-cyclopenta[e]pyrazolo[1,5-a]pyrimidine-6-carboxamido) pyridin-2-yl)-2H-1,2,3-triazole-4-carboxylate (300 mg, 76% yield) as a yellow solid. $^1$H NMR (400 MHz, Chloroform-d) 6: 8.74 (s, 1H), 8.55-8.59 (m, 2H), 8.36 (s, 1H), 6.75 (s, 1H), 4.36-4.40 (m, 1H), 2.85 (s, 3H), 2.46-2.63 (m, 2H), 1.79 (s, 3H), 1.64 (s, 3H). LC-MS: m/z 501[M+H]$^+$.

Step 4: 2-chloro-N-(5-chloro-6-(4-(hydroxymethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide

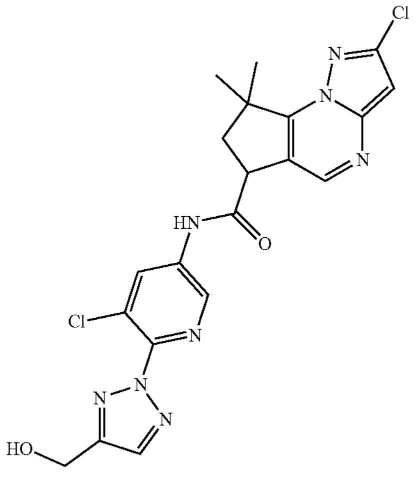 [SMILES: CC1(C)CC(C(=O)Nc2cnc(-n3ncc(CO)n3)c(Cl)c2)c2cnc3cc(Cl)nn3c21]

To a stirred solution of methyl 2-(3-chloro-5-(2-chloro-8,8-dimethyl-7,8-dihydro-6H-cyclopenta[e]pyrazolo[1,5-a]pyrimidine-6-carboxamido) pyridin-2-yl)-2H-1,2,3-triazole-4-carboxylate (50 mg, 95.8 μmol) in THE (5 mL) at 0° C. was added $LiAlH_4$ (4 mg, 114.9 μmol) slowly. The reaction mixture was stirred at 0° C. for 1 h. The resulting mixture was quenched with a saturated aqueous solution of $NH_4Cl$(5 mL) and extracted with EtOAc (3×5 mL). The combined organic layers were washed with brine (15 mL), dried over anhydrous $Na_2SO_4$ and concentrated under reduced pressure. The residue was submitted to Prep-HPLC purification and the collected fractions were lyophilized to give 2-chloro-N-(5-chloro-6-(4-(hydroxymethyl)-2H-1,2,3-triazol-2-yl) pyridin-3-yl)-8,8-dimethyl-7,8-dihydro-6H-cyclopenta[e]pyrazolo[1,5-a]pyrimidine-6-carboxamide [7.3.0.02,6]dodeca-2(6),7,9,11-tetraene-5-carboxamide (40 mg, 86% yield) as a white solid. $^1$H NMR (300 MHz, Chloroform-d) δ 8.65 (d, J=2.0 Hz, 1H), 8.48 (s, 1H), 8.45 (d, J=2.3 Hz, 1H), 7.92 (s, 1H), 7.87 (s, 1H), 6.70 (s, 1H), 4.93 (s, 2H), 4.18-4.32 (m, 1H), 2.59 (dd, J=13.1, 8.9 Hz, 1H), 2.45 (dd, J=13.1, 6.9 Hz, 1H), 1.78 (s, 3H), 1.62 (s, 3H). LC-MS: m/z 473 [M+H]$^+$.

Step 5: Separation of Enantiomers to Obtain (R)-2-chloro-N-(5-chloro-6-(4-(hydroxymethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(4-(hydroxymethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide Example 30

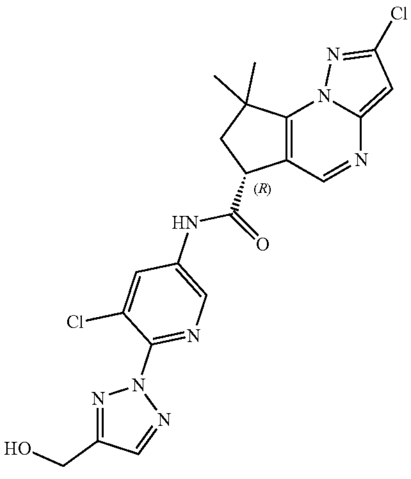

and

-continued

Example 31

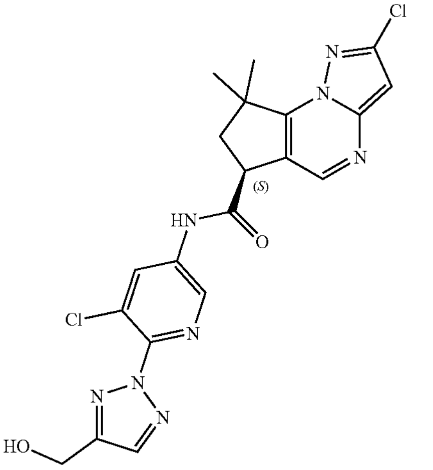

40 mg of 2-chloro-N-(5-chloro-6-(4-(hydroxymethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide were submitted to chiral HPLC purification (CHIRALPAK ID, 2*25 cm(5 um); Mobile Phase A:MTBE (0.5% 2M $NH_3$-MeOH), Mobile Phase B:EtOH; Flow rate: 15 mL/min; isocratic: 50 B; 220/254 nm; RT1:10.067; RT2:13.408; Injection Volume: 1.5 ml; Number Of Runs: 2). The first eluting isomer was concentrated and lyophilized to afford Example 30 (6.5 mg, 32% yield) as a white solid. The second eluting isomer was concentrated and lyophilized to afford Example 31 (6.3 mg, 32% yield) as a white solid.

Example 30: $^1$H NMR (400 MHz, Methanol-$d_4$) δ: 8.68 (d, J=2.3 Hz, 1H), 8.62 (d, J=2.3 Hz, 1H), 8.52 (s, 1H), 7.97 (s, 1H), 6.70 (s, 1H), 4.79 (s, 2H), 4.42 (dd, J=9.1, 6.6 Hz, 1H), 2.63 (dd, J=13.2, 9.1 Hz, 1H), 2.42 (dd, J=13.2, 6.7 Hz, 1H), 1.73 (s, 3H), 1.63 (s, 3H). LC-MS: m/z 473 $[M+H]^+$.

Example 31: $^1$H NMR (400 MHz, Methanol-$d_4$) δ: 8.68 (d, J=2.3 Hz, 1H), 8.62 (d, J=2.2 Hz, 1H), 8.52 (s, 1H), 7.98 (s, 1H), 6.70 (s, 1H), 4.79 (s, 2H), 4.42 (dd, J=9.1, 6.7 Hz, 1H), 2.63 (dd, J=13.2, 9.1 Hz, 1H), 2.42 (dd, J=13.2, 6.7 Hz, 1H), 1.73 (s, 3H), 1.63 (s, 3H). LC-MS: m/z 473$[M+H]^+$.

The absolute stereochemistry for each separated isomer was not determined.

Method O1

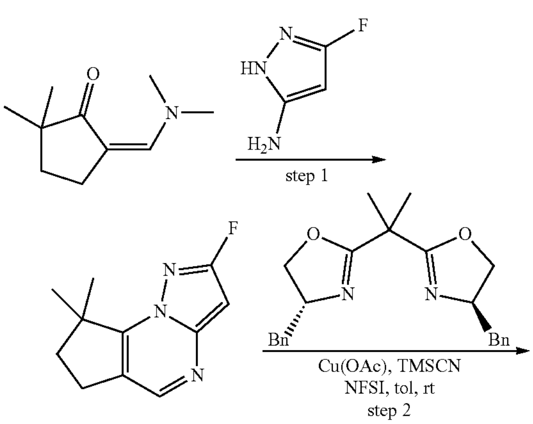

-continued

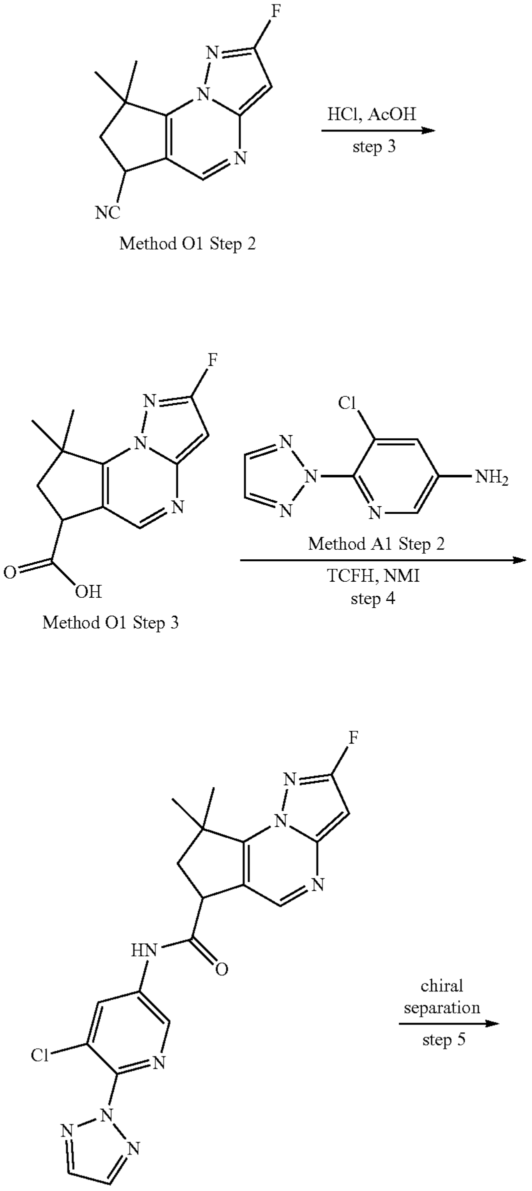

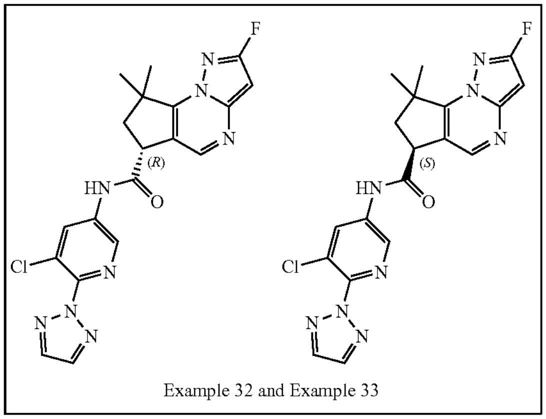

Example 32 and Example 33

Examples 32 and 33: Single Enantiomers Obtained from a Racemic Mixture Containing (R)—N-(5-chloro-6-(2H-1,2,3-triazol-2-yl)pyridin-3-yl)-2-fluoro-8,8-dimethyl-7,8-dihydro-611-cyclopenta[e]pyrazolo[1,5-a]pyrimidine-6-carboxamide and (S)—N-(5-chloro-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide Step 1: 2-fluoro-8,8-dimethyl-7,8-dihydro-6H-cyclopenta[e]pyrazolo[1,5-a]pyrimidine

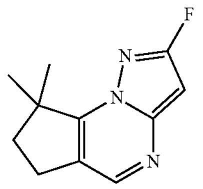

To a stirred solution of 5-((dimethylamino)methyl ene)-2,2-dimethylcyclopentan-1-one (Method A1 Step 3; 7.45 g, 44.5 mmol) in toluene (150 mL) were added 3-fluoro-1H-pyrazol-5-amine (3.75 g, 37.1 mmol) and AcOH (15 mL) at rt. The resulting mixture was stirred for 5 h at 90° C. under nitrogen. The mixture was allowed to cool down to r.t. and concentrated under reduced pressure. The residue was diluted with water (100 mL). The pH was adjusted to 6-7 with sodium bicarbonate (sat., aq.). The resulting solution was extracted with EtOAc (2×100 mL), dried over anhydrous $Na_2SO_4$ and concentrated under vacuum. The residue was applied onto a silica gel column and eluted with EtOAc/PE (1:5) to give 2-fluoro-8,8-dimethyl-7,8-dihydro-6H-cyclopenta[e]pyrazolo[1,5-a]pyrimidine (3 g, 39% yield) as a yellow solid. $^1H$ NMR (400 MHz, Chloroform-d) δ: 8.37 (s, 1H), 6.18 (d, J=4.8 Hz, 1H), 3.00 (t, J=7.6 Hz, 2H), 2.13 (t, J=7.6 Hz, 2H), 1.58 (s, 6H). LC-MS: m/z 206 $[M+H]^+$.

Step 2: 2-fluoro-8,8-dimethyl-7,8-dihydro-6H-cyclopenta[e]pyrazolo[1,5-a]pyrimidine-6-carbonitrile

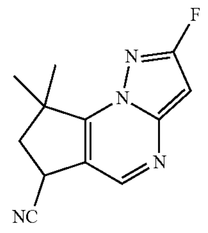 [SMILES: CC1(C)CC(C#N)c2cnc3cc(F)nn3c21]

To a stirred solution of 2-fluoro-8,8-dimethyl-7,8-dihydro-6H-cyclopenta[e]pyrazolo[1,5-a]pyrimidine (3 g, 14.6 mmol) in toluene (60 mL) were added (4R)-4-benzyl-2-[1-[(4R)-4-benzyl-4,5-dihydrooxazol-2-yl]-1-methylethyl]-4,5-dihydrooxazole (636 mg, 1.8 mmol), acetoxycopper (359 mg, 2.9 mmol), N-fluorobenzenesulfonimide (6.91 g, 21.9 mmol), and TMSCN (7.25 g, 73.1 mmol). The reaction was stirred at r.t. for 16 h under nitrogen. The solvent was removed under vacuum and the residue was applied onto a silica gel column and eluted with EtOAc/PE (1:5) to give 2-fluoro-8,8-dimethyl-7,8-dihydro-6H-cyclopenta[e]pyrazolo[1,5-a]pyrimidine-6-carbonitrile (Method 01 Step 2; 5.5 g, 33% yield) as a yellow solid. LC-MS: m/z 231 $[M+H]^+$.

Step 3: 2-fluoro-8,8-dimethyl-7,8-dihydro-6H-cyclopenta[e]pyrazolo[1,5-a]pyrimidine-6-carboxylic acid

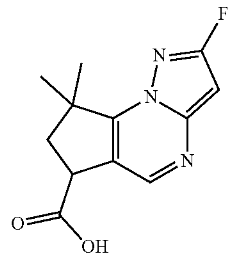 [SMILES: CC1(C)CC(C(=O)O)c2cnc3cc(F)nn3c21]

To a 30 mL vial was added 2-fluoro-8,8-dimethyl-7,8-dihydro-6H-cyclopenta[e]pyrazolo[1,5-a]pyrimidine-6-carbonitrile (5.2 g, 22.6 mmol) in AcOH (52 mL) and HCl (52 mL). The resulting mixture was stirred for 1.5 h at 100° C. The mixture was allowed to cool down to r.t. and concentrated under vacuum. The residue was diluted with water (300 ml) and the pH was adjusted to 5-6 with $NaHCO_3$(sat., aq.). The resulting solution was extracted with EtOAc (3×200 mL), dried over anhydrous $Na_2SO_4$ and concentrated under vacuum. The residue was applied onto a silica gel column and eluted with DCM/MeOH (10:1) to give 2-fluoro-8,8-dimethyl-7,8-dihydro-6H-cyclopenta[e]pyrazolo[1,5-a]pyrimidine-6-carboxylic acid (Method 01 Step 3; 450 mg, 56% purity) as an off-white solid. LC-MS: m/z 250 $[M+H]^+$.

Step 4: N-(5-chloro-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide

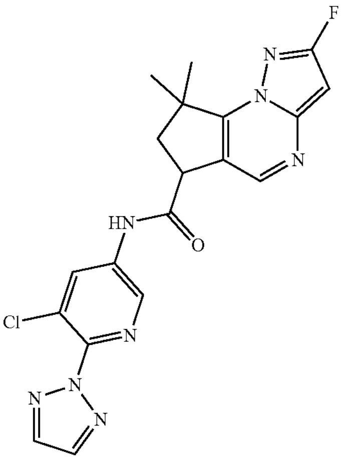 [SMILES: CC1(C)CC(C(=O)Nc2cnc(-n3nccn3)c(Cl)c2)c2cnc3cc(F)nn3c21]

To a stirred solution of 2-fluoro-8,8-dimethyl-7,8-dihydro-6H-cyclopenta[e]pyrazolo[1,5-a]pyrimidine-6-carboxylic acid (400 mg, 1.6 mmol) in ACN (5 mL) were added 5-chloro-6-(triazol-2-yl)pyridin-3-amine (250 mg, 1.3 mmol), TCFH (1.80 g, 6.4 mmol), NMI (525 mg, 6.4 mmol). The resulting mixture was stirred for 16 h at room temperature. The reaction mixture was quenched with water (10 mL). The resulting solution was extracted with EtOAc (3×20 mL), dried over anhydrous $Na_2SO_4$ and concentrated under vacuum. The residue was submitted to Prep-HPLC purification and the collected fractions were lyophilized to give N-(5-chloro-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide (83.4 mg, 12% yield) as a white solid. LC-MS: m/z 427 $[M+H]^+$.

Step 5: Separation of Enantiomers to Obtain (R)—N-(5-chloro-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide Example 32

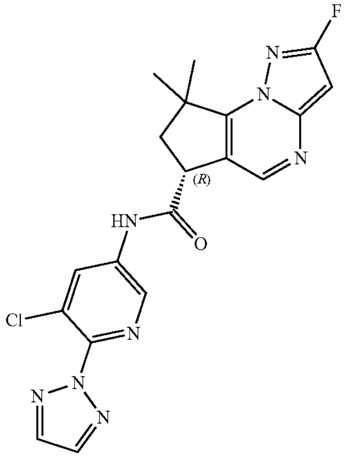

and

Example 33

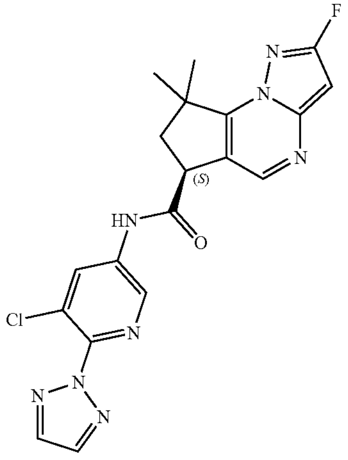

83.4 mg of N-(5-chloro-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide were submitted to chiral HPLC purification (CHIRALPAK ID, 2*25 cm(5 um); Mobile Phase A:MTBE (0.5% 2M $NH_3$-MeOH), Mobile Phase B:EtOH; Flow rate: 13 mL/min; isocratic: 50 B; 220/254 nm; RT1:6.691; RT2:9.683; Injection Volume: 3 ml; Number of Runs: 4). The first eluting isomer was concentrated and lyophilized to afford Example 32 as a white solid (33.6 mg, 41% yield). The second eluting isomer was concentrated and lyophilized to afford Example 33 as a white solid (37.8 mg, 47% yield).

Example 32: $^1$H NMR (400 MHz, Chloroform-d) δ: 8.67 (d, J=2.4 Hz, 1H), 8.56 (s, 1H), 8.50 (d, J=2.4 Hz, 1H), 8.03 (s, 1H), 7.94 (s, 2H), 6.30 (d, J=4.8 Hz, 1H), 4.29 (dd, J=8.8, 7.2 Hz, 1H), 2.58 (dd, J=13.2, 8.8 Hz, 1H), 2.47 (dd, J=13.2, 6.8 Hz, 1H), 1.77 (s, 3H), 1.61 (s, 3H). LC-MS: m/z 427 $[M+H]^+$.

Example 33: $^1$H NMR (400 MHz, Chloroform-d) δ: 8.67 (s, 1H), 8.58 (s, 1H), 8.51 (s, 1H), 8.09 (s, 1H), 7.94 (s, 2H), 6.31 (d, J=5.2 Hz, 1H), 4.30 (dd, J=6.8, 8.8 Hz, 1H), 2.58 (dd, J=13.2, 8.8 Hz, 1H), 2.48 (dd, J=13.2, 6.8 Hz, 1H), 1.77 (s, 3H), 1.61 (s, 3H). LC-MS: m/z 427 $[M+H]^+$.

The absolute stereochemistry for each separated isomer was not determined.

Method P1

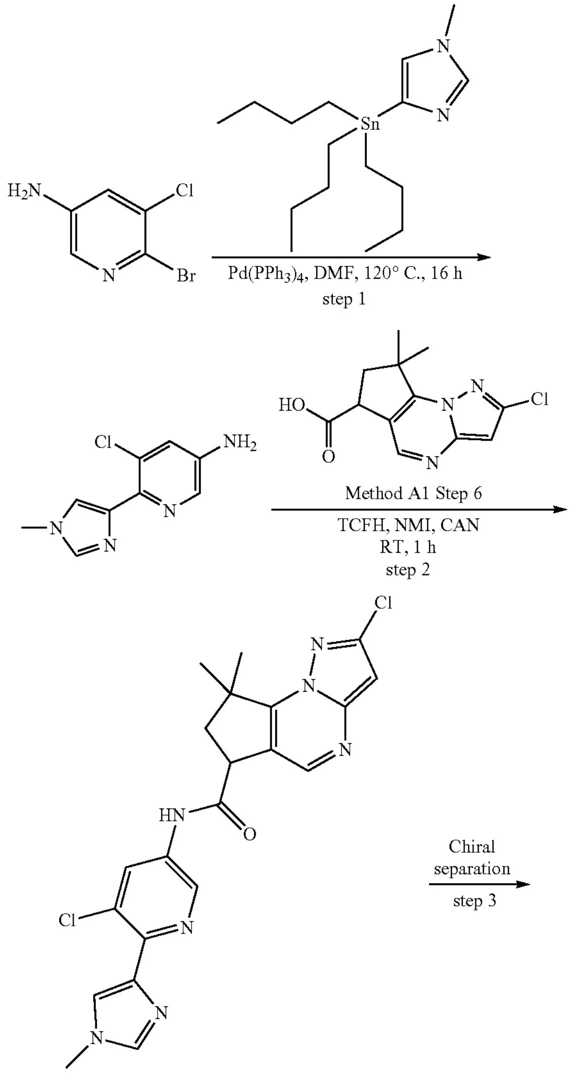

-continued

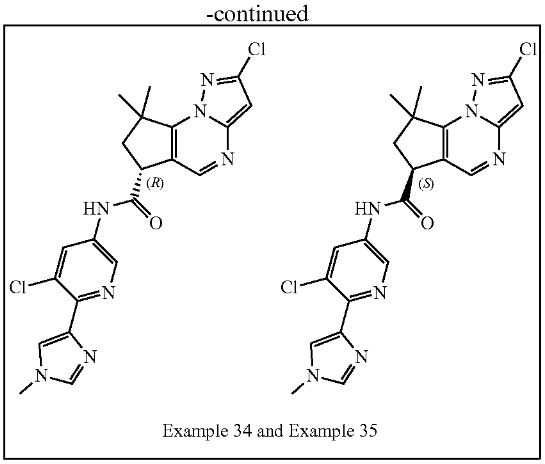

Example 34 and Example 35

Examples 34 and 35: Single Enantiomers Obtained from a Racemic Mixture Containing (R)-2-chloro-N-(5-chloro-6-(1-methyl-1H-imidazol-4-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(1-methyl-1H-imidazol-4-yl)pyridin-3-yl)-8,8-dimethyl-7,8-dihydro-6H-cyclopenta[e]pyrazolo[1,5-a]pyrimidine-6-carboxamide Step 1: 5-chloro-6-(1-methyl-1H-imidazol-4-yl)pyridin-3-amine

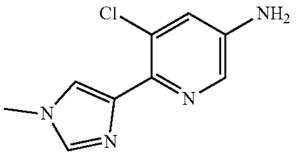

To a stirred solution of 6-bromo-5-chloro-pyridin-3-amine (200 mg, 964.1 μmol) in DMF (5 mL) were added 1-methyl-4-(tributylstannyl)-1H-imidazole (429 mg, 1.16 mmol) and $Pd(PPh_3)_4$ (111 mg, 96.3 μmol) under nitrogen. The reaction was stirred at 120° C. for 16 h. The reaction mixture was quenched with water (10 mL). The resulting solution was extracted with EtOAc (3×5 mL). The combined organic layers were dried over anhydrous $Na_2SO_4$ and concentrated under vacuum. The residue was purified with reserve phase column to give 5-chloro-6-(1-methylimidazol-4-yl)pyridin-3-amine (120 mg, 51% yield) as a light-yellow solid. H NMR (300 MHz, DMSO-$d_6$) δ 9.15 (d, J=1.4 Hz, 1H), 8.20 (d, J=1.4 Hz, 1H), 8.06 (d, J=2.4 Hz, 1H), 7.17 (d, J=2.4 Hz, 1H), 3.91 (s, 3H). LC-MS: m/z 209 $[M+H]^+$.

Step 2. 2-chloro-N-(5-chloro-6-(1-methyl-1H-imidazol-4-yl)pyridin-3-yl)-8,8-dimethyl-7,8-dihydro-6H-cyclopenta[e]pyrazolo[1,5-a]pyrimidine-6-carboxamide

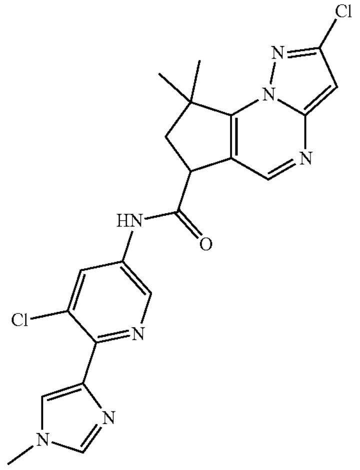 [SMILES: Cn1cnc(-c2ncc(NC(=O)C3CC(C)(C)c4c3cnc3cc(Cl)nn43)cc2Cl)c1]

A mixture of 5-chloro-6-(1-methylimidazol-4-yl)pyridin-3-amine (111 mg, 451.7 μmol), 2-chloro-8,8-dimethyl-7,8-dihydro-6H-cyclopenta[e]pyrazolo[1,5-a]pyrimidine-6-carboxylic acid (80 mg, 301.1 μmol), TCFH (338 mg, 1.2 mmol) and NMI (97 mg, 1.2 mmol) in ACN (5 mL) was stirred at 25° C. for 1 hr. The resulting mixture was concentrated under reduced pressure. Water (5 mL) was added and the mixture was extracted with EtOAc (3×3 mL). The combined organic layers were washed with brine (3 mL), dried over $Na_2SO_4$ and concentrated under reduced pressure. The residue was purified with Prep-HPLC to give 2-chloro-N-(5-chloro-6-(1-methyl-1H-imidazol-4-yl)pyridin-3-yl)-8, 8-dimethyl-7,8-dihydro-6H-cyclopenta[e]pyrazolo[1,5-a]pyrimidine-6-carboxamide (30.4 mg, 21% yield) as a white solid. $^{1}H$ NMR (300 MHz, DMSO-$d_6$) δ 10.74 (s, 1H), 8.61-8.72 (m, 2H), 8.29 (d, J=2.2 Hz, 1H), 7.72 (s, 1H), 7.68 (s, 1H), 6.95 (s, 1H), 4.41 (dd, J=9.0, 6.3 Hz, 1H), 3.73 (s, 3H), 2.51-2.62 (m, 1H), 2.27-2.34 (m, 1H), 1.65 (s, 3H), 1.56 (s, 3H). LC-MS: m/z 456 $[M+H]^+$.

Step 3: Separation of Enantiomers to Obtain (R)-2-chloro-N-(5-chloro-6-(1-methyl-1H-imidazol-4-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(1-methyl-1H-imidazol-4-yl)pyridin-3-yl)-8,8-dimethyl-7,8-dihydro-6H-cyclopenta[e]pyrazolo[1,5-a]pyrimidine-6-carboxamide Example 34

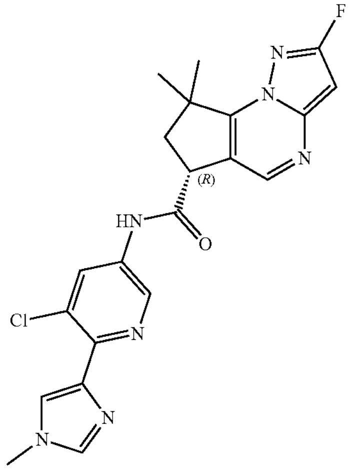

and

-continued

Example 35

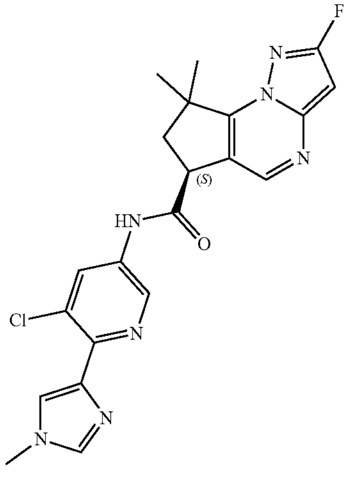

30 mg of 2-chloro-N-(5-chloro-6-(1-methyl-1H-imidazol-4-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IE, 2*25 cm, 5 um; Mobile Phase A:Hex:DCM=3:1 (0.5% 2M $NH_3$-MeOH), Mobile Phase B:EtOH; Flow rate: 17 mL/min; isocratic: 50 B; 254/220 nm; RT1:13.034; RT2:19.681; Injection Volume: 1.8 ml; Number of Runs: 1). The first eluting isomer was concentrated and lyophilized to afford Example 34 (5.3 mg, 18% yield). The second eluting isomer was concentrated and lyophilized to afford Example 35 (5.8 mg, 20% yield) as a white solid.

Example 34: $^{1}H$ NMR (300 MHz, DMSO-$d_6$) δ 10.74 (s, 1H), 8.61-8.72 (m, 2H), 8.29 (d, J=2.2 Hz, 1H), 7.69-7.73 (m, 2H), 6.95 (s, 1H), 4.41 (dd, J=9.0, 6.4 Hz, 1H), 3.73 (s, 3H), 2.51-2.62 (m, 1H), 2.35-2.40 (m, 1H), 1.65 (s, 3H), 1.56 (s, 3H). LC-MS: m/z 456 $[M+H]^+$.

Example 35: $^{1}H$ NMR (300 MHz, DMSO-$d_6$) δ 10.75 (s, 1H), 8.61-8.72 (m, 2H), 8.29 (d, J=2.2 Hz, 1H), 7.68-7.73 (m, 2H), 6.95 (s, 1H), 4.42 (dd, J=9.0, 6.3 Hz, 1H), 3.73 (s, 3H), 2.51-2.62 (m, 1H), 2.28-2.34 (m, 1H), 1.65 (s, 3H), 1.56 (s, 3H). LC-MS: m/z 456 $[M+H]^+$.

The absolute stereochemistry for each separated isomer was not determined.

Method Q1

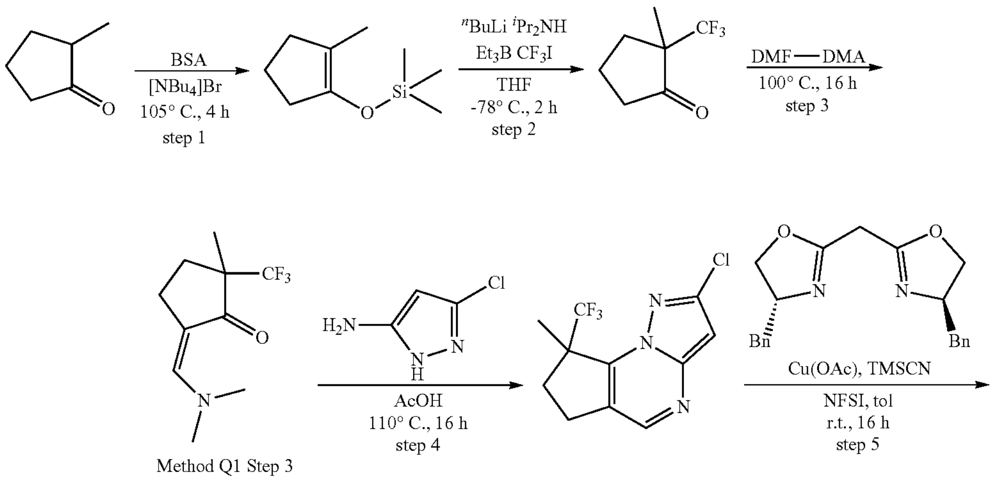

Method Q1 Step 3

-continued
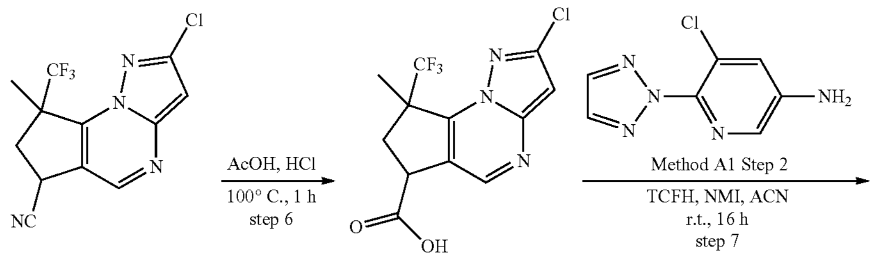
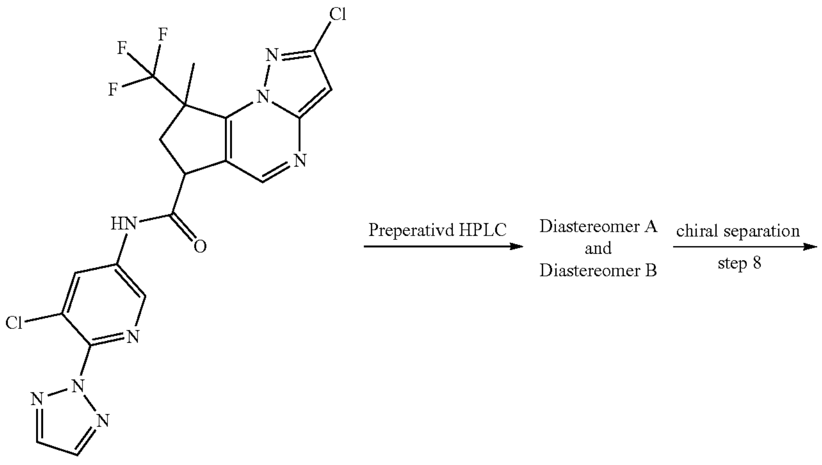
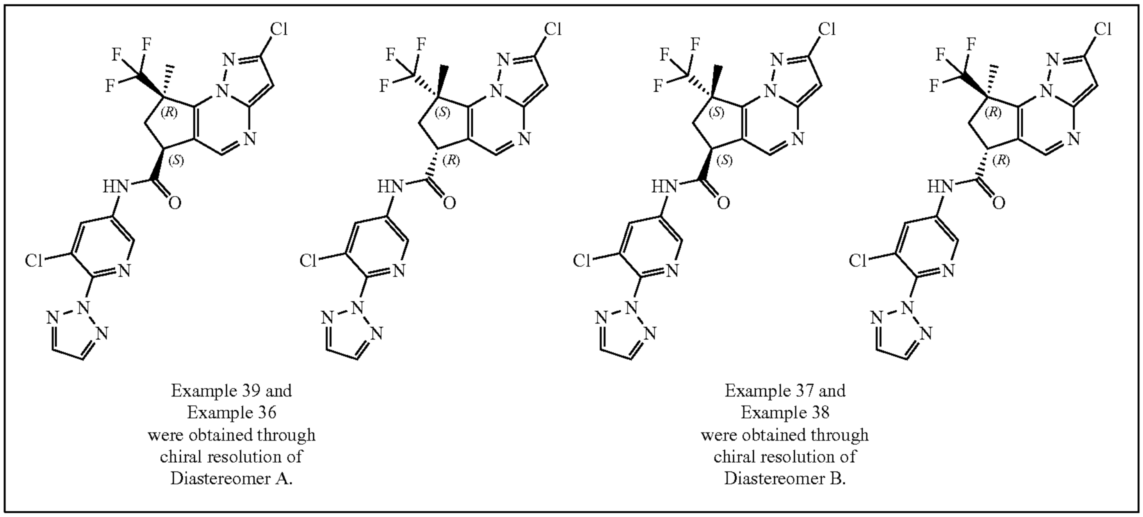
Example 39 and
Example 36
were obtained through
chiral resolution of
Diastereomer A.
Example 37 and
Example 38
were obtained through
chiral resolution of
Diastereomer B.

Examples 39, 36, 37 and 38: Single Enantiomers Obtained from Racemic Mixtures containing (6S, 8R)-2-chloro-N-(5-chloro-6-(2H-1,2,3-triazol-2-yl) pyridin-3-yl)-8-methyl-8-(trifluoromethyl)-7,8-dihydro-6H-cyclopenta[e]pyrazolo[1,5-a]pyrimidine-6-carboxamide, (6R,8S)-2-chloro-N-(5-chloro-6-(2H-1,2,3-triazol-2-yl)pyridin-3-yl)-8-methyl-8-(trifluoromethyl)-7,8-dihydro-6H-cyclopenta[e] pyrazolo[1,5-a]pyrimidine-6-carboxamide, (65,85)-2-chloro-N-(5-chloro-6-(2H-1,2,3-triazol-2-yl) pyridin-3-yl)-8-methyl-8-(trifluoromethyl)-7,8-dihydro-6H-cyclopenta[e]pyrazolo[1,5-a] pyrimidine-6-carboxamide and (6R,8R)-2-chloro-N-(5-chloro-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide Step 1: trimethyl((2-methylcyclopent-1-en-1-yl)oxy)silane

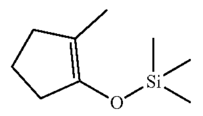

A mixture of 2-methylcyclopentan-1-one (10 g, 101.9 mmol), TBAB (82.2 g, 254.7 mmol) and trimethylsilyl (E)-N-(trimethylsilyl)acetimidate (24.9 g, 122.3 mmol) was stirred at 105° C. for 4 h. The mixture was directly distilled under reduced pressure without any workup to give trimethyl((2-methylcyclopent-1-en-1-yl)oxy)silane (15 g, crude) as yellow oil which was used to the next step directly. $^1$H NMR (400 MHz, Chloroform-d) δ 2.18-2.29 (m, 4H), 1.75-1.81 (m, 2H), 1.51 (s, 3H), 0.17 (s, 9H).

Step 2. 2-methyl-2-(trifluoromethyl)cyclopentan-1-one

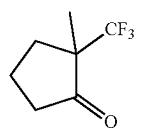

To a solution of trimethyl((2-methylcyclopent-1-en-1-yl) oxy)silane (5 g, 29.4 mmol) in anhydrous THF (185 mL) was added n-BuLi (18.8 mL, 47.0 mmol, 2.5 M in hexane) at 0° C. under nitrogen. Diisopropylamine (4.8 g, 47.0 mmol) was added to the solution, and the reaction mixture was stirred for another 20 min at the same temperature. Trifluoroiodomethane (28.8 g, 146.8 mmol) was added to the reaction mixture with a cannula followed by triethylborane (1 M, 29.4 mmol) at −78° C. The resulting mixture was stirred for 2 h at −78° C. The reaction mixture was quenched by acetic acid (18 mL, 5 M in THF). The mixture was diluted with water (100 mL), extracted with $Et_2O$ (3×200 mL) and dried over $Na_2SO_4$. The resulting mixture was concentrated under vacuum to afford 2-methyl-2-(trifluoromethyl)cyclopentan-1-one (5 g, crude) as a brown oil which was used to the next step directly. $^1$H NMR (400 MHz, Chloroform-d) δ 2.19-2.43 (m, 2H), 1.99-2.17 (m, 2H), 1.34-1.52 (m, 2H), 0.89 (s, 3H).

Step 3: (Z)-5-((dimethyl amino)methylene)-2-methyl-2-(trifluoromethyl)cyclopentan-1-one

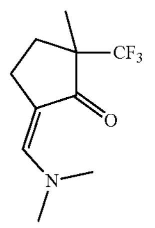

A solution of 2-methyl-2-(trifluoromethyl)cyclopentan-1-one (5 g, 22.6 mmol) in DMF-DMA (25 mL) was stirred for 16 h at 100° C. The mixture was allowed to cool down to room temperature and concentrated under reduced pressure. The residue was applied onto a silica gel column and eluted with EtOAc/PE (1:1) to afford (Z)-5-((dimethylamino)methylene)-2-methyl-2-(trifluoromethyl)cyclopentan-1-one as a yellow solid (Method Q1, step 3; 400 mg, 6% yield). LC-MS: m/z 222 [M+H]$^+$.

Step 4: 2-chloro-8-methyl-8-(trifluoromethyl)-7,8-dihydro-6H-cyclopenta[e]pyrazolo[1,5-a]pyrimidine

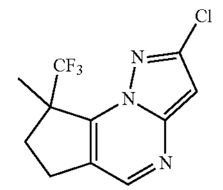 [SMILES: CC1(C(F)(F)F)CCc2cnc3cc(Cl)nn3c21]

To a solution of (Z)-5-((dimethylamino)methylene)-2-methyl-2-(trifluoromethyl) cyclopentan-1-one (400 mg, 1.8 mmol) in AcOH (10 mL) was added 3-chloro-1H-pyrazol-5-amine (427 mg, 3.6 mmol) at room temperature. The resulting mixture was stirred for 16 h at 110° C. The mixture was allowed to cool down to room temperature and concentrated under reduced pressure. The residue was diluted with water (50 mL). The pH was adjusted to 6-7 with sodium bicarbonate (sat., aq.). The resulting solution was extracted with EtOAc (2×50 mL), dried over anhydrous $Na_2SO_4$ and concentrated under vacuum. The residue was applied onto a silica gel column and eluted with EtOAc/PE (1:3) to give 2-chloro-8-methyl-8-(trifluoromethyl)-7,8-dihydro-6H-cyclopenta[e]pyrazolo[1,5-a]pyrimidine (300 mg, 60% yield) as a yellow solid. $^1$H NMR (400 MHz, DMSO-$d_6$) δ 8.70 (s, 1H), 7.01 (s, 1H), 3.06-3.10 (m, 2H), 2.62-2.68 (m, 1H), 2.24-2.32 (m, 1H), 1.84 (s, 3H). LC-MS: m/z 276 [M+H]$^+$.

Step 5: 2-chloro-8-methyl-8-(trifluoromethyl)-7,8-dihydro-6H-cyclopenta[e]pyrazolo[1,5-a]pyrimidine-6-carbonitrile

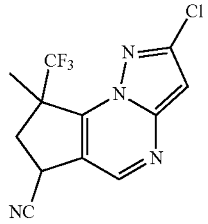 [SMILES: CC1(C(F)(F)F)CC(C#N)c2cnc3cc(Cl)nn3c21]

To a stirred solution of 2-fluoro-8,8-dimethyl-7,8-dihydro-6H-cyclopenta[e]pyrazolo[1,5-a]pyrimidine (230 mg, 0.8 mmol) in toluene (15 mL) were added bis((R)-4-benzyl-4,5-dihydrooxazol-2-yl)methane (37 mg, 0.1 mmol), acetoxycopper (21 mg, 0.2 mmol), NFSI (396 mg, 2.0 mmol), and TMSCN (414 mg, 4.0 mmol). The reaction was stirred at room temperature for 16 h under nitrogen. The solvent was removed under vacuum and the residue was applied onto a silica gel column and eluted with EtOAc/PE (1:3) to give the crude product. The product was submitted to Prep-HPLC purification and the collected fractions were lyophilized to give 2-chloro-8-methyl-8-(trifluoromethyl)-7,8-dihydro-6H-cyclopenta[e]pyrazolo[1,5-a]pyrimidine-6-carbonitrile (33 mg, 13% yield) as a white solid. LC-MS: m/z 301 $[M+H]^+$.

Step 6: 2-chloro-8-methyl-8-(trifluoromethyl)-7,8-dihydro-6H-cyclopenta[e]pyrazolo[1,5-a]pyrimidine-6-carboxylic acid

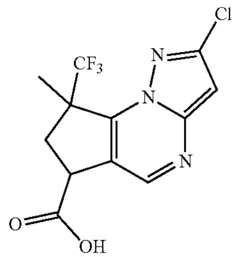 [SMILES: CC1(C(F)(F)F)CC(C(=O)O)c2cnc3cc(Cl)nn3c21]

To a 8 mL vial was added 2-fluoro-8,8-dimethyl-7,8-dihydro-6H-cyclopenta[e]pyrazolo[1,5-a]pyrimidine-6-carbonitrile (33 mg, 0.1 mmol) in AcOH (1 mL) and HCl (1 mL). The resulting mixture was stirred for 1 h at 100° C. The mixture was allowed to cool down to room temperature and concentrated under vacuum. The residue was diluted with water (20 mL) and the pH was adjusted to 5-6 with $NaHCO_3$ (aq., sat.). The resulting solution was extracted with EtOAc (3×30 mL), dried over $Na_2SO_4$ and concentrated under vacuum to afford 2-chloro-8-methyl-8-(trifluoromethyl)-7,8-dihydro-6H-cyclopenta[e]pyrazolo[1,5-a]pyrimidine-6-carboxylic acid (30 mg, crude) as a yellow oil, which was used directly in the next step. LC-MS: m/z 320 $[M+H]^+$.

Step 7: 2-chloro-N-(5-chloro-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide

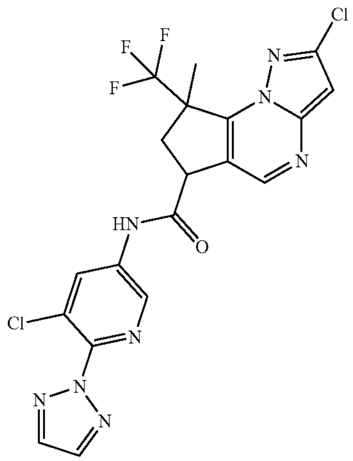 [SMILES: CC1(C(F)(F)F)CC(C(=O)Nc2cnc(-n3nccn3)c(Cl)c2)c2cnc3cc(Cl)nn3c21]

To a stirred solution of 2-chloro-8-methyl-8-(trifluoromethyl)-7,8-dihydro-6H-cyclopenta[e]pyrazolo[1,5-a]pyrimidine-6-carboxylic acid (30 mg, 93.9 μmol) in ACN (3 mL) were added 5-chloro-6-(triazol-2-yl)pyridin-3-amine (Method A1, step 2; 28 mg, 140.8 μmol), TCFH (120 mg, 375.6 μmol), NMI (525 mg, 375.6 μmol). The resulting mixture was stirred for 16 h at room temperature. The reaction mixture was quenched by water (10 mL). The resulting solution was extracted with EtOAc (3×20 mL), dried over anhydrous $Na_2SO_4$ and concentrated under vacuum. The residue was applied onto a silica gel column and eluted with EtOAc/PE (1:1) to give 2-chloro-N-(5-chloro-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide as a mixture of two racemic diastereomeric pairs as white solid. LC-MS: m/z 497 $[M+H]^+$. This mixture was submitted to Prep-HPLC to obtain the separated racemic mixtures of Diastereomer A and Diastereomer B.

Step 8: Separation of Enantiomers to Obtain (6S, 8R)-2-chloro-N-(5-chloro-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide, (6R,8S)-2-chloro-N-(5-chloro-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide, (6S,8S)-2-chloro-N-(5-chloro-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide and (6R,8R)-2-chloro-N-(5-chloro-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide Example 39

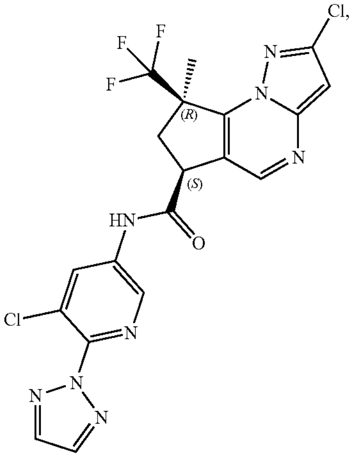

Example 36

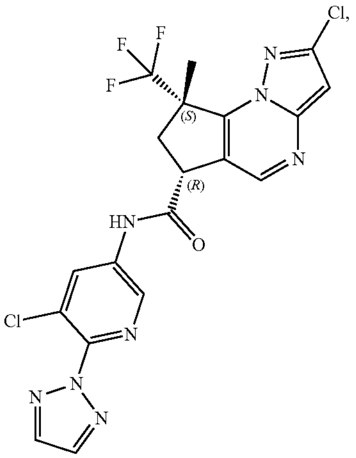

-continued

Example 37

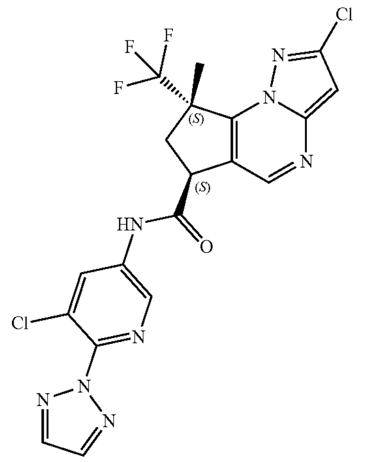

and

Example 38

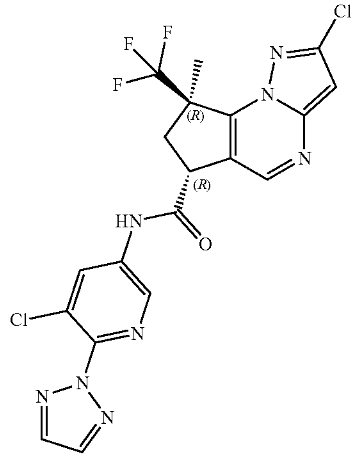

12 mg of Diastereomer A were submitted to chiral HPLC purification (Column: CHIRALPAK IF, 2*25 cm, 5 um; Mobile Phase A:Hex(0.5% 2M $NH_3$-MeOH), Mobile Phase B:EtOH; Flow rate: 13 mL/min; isocratic: 50 B; 220/254 nm; RT1:12.603; RT2:16.474; Injection Volume: 3 ml; Number of Runs: 1). The first eluting isomer was concentrated and lyophilized to afford Example 39 (4.7 mg, 10% yield) as a white solid. The second eluting isomer was concentrated and lyophilized to afford Example 36 (4.7 mg, 10% yield) as a white solid.

6 mg of Diastereomer B were submitted to chiral HPLC purification (Column CHIRALPAK IF, 2*25 cm, 5 um; Mobile Phase A:Hex(0.5% 2M $NH_3$-MeOH), Mobile Phase B:EtOH; Flow rate: 13 mL/min; isocratic: 50 B; 220/254 nm; RT1:9.265; RT2:13.315; Injection Volume: 2 ml; Number of Runs: 1). The first eluting isomer was concentrated and lyophilized to afford Example 37 (2.4 mg, 4% yield) as a white solid. The second eluting isomer was concentrated and lyophilized to afford Example 38 (2.5 mg, 4% yield) as a white solid.

Example 39: $^1$H NMR (300 MHz, Methanol-$d_4$) δ: 8.63-8.71 (m, 3H), 8.02 (s, 2H), 6.81 (s, 1H), 4.50-4.55 (m, 1H), 3.07-3.20 (m, 1H), 2.50-2.58 (m, 1H), 2.00 (s, 3H). LC-MS: m/z 473 $[M+H]^+$.

Example 36: $^1$H NMR (300 MHz, Methanol-$d_4$) δ: 8.63-8.71 (m, 3H), 8.02 (s, 2H), 6.81 (s, 1H), 4.50-4.55 (m, 1H), 3.07-3.20 (m, 1H), 2.50-2.58 (m, 1H), 2.00 (s, 3H). LC-MS: m/z 473 $[M+H]^+$.

Example 37: $^1$H NMR (300 MHz, Methanol-$d_4$) δ: 8.61-8.70 (m, 3H), 8.02 (s, 2H), 6.81 (s, 1H), 4.49-4.51 (m, 1H), 2.97-3.02 (m, 1H), 2.77-2.81 (m, 1H), 1.89 (s, 3H). LC-MS: m/z 473 $[M+H]^+$.

Example 38: $^1$H NMR (400 MHz, Methanol-$d_4$) δ: 8.61-8.70 (m, 3H), 8.02 (s, 2H), 6.81 (s, 1H), 4.49-4.51 (m, 1H), 2.97-3.02 (m, 1H), 2.77-2.81 (m, 1H), 1.89 (s, 3H). LC-MS: m/z 473 $[M+H]^+$.

The absolute stereochemistry for each separated isomer was not determined.

Method R1

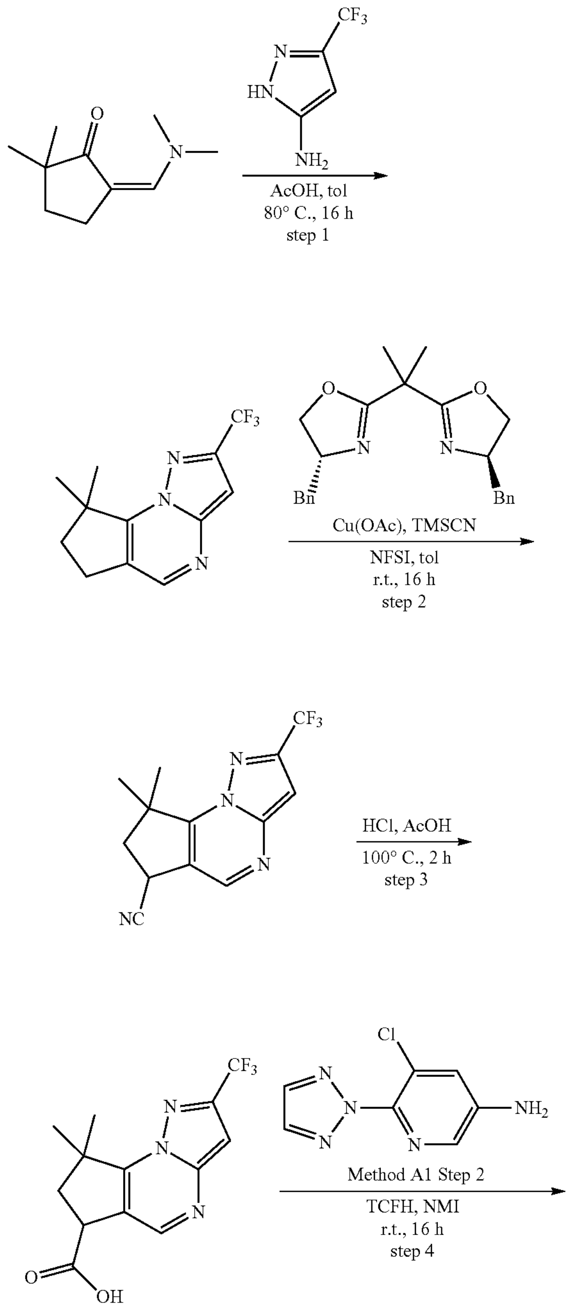

-continued

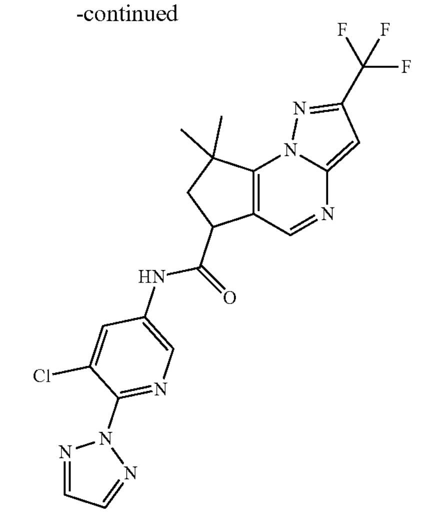

Example 40

Step 1: 8,8-dimethyl-2-(trifluoromethyl)-7,8-dihydro-6H-cyclopenta[e]pyrazolo[1,5-a]pyrimidine

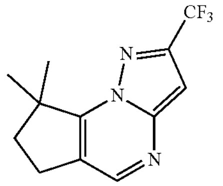 [SMILES: CC1(C)CCc2cnc3cc(C(F)(F)F)nn3c21]

To a stirred solution of 5-((dimethylamino)methylene)-2,2-dimethylcyclopentan-1-one (Method A1 step 3; 4.98 g, 29.8 mmol) in toluene (100 mL) were added 3-(trifluoromethyl)-1H-pyrazol-5-amine (4.5 g, 29.8 mmol) and AcOH (10 mL) at rt. The resulting mixture was stirred for 16 h at 80° C. The mixture was allowed to cool down to r.t. and concentrated under reduced pressure. The residue was diluted with water (200 mL). The pH was adjusted to 6-7 with sodium bicarbonate (sat., aq.). The resulting solution was extracted with EtOAc (2×100 mL). The combined organic layers were dried over anhydrous $Na_2SO_4$ and concentrated under vacuum. The residue was applied onto a silica gel column and eluted with EtOAc/PE (1:5) to give 8,8-dimethyl-2-(trifluoromethyl)-7,8-dihydro-6H-cyclopenta[e]pyrazolo[1,5-a]pyrimidine (2 g, 26% yield for two steps) as a yellow solid. $^1$H NMR (400 MHz, Chloroform-d) δ: 8.49 (s, 1H), 6.95 (s, 1H), 3.05 (t, J=7.2 Hz, 2H), 2.18 (t, J=7.2 Hz, 2H), 1.62 (s, 6H). LC-MS: m/z 256 $[M+H]^+$.

Step 2: 8,8-dimethyl-2-(trifluoromethyl)-7,8-dihydro-6H-cyclopenta[e]pyrazolo[1,5-a]pyrimidine-6-carbonitrile

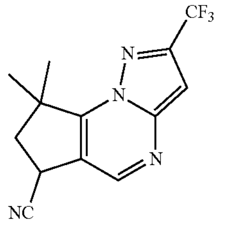 [SMILES: CC1(C)CC(C#N)c2cnc3cc(C(F)(F)F)nn3c21]

To a stirred solution of 8,8-dimethyl-2-(trifluoromethyl)-7,8-dihydro-6H-cyclopenta[e]pyrazolo[1,5-a]pyrimidine (1.9 g, 7.4 mmol) in toluene (38 mL) were added (4R)-4-benzyl-2-[1-[(4R)-4-benzyl-4,5-dihydrooxazol-2-yl]-1-methyl-ethyl]-4,5-dihydrooxazole (324 mg, 893.3 μmol), acetoxycopper (182 mg, 1.5 mmol), N-fluorobenzenesulfonimide (3.5 g, 11.2 mmol) and TMSCN (3.7 g, 37.2 mmol). The reaction was stirred at r.t. for 16 h under nitrogen.

The solvent was removed under vacuum and the residue was applied onto a silica gel column and eluted with EtOAc/PE (1:5) to give 8,8-dimethyl-2-(trifluoromethyl)-7,8-dihydro-6H-cyclopenta[e]pyrazolo[1,5-a]pyrimidine-6-carbonitrile (1.9 g, 91% yield) as a yellow solid. $^1$H NMR (400 MHz, Chloroform-d) δ: 8.67 (s, 1H), 7.10 (s, 1H), 4.32 (dd, J=8.8, 6.4 Hz, 1H), 2.64 (dd, J=13.6, 8.8 Hz, 1H), 2.53 (dd, J=13.6, 6.4 Hz, 1H), 1.79 (s, 3H), 1.64 (s, 3H). LC-MS: m/z 281 [M+H]$^+$.

Step 3: 8,8-dimethyl-2-(trifluoromethyl)-7,8-dihydro-6H-cyclopenta[e]pyrazolo[1,5-a]pyrimidine-6-carboxylic acid

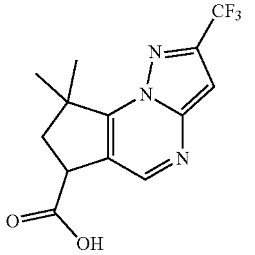 [SMILES: CC1(C)CC(C(=O)O)c2cnc3cc(C(F)(F)F)nn3c21]

To a 30 mL vial was added 8,8-dimethyl-2-(trifluoromethyl)-7,8-dihydro-6H-cyclopenta[e]pyrazolo[1,5-a]pyrimidine-6-carbonitrile (900 mg, 3.2 mmol) in AcOH (9 mL) and HCl (9 mL). The resulting mixture was stirred for 2 h at 100° C. The mixture was allowed to cool down to r.t. and concentrated under vacuum. The residue was diluted with water (100 mL) and the pH was adjusted to 5-6 with $NaHCO_3$(aq., sat.). The resulting solution was extracted with EtOAc (3×100 mL). The combined organic layers were dried over anhydrous $Na_2SO_4$ and concentrated under vacuum. The residue was applied onto a silica gel column and eluted with DCM/MeOH (10:1) to give 8,8-dimethyl-2-(trifluoromethyl)-7,8-dihydro-6H-cyclopenta[e]pyrazolo[1,5-a]pyrimidine-6-carboxylic acid (100 mg, 10% yield) as a yellow solid. $^1$H NMR (400 MHz, Chloroform-d) δ: 8.72 (s, 1H), 7.02 (s, 1H), 4.29 (dd, J=9.2, 6.4 Hz, 1H), 2.46-2.60 (m, 2H), 1.72 (s, 3H), 1.64 (s, 3H). LC-MS: m/z 300 [M+H]$^+$.

Step 4: N-(5-chloro-6-(2H-1,2,3-triazol-2-yl)pyridin-3-yl)-8,8-dimethyl-2-(trifluoromethyl)-7,8-dihydro-6H-cyclopenta[e]pyrazolo[1,5-a]pyrimidine-6-carboxamide Example 40

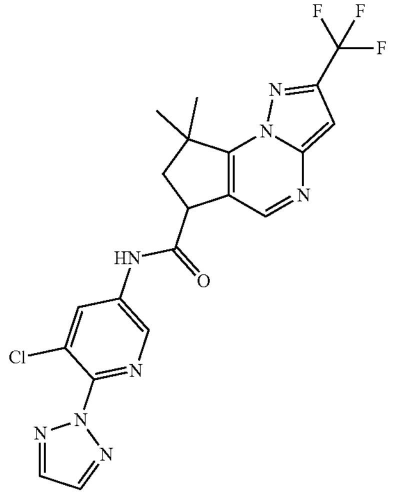

To a stirred solution of 8,8-dimethyl-2-(trifluoromethyl)-7,8-dihydro-6H-cyclopenta[e]pyrazolo[1,5-a]pyrimidine-6-carboxylic acid (100 mg, 334.2 μmol) in ACN (2 mL) were added 5-chloro-6-(triazol-2-yl)pyridin-3-amine (Method A1, step 2; 98 mg, 501.3 μmol), TCFH (375 mg, 1.3 mmol) and NMI (110 mg, 1.3 mmol). The resulting mixture was stirred for 16 h at r.t. The reaction mixture was quenched with water (20 mL). The resulting solution was extracted with EtOAc (3×20 mL). The combined organic layers were dried over anhydrous $Na_2SO_4$ and concentrated under vacuum. The residue was submitted to Prep-HPLC purification and the collected fractions were lyophilized to give N-(5-chloro-6-(2H-1,2,3-triazol-2-yl)pyridin-3-yl)-8,8-dimethyl-2-(trifluoromethyl)-7,8-dihydro-6H-cyclopenta[e]pyrazolo[1,5-a]pyrimidine-6-carboxamide (40 mg, 25% yield) as a white solid.

Example 40: $^1$H NMR (400 MHz, Chloroform-d) δ: 8.68 (s, 1H), 8.63 (s, 1H), 8.48 (s, 1H), 7.94 (s, 2H), 7.85 (s, 1H), 7.05 (s, 1H), 4.32 (t, J=8.0 Hz, 1H), 2.63 (dd, J=13.2, 9.2 Hz, 1H), 2.49 (dd, J=13.2, 7.2 Hz, 1H), 1.81 (s, 3H), 1.65 (s, 3H). LC-MS: m/z 477 [M+H]$^+$.

Method S1

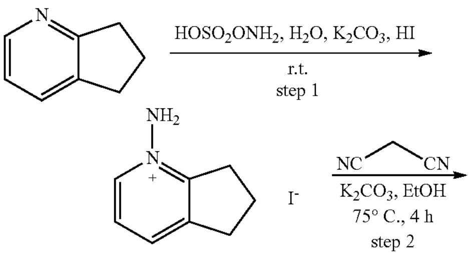

-continued

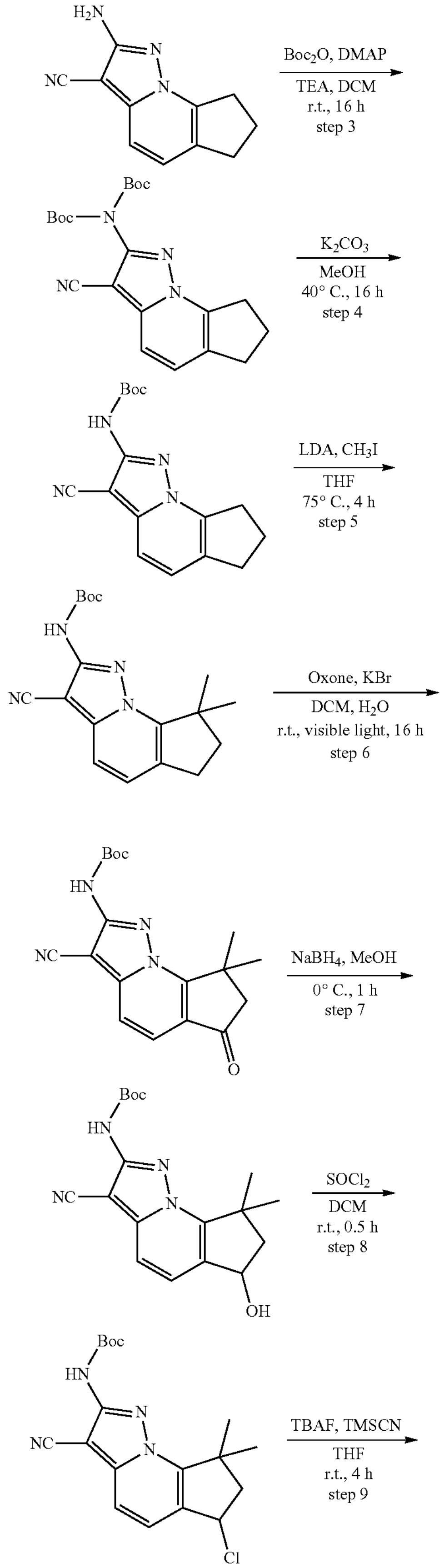

-continued

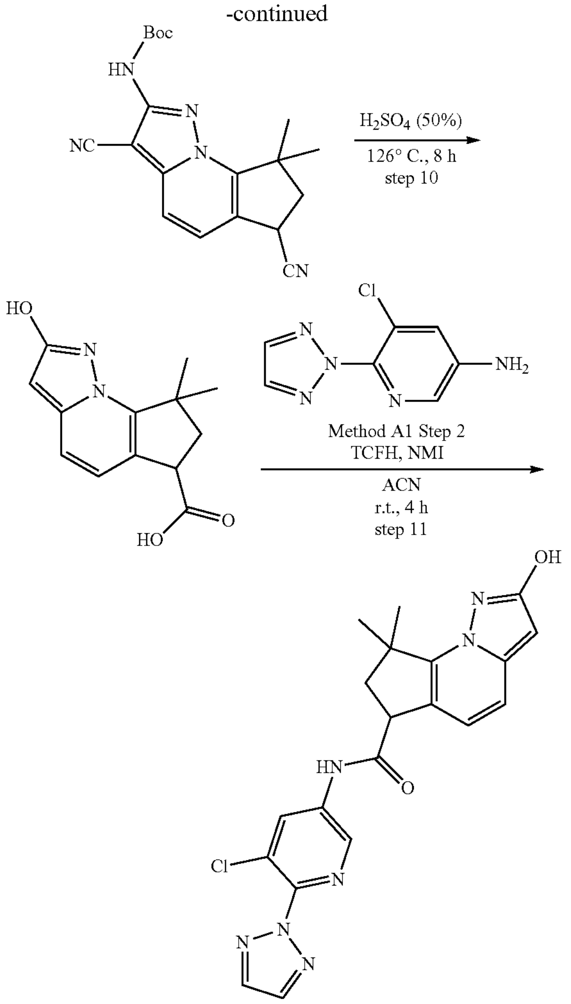

Example 41

Example 41: N-(5-chloro-6-(2H-1,2,3-triazol-2-yl)pyridin-3-yl)-2-hydroxy-8,8-dimethyl-7,8-dihydro-6H-cyclopenta[e]pyrazolo[1,5-a]pyridine-6-carboxamide Step 1: 1-amino-6,7-dihydro-5H-cyclopenta[b]pyridin-1-ium iodide

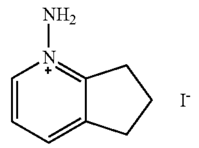

To a stirred solution of (aminooxy)sulfonic acid (113 g, 1.0 mol) in $H_2O$ (500 mL) was added 6,7-dihydro-5H-cyclopenta[b]pyridine (360 g, 3.0 mol). The resulting mixture was stirred for 120 min at 90° C. under an atmosphere of nitrogen. The reaction was cooled to −5° C. To the above mixture was added $K_2CO_3$ (138 g, 1.0 mol) in several portions over 10 min at −5° C. The resulting mixture was concentrated under reduced pressure. The residue was diluted with ethanol (450 mL). The solid was filtered out. To the filtrate was added hydriodic acid (140 mL, 57% purity) dropwise over 10 min at −5° C. The resulting mixture was stirred for 20 min at −5° C. The solid was collected by filtration to give 1-amino-6,7-dihydro-5H-cyclopenta[b]pyridin-1-ium iodide (60 g, 22.68% yield) as a black solid. LC-MS: m/z 135 $[M+H]^+$.

Step 2: 2-amino-7,8-dihydro-6H-cyclopenta[e]pyrazolo[1,5-a]pyridine-3-carbonitrile

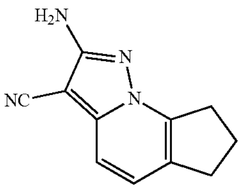 [SMILES: N#Cc1c(N)nn2c3c(ccc12)CCC3]

To a stirred solution of malononitrile (1.0 g, 15.3 mmol) in EtOH (150 mL) was added 1-amino-6,7-dihydro-5H-cyclopenta[b]pyridin-1-ium iodide (5 g, 19.1 mmol, I), $K_2CO_3$ (2.6 g, 19.1 mmol) in portions at room temperature. The resulting mixture was stirred for 1 h at 90° C. under an atmosphere of nitrogen. The reaction mixture was cooled to room temperature. The solid was filtered out and re-crystallized from methanol (100 mL) and water (100 mL) to afford 2-amino-7,8-dihydro-6H-cyclopenta[e]pyrazolo[1,5-a]pyridine-3-carbonitrile (1.0 g, 22.4% yield) as a black solid. LC-MS: m/z 199 $[M+H]^+$.

Step 3: tert-butyl N-[(tert-butoxy)carbonyl]-N-{10-cyano-1,12-diazatricyclo[7.3.0.0$^{2,6}$]dodeca-2 (6),7,9,11-tetraen-11-yl}carbamate

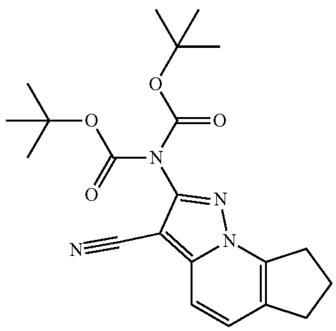 [SMILES: CC(C)(C)OC(=O)N(C(=O)OC(C)(C)C)c1nn2c3c(ccc2c1C#N)CCC3]

To a stirred mixture of 2-amino-7,8-dihydro-6H-cyclopenta[e]pyrazolo[1,5-a]pyridine-3-carbonitrile (1.0 g, 5.1 mmol) and triethylamine (1.5 g, 15.1 mmol) in DCM (10 mL) was added $Boc_2O$ (3.3 g, 15.1 mmol) in portions at room temperature under an atmosphere of nitrogen. To the above mixture was added DMAP (61.6 mg, 504.5 μmol) in portions at room temperature. The resulting mixture was stirred for additional 16 hours at room temperature. The reaction mixture was concentrated under reduced pressure. The residue was applied onto a silica gel column and eluted with EtOAc/PE (1:3) to give tert-butyl N-[(tert-butoxy)carbonyl]-N-{10-cyano-1,12-diazatricyclo[7.3.0.0$^{2,6}$]dodeca-2 (6),7,9,11-tetraen-11-yl}carbamate (1.0 g, 23.9% yield) as a yellow solid. $^1H$ NMR (400 MHz, DMSO-$d_6$) δ: 7.78 (d, J=8.8 Hz, 1H), 7.68 (d, J=8.8 Hz, 1H), 3.24-3.32 (m, 2H), 3.02-3.11 (m, 2H), 2.21-2.34 (m, 2H), 1.43 (s, 18H). LC-MS: m/z 399 $[M+H]^+$.

Step 4: tert-butyl (3-cyano-7,8-dihydro-6H-cyclopenta[e]pyrazolo[1,5-a]pyridin-2-yl)carbamate

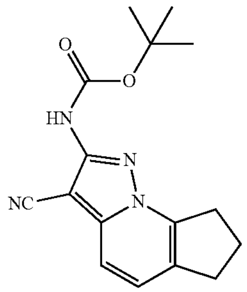 [SMILES: CC(C)(C)OC(=O)Nc1nn2c3c(ccc2c1C#N)CCC3]

To a stirred solution of tert-butyl N-[(tert-butoxy)carbonyl]-N-{10-cyano-1,12-diazatricyclo[7.3.0.0$^{2,6}$]dodeca-2 (6),7,9,11-tetraen-11-yl}carbamate (1.0 g, 2.5 mmol) in methanol (10 mL) was added potassium carbonate (345.8 mg, 2.5 mmol) in portions at room temperature. The resulting mixture was stirred overnight at 40° C. under an atmosphere of nitrogen. The resulting mixture was concentrated under reduced pressure. The residue was applied onto a silica gel column and eluted with EtOAc/PE (1:3) to give tert-butyl(3-cyano-7,8-dihydro-6H-cyclopenta[e]pyrazolo[1,5-a]pyridin-2-yl)carbamate (675 mg, 90% yield) as a yellow solid. $^1H$ NMR (400 MHz, DMSO-$d_6$) δ: 10.21 (s, 1H), 7.57 (s, 2H), 3.22 (t, J=7.6 Hz, 2H), 3.02 (t, J=7.4 Hz, 2H), 2.24-2.27 (m, 2H), 1.49 (s, 9H). LC-MS: m/z 299 $[M+H]^+$.

Step 5: tert-butyl (3-cyano-8,8-dimethyl-7,8-dihydro-6H-cyclopenta[e]pyrazolo[1,5-a]pyridine-2-yl)carbamate

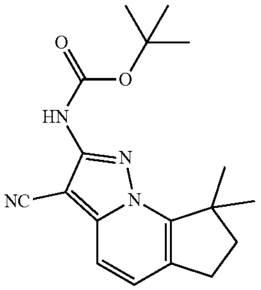 [SMILES: CC(C)(C)OC(=O)Nc1nn2c3c(ccc2c1C#N)CCC3(C)C]

To a solution of tert-butyl(3-cyano-7,8-dihydro-6H-cyclopenta[e]pyrazolo[1,5-a]pyridin-2-yl)carbamate (300 mg, 1.0 mmol) in THF (10 mL) was added a solution of lithium diisopropylamide (2.5 mL, 2 M in THF, 5.0 mmol) in THF dropwise at −20° C. under an atmosphere of nitrogen. The reaction mixture was stirred at −20° C. for 0.5 h. Then, a solution of iodomethane (428.19 mg, 3.0 mmol) in THF (0.5 mL) was added dropwise and the mixture was stirred for another 1 h. The reaction was quenched with saturated aqueous $NH_4Cl$(100 mL) and the mixture was extracted with EtOAc (3×100 mL). The combined organic extracts were washed with brine (100 mL), dried over anhydrous $Na_2SO_4$ and concentrated under vacuum. The residue was applied onto a silica gel column and eluted with EtOAc/PE (1:1) to give tert-butyl (3-cyano-8,8-dimethyl-7,8-dihydro-6H-cyclopenta[e]pyrazolo[1,5-a]pyridine-2-yl)carbamate (200 mg, 58.2% yield) as a yellow solid. $^1H$ NMR (400 MHz, Chloroform-d) δ: 7.49 (d, J=8.8 Hz, 1H), 7.32 (d, J=8.8 Hz, 1H), 7.06 (s, 1H), 2.98 (t, J=7.2 Hz, 2H), 2.14 (t, J=7.2 Hz, 2H), 1.59 (s, 9H), 1.56 (s, 6H). LC-MS: m/z 327 $[M+H]^+$.

Step 6: tert-butyl (3-cyano-8,8-dimethyl-6-oxo-7,8-dihydro-6H-cyclopenta[e]pyrazolo[1,5-a]pyridin-2-yl)carbamate

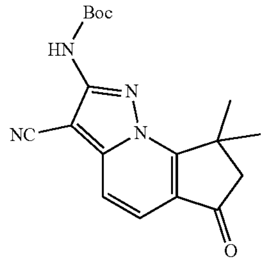 [SMILES: CC(C)(C)OC(=O)Nc1nn2c3c(ccc2c1C#N)C(=O)CC3(C)C]

To a stirred solution of tert-butyl (3-cyano-8,8-dimethyl-7,8-dihydro-6H-cyclopenta[e]pyrazolo[1,5-a]pyridine-2-yl) carbamate (100 mg, 306.4 μmol) in DCM (10 mL) and $H_2O$ (10 mL) were added oxone (188.3 mg, 306.4 μmol) and potassium bromide (36.5 mg, 306.4 μmol). The reaction was stirred at 25° C. for 16 h under sunlight (20W). The reaction was quenched with saturated aqueous $Na_2SO_3$ (50 mL) and the mixture was extracted with EtOAc (3×50 mL). The combined organic layers were washed with brine (50 mL), dried over anhydrous $Na_2SO_4$ and concentrated under vacuum. The residue was applied onto a silica gel column and eluted with EtOAc/PE (1:5) to give tert-butyl (3-cyano-8,8-dimethyl-6-oxo-7,8-dihydro-6H-cyclopenta[e]pyrazolo[1,5-a]pyridin-2-yl)carbamate (70 mg, 66.4% yield) as a brown solid. $^1H$ NMR (400 MHz, DMSO-$d_6$) δ: 10.56 (s, 1H), 7.73 (d, J=9.0 Hz, 1H), 7.66 (d, J=9.0 Hz, 1H), 2.75 (s, 2H), 1.62 (s, 6H), 1.49 (s, 9H); LC-MS: m/z 341 $[M+H]^+$.

Step 7: tert-butyl (3-cyano-6-hydroxy-8,8-dimethyl-7,8-dihydro-6H-cyclopenta[e]pyrazolo[1,5-a]pyridin-2-yl)carbamate

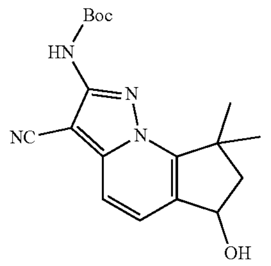 [SMILES: CC(C)(C)OC(=O)Nc1nn2c3c(ccc2c1C#N)C(O)CC3(C)C]

To a solution of tert-butyl (3-cyano-8,8-dimethyl-6-oxo-7,8-dihydro-6H-cyclopenta[e]pyrazolo[1,5-a]pyridin-2-yl) carbamate (400 mg, 1.2 mmol) in MeOH (40 mL) was added sodium borohydride (88.9 mg, 2.4 mmol) in several portions at 0° C. under an atmosphere of nitrogen. The reaction mixture was stirred at 20° C. for 0.5 h. The reaction was quenched with water/ice (100 mL) and extracted with EtOAc (3×150 mL). The combined organic layers were washed with brine (200 mL), dried over anhydrous $Na_2SO_4$, and concentrated under vacuum. The residue was applied onto a silica gel column and eluted with MeOH/DCM (1:10) to give tert-butyl (3-cyano-6-hydroxy-8,8-dimethyl-7,8-dihydro-6H-cyclopenta[e]pyrazolo[1,5-a]pyridin-2-yl) carbamate (300 mg, 68.6% yield) as an off yellow solid. $^1H$ NMR (400 MHz, DMSO-$d_6$) δ: 10.21 (s, 1H), 7.65 (d, J=8.8 Hz, 1H), 7.59 (d, J=8.8 Hz, 1H), 5.56 (s, 1H), 5.16 (s, 1H), 2.44 (dd, J=13.2, 7.4 Hz, 1H), 1.92 (dd, J=13.2, 5.0 Hz, 1H), 1.60 (s, 3H), 1.50 (s, 9H), 1.45 (s, 3H). LC-MS: m/z 343 $[M+H]^+$.

Step 8: tert-butyl (6-chloro-3-cyano-8,8-dimethyl-7,8-dihydro-6H-cyclopenta[e]pyrazolo[1,5-a]pyridin-2-yl)carbamate

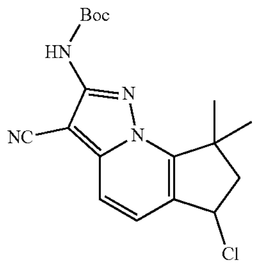 [SMILES: CC(C)(C)OC(=O)Nc1nn2c3c(ccc2c1C#N)C(Cl)CC3(C)C]

To a stirred solution of tert-butyl (3-cyano-6-hydroxy-8,8-dimethyl-7,8-dihydro-6H-cyclopenta[e]pyrazolo[1,5-a]pyridin-2-yl)carbamate (300 mg, 876.2 μmol) in DCM (20 mL) was added $SOCl_2$ (202.3 mg, 1.7 mmol) dropwise at 0° C. under an atmosphere of nitrogen. The resulting mixture was stirred for 30 min at 25° C. under an atmosphere of nitrogen. The resulting mixture was concentrated under vacuum to afford tert-butyl (6-chloro-3-cyano-8,8-dimethyl-7,8-dihydro-6H-cyclopenta[e]pyrazolo[1,5-a]pyridin-2-yl) carbamate (500 mg, crude) as a yellow oil. The product was used directly without further purification in the next step. LC-MS: m/z 361 $[M+H]^+$.

Step 9: tert-butyl (3,6-dicyano-8,8-dimethyl-7,8-dihydro-6H-cyclopenta[e]pyrazolo[1,5-a]pyridin-2-yl)carbamate

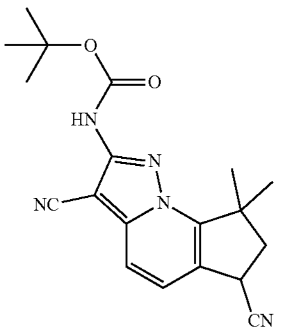 [SMILES: CC(C)(C)OC(=O)Nc1nn2c3c(ccc2c1C#N)C(C#N)CC3(C)C]

To a stirred solution of TMSCN (260.7 mg, 2.6 mmol) and TBAF (2.6 mL, 1 M in THF, 2.6 mmol) in THF (20 mL) was added tert-butyl (6-chloro-3-cyano-8,8-dimethyl-7,8-dihydro-6H-cyclopenta[e]pyrazolo[1,5-a]pyridin-2-yl)carbamate (500 mg, 2.6 mmol) in THF (2 mL) dropwise at 0° C. under an atmosphere of nitrogen. The resulting mixture was stirred for 2 h at 25° C. under an atmosphere of nitrogen. The resulting mixture was concentrated under vacuum. The residue was applied onto a silica gel column and eluted with EtOAc/PE (1:1) to give tert-butyl (3,6-dicyano-8,8-dimethyl-7,8-dihydro-6H-cyclopenta[e]pyrazolo[1,5-a]pyridin-2-yl) carbamate (130 mg, 42.2% yield) as a brown oil. $^1$H NMR (400 MHz, Chloroform-d) δ: 7.65 (d, J=8.8 Hz, 1H), 7.49 (d, J=8.8 Hz, 1H), 7.07 (s, 1H), 4.23 (dd, J=8.8, 6.8 Hz, 1H), 2.60 (dd, J=13.2, 8.8 Hz, 1H), 2.49 (dd, J=13.2, 6.8 Hz, 1H), 1.73 (s, 3H), 1.60 (s, 9H), 1.56 (s, 3H); LC-MS: m/z 352 [M+H]$^+$.

Step 10: 2-hydroxy-8,8-dimethyl-7,8-dihydro-6H-cyclopenta[e]pyrazolo[1,5-a]pyridine-6-carboxylic acid

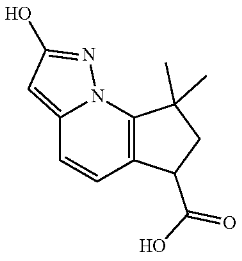 [SMILES: CC1(C)CC(C(=O)O)c2ccc3cc(O)nn3c21]

To a stirred solution of tert-butyl (3,6-dicyano-8,8-dimethyl-7,8-dihydro-6H-cyclopenta[e]pyrazolo[1,5-a]pyridin-2-yl) carbamate (100 mg, 284.6 μmol) in water (3 mL) was added H2504 (3 mL). The reaction was stirred at 126° C. for 16 h under an atmosphere of nitrogen. The reaction mixture was poured into 50 g of crushed ice and the pH was adjusted to 6-7 with aqueous solution of sodium hydroxide (4 M). The resulting mixture was concentrated under vacuum. The residue was diluted with ACN (10 mL). The solid was filtered out. The filtrate was concentrated under vacuum. The residue was applied onto a silica gel column and eluted with MeOH/DCM (1:10) to afford 2-hydroxy-8,8-dimethyl-7,8-dihydro-6H-cyclopenta[e]pyrazolo[1,5-a]pyridine-6-carboxylic acid (30 mg, 42.81% yield) as a yellow solid. $^1$H NMR (300 MHz, Chloroform-d) δ: 7.35 (d, J=8.8 Hz, 1H), 7.28 (d, J=8.8 Hz, 1H), 5.90 (s, 1H), 4.14 (dd, J=8.8, 6.2 Hz, 1H), 2.48 (qd, J=13.2, 7.6 Hz, 2H), 1.67 (s, 3H), 1.58 (s, 3H); LC-MS: m/z 247 [M+H]$^+$.

Step 11: N-(5-chloro-6-(2H-1,2,3-triazol-2-yl)pyridin-3-yl)-2-hydroxy-8,8-dimethyl-7,8-dihydro-6H-cyclopenta[e]pyrazolo[1,5-a]pyridine-6-carboxamide Example 41

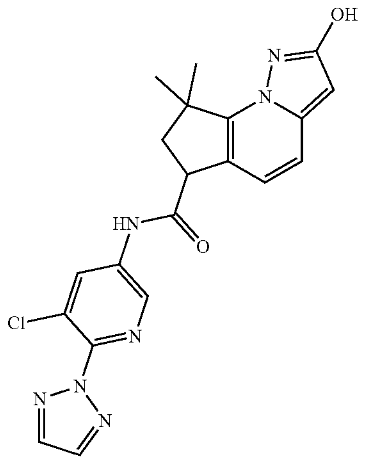

To a stirred solution of 5-chloro-6-(2H-1,2,3-triazol-2-yl)pyridin-3-amine (Method A1, step 2; 28.6 mg, 146.2 μmol) and 2-hydroxy-8,8-dimethyl-7,8-dihydro-6H-cyclopenta[e]pyrazolo[1,5-a]pyridine-6-carboxylic acid (30 mg, 121.8 μmol) in ACN (2 mL) was added TCFH (136.7 mg, 487.3 μmol) and NMI (40 mg, 487.3 μmol) in portions at room temperature. The resulting mixture was stirred for 16 hours at room temperature under an atmosphere of nitrogen. The resulting mixture was concentrated under reduced pressure. The residue was applied onto a silica gel column and eluted with MeOH/DCM (1:10) to give the crude product (10 mg). The crude product was submitted to Prep-HPLC purification and the collected fractions were lyophilized to afford N-(5-chloro-6-(2H-1,2,3-triazol-2-yl)pyridin-3-yl)-2-hydroxy-8,8-dimethyl-7,8-dihydro-6H-cyclopenta[e]pyrazolo[1,5-a]pyridine-6-carboxamide (4.5 mg, 7.8% yield) as an off white solid.

Example 41: $^1$H NMR (300 MHz, Methanol-d$_4$) δ: 8.69 (d, J=2.4 Hz, 1H), 8.64 (d, J=2.4 Hz, 1H), 8.02 (s, 2H), 7.24 (d, J=9.0 Hz, 1H), 7.06 (d, J=9.0 Hz, 1H), 4.19-4.24 (m, 1H), 2.42-2.46 (m, 2H), 1.73 (s, 3H), 1.56 (s, 3H); LC-MS: m/z 424 [M+H]$^+$ Method T1

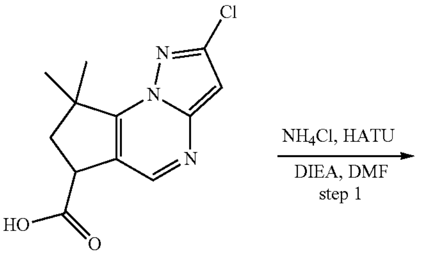

Method A1 Step 6

-continued

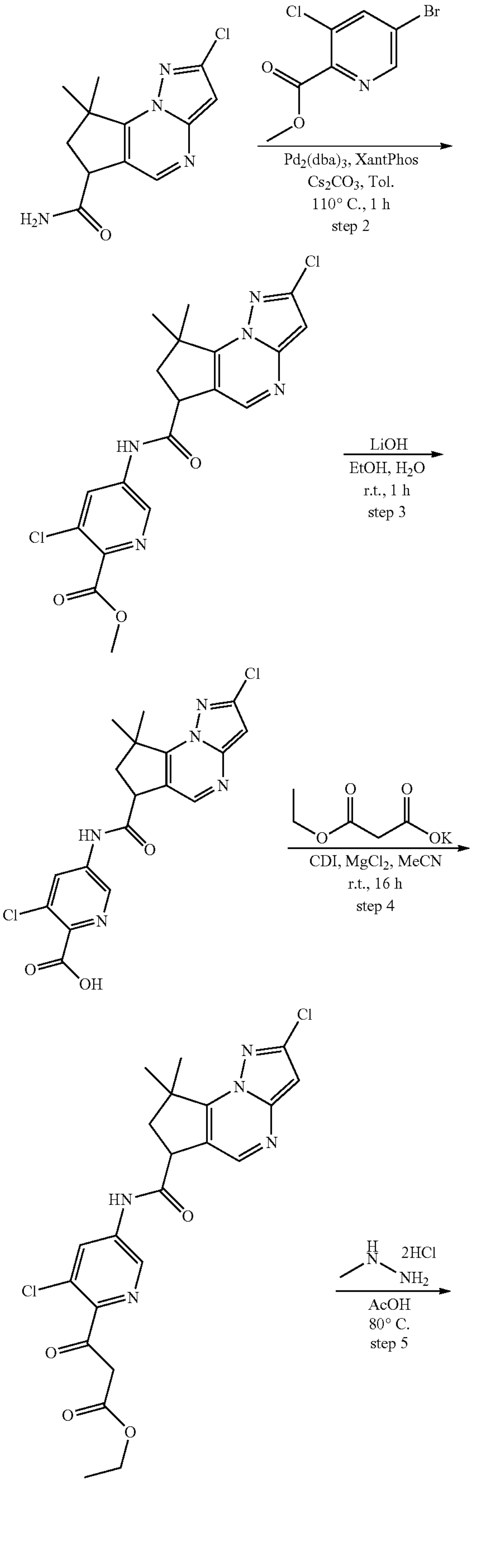

-continued

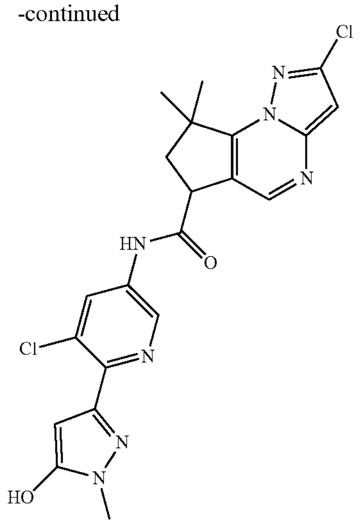

Example 42

Step 1: 2-chloro-8,8-dimethyl-7,8-dihydro-6H-cyclopenta[e]pyrazolo[1,5-a]pyrimidine-6-carboxamide

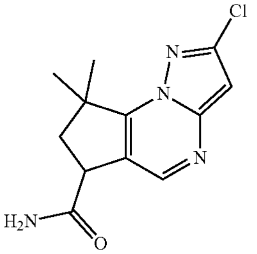 [SMILES: CC1(C)CC(C(N)=O)c2cnc3cc(Cl)nn3c21]

To a stirred mixture of 2-chloro-8,8-dimethyl-7,8-dihydro-6H-cyclopenta[e]pyrazolo[1,5-a]pyrimidine-6-carboxylic acid (Method A1, step 6; 600 mg, 2.3 mmol) in DMF (10 mL) was added $NH_4C1$(305 mg, 5.6 mmol), HATU (1.29 g, 3.4 mmol) and DIEA (583 mg, 4.5 mmol). The mixture was stirred at 25° C. for 1 hr. Water (30 mL) was added and the mixture was extracted with ethyl acetate (10 mL×3). The organic layers were washed with brine (10 mL), dried over anhydrous sodium sulfate and the solvent was removed under reduced pressure. The residue was purified by silica gel column chromatography, eluted with (PE/EtOAc 100:0 to 0:100) to afford 2-chloro-8,8-dimethyl-7,8-dihydro-6H-cyclopenta[e]pyrazolo[1,5-a]pyrimidine-6-carboxamide (500 mg, 75% yield) as an off-white solid. LC-MS: m/z 265 $[M+H]^+$.

Step 2: methyl 3-chloro-5-(2-chloro-8,8-dimethyl-7,8-dihydro-6H-cyclopenta[e]pyrazolo[1,5-a]pyrimidine-6-carboxamido)picolinate

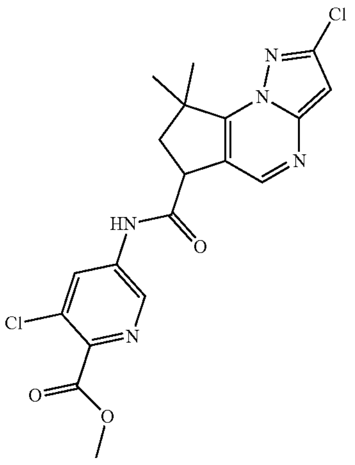 [SMILES: COC(=O)c1ncc(NC(=O)C2CC(C)(C)c3c2cnc2cc(Cl)nn32)cc1Cl]

To a mixture of methyl 5-bromo-3-chloropicolinate (100 mg, 399.2 μmol) in toluene (5 mL) was added 2-chloro-8,8-dimethyl-7,8-dihydro-6H-cyclopenta[e]pyrazolo[1,5-a]pyrimidine-6-carboxamide (106 mg, 399.2 μmol), $Pd_2(dba)_3$ (36 mg, 39.9 μmol), XantPhos (23 mg, 39.9 μmol) and cesium carbonate (260 mg, 798.5 μmol). The reaction mixture was stirred at 110° C. for 1 h under nitrogen. The mixture was allowed to cool down to room temperature and sodium bicarbonate (sat., aq.) (3 mL) was added. The mixture was extracted with EtOAc (3×2 mL). The combined organic layers were washed with brine (3 mL), dried over anhydrous $Na_2SO_4$, and concentrated under reduced pressure. The residue was purified by Prep-TLC with EtOAc/PE (1:1) to give methyl 3-chloro-5-(2-chloro-8,8-dimethyl-7,8-dihydro-6H-cyclopenta[e]pyrazolo[1,5-a]pyrimidine-6-carboxamido)picolinate (120 mg, 55% yield) as a light-yellow oil. LC-MS: m/z 434 $[M+H]^+$.

Step 3: 3-chloro-5-(2-chloro-8,8-dimethyl-7,8-dihydro-6H-cyclopenta[e]pyrazolo[1,5-a]pyrimidine-6-carboxamido)picolinic acid

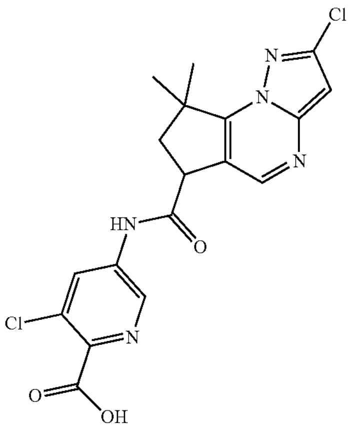 [SMILES: CC1(C)CC(C(=O)Nc2cnc(C(=O)O)c(Cl)c2)c2cnc3cc(Cl)nn3c21]

To a stirred mixture of methyl 3-chloro-5-(2-chloro-8,8-dimethyl-7,8-dihydro-6H-cyclopenta[e]pyrazolo[1,5-a]pyrimidine-6-carboxamido)picolinate (100 mg, 184.2 μmol) in EtOH (1 mL) and water (0.5 mL) was added lithium hydroxide (9 mg, 368.4 μmol). The mixture was stirred at room temperature for 1 h. The reaction mixture was neutralized with 1 N HCl and the mixture was extracted with EtOAc (3×2 mL). The combined organic layers were dried over anhydrous $Na_2SO_4$ and concentrated under reduced pressure to give 3-chloro-5-(2-chloro-8,8-dimethyl-7,8-dihydro-6H-cyclopenta[e]pyrazolo[1,5-a]pyrimidine-6-carboxamido)picolinic acid (80 mg, 99% yield) as an off-white solid. $^1H$ NMR (400 MHz, DMSO-$d_6$) M3.53 (br, 1H), 10.98 (s, 1H), 8.71 (d, J=2.4 Hz, 1H), 8.63 (s, 1H), 8.38 (d, J=2.4 Hz, 1H), 6.95 (s, 1H), 4.43 (dd, J=6.4, 9.2 Hz, 1H), 2.55 (dd, J=9.2, 13.2 Hz, 1H), 2.31 (dd, J=6.4, 13.2 Hz, 1H), 1.63 (s, 3H), 1.55 (s, 3H). LC-MS: m/z 420 $[M+H]^+$.

Step 4: ethyl 3-(3-chloro-5-(2-chloro-8,8-dimethyl-7,8-dihydro-6H-cyclopenta[e]pyrazolo[1,5-a]pyrimidine-6-carboxamido)pyridin-2-yl)-3-oxopropanoate

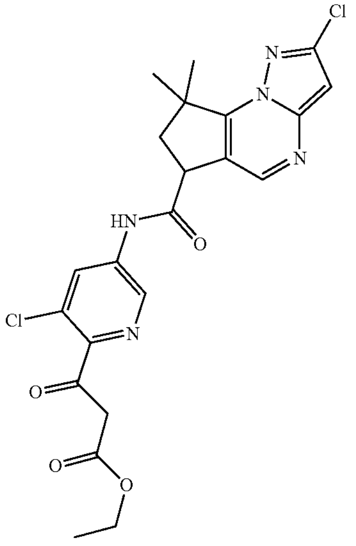 [SMILES: CCOC(=O)CC(=O)c1ncc(NC(=O)C2CC(C)(C)c3c2cnc2cc(Cl)nn32)cc1Cl]

To a mixture of 3-chloro-5-(2-chloro-8,8-dimethyl-7,8-dihydro-6H-cyclopenta[e]pyrazolo[1,5-a]pyrimidine-6-carboxamido)picolinic acid (30 mg, 68.5 μmol) in acetonitrile (1 mL) was added CDI (13 mg, 82.2 μmol), and the mixture was stirred at room temperature for 2.5 h under nitrogen. To the mixture was added potassium 3-ethoxy-3-oxopropanoate (13 mg, 78.8 μmol) and $MgCl_2$ (7 mg, 78.8 μmol). The mixture was stirred at room temperature for 16 h. Then 5% of citric acid aqueous solution (3 mL) was added, and the mixture was extracted with EtOAc (3×2 mL). The combined organic layers were washed with brine (2 mL), dried over anhydrous $Na_2SO_4$ and concentrated under reduced pressure. The residue was purified by Prep-TLC with EtOAc/PE (1:1) to give ethyl 3-(3-chloro-5-(2-chloro-8,8-dimethyl-7,8-dihydro-6H-cyclopenta[e]pyrazolo[1,5-a]pyrimidine-6-carboxamido)pyridin-2-yl)-3-oxopropanoate (10 mg, 27% yield) as an off-white solid. LC-MS: m/z 490 $[M+H]^+$.

Step 5: 2-chloro-N-(5-chloro-6-(5-hydroxy-1-methyl-1H-pyrazol-3-yl)pyridin-3-yl)-8,8-dimethyl-7,8-dihydro-6H-cyclopenta[e]pyrazolo[1,5-a]pyrimidine-6-carboxamide Example 42

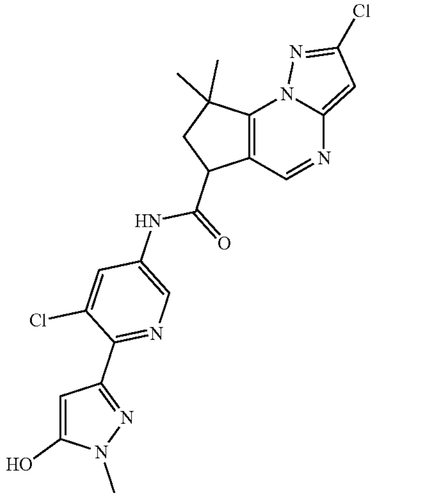

To a solution of ethyl 3-(3-chloro-5-(2-chloro-8,8-dimethyl-7,8-dihydro-6H-cyclopenta[e]pyrazolo[1,5-a]pyrimidine-6-carboxamido)pyridin-2-yl)-3-oxopropanoate (10 mg, 18.3 μmol) in AcOH (1 mL) was added methylhydrazine hydrochloride (3.0 mg, 22.0 μmol). The mixture was stirred at 80° C. for 2 h. The resulting mixture was purified with Prep-HPLC purification and the collected fractions were lyophilized to give 2-chloro-N-(5-chloro-6-(5-hydroxy-1-methyl-1H-pyrazol-3-yl)pyridin-3-yl)-8,8-dimethyl-7,8-dihydro-6H-cyclopenta[e]pyrazolo[1,5-a]pyrimidine-6-carboxamide (1.3 mg, 14% yield) as a yellow solid.

Example 42: $^1$H NMR (300 MHz, DMSO-$d_6$) δ 10.78 (s, 1H), 8.68 (d, J=2.1 Hz, 1H), 8.63 (s, 1H), 8.29 (d, J=2.1 Hz, 1H), 6.94 (s, 1H), 5.83 (s, 1H), 4.41 (dd, J=9.0, 6.3 Hz, 1H), 3.57 (s, 3H), 2.27-2.37 (m, 2H), 1.64 (s, 3H), 1.55 (s, 3H). LC-MS: m/z 472 [M+H]$^+$.

Method U1

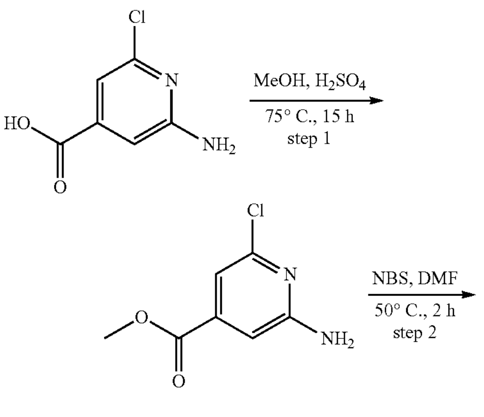

-continued

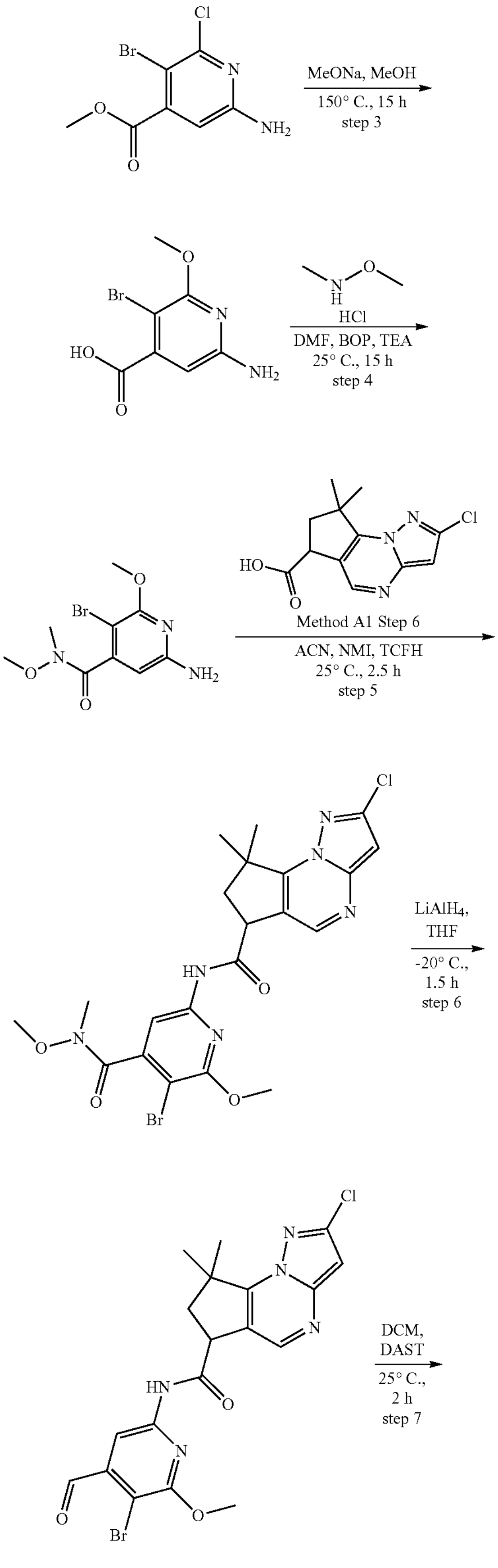

-continued

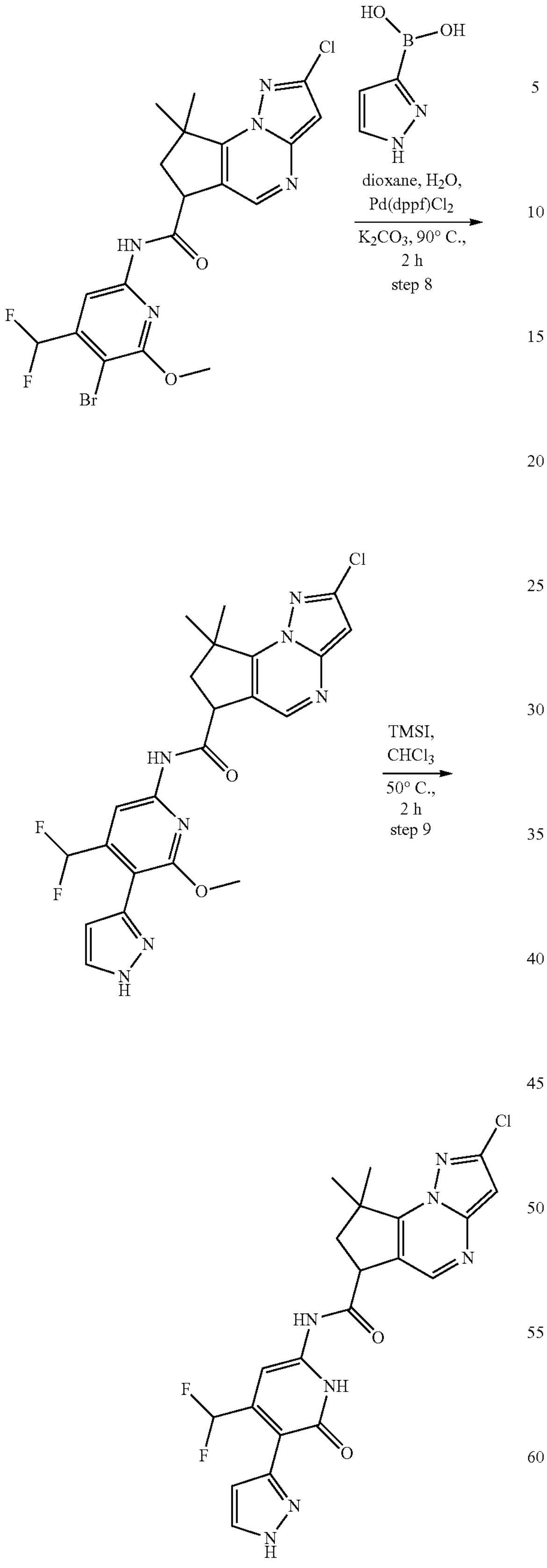

Example 43

Example 43: 2-chloro-N-(4-(difluoromethyl)-6-oxo-5~(1H-pyrazol-3-yl)-1,6-dihydropyridin-2-yl)-8,8-dimethyl-7,8-dihydro-6H-cyclopenta[e]pyrazolo[1,5a]pyrimidine-6-carboxamide Step 1: methyl 2-amino-6-chloroisonicotinate

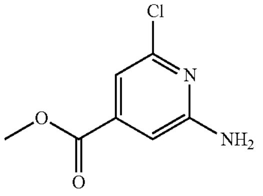

A solution of 2-amino-6-chloroisonicotinic acid (20 g, 116.3 mmol) in MeOH (200 mL) and concentrated H2504 (20 mL) was stirred at 75° C. for 15 h. The mixture was allowed to cool down to 25° C. The resulting mixture was concentrated under vacuum. The residue was diluted with ice water (400 mL). The pH was adjusted to 7-8 with saturated aqueous sodium bicarbonate solution. The resulting solution was extracted with EtOAc (3×400 mL), dried over anhydrous sodium sulfate and concentrated under vacuum. The residue was applied onto a silica gel column and eluted with EtOAc/PE (1:2) to give methyl 2-amino-6-chloroisonicotinate (13 g, 60% yield) as a yellow solid. $^1H$ NMR (400 MHz, DMSO-$d_6$) δ: 6.91 (d, J=1.2 Hz, 1H), 6.83 (d, J=1.2 Hz, 1H), 6.81 (br, 2H), 3.85 (s, 3H). LC-MS: m/z 187 $[M+H]^+$.

Step 2: methyl 6-amino-3-bromo-2-chloroisonicotinate

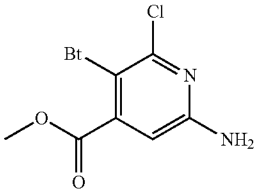

To a stirred solution of methyl 2-amino-6-chloroisonicotinate (2.8 g, 15.2 mmol) in DMF (30 mL) was added 1-bromopyrrolidine-2,5-dione (2.7 g, 15.2 mmol). The mixture was stirred at 50° C. for 2 h. The mixture was cooled to 25° C. The mixture was poured into water (100 mL) and extracted with EtOAc (3×100 mL). The combined organic layers were washed with brine (3×100 mL), dried over anhydrous sodium sulfate and concentrated under vacuum. The residue was applied onto a silica gel column and eluted with EtOAc/PE (1:2) to give methyl 6-amino-3-bromo-2-chloroisonicotinate (3.2 g, 80% yield) as a yellow solid. $^1H$ NMR (300 MHz, DMSO-$d_6$) δ: 6.92 (br, 2H), 6.63 (s, 1H), 3.87 (s, 3H). LC-MS: m/z 265 $[M+H]^+$.

Step 3: 6-amino-3-bromo-2-methoxyisonicotinic acid

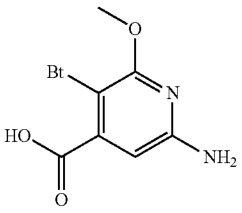

To a stirred solution of methyl 6-amino-3-bromo-2-chloroisonicotinate (1.9 g, 7.2 mmol) in MeOH (50 mL) was added sodium methanolate (5.8 g, 107.4 mmol). The mixture was stirred at 150° C. for 15 h. The mixture was allowed to cool down to 25° C. The mixture was concentrated under vacuum. The residue was diluted with water (20 mL), and the pH was adjusted to 3-4 with HCl (1 M). The resulting solution was concentrated under vacuum. The residue was submitted to Prep-HPLC purification and the collected fractions were lyophilized to give 6-amino-3-bromo-2-methoxyisonicotinic acid (1.2 g, 67% yield) as a brown solid. LC-MS: m/z 247 $[M+H]^+$.

Step 4: 6-amino-3-bromo-N-2-dimethoxy-N-methylisonicotinamide

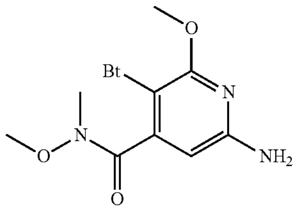

To a stirred solution of 6-amino-3-bromo-2-methoxyisonicotinic acid (6.5 g, 26.4 mmol) in DMF (70 mL) were added N,O-dimethylhydroxylamine hydrochloride (3.8 g, 39.2 mmol), TEA (10.7 g, 105.7 mmol) and BOP (12.9 g, 29.1 mmol) at 0° C. The mixture was stirred at 25° C. for 15 h. The reaction mixture was quenched with saturated aqueous sodium bicarbonate solution (200 mL) and extracted with EtOAc (3×200 mL). The combined organic layers were washed with brine (3×400 mL), dried over anhydrous sodium sulfate and concentrated under vacuum. The residue was applied onto a silica gel column and eluted with MeOH/DCM (1:10) to give 6-amino-3-bromo-N,2-dimethoxy-N-methylisonicotinamide (6.9 g, 90% yield) as a yellow solid. LC-MS: m/z 290 $[M+H]^+$.

Step 5: N-(5-bromo-6-methoxy-4-(methoxy(methyl)carbamoyl)pyridin-2-yl)-2-chloro-8,8-dimethyl-7,8-dihydro-6H-cyclopenta[e]pyrazolo[1,5-a]pyrimidine-6-carboxamide

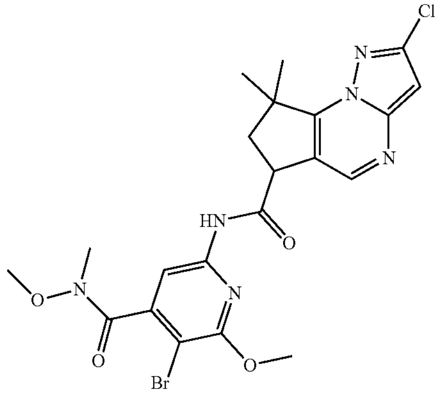 [SMILES: COc1nc(NC(=O)C2CC(C)(C)c3c2cnc2cc(Cl)nn32)cc(C(=O)N(C)OC)c1Br]

To a solution of 6-amino-3-bromo-N,2-dimethoxy-N-methylisonicotinamide (872 mg, 3.0 mmol) in acetonitrile (25 mL) were added 2-chloro-8,8-dimethyl-7,8-dihydro-6H-cyclopenta[e]pyrazolo[1,5-a]pyrimidine-6-carboxylic acid (800 mg, 3.0 mmol), TCFH (2.5 g, 9.1 mmol) and NMI (743 mg, 9.1 mmol). The resulting mixture was stirred at 25° C. for 2.5 h. The reaction mixture was concentrated under vacuum. The residue was applied onto a silica gel column and eluted with EtOAc/PE (1:1) to give N-(5-bromo-6-methoxy-4-(methoxy(methyl)carbamoyl)pyridin-2-yl)-2-chloro-8,8-dimethyl-7,8-dihydro-6H-cyclopenta[e]pyrazolo[1,5-a]pyrimidine-6-carboxamide (1.2 g, 68% yield) as a white solid. LC-MS: m/z 537 $[M+H]^+$.

Step 6: N-(5-bromo-4-formyl-6-methoxypyridin-2-yl)-2-chloro-8,8-dimethyl-7,8-dihydro-6H-cyclopenta[e]pyrazolo[1,5-a]pyrimidine-6-carboxamide

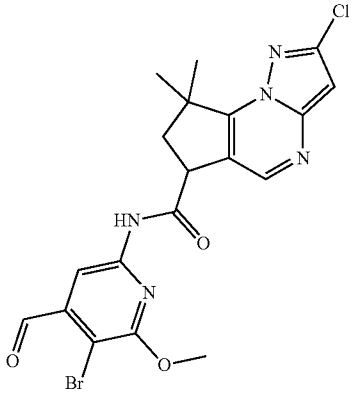 [SMILES: COc1nc(NC(=O)C2CC(C)(C)c3c2cnc2cc(Cl)nn32)cc(C=O)c1Br]

To a solution of N-(5-bromo-6-methoxy-4-(methoxy(methyl)carbamoyl)-pyridin-2-yl)-2-chloro-8,8-dimethyl-7,8-dihydro-6H-cyclopenta[e]pyrazolo[1,5-a]pyrimidine-6-carboxamide (800 mg, 1.5 mmol) in THE (20 mL) was added $LiAlH_4$ (85 mg, 2.2 mmol) slowly at −30° C. The reaction mixture was stirred at −20° C. for 1.5 h. While stirring, $H_2O$ (85 mg) and an aqueous solution of NaOH (85 mg, 10%) were added, followed by the addition of $H_2O$ (85 mg). The mixture was stirred for 10 min at 25° C. and the precipitate was filtered off. The filtrate was concentrated under vacuum and applied onto a silica gel column and eluted with EtOAc/PE (1:3) to give N-(5-bromo-4-formyl-6-methoxypyridin-2-yl)-2-chloro-8,8-dimethyl-7,8-dihydro-6H-cyclopenta[e]pyrazolo[1,5-a]pyrimidine-6-carboxamide (330 mg, 46% yield) as a yellow solid. LC-MS: m/z 478 $[M+H]^+$.

Step 7: N-(5-bromo-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide

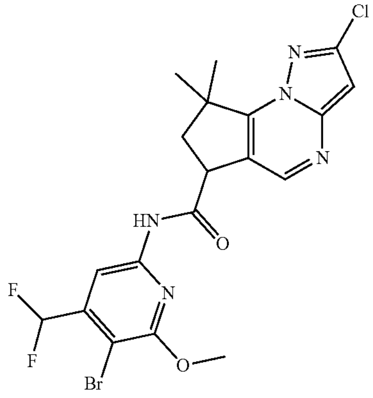 [SMILES: COc1nc(NC(=O)C2CC(C)(C)c3c2cnc2cc(Cl)nn32)cc(C(F)F)c1Br]

To a solution of N-(5-bromo-4-formyl-6-methoxypyridin-2-yl)-2-chloro-8,8-dimethyl-7,8-dihydro-6H-cyclopenta[e]pyrazolo[1,5-a]pyrimidine-6-carboxamide (330 mg, 691.8 μmol) in DCM (8 mL) was added DAST (223 mg, 1.4 mmol) slowly at 0° C. The reaction mixture was warmed up to 25° C. and stirred for 2 h. The reaction mixture was quenched with water (50 mL). The resulting solution was extracted with EtOAc (3×50 mL). The combined organic layers were dried over anhydrous sodium sulfate and concentrated under vacuum. The residue was applied onto a silica gel column and eluted with EtOAc/PE (1:3) to give N-(5-bromo-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (100 mg, 29% yield) as a yellow solid. LC-MS: m/z 500 $[M+H]^+$.

Step 8: 2-chloro-N-(4-(difluoromethyl)-6-methoxy-5~(1H-pyrazol-3-yl)-pyridin-2-yl)-8,8-dimethyl-7,8-dihydro-6H-cyclopenta[e]pyrazolo[1,5-a]pyrimidine-6-carboxamide

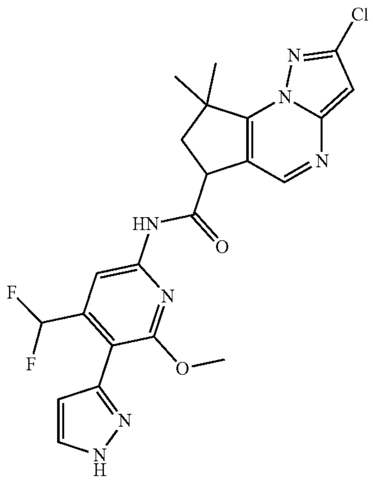 [SMILES: COc1nc(NC(=O)C2CC(C)(C)c3c2cnc2cc(Cl)nn32)cc(C(F)F)c1-c1cc[nH]n1]

To a stirred solution of N-(5-bromo-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (49 mg, 98.6 μmol) and (1H-pyrazol-3-yl)boronic acid (33 mg, 294.6 μmol) in dioxane (8 mL) and $H_2O$ (2 mL) were added $K_2CO_3$ (41 mg, 294.9 μmol) and Pd(dppf)C12 (7 mg, 9.7 μmol). The mixture was stirred at 90° C. for 2 h under nitrogen. The mixture was allowed to cool down to room temperature and concentrated under vacuum. The residue was applied onto a silica gel column and eluted with MeOH/DCM (1:20) to give 2-chloro-N-(4-(difluoromethyl)-6-methoxy-5~(1H-pyrazol-3-yl)pyridin-2-yl)-8,8-dimethyl-7,8-dihydro-6H-cyclopenta[e]pyrazolo[1,5-a]pyrimidine-6-carboxamide (40 mg, 80% yield) as a yellow solid. LC-MS: m/z 488 $[M+H]^+$.

Step 9: 2-chloro-N-(4-(difluoromethyl)-6-oxo-5~(1H-pyrazol-3-yl)-1,6-dihydropyridin-2-yl)-8,8-dimethyl-7,8-dihydro-6H-cyclopenta[e]pyrazolo[1,5-a]-pyrimidine-6-carboxamide Example 43

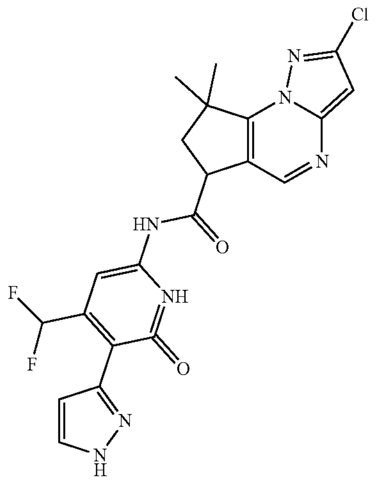

To a stirred solution of 2-chloro-N-(4-(difluoromethyl)-6-methoxy-5~(1H-pyrazol-3-yl)pyridin-2-yl)-8,8-dimethyl-7,8-dihydro-6H-cyclopenta[e]pyrazolo[1,5-a]pyrimidine-6-carboxamide (39 mg, 80.1 μmol) in chloroform (6 mL) was added iodotrimethylsilane (160 mg, 800.0 μmol) at 25° C. The resulting mixture was stirred at 50° C. for 2 h. The reaction mixture was cooled to 25° C. The reaction mixture was quenched with MeOH (10 mL) and concentrated under reduced pressure. The residue was submitted to Prep-HPLC purification and the collected fractions were lyophilized to give 2-chloro-N-(4-(difluoromethyl)-6-oxo-5~(1H-pyrazol-3-yl)-1,6-dihydropyridin-2-yl)-8,8-dimethyl-7,8-dihydro-6H-cyclopenta[e]pyrazolo[1,5-a]pyrimidine-6-carboxamide (3.7 mg, 10% yield) as a yellow solid.

Example 43: $^1$H NMR (400 MHz, DMSO-$d_6$) δ: 13.07 (br, 1H), 11.50 (br, 1H), 10.82 (br, 1H), 8.63 (s, 1H), 7.83 (s, 2H), 7.13 (t, J=51.2 Hz, 1H), 6.94 (s, 1H), 6.66 (s, 1H), 4.51 (s, 1H), 2.66-2.68 (m, 1H), 2.28-2.33 (m, 1H), 1.63 (s, 3H), 1.55 (s, 3H). LC-MS: m/z 474 $[M+H]^+$.

Method V1

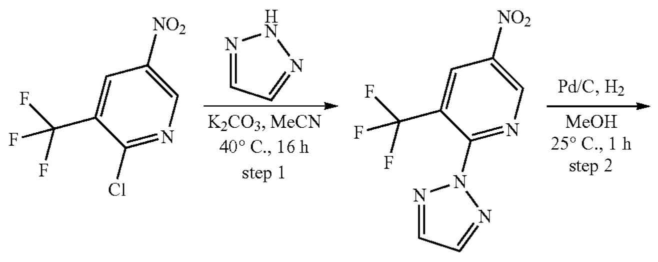

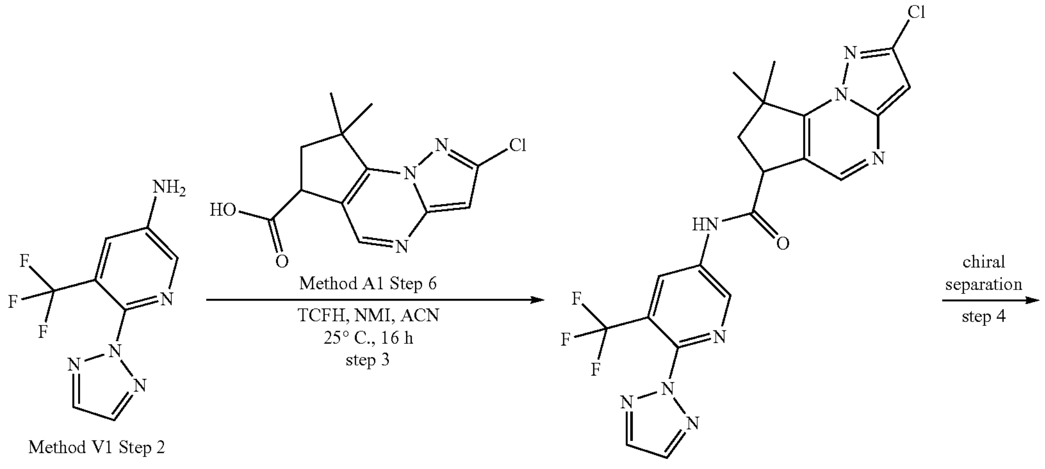

-continued

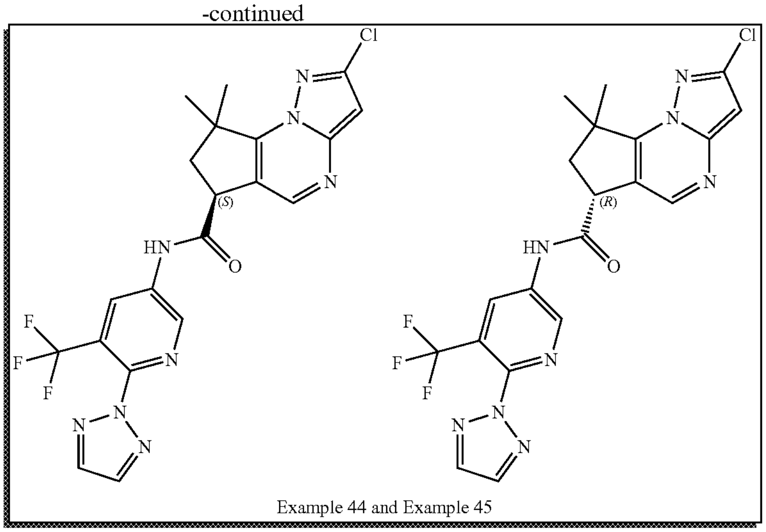

Example 44 and Example 45

Examples 44 and 45: Single Enantiomers Obtained from a Racemic Mixture Containing (S)—N-(6-(2H-1,2,3-triazol-2-yl)-5~(trifluoromethyl)pyridin-3-yl)-2-chloro-8,8-dimethyl-7,8-dihydro-6H-cyclopenta[e]pyrazolo[1,5-a]pyrimidine-6-carboxamide and (R)—N-(6-(2H-1,2,3-triazol-2-yl)-5~(trifluoromethyl)pyridin-3-yl)-2-chloro-8,8-dimethyl-7,8-dihydro-6H-cyclopenta[e]pyrazolo[1,5-a]pyrimidine-6-carboxamide Step 1: 5-nitro-2-(2H-1,2,3-triazol-2-yl)-3-(trifluoromethyl)pyridine

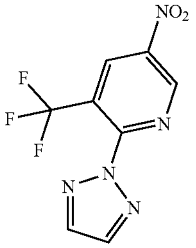 [SMILES: O=[N+]([O-])c1cnc(-n2nccn2)c(C(F)(F)F)c1]

To a stirred solution of 2-chloro-5-nitro-3-(trifluoromethyl)pyridine (2 g, 8.8 mmol) in MeCN (40 mL) were added 2H-triazole (670 mg, 9.7 mmol) and $K_2CO_3$ (2.4 g, 51.8 mmol). The resulting mixture was stirred for 16 h at 40° C. The mixture was allowed to cool down to 25° C. The reaction mixture was filtered and the collected solid was washed with EtOAc (3×50 mL). The combined organic layers were concentrated under reduced pressure. The residue was applied on a silica gel column chromatography and eluted with EtOAc/PE (1:3) to give 5-nitro-2-(2H-1,2,3-triazol-2-yl)-3-(trifluoromethyl)pyridine (1.2 g, 52% yield) as a white solid. $^1$H NMR (300 MHz, DMSO-$d_6$) δ: 9.70 (d, J=4 Hz, 1H), 9.17 (d, J=4 Hz, 1H), 8.87 (s, 2H). LC-MS: m/z 260 $[M+H]^+$.

Step 2: 6-(2H-1,2,3-triazol-2-yl)-5~(trifluoromethyl) pyridin-3-amine

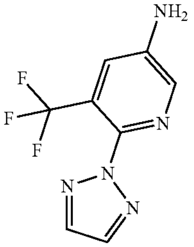 [SMILES: Nc1cnc(-n2nccn2)c(C(F)(F)F)c1]

To a solution of 5-nitro-2-(2H-1,2,3-triazol-2-yl)-3-(trifluoromethyl)pyridine (1.2 g, 4.4 mmol) was added Pd/C (10%, 236 mg) at 25° C. The flask was evacuated and flushed three times with nitrogen, followed by flushing with hydrogen. The mixture was stirred 1 h at room temperature under an atmosphere of hydrogen. The solid was filtered out. The filtrate was concentrated under reduced pressure. The residue was applied on a silica gel column chromatography and eluted with EtOAc/PE (1:1) to afford 6-(2H-1,2,3-triazol-2-yl)-5-(trifluoromethyl)pyridin-3-amine (Method V1 Step 2; 800 mg, 78% yield) as yellow oil. LC-MS: m/z 230 $[M+H]^+$.

Step 3: N-(6-(2H-1,2,3-triazol-2-yl)-5~(trifluoromethyl)pyridin-3-yl)-2-chloro-8,8-dimethyl-7,8-dihydro-6H-cyclopenta[e]pyrazolo[1,5-a]pyrimidine-6-carboxamide

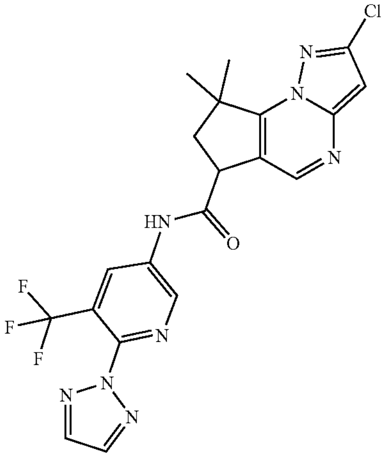

To a stirred solution of 6-(2H-1,2,3-triazol-2-yl)-5~(trifluoromethyl) pyridin-3-amine (86 mg, 376.4 μmol) and 2-chloro-8,8-dimethyl-7,8-dihydro-6H-cyclopenta[e]pyrazolo[1,5-a]pyrimidine-6-carboxylic acid (Method A1 Step 6; 100 mg, 376.4 μmol) in acetonitrile (5 mL) were added TCFH (421 mg, 1.5 mmol) and NMI (123 mg, 1.5 mmol). The mixture was stirred at 25° C. for 16 h. The resulting mixture was concentrated under reduced pressure. The residue was submitted to Prep-HPLC purification and the collected fractions were lyophilized to give N-(6 (2H-1,2,3-triazol-2-yl)-5~(trifluoromethyl)pyridin-3-yl)-2-chloro-8,8-dimethyl-7,8-dihydro-6H-cyclopenta[e]pyrazolo[1,5-a] pyrimidine-6-carboxamide (70 mg, 39% yield) as a white solid. LC-MS: m/z 477 $[M+H]^+$.

Step 4: Separation of Enantiomers to Obtain (S)—N-(6-(2H-1,2,3-triazol-2-yl)-5-(trifluoromethyl)pyridin-3-yl)-2-chloro-8,8-dimethyl-7,8-dihydro-6H-cyclopenta[e]pyrazolo[1,5-a]pyrimidine-6-carboxamide and (R)—N-(6-(2H-1,2,3-triazol-2-yl)-5-(trifluoromethyl)pyridin-3-yl)-2-chloro-8,8-dimethyl-7,8-dihydro-6H-cyclopenta[e]pyrazolo[1,5-a]pyrimidine-6-carboxamide Example 44

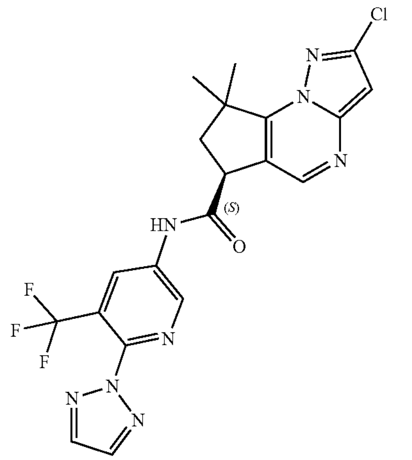

and

Example 45

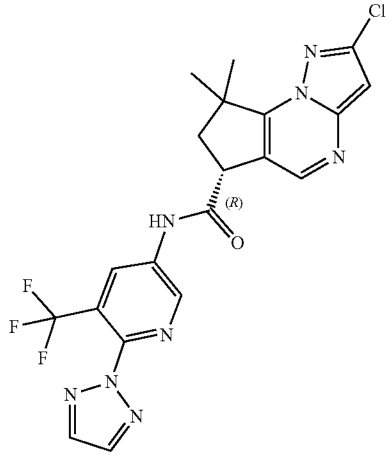

70 mg of N-(6-(2H-1,2,3-triazol-2-yl)-5~(trifluoromethyl)pyridin-3-yl)-2-chloro-8,8-dimethyl-7,8-dihydro-6H-cyclopenta[e]pyrazolo[1,5-a]pyrimidine-6-carboxamide were submitted to chiral HPLC purification (Column: CHIRAL ART Cellulose-SB, 2*25 cm, 5 um; Mobile Phase A:Hex(0.5% 2M $NH_3$-MeOH), Mobile Phase B:EtOH; Flow rate: 20 mL/min; isocratic 50% B 21 min; 254/220 nm; RT1:12.167; RT2:17.18; Injection Volume: 1 ml; Number of Runs: 3). The first eluting isomer was concentrated and lyophilized to afford Example 44 as a white solid (21.6 mg, 31% yield). The second eluting isomer was concentrated and lyophilized to afford Example 45 as a white solid (15.2 mg, 22% yield).

Example 44: $^1H$ NMR (300 MHz, DMSO-$d_6$) δ: 11.22 (s, 1H), 9.03 (d, J=2.4 Hz, 1H), 8.82 (d, J=2.4 Hz, 1H), 8.68 (s, 1H), 8.20 (s, 2H), 6.96 (s, 1H), 4.49 (dd, J=6.3, 9.3 Hz, 1H), 2.59 (dd, J=9.3, 13.2 Hz, 1H), 2.37 (dd, J=6.3, 13.2 Hz, 1H), 1.66 (s, 3H), 1.58 (s, 3H). LC-MS: m/z 477 $[M+H]^+$.
Example 45: $^1$H NMR (300 MHz, DMSO-$d_6$) δ: 11.23 (s, 1H), 9.03 (d, J=2.1 Hz, 1H), 8.82 (d, J=2.1 Hz, 1H), 8.68 (s, 1H), 8.20 (s, 2H), 6.96 (s, 1H), 4.49 (dd, J=6.3, 9.3 Hz, 1H), 2.59 (dd, J=9.3, 13.2 Hz, 1H), 2.37 (dd, J=6.3, 13.2 Hz, 1H), 1.66 (s, 3H), 1.58 (s, 3H). LC-MS: m/z 477 $[M+H]^+$
The absolute stereochemistry for each separated isomer was not determined.
Method W1
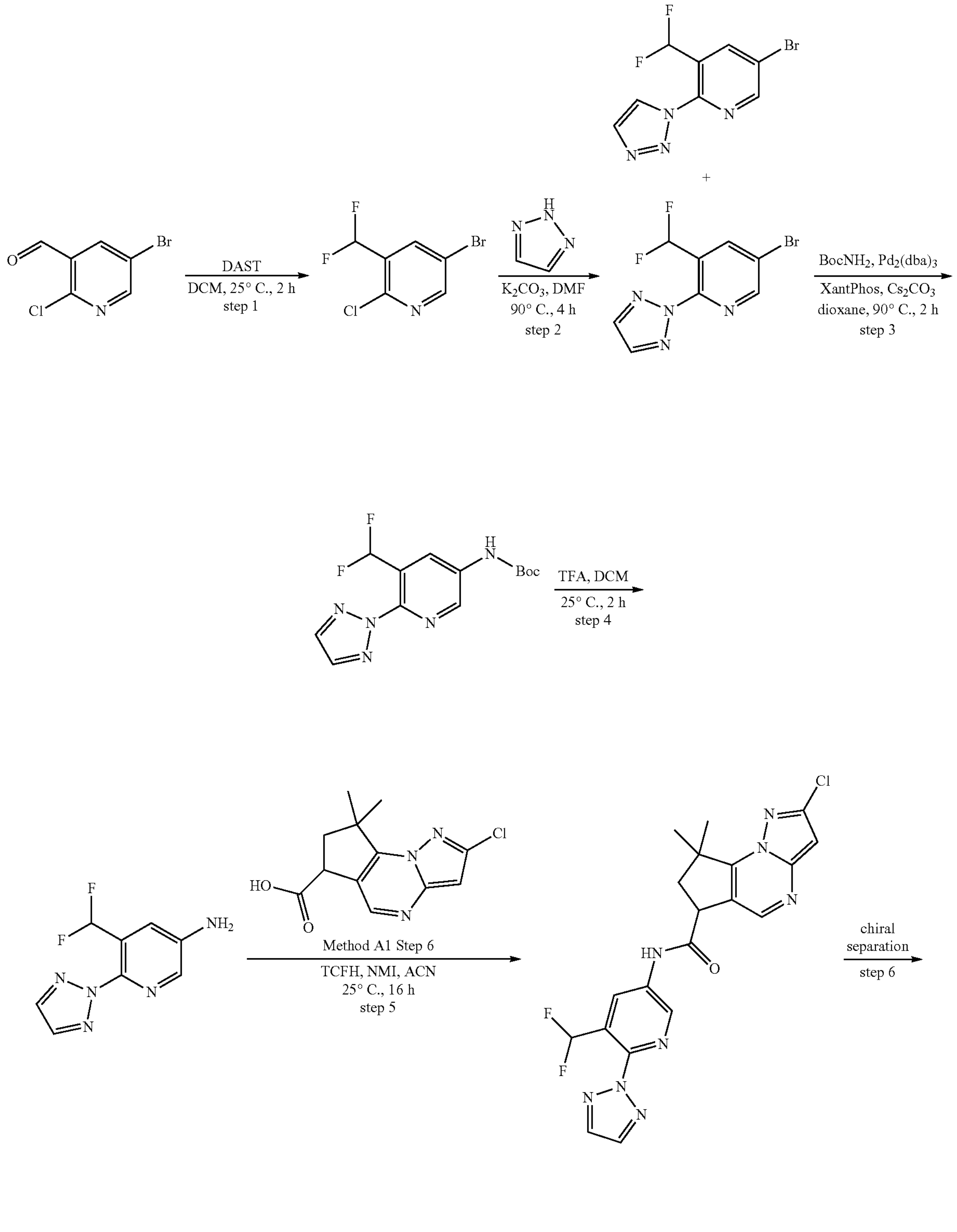

-continued

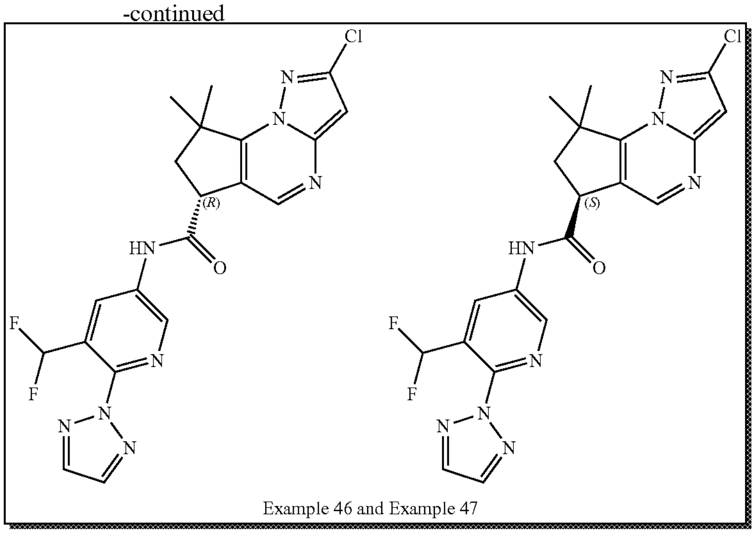

Example 46 and Example 47

Examples 46 and 47: Single Enantiomers Obtained from a Racemic Mixture Containing (R)-2-chloro-N-(5-(difluoromethyl)-6-(2H-1,2,3-triazol-2-yl) pyridin-3-yl)-8,8-dimethyl-7,8-dihydro-6H-cyclopenta [e]pyrazolo[1,5-a]pyrimidine-6-carboxamide and (S)-2-chloro-N-(5-(difluoromethyl)-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide Step 1: 5-bromo-2-chloro-3-(difluoromethyl)pyridine

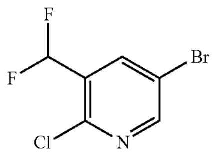 [SMILES: FC(F)c1cc(Br)cnc1Cl]

To a stirred solution of 5-bromo-2-chloronicotinaldehyde (2.5 g, 11.3 mmol) in DCM (50 mL) was added DAST (3.6 g, 22.6 mmol) dropwise at 0° C. The reaction mixture was stirred at 25° C. for 2 h. The pH of the mixture was adjusted to 8 with saturated aqueous $NaHCO_3$. The resulting mixture was extracted with DCM (3×100 mL). The combined organic layers were washed with brine (100 mL), dried over anhydrous $Na_2SO_4$, filtered and concentrated under reduced pressure to afford crude 5-bromo-2-chloro-3-(difluoromethyl)pyridine (1.5 g, 55% yield) as a light-yellow oil. $^1H$ NMR (400 MHz, Chloroform-d) δ: 8.55-8.59 (m, 1H), 8.09-8.14 (m, 1H), 6.87 (t, J=54.0 Hz, 1H). LC-MS: m/z 242 $[M+H]^+$.

Step 2: 5-bromo-3-(difluoromethyl)-2-(2H-1,2,3-triazol-2-yl)pyridine and 5-bromo-3-(difluoromethyl)-2-(1H-1,2,3-triazol-1-yl)pyridine

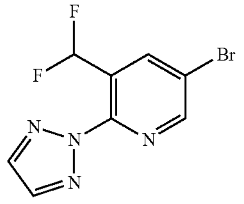

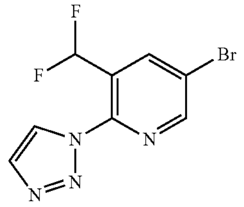

To a stirred solution of 5-bromo-2-chloro-3-(difluoromethyl)pyridine (1.5 g, 6.2 mmol) in DMF (20 mL) were added $K_2CO_3$ (1.7 g, 12.8 mmol) and 2H-1,2,3-triazole (512 mg, 7.4 mmol). The reaction mixture was stirred at 90° C. for 4 h. The mixture was poured into water (30 mL) and extracted with EtOAc (3×100 mL). The combined organic layers were washed with brine (3×100 mL), dried over anhydrous $Na_2SO_4$. After filtration, the filtrate was concentrated under reduced pressure. The residue was applied onto a silica gel column and eluting with EtOAc/PE (1:3) to afford a mixture of 5-bromo-3-(difluoromethyl)-2-(2H-1,2,3-triazol-2-yl)pyridine and 5-bromo-3-(difluoromethyl)-2-(1H-1,2,3-triazol-1-yl)pyridine (1.6 g, 94% yield) as a yellow solid. LC-MS: m/z 275 $[M+H]^+$.

Step 3: tert-butyl (5-(difluoromethyl)-6-(2H-1,2,3-triazol-2-yl)pyridin-3-yl)carbamate and tert-butyl (5-(difluoromethyl)-6-(1H-1,2,3-triazol-1-yl)pyridine-3-yl)carbamate

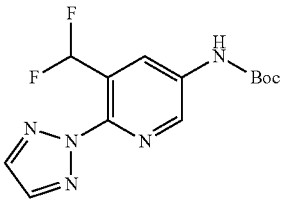

-continued

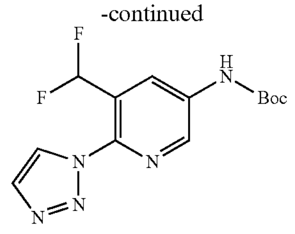

To a stirred solution of the mixture of 5-bromo-3-(difluoromethyl)-2-(2H-1,2,3-triazol-2-yl)pyridine and 5-bromo-3-(difluoromethyl)-2-(1H-1,2,3-triazol-1-yl)pyridine (1.6 g, 5.8 mmol) in dioxane (160 mL) were added tert-butyl carbamate (1.02 g, 8.7 mmol), xantphos (1.01 g, 1.7 mmol), $Pd_2(dba)_3$ (668 mg, 1.2 mmol) and $Cs_2CO_3$ (5.7 g, 17.4 mmol). The reaction mixture was stirred at 90° C. for 2 h under N2. The mixture was allowed to cool down to room temperature. The resulting mixture was filtered. The filter cake was washed with EtOAc (3×100 mL). The filtrate was concentrated under reduced pressure. The residue was applied onto a silica gel column and eluted with EtOAc/PE (1:4) to afford tert-butyl (5-(difluoromethyl)-6-(2H-1,2,3-triazol-2-yl)pyridin-3-yl)carbamate (700 mg, 38.7% yield) as a yellow solid and tert-butyl (5-(difluoromethyl)-6-(1H-1,2,3-triazol-1-yl) pyridin-3-yl)carbamate (600 mg, 33% yield) as a yellow solid.

Tert-butyl (5-(difluoromethyl)-6-(2H-1,2,3-triazol-2-yl) pyridin-3-yl)carbamate: $^1H$ NMR (400 MHz, Methanol-$d_4$) δ: 8.69 (d, J=2.4 Hz, 1H), 8.50 (d, J=2.4 Hz, 1H), 8.04 (s, 2H), 7.45 (t, J=54.8 Hz, 1H), 1.55 (s, 9H). LC-MS: m/z 312 $[M+H]^+$ Tert-butyl (5-(difluoromethyl)-6-(1H-1,2,3-triazol-1-yl) pyridin-3-yl)carbamate $^1H$ NMR (400 MHz, Methanol-$d_4$) δ: 8.72 (d, J=2.4 Hz, 1H), 8.59 (d, J=1.2 Hz, 1H), 8.50 (d, J=2.4 Hz, 1H), 7.91 (d, J=1.2 Hz, 1H), 7.60 (t, J=54.8 Hz, 1H), 1.56 (s, 9H). LC-MS: m/z 312 $[M+H]^+$.

Step 4: 5-(difluoromethyl)-6-(2H-1,2,3-triazol-2-yl) pyridin-3-amine

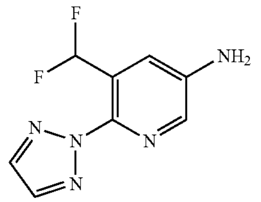 [SMILES: Nc1cnc(-n2nccn2)c(C(F)F)c1]

To a stirred solution of tert-butyl (5-(difluoromethyl)-6-(2H-1,2,3-triazol-2-yl)pyridin-3-yl)carbamate (200 mg, 643 μmol) in DCM (20 mL) was added TFA (2.9 g, 25.7 mmol). The mixture was stirred at 25 for 2 h. The resulting mixture was concentrated under vacuum. The residue was applied onto a silica gel column chromatography and eluted with EtOAc/PE (1:1) to afford 5-(difluoromethyl)-6-(2H-1,2,3-triazol-2-yl)pyridin-3-amine (110 mg, 81% yield) as a yellow solid. $^1H$ NMR (300 MHz, Methanol-$d_4$) δ: 8.00 (d, J=2.7 Hz, 1H), 7.96 (s, 2H), 7.08 (t, J=55.2 Hz, 1H). LC-MS: m/z 212 $[M+H]^+$.

Step 5: 2-chloro-N-(5-(difluoromethyl)-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

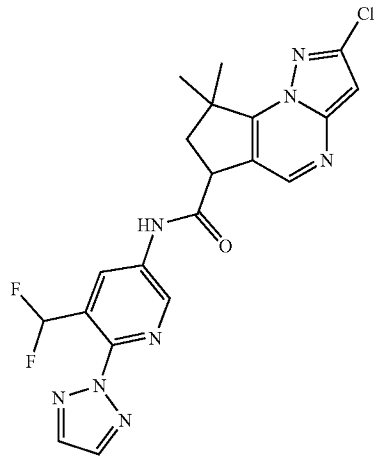

To a stirred solution of 5-(difluoromethyl)-6-(2H-1,2,3-triazol-2-yl)pyridin-3-amine (110 mg, 520.9 μmol) and 2-chloro-8,8-dimethyl-7,8-dihydro-6H-cyclopenta[e]pyrazolo[1,5-a]pyrimidine-6-carboxylic acid (Method A1 Step 6; 138 mg, 520.9 μmol) in acetonitrile (5 mL) were added TCFH (588 mg, 2.1 mmol) and NMI (171 mg, 2.1 mmol). The mixture was stirred at 25° C. for 16 h. The resulting mixture was concentrated under reduced pressure. The residue was submitted to Prep-HPLC purification and the collected fractions were lyophilized to give 2-chloro-N-(5-(difluoromethyl)-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide (100 mg, 42% yield) as a white solid. LC-MS: m/z 459 $[M+H]^+$.

Step 6: Separation of Enantiomers to Obtain (R)-2-chloro-N-(5-(difluoromethyl)-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-(difluoromethyl)-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide Example 46

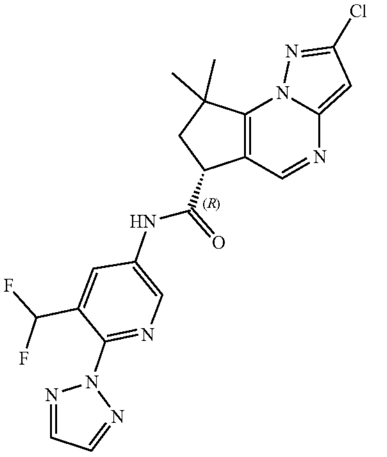

and

Example 47

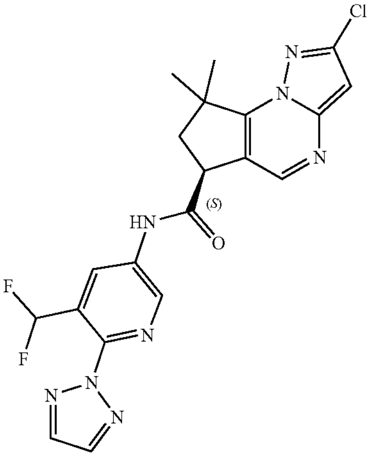

100 mg of 2-chloro-N-(5-(difluoromethyl)-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IA, 2*25 cm, 5 um; Mobile Phase A:Hex(0.5% 2M $NH_3$-MeOH), Mobile Phase B:EtOH; Flow rate: 20 mL/min; isocratic 50% B 20 min; 254/220 nm; RT1: 7.229; RT2: 13.27; Injection Volume: 1 ml; Number of Runs: 3). The first eluting isomer was concentrated and lyophilized to afford Example 46 as a white solid (29.2 mg, 29% yield). The second eluting isomer was concentrated and lyophilized to afford Example 47 as a white solid (35.8 mg, 36% yield).

Example 46: $^1H$ NMR (300 MHz, DMSO-$d_6$) δ: 11.06 (s, 1H), 8.93 (d, J=2.4 Hz, 1H), 8.69 (d, J=2.4 Hz, 1H), 8.68 (s, 1H), 8.22 (s, 2H), 7.35 (t, J=54.3 Hz, 1H), 6.96 (s, 1H), 4.47 (dd, J=6.3, 9.3 Hz, 1H), 2.58 (dd, J=9.3, 13.2 Hz, 1H), 2.36 (dd, J=6.3, 13.2 Hz, 1H), 1.65 (s, 3H), 1.57 (s, 3H). LC-MS: m/z 459 $[M+H]^+$.

Example 47: $^1H$ NMR (300 MHz, DMSO-$d_6$) δ: 11.06 (s, 1H), 8.93 (d, J=2.4 Hz, 1H), 8.69 (d, J=2.4 Hz, 1H), 8.68 (s, 1H), 8.22 (s, 2H), 7.35 (t, J=54.3 Hz, 1H), 6.96 (s, 1H), 4.47 (dd, J=6.3, 9.3 Hz, 1H), 2.58 (dd, J=9.3, 13.2 Hz, 1H), 2.36 (dd, J=6.3, 13.2 Hz, 1H), 1.66 (s, 3H), 1.57 (s, 3H). LC-MS: m/z 459 $[M+H]^+$.

The absolute stereochemistry for each separated isomer was not determined.

Method X1

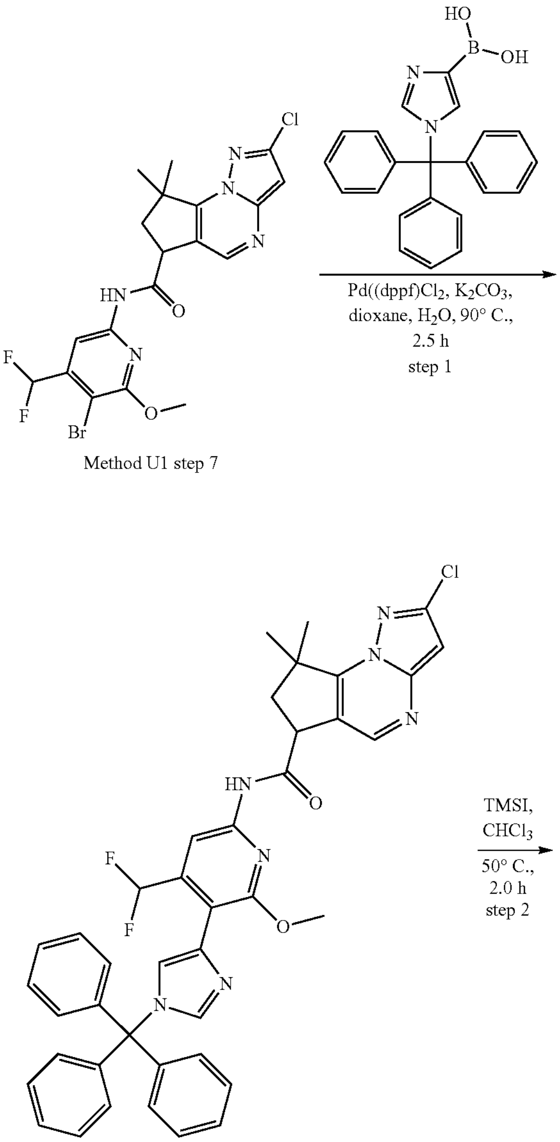

-continued

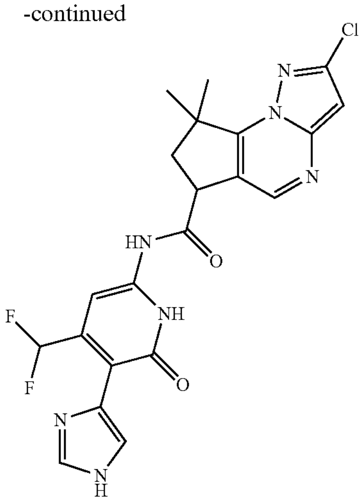

Example 48

Example 48: 2-chloro-N-(4-(difluoromethyl)-5~(1H-imidazol-4-yl)-6-oxo-1,6-dihydropyridin-2-yl)-8,8-dimethyl-7,8-dihydro-6H-cyclopenta[e]pyrazolo[1,5-a]pyrimidine-6-carboxamide Step 1: 2-chloro-N-(4-(difluoromethyl)-6-methoxy-5~(1-trityl-1H-imidazol-4-yl)pyridin-2-yl)-8,8-dimethyl-7,8-dihydro-6H-cyclopenta[e]pyrazolo[1,5-a]pyrimidine-6-carboxamide

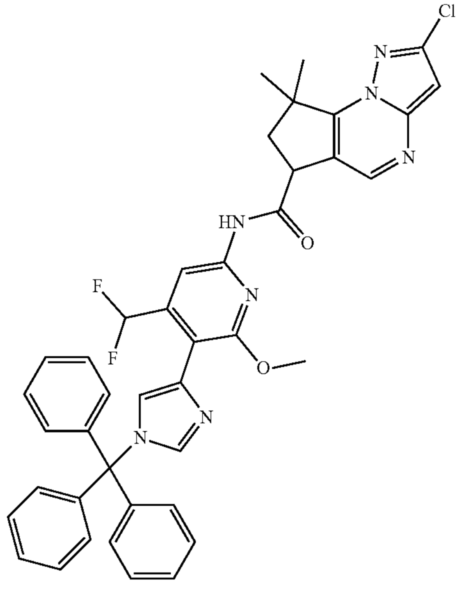

To a solution of N-(5-bromo-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (Method U1 step 7; 80 mg, 159.7 μmol) in dioxane (9 mL)

and $H_2O$ (3 mL) were added (1-trityl-1H-imidazol-4-yl) boronic acid (170 mg, 479.3 μmol), Pd(dppf)C12 (12 mg, 15.9 μmol) and $K_2CO_3$ (22 mg, 159.7 μmol) under nitrogen. The reaction was stirred for 2.5 h at 90° C. The mixture was cooled to 25° C. The reaction mixture was concentrated, and the residue was applied onto a silica gel column and eluted with EtOAc/PE (1:1) to obtain 2-chloro-N-(4-(difluoromethyl)-6-methoxy-5-(1-trityl-1H-imidazol-4-yl)pyridin-2-yl)-8,8-dimethyl-7,8-dihydro-6H-cyclopenta[e]pyrazolo[1,5-a]pyrimidine-6-carboxamide (84 mg, 65% yield) as a white solid. LC-MS: m/z 730 $[M+H]^+$.

Step 2: 2-chloro-N-(4-(difluoromethyl)-5~(1H-imidazol-4-yl)-6-oxo-1,6-dihydropyridin-2-yl)-8,8-dimethyl-7,8-dihydro-6H-cyclopenta[e]pyrazolo[1,5-a]pyrimidine-6-carboxamide Example 48

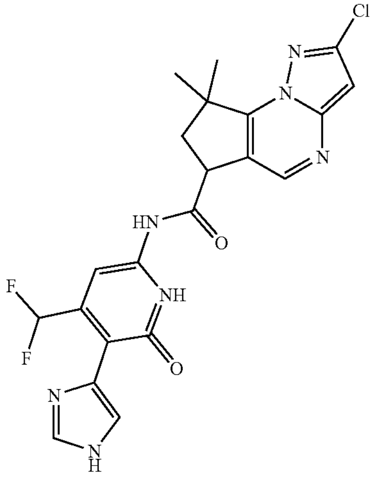

To a solution of 2-chloro-N-(4-(difluoromethyl)-6-methoxy-5-(1-trityl-1H-imidazol-4-yl)pyridin-2-yl)-8,8-dimethyl-7,8-dihydro-6H-cyclopenta[e]pyrazolo[1,5-a]pyrimidine-6-carboxamide (84 mg, 115.1 μcool) in chloroform (5 mL) was added iodotrimethylsilane (230 mg, 1.2 mmol) at 25° C. The resulting mixture was stirred at 50° C. for 2 h. The mixture was cooled to 25° C. The reaction mixture was quenched with MeOH (10 mL) and concentrated under reduced pressure. The residue was submitted to Prep-HPLC purification and the collected fractions were lyophilized to give 2-chloro-N-(4-(difluoromethyl)-5~(1H-imidazol-4-yl)-6-oxo-1,6-dihydropyridin-2-yl)-8,8-dimethyl-7,8-dihydro-6H-cyclopenta[e]pyrazolo[1,5-a]pyrimidine-6-carboxamide (9.4 mg, 17% yield) as a light yellow solid.

Example 48: $^1H$ NMR (400 MHz, DMSO-$d_6$) δ: 13.39 (br, 2H), 10.95 (s, 1H), 8.69 (br, 1H), 8.62 (s, 1H), 7.67 (s, 1H), 7.08-7.43 (m, 2H), 6.93 (s, 1H), 4.51 (t, J=8.4 Hz, 1H), 2.51-2.57 (m, 1H), 2.28-2.33 (m, 1H), 1.63 (s, 3H), 1.55 (s, 3H). LC-MS: m/z 474 $[M+H]^+$.

Method Y1
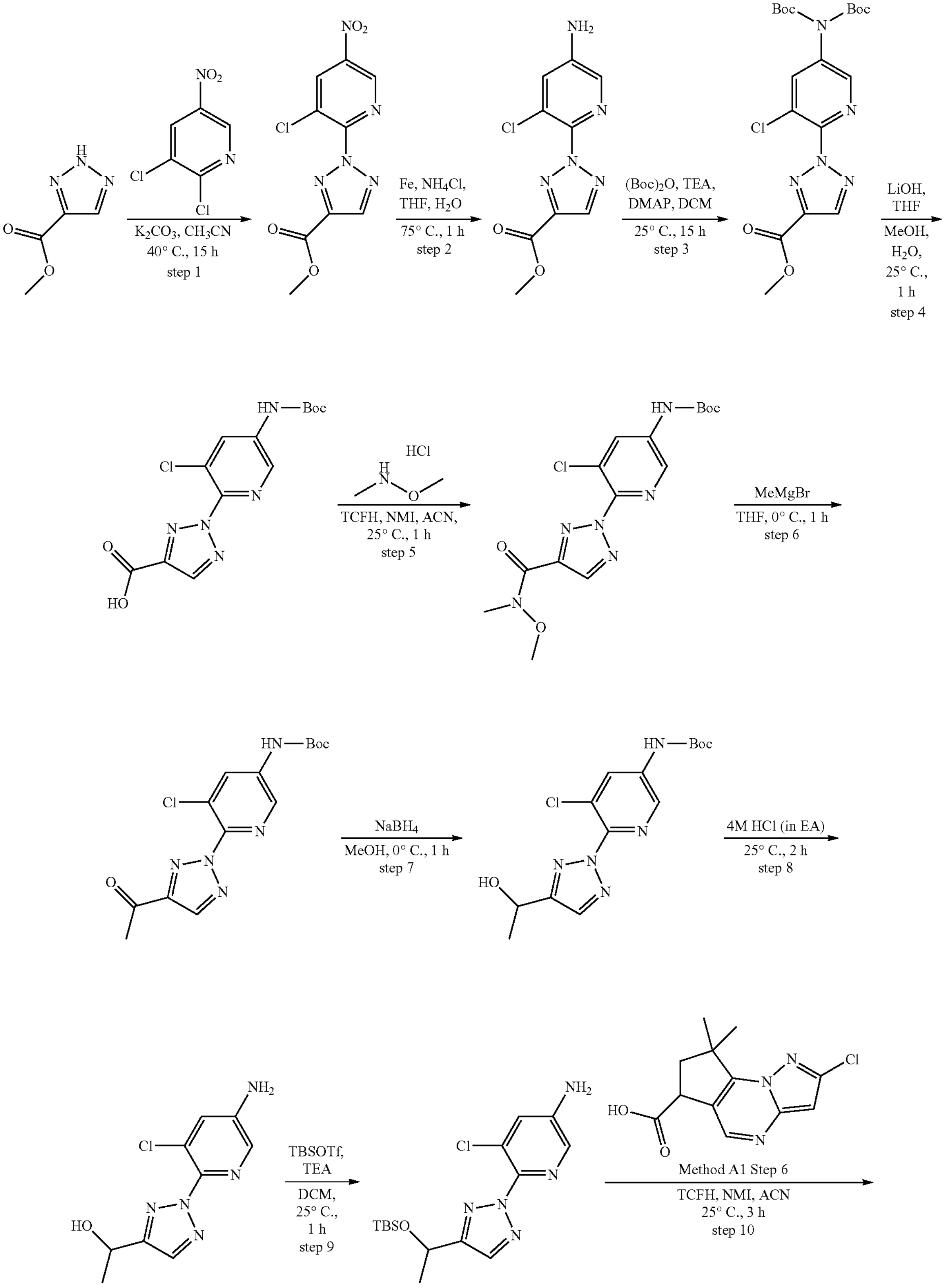
Method Y1 Step 8

-continued
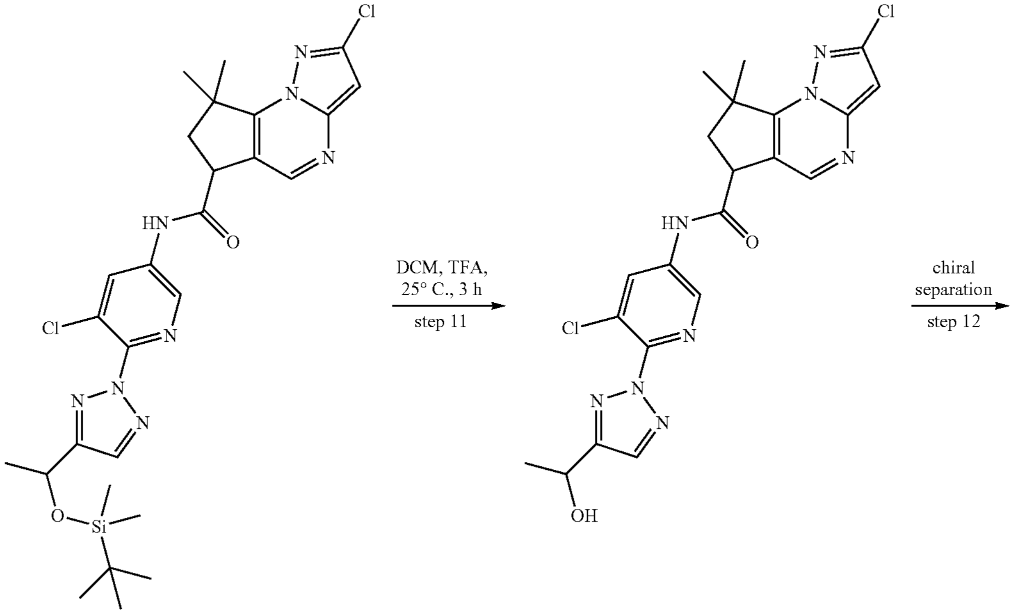
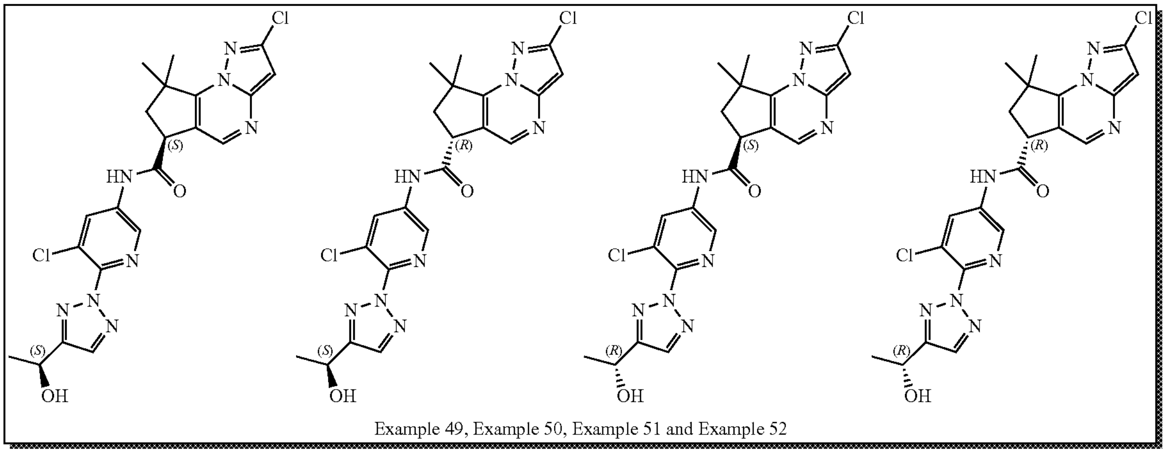
Example 49, Example 50, Example 51 and Example 52

Examples 49, 50, 51 and 52: Single Enantiomers Obtained from Racemic Mixtures containing (S)-2-chloro-N-(5-chloro-6-(4-((S)-1-hydroxyethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide, (S)-2-chloro-N-(5-chloro-6-(4-((R)-1-hydroxyethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide, (R)-2-chloro-N-(5-chloro-6-(4-((S)-1-hydroxyethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide and (R)-2-chloro-N-(5-chloro-6-(4-((R)-1-hydroxyethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide Step 1: methyl 2-(3-chloro-5-nitropyridin-2-yl)-2H-1,2,3-triazole-4-carboxylate

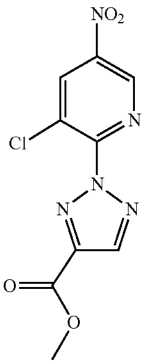 [SMILES: COC(=O)c1cnn(-c2ncc([N+](=O)[O-])cc2Cl)n1]

Into a 500 mL flask were placed methyl 2H-1,2,3-triazole-4-carboxylate (6.5 g, 51.5 mmol), acetonitrile (150 mL), 2,3-dichloro-5-nitropyridine (9.0 g, 46.9 mmol) and $K_2CO_3$ (8.4 g, 60.9 mmol). The reaction mixture was stirred at 40° C. for 15 h. The solid was filtered out. The filtrate was concentrated under vacuum. The residue was purified by Prep-HPLC purification and the collected fractions were concentrated to afford methyl 2-(3-chloro-5-nitropyridin-2-yl)-2H-1,2,3-triazole-4-carboxylate (4.9 g, 33.8% yield) as a white solid. $^1$H NMR (300 MHz, Chloroform-d) δ: 9.36 (d, J=2.3 Hz, 1H), 8.83 (d, J=2.3 Hz, 1H), 8.44 (s, 1H), 4.05 (s, 3H). LC-MS: m/z 284 $[M+H]^+$.

Step 2: methyl 2-(5-amino-3-chloropyridin-2-yl)-2H-1,2,3-triazole-4-carboxylate

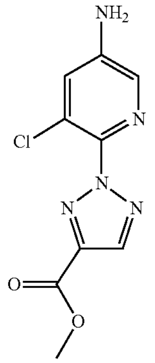 [SMILES: COC(=O)c1cnn(-c2ncc(N)cc2Cl)n1]

Into a 250 mL flask was placed methyl 2-(3-chloro-5-nitropyridin-2-yl)-2H-1,2,3-triazole-4-carboxylate (1.3 g, 4.6 mmol), tetrahydrofuran (20 mL), water (10 mL), $NH_4Cl$ (1.2 g, 22.9 mmol), and Fe (1.3 g, 22.9 mmol). The mixture was stirred at 75° C. for 1 h. The reaction was cooled to 25° C. The solid was filtered out. The filtrate was concentrated under vacuum. The resulting mixture was diluted with water (100 mL). The resulting mixture was extracted with ethyl acetate (3×100 mL). The combined organic layers were dried over anhydrous sodium sulfate and concentrated under vacuum. The residue was purified by column chromatography on silica gel using 97% dichloromethane and 3% methanol as eluent to afford methyl 2-(5-amino-3-chloropyridin-2-yl)-2H-1,2,3-triazole-4-carboxylate (844 mg, 72.8% yield) as a white solid. $^1$H NMR (400 MHz, Chloroform-d) δ: 8.30 (s, 1H), 7.90 (d, J=2.6 Hz, 1H), 7.16 (d, J=2.5 Hz, 1H), 3.98 (s, 3H). LC-MS: m/z 254 $[M+H]^+$.

Step 3: methyl 2-[5~[bis(tert-butoxycarbonyl)amino]-3-chloro-2-pyridyl]triazole-4-carboxylate

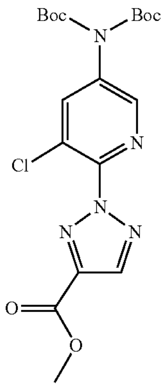 [SMILES: COC(=O)c1cnn(-c2ncc(N(C(=O)OC(C)(C)C)C(=O)OC(C)(C)C)cc2Cl)n1]

Into a 100 mL flask was placed methyl 2-(5-amino-3-chloropyridin-2-yl)-2H-1,2,3-triazole-4-carboxylate (844 mg, 3.3 mmol), dichloromethane (20 mL), TEA (673.4 mg, 6.7 mmol) and N,N-dimethylpyridin-4-amine (40.7 mg, 332.8 μmol). The reaction was cooled to 0° C. Then di-tert-butyl dicarbonate (1.5 g, 6.7 mmol) was added. The reaction was warmed to room temperature and stirred for 15 h. The resulting mixture was diluted with water (100 mL). The resulting mixture was extracted with dichloromethane (3×100 mL). The combined organic layers were dried over anhydrous sodium sulfate and concentrated under vacuum. The residue was purified by column chromatography on silica gel using 65% petroleum ether and 35% ethyl acetate as eluent to afford methyl 2-[5~[bis(tert-butoxycarbonyl)amino]-3-chloro-2-pyridyl]triazole-4-carboxylate (912 mg, 60.4% yield) as a white solid. $^1$H NMR (400 MHz, Chloroform-d) δ: 8.36 (s, 1H), 8.35 (d, J=2.2 Hz, 1H), 7.83 (d, J=2.3 Hz, 1H), 4.00 (s, 3H), 1.45 (s, 18H). LC-MS: m/z 454 $[M+H]^+$.

Step 4: 2-(5-((tert-butoxycarbonyl)amino)-3-chloropyridin-2-yl)-2H-1,2,3-triazole-4-carboxylic acid

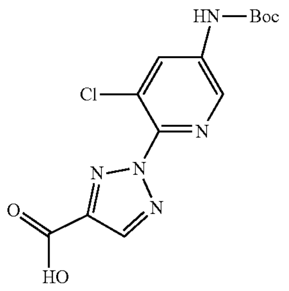 [SMILES: CC(C)(C)OC(=O)Nc1cnc(-n2ncc(C(=O)O)n2)c(Cl)c1]

To a stirred solution of methyl 2-(5-{bis[(tert-butoxy)carbonyl]amino}-3-chloropyridin-2-yl)-2H-1,2,3-triazole-4-carboxylate (1.8 g, 3.9 mmol) in methanol (10 mL) and tetrahydrofuran (20 mL) was added LiOH (190 mg, 7.9 mmol) in water (10 mL). The reaction was stirred at 25° C. for 1 h. The reaction was diluted with water (50 mL). The pH was adjusted to 4-5 with HCl (4 M). The mixture was extracted with ethyl acetate (2×100 mL). The organic layers were combined, dried over anhydrous sodium sulfate and concentrated under vacuum to give 2-(5~((tert-butoxycarbonyl)amino)-3-chloropyridin-2-yl)-2H-1,2,3-triazole-4-carboxylic acid (1.5 g, 94% yield) as a white solid. $^1$H NMR (300 MHz, DMSO-$d_6$) δ: 13.02 (s, 1H), 10.26 (s, 1H), 8.59 (d, J=2.3 Hz, 1H), 8.55 (s, 1H), 8.35 (d, J=2.3 Hz, 1H), 1.52 (s, 9H). LC-MS: m/z 340 $[M+H]^+$.

Step 5: tert-butyl (5-chloro-6-(4-(methoxy(methyl)carbamoyl)-2H-1,2,3-triazol-2-yl)pyridin-3-yl)carbamate

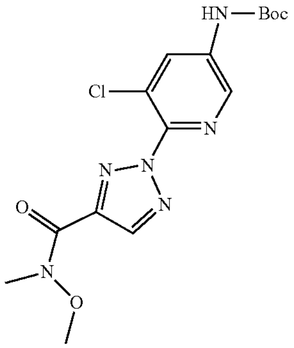 [SMILES: CON(C)C(=O)c1cnn(-c2ncc(NC(=O)OC(C)(C)C)cc2Cl)n1]

To a stirred solution of 2-(5~((tert-butoxycarbonyl)amino)-3-chloropyridin-2-yl)-2H-1,2,3-triazole-4-carboxylic acid (400 mg, 1.2 mmol) in acetonitrile were added N,O-dimethylhydroxylamine; hydrochloride (229 mg, 2.3 mmol), N-(chloro(dimethylamino)methylene)-N-methylmethanaminium hexafluorophosphate (991 mg, 3.5 mmol) and 1-methyl-1H-imidazole (676 mg, 8.2 mmol). The mixture was stirred at 25° C. for 1 h. The mixture was concentrated under vacuum. The residue was purified by column chromatography on silica gel using 75% petroleum ether and 25% ethyl acetate as eluent to afford tert-butyl (5-chloro-6-(4-(methoxy(methyl)carbamoyl)-2H-1,2,3-triazol-2-yl)pyridin-3-yl)carbamate (300 mg, 59% yield) as a white solid. $^1$H NMR (400 MHz, DMSO-$d_6$) δ: 10.25 (s, 1H), 8.57 (d, J=2.3 Hz, 1H), 8.44 (s, 1H), 8.33 (d, J=2.3 Hz, 1H), 3.74 (s, 3H), 2.67 (s, 3H), 1.50 (s, 9H). LC-MS: m/z 383 $[M+H]^+$.

Step 6: tert-butyl (6-(4-acetyl-2H-1,2,3-triazol-2-yl)-5-chloropyridin-3-yl) carbamate

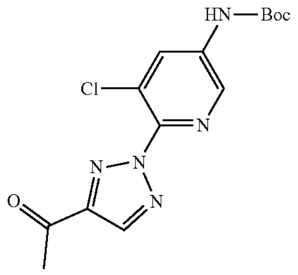 [SMILES: CC(=O)c1cnn(-c2ncc(NC(=O)OC(C)(C)C)cc2Cl)n1]

To a stirred solution of tert-butyl (5-chloro-6-(4-(methoxy(methyl) carbamoyl)-2H-1,2,3-triazol-2-yl)pyridin-3-yl)carbamate (280 mg, 731.1 μmol) in tetrahydrofuran (20 mL) was added methyl magnesium bromide (0.5 mL, 1.5 mmoL, 3 M in diethyl ether) dropwise at 0° C. under an atmosphere of nitrogen. The reaction was stirred at 0° C. for 1 h. The reaction was quenched with saturated aqueous $NH_4C1$ solution (50 mL). The resulted mixture was extracted with ethyl acetate (3×50 mL). The organic layers were combined, washed with brine, dried over anhydrous sodium sulfate and concentrated under vacuum. The residue was purified by column chromatography on silica gel using 70% petroleum ether and 30% ethyl acetate as eluent to afford tert-butyl (6-(4-acetyl-2H-1,2,3-triazol-2-yl)-5-chloropyridin-3-yl) carbamate (170 mg, 61% yield) as a white solid. $^1$H NMR (400 MHz, DMSO-$d_6$) δ: 10.27 (s, 1H), 8.48-8.67 (m, 2H), 8.34 (d, J=2.3 Hz, 1H), 2.59 (s, 3H), 1.50 (s, 9H). LC-MS: m/z 338 $[M+H]^+$.

Step 7: tert-butyl (5-chloro-6-(4-(1-hydroxyethyl)-2H-1,2,3-triazol-2-yl)pyridin-3-yl)carbamate

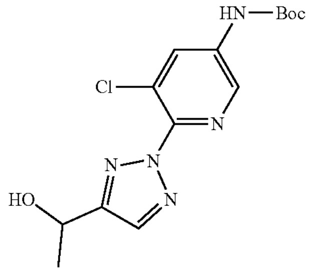 [SMILES: CC(O)c1cnn(-c2ncc(NC(=O)OC(C)(C)C)cc2Cl)n1]

To a stirred solution of tert-butyl (6-(4-acetyl-2H-1,2,3-triazol-2-yl)-5-chloropyridin-3-yl)carbamate (140 mg, 414.5 μmol) in methanol (4 mL) was added NaBH4 (19 mg, 497.4 μmol) at 0° C. The reaction was stirred at 0° C. for 1 h. The solvent was removed under vacuum. The residue was purified by Prep-TLC using 90% dichloromethane and 10% methanol as eluent to afford tert-butyl (5-chloro-6-(4-(1-hydroxyethyl)-2H-1,2,3-triazol-2-yl)pyridin-3-yl) carbamate (140 mg, 94% yield) as a white solid. $^1$H NMR (400 MHz, DMSO-$d_6$) δ: 10.16 (s, 1H), 8.53 (d, J=2.3 Hz, 1H), 8.28 (d, J=2.3 Hz, 1H), 7.98 (s, 1H), 5.50 (d, J=5.1 Hz, 1H), 4.88-4.94 (m, 1H), 1.49 (s, 9H), 1.43 (d, J=6.5 Hz, 3H). LC-MS: m/z 340 $[M+H]^+$.

Step 8: 1-(2-(5-amino-3-chloropyridin-2-yl)-2H-1,2,3-triazol-4-yl)ethan-1-ol

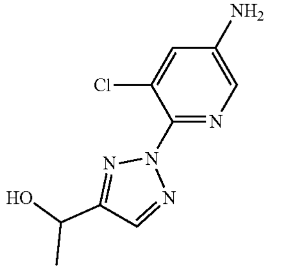 [SMILES: CC(O)c1cnn(-c2ncc(N)cc2Cl)n1]

To a stirred solution of tert-butyl (5-chloro-6-(4-(1-hydroxyethyl)-2H-1,2,3-triazol-2-yl)pyridin-3-yl)carbamate (100 mg, 220.2 μmol) in ethyl acetate (2 mL) was added HCl (2.2 mL, 4 M in ethyl acetate). The reaction was stirred at 25° C. for 2 h. The solvent was removed under vacuum. The residue was diluted with ethyl acetate (50 mL) and quenched by saturated aqueous $NaHCO_3$ solution (50 mL). The aqueous layer was extracted with ethyl acetate (2×50 mL). The combined organic layers were dried over anhydrous sodium sulfate and concentrated under vacuum. The residue was purified by Prep-TLC using 95% dichloromethane and 5% methanol as eluent to afford 1-(2-(5-amino-3-chloropyridin-2-yl)-2H-1,2,3-triazol-4-yl)ethan-1-ol (Method Y1 step 8; 38 mg, 54% yield) as a colorless oil. $^1$H NMR (300 MHz, DMSO-$d_6$) δ: 7.87 (s, 1H), 7.79 (d, J=2.5 Hz, 1H), 7.17 (d, J=2.5 Hz, 1H), 6.14 (s, 2H), 5.43 (s, 1H), 4.89 (s, 1H), 1.42 (d, J=6.5 Hz, 3H). LC-MS: m/z 240 $[M+H]^+$.

Step 9: 6-(4-(1-((tert-butyldimethylsilyl)oxy)ethyl)-2H-1,2,3-triazol-2-yl)-5-chloropyridin-3-amine

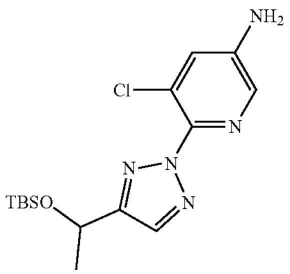 [SMILES: CC(O[Si](C)(C)C(C)(C)C)c1cnn(-c2ncc(N)cc2Cl)n1]

To a stirred solution of 1-(2-(5-amino-3-chloropyridin-2-yl)-2H-1,2,3-triazol-4-yl)ethan-1-ol (50 mg, 208.6 μmol) in dichloromethane (7 mL) was added trifluoromethanesulfonic acid tert-butyldimethylsilyl ester (72 mg, 271.2 μmol) and 2,6-dimethylpyridine (63 mg, 625.9 μmol) at 0° C. The reaction was stirred at 25° C. for 1 h. The solvent was removed under vacuum. The residue was purified by Prep-TLC using 50% petroleum ether and 50% methanol as eluent to afford 6-(4-(1-((tert-butyldimethylsilyl)oxy)ethyl)-2H-1,2,3-triazol-2-yl)-5-chloropyridin-3-amine (40 mg, 51% yield) as a white solid. LC-MS: m/z 354 $[M+H]^+$.

Step 10: N-(6-(4-(1-((tert-butyldimethylsilyl)oxy)ethyl)-2H-1,2,3-triazol-2-yl)-5-chloropyridin-3-yl)-2-chloro-8,8-dimethyl-7,8-dihydro-6H-cyclopenta[e]pyrazolo[1,5-a]pyrimidine-6-carboxamide

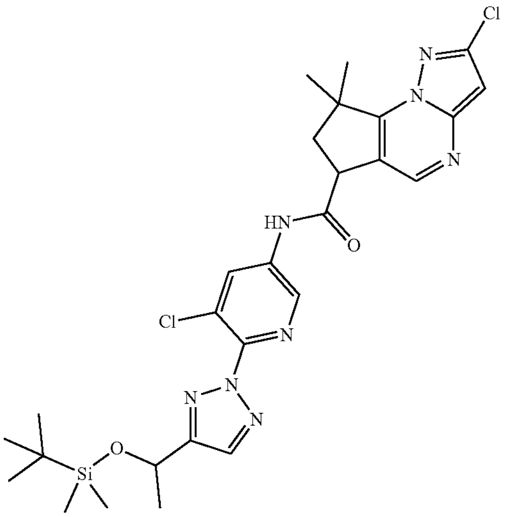 [SMILES: CC(O[Si](C)(C)C(C)(C)C)c1cnn(-c2ncc(NC(=O)C3CC(C)(C)c4c3cnc3cc(Cl)nn43)cc2Cl)n1]

To a solution of 6-(4-(1-((tert-butyldimethylsilyl)oxy)ethyl)-2H-1,2,3-triazol-2-yl)-5-chloropyridin-3-amine (400 mg, 1.7 mmol) in acetonitrile (15 mL) were added 2-chloro-8,8-dimethyl-7,8-dihydro-6H-cyclopenta[e]pyrazolo[1,5-a]pyrimidine-6-carboxylic acid (Method A1 step 6; 453 mg, 1.7 mmol), TCFH (1.4 g, 5.1 mmol) and NMI (420 mg, 5.1 mmol). The resulting mixture was stirred at 25° C. for 3 h. The reaction mixture was concentrated under vacuum. The residue was applied onto a silica gel column and eluted with EtOAc/PE (1:1) to give N-(6-(4-(1-((tert-butyl dimethyl silyl)oxy)ethyl)-2H-1,2,3-triazol-2-yl)-5-chloropyridin-3-yl)-2-chloro-8,8-dimethyl-7,8-dihydro-6H cyclopenta[e]pyrazolo[1,5-a]pyrimidine-6-carboxamide (500 mg, 66% yield) as a white solid. LC-MS: m/z 601 $[M+H]^+$.

Step 11: 2-chloro-N-(5-chloro-6-(4-(1-hydroxyethyl)-2H-1,2,3-triazol-2-yl) pyridin-3-yl)-8,8-dimethyl-7,8-dihydro-6H-cyclopenta[e]pyrazolo[1,5-a] pyrimidine-6-carboxamide To a solution of N-(6-(4-(1-((tert-butyldimethylsilyl)oxy) ethyl)-2H-1,2,3-triazol-2-yl)-5-chloropyridin-3-yl)-2-chloro-8,8-dimethyl-7,8-dihydro-6H-cyclopenta[e]pyrazolo [1,5

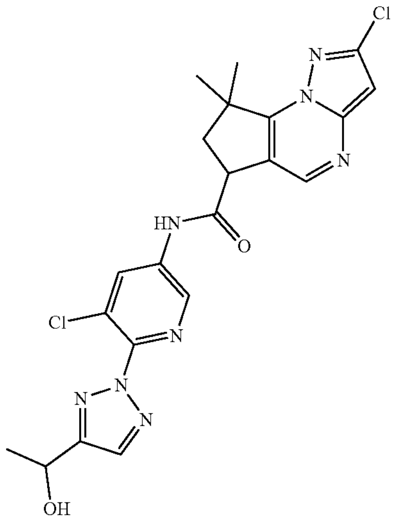 [SMILES: CC(O)c1cnn(-c2ncc(NC(=O)C3CC(C)(C)c4c3cnc3cc(Cl)nn43)cc2Cl)n1]

a]pyrimidine-6-carboxamide (450 mg, 748.0 μmol) in DCM (6 mL) was added TFA (2 mL). The resulting mixture was stirred at 25° C. for 3 h. The reaction solution was concentrated under vacuum. The residue was diluted with water (100 mL). The pH was adjusted to 7-8 with saturated aqueous sodium bicarbonate solution. The resulting mixture was extracted with EtOAc (3×100 mL). The combined organic layers were dried over anhydrous sodium sulfate and concentrated under vacuum. The residue was applied onto a silica gel column and eluted with MeOH/DCM (1:10) to give 370 mg of crude product. The crude product was submitted to Prep-HPLC purification and the collected fractions were lyophilized to give 2-chloro-N-(5-chloro-6-(4-(1-hydroxyethyl)-2H-1,2,3-triazol-2-yl)pyridin-3-yl)-8,8-dimethyl-7,8-dihydro-6H-cyclopenta[e]pyrazolo[1,5-a] pyrimidine-6-carboxamide (200 mg, 46% yield) as a white solid. LC-MS: m/z 487 [M+H]$^+$.

Step 12: Separation of Enantiomers to Obtain (S)-2-chloro-N-(5-chloro-6-(4-((S)-1-hydroxyethyl)-2H-1,2,3-triazol-2-yl)pyridin-3-yl)-8,8-dimethyl-7,8-dihydro-6H-cyclopenta[e]pyrazolo[1,5-a] pyrimidine-6-carboxamide, (R)-2-chloro-N-(5-chloro-6-(4-((S)-1-hydroxyethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide, (S)-2-chloro-N-(5-chloro-6-(4-((R)-1-hydroxyethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide and (R)-2-chloro-N-(5-chloro-6-(4-((R)-1-hydroxyethyl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide Example 49

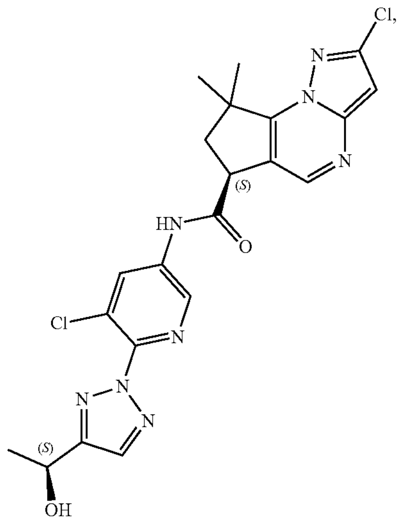

Example 50

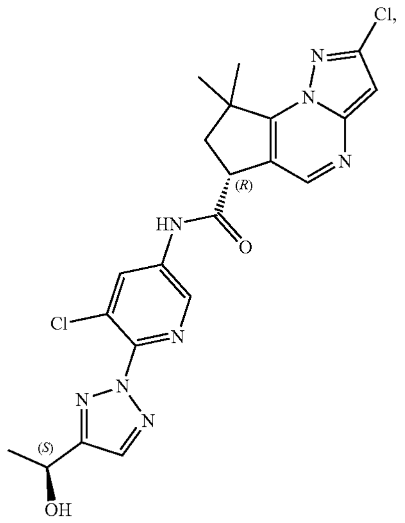

-continued

Example 51

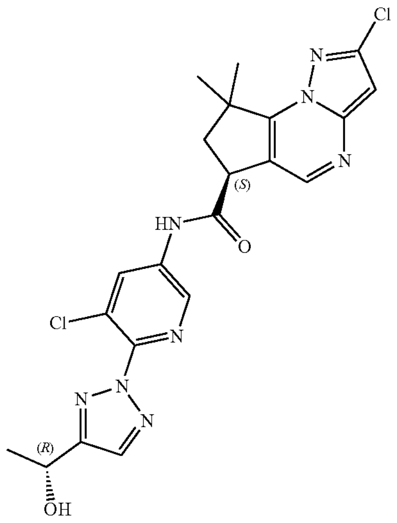

and

Example 52

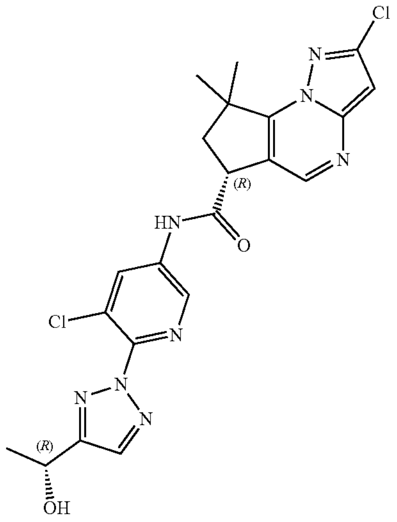

200 mg of 2-chloro-N-(5-chloro-6-(4-(1-hydroxyethyl)-2H-1,2,3-triazol-2-yl) pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRAL ART Cellulose-SB, 5*25 cm, 10 μm; Mobile Phase A: Hex (0.5% 2M $NH_3$-MeOH), Mobile Phase B: EtOH; Flow rate: 20 mL/min; isocratic 40% B 21.5 min; 220/254 nm; RT1:12.594; RT2:14.454; Injection Volume: 0.5 ml; Number of Runs: 9). The first eluting isomer was concentrated and lyophilized to afford Example 49 as a white solid (27.8 mg, 14% yield). The third eluting isomer was concentrated and lyophilized to afford Example 52 as a white solid (20.1 mg, 10% yield). Fractions containing a mixture of the two other isomers were concentrated and submitted to chiral HPLC purification (Column: CHIRALPAK IF, 2*25 cm, 5 μm; Mobile Phase A: Hex (0.5% 2M $NH_3$-MeOH), Mobile Phase B: EtOH; Flow rate: 18 mL/min; isocratic 40% B 21 min; 220/254 nm; RT1:9.826; RT2:16.854; Injection Volume: 4 ml; Number of Runs: 2). The first eluting isomer was concentrated and lyophilized to afford Example 50 as a white solid (30.4 mg, 15% yield). The second eluting isomer was concentrated and lyophilized to afford Example 51 as a white solid (38.5 mg, 19% yield).

Example 49: $^1$H NMR (400 MHz, DMSO-$d_6$) δ: 11.07 (br, 1H), 8.72 (d, J=2.4 Hz, 1H), 8.65 (s, 1H), 8.57 (d, J=2.4 Hz, 1H), 8.03 (s, 1H), 6.95 (s, 1H), 5.54 (br, 1H), 4.93-4.97 (m, 1H), 4.44-4.48 (m, 1H), 2.50-2.60 (m, 1H), 2.32-2.36 (m, 1H), 1.65 (s, 3H), 1.57 (s, 3H), 1.47 (d, J=6.4 Hz, 3H). LC-MS: m/z 487 $[M+H]^+$.

Example 50: $^1$H NMR (400 MHz, DMSO-$d_6$) δ: 11.06 (br, 1H), 8.72 (d, J=2.4 Hz, 1H), 8.66 (s, 1H), 8.57 (d, J=2.4 Hz, 1H), 8.04 (s, 1H), 6.95 (s, 1H), 5.49 (br, 1H), 4.92-4.97 (m, 1H), 4.44-4.48 (m, 1H), 2.51-2.60 (m, 1H), 2.31-2.36 (m, 1H), 1.65 (s, 3H), 1.56 (s, 3H), 1.46 (d, J=6.8 Hz, 3H). LC-MS: m/z 487 $[M+H]^+$.

Example 51: $^1$H NMR (400 MHz, DMSO-$d_6$) δ: 11.06 (br, 1H), 8.69 (d, J=2.4 Hz, 1H), 8.66 (s, 1H), 8.57 (d, J=2.4 Hz, 1H), 8.03 (s, 1H), 6.95 (s, 1H), 5.53 (br, 1H), 4.92-4.97 (m, 1H), 4.44-4.48 (m, 1H), 2.57-2.68 (m, 1H), 2.30-2.36 (m, 1H), 1.65 (s, 3H), 1.56 (s, 3H), 1.46 (d, J=6.4 Hz, 3H). LC-MS: m/z 487 $[M+H]^+$.

Example 52: $^1$H NMR (400 MHz, DMSO-$d_6$) δ: 11.06 (br, 1H), 8.71 (d, J=2.4 Hz, 1H), 8.68 (s, 1H), 8.65 (d, J=2.4 Hz, 1H), 8.02 (s, 1H), 6.95 (s, 1H), 5.54 (br, 1H), 4.92-4.97 (m, 1H), 4.44-4.48 (m, 1H), 2.51-2.68 (m, 1H), 2.31-2.36 (m, 1H), 1.65 (s, 3H), 1.56 (s, 3H), 1.46 (d, J=6.8 Hz, 3H). LC-MS: m/z 487 $[M+H]^+$.

The absolute stereochemistry for each separated isomer was not determined.

Method Z1
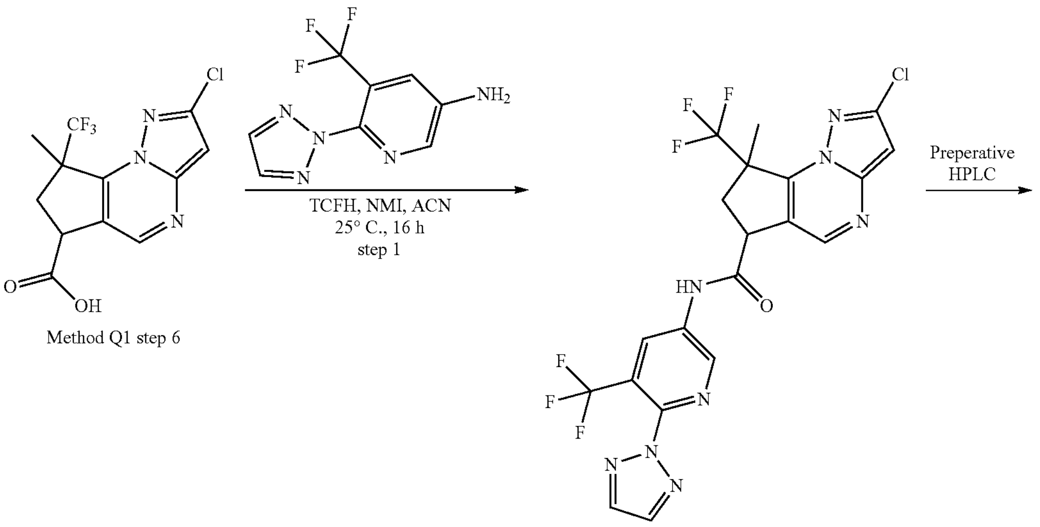
Diastereomer A
and
Diastereomer B
chiral separation
step 2
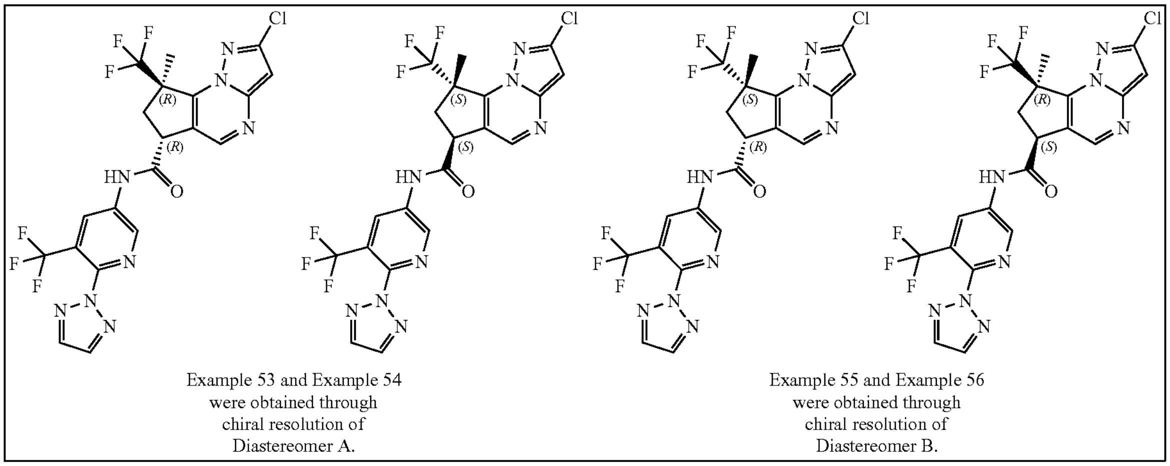
Example 53 and Example 54 were obtained through chiral resolution of Diastereomer A.
Example 55 and Example 56 were obtained through chiral resolution of Diastereomer B.

Examples 53, 54, 55 and 56: Single Enantiomers Obtained from Racemic Mixtures Containing (6R, 8R)—N-(6-(2H-1,2,3-triazol-2-yl)-5~(trifluoromethyl) pyridin-3-yl)-2-chloro-8-methyl-8-(trifluoromethyl)-7,8-dihydro-6H-cyclopenta[e]pyrazolo[1,5-a]pyrimidine-6-carboxamide, (6S,8S)—N-(6-(2H-1,2,3-triazol-2-yl)-5~(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide, (6R,8S)—N-(6-(2H-1,2,3-triazol-2-yl)-5-(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide and (6S,8R)—N-(6-(2H-1,2,3-triazol-2-yl)-5~(trifluoromethyl)pyridin-3-yl)-2-chloro-8-methyl-8-(trifluoromethyl)-7,8-dihydro-611-cyclopenta[e]pyrazolo[1,5-a]pyrimidine-6-carboxamide Step 1: N-(6-(2H-1,2,3-triazol-2-yl)-5~(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide

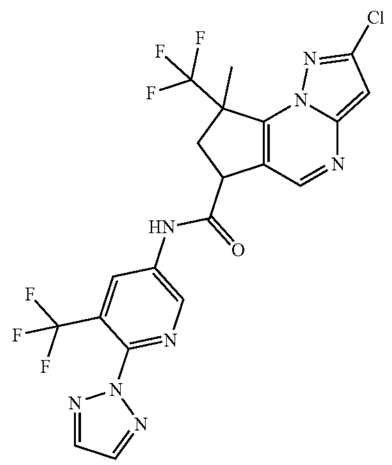 [SMILES: CC1(C(F)(F)F)CC(C(=O)Nc2cnc(-n3nccn3)c(C(F)(F)F)c2)c2cnc3cc(Cl)nn3c21]

To a stirred solution of 2-chloro-8-methyl-8-(trifluoromethyl)-7,8-dihydro-6H-cyclopenta[e]pyrazolo[1,5-a]pyrimidine-6-carboxylic acid (Method Q1 step 6; 160 mg, 501.6 μmol) in acetonitrile (10 mL) were added 6-(2H-1,2,3-triazol-2-yl)-5~(trifluoromethyl)pyridin-3-amine (138 mg, 601.9 μmol), TCFH (564 mg, 2.0 mmol) and NMI (163 mg, 2.0 mmol). The resulting mixture was stirred for 16 h at 25° C. The reaction mixture was quenched with water (50 mL). The resulting solution was extracted with EtOAc (3×30 mL), dried over anhydrous sodium sulfate and concentrated under vacuum. The residue was applied onto a silica gel column and eluted with EtOAc/PE (1:1) to give N-(6-(2H-1,2,3-triazol-2-yl)-5~(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide as a mixture of two racemic diastereomeric pairs as white solid. LC-MS: m/z 531 $[M+H]^+$. This mixture was submitted to Prep-HPLC to obtain the separated racemic mixtures of Diastereomer A and Diastereomer B.

Step 8: Separation of Enantiomers to Obtain (6R, 8R)—N-(6-(2H-1,2,3-triazol-2-yl)-5-(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide, (6S,8S)—N-(6-(2H-1,2,3-triazol-2-yl)-5-(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide, (6R,8S)—N-(6-(2H-1,2,3-triazol-2-yl)-5-(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide and (6S,8R)—N-(6-(2H-1,2,3-triazol-2-yl)-5~(trifluoromethyl)pyridin-3-yl)-2-chloro-8-methyl-8-(trifluoromethyl)-7,8-dihydro-6H-cyclopenta[e]pyrazolo[1,5-a]pyrimidine-6-carboxamide Example 53

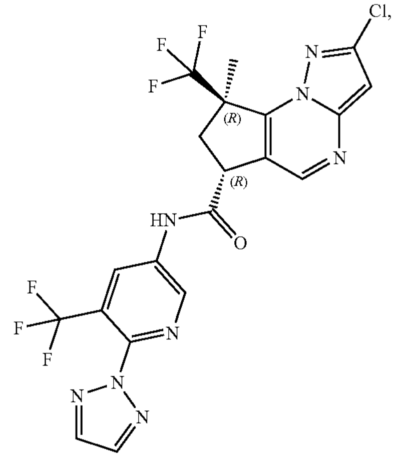

Example 54

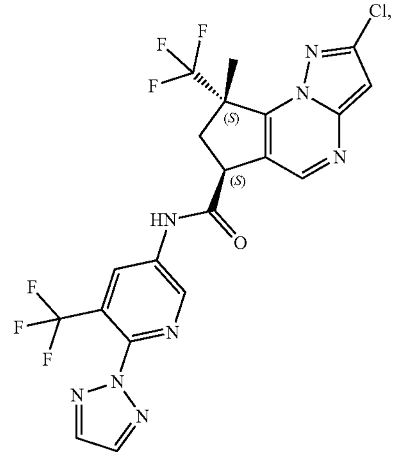

-continued

Example 55

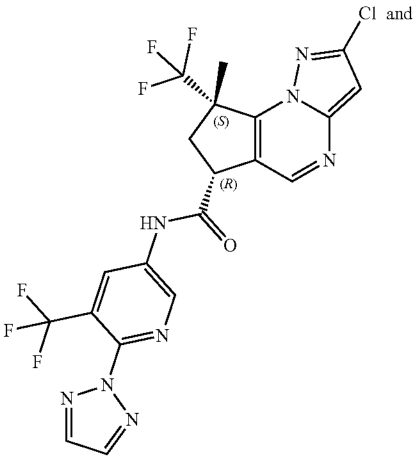

and

Example 56

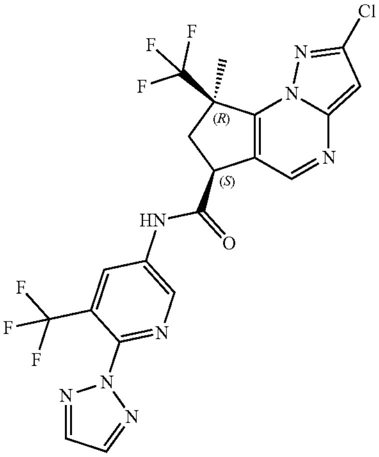

60 mg of Diastereomer A were submitted to chiral HPLC purification (Column: CHIRALPAK IG, 2*25 cm, 5 um; Mobile Phase A: Hex (0.1% FA), Mobile Phase B: EtOH; Flow rate: 20 mL/min; isocratic 20% B 20 min; 254/220 nm; RT1: 6.443; RT2:16.149; Injection Volume: 1.5 ml; Number of Runs: 2). The first eluting isomer was concentrated and lyophilized to afford Example 53 (23.8 mg, 9% yield) as a white solid. The second eluting isomer was concentrated and lyophilized to afford Example 54 (30.6 mg, 12% yield) as a white solid.

40 mg of Diastereomer B were submitted to chiral HPLC purification (Column: CHIRALPAK IA, 2*25 cm, 5 um; Mobile Phase A: Hex (0.1% FA), Mobile Phase B: EtOH; Flow rate: 20 mL/min; isocratic 30% B 19 min; 254/220 nm; RT1: 7.153; RT2:11.261; Injection Volume: 2 ml; Number of Runs: 1). The first eluting isomer was concentrated and lyophilized to afford Example 55 (7 mg, 3% yield) as an off white solid. The second eluting isomer was concentrated and lyophilized to afford Example 56 (18.4 mg, 7% yield) as a white solid.

Example 53: $^1$H NMR (400 MHz, DMSO-$d_6$) δ:11.33 (s, 1H), 9.02 (d, J=2.4 Hz, 1H), 8.82 (d, J=2.4 Hz, 1H), 8.79 (s, 1H), 8.20 (s, 2H), 7.09 (s, 1H), 4.56-4.60 (m, 1H), 3.08-3.13 (m, 1H), 2.54-2.58 (m, 1H), 1.94 (s, 3H). LC-MS: m/z 531 $[M+H]^+$.

Example 54: $^1$H NMR (400 MHz, DMSO-$d_6$) δ:11.33 (s, 1H), 9.02 (d, J=2.4 Hz, 1H), 8.82 (d, J=2.4 Hz, 1H), 8.79 (s, 1H), 8.20 (s, 2H), 7.09 (s, 1H), 4.56-4.60 (m, 1H), 3.08-3.13 (m, 1H), 2.54-2.58 (m, 1H), 1.94 (s, 3H). LC-MS: m/z 531 $[M+H]^+$.

Example 55: $^1$H NMR (400 MHz, DMSO-$d_6$) δ:11.24 (s, 1H), 9.03 (d, J=2.4 Hz, 1H), 8.79 (s, 2H), 8.19 (s, 2H), 7.09 (s, 1H), 4.57-4.61 (m, 1H), 2.91-2.94 (m, 1H), 2.73-2.90 (m, 1H), 1.84 (s, 3H). LC-MS: m/z 531 $[M+H]^+$.

Example 56: $^1$H NMR (400 MHz, DMSO-$d_6$) δ:11.23 (s, 1H), 9.02 (d, J=2.4 Hz, 1H), 8.79 (s, 2H), 8.20 (s, 2H), 7.09 (s, 1H), 4.57-4.61 (m, 1H), 2.91-2.94 (m, 1H), 2.73-2.90 (m, 1H), 1.84 (s, 3H). LC-MS: m/z 531 $[M+H]^+$.

The absolute stereochemistry for each separated isomer was not determined.

Method A2

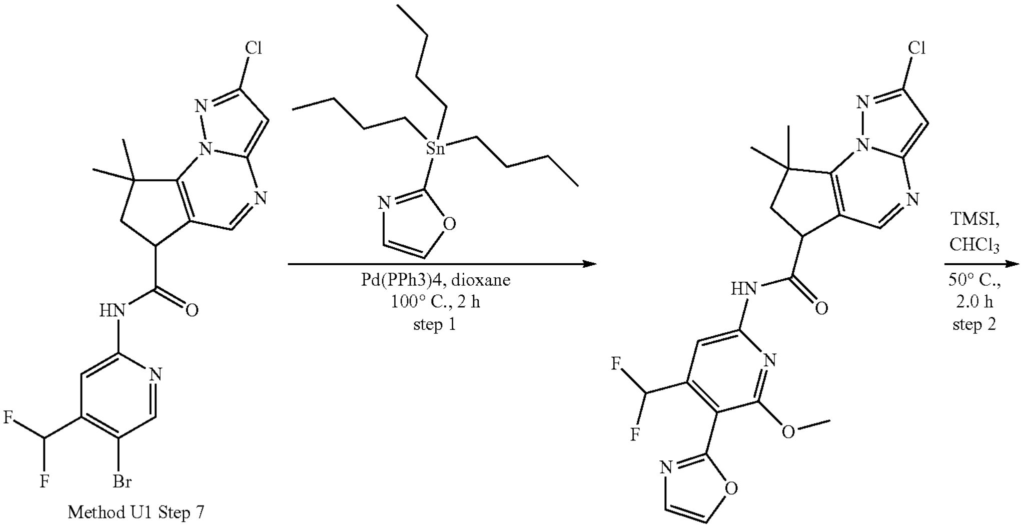

Method U1 Step 7

-continued
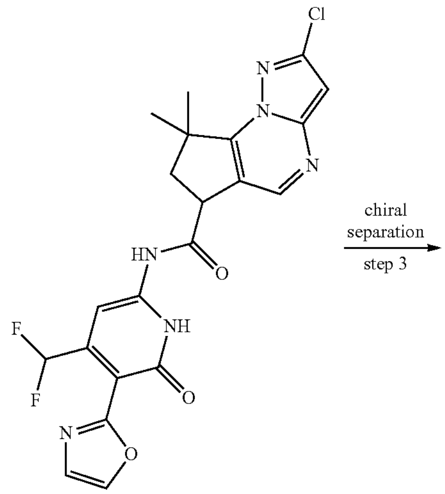
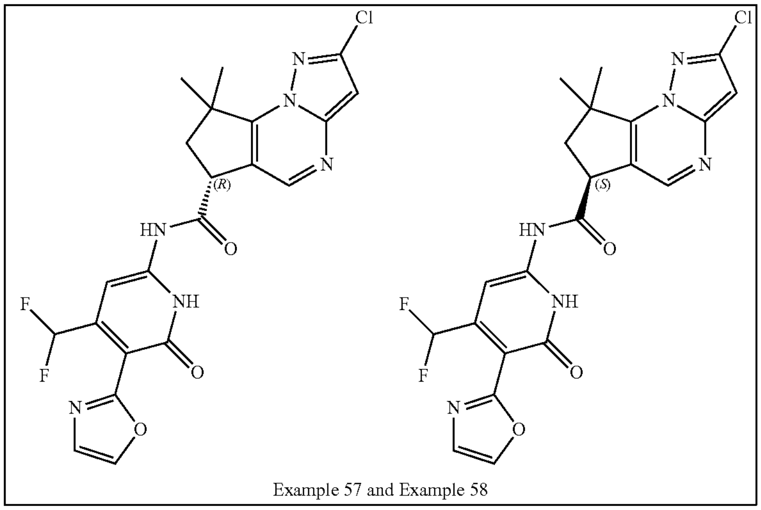
Example 57 and Example 58

Examples 57 and 58: Single Enantiomers Obtained from a Racemic Mixture Containing (R)-2-chloro-N-(4-(difluoromethyl)-5~(oxazol-2-yl)-6-oxo-1,6-dihydropyridin-2-yl)-8,8-dimethyl-7,8-dihydro-6H-cyclopenta[e]pyrazolo[1,5-a]pyrimidine-6-carboxamide and (S)-2-chloro-N-(4-(difluoromethyl)-5~(oxazol-2-yl)-6-oxo-1,6-dihydropyridin-2-yl)-8,8-dimethyl-7,8-dihydro-6H-cyclopenta[e]pyrazolo[1,5-a]pyrimidine-6-carboxamide Step 1: 2-chloro-N-(4-(difluoromethyl)-6-methoxy-5~(oxazol-2-yl)pyridin-2-yl)-8,8-dimethyl-7,8-dihydro-6H-cyclopenta[e]pyrazolo[1,5-a]pyrimidine-6-carboxamide

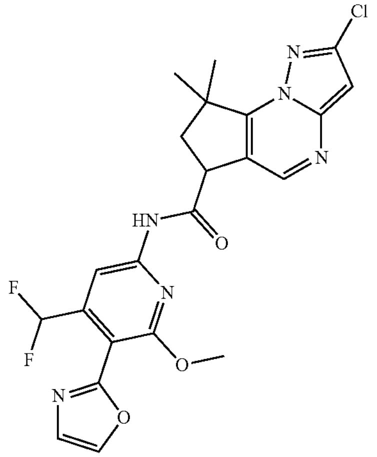 [SMILES: COc1nc(NC(=O)C2CC(C)(C)c3c2cnc2cc(Cl)nn32)cc(C(F)F)c1-c1ncco1]

To a stirred solution of N-(5-bromo-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (Method U1 Step 7; 100 mg, 199.7 μmol) in dioxane (10 mL) was added 2-(tributylstannyl)oxazole (71.5 mg, 199.7 μmol) and $Pd(PPh_3)_4$ (49.7 mg, 39.9 μmol) at 25° C. The resulting mixture was stirred at 90° C. for 2 h under nitrogen. The mixture was cooled to 25° C. The reaction mixture was concentrated under reduced pressure. The residue was applied on a silica gel column and eluted with EtOAc/PE (2:1) to give 2-chloro-N-(4-(difluoromethyl)-6-methoxy-5~(oxazol-2-yl)pyridin-2-yl)-8,8-dimethyl-7,8-dihydro-6H-cyclopenta[e]pyrazolo[1,5-a]pyrimidine-6-carboxamide (40 mg, 40% yield) as a brown solid. LC-MS: m/z 489 $[M+H]^+$.

Step 2: 2-chloro-N-(4-(difluoromethyl)-5~(oxazol-2-yl)-6-oxo-1,6-dihydropyridin-2-yl)-8,8-dimethyl-7,8-dihydro-6H-cyclopenta[e]pyrazolo[1,5-a]pyrimidine-6-carboxamide

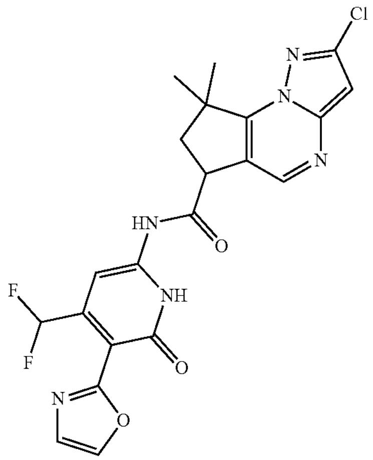

To a stirred mixture of 2-chloro-N-(4-(difluoromethyl)-6-methoxy-5~(oxazol-2-yl)pyridin-2-yl)-8,8-dimethyl-7,8-dihydro-6H-cyclopenta[e]pyrazolo[1,5-a]pyrimidine-6-carboxamide (100 mg, 204.5 μmol) in chloroform (10 mL) was added iodotrimethylsilane (409 mg, 2.1 mmol) in portions at 25° C. under nitrogen. The resulting mixture was stirred at 50° C. for 2 h under nitrogen. The mixture was cooled to 25° C., diluted with water (50 mL) and then extracted with DCM (3×50 mL). The organic layers were combined, washed with brine, dried and concentrated under vacuum. The crude product (50 mg) was purified by Prep-HPLC to afford 2-chloro-N-(4-(difluoromethyl)-5~(oxazol-2-yl)-6-oxo-1,6-dihydropyridin-2-yl)-8,8-dimethyl-7,8-dihydro-6H-cyclopenta[e]pyrazolo[1,5-a]pyrimidine-6-carboxamide (30 mg, 22% yield) as a white solid. LC-MS: m/z 475 $[M+H]^+$.

Step 3: Separation of Enantiomers to Obtain (R)-2-chloro-N-(4-(difluoromethyl)-5-(oxazol-2-yl)-6-oxo-1,6-dihydropyridin-2-yl)-8,8-dimethyl-7,8-dihydro-6H-cyclopenta[e]pyrazolo[1,5-a]pyrimidine-6-carboxamide and (S)-2-chloro-N-(4-(difluoromethyl)-5~(oxazol-2-yl)-6-oxo-1,6-dihydropyridin-2-yl)-8,8-dimethyl-7,8-dihydro-6H-cyclopenta[e]pyrazolo[1,5-a]pyrimidine-6-carboxamide Example 57

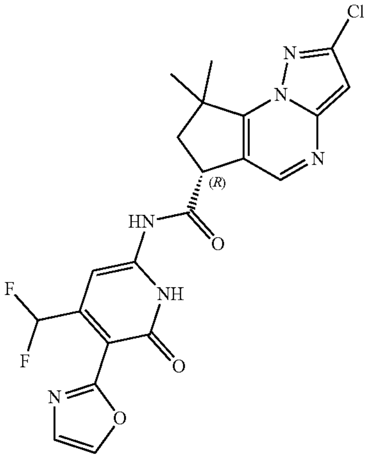 [SMILES: CC1(C)CC(C(=O)Nc2cc(C(F)F)c(-c3ncco3)c(=O)[nH]2)c2cnc3cc(Cl)nn3c21]

and

Example 58

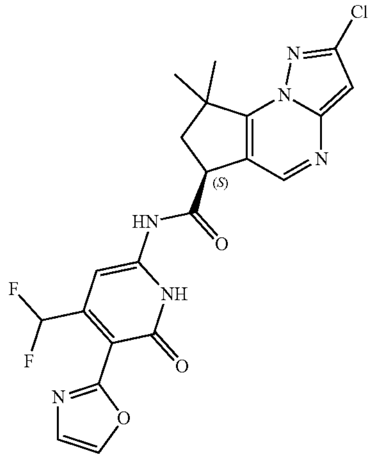

30 mg of racemic 2-chloro-N-(4-(difluoromethyl)-5~(oxazol-2-yl)-6-oxo-1,6-dihydropyridin-2-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IG, 2*25 cm, 5 um; Mobile Phase A:Hex(0.3% FA), Mobile Phase B:EtOH; Flow rate: 16 mL/min; isocratic 50% B 30 min; 220/254 nm; RT1:11.977; RT2:24.831; Injection Volume: 1 ml; Number of Runs: 3). The first eluting isomer was concentrated and lyophilized to afford Example 57 (8.3 mg, 27.6% yield) as a purple solid. The second eluting isomer was concentrated and lyophilized to afford Example 58 (4.6 mg, 15.3% yield) as a pink solid.

Example 57: $^1$HNMR (400 MHz, DMSO-$d_6$) δ: 12.01 (br, 1H), 11.47 (br, 1H), 8.62 (s, 1H), 8.30 (s, 1H), 7.81 (s, 1H), 7.46 (s, 1H), 7.30 (t, J=56 Hz, 1H), 6.93 (s, 1H), 4.54-4.52 (m, 1H), 2.51-2.68 (m, 1H), 2.27-2.34 (m, 1H), 1.63 (s, 3H), 1.54 (s, 3H). LCMS (ES, m/z): 475[M+H]$^+$.

Example 58: $^1$HNMR (400 MHz, DMSO-$d_6$) δ: 12.01 (br, 1H), 11.47 (br, 1H), 8.62 (s, 1H), 8.30 (s, 1H), 7.80 (s, 1H), 7.46 (s, 1H), 7.31 (t, J=56 Hz, 1H), 6.93 (s, 1H), 4.54-4.51 (m, 1H), 2.54-2.68 (m, 1H), 2.27-2.33 (m, 1H), 1.63 (s, 3H), 1.54 (s, 3H). LC-MS (ES, m/z): 475[M+H]$^+$.

The absolute stereochemistry for each separated isomer was not determined.

Method B2

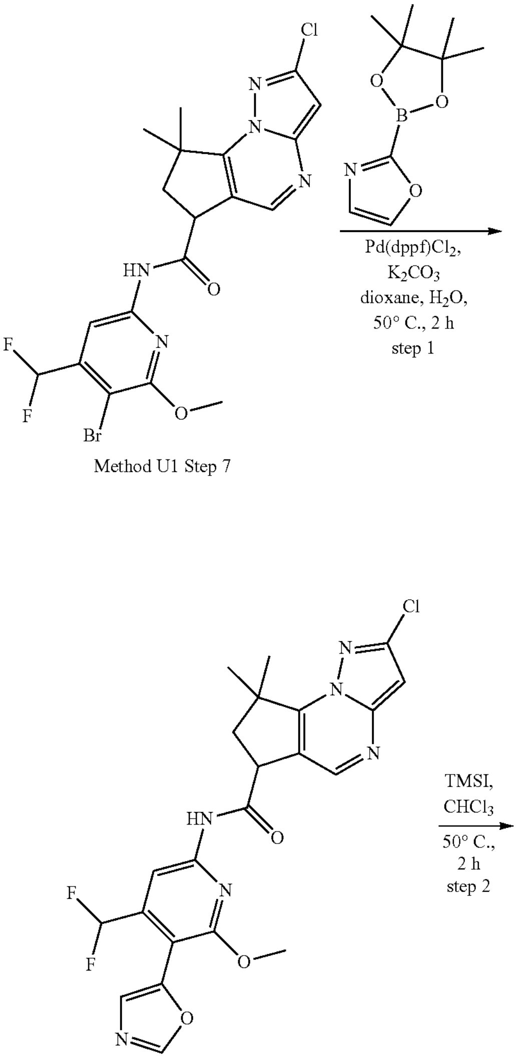

-continued

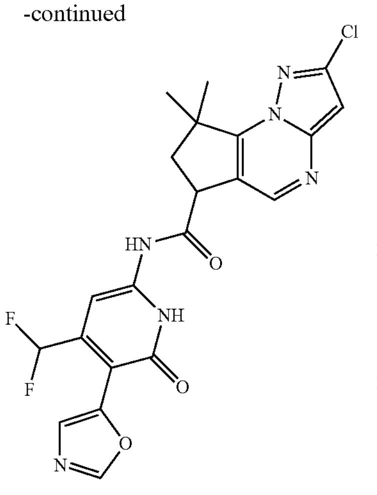

Example 59

Examples 59: 2-chloro-N-(4-(difluoromethyl)-5~(oxazol-5-yl)-6-oxo-1,6-dihydropyridin-2-yl)-8,8-dimethyl-7,8-dihydro-6H-cyclopenta[e]pyrazolo[1,5-a]pyrimidine-6-carboxamide Step 1: 2-chloro-N-(4-(difluoromethyl)-6-methoxy-5~(oxazol-5-yl)pyridin-2-yl)-8,8-dimethyl-7,8-dihydro-6H-cyclopenta[e]pyrazolo[1,5-a]pyrimidine-6-carboxamide

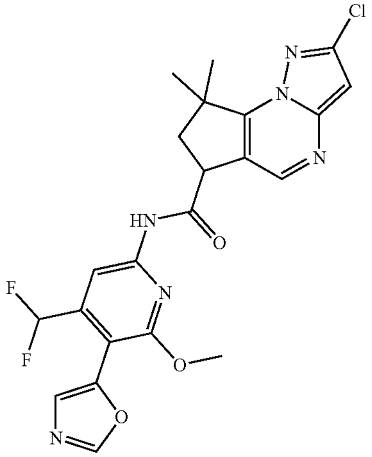 [SMILES: COc1nc(NC(=O)C2CC(C)(C)c3c2cnc2cc(Cl)nn32)cc(C(F)F)c1-c1cnco1]

To a stirred mixture of 5~(4,4,5,5-tetramethyl-1,3,2-dioxaborolan-2-yl)oxazole (70 mg, 359.5 μmol) and N-(5-bromo-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (Method U1 Step 7; 60 mg, 119.8 μmol) in dioxane (4 mL) were added Pd(dppf)C12 (18 mg, 23.9 μmol), $K_2CO_3$ (50 mg, 359.5 μmol) and $H_2O$ (1 mL) at 25° C. The resulting mixture was stirred at 50° C. for 2 h under nitrogen. The mixture was cooled to 25° C. The resulting solution was diluted with water (50 mL) and extracted with DCM (3×50 mL). The combined organic layers were dried over anhydrous sodium sulfate and concentrated under vacuum. The residue was applied on a silica gel column and eluted with EtOAc/PE (3:1) to give 2-chloro-N-(4-(difluoromethyl)-6-methoxy-5-(oxazol-5-yl)pyridin-2-yl)-8,8-dimethyl-7,8-dihydro-6H-cyclopenta[e]pyrazolo[1,5-a]pyrimidine-6-carboxamide (40 mg, 61% yield) as a light yellow solid. LC-MS: m/z 489 $[M+H]^+$.

Step 2: 2-chloro-N-(4-(difluoromethyl)-5~(oxazol-5-yl)-6-oxo-1,6-dihydropyridin-2-yl)-8,8-dimethyl-7,8-dihydro-6H-cyclopenta[e]pyrazolo[1,5-a]pyrimidine-6-carboxamide Example 59

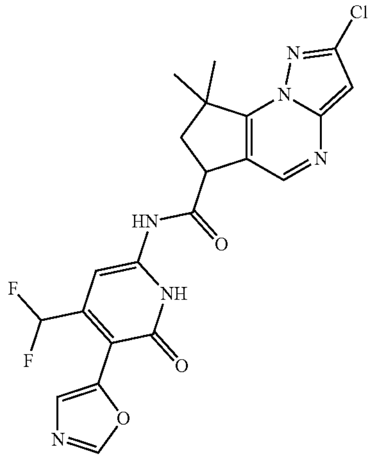

To a stirred mixture of 2-chloro-N-(4-(difluoromethyl)-6-methoxy-5~(oxazol-5-yl)pyridin-2-yl)-8,8-dimethyl-7,8-dihydro-6H-cyclopenta[e]pyrazolo[1,5-a]pyrimidine-6-carboxamide (30 mg, 61.5 μmol) in chloroform (5 mL) were added iodotrimethylsilane (41 mg, 0.6 mmol) in portions at 25° C. under nitrogen. The resulting mixture was stirred at 50° C. for 2 h under nitrogen. The mixture was cooled to 25° C. The reaction mixture was diluted with water (20 mL), and then extracted with DCM (3×20 mL). The organic layers were combined, washed with brine, dried over anhydrous sodium sulfate and concentrated under vacuum. The crude product (20 mg) was purified by Prep-HPLC to afford 2-chloro-N-(4-(difluoromethyl)-5~(oxazol-5-yl)-6-oxo-1,6-dihydropyridin-2-yl)-8,8-dimethyl-7,8-dihydro-6H-cyclopenta[e]pyrazolo[1,5-a]pyrimidine-6-carboxamide (14 mg, 47% yield) as a yellow solid.

Example 59: $^1H$ NMR (400 MHz, DMSO-$d_6$) δ: 11.91 (br, 1H), 10.94 (br, 1H), 8.63 (s, 1H), 8.50 (s, 1H), 7.97 (s, 1H), 7.56 (s, 1H), 7.28 (t, J=54 Hz, 1H), 6.94 (s, 1H), 4.44-4.58 (m, 1H), 2.51-2.59 (m, 1H), 2.32-2.33 (m, 1H), 1.63 (s, 3H), 1.55 (s, 3H). LC-MS: m/z 475 $[M+H]^+$.

Method C2
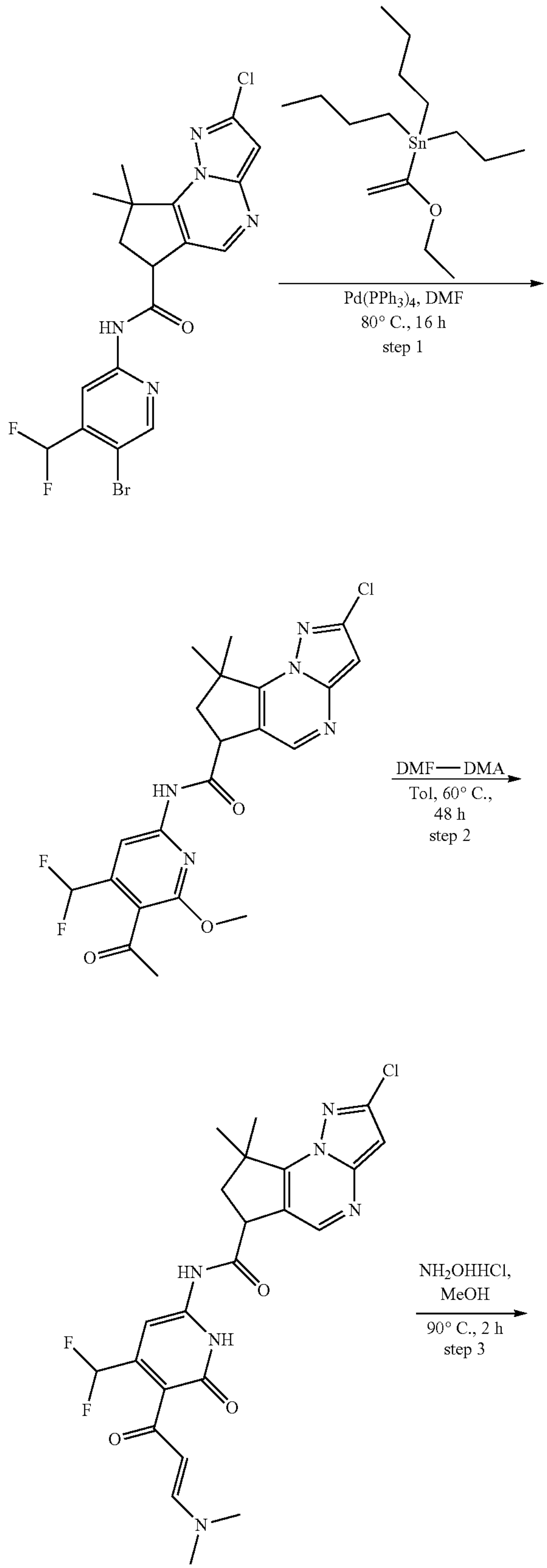
-continued
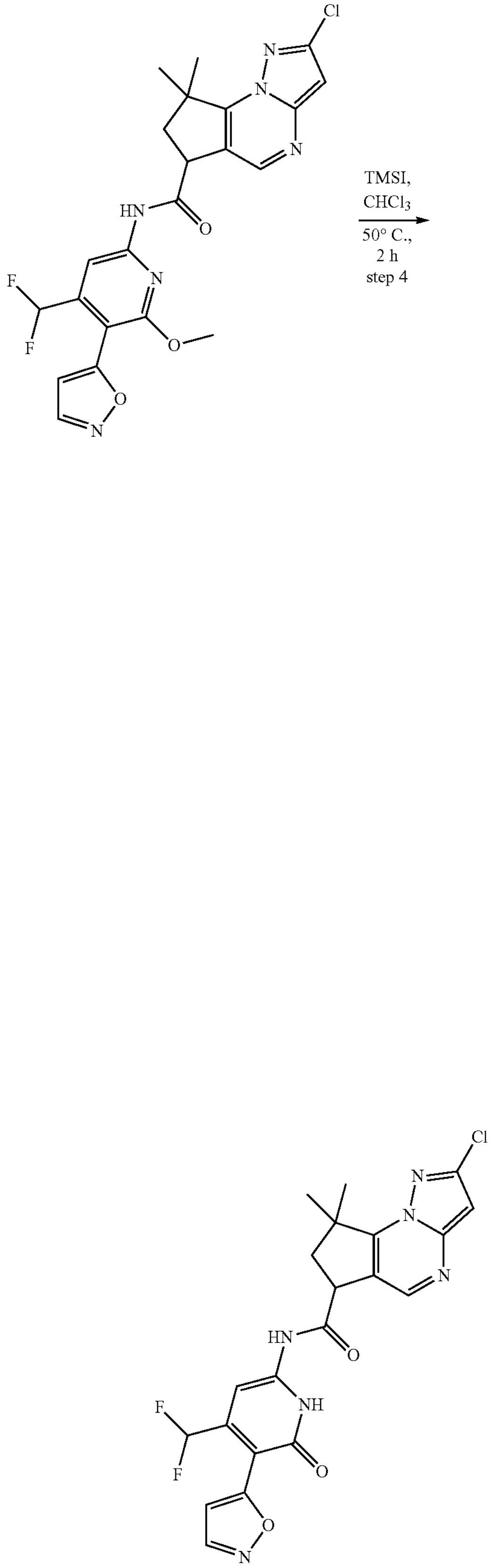
Example 60

Examples 60: 2-chloro-N-(4-(difluoromethyl)-5-(isoxazol-5-yl)-6-oxo-1,6-dihydropyridin-2-yl)-8,8-dimethyl-7,8-dihydro-6H-cyclopenta[e]pyrazolo[1,5-a]pyrimidine-6-carboxamide Step 1: N-(5-acetyl-4-(difluoromethyl)-6-methoxy-pyridin-2-yl)-2-chloro-8,8-dimethyl-7,8-dihydro-6H-cyclopenta[e]pyrazolo[1,5-a]pyrimidine-6-carboxamide

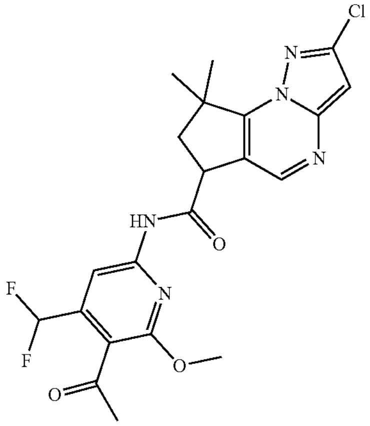 [SMILES: COc1nc(NC(=O)C2CC(C)(C)c3c2cnc2cc(Cl)nn32)cc(C(F)F)c1C(C)=O]

To a stirred mixture of N-(5-bromo-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (Method U1 Step 7; 200 mg, 399.4 μmol) in DMF (5 mL) were added tributyl(1-ethoxyvinyl)stannane (288 mg, 798.8 μmol) and $Pd(PPh_3)_4$ (99 mg, 79.8 μmol) at 25° C. under nitrogen. The resulting mixture was stirred at 80° C. for 6 h under nitrogen. The mixture was cooled to 25° C. The residue was quenched with HCl (50 mL, 2 M). The resulting mixture were extracted with EtOAc (3×200 mL), dried over anhydrous sodium sulfate and concentrated under vacuum. The residue was applied on a silica gel column and eluted with EtOAc/PE (2:1) to give N-(5-acetyl-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (180 mg, 74% yield) as a yellow solid. $^1H$ NMR (300 MHz, DMSO-$d_6$) δ: 11.21 (br, 1H), 8.58 (s, 1H), 8.00 (s, 1H), 7.01 (t, J=54 Hz, 1H) 6.80 (s, 1H), 4.51-4.58 (m, 1H), 3.78 (s, 3H), 2.52-2.55 (m, 1H), 2.52 (s, 3H), 2.25-2.31 (m, 1H), 1.62 (s, 3H), 1.54 (s, 3H). LC-MS: m/z 464 $[M+H]^+$.

Step 2: (E)-2-chloro-N-(4-(difluoromethyl)-5~(3-(dimethylamino)acryloyl)-6-oxo-1,6-dihydropyridin-2-yl)-8,8-dimethyl-7,8-dihydro-6H-cyclopenta[e]pyrazolo[1,5-a]pyrimidine-6-carboxamide

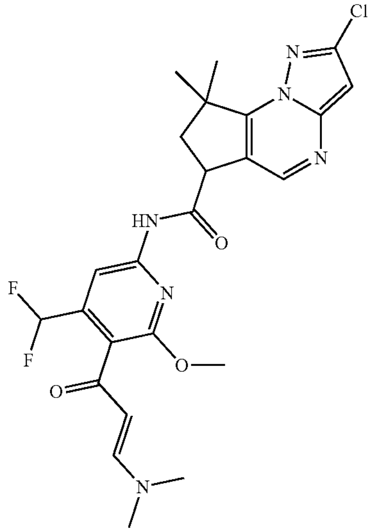 [SMILES: COc1nc(NC(=O)C2CC(C)(C)c3c2cnc2cc(Cl)nn32)cc(C(F)F)c1C(=O)/C=C/N(C)C]

To a stirred mixture of N-(5-acetyl-4-(difluoromethyl)-6-methoxypyridin-2-yl)-2-chloro-8,8-dimethyl-7,8-dihydro-6H-cyclopenta[e]pyrazolo[1,5-a]pyrimidine-6-carboxamide (150 mg, 323.4 μmol) in toluene (10 mL) was added DMF-DMA (192 mg, 1.6 mmol) at 25° C. under nitrogen. The resulting mixture was stirred at 60° C. for 48 h under nitrogen. The mixture was cooled to 25° C. The residue was concentrated under vacuum. The residue was applied on a silica gel column and eluted with EtOAc/PE (2:1) to give (E)-2-chloro-N-(4-(difluoromethyl)-5~(3-(dimethylamino)acryloyl)-6-oxo-1,6-dihydropyridin-2-yl)-8,8-dimethyl-7,8-dihydro-6H-cyclopenta[e]pyrazolo[1,5-a]pyrimidine-6-carboxamide (20 mg, 10% yield) as a yellow solid. LC-MS: m/z 519 $[M+H]^+$.

Step 3: 2-chloro-N-(4-(difluoromethyl)-5-(isoxazol-5-yl)-6-methoxypyridin-2-yl)-8,8-dimethyl-7,8-dihydro-6H-cyclopenta[e]pyrazolo[1,5-a]pyrimidine-6-carboxamide

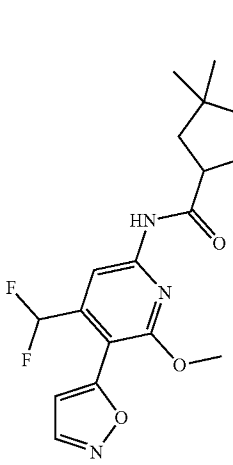

To a stirred mixture of (E)-2-chloro-N-(4-(difluoromethyl)-5~(3-(dimethylamino)acryloyl)-6-oxo-1,6-dihydropyridin-2-yl)-8,8-dimethyl-7,8-dihydro-6H-cyclopenta[e]pyrazolo[1,5-a]pyrimidine-6-carboxamide (35 mg, 67.4 μmol) in ethanol (4 mL) was added hydroxylamine hydrochloride (7 mg, 101.2 μmol) at 25° C. under nitrogen. The resulting mixture was stirred at 90° C. for 2 h under nitrogen. The mixture was cooled to 25° C. The resulting solution was diluted with water (50 mL) and extracted with DCM (3×50 mL). The combined organic layers were dried over anhydrous sodium sulfate and concentrated under vacuum. The residue was applied on a silica gel column and eluted with EtOAc/PE (5:1) to give 2-chloro-N-(4-(difluoromethyl)-5-(isoxazol-5-yl)-6-methoxypyridin-2-yl)-8,8-dimethyl-7,8-dihydro-6H-cyclopenta[e]pyrazolo[1,5-a]pyrimidine-6-carboxamide (15 mg, 45% yield) as an off white solid. LC-MS: m/z 489 $[M+H]^+$.

Step 4: 2-chloro-N-(4-(difluoromethyl)-5-(isoxazol-5-yl)-6-oxo-1,6-dihydropyridin-2-yl)-8,8-dimethyl-7,8-dihydro-6H-cyclopenta[e]pyrazolo[1,5-a]pyrimidine-6-carboxamide Example 60

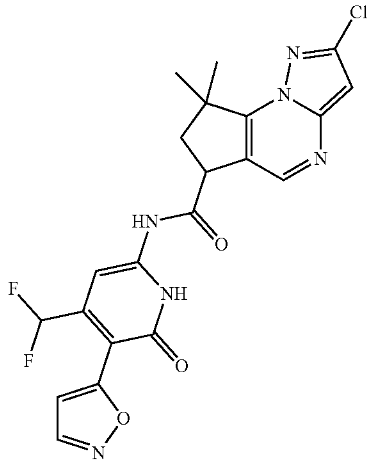 [SMILES: COc1nc(NC(=O)C2CC(C)(C)c3c2cnc2cc(Cl)nn32)cc(C(F)F)c1-c1ccno1]

To a stirred mixture of 2-chloro-N-(4-(difluoromethyl)-5-(isoxazol-5-yl)-6-methoxypyridin-2-yl)-8,8-dimethyl-7,8-dihydro-6H-cyclopenta[e]pyrazolo[1,5-a]pyrimidine-6-carboxamide (23 mg, 47.1 μmol) in chloroform (6 mL) was added iodotrimethylsilane (94 mg, 470.5 mmol) in portions at 25° C. under nitrogen. The resulting mixture was stirred at 50° C. for 2 h under nitrogen. The mixture was cooled to 25° C. The reaction mixture was diluted with water (15 mL), and then extracted with DCM (3×15 mL). The combined organic layers were washed with brine (40 mL), dried over anhydrous sodium sulfate and concentrated under vacuum. The crude product (20 mg) was purified by Prep-HPLC to afford 2-chloro-N-(4-(difluoromethyl)-5-(isoxazol-5-yl)-6-oxo-1,6-dihydropyridin-2-yl)-8,8-dimethyl-7,8-dihydro-6H-cyclopenta[e]pyrazolo[1,5-a]pyrimidine-6-carboxamide (9.5 mg, 42% yield) as an off white solid.

Example 60: $^1H$ NMR (400 MHz, DMSO-$d_6$) δ: 12.00 (br, 1H), 11.06 (s, 1H), 8.65-8.70 (m, 2H), 7.24 (t, J=54 Hz, 1H), 6.95 (s, 1H), 6.90 (bs, 1H), 4.51-4.60 (m, 1H), 2.55-2.62 (m, 1H), 2.29-2.33 (m, 1H), 1.64 (s, 3H), 1.56 (s, 3H). LC-MS: m/z 475 $[M+H]^+$ Method D2

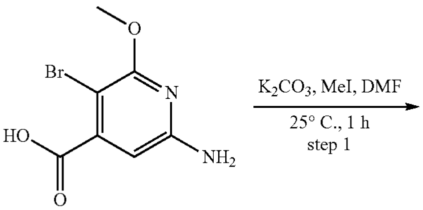

Method U1 Step 3

-continued
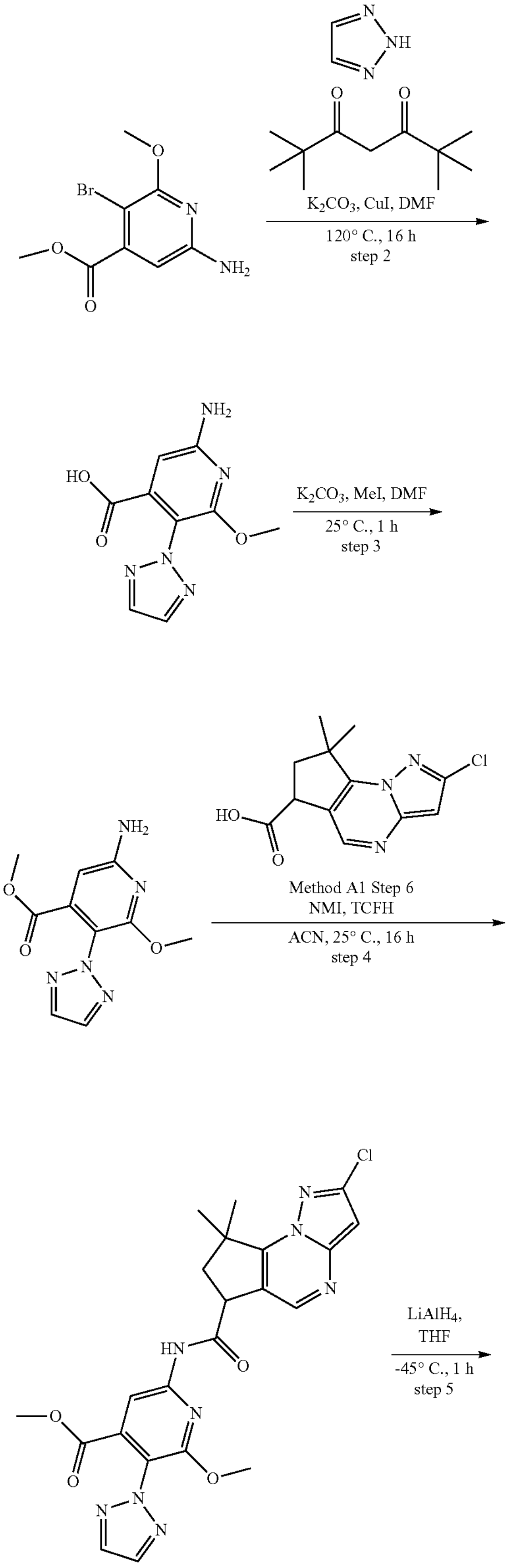
-continued
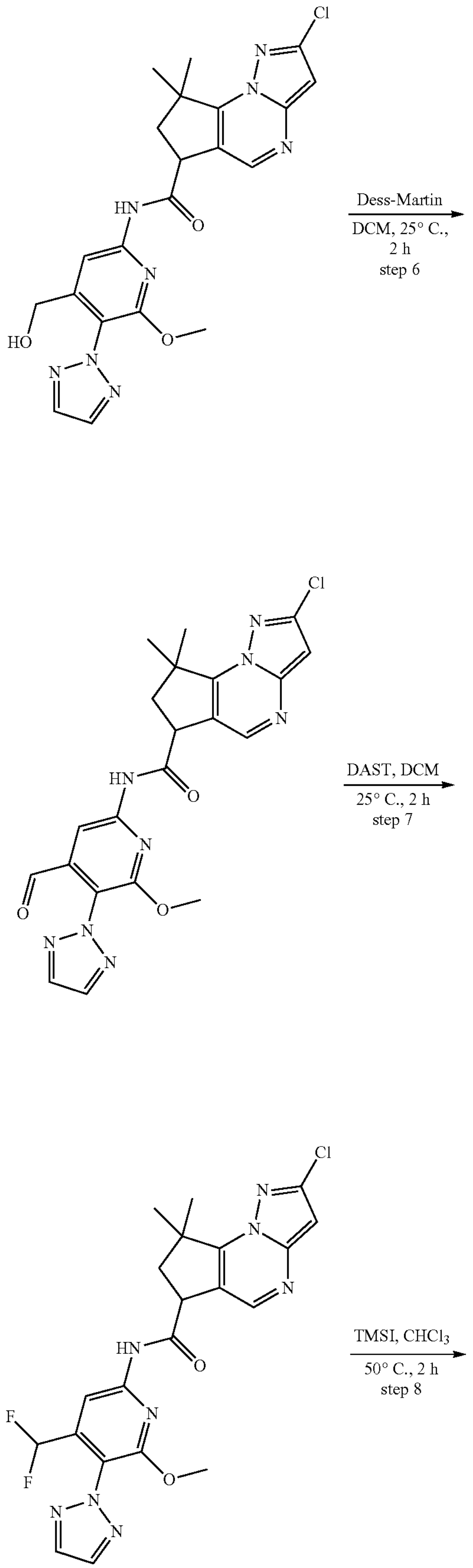

-continued

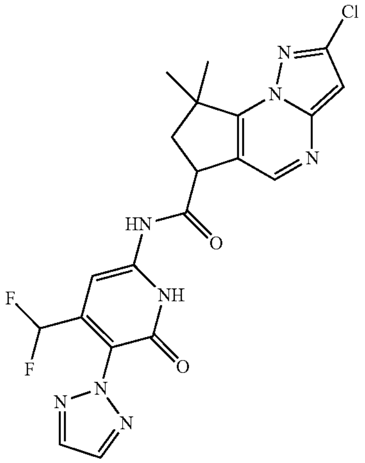

Example 61

Examples 61: 2-chloro-N-(4-(difluoromethyl)-6-oxo-5~(2H-1,2,3-triazol-2-yl)-1,6-dihydropyridin-2-yl)-8,8-dimethyl-7,8-dihydro-6H-cyclopenta[e]pyrazolo[1,5-a]pyrimidine-6-carboxamide Step 1: methyl 6-amino-3-bromo-2-methoxyisonicotinate

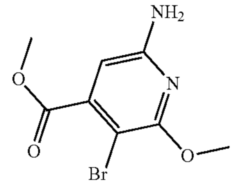

To a stirred solution of 6-amino-3-bromo-2-methoxyisonicotinic acid (Method U1 Step 3; 10 g, 40.6 mmol) in DMF (50 mL) were added iodomethane (7.1 g, 50.2 mmol) and $K_2CO_3$ (11.2 g, 81.2 mmol). The mixture was stirred at 25° C. for 4 h. The resulting mixture was poured into water (400 mL) and extracted with EtOAc (3×400 mL). The combined organic layers were washed with water (3×400 mL), dried over anhydrous sodium sulfate and concentrated under reduced pressure. The residue was applied on a silica gel column and eluted with EtOAc/PE (1:5) to give methyl 6-amino-3-bromo-2-methoxyisonicotinate (5 g, 47% yield) as a yellow solid. LC-MS: m/z 261 $[M+H]^+$.

Step 2: 6-amino-2-methoxy-3-(2H-1,2,3-triazol-2-yl)isonicotinic acid

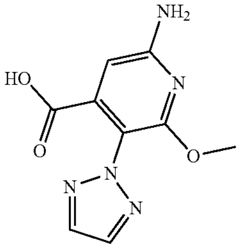 [SMILES: COc1nc(N)cc(C(=O)O)c1-n1nccn1]

To a stirred solution of methyl 6-amino-3-bromo-2-methoxyisonicotinate (4.1 g, 15.7 mmol) and 2H-1,2,3-triazole (1.6 g, 25.6 mmol) in DMF (20 mL) were added 2,2,6,6-tetramethylheptane-3,5-dione (578 mg, 3.2 mmol), CuI (598 mg, 3.2 mmol) and $K_2CO_3$ (4.4 g, 31.4 mmol). The mixture was stirred at 25° C. for 16 h. The resulting mixture was poured into water (200 mL) and extracted with EtOAc (3×200 mL). The combined organic layers were washed with water (3×500 mL), dried over anhydrous sodium sulfate, and concentrated under reduced pressure. The residue was applied on a silica gel column and eluted with EtOAc/PE (2:1) to give 6-amino-2-methoxy-3-(2H-1,2,3-triazol-2-yl)isonicotinic acid (1 g, 27% yield) as a yellow solid. LC-MS: m/z 236 $[M+H]^+$.

Step 3: methyl 6-amino-2-methoxy-3-(2H-1,2,3-triazol-2-yl)isonicotinate

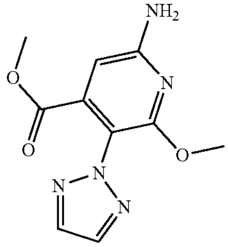 [SMILES: COC(=O)c1cc(N)nc(OC)c1-n1nccn1]

To a stirred solution of 6-amino-2-methoxy-3-(2H-1,2,3-triazol-2-yl)isonicotinic acid (1 g, 4.3 mmol) in DMF (10 mL) were added iodomethane (905 mg, 6.4 mmol) and $K_2CO_3$ (1.2 g, 8.5 mmol). The mixture was stirred at 25° C. for 4 h. The resulting mixture was poured into water (100 mL) and extracted with EtOAc (3×100 mL). The combined organic layers were washed with water (3×200 mL), dried over anhydrous sodium sulfate, and concentrated under reduced pressure. The residue was applied on a silica gel column and eluted with EtOAc/PE (1:3) to give methyl 6-amino-2-methoxy-3-(2H-1,2,3-triazol-2-yl)isonicotinate (340 mg, 32% yield) as a yellow solid. $^1$H NMR (300 MHz, DMSO-$d_6$) δ: 7.90 (s, 2H), 6.82 (br, 2H), 6.41 (s, 1H), 3.84 (s, 3H), 3.50 (s, 3H). LC-MS: m/z 250 $[M+H]^+$.

Step 4: methyl 6-(2-chloro-8,8-dimethyl-7,8-dihydro-6H-cyclopenta[e]pyrazolo[1,5-a]pyrimidine-6-carboxamido)-2-methoxy-3-(2H-1,2,3-triazol-2-yl) isonicotinate

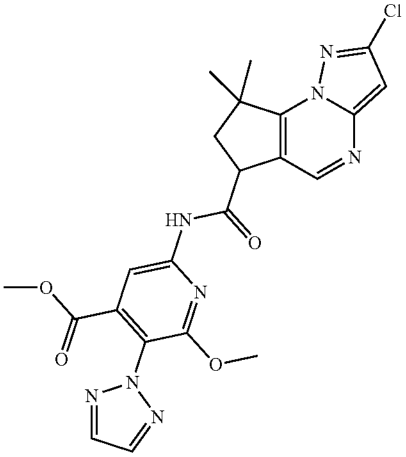 [SMILES: COC(=O)c1cc(NC(=O)C2CC(C)(C)c3c2cnc2cc(Cl)nn32)nc(OC)c1-n1nccn1]

To a stirred solution of methyl 6-amino-2-methoxy-3-(2H-1,2,3-triazol-2-yl)isonicotinate (330 mg, 1.3 mmol) and 2-chloro-8,8-dimethyl-7,8-dihydro-6H-cyclopenta[e]pyrazolo[1,5-a]pyrimidine-6-carboxylic acid (Method A1 step 6; 492 mg, 1.8 mmol) in acetonitrile (10 mL) were added TCFH (1.1 g, 3.9 mmol) and NMI (326 mg, 3.9 mmol). The resulting mixture was stirred at 25° C. for 16 h. The reaction mixture was quenched with water (50 mL). The resulting solution was extracted with EtOAc (3×50 mL). The combined organic layers were dried over anhydrous sodium sulfate and concentrated under vacuum. The residue was applied on a silica gel column and eluted with EtOAc/PE (1:1) to give methyl 6-(2-chloro-8,8-dimethyl-7,8-dihydro-6H-cyclopenta[e]pyrazolo[1,5-a]pyrimidine-6-carboxamido)-2-methoxy-3-(2H-1,2,3-triazol-2-yl)isonicotinate (400 mg, 38% yield) as a yellow solid. LC-MS: m/z 497 $[M+H]^+$.

Step 5: 2-chloro-N-(4-(hydroxymethyl)-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide

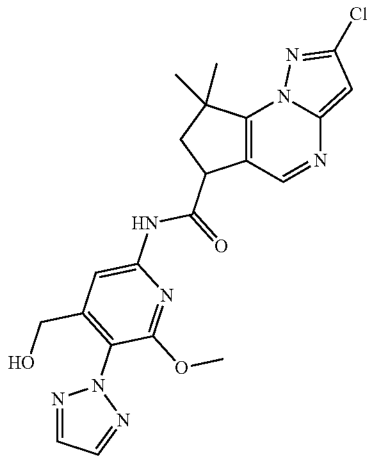 [SMILES: COc1nc(NC(=O)C2CC(C)(C)c3c2cnc2cc(Cl)nn32)cc(CO)c1-n1nccn1]

To a stirred solution of methyl 6-(2-chloro-8,8-dimethyl-7,8-dihydro-6H-cyclopenta[e]pyrazolo[1,5-a]pyrimidine-6-carboxamido)-2-methoxy-3-(2H-1,2,3-triazol-2-yl)isonicotinate (230 mg, 463 μmol) in THE (20 mL) at −40° C. was added $LiAlH_4$ (53 mg, 1.4 mmol) slowly. The reaction mixture was stirred at −40° C. for 1 h. Water (53 mg) and NaOH (53 mg, 10% in water) were added. Another batch of water (53 mg) was added into the mixture, and it was stirred for 5 min. The solid was filtered off and the filtrate was concentrated under vacuum. The residue was applied on a silica gel column and eluted with EtOAc/PE (5:1) to give 2-chloro-N-(4-(hydroxymethyl)-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide (100 mg, 36% yield) as a yellow solid. LC-MS: m/z 469 $[M+H]^+$.

Step 6: 2-chloro-N-(4-formyl-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide

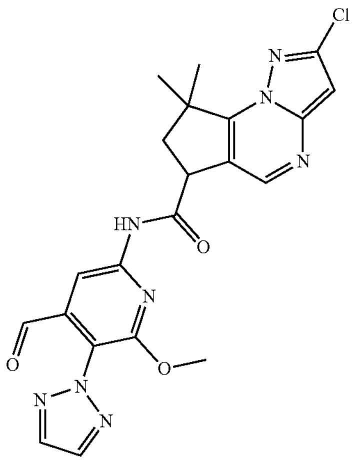 [SMILES: COc1nc(NC(=O)C2CC(C)(C)c3c2cnc2cc(Cl)nn32)cc(C=O)c1-n1nccn1]

To a stirred solution of 2-chloro-N-(4-(hydroxymethyl)-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide (100 mg, 213 μmol) in DCM (5 mL) at 0° C. was slowly added Dess-Martin periodinane (361 mg, 853 μmol). The reaction mixture was stirred at 25° C. for 1 h. The solid was filtered off and the filtrate was concentrated under vacuum. The residue was applied on a silica gel column and eluted with EtOAc/PE (5:1) to give 2-chloro-N-(4-formyl-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide (30 mg, 30% yield) as a yellow solid. LC-MS: m/z 467 $[M+H]^+$.

Step 7: 2-chloro-N-(4-(difluoromethyl)-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide

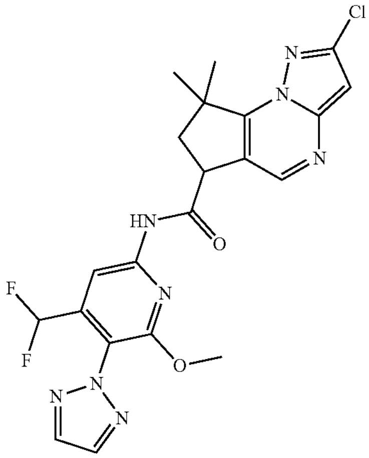 [SMILES: COc1nc(NC(=O)C2CC(C)(C)c3c2cnc2cc(Cl)nn32)cc(C(F)F)c1-n1nccn1]

To a stirred solution of 2-chloro-N-(4-formyl-6-methoxy-5-(2H-1,2,3-triazol-2-yl)pyridin-2-yl)-8,8-dimethyl-7,8-dihydro-6H-cyclopenta[e]pyrazolo[1,5-a]pyrimidine-6-carboxamide (30 mg, 64 μmol) in DCM (5 mL) at −20° C. was slowly added diethylaminosulfur trifluoride (20 mg, 128 μmol). The reaction mixture was stirred at 25° C. for 1 h. The resulting mixture was poured into crushed ice (10 mL) and extracted with DCM (3×10 mL). The combined organic layers were concentrated under vacuum. The residue was applied on a silica gel column and eluted with EtOAc/PE (5:1) to give 2-chloro-N-(4-(difluoromethyl)-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide (8 mg, 16% yield) as a yellow solid. LC-MS: m/z 489 $[M+H]^+$.

Step 8: 2-chloro-N-(4-(difluoromethyl)-6-oxo-5~(2H-1,2,3-triazol-2-yl)-1,6-dihydropyridin-2-yl)-8,8-dimethyl-7,8-dihydro-6H-cyclopenta[e]pyrazolo[1,5-a]pyrimidine-6-carboxamide Example 61

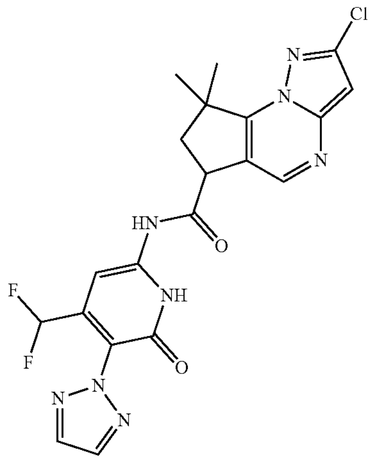

To a stirred mixture of 2-chloro-N-(4-(difluoromethyl)-6-methoxy-5~(2H-1,2,3-triazol-2-yl)pyridin-2-yl)-8,8-dimethyl-7,8-dihydro-6H-cyclopenta[e]pyrazolo[1,5-a]pyrimidine-6-carboxamide (8 mg, 16.2 μmol) in chloroform (4 mL) was added iodotrimethylsilane (33 mg, 162 mmol) in portions at 25° C. under nitrogen. The resulting mixture was stirred for 2 h at 50° C. under nitrogen. The mixture was cooled to 25° C. The reaction mixture was diluted with water (10 mL), and then extracted with DCM (3×10 mL). The combined organic layers were washed with brine (30 mL), dried over anhydrous sodium sulfate and concentrated under vacuum. The crude product (6 mg) was purified by Prep-HPLC to afford 2-chloro-N-(4-(difluoromethyl)-6-oxo-5~(2H-1,2,3-triazol-2-yl)-1,6-dihydropyridin-2-yl)-8,8-dimethyl-7,8-dihydro-6H-cyclopenta[e]pyrazolo[1,5-a]pyrimidine-6-carboxamide (3 mg, 38% yield) as an off-white solid.

Example 61: $^1H$ NMR (300 MHz, DMSO-$d_6$) δ: 11.91 (br, 1H), 11.10 (s, 1H), 8.65 (s, 1H), 8.10 (s, 2H), 7.65 (br, 1H), 6.95 (s, 1H), 6.59 (t, J=54 Hz, 1H), 4.50-4.62 (m, 1H), 2.50-2.58 (m, 1H), 2.27-2.35 (m, 1H), 1.65 (s, 3H), 1.56 (s, 3H). LC-MS: m/z 475 $[M+H]^+$.
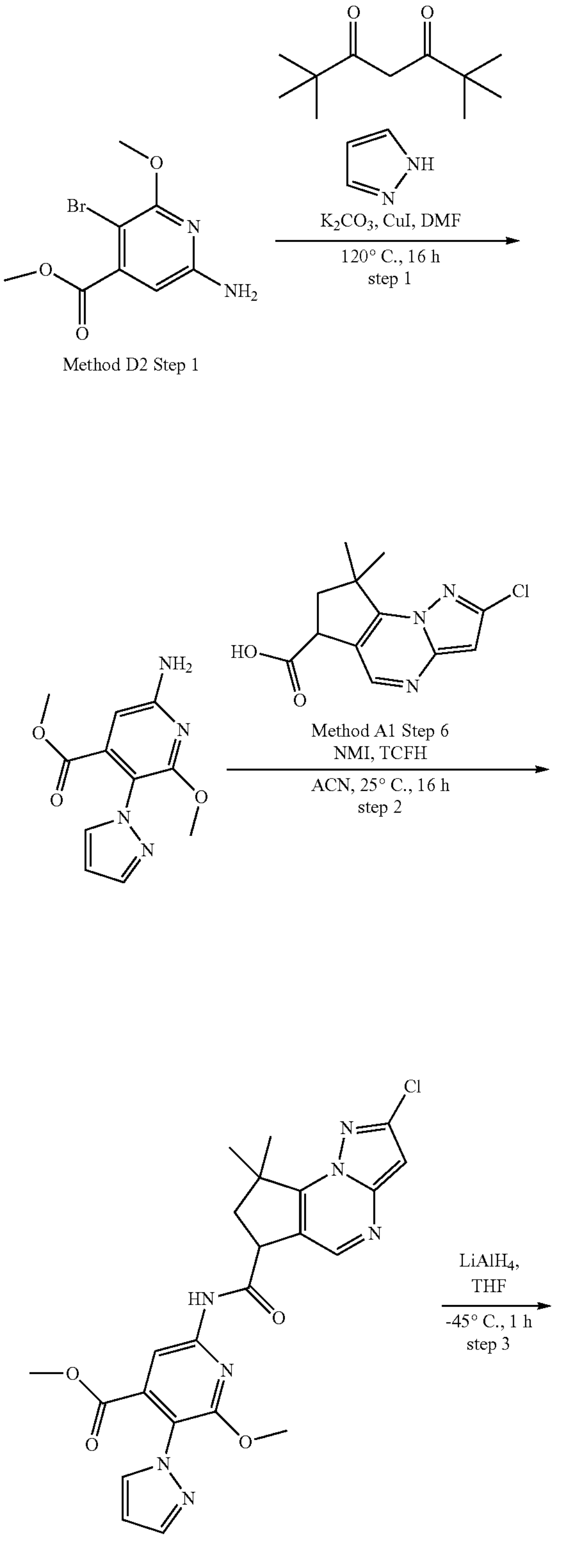
-continued
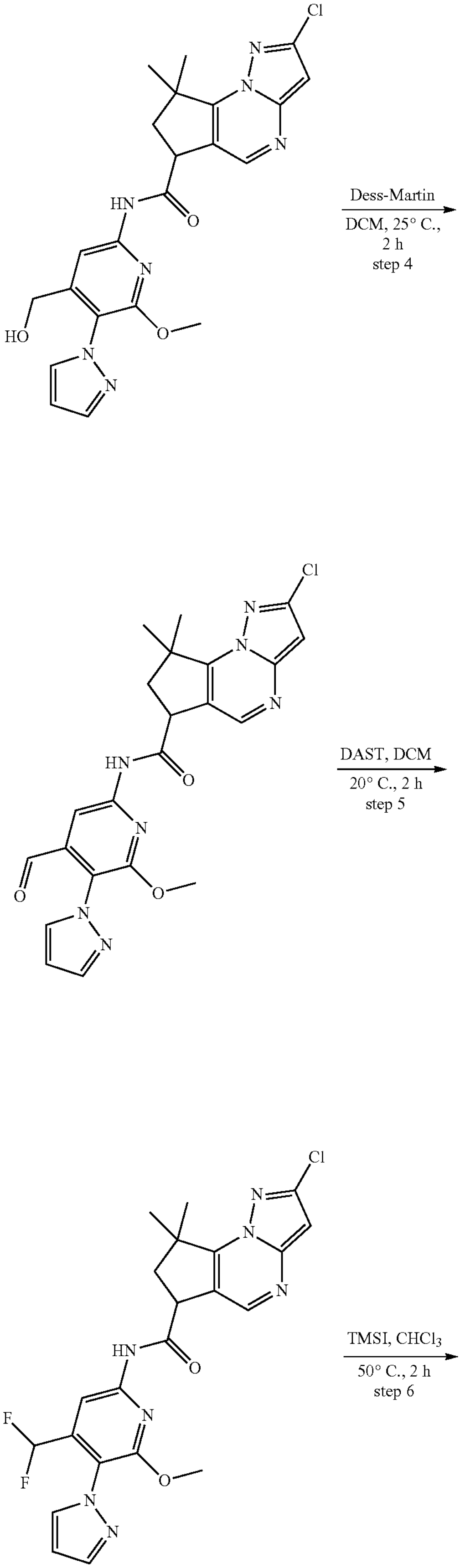

-continued

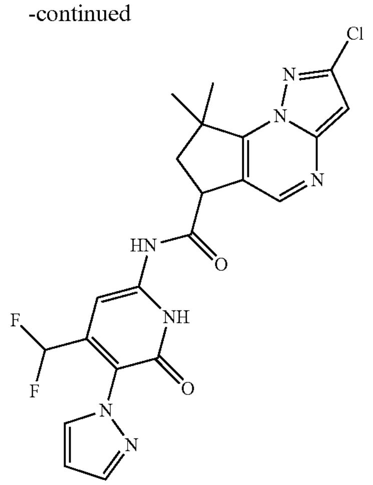

Example 62

Method E2

Examples 62: 2-chloro-N-(4-(difluoromethyl)-6-oxo-5-(1H-pyrazol-1-yl)-1,6-dihydropyridin-2-yl)-8,8-dimethyl-7,8-dihydro-6H-cyclopenta[e]pyrazolo[1,5-a]pyrimidine-6-carboxamide Step 1: methyl 6-amino-2-methoxy-3-(1H-pyrazol-1-yl)isonicotinate

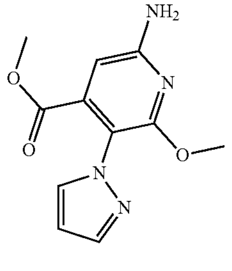 [SMILES: COC(=O)c1cc(N)nc(OC)c1-n1cccn1]

To a stirred solution of methyl 6-amino-3-bromo-2-methoxyisonicotinate (Method D2

Step 1; 2 g, 7.6 mmol) and 1H-pyrazole (782 mg, 17.5 mmol) in DMF (20 mL) were added 2,2,6,6-tetramethylheptane-3,5-dione (279 mg, 1.6 mmol), CuI (300 mg, 1.6 mmol) and $K_2CO_3$ (2.2 g, 16.2 mmol). The mixture was stirred at 25° C. for 16 h. The resulting mixture was poured into water (200 mL) and extracted with EtOAc (3×200 mL). The combined organic layers were washed with water (3×500 mL), dried over anhydrous sodium sulfate, and concentrated under reduced pressure. The residue was applied on a silica gel column and eluted with EtOAc/PE (1:1) to give methyl 6-amino-2-methoxy-3-(1H-pyrazol-1-yl)isonicotinate (650 mg, 33% yield) as a brown solid. $^1H$ NMR (300 MHz, DMSO-$d_6$) δ: 7.78 (s, 1H), 7.54 (s, 1H), 6.61 (s, 2H), 6.31 (br, 2H), 3.80 (s, 3H), 3.52 (s, 3H). LC-MS: m/z 249 $[M+H]^+$ Step 2: methyl 6-(2-chloro-8,8-dimethyl-7,8-dihydro-6H-cyclopenta[e]pyrazolo[1,5-a]pyrimidine-6-carboxamido)-2-methoxy-3-(1H-pyrazol-1-yl)isonicotinate

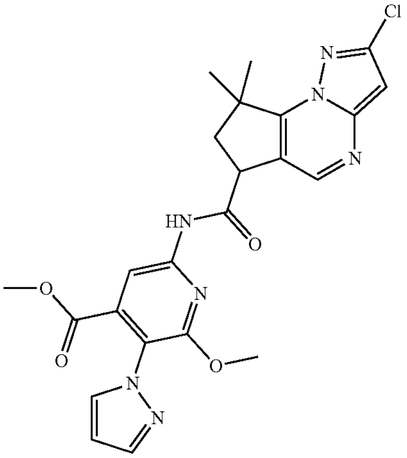 [SMILES: COC(=O)c1cc(NC(=O)C2CC(C)(C)c3c2cnc2cc(Cl)nn32)nc(OC)c1-n1cccn1]

To a stirred solution of methyl 6-amino-2-methoxy-3-(2H-1,2,3-triazol-2-yl)isonicotinate (650 mg, 2.6 mmol) and 2-chloro-8,8-dimethyl-7,8-dihydro-6H-cyclopenta[e]pyrazolo[1,5-a]pyrimidine-6-carboxylic acid (Method A1 step 6; 984 mg, 3.6 mmol) in acetonitrile (20 mL) were added TCFH (2.2 g, 7.8 mmol) and NMI (652 mg, 7.8 mmol). The resulting mixture was stirred at 25° C. for 16 h. The reaction mixture was quenched with water (100 mL). The resulting solution was extracted with EtOAc (3×100 mL). The combined organic layers were dried over anhydrous sodium sulfate and concentrated under vacuum. The residue was applied on a silica gel column and eluted with EtOAc/PE (5:1) to give methyl 6-(2-chloro-8,8-dimethyl-7,8-dihydro-6H-cyclopenta [e]pyrazolo[1,5-a]pyrimidine-6-carboxamido)-2-methoxy-3-(1H-pyrazol-1-yl)isonicotinate (500 mg, 34% yield) as a yellow oil. $^1H$ NMR (400 MHz, DMSO-$d_6$) δ: 11.19 (br, 1H), 8.61 (s, 1H), 8.05-7.95 (m, 2H), 7.66 (d, J=1.8 Hz, 1H), 6.95 (s, 1H), 6.48 (t, J=2.1 Hz, 1H), 4.53-4.56 (m, 1H), 3.99 (s, 3H), 3.55 (s, 3H), 2.49-2.53 (m, 1H), 2.23-2.36 (m, 1H), 1.65 (s, 3H), 1.57 (s, 3H). LC-MS: m/z 496 $[M+H]^+$.

Step 3: 2-chloro-N-(4-(hydroxymethyl)-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide

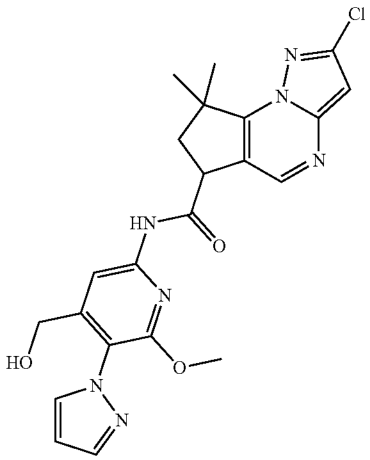 [SMILES: COc1nc(NC(=O)C2CC(C)(C)c3c2cnc2cc(Cl)nn32)cc(CO)c1-n1cccn1]

To a stirred solution of methyl 6-(2-chloro-8,8-dimethyl-7,8-dihydro-6H-cyclopenta[e]pyrazolo[1,5-a]pyrimidine-6-carboxamido)-2-methoxy-3-(1H-pyrazol-1-yl)isonicotinate (600 mg, 1.2 mmol) in THE (20 mL) at −45° C. was added slowly $LiAlH_4$ (91 mg, 2.4 mmol). The reaction mixture was stirred at −45° C. for 1 h. Water (91 mg) and NaOH (91 mg, 10% in water) were added. Another batch of water (91 mg) was added into the mixture and it was stirred for 5 min. The solid was filtered off and the filtrate was concentrated under vacuum. The residue was applied on a silica gel column and eluted with EtOAc/PE (10:1) to give 2-chloro-N-(4-(hydroxymethyl)-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide (280 mg, 30% yield) as a light yellow solid. LC-MS: m/z 468 $[M+H]^+$.

Step 4: 2-chloro-N-(4-formyl-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide

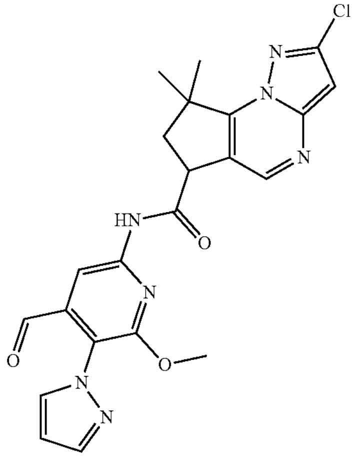 [SMILES: COc1nc(NC(=O)C2CC(C)(C)c3c2cnc2cc(Cl)nn32)cc(C=O)c1-n1cccn1]

To a stirred solution of 2-chloro-N-(4-(hydroxymethyl)-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide (280 mg, 598 μmol) in DCM (10 mL) at 0° C. was slowly added Dess-martin periodinane (380 mg, 897 μmol). The reaction mixture was stirred at 25° C. for 1 h. The solid was filtered off and the filtrate was concentrated under vacuum. The residue was applied on a silica gel column and eluted with EtOAc/PE (5:1) to give 2-chloro-N-(4-formyl-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide (120 mg, 32% yield) as a yellow solid. LC-MS: m/z 466 $[M+H]^+$.

Step 5: 2-chloro-N-(4-(difluoromethyl)-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide

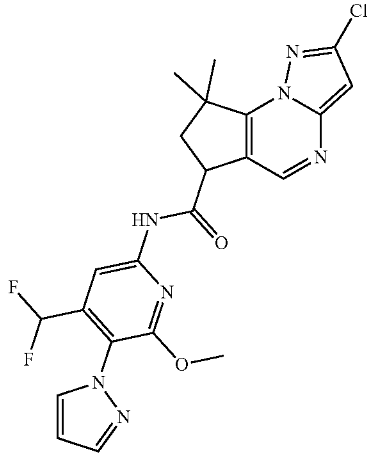 [SMILES: COc1nc(NC(=O)C2CC(C)(C)c3c2cnc2cc(Cl)nn32)cc(C(F)F)c1-n1cccn1]

To a stirred solution of 2-chloro-N-(4-formyl-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide (100 mg, 214 μmol) in DCM (10 mL) at −20° C. was slowly added diethylaminosulfur trifluoride (69 mg, 428 μmol). The reaction mixture was stirred at 25° C. for 1 h. The resulting mixture was poured into crushed ice (15 mL) and extracted with DCM (3×15 mL). The combined organic layers were concentrated under vacuum. The residue was applied on a silica gel column and eluted with EtOAc/PE (5:1) to give 2-chloro-N-(4-(difluoromethyl)-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide (10 mg, 9% yield) as a yellow solid. LC-MS: m/z 488 $[M+H]^+$.

Step 6: 2-chloro-N-(4-(difluoromethyl)-6-oxo-5~(1H-pyrazol-1-yl)-1,6-dihydropyridin-2-yl)-8,8-dimethyl-7,8-dihydro-6H-cyclopenta[e]pyrazolo[1,5-a]pyrimidine-6-carboxamide Example 62

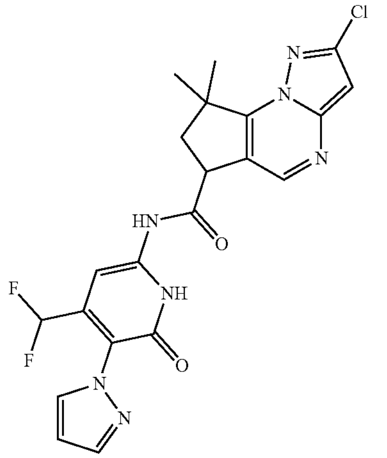

To a stirred mixture of 2-chloro-N-(4-(difluoromethyl)-6-methoxy-5~(1H-pyrazol-1-yl)pyridin-2-yl)-8,8-dimethyl-7,8-dihydro-6H-cyclopenta[e]pyrazolo[1,5-a]pyrimidine-6-carboxamide (10 mg, 20.4 μmol) in chloroform (4 mL) was added iodotrimethylsilane (40 mg, 204 μmol) in portions at 25° C. under nitrogen. The resulting mixture was stirred at 50° C. for 2 h under nitrogen. The mixture was cooled to 25° C. The reaction mixture was diluted with water (12 mL), and then extracted with DCM (3x12 mL). The organic layers were combined, washed with brine (30 mL), dried over anhydrous sodium sulfate and concentrated under vacuum. The crude product (7 mg) was purified by Prep-HPLC to afford 2-chloro-N-(4-(difluoromethyl)-6-oxo-5-(1H-pyrazol-1-yl)-1,6-dihydropyridin-2-yl)-8,8-dimethyl-7,8-dihydro-6H-cyclopenta[e]pyrazolo[1,5-a]pyrimidine-6-carboxamide (4 mg, 51% yield) as a white solid.

Example 62: $^{1}$H NMR (300 MHz, DMSO-$d_6$) δ: 11.89 (br, 1H), 10.98 (s, 1H), 8.65 (s, 1H), 8.00 (d, J=2.1 Hz, 1H), 7.90 (br, 1H), 7.74 (d, J=2.1 Hz, 1H), 6.96 (s, 1H), 6.75 (t, J=54 Hz, 1H), 6.50-6.51 (m, 1H), 4.50-4.61 (m, 1H), 2.50-2.59 (m, 1H), 2.38-2.49 (m, 1H), 1.65 (s, 3H), 1.57 (s, 3H). LC-MS: m/z 474 [M+H]$^+$.

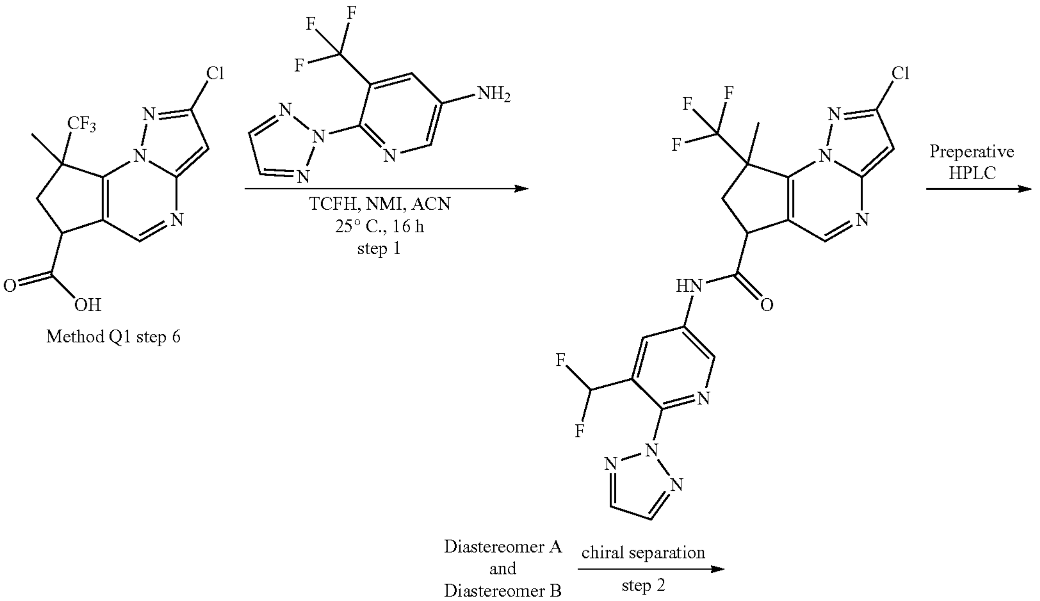

Method Q1 step 6

Diastereomer A
and
Diastereomer B

-continued

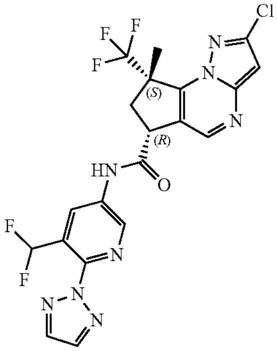

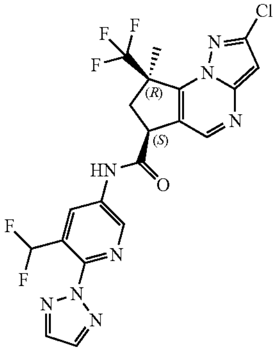

Example 63 and Example 64 were obtained through chiral resolution of Diastereomer A.

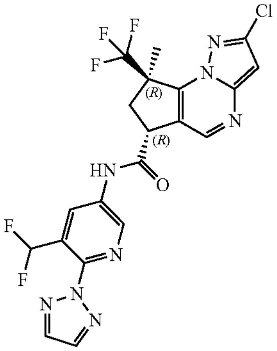

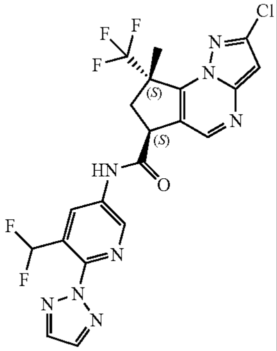

Example 65 and Example 66 were obtained through chiral resolution of Diastereomer B.

Examples 63, 64, 65 and 66: Single Enantiomers Obtained from Racemic Mixtures Containing (6R,8S)-2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide, (6S,8R)-2-chloro-N-(5-(difluoro-methyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide, (6R,8R)-2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide and (6S,8S)-2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide

Step 1: 2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide

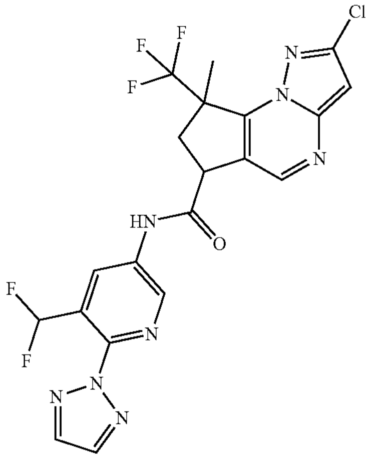 [SMILES: CC1(C(F)(F)F)CC(C(=O)Nc2cnc(-n3nccn3)c(C(F)F)c2)c2cnc3cc(Cl)nn3c21]

To a stirred solution of 2-chloro-8-methyl-8-(trifluoromethyl)-7,8-dihydro-6H-cyclopenta[e]pyrazolo[1,5-a]pyrimidine-6-carboxylic acid (Method Q1 step 6; 50 mg, 156.7 μmol) in acetonitrile (8 mL) were added 5-(difluoromethyl)-6-(2H-1,2,3-triazol-2-yl)pyridin-3-amine (Method W1 step 4; 50 mg, 235.1 μmol), TCFH (176 mg, 627.0 μmol), NMI (51 mg, 627.0 μmol). The resulting mixture was stirred for 16 h at 25° C. The reaction mixture was quenched with water (50 mL). The resulting solution was extracted with EtOAc (3×30 mL), dried over anhydrous sodium sulfate, and concentrated under vacuum. The residue was applied onto a silica gel column and eluted with EtOAc/PE (1:1) to give 2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide as a mixture of two racemic diastereomeric pairs as white solid. LC-MS: m/z 513 $[M+H]^+$. This mixture was submitted to Prep-HPLC to obtain the separated racemic mixtures of Diastereomer A and Diastereomer B.

Step 2: Separation of Enantiomers to Obtain (6R,8S)-2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide, (6S,8R)-2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide, (6R,8R)-2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide and (6S,8S)-2-chloro-N-(5-(difluoromethyl)-6-(2H-1,2,3-triazol-2-yl)pyridin-3-yl)-8-methyl-8-(trifluoromethyl)-7,8-dihydro-6H-cyclopenta[e]pyrazolo[1,5-a]pyrimidine-6-carboxamide Example 63

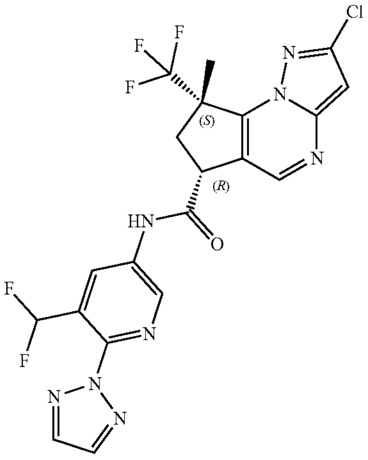

-continued

Example 64

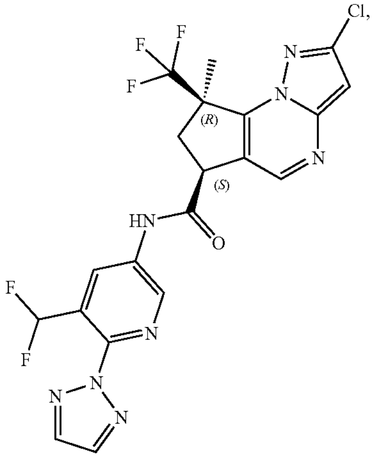
,

Example 65

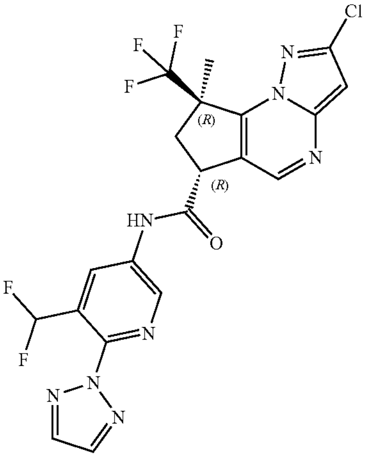
and

Example 66

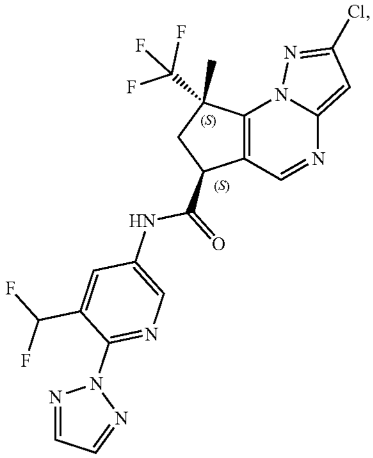
, 30 mg of Diastereomer A were submitted to chiral HPLC purification (Column: CHIRALPAK IA, 2*25 cm, 5 um; Mobile Phase A: Hex (0.1% FA), Mobile Phase B: EtOH; Flow rate: 20 mL/min; isocratic 30% B 15 min; 254/220 nm; RT1: 7.109; RT2:11.874; Injection Volume: 1.2 ml; Number of Runs: 2). The first eluting isomer was concentrated and lyophilized to afford Example 63 (11.3 mg, 14% yield) as a white solid. The second eluting isomer was concentrated and lyophilized to afford Example 64 (10.3 mg, 13% yield) as an off-white solid. 15 mg of Diastereomer B were submitted to chiral HPLC purification (Column: CHIRALPAK IA, 2*25 cm, 5 um; Mobile Phase A: Hex (0.1% FA), Mobile Phase B: EtOH; Flow rate: 20 mL/min; isocratic 30% B 19 min; 254/220 nm; RT1: 7.153; RT2:11.261; Injection Volume: 2 ml; Number of Runs: 1). The first eluting isomer was concentrated and lyophilized to afford Example 65 (6 mg, 11% yield) as a white solid. The second eluting isomer was concentrated and lyophilized to afford Example 66 (5.4 mg, 10% yield) as an off-white solid.

Example 63: $^1$H NMR (400 MHz, DMSO-$d_6$) δ: 11.18 (br, 1H), 8.93 (d, J=2.4 Hz, 1H), 8.79 (s, 1H), 8.70 (d, J=2.4 Hz, 1H), 8.23 (s, 2H), 7.35 (t, J=54.4 Hz, 1H), 7.09 (s, 1H), 4.55-4.59 (m, 1H), 3.08-3.14 (m, 1H), 2.07-2.68 (m, 1H), 1.94 (s, 3H). LC-MS: m/z 513 $[M+H]^+$.

Example 64: $^1$H NMR (400 MHz, DMSO-$d_6$) δ: 11.22 (br, 1H), 8.93 (d, J=2.4 Hz, 1H), 8.79 (s, 1H), 8.69 (d, J=2.4 Hz, 1H), 8.23 (s, 2H), 7.36 (t, J=54.4 Hz, 1H), 7.09 (s, 1H), 4.55-4.59 (m, 1H), 3.08-3.14 (m, 1H), 2.07-2.68 (m, 1H), 1.94 (s, 3H). LC-MS: m/z 513 $[M+H]^+$.

Example 65: $^1$H NMR (400 MHz, DMSO-$d_6$) δ: 11.06 (br, 1H), 8.93 (d, J=2.4 Hz, 1H), 8.79 (s, 1H), 8.67 (d, J=2.4 Hz, 1H), 8.22 (s, 2H), 7.35 (t, J=54 Hz, 1H), 7.09 (s, 1H), 4.56-4.59 (m, 1H), 2.88-2.93 (m, 1H), 2.75-2.79 (m, 1H), 1.83 (s, 3H). LC-MS: m/z 513 $[M+H]^+$.

Example 66: $^1$H NMR (400 MHz, DMSO-$d_6$) δ: 11.05 (br, 1H), 8.93 (d, J=2.4 Hz, 1H), 8.79 (s, 1H), 8.67 (d, J=2.4 Hz, 1H), 8.22 (s, 2H), 7.35 (t, J=54 Hz, 1H), 7.09 (s, 1H), 4.56-4.59 (m, 1H), 2.88-2.93 (m, 1H), 2.75-2.79 (m, 1H), 1.83 (s, 3H). LC-MS: m/z 513 $[M+H]^+$.

The absolute stereochemistry for each separated isomer was not determined.

Method G2

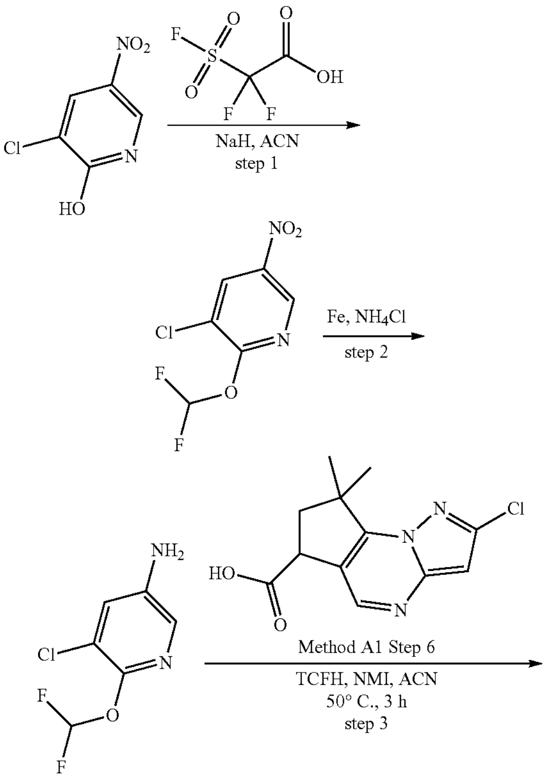

-continued

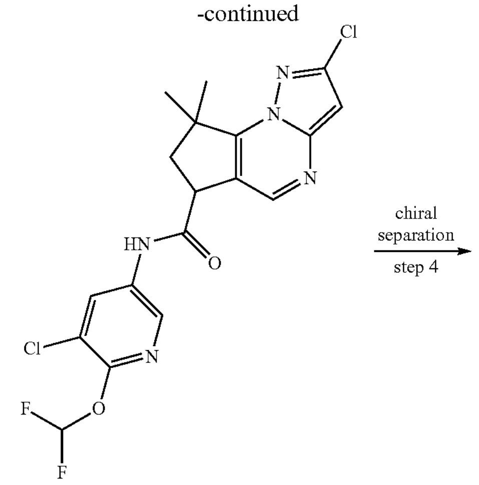

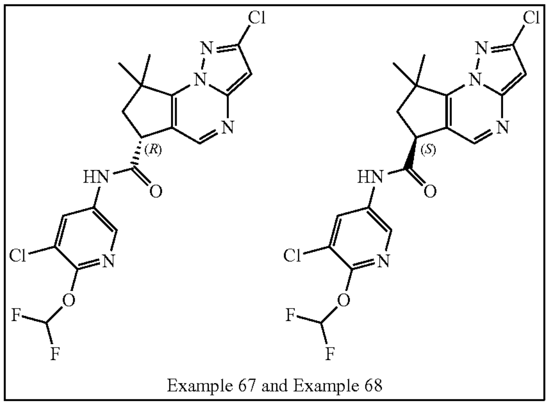

Example 67 and Example 68

Examples 67 and 68: Single Enantiomers Obtained from a Racemic Mixture Containing (R)-2-chloro-N-(5-chloro-6-(difluoromethoxy)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(difluoromethoxy)pyridin-3-yl)-8,8-dimethyl-7,8-dihydro-6H-cyclopenta[e]pyrazolo[1,5-a]pyrimidine-6-carboxamide Step 1: 3-chloro-2-(difluoromethoxy)-5-nitro-pyridine

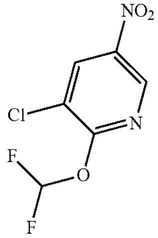 [SMILES: O=[N+]([O-])c1cnc(OC(F)F)c(Cl)c1]

To a stirred solution of 3-chloro-5-nitro-pyridin-2-ol (1 g, 5.7 mmol) in acetonitrile (50 mL) was added sodium hydride (618 mg, 15.4 mmol, 60% in mineral oil) at 0° C. The reaction mixture was stirred at 23° C. for 0.5 h. 2,2-difluoro-2-fluorosulfonyl-acetic acid (1.7 g, 9.7 mmol) was added and the mixture was stirred at 23° C. for 18 h. The reaction was quenched by the addition of water (50 mL), and the mixture was extracted with EtOAc (3×50 mL). The combined organic layers were washed with brine, dried over anhydrous sodium sulfate and concentrated. The residue was purified by prep-TLC (Petroleum ether:EtOAc=6:1) to afford 3-chloro-2-(difluoromethoxy)-5-nitro-pyridine (260 mg, 18% yield) as a colorless oil. $^1$H NMR (400 MHz, Chloroform-d) δ: 8.98 (d, J=2.4 Hz, 1H), 8.60 (d, J=2.4 Hz, 1H), 7.52 (t, J=71.2 Hz, 1H).

Step 2: 5-chloro-6-(difluoromethoxy)pyridin-3-amine

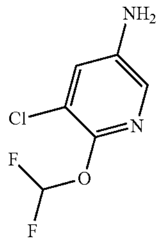 [SMILES: Nc1cnc(OC(F)F)c(Cl)c1]

To a mixture of 3-chloro-2-(difluoromethoxy)-5-nitro-pyridine (210 mg, 0.9 mmol) in ethanol (7.5 mL) and water (2.5 mL) were added ammonium chloride (100 mg, 1.9 mmol) and iron (313 mg, 5.6 mmol). The reaction mixture was stirred at 80° C. for 2 h. The reaction mixture was cooled and filtered, and the ethanol was removed under vacuum. The residue was extracted with EtOAc (3×10 mL), and the combined organic layers were washed with saturated aqueous ammonium chloride solution, dried over anhydrous sodium sulfate, and concentrated under vacuum. The residue was applied onto a silica gel column and eluted with PE/EtOAc (3:1) to afford 5-chloro-6-(difluoromethoxy)pyridin-3-amine (140 mg, 50% yield) as a colorless oil. LC-MS: m/z 195 [M+H]$^+$.

Step 3: 2-chloro-N-(5-chloro-6-(difluoromethoxy) pyridin-3-yl)-8,8-dimethyl-7,8-dihydro-6H-cyclopenta[e]pyrazolo[1,5-a]pyrimidine-6-carboxamide

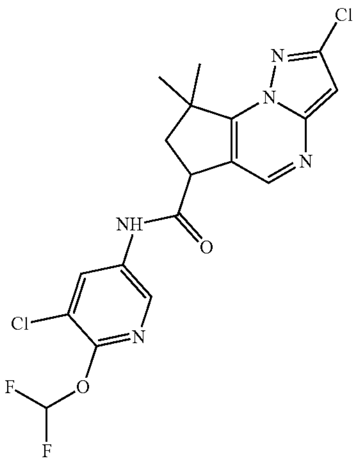 [SMILES: CC1(C)CC(C(=O)Nc2cnc(OC(F)F)c(Cl)c2)c2cnc3cc(Cl)nn3c21]

To a stirred mixture of 5-chloro-6-(difluoromethoxy)pyridin-3-amine (195 mg, 155 μmol) and 2-chloro-8,8-dimethyl-7,8-dihydro-6H-cyclopenta[e]pyrazolo[1,5-a]pyrimidine-6-carboxylic acid (Method A1 Step 6; 265 mg, 212 μmol) in acetonitrile (10 mL) were added TCFH (674 mg, 2.4 mmol) and NMI (197 mg, 2.4 mmol). The resulting mixture was stirred at 25° C. for 3 h. The resulting mixture was concentrated under reduced pressure. The residue was diluted with water (100 mL) and then extracted with DCM (3×100 mL). The organic layers were combined, washed with brine (300 mL), dried over anhydrous sodium sulfate, and concentrated under vacuum. The crude product (150 mg) was purified by Prep-HPLC to afford 2-chloro-N-(5-chloro-6-(difluoromethoxy)pyridin-3-yl)-8,8-dimethyl-7,8-dihydro-6H-cyclopenta[e]pyrazolo[1,5-a]pyrimidine-6-carboxamide (50 mg, 14% yield) as a white solid. LC-MS: m/z 442 [M+H]$^+$.

Step 4: Separation of Enantiomers to Obtain (R)-2-chloro-N-(5-chloro-6-(difluoromethoxy)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(difluoromethoxy) pyridin-3-yl)-8,8-dimethyl-7,8-dihydro-6H-cyclopenta[e] pyrazolo[1,5-a]pyrimidine-6-carboxamide Example 67

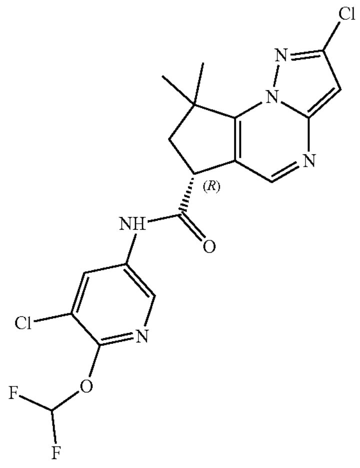

and

Example 68

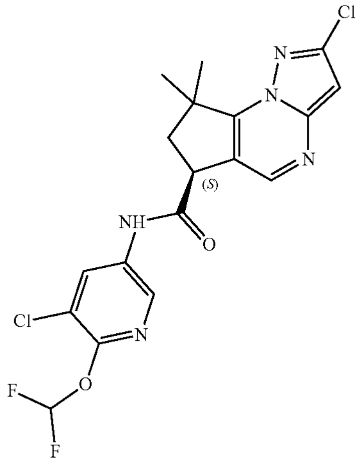

30 mg of 2-chloro-N-(5-chloro-6-(difluoromethoxy)pyridin-3-yl)-8,8-dimethyl-7,8-dihydro-6H-cyclopenta[e]pyrazolo[1,5-a]pyrimidine-6-carboxamide were submitted to chiral HPLC purification (Column: Reg-AD, 3*25 cm, 5

μm; Mobile Phase A:Hex(0.5% 2M $NH_3$-MeOH), Mobile Phase B:EtOH; Flow rate: 45 mL/min; isocratic 20% B 17 min; 220/254 nm; RT1:11.229; RT2:13.438; Injection Volume: 0.5 ml; Number of Runs: 10). Fractions containing the first eluting isomer were concentrated and lyophilized to afford Example 67 as a white solid (8 mg, 26% yield). Fractions containing the second eluting isomer were concentrated and lyophilized to obtain Example 68 as a white solid (7 mg, 23% yield).

Example 67: $^1$H NMR (300 MHz, DMSO-$d_6$) δ: 11.15 (br, 1H), 8.65 (s, 1H), 8.44-8.48 (m, 2H), 7.70 (t, J=72 Hz, 1H), 6.94 (s, 1H), 4.44-4.49 (m, 1H), 2.51-2.58 (m, 1H), 2.24-2.33 (m, 1H), 1.64 (s, 3H), 1.56 (s, 3H). LC-MS: m/z 442 $[M+H]^+$.

Example 68: $^1$H NMR (300 MHz, DMSO-$d_6$) δ: 11.18 (br, 1H), 8.66 (s, 1H), 8.44-8.49 (m, 2H), 7.70 (t, J=72 Hz, 1H), 6.94 (s, 1H), 4.49-4.53 (m, 1H), 2.51-2.58 (m, 1H), 2.26-2.37 (m, 1H), 1.65 (s, 3H), 1.55 (s, 3H). LC-MS: m/z 442 $[M+H]^+$. The absolute stereochemistry for each separated isomer was not determined.

Method H2

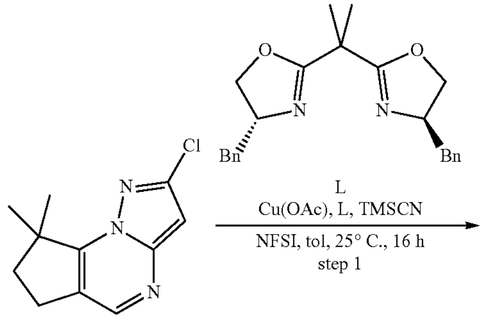

Method A1 Step 4

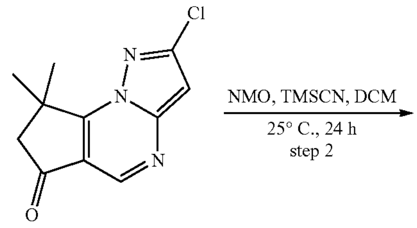

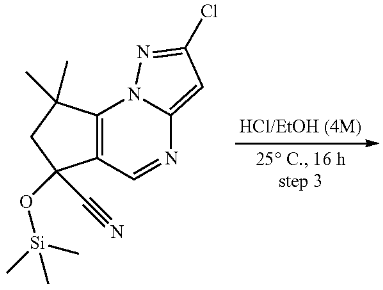

-continued

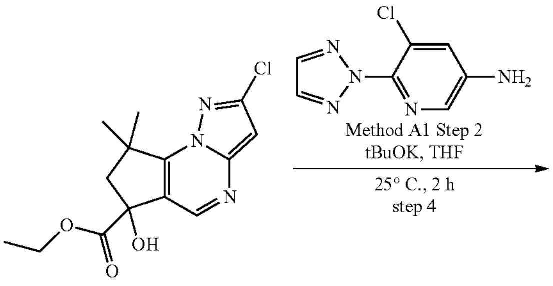

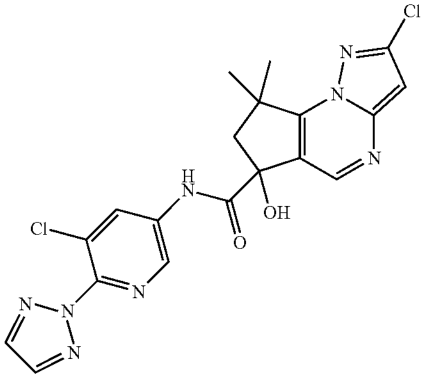

Example 69

Example 69: 2-chloro-N-(5-chloro-6-(2H-1,2,3-triazol-2-yl)pyridin-3-yl)-6-hydroxy-8,8-dimethyl-7,8-dihydro-6H-cyclopenta[e]pyrazolo[1,5-a]pyrimidine-6-carboxamide Step 1: 2-chloro-8,8-dimethyl-7,8-dihydro-6H-cyclopenta[e]pyrazolo[1,5-a]pyrimidin-6-one

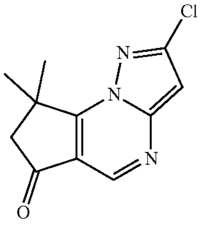 [SMILES: CC1(C)CC(=O)c2cnc3cc(Cl)nn3c21]

To a stirred solution of 2-chloro-8,8-dimethyl-7,8-dihydro-6H-cyclopenta[e]pyrazolo[1,5-a]pyrimidine (Method A1 Step 4; 2.0 g, 9.0 mmol) in toluene (30 mL) were added (4R)-4-benzyl-2-[1-[(4R)-4-benzyl-4,5-dihydrooxazol-2-yl]-1-methyl-ethyl]-4,5-dihydrooxazole (362 mg, 1.0 mmol), acetoxycopper (132 mg, 1.0 mmol), N-Fluorobenzenesulfonimide (4.3 g, 13.5 mmol) and TMSCN (4.5 g, 45.1 mmol). The reaction was stirred at 25° C. for 16 h under oxygen (balloon).

The solvent was removed under vacuum and the residue was applied on a silica gel column and eluted with EtOAc/PE (1:5) to give 2-chloro-8,8-dimethyl-7,8-dihydro-6H-cyclopenta[e]pyrazolo[1,5-a]pyrimidin-6-one (700 mg, 32% yield) as a white solid. LC-MS (ES, m/z): $236[M+H]^+$.

Step 2: 2-chloro-8,8-dimethyl-6-((trimethylsilyl) oxy)-7,8-dihydro-6H-cyclopenta[e]pyrazolo[1,5-a] pyrimidine-6-carbonitrile

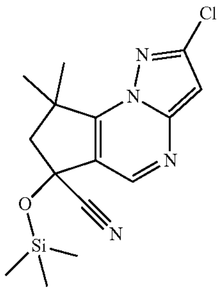 [SMILES: CC1(C)CC(C#N)(O[Si](C)(C)C)c2cnc3cc(Cl)nn3c21]

To a stirred solution of 2-chloro-8,8-dimethyl-7,8-dihydro-6H-cyclopenta[e]pyrazolo[1,5-a]pyrimidin-6-one (200 mg, 0.8 mmol) in DCM (20 mL) were added 4-methylmorpholine 4-oxide (1 g, 8.5 mmol) and TMSCN (0.9 g, 8.5 mmol). The reaction was stirred at 25° C. for 16 h under nitrogen. The solvent was removed under vacuum and the residue was applied on a silica gel column and eluted with EtOAc/PE (1:2) to give 2-chloro-8,8-dimethyl-6-((trimethylsilyl)oxy)-7,8-dihydro-6H-cyclopenta[e]pyrazolo[1,5-a] pyrimidine-6-carbonitrile (40 mg, 9% yield). $^{1}$HNMR (300 MHz, Chloroform-d) δ: 8.62 (s, 1H), 6.76 (s, 1H), 2.74-2.91 (m, 1H), 2.48-2.51 (m, 1H), 1.73 (d, J=2.7 Hz, 6H), 0.34 (s, 9H). LC-MS (ES, m/z): 335[M+H]$^+$.

Step 3: ethyl 2-chloro-6-hydroxy-8,8-dimethyl-7,8-dihydro-6H-cyclopenta[e]pyrazolo[1,5-a]pyrimidine-6-carboxylate

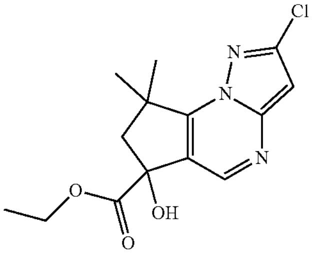 [SMILES: CCOC(=O)C1(O)CC(C)(C)c2c1cnc1cc(Cl)nn21]

A solution of 2-chloro-8,8-dimethyl-6-((trimethylsilyl) oxy)-7,8-dihydro-6H-cyclopenta[e]pyrazolo[1,5-a]pyrimidine-6-carbonitrile (52 mg, 155 μmol) in HCl (5 mL, 4M in ethanol) was stirred at 25° C. for 4 h. The mixture was cooled to 25° C. The resulting mixture was concentrated under reduced pressure. The residue was applied on a silica gel column and eluted with EtOAc/PE (1:1) to give ethyl 2-chloro-6-hydroxy-8,8-dimethyl-7,8-dihydro-6H-cyclopenta[e]pyrazolo[1,5-a]pyrimidine-6-carboxylate (45 mg, 66% yield). LC-MS (ES, m/z): 310[M+H]$^+$.

Step 4: 2-chloro-N-(5-chloro-6-(2H-1,2,3-triazol-2-yl)pyridin-3-yl)-6-hydroxy-8,8-dimethyl-7,8-dihydro-6H-cyclopenta[e]pyrazolo[1,5-a]pyrimidine-6-carboxamide Example 69

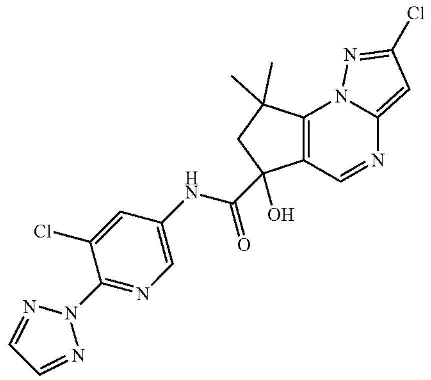

To a stirred solution of 2-chloro-6-hydroxy-8,8-dimethyl-7,8-dihydro-6H-cyclopenta[e]pyrazolo[1,5-a]pyrimidine-6-carboxylate (16 mg, 53 μmol) and 5-chloro-6-(2H-1,2,3-triazol-2-yl)pyridin-3-amine (Method A1 step 2; 13 mg, 65 μmol) in THE (5 mL) was added potassium tert-butoxide (12 mg, 106 mmol). The reaction mixture was stirred at 25° C. for 2 h. The resulting mixture was concentrated under reduced pressure. The residue was diluted with water (30 mL), and then extracted with DCM (3x30 mL). The combined organic layers were washed with brine (90 mL), dried over anhydrous sodium sulfate and concentrated under vacuum. The residue was purified by Prep-HPLC to afford 2-chloro-N-(4-(difluoromethyl)-6-oxo-5~(1H-pyrazol-1-yl)-1,6-dihydropyridin-2-yl)-8,8-dimethyl-7,8-dihydro-6H-cyclopenta[e]pyrazolo[1,5-a]pyrimidine-6-carboxamide (10.5 mg, 42% yield) as an off white solid.

Example 69: $^{1}$H NMR (400 MHz, DMSO-$d_6$) δ: 10.93 (br, 1H), 9.00 (d, J=2 Hz, 1H), 8.72 (d, J=2 Hz, 1H), 8.68 (s, 1H), 8.17 (s, 2H), 7.09 (br, 1H), 7.01 (s, 1H), 2.81 (d, J=14.0 Hz, 1H), 2.33 (d, J=14.0 Hz, 1H), 1.69 (s, 3H), 1.64 (s, 3H). LC-MS: m/z 459 [M+H]$^+$.

Method I2

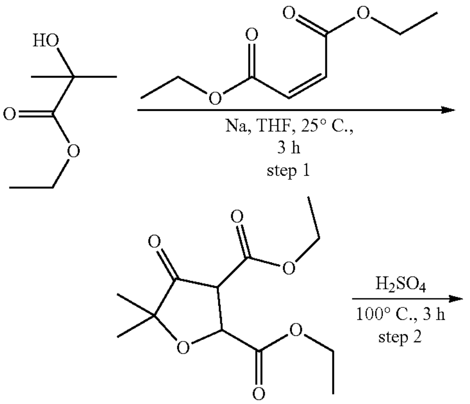

-continued

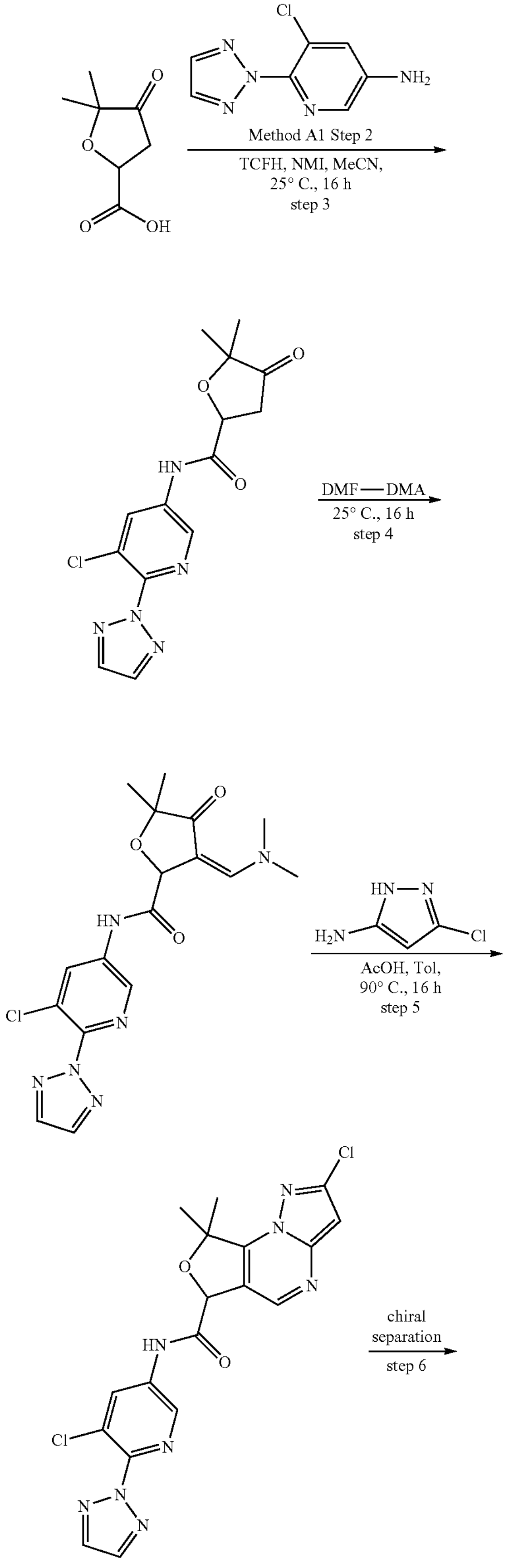

-continued

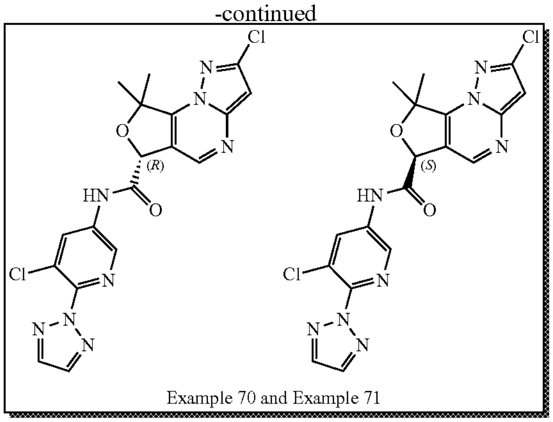

Example 70 and Example 71

Examples 70 and 71: Single Enantiomers Obtained from a Racemic Mixture Containing (R)-2-chloro-N-(5-chloro-6-(2H-1,2,3-triazol-2-yl)pyridin-3-yl)-8,8-dimethyl-6,8-dihydrofuro[3,4-e]pyrazolo[1,5-a]pyrimidine-6-carboxamide and (S)-2-chloro-N-(5-chloro-6-(2H-1,2,3-triazol-2-yl)pyridin-3-yl)-8,8-dimethyl-6,8-dihydrofuro[3,4-e]pyrazolo[1,5-a]pyrimidine-6-carboxamide Step 1: diethyl 5,5-dimethyl-4-oxotetrahydrofuran-2,3-dicarboxylate

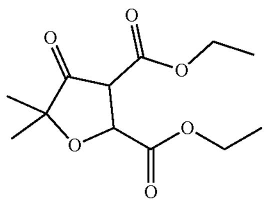 [SMILES: CCOC(=O)C1OC(C)(C)C(=O)C1C(=O)OCC]

To a stirred mixture of sodium (1.0 g, 43.6 mmol) in THF (100 mL) were added ethyl 2-hydroxy-2-methylpropanoate (9.6 g, 72.6 mmol) and diethyl maleate (5.0 g, 29.0 mmol) at 0° C. The reaction mixture was stirred at 25° C. for 3 h. The pH was adjusted to 2-3 with H2504 (2 M). The resulting mixture was extracted with DCM (100 mL×2). The combined organic layers were dried over anhydrous sodium sulfate and concentrated under vacuum to give diethyl 5,5-dimethyl-4-oxotetrahydrofuran-2,3-dicarboxylate (8.0 g, 85% yield) as a yellow oil which was used directly without further purification. $^1$H NMR (400 MHz, Chloroform-d) δ: 5.08 (d, J=9.2 Hz, 1H), 4.28 (q, J=7.2 Hz, 4H), 3.75 (d, J=9.2 Hz, 1H), 1.37 (s, 3H), 1.31 (t, J=7.2 Hz, 6H), 1.30 (s, 3H).

Step 2: 5,5-dimethyl-4-oxotetrahydrofuran-2-carboxylic acid

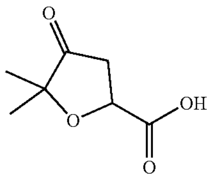

A mixture of diethyl 5,5-dimethyl-4-oxotetrahydrofuran-2,3-dicarboxylate (8.0 g, 31.0 mmol) in H2504 (120 mL, 2 M) was stirred at 100° C. for 3 h. The reaction mixture was diluted with water (100 mL) and extracted with DCM (2×100 mL). The combined organic layers were dried over anhydrous sodium sulfate and concentrated under vacuum to give 5,5-dimethyl-4-oxotetrahydrofuran-2-carboxylic acid (3.0 g, 61% yield) as a yellow oil. $^1$H NMR (400 MHz, Chloroform-d) δ: 4.83 (t, J=8.4 Hz, 1H), 2.94 (dd, J=18.8, 8.4 Hz, 1H), 2.81 (dd, J=18.8, 8.0 Hz, 1H), 1.37 (s, 3H), 1.29 (s, 3H).

Step 3: N-(5-chloro-6-(2H-1,2,3-triazol-2-yl)pyridin-3-yl)-5,5-dimethyl-4-oxotetrahydrofuran-2-carboxamide

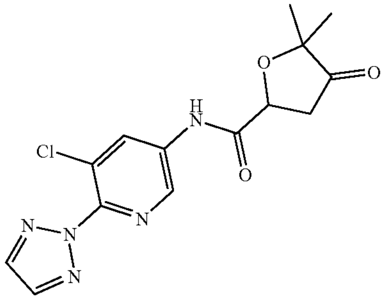 [SMILES: CC1(C)OC(C(=O)Nc2cnc(-n3nccn3)c(Cl)c2)CC1=O]

To a stirred solution of 5,5-dimethyl-4-oxotetrahydrofuran-2-carboxylic acid (1.2 g, 7.7 mmol) and 5-chloro-6-(2H-1,2,3-triazol-2-yl)pyridin-3-amine (Method A1 step 2; 1.0 g, 5.1 mmol) in acetonitrile (30 mL) were added TCFH (5.7 g, 20.4 mmol) and NMI (1.7 g, 20.4 mmol). The mixture was stirred at 25° C. for 16 h. The resulting mixture was concentrated under reduced pressure. The residue was applied onto a silica gel column and eluted with DCM/MeOH (93:7) to give N-(5-chloro-6-(2H-1,2,3-triazol-2-yl)pyridin-3-yl)-5,5-dimethyl-4-oxotetrahydrofuran-2-carboxamide (320 mg, 10% yield) as a yellow oil. LC-MS: m/z 336 [M+H]$^+$.

Step 4: N-(5-chloro-6-(2H-1,2,3-triazol-2-yl)pyridin-3-yl)-3-((dimethylamino) methyl ene)-5,5-dimethyl-4-oxotetrahydrofuran-2-carboxamide

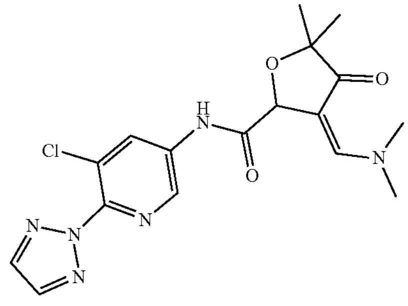 [SMILES: CN(C)/C=C1\C(=O)C(C)(C)OC1C(=O)Nc1cnc(-n2nccn2)c(Cl)c1]

A solution of N-(5-chloro-6-(2H-1,2,3-triazol-2-yl)pyridin-3-yl)-5,5-dimethyl-4-oxotetrahydrofuran-2-carboxamide (320 mg, 953.1 μmol) in DMF-DMA (10 mL) was stirred for 16 h at 25° C. The resulting mixture was concentrated under reduced pressure. This resulted in N-(5-chloro-6-(2H-1,2,3-triazol-2-yl)pyridin-3-yl)-3-((dimethylamino)methylene)-5,5-dimethyl-4-oxotetrahydrofuran-2-carboxamide (300 mg, 37% yield) as a yellow oil which was used directly without further purification. LCMS (ES, m/z): 391 [M+H]$^+$.

Step 5: 2-chloro-N-(5-chloro-6-(2H-1,2,3-triazol-2-yl)pyridin-3-yl)-8,8-dimethyl-6,8-dihydrofuro[3,4-e]pyrazolo[1,5-a]pyrimidine-6-carboxamide

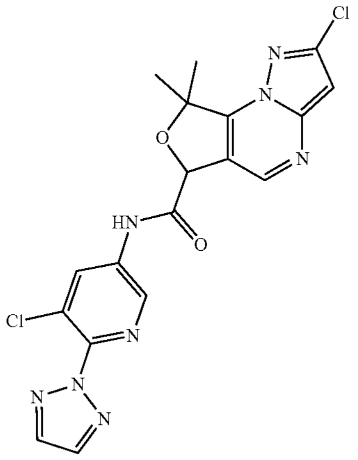

To a stirred solution of N-(5-chloro-6-(2H-1,2,3-triazol-2-yl)pyridin-3-yl)-3-((dimethylamino)methylene)-5,5-dimethyl-4-oxotetrahydrofuran-2-carboxamide (300 mg, 353.1 μmol) and 3-chloro-1H-pyrazol-5-amine (42 mg, 353.1 μmol) in toluene (4 mL) was added AcOH (0.4 mL) at 25° C. The resulting mixture was stirred at 90° C. for 16 h. The mixture was cooled to 25° C. The reaction mixture was concentrated under reduced pressure. The residue was applied on a silica gel column and eluted with EtOAc/PE (1:4) to give 100 mg of crude product. The crude product was submitted to Prep-HPLC purification and the collected fractions were lyophilized to give 2-chloro-N-(5-chloro-6-(2H-1,2,3-triazol-2-yl)pyridin-3-yl)-8,8-dimethyl-6,8-dihydrofuro[3,4-e]pyrazolo[1,5-a]pyrimidine-6-carboxamide (45 mg, 28% yield) as a white solid. LC-MS: m/z 445 $[M+H]^+$.

Step 6: Separation of Enantiomers to Obtain (R)-2-chloro-N-(5-chloro-6-(2H-1,2,3-triazol-2-yl)pyridin-3-yl)-8,8-dimethyl-6,8-dihydrofuro[3,4-e]pyrazolo[1,5-a]pyrimidine-6-carboxamide and (S)-2-chloro-N-(5-chloro-6-(2H-1,2,3-triazol-2-yl)pyridin-3-yl)-8,8-dimethyl-6,8-dihydrofuro[3,4-e]pyrazolo[1,5-a]pyrimidine-6-carboxamide Example 70

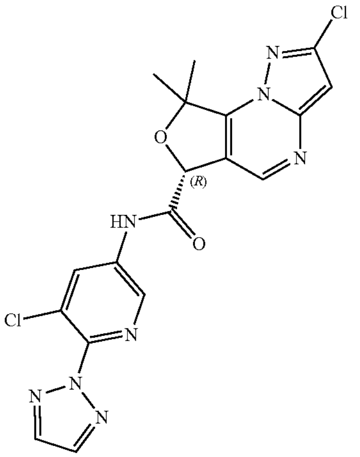

and

Example 71

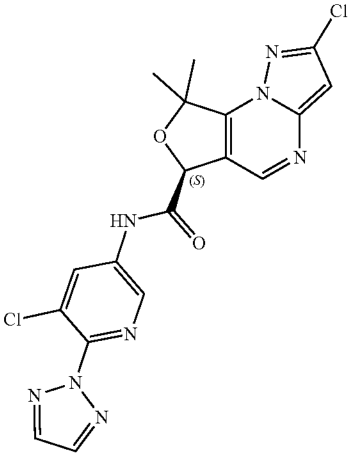

45 mg of N-(2-(difluoromethyl)pyridin-4-yl)-2-fluoro-8-methyl-8-(trifluoro-methyl)-7,8-dihydro-6H-pyrazolo[1,5-a]pyrrolo[2,3-e]pyrimidine-6-carboxamide were submitted to chiral HPLC purification (Column: CHIRALPAK IF, 2*25 cm, 5 um; Mobile Phase A:MTBE (0.5% 2M $NH_3$-MeOH), Mobile Phase B:EtOH; Flow rate: 20 mL/min; isocratic, 10% B in 11 min; 220/254 nm; RT1:7.523; RT2: 8.35; Injection Volume: 0.5 ml; Number of Runs: 15). The first eluting isomer was concentrated and lyophilized to afford Example 70 as an off-white solid (10.1 mg, 22% yield). The second eluting isomer was concentrated and lyophilized to afford Example 71 as an off-white solid (7.9 mg, 17% yield).

Example 70: $^1H$ NMR (400 MHz, Chloroform-d) δ: 8.83 (s, 1H), 8.75 (s, 1H), 8.64 (d, J=2.4 Hz, 1H), 8.50 (d, J=2.4 Hz, 1H), 7.93 (s, 2H), 6.78 (s, 1H), 5.83 (s, 1H), 2.04 (s, 3H), 1.91 (s, 3H). LC-MS: m/z 445 $[M+H]^+$.

Example 71: $^1H$ NMR (400 MHz, Chloroform-d) δ: 8.83 (s, 1H), 8.75 (s, 1H), 8.64 (d, J=2.4 Hz, 1H), 8.50 (d, J=2.0 Hz, 1H), 7.93 (s, 2H), 6.78 (s, 1H), 5.83 (s, 1H), 2.04 (s, 3H), 1.91 (s, 3H). LC-MS: m/z 445 $[M+H]^+$.

Method J2

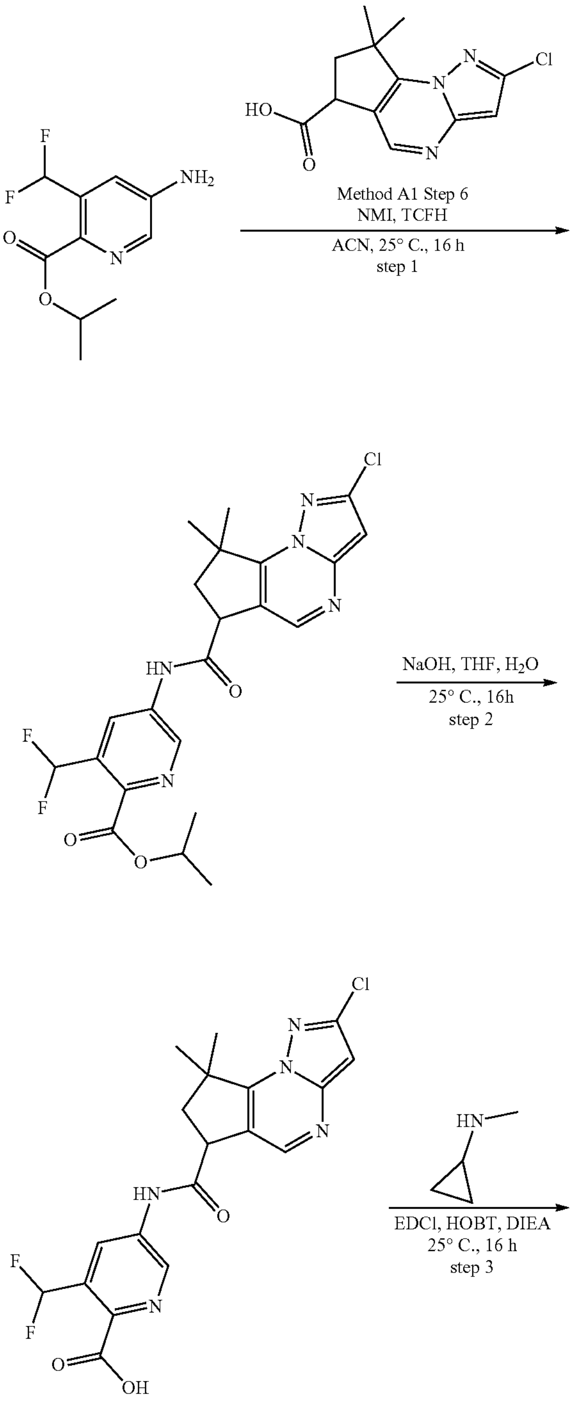

Method J2 Step 2

-continued

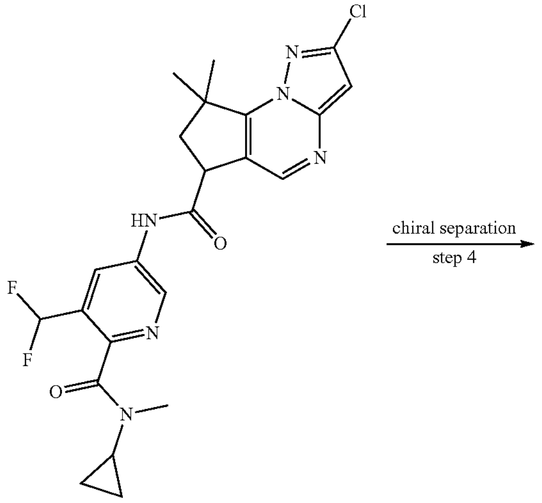

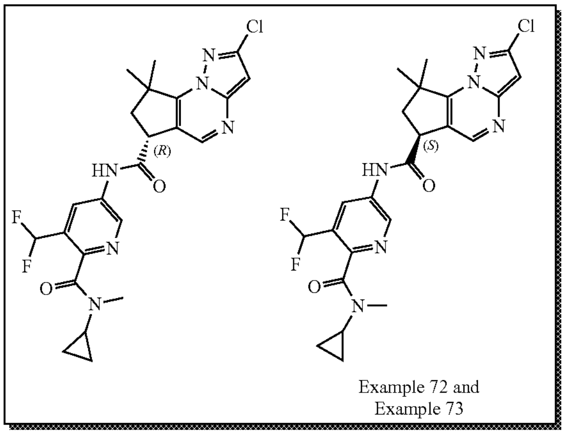

Example 72 and Example 73

Examples 72 and 73: Single Enantiomers Obtained from a Racemic Mixture Containing (R)-2-chloro-N-(6-(cyclopropyl(methyl)carbamoyl)-5-(difluoromethyl)pyridin-3-yl)-8,8-dimethyl-7,8-dihydro-6H-cyclopenta[e]pyrazolo[1,5-a]pyrimidine-6-carboxamide and (S)-2-chloro-N-(6-(cyclopropyl(methyl)carbamoyl)-5-(difluoromethyl)pyridin-3-yl)-8,8-dimethyl-7,8-dihydro-6H-cyclopenta[e]pyrazolo[1,5-a]pyrimidine-6-carboxamide

Step 1: isopropyl 5~(2-chloro-8,8-dimethyl-7,8-dihydro-6H-cyclopenta[e]pyrazolo[1,5-a]pyrimidine-6-carboxamido)-3-(difluoromethyl)picolinate

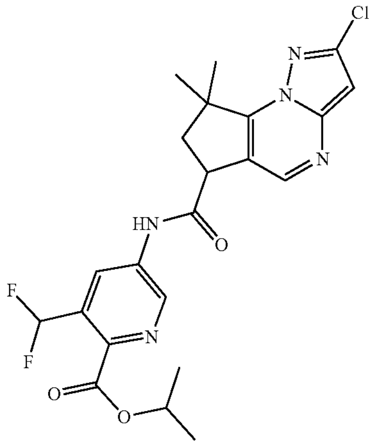 [SMILES: CC(C)OC(=O)c1ncc(NC(=O)C2CC(C)(C)c3c2cnc2cc(Cl)nn32)cc1C(F)F]

To a stirred solution of isopropyl 5-amino-3-(difluoromethyl)picolinate (300 mg, 1.3 mmol) and 2-chloro-8,8-dimethyl-7,8-dihydro-6H-cyclopenta[e]pyrazolo[1,5-a]pyrimidine-6-carboxylic acid (Method A1 Step 6; 346 mg, 1.3 mmol) in acetonitrile (10 mL) were added TCFH (1.46 g, 5.2 mmol) and NMI (427 mg, 5.2 mmol). The mixture was stirred at 25° C. for 16 h. The resulting mixture was concentrated. The residue was applied onto a silica gel column and eluted with EtOAc/PE (3:2) to give isopropyl 5~(2-chloro-8,8-dimethyl-7,8-dihydro-6H-cyclopenta[e]pyrazolo[1,5-a]pyrimidine-6-carboxamido)-3-(difluoromethyl)picolinate (400 mg, 44% yield) as a yellow solid. LC-MS: m/z 478 $[M+H]^+$.

Step 2: 5-(2-chloro-8,8-dimethyl-7,8-dihydro-6H-cyclopenta[e]pyrazolo[1,5-a]pyrimidine-6-carboxamido)-3-(difluoromethyl)picolinic acid

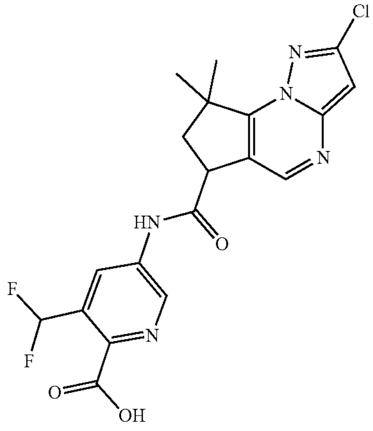 [SMILES: CC1(C)CC(C(=O)Nc2cnc(C(=O)O)c(C(F)F)c2)c2cnc3cc(Cl)nn3c21]

To a stirred solution of isopropyl 5~(2-chloro-8,8-dimethyl-7,8-dihydro-6H-cyclopenta[e]pyrazolo[1,5-a]pyrimidine-6-carboxamido)-3-(difluoromethyl)picolinate (390 mg, 816 µcool) in tetrahydrofuran (10 mL) and water (5 mL) was added sodium hydroxide (163 mg, 4.1 mmol) at 0° C. The reaction mixture was stirred at 25° C. for 16 h. The pH was adjusted to 3 with HCl (1 M). The mixture was extracted with EtOAc (3x30 mL). The combined organic layers were dried over anhydrous sodium sulfate and concentrated under vacuum to afford 5~(2-chloro-8,8-dimethyl-7,8-dihydro-6H-cyclopenta[e]pyrazolo[1,5-a]pyrimidine-6-carboxamido)-3-(difluoromethyl)picolinic acid (Method J2 Step 2; 300 mg, 84% yield) as a yellow solid. LC-MS: m/z 436 $[M+H]^+$.

Step 3: 2-chloro-N-(6-(cyclopropyl(methyl)carbamoyl)-5-(difluoromethyl)pyridin-3-yl)-8,8-dimethyl-7,8-dihydro-6H-cyclopenta[e]pyrazolo[1,5-a]pyrimidine-6-carboxamide

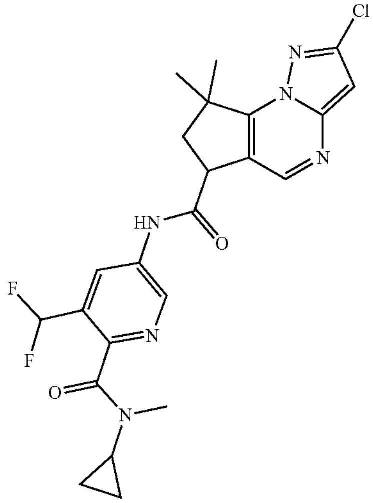 [SMILES: CN(C(=O)c1ncc(NC(=O)C2CC(C)(C)c3c2cnc2cc(Cl)nn32)cc1C(F)F)C1CC1]

To a stirred solution of 5~(2-chloro-8,8-dimethyl-7,8-dihydro-6H-cyclopenta[e]pyrazolo[1,5-a]pyrimidine-6-carboxamido)-3-(difluoromethyl)picolinic acid (240 mg, 550 µmol) in N,N-dimethylformamide (5 mL) were added N-methylcyclopropanamine (39 mg, 550 µmol), EDCI (137 mg, 716 µmol), HOBt (96 mg, 716 µmol) and DIEA (284 mg, 2.2 mmol). The reaction mixture was stirred at 25° C. for 16 h. The reaction mixture was quenched with water (30 mL). The resulting solution was extracted with EtOAc (3x30 mL). The combined organic layers were washed with brine (50 mL), dried over anhydrous sodium sulfate, and concentrated under vacuum. The residue was purified by Prep-HPLC and the collected fractions were lyophilized to afford 2-chloro-N-(6-(cyclopropyl(methyl)carbamoyl)-5-(difluoromethyl)pyridin-3-yl)-8,8-dimethyl-7,8-dihydro-6H-cyclopenta[e]pyrazolo[1,5-a]pyrimidine-6-carboxamide (90 mg, 32% yield) as an off-white solid. LC-MS: m/z 489 $[M+H]^+$.

Step 4: Separation of Enantiomers to Obtain (R)-2-chloro-N-(6-(cyclopropyl(methyl)carbamoyl)-5-(difluoromethyl)pyridin-3-yl)-8,8-dimethyl-7,8-dihydro-6H-cyclopenta[e]pyrazolo[1,5-a]pyrimidine-6-carboxamide and (S)-2-chloro-N-(6-(cyclopropyl(methyl)carbamoyl)-5-(difluoromethyl)pyridin-3-yl)-8,8-dimethyl-7,8-dihydro-6H-cyclopenta[e]pyrazolo[1,5-a]pyrimidine-6-carboxamide Example 72

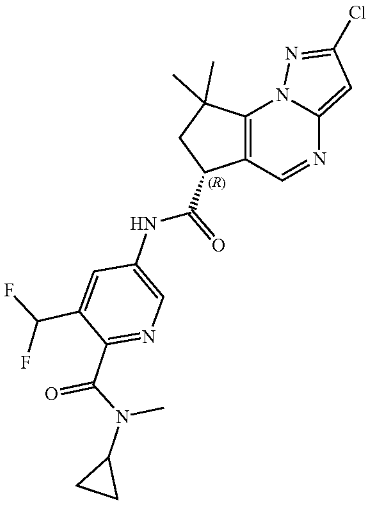

and

-continued

Example 73

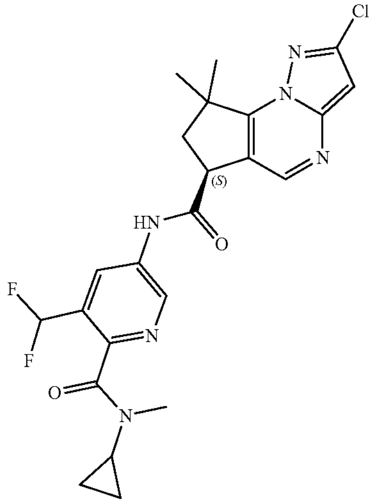

87 mg of 2-chloro-N-(6-(cyclopropyl(methyl)carbamoyl)-5-(difluoromethyl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IF, 5×25 cm, 5 μm; Mobile Phase A: MTBE (0.5% 2M $NH_3$-MeOH), Mobile Phase B: EtOH; Flow rate: 20 mL/min; Gradient: 25% B to 25% B in 20 min; Wave Length: 220/254 nm; RT1(min): 8.786; RT2(min): 13.978; Sample Solvent: EtOH; Injection Volume: 2 mL; Number Of Runs: 2). The first eluting isomer was concentrated and lyophilized to afford Example 72 as an off-white solid (36.6 mg, 42% yield). The second eluting isomer was concentrated and lyophilized to afford Example 73 as an off-white solid (37.3 mg, 43% yield).

Example 72: $^1$H NMR (400 MHz, DMSO-$d_6$) δ: 10.91 (s, 1H), 8.89 (d, J=2.0 Hz, 1H), 8.65 (s, 1H), 8.47 (d, J=2.0 Hz, 1H), 7.12 (t, J=54.8 Hz, 1H), 6.94 (s, 1H), 4.43 (dd, J=6.4, 9.2 Hz, 1H), 3.01 (s, 3H), 2.79-2.86 (m, 1H), 2.53-2.60 (m, 1H), 2.29-2.36 (m, 1H), 1.64 (s, 3H), 1.56 (s, 3H), 0.37-0.45 (m, 4H). LC-MS: m/z 489 $[M+H]^+$.

Example 73: $^1$H NMR (400 MHz, DMSO-$d_6$) δ: 10.90 (s, 1H), 8.90 (d, J=2.0 Hz, 1H), 8.65 (s, 1H), 8.48 (d, J=2.0 Hz, 1H), 7.12 (t, J=54.8 Hz, 1H), 6.95 (s, 1H), 4.43 (dd, J=6.4, 9.2 Hz, 1H), 3.01 (s, 3H), 2.71-2.83 (m, 1H), 2.55-2.60 (m, 1H), 2.29-2.36 (m, 1H), 1.65 (s, 3H), 1.56 (s, 3H), 0.39-0.44 (m, 4H). LC-MS: m/z 489 $[M+H]^+$.

Method $K_2$

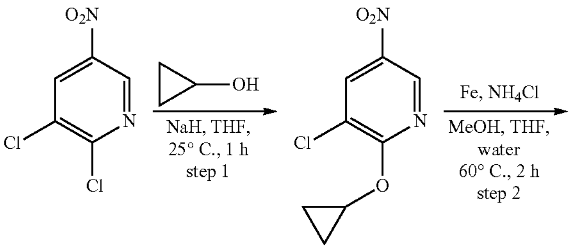

-continued

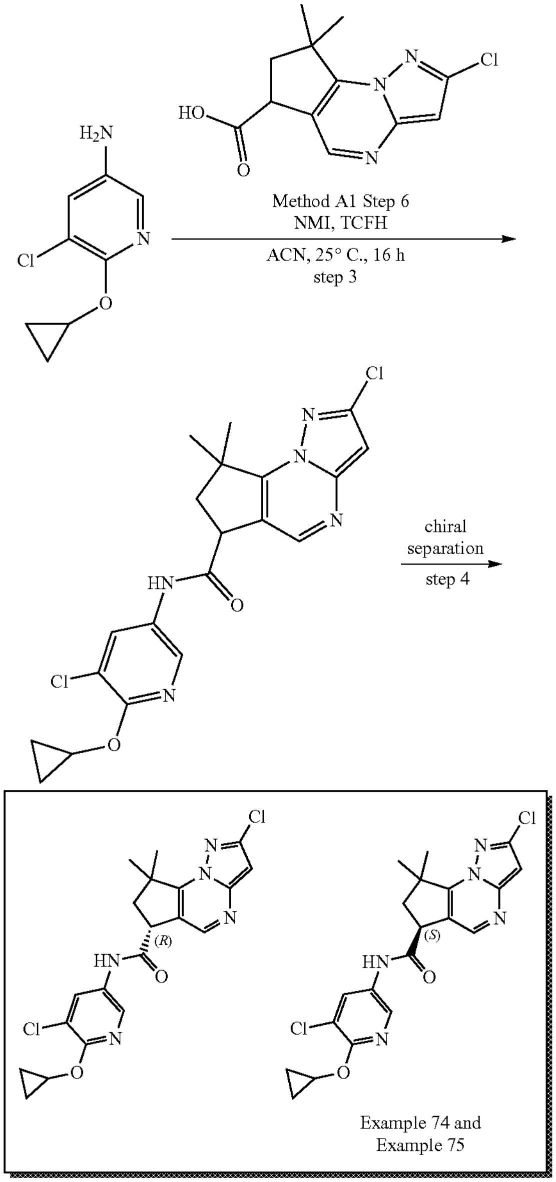

Example 74 and
Example 75

Examples 74 and 75: Single enantiomers obtained from racemic mixtures containing (R)-2-chloro-N-(5-chloro-6-cyclopropoxypyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-cyclopropoxypyridin-3-yl)-8,8-dimethyl-7,8-dihydro-6H-cyclopenta[e]pyrazolo[1,5-a]pyrimidine-6-carboxamide Step 1: 3-chloro-2-cyclopropoxy-5-nitropyridine

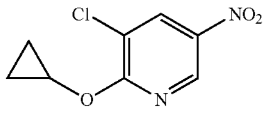 [SMILES: O=[N+]([O-])c1cnc(OC2CC2)c(Cl)c1]

To a stirred mixture of cyclopropanol (1.9 g, 34.2 mmol) in tetrahydrofuran (100 mL) was added NaH (2.0 g, 51.3 mmol, 60% in mineral oil) at 0° C. The reaction mixture was stirred at 40° C. for 1 h. The reaction was cooled to 0° C. To the above mixture was added a solution of 2,3-dichloro-5-nitropyridine (6.6 g, 34.2 mmol) in tetrahydrofuran (10 mL) at 0° C. The reaction was stirred at 25° C. for 1 h. The reaction mixture was quenched with water (200 mL). The resulting solution was extracted with EtOAc (3×200 mL). The combined organic layers were dried over anhydrous sodium sulfate and concentrated under vacuum. The residue was applied onto a silica gel column and eluted with EtOAc/PE (1:2) to give 3-chloro-2-cyclopropoxy-5-nitropyridine (3.1 g, 21% yield) as a yellow oil. LC-MS: m/z 215 $[M+H]^+$.

Step 2: 5-chloro-6-cyclopropoxypyridin-3-amine

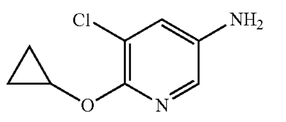 [SMILES: Nc1cnc(OC2CC2)c(Cl)c1]

To a stirred solution of 3-chloro-2-cyclopropoxy-5-nitropyridine (2.6 g, 12.3 mmol) in tetrahydrofuran (40 mL) and methanol (20 mL) were added Fe (3.4 g, 61.9 mmol), $NH_4Cl$ (3.3 g, 61.9 mmol) and water (10 mL). The mixture was stirred at 60° C. for 2 h. After cooled to 25° C., the solid was filtered off. The filtrate was concentrated under vacuum. The residue was diluted with water (100 mL), and the resulting solution was extracted with EtOAc (3×100 mL). The combined organic layers were washed with brine (100 mL), dried over anhydrous sodium sulfate, and concentrated under vacuum. The residue was applied onto a silica gel column and eluted with EtOAc/PE (1:3) to give 5-chloro-6-cyclopropoxypyridin-3-amine (400 mg, 16% yield) as a yellow solid. LC-MS: m/z 185 $[M+H]^+$.

Step 3: 2-chloro-N-(5-chloro-6-cyclopropoxypyridin-3-yl)-8,8-dimethyl-7,8-dihydro-6H-cyclopenta[e]pyrazolo[1,5-a]pyrimidine-6-carboxamide

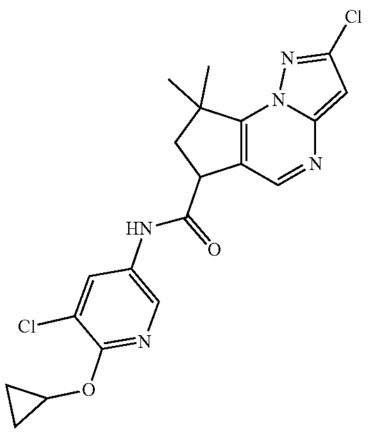 [SMILES: CC1(C)CC(C(=O)Nc2cnc(OC3CC3)c(Cl)c2)c2cnc3cc(Cl)nn3c21]

To a stirred solution of 5-chloro-6-cyclopropoxypyridin-3-amine (200 mg, 1.0 mmol) in acetonitrile (20 mL) were added 2-chloro-8,8-dimethyl-7,8-dihydro-6H-cyclopenta[e]pyrazolo[1,5-a]pyrimidine-6-carboxylic acid (Method A1 Step 6; 287 mg, 1.0 mmol), NMI (622 mg, 7.5 mmol) and TCFH (1.2 g, 4.3 mmol). The reaction mixture was stirred at 25° C. for 1 h. The mixture was concentrated under vacuum. The residue was diluted with water (50 mL), and the resulting mixture was extracted with EtOAc (3×50 mL). The combined organic layers were washed with brine (3×50 mL), dried over anhydrous sodium sulfate, and concentrated under vacuum. The residue was applied onto a silica gel column and eluted with EtOAc/PE (4:6) to give 150 mg of crude product. The crude product was submitted to Prep-HPLC purification and the collected fractions were lyophilized to give 2-chloro-N-(5-chloro-6-cyclopropoxypyridin-3-yl)-8,8-dimethyl-7,8-dihydro-6H-cyclopenta[e]pyrazolo[1,5-a]pyrimidine-6-carboxamide (60 mg, 12% yield) as a white solid. LC-MS: m/z 432 $[M+H]^+$.

Step 4: Separation of Enantiomers to Obtain (R)-2-chloro-N-(5-chloro-6-cyclopropoxypyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-cyclopropoxypyridin-3-yl)-8,8-dimethyl-7,8-dihydro-6H-cyclopenta[e]pyrazolo[1,5-a]pyrimidine-6-carboxamide Example 74

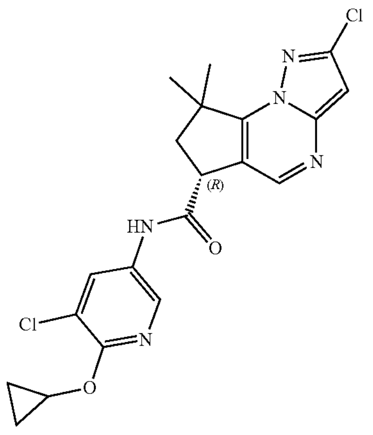

and

Example 75

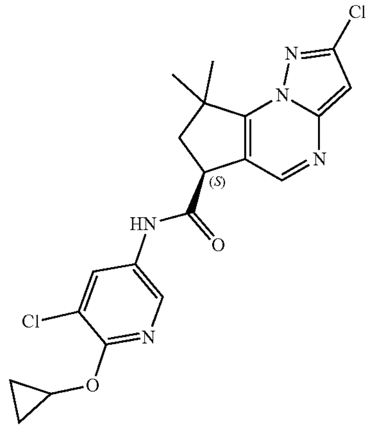

58 mg of 2-chloro-N-(5-chloro-6-cyclopropoxypyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IA, 2*25 cm, 5

μm; Mobile Phase A: Hex(0.5% 2M $NH_3$-MeOH), Mobile Phase B: EtOH; Flow rate: 16 mL/min; isokratic 50% B, 20 min; Wave Length: 220/254 nm; RT1(min): 6.008; RT2 (min): 14.76; Sample Solvent: EtOH; Injection Volume: 2.5 mL; Number of Runs: 2). The first eluting isomer was concentrated and lyophilized to afford Example 74 as a white solid (23.9 mg, 40% yield). The second eluting isomer was concentrated and lyophilized to afford Example 75 as a white solid (23.5 mg, 40% yield).

Example 74: $^1$H NMR (400 MHz, DMSO-$d_6$) δ: 10.56 (br, 1H), 8.61 (s, 1H), 8.33 (d, J=2.4 Hz, 1H), 8.21 (d, J=2.4 Hz, 1H), 6.93 (s, 1H), 4.34-4.38 (m, 1H), 4.27-4.31 (m, 1H), 2.51-2.54 (m, 1H), 2.27-2.33 (m, 1H), 1.63 (s, 3H), 1.54 (s, 3H), 0.76-0.85 (m, 2H), 0.68-0.74 (m, 2H).

LC-MS: m/z 432 $[M+H]^+$.

Example 75: $^1$H NMR (400 MHz, DMSO-$d_6$) δ: 10.56 (br, 1H), 8.60 (s, 1H), 8.33 (d, J=1.7 Hz, 1H), 8.21 (d, J=1.7 Hz, 1H), 6.93 (s, 1H), 4.34-4.38 (m, 1H), 4.27-4.31 (m, 1H), 2.51-2.54 (m, 1H), 2.27-2.33 (m, 1H), 1.63 (s, 3H), 1.54 (s, 3H), 0.76-0.81 (m, 2H), 0.68-0.75 (m, 2H). LC-MS: m/z 432 $[M+H]^+$.

The absolute stereochemistry for each separated isomer was not determined.

Method L2

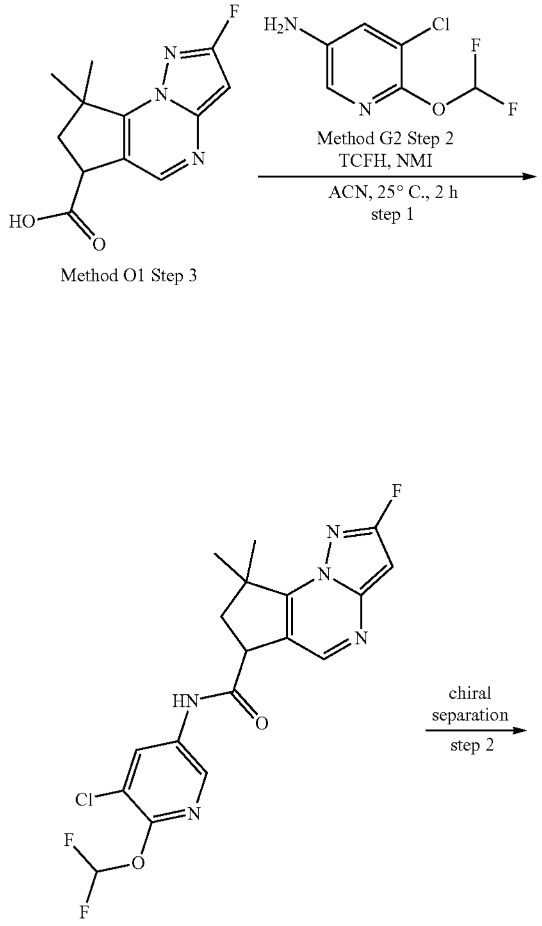

-continued

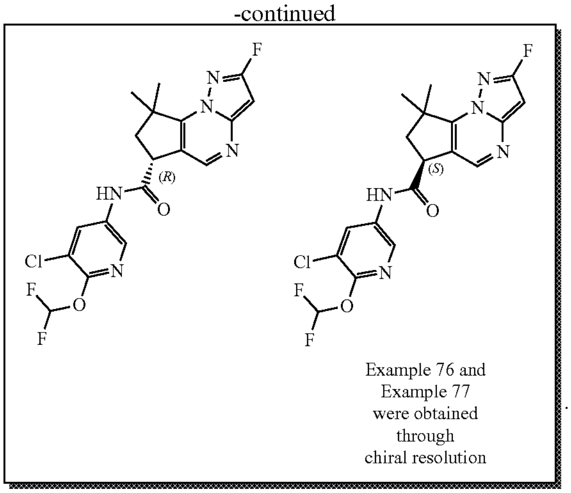

Examples 76 and 77: Single Enantiomers Obtained from a Racemic Mixture Containing (R)—N-(5-chloro-6-(difluoromethoxy)pyridin-3-yl)-2-fluoro-8,8-dimethyl-7,8-dihydro-6H-cyclopenta[e]pyrazolo[1,5-a]pyrimidine-6-carboxamide and (S)—N-(5-chloro-6-(difluoromethoxy)pyridin-3-yl)-2-fluoro-8,8-dimethyl-7,8-dihydro-6H-cyclopenta[e]pyrazolo[1,5-a]pyrimidine-6-carboxamide Step 1: N-(5-chloro-6-(difluoromethoxy)pyridin-3-yl)-2-fluoro-8,8-dimethyl-7,8-dihydro-6H-cyclopenta[e]pyrazolo[1,5-a]pyrimidine-6-carboxamide

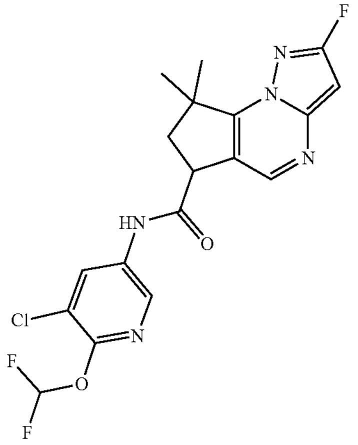 [SMILES: CC1(C)CC(C(=O)Nc2cnc(OC(F)F)c(Cl)c2)c2cnc3cc(F)nn3c21]

To a stirred solution of 2-fluoro-8,8-dimethyl-7,8-dihydro-6H-cyclopenta[e]pyrazolo[1,5-a]pyrimidine-6-carboxylic acid (Method O1 Step 3; 20 mg, 80.2 μmol) and 5-chloro-6-(difluoromethoxy)pyridin-3-amine (Method G2 Step 2; 16 mg, 80.2 μmol) in acetonitrile (1 mL) were added TCFH (68 mg, 240.7 μmol) and NMI (20 mg, 240.7 μmol). The mixture was stirred at 25° C. for 2 h. The resulting mixture was concentrated under reduced pressure. The residue was submitted to Prep-HPLC purification and the collected fractions were lyophilized to give N-(5-chloro-6-(difluoromethoxy)pyridin-3-yl)-2-fluoro-8,8-dimethyl-7,8- dihydro-6H-cyclopenta[e]pyrazolo[1,5-a]pyrimidine-6-carboxamide (26.3 mg, 76% yield) as a white solid. LC-MS: m/z 426 $[M+H]^+$.

Step 2: Separation of Enantiomers to Obtain (R)—N-(5-chloro-6-(difluoromethoxy)pyridin-3-yl)-2-fluoro-8,8-dimethyl-7,8-dihydro-6H-cyclopenta[e]pyrazolo[1,5-a]pyrimidine-6-carboxamide and (S)—N-(5-chloro-6-(difluoromethoxy)pyridin-3-yl)-2-fluoro-8,8-dimethyl-7,8-dihydro-6H-cyclopenta[e]pyrazolo[1,5-a]pyrimidine-6-carboxamide Example 76

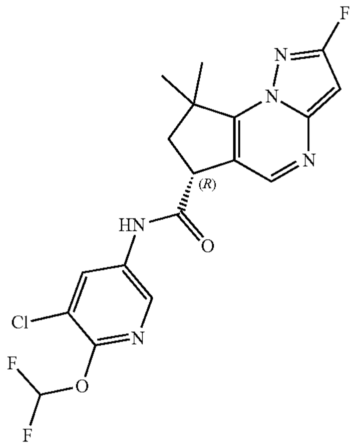

and

Example 77

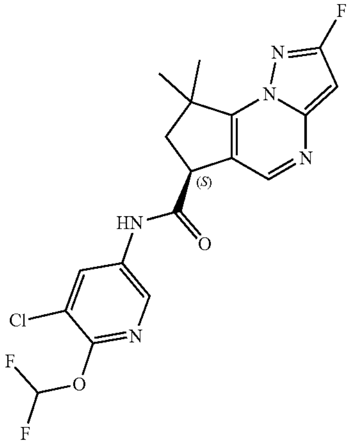

24 mg of N-(5-chloro-6-(difluoromethoxy)pyridin-3-yl)-2-fluoro-8,8-dimethyl-7,8-dihydro-6H-cyclopenta[e]pyrazolo[1,5-a]pyrimidine-6-carboxamide were submitted to chiral HPLC purification (Column: CHIRALPAK IA, 2*25 cm, 5 μm; Mobile Phase A: Hex(0.1% FA), Mobile Phase B: EtOH; Flow rate: 20 mL/min; isocratic 10% B, 26 min; Wave Length: 220/254 nm; RT1(min): 13.67; RT2(min): 19.76; Sample Solvent: EtOH; Injection Volume: 0.8 mL; Number of Runs: 5). The first eluting isomer was concentrated and lyophilized to afford Example 76 as a white solid (4.5 mg, 18% yield). The second eluting isomer was concentrated and lyophilized to afford Example 77 as a white solid (6.2 mg, 25% yield).

Example 76: $^1$H NMR (400 MHz, Chloroform-d) δ: 8.54 (s, 1H), 8.31 (s, 1H), 8.14 (s, 1H), 7.49 (s, 1H), 7.40 (t, J=72.4 Hz, 1H), 6.30 (d, J=5.2 Hz, 1H), 4.13-4.24 (m, 1H), 2.38-2.61 (m, 2H), 1.75 (s, 3H), 1.61 (s, 3H). LC-MS: m/z 426 $[M+H]^+$.

Example 77: $^1$H NMR (400 MHz, Chloroform-d) δ: 8.56 (s, 1H), 8.31 (s, 1H), 8.15 (s, 1H), 7.52 (s, 1H), 7.40 (t, J=72.4 Hz, 1H), 6.31 (d, J=5.2 Hz, 1H), 4.13-4.25 (m, 1H), 2.39-2.63 (m, 2H), 1.76 (s, 3H), 1.61 (s, 3H). LC-MS: m/z 426 $[M+H]^+$.

Method M2

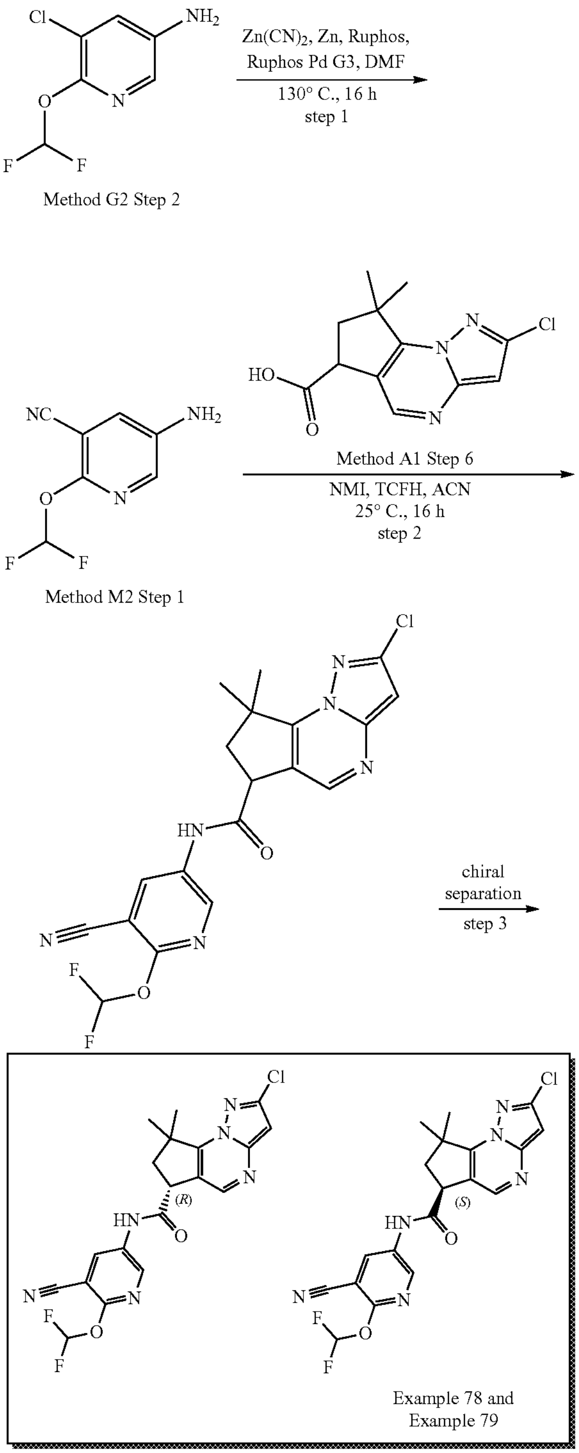

Example 78 and Example 79

Examples 78 and 79: Single Enantiomers Obtained from a Racemic Mixture Containing (R)-2-chloro-N-(5-cyano-6-(difluoromethoxy)pyridin-3-yl)-8,8-dimethyl-7,8-dihydro-6H-cyclopenta[e]pyrazolo[1,5-a]pyrimidine-6-carboxamide and (S)-2-chloro-N-(5-cyano-6-(difluoromethoxy)pyridin-3-yl)-8,8-dimethyl-7,8-dihydro-6H-cyclopenta[e]pyrazolo[1,5-a]pyrimidine-6-carboxamide Step 1: 5-amino-2-(difluoromethoxy)nicotinonitrile

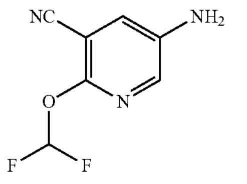 [SMILES: N#Cc1cc(N)cnc1OC(F)F]

To a stirred solution of 5-chloro-6-(difluoromethoxy)pyridin-3-amine (Method G2 Step 2; 100 mg, 513.9 μmol) in N,N-Dimethylformamide (2 mL) were added $Zn(CN)_2$ (66 mg, 565.3 μcool) Ruphos (24 mg, 51.4 μcool), Ruphos Pd G3 (43 mg, 51.4 μmol) and Zinc (2 mg, 25.7 μmol) under nitrogen. The reaction mixture was stirred at 130° C. for 16 h. The reaction mixture was cooled to 25° C. The solid was filtered off, and the filtrate was concentrated under vacuum. The residue was applied onto a silica gel column and eluted with EtOAc/PE (1:3) to afford 5-amino-2-(difluoromethoxy)nicotinonitrile (Method M2 Step 1; 65 mg, 68% yield) as a yellow oil. LC-MS: m/z 186 $[M+H]^+$.

Step 2: 2-chloro-N-(5-cyano-6-(difluoromethoxy)pyridin-3-yl)-8,8-dimethyl-7,8-dihydro-6H-cyclopenta[e]pyrazolo[1,5-a]pyrimidine-6-carboxamide

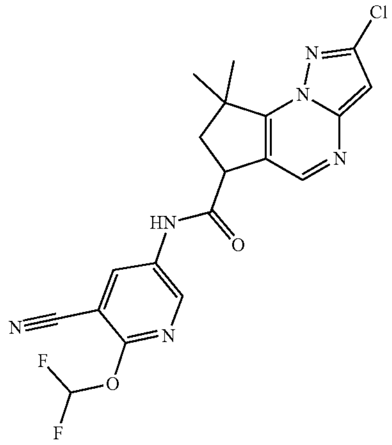 [SMILES: CC1(C)CC(C(=O)Nc2cnc(OC(F)F)c(C#N)c2)c2cnc3cc(Cl)nn3c21]

To a stirred solution of 5-amino-2-(difluoromethoxy)nicotinonitrile (Method M2 Step 1; 60 mg, 324.1 μmol) and 2-chloro-8,8-dimethyl-7,8-dihydro-6H-cyclopenta[e]pyrazolo[1,5-a]pyrimidine-6-carboxylic acid (Method A1 Step 6; 129 mg, 486.1 μmol) in acetonitrile (10 mL) were added TCFH (272.8 mg, 972.2 μmol) and NMI (133.0 mg, 1.6 mmol). The mixture was stirred at 25° C. for 16 h. The reaction mixture was concentrated under vacuum. The residue was submitted to Prep-HPLC purification and the collected fractions were lyophilized to give 2-chloro-N-(5-cyano-6-(difluoromethoxy)pyridin-3-yl)-8,8-dimethyl-7,8-dihydro-6H-cyclopenta[e]pyrazolo[1,5-a]pyrimidine-6-carboxamide (65 mg, 46% yield) as a white solid. LC-MS: m/z 433 $[M+H]^+$.

Step 3: Separation of Enantiomers to Obtain (R)-2-chloro-N-(5-cyano-6-(difluoromethoxy) pyridin-3-yl)-8,8-dimethyl-7,8-dihydro-6H-cyclopenta[e]pyrazolo[1,5-a]pyrimidine-6-carboxamide and (S)-2-chloro-N-(5-cyano-6-(difluoromethoxy)pyridin-3-yl)-8,8-dimethyl-7,8-dihydro-6H-cyclopenta[e]pyrazolo[1,5-a]pyrimidine-6-carboxamide Example 78

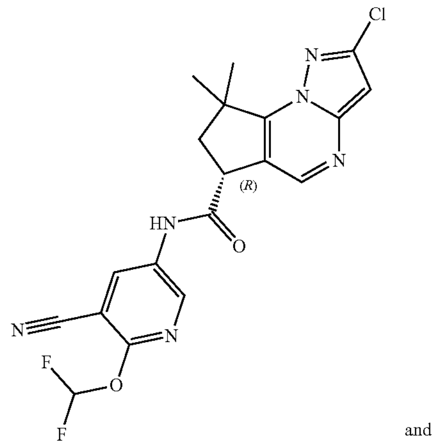

and

Example 79

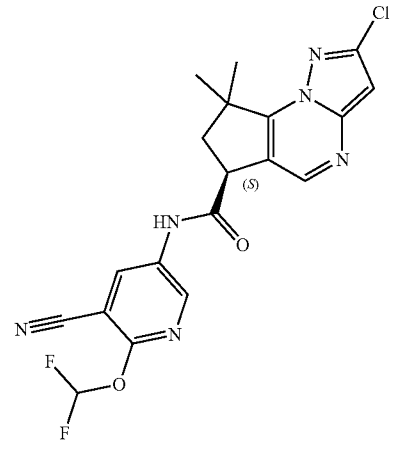

2-chloro-N-(5-cyano-6-(difluoromethoxy)pyridin-3-yl)-8,8-dimethyl-7,8-dihydro-6H-cyclopenta[e]pyrazolo[1,5-a]pyrimidine-6-carboxamide (65 mg, 148.8 μmol) was submitted to chiral-HPLC (Column: CHIRAL ART Cellulose-SC, 2×25 cm, 5 μm; Mobile Phase A: Hex (0.1% FA), Mobile Phase B: EtOH; Flow rate: 20 mL/min; isocratic 20% B, 10 min; Wave Length: 220/254 nm; RT1(min): 6.86; RT2(min): 8.27; Sample Solvent: EtOH; Injection Volume: 0.8 mL; Number of Runs: 6). The first eluting isomer was concentrated and lyophilized to afford Example 78 (20.9 mg, 34.% yield) as a white solid. The second eluting isomer was concentrated and lyophilized to afford Example 79 (22.3 mg, 36% yield) as a white solid.

Examples 78: $^{1}$H NMR (400 MHz, DMSO-$d_6$) δ: 10.86 (br, 1H), 8.68 (d, J=2.4 Hz, 1H), 8.62 (d, J=3.2 Hz, 2H), 7.74 (t, J=71.6 Hz, 1H), 6.94 (s, 1H), 4.37-4.42 (m, 1H), 2.51-2.56 (m, 1H), 2.27-2.34 (m, 1H), 1.63 (s, 3H), 1.55 (s, 3H). LC-MS: m/z 433 $[M+H]^+$.

Examples 79: $^{1}$H NMR (400 MHz, DMSO-$d_6$) δ: 10.86 (br, 1H), 8.68 (d, J=2.4 Hz, 1H), 8.62 (d, J=2.8 Hz, 2H), 7.73 (t, J=71.2 Hz, 1H), 6.93 (s, 1H), 4.36-4.42 (m, 1H), 2.51-2.56 (m, 1H), 2.27-2.33 (m, 1H), 1.63 (s, 3H), 1.55 (s, 3H). LC-MS: m/z 433 $[M+H]^+$.

The absolute stereochemistry for each separated isomer was not determined.

Method N2

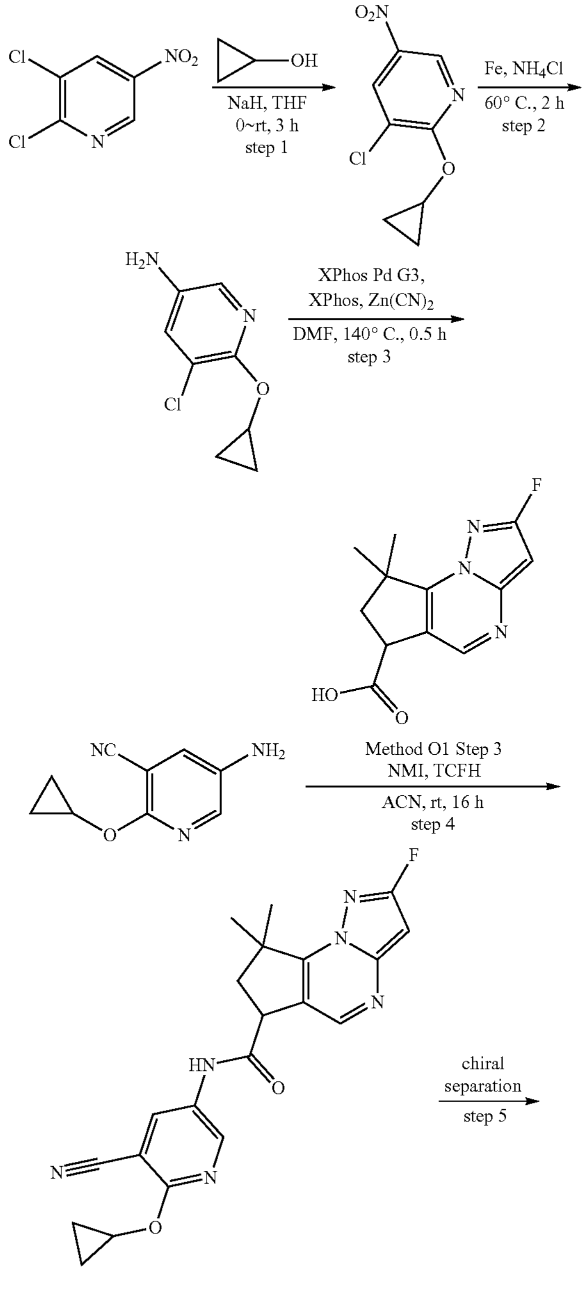

-continued

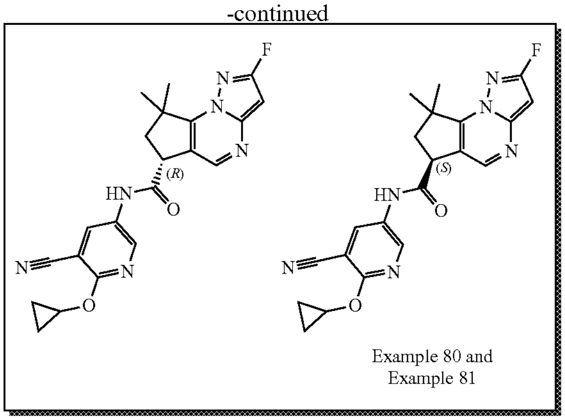

Example 80 and Example 81

Example 80 and Example 81: Single Enantiomers Obtained from a Racemic Mixture Containing (R)—N-(5-cyano-6-cyclopropoxypyridin-3-yl)-2-fluoro-8,8-dimethyl-7,8-dihydro-611-cyclopenta[e]pyrazolo[1,5-a]pyrimidine-6-carboxamide and (S)—N-(5-cyano-6-cyclopropoxypyridin-3-yl)-2-fluoro-8,8-dimethyl-7,8-dihydro-6H-cyclopenta[e]pyrazolo[1,5-a]pyrimidine-6-carboxamide Step 1: 3-chloro-2-cyclopropoxy-5-nitropyridine

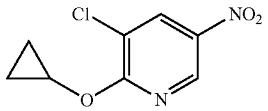

To a stirred solution of cyclopropanol (1.99 g, 34.2 mmol) in THF (100 mL) was added NaH (2.05 g, 51.3 mmol, 60% in mineral oil) at 0° C. The reaction mixture was stirred at 0° C. for 1 h. 2,3-dichloro-5-nitropyridine (6.6 g, 34.2 mmol) was added and the reaction was stirred at 25° C. for 3 h. The reaction mixture was quenched with water (200 mL). The resulting solution was extracted with ethyl acetate (3×100 mL). The combined organic layers were dried over anhydrous sodium sulfate and concentrated under reduced pressure. The residue was applied onto a silica gel column and eluted with PE/EtOAc (5:1) to afford 3-chloro-2-cyclopropoxy-5-nitropyridine (5.9 g, 79% yield) as a yellow solid. LC-MS: m/z 215 $[M+H]^+$.

Step 2: 5-chloro-6-cyclopropoxypyridin-3-amine

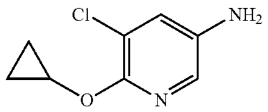

To a stirred solution of 3-chloro-2-cyclopropoxy-5-nitropyridine (5.9 g, 27.5 mmol) in methanol (60 mL) and water (30 mL) were added Fe (7.7 g, 137.5 mmol) and Ammonium chloride (7.4 g, 137.5 mmol). The resulting mixture was stirred at 60 0° C. for 2 h. The reaction mixture was quenched by the addition of water (100 mL). The resulting solution was extracted with ethyl acetate (3×100 mL). The combined organic layers were dried over anhydrous sodium sulfate and concentrated under reduced pressure to afford 5-chloro-6-cyclopropoxypyridin-3-amine (4.9 g, 77% yield) as a light brown solid. LC-MS: m/z 185 $[M+H]^+$.

Step 3: 5-amino-2-cyclopropoxynicotinonitrile $NCNH_2$

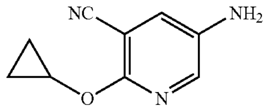 [SMILES: N#Cc1cc(N)cnc1OC1CC1]

To a stirred solution of 5-chloro-6-cyclopropoxypyridin-3-amine (200 mg, 1.1 mmol) in N,N-Dimethylformamide (1 mL) were added $Zn(CN)_2$ (254 mg, 2.2 mmol), Xphos (155 mg, 325.6 μmol) and Xphos Pd G3 (183 mg, 325.6 μmol) under nitrogen atmosphere. The reaction mixture was heated in a microwave reactor at 140° C. for 0.5 h. After cooled to 25° C., the solid was filtered out. The filtrate was quenched with water (50 mL). The resulting solution was extracted with ethyl acetate (3×50 mL). The combined organic layers were washed with brine (3×50 mL), dried over anhydrous sodium sulfate, and concentrated under reduced pressure. The residue was applied onto a silica gel column and eluted with PE/EtOAc (3:1) to afford 5-amino-2-cyclopropoxynicotinonitrile (60 mg, 24% yield) as a yellow solid. LC-MS: m/z 176 $[M+H]^+$.

Step 4: N-(5-cyano-6-cyclopropoxypyridin-3-yl)-2-fluoro-8,8-dimethyl-7,8-dihydro-6H-cyclopenta[e]pyrazolo[1,5-a]pyrimidine-6-carboxamide

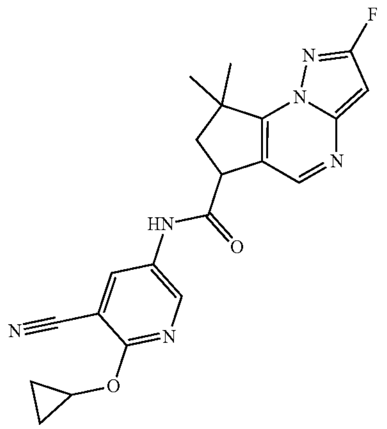 [SMILES: CC1(C)CC(C(=O)Nc2cnc(OC3CC3)c(C#N)c2)c2cnc3cc(F)nn3c21]

To a solution of 5-amino-2-cyclopropoxynicotinonitrile (50 mg, 284.1 μmol) in acetonitrile (2 mL) were added 2-fluoro-8,8-dimethyl-7,8-dihydro-6H-cyclopenta[e]pyrazolo[1,5-a]pyrimidine-6-carboxylic acid (Method 01 Step 3; 71 mg, 284.1 μmol), TCFH (320 mg, 1.1 mmol) and NMI (93 mg, 1.1 mmol). The resulting mixture was stirred at 25° C. for 16 h. The reaction mixture was concentrated under reduced pressure. The residue was submitted to Prep-HPLC purification to give N-(5-cyano-6-cyclopropoxypyridin-3-yl)-2-fluoro-8,8-dimethyl-7,8-dihydro-6H-cyclopenta[e]pyrazolo[1,5-a]pyrimidine-6-carboxamide (50 mg, 42% yield) as a white solid. LC-MS: m/z 407 $[M+H]^+$.

Step 5: Separation of Enantiomers to Obtain (R)—N-(5-cyano-6-cyclopropoxypyridin-3-yl)-2-fluoro-8,8-dimethyl-7,8-dihydro-6H-cyclopenta[e]pyrazolo[1,5-a]pyrimidine-6-carboxamide and (S)—N-(5-cyano-6-cyclopropoxypyridin-3-yl)-2-fluoro-8,8-dimethyl-7,8-dihydro-6H-cyclopenta[e]pyrazolo[1,5-a]pyrimidine-6-carboxamide Example 80

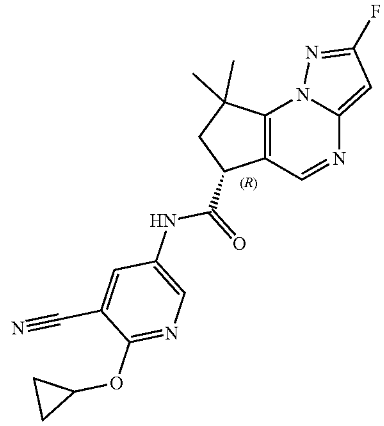

and

Example 81

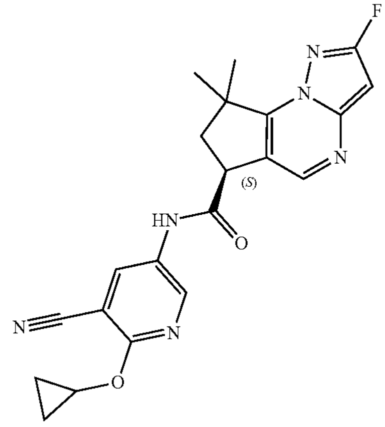

N-(5-cyano-6-cyclopropoxypyridin-3-yl)-2-fluoro-8,8-dimethyl-7,8-dihydro-6H-cyclopenta[e]pyrazolo[1,5-a]pyrimidine-6-carboxamide (45 mg, 110.6 mmol) was submitted to chiral HPLC purification (Column: CHIRALPAK IE, 2×25 cm, 5 μm; Mobile Phase A: Hex(0.1% FA)-HPLC, Mobile Phase B: EtOH-HPLC; Flow rate: 18 mL/min; isocratic 50% B in 14 min; Wave Length: 254/220 nm; RT1(min): 7.51; RT2(min): 9.37; Sample Solvent: EtOH-HPLC; Injection Volume: 1.5 mL; Number Of Runs: 3). The first eluting isomer was concentrated and lyophilized to afford Example 80 (14.3 mg, 31% yield) as a white solid. The second eluting isomer was concentrated and lyophilized to afford Example 81 (12.8 mg, 28% yield) as a white solid.

Example 80: $^1H$ NMR (400 MHz, DMSO-$d_6$) δ: 10.68 (s, 1H), 8.60-8.63 (m, 2H), 8.45 (d, J=2.4 Hz, 1H), 6.56 (d, J=4.8 Hz, 1H), 4.34-4.39 (m, 2H), 2.48-2.53 (m, 1H), 2.27-2.32 (m, 1H), 1.61 (s, 3H), 1.53 (s, 3H), 0.73-0.84 (m, 4H). LC-MS: m/z 407.2 $[M+H]^+$.

Example 81: $^1$H NMR (400 MHz, DMSO-$d_6$) δ: 10.68 (s, 1H), 8.60-8.63 (m, 2H), 8.45 (d, J=2.8 Hz, 1H), 6.56 (d, J=4.8 Hz, 1H), 4.34-4.39 (m, 2H), 2.48-2.53 (m, 1H), 2.27-2.32 (m, 1H), 1.61 (s, 3H), 1.53 (s, 3H), 0.73-0.84 (m, 4H). LC-MS: m/z 407.2 [M+H]$^+$.

The absolute stereochemistry for each separated isomer was not determined.

Method 02

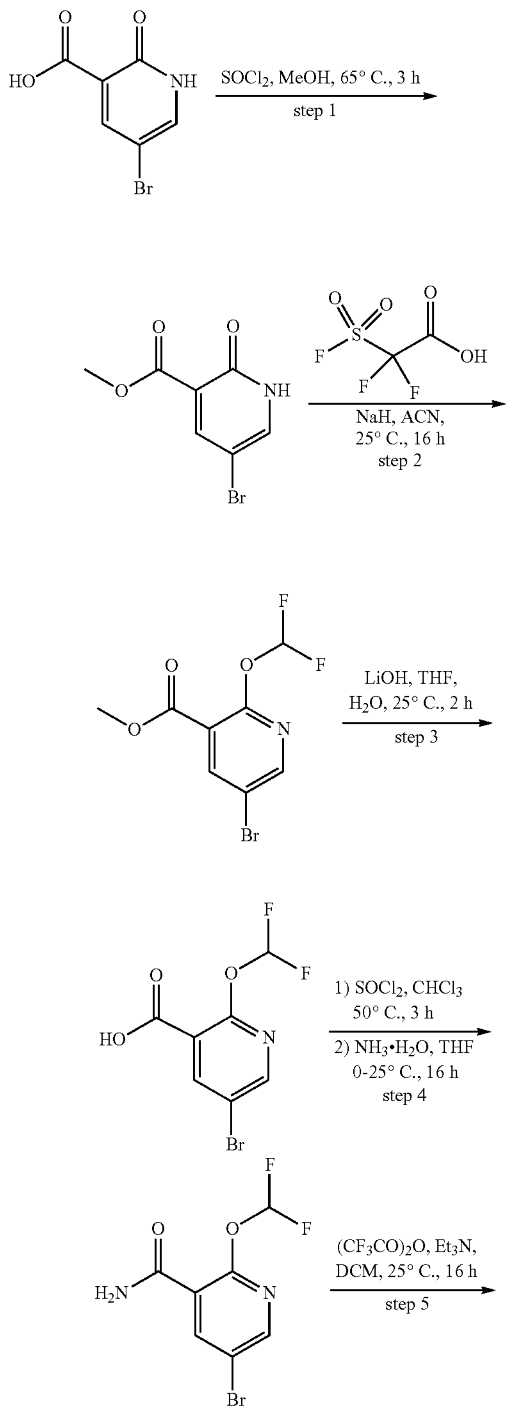

-continued

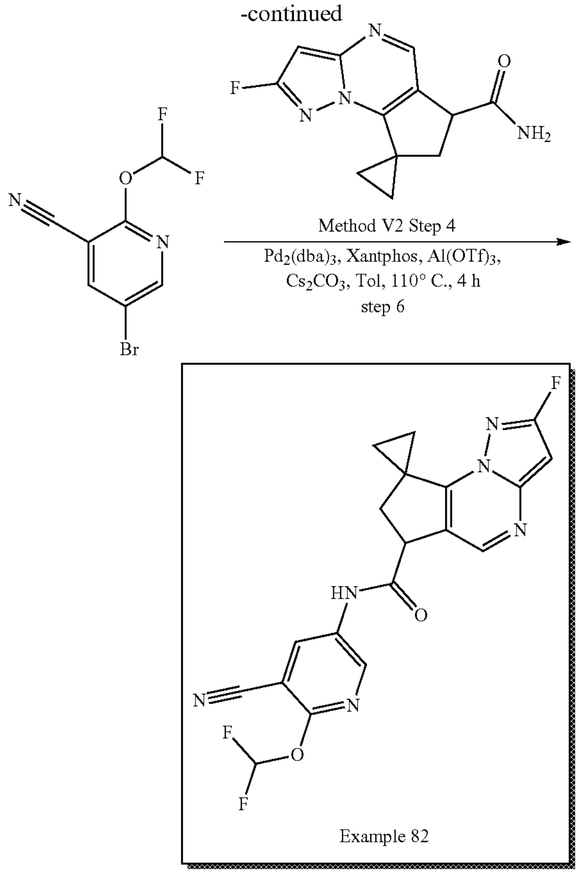

Example 82

Example 82: N-(5-cyano-6-(difluoromethoxy)pyridin-3-yl)-2-fluoro-6,7-dihydrospiro[cyclopenta[e]pyrazolo[1,5-a]pyrimidine-8,1'-cyclopropane]-6-carboxamide Step 1: methyl 5-bromo-2-oxo-1,2-dihydropyridine-3-carboxylate

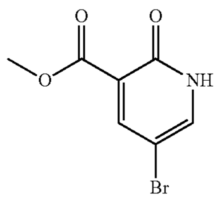

To a stirred solution of 5-bromo-2-oxo-1,2-dihydropyndine-3-carboxylic acid (10 g, 45.9 mmol) in MeOH (130 mL) was added dropwise sulfurous dichloride (13.4 g, 112.6 mmol). The reaction mixture was stirred at 65° C. for 3 h. The reaction mixture was concentrated under reduced pressure. The residue was diluted with EtOAc (50 mL) and water (20 mL). The precipitated solid was filtered and triturated with 2-methoxy-2-methylpropane (50 mL). The solid was filtered and dried to afford methyl 5-bromo-2-oxo-1,2-dihydropyridine-3-carboxylate (9.5 g, 89% yield) as a white solid. LC-MS: m/z 232 [M+H]$^+$.

Step 2: methyl 5-bromo-2-(difluoromethoxy)nicotinate

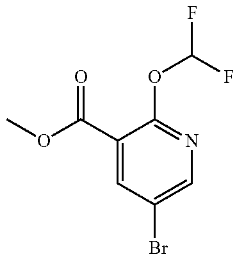

To a stirred solution of methyl 5-bromo-2-oxo-1,2-dihydropyridine-3-carboxylate (1.0 g, 4.3 mmol) in acetonitrile (50 mL) was added NaH (474 mg, 11.8 mmol, 60% in mineral oil) at 0° C. The reaction mixture was stirred at 0° C. for 1 h. 2,2-difluoro-2-(fluorosulfonyl)acetic acid (1.3 g, 7.3 mmol) was added at 0° C. and the reaction mixture was stirred at 25° C. for 16 h. The reaction mixture was quenched with water (50 mL). The resulting solution was extracted with ethyl acetate (3×50 mL). The combined organic layers were dried over anhydrous sodium sulfate and concentrated under reduced pressure. The residue was applied onto a silica gel column and eluted with PE/EtOAc (5:1) to afford methyl 5-bromo-2(difluoromethoxy)nicotinate (1.0 g, 82% yield) as a white solid. $^1$H NMR (300 MHz, DMSO-$d_6$) δ: 8.65 (d, J=2.4 Hz, 1H), 8.48 (d, J=2.4 Hz, 1H), 7.73 (t, J=71.7 Hz, 1H), 3.87 (s, 3H). LC-MS: m/z 282 $[M+H]^+$.

Step 3: 5-bromo-2-(difluoromethoxy)nicotinic acid

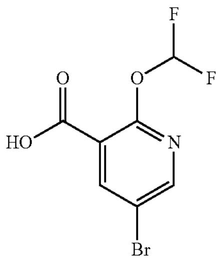 [SMILES: O=C(O)c1cc(Br)cnc1OC(F)F]

To a stirred solution of methyl 5-bromo-2-(difluoromethoxy)nicotinate (1.0 g, 3.6 mmol) in THF (5 mL) and water (5 mL) was added lithium hydroxide (255 mg, 10.6 mmol). The reaction mixture was stirred at 25° C. for 2 h. The pH was adjusted to 2 with HCl (12 M). The resulting solution was extracted with DCM (3×20 mL). The combined organic layers were dried over anhydrous sodium sulfate and concentrated under reduced pressure to afford 5-bromo-2-(difluoromethoxy)nicotinic acid (900 mg, 94% yield) as a white solid. LC-MS: m/z 268 $[M+H]^+$.

Step 4: 5-bromo-2-(difluoromethoxy)nicotinamide

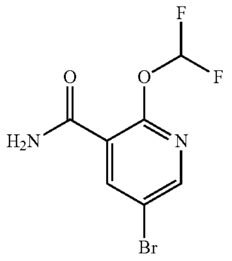 [SMILES: NC(=O)c1cc(Br)cnc1OC(F)F]

To a stirred solution of 5-bromo-2-(difluoromethoxy) nicotinic acid (700 mg, 2.6 mmol) in chloroform (10 mL) was added sulfurous dichloride (4 mL) at 0° C. The reaction mixture was stirred at 50° C. for 2 h. The reaction mixture was concentrated under reduced pressure. The residue was re-dissolved in THF (5 mL) and the mixture was added to ammonium hydroxide solution (10 mL) at 0° C. The reaction mixture was stirred at 25° C. for 16 h. The organic solvent was removed under reduced pressure. The precipitated solid was collected by filtration, washed with water (50 mL) and dried to afford 5-bromo-2-(difluoromethoxy)nicotinamide (600 mg, 86% yield) as a white solid. LC-MS: m/z 267 $[M+H]^+$.

Step 5: 5-bromo-2-(difluoromethoxy)nicotinonitrile

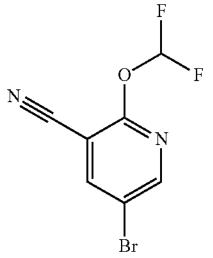 [SMILES: N#Cc1cc(Br)cnc1OC(F)F]

To a stirred solution of 5-bromo-2-(difluoromethoxy) nicotinamide (600 mg, 2.2 mmol) in DCM (10 mL) was added TEA (1.54 g, 15.2 mmol) and trifluoromethanesulfonic anhydride (1.2 g, 4.2 mmol) at 0° C. The reaction mixture was stirred at 25° C. for 16 h. The resulting mixture was poured into crushed ice (20 mL) and extracted with DCM (3×20 mL). The combined organic layers were concentrated under reduced pressure. The residue was applied onto a silica gel column and eluted with PE/EtOAc (3:1) to afford 5-bromo-2-(difluoromethoxy)nicotinonitrile (300 mg, 53% yield) as a white solid. $^1$H NMR (300 MHz, Methanol-$d_4$) δ: 8.57 (d, J=2.7 Hz, 1H), 8.51 (d, J=2.4 Hz, 1H), 7.60 (d, J=71.4 Hz, 1H).

Step 6: N-(5-cyano-6-(difluoromethoxy)pyridin-3-yl)-2-fluoro-6,7-dihydrospiro[cyclopenta[e]pyrazolo[1,5-a]pyrimidine-8,1'-cyclopropane]-6-carboxamide Example 82

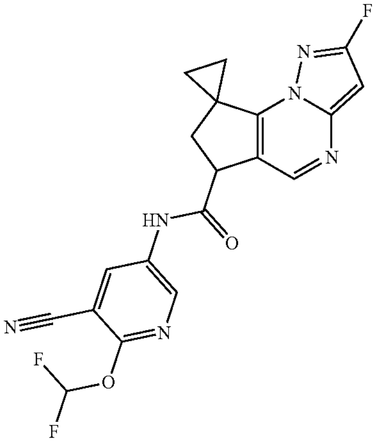

To a stirred solution of 2-fluoro-6,7-dihydrospiro[cyclopenta[e]pyrazolo[1,5-a]pyrimidine-8,1'-cyclopropane]-6-carboxamide (Method V2 Step 4; 30 mg, 96.2 μmol) in toluene (10 mL) was added 5-bromo-2-(difluoromethoxy)nicotinonitrile (48 mg, 192.5 μmol), $Pd_2(dba)_3$ (9 mg, 9.6 μmol), XantPhos (6 mg, 9.6 μmol), $A1(OTf)_3$ (5 mg, 9.6 μmol) and cesium carbonate (47 mg, 144.4 μmol). The reaction mixture was stirred at 110° C. for 4 h. The resulting mixture was extracted with ethyl acetate (3×10 mL). The combined organic layers were dried over anhydrous sodium sulfate and concentrated under reduced pressure. The residue was applied on a silica gel column and eluted with EtOAc/PE (1:10) to give the crude product. The crude product was submitted to Prep-HPLC purification to give N-(5-cyano-6-(difluoromethoxy)pyridin-3-yl)-2-fluoro-6,7-dihydrospiro[cyclopenta[e]pyrazolo[1,5-a]pyrimidine-8,1'-cyclopropane]-6-carboxamide (1.9 mg, 4% yield) as a white solid.

Example 82: $^1$H NMR (400 MHz, DMSO-$d_6$) δ: 10.92 (s, 1H), 8.69 (d, J=2.4 Hz, 1H), 8.62 (d, J=2.9 Hz, 1H), 8.56 (s, 1H), 7.74 (t, J=71.6 Hz, 1H), 6.40-6.52 (m, 1H), 4.44-4.53 (m, 1H), 2.60-2.70 (m, 1H), 2.53-2.55 (m, 1H), 2.04-2.16 (m, 2H), 1.14-1.25 (m, 2H). LC-MS: m/z 415.2 $[M+H]^+$.

Method P2

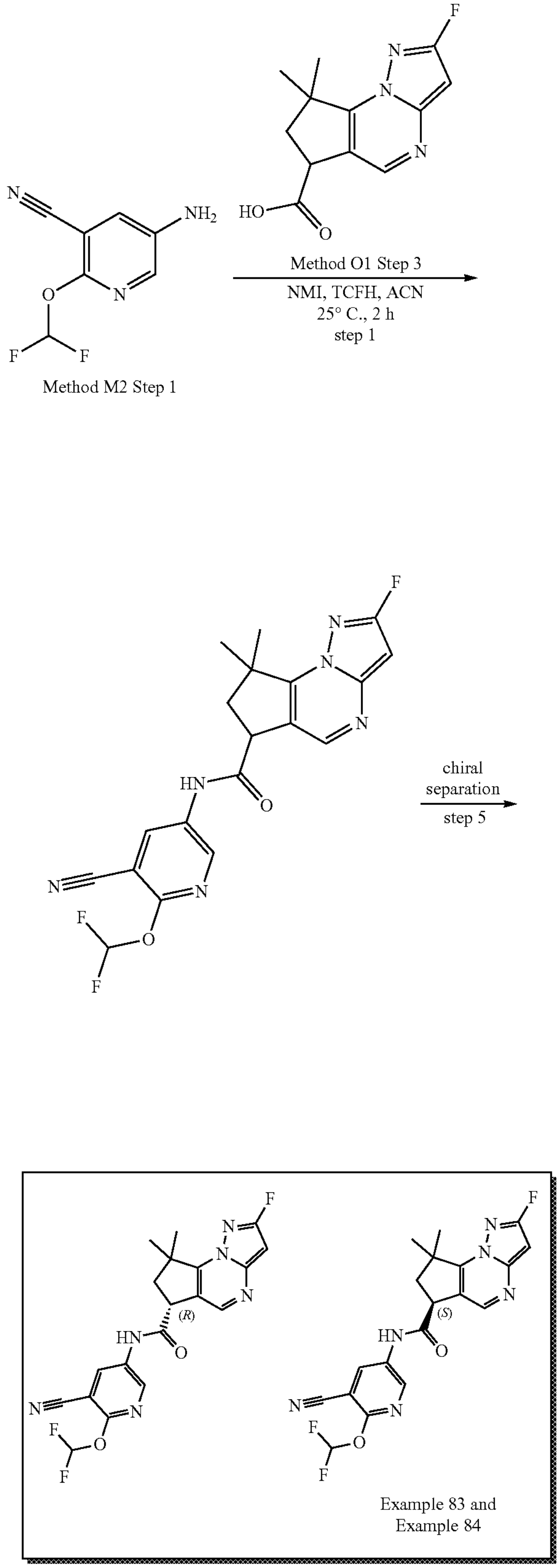

Example 83 and Example 84

Example 83 and 84: Single Enantiomers Obtained from Racemic Mixtures Containing (R)—N-(5-cyano-6-(difluoromethoxy)pyridin-3-yl)-2-fluoro-8,8-dimethyl-7,8-dihydro-6H-cyclopenta[e]pyrazolo[1,5-a]pyrimidine-6-carboxamide and (S)—N-(5-cyano-6-(difluoromethoxy)pyridin-3-yl)-2-fluoro-8,8-dimethyl-7,8-dihydro-6H-cyclopenta[e]pyrazolo[1,5-a]pyrimidine-6-carboxamide Step 1: N-(5-cyano-6-(difluoromethoxy)pyridin-3-yl)-2-fluoro-8,8-dimethyl-7,8-dihydro-6H-cyclopenta[e]pyrazolo[1,5-a]pyrimidine-6-carboxamide

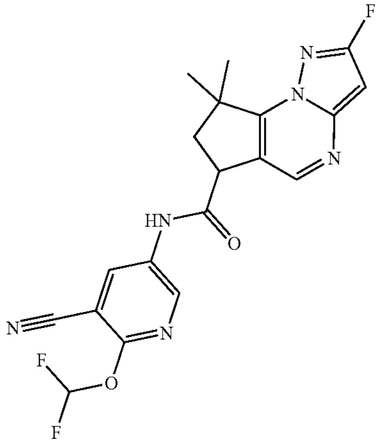 [SMILES: CC1(C)CC(C(=O)Nc2cnc(OC(F)F)c(C#N)c2)c2cnc3cc(F)nn3c21]

To a stirred solution of 5-amino-2-(difluoromethoxy) nicotinomtrile (Method M1 Step 1; 50 mg, 270 μmol) in acetonitrile (1 mL) was added 2-fluoro-8,8-dimethyl-7,8-dihydro-6H-cyclopenta[e]pyrazolo[1,5-a]pyrimidine-6-carboxylic acid (Method 01 Step 3; 67.31 mg, 270 μmol), NMI (89 mg, 1.1 mmol) and TCFH (303 mg, 1.1 mmol). The reaction mixture was stirred at 25° C. for 12 h. The mixture was concentrated under reduced pressure. The residue was diluted with water (5 mL), and the resulting solution was extracted with ethyl acetate (3×5 mL). The combined organic layers were washed with brine (3×5 mL), dried over anhydrous sodium sulfate and concentrated under reduced pressure. The residue was submitted to Prep-HPLC purification to give N-(5-cyano-6-(difluoromethoxy)pyridin-3-yl)-2-fluoro-8,8-dimethyl-7,8-dihydro-6H-cyclopenta[e]pyrazolo[1,5-a]pyrimidine-6-carboxamide (50 mg, 44% yield) as a white solid. LC-MS: m/z 417 $[M+H]^+$.

Step 2: Separation of Enantiomers to Obtain (R)—N-(5-cyano-6-(difluoromethoxy)pyridin-3-yl)-2-fluoro-8,8-dimethyl-7,8-dihydro-6H-cyclopenta[e]pyrazolo[1,5-a]pyrimidine-6-carboxamide and (S)—N-(5-cyano-6-(difluoromethoxy)pyridin-3-yl)-2-fluoro-8,8-dimethyl-7,8-dihydro-6H-cyclopenta[e]pyrazolo[1,5-a]pyrimidine-6-carboxamide Example 83

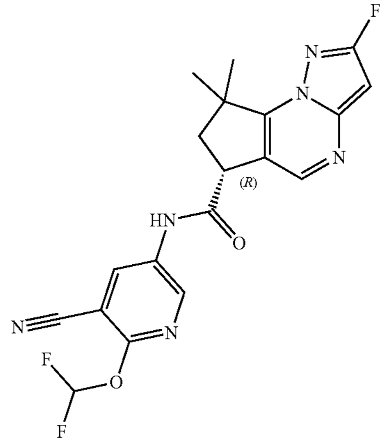

and

Example 84

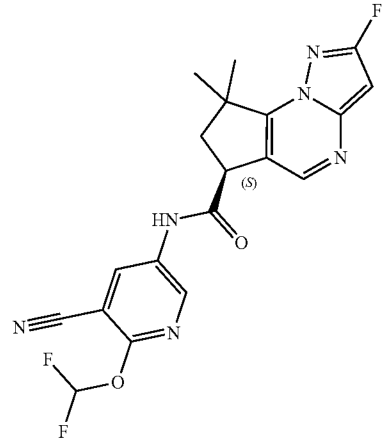

45 mg of N-(5-cyano-6-(difluoromethoxy)pyridin-3-yl)-2-fluoro-8,8-dimethyl-7,8-dihydro-6H-cyclopenta[e]pyrazolo[1,5-a]pyrimidine-6-carboxamide were submitted to chiral HPLC purification (Column: CHIRAL ART Cellulose-SC, 2*25 cm, 5 μm; Mobile Phase A: Hex(0.1% FA)-HPLC, Mobile Phase B: EtOH-HPLC; Flow rate: 20 mL/min; isocratic 20% B in 10 min; Wave Length: 220/254 nm; RT1(min): 7.45; RT2(min): 8.89; Sample Solvent: EtOH-HPLC; Injection Volume: 0.8 mL; Number Of Runs: 8). The first eluting isomer was concentrated and lyophilized to afford Example 83 (14.9 mg, 66% yield) as a white solid. The second eluting isomer was concentrated and lyophilized to afford Example 84 (8.5 mg, 37% yield) as a white solid.

Example 83: $^1H$ NMR (300 MHz, DMSO-$d_6$) δ: 10.88 (s, 1H), 8.69 (d, J=2.7 Hz, 1H), 8 0.60-8.64 (m, 2H), 7.75 (t, J=72.0 Hz, 1H), 6.56 (d, J=4.5 Hz, 1H), 4.37-4.44 (m, 1H), 2.51-2.62 (m, 1H), 2.32-2.41 (m, 1H), 1.63 (s, 3H), 1.55 (s, 3H). LC-MS: m/z 417.1 $[M+H]^+$.

Example 84: $^1H$ NMR (300 MHz, DMSO-$d_6$) δ: 10.87 (s, 1H), 8.69 (d, J=2.7 Hz, 1H), 8 0.61-8.64 (m, 2H), 7.75 (t, J=71.7 Hz, 1H), 6.56 (d, J=4.8 Hz, 1H), 4.37-4.44 (m, 1H), 2.51-2.61 (m, 1H), 2.32-2.40 (m, 1H), 1.63 (s, 3H), 1.55 (s, 3H). LC-MS: m/z 417.2 $[M+H]^+$.
The absolute stereochemistry for each separated isomer was not determined.
Method Q2
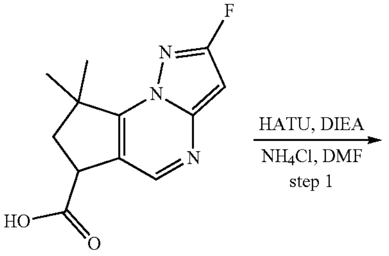
Method O1 Step 3
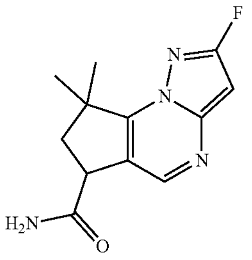
Method Q2 Step 1
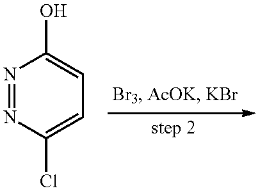
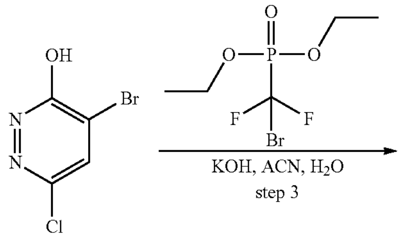
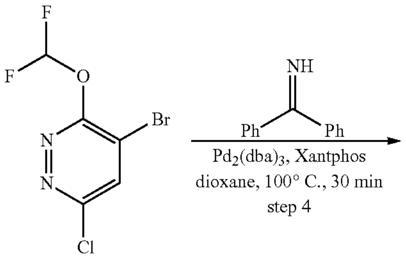
-continued
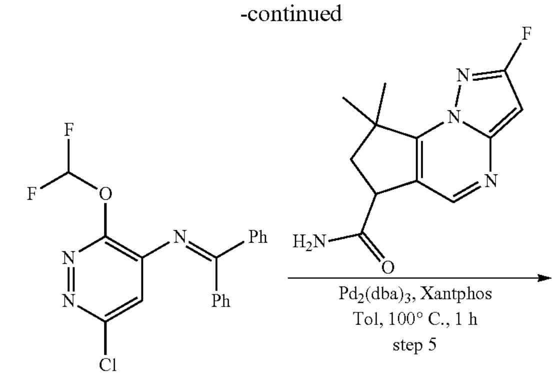
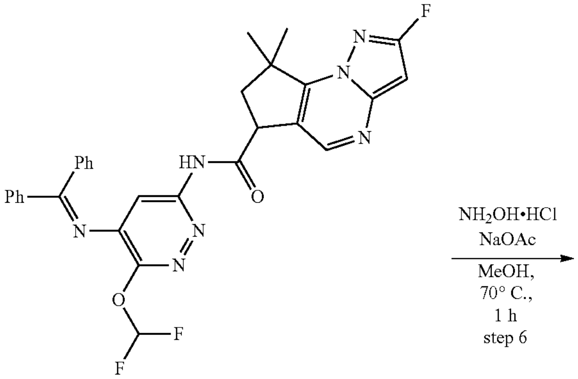
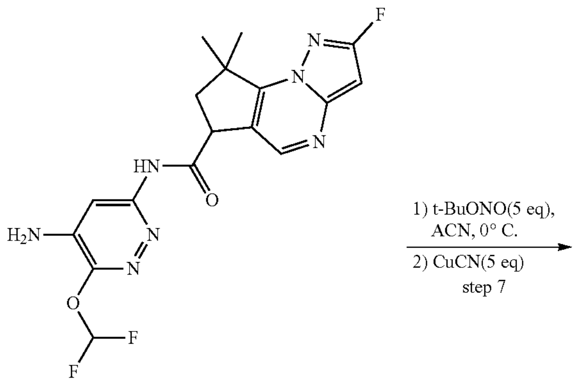
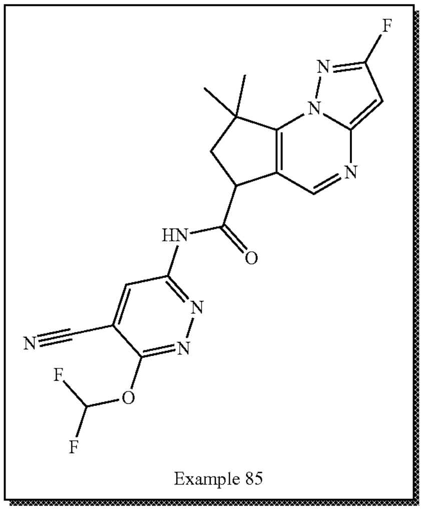
Example 85

Example 85: N-(5-cyano-6-(difluoromethoxy) pyridazin-3-yl)-2-fluoro-8,8-dimethyl-7,8-dihydro-6H-cyclopenta[e]pyrazolo[1,5-a]pyrimidine-6-carboxamide Step 1: 2-Fluoro-8,8-dimethyl-7,8-dihydro-6H-cyclopenta[e]pyrazolo[1,5-a]pyrimidine-6-carboxamide

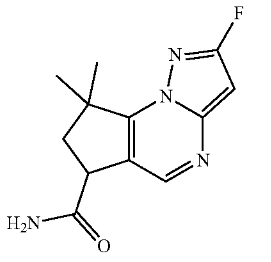 [SMILES: CC1(C)CC(C(N)=O)c2cnc3cc(F)nn3c21]

To a stirred solution of 2-fluoro-8,8-dimethyl-7,8-dihydro-6H-cyclopenta[e]pyrazolo[1,5-a]pyrimidine-6-carboxylic acid (Method 01 Step 3; 100 mg, 401 μmol) and 2-(3H-[1,2,3]triazolo[4,5-b]pyridin-3-yl)-1,1,3,3-tetramethylisouronium (HATU) (229 mg, 602 μmol) in N,N-Dimethylformamide (5 mL) were added ammonia hydrochloride (43 mg, 802 μmol) and N-ethyl-N-isopropyl-propan-2-amine (156 mg, 1.2 mmol). The mixture was stirred at 25° C. for 1 h.

The reaction mixture was quenched with water (10 mL). The resulting solution was extracted with ethyl acetate (3×10 mL). The combined organic layers were dried over anhydrous sodium sulfate and concentrated under reduced pressure. The residue was applied onto a silica gel column and eluted with EtOAc/PE (1:1) to give 2-fluoro-8,8-dimethyl-7,8-dihydro-6H-cyclopenta[e]pyrazolo[1,5-a]pyrimidine-6-carboxamide (Method Q2 Step 1; 80 mg, 73.9% yield) as a yellow oil. LCMS (ES, m/z): 249 $[M+H]^+$.

Step 2: 4-Bromo-6-chloro-pyridazin-3-ol

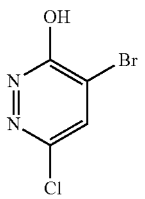

To a stirred mixture of 6-chloropyridazin-3-ol (20 g, 153.2 mmol) and potassium bromide (54.7 g, 459.7 mmol) in water (170 mL) were added potassium acetate (22.6 g, 229.8 mmol) and bromine (73.5 g, 459.7 mmol) at 25° C. The resulting mixture was stirred at 100° C. for 2 h. The mixture was allowed to cool down to room temperature. The reaction was quenched by the addition of sodium sulfite (sat., aq.) at 0° C. The precipitated solids were collected by filtration and washed with water (3×50 mL) to afford 4-bromo-6-chloro-pyridazin-3-ol (16 g, 49% yield) as a yellow solid. LCMS (ES, m/z): 209 $[M+H]^+$.

Step 3: 4-Bromo-6-chloro-3-(difluoromethoxy)pyridazine

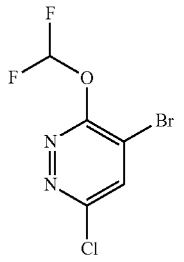 [SMILES: FC(F)Oc1nnc(Cl)cc1Br]

To a mixture of 4-bromo-6-chloro-pyridazin-3-ol (14 g, 66.9 mmol) in ACN (308 mL) was added potassium hydroxide (75.0 g, 1.3 mol) in water (300 mL) at 0° C. The mixture was stirred for 5 min. Diethyl (bromodifluoromethyl)phosphonate (53.6 g, 200.6 mmol) was added at 0° C. and the mixture was stirred for additional 1 h at 10° C. The reaction mixture was quenched with water (600 mL). The resulting solution was extracted with ethyl acetate (3×400 mL). The combined organic layers were washed with brine (500 mL), dried over anhydrous sodium sulfate and concentrated under reduced pressure. The residue was applied onto a silica gel column and eluted with EtOAc/PE (1:4) to give 4-bromo-6-chloro-3-(difluoromethoxy)pyridazine (2.5 g, 14% yield) as a yellow solid. $^1H$ NMR (300 MHz, DMSO-$d_6$) δ 8.63 (s, 1H), 7.85 (t, J=70.7 Hz, 1H). LCMS (ES, m/z): 259 $[M+H]^+$.

Step 4: N-[6-chloro-3-(difluoromethoxy)pyridazin-4-yl]-1,1-diphenyl-methanimine

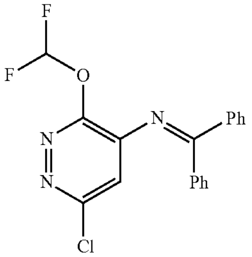 [SMILES: FC(F)Oc1nnc(Cl)cc1N=C(c1ccccc1)c1ccccc1]

To a mixture of 4-bromo-6-chloro-3-(difluoromethoxy) pyridazine (100 mg, 385 μmol) in dioxane (5 mL) were added diphenylmethanimine (56 mg, 308 μmol), $Pd_2(dba)_3$ (35 mg, 38.6 μmol) XantPhos (45 mg, 77.1 μmol) and cesium carbonate (251 mg, 770.9 μmol). The reaction mixture was stirred at 100° C. for 30 min under nitrogen. The mixture was allowed to cool down to room temperature and water (20 mL) was added. The mixture was extracted with ethyl acetate (20 mL×2). The combined organic layers were washed with brine (3 mL), dried over anhydrous sodium sulfate and concentrated under reduced pressure. The residue was purified by Prep-TLC with EtOAc/PE (1:3) to give N-[6-chloro-3-(difluoromethoxy)pyridazin-4-yl]-1,1-diphenyl-methanimine (100 mg, 66% yield) as a yellow oil. LCMS (ES, m/z): 360 $[M+H]^+$.

Step 5: N-(6-(difluoromethoxy)-5-((diphenylmethylene)amino)pyridazin-3-yl)-2-fluoro-8,8-dimethyl-7,8-dihydro-6H-cyclopenta[e]pyrazolo[1,5-a]pyrimidine-6-carboxamide

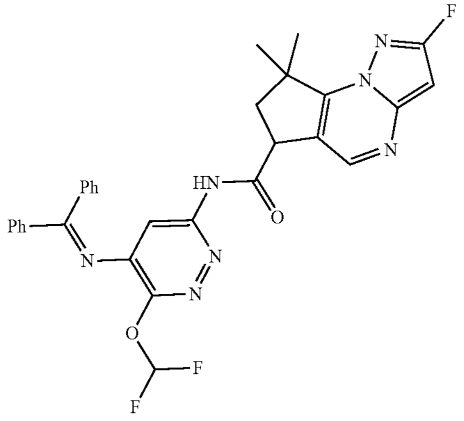 [SMILES: CC1(C)CC(C(=O)Nc2cc(N=C(c3ccccc3)c3ccccc3)c(OC(F)F)nn2)c2cnc3cc(F)nn3c21]

To a mixture of N-[6-chloro-3-(difluoromethoxy)pyridazin-4-yl]-1,1-diphenyl-methanimine (100 mg, 277.9 μmol) in toluene (5 mL) was added 2-fluoro-8,8-dimethyl-7,8-dihydro-6H-cyclopenta[e]pyrazolo[1,5-a]pyrimidine-6-carboxamide (76 mg, 305.8 μmol), $Pd_2(dba)_3$ (26 mg, 27.8 μmol), XantPhos (32 mg, 55.6 μmol) and cesium carbonate (272 mg, 833.9 μmol). The reaction mixture was stirred at 110° C. for 1 h under nitrogen. The mixture was allowed to cool down to room temperature and water (20 mL) was added. The mixture was extracted with ethyl acetate (20 mL×3). The combined organic layers were dried over anhydrous $Na_2SO_4$ and concentrated under reduced pressure. The residue was applied onto a silica gel column and eluted with PE/EtOAc (1:1) to afford N-(6-(difluoromethoxy)-5-((diphenylmethylene)amino)pyridazin-3-yl)-2-fluoro-8,8-dimethyl-7,8-dihydro-6H-cyclopenta[e]pyrazolo[1,5-a]pyrimidine-6-carboxamide (60 mg, 36% yield) as a yellow oil. $^1H$ NMR (300 MHz, DMSO-$d_6$) δ 11.4 (s, 1H), 8.54 (s, 1H), 7.47-7.76 (m, 12H), 6.54 (d, J=6 Hz, 1H), 4.45-4.50 (m, 1H), 2.49-2.46 (m, 1H), 2.20-2.26 (m, 1H), 1.58 (s, 3H), 1.51 (s, 3H). LCMS (ES, m/z): 572 $[M+H]^+$.

Step 6: N-(5-amino-6-(difluoromethoxy)pyridazin-3-yl)-2-fluoro-8,8-dimethyl-7,8-dihydro-6H-cyclopenta[e]pyrazolo[1,5-a]pyrimidine-6-carboxamide

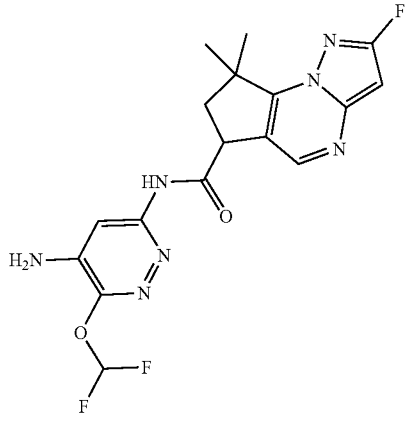 [SMILES: CC1(C)CC(C(=O)Nc2cc(N)c(OC(F)F)nn2)c2cnc3cc(F)nn3c21]

To a stirred solution of N-(6-(difluoromethoxy)-5-((diphenylmethylene)amino)pyridazin-3-yl)-2-fluoro-8,8-dimethyl-7,8-dihydro-6H-cyclopenta[e]pyrazolo[1,5-a]pyrimidine-6-carboxamide (60 mg, 104.9 μmol) in methanol (3 mL) were added hydroxylamine hydrochloride (36 mg, 524.9 μmol) and sodium acetate (43 mg, 524.9 μmol). The mixture was stirred at 70° C. for 1 h. The reaction mixture was cooled down to room temperature and concentrated under reduced pressure. The residue was purified by Prep-TLC with EtOAc/PE (1:1) to give N-(5-amino-6-(difluoromethoxy)pyridazin-3-yl)-2-fluoro-8,8-dimethyl-7,8-dihydro-6H-cyclopenta[e]pyrazolo[1,5-a]pyrimidine-6-carboxamide (30 mg, 64% yield) as a white solid. LCMS (ES, m/z): 408 $[M+H]^+$.

Step 7: N-(5-cyano-6-(difluoromethoxy)pyridazin-3-yl)-2-fluoro-8,8-dimethyl-7,8-dihydro-6H-cyclopenta[e]pyrazolo[1,5-a]pyrimidine-6-carboxamide Example 85

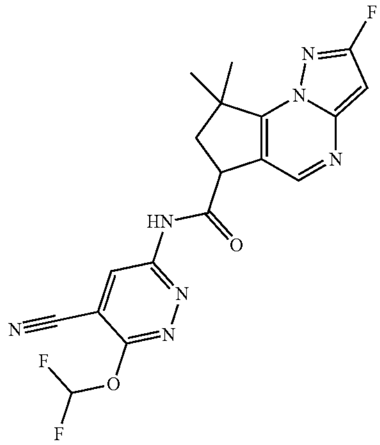

To a stirred solution of tert-butyl nitrite (6 mg, 61.4 μmol) and cuprous cyanide (5.5 mg, 61.2 μmol) in ACN (2 mL) was added a solution of N-(5-amino-6-(difluoromethoxy)pyridazin-3-yl)-2-fluoro-8,8-dimethyl-7,8-dihydro-6H-cyclopenta[e]pyrazolo[1,5-a]pyrimidine-6-carboxamide (5 mg, 12.3 μmol) in ACN (0.2 mL) at 50° C. The reaction mixture was stirred at 50° C. for 3 h. The reaction mixture was quenched with water (10 mL). The resulting solution was extracted with ethyl acetate (2×10 mL). The combined organic layers were dried over anhydrous sodium sulfate and concentrated under reduced pressure. The residue was purified by Prep-TLC with EtOAc/PE (1:1) to give the crude product. The crude product was submitted to Prep-HPLC purification and the collected fractions were lyophilized to give N-(5-cyano-6-(difluoromethoxy)pyridazin-3-yl)-2-fluoro-8,8-dimethyl-7,8-dihydro-6H-cyclopenta[e]pyrazolo[1,5-a]pyrimidine-6-carboxamide (0.8 mg, 15% yield) as a white solid.

Example 85: $^{1}$H NMR (300 MHz, $CDCl_3$) δ 8.97 (s, 1H), 8.91 (s, 1H), 8.56 (s, 1H), 7.59 (t, J=70.5 Hz, 1H), 6.33 (d, J=4.8 Hz, 1H), 4.36-4.41 (m, 1H), 2.58-2.66 (m, 1H), 2.43-2.50 (m, 1H), 1.76 (s, 3H), 1.63 (s, 3H). LCMS (ES, m/z): 418.0 [M+H]$^+$.

Method R2

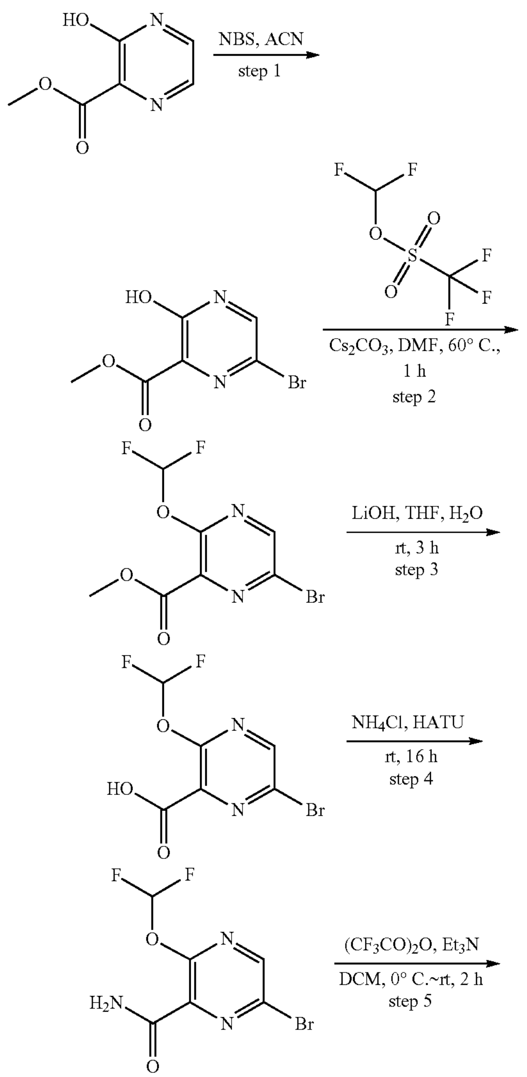

-continued

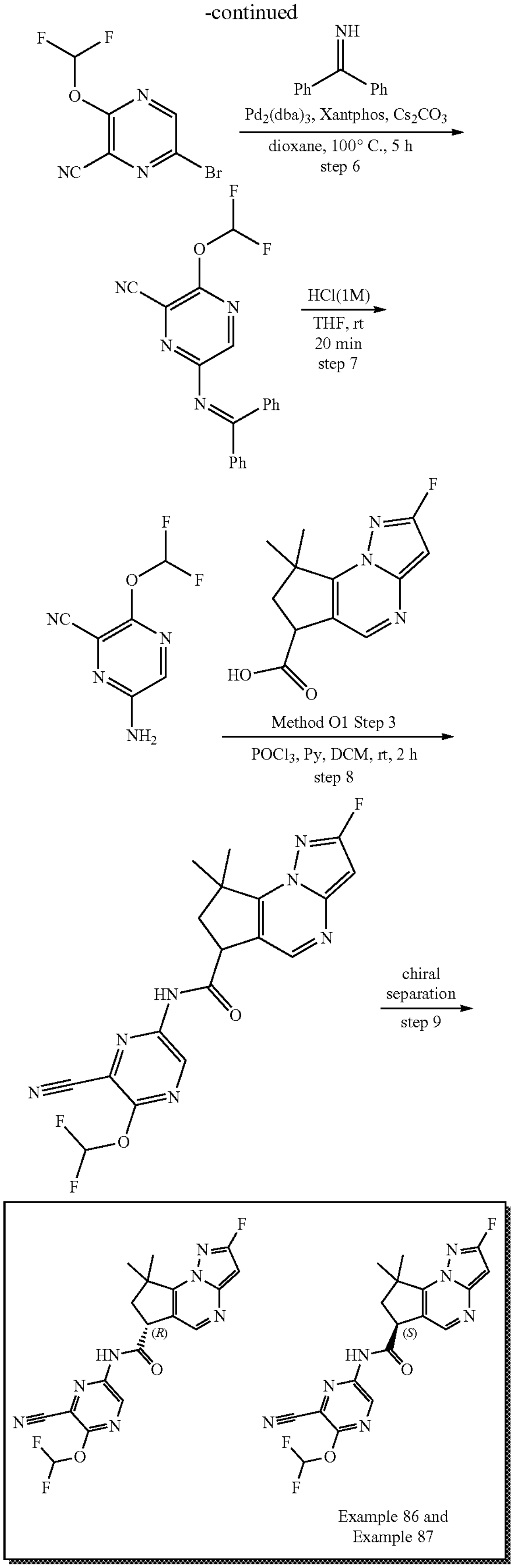

Example 86 and Example 87

Example 86 and Example 87: Single Enantiomers Obtained from a Racemic Mixture Containing (R)—N-(6-cyano-5-(difluoromethoxy)pyrazin-2-yl)-2-fluoro-8,8-dimethyl-7,8-dihydro-6H-cyclopenta[e]pyrazolo[1,5-a]pyrimidine-6-carboxamide and (S)—N-(6-cyano-5-(difluoromethoxy)pyrazin-2-yl)-2-fluoro-8,8-dimethyl-7,8-dihydro-6H-cyclopenta[e]pyrazolo[1,5-a]pyrimidine-6-carboxamide Step 1: methyl 6-bromo-3-hydroxypyrazine-2-carboxylate

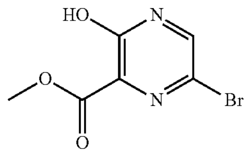

To a stirred solution of methyl 3-hydroxypyrazine-2-carboxylate (9 g, 58.4 mmol) in ACN (150 mL) was added NBS (15.6 g, 87.6 mmol). The reaction was stirred at 25° C. for 16 h. The reaction mixture was quenched with water (200 mL). The resulting solution was extracted with ethyl acetate (3×200 mL). The combined organic layers were dried over anhydrous sodium sulfate and concentrated under reduced pressure. The residue was applied onto a silica gel column and eluted with EtOAc/PE (1:1) to give methyl 6-bromo-3-hydroxypyrazine-2-carboxylate (6 g, 39% yield) as a white solid. $^1$H NMR (400 MHz, $CDCl_3$) δ: 11.20 (br, 1H), 8.54 (s, 1H), 4.10 (s, 3H). LC-MS: m/z 233 $[M+H]^+$.

Step 2: methyl 6-bromo-3-(difluoromethoxy)pyrazine-2-carboxylate

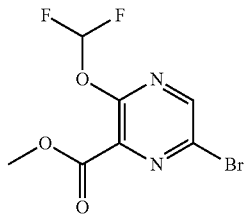

To a stirred solution of methyl 6-bromo-3-hydroxy-pyrazine-2-carboxylate (1 g, 3.9 mmol) in DMF (30 mL) were added cesium carbonate (3.8 g, 11.7 mmol) and difluoromethyl trifluoromethanesulfonate (3.1 g, 15.6 mmol). The resulting mixture was stirred at 60° C. for 1 h. The reaction mixture was quenched by the addition of water (100 mL). The resulting solution was extracted with ethyl acetate (3×100 mL). The combined organic layers were dried over anhydrous sodium sulfate and concentrated under reduced pressure. The residue was applied onto a silica gel column and eluted with EtOAc/PE (1:4) to give methyl 6-bromo-3-(difluoromethoxy)pyrazine-2-carboxylate (200 mg, 18% yield) as a yellow solid. $^1$H NMR (300 MHz, DMSO-$d_6$) δ: 8.84 (s, 1H), 7.70 (t, J=71.0 Hz, 1H), 3.92 (s, 3H). LC-MS: m/z 283 $[M+H]^+$.

Step 3: 6-bromo-3-(difluoromethoxy)pyrazine-2-carboxylic acid

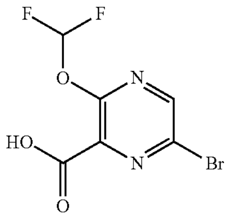 [SMILES: O=C(O)c1nc(Br)cnc1OC(F)F]

To a stirred mixture of methyl 6-bromo-3-(difluoromethoxy)pyrazine-2-carboxylate (440 mg, 1.6 mmol) in THE (10 mL) and water (10 mL) was added lithium hydroxide (186 mg, 7.8 mmol). The mixture was stirred at room temperature for 3 h. The pH was adjusted to 3-4 with HCl (2 M). The mixture was extracted with ethyl acetate (3×20 mL). The combined organic layers were dried over anhydrous $Na_2SO_4$ and concentrated under reduced pressure to give 6-bromo-3-(difluoromethoxy)pyrazine-2-carboxylic acid (400 mg, 74% yield) as a yellow oil. LC-MS: m/z 269 $[M+H]^+$.

Step 4: 6-bromo-3-(difluoromethoxy)pyrazine-2-carboxamide

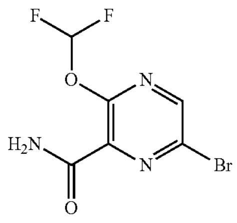 [SMILES: NC(=O)c1nc(Br)cnc1OC(F)F]

To a solution of 6-bromo-3-(difluoromethoxy)pyrazine-2-carboxylic acid (400 mg, 1.5 mmol) in DMF (10 mL) were added $NH_4Cl$ (576 mg, 4.5 mmol), DIEA (577 mg, 4.5 mmol) and HATU (848 mg, 2.2 mmol). The resulting mixture was stirred at 25° C. for 16 h. The reaction mixture was quenched by the addition of water (50 mL). The resulting solution was extracted with ethyl acetate (3×50 mL). The combined organic layers were dried over anhydrous sodium sulfate and concentrated under reduced pressure. The residue was applied onto a silica gel column and eluted with EtOAc/PE (1:1) to give 6-bromo-3-(difluoromethoxy)pyrazine-2-carboxamide (180 mg, 45% yield) as a yellow solid. LC-MS: m/z 268 $[M+H]^+$.

Step 5: 6-bromo-3-(difluoromethoxy)pyrazine-2-carbonitrile

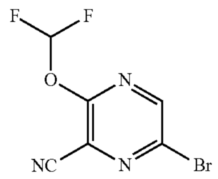 [SMILES: N#Cc1nc(Br)cnc1OC(F)F]

To a solution of 6-bromo-3-(difluoromethoxy)pyrazine-2-carboxamide (180 mg, 671.6 μmol) in DCM (10 mL) were added $Et_3N$ (1.0 g, 10 mmol) and 2,2,2-trifluoroacetic anhydride (2.3 g, 8.1 mmol) at 0° C. The resulting mixture was stirred at 25° C. for 16 h. The reaction mixture was quenched by the addition of water (50 mL). The resulting solution was extracted with DCM (3×50 mL). The combined organic layers were dried over anhydrous sodium sulfate and concentrated under reduced pressure. The residue was applied onto a silica gel column and eluted with EtOAc/PE (1:4) to give 6-bromo-3-(difluoromethoxy)pyrazine-2-carbonitrile (107 mg, 63% yield) as a yellow solid. $^1H$ NMR (400 MHz, DMSO-$d_6$) δ: 8.95 (s, 1H), 7.72 (t, J=70.2 Hz, 1H).

Step 6: 3-(difluoromethoxy)-6-((diphenylmethylene) amino)pyrazine-2-carbonitrile

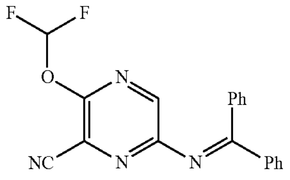 [SMILES: N#Cc1nc(N=C(c2ccccc2)c2ccccc2)cnc1OC(F)F]

To a stirred solution of methyl 6-bromo-3-(difluoromethoxy)pyrazine-2-carbonitrile (100 mg, 400.0 μmol) in dioxane (3 mL) were added diphenylmethanimine (145 mg, 800.0 μmol), cesium carbonate (261 mg, 800.0 μmol), Xantphos (46 mg, 80.0 μmol) and $Pd_2(dba)_3$ (83 mg, 80.0 μmol). The resulting mixture was stirred at 100° C. for 5 h under nitrogen. The reaction mixture was quenched by the addition of water (50 mL). The resulting solution was extracted with ethyl acetate (3×50 mL). The combined organic layers were dried over anhydrous sodium sulfate and concentrated under reduced pressure. The residue was applied onto a silica gel column and eluted with EtOAc/PE (1:4) to give 3-(difluoromethoxy)-6-((diphenylmethylene) amino)pyrazine-2-carbonitrile (80 mg, 45% yield) as a yellow solid. LC-MS: m/z 351 $[M+H]^+$.

Step 7: 6-amino-3-(difluoromethoxy)pyrazine-2-carbonitrile

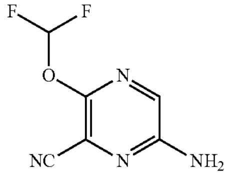 [SMILES: N#Cc1nc(N)cnc1OC(F)F]

To a solution of 3-(difluoromethoxy)-6-((diphenylmethylene)amino)pyrazine-2-carbonitrile (63 mg, 179.8 μmol) in THE (5 mL) was added 1 M HCl (1 mL) at 0° C. The resulting mixture was stirred at 25° C. for 20 min. The pH was adjusted to 7-8 with saturated aqueous sodium bicarbonate solution. The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:4) to give 6-amino-3-(difluoromethoxy)pyrazine-2-carbonitrile (30 mg, 89% yield) as a yellow solid. $^1H$ NMR (400 MHz, DMSO-$d_6$) δ: 7.95 (s, 1H), 7.55 (t, J=72.0 Hz, 1H), 7.11 (s, 2H). LC-MS: m/z 187 $[M+H]^+$.

Step 8: N-(6-cyano-5-(difluoromethoxy)pyrazin-2-yl)-2-fluoro-8,8-dimethyl-7,8-dihydro-6H-cyclopenta[e]pyrazolo[1,5-a]pyrimidine-6-carboxamide

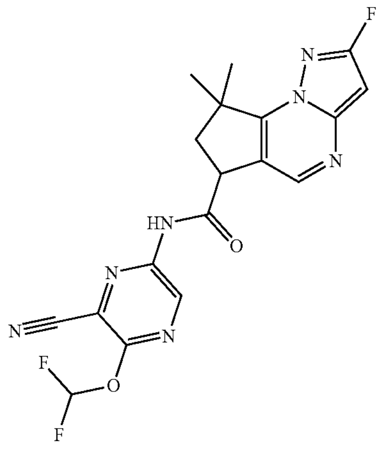

To a stirred solution of 2-fluoro-8,8-dimethyl-7,8-dihydro-6H-cyclopenta[e]pyrazolo[1,5-a]pyrimidine-6-carboxylic acid (Method 01 Step 3; 32 mg, 129 μmol) in DCM (2 mL) were added pyridine (102 mg, 1.3 mmol) and phosphoryl trichloride (82 mg, 537.3 μmol) at 0° C. The mixture was stirred at 0° C. for 1 h. 6-amino-3-(difluoromethoxy)pyrazine-2-carbonitrile (20 mg, 107.5 μmol) was added, and the mixture was stirred at 25° C. for 16 h. The reaction mixture was concentrated under reduced pressure. The residue was purified by Prep-HPLC and the collected fractions were concentrated under reduced pressure to afford N-(6-cyano-5-(difluoromethoxy)pyrazin-2-yl)-2-fluoro-8,8-dimethyl-7,8-dihydro-6H-cyclopenta[e]pyrazolo[1,5-a]pyrimidine-6-carboxamide (17 mg, 38% yield) as a white solid. LC-MS: m/z 418 $[M+H]^+$.

Step 9: Separation of Enantiomers to Obtain (R)—N-(6-cyano-5-(difluoromethoxy)pyrazin-2-yl)-2-fluoro-8,8-dimethyl-7,8-dihydro-6H-cyclopenta[e]pyrazolo[1,5-a]pyrimidine-6-carboxamide and (S)—N-(6-cyano-5-(difluoromethoxy)pyrazin-2-yl)-2-fluoro-8,8-dimethyl-7,8-dihydro-6H-cyclopenta[e]pyrazolo[1,5-a]pyrimidine-6-carboxamide Example 86

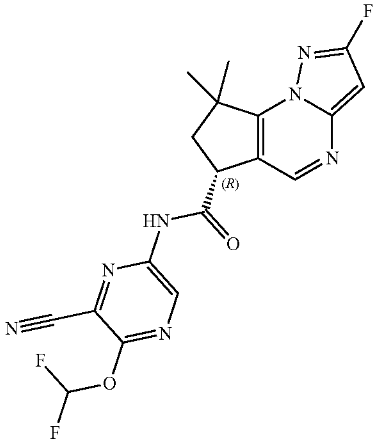

and

Example 87

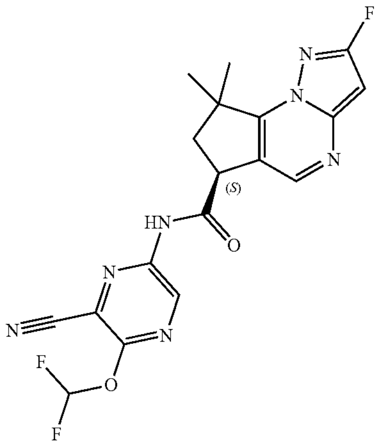

N-(6-cyano-5-(difluoromethoxy)pyrazin-2-yl)-2-fluoro-8,8-dimethyl-7,8-dihydro-6H-cyclopenta[e]pyrazolo[1,5-a]pyrimidine-6-carboxamide (15 mg, 35.9 mmol) was separated by Chiral-HPLC (Column: CHIRAL ART Cellulose-SA, 2×25 cm, 5 μm; Mobile Phase A: Hex(0.1% FA)-HPLC, Mobile Phase B: EtOH-HPLC; Flow rate: 20 mL/min; isocratic 50% B in 11 min; Wave Length: 220/254 nm; RT1(min): 6.68; RT2(min): 8.83; Sample Solvent: EtOH-HPLC; Injection Volume: 1 mL; Number Of Runs: 2). The first eluting isomer was concentrated and lyophilized to afford Example 86 (6.9 mg, 46% yield) as a white solid. The second eluting isomer was concentrated and lyophilized to afford Example 87 (6.2 mg, 41% yield) as a white solid.

Example 86: $^1$H NMR (400 MHz, DMSO-d$_6$) δ: 11.7 (s, 1H), 9.22 (s, 1H), 8.59 (s, 1H), 7.71 (t, J=70.8 Hz, 1H), 6.56 (d, J=4.8 Hz, 1H), 4.48-4.52 (m, 1H), 2.51-2.57 (m, 1H), 2.27-2.32 (m, 1H), 1.61 (s, 3H), 1.53 (s, 3H). LC-MS: m/z 418.0 [M+H]$^+$.

Example 87: $^1$H NMR (400 MHz, DMSO-d$_6$) δ: 11.7 (s, 1H), 9.22 (s, 1H), 8.59 (s, 1H), 7.71 (t, J=70.8 Hz, 1H), 6.56 (d, J=4.8 Hz, 1H), 4.48-4.52 (m, 1H), 2.51-2.57 (m, 1H), 2.28-2.32 (m, 1H), 1.61 (s, 3H), 1.53 (s, 3H). LC-MS: m/z 418.0 [M+H]$^+$.

The absolute stereochemistry for each separated isomer was not determined.

Method S2

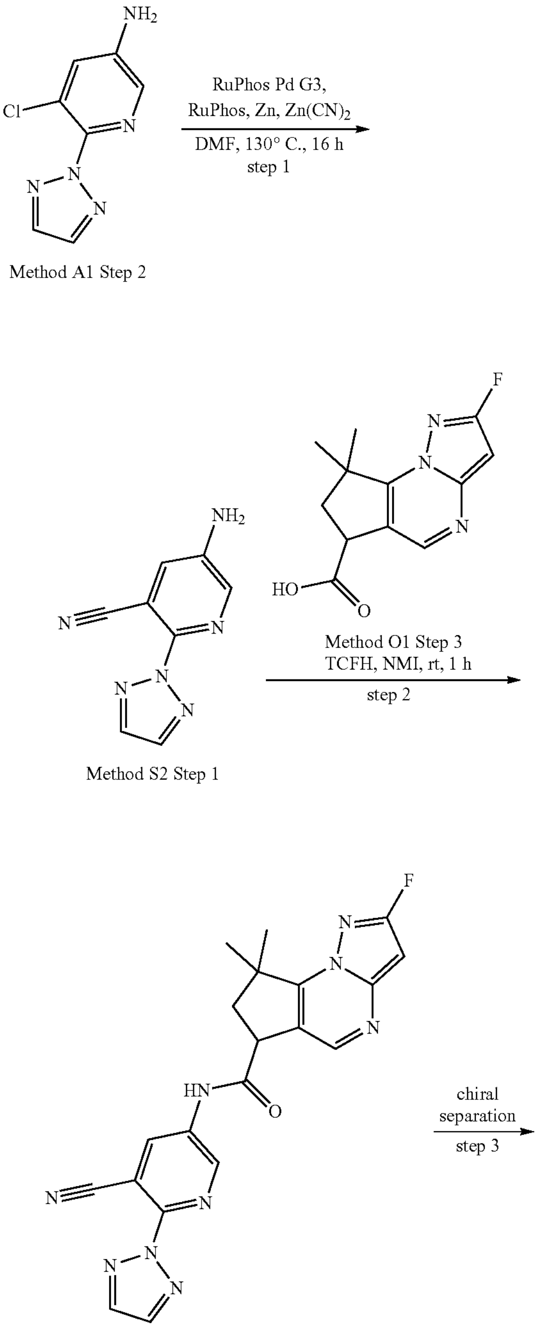

-continued

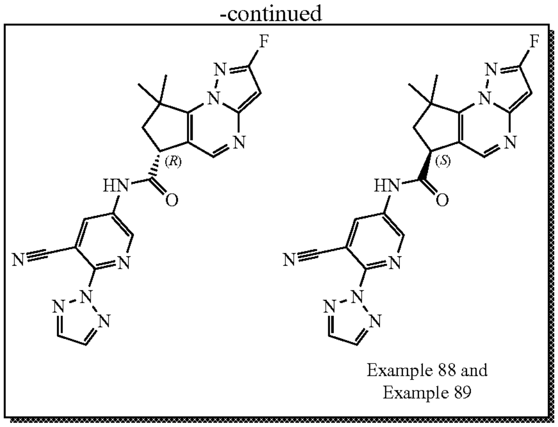

Example 88 and Example 89

Examples 88 and 89: Single enantiomers obtained from racemic mixture containing (R)—N-(5-cyano-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide and (S)—N-(5-cyano-6-(2H-1,2,3-triazol-2-yl)pyridin-3-yl)-2-fluoro-8,8-dimethyl-7,8-dihydro-6H-cyclopenta[e]pyrazolo[1,5a]pyrimidine-6-carboxamide Step 1: 5-amino-2-(2H-1,2,3-triazol-2-yl)nicotinonitrile

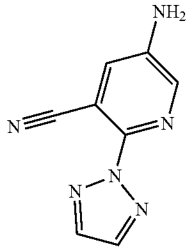 [SMILES: N#Cc1cc(N)cnc1-n1nccn1]

To a stirred solution of 5-chloro-6-(2H-1,2,3-triazol-2-yl)pyridin-3-amine (Method A1 step 2; 1.0 g, 5.1 mmol) in DMF (5 mL) were added $Zn(CN)_2$ (660 mg, 5.6 mmol), RuPhos (239 mg, 513.8 μcool), RuPhos Pd G3 (430 mg, 513.8 μmol) and Zinc (16 mg, 256.9 μmol) under nitrogen atmosphere. The mixture was stirred at 130° C. for 16 h. The mixture was allowed to cool down to room temperature. The resulting mixture was filtered and the filter cake was washed with MeOH (3×10 ml). The filtrate was concentrated under reduced pressure. Water (100 mL) was added and the mixture was extracted with ethyl acetate (3×100 mL). The combined organic layers were washed with brine (3×100 mL), dried over anhydrous sodium sulfate and concentrated under reduced pressure. The residue was purified by Prep-HPLC and the collected fractions were concentrated under reduced pressure to afford 5-amino-2-(2H-1,2,3-triazol-2-yl)nicotinonitrile (Method S2 step 1; 200 mg, 21% yield) as white solid. LC-MS: m/z 187 $[M+H]^+$.

Step 2: N-(5-cyano-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide

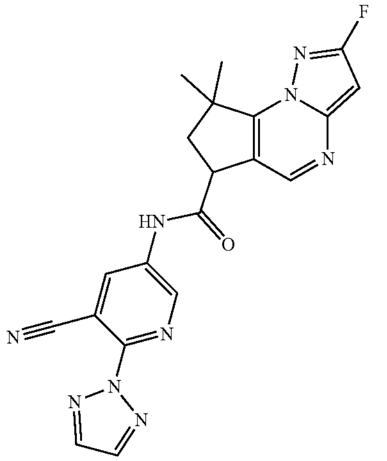 [SMILES: CC1(C)CC(C(=O)Nc2cnc(-n3nccn3)c(C#N)c2)c2cnc3cc(F)nn3c21]

To a solution of 5-amino-2-(2H-1,2,3-triazol-2-yl)nicotinonitrile (89 mg, 481.4 μmol) in ACN (1 mL) were added 2-fluoro-8,8-dimethyl-7,8-dihydro-6H-cyclopenta[e]pyrazolo[1,5-a]pyrimidine-6-carboxylic acid (Method 01 step 3; 100 mg, 401.2 μmol), TCFH (337 mg, 1.2 mmol) and NMI (164 mg, 2.0 mmol). The resulting mixture was stirred at 25° C. for 1 h. The reaction mixture was concentrated under reduced pressure. The residue was applied onto a silica gel column and eluted with EtOAc/PE (1:1) to afford the crude product. The residue was purified by Prep-HPLC and the collected fractions were concentrated under reduced pressure to afford N-(5-cyano-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide (53 mg, 31% yield) as a white solid. LC-MS: m/z 418 $[M+H]^+$.-

Step 3: Separation of Enantiomers to Obtain (R)—N-(5-cyano-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide and (S)—N-(5-cyano-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide Example 88

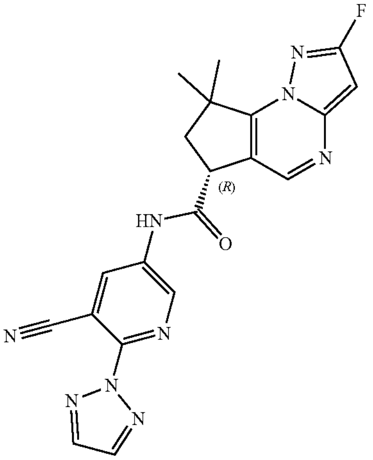

and

-continued

Example 89

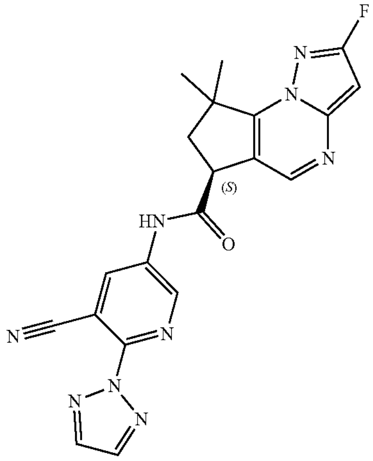

50 mg of N-(5-cyano-6-(2H-1,2,3-triazol-2-yl)pyridin-3-yl)-2-fluoro-8,8-dimethyl-7,8-dihydro-6H-cyclopenta[e]pyrazolo[1,5-a]pyrimidine-6-carboxamide were submitted to chiral HPLC purification. (Column: CHIRAL ART Amylose-SA, 2×25 cm, 5 μm; Mobile Phase A: Hex(0.1% FA)-HPLC, Mobile Phase B: EtOH-HPLC; Flow rate: 20 mL/min; isocratic 50% B in 22 min; Wave Length: 254/220 nm; RT1(min): 11.07; RT2(min): 16.29; Sample Solvent: EtOH-HPLC; Injection Volume: 1 mL). The first eluting isomer was concentrated and lyophilized to afford Example 88 (17.2 mg, 28% yield) as a white solid. The second eluting isomer was concentrated and lyophilized to afford Example 89 (9.3 mg, 15% yield) as a white solid.

Example 88: $^{1}$H NMR (400 MHz, DMSO-$d_6$) δ: 11.14 (s, 1H), 8.98 (d, J=2.8 Hz, 1H), 8.78 (d, J=2.4 Hz, 1H), 8.64 (s, 1H), 8.29 (s, 2H), 6.56 (d, J=5.2 Hz, 1H), 4.43-4.47 (m, 1H), 2.55-2.58 (m, 1H), 2.31-2.36 (m, 1H), 1.63 (s, 3H), 1.55 (s, 3H). LC-MS: m/z 418.0 $[M+H]^+$.

Example 89: $^{1}$H NMR (400 MHz, DMSO-$d_6$) δ: 11.12 (s, 1H), 8.98 (d, J=2.8 Hz, 1H), 8.78 (d, J=2.4 Hz, 1H), 8.64 (s, 1H), 8.30 (s, 2H), 6.57 (d, J=5.2 Hz, 1H), 4.44-4.48 (m, 1H), 2.55-2.59 (m, 1H), 2.32-2.36 (m, 1H), 1.63 (s, 3H), 1.55 (s, 3H). LC-MS: m/z 418.0 $[M+H]^+$ The absolute stereochemistry for each separated isomer was not determined.

Method T2

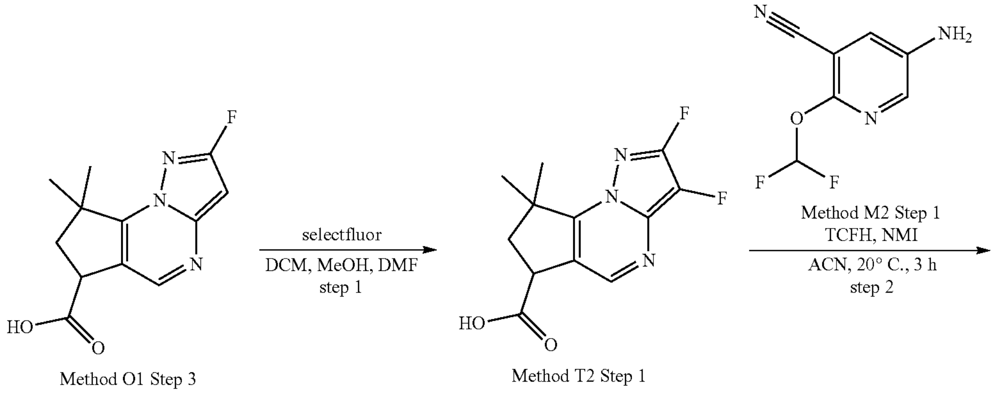

-continued

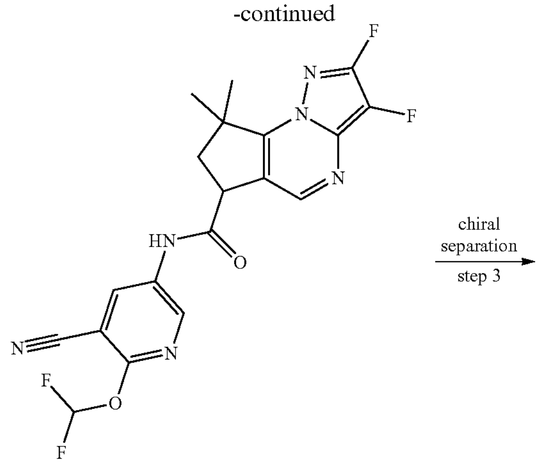

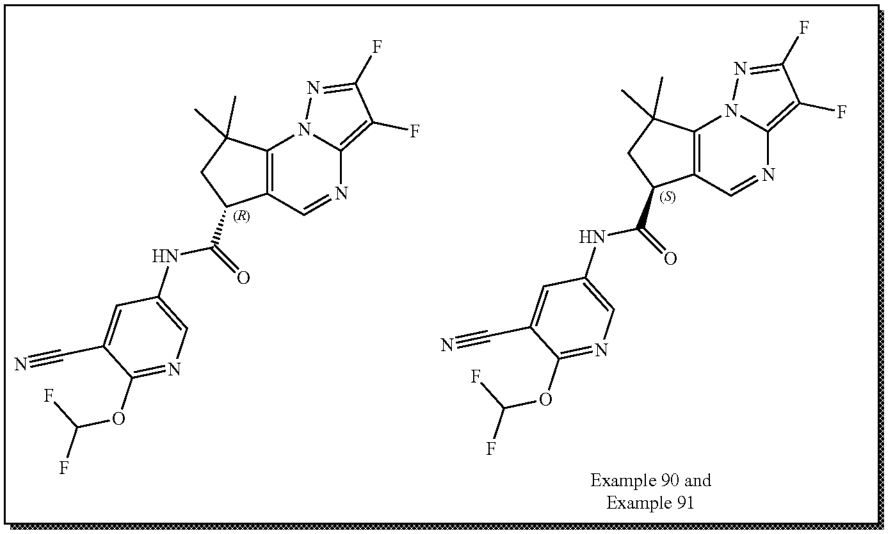

Example 90 and
Example 91

Examples 90 and 91: Single Enantiomers Obtained from a Racemic Mixture Containing (R)—N-(5-cyano-6-(difluoromethoxy)pyridin-3-yl)-2,3-difluoro-8,8-dimethyl-7,8-dihydro-611-cyclopenta[e]pyrazolo[1,5-a]pyrimidine-6-carboxamide and (S)—N-(5-cyano-6-(difluoromethoxy)pyridin-3-yl)-2,3-difluoro-8,8-dimethyl-7,8-dihydro-6H-cyclopenta[e]pyrazolo[1,5-a]pyrimidine-6-carboxamide

Step 1: 2,3-difluoro-8,8-dimethyl-7,8-dihydro-6H-cyclopenta[e]pyrazolo[1,5-a]pyrimidine-6-carboxylic acid

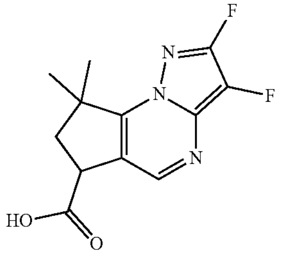 [SMILES: CC1(C)CC(C(=O)O)c2cnc3c(F)c(F)nn3c21]

To a stirred solution of 2-fluoro-8,8-dimethyl-7,8-dihydro-6H-cyclopenta[e]pyrazolo[1,5-a]pyrimidine-6-carboxylic acid (Method 01 step 3; 300 mg, 1.2 mmol) in DCM (6 mL) and MeOH (6 mL) was added selectfluor (852 mg, 2.4 mmol) in DMF (2 mL) at −20° C. The reaction mixture was stirred at 25° C. for 16 h. The resulting mixture was concentrated under reduced pressure. The residue was diluted with water (100 mL) and extracted with ethyl acetate (3×100 mL). The combined organic layers were dried over anhydrous sodium sulfate and concentrated under reduced pressure. The residue was applied onto a silica gel column and eluted with EtOAc/PE (4:1) to give 2,3-difluoro-8,8-dimethyl-7,8-dihydro-6H-cyclopenta[e]pyrazolo[1,5-a]pyrimidine-6-carboxylic acid (Method T2 step 1; 40 mg, 11% yield) as a yellow oil. LC-MS: m/z 268 $[M+H]^+$.

Step 2: N-(5-cyano-6-(difluoromethoxy)pyridin-3-yl)-2,3-difluoro-8,8-dimethyl-7,8-dihydro-6H-cyclopenta[e]pyrazolo[1,5-a]pyrimidine-6-carboxamide

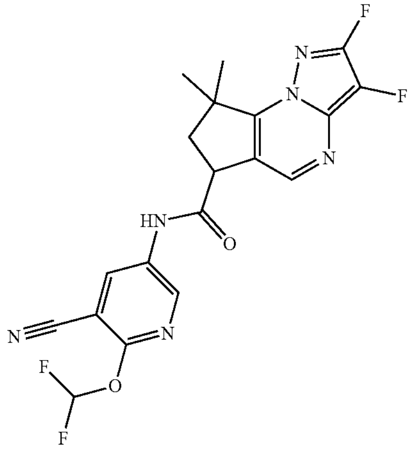 [SMILES: CC1(C)CC(C(=O)Nc2cnc(OC(F)F)c(C#N)c2)c2cnc3c(F)c(F)nn3c21]

To a solution of 2,3-difluoro-8,8-dimethyl-7,8-dihydro-6H-cyclopenta[e]pyrazolo[1,5-a]pyrimidine-6-carboxylic acid (35 mg, 130.9 μmol) in ACN (2 mL) were added 5-amino-2-(difluoromethoxy)pyridine-3-carbonitrile (Method M2 step 1; 24 mg, 130.9 μmol), TCFH (146 mg, 523.8 μmol) and NMI (43 mg, 523.8 μmol). The resulting mixture was stirred at 25° C. for 3 h. The reaction mixture was quenched with water (10 mL). The resulting solution was extracted with dichloromethane (3×10 mL). The combined organic layers were dried over anhydrous sodium sulfate and concentrated under reduced pressure. The residue was purified by Prep-HPLC and the collected fractions were lyophilized to afford N-(5-cyano-6-(difluoromethoxy)pyridin-3-yl)-2,3-difluoro-8,8-dimethyl-7,8-dihydro-6H-cyclopenta[e]pyrazolo[1,5-a]pyrimidine-6-carboxamide (2.3 mg, 4.% yield) as an off-white solid. LC-MS: m/z 435 $[M+H]^+$.

Step 3: Separation of Enantiomers to Obtain (R)—N-(5-cyano-6-(difluoromethoxy)pyridin-3-yl)-2,3-difluoro-8,8-dimethyl-7,8-dihydro-6H-cyclopenta[e]pyrazolo[1,5-a]pyrimidine-6-carboxamide and (S)—N-(5-cyano-6-(difluoromethoxy)pyridin-3-yl)-2,3-difluoro-8,8-dimethyl-7,8-dihydro-6H-cyclopenta[e]pyrazolo[1,5-a]pyrimidine-6-carboxamide Example 90

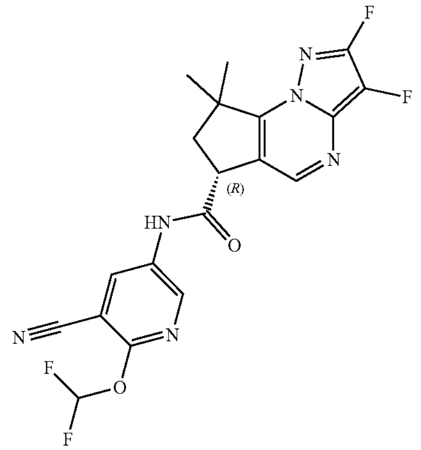

and

Example 91

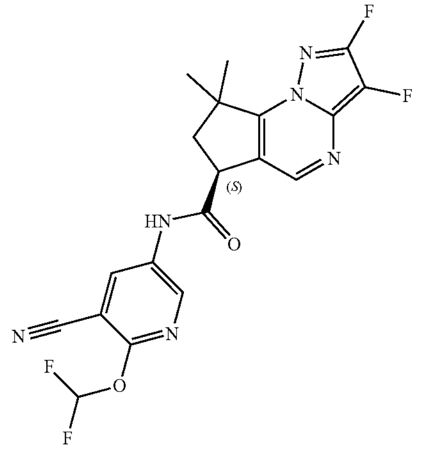

15 mg of N-(5-cyano-6-(difluoromethoxy)pyridin-3-yl)-2,3-difluoro-8,8-dimethyl-7,8-dihydro-6H-cyclopenta[e]pyrazolo[1,5-a]pyrimidine-6-carboxamide were submitted to chiral HPLC purification. (Column: CHIRALPAK IG, 2*25 cm, 5 μm; Mobile Phase A: MtBE(0.5% 2M $NH_3$-MeOH)-HPLC, Mobile Phase B: EtOH-HPLC; Flow rate: 20 mL/min; isocratic 70% B in 6.5 min; Wave Length: 220/254 nm; RT1(min): 4.49; RT2(min): 6.064; Sample Solvent: EtOH-HPLC; Injection Volume: 1.6 mL; Number Of Runs: 3). The first eluting isomer was concentrated and lyophilized to afford Example 90 (1.7 mg, 11% yield) as a yellow solid. The second eluting isomer was concentrated and lyophilized to afford Example 91 (2.2 mg, 14% yield) as a yellow solid.

Example 90: $^1$H NMR (400 MHz, DMSO-$d_6$) δ 10.85 (br, 1H), 8.60-8.67 (m, 3H), 7.74 (t, J=71.2 Hz, 1H), 4.37-4.41 (m, 1H), 2.50-2.55 (m, 1H), 2.26-2.32 (m, 1H), 1.60 (s, 3H), 1.52 (s, 3H); LC-MS: m/z 435.1 $[M+H]^+$.

Example 91: $^1$H NMR (400 MHz, DMSO-$d_6$) δ 10.86 (br, 1H), 8.60-8.67 (m, 3H), 7.74 (t, J=71.4 Hz, 1H), 4.37-4.42

(m, 1H), 2.50-2.56 (m, 1H), 2.26-2.32 (m, 1H), 1.60 (s, 3H), 1.52 (s, 3H). LC-MS: m/z 435.0 $[M+H]^+$.
The absolute stereochemistry for each separated isomer was not determined.
Method U2
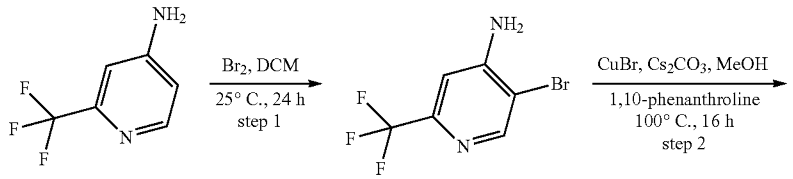
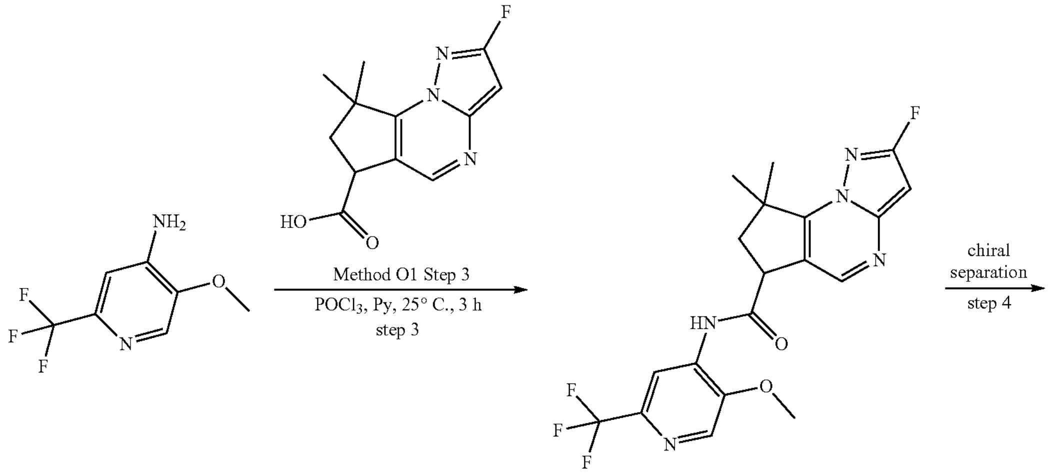
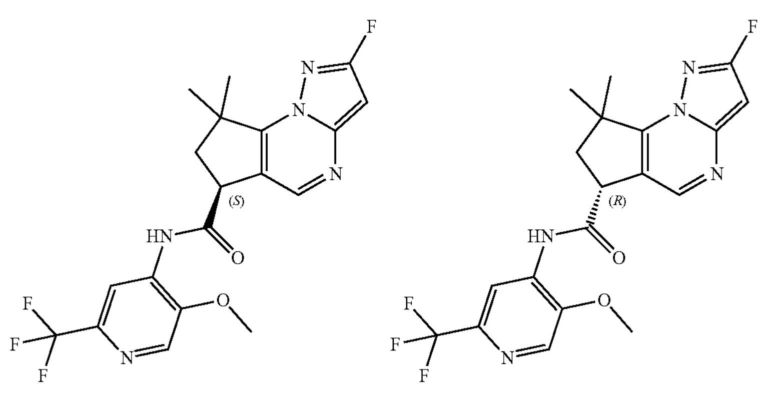
Example 92 and
Example 93

Examples 92 and 93: Single Enantiomers Obtained from a Racemic Mixture Containing (S)-2-fluoro-N-(5-methoxy-2-(trifluoromethyl)pyridin-4-yl)-8,8-dimethyl-7,8-dihydro-6H-cyclopenta[e]pyrazolo[1,5-a]pyrimidine-6-carboxamide and (R)-2-fluoro-N-(5-methoxy-2-(trifluoromethyl)pyridin-4-yl)-8,8-dimethyl-7,8-dihydro-6H-cyclopenta[e]pyrazolo[1,5-a]pyrimidine-6-carboxamide Step 1: 5-bromo-2-(trifluoromethyl)pyridin-4-amine

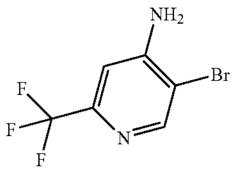 [SMILES: Nc1cc(C(F)(F)F)ncc1Br]

To a stirred mixture of 2-(trifluoromethyl)pyridin-4-amine (5.0 g, 30.8 mmol) in DCM (80 mL) was added bromine (4.9 g, 30.8 mmol). The reaction mixture was stirred at 25° C. for 24 h. The reaction mixture was quenched with water (50 mL). The resulting solution was extracted with DCM (3x100 mL). The combined organic layers were dried over anhydrous sodium sulfate and concentrated under reduced pressure to afford 5-bromo-2-(trifluoromethyl)pyridin-4-amine (7.8 g, 83% yield) as a yellow solid. LC-MS: m/z 241 $[M+H]^+$.

Step 2: 5-methoxy-2-(trifluoromethyl)pyridin-4-amine

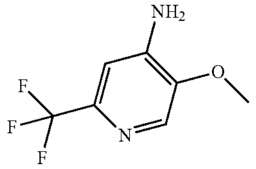

To a stirred mixture of 5-bromo-2-(trifluoromethyl)pyridin-4-amine (7.6 g, 25.2 mmol) in MeOH (100 mL) was added cuprous bromide (2.2 g, 15.1 mmol), cesium carbonate (16.4 g, 50.4 mmol) and 1,10-phenanthroline (1.4 g, 7.6 mmol). The reaction mixture was stirred at 100° C. for 24 h. The reaction mixture was quenched with water (100 mL). The resulting solution was extracted with ethyl acetate (3x100 mL). The combined organic layers were dried over anhydrous sodium sulfate and concentrated under reduced pressure. The residue was applied onto a silica gel column and eluted with EtOAc/PE (1:1) to give 5-methoxy-2-(trifluoromethyl)pyridin-4-amine (1.5 g, 22% yield) as a yellow solid. $^1H$ NMR (400 MHz, DMSO-$d_6$) δ: 7.99 (s, 1H), 6.97 (s, 1H), 6.20 (br, 2H), 3.90 (s, 3H). LC-MS: m/z 193 $[M+H]^+$.

Step 3: 2-fluoro-N-(5-methoxy-2-(trifluoromethyl)pyridin-4-yl)-8,8-dimethyl-7,8-dihydro-6H-cyclopenta[e]pyrazolo[1,5-a]pyrimidine-6-carboxamide

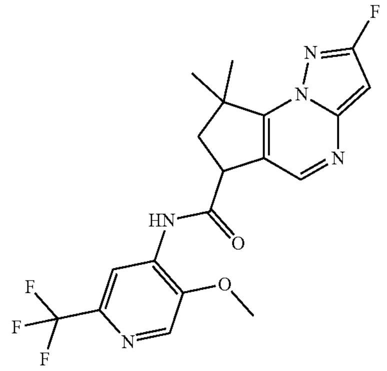 [SMILES: COc1cnc(C(F)(F)F)cc1NC(=O)C1CC(C)(C)c2c1cnc1cc(F)nn21]

To a stirred mixture of 2-fluoro-8,8-dimethyl-7,8-dihydro-6H-cyclopenta[e]pyrazolo[1,5-a]pyrimidine-6-carboxylic acid (Method 01 step 3; 73 mg, 292.6 μmol) in DCM (2 mL) was added phosphoryl trichloride (224 mg, 1.5 mmol). The reaction mixture was stirred at 25° C. for 30 min. To the above reaction mixture was added 5-methoxy-2-(trifluoromethyl)pyridin-4-amine (77 mg, 292.6 μmol) and pyridine (278 mg, 3.5 mmol). The reaction mixture was stirred at 25° C. for 3 h. The reaction mixture was quenched with water (10 mL). The resulting solution was extracted with ethyl acetate (3x10 mL). The combined organic layers were dried over anhydrous sodium sulfate and concentrated under reduced pressure. The residue was submitted to Prep-HPLC purification and the collected fractions were lyophilized to give 2-fluoro-N-(5-methoxy-2-(trifluoromethyl)pyridin-4-yl)-8,8-dimethyl-7,8-dihydro-6H-cyclopenta[e]pyrazolo[1,5-a]pyrimidine-6-carboxamide (32 mg, 25% yield) as a white solid. LC-MS: m/z 424 $[M+H]^+$.

Step 4: Separation of Enantiomers to Obtain (S)-2-fluoro-N-(5-methoxy-2-(trifluoromethyl)pyridin-4-yl)-8,8-dimethyl-7,8-dihydro-6H-cyclopenta[e]pyrazolo[1,5-a]pyrimidine-6-carboxamide and (R)-2-fluoro-N-(5-methoxy-2-(trifluoromethyl)pyridin-4-yl)-8,8-dimethyl-7,8-dihydro-6H-cyclopenta[e]pyrazolo[1,5-a]pyrimidine-6-carboxamide Example 92

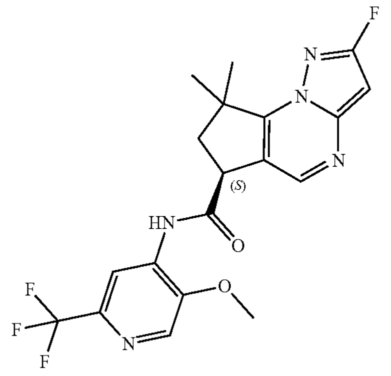

and

-continued

Example 93

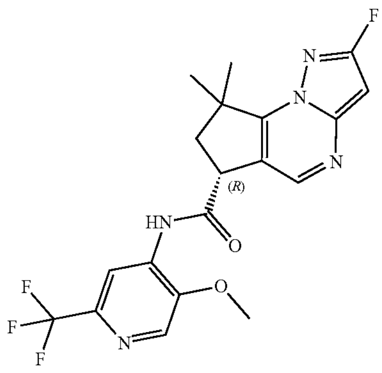

30 mg of 2-fluoro-N-(5-methoxy-2-(trifluoromethyl)pyridin-4-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IG, 2*25 cm, 5 μm; Mobile Phase A: Hex(0.1% FA)-HPLC, Mobile Phase B: EtOH-HPLC; Flow rate: 20 mL/min; isocratic 20% B in 10 min; Wave Length: 220/254 nm; RT1(min): 6.34; RT2(min): 8.43; Sample Solvent: EtOH-HPLC; Injection Volume: 0.5 mL; Number Of Runs: 4). The first eluting isomer was concentrated and lyophilized to afford Example 93 (3.1 mg, 10% yield) as a white solid. The second eluting isomer was concentrated and lyophilized to afford Example 92 (2.9 mg, 9% yield) as a white solid.

Example 92: $^1$H NMR (400 MHz, DMSO-$d_6$) δ: 10.35 (s, 1H), 8.63 (s, 1H), 8.57 (s, 1H), 8.55 (s, 1H), 6.54 (d, J=4.8 Hz, 1H), 4.71 (dd, J=9.2, 6.4 Hz, 1H), 4.11 (s, 3H), 2.52-2.56 (m, 1H), 2.25 (dd, J=13.2, 6.4 Hz, 1H), 1.61 (s, 3H), 1.52 (s, 3H). LC-MS: m/z 424.1 $[M+H]^+$.

Example 93: $^1$H NMR (400 MHz, DMSO-$d_6$) δ: 10.35 (s, 1H), 8.63 (s, 1H), 8.57 (s, 1H), 8.55 (s, 1H), 6.55 (d, J=4.8 Hz, 1H), 4.72 (dd, J=8.8, 6.0 Hz, 1H), 4.11 (s, 3H), 2.52-2.57 (m, 1H), 2.25 (dd, J=13.2, 6.4 Hz, 1H), 1.61 (s, 3H), 1.52 (s, 3H). LC-MS: m/z 424.1 $[M+H]^+$.

Method V2

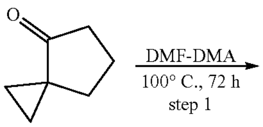

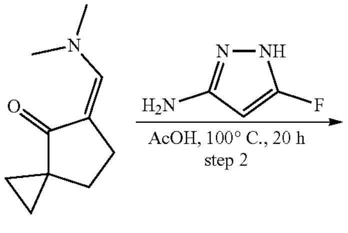

-continued

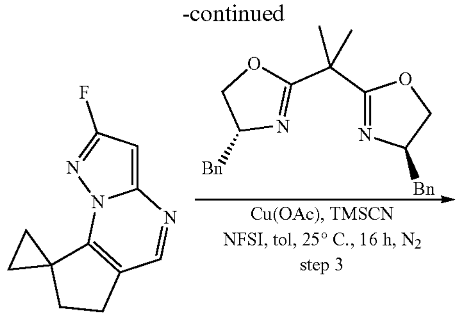

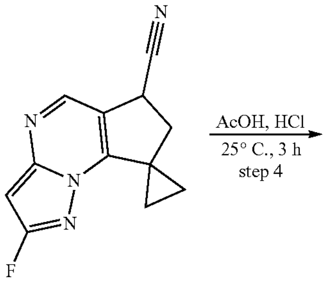

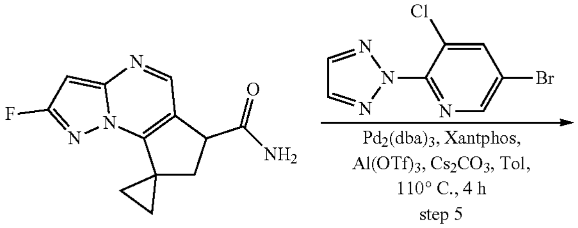

Method V2 Step 4

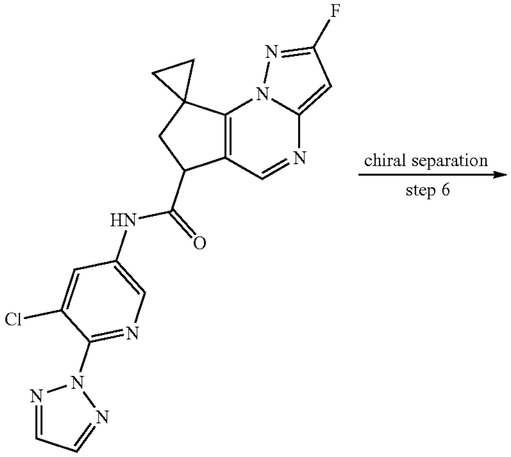

-continued

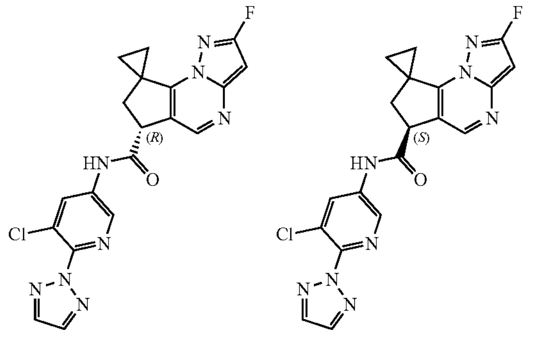

Example 94 and Example 95 were obtained through chiral resolution

Examples 94 and 95: Single Enantiomers Obtained from a Racemic Mixture Containing (R)—N-(5-chloro-6-(2H-1,2,3-triazol-2-yl)pyridin-3-yl)-2-fluoro-6,7-dihydrospiro[cyclopenta[e]pyrazolo[1,5-a]pyrimidine-8,1'-cyclopropane]-6-carboxamide and (S)—N-(5-chloro-6-(2H-1,2,3-triazol-2-yl)pyridin-3-yl)-2-fluoro-6,7-dihydrospiro[cyclopenta[e]pyrazolo[1,5-a]pyrimidine-8,1'-cyclopropane]-6-carboxamide Step 1: 5-((dimethylamino)methylene)spiro[2.4]heptan-4-one

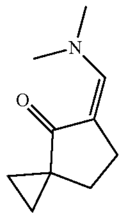

A mixture of spiro[2.4]heptan-4-one (3.0 g, 27.2 mmol) in 1,1-dimethoxy-N,N-dimethylmethanamine (26.7 g, 224.1 mmol) was stirred at 100° C. for 72 h. The reaction mixture was concentrated under reduced pressure to give 5-((dimethylamino)methylene)spiro[2.4]heptan-4-one (4.5 g, 70% yield) as a yellow solid. LC-MS: m/z 166 [M+H]$^+$.

Step 2: 2-fluoro-6,7-dihydrospiro[cyclopenta[e]pyrazolo[1,5-a]pyrimidine-8,1'-cyclopropane]

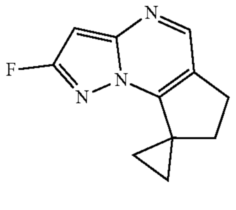 [SMILES: Fc1cc2ncc3c(n2n1)C1(CC3)CC1]

A mixture of 5-fluoro-1H-pyrazol-3-amine (2.0 g, 19.8 mmol) and 5-((dimethylamino)methylene)spiro[2.4]heptan-4-one (3.9 g, 23.7 mmol) in AcOH (60 mL) were stirred at 100° C. for 20 h. The reaction mixture was concentrated under reduced pressure. The residue was applied on a silica gel column and eluted with EtOAc/PE (1:2) to give 2-fluoro-6,7-dihydrospiro[cyclopenta[e]pyrazolo[1,5-a]pyrimidine-8,1'-cyclopropane] (1.5 g, 37% yield) as a yellow solid. $^{1}$H NMR (400 MHz, DMSO-$d_6$) δ: 8.44 (s, 1H), 6.37 (d, J=4.8 Hz, 1H), 3.09 (t, J=7.6 Hz, 2H), 2.23-2.29 (m, 2H), 1.99-2.04 (m, 2H), 1.05-1.10 (m, 2H). LC-MS: m/z 204 [M+H]$^+$.

Step 3: 2-fluoro-6,7-dihydrospiro[cyclopenta[e]pyrazolo[1,5-a]pyrimidine-8,1'-cyclopropane]-6-carbonitrile

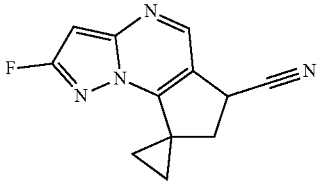 [SMILES: N#CC1CC2(CC2)c2c1cnc1cc(F)nn21]

To a stirred solution of 2-fluoro-6,7-dihydrospiro[cyclopenta[e]pyrazolo[1,5-a]pyrimidine-8,1'-cyclopropane] (1.6 g, 7.9 mmol) in toluene (30 mL) was added (4R,4'R)-2,2'-(propane-2,2-diyl)bis(4-benzyl-4,5-dihydrooxazole) (428 mg, 1.2 mmol), acetoxycopper (193 mg, 1.6 mmol), N-fluoro-N-(phenylsulfonyl)benzenesulfonamide (3.7 g, 11.8 mmol) and TMSCN (3.9 g, 39.4 mmol). The reaction mixture was stirred at 25° C. for 16 h under nitrogen. The resulting mixture was concentrated under reduced pressure. The residue was applied on a silica gel column and eluted with EtOAc/PE (1:2) to give 2-fluoro-6,7-dihydrospiro[cyclopenta[e]pyrazolo[1,5-a]pyrimidine-8,1'-cyclopropane]-6-carbonitrile (150 mg, 3% yield) as a white solid. LC-MS: m/z 229 [M+H]$^+$.

Step 4: 2-fluoro-6,7-dihydrospiro[cyclopenta[e]pyrazolo[1,5-a]pyrimidine-8,1'-cyclopropane]-6-carboxamide

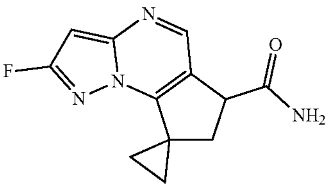 [SMILES: NC(=O)C1CC2(CC2)c2c1cnc1cc(F)nn21]

A mixture of 2-fluoro-6,7-dihydrospiro[cyclopenta[e]pyrazolo[1,5-a]pyrimidine-8,1'-cyclopropane]-6-carbonitrile (150 mg, 657.2 μmol) in HCl (2 mL) and AcOH (4 mL) was stirred at 25° C. for 3 h. The pH was adjusted to 6-7 with saturated aqueous sodium bicarbonate solution. The resulting solution was extracted with ethyl acetate (3×10 mL). The combined organic layers were dried over anhydrous sodium sulfate and concentrated under reduced pressure. The residue was applied on a silica gel column and eluted with MeOH/DCM (1:10) to give 2-fluoro-6,7-dihydrospiro[cyclopenta[e]pyrazolo[1,5-a]pyrimidine-8,1'-cyclopropane]-

6-carboxamide (Method V2 step 4; 40 mg, 22% yield) as a yellow solid. LC-MS: m/z 247 $[M+H]^+$.

Step 5: N-(5-chloro-6-(2H-1,2,3-triazol-2-yl)pyridin-3-yl)-2-fluoro-6,7-dihydrospiro[cyclopenta[e]pyrazolo[1,5-a]pyrimidine-8,1'-cyclopropane]-6-carboxamide

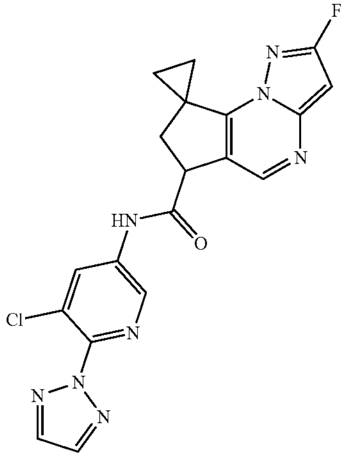 [SMILES: O=C(Nc1cnc(-n2nccn2)c(Cl)c1)C1CC2(CC2)c2c1cnc1cc(F)nn21]

To a stirred solution of 2-fluoro-6,7-dihydrospiro[cyclopenta[e]pyrazolo[1,5-a]pyrimidine-8,1'-cyclopropane]-6-carboxamide (Method V2 step 4; 40 mg, 162.4 μmol) in toluene (1 mL) was added XantPhos (19 mg, 32.5 μmol), $Pd_2(dba)_3$ (30 mg, 32.5 μmol), cesium carbonate (79 mg, 243.7 μmol), $A1(OTf)_3$ (8 mg, 16.2 μmol) and 5-bromo-3-chloro-2-(2H-1,2,3-triazol-2-yl)pyridine (42 mg, 162.4 μmol). The reaction mixture was stirred at 110° C. for 4 h under nitrogen. The reaction mixture was quenched with water (10 mL). The resulting solution was extracted with ethyl acetate (3×10 mL). The combined organic layers were dried over anhydrous sodium sulfate and concentrated under reduced pressure. The residue was applied on a silica gel column and eluted with EtOAc/PE (1:2) to give the crude product. The crude product was submitted to Prep-HPLC and the collected fractions were lyophilized to afford N-(5-chloro-6-(2H-1,2,3-triazol-2-yl)pyridin-3-yl)-2-fluoro-6,7-dihydrospiro[cyclopenta[e]pyrazolo[1,5-a]pyrimidine-8,1'-cyclopropane]-6-carboxamide (17 mg, 22% yield) as a white solid. LC-MS: m/z 425 $[M+H]^+$.

Step 6: Separation of Enantiomers to Obtain (R)—N-(5-chloro-6-(2H-1,2,3-triazol-2-yl)pyridin-3-yl)-2-fluoro-6,7-dihydrospiro[cyclopenta[e]pyrazolo[1,5-a]pyrimidine-8,1'-cyclopropane]-6-carboxamide and (S)—N-(5-chloro-6-(2H-1,2,3-triazol-2-yl)pyridin-3-yl)-2-fluoro-6,7-dihydrospiro[cyclopenta[e]pyrazolo[1,5-a]pyrimidine-8,1'-cyclopropane]-6-carboxamide

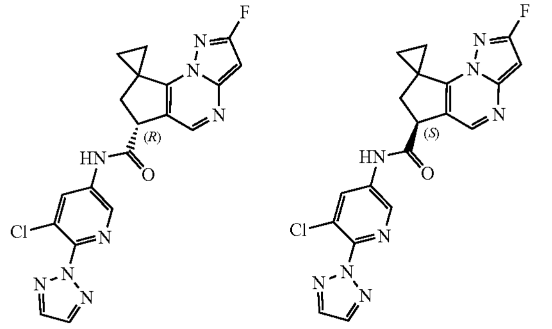

Example 94
and Example 95

15 mg of N-(5-chloro-6-(2H-1,2,3-triazol-2-yl)pyridin-3-yl)-2-fluoro-6,7-dihydrospiro[cyclopenta[e]pyrazolo[1,5-a]pyrimidine-8,1'-cyclopropane]-6-carboxamide were submitted to chiral HPLC purification (Column: Chiral ART Cellulose-SA, 2*25 cm, 5 μm; Mobile Phase A: Hex(0.5% 2M $NH_3$-MeOH)-HPLC, Mobile Phase B: EtOH—HPLC; Flow rate: mL/min; isocratic 50% B in 18 min; Wave Length: 254/220 nm; RT1(min): 8.26; RT2(min): 14.82; Sample Solvent: EtOH-HPLC; Injection Volume: 1 mL; Number Of Runs: 3). The first eluting isomer was concentrated and lyophilized to afford Example 94 (7.3 mg, 42% yield) as a white solid. The second eluting isomer was concentrated and lyophilized to afford Example 95 (6.2 mg, 36% yield) as a white solid.

Example 94: $^1H$ NMR (400 MHz, DMSO-$d_6$) δ: 11.10 (s, 1H), 8.73 (d, J=2.4 Hz, 1H), 8.59 (s, 1H), 8.58 (d, J=2.4 Hz, 1H), 8.17 (s, 2H), 6.49 (d, J=4.8 Hz, 1H), 4.54 (dd, J=9.6, 5.2 Hz, 1H), 2.64-2.74 (m, 1H), 2.52-2.60 (m, 1H), 2.05-2.16 (m, 2H), 1.16-1.27 (m, 2H). LC-MS: m/z 425.1 $[M+H]^+$.

Example 95: $^1H$ NMR (400 MHz, DMSO-$d_6$) δ: 11.10 (s, 1H), 8.73 (d, J=2.4 Hz, 1H), 8.59 (s, 1H), 8.58 (d, J=2.4 Hz, 1H), 8.17 (s, 2H), 6.49 (d, J=5.2 Hz, 1H), 4.54 (dd, J=9.6, 5.2 Hz, 1H), 2.65-2.73 (m, 1H), 2.53-2.59 (m, 1H), 2.05-2.17 (m, 2H), 1.17-1.26 (m, 2H). LC-MS: m/z 425.1 $[M+H]^+$.

The absolute stereochemistry for each separated isomer was not determined.

Method W2

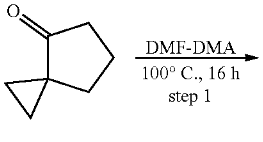

-continued

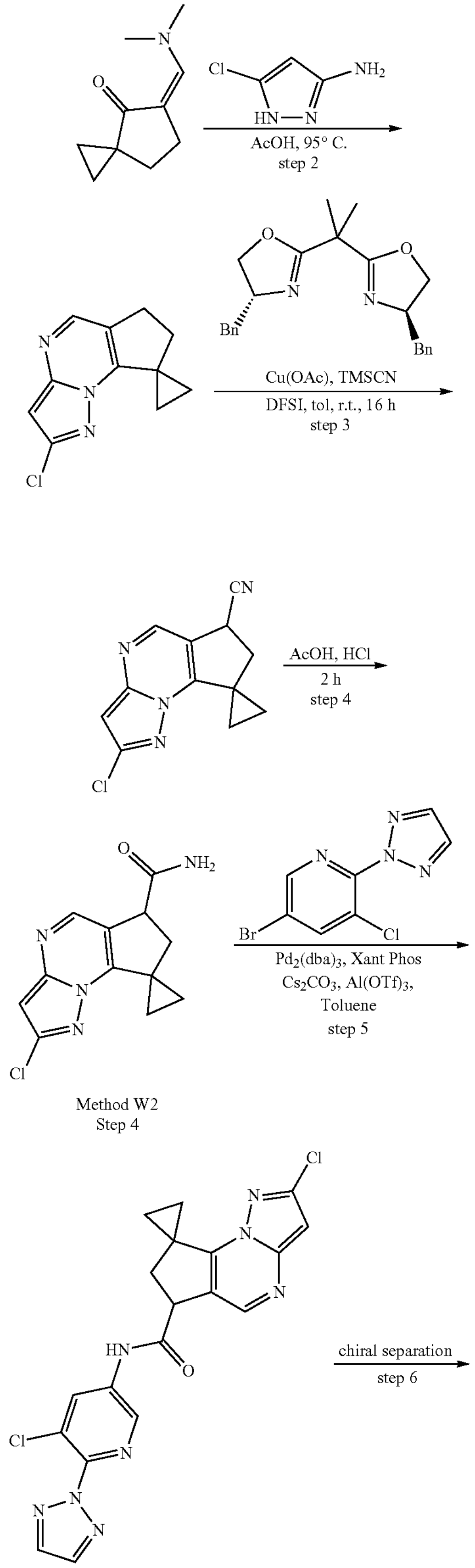

-continued

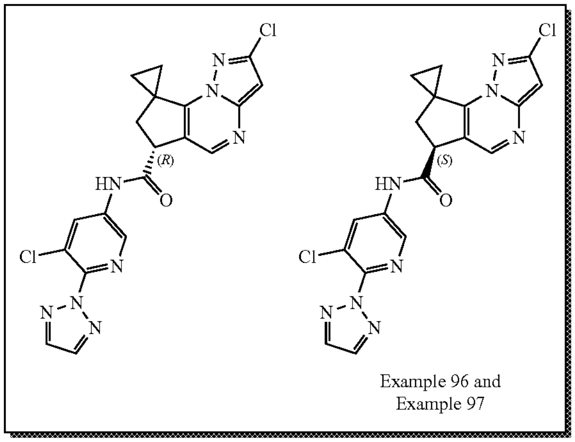

Example 96 and Example 97

Examples 96 and 97: Single Enantiomers Obtained from a Racemic Mixture Containing (R)-2-chloro-N-(5-chloro-6-(2H-1,2,3-triazol-2-yl)pyridin-3-yl)-6,7-dihydrospiro[cyclopenta[e]pyrazolo[1,5-a]pyrimidine-8,1'-cyclopropane]-6-carboxamide and (S)-2-chloro-N-(5-chloro-6-(2H-1,2,3-triazol-2-yl)pyridin-3-yl)-6,7-dihydrospiro[cyclopenta[e]pyrazolo[1,5-a]pyrimidine-8,1'-cyclopropane]-6-carboxamide Step 1: (Z)-5-((dimethylamino)methylene)spiro[2.4]heptan-4-one

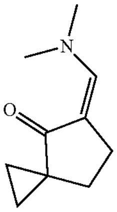

A solution of spiro[2.4]heptan-4-one (5 g, 45.4 mmol) in DMF-DMA (20 mL) was stirred at 100° C. for 16 h. The mixture was allowed to cool down to 25° C. The resulting mixture was concentrated under reduced pressure to give (Z)-5-((dimethylamino)methylene)spiro[2.4]heptan-4-one (6 g, crude) as a yellow oil which was used in the next step without purification. LCMS (ES, m/z): 166 $[M+H]^+$.

Step 2: 2-chloro-6,7-dihydrospiro[cyclopenta[e]pyrazolo[1,5-a]pyrimidine-8,1'-cyclopropane]

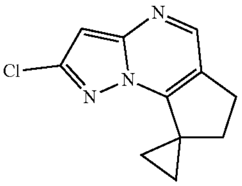

To a stirred solution of (Z)-5-((dimethylamino)methylene)spiro[2.4]heptan-4-one (1 g, 6 mmol) in AcOH (60 mL)

were added 5-chloro-1H-pyrazol-3-amine (0.9 g, 7.8 mmol) at 25° C. The resulting mixture was stirred at 95° C. for 1 h. The mixture was allowed to cool down to 25° C. The reaction mixture was concentrated under reduced pressure. The residue was diluted with water (100 mL). The pH was adjusted to 6-7 with saturated aqueous sodium bicarbonate solution. The resulting solution was extracted with ethyl acetate (2×100 mL). The combined organic layers were dried over anhydrous sodium sulfate and concentrated under reduced pressure. The residue was applied onto a silica gel column and eluted with EtOAc/PE (1:3) to give 2-chloro-6,7-dihydrospiro[cyclopenta[e]pyrazolo[1,5-a]pyrimidine-8,1'-cyclopropane] (500 mg, 37% yield) as a yellow solid. $^{1}$H NMR (300 MHz, DMSO-$d_6$) δ: 8.45 (s, 1H), 6.76 (s, 1H), 3.08-3.13 (m, 2H), 2.25-2.30 (m, 2H), 2.03-2.07 (m, 2H), 1.07-1.11 (m, 2H). LC-MS (ES, m/z):220 $[M+H]^+$.

Step 3: 2-chloro-6,7-dihydrospiro[cyclopenta[e]pyrazolo[1,5-a]pyrimidine-8,1'-cyclopropane]-6-carbonitrile

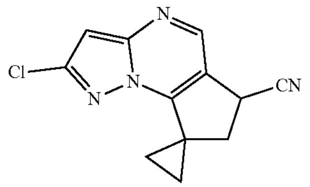 [SMILES: N#CC1CC2(CC2)c2c1cnc1cc(Cl)nn21]

To a stirred solution of 2-chloro-6,7-dihydrospiro[cyclopenta[e]pyrazolo[1,5-a]pyrimidine-8,1'-cyclopropane] (2 g, 9.1 mmol) in toluene (50 mL) was added (4R)-4-benzyl-2-[1-[(4R)-4-benzyl-4,5-dihydrooxazol-2-yl]-1-methyl-ethyl]-4,5-dihydrooxazole (396 mg, 1.1 mmol), acetoxycopper (223 mg, 1.8 mmol), N-Fluorobenzenesulfonimide (4.3 g, 13.6 mmol) and TMSCN (4.5 g, 45.5 mmol). The reaction was stirred at 25° C. for 16 h under nitrogen atmosphere. The resulting mixture was concentrated under reduced pressure. The residue was applied onto a silica gel column and eluted with EtOAc/PE (1:4) to give 2-chloro-6,7-dihydrospiro[cyclopenta[e]pyrazolo[1,5-a]pyrimidine-8,1'-cyclopropane]-6-carbonitrile (500 mg, 22% yield) as a yellow solid. LC-MS (ES, m/z): 245 $[M+H]^+$.

Step 4: 2-chloro-6,7-dihydrospiro[cyclopenta[e]pyrazolo[1,5-a]pyrimidine-8,1'-cyclopropane]-6-carboxamide

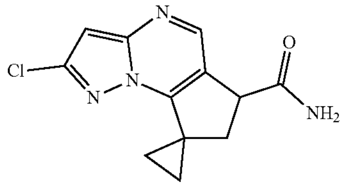 [SMILES: NC(=O)C1CC2(CC2)c2c1cnc1cc(Cl)nn21]

A mixture of 2-chloro-6,7-dihydrospiro[cyclopenta[e]pyrazolo[1,5-a]pyrimidine-8,1'-cyclopropane]-6-carbonitrile (900 mg, 3.7 mmol) in AcOH (10 mL) and 12 M HCl (5 mL) was stirred at 25° C. for 2 h. The mixture was allowed to cool down to 25° C. The resulting mixture was concentrated under reduced pressure. The residue was diluted with water (50 mL). The pH was adjusted to 5-6 with saturated aqueous sodium bicarbonate solution. The resulting solution was extracted with ethyl acetate (3×50 mL). The combined organic layers were dried over anhydrous sodium sulfate and concentrated under reduced pressure. The residue was applied onto a silica gel column and eluted with MeOH/DCM (1:10) to give 2-chloro-6,7-dihydrospiro[cyclopenta[e]pyrazolo[1,5-a]pyrimidine-8,1'-cyclopropane]-6-carboxamide (Method W2 step 4; 160 mg, 16% yield) as a yellow solid. LC-MS (ES, m/z): 263 $[M+H]^+$.

Step 5: 2-chloro-N-(5-chloro-6-(2H-1,2,3-triazol-2-yl)pyridin-3-yl)-6,7-dihydrospiro[cyclopenta[e]pyrazolo[1,5-a]pyrimidine-8,1'-cyclopropane]-6-carboxamide

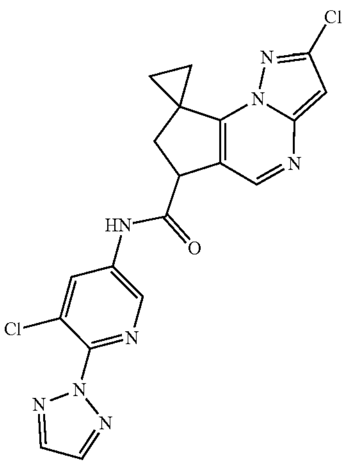

To a stirred mixture of 5-bromo-3-chloro-2-(2H-1,2,3-triazol-2-yl)pyridine (30 mg, 114 μmol) in toluene (5 mL) were added 2-chloro-6,7-dihydrospiro[cyclopenta[e]pyrazolo[1,5-a]pyrimidine-8,1'-cyclopropane]-6-carboxamide (30 mg, 114 μmol), XantPhos (13 mg, 23 μmol), $Pd_2(dba)_3$ (21 mg, 22.9 μmol), $Cs_2CO_3$ (55.8 mg, 171.3 μmol) and $Al(OTf)_3$ (5.4 mg, 11.4 μmol) at 25° C. under nitrogen atmosphere. The resulting mixture was stirred at 110° C. for 12 h under nitrogen atmosphere. The mixture was allowed to cool down to 25° C. The reaction mixture was diluted with water (50 mL). The resulting solution was extracted with DCM (3×50 mL). The combined organic layers were dried over anhydrous sodium sulfate and concentrated under reduced pressure. The residue was submitted to Prep-HPLC purification and the collected fractions were lyophilized to give 2-chloro-N-(5-chloro-6-(2H-1,2,3-triazol-2-yl)pyridin-3-yl)-6,7-dihydrospiro[cyclopenta[e]pyrazolo[1,5-a]pyrimidine-8,1'-cyclopropane]-6-carboxamide (10 mg, 20% yield) as a white solid. LC-MS: m/z 441.1 $[M+H]^+$.

Step 6: Separation of Enantiomers to Obtain (R)-2-chloro-N-(5-chloro-6-(2H-1,2,3-triazol-2-329yridinedin-3-yl)-6,7-dihydrospiro[cyclopenta[e]pyrazolo[1,5-a]pyrimidine-',1'-cyclopropane]-6-carboxamide and (S)-2-chloro-N-(5-chloro-6-(2H-1,2,3-triazol-2-329yridinedin-3-yl)-6,7-dihydrospiro[cyclopenta[e]pyrazolo[1,5-a]pyrimidine-',1'-cyclopropane]-6-carboxamide

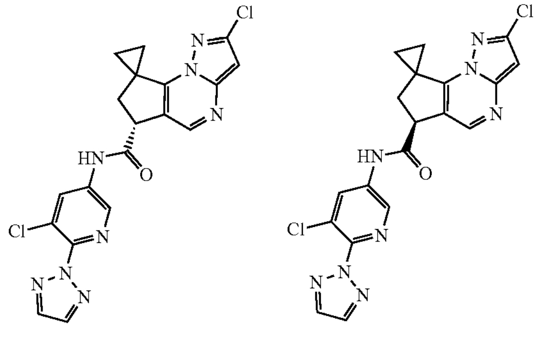

Example 96
and Example 97

15 mg of 2-chloro-N-(5-chloro-6-(2H-1,2,3-triazol-2-329yridinedin-3-yl)-6,7-dihydrospiro[cyclopenta[e]pyrazolo[1,5-a]pyrimidine-',1'-cyclopropane]-6-carboxamide were submitted to chiral HPLC purification (Column: CHIRAL ART Cellulose-SA, 2*25 cm, 5 μm; Mobile Phase A: Hex(0.1%-)-HPLC, Mobile Phase B: E-H-HPLC; Flow rate: 20 mL/min; isocratic 50% B in 31 min; Wave Length: 254/220 nm; RT1(min): 11.02; RT2(min): 24.93; Sample Solvent: E-H-HPLC; Injection Volume: 3 mL; Number Of Runs: 4). The first eluting isomer was concentrated and lyophilized to afford Example 96 (3.6 mg, 23% yield) as a white solid. The second eluting isomer was concentrated and lyophilized to afford Example 97 (3.5 mg, 23% yield) as a white solid.

Example 96: $^{1}$H NMR (400 MHz, DMSO-$d_6$) δ: 11.12 (br, 1H), 8.73 (d, J=2.4 Hz, 1H), 8.57-8.60 (m, 2H), 8.17 (s, 2H), 6.86 (s, 1H), 4.50-4.57 (m, 1H), 2.67-2.72 (m, 1H), 2.54-2.58 (m, 1H), 2.11-2.18 (m, 2H), 1.20-1.23 (m, 2H). LC-MS: m/z 441.1 $[M+H]^+$.

Example 97: $^{1}$H NMR (400 MHz, DMSO-$d_6$) δ: 11.16 (br, 1H), 8.73 (d, J=2.0 Hz, 1H), 8.58-8.60 (m, 2H), 8.17 (s, 2H), 6.86 (s, 1H), 4.50-4.57 (m, 1H), 2.66-2.72 (m, 1H), 2.54-2.58 (m, 1H), 2.11-2.17 (m, 2H), 1.20-1.23 (m, 2H). LC-MS: m/z 441.1 $[M+H]^+$.

The absolute stereochemistry for each separated isomer was not determined.

Method X2

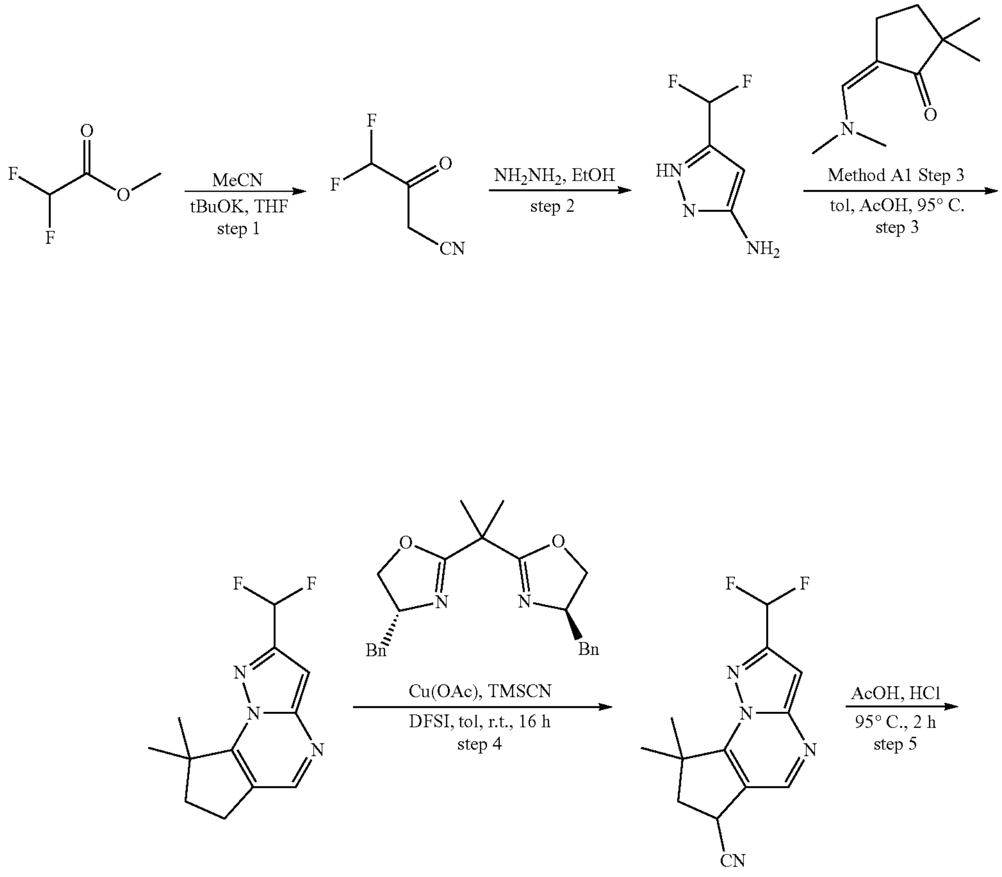

-continued

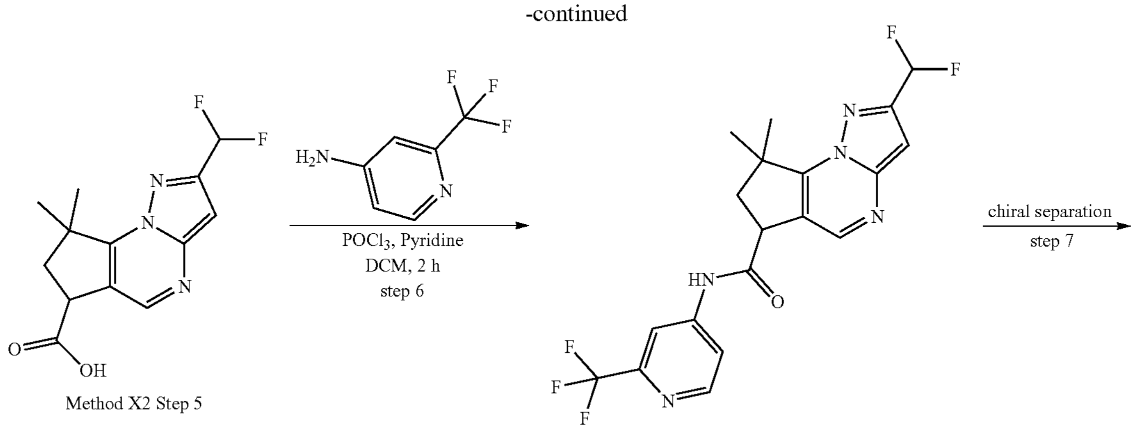

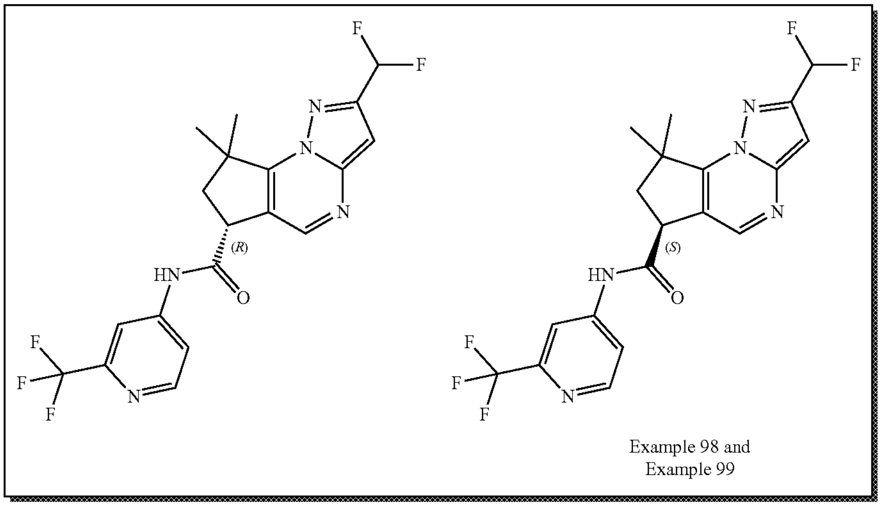

Example 98 and Example 99

Examples 98 and 99: Single Enantiomers Obtained from a Racemic Mixture Containing (R)-2-(difluoromethyl)-8,8-dimethyl-N-(2-(trifluoromethyl)pyridin-4-yl)-7,8-dihydro-6H-cyclopenta[e]pyrazolo[1,5-a]pyrimidine-6-carboxamide and (S)-2-(difluoromethyl)-8,8-dimethyl-N-(2-(trifluoromethyl)pyridin-4-yl)-7,8-dihydro-6H-cyclopenta[e]pyrazolo[1,5-a]pyrimidine-6-carboxamide Step 1: 4,4-difluoro-3-oxobutanenitrile

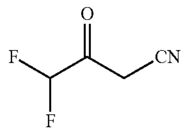

To a stirred solution of t-BuOK (38.2 g, 340.7 mmol) in THF (300 mL) was added 2,2-difluoroacetate (28.2 g, 227.1 mmol) and acetonitrile (13.9 g, 340.7 mmol) dropwise at 0° C. The resulting mixture was stirred at 25° C. for 18 h. The reaction mixture was quenched with water (300 mL). The resulting solution was extracted with ethyl acetate (2×300 mL). The combined organic layers were dried over anhydrous sodium sulfate and concentrated under reduced pressure to give 4,4-difluoro-3-oxobutanenitrile (12.5 g, crude) as a yellow oil which was used to the next step without purification. LCMS (ES, m/z): 120 $[M+H]^+$.

Step 2: 5-(difluoromethyl)-1H-pyrazol-3-amine

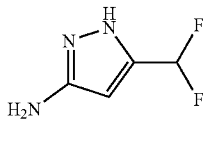

To a stirred solution of 4,4-difluoro-3-oxobutanenitrile (42.0 g, 352.7 mmol) in Ethanol (500 mL) was added Hydrazinium hydroxide solution (44.2 g, 705.5 mmol, 80% in water) at room temperature. The resulting mixture was stirred at 90° C. for 16 h. The mixture was allowed to cool down to room temperature. The reaction mixture was concentrated under reduced pressure. The residue was applied onto a silica gel column and eluted with EtOAc/PE (1:1) to give 5-(difluoromethyl)-1H-pyrazol-3-amine (3.0 g, 5.1% yield) as a yellow oil. LC-MS (ES, m/z):134 $[M+H]^+$.

Step 3: 2-(difluoromethyl)-8,8-dimethyl-7,8-dihydro-6H-cyclopenta[e]pyrazolo[1,5-a]pyrimidine

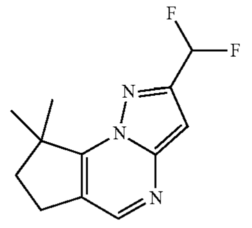

To a stirred solution of (Z)-5-((dimethylamino)methylene)-2,2-dimethylcyclopentan-1-one (Method A1 step 3; 3.7 g, 22.5 mmol) in Toluene (20 mL) was added 5-(difluoromethyl)-1H-pyrazol-3-amine (3.0 g, 22.5 mmol) and AcOH (2 mL) at room temperature. The resulting mixture was stirred at 95° C. for 16 h. The mixture was allowed to cool down to room temperature. The reaction mixture was concentrated under reduced pressure. The residue was diluted with water (200 mL). The pH was adjusted to 6-7 with sodium bicarbonate (sat., aq.). The resulting solution was extracted with ethyl acetate (2×200 mL). The combined organic layers were dried over anhydrous sodium sulfate and concentrated under reduced pressure. The residue was applied onto a silica gel column and eluted with EtOAc/PE (1:4) to give 2-(difluoromethyl)-8,8-dimethyl-7,8-dihydro-6H-cyclopenta[e]pyrazolo[1,5-a]pyrimidine (3.0 g, 50% yield). $^1$H NMR (300 MHz, DMSO-$d_6$) δ: 8.60 (s, 1H), 7.30 (t, J=54.0 Hz, 1H), 6.99 (s, 1H), 3.02 (t, J=6.0 Hz, 2H), 2.10 (t, J=6.0 Hz, 2H), 1.53 (s, 6H). LC-MS (ES, m/z):238 [M+H]$^+$.

Step 4: 2-(difluoromethyl)-8,8-dimethyl-7,8-dihydro-6H-cyclopenta[e]pyrazolo[1,5-a]pyrimidine-6-carbonitrile

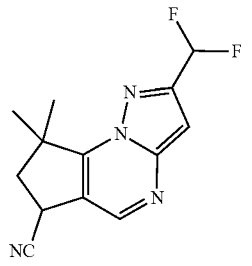

To a stirred solution of 2-(difluoromethyl)-8,8-dimethyl-7,8-dihydro-6H-cyclopenta[e]pyrazolo[1,5-a]pyrimidine (2.0 g, 8.4 mmol) in toluene (200 mL) was added (4R)-4-benzyl-2-[1-[(4R)-4-benzyl-4,5-dihydrooxazol-2-yl]-1-methyl-ethyl]-4,5-dihydrooxazole (366 mg, 1.0 mmol), acetoxycopper (206 mg, 1.7 mmol), N-Fluorobenzenesulfonimide (4 g, 12.6 mmol), TMSCN (4.2 g, 42.2 mmol). The reaction was stirred at room temperature for 16 h under nitrogen. The solvent was removed under reduced pressure and the residue was applied onto a silica gel column and eluted with EtOAc/PE (1:1) to give 2-(difluoromethyl)-8,8-dimethyl-7,8-dihydro-6H-cyclopenta[e]pyrazolo[1,5-a]pyrimidine-6-carbonitrile (1.2 g, 32% yield). LC-MS (ES, m/z): 263 [M+H]$^+$.

Step 5: 2-(difluoromethyl)-8,8-dimethyl-7,8-dihydro-6H-cyclopenta[e]pyrazolo[1,5-a]pyrimidine-6-carboxylic acid

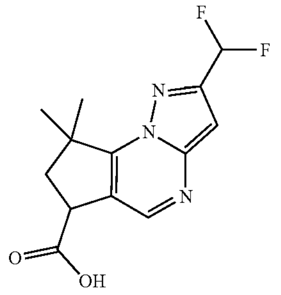

A mixture of 2-(difluoromethyl)-8,8-dimethyl-7,8-dihydro-6H-cyclopenta[e]pyrazolo[1,5-a]pyrimidine-6-carbonitrile (2.0 g, 4.6 mmol) in AcOH (8 mL) and 12 M HCl (8 mL) was stirred for 2 h at 100° C. The mixture was allowed to cool down to room temperature. The solvent was concentrated under reduced pressure and the residue was diluted with 300 ml water. The resulting solution was extracted with ethyl acetate (300 mL×3). The combined organic layers were dried over anhydrous sodium sulfate and concentrated under reduced pressure. The residue was applied onto a silica gel column and eluted with MeOH/DCM (1:10) to give 2-(difluoromethyl)-8,8-dimethyl-7,8-dihydro-6H-cyclopenta[e]pyrazolo[1,5-a]pyrimidine-6-carboxylic acid (Method X2 step 5; 400 mg, 27% yield) as a yellow solid. LC-MS (ES, m/z): 282 [M+H]$^+$.

Step 6: 2-(difluoromethyl)-8,8-dimethyl-N-(2-(trifluoromethyl)pyridin-4-yl)-7,8-dihydro-6H-cyclopenta[e]pyrazolo[1,5-a]pyrimidine-6-carboxamide

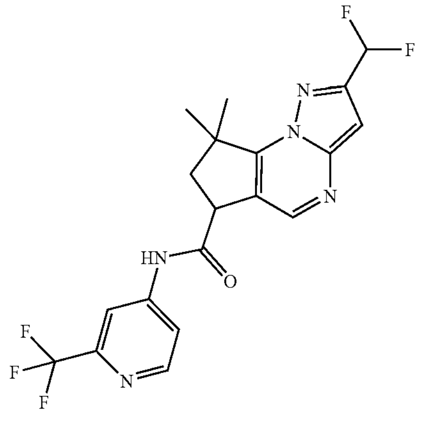

To a stirred solution of 2-(difluoromethyl)-8,8-dimethyl-7,8-dihydro-6H-cyclopenta[e]pyrazolo[1,5-a]pyrimidine-6-carboxylic acid (30 mg, 106 μmol) in DCM (5 mL) were added pyridine (84 mg, 1.0 mmol) and phosphoryl trichloride (49 mg, 320 μmol) at 0° C. The mixture was stirred at 0° C. for 0.5 h. 2-(trifluoromethyl)pyridin-4-amine (17 mg, 106 μmol) was added, and the mixture was stirred at 25° C. for 1 h. The reaction mixture was concentrated under reduced pressure. The residue was purified by Prep-HPLC and the collected fractions were concentrated under reduced pressure to afford 2-(difluoromethyl)-8,8-dimethyl-N-(2-(trifluoromethyl)pyridin-4-yl)-7,8-dihydro-6H-cyclopenta[e]pyrazolo[1,5-a]pyrimidine-6-carboxamide (26 mg, 56% yield) as a white solid. LC-MS: m/z 426 [M+H]$^+$.

Step 7: Separation of Enantiomers to Obtain (R)-2-(difluoromethyl)-8,8-dimethyl-N-(2-(trifluoromethyl)pyridin-4-yl)-7,8-dihydro-6H-cyclopenta[e]pyrazolo[1,5-a]pyrimidine-6-carboxamide and (S)-2-(difluoromethyl)-8,8-dimethyl-N-(2-(trifluoromethyl)pyridin-4-yl)-7,8-dihydro-6H-cyclopenta[e]pyrazolo[1,5-a]pyrimidine-6-carboxamide

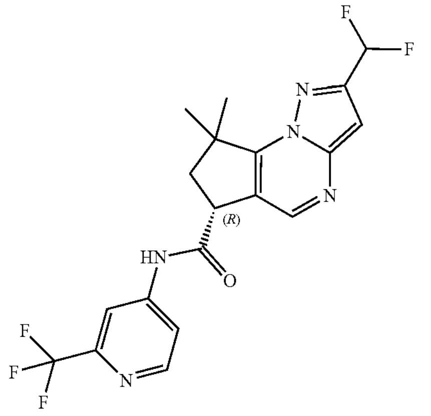

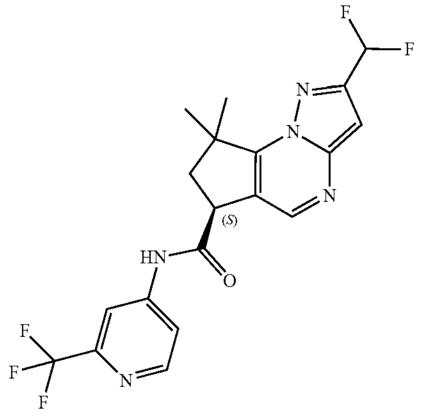

Example 98 and
Example 99

60 mg of 2-(difluoromethyl)-8,8-dimethyl-N-(2-(trifluoromethyl)pyridin-4-yl)-7,8-dihydro-6H-cyclopenta[e]pyrazolo[1,5-a]pyrimidine-6-carboxamide were submitted to chiral HPLC purification (Column: CHIRAL ART Cellulose-SC, 2*25 cm, 5 μm; Mobile Phase A: Hex(0.1% FA)-HPLC, Mobile Phase B: EtOH-HPLC; Flow rate: 20 mL/min; isocratic 90% B in 13 min; Wave Length: 254/220 nm; RT1(min): 7.597; RT2(min): 9.569; Sample Solvent: ETOH:DCM=1:1; Injection Volume: 0.3 mL; Number Of Runs: 4). The first eluting isomer was concentrated and lyophilized to afford Example 98 (14.3 mg, 23% yield) as a white solid. The second eluting isomer was concentrated and lyophilized to afford Example 99 (14 mg, 23% yield) as a white solid.

Example 98: $^1$H NMR (300 MHz, DMSO-$d_6$) δ 11.08 (br, 1H), 8.69 (s, 1H), 8.64 (d, J=5.4 Hz, 1H), 8.17 (d, J=1.5 Hz, 1H), 7.82 (dd, J=1.5, 5.4 Hz, 1H), 7.30 (t, J=54.3 Hz, 1H), 7.07 (s, 1H), 4.44-4.49 (m, 1H), 2.50-2.62 (m, 1H), 2.28-2.35 (m, 1H), 1.65 (s, 3H), 1.58 (s, 3H). LCMS (ES, m/z): 426.1 [M+H]$^+$.

Example 99: $^1$H NMR (300 MHz, DMSO-$d_6$) δ 11.08 (br, 1H), 8.69 (s, 1H), 8.64 (d, J=5.7 Hz, 1H), 8.17 (d, J=1.8 Hz, 1H), 7.81 (dd, J=1.5, 5.4 Hz, 1H), 7.29 (t, J=54.0 Hz, 1H), 7.08 (s, 1H), 4.44-4.49 (m, 1H), 2.50-2.63 (m, 1H), 2.29-2.35 (m, 1H), 1.66 (s, 3H), 1.58 (s, 3H). LC-MS (ES, m/z): 426.1 [M+H]$^+$.

The absolute stereochemistry for each separated isomer was not determined

Method Y2

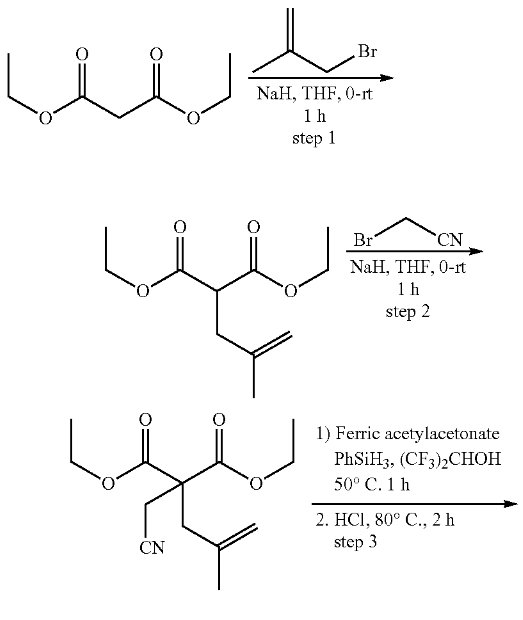

-continued

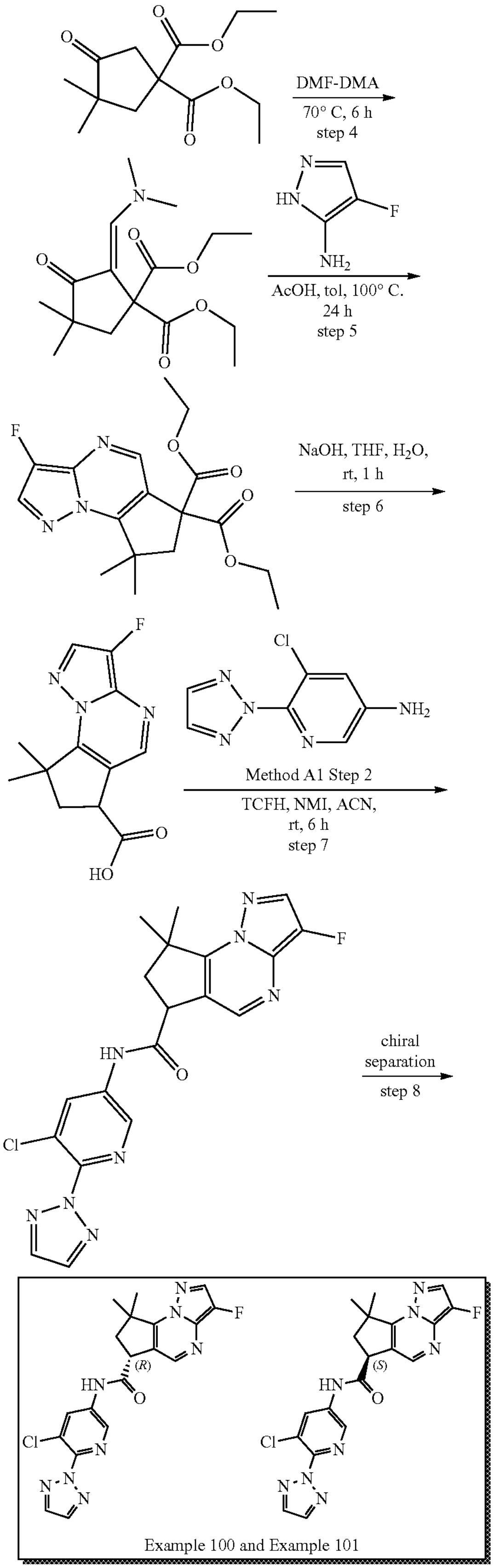

Example 100 and Example 101

Examples 100 and 101: Single Enantiomers Obtained from a Racemic Mixture Containing (R)—N-(5-chloro-6-(2H-1,2,3-triazol-2-yl)pyridin-3-yl)-3-fluoro-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-3-fluoro-8,8-dimethyl-7,8-dihydro-6H-cyclopenta[e]pyrazolo[1,5-a]pyrimidine-6-carboxamide Step 1: diethyl 2-(2-methylallyl)malonate

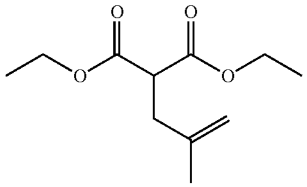

To a mixture of diethyl malonate (20.0 g, 124.8 mmol) in tetrahydrofuran (300 mL) was added sodium hydride (5.0 g, 124.8 mmol, 60% in mineral oil) at 0° C. under nitrogen atmosphere. The mixture was stirred for 30 min. 3-bromo-2-methylprop-1-ene (25.0 g, 187.3 mmol) was added and the mixture was allowed to warm to 25° C. and stirred for 1 h. The reaction mixture was quenched with water (400 mL). The resulting solution was extracted with ethyl acetate (3×500 mL). The combined organic layers were washed with brine (200 mL), dried over anhydrous sodium sulfate and concentrated under reduced pressure. The residue was applied on a silica gel column and eluted with EtOAc/PE (1:3) to give diethyl 2-(2-methylallyl)malonate (15.0 g, crude) as a white oil. LC-MS: m/z 215 $[M+H]^+$.

Step 2: diethyl 2-(cyanomethyl)-2-(2-methylallyl)malonate

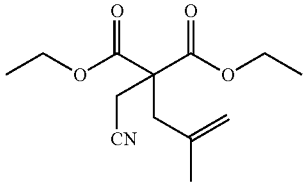 [SMILES: C=C(C)CC(CC#N)(C(=O)OCC)C(=O)OCC]

To a mixture of diethyl 2-(2-methylallyl)malonate (25.0 g, 116.6 mmol) in tetrahydrofuran (300 mL) was added sodium hydride (7.0 g, 175.0 mmol, 60% in mineral oil) at 0° C. under nitrogen atmosphere. The mixture was stirred for 30 min. 2-bromoacetonitrile (21.0 g, 175.0 mmol) was added and the mixture was allowed to warm to 25° C. and stirred for 1 h. The reaction mixture was quenched with water (100 mL). The resulting solution was extracted with ethyl acetate (3×200 mL). The combined organic layers were washed with brine (200 mL), dried over anhydrous sodium sulfate and concentrated under reduced pressure. The residue was applied on a silica gel column and eluted with EtOAc/PE (1:3) to afford diethyl 2-(cyanomethyl)-2-(2-methylallyl) malonate (18.0 g, crude) as a white oil. LC-MS: m/z 254 $[M+H]^+$.

Step 3: diethyl 3,3-dimethyl-4-oxocyclopentane-1,1-dicarboxylate

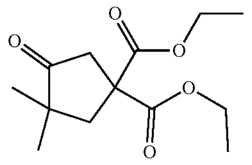 [SMILES: CCOC(=O)C1(C(=O)OCC)CC(=O)C(C)(C)C1]

To a stirred mixture of diethyl 2-(cyanomethyl)-2-(2-methylallyl)malonate (9 g, 31.4 mmol) and ferric (Z)-4-oxopent-2-en-2-olate (5.6 g, 15.8 mmol) was added phenylsilane (10.6 g, 97.8 mmol) in ethyl acetate (22 mL) and 1,1,1,3,3,3-Hexafluoro-2-propanol (22 mL) at 25° C. under nitrogen atmosphere. The resulting mixture was stirred for 1 h at 50° C. under nitrogen atmosphere. To the above mixture was added hydrogen chloride (2 M, 80 mL). The resulting mixture was stirred for additional 2 h at 80° C. The mixture was allowed to cool down to room temperature. The reaction mixture was quenched with water (400 mL). The resulting solution was extracted with ethyl acetate (3×400 mL). The combined organic layers were washed with brine (400 mL), dried over anhydrous sodium sulfate and concentrated under reduced pressure. The residue was applied on a silica gel column and eluted with EtOAc/PE (1:3) to afford diethyl 3,3-dimethyl-4-oxocyclopentane-1,1-dicarboxylate (1.9 g, crude) as a yellow oil. LC-MS: m/z 257 $[M+H]^+$.

Step 4: diethyl (E)-2-((dimethylamino)methylene)-4,4-dimethyl-3-oxocyclopentane-1,1-dicarboxylate

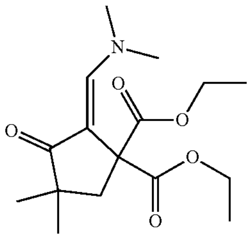 [SMILES: CCOC(=O)C1(C(=O)OCC)CC(C)(C)C(=O)/C1=C/N(C)C]

A solution of diethyl 3,3-dimethyl-4-oxocyclopentane-1,1-dicarboxylate (2.8 g, 10.9 mmol) in N,N-Dimethylformamide dimethyl acetal (30 mL) was stirred at 70° C. for 6 h. The mixture was allowed to cool down to room temperature. The resulting mixture was concentrated under reduced pressure to afford diethyl (E)-2-((dimethylamino)methylene)-4,4-dimethyl-3-oxocyclopentane-1,1-dicarboxylate (3.1 g, crude) as a yellow oil. The crude product was used in next step immediately without any further purification. LC-MS: m/z 312 $[M+H]^+$.

Step 5: diethyl 3-fluoro-8,8-dimethyl-7,8-dihydro-6H-cyclopenta[e]pyrazolo[1,5-a]pyrimidine-6,6-dicarboxylate

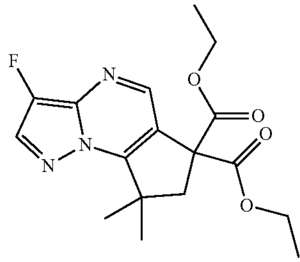 [SMILES: CCOC(=O)C1(C(=O)OCC)CC(C)(C)c2c1cnc1c(F)cnn21]

A solution of diethyl (E)-2-((dimethylamino)methylene)-4,4-dimethyl-3-oxocyclopentane-1,1-dicarboxylate (874 mg, 2.8 mmol) and 4-fluoro-1H-pyrazol-5-amine (110 mg, 935.2 μmol) in acetic acid (1 mL) and toluene (10 mL) was stirred for 24 h at 100° C. under nitrogen atmosphere. The mixture was allowed to cool down to room temperature. The reaction mixture was quenched with water (40 mL). The resulting solution was extracted with ethyl acetate (3×50 mL). The combined organic layers were washed with brine (60 mL), dried over anhydrous sodium sulfate and concentrated under reduced pressure. The residue was applied on a silica gel column and eluted with EtOAc/PE (2:3) to afford diethyl 3-fluoro-8,8-dimethyl-7,8-dihydro-6H-cyclopenta[e]pyrazolo[1,5-a]pyrimidine-6,6-dicarboxylate (240 mg, 64% yield) as a yellow oil. $^1$H NMR (300 MHz, DMSO-$d_6$): δ 8.60 (s, 1H), 8.45 (d, J=3.0 Hz, 1H), 4.19-4.26 (m, 4H), 2.73 (s, 2H), 1.57 (s, 6H), 1.18-1.24 (m, 6H). LC-MS: m/z 350 $[M+H]^+$.

Step 6: 3-fluoro-8,8-dimethyl-7,8-dihydro-6H-cyclopenta[e]pyrazolo[1,5-a]pyrimidine-6-carboxylic acid

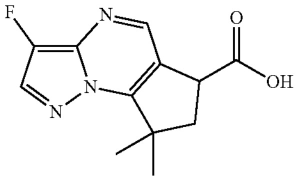 [SMILES: CC1(C)CC(C(=O)O)c2cnc3c(F)cnn3c21]

To a stirred mixture of diethyl 3-fluoro-8,8-dimethyl-7,8-dihydro-6H-cyclopenta[e]pyrazolo[1,5-a]pyrimidine-6,6-dicarboxylate (160 mg, 457.9 μmol) in tetrahydrofuran (1 mL) was added sodium hydroxide (91 mg, 2.2 mmol) in water (1 mL) at room temperature. The resulting mixture was stirred for 1 h at 25° C. The pH value was adjusted to 6 with hydrochloric acid (1 M). The resulting mixture was extracted with ethyl acetate (3×25 mL). The combined organic layers were washed with brine (20 mL), dried over anhydrous sodium sulfate and concentrated under reduced pressure to afford 3-fluoro-8,8-dimethyl-7,8-dihydro-6H-cyclopenta[e]pyrazolo[1,5-a]pyrimidine-6-carboxylic acid (72 mg, 63% yield) as a yellow solid. $^1$H NMR (400 MHz, DMSO-$d_6$): δ 12.87 (s, 1H), 8.57 (s, 1H), 8.38 (d, J=3.2 Hz, 1H), 4.25-4.28 (m, 1H), 2.40-2.48 (m, 1H), 2.28-2.33 (m, 1H), 1.57 (s, 3H), 1.53 (s, 3H). LC-MS: m/z 250 $[M+H]^+$.

Step 7: N-(5-chloro-6-(2H-1,2,3-triazol-2-yl)pyridin-3-yl)-3-fluoro-8,8-dimethyl-7,8-dihydro-6H-cyclopenta[e]pyrazolo[1,5-a]pyrimidine-6-carboxamide

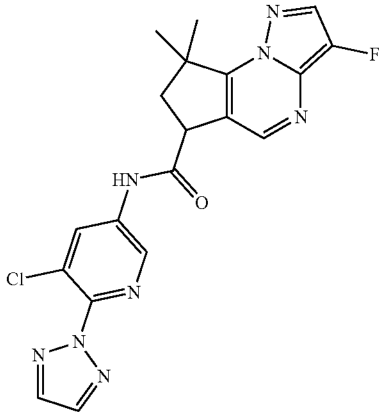 [SMILES: CC1(C)CC(C(=O)Nc2cnc(-n3nccn3)c(Cl)c2)c2cnc3c(F)cnn3c21]

To a stirred solution of 3-fluoro-8,8-dimethyl-7,8-dihydro-6H-cyclopenta[e]pyrazolo[1,5-a]pyrimidine-6-carboxylic acid (72 mg, 300.9 μmol) in acetonitrile (2 mL) were added 5-chloro-6-(2H-1,2,3-triazol-2-yl)pyridin-3-amine (Method A1 step 2; 88 mg, 451.3 μmol), TCFH (337 mg, 1.2 mmol) and NMI (98 mg, 1.2 mmol) at 25° C. The mixture was stirred for 6 h at 25° C.

The reaction mixture was concentrated under reduced pressure. The crude product was submitted to Prep-HPLC and the collected fractions were lyophilized to afford N-(5-chloro-6-(2H-1,2,3-triazol-2-yl)pyridin-3-yl)-3-fluoro-8,8-dimethyl-7,8-dihydro-6H-cyclopenta[e]pyrazolo[1,5-a]pyrimidine-6-carboxamide (37 mg, 31% yield) as a white solid. LC-MS: m/z 427 $[M+H]^+$.

Step 8: Separation of Enantiomers to Obtain (R)—N-(5-chloro-6-(2H-1,2,3-triazol-2-yl)pyridin-3-yl)-3-fluoro-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-3-fluoro-8,8-dimethyl-7,8-dihydro-6H-cyclopenta[e]pyrazolo[1,5-a]pyrimidine-6-carboxamide Example 100 and Example 101

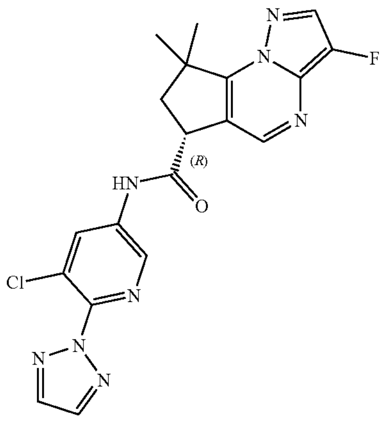

-continued

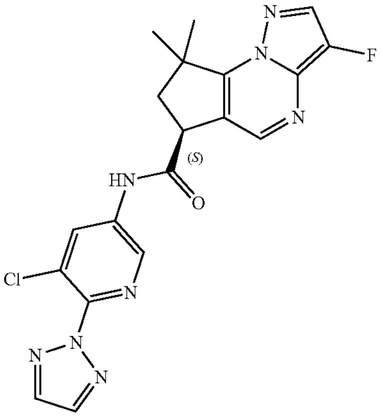

37 mg of N-(5-chloro-6-(2H-1,2,3-triazol-2-yl)pyridin-3-yl)-3-fluoro-8,8-dimethyl-7,8-dihydro-6H-cyclopenta[e]pyrazolo[1,5-a]pyrimidine-6-carboxamide were submitted to chiral HPLC purification (Column: CHIRAL ART Amylose-SA, 2*25 cm, 5 μm; Mobile Phase A: Hex(0.5% 2M $NH_3$-MeOH)-HPLC, Mobile Phase B: EtOH-HPLC; Flow rate: 16 mL/min; isocratic 50% B in 25 min; Wave Length: 220/254 nm; RT1(min): 13.22; RT2(min): 18.80; Sample Solvent: EtOH-HPLC; Injection Volume: 1.5 mL; Number Of Runs: 2). The first eluting isomer was concentrated and lyophilized to afford Example 100 (11 mg, 29% yield) as a white solid yield. The second eluting isomer was concentrated and lyophilized to afford Example 101 (9.5 mg, 25% yield) as a white solid.

Example 100: $^1H$ NMR (400 MHz, DMSO-$d_6$) δ: 11.09 (s, 1H), 8.74 (d, J=2.4 Hz, 1H), 8.59-8.61 (m, 2H), 8.41 (d, J=3.6 Hz, 1H), 8.17 (s, 2H), 4.44-4.48 (m, 1H), 2.51-2.60 (m, 1H), 2.32-2.37 (m, 1H), 1.67 (s, 3H), 1.58 (s, 3H). LC-MS: m/z 427.1 $[M+H]^+$.

Example 101: $^1H$ NMR (400 MHz, DMSO-$d_6$) δ: 11.09 (s, 1H), 8.73 (d, J=2.4 Hz, 1H), 8.58-8.61 (m, 2H), 8.41 (d, J=3.6 Hz, 1H), 8.18 (s, 2H), 4.44-4.48 (m, 1H), 2.51-2.60 (m, 1H), 2.32-2.37 (m, 1H), 1.67 (s, 3H), 1.59 (s, 3H). LC-MS: m/z 427.0 $[M+H]^+$. The absolute stereochemistry for each separated isomer was not determined.

Method Z2

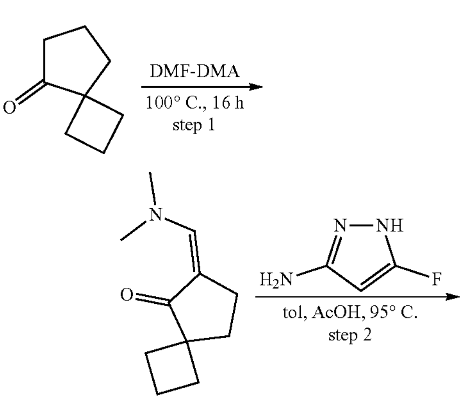

-continued

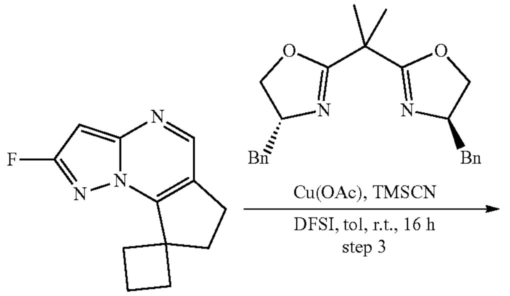

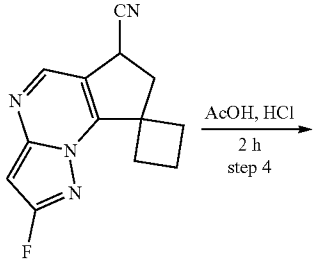

Method Z2 Step 3

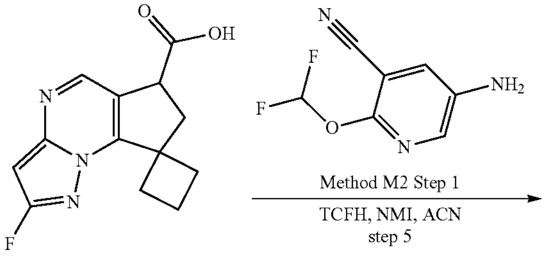

Method Z2 Step 4

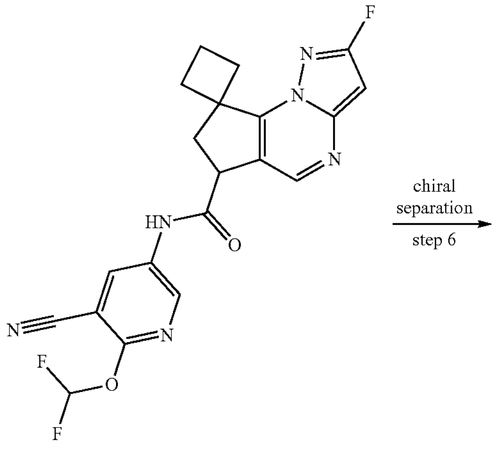

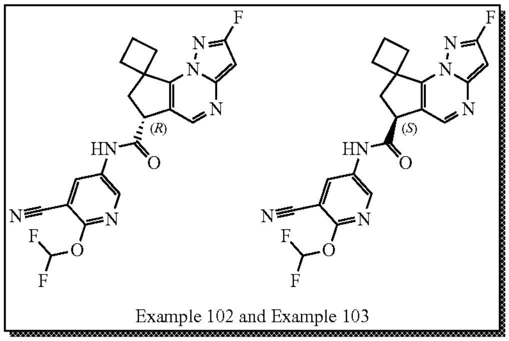

Example 102 and Example 103

Examples 102 and 103: Single Enantiomers Obtained from a Racemic Mixture Containing (R)—N-(5-Cyano-6-(Difluoromethoxy)Pyridin-3-Yl)-2'-Fluoro-6',7'-dihydrospiro[cyclobutane-1,8'-cyclopenta[a]pyrazolo[1,5-a]pyrimidine]-6'-carboxamide and (S)—N-(5-cyano-6-(difluoromethoxy)pyridin-3-yl)-2'-fluoro-6',7'-dihydrospiro[cyclobutane-1,8'-cyclopenta[a]pyrazolo[1,5-a]pyrimidine]-6'-carboxamide Step 1: (Z)-6-((dimethylamino)methylene)spiro[3.4]octan-5-one

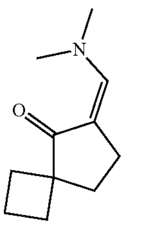

A solution of spiro[3.4]octan-5-one (5 g, 40.3 mmol) in DMF-DMA (20 mL) was stirred for 16 h at 100° C. The mixture was allowed to cool down to room temperature. The resulting mixture was concentrated under reduced pressure. This resulted in (Z)-6-((dimethylamino)methylene)spiro[3.4]octan-5-one (6 g, crude) as a yellow oil which was used to the next step without purification. LCMS (ES, m/z): 180 $[M+H]^+$.

Step 2: 2'-fluoro-6',7'-dihydrospiro[cyclobutane-1,8'-cyclopenta[e]pyrazolo[1,5-a]pyrimidine]

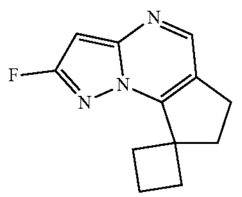 [SMILES: Fc1cc2ncc3c(n2n1)C1(CCC1)CC3]

To a stirred solution of (Z)-6-((dimethylamino)methylene)spiro[3.4]octan-5-one (1.0 g, 5.5 mmol) in Toluene (20 mL) were added 5-fluoro-1H-pyrazol-3-amine (670 mg, 6.6 mmol) and AcOH (2 mL) at room temperature. The resulting mixture was stirred at 95° C. for 16 h. The mixture was allowed to cool down to room temperature. The reaction mixture was concentrated under reduced pressure. The residue was diluted with water (100 mL). The pH was adjusted to 6-7 with sodium bicarbonate (sat., aq.). The resulting solution was extracted with ethyl acetate (2×100 mL), The combined organic layers were dried over anhydrous sodium sulfate and concentrated under reduced pressure. The residue was applied onto a silica gel column and eluted with EtOAc/PE (1:3) to give 2'-fluoro-6',7'-dihydrospiro[cyclobutane-1,8'-cyclopenta[e]pyrazolo[1,5-a]pyrimidine] (900 mg, 75% yield). $^1H$ NMR (400 MHz, DMSO-$d_6$) δ: 8.48 (s, 1H), 6.46 (d, J=4.8 Hz, 1H), 2.99-3.08 (m, 2H), 2.87-2.98 (m, 2H), 2.40-2.46 (m, 2H), 1.9-2.23 (m, 4H). LC-MS (ES, m/z): 218 $[M+H]^+$.

Step 3: 2'-fluoro-6',7'-dihydrospiro[cyclobutane-1,8'-cyclopenta[e]pyrazolo[1,5-a]pyrimidine]-6'-carbonitrile

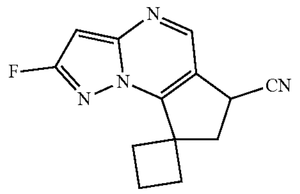 [SMILES: N#CC1CC2(CCC2)c2c1cnc1cc(F)nn21]

To a stirred solution of 2'-fluoro-6',7'-dihydrospiro[cyclobutane-1,8'-cyclopenta[e]pyrazolo[1,5-a]pyrimidine] (2.5 g, 11.5 mmol) in Toluene (300 mL) was added (4R)-4-benzyl-2-[1-[(4R)-4-benzyl-4,5-dihydrooxazol-2-yl]-1-methyl-ethyl]-4,5-dihydrooxazole (500 mg, 1.3 mmol), acetoxycopper (282 mg, 2.3 mmol), N-Fluorobenzenesulfonimide (5.4 g, 17.3 mmol), TMSCN (5.8 g, 57.5 mmol). The reaction was stirred at 25° C. for 16 h under nitrogen. The solvent was removed under reduced pressure and the residue was applied onto a silica gel column and eluted with EtOAc/PE (1:3) to get 2'-fluoro-6',7'-dihydrospiro[cyclobutane-1,8'-cyclopenta[e]pyrazolo[1,5-a]pyrimidine]-6'-carbonitrile (Method Z2 step 3; 1.1 g, 25% yield) as a yellow solid. LC-MS (ES, m/z): 243 $[M+H]^+$.

Step 4: 2'-fluoro-6',7'-dihydrospiro[cyclobutane-1,8'-cyclopenta[e]pyrazolo[1,5-a]pyrimidine]-6'-carboxylic acid

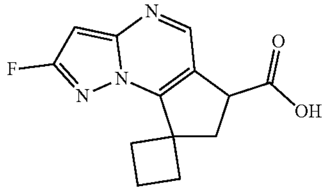 [SMILES: O=C(O)C1CC2(CCC2)c2c1cnc1cc(F)nn21]

A mixture of 2'-fluoro-6',7'-dihydrospiro[cyclobutane-1,8'-cyclopenta[e]pyrazolo[1,5-a]pyrimidine]-6'-carbonitrile (100 mg, 206 μmol) in AcOH (5 mL) and HCl (5 mL) was stirred at 100° C. for 2 h. The mixture was allowed to cool down to room temperature. The solvent was concentrated under reduced pressure and the residue was diluted with 50 ml water. The resulting solution was extracted with ethyl acetate (50 mL×3). The combined organic layers were dried over anhydrous sodium sulfate and concentrated under reduced pressure. The residue was applied onto a silica gel column and eluted with MeOH/DCM (1:10) to give 2'-fluoro-6',7'-dihydrospiro[cyclobutane-1,8'-cyclopenta[e]pyrazolo[1,5-a]pyrimidine]-6'-carboxylic acid (Method Z2 step 4; 35 mg, 27% yield) as a yellow solid. LC-MS (ES, m/z): 262 $[M+H]^+$.

Step 5: N-(5-cyano-6-(difluoromethoxy)pyridin-3-yl)-2'-fluoro-6',7'-dihydrospiro[cyclobutane-1,8'-cyclopenta[e]pyrazolo[1,5-a]pyrimidine]-6'-carboxamide

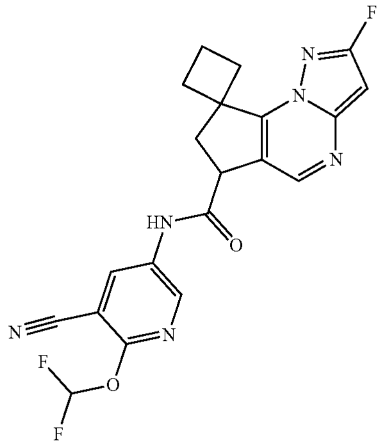 [SMILES: N#Cc1cc(NC(=O)C2CC3(CCC3)c3c2cnc2cc(F)nn32)cnc1OC(F)F]

To a stirred solution of 2'-fluoro-6',7'-dihydrospiro[cyclobutane-1,8'-cyclopenta[e]pyrazolo[1,5-a]pyrimidine]-6'-carboxylic acid (35 mg, 133 μmol) in ACN (4 mL) was added 5-amino-2-(difluoromethoxy)nicotinonitrile (Method M2 step 1; 30 mg, 160 μmol), TCFH (44 mg, 535 μmol) and NMI (150 mg, 535 μmol). The resulting mixture was stirred at 25° C. for 16 h. The reaction mixture was quenched with water (40 mL). The resulting solution was extracted with ethyl acetate (40 mL×3). The combined organic layers were dried over anhydrous sodium sulfate and concentrated under reduced pressure. The residue was submitted to Prep-HPLC and the collected fraction was lyophilized to give N-(5-cyano-6-(difluoromethoxy)pyridin-3-yl)-2'-fluoro-6',7'-dihydrospiro[cyclobutane-1,8'-cyclopenta[e]pyrazolo[1,5-a]pyrimidine]-6'-carboxamide (30 mg, 52% yield) as a white solid. LC-MS (ES, m/z): 429[M+H].

Step 6: Separation of Enantiomers to Obtain (R)—N-(5-cyano-6-(difluoromethoxy)pyridin-3-yl)-2'-fluoro-6',7'-dihydrospiro[cyclobutane-1,8'-cyclopenta[e]pyrazolo[1,5-a]pyrimidine]-6'-carboxamide, (S)—N-(5-cyano-6-(difluoromethoxy)pyridin-3-yl)-2'-fluoro-6',7'-dihydrospiro[cyclobutane-1,8'-cyclopenta[e]pyrazolo[1,5-a]pyrimidine]-6'-carboxamide Example 102 and Example 103

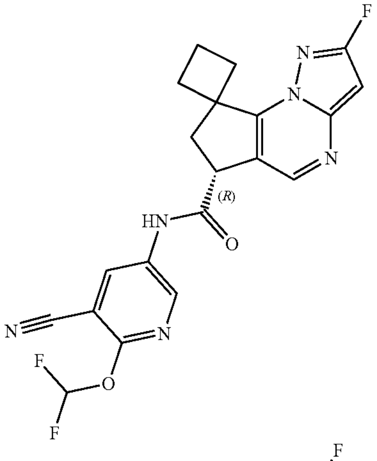

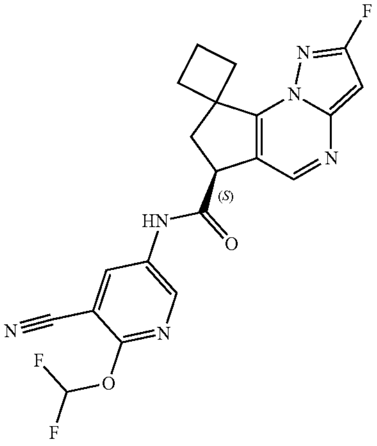

30 mg of N-(5-cyano-6-(difluoromethoxy)pyridin-3-yl)-2'-fluoro-6',7'-dihydrospiro[cyclobutane-1,8'-cyclopenta[e]pyrazolo[1,5-a]pyrimidine]-6'-carboxamide were submitted to chiral HPLC purification (Column: CHIRAL ART Cellulose-SC, 2*25 cm, 5 μm; Mobile Phase A: Hex(0.1% FA)-HPLC, Mobile Phase B: EtOH-HPLC; Flow rate: 20 mL/min; isocratic 30% B in 8.5 min; Wave Length: 254/220 nm; RT1(min): 5.69; RT2(min): 6.97; Sample Solvent: EtOH-HPLC; Injection Volume: 1.6 mL; Number Of Runs: 3). The first eluting isomer was concentrated and lyophilized to afford Example 102 (9.3 mg, 31% yield) as a white solid. The second eluting isomer was concentrated and lyophilized to afford Example 103 (7.7 mg, 25% yield) as a white solid.

Example 102: $^1$H NMR (300 MHz, DMSO-$d_6$) δ: 10.86 (br, 1H), 8.66 (d, J=2.7 Hz, 1H), 8.60-8.63 (m, 2H), 7.74 (t, J=71.4 Hz, 1H), 6.59 (d, J=5.1 Hz, 1H), 4.28-4.39 (m, 1H), 3.07-3.18 (m, 2H), 2.81-2.90 (m, 1H), 2.62-2.71 (m, 1H), 2.06-2.23 (m, 4H). LCMS (ES, m/z): 429.1 $[M+H]^+$.

Example 103: $^1$H NMR (300 MHz, DMSO-$d_6$) δ: 10.91 (br, 1H), 8.67 (d, J=3.0 Hz, 1H), 8.61-8.64 (m, 2H), 7.74 (t, J=71.4 Hz, 1H), 6.59 (d, J=4.8 Hz, 1H), 4.30-4.49 (m, 1H), 3.07-3.21 (m, 2H), 2.81-2.90 (m, 1H), 2.64-2.74 (m, 1H), 2.02-2.23 (m, 4H). LC-MS (ES, m/z): 429.1 $[M+H]^+$.

The absolute stereochemistry for each separated isomer was not determined.

Method A3

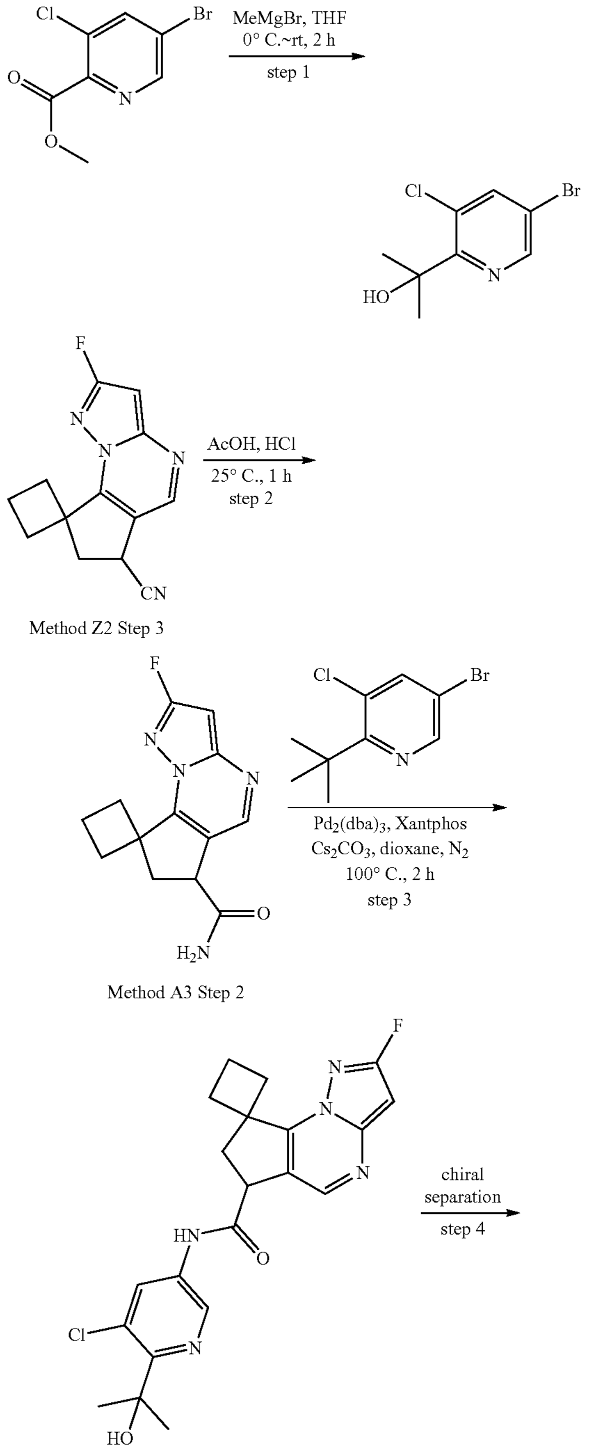

-continued

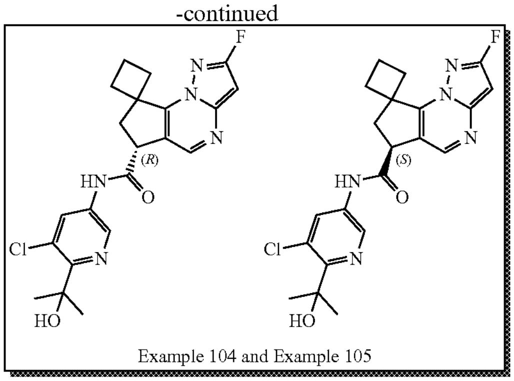

Example 104 and Example 105

Examples 104 and 105: Single Enantiomers Obtained from a Racemic Mixture Containing (R)—N-(5-chloro-6-(2-hydroxypropan-2-yl)pyridin-3-yl)-2'-fluoro-6',7'-dihydrospiro[cyclobutane-1,8'-cyclopenta[a]pyrazolo[1,5-a]pyrimidine]-6'-carboxamide and (S)—N-(5-chloro-6-(2-hydroxypropan-2-yl)pyridin-3-yl)-2'-fluoro-6',7'-dihydrospiro[cyclobutane-1,8'-cyclopenta[a]pyrazolo[1,5-a]pyrimidine]-6'-carboxamide Step 1: 2-(5-bromo-3-chloropyridin-2-yl)propan-2-ol

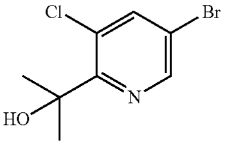

To a stirred solution of methyl 5-bromo-3-chloropicolinate (1 g, 4.0 mmol) in THF (10 mL) was added methylmagnesium bromide (8.8 mL, 8.8 mmol, 1M in THF) at 0° C. The reaction was stirred at 25° C. for 2 h. The reaction mixture was quenched with water (10 mL). The resulting solution was extracted with ethyl acetate (3×10 mL). The combined organic layers were dried over anhydrous sodium sulfate and concentrated under reduced pressure. The residue was applied onto a silica gel column and eluted with EtOAc/PE (4:1) to give 2-(5-bromo-3-chloropyridin-2-yl)propan-2-ol (500 mg, 50% yield) as a white solid. $^1H$ NMR (300 MHz, Chloroform-d) δ: 8.51 (d, J=2.0 Hz, 1H), 7.90 (d, J=1.9 Hz, 1H), 4.78 (br, 1H), 1.67 (s, 6H). LC-MS: m/z 250 $[M+H]^+$.

Step 2: 2'-fluoro-6',7'-dihydrospiro[cyclobutane-1,8'-cyclopenta[e]pyrazolo[1,5-a]pyrimidine]-6'-carboxamide

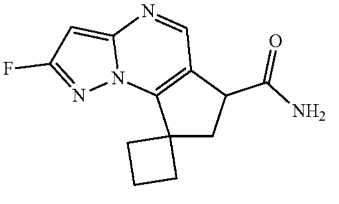 [SMILES: NC(=O)C1CC2(CCC2)c2c1cnc1cc(F)nn21]

To a solution of 2'-fluoro-6',7'-dihydrospiro[cyclobutane-1,8'-cyclopenta[e]pyrazolo[1,5-a]pyrimidine]-6'-carbonitrile (Method Z2 step 3; 600 mg, 1.2 mmol) in 12 M hydrogen chloride (6 mL) was added acetic acid (6 mL). The resulting mixture was stirred at 25° C. for 1 h. The reaction mixture was diluted with water (100 mL). The pH was adjusted to 5-6 with saturated aqueous sodium bicarbonate solution. The resulting solution was extracted with ethyl acetate (3×100 mL). The combined organic layers were dried over anhydrous sodium sulfate and concentrated under reduced pressure. The residue was applied onto a silica gel column and eluted with MeOH/DCM (1:10) to give 2'-fluoro-6',7'-dihydrospiro[cyclobutane-1,8'-cyclopenta[e]pyrazolo[1,5-a]pyrimidine]-6'-carboxamide (Method A3 step 2; 250 mg, 77% yield) as an off-white solid. LC-MS: m/z 261 $[M+H]^+$.

Step 3: N-(5-chloro-6-(2-hydroxypropan-2-yl)pyridin-3-yl)-2'-fluoro-6',7'-dihydrospiro[cyclobutane-1,8'-cyclopenta[e]pyrazolo[1,5-a]pyrimidine]-6'-carboxamide

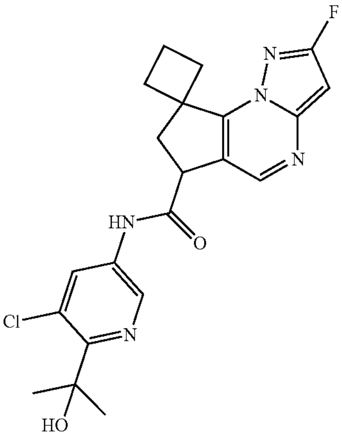 [SMILES: CC(C)(O)c1ncc(NC(=O)C2CC3(CCC3)c3c2cnc2cc(F)nn32)cc1Cl]

To a stirred mixture of 2'-fluoro-6',7'-dihydrospiro[cyclobutane-1,8'-cyclopenta[e]pyrazolo[1,5-a]pyrimidine]-6'-carboxamide (40 mg, 153.7 μmol) in dioxane (2 mL) was added 2-(5-bromo-3-chloropyridin-2-yl)propan-2-ol (77 mg, 307.4 μmol), $Cs_2CO_3$ (100 mg, 307.4 μmol), Xantphos (18 mg, 30.7 μmol) and $Pd_2(dba)_3$ (32 mg, 30.7 μmol). The mixture was stirred at 100° C. for 2 h under nitrogen atmosphere. The mixture was cooled to 25° C. The reaction mixture was diluted with water (10 mL). The resulting solution was extracted with ethyl acetate (3×10 mL). The combined organic layers were dried over anhydrous sodium sulfate and concentrated under reduced pressure. The residue was applied onto a silica gel column and eluted with EtOAc/PE (1:1) to give the crude product. The crude product was purified by Prep-HPLC and the collected fractions were lyophilized to afford N-(5-chloro-6-(2-hydroxypropan-2-yl)pyridin-3-yl)-2'-fluoro-6',7'-dihydrospiro[cyclobutane-1,8'-cyclopenta[e]pyrazolo[1,5-a]pyrimidine]-6'-carboxamide (24 mg, 36% yield) as a white solid. LC-MS: m/z 430 $[M+H]^+$.

Step 4: Separation of Enantiomers to Obtain (R)—N-(5-chloro-6-(2-hydroxypropan-2-yl)pyridin-3-yl)-2'-fluoro-6',7'-dihydrospiro[cyclobutane-1,8'-cyclopenta[e]pyrazolo[1,5-a]pyrimidine]-6'-carboxamide and (S)—N-(5-chloro-6-(2-hydroxypropan-2-yl)pyridin-3-yl)-2'-fluoro-6',7'-dihydrospiro[cyclobutane-1,8'-cyclopenta[e]pyrazolo[1,5-a]pyrimidine]-6'-carboxamide

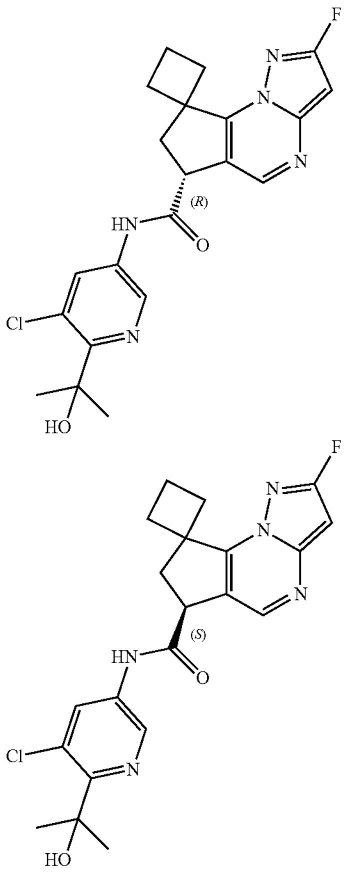

Example 104 and 105

22 mg of N-(5-chloro-6-(2-hydroxypropan-2-yl)pyridin-3-yl)-2-fluoro-6',7'-dihydrospiro[cyclobutane-1,8'-cyclopenta[e]pyrazolo[1,5-a]pyrimidine]-6'-carboxamide were submitted to chiral HPLC purification (Column: CHIRAL ART Cellulose-SA, 2×25 cm, 5 μm; Mobile Phase A: Hex(0.1% FA)-HPLC, Mobile Phase B: EtOH-HPLC; Flow rate: 20 mL/min; isocratic 30% B in 8 min; Wave Length: 220/254 nm; RT1(min): 4.29; RT2(min): 5.94; Sample Solvent: EtOH-HPLC; Injection Volume: 0.4 mL; Number Of Runs: 7). The first eluting isomer was concentrated and lyophilized to afford Example 104 (8.1 mg, 37% yield) as a white solid. The second eluting isomer was concentrated and lyophilized to afford Example 105 (7.9 mg, 35% yield) as a white solid.

Example 104: $^1$H NMR (400 MHz, DMSO-$d_6$) δ: 10.72 (s, 1H), 8.60-8.62 (m, 2H), 8.22 (d, J=2.0 Hz, 1H), 6.58 (d, J=4.8 Hz, 1H), 5.35 (s, 1H), 4.32-4.33 (m, 1H), 3.09-3.17 (m, 2H), 2.83-2.88 (m, 1H), 2.65-2.69 (m, 1H), 2.13-2.20 (m, 4H), 1.56 (s, 6H). LC-MS: m/z 430.0 [M+H]$^+$.

Example 105: $^1$H NMR (400 MHz, DMSO-$d_6$) δ: 10.72 (s, 1H), 8.60-8.62 (m, 2H), 8.22 (d, J=2.0 Hz, 1H), 6.58 (d, J=4.8 Hz, 1H), 5.34 (br, 1H), 4.32-4.35 (m, 1H), 3.10-3.18 (m, 2H), 2.83-2.89 (m, 1H), 2.65-2.70 (m, 1H), 2.10-2.22 (m, 4H), 1.56 (s, 6H). LC-MS: m/z 430.0 [M+H]$^+$.

Method B3

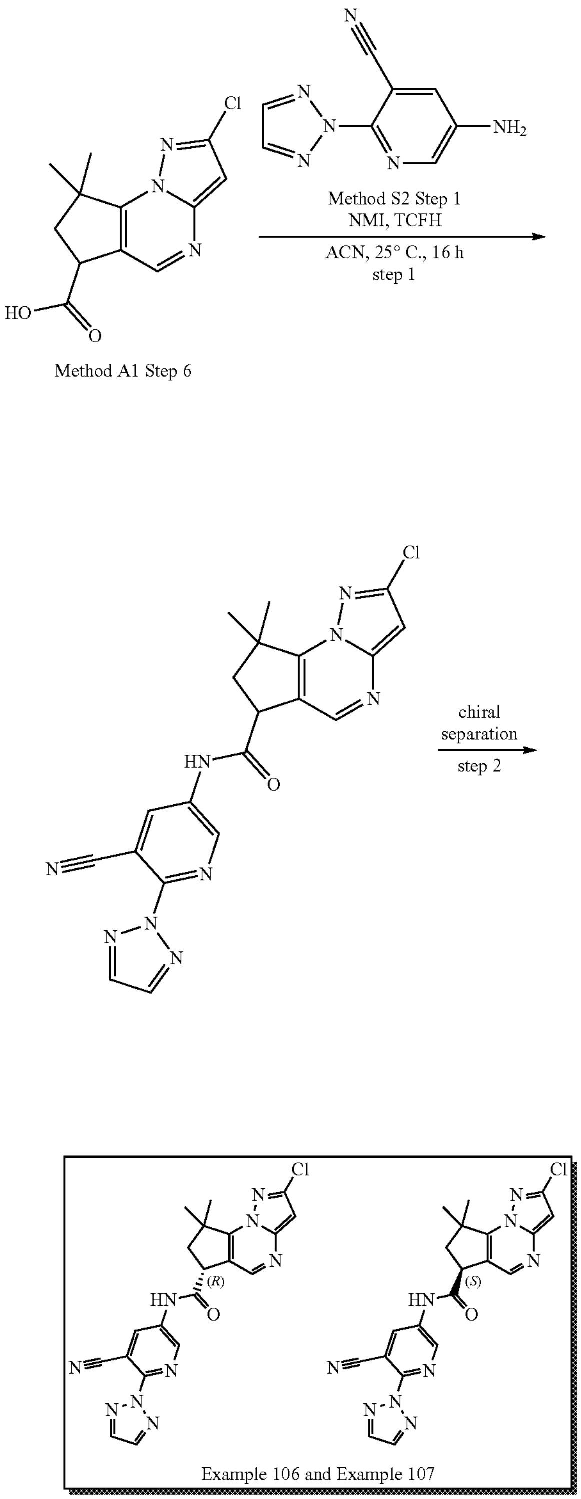

Examples 106 and 107: Single Enantiomers Obtained from a Racemic Mixture Containing (R)-2-chloro-N-(5-cyano-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-cyano-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

Step 1: 2-chloro-N-(5-cyano-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

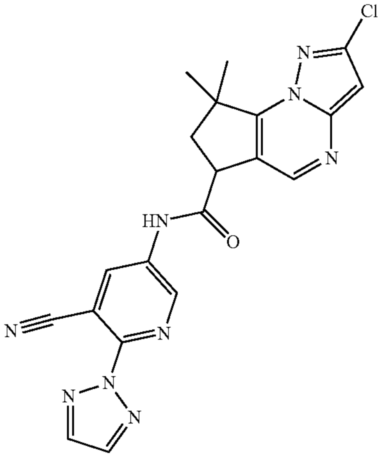 [SMILES: CC1(C)CC(C(=O)Nc2cnc(-n3nccn3)c(C#N)c2)c2cnc3cc(Cl)nn3c21]

To a stirred solution of 5-amino-2-(2H-1,2,3-triazol-2-yl)nicotinonitrile (Method S2 step 1; 70 mg, 376.4 μmol) and 2-chloro-8,8-dimethyl-7,8-dihydro-6H-cyclopenta[e]pyrazolo[1,5-a]pyrimidine-6-carboxylic acid (Method A1 step 6; 100 mg, 376.4 μmol) in ACN (2 mL) was added TCFH (317 mg, 1.1 mmol) and NMI (93 mg, 1.1 mmol). The reaction mixture was stirred at 25° C. for 16 h. The resulting mixture was concentrated under reduced pressure. The residue was submitted to Prep-HPLC purification and the collected fractions were lyophilized to give 2-chloro-N-(5-cyano-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide (50 mg, 30% yield) as a white solid. LC-MS: m/z 434 $[M+H]^+$.

Step 2: Separation of Enantiomers to Obtain (R)-2-chloro-N-(5-cyano-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-cyano-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide

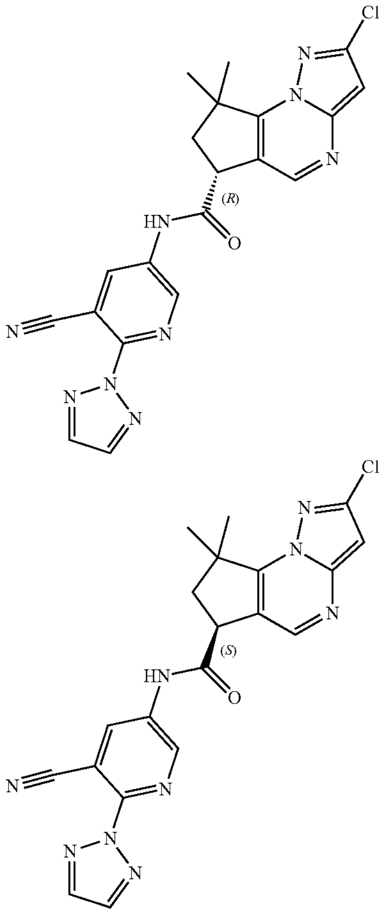

Example 106 and Example 107

50 mg of 2-chloro-N-(5-cyano-6-(2H-1,2,3-triazol-2-yl)pyridin-3-yl)-8,8-dimethyl-7,8-dihydro-6H-cyclopenta[e]pyrazolo[1,5-a]pyrimidine-6-carboxamide were submitted to chiral HPLC (Column: CHIRAL ART Amylose-SA, 2*25 cm, 5 μm; Mobile Phase A: Hex:DCM=3:1 (0.5% 2M $NH_3$-MeOH)-HPLC, Mobile Phase B: EtOH-HPLC; Flow rate: 20 mL/min; isocratic 30% B in 9.5 min; Wave Length: 220/254 nm; RT1(min): 6.28; RT2(min): 8.51; Sample Solvent: ETOH:DCM=1:1; Injection Volume: 1 mL; Number Of Runs: 5). The first eluting isomer was concentrated and lyophilized to afford Example 106 (22.2 mg, 43% yield) as a white solid. The second eluting isomer was concentrated and lyophilized to afford Example 107 (21.2 mg, 42% yield) as a white solid.

Example 106: $^1H$ NMR (400 MHz, Chloroform-d) δ: 8.90 (d, J=2.4 Hz, 1H), 8.87 (d, J=2.4 Hz, 1H), 8.72 (s, 1H), 8.38 (s, 1H), 8.01 (s, 2H), 6.76 (s, 1H), 4.38 (dd, J=6.8, 8.8 Hz, 1H), 2.62 (dd, J=9.2, 13.2 Hz, 1H), 2.54 (dd, J=6.8, 13.2 Hz, 1H), 1.82 (s, 3H), 1.66 (s, 3H). LC-MS: m/z 434.0 $[M+H]^+$.

Example 107: $^{1}$H NMR (400 MHz, Chloroform-d) δ: 8.90 (d, J=2.4 Hz, 1H), 8.87 (d, J=2.4 Hz, 1H), 8.70 (s, 1H), 8.38 (s, 1H), 8.01 (s, 2H), 6.75 (s, 1H), 4.37 (dd, J=6.8, 8.8 Hz, 1H), 2.62 (dd, J=8.8, 13.2 Hz, 1H), 2.54 (dd, J=6.4, 12.8 Hz, 1H), 1.81 (s, 3H), 1.66 (s, 3H). LC-MS: m/z 434.0 [M+H]$^{+}$.

The absolute stereochemistry for each separated isomer was not determined.

Method C3

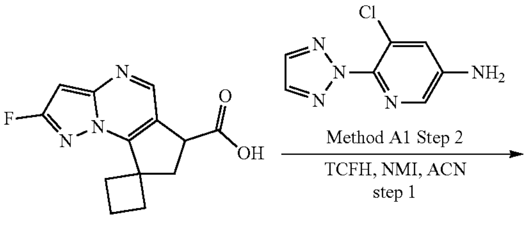

Method Z2 Step 4

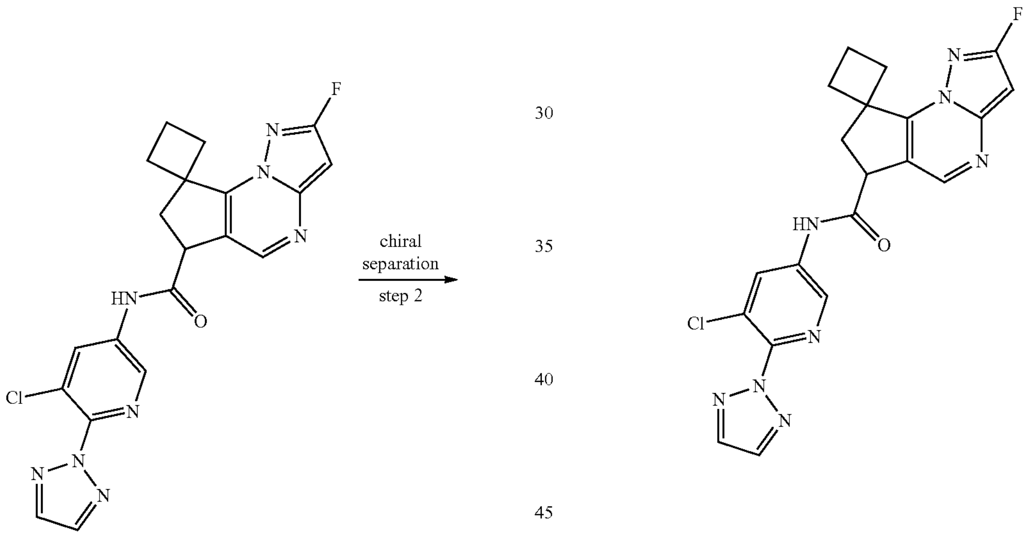

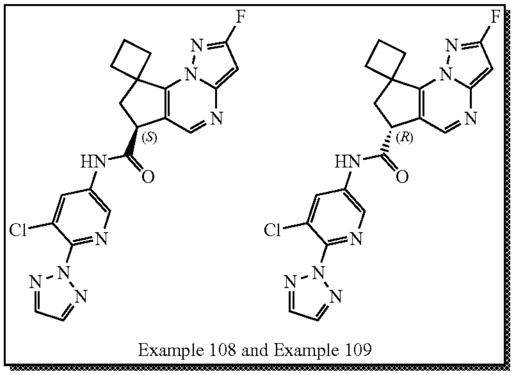

Example 108 and Example 109

Examples 108 and 109: Single Enantiomers Obtained from a Racemic Mixture Containing (S)—N-(5-chloro-6-(2H-1,2,3-triazol-2-yl)pyridin-3-yl)-2'-fluoro-6',7'-dihydrospiro[cyclobutane-1,8'-cyclopenta[a]pyrazolo[1,5-a]pyrimidine]-6'-carboxamide and (R)—N-(5-chloro-6-(2H-1,2,3-triazol-2-yl)pyridin-3-yl)-2'-fluoro-6',7'-dihydrospiro[cyclobutane-1,8'-cyclopenta[a]pyrazolo[1,5-a]pyrimidine]-6'-carboxamide Step 1: N-(5-chloro-6-(2H-1,2,3-triazol-2-yl)pyridin-3-yl)-2'-fluoro-6',7'-dihydrospiro[cyclobutane-1,8'-cyclopenta[e]pyrazolo[1,5-a]pyrimidine]-6'-carboxamide To a stirred solution of 2'-fluoro-6',7'-dihydrospiro[cyclobutane-1,8'-cyclopenta[e]pyrazolo[1,5-a]pyrimidine]-6'-carboxylic acid (Method Z2 step 4; 120 mg, 459.5 μmol) in ACN (10 mL) was added 5-chloro-6-(2H-1,2,3-triazol-2-yl)pyridin-3-amine (Method A1 step 2; 90 mg, 459.5 μmol), TCFH (515 mg, 1.8 mmol) and NMI (150 mg, 1.8 mmol). The resulting mixture was stirred at 25° C. for 16 h. The resulting mixture was concentrated under reduced pressure. The residue was submitted to Prep-HPLC purification and the collected fractions were lyophilized to give N-(5-chloro-6-(2H-1,2,3-triazol-2-yl)pyridin-3-yl)-2'-fluoro-6',7'-dihydrospiro[cyclobutane-1,8'-cyclopenta[e]pyrazolo[1,5-a]pyrimidine]-6'-carboxamide (60 mg, 30% yield) as a white solid. LC-MS (ES, m/z): 439[M+H].

Step 2: Separation of Enantiomers to Obtain (S)—N-(5-chloro-6-(2H-1,2,3-triazol-2-yl)pyridin-3-yl)-2'-fluoro-6',7'-dihydrospiro[cyclobutane-1,8'-cyclopenta[e]pyrazolo[1,5-a]pyrimidine]-6'-carboxamide and (R)—N-(5-chloro-6-(2H-1,2,3-triazol-2-yl)pyridin-3-yl)-2'-fluoro-6',7'-dihydrospiro[cyclobutane-1,8'-cyclopenta[e]pyrazolo[1,5-a]pyrimidine]-6'-carboxamide

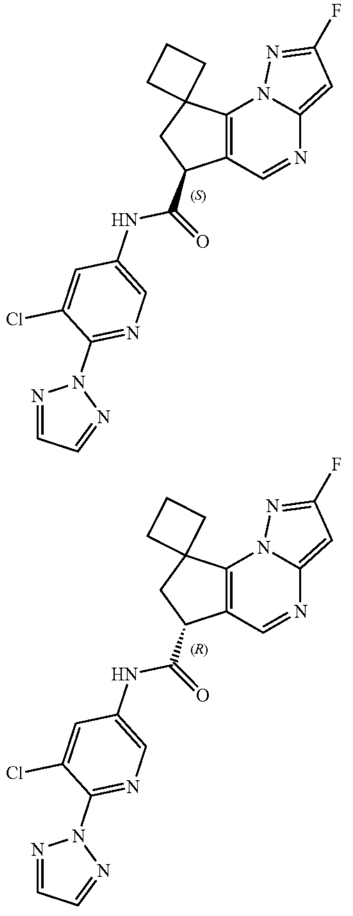

Example 108 and Example 109

58 mg of N-(5-chloro-6-(2H-1,2,3-triazol-2-yl)pyridin-3-yl)-2'-fluoro-6',7'-dihydrospiro[cyclobutane-1,8'-cyclopenta[e]pyrazolo[1,5-a]pyrimidine]-6'-carboxamide were submitted to chiral HPLC purification (Column: CHIRAL ART Cellulose-SC, 2*25 cm, 5 μm; Mobile Phase A: Hex(0.1% FA)-HPLC, Mobile Phase B: EtOH-HPLC; Flow rate: 20 mL/min; isocratic 50% B in 16 min; Wave Length: 220/254 nm; RT1(min): 11.11; RT2(min): 13.15; Sample Solvent: EtOH-HPLC; Injection Volume: 0.5 mL; Number Of Runs: 6). The first eluting isomer was concentrated and lyophilized to afford Example 108 (20.6 mg, 36% yield) as an off white solid. The second eluting isomer was concentrated and lyophilized to afford Example 109 (20.6 mg, 36% yield) as an off white solid.

Example 108: $^1$H NMR (300 MHz, DMSO-$d_6$) δ: 11.07 (s, 1H), 8.73 (d, J=2.4 Hz, 1H), 8.64 (s, 1H), 8.57 (d, J=2.4 Hz, 1H), 8.18 (s, 2H), 6.60 (d, J=4.8 Hz, 1H), 4.37-4.42 (m, 1H), 3.06-3.20 (m, 2H), 2.82-2.93 (m, 1H), 2.69-2.77 (m, 1H), 2.08-2.24 (m, 4H). LCMS (ES, m/z): 439.1 [M+H]$^+$.

Example 109: $^1$H NMR (300 MHz, DMSO-$d_6$) δ: 11.07 (s, 1H), 8.72 (d, J=2.1 Hz, 1H), 8.65 (s, 1H), 8.57 (d, J=2.1 Hz, 1H), 8.18 (s, 2H), 6.61 (d, J=5.1 Hz, 1H), 4.34-4.42 (m, 1H), 3.08-3.22 (m, 2H), 2.86-2.93 (m, 1H), 2.69-2.75 (m, 1H), 2.18-2.28 (m, 4H). LC-MS (ES, m/z): 439.1 [M+H]$^+$.

The absolute stereochemistry for each separated isomer was not determined.

Method D3

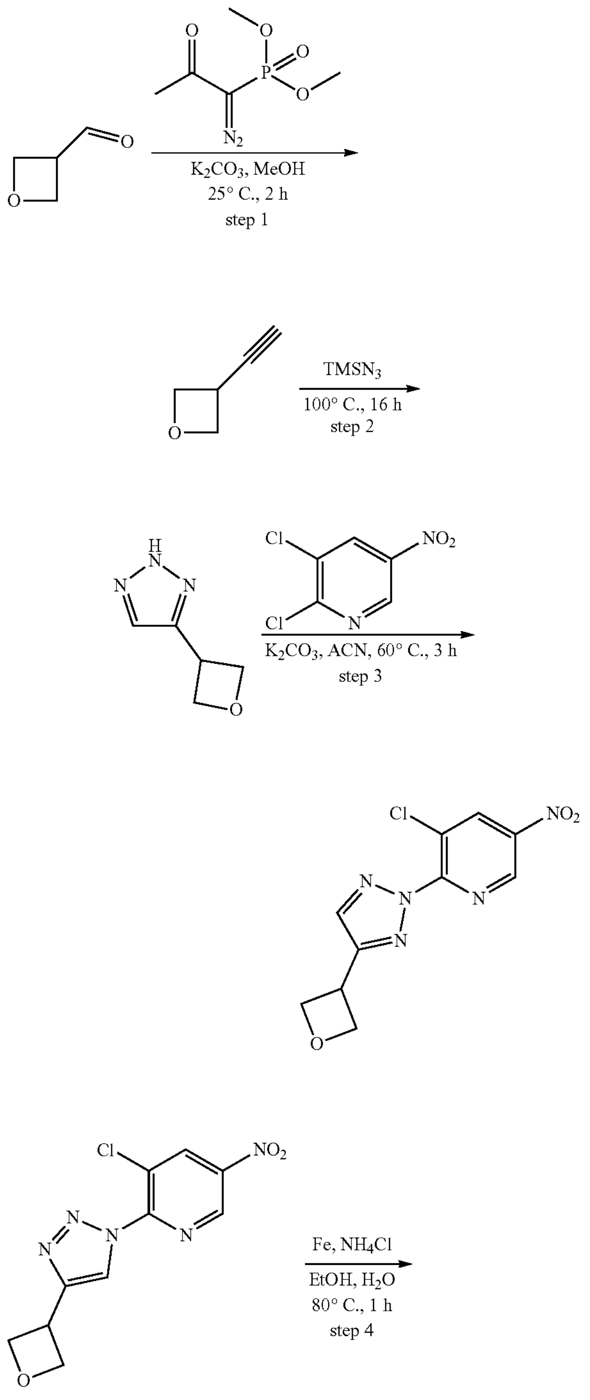

Method D3 Step 3-I

-continued

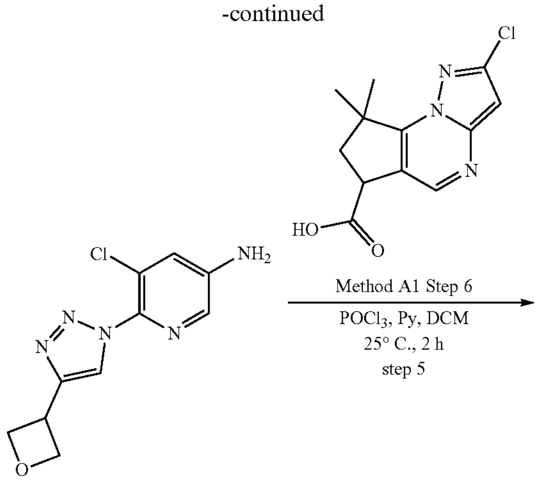

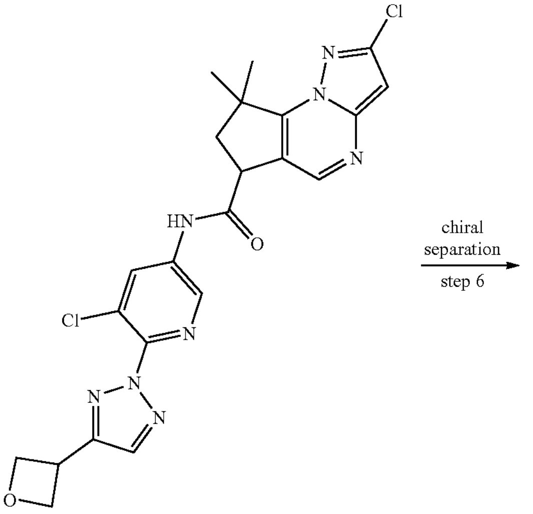

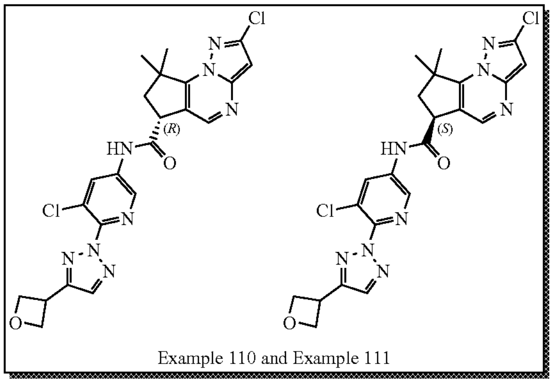

Example 110 and Example 111

Examples 110 and 111: Single Enantiomers Obtained from a Racemic Mixture Containing (R)-2-chloro-N-(5-chloro-6-(4-(oxetan-3-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(4-(oxetan-3-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide Step 1: 3-ethynyloxetane

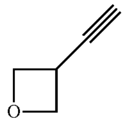

To a stirred solution of dimethyl (1-diazo-2-oxopropyl) phosphonate (15.6 g, 81.3 mmol) in MeOH (7.5 mL) was added $K_2CO_3$ (18.5 g, 133.6 mmol) and oxetane-3-carbaldehyde (5 g, 58.1 mmol) at 0° C. The reaction was stirred at 25° C. for 2 h. The reaction mixture was quenched with water (15 mL). The resulting solution was extracted with DCM (2×30 mL). The combined organic layers were dried over anhydrous sodium sulfate and concentrated to afford 3-ethynyloxetane (9.0 g, crude) as a yellow oil. $^1$H NMR (400 MHz, Chloroform-d) δ: 4.78-4.82 (m, 2H), 4.70-4.75 (m, 2H), 3.83-3.91 (m, 1H), 2.36 (d, J=2.4 Hz, 1H).

Step 2: 4-(oxetan-3-yl)-2H-1,2,3-triazole

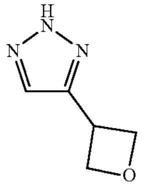

A solution of 3-ethynyloxetane (9 g, 109.6 mmol) in azidotrimethylsilane (9 mL) was stirred at 100° C. for 16 h. The reaction mixture was concentrated under reduced pressure. The residue was purified by prep-HPLC and the collected fractions were concentrated under reduced pressure to give 4-(oxetan-3-yl)-2H-1,2,3-triazole (200 mg, 1% yield) as a yellow oil. $^1$H NMR (400 MHz, Chloroform-d) δ: 7.71 (s, 1H), 5.04-5.09 (m, 2H), 4.83-4.87 (m, 2H), 4.39-4.50 (m, 1H). LC-MS: m/z 126 [M+H]$^+$.

Step 3: 3-chloro-5-nitro-2-(4-(oxetan-3-yl)-2H-1,2,3-triazol-2-yl)pyridine and 3-chloro-5-nitro-2-(4-(oxetan-3-yl)-1H-1,2,3-triazol-1-yl)pyridine

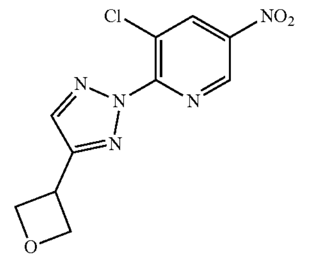

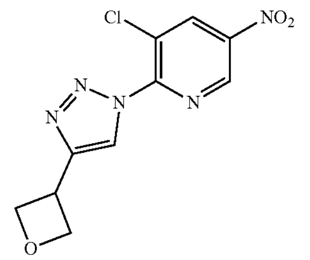

To a solution of 4-(oxetan-3-yl)-2H-1,2,3-triazole (200 mg, 1.3 mmol) and 2,3-dichloro-5-nitro-pyridine (247 mg, 1.3 mmol) in ACN (10 mL) was added $K_2CO_3$ (530 mg, 3.8 mmol). The mixture was stirred at 60° C. for 3 h. The reaction mixture was diluted with water (30 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:1) to give 3-chloro-5-nitro-2-(4-(oxetan-3-yl)-2H-1,2,3-triazol-2-yl)pyridine (200 mg, 55% yield) as a yellow oil and 3-chloro-5-nitro-2-(4-(oxetan-3-yl)-1H-1,2,3-triazol-1-yl)pyridine (Method D3 step 3-i; 100 mg, 27% yield) as a yellow oil. LC-MS: m/z 282 $[M+H]^+$.

Step 4: 5-chloro-6-(4-(oxetan-3-yl)-2H-1,2,3-triazol-2-yl)pyridin-3-amine

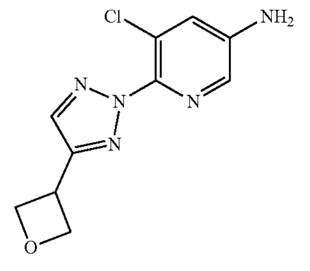 [SMILES: Nc1cnc(-n2ncc(C3COC3)n2)c(Cl)c1]

To a solution of 3-chloro-5-nitro-2-(4-(oxetan-3-yl)-2H-1,2,3-triazol-2-yl)pyridine (200 mg, 710.1 μmol) in EtOH (9 mL) and water (3 mL) was added Fe (198 mg, 3.6 mmol) and Ammonium chloride (114 mg, 2.1 mmol). The mixture was stirred at 80° C. for 1 h. After cooled to 25° C., the solid was filtered out. The filtrate was concentrated under reduced pressure. The residue was diluted with water (10 mL), and the resulting solution was extracted with ethyl acetate (3×10 mL). The combined organic layers were dried over anhydrous sodium sulfate and concentrated under reduced pressure to give 5-chloro-6-(4-(oxetan-3-yl)-2H-1,2,3-triazol-2-yl)pyridin-3-amine (160 mg, 89% yield) as a light brown solid. LC-MS: m/z 252 $[M+H]^+$.

Step 5: 2-chloro-N-(5-chloro-6-(4-(oxetan-3-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide

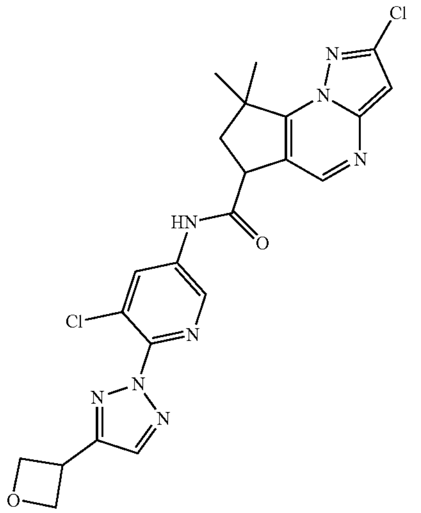

To a solution of 2-chloro-8,8-dimethyl-7,8-dihydro-6H-cyclopenta[e]pyrazolo[1,5-a]pyrimidine-6-carboxylic acid (Method A1 step 6; 105 mg, 397 μmol) in DCM (2 mL) was added phosphoryl trichloride (183 mg, 1.2 mmol) at 0° C. The resulting mixture was stirred at 25° C. for 1 h. Then 5-chloro-6-(4-(oxetan-3-yl)-2H-1,2,3-triazol-2-yl)pyridin-3-amine (100 mg, 397 μmol) and pyridine (314 mg, 4.0 mmol) were added. The resulting mixture was stirred at 25° C. for 2 h.

The reaction mixture was quenched with water (20 mL). The resulting solution was extracted with DCM (3×20 mL). The combined organic layers were dried over anhydrous sodium sulfate and concentrated under reduced pressure. The residue was submitted to Prep-HPLC purification and the collected fractions were lyophilized to give 2-chloro-N-(5-chloro-6-(4-(oxetan-3-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide (18 mg, 9% yield) as a white solid. LC-MS: m/z 499 $[M+H]^+$.

Step 6: Separation of Enantiomers to Obtain (R)-2-chloro-N-(5-chloro-6-(4-(oxetan-3-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(4-(oxetan-3-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide

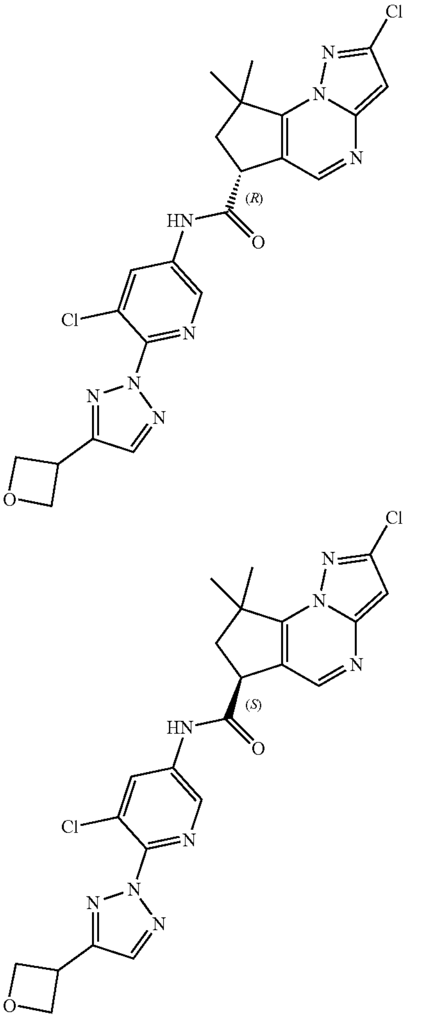

Example 110 and Example 111

18 mg of 2-chloro-N-(5-chloro-6-(4-(oxetan-3-yl)-2H-1,2,3-triazol-2-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IG, 2*25 cm, 5 μm; Mobile Phase A: Hex:DCM=3:1 (0.5% 2M $NH_3$-MeOH)-HPLC, Mobile Phase B: EtOH-HPLC; Flow rate: 20 mL/min; isocratic 30% B in 29 min; Wave Length: 220/254 nm; RT1(min): 15.61; RT2 (min): 25.30; Sample Solvent: ETOH:DCM=1:1; Injection Volume: 3 mL; Number Of Runs: 1). The first eluting isomer was concentrated and lyophilized to afford Example 110 (5.1 mg, 28% yield) as a white solid. The second eluting isomer was concentrated and lyophilized to afford Example 111 (3.4 mg, 19% yield) as a light yellow solid.

Example 110: $^1H$ NMR (400 MHz, DMSO-$d_6$) δ: 11.07 (s, 1H), 8.72 (d, J=2.4 Hz, 1H), 8.66 (s, 1H), 8.57 (d, J=2.0 Hz, 1H), 8.21 (s, 1H), 6.95 (s, 1H), 4.94-4.97 (m, 2H), 4.73-4.76 (m, 2H), 4.45-4.52 (m, 2H), 2.54-2.60 (m, 1H), 2.33-2.36 (m, 1H), 1.64 (s, 3H), 1.56 (s, 3H). LC-MS: m/z 499.1 $[M+H]^+$.

Example 111: $^1H$ NMR (400 MHz, DMSO-$d_6$) δ: 11.07 (s, 1H), 8.72 (d, J=1.6 Hz, 1H), 8.66 (s, 1H), 8.57 (d, J=1.6 Hz, 1H), 8.21 (s, 1H), 6.95 (s, 1H), 4.94-4.97 (m, 2H), 4.73-4.76 (m, 2H), 4.43-4.52 (m, 2H), 2.54-2.61 (m, 1H), 2.33-2.36 (m, 1H), 1.64 (s, 3H), 1.56 (s, 3H). LC-MS: m/z 499.1 $[M+H]^+$.

The absolute stereochemistry for each separated isomer was not determined.

Method E3

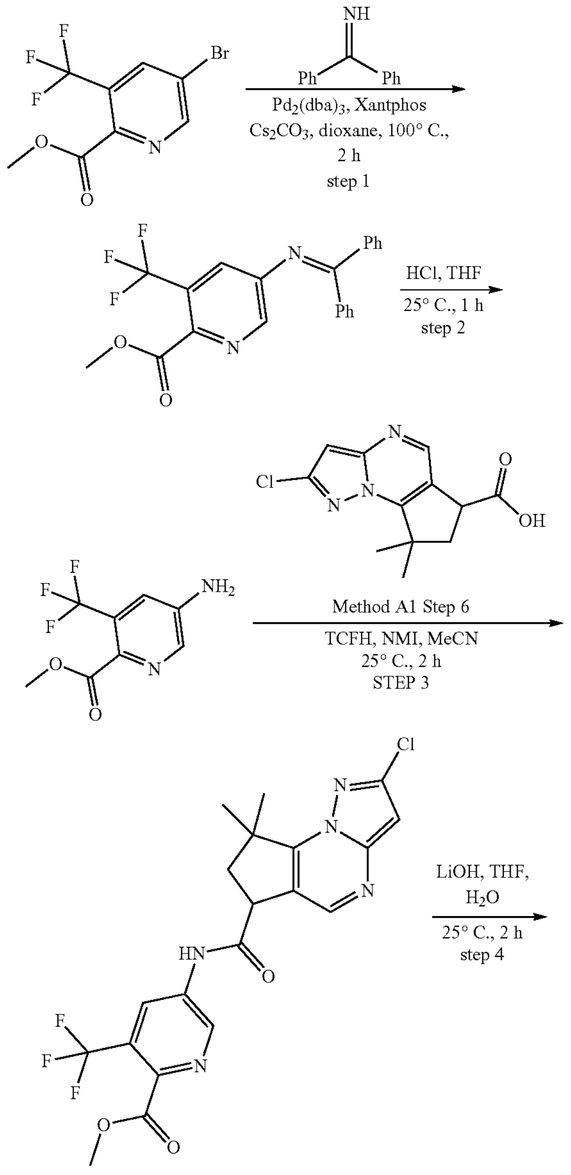

-continued

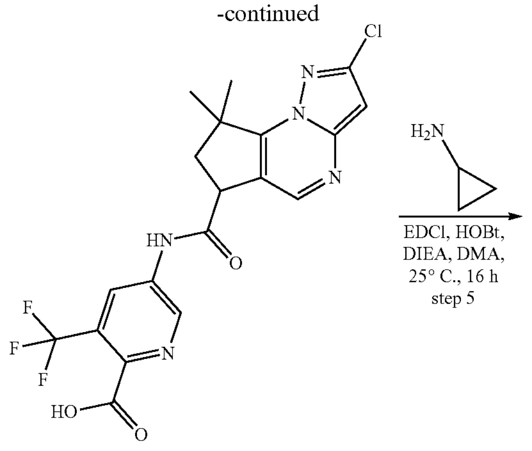

Method E3 Step 4

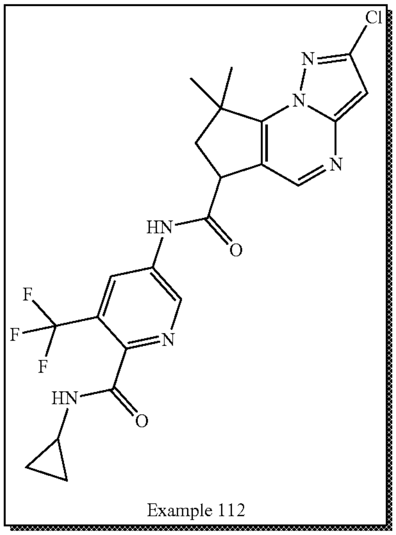

Example 112

Example 112: 2-chloro-N-(6-(cyclopropylcarbamoyl)-5~(trifluoromethyl)pyridin-3-yl)-8,8-dimethyl-7,8-dihydro-6H-cyclopenta[e]pyrazolo[1,5-a]pyrimidine-6-carboxamide Step 1: methyl 5-((diphenylmethylene)amino)-3-(trifluoromethyl)picolinate

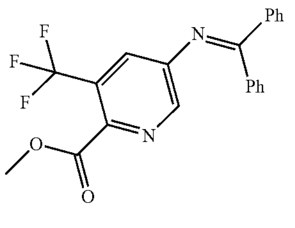 [SMILES: COC(=O)c1ncc(N=C(c2ccccc2)c2ccccc2)cc1C(F)(F)F]

To a mixture of methyl 5-bromo-3-(trifluoromethyl)picolinate (500 mg, 1.8 mmol) in dioxane (5 mL) were added cesium carbonate (1.2 g, 3.5 mmol), diphenylmethanimine (638 mg, 3.5 mmol), XantPhos (204 mg, 352.1 μmol) and $Pd_2(dba)_3$ (180 mg, 176. μmol). The mixture was stirred at 100° C. for 2 h. The reaction solution was concentrated under reduced pressure. The residue was diluted with water (30 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:1) to give methyl 5-((diphenylmethylene)amino)-3-(trifluoromethyl)picolinate (400 mg, 59% yield) as a white solid. LC-MS: m/z 385 $[M+H]^+$.

Step 2: methyl 5-amino-3-(trifluoromethyl)picolinate

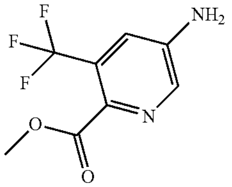

To a mixture of methyl 5-((diphenylmethylene)amino)-3-(trifluoromethyl)picolinate (400 mg, 1.0 mmol) in THE (5 mL) was added 1M HCl (4 mL). The mixture was stirred at 25° C. for 1 h. The reaction solution was concentrated under reduced pressure. The residue was diluted with water (30 mL). The pH was adjusted to 7-8 with saturated aqueous sodium bicarbonate solution. The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:1) to give methyl 5-amino-3-(trifluoromethyl)picolinate (220 mg, 96% yield) as a yellow oil. LC-MS: m/z 221 $[M+H]^+$.

Step 3: methyl 5~(2-chloro-8,8-dimethyl-7,8-dihydro-6H-cyclopenta[e]pyrazolo[1,5-a]pyrimidine-6-carboxamido)-3-(trifluoromethyl)picolinate

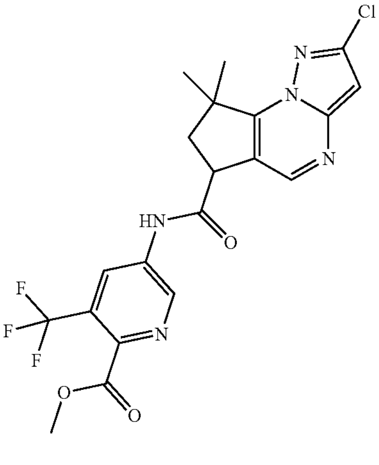 [SMILES: COC(=O)c1ncc(NC(=O)C2CC(C)(C)c3c2cnc2cc(Cl)nn32)cc1C(F)(F)F]

To a solution of methyl 5-amino-3-(trifluoromethyl)picolinate (200 mg, 908.5 μmol) in ACN (2 mL), was added 2-chloro-8,8-dimethyl-7,8-dihydro-6H-cyclopenta[e]pyrazolo[1,5-a]pyrimidine-6-carboxylic acid (Method A1 step 6; 241 mg, 908.5 μmol), NMI (302 mg, 3.6 mmol) and TCFH (1.0 g, 3.6 mmol). The resulting mixture was stirred at 25°

C. for 2 h. The reaction mixture was quenched with water (50 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:1) to give methyl 5~(2-chloro-8,8-dimethyl-7,8-dihydro-6H-cyclopenta[e]pyrazolo[1,5-a]pyrimidine-6-carboxamido)-3-(trifluoromethyl)picolinate (400 mg, 75% yield) as a light yellow oil. LC-MS: m/z 468 $[M+H]^+$.

Step 4: 5-(2-chloro-8,8-dimethyl-7,8-dihydro-6H-cyclopenta[e]pyrazolo[1,5-a]pyrimidine-6-carboxamido)-3-(trifluoromethyl)picolinic acid

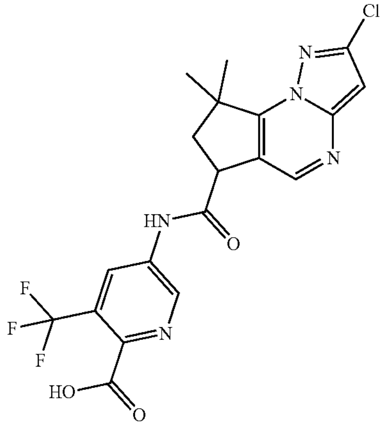 [SMILES: CC1(C)CC(C(=O)Nc2cnc(C(=O)O)c(C(F)(F)F)c2)c2cnc3cc(Cl)nn3c21]

To a solution of methyl 5~(2-chloro-8,8-dimethyl-7,8-dihydro-6H-cyclopenta[e]pyrazolo[1,5-a]pyrimidine-6-carboxamido)-3-(trifluoromethyl)picolinate (500 mg, 8551 μmol) in THE (3.2 mL), water (0.8 mL) and EtOH (0.8 mL) was added lithium hydroxide (205 mg, 8.6 mmol). The resulting mixture was stirred at 25° C. for 2 h. The mixture was concentrated under reduced pressure. The residue was diluted with water (20 mL). The pH was adjusted to 3-4 with 1M HCl. The resulting solution was extracted with ethyl acetate (3×20 mL). The combined organic layers were dried over anhydrous sodium sulfate and concentrated under reduced pressure afford 5~(2-chloro-8,8-dimethyl-7,8-dihydro-6H-cyclopenta[e]pyrazolo[1,5-a]pyrimidine-6-carboxamido)-3-(trifluoromethyl)picolinic acid (Method E3 step 4; 150 mg, 31% yield) as a white solid. LC-MS: m/z 454 $[M+H]^+$.

Step 5: 2-chloro-N-(6-(cyclopropylcarbamoyl)-5~(trifluoromethyl)pyridin-3-yl)-8,8-dimethyl-7,8-dihydro-6H-cyclopenta[e]pyrazolo[1,5-a]pyrimidine-6-carboxamide Example 112

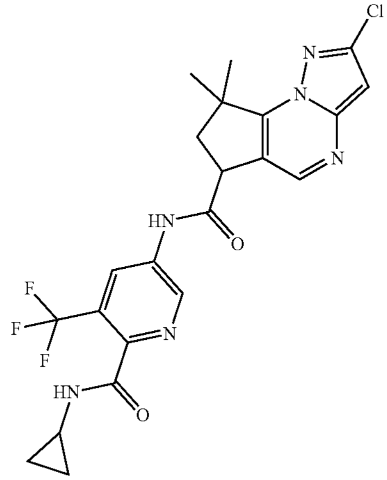

To a solution of 5~(2-chloro-8,8-dimethyl-7,8-dihydro-6H-cyclopenta[e]pyrazolo[1,5-a]pyrimidine-6-carboxamido)-3-(trifluoromethyl)picolinic acid (30 mg, 66.1 μmol) in DMF (0.5 mL) were added Cyclopropylamine (7.4 mg, 79.3 μmol), EDCI (19 mg, 99.2 μmol), HOBT (13.4 mg, 99.2 μmol) and DIEA (12.8 mg, 99.2 μmol). The resulting mixture was stirred at 25° C. for 16 h. The mixture was concentrated under reduced pressure. The residue was submitted to Prep-HPLC purification and the collected fractions were lyophilized to give Example 112 (2.2 mg, 7% yield) as a white solid.

Example 112: $^1H$ NMR (400 MHz, Chloroform-d) δ: 9.00 (s, 1H), 8.51 (s, 1H), 8.39-8.42 (m, 2H), 7.71 (d, J=2.4 Hz, 1H), 6.71 (s, 1H), 4.31-4.36 (m, 1H), 2.87-2.90 (m, 1H), 2.56-2.63 (m, 1H), 2.44-2.51 (m, 1H), 1.80 (s, 3H), 1.64 (s, 3H), 0.85-0.94 (m, 2H), 0.65-0.74 (m, 2H). LC-MS: m/z 493.2 $[M+H]^+$.

Method F3

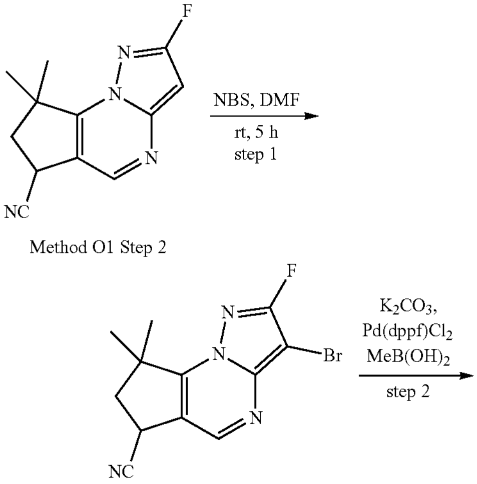

-continued

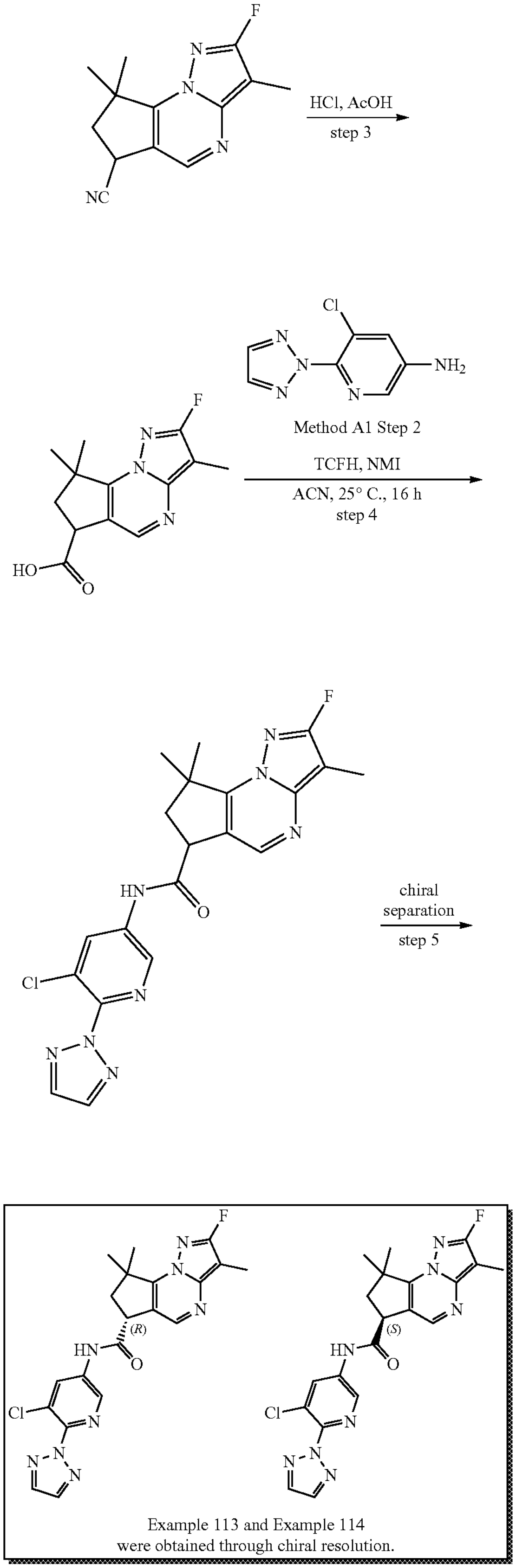

Example 113 and Example 114
were obtained through chiral resolution.

Examples 113 and 114: Single Enantiomers Obtained from a Racemic Mixture Containing (R)—N-(5-chloro-6-(2H-1,2,3-triazol-2-yl)pyridin-3-yl)-2-fluoro-3,8,8-trimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-fluoro-3,8,8-trimethyl-7,8-dihydro-6H-cyclopenta[e]pyrazolo[1,5-a]pyrimidine-6-carboxamide Step 1: 3-bromo-2-fluoro-8,8-dimethyl-7,8-dihydro-6H-cyclopenta[e]pyrazolo[1,5-a]pyrimidine-6-carbonitrile

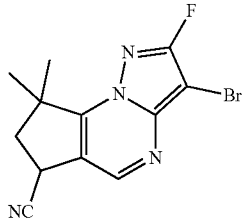 [SMILES: CC1(C)CC(C#N)c2cnc3c(Br)c(F)nn3c21]

To a stirred solution of 2-fluoro-8,8-dimethyl-7,8-dihydro-6H-cyclopenta[e]pyrazolo[1,5-a]pyrimidine-6-carbonitrile (Method 01 step 2; 370 mg, 1.6 mmol) in DMF (3 mL) was added NBS (372 mg, 2.1 mmol). The mixture was stirred at 25° C. for 5 h. The reaction mixture was quenched with water (20 mL). The resulting solution was extracted with ethyl acetate (3x20 mL). The combined organic layers were washed with brine (3x20 mL), dried over anhydrous sodium sulfate and concentrated under reduced pressure. This resulted in 3-bromo-2-fluoro-8,8-dimethyl-7,8-dihydro-6H-cyclopenta[e]pyrazolo[1,5-a]pyrimidine-6-carbonitrile (460 mg, crude) as a yellow solid which was used in the next step without further purification. LCMS (ES, m/z): 309 $[M+H]^+$.

Step 2: 2-fluoro-3,8,8-trimethyl-7,8-dihydro-6H-cyclopenta[e]pyrazolo[1,5-a]pyrimidine-6-carbonitrile

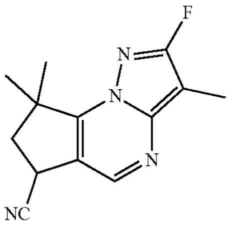

To a stirred solution of 3-bromo-2-fluoro-8,8-dimethyl-7,8-dihydro-6H-cyclopenta[e]pyrazolo[1,5-a]pyrimidine-6-carbonitrile (120 mg, 0.39 mmol) in dioxane (5 mL) and water (0.5 mL) was added methylboronic acid (82.7 mg, 1.38 mmol), Pd(dppf)C12 (21.6 mg, 26.44 μmol) and $K_2CO_3$ (180 mg, 1.3 mmol). The reaction mixture was stirred at 100° C. for 2 h under nitrogen atmosphere. The mixture was allowed to cool down to 25° C. and concentrated under reduced pressure. The residue was submitted to Prep-HPLC purification and the collected fractions were lyophilized to afford 2-fluoro-3,8,8-trimethyl-7,8-dihydro-6H-cyclopenta[e]pyrazolo[1,5-a]pyrimidine-6-carbonitrile (29 mg, 31% yield) as a yellow solid. LC-MS: m/z 245 $[M+H]^+$.

Step 3: 2-fluoro-3,8,8-trimethyl-7,8-dihydro-6H-cyclopenta[e]pyrazolo[1,5-a]pyrimidine-6-carboxylic acid

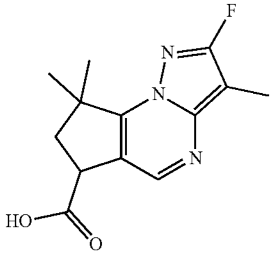 [SMILES: Cc1c(F)nn2c3c(cnc12)C(C(=O)O)CC3(C)C]

A mixture of 2-fluoro-3,8,8-trimethyl-7,8-dihydro-6H-cyclopenta[e]pyrazolo[1,5-a]pyrimidine-6-carbonitrile (69 mg, 282.5 μmol) in AcOH (1 mL) and 12M HCl (1 mL) was stirred at 100° C. for 2 h. The mixture was allowed to cool down to 25° C. The reaction mixture was diluted with water (30 mL). The resulting solution was extracted with ethyl acetate (50 mL×3).

The combined organic layers were dried over anhydrous sodium sulfate and concentrated under reduced pressure. The residue was applied onto a silica gel column and eluted with MeOH/DCM (1:10) to give 2-fluoro-3,8,8-trimethyl-7,8-dihydro-6H-cyclopenta[e]pyrazolo[1,5-a]pyrimidine-6-carboxylic acid (72 mg, 96.8% yield) as a yellow solid. LC-MS: m/z 264 $[M+H]^+$.

Step 4: N-(5-chloro-6-(2H-1,2,3-triazol-2-yl)pyridin-3-yl)-2-fluoro-3,8,8-trimethyl-7,8-dihydro-6H-cyclopenta[e]pyrazolo[1,5-a]pyrimidine-6-carboxamide

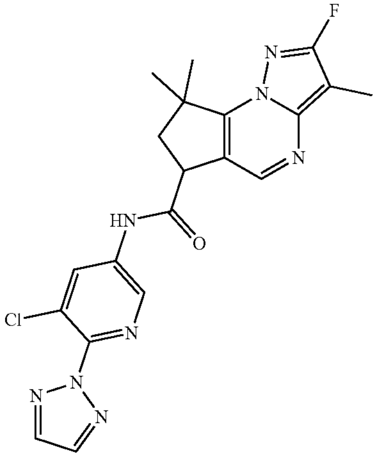 [SMILES: Cc1c(F)nn2c3c(cnc12)C(C(=O)Nc1cnc(-n2nccn2)c(Cl)c1)CC3(C)C]

To a stirred solution of 2-fluoro-3,8,8-trimethyl-7,8-dihydro-6H-cyclopenta[e]pyrazolo[1,5-a]pyrimidine-6-carboxylic acid (72 mg, 273.5 μmol) and 5-chloro-6-(2H-1,2,3-triazol-2-yl)pyridin-3-amine (Method A1 step 2; 53 mg, 273.5 μmol) in ACN (5 mL) were added TCFH (230 mg, 820.5 μmol) and NMI (67 mg, 820.5 μmol). The mixture was stirred at 25° C. for 16 h. The resulting mixture was concentrated under reduced pressure. The residue was submitted to Prep-HPLC purification and the collected fractions were lyophilized to give N-(5-chloro-6-(2H-1,2,3-triazol-2-yl)pyridin-3-yl)-2-fluoro-3,8,8-trimethyl-7,8-dihydro-6H-cyclopenta[e]pyrazolo[1,5-a]pyrimidine-6-carboxamide (45 mg, 37% yield) as a white solid. LC-MS: m/z 441 $[M+H]^+$.

Step 5: Separation of Enantiomers to Obtain (R)—N-(5-chloro-6-(2H-1,2,3-triazol-2-yl)pyridin-3-yl)-2-fluoro-3,8,8-trimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2-fluoro-3,8,8-trimethyl-7,8-dihydro-6H-cyclopenta[e]pyrazolo[1,5-a]pyrimidine-6-carboxamide Example 113

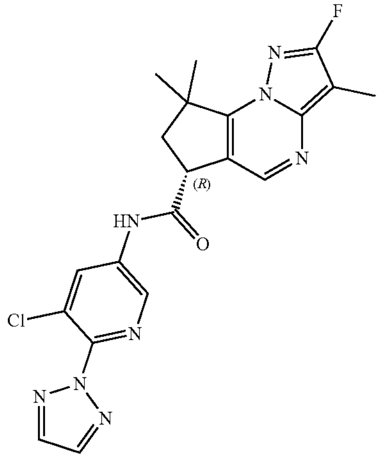

and

Example 114

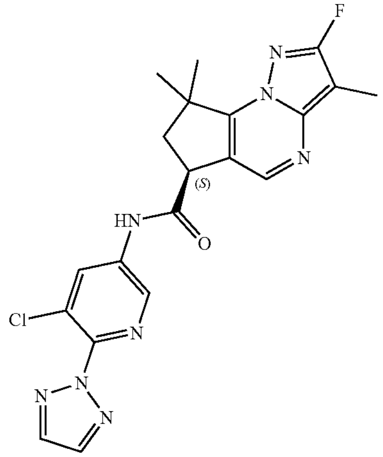

42 mg of N-(5-chloro-6-(2H-1,2,3-triazol-2-yl)pyridin-3-yl)-2-fluoro-3,8,8-trimethyl-7,8-dihydro-6H-cyclopenta[e]pyrazolo[1,5-a]pyrimidine-6-carboxamide were submitted to chiral HPLC purification (Column: CHIRALPAK IA, 2*25 cm, 20 μm; Mobile Phase A: Hex(0.1% FA)-HPLC, Mobile Phase B: EtOH-HPLC; Flow rate: 20 mL/min; isocratic 50% B in 9 min; Wave Length: 220/254 nm; RT1(min): 5.43; RT2(min): 7.63; Sample Solvent: EtOH- HPLC; Injection Volume: 0.8 mL; Number Of Runs: 6). The first eluting isomer was concentrated and lyophilized to afford Example 113 (13.7 mg, 25% yield) as a white solid. The second eluting isomer was concentrated and lyophilized to afford Example 114 (11.7 mg, 22% yield) as a white solid.

Example 113: $^1H$ NMR (400 MHz, DMSO-$d_6$) δ: 11.08 (br, 1H), 8.73 (d, J=2.0 Hz, 1H), 8.58-8.59 (m, 2H), 8.17 (s, 2H), 4.41-4.45 (m, 1H), 2.55-2.67 (m, 1H), 2.32-2.35 (m, 1H), 2.22 (s, 3H), 1.62 (s, 3H), 1.54 (s, 3H). LC-MS: m/z 441.1 $[M+H]^+$.

Example 114: $^1H$ NMR (400 MHz, DMSO-$d_6$) δ: 11.09 (br, 1H), 8.73 (d, J=2.0 Hz, 1H), 8.58-8.59 (m, 2H), 8.18 (s, 2H), 4.42-4.45 (m, 1H), 2.54-2.57 (m, 1H), 2.32-2.35 (m, 1H), 2.22 (s, 3H), 1.62 (s, 3H), 1.54 (s, 3H). LC-MS: m/z 441.1 $[M+H]^+$.

The absolute stereochemistry for each separated isomer was not determined.

Method G3

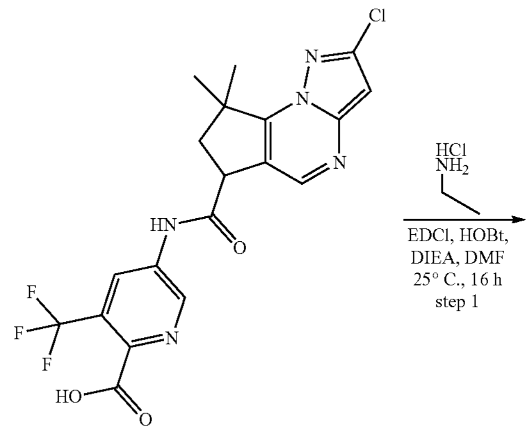

Method E3 Step 4

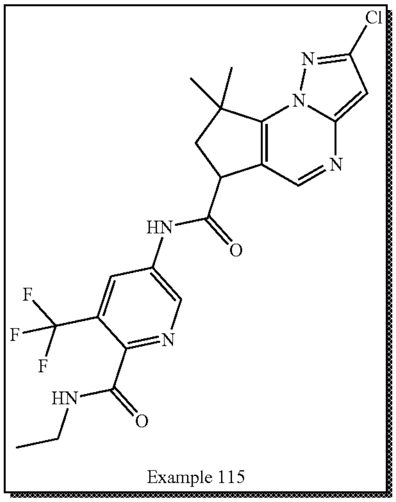

Example 115

Example 115: 2-chloro-N-(6-(ethylcarbamoyl)-5-(trifluoromethyl)pyridin-3-yl)-8,8-dimethyl-7,8-dihydro-6H-cyclopenta[e]pyrazolo[1,5-a]pyrimidine-6-carboxamide Step 1: 2-chloro-N-(6-(ethylcarbamoyl)-5-(trifluoromethyl)pyridin-3-yl)-8,8-dimethyl-7,8-dihydro-6H-cyclopenta[e]pyrazolo[1,5-a]pyrimidine-6-carboxamide Example 115

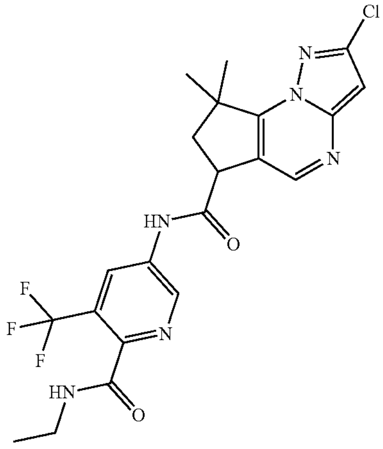

To a solution of 5-(2-chloro-8,8-dimethyl-7,8-dihydro-6H-cyclopenta[e]pyrazolo[1,5-a]pyrimidine-6-carboxamido)-3-(trifluoromethyl)picolinic acid (Method E3 step 4; 37 mg, 66.1 μmol) in DMF (0.5 mL) were added ethylamine hydrochloride salt (6.5 mg, 79.3 μmol), EDCI (19 mg, 99.2 μmol), HOBT (13.4 mg, 99.2 μmol) and DIEA (12.8 mg, 99.2 μmol). The mixture was stirred at 25° C. for 16 h. The resulting mixture was concentrated under reduced pressure. The residue was submitted to Prep-HPLC purification and the collected fractions were lyophilized to give Example 115 (3.5 mg, 11% yield) as a white solid.

Example 115: $^1H$ NMR (400 MHz, DMSO-$d_6$) δ: 11.02 (s, 1H), 8.99 (d, J=2.0 Hz, 1H), 8.61-8.67 (m, 2H), 8.57 (d, J=2.4 Hz, 1H), 6.95 (s, 1H), 4.40-4.49 (m, 1H), 3.25-3.28 (m, 2H), 2.54-2.65 (m, 1H), 2.29-2.37 (m, 1H), 1.63 (s, 3H), 1.56 (s, 3H), 1.11 (t, J=7.2 Hz, 3H). LC-MS: m/z 481.1 $[M+H]^+$.

Method 113

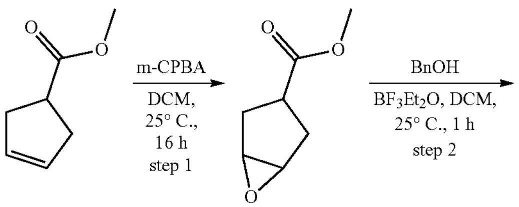

-continued
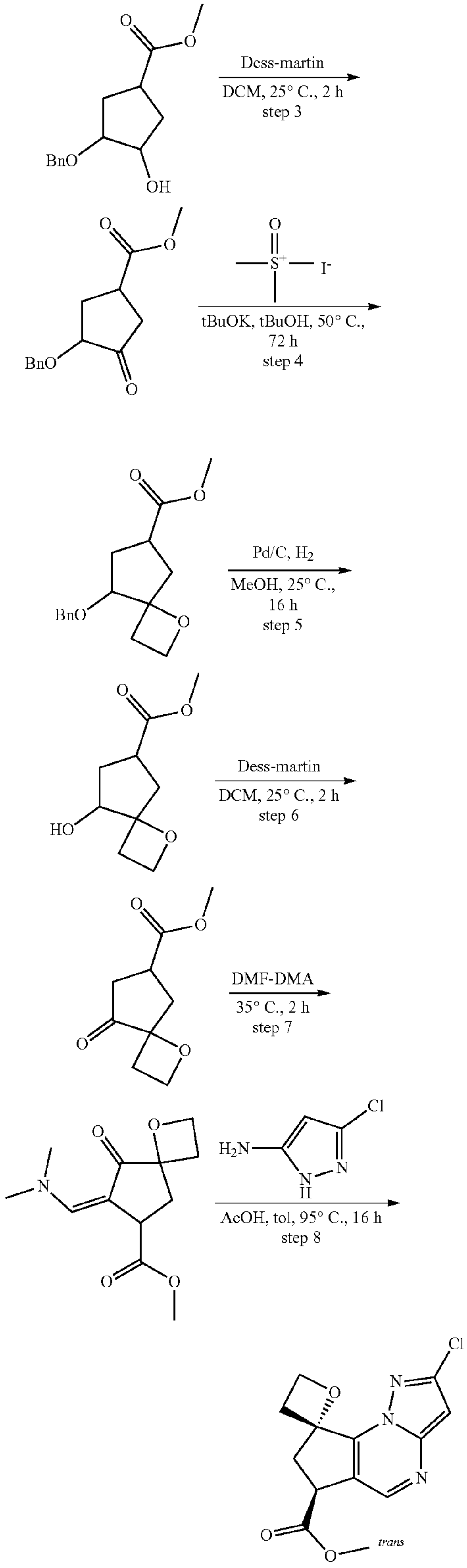
-continued
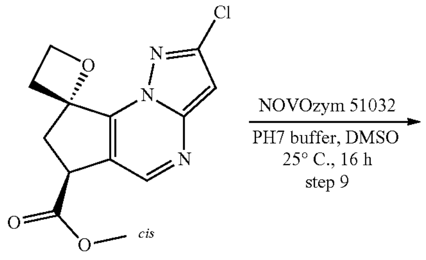
Method H3 Step 8-c
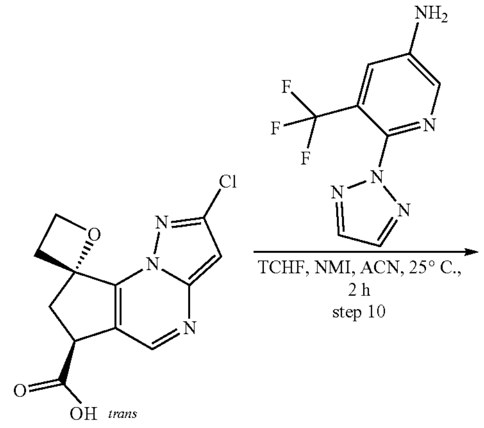
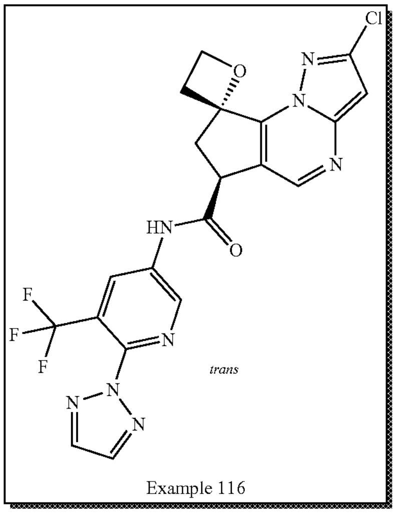
Example 116

Example 116: (trans)-N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,2'-oxetane]-6-carboxamide (racemic)

Step 1: methyl 6-oxabicyclo[3.1.0]hexane-3-carboxylate

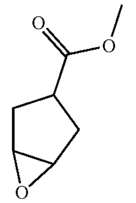

To a stirred solution of methyl cyclopent-3-ene-1-carboxylate (25.0 g, 198.4 mmol) in DCM (200 mL) were added 3-chloroperoxybenzoic acid (51.1 g, 297.6 mmol) at 0° C. The mixture was stirred at 25° C. for 16 h. The solid was filtered out and the filtrate was concentrated under reduced pressure to give methyl 6-oxabicyclo[3.1.0]hexane-3-carboxylate (26 g, 92% yield) as a colorless oil. LC-MS: m/z 143 $[M+H]^+$.

Step 2: methyl 3-(benzyloxy)-4-hydroxycyclopentane-1-carboxylate

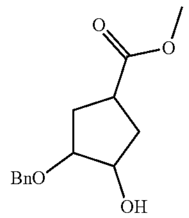 [SMILES: COC(=O)C1CC(O)C(OCc2ccccc2)C1]

To a stirred solution of methyl 6-oxabicyclo[3.1.0]hexane-3-carboxylate (26.0 g, 183.1 mmol) in DCM (200 mL) were added benzyl alcohol (29.6 g, 274.6 mmol) and boron trifluoride etherate (2.6 g, 18.3 mmol) at 0° C. The mixture was stirred at 25° C. for 1 h. The reaction mixture was quenched with ice water (200 mL). The resulting solution was extracted with DCM (3×100 mL). The combined organic layers were dried over anhydrous sodium sulfate and concentrated under reduced pressure. The residue was applied on a silica gel column and eluted with EtOAc/PE (1:3) to give methyl 3-(benzyloxy)-4-hydroxycyclopentane-1-carboxylate (25 g, 54% yield) as a colorless oil. LC-MS: m/z 251 $[M+H]^+$.

Step 3: methyl 3-(benzyloxy)-4-oxocyclopentane-1-carboxylate

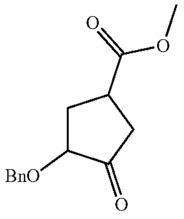 [SMILES: COC(=O)C1CC(=O)C(OCc2ccccc2)C1]

To a stirred solution of methyl 3-(benzyloxy)-4-hydroxycyclopentane-1-carboxylate (25.0 g, 100.0 mmol) in DCM (500 mL) was added Dess-Martin periodinane (106.1 g, 250.0 mmol) in portions at 0° C. The reaction mixture was stirred at 25° C. for 2 h. The solid was filtered out and the filtrate was concentrated under reduced pressure. The residue was applied on a silica gel column and eluted with EtOAc/PE (1:3) to give methyl 3-(benzyloxy)-4-oxocyclopentane-1-carboxylate (20 g, 81% yield) as a colorless oil. LC-MS: m/z 249 $[M+H]^+$.

Step 4: methyl 8-(benzyloxy)-1-oxaspiro[3.4]octane-6-carboxylate

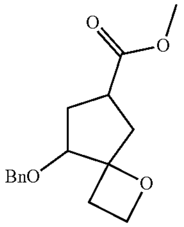 [SMILES: COC(=O)C1CC(OCc2ccccc2)C2(CCO2)C1]

To a stirred solution of methyl trimethylsulfoxonium iodide (17.6 g, 80.3 mmol) in t-BuOH (100 mL) was added potassium tert-butoxide (9.3 g, 80.3 mmol) in portions at 25° C. The reaction mixture was stirred at 50° C. for 30 min. Then a solution of methyl 3-(benzyloxy)-4-oxocyclopentane-1-carboxylate (20.0 g, 80.3 mmol) in t-BuOH (10 mL) was added. The reaction mixture was stirred at 50° C. for 72 h. The reaction mixture was quenched with ice water (200 mL).

The resulting solution was extracted with ethyl acetate (3×100 mL). The combined organic layers were dried over anhydrous sodium sulfate and concentrated under reduced pressure. The residue was applied on a silica gel column and eluted with EtOAc/PE (1:2) to give methyl methyl 8-(benzyloxy)-1-oxaspiro[3.4]octane-6-carboxylate (18 g, 81% yield) as a colorless oil. LC-MS: m/z 277 $[M+H]^+$.

Step 5: methyl 8-hydroxy-1-oxaspiro[3.4]octane-6-carboxylate

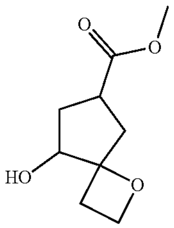

To a stirred solution of methyl 8-(benzyloxy)-1-oxaspiro[3.4]octane-6-carboxylate (18.0 g, 64.9 mmol) in methanol (200 mL) was added Pd/C (9.0 g, 10%) at 25° C. The reaction mixture was stirred at 25° C. for 16 h under hydrogen atmosphere. The solid was filtered out and the filtrate was concentrated under reduced pressure. The residue was applied on a silica gel column and eluted with EtOAc/PE (1:1) to give methyl 8-hydroxy-1-oxaspiro[3.4]octane-6-carboxylate (10 g, 83% yield) as a colorless oil. LC-MS: m/z 187 $[M+H]^+$.

Step 6: methyl 8-oxo-1-oxaspiro[3.4]octane-6-carboxylate

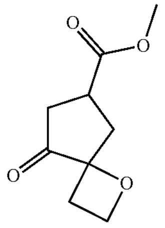

To a stirred solution of methyl 8-hydroxy-1-oxaspiro[3.4]octane-6-carboxylate (10.0 g, 53.4 mmol) in DCM (100 mL) was added Dess-Martin periodinane (5.6 g, 133.6 mmol) in portions at 0° C. The reaction mixture was stirred at 25° C. for 2 h. The solid was filtered out and the filtrate was concentrated under reduced pressure. The residue was applied on a silica gel column and eluted with EtOAc/PE (1:2) to give methyl 8-oxo-1-oxaspiro[3.4]octane-6-carboxylate (7 g, 71% yield) as a colorless oil. $^1H$ NMR (400 MHz, Chloroform-d) δ 4.69-4.74 (m, 1H), 4.48-4.56 (m, 1H), 3.73 (s, 3H), 3.12-3.22 (m, 1H), 2.76-2.86 (m, 1H), 2.64-2.75 (m, 1H), 2.50-2.64 (m, 3H), 2.26-2.34 (m, 1H). LC-MS: m/z 185 $[M+H]^+$.

Step 7: methyl (Z)-7-((dimethylamino)methylene)-8-oxo-1-oxaspiro[3.4]octane-6-carboxylate

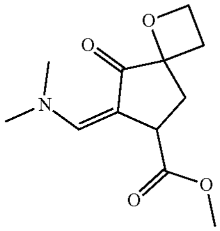

A solution of methyl 8-oxo-1-oxaspiro[3.4]octane-6-carboxylate (7.0 g, 37.8 mmol) in DMF-DMA (100 mL) was stirred at 35° C. for 2 h. The mixture was allowed to cool down to 25° C. and concentrated to give methyl (Z)-7-((dimethylamino)methylene)-8-oxo-1-oxaspiro[3.4]octane-6-carboxylate (6.0 g, crude) as yellow oil which was used in the next step without purification. LC-MS: m/z 240 $[M+H]^+$.

Step 8: methyl (trans)-2-chloro-6,7-dihydrospiro[cyclopenta[e]pyrazolo[1,5-a]pyrimidine-8,2'-oxetane]-6-carboxylate and methyl (cis)-2-chloro-6,7-dihydrospiro[cyclopenta[e]pyrazolo[1,5-a]pyrimidine-8,2'-oxetane]-6-carboxylate

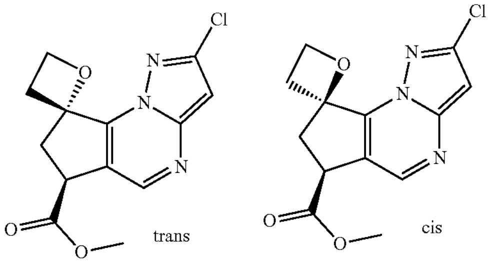 [SMILES: COC(=O)[C@H]1C[C@@]2(CCO2)c2c1cnc1cc(Cl)nn21 ; COC(=O)[C@H]1C[C@]2(CCO2)c2c1cnc1cc(Cl)nn21]

trans cis

To a stirred solution of methyl (Z)-7-((dimethylamino)methylene)-8-oxo-1-oxaspiro[3.4]octane-6-carboxylate (6.0 g, 22.0 mmol) in toluene (30 mL) and AcOH (3 mL) was added 3-chloro-1H-pyrazol-5-amine (2.5 g, 22.0 mmol). The resulting mixture was stirred at 95° C. for 16 h. The mixture was cooled to 25° C. and concentrated under reduced pressure. The residue was diluted with water (100 mL). The pH was adjusted to 6-7 with aqueous saturated sodium bicarbonate. The resulting solution was extracted with ethyl acetate (2×100 mL). The combined organic layers were dried over anhydrous sodium sulfate and concentrated under reduced pressure. The residue was applied on a silica gel column and eluted with EtOAc/PE (1:1) to give methyl (trans)-2-chloro-6,7-dihydrospiro[cyclopenta[e]pyrazolo[1,5-a]pyrimidine-8,2'-oxetane]-6-carboxylate (1.5 g, 23% yield) as a white solid and methyl (cis)-2-chloro-6,7-dihydrospiro[cyclopenta[e]pyrazolo[1,5-a]pyrimidine-8,2'-oxetane]-6-carboxylate (Method 113 step 8-c; 1.0 g, 14% yield) as a white solid. LCMS (ES, m/z): 294 $[M+H]^+$.

Step 9: (trans)-2-chloro-6,7-dihydrospiro[cyclopenta[e]pyrazolo[1,5-a]pyrimidine-8,2'-oxetane]-6-carboxylic acid

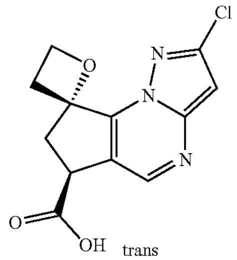 [SMILES: O=C(O)[C@H]1C[C@@]2(CCO2)c2c1cnc1cc(Cl)nn21]

trans

A solution of methyl (trans)-2-chloro-6,7-dihydrospiro[cyclopenta[e]pyrazolo[1,5-a]pyrimidine-8,2'-oxetane]-6-carboxylate (1.5 g, 5.1 mmol) in DMSO (2 mL) was added PBS buffer (40 mL, pH=7). The mixture was stirred at 25° C. for 30 min. Then Novozym51032 (1.5 g) was added. The mixture was stirred at 25° C. for 16 h. The reaction mixture was submitted to Prep-HPLC purification and the collected fractions were lyophilized to give (trans)-2-chloro-6,7-dihydrospiro[cyclopenta[e]pyrazolo[1,5-a]pyrimidine-8,2'-oxetane]-6-carboxylic acid (800 mg, 57% yield) as a white solid. LCMS (ES, m/z): 280 [M+H]$^+$.

Step 10: (trans)-N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,2'-oxetane]-6-carboxamide Example 116

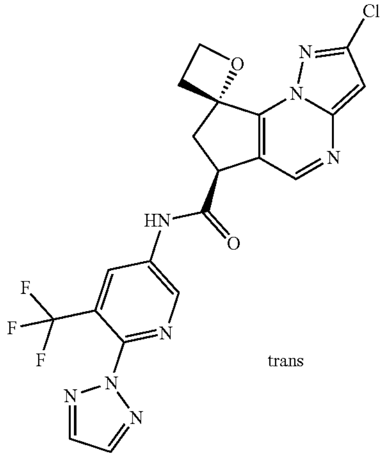

trans

To a solution of (trans)-2-chloro-6,7-dihydrospiro[cyclopenta[e]pyrazolo[1,5-a]pyrimidine-8,2'-oxetane]-6-carboxylic acid (200 mg, 716 μmol) in ACN (10 mL) were added 6-(2H-1,2,3-triazol-2-yl)-5~(trifluoromethyl)pyridin-3-amine (164 mg, 716 μmol), TCFH (784 mg, 2.8 mmol) and NMI (229 mg, 2.8 mmol). The resulting mixture was stirred at 25° C. for 2 h. The reaction mixture was concentrated under reduced pressure. The residue was submitted to Prep- HPLC purification and the collected fractions were lyophilized to give Example 116 (4.0 mg, 1% yield) as a white solid.

Example 116: $^1$H NMR (300 MHz, DMSO-$d_6$) δ 11.26 (br, 1H), 8.99-9.03 (m, 1H), 8.83-8.74 (m, 2H), 8.18 (s, 2H), 7.11 (s, 1H), 4.96-5.04 (m, 1H), 4.51-4.56 (m, 2H), 3.38-3.52 (m, 1H), 3.10-3.13 (m, 2H), 2.89-2.93 (m, 1H). LC-MS: m/z 491.0 [M+H]$^+$.

Method I3

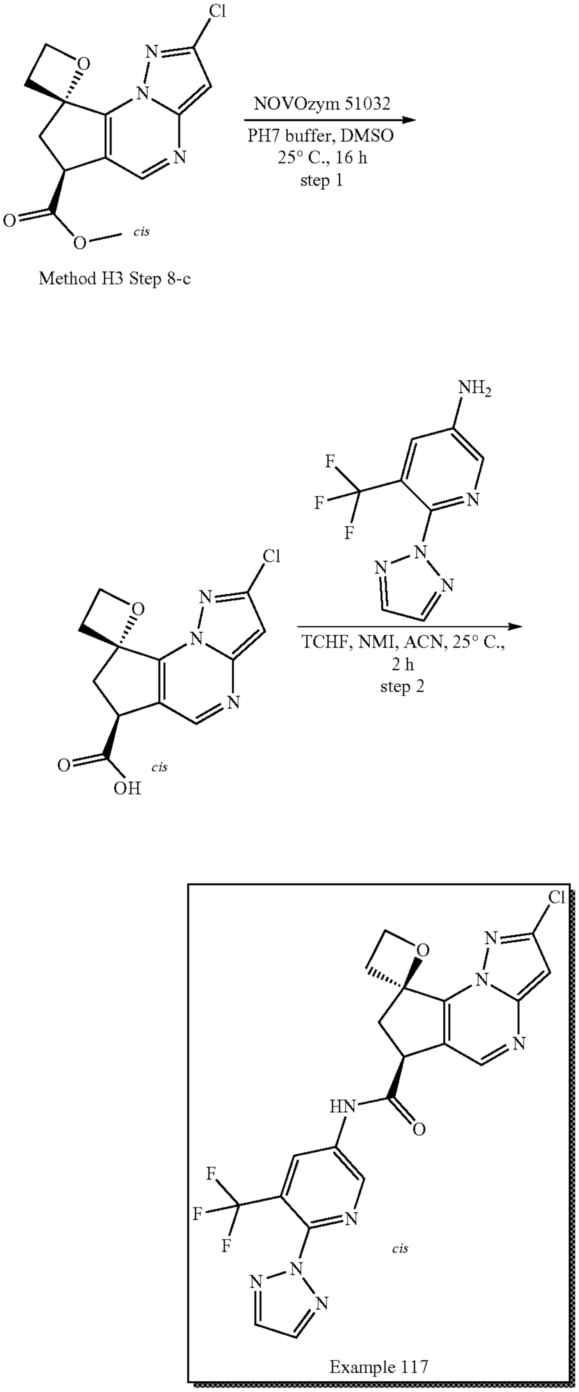

Example 117: (cis)-N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,2'-oxetane]-6-carboxamide (racemic)

Step 1: (cis)-2-chloro-6,7-dihydrospiro[cyclopenta[e]pyrazolo[1,5-a]pyrimidine-8,2'-oxetane]-6-carboxylic acid

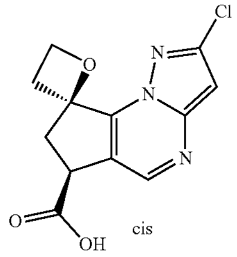 [SMILES: O=C(O)[C@H]1C[C@]2(CCO2)c2c1cnc1cc(Cl)nn21]

cis

To a solution of methyl (cis)-2-chloro-6,7-dihydrospiro[cyclopenta[e]pyrazolo[1,5-a]pyrimidine-8,2'-oxetane]-6-carboxylate (Method 113 step 8-c; 1.0 g, 3.4 mmol) in DMSO (2 mL) was added PBS buffer (40 mL, pH=7). The mixture was stirred at 25° C. for 30 min. Then Novozym51032 (1.0 g) was added. The mixture was stirred at 25° C. for 16 h. The reaction mixture was submitted to Prep-HPLC purification and the collected fractions were lyophilized to give (cis)-2-chloro-6,7-dihydrospiro[cyclopenta[e]pyrazolo[1,5-a]pyrimidine-8,2'-oxetane]-6-carboxylic acid (400 mg, 42% yield) as a white solid. LCMS (ES, m/z): 280 $[M+H]^+$.

Step 2: (cis)-N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,2'-oxetane]-6-carboxamide Example 117

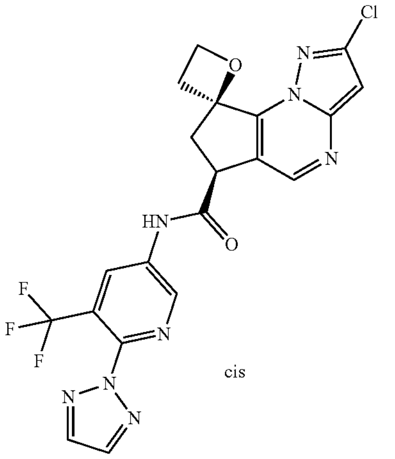

cis

To a solution of (cis)-2-chloro-6,7-dihydrospiro[cyclopenta[e]pyrazolo[1,5-a]pyrimidine-8,2'-oxetane]-6-carboxylic acid (200 mg, 716 μmol) in ACN (10 mL) were added 6-(2H-1,2,3-triazol-2-yl)-5~(trifluoromethyl)pyridin-3-amine (164 mg, 716 μmol), TCFH (784 mg, 2.8 mmol) and NMI (229 mg, 2.8 mmol). The resulting mixture was stirred at 25° C. for 2 h. The reaction mixture was concentrated under reduced pressure. The residue was submitted to Prep-HPLC purification and the collected fractions were lyophilized to give Example 117 (1.7 mg, 0.5% yield) as a white solid.

Example 117: $^1$H NMR (400 MHz, DMSO-$d_6$) δ 11.27 (s, 1H), 9.02 (d, J=2.4 Hz, 1H), 8.80 (d, J=2.4 Hz, 1H), 8.77 (s, 1H), 8.20 (s, 2H), 7.11 (s, 1H), 5.01-5.06 (m, 1H), 4.55-4.61 (m, 1H), 4.32-4.36 (m, 1H), 3.41-3.48 (m, 1H), 3.03-3.17 (m, 2H), 2.75-2.82 (m, 1H). LC-MS: m/z 491.1 $[M+H]^+$.

Method J3

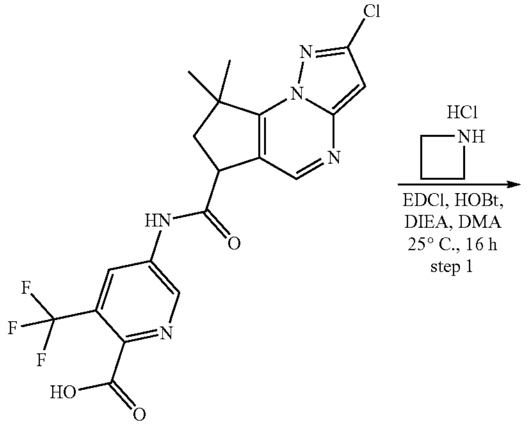

Method E3 Step 4

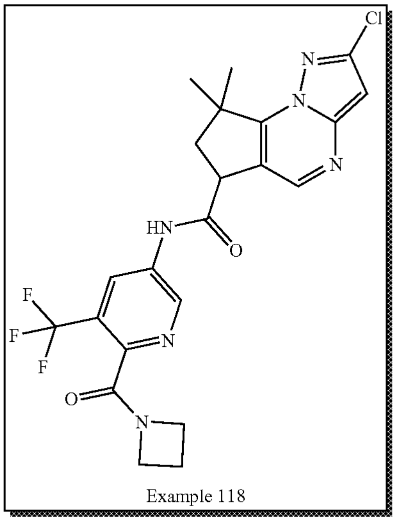

Example 118

Example 118: N-(6-(azetidine-1-carbonyl)-5~(trifluoromethyl)pyridin-3-yl)-2-chloro-8,8-dimethyl-7,8-dihydro-6H-cyclopenta[e]pyrazolo[1,5-a]pyrimidine-6-carboxamide Step 1: N-(6-(azetidine-1-carbonyl)-5~(trifluoromethyl)pyridin-3-yl)-2-chloro-8,8-dimethyl-7,8-dihydro-6H-cyclopenta[e]pyrazolo[1,5-a]pyrimidine-6-carboxamide Example 118

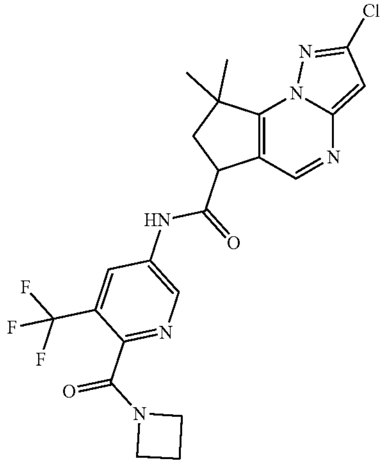

To a solution of 5~(2-chloro-8,8-dimethyl-7,8-dihydro-6H-cyclopenta[e]pyrazolo[1,5-a]pyrimidine-6-carboxamido)-3-(trifluoromethyl)picolinic acid (Method E3 step 4; 30 mg, 66.1 μmol) in DMF (0.5 mL) were added azetidine hydrogen chloride salt (7 mg, 79.3 μmol), EDCI (19 mg, 99.2 μmol), HOBT (13 mg, 99.2 μmol) and DIEA (43 mg, 330.5 μmol). The resulting mixture was stirred at 25° C. for 16 h. The reaction mixture was concentrated under reduced pressure. The residue was submitted to Prep-HPLC purification and the collected fractions were lyophilized to give Example 118 (4.4 mg, 13% yield) as a white solid.

Example 118: $^1$H NMR (400 MHz, DMSO-$d_6$) δ: 11.03 (s, 1H), 8.98 (d, J=2.0 Hz, 1H), 8.65 (s, 1H), 8.58 (d, J=2.0 Hz, 1H), 6.95 (s, 1H), 4.42-4.45 (m, 1H), 3.97-4.08 (m, 4H), 2.54-2.58 (m, 1H), 2.27-2.35 (m, 3H), 1.63 (s, 3H), 1.56 (s, 3H). LC-MS: m/z 493.1 [M+H]$^+$.

Method $K_3$

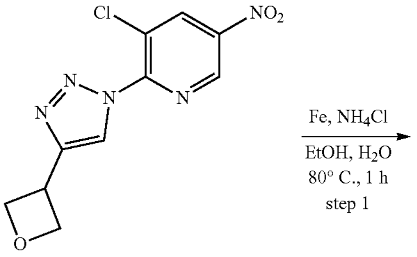

Method D3 Step 3-I

-continued

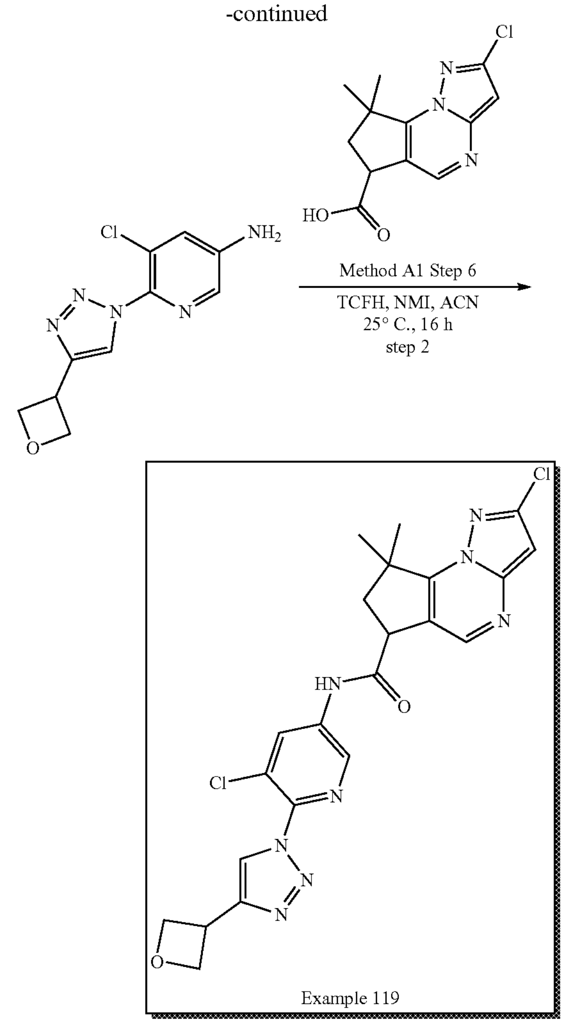

Example 119

Example 119: 2-chloro-N-(5-chloro-6-(4-(oxetan-3-yl)-111-1,2,3-triazol-1-yl)pyridin-3-yl)-8,8-dimethyl-7,8-dihydro-6H-cyclopenta[e]pyrazolo[1,5-a]pyrimidine-6-carboxamide Step 1: 5-chloro-6-(4-(oxetan-3-yl)-1H-1,2,3-triazol-1-yl)pyridin-3-amine

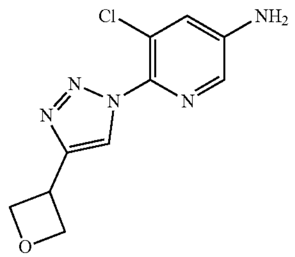 [SMILES: Nc1cnc(-n2cc(C3COC3)nn2)c(Cl)c1]

To a solution of 3-chloro-5-nitro-2-(4-(oxetan-3-yl)-1H-1,2,3-triazol-1-yl)pyridine (Method D3 step 3-i; 100 mg, 355.0 μmol) in EtOH (3 mL) and water (1 mL) was added Fe (99 mg, 1.8 mmol) and Ammonium chloride (57 mg, 1.1 mmol). The mixture was stirred at 80° C. for 1 h. After cooled to 25° C., the solid was filtered out. The filtrate was concentrated under reduced pressure. The residue was diluted with water (10 mL). The resulting solution was extracted with ethyl acetate (3×20 mL). The combined organic layers were dried over anhydrous sodium sulfate and concentrated under reduced pressure to give 5-chloro-6-(4-(oxetan-3-yl)-1H-1,2,3-triazol-1-yl)pyridin-3-amine (80 mg, 89% yield) as a light brown solid. LC-MS: m/z 252 $[M+H]^+$.

Step 2: 2-chloro-N-(5-chloro-6-(4-(oxetan-3-yl)-1H-1,2,3-triazol-1-yl)pyridin-3-yl)-8,8-dimethyl-7,8-dihydro-6H-cyclopenta[e]pyrazolo[1,5-a]pyrimidine-6-carboxamide Example 119

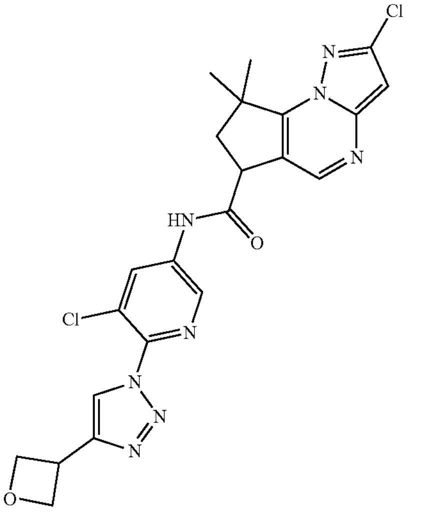

To a solution of 5-chloro-6-(4-(oxetan-3-yl)-1H-1,2,3-triazol-1-yl)pyridin-3-amine (10 mg, 39.7 μmol) in ACN (1 mL) were added 2-chloro-8,8-dimethyl-7,8-dihydro-6H-cyclopenta[e]pyrazolo[1,5-a]pyrimidine-6-carboxylic acid (Method A1 step 6; 11 mg, 39.7 μmol), TCFH (17 mg, 59.6 μmol) and NMI (10 mg, 119.2 μmol). The resulting mixture was stirred at 25° C. for 16 h. The reaction mixture was concentrated under reduced pressure. The residue was submitted to Prep-HPLC purification and the collected fractions were lyophilized to give Example 119 (1.3 mg, 6% yield) as a white solid.

Example 119: $^1$H NMR (400 MHz, DMSO-$d_6$) δ: 11.08 (br, 1H), 8.75 (d, J=2.0 Hz, 1H), 8.65 (s, 1H), 8.58-8.60 (m, 2H), 6.95 (s, 1H), 4.91-4.97 (m, 2H), 4.76-4.79 (m, 2H), 4.44-4.52 (m, 2H), 2.54-2.60 (m, 1H), 2.31-2.36 (m, 1H), 1.64 (s, 3H), 1.57 (s, 3H). LC-MS: m/z 499.1 $[M+H]^+$.

Method L3

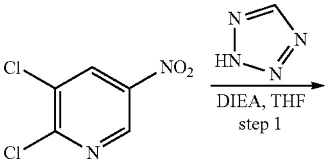

-continued

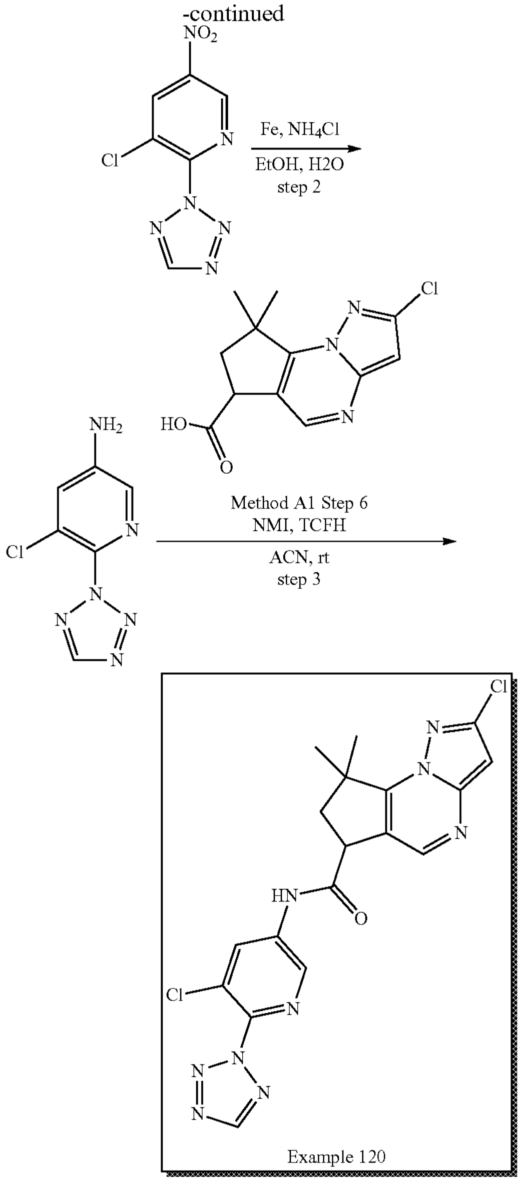

Example 120

Example 120: 2-chloro-N-(5-chloro-6-(2H-tetrazol-2-yl)pyridin-3-yl)-8,8-dimethyl-7,8-dihydro-6H-cyclopenta[e]pyrazolo[1,5-a]pyrimidine-6-carboxamide Step 1: 3-chloro-5-nitro-2-(2H-tetrazol-2-yl)pyridine

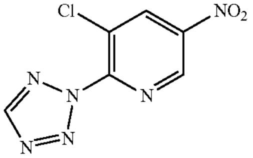 [SMILES: O=[N+]([O-])c1cnc(-n2ncnn2)c(Cl)c1]

To a stirred mixture of 2,3-dichloro-5-nitro-pyridine (1 g, 5.18 mmol) in THE (15 mL) was added 2H-tetrazole (13.8 mL, 6.22 mmol, 0.45 M in ACN) and DIEA (2.0 g, 15.6 mmol). The resulting mixture was stirred at 25° C. for 15 h.

The resulting mixture was concentrated under reduced pressure. The residue was applied on a silica gel column and eluted with EtOAc/PE (1:1) to give 3-chloro-5-nitro-2-(2H-tetrazol-2-yl)pyridine (400 mg, 34% yield) as a yellow solid. $^1$H NMR (400 MHz, DMSO-$d_6$) δ: 10.15 (s, 1H), 9.44 (s, 1H), 9.25 (s, 1H). LC-MS: m/z 227 $[M+H]^+$.

Step 2:
5-chloro-6-(2H-tetrazol-2-yl)pyridin-3-amine

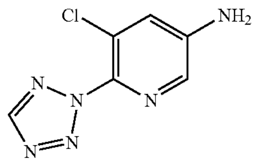 [SMILES: Nc1cnc(-n2ncnn2)c(Cl)c1]

To a stirred mixture of 3-chloro-5-nitro-2-(2H-tetrazol-2-yl)pyridine (300 mg, 1.3 mmol) in EtOH (10 mL) and water (10 mL) were added Fe (311 mg, 5.6 mmol) and Ammonium chloride (297 mg, 5.6 mmol). The resulting mixture was stirred at 95° C. for 1 h. After cooled to 25° C., the solid was filtered out. The filtrate was concentrated under reduced pressure. The residue was diluted with water (10 mL). The resulting solution was extracted with DCM/MeOH (10:1) (3×50 mL). The combined organic layers were dried over anhydrous sodium sulfate and concentrated under reduced pressure. The residue was applied on a silica gel column and eluted with MeOH/DCM (1:10) to give 5-chloro-6-(2H-tetrazol-2-yl)pyridin-3-amine (200 mg, 77% yield) as a yellow solid. LC-MS: m/z 197 $[M+H]^+$.

Step 3: 2-chloro-N-(5-chloro-6-(2H-tetrazol-2-yl)pyridin-3-yl)-8,8-dimethyl-7,8-dihydro-6H-cyclopenta[e]pyrazolo[1,5-a]pyrimidine-6-carboxamide Example 120

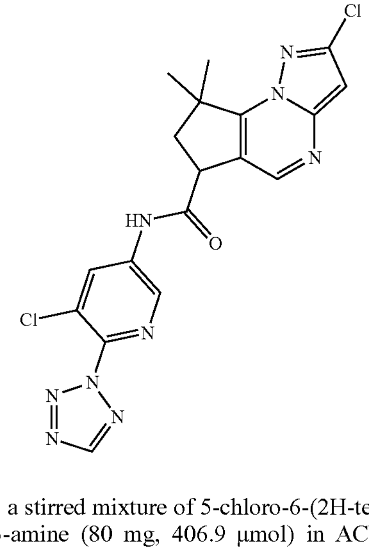

To a stirred mixture of 5-chloro-6-(2H-tetrazol-2-yl)pyridin-3-amine (80 mg, 406.9 μmol) in ACN (8 mL) were added 2-chloro-8,8-dimethyl-7,8-dihydro-6H-cyclopenta[e]pyrazolo[1,5-a]pyrimidine-6-carboxylic acid (Method A1 step 6; 130 mg, 488.3 μmol), TCFH (343 mg, 1.2 mmol) and NMI (167 mg, 2.0 mmol). The resulting mixture was stirred at 25° C. for 3 h. The reaction mixture was concentrated under reduced pressure. The residue was submitted to Prep-HPLC purification and the collected fractions were lyophilized to give Example 120 (19.0 mg, 10% yield) as a white solid.

Example 120: $^1$H NMR (400 MHz, DMSO-$d_6$) δ: 11.15 (s, 1H), 10.02 (s, 1H), 8.78 (d, J=2.4 Hz, 1H), 8.66 (s, 1H), 8.64 (d, J=2.4 Hz, 1H), 6.94-6.97 (m, 1H), 4.41-4.52 (m, 1H), 2.54-2.63 (m, 1H), 2.41-2.29 (1H), 1.64 (s, 3H), 1.57 (s, 3H). LC-MS: m/z 444.1 $[M+H]^+$.

Method M3

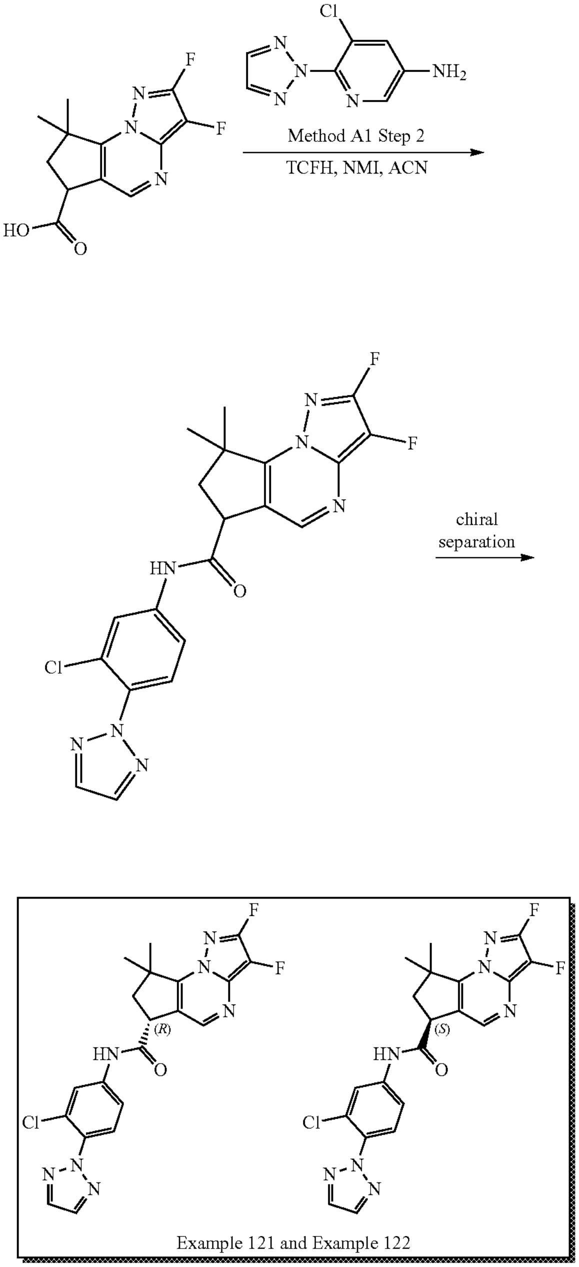

Example 121 and Example 122

Examples 121 and 122: Single Enantiomers Obtained from a Racemic Mixture Containing (R)—N-(5-chloro-6-(2H-1,2,3-triazol-2-yl)pyridin-3-yl)-2,3-difluoro-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2,3-difluoro-8,8-dimethyl-7,8-dihydro-6H-cyclopenta[e]pyrazolo[1,5-a]pyrimidine-6-carboxamide

Step 1: N-(5-chloro-6-(2H-1,2,3-triazol-2-yl)pyridin-3-yl)-2,3-difluoro-8,8-dimethyl-7,8-dihydro-6H-cyclopenta[e]pyrazolo[1,5-a]pyrimidine-6-carboxamide

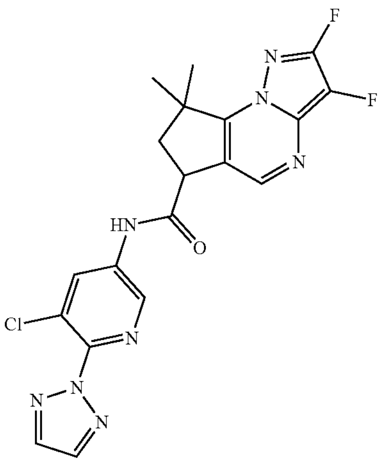 [SMILES: CC1(C)CC(C(=O)Nc2cnc(-n3nccn3)c(Cl)c2)c2cnc3c(F)c(F)nn3c21]

To a solution of 2,3-difluoro-8,8-dimethyl-7,8-dihydro-6H-cyclopenta[e]pyrazolo[1,5-a]pyrimidine-6-carboxylic acid (Method T2 step 1; 100 mg, 374.2 μmol) in ACN (2 mL) was added 5-chloro-6-(2H-1,2,3-triazol-2-yl)pyridin-3-amine (Method A1 step 2; 73 mg, 374.2 μmol), NMI (92 mg, 1.1 mmol) and TCFH (157 mg, 561.3 μmol). The resulting solution was stirred at 25° C. for 3 h. The resulting mixture was concentrated under reduced pressure. The residue was submitted to Prep-HPLC purification and the collected fractions were lyophilized to give N-(5-chloro-6-(2H-1,2,3-triazol-2-yl)pyridin-3-yl)-2,3-difluoro-8,8-dimethyl-7,8-dihydro-6H-cyclopenta[e]pyrazolo[1,5-a]pyrimidine-6-carboxamide (95 mg, 57% yield) as a white solid. LC-MS: m/z 445 $[M+H]^+$.

Step 2: Separation of Enantiomers to Obtain (R)—N-(5-chloro-6-(2H-1,2,3-triazol-2-yl)pyridin-3-yl)-2,3-difluoro-8,8-dimethyl-7,8-dihydro-6H-cyclopenta[e]pyrazolo[1,5-a]pyrimidine-6-carboxamide and (S)—N-(5-chloro-6-(2H-1,2,3-triazol-2-yl)pyridin-3-yl)-2,3-difluoro-8,8-dimethyl-7,8-dihydro-6H-cyclopenta[e]pyrazolo[1,5-a]pyrimidine-6-carboxamide

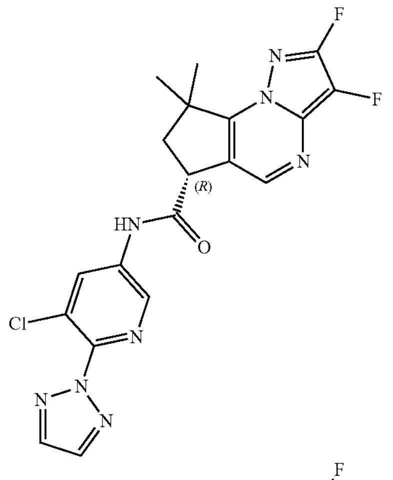

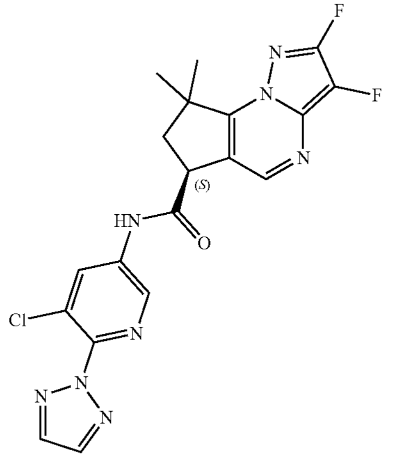

Example 121 and Example 122

95 mg of N-(5-chloro-6-(2H-1,2,3-triazol-2-yl)pyridin-3-yl)-2,3-difluoro-8,8-dimethyl-7,8-dihydro-6H-cyclopenta[e]pyrazolo[1,5-a]pyrimidine-6-carboxamide were submitted to chiral HPLC purification (Column: CHIRALPAK IA, 2*25 cm, 5 μm; Mobile Phase A: Hex(0.1% FA)-HPLC, Mobile Phase B: EtOH-HPLC; Flow rate: 20 mL/min; isocratic 50% B in 10 min; Wave Length: 220/254 nm; RT1(min): 5.09; RT2(min): 7.97; Sample Solvent: EtOH-HPLC; Injection Volume: 1.5 mL; Number Of Runs: 4). The first eluting isomer was concentrated and lyophilized to afford Example 121 (13 mg, 13% yield) as a white solid. The second eluting isomer was concentrated and lyophilized to afford Example 122 (14.8 mg, 15% yield) as a white solid.

Example 121: $^1H$ NMR (300 MHz, DMSO-$d_6$) δ 11.07 (s, 1H), 8.72 (d, J=2.4 Hz, 1H), 8.68 (s, 1H), 8.57 (d, J=2.1 Hz, 1H), 8.17 (s, 2H), 4.45 (dd, J=6.3, 9.0 Hz, 1H), 2.56 (dd, J=9.0, 13.2 Hz, 1H), 2.33 (dd, J=6.3, 13.2 Hz, 1H), 1.62 (s, 3H), 1.54 (s, 3H). LC-MS: m/z 445.0 $[M+H]^+$.

Example 122: $^1H$ NMR (300 MHz, DMSO-$d_6$) δ 11.07 (s, 1H), 8.72 (d, J=2.1 Hz, 1H), 8.68 (s, 1H), 8.57 (d, J=2.1 Hz, 1H), 8.17 (s, 2H), 4.45 (dd, J=6.3, 9.0 Hz, 1H), 2.56 (dd, J=9.0, 13.2 Hz, 1H), 2.32 (dd, J=6.3, 13.2 Hz, 1H), 1.62 (s, 3H), 1.54 (s, 3H). LC-MS: m/z 445.0 $[M+H]^+$.
The absolute stereochemistry for each separated isomer was not determined.
Method N3
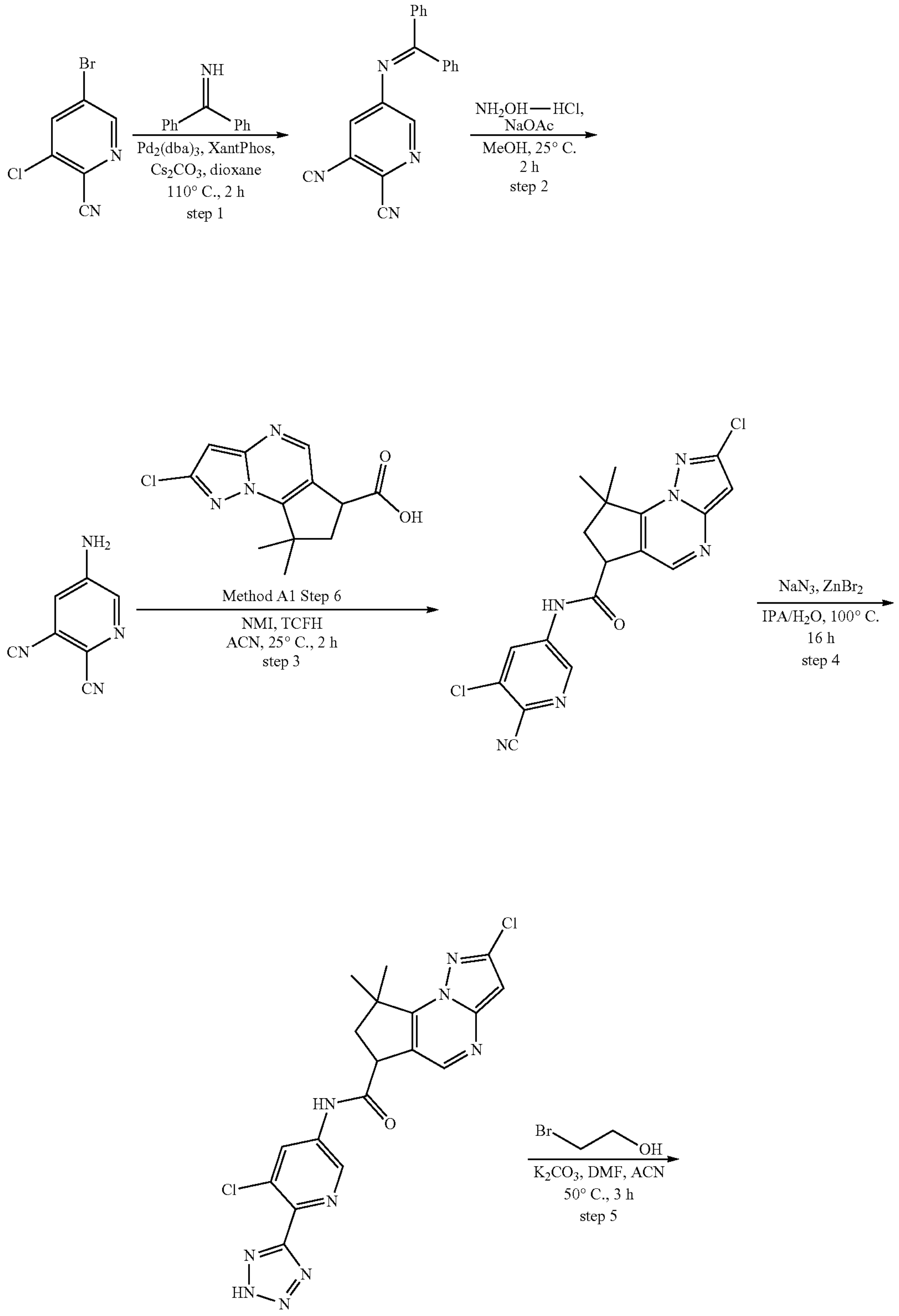

-continued

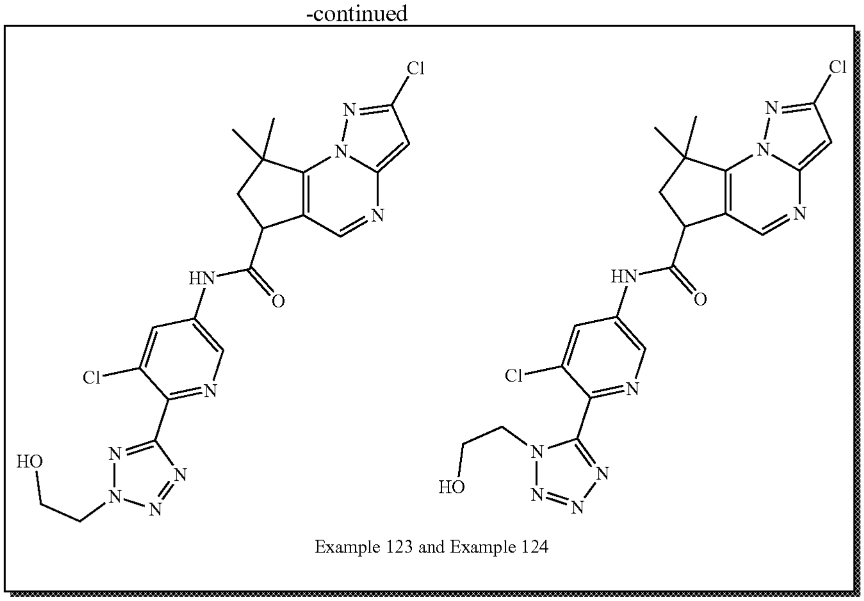

Example 123 and Example 124

Examples 123 and 124: 2-chloro-N-(5-chloro-6-(2-(2-hydroxyethyl)-2H-tetrazol-5-yl)pyridin-3-yl)-8,8-dimethyl-7,8-dihydro-6H-cyclopenta[e]pyrazolo[1,5-a]pyrimidine-6-carboxamide and 2-chloro-N-(5-chloro-6-(1-(2-hydroxyethyl)-1H-tetrazol-5-yl) pyridin-3-yl)-8,8-dimethyl-7,8-dihydro-6H-cyclopenta[e]pyrazolo[1,5-a]pyrimidine-6-carboxamide Step 1: 3-chloro-5-((diphenylmethylene)amino)picolinonitrile

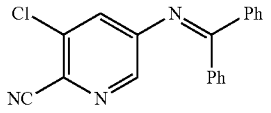 [SMILES: N#Cc1ncc(N=C(c2ccccc2)c2ccccc2)cc1Cl]

To a stirred solution of 5-bromo-3-chloropicolinomtrile (10.0 g, 46.1 mmol) and diphenylmethanimine (16.6 g, 92.2 mmol) in dioxane (100 mL) were added $Cs_2CO_3$ (29.9 g, 92.2 mmol), XantPhos (5.3 g, 9.2 mmol) and $Pd_2(dba)_3$ (4.7 g, 4.6 mmol). The mixture was stirred at 110° C. for 2 h. The reaction was cooled to 25° C. The reaction mixture was quenched with water (500 mL). The resulting solution was extracted with ethyl acetate (3×300 mL). The combined organic layers were dried over anhydrous sodium sulfate and concentrated under reduced pressure. The residue was applied onto a silica gel column and eluted with EtOAc/PE (1:3) to give 3-chloro-5-((diphenylmethylene)amino)picolinonitrile (11.5 g, 78% yield) as a yellow oil. LC-MS: m/z 318 $[M+H]^+$.

Step 2: 5-amino-3-chloropicolinonitrile

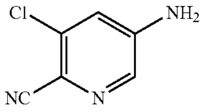

To a stirred solution of 3-chloro-5-((diphenylmethylene) amino)picolinonitrile (11.5 g, 36.2 mmol) in methanol (100 mL) were added hydroxylamine hydrochloride (4.9 g, 72.4 mmol) and sodium acetate (6.1 g, 72.4 mmol). The mixture was stirred at 25° C. for 2 h. The reaction mixture was quenched with water (500 mL). The resulting solution was extracted with ethyl acetate (3×300 mL). The combined organic layers were dried over anhydrous sodium sulfate and concentrated under reduced pressure. The residue was applied onto a silica gel column and eluted with EtOAc/PE (1:1) to give 5-amino-3-chloropicolinonitrile (3.2 g, 58% yield) as a white solid. LC-MS: m/z 154 $[M+H]^+$.

Step 3: 2-chloro-N-(5-chloro-6-cyanopyridin-3-yl)-8,8-dimethyl-7,8-dihydro-6H-cyclopenta[e]pyrazolo[1,5-a]pyrimidine-6-carboxamide

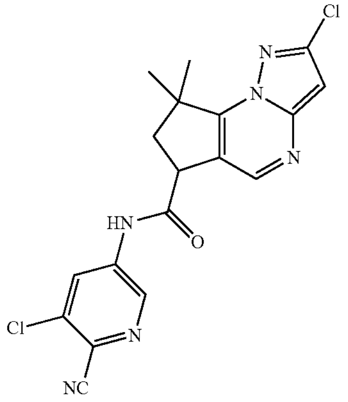 [SMILES: CC1(C)CC(C(=O)Nc2cnc(C#N)c(Cl)c2)c2cnc3cc(Cl)nn3c21]

To a solution of 5-amino-3-chloropicolinonitrile (3.2 g, 20.9 mmol) in ACN (50 mL) were added 2-chloro-8,8-dimethyl-7,8-dihydro-6H-cyclopenta[e]pyrazolo[1,5-a]pyrimidine-6-carboxylic acid (Method A1 step 6; 5.5 g, 20.9 mmol), TCFH (23.4 g, 83.6 mmol) and NMI (6.8 g, 83.6 mmol). The resulting mixture was stirred at 25° C. for 2 h. The reaction mixture was concentrated under reduced pressure. The residue was applied onto a silica gel column and eluted with EtOAc/PE (1:1) to give 2-chloro-N-(5-chloro-6-cyanopyridin-3-yl)-8,8-dimethyl-7,8-dihydro-6H-cyclopenta[e]pyrazolo[1,5-a]pyrimidine-6-carboxamide (5.0 g, 60% yield) as a white solid. LC-MS: m/z 401 $[M+H]^+$.

Step 4: 2-chloro-N-(5-chloro-6-(2H-tetrazol-5-yl)pyridin-3-yl)-8,8-dimethyl-7,8-dihydro-6H-cyclopenta[e]pyrazolo[1,5-a]pyrimidine-6-carboxamide

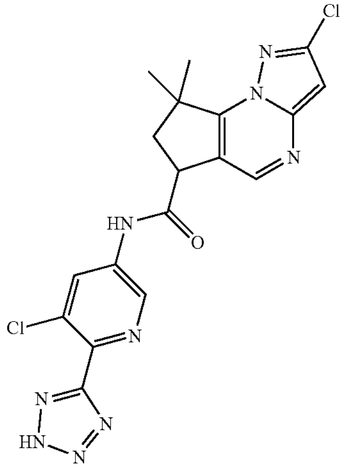 [SMILES: CC1(C)CC(C(=O)Nc2cnc(-c3nn[nH]n3)c(Cl)c2)c2cnc3cc(Cl)nn3c21]

To a stirred solution of 2-chloro-N-(5-chloro-6-cyanopyridin-3-yl)-8,8-dimethyl-7,8-dihydro-6H-cyclopenta[e]pyrazolo[1,5-a]pyrimidine-6-carboxamide (5.0 g, 12.5 mmol) and zinc(II) bromide (2.8 g, 12.5 mmol) in isopropyl alcohol (50 mL) and water (5 mL) were added sodium azide (2.4 g, 37.5 mmol). The mixture was stirred at 100° C. for 16 h. The reaction was cooled to 25° C. The reaction mixture was quenched with water (200 mL). The resulting solution was extracted with ethyl acetate (3×200 mL). The combined organic layers were washed with water (3×500 mL), dried over anhydrous sodium sulfate and concentrated under reduced pressure. The residue was applied on a silica gel column and eluted with MeOH/DCM (1:5) to give 2-chloro-N-(5-chloro-6-(2H-tetrazol-5-yl)pyridin-3-yl)-8,8-dimethyl-7,8-dihydro-6H-cyclopenta[e]pyrazolo[1,5-a]pyrimidine-6-carboxamide (2.0 g, 36% yield) as a white solid. LC-MS: m/z 444 $[M+H]^+$.

Step 5: 2-chloro-N-(5-chloro-6-(2-(2-hydroxyethyl)-2H-tetrazol-5-yl)pyridin-3-yl)-8,8-dimethyl-7,8-dihydro-6H-cyclopenta[e]pyrazolo[1,5-a]pyrimidine-6-carboxamide and 2-chloro-N-(5-chloro-6-(1-(2-hydroxyethyl)-1H-tetrazol-5-yl)pyridin-3-yl)-8,8-dimethyl-7,8-dihydro-6H-cyclopenta[e]pyrazolo[1,5-a]pyrimidine-6-carboxamide

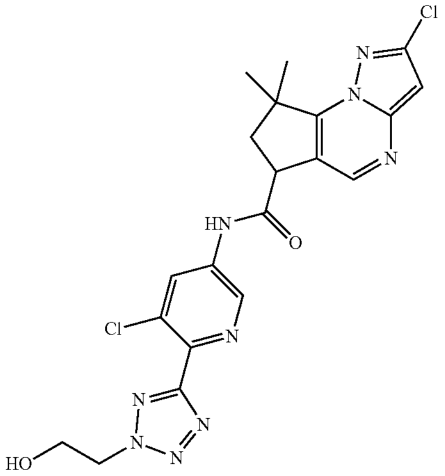

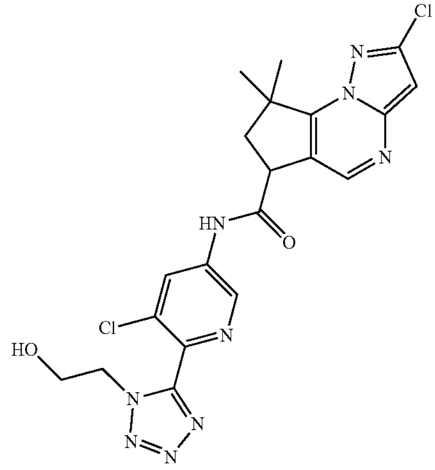

Example 123 and
Example 124

To a stirred solution of 2-chloro-N-(5-chloro-6-(2H-tetrazol-5-yl)pyridin-3-yl)-8,8-dimethyl-7,8-dihydro-6H-cyclopenta[e]pyrazolo[1,5-a]pyrimidine-6-carboxamide (300 mg, 675.6 μmol) in DMF (30 mL) and ACN (3 mL) were added 2-bromoethan-1-ol (253 mg, 2.0 mmol) and $K_2CO_3$ (280 mg, 2.0 mmol). The mixture was stirred at 50° C. for 3 h. The reaction mixture was quenched with water (50 mL). The resulting solution was extracted with ethyl acetate (3×50 mL). The combined organic layers were washed with water (3×40 mL), dried over anhydrous sodium sulfate and concentrated under reduced pressure. The residue was submitted to Prep-HPLC purification and the collected fractions were lyophilized to give Example 123 (1.0 mg, 0.3% yield) as an off-white solid and Example 124 (2.1 mg, 0.6% yield) as an off-white solid.

Example 123: $^1$H NMR (300 MHz, DMSO-$d_6$) δ 10.99 (s, 1H), 8.85 (d, J=2.1 Hz, 1H), 8.65 (s, 1H), 8.49 (d, J=2.1 Hz, 1H), 6.94 (s, 1H), 5.10 (t, J=5.5 Hz, 1H), 4.80 (t, J=5.2 Hz, 2H), 4.42-4.47 (m, 1H), 3.94-3.99 (m, 2H), 2.53-2.56 (m, 1H), 2.29-2.39 (m, 1H), 1.64 (s, 3H), 1.56 (s, 3H). LC-MS: m/z 488.1 [M+H]$^+$.

Example 124: $^1$H NMR (300 MHz, DMSO-$d_6$) δ 11.08 (s, 1H), 8.90 (d, J=2.1 Hz, 1H), 8.64 (s, 1H), 8.52 (d, J=2.1 Hz, 1H), 6.94 (s, 1H), 4.89 (t, J=5.5 Hz, 1H), 4.59 (t, J=5.2 Hz, 2H), 4.42-4.48 (m, 1H), 3.68-3.70 (m, 2H), 2.53-2.56 (m, 1H), 2.29-2.39 (m, 1H), 1.64 (s, 3H), 1.56 (s, 3H). LC-MS: m/z 488.1 [M+H]$^+$ The position of the hydroxyethyl group on the triazole moiety was not determined.

Method O3

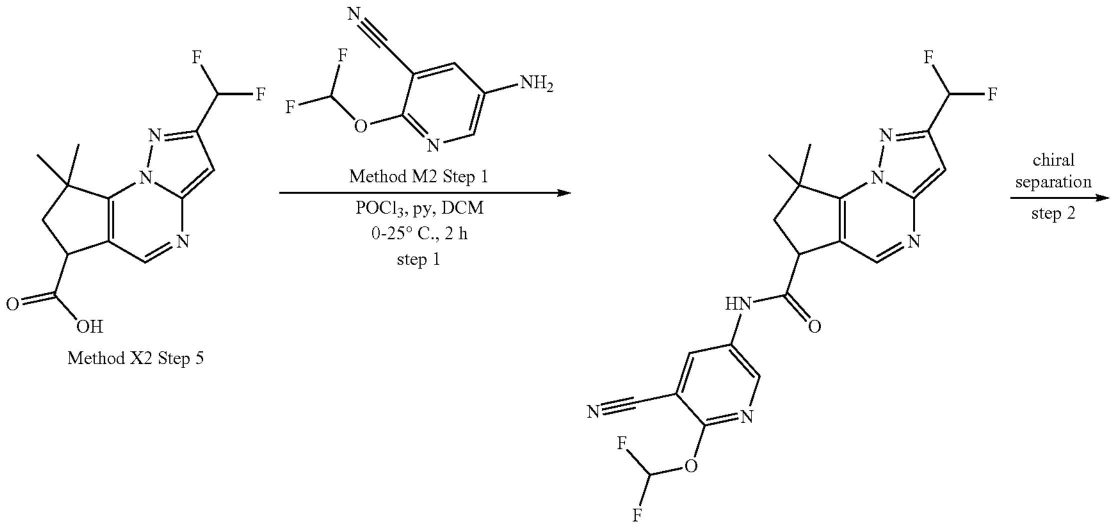

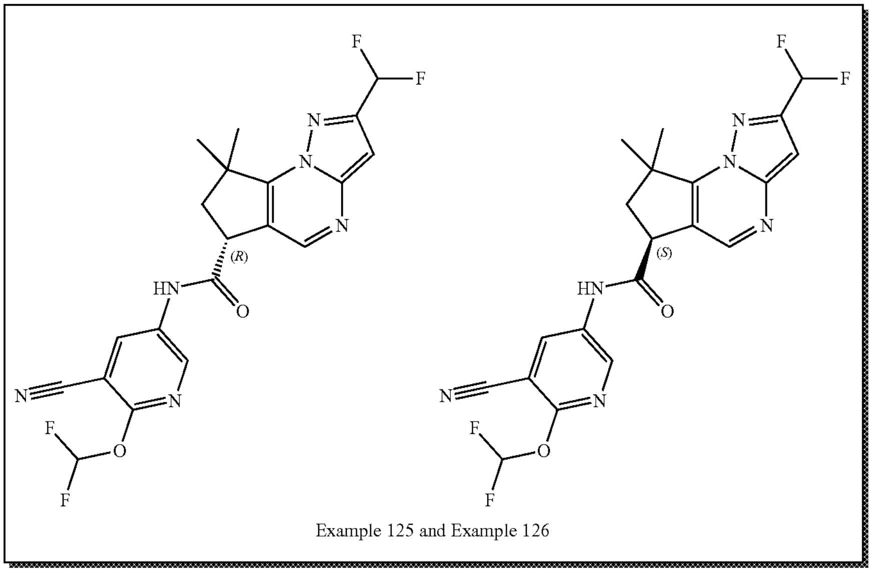

Example 125 and Example 126

Examples 125 and 126: Single Enantiomers Obtained from a Racemic Mixture Containing (R)—N-(5-cyano-6-(difluoromethoxy)pyridin-3-yl)-2-(difluoromethyl)-8,8-dimethyl-7,8-dihydro-6H-cyclopenta[e]pyrazolo[1,5-a]pyrimidine-6-carboxamide and (S)—N-(5-cyano-6-(difluoromethoxy)pyridin-3-yl)-2-(difluoromethyl)-8,8-dimethyl-7,8-dihydro-611-cyclopenta[e]pyrazolo[1,5-a]pyrimidine-6-carboxamide

Step 1: N-(5-cyano-6-(difluoromethoxy)pyridin-3-yl)-2-(difluoromethyl)-8,8-dimethyl-7,8-dihydro-6H-cyclopenta[e]pyrazolo[1,5-a]pyrimidine-6-carboxamide

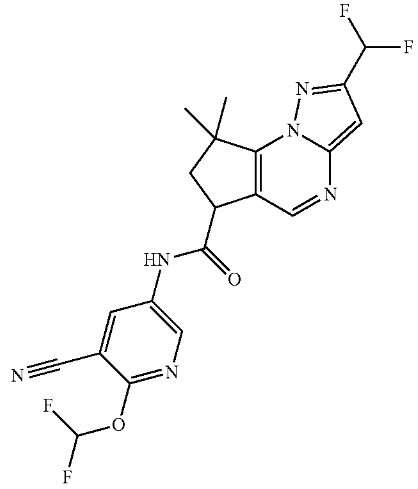 [SMILES: CC1(C)CC(C(=O)Nc2cnc(OC(F)F)c(C#N)c2)c2cnc3cc(C(F)F)nn3c21]

To a stirred solution of 2-(difluoromethyl)-8,8-dimethyl-7,8-dihydro-6H-cyclopenta[e]pyrazolo[1,5-a]pyrimidine-6-carboxylic acid (Method X2 step 5; 100 mg, 355.5 μmol) in DCM (4 mL) were added pyridine (281 mg, 3.5 mmol) and phosphoryl trichloride (163 mg, 1.0 mmol) at 0° C. The mixture was stirred at 0° C. for 0.5 h. Then 5-amino-2-(difluoromethoxy)nicotinonitrile (Method M2 step 1; 72 mg, 391.1 μmol) was added. The mixture was stirred at 25° C. for 2 h. The reaction mixture was quenched with water (20 mL). The resulting solution was extracted with DCM (3×20 mL). The combined organic layers were dried over anhydrous sodium sulfate and concentrated under reduced pressure. The residue was purified by Prep-HPLC and the collected fractions were concentrated under reduced pressure to afford N-(5-cyano-6-(difluoromethoxy)pyridin-3-yl)-2-(difluoromethyl)-8,8-dimethyl-7,8-dihydro-6H-cyclopenta[e]pyrazolo[1,5-a]pyrimidine-6-carboxamide (15 mg, 9% yield) as a white solid. LC-MS: m/z 449 [M+H]$^+$.

Step 2: Separation of Enantiomers to Obtain (R)—N-(5-cyano-6-(difluoromethoxy)pyridin-3-yl)-2-(difluoromethyl)-8,8-dimethyl-7,8-dihydro-6H-cyclopenta[e]pyrazolo[1,5-a]pyrimidine-6-carboxamide and (S)—N-(5-cyano-6-(difluoromethoxy)pyridin-3-yl)-2-(difluoromethyl)-8,8-dimethyl-7,8-dihydro-6H-cyclopenta[e]pyrazolo[1,5-a]pyrimidine-6-carboxamide

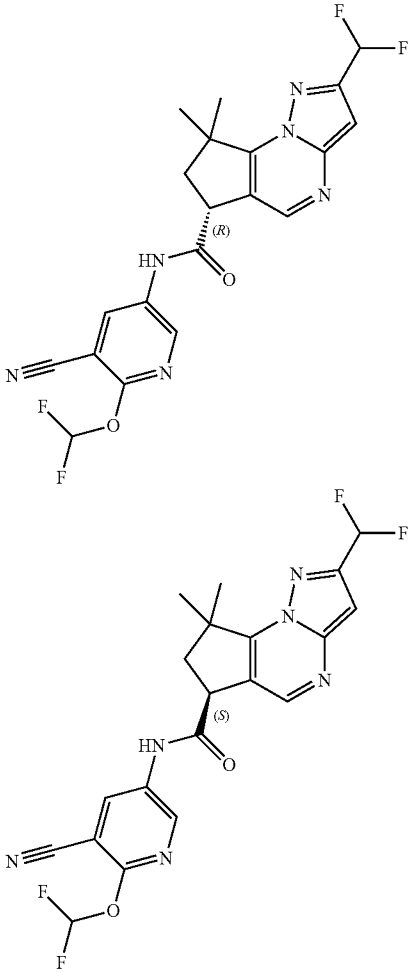

Example 125 and
Example 126

15 mg of N-(5-cyano-6-(difluoromethoxy)pyridin-3-yl)-2-(difluoromethyl)-8,8-dimethyl-7,8-dihydro-6H-cyclopenta[e]pyrazolo[1,5-a]pyrimidine-6-carboxamide were submitted to chiral HPLC purification (Column: CHIRALPAK IG, 2*25 cm, 5 μm; Mobile Phase A: Hex(0.1% FA)-HPLC, Mobile Phase B: EtOH-HPLC; Flow rate: 20 mL/min; isocratic 50% B in 9.5 min; Wave Length: 254/220 nm; RT1(min): 5.392; RT2(min): 6.994; Sample Solvent: ETOH:DCM=1:1; Injection Volume: 2 mL; Number Of Runs: 4). The first eluting isomer was concentrated and lyophilized to afford Example 125 (4.0 mg, 26% yield) as an off-white solid. The second eluting isomer was concentrated and lyophilized to afford Example 126 (4.6 mg, 30% yield) as a light yellow solid.

Example 125: $^1$H NMR (400 MHz, DMSO-$d_6$) δ:10.88 (br, 1H), 8.68-8.69 (m, 2H), 8.63 (d, J=2.4 Hz, 1H), 7.75 (t, J=71.2 Hz, 1H), 7.30 (t, J=54.4 Hz, 1H), 7.08 (s, 1H), 4.42-4.46 (m, 1H), 2.53-2.59 (m, 1H), 2.31-2.36 (m, 1H), 1.67 (s, 3H), 1.58 (s, 3H). LC-MS: m/z 449.1 $[M+H]^+$.
Example 126: $^1H$ NMR (400 MHz, DMSO-$d_6$) δ: 10.88 (br, 1H), 8.68-8.69 (m, 2H), 8.63 (d, J=2.8 Hz, 1H), 7.75 (t, J=71.2 Hz, 1H), 7.30 (t, J=54.4 Hz, 1H), 7.08 (s, 1H), 4.42-4.46 (m, 1H), 2.53-2.59 (m, 1H), 2.31-2.36 (m, 1H), 1.67 (s, 3H), 1.58 (s, 3H). LC-MS: m/z 449.1 $[M+H]^+$.
The absolute stereochemistry for each separated isomer was not determined.
Method P3
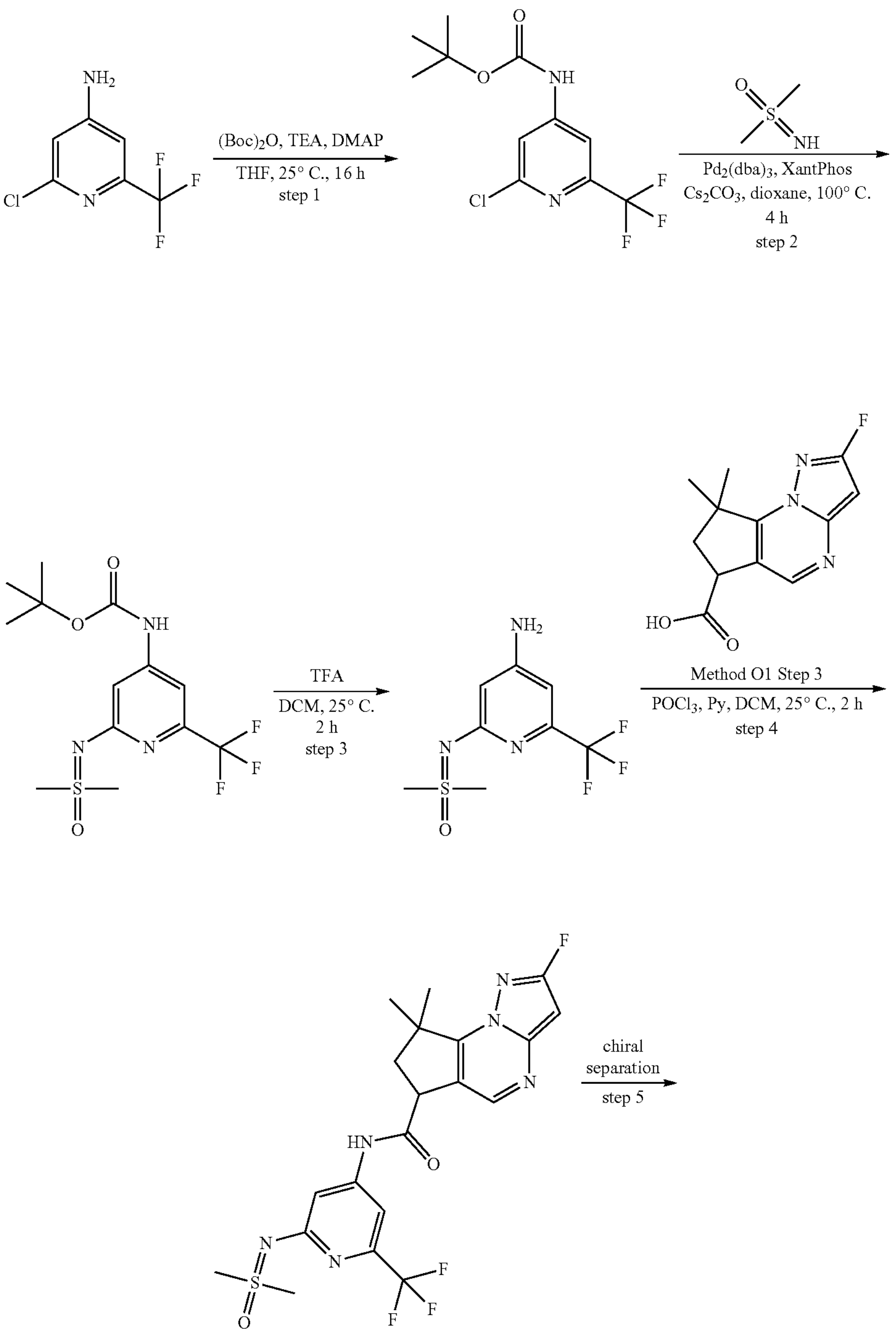

-continued

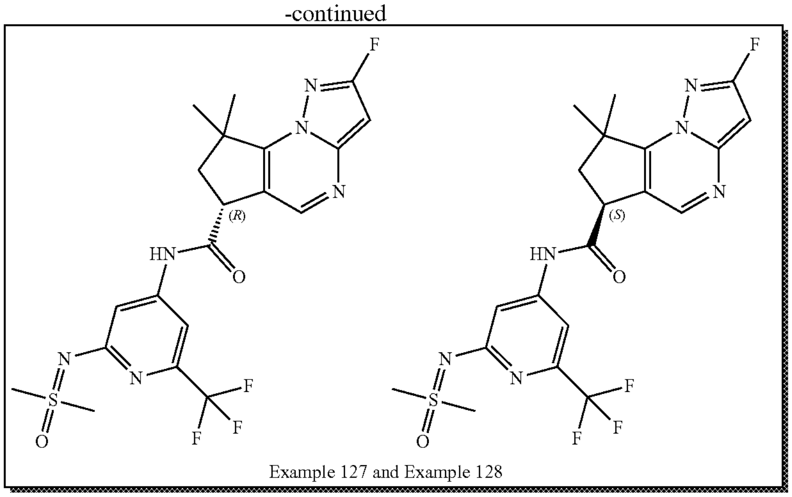

Example 127 and Example 128

Examples 127 and 128: Single Enantiomers Obtained from a Racemic Mixture Containing (R)—N-(2-((dimethyl(oxo)-λ$^6$-sulfaneylidene) amino)-6-(trifluoromethyl)pyridin-4-yl)-2-fluoro-8,8-dimethyl-7,8-dihydro-6H-cyclopenta[e]pyrazolo[1,5-a]pyrimidine-6-carboxamide and (S)—N-(2-((dimethyl(oxo)-λ$^6$-sulfaneylidene)amino)-6-(trifluoromethyl)pyridin-4-yl)-2-fluoro-8,8-dimethyl-7,8-dihydro-6H-cyclopenta[e]pyrazolo[1,5-a]pyrimidine-6-carboxamide

Step 1: tert-butyl (2-chloro-6-(trifluoromethyl)pyridin-4-yl)carbamate

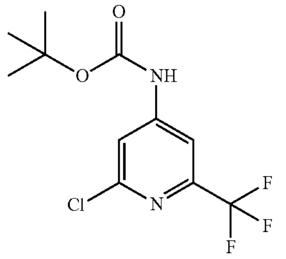 [SMILES: CC(C)(C)OC(=O)Nc1cc(Cl)nc(C(F)(F)F)c1]

To a stirred solution of 2-chloro-6-(trifluoromethyl)pyridin-4-amine (10 g, 50.9 mmol) in THF (250 mL) were added di-tertbutyl dicarbonate (16.7 g, 76.3 mmol), trimethylamine (12.9 g, 127.2 mmol) and 4-Dimethylaminopyridine (0.6 g, 5.1 mmol). The resulting mixture was stirred at 25° C. for 16 h. The reaction mixture was concentrated under reduced pressure. The residue was applied onto a silica gel column and eluted with EtOAc/PE (1:10) to give tert-butyl (2-chloro-6-(trifluoromethyl)pyridin-4-yl)carbamate (5.2 g, 33% yield) as a white solid. $^1$H NMR (300 MHz, DMSO-d$_6$) δ: 10.52 (s, 1H), 7.89 (d, J=1.5 Hz, 1H), 7.73 (d, J=1.8 Hz, 1H), 1.50 (s, 9H); LC-MS: m/z 297 [M+H]$^+$.

Step 2: tert-butyl (2-((dimethyl(oxo)-λ$^6$-sulfaneylidene)amino)-6-(trifluoromethyl)pyridin-4-yl)carbamate

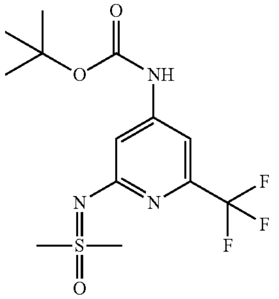 [SMILES: CC(C)(C)OC(=O)Nc1cc(N=S(C)(C)=O)nc(C(F)(F)F)c1]

To a stirred solution of tert-butyl (2-chloro-6-(trifluoromethyl)pyridin-4-yl)carbamate (600 mg, 2.0 mmol) in dioxane (12 mL) were added iminodimethyl-λ$^6$-sulfanone (226 mg, 2.4 mmol), $Pd_2(dba)_3$ (186 mg, 0.2 mmol), Xant-Phos (235 mg, 0.4 mmol) and $Cs_2CO_3$ (989 mg, 0.4 mmol). The resulting mixture was stirred at 100° C. for 4 h under nitrogen atmosphere. The mixture was allowed to cool down to 25° C. and concentrated under reduced pressure. The residue was applied onto a silica gel column and eluted with EtOAc/PE (1:1) to give tert-butyl (2-((dimethyl(oxo)-λ$^6$-sulfaneylidene)amino)-6-(trifluoromethyl)pyridin-4-yl)carbamate (600 mg, 82% yield) as a yellow solid. $^1$H NMR (300 MHz, Chloroform-d) δ: 9.96 (s, 1H), 7.45 (d, J=3.0 Hz, 1H), 6.88 (d, J=3.0 Hz, 1H), 3.38 (s, 6H), 1.49 (s, 9H). LC-MS: m/z 354 [M+H]$^+$.

Step 3: ((4-Amino-6-(trifluoromethyl)pyridin-2-yl)imino)dimethyl-λ$^6$-sulfanone

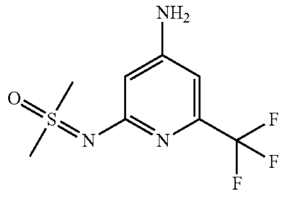 [SMILES: CS(C)(=O)=Nc1cc(N)cc(C(F)(F)F)n1]

To a stirred solution of tert-butyl (2-((dimethyl(oxo)-λ$^6$-sulfaneylidene)amino)-6-(trifluoromethyl)pyridin-4-yl)carbamate (100 mg, 282.5 μmol) in DCM (9.6 mL) was added TFA (2.4 mL). The mixture was stirred at 25° C. for 2 h. The resulting mixture was concentrated under reduced pressure. The pH was adjusted to 5-6 with saturated aqueous sodium bicarbonate solution. The resulting solution was extracted with ethyl acetate (3×20 mL). The combined organic layers were washed with brine (50 mL), dried over anhydrous sodium sulfate and concentrated under reduced pressure. The residue was applied onto a silica gel column and eluted with EtOAc/PE (1:1) to give ((4-amino-6-(trifluoromethyl)pyridin-2-yl)imino)dimethyl-λ$^6$-sulfanone (60 mg, 83% yield) as a white solid. LC-MS: m/z 254 $[M+H]^+$.

Step 4: N-(2-((dimethyl(oxo)-λ$^6$-sulfaneylidene)amino)-6-(trifluoromethyl)pyridin-4-yl)-2-fluoro-8,8-dimethyl-7,8-dihydro-6H-cyclopenta[e]pyrazolo[1,5-a]pyrimidine-6-carboxamide

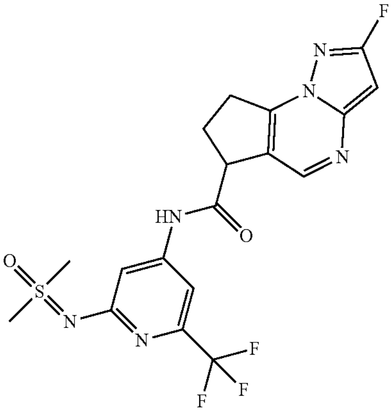 [SMILES: CS(C)(=O)=Nc1cc(NC(=O)C2CCc3c2cnc2cc(F)nn32)cc(C(F)(F)F)n1]

To a stirred solution of 2-fluoro-8,8-dimethyl-7,8-dihydro-6H-cyclopenta[e]pyrazolo[1,5-a]pyrimidine-6-carboxylic acid (Method 01 step 3; 35 mg, 140.6 μmol) in DCM (8 mL) were added pyridine (111 mg, 1.4 mmol) and phosphoryl trichloride (65 mg, 421.8 μmol) at 0° C. The resulting mixture was stirred at 0° C. for 1 h. Then ((4-amino-6-(trifluoromethyl)pyridin-2-yl)imino)dimethyl-λ$^6$-sulfanone (47 mg, 182.3 μmol) was added. The resulting mixture was stirred at 25° C. for 2 h. The reaction mixture was quenched with water (20 mL). The resulting solution was extracted with DCM (3×30 mL). The combined organic layers were dried over anhydrous sodium sulfate and concentrated under reduced pressure. The residue was submitted to Prep-HPLC purification and the collected fractions were lyophilized to give N-(2-((dimethyl(oxo)-λ$^6$-sulfaneylidene)amino)-6-(trifluoromethyl)pyridin-4-yl)-2-fluoro-8,8-dimethyl-7,8-dihydro-6H-cyclopenta[e]pyrazolo[1,5-a]pyrimidine-6-carboxamide (35 mg, 95% yield) as a yellow oil. LC-MS: m/z 485 $[M+H]^+$.

Step 5: Separation of Enantiomers to Obtain (R)—N-(2-((dimethyl(oxo)-λ$^6$-sulfaneylidene)amino)-6-(trifluoromethyl)pyridin-4-yl)-2-fluoro-8,8-dimethyl-7,8-dihydro-6H-cyclopenta[e]pyrazolo[1,5-a]pyrimidine-6-carboxamide and (S)—N-(2-((dimethyl(oxo)-λ$^6$-sulfaneylidene)amino)-6-(trifluoromethyl)pyridin-4-yl)-2-fluoro-8,8-dimethyl-7,8-dihydro-6H-cyclopenta[e]pyrazolo[1,5-a]pyrimidine-6-carboxamide

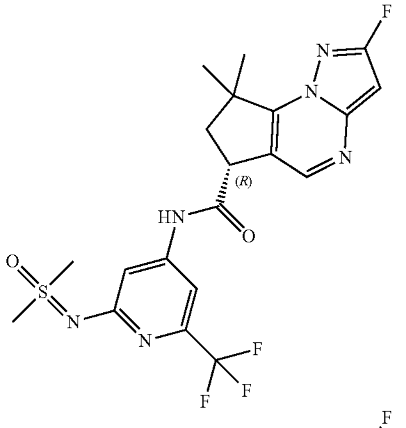

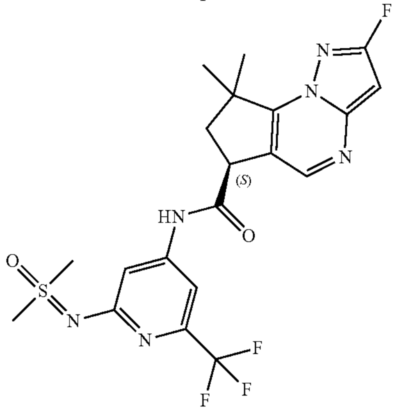

Example 127
and
Example 128

30 mg of N-(2-((dimethyl(oxo)-16-sulfaneylidene)amino)-6-(trifluoromethyl)pyridin-4-yl)-2-fluoro-8,8-dimethyl-7,8-dihydro-6H-cyclopenta[e]pyrazolo[1,5-a]pyrimidine-6-carboxamide were submitted to chiral HPLC purification (Column: CHIRAL ART Amylose-SA, 2*25 cm, 5 μm; Mobile Phase A: Hex(0.1% FA)-HPLC, Mobile Phase B: EtOH-HPLC; Flow rate: 20 mL/min; isocratic 50% B in 15 min; Wave Length: 220/254 nm; RT1(min): 5.972; RT2(min): 12.782; Sample Solvent: EtOH-HPLC; Injection Volume: 2 mL; Number Of Runs: 2).

The first eluting isomer was concentrated and lyophilized to afford Example 127 (10.4 mg, 11% yield) as a white solid. The second eluting isomer was concentrated and lyophilized to afford Example 128 (8.3 mg, 9% yield) as a white solid.

Example 127: $^1H$ NMR (400 MHz, DMSO-$d_6$) δ: 10.78 (s, 1H), 8.59 (s, 1H), 7.54 (d, J=1.6 Hz, 1H), 7.14 (d, J=1.2 Hz, 1H), 6.56 (d, J=4.8 Hz, 1H), 4.35-4.39 (m, 1H), 3.40 (s, 6H), 2.52-2.56 (m, 1H), 2.24-2.29 (m, 1H), 1.60 (s, 3H), 1.53 (s, 3H). LC-MS: m/z 485.1 $[M+H]^+$.
Example 128: $^1H$ NMR (400 MHz, DMSO-$d_6$) δ: 10.78 (s, 1H), 8.59 (s, 1H), 7.54 (d, J=1.6 Hz, 1H), 7.14 (d, J=1.2 Hz, 1H), 6.56 (d, J=4.8 Hz, 1H), 4.35-4.39 (m, 1H), 3.40 (s, 6H), 2.52-2.56 (m, 1H), 2.24-2.29 (m, 1H), 1.60 (s, 3H), 1.53 (s, 3H). LC-MS: m/z 485.1 $[M+H]^+$.
The absolute stereochemistry for each separated isomer was not determined.
Method Q3
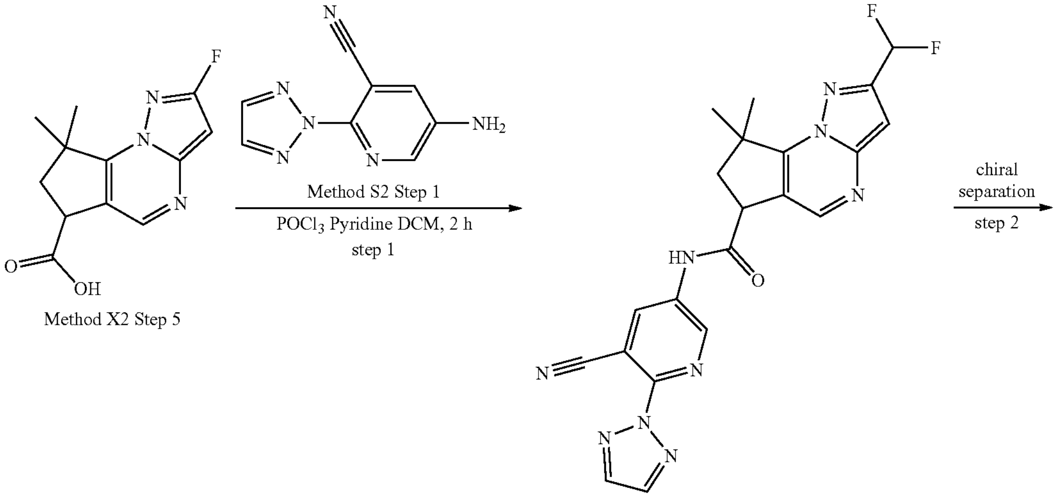
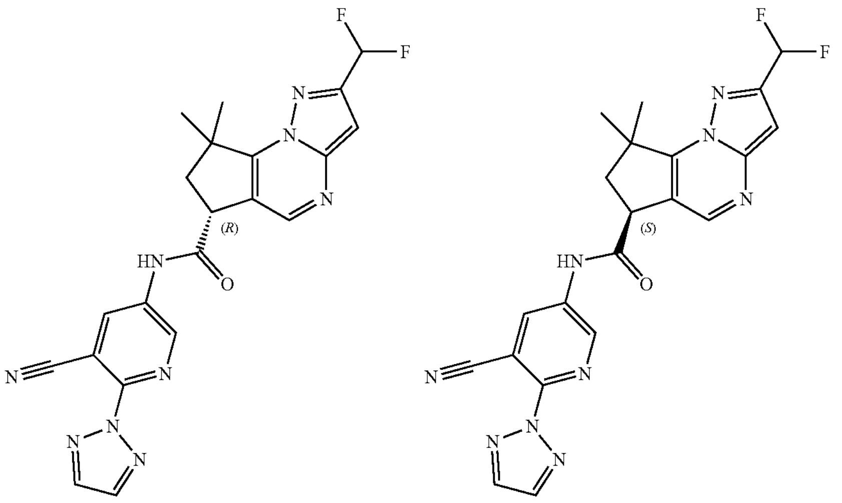
Example 129 and Example 130

Examples 129 and 130: Single Enantiomers Obtained from a Racemic Mixture Containing (R)—N-(5-cyano-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide and (S)—N-(5-cyano-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide Step 1: N-(5-cyano-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide

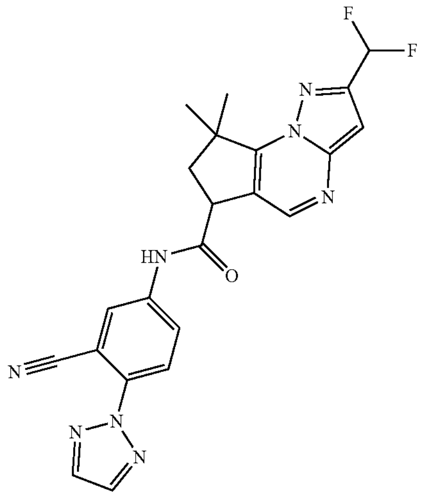 [SMILES: CC1(C)CC(C(=O)Nc2ccc(-n3nccn3)c(C#N)c2)c2cnc3cc(C(F)F)nn3c21]

To a stirred solution of 2-(difluoromethyl)-8,8-dimethyl-7,8-dihydro-6H-cyclopenta[e]pyrazolo[1,5-a]pyrimidine-6-carboxylic acid (Method X2 step 5; 60 mg, 213.3 μmol) in DCM (8 mL) were added pyridine (168 mg, 2.1 mmol) and phosphoryl trichloride (98 mg, 640.8 μmol) at 0° C. The mixture was stirred at 0° C. for 0.5 h. Then 5-amino-2-(2H-1,2,3-triazol-2-yl)nicotinonitrile (Method S2 step 1; 40 mg, 213.4 μmol) was added at 0° C. The mixture was stirred at 25° C. for 2 h. The reaction mixture was concentrated under reduced pressure. The residue was submitted to Prep-HPLC purification and the collected fractions were lyophilized to give N-(5-cyano-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide (62 mg, 65% yield) as a white solid. LC-MS: m/z 450 [M+H]$^+$.

Step 2: Separation of Enantiomers to Obtain (R)—N-(5-cyano-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide and (S)—N-(5-cyano-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide

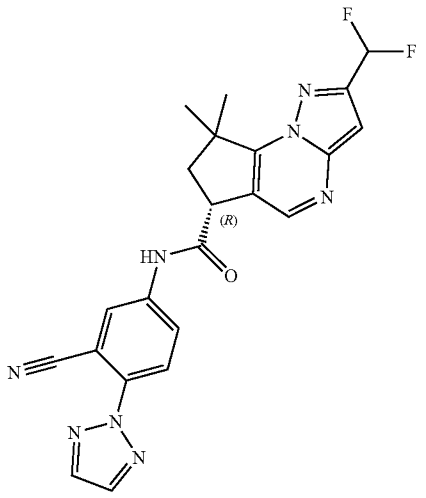

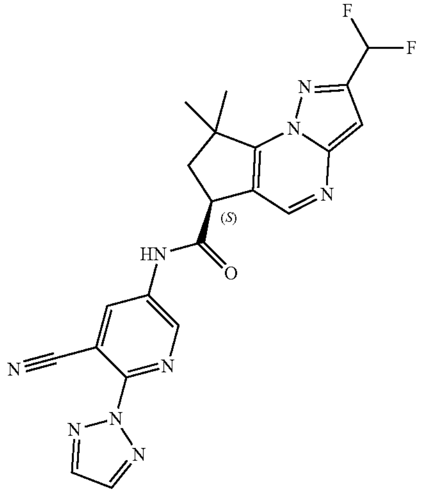

Example 129 and Example 130

60 mg of N-(5-cyano-6-(2H-1,2,3-triazol-2-yl)pyridin-3-yl)-2-(difluoromethyl)-8,8-dimethyl-7,8-dihydro-6H-cyclopenta[e]pyrazolo[1,5-a]pyrimidine-6-carboxamide were submitted to chiral HPLC purification (Column: CHIRAL ART Cellulose-SC, 2*25 cm, 5 μm; Mobile Phase A: Hex (0.5% 2M $NH_3$-MeOH)-HPLC, Mobile Phase B: EtOH-HPLC; Flow rate: 20 mL/min; isocratic 50% B in 20 min; Wave Length: 220/254 nm; RT1(min): 13.43; RT2(min): 17.52; Sample Solvent: EtOH-HPLC; Injection Volume: 0.3 mL; Number Of Runs: 7). The first eluting isomer was concentrated and lyophilized to afford Example 129 (18.3 mg, 30% yield) as a white solid. The second eluting isomer was concentrated and lyophilized to afford Example 130 (20.6 mg, 33% yield) as a white solid.

Example 129: $^1$H NMR (300 MHz, DMSO-$d_6$) δ: 11.13 (s, 1H), 8.99 (d, J=2.7 Hz, 1H), 8.78 (d, J=2.7 Hz, 1H), 8.72

(s, 1H), 8.30 (s, 2H), 7.30 (t, J=54.3 Hz, 1H), 7.08 (s, 1H), 4.47-4.52 (m, 1H), 2.56-2.64 (m, 1H), 2.33-2.40 (m, 1H), 1.68 (s, 3H), 1.60 (s, 3H). LCMS (ES, m/z): 450.0 $[M+H]^+$.
Example 130: $^1$H NMR (300 MHz, DMSO-$d_6$) δ: 11.13 (s, 1H), 8.99 (d, J=2.7 Hz, 1H), 8.78 (d, J=2.4 Hz, 1H), 8.72 (s, 1H), 8.29 (s, 2H), 7.30 (t, J=54.3 Hz, 1H), 7.08 (s, 1H), 4.47-4.52 (m, 1H), 2.56-2.63 (m, 1H), 2.33-2.40 (m, 1H), 1.68 (s, 3H), 1.59 (s, 3H). LC-MS (ES, m/z): 450.0 $[M+H]^+$.
The absolute stereochemistry for each separated isomer was not determined.
Method R3
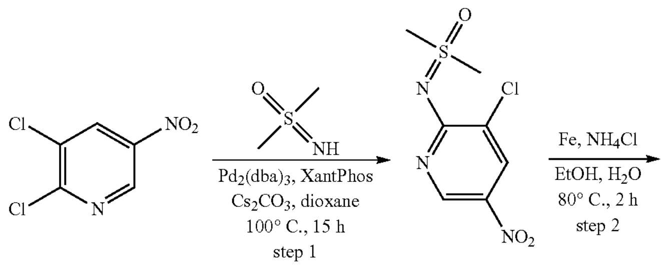
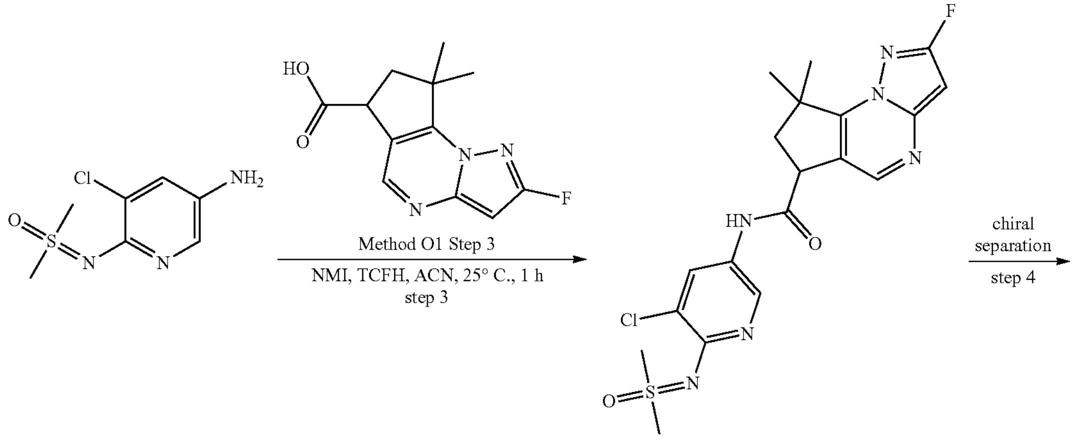
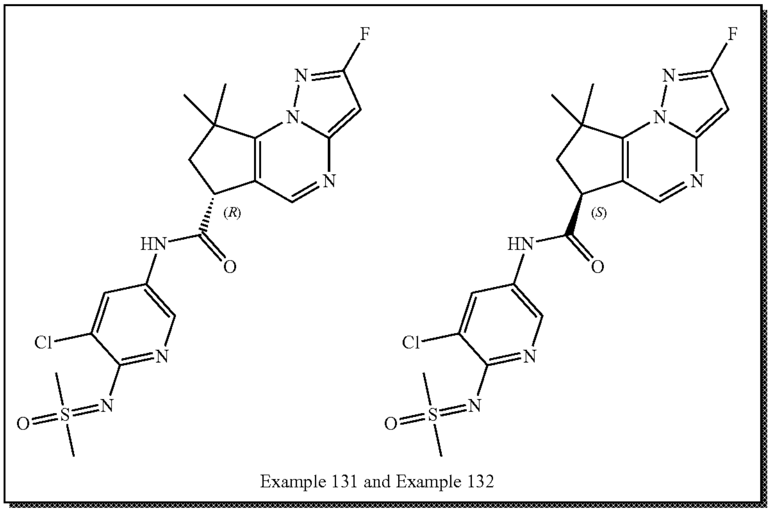
Example 131 and Example 132

Examples 131 and 132: Single Enantiomers Obtained from a Racemic Mixture Containing (R)—N-(5-chloro-6-((dimethyl(oxo)λ$^6$-sulfaneylidene)amino)pyridin-3-yl)-2-fluoro-8,8-dimethyl-7,8-dihydro-6H-cyclopenta[e]pyrazolo[1,5-a]pyrimidine-6-carboxamide and (S)—N-(5-chloro-6-((dimethyl(oxo)λ$^6$-sulfaneylidene)amino)pyridin-3-yl)-2-fluoro-8,8-dimethyl-7,8-dihydro-6H-cyclopenta[e]pyrazolo[1,5-a]pyrimidine-6-carboxamide Step 1: ((3-chloro-5-nitropyridin-2-yl)imino)dimethyl-λ$^6$-sulfanone

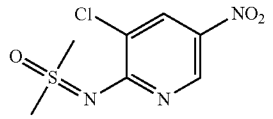

To a stirred solution of 2,3-dichloro-5-nitropyridine (600 mg, 3.1 mmol) in dioxane (12 mL) were added iminodimethyl-λ$^6$-sulfanone (577 mg, 6.2 mmol), $Pd_2(dba)_3$ (186 mg, 310 μmol), XantPhos (359 mg, 620 μmol) and $Cs_2CO_3$ (1.5 g, 4.7 mmol). The resulting mixture was stirred at 100° C. for 15 h under nitrogen atmosphere. The mixture was allowed to cool down to 25° C. and concentrated under reduced pressure. The residue was applied onto a silica gel column and eluted with EtOAc/PE (1:1) to give ((3-chloro-5-nitropyridin-2-yl)imino)dimethyl-λ$^6$-sulfanone (680 mg, 74% yield) as a yellow solid. LC-MS: m/z 250 $[M+H]^+$.

Step 2: ((5-amino-3-chloropyridin-2-yl)imino)dimethyl-λ$^6$-sulfanone

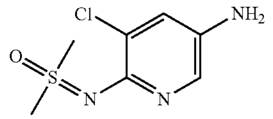

To a stirred solution of ((3-chloro-5-nitropyridin-2-yl)imino)dimethyl-λ$^6$-sulfanone (300 mg, 1.2 mmol) in EtOH (7 mL) and water (7 mL) were added Fe (269 mg, 4.8 mmol) and Ammonium chloride (260 mg, 4.8 mmol). The mixture was stirred at 80° C. for 2 h. After cooled to 25° C., the solid was filtered out. The filtrate was concentrated under reduced pressure. The residue was diluted with water (10 mL). The resulting solution was extracted with ethyl acetate (3×10 mL). The combined organic layers were dried over anhydrous sodium sulfate and concentrated under reduced pressure. The residue was applied onto a silica gel column and eluted with MeOH/DCM (1:10) to give ((5-amino-3-chloropyridin-2-yl)imino)dimethyl-λ$^6$-sulfanone (60 mg, 83% yield) as a white solid. LC-MS: m/z 220 $[M+H]^+$.

Step 3: N-(5-chloro-6-((dimethyl(oxo)-λ$^6$-sulfaneylidene)amino)pyridin-3-yl)-2-fluoro-8,8-dimethyl-7,8-dihydro-6H-cyclopenta[e]pyrazolo[1,5-a]pyrimidine-6-carboxamide

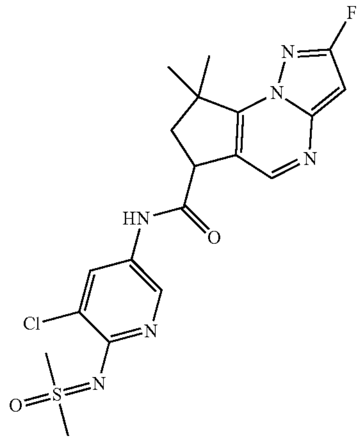 [SMILES: CC1(C)CC(C(=O)Nc2cnc(N=S(C)(C)=O)c(Cl)c2)c2cnc3cc(F)nn3c21]

To a stirred solution of ((5-amino-3-chloropyridin-2-yl)imino)dimethyl-λ$^6$-sulfanone (30 mg, 136 μmol) in ACN (2 mL) were added 2-fluoro-8,8-dimethyl-7,8-dihydro-6H-cyclopenta[e]pyrazolo[1,5-a]pyrimidine-6-carboxylic acid (Method 01 step 3; 60 mg, 272 μmol), TCFH (114 mg, 408 μmol) and NMI (100 mg, 1.1 mmol). The mixture was stirred for at 25° C. 1 h. The resulting mixture was concentrated under reduced pressure. The residue was submitted to Prep-HPLC purification and the collected fractions were lyophilized to give N-(5-chloro-6-((dimethyl(oxo)-λ$^6$-sulfaneylidene)amino)pyridin-3-yl)-2-fluoro-8,8-dimethyl-7,8-dihydro-6H-cyclopenta[e]pyrazolo[1,5-a]pyrimidine-6-carboxamide (30 mg, 42% yield) as a white solid. LC-MS: m/z 451 $[M+H]^+$.

Step 4: Separation of Enantiomers to Obtain (R)—N-(5-chloro-6-((dimethyl(oxo)-λ$^6$-sulfaneylidene)amino)pyridin-3-yl)-2-fluoro-8,8-dimethyl-7,8-dihydro-6H-cyclopenta[e]pyrazolo[1,5-a]pyrimidine-6-carboxamide and (S)—N-(5-chloro-6-((dimethyl(oxo)-λ$^6$sulfaneylidene)amino)pyridin-3-yl)-2-fluoro-8,8-dimethyl-7,8-dihydro-6H-cyclopenta[e]pyrazolo[1,5-a]pyrimidine-6-carboxamide Example 131

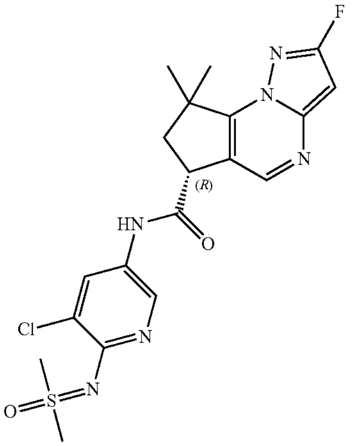

and

-continued

Example 132

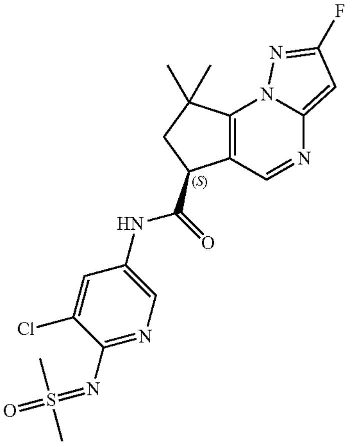

30 mg of N-(5-chloro-6-((dimethyl(oxo)-λ$^6$-sulfaneylidene)amino)pyridin-3-yl)-2-fluoro-8,8-dimethyl-7,8-dihydro-6H-cyclopenta[e]pyrazolo[1,5-a]pyrimidine-6-carboxamide were submitted to chiral HPLC purification (Column: CHIRAL ART Amylose-SA, 2×25 cm, 5 μm; Mobile Phase A: Hex(0.1% FA)-HPLC, Mobile Phase B: EtOH-HPLC; Flow rate: 20 mL/min; isocratic 50% B in 15 min; Wave Length: 220/254 nm; RT1(min): 6.196; RT2 (min): 14.59; Sample Solvent: EtOH-HPLC; Injection Volume: 2 mL; Number Of Runs: 3). The first eluting isomer was concentrated and lyophilized to afford Example 131 (12.6 mg, 19% yield) as a white solid. The second eluting isomer was concentrated and lyophilized to afford Example 132 (10.8 mg, 17% yield) as a white solid.

Example 131: $^1$H NMR (400 MHz, DMSO-d$_6$) δ: 10.40 (s, 1H), 8.58 (s, 1H), 8.24 (d, J=2.4 Hz, 1H), 8.09 (d, J=2.4 Hz, 1H), 6.55 (d, J=4.8 Hz, 1H), 4.31-4.35 (m, 1H), 3.40 (s, 6H), 2.46-2.49 (m, 1H), 2.26-2.31 (m, 1H) 1.61 (s, 3H), 1.52 (s, 3H). LC-MS: m/z 451.1 [M+H]$^+$.

Example 132: $^1$H NMR (400 MHz, DMSO-d$_6$) δ: 10.40 (s, 1H), 8.58 (s, 1H), 8.24 (d, J=2.4 Hz, 1H), 8.09 (d, J=2.4 Hz, 1H), 6.55 (d, J=4.8 Hz, 1H), 4.31-4.35 (m, 1H), 3.40 (s, 6H), 2.46-2.49 (m, 1H), 2.26-2.31 (m, 1H) 1.61 (s, 3H), 1.52 (s, 3H). LC-MS: m/z 451.1 [M+H]$^+$.

The absolute stereochemistry for each separated isomer was not determined.

Method S3

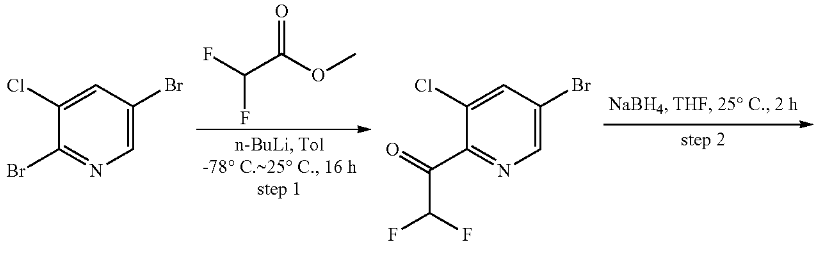

-continued

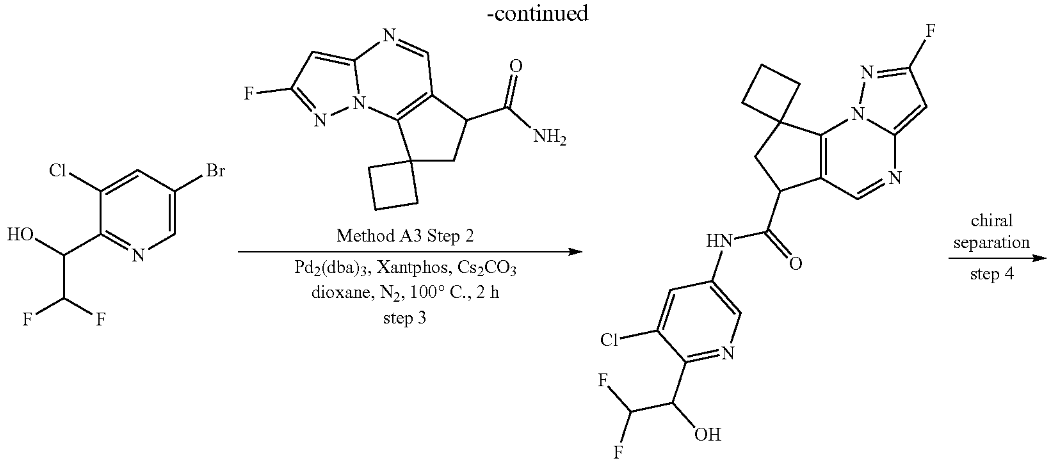

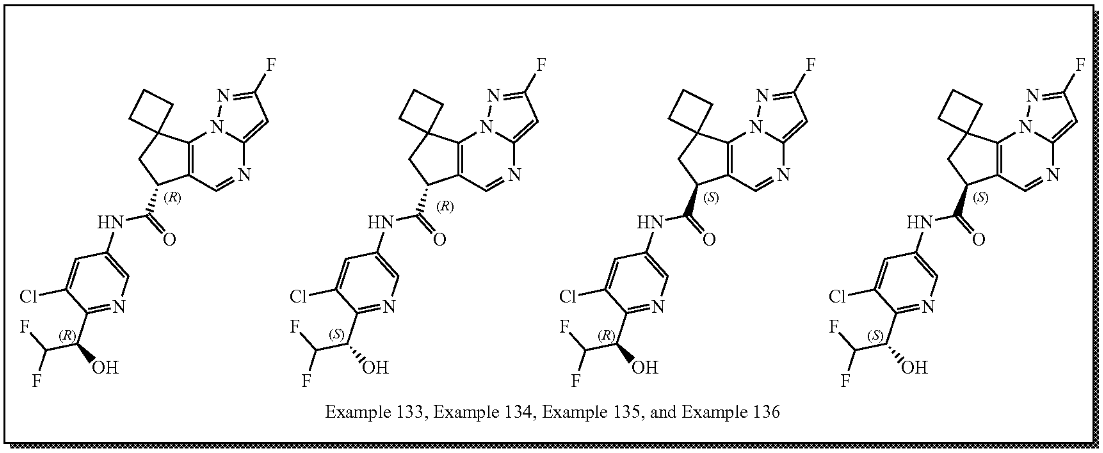

Example 133, Example 134, Example 135, and Example 136

Examples 133,134,135 and 136: Single Enantiomers Obtained from a Racemic Mixture Containing (R)—N-(5-chloro-6-((R)-2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide, (R)—N-(5-chloro-6-((S)-2,2-difluoro-1-hydroxyethyl)pyridin-3-yl)-2'-fluoro-6',7'-dihydrospiro[cyclobutane-1,8'-cyclopenta[a]pyrazolo[1,5-a]pyrimidine]-6'-carboxamide, (S)—N-(5-chloro-6-((R)-2,2-difluoro-1-hydroxyethyl)pyridin-3-yl)-2'-fluoro-6',7'-dihydrospiro[cyclo-butane-1,8'-cyclopenta[e]pyrazolo[1,5-a]pyrimidine]-6'-carboxamide and (S)—N-(5-chloro-6-((S)-2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide Step 1:1-(5-bromo-3-chloropyridin-2-yl)-2,2-difluoroethan-1-one

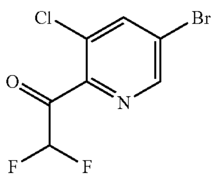 [SMILES: O=C(c1ncc(Br)cc1Cl)C(F)F]

To a stirred solution of 2,5-dibromo-3-chloro-pyridine (1 g, 3.7 mmol) in Toluene (20 mL) was added n-BuLi (1.6 mL, 2.5 N) at −78° C. dropwise under nitrogen atmosphere. Then Methyl 2,2-difluoroacetate (486 mg, 4.4 mmol) was added. The reaction mixture was stirred at 25° C. for 16 h under nitrogen atmosphere. The reaction mixture was stirred at −78° C. for 1 h. The reaction mixture was quenched with water (10 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:3) to give 1-(5-bromo-3-chloropyridin-2-yl)-2,2-difluoroethan-1-one (500 mg, 50% yield) as a colorless oil. $^1H$ NMR (400 MHz, DMSO-$d_6$) δ: 8.92 (d, J=1.9 Hz, 1H), 8.63 (d, J=1.9 Hz, 1H), 7.13 (t, J=53.2 Hz, 1H). LC-MS: m/z 270 $[M+H]^+$.

Step 2:1-(5-bromo-3-chloropyridin-2-yl)-2,2-difluoroethan-1-ol

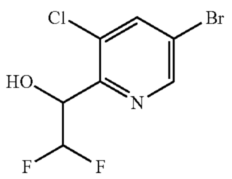 [SMILES: OC(c1ncc(Br)cc1Cl)C(F)F]

To a stirred solution of 1-(5-bromo-3-chloropyridin-2-yl)-2,2-difluoroethan-1-one (600 mg, 2.2 mmol) in THE (10 mL) was added $NaBH_4$ (84 mg, 2.2 mmol). The resulting mixture was stirred at 25° C. for 2 h. The reaction mixture was quenched with water (20 mL). The resulting solution was extracted with ethyl acetate (3×20 mL). The combined organic layers were dried over anhydrous sodium sulfate and concentrated under reduced pressure. The residue was applied onto a silica gel column and eluted with EtOAc/PE (1:4) to give 1-(5-bromo-3-chloropyridin-2-yl)-2,2-difluoroethan-1-ol (300 mg, 49% yield) as a colorless oil. LC-MS: m/z 272 $[M+H]^+$.

Step 3: N-(5-chloro-6-(2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide

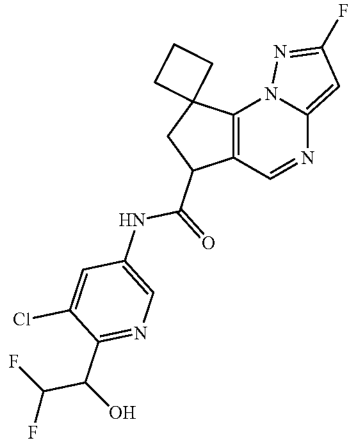 [SMILES: O=C(Nc1cnc(C(O)C(F)F)c(Cl)c1)C1CC2(CCC2)c2c1cnc1cc(F)nn21]

To a stirred mixture of 1-(5-bromo-3-chloropyridin-2-yl)-2,2-difluoroethan-1-ol (209 mg, 768 μmol) in dioxane (5 mL) was added 2'-fluoro-6',7'-dihydrospiro[cyclobutane-1,8'-cyclopenta[e]pyrazolo[1,5-a]pyrimidine]-6'-carboxamide (Method A3 step 2; 200 mg, 768.4 μmol) $Cs_2CO_3$ (500 mg, 1.5 mmol), XantPhos (89 mg, 153.7 μmol) and $Pd_2(dba)_3$ (159 mg, 153.7 μmol). The mixture was stirred at 100° C. for 2 h under nitrogen atmosphere. The mixture was cooled to 25° C. The residue was diluted with water (20 mL). The resulting solution was extracted with ethyl acetate (3×20 mL). The combined organic layers were dried over anhydrous sodium sulfate and concentrated under reduced pressure. The residue was applied onto a silica gel column and eluted with EtOAc/PE (1:3) to give the crude product. The crude product was submitted to Prep-HPLC purification and the collected fractions were lyophilized to give N-(5-chloro-6-(2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide (120 mg, 34% yield) as a white solid. LC-MS: m/z 452 $[M+H]^+$.

Step 4: Separation of Enantiomers to Obtain (R)—N-(5-chloro-6-((R)-2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide, (R)—N-(5-chloro-6-((S)-2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide, (S)—N-(5-chloro-6-((R)-2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide and (S)—N-(5-chloro-6-((S)-2,2-difluoro-1-hydroxyethyl)pyridin-3-yl)-2'-fluoro-6',7'-dihydrospiro[cyclobutane-1,8'-cyclopenta[e]pyrazolo[1,5-a]pyrimidine]-6'-carboxamide Example 133

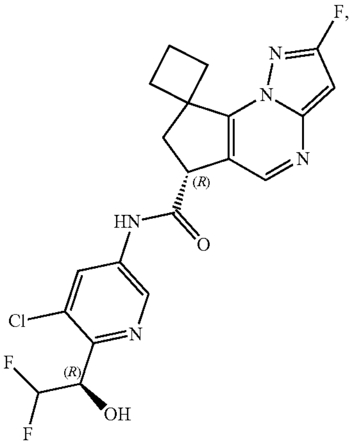

,

Example 134

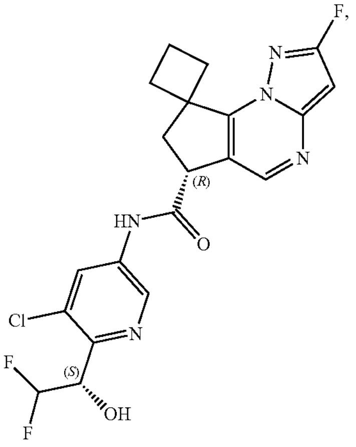

,

-continued

Example 135

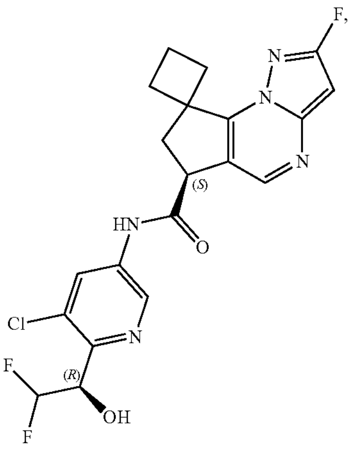

and

Example 136

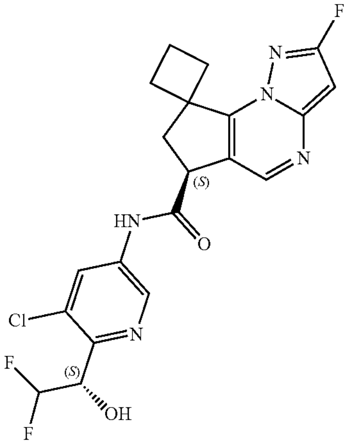

120 mg of N-(5-chloro-6-(2,2-difluoro-1-hydroxyethyl) pyridin-3-yl)-2'-fluoro-6',7'-dihydrospiro[cyclobutane-1,8'-cyclopenta[e]pyrazolo[1,5-a]pyrimidine]-6'-carboxamide were submitted to chiral HPLC purification (Column: CHIRALPAK IG, 2*25 cm, 5 μm; Mobile Phase A: Hex(0.5% 2M $NH_3$-MeOH)-HPLC, Mobile Phase B: EtOH-HPLC; Flow rate: 20 mL/min; isocratic 50% B in 16 min; Wave Length: 220/254 nm; RT1(min): 6.10; RT2(min): 7.67; Sample Solvent: EtOH-HPLC; Injection Volume: 0.5 mL; Number Of Runs: 9). The first eluting isomer was concentrated and lyophilized to afford Example 133 (17.4 mg, 14% yield) as a white solid. The second eluting isomer was concentrated and lyophilized to afford Example 134 (13.4 mg, 11% yield) as a white solid. Fractions containing a mixture of the two other isomers were concentrated and submitted to chiral HPLC purification (Column: CHIRALPAK IG, 2×25 cm, 5 μm; Mobile Phase A: Hex(0.1% FA)-HPLC, Mobile Phase B: EtOH-HPLC; Flow rate: 20 mL/min; isocratic 30% B in 28 min; Wave Length: 220/254 nm; RT1(min): 9.91; RT2(min): 11.66; Sample Solvent: EtOH-HPLC; Injection Volume: 0.5 mL; Number Of Runs: 5). The first eluting isomer was concentrated and lyophilized to afford Example 135 (15.1 mg, 12% yield) as a white solid. The second eluting isomer was concentrated and lyophilized to afford Example 136 (17.0 mg, 14% yield) as a white solid.

Example 133: $^1$H NMR (400 MHz, DMSO-$d_6$) δ: 10.82 (s, 1H), 8.70 (d, J=2.4 Hz, 1H), 8.61 (s, 1H), 8.31 (d, J=2.0 Hz, 1H), 6.58 (d, J=4.8 Hz, 1H), 6.14-6.44 (m, 2H), 5.01-5.07 (m, 1H), 4.33-4.36 (m, 1H), 3.07-3.18 (m, 2H), 2.83-2.89 (m, 1H), 2.67-2.71 (m, 1H), 2.08-2.23 (m, 4H). LC-MS: m/z 452.0 $[M+H]^+$.

Example 134: $^1$H NMR (400 MHz, DMSO-$d_6$) δ: 10.83 (s, 1H), 8.71 (d, J=2.0 Hz, 1H), 8.61 (s, 1H), 8.31 (d, J=2.0 Hz, 1H), 6.58 (d, J=4.8 Hz, 1H), 6.14-6.44 (m, 2H), 5.01-5.07 (m, 1H), 4.33-4.36 (m, 1H), 3.07-3.18 (m, 2H), 2.83-2.89 (m, 1H), 2.66-2.70 (m, 1H), 2.08-2.24 (m, 4H). LC-MS: m/z 452.0 $[M+H]^+$.

Example 135: $^1$H NMR (400 MHz, DMSO-$d_6$) δ: 10.83 (s, 1H), 8.71 (d, J=2.0 Hz, 1H), 8.61 (s, 1H), 8.31 (d, J=2.0 Hz, 1H), 6.58 (d, J=4.8 Hz, 1H), 6.14-6.44 (m, 2H), 5.02-5.07 (m, 1H), 4.33-4.36 (m, 1H), 3.07-3.17 (m, 2H), 2.84-2.90 (m, 1H), 2.67-2.70 (m, 1H), 2.06-2.24 (m, 4H). LC-MS: m/z 452.0 $[M+H]^+$.

Example 136: $^1$H NMR (400 MHz, DMSO-$d_6$) δ: 10.83 (s, 1H), 8.71 (d, J=2.0 Hz, 1H), 8.61 (s, 1H), 8.31 (d, J=2.0 Hz, 1H), 6.58 (d, J=4.8 Hz, 1H), 6.14-6.44 (m, 2H), 5.02-5.07 (m, 1H), 4.33-4.37 (m, 1H), 3.08-3.17 (m, 2H), 2.83-2.90 (m, 1H), 2.66-2.74 (m, 1H), 2.07-2.24 (m, 4H). LC-MS: m/z 452.0 $[M+H]^+$.

The absolute and relative stereochemistry for each separated isomer was not determined.

Method T3

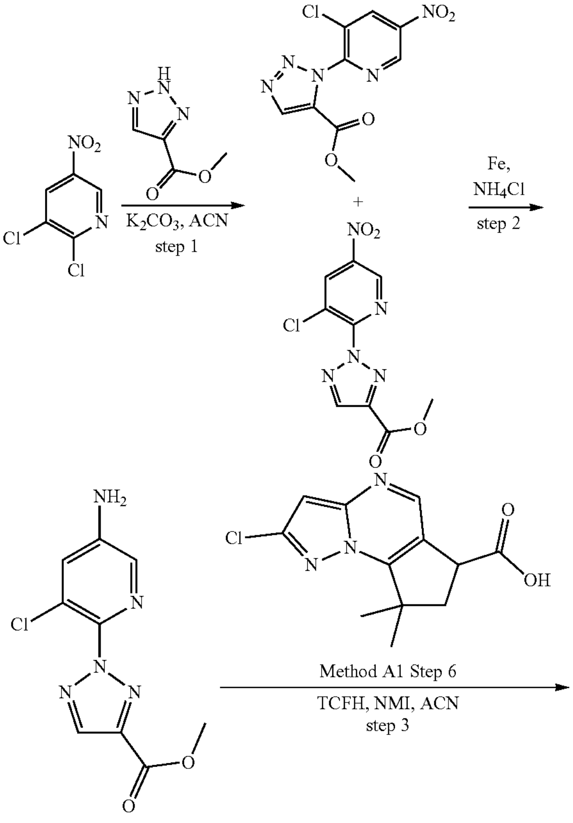

-continued

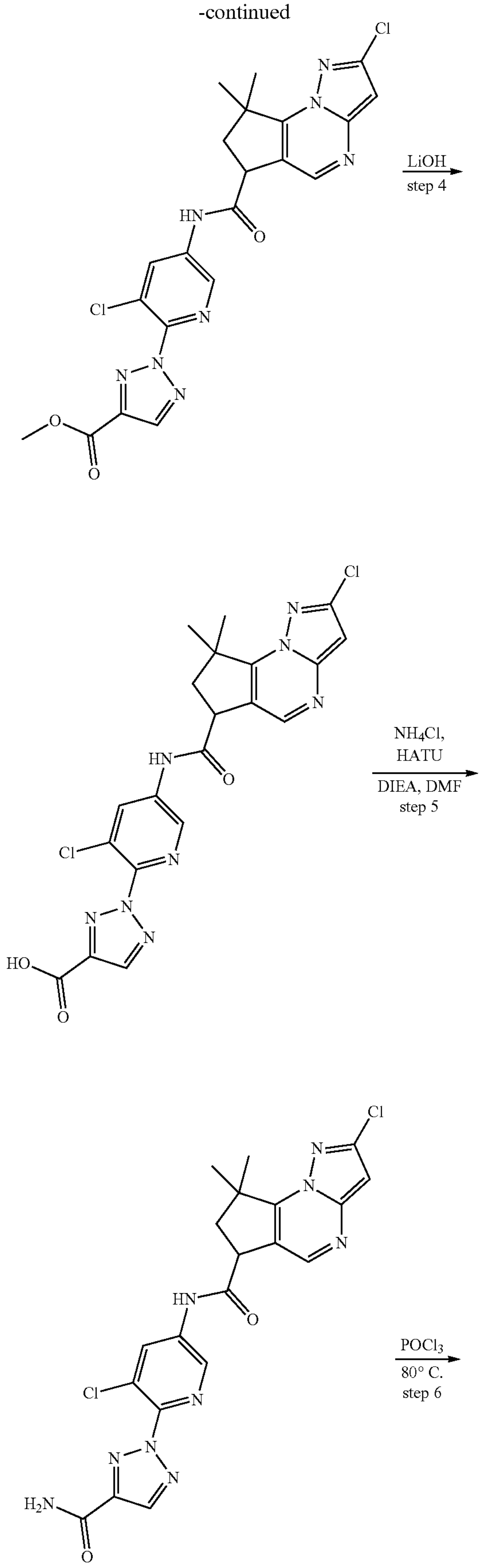

-continued

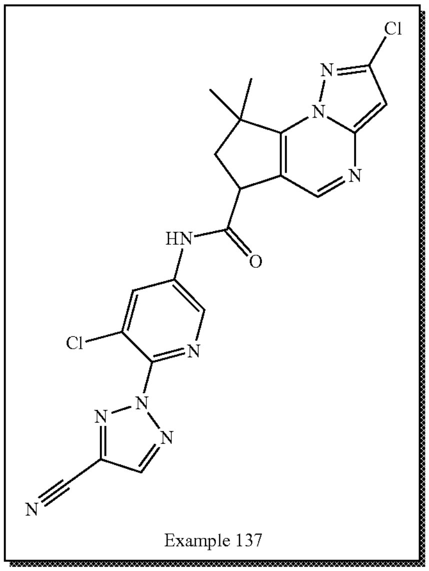

Example 137

Example 137: 2-chloro-N-(5-chloro-6-(4-cyano-2H-1,2,3-triazol-2-yl)pyridin-3-yl)-8,8-dimethyl-7,8-dihydro-6H-cyclopenta[e]pyrazolo[1,5-a]pyrimidine-6-carboxamide Step 1: mixture of methyl 2-(3-chloro-5-nitropyridin-2-yl)-2H-1,2,3-triazole-4-carboxylate and methyl 1-(3-chloro-5-nitropyridin-2-yl)-1H-1,2,3-triazole-5-carboxylate

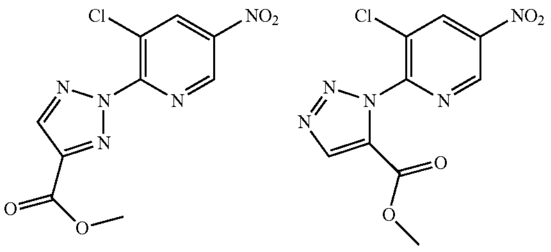 [SMILES: COC(=O)c1cnn(-c2ncc([N+](=O)[O-])cc2Cl)n1 ; COC(=O)c1cnnn1-c1ncc([N+](=O)[O-])cc1Cl]

To a stirred solution of 2,3-dichloro-5-nitropyridine (5.0 g, 25.9 mmol) in ACN (150 mL) was added methyl 2H-1,2,3-triazole-4-carboxylate (3.6 g, 28.5 mmol) and potassium carbonate (10.7 g, 77.7 mmol). The reaction mixture was stirred at 60° C. for 16 h. The resulting mixture was filtrated, and the filtrate was concentrated under reduced pressure. The residue was applied onto a silica gel column and eluted with EtOAc/PE (1:4) to give a mixture of methyl 2-(3-chloro-5-nitropyridin-2-yl)-2H-1,2,3-triazole-4-carboxylate and methyl 1-(3-chloro-5-nitropyridin-2-yl)-1H-1,2,3-triazole-5-carboxylate (4.5 g, 33% yield) as a yellow solid. LC-MS: m/z 284 $[M+H]^+$.

Step 2: methyl 2-(5-amino-3-chloropyridin-2-yl)-2H-1,2,3-triazole-4-carboxylate

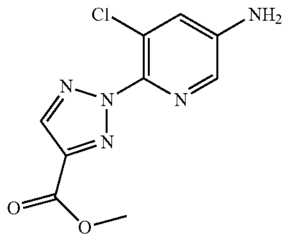 [SMILES: COC(=O)c1cnn(-c2ncc(N)cc2Cl)n1]

To a stirred solution of a mixture of methyl 2-(3-chloro-5-nitropyridin-2-yl)-2H-1,2,3-triazole-4-carboxylate and methyl 1-(3-chloro-5-nitropyridin-2-yl)-1H-1,2,3-triazole-5-carboxylate (4.5 g, 15.9 mmol) in THF (20 mL) and water (10 mL) was added Fe (4.4 g, 79.3 mmol) and $NH_4Cl$ (4.2 g, 79.3 mmol). The reaction mixture was stirred at 60° C. for 2 h. The reaction mixture was filtered and the filtrate was concentrated under reduced pressure. The residue was applied onto a silica gel column and eluted with EtOAc/PE (1:1) to give methyl 2-(5-amino-3-chloropyridin-2-yl)-2H-1,2,3-triazole-4-carboxylate (600 mg, 30% yield) as a yellow solid. $^1H$ NMR (300 MHz, Chloroform-d) δ 8.30 (s, 1H), 7.92 (d, J=2.7 Hz, 1H), 7.17 (d, J=2.7 Hz, 1H), 4.13 (br, 2H), 3.99 (s, 3H). LC-MS: m/z 254 $[M+H]^+$.

Step 3: methyl 2-(3-chloro-5-(2-chloro-8,8-dimethyl-7,8-dihydro-6H-cyclopenta[e]pyrazolo[1,5-a]pyrimidine-6-carboxamido)pyridin-2-yl)-2H-1,2,3-triazole-4-carboxylate

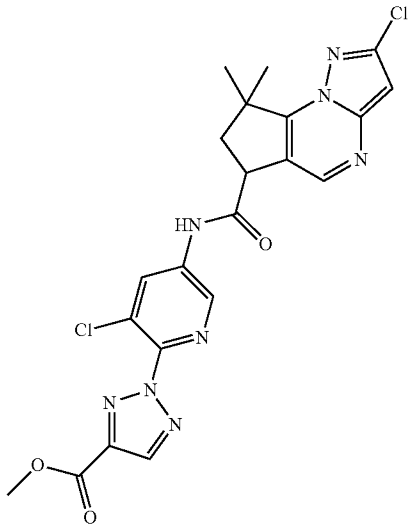 [SMILES: COC(=O)c1cnn(-c2ncc(NC(=O)C3CC(C)(C)c4c3cnc3cc(Cl)nn43)cc2Cl)n1]

To a mixture of methyl 2-(5-amino-3-chloropyridin-2-yl)-2H-1,2,3-triazole-4-carboxylate (300 mg, 1.2 mmol) in ACN (5 mL) was added 2-chloro-8,8-dimethyl-7,8-dihydro-6H-cyclopenta[e]pyrazolo[1,5-a]pyrimidine-6-carboxylic acid (Method A1 step 6; 314 mg, 1.2 mmol), TCFH (1.3 g, 4.7 mmol) and NMI (388 mg, 4.7 mmol). The resulting mixture stirred at 25° C. for 3 h. The mixture was concentrated under reduced pressure. The residue was applied onto a silica gel column and eluted with MeOH/DCM (1:10) to give methyl 2-(3-chloro-5-(2-chloro-8,8-dimethyl-7,8-dihydro-6H-cyclopenta[e]pyrazolo[1,5-a]pyrimidine-6-carboxamido)pyridin-2-yl)-2H-1,2,3-triazole-4-carboxylate (500 mg, 84% yield) as a yellow oil. LC-MS: m/z 501 $[M+H]^+$.

Step 4: 2-(3-chloro-5-(2-chloro-8,8-dimethyl-7,8-dihydro-6H-cyclopenta[e]pyrazolo[1,5-a]pyrimidine-6-carboxamido)pyridin-2-yl)-2H-1,2,3-triazole-4-carboxylic acid

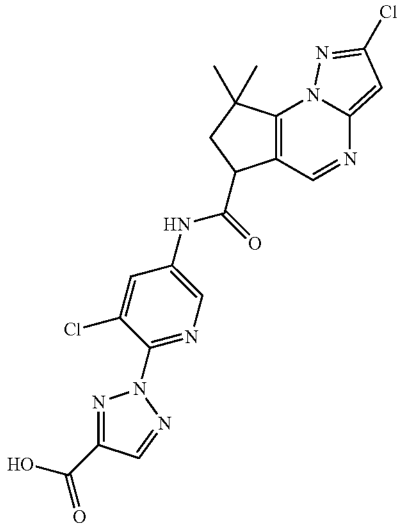 [SMILES: CC1(C)CC(C(=O)Nc2cnc(-n3ncc(C(=O)O)n3)c(Cl)c2)c2cnc3cc(Cl)nn3c21]

To a stirred solution of methyl 2-(3-chloro-5-(2-chloro-8,8-dimethyl-7,8-dihydro-6H-cyclopenta[e]pyrazolo[1,5-a]pyrimidine-6-carboxamido)pyridin-2-yl)-2H-1,2,3-triazole-4-carboxylate (500 mg, 997 μmol) in THF (10 mL) was added LiOH (287 mg, 12.0 mmol) in water (5 mL). The reaction mixture was stirred at 25° C. for 16 h. The pH was adjusted to 5-6 with 2M HCl. The resulting solution was extracted with ethyl acetate (3×10 mL). The combined organic layers were dried over anhydrous sodium sulfate and concentrated under reduced pressure to afford 2-(3-chloro-5-(2-chloro-8,8-dimethyl-7,8-dihydro-6H-cyclopenta[e]pyrazolo[1,5-a]pyrimidine-6-carboxamido)pyridin-2-yl)-2H-1,2,3-triazole-4-carboxylic acid (600 mg, 79% yield) as a yellow oil. LC-MS: m/z 487 $[M+H]^+$.

Step 5: N-(6-(4-carbamoyl-2H-1,2,3-triazol-2-yl)-5-chloropyridin-3-yl)-2-chloro-8,8-dimethyl-7,8-dihydro-6H-cyclopenta[e]pyrazolo[1,5-a]pyrimidine-6-carboxamide

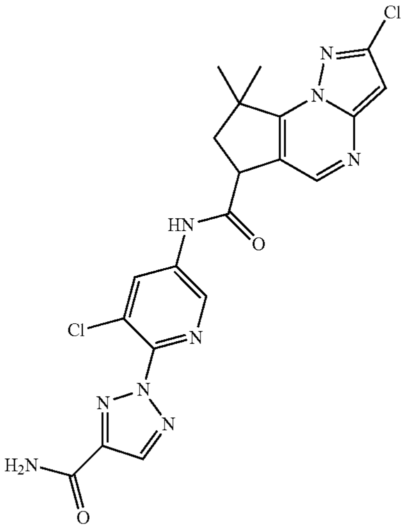 [SMILES: CC1(C)CC(C(=O)Nc2cnc(-n3ncc(C(N)=O)n3)c(Cl)c2)c2cnc3cc(Cl)nn3c21]

To a solution of 2-(3-chloro-5-(2-chloro-8,8-dimethyl-7,8-dihydro-6H-cyclopenta[e]pyrazolo[1,5-a]pyrimidine-6-carboxamido)pyridin-2-yl)-2H-1,2,3-triazole-4-carboxylic acid (600 mg, 1.2 mmol) in DMF (5 mL) was added ammonium chloride (132 mg, 2.5 mmol), HATU (562 mg, 1.5 mmol) and DIEA (477 mg, 3.7 mmol). The resulting mixture was stirred at 25° C. for 3 h. The mixture was concentrated under reduced pressure. The residue was applied onto a silica gel column and eluted with MeOH/DCM (1:10) to give N-(6-(4-carbamoyl-2H-1,2,3-triazol-2-yl)-5-chloropyridin-3-yl)-2-chloro-8,8-dimethyl-7,8-dihydro-6H-cyclopenta[e]pyrazolo[1,5-a]pyrimidine-6-carboxamide (50 mg, 8% yield) as a white solid. LC-MS: m/z 486 [M+H]+.

Step 6: 2-chloro-N-(5-chloro-6-(4-cyano-2H-1,2,3-triazol-2-yl)pyridin-3-yl)-8,8-dimethyl-7,8-dihydro-6H-cyclopenta[e]pyrazolo[1,5-a]pyrimidine-6-carboxamide Example 137

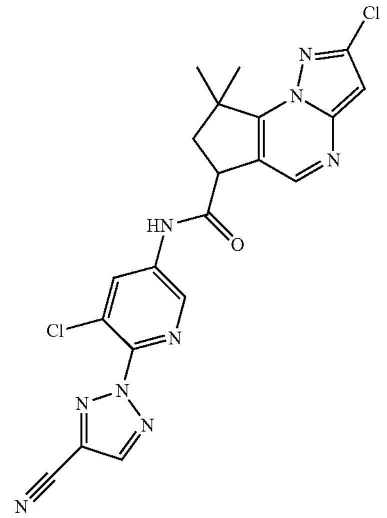

A solution of N-(6-(4-carbamoyl-2H-1,2,3-triazol-2-yl)-5-chloropyridin-3-yl)-2-chloro-8,8-dimethyl-7,8-dihydro-6H-cyclopenta[e]pyrazolo[1,5-a]pyrimidine-6-carboxamide (45 mg, 92.5 μmol) in phosphoryl trichloride (5 mL) was stirred at 80° C. for 3 h. The reaction mixture was quenched with water (15 mL). The pH was adjusted to 7 with saturated aqueous sodium bicarbonate solution. The resulting solution was extracted with ethyl acetate (3×20 mL). The combined organic layers were washed with brine, dried over anhydrous sodium sulfate and concentrated under reduced pressure. The residue was applied onto a silica gel column and eluted with MeOH/DCM (1:10) to give the crude product. The crude product was submitted to Prep-HPLC purification and the collected fractions were lyophilized to give Example 137 (2 mg, 4% yield) as a yellow solid.

Example 137: $^1$H NMR (400 MHz, DMSO-$d_6$) δ 10.21 (d, J=2.0 Hz, 1H), 9.84 (s, 1H), 8.72 (s, 1H), 8.66 (d, J=2.0 Hz, 1H), 6.97 (s, 1H), 4.51-4.57 (m, 1H), 2.60-2.69 (m, 1H), 2.41-2.52 (m, 1H), 1.67 (s, 3H), 1.60 (s, 3H). LC-MS: m/z 468.1 [M+H]+.

Method U3

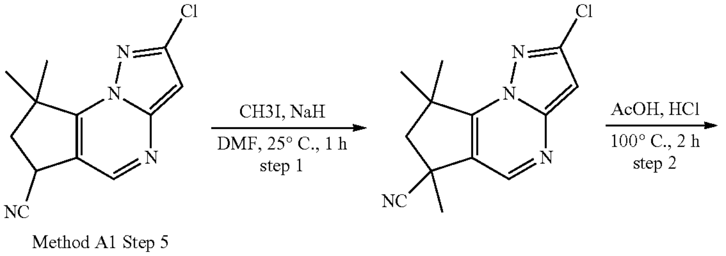

-continued

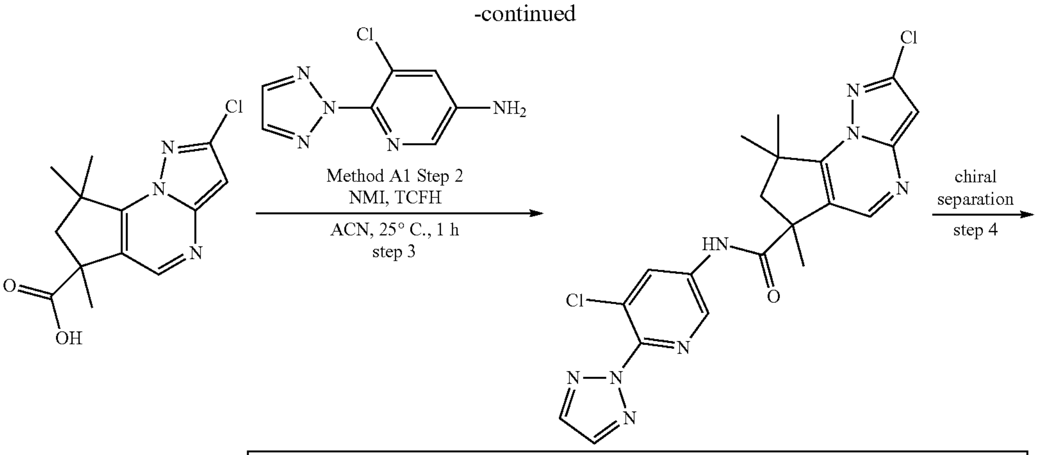

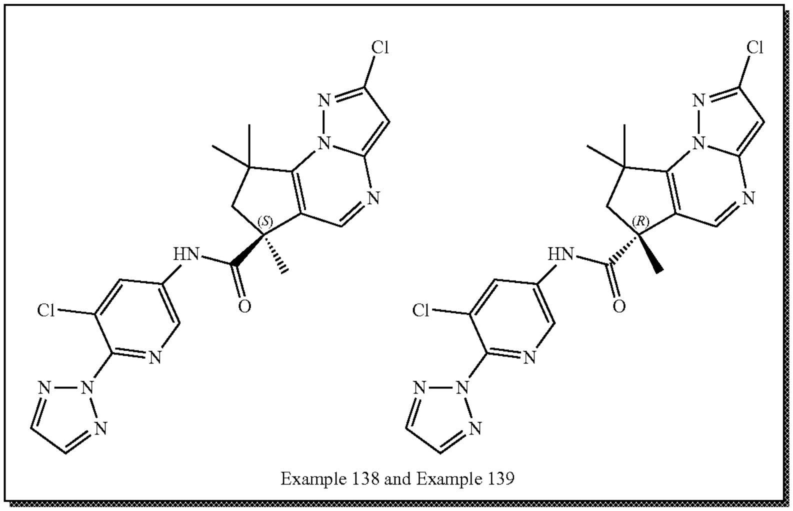

Example 138 and Example 139

Examples 138 and 139: Single Enantiomers Obtained from a Racemic Mixture Containing (8)-2-chloro-N-(5-chloro-6-(2H-1,2,3-triazol-2-yl)pyridin-3-yl)-6,8,8-trimethyl-7,8-dihydro-6H-cyclopenta[e]pyrazolo[1,5-a]pyrimidine-6-carboxamide and (R)-2-chloro-N-(5-chloro-6-(2H-1,2,3-triazol-2-yl)pyridin-3-yl)-6,8,8-trimethyl-7,8-dihydro-6H-cyclopenta[e]pyrazolo[1,5-a]pyrimidine-6-carboxamide Step 1: 2-chloro-6,8,8-trimethyl-7,8-dihydro-6H-cyclopenta[e]pyrazolo[1,5-a]pyrimidine-6-carbonitrile

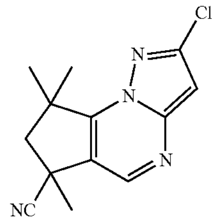 [SMILES: CC1(C)CC(C)(C#N)c2cnc3cc(Cl)nn3c21]

To a stirred solution of 2-chloro-8,8-dimethyl-7,8-dihydro-6H-cyclopenta[e]pyrazolo[1,5-a]pyrimidine-6-carbonitrile (Method A1 step 5; 2.0 g, 8.1 mmol) in DMF (20 mL) was added NaH (424 mg, 10.6 mmol, 60% in mineral oil) in portions at 0° C. The mixture was stirred at 25° C. for 1 h. Iodomethane (1.2 g, 8.3 mmol) was added dropwise at 0° C., and the resulting mixture was stirred at 25° C. for 1 h. The reaction mixture was quenched with water (100 mL). The resulting solution was extracted with ethyl acetate (3×100 mL). The combined organic layers were dried over anhydrous sodium sulfate and concentrated under reduced pressure. The residue was applied onto a silica gel column and eluted with EtOAc/PE (1:2) to give 2-chloro-6,8,8-trimethyl-7,8-dihydro-6H-cyclopenta[e]pyrazolo[1,5-a]pyrimidine-6-carbonitrile (800 mg, 37% yield) as a yellow solid. $^1H$ NMR (300 MHz, Chloroform-d) δ: 8.54 (s, 1H), 6.75 (s, 1H), 2.81 (d, J=12 Hz, 1H), 2.22 (d, J=12 Hz, 1H), 1.87 (s, 3H) 1.74 (s, 6H). LC-MS (ES, m/z): 261 $[M+H]^+$.

Step 2: 2-chloro-6,8,8-trimethyl-7,8-dihydro-6H-cyclopenta[e]pyrazolo[1,5-a]pyrimidine-6-carboxylic acid

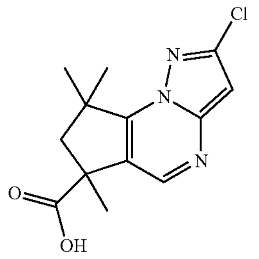 [SMILES: CC1(C)CC(C)(C(=O)O)c2cnc3cc(Cl)nn3c21]

To a stirred solution of 2-chloro-6,8,8-trimethyl-7,8-dihydro-6H-cyclopenta[e]pyrazolo[1,5-a]pyrimidine-6-carbonitrile (260 mg, 1.0 mmol) in AcOH (6 mL) was added 12 M HCl (6 mL). The resulting mixture was stirred at 100° C. for 2 h. The mixture was allowed to cool down to 25° C. The mixture was concentrated under reduced pressure and the residue was diluted with water (100 ml). The resulting solution was extracted with ethyl acetate (3×100 mL). The combined organic layers were dried over anhydrous sodium sulfate and concentrated under reduced pressure. The residue was applied onto a silica gel column and eluted with MeOH/DCM (1:10) to give 2-chloro-6,8,8-trimethyl-7,8-dihydro-6H-cyclopenta[e]pyrazolo[1,5-a]pyrimidine-6-carboxylic acid (150 mg, 53% yield) as an off white solid. LC-MS (ES, m/z): 280 $[M+H]^+$.

Step 3: 2-chloro-N-(5-chloro-6-(2H-1,2,3-triazol-2-yl)pyridin-3-yl)-6,8,8-trimethyl-7,8-dihydro-6H-cyclopenta[e]pyrazolo[1,5-a]pyrimidine-6-carboxamide

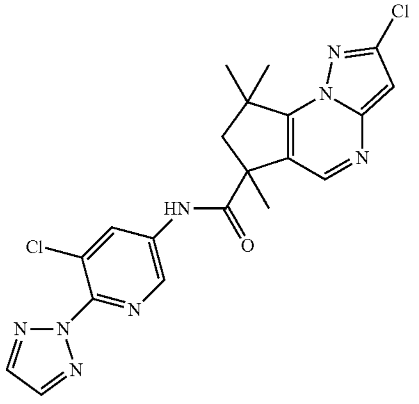 [SMILES: CC1(C)CC(C)(C(=O)Nc2cnc(-n3nccn3)c(Cl)c2)c2cnc3cc(Cl)nn3c21]

To a stirred solution of 2-chloro-6,8,8-trimethyl-7,8-dihydro-6H-cyclopenta[e]pyrazolo[1,5-a]pyrimidine-6-carboxylic acid (130 mg, 464.3 μmol) in ACN (10 mL) was added 5-chloro-6-(2H-1,2,3-triazol-2-yl)pyridin-3-amine (Method A1 step 2; 90 mg, 464.5 μmol), TCFH (391 mg, 1.4 mmol) and NMI (190 mg, 2.3 mmol). The resulting mixture was stirred at 25° C. for 1 h. The reaction mixture was concentrated under reduced pressure. The residue was submitted to Prep-HPLC purification and the collected fractions were lyophilized to give 2-chloro-N-(5-chloro-6-(2H-1,2,3-triazol-2-yl)pyridin-3-yl)-6,8,8-trimethyl-7,8-dihydro-6H-cyclopenta[e]pyrazolo[1,5-a]pyrimidine-6-carboxamide (90 mg, 43% yield) as a white solid. LC-MS (ES, m/z): 457 $[M+H]^+$.

Step 4: Separation of Enantiomers to Obtain (S)-2-chloro-N-(5-chloro-6-(2H-1,2,3-triazol-2-yl)pyridin-3-yl)-6,8,8-trimethyl-7,8-dihydro-6H-cyclopenta[e]pyrazolo[1,5-a]pyrimidine-6-carboxamide and (R)-2-chloro-N-(5-chloro-6-(2H-1,2,3-triazol-2-yl)pyridin-3-yl)-6,8,8-trimethyl-7,8-dihydro-6H-cyclopenta[e]pyrazolo[1,5-a]pyrimidine-6-carboxamide Example 138

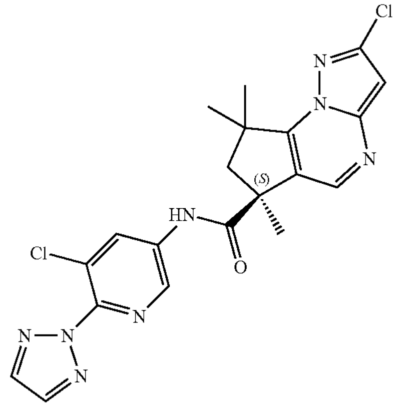

and

Example 139

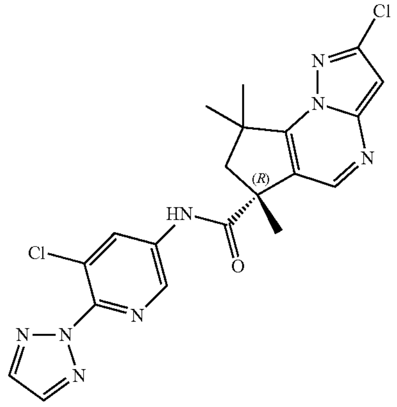

90 mg of 2-chloro-N-(5-chloro-6-(2H-1,2,3-triazol-2-yl)pyridin-3-yl)-6,8,8-trimethyl-7,8-dihydro-6H-cyclopenta[e]pyrazolo[1,5-a]pyrimidine-6-carboxamide were submitted to chiral HPLC purification (Column: CHIRAL ART Cellulose-SC, 2*25 cm, 5 μm; Mobile Phase A: Hex(0.1% FA)-HPLC, Mobile Phase B: EtOH-HPLC; Flow rate: 20 mL/min; isocratic 30% B in 21 min; Wave Length: 220/254 nm; RT1(min): 12.93; RT2(min): 17.84; Sample Solvent: EtOH-HPLC; Injection Volume: 0.5 mL; Number Of Runs: 8). The first eluting isomer was concentrated and lyophilized to afford Example 138 (38.6 mg, 42% yield) as a white solid. The second eluting isomer was concentrated and lyophilized to afford Example 139 (34.3 mg, 38% yield) as a white solid.

Example 138: $^1$H NMR (400 MHz, DMSO-$d_6$) δ: 10.15 (s, 1H), 8.78 (d, J=2.4 Hz, 1H), 8.72 (s, 1H), 8.52 (d, J=2.4 Hz, 1H), 8.16 (s, 2H), 6.96 (s, 1H), 2.70 (d, J=14.0 Hz, 1H), 2.29 (d, J=14.0 Hz, 1H), 1.78 (s, 3H), 1.64 (s, 3H), 1.53 (s, 3H). LCMS (ES, m/z): 457.1 $[M+H]^+$.

Example 139: $^1H$ NMR (400 MHz, DMSO-$d_6$) δ: 10.14 (s, 1H), 8.78 (d, J=2.4 Hz, 1H), 8.72 (s, 1H), 8.52 (d, J=2.4 Hz, 1H), 8.17 (s, 2H), 6.96 (s, 1H), 2.71 (d, J=13.6 Hz, 1H), 2.29 (d, J=13.6 Hz, 1H), 1.78 (s, 3H), 1.63 (s, 3H), 1.52 (s, 3H). LC-MS (ES, m/z): 457.1 $[M+H]^+$.

The absolute stereochemistry for each separated isomer was not determined.

Method V3

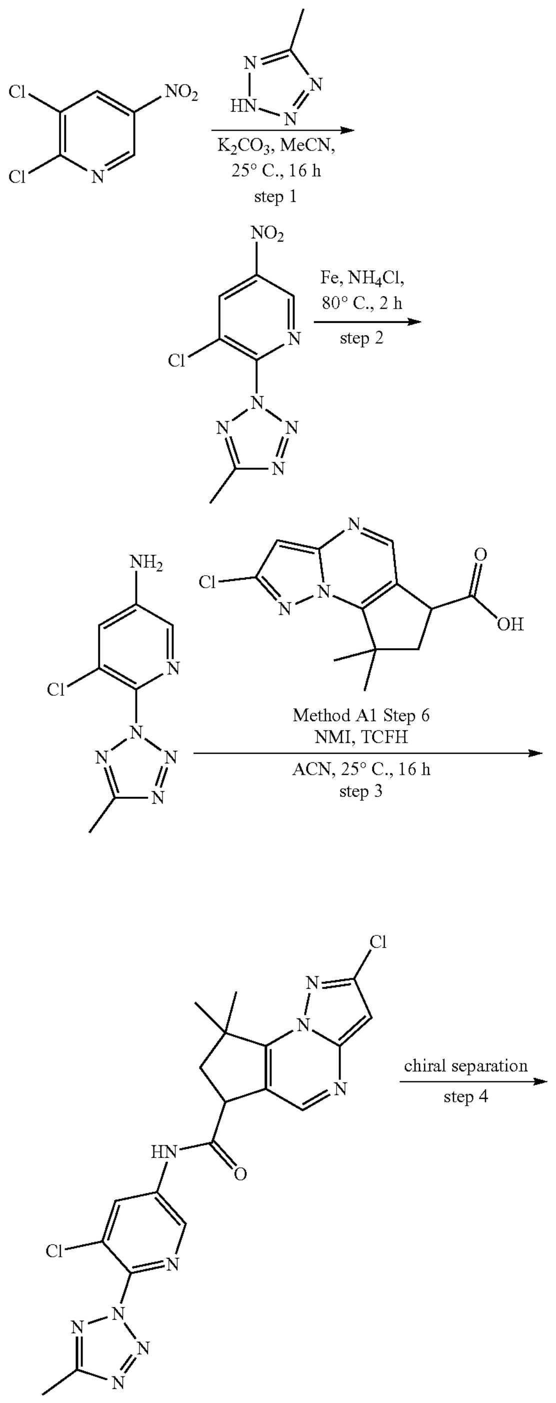

-continued

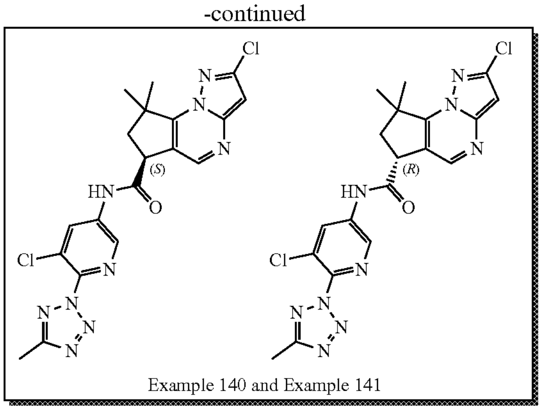

Example 140 and Example 141

Examples 140 and 141: Single Enantiomers Obtained from a Racemic Mixture Containing (S)-2-chloro-N-(5-chloro-6-(5-methyl-2H-tetrazol-2-yl)pyridin-3-yl)-8,8-dimethyl-7,8-dihydro-6H-cyclopenta[e]pyrazolo[1,5-a]pyrimidine-6-carboxamide and (R)-2-chloro-N-(5-chloro-6-(5-methyl-2H-tetrazol-2-yl)pyridin-3-yl)-8,8-dimethyl-7,8-dihydro-611-cyclopenta[e]pyrazolo[1,5-a]pyrimidine-6-carboxamide Step 1: 3-chloro-2-(5-methyl-2H-tetrazol-2-yl)-5-nitropyridine

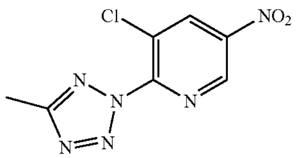 [SMILES: Cc1nnn(-c2ncc([N+](=O)[O-])cc2Cl)n1]

To a mixture of 2,3-dichloro-5-nitropyridine (100 mg, 518.2 μmol) in ACN (1 mL) was added 5-methyl-2H-tetrazole (52 mg, 621.8 μmol) and $K_2CO_3$ (214 mg, 1.5 mmol). The reaction mixture was stirred at 25° C. for 16 h. The resulting mixture was filtrated, and the filtrate was concentrated under reduced pressure. The residue was diluted with water (10 mL). The resulting solution was extracted with ethyl acetate (3×10 mL). The combined organic layers were dried over anhydrous sodium sulfate and concentrated under reduced pressure. The residue was applied on a silica gel column and eluted with EtOAc/PE (1:1) to give 3-chloro-2-(5-methyl-2H-tetrazol-2-yl)-5-nitropyridine (80 mg, 60% yield) as a white solid. $^1H$ NMR (400 MHz, Chloroform-d) δ: 9.38 (d, J=2.4 Hz, 1H), 8.86 (d, J=2.4 Hz, 1H), 2.69 (s, 3H). LC-MS: m/z 241 $[M+H]^+$.

Step 2: 5-chloro-6-(5-methyl-2H-tetrazol-2-yl)pyridin-3-amine

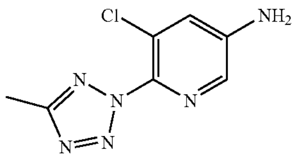

To a stirred solution of 3-chloro-2-(5-methyl-2H-tetrazol-2-yl)-5-nitropyridine (80 mg, 332.5 μmol) and ammonium chloride (89 mg, 1.7 mmol) in EtOH (3 mL) and water (1 mL) was added Fe (56 mg, 997.5 μmol). The reaction mixture was stirred at 80° C. for 2 h. The solid was filtered out and the filtrate was concentrated under reduced pressure to give 5-chloro-6-(5-methyl-2H-tetrazol-2-yl)pyridin-3-amine (40 mg, 57% yield) as a yellow solid. LC-MS: m/z 211 $[M+H]^+$.

Step 3: 2-chloro-N-(5-chloro-6-(5-methyl-2H-tetrazol-2-yl)pyridin-3-yl)-8,8-dimethyl-7,8-dihydro-6H-cyclopenta[e]pyrazolo[1,5-a]pyrimidine-6-carboxamide

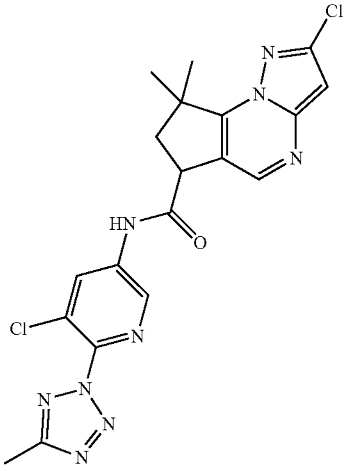 [SMILES: Cc1nnn(-c2ncc(NC(=O)C3CC(C)(C)c4c3cnc3cc(Cl)nn43)cc2Cl)n1]

To a stirred solution of 5-chloro-6-(5-methyl-2H-tetrazol-2-yl)pyridin-3-amine (40 mg, 189.9 μmol) and 2-chloro-8,8-dimethyl-7,8-dihydro-6H-cyclopenta[e]pyrazolo[1,5-a]pyrimidine-6-carboxylic acid (Method A1 step 6; 50 mg, 189.9 μmol) in ACN (1 mL) was added TCFH (160 mg, 569.7 μmol) and NMI (47 mg, 569.7 μmol). The reaction mixture was stirred at 25° C. for 16 h. The resulting mixture was concentrated under reduced pressure. The residue was submitted to Prep-HPLC purification and the collected fractions were lyophilized to give 2-chloro-N-(5-chloro-6-(5-methyl-2H-tetrazol-2-yl)pyridin-3-yl)-8,8-dimethyl-7,8-dihydro-6H-cyclopenta[e]pyrazolo[1,5-a]pyrimidine-6-carboxamide (36 mg, 41% yield) as a white solid. LC-MS: m/z 458 $[M+H]^+$.

Step 4: Separation of Enantiomers to Obtain (S)-2-chloro-N-(5-chloro-6-(5-methyl-2H-tetrazol-2-yl)pyridin-3-yl)-8,8-dimethyl-7,8-dihydro-6H-cyclopenta[e]pyrazolo[1,5-a]pyrimidine-6-carboxamide and (R)-2-chloro-N-(5-chloro-6-(5-methyl-2H-tetrazol-2-yl)pyridin-3-yl)-8,8-dimethyl-7,8-dihydro-6H-cyclopenta[e]pyrazolo[1,5-a]pyrimidine-6-carboxamide

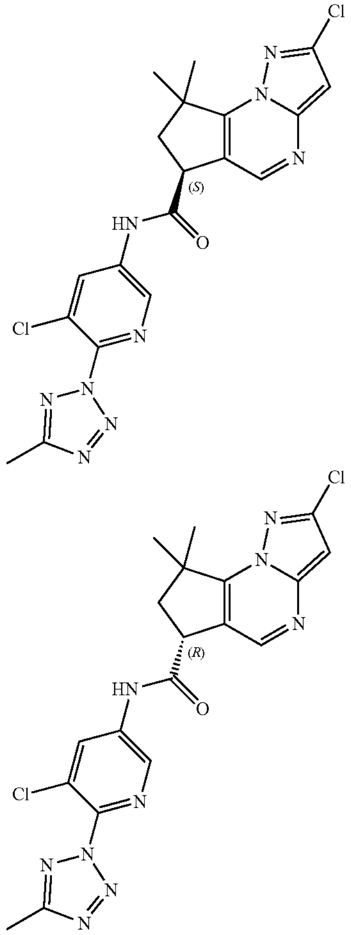

Example 140 and
Example 141

34 mg of 2-chloro-N-(5-chloro-6-(5-methyl-2H-tetrazol-2-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IG, 2*25 cm, 5 μm; Mobile Phase A: Hex:DCM=3:1 (0.5% 2M $NH_3$-MeOH)-HPLC, Mobile Phase B: EtOH-HPLC; Flow rate: 20 mL/min; isocratic 10% B in 25 min; Wave Length: 220/254 nm; RT1(min): 12.80; RT2(min): 20.52; Sample Solvent: EtOH-HPLC; Injection Volume: 1.2 mL; Number Of Runs: 3). The first eluting isomer was concentrated and lyophilized to afford Example 140 (4.4 mg, 12% yield) as a white solid. The second eluting isomer was concentrated and lyophilized to afford Example 141 (11.0 mg, 23% yield) as a white solid.

Example 140: $^1H$ NMR (400 MHz, Chloroform-d) δ: 9.09 (s, 1H), 8.74 (d, J=2.0 Hz, 1H), 8.70 (d, J=2.0 Hz, 1H), 8.61 (s, 1H), 6.72 (s, 1H), 4.48 (dd, J=7.2, 8.4 Hz, 1H), 2.64 (dd, J=8.8, 13.2 Hz, 1H), 2.57 (s, 3H), 2.51 (dd, J=6.8, 13.2 Hz, 1H), 1.80 (s, 3H), 1.64 (s, 3H). LC-MS: m/z 458.0 $[M+H]^+$.
Example 141: $^1H$ NMR (400 MHz, Chloroform-d) δ: 9.08 (s, 1H), 8.74 (d, J=2.4 Hz, 1H), 8.70 (d, J=2.4 Hz, 1H), 8.58 (s, 1H), 6.71 (s, 1H), 4.47 (dd, J=6.8, 8.8 Hz, 1H), 2.64 (dd, J=9.2, 13.2 Hz, 1H), 2.57 (s, 3H), 2.50 (dd, J=6.4, 13.2 Hz, 1H), 1.79 (s, 3H), 1.64 (s, 3H). LC-MS: m/z 458.0 $[M+H]^+$.
The absolute stereochemistry for each separated isomer was not determined.
Method W3
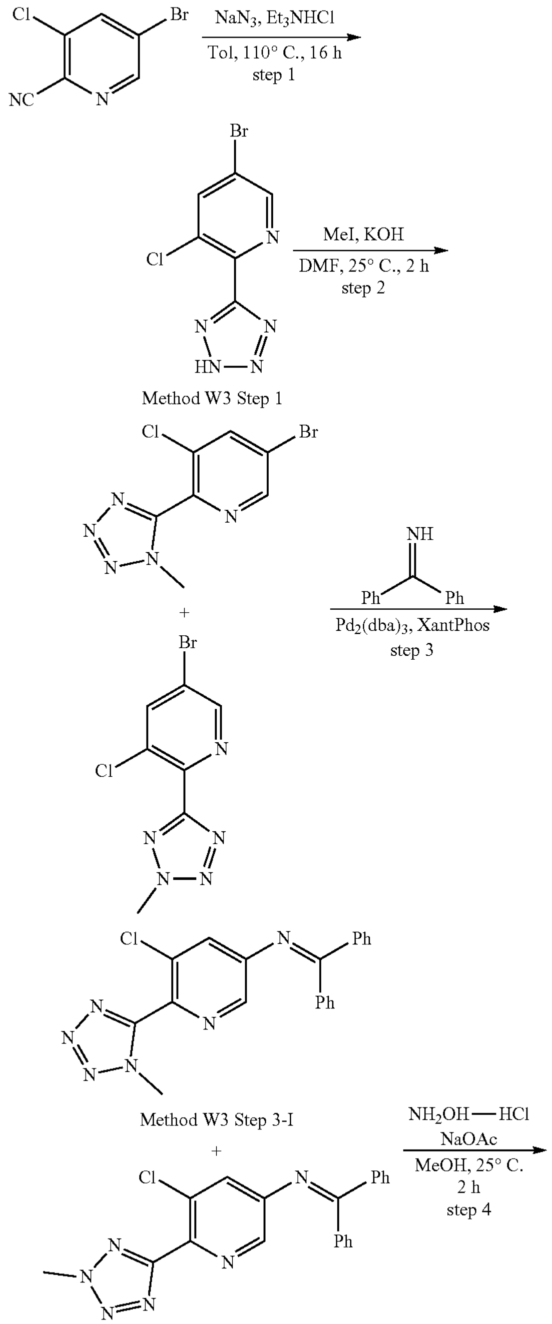
-continued
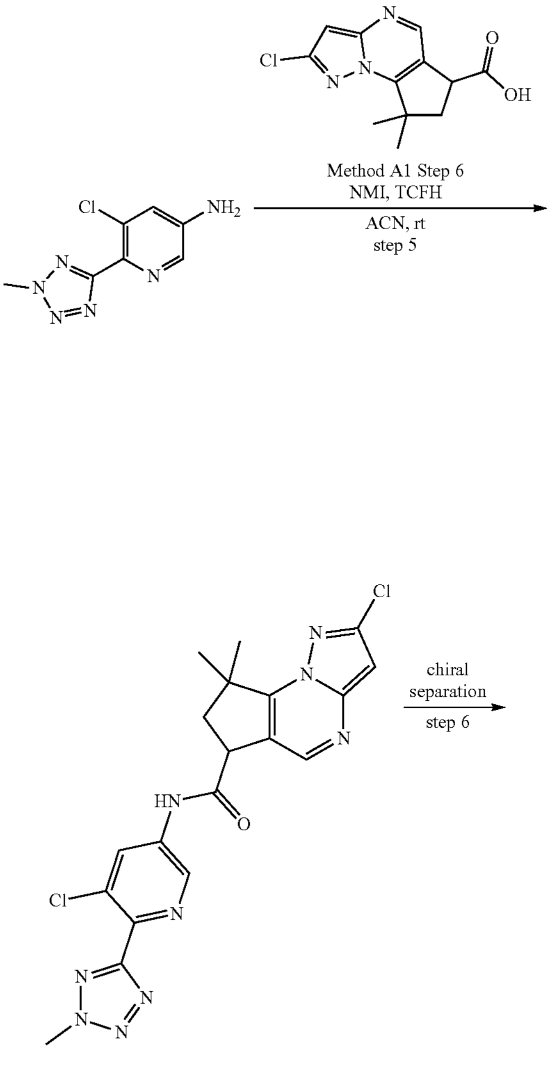
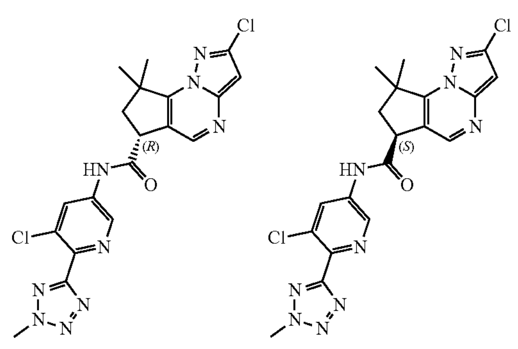
Example 142 and Example 143

Examples 142 and 143: Single Enantiomers Obtained from a Racemic Mixture Containing (R)-2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide Step 1: 5-bromo-3-chloro-2-(2H-tetrazol-5-yl)pyridine

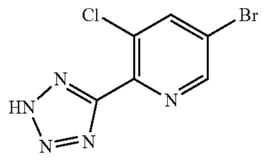 [SMILES: Clc1cc(Br)cnc1-c1nn[nH]n1]

To a stirred solution of 5-bromo-3-chloropicolinonitrile (10.0 g, 46.5 mmol) and triethylamine hydrochloride salt (19.1 g, 139.5 mmol) in Toluene (200 mL) was added sodium azide (3.6 g, 56.0 mmol). The mixture was stirred at 110° C. for 16 h. The reaction mixture was cooled to 25° C. and quenched with water (200 mL). The resulting solution was extracted with ethyl acetate (3×200 mL). The combined organic layers were washed with water (3×500 mL), dried over anhydrous sodium sulfate and concentrated under reduced pressure. The residue was applied onto a silica gel column and eluted with MeOH/DCM (1:5) to give 5-bromo-3-chloro-2-(2H-tetrazol-5-yl)pyridine (Method W3 step 1; 9.0 g, 75% yield) as a yellow solid. $^1$H NMR (400 MHz, DMSO-$d_6$) δ 9.42 (s, 1H), 8.73 (d, J=2.2 Hz, 1H), 8.38 (d, J=2.2 Hz, 1H). LC-MS: m/z 260 $[M+H]^+$.

Step 2: mixture of 5-bromo-3-chloro-2-(2-methyl-2H-tetrazol-5-yl)pyridine and 5-bromo-3-chloro-2-(1-methyl-1H-tetrazol-5-yl)pyridine

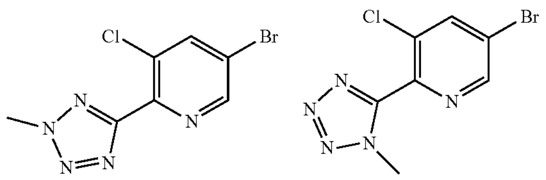

To a stirred solution of 5-bromo-3-chloro-2-(2H-tetrazol-5-yl)pyridine (4.0 g, 15.3 mmol) in DMF (30 mL) were added iodomethane (4.3 g, 30.7 mmol) and potassium hydroxide (1.7 g, 30.7 mmol). The mixture was stirred at 25° C. for 2 h. The reaction mixture was quenched with water (200 mL). The resulting solution was extracted with ethyl acetate (3×200 mL). The combined organic layers were washed with water (3×400 mL), dried over anhydrous sodium sulfate and concentrated under reduced pressure. The residue was applied onto a silica gel column and eluted with EtOAc/PE (1:1) to give a mixture of 5-bromo-3-chloro-2-(2-methyl-2H-tetrazol-5-yl)pyridine and 5-bromo-3-chloro-2-(1-methyl-1H-tetrazol-5-yl)pyridine (3.6 g, 85% yield) as a white solid. LC-MS: m/z 274 $[M+H]^+$.

Step 3: N-(5-chloro-6-(2-methyl-2H-tetrazol-5-yl)pyridin-3-yl)-1,1-diphenylmethanimine and N-(5-chloro-6-(1-methyl-1H-tetrazol-5-yl)pyridin-3-yl)-1,1-diphenylmethanimine

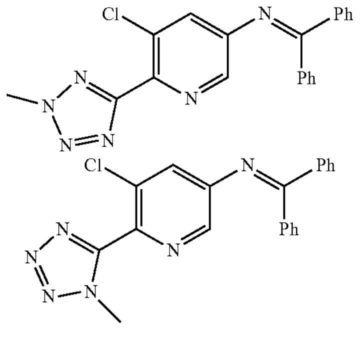

To a stirred solution of a mixture of 5-bromo-3-chloro-2-(2-methyl-2H-tetrazol-5-yl)pyridine and 5-bromo-3-chloro-2-(1-methyl-1H-tetrazol-5-yl)pyridine (2.0 g, 7.3 mmol) in dioxane (30 mL) were added diphenylmethanimine (2.6 g, 14.6 mmol), $Cs_2CO_3$ (4.7 g, 14.6 mmol), XantPhos (843.8 mg, 1.5 mmol) and $Pd_2(dba)_3$ (755.5 mg, 0.7 mmol). The mixture was stirred at 110° C. for 2 h. The reaction mixture was cooled to 25° C. and quenched with water (50 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:2) to give N-(5-chloro-6-(2-methyl-2H-tetrazol-5-yl)pyridin-3-yl)-1,1-diphenylmethanimine (1.7 g, 62% yield) as a yellow solid and N-(5-chloro-6-(1-methyl-1H-tetrazol-5-yl)pyridin-3-yl)-1,1-diphenylmethanimine (Method W3 step 3-i; 900 mg, 59% yield) as a yellow solid. LC-MS: m/z 375 $[M+H]^+$.

Step 4: 5-chloro-6-(2-methyl-2H-tetrazol-5-yl)pyridin-3-amine

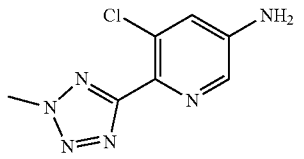

To a stirred solution of N-(5-chloro-6-(2-methyl-2H-tetrazol-5-yl)pyridin-3-yl)-1,1-diphenylmethanimine (1.0 g, 2.6 mmol) in MeOH (20 mL) were added hydroxylamine hydrochloride (358.8 mg, 5.2 mmol) and sodium acetate (426.4 mg, 5.2 mmol). The mixture was stirred at 25° C. for 2 h. The reaction mixture was quenched with water (50 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:1) to give 5-chloro-6-(2-methyl-2H-tetrazol-5-yl)pyridin-3-amine (400 mg, 73% yield) as a white solid. $^1$H NMR (400 MHz, DMSO-$d_6$) δ 8.01 (d, J=2.4 Hz, 1H), 7.11 (d, J=2.4 Hz, 1H), 6.12 (s, 2H), 4.42 (s, 3H). LC-MS: m/z 211 $[M+H]^+$.

Step 5: 2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide

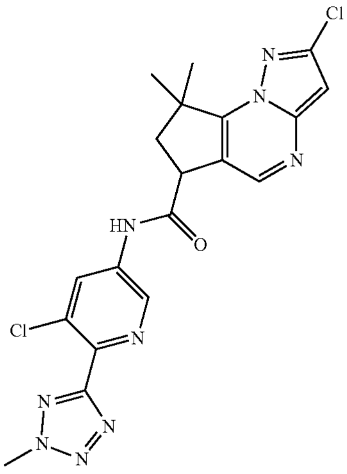 [SMILES: Cn1nnc(-c2ncc(NC(=O)C3CC(C)(C)c4c3cnc3cc(Cl)nn43)cc2Cl)n1]

To a solution of 5-chloro-6-(2-methyl-2H-tetrazol-5-yl)pyridin-3-amine (400 mg, 1.9 mmol) in ACN (25 mL) were added 2-chloro-8,8-dimethyl-7,8-dihydro-6H-cyclopenta[e]pyrazolo[1,5-a]pyrimidine-6-carboxylic acid (Method A1 step 6; 502.3 mg, 1.9 mmol), TCFH (2.1 g, 7.6 mmol) and NMI (623.2 mg, 7.6 mmol). The resulting mixture was stirred at 25° C. for 2 h. The reaction mixture was concentrated under reduced pressure. The residue was applied onto a silica gel column and eluted with EtOAc/PE (1:1) to give 2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide (100 mg, 11% yield) as a white solid. LC-MS: m/z 458 $[M+H]^+$.

Step 6: Separation of Enantiomers to Obtain (R)-2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide

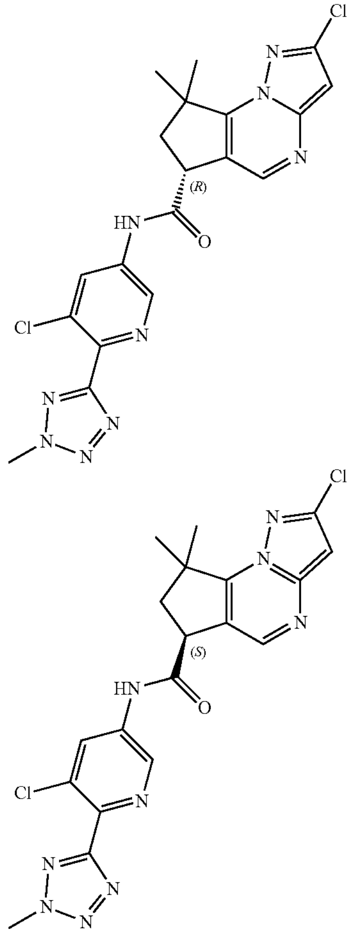

Example 142 and
Example 143

100 mg of 2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK ID, 2*25 cm, 5 μm; Mobile Phase A: Hex(0.1% FA)-HPLC, Mobile Phase B: EtOH-HPLC; Flow rate: 17 mL/min; isocratic 50% B in 16 min; Wave Length: 220/254 nm; RT1(min): 10.16; RT2(min): 12.68; Sample Solvent: EtOH-HPLC; Injection Volume: 0.5 mL; Number Of Runs: 12). The first eluting isomer was concentrated and lyophilized to afford Example 142 (38.2 mg, 38% yield) as a white solid. The second eluting isomer was concentrated and lyophilized to afford Example 143 (29.8 mg, 30% yield) as a white solid.

Example 142: $^1H$ NMR (400 MHz, DMSO-$d_6$) δ 11.07 (s, 1H), 8.91 (d, J=2.0 Hz, 1H), 8.65 (s, 1H), 8.55 (d, J=2.0 Hz, 1H), 6.95 (s, 1H), 4.46-4.48 (m, 1H), 4.15 (s, 3H), 2.52-2.58 (m, 1H), 2.30-2.35 (m, 1H), 1.64 (s, 3H), 1.56 (s, 3H). LC-MS: m/z 458.0 $[M+H]^+$.

Example 143: $^1$H NMR (400 MHz, DMSO-$d_6$) δ 11.07 (s, 1H), 8.91 (d, J=2.0 Hz, 1H), 8.65 (s, 1H), 8.55 (d, J=2.0 Hz, 1H), 6.95 (s, 1H), 4.46-4.48 (m, 1H), 4.14 (s, 3H), 2.54-2.58 (m, 1H), 2.30-2.35 (m, 1H), 1.64 (s, 3H), 1.56 (s, 3H). LC-MS: m/z 458.0 $[M+H]^+$.

The absolute stereochemistry for each separated isomer was not determined.

Method X3

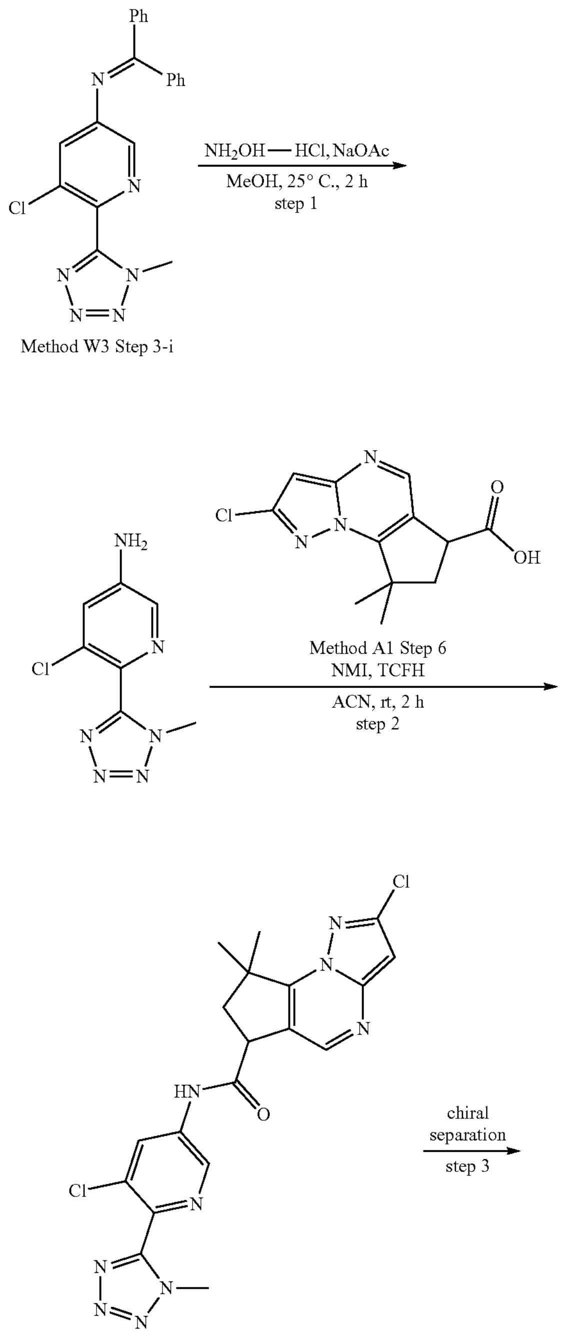

-continued

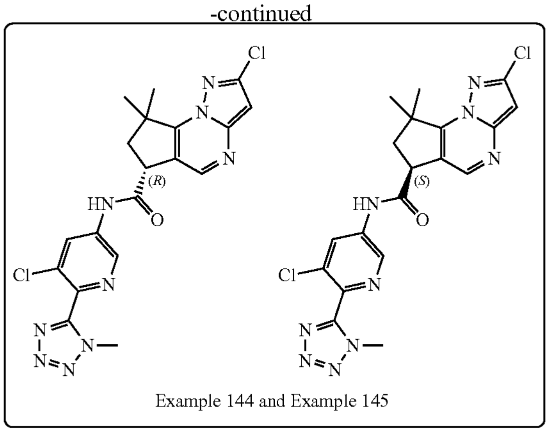

Example 144 and Example 145

Examples 144 and 145: Single Enantiomers Obtained from a Racemic Mixture Containing (R)-2-chloro-N-(5-chloro-6-(1-methyl-1H-tetrazol-5-yl)pyridin-3-yl)-8,8-dimethyl-7,8-dihydro-6H-cyclopenta[e]pyrazolo[1,5-a]pyrimidine-6-carboxamide and (S)-2-chloro-N-(5-chloro-6-(1-methyl-1H-tetrazol-5-yl)pyridin-3-yl)-8,8-dimethyl-7,8-dihydro-611-cyclopenta[e]pyrazolo[1,5-a]pyrimidine-6-carboxamide Step 1: 5-chloro-6-(1-methyl-1H-tetrazol-5-yl)pyridin-3-amine

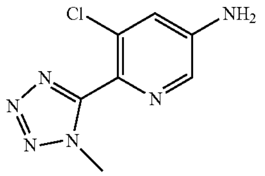

To a stirred solution of N-(5-chloro-6-(1-methyl-1H-tetrazol-5-yl)pyridin-3-yl)-1,1-diphenylmethanimine (Method W3 step 3-i; 500 mg, 1.3 mmol) in MeOH (10 mL) were added hydroxylamine hydrochloride (179 mg, 2.6 mmol) and sodium acetate (213 mg, 2.6 mmol). The mixture was stirred at 25° C. for 2 h. The reaction mixture was quenched with water (50 mL). The resulting solution was extracted with ethyl acetate (3x30 mL). The combined organic layers were dried over anhydrous sodium sulfate and concentrated under reduced pressure. The residue was applied onto a silica gel column and eluted with EtOAc/PE (1:1) to give 5-chloro-6-(1-methyl-1H-tetrazol-5-yl)pyridin-3-amine (150 mg, 54% yield) as a white solid. $^1$H NMR (400 MHz, DMSO-$d_6$) δ 8.05 (d, J=2.4 Hz, 1H), 7.17 (d, J=2.4 Hz, 1H), 6.34 (s, 2H), 4.08 (s, 3H). LC-MS: m/z 211 $[M+H]^+$.

Step 2: 2-chloro-N-(5-chloro-6-(1-methyl-1H-tetrazol-5-yl)pyridin-3-yl)-8,8-dimethyl-7,8-dihydro-6H-cyclopenta[e]pyrazolo[1,5-a]pyrimidine-6-carboxamide

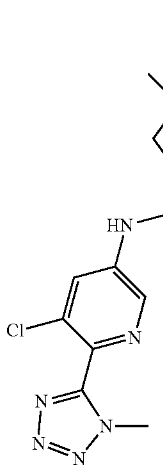

To a solution of 5-chloro-6-(1-methyl-1H-tetrazol-5-yl) pyridin-3-amine (150.0 mg, 0.7 mmol) in ACN (15 mL) were added 2-chloro-8,8-dimethyl-7,8-dihydro-6H-cyclopenta[e]pyrazolo[1,5-a]pyrimidine-6-carboxylic acid (Method A1 step 6; 185 mg, 0.7 mmol), TCFH (784 mg, 2.8 mmol) and NMI (230 mg, 2.8 mmol). The resulting mixture was stirred at 25° C. for 2 h. The reaction mixture was concentrated under reduced pressure. The residue was applied onto a silica gel column and eluted with EtOAc/PE (1:1) to give 2-chloro-N-(5-chloro-6-(2-methyl-2H-tetrazol-5-yl)pyridin-3-yl)-8,8-dimethyl-7,8-dihydro-6H-cyclopenta[e]pyrazolo[1,5-a]pyrimidine-6-carboxamide (40 mg, 12% yield) as a white solid. LC-MS: m/z 458 $[M+H]^+$.

Step 3: Separation of Enantiomers to Obtain (R)-2-chloro-N-(5-chloro-6-(1-methyl-1H-tetrazol-5-yl)pyridin-3-yl)-8,8-dimethyl-7,8-dihydro-6H-cyclopenta[e]pyrazolo[1,5-a]pyrimidine-6-carboxamide and (5)-2-chloro-N-(5-chloro-6-(1-methyl-1H-tetrazol-5-yl)pyridin-3-yl)-8,8-dimethyl-7,8-dihydro-6H-cyclopenta[e]pyrazolo[1,5-a]pyrimidine-6-carboxamide

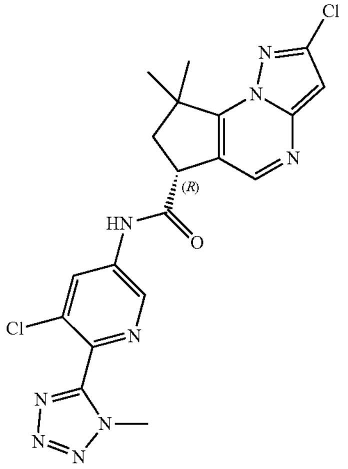

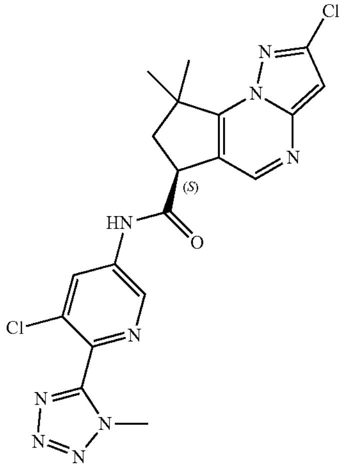

Example 144 and Example 145

40 mg of 2-chloro-N-(5-chloro-6-(1-methyl-1H-tetrazol-5-yl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IA, 2*25 cm, 20 μm; Mobile Phase A: Hex:DCM=3:1 (0.1% TFA)-HPLC, Mobile Phase B: EtOH-HPLC; Flow rate: 20 mL/min; isocratic 50% B in 15 min; Wave Length: 220/254 nm; RT1(min): 5.68; RT2(min): 9.69; Sample Solvent: EtOH-HPLC; Injection Volume: 1.5 mL; Number Of Runs: 2). The first eluting isomer was concentrated and lyophilized to afford Example 144 (6.2 mg, 15% yield) as a white solid. The second eluting isomer was concentrated and lyophilized to afford Example 145 (5.3 mg, 13% yield) as a white solid.

Example 144: $^1H$ NMR (400 MHz, DMSO-$d_6$) δ 11.02 (s, 1H), 8.84 (d, J=2.2 Hz, 1H), 8.65 (s, 1H), 8.50 (d, J=2.2 Hz, 1H), 6.95 (s, 1H), 4.47 (s, 3H), 4.44-4.45 (m, 1H), 2.56-2.67 m, 1H), 2.30-2.35 (m, 1H), 1.64 (s, 3H), 1.56 (s, 3H). LC-MS: m/z 458.0 $[M+H]^+$.

Example 145: $^1$H NMR (400 MHz, DMSO-$d_6$) δ 11.01 (s, 1H), 8.84 (d, J=2.2 Hz, 1H), 8.65 (s, 1H), 8.50 (d, J=2.2 Hz, 1H), 6.95 (s, 1H), 4.47 (s, 3H), 4.44-4.45 (m, 1H), 2.56-2.67 (m, 1H), 2.30-2.35 (m, 1H), 1.64 (s, 3H), 1.56 (s, 3H). LC-MS: m/z 458.0 [M+H]$^+$.
The absolute stereochemistry for each separated isomer was not determined.
Method Y3
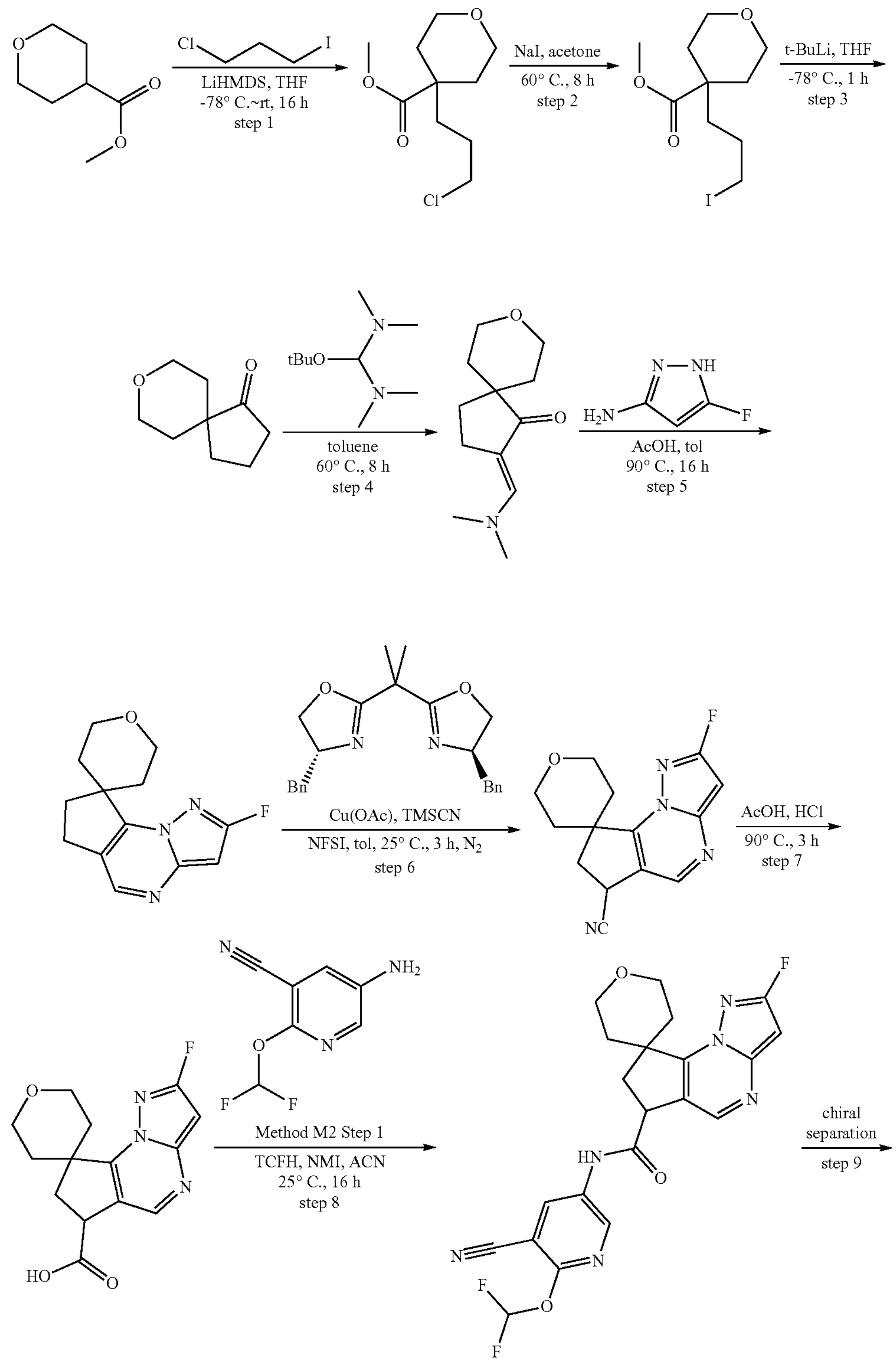

-continued

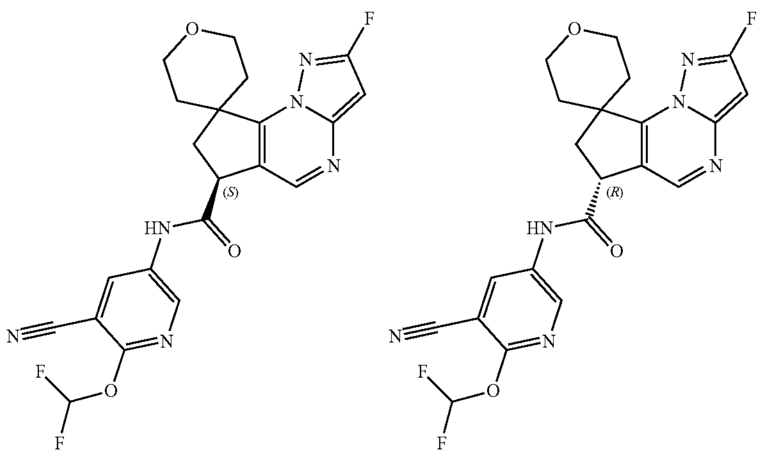

Example 146 and Example 147

Examples 146 and 147: Single Enantiomers Obtained from a Racemic Mixture Containing (S)—N-(5-cyano-6-(difluoromethoxy)pyridin-3-yl)-2-fluoro-2',3',5',6,6',7-hexahydrospiro[cyclopenta[e]pyrazolo[1,5-a]pyrimidine-8,4'-pyran]-6-carboxamide and (R)—N-(5-cyano-6-(difluoromethoxy)pyridin-3-yl)-2-fluoro-2',3',5',6,6',7-hexahydrospiro[cyclopenta[e]pyrazolo[1,5-a]pyrimidine-8,4'-pyran]-6-carboxamide Step 1: methyl 4-(3-chloropropyl)tetrahydro-2H-pyran-4-carboxylate

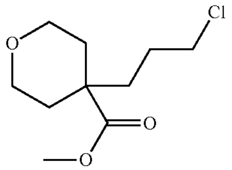

To a solution of methyl tetrahydro-2H-pyran-4-carboxylate (10 g, 69.4 mmol) in THF (150 mL) was added LiHMDS (70.0 mL, 1 M in THF) dropwise at −78° C. The mixture was stirred at 78° C. for 1 h. Then 1-chloro-3-iodopropane (14.2 g, 69.4 mmol) was added dropwise at −78° C. The mixture was warmed to 25° C. and stirred at 25° C. for 16 h. The reaction mixture was diluted with 2-methoxy-2-methylpropane (200 mL). The resulting mixture was washed with aqueous sodium thiosulfate solution (100 mL) and saturated aqueous sodium bicarbonate solution. The organic layers were dried over anhydrous sodium sulfate and concentrated under reduced pressure to give methyl 4-(3-chloropropyl)tetrahydro-2H-pyran-4-carboxylate (17 g, 89% yield) as a yellow oil. $^1$H NMR (400 MHz, $CDCl_3$) δ: 3.74-3.81 (m, 2H), 3.68 (s, 3H), 3.33-3.46 (m, 4H), 2.00-2.07 (m, 2H), 1.75-1.84 (m, 1H), 1.61-1.65 (m, 3H), 1.42-1.52 (m, 2H).

Step 2: methyl 4-(3-iodopropyl)tetrahydro-2H-pyran-4-carboxylate

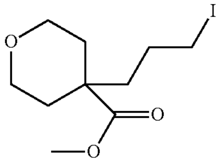

A mixture of methyl 4-(3-chloropropyl)tetrahydro-2H-pyran-4-carboxylate (15 g, 68.0 mmol) and sodium iodide (14.3 g, 95.2 mmol) in acetone (100 mL) was stirred at 60° C. for 8 h. The reaction mixture was quenched with water (100 mL). The resulting solution was extracted with ethyl acetate (3×100 mL). The combined organic layers were washed with aqueous sodium thiosulfate solution (2×100 mL), dried over anhydrous sodium sulfate and concentrated under reduced pressure. The residue was applied onto a silica gel column and eluted with EtOAc/PE (1:2) to give methyl 4-(3-iodopropyl)tetrahydro-2H-pyran-4-carboxylate (11.8 g, 56% yield) as a yellow oil. LC-MS: m/z 313 $[M+H]^+$.

Step 3: 8-oxaspiro[4.5]decan-1-one

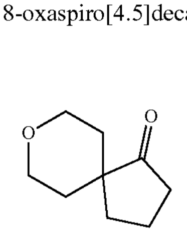

To a stirred mixture of methyl 4-(3-iodopropyl)tetrahydro-2H-pyran-4-carboxylate (5 g, 16.0 mmol) in THE (150 mL) was added tert-butyllithium (12.8 mL, 2.5 M in pentane) dropwise at −78° C. The resulting mixture was stirred at −78° C. for 1 h. The reaction was quenched by adding saturated aqueous ammonium chloride solution (20 mL). The mixture was extracted with ethyl acetate (3×100 mL). The combined organic layers were washed with aqueous sodium thiosulfate solution (2×100 mL), dried over anhydrous sodium sulfate and concentrated under reduced pressure. The residue was applied onto a silica gel column and eluted with EtOAc/PE (1:1) to give 8-oxaspiro[4.5]decan-1-one (2.4 g, 97% yield) as a colorless oil. LC-MS: m/z 155 $[M+H]^+$.

Step 4: (E)-2-((dimethylamino)methylene)-8-oxaspiro[4.5]decan-1-one

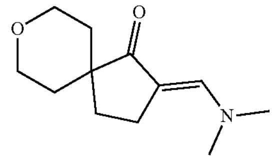

A mixture of 8-oxaspiro[4.5]decan-1-one (1 g, 6.5 mmol) and 1-tert-butoxy-N,N,N',N'-tetramethylmethanediamine (2.3 g, 13.00 mmol) in toluene (10 mL) was stirred at 60° C. for 8 h. The mixture was allowed to cool down to 25° C. and concentrated under reduced pressure to give (E)-2-((dimethylamino)methylene)-8-oxaspiro[4.5]decan-1-one (1.2 g, crude) as a white solid. LC-MS: m/z 210 $[M+H]^+$.

Step 5: 2-fluoro-2',3',5',6,6',7-hexahydrospiro[cyclopenta[e]pyrazolo[1,5-a]pyrimidine-8,4'-pyran]

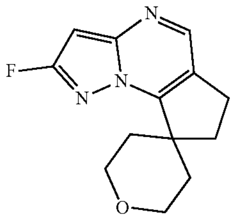 [SMILES: Fc1cc2ncc3c(n2n1)C1(CCOCC1)CC3]

To a solution of (E)-2-((dimethylamino)methylene)-8-oxaspiro[4.5]decan-1-one (1.1 g, 5.3 mmol) in AcOH (2 mL) and toluene (20 mL) was added 5-fluoro-1H-pyrazol-3-amine (531 mg, 5.3 mmol). The resulting mixture was stirred at 90° C. for 16 h. The mixture was allowed to cool down to 25° C. The resulting mixture was concentrated under reduced pressure. The residue was applied onto a silica gel column and eluted with EtOAc/PE (3:2) to give 900 mg of the crude product. The crude product was submitted to Prep-HPLC purification and the collected fractions were concentrated under reduced pressure to give 2-fluoro-2',3',5',6,6',7-hexahydrospiro[cyclopenta[e]pyrazolo[1,5-a]pyrimidine-8,4'-pyran] (0.48 g, 37% yield) as a white solid. LC-MS: m/z 248 $[M+H]^+$.

Step 6: 2-fluoro-2',3',5',6,6',7-hexahydrospiro[cyclopenta[e]pyrazolo[1,5-a]pyrimidine-8,4'-pyran]-6-carbonitrile

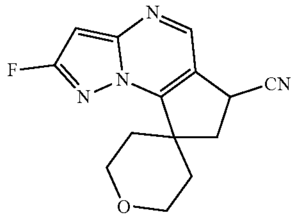 [SMILES: N#CC1CC2(CCOCC2)c2c1cnc1cc(F)nn21]

To a stirred solution of 2-fluoro-2',3',5',6,6',7-hexahydrospiro[cyclopenta[e]pyrazolo[1,5-a]pyrimidine-8,4'-pyran] (300 mg, 1.2 mmol) in toluene (20 mL) was added (4R)-4-benzyl-2-[1-[(4R)-4-benzyl-4,5-dihydrooxazol-2-yl]-1-methyl-ethyl]-4,5-dihydrooxazole (53 mg, 145.6 μmol) acetoxycopper (30 mg, 242.6 μmol), N-fluorobenzenesulfonimide (574 mg, 1.8 mmol), TMSCN (602 mg, 6.1 mmol). The resulting mixture was stirred at 25° C. for 3 h under nitrogen.

The mixture was concentrated under reduced pressure. The residue applied on a silica gel column and eluted with EtOAc/PE (3:2) to give 2-fluoro-2',3',5',6,6',7-hexahydrospiro[cyclopenta[e]pyrazolo[1,5-a]pyrimidine-8,4'-pyran]-6-carbonitrile (105 mg, 27% yield) as a white solid. LC-MS: m/z 273 $[M+H]^+$.

Step 7: 2-fluoro-2',3',5',6,6',7-hexahydrospiro[cyclopenta[e]pyrazolo[1,5-a]pyrimidine-8,4'-pyran]-6-carboxylic acid

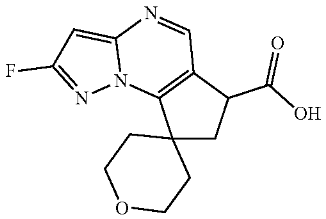 [SMILES: O=C(O)C1CC2(CCOCC2)c2c1cnc1cc(F)nn21]

To a stirred solution of 2-fluoro-2',3',5',6,6',7-hexahydrospiro[cyclopenta[e]pyrazolo[1,5-a]pyrimidine-8,4'-pyran]-6-carbonitrile (123 mg, 385.6 μmol) in AcOH (10 mL) was added 12 M HCl (10 mL). The resulting mixture was stirred at 90° C. for 3 h. The mixture was cooled to 25° C. The reaction mixture was diluted with water (50 mL). The resulting solution was extracted with ethyl acetate (50 mL×3). The combined organic layers were dried over anhydrous sodium sulfate and concentrated under reduced pressure to give 2-fluoro-2',3',5',6,6',7-hexahydrospiro[cyclopenta[e]pyrazolo[1,5-a]pyrimidine-8,4'-pyran]-6-carboxylic acid (105 mg, 79% yield) as a yellow solid. LC-MS: m/z 292 $[M+H]^+$.

Step 8: N-(5-cyano-6-(difluoromethoxy)pyridin-3-yl)-2-fluoro-2',3',5',6,6',7-hexahydrospiro[cyclopenta[e]pyrazolo[1,5-a]pyrimidine-8,4'-pyran]-6-carboxamide

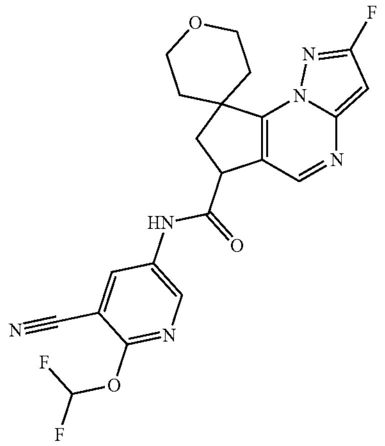 [SMILES: N#Cc1cc(NC(=O)C2CC3(CCOCC3)c3c2cnc2cc(F)nn32)cnc1OC(F)F]

To a solution of 2-fluoro-2',3',5',6,6',7-hexahydrospiro[cyclopenta[e]pyrazolo[1,5-a]pyrimidine-8,4'-pyran]-6-carboxylic acid (143 mg, 343.3 μcool) in ACN (13 mL) were added 5-amino-2-(difluoromethoxy)nicotinonitrile (Method M2 step 1; 95 mg, 514.9 μcool), TCFH (289 mg, 1.0 mmol) and NMI (225 mg, 2.8 mmol). The resulting mixture was stirred at 25° C. for 16 h.

The reaction mixture was concentrated under reduced pressure. The residue was submitted to Prep-HPLC purification and the collected fractions were lyophilized to afford N-(5-cyano-6-(difluoromethoxy)pyridin-3-yl)-2-fluoro-2',3',5',6,6',7-hexahydrospiro[cyclopenta[e]pyrazolo[1,5-a]pyrimidine-8,4'-pyran]-6-carboxamide (53 mg, 34% yield) as a white solid. LC-MS: m/z 459 $[M+H]^+$.

Step 9: Separation of Enantiomers to Obtain (S)—N-(5-cyano-6-(difluoromethoxy)pyridin-3-yl)-2-fluoro-2',3',5',6,6',7-hexahydrospiro[cyclopenta[e]pyrazolo[1,5-a]pyrimidine-8,4'-pyran]-6-carboxamide and (R)—N-(5-cyano-6-(difluoromethoxy)pyridin-3-yl)-2-fluoro-2',3',5',6,6',7-hexahydrospiro[cyclopenta[e]pyrazolo[1,5-a]pyrimidine-8,4'-pyran]-6-carboxamide

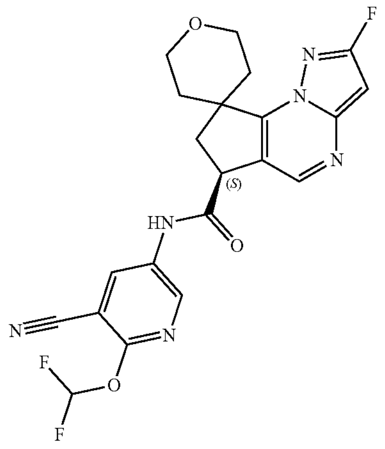

-continued

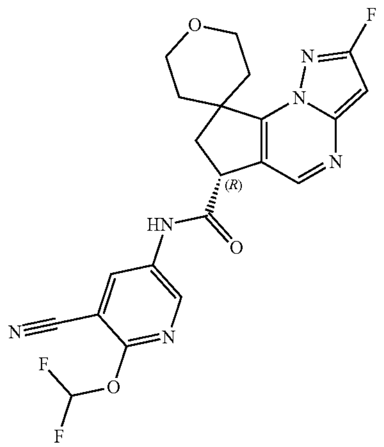

Example 146 and Example 147

53 mg of N-(5-cyano-6-(difluoromethoxy)pyridin-3-yl)-2-fluoro-2',3',5',6,6',7-hexahydrospiro[cyclopenta[e]pyrazolo[1,5-a]pyrimidine-8,4'-pyran]-6-carboxamide were submitted to chiral HPLC purification (Column: CHIRALPAK IG, 2*25 cm, 5 μm; Mobile Phase A: Hex(0.1% FA)-HPLC, Mobile Phase B: EtOH-HPLC; Flow rate: 20 mL/min; isocratic 40% B in 16 min; Wave Length: 220/254 nm; RT1(min): 6.53; RT2(min): 13.91; Sample Solvent: EtOH-HPLC; Injection Volume: 2 mL; Number Of Runs: 1). The first eluting isomer was concentrated and lyophilized to afford Example 146 (6.3 mg, 12% yield) as a white solid. The second eluting isomer was concentrated and lyophilized to afford Example 147 (7.5 mg, 14% yield) as a white solid.

Example 146: $^1H$ NMR (400 MHz, DMSO-$d_6$) δ: 10.94 (s, 1H), 8.68 (d, J=2.4 Hz, 1H), 8.66 (s, 1H), 8.62 (d, J=2.4 Hz, 1H), 7.75 (t, J=71.6 Hz, 1H), 6.59 (d, J=4.8 Hz, 1H), 4.41-4.46 (m, 1H), 3.89-3.99 (m, 2H), 3.49-3.61 (m, 2H), 2.82-2.92 (m, 1H), 2.70-2.81 (m, 2H), 2.46-2.49 (m, 1H), 1.52-1.58 (m, 1H), 1.41-1.46 (m, 1H). LC-MS: m/z 459.2 $[M+H]^+$.

Example 147: $^1H$ NMR (400 MHz, DMSO-$d_6$) δ: 10.91 (s, 1H), 8.69 (d, J=2.7 Hz, 1H), 8.66 (s, 1H), 8.62 (d, J=2.7 Hz, 1H), 7.74 (t, J=70.8 Hz, 1H), 6.59 (d, J=5.2 Hz, 1H), 4.39-4.46 (m, 1H), 3.89-3.98 (m, 2H), 3.51-3.62 (m, 2H), 2.82-2.93 (m, 1H), 2.68-2.78 (m, 2H), 2.44-2.48 (m, 1H), 1.53-1.58 (m, 1H), 1.42-1.47 (m, 1H). LC-MS: m/z 459.2 $[M+H]^+$.

The absolute stereochemistry for each separated isomer was not determined.

Method Z3
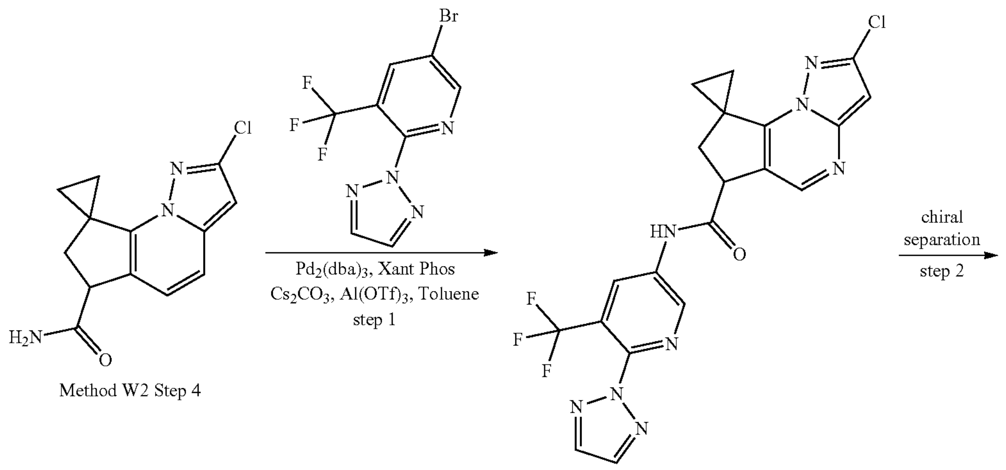
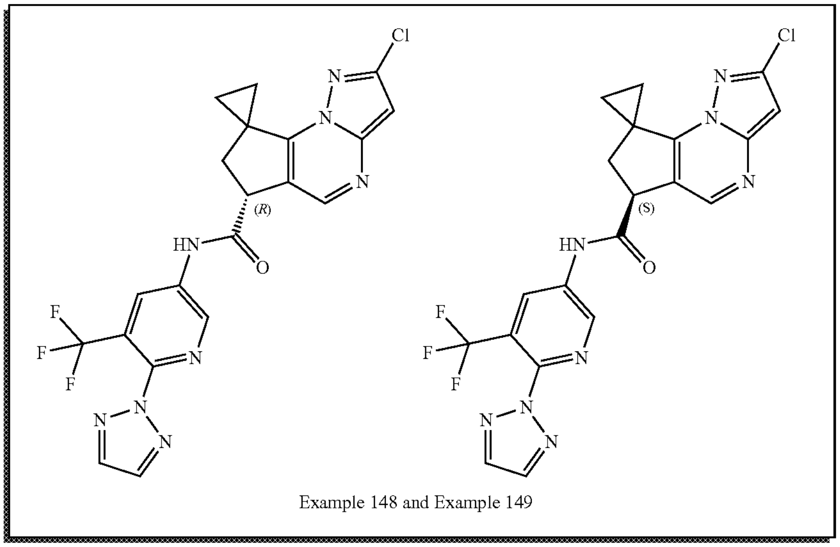
Example 148 and Example 149

Examples 148 and 149: Single Enantiomers Obtained from a Racemic Mixture Containing (R)—N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,1'-cyclopropane]-6-carboxamide and (S)—N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,1'-cyclopropane]-6-carboxamide Step 1: N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,1'-cyclopropane]-6-carboxamide

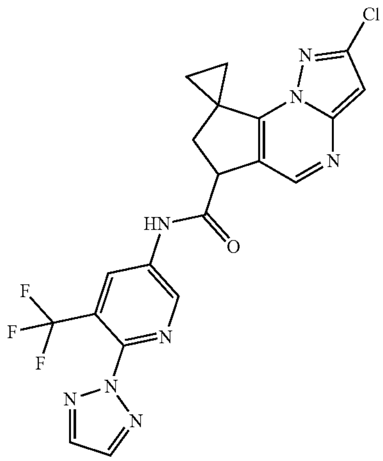 [SMILES: O=C(Nc1cnc(-n2nccn2)c(C(F)(F)F)c1)C1CC2(CC2)c2c1cnc1cc(Cl)nn21]

To a stirred mixture of 5-bromo-2-(2H-1,2,3-triazol-2-yl)-3-(trifluoromethyl)pyridine (55.8 mg, 190 μmol) and 2-chloro-6,7-dihydrospiro[cyclopenta[e]pyrazolo[1,5-a]pyrimidine-8,1'-cyclopropane]-6-carboxamide (Method W2 step 4; 50 mg, 190 μmol) in toluene (2 mL) were added XantPhos (22 mg, 38 μmol), $Pd_2(dba)_3$ (34.8 mg, 38 μmol), $Cs_2CO_3$ (93 mg, 285.5 μmol), and $Al(OTf)_3$ (9 mg, 19 μmol) at 25° C. The resulting mixture was stirred at 110° C. for 12 h under nitrogen atmosphere. The mixture was allowed to cool down to 25° C. The reaction mixture was diluted with water (50 mL). The resulting solution was extracted with DCM (3×50 mL). The combined organic layers were dried over anhydrous sodium sulfate and concentrated under reduced pressure. The residue was submitted to Prep-HPLC purification and the collected fractions were lyophilized to give N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,1'-cyclopropane]-6-carboxamide (11 mg, 13% yield) as a white solid. LC-MS: m/z 475 $[M+H]^+$.

Step 2: Separation of Enantiomers to Obtain (R)—N-(6-(2H-1,2,3-triazol-2-yl)-5-(trifluoromethyl)pyridin-3-yl)-2-chloro-6,7-dihydrospiro[cyclopenta[e]pyrazolo[1,5-a]pyrimidine-8,1'-cyclopropane]-6-carboxamide and (S)—N-(6-(2H-1,2,3-triazol-2-yl)-5-(trifluoromethyl)pyridin-3-yl)-2-chloro-6,7-dihydrospiro[cyclopenta[e]pyrazolo[1,5-a]pyrimidine-8,1'-cyclopropane]-6-carboxamide

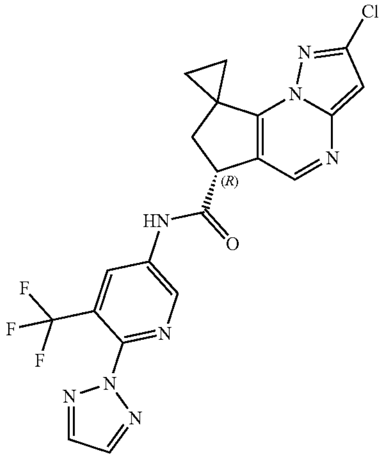

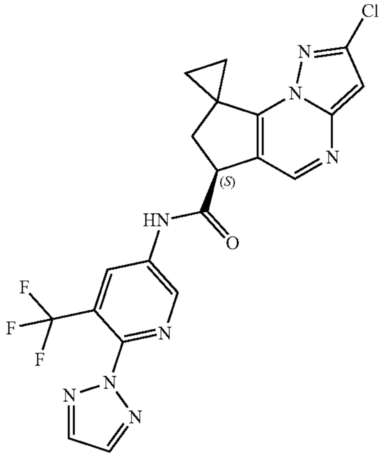

Example 148 and Example 149

10 mg of N-(6-(2H-1,2,3-triazol-2-yl)-5~(trifluoromethyl)pyridin-3-yl)-2-chloro-6,7-dihydrospiro[cyclopenta[e]pyrazolo[1,5-a]pyrimidine-8,1'-cyclopropane]-6-carboxamide were submitted to chiral HPLC purification (Column: CHIRAL ART Cellulose-SA, 2*25 cm, 5 μm; Mobile Phase A: Hex:DCM=3:1(0.1% TFA)-HPLC, Mobile Phase B: EtOH-HPLC; Flow rate: 20 mL/min; isocratic 20% B in 9 min; Wave Length: 254/220 nm; RT1(min): 5.93; RT2(min): 8.13; Sample Solvent: EtOH-HPLC; Injection Volume: 1.5 mL; Number Of Runs: 2). The first eluting isomer was concentrated and lyophilized to afford Example 148 (1 mg, 9% yield) as a white solid. The second eluting isomer was concentrated and lyophilized to afford Example 149 (1.3 mg, 12.5% yield) as a white solid.

Example 148: $^1H$ NMR (400 MHz, DMSO-$d_6$) δ: 11.25 (br, 1H), 9.03 (d, J=2 Hz, 1H), 8.81 (d, J=2.4 Hz, 1H), 8.62 (s, 1H), 8.19 (s, 2H), 6.87 (s, 1H), 4.55-4.59 (m, 1H), 2.70-2.74 (m, 1H), 2.67-2.68 (m, 1H), 2.11-2.16 (m, 2H), 1.23-1.26 (m, 2H). LC-MS: m/z 475.1 $[M+H]^+$.
Example 149: $^1$H NMR (400 MHz, DMSO-$d_6$) δ: 11.23 (br, 1H), 9.02 (d, J=2 Hz, 1H), 8.81 (d, J=2.4 Hz, 1H), 8.62 (s, 1H), 8.19 (s, 2H), 6.87 (s, 1H), 4.55-4.59 (m, 1H), 2.68-2.74 (m, 1H), 2.56-2.60 (m, 1H), 2.09-2.16 (m, 2H), 1.19-1.26 (m, 2H). LC-MS: m/z 475.1 $[M+H]^+$.
The absolute stereochemistry for each separated isomer was not determined.
Method A4
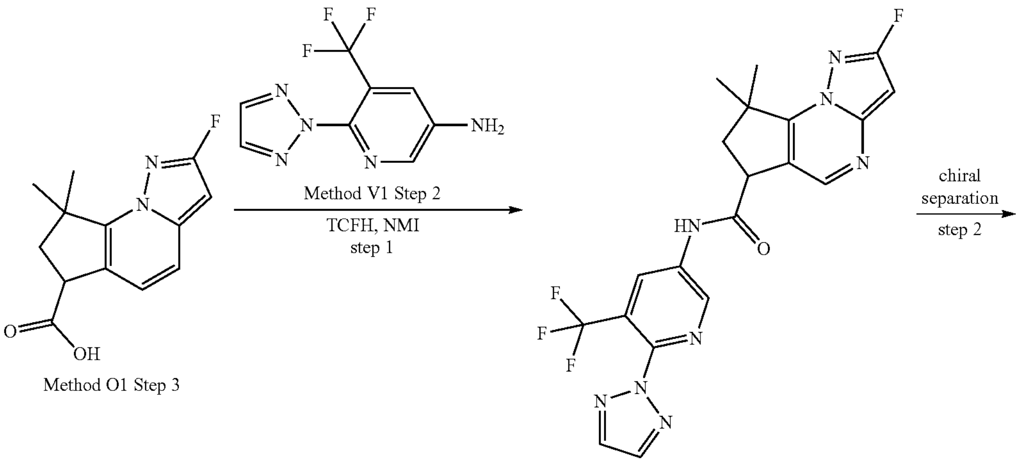
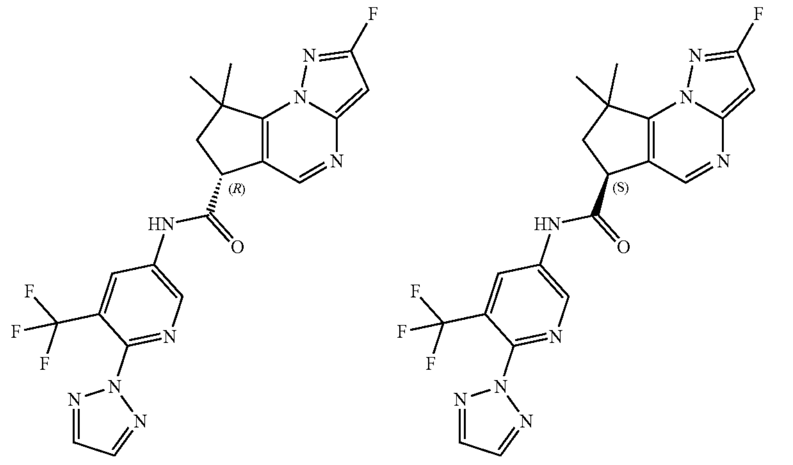
Example 150 and Example 151

Examples 150 and 151: Single Enantiomers Obtained from a Racemic Mixture Containing (R)—N-(6-(2H-1,2,3-triazol-2-yl)-5~(trifluoromethyl)pyridin-3-yl)-2-fluoro-8,8-dimethyl-7,8-dihydro-6H-cyclopenta[e]pyrazolo[1,5-a]pyrimidine-6-carboxamide and (S)—N-(6-(2H-1,2,3-triazol-2-yl)-5~(trifluoromethyl)pyridin-3-yl)-2-fluoro-8,8-dimethyl-7,8-dihydro-6H-cyclopenta[e]pyrazolo[1,5-a]pyrimidine-6-carboxamide Step 1: N-(6-(2H-1,2,3-triazol-2-yl)-5~(trifluoromethyl)pyridin-3-yl)-2-fluoro-8,8-dimethyl-7,8-dihydro-6H-cyclopenta[e]pyrazolo[1,5-a]pyrimidine-6-carboxamide

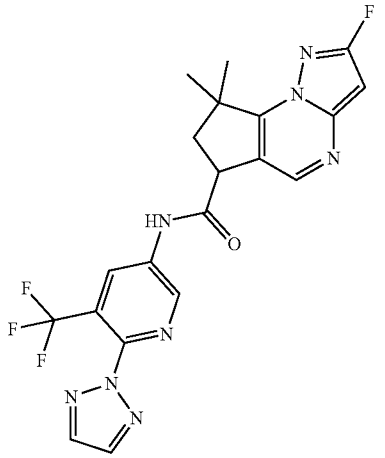

To a stirred solution of 2-fluoro-8,8-dimethyl-7,8-dihydro-6H-cyclopenta[e]pyrazolo[1,5-a]pyrimidine-6-carboxylic acid (Method 01 step 3; 300 mg, 1.2 mmol) in ACN (20 mL) was added 6-(2H-1,2,3-triazol-2-yl)-5~(trifluoromethyl)pyridin-3-amine (Method VI step 2; 276 mg, 1.2 mmol), TCFH (1.4 g, 4.8 mmol) and NMI (396 mg, 4.8 mmol). The resulting mixture was stirred at 25° C. for 16 h. The resulting mixture was concentrated under reduced pressure. The residue was submitted to Prep-HPLC purification and the collected fractions were lyophilized to give N-(6-(2H-1,2,3-triazol-2-yl)-5~(trifluoromethyl)pyridin-3-yl)-2-fluoro-8,8-dimethyl-7,8-dihydro-6H-cyclopenta[e]pyrazolo[1,5-a]pyrimidine-6-carboxamide (103 mg, 18.6% yield) as a white solid. LC-MS: m/z 461 $[M+H]^+$.

Step 2: Separation of Enantiomers to Obtain (R)—N-(6-(2H-1,2,3-triazol-2-yl)-5-(trifluoromethyl)pyridin-3-yl)-2-fluoro-8,8-dimethyl-7,8-dihydro-6H-cyclopenta[e]pyrazolo[1,5-a]pyrimidine-6-carboxamide and (S)—N-(6-(2H-1,2,3-triazol-2-yl)-5~(trifluoromethyl)pyridin-3-yl)-2-fluoro-8,8-dimethyl-7,8-dihydro-6H-cyclopenta[e]pyrazolo[1,5-a]pyrimidine-6-carboxamide

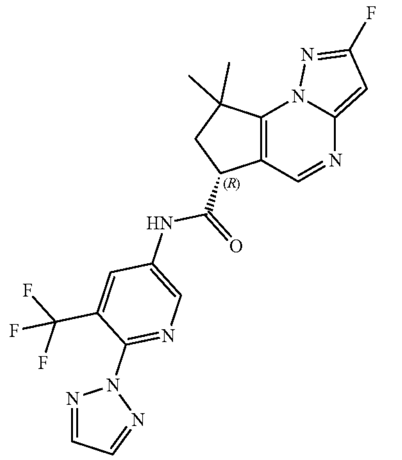

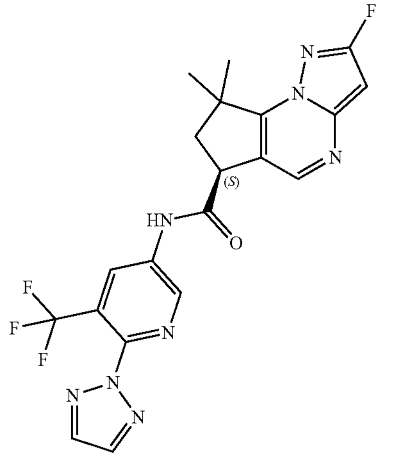

Example 150 and
Example 151

100 mg of N-(6-(2H-1,2,3-triazol-2-yl)-5~(trifluoromethyl)pyridin-3-yl)-2-fluoro-8,8-dimethyl-7,8-dihydro-6H-cyclopenta[e]pyrazolo[1,5-a]pyrimidine-6-carboxamide were submitted to chiral HPLC purification (Column: CHIRAL ART Amylose-SA, 2*25 cm, 5 μm; Mobile Phase A: Hex(0.1% FA)-HPLC, Mobile Phase B: EtOH-HPLC; Flow rate: 20 mL/min; isocratic 40% B in 12 min; Wave Length: 254/220 nm; RT1(min): 5.17; RT2(min): 8.61; Sample Solvent: EtOH-HPLC; Injection Volume: 1.2 mL; Number Of Runs: 3). The first eluting isomer was concentrated and lyophilized to afford Example 150 (36.6 mg, 36% yield) as a white solid. The second eluting isomer was concentrated and lyophilized to afford Example 151 (34.2 mg, 34% yield) as a white solid.

Example 150: $^1H$ NMR (300 MHz, DMSO-$d_6$) δ: 11.22 (s, 1H), 9.04 (s, 1H), 8.82 (s, 1H), 8.67 (s, 1H), 8.20 (s, 2H), 6.58 (d, J=4.2 Hz, 1H), 4.46-4.51 (m, 1H), 2.57-2.62 (m, 1H), 2.28-2.41 (m, 1H), 1.64 (s, 3H), 1.57 (s, 3H). LCMS (ES, m/z): 461.1 $[M+H]^+$.

Example 151: $^1$H NMR (300 MHz, DMSO-$d_6$) δ: 11.22 (s, 1H), 9.04 (s, 1H), 8.82 (s, 1H), 8.67 (s, 1H), 8.20 (s, 2H), 6.58 (d, J=4.5 Hz, 1H), 4.46-4.51 (m, 1H), 2.57-2.62 (m, 1H), 2.28-2.41 (m, 1H), 1.64 (s, 3H), 1.57 (s, 3H). LC-MS (ES, m/z): 461.1 [M+H]$^+$.
The absolute stereochemistry for each separated isomer was not determined.
Method B4
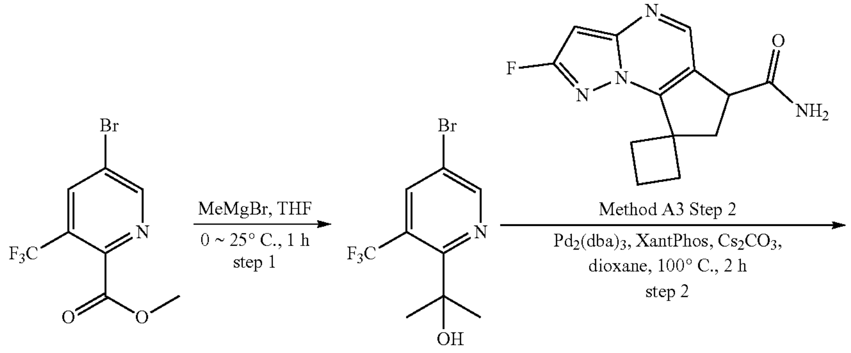
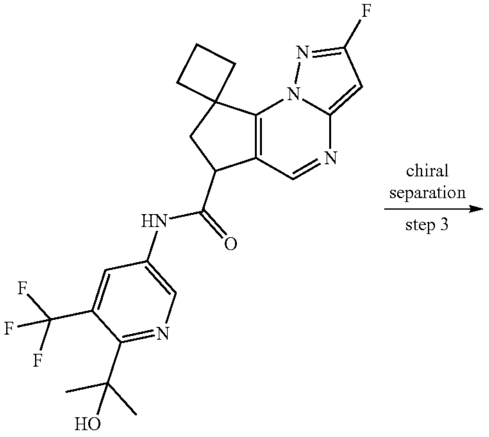
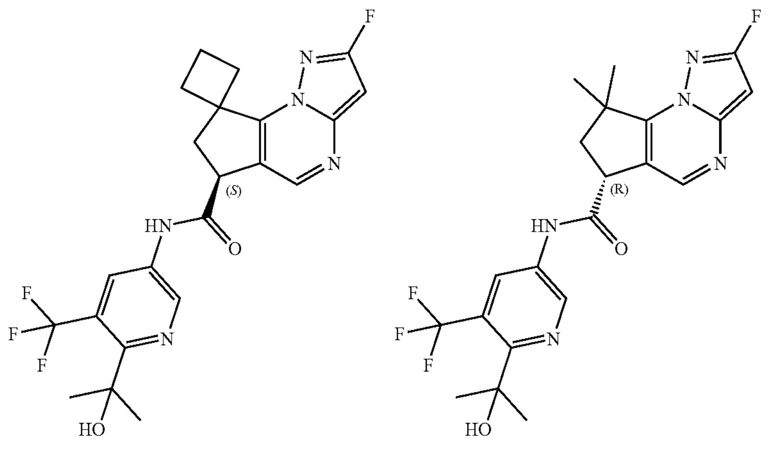
Example 152 and Example 153

Examples 152 and 153: Single Enantiomers Obtained from a Racemic Mixture Containing (S)-2'-fluoro-N-(6-(2-hydroxypropan-2-yl)-5~(trifluoromethyl)pyridin-3-yl)-6',7'-dihydrospiro[cyclobutane-1,8'-cyclopenta[a]pyrazolo[1,5-a]pyrimidine]-6'-carboxamide and (R)-2'-fluoro-N-(6-(2-hydroxypropan-2-yl)-5~(trifluoromethyl)pyridin-3-yl)-6',7'-dihydrospiro[cyclobutane-1,8'-cyclopenta[a]pyrazolo[1,5-a]pyrimidine]-6'-carboxamide Step 1: 2-(5-bromo-3-(trifluoromethyl)pyridin-2-yl)propan-2-ol

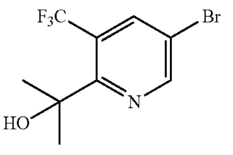

To a stirred solution of methyl 5-bromo-3-(trifluoromethyl)picolinate (2 g, 7.0 mmol) in THF (20 mL) was added Methylmagnesium bromide (15.5 mL, 1M in THF) at 0° C. The mixture was stirred at 25° C. for 1 h. The reaction mixture was quenched with water (30 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (3:1) to give 2-(5-bromo-3-(trifluoromethyl)pyridin-2-yl)propan-2-ol (1.4 g, 70% yield) as a light-yellow oil. LC-MS: m/z 284 $[M+H]^+$.

Step 2: 2'-fluoro-N-(6-(2-hydroxypropan-2-yl)-5~(trifluoromethyl)pyridin-3-yl)-6',7'-dihydrospiro[cyclobutane-1,8'-cyclopenta[e]pyrazolo[1,5-a]pyrimidine]-6'-carboxamide

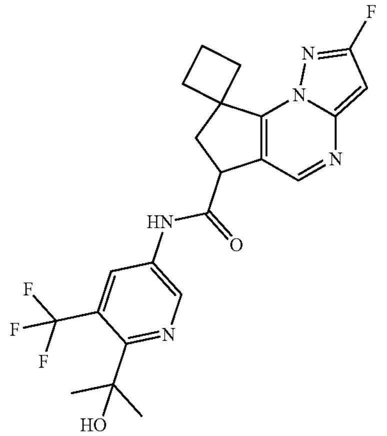

To a solution of 2'-fluoro-6',7'-dihydrospiro[cyclobutane-1,8'-cyclopenta[e]pyrazolo[1,5-a]pyrimidine]-6'-carboxamide (Method A3 step 2; 40 mg, 153.7 μmol) in dioxane (5 mL) was added 2-[5-bromo-3-(trifluoromethyl)-2-pyridyl]propan-2-ol (87 mg, 307.4 μmol), $Cs_2CO_3$ (100 mg, 307.4 μmol), Xantphos (18 mg, 30.7 μmol) and $Pd_2(dba)_3$ (16 mg, 15.4 μmol). The resulting mixture was stirred at 100° C. for 2 h under nitrogen. The reaction mixture was diluted with water (20 mL). The resulting solution was extracted with ethyl acetate (3×20 mL). The combined organic layers were dried over anhydrous sodium sulfate and concentrated under reduced pressure. The residue was submitted to Prep-HPLC purification and the collected fractions were lyophilized to give 2'-fluoro-N-(6-(2-hydroxypropan-2-yl)-5~(trifluoromethyl)pyridin-3-yl)-6',7'-dihydrospiro[cyclobutane-1,8'-cyclopenta[e]pyrazolo[1,5-a]pyrimidine]-6'-carboxamide (14.6 mg, 20% yield) as a white solid. LC-MS: m/z 464 $[M+H]^+$.

Step 3: Separation of Enantiomers to Obtain (S)-2'-fluoro-N-(6-(2-hydroxypropan-2-yl)-5-(trifluoromethyl)pyridin-3-yl)-6',7'-dihydrospiro[cyclobutane-1,8'-cyclopenta[e]pyrazolo[1,5-a]pyrimidine]-6'-carboxamide and (R)-2'-fluoro-N-(6-(2-hydroxypropan-2-yl)-5-(trifluoromethyl)pyridin-3-yl)-6',7'-dihydrospiro[cyclobutane-1,8'-cyclopenta[e]pyrazolo[1,5-a]pyrimidine]-6'-carboxamide

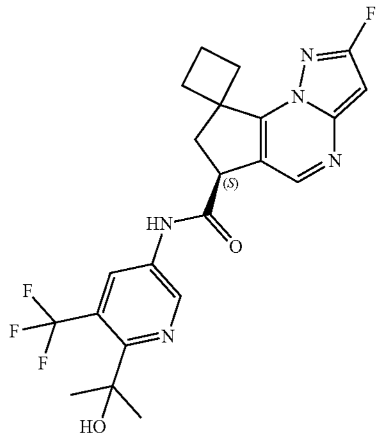

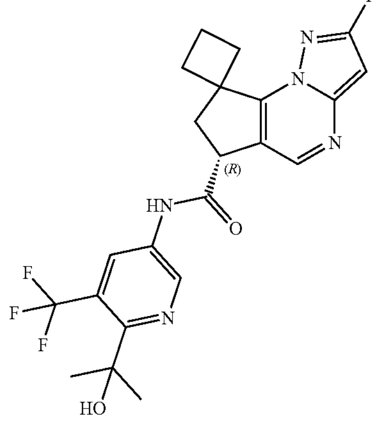

Example 152 and
Example 153

12.5 mg of 2'-fluoro-N-(6-(2-hydroxypropan-2-yl)-5~(trifluoromethyl)pyridin-3-yl)-6',7'-dihydrospiro[cyclobutane-1,8'-cyclopenta[e]pyrazolo[1,5-a]pyrimidine]-6'-carboxamide were submitted to chiral HPLC purification (Column: CHIRAL ART Cellulose-SA, 2*25 cm, 5 μm; Mobile Phase A: Hex(0.1% FA)-HPLC, Mobile Phase B: EtOH-HPLC; Flow rate: 20 mL/min; isocratic 20% B in 17 min; Wave Length: 220/254 nm; RT1(min): 8.73; RT2(min): 15.13;

Sample Solvent: EtOH-HPLC; Injection Volume: 1 mL; Number Of Runs: 2). The first eluting isomer was concentrated and lyophilized to afford Example 153 (2.8 mg, 22% yield) as a white solid. The second eluting isomer was concentrated and lyophilized to afford Example 152 (2.7 mg, 22% yield) as a white solid.

Example 152: $^{1}$H NMR (400 MHz, DMSO-$d_6$) δ: 10.79 (s, 1H), 8.88 (d, J=2.0 Hz, 1H), 8.61 (s, 1H), 8.49 (d, J=2.4 Hz, 1H), 6.59 (d, J=4.8 Hz, 1H), 5.21 (s, 1H), 4.30-4.38 (m, 1H), 3.04-3.23 (m, 2H), 2.79-2.93 (m, 1H), 2.63-2.75 (m, 1H), 2.06-2.29 (m, 4H), 1.51 (s, 6H). LC-MS: m/z 464.2 $[M+H]^+$.

Example 153: $^{1}$H NMR (400 MHz, DMSO-$d_6$) δ: 10.79 (s, 1H), 8.88 (d, J=2.0 Hz, 1H), 8.61 (s, 1H), 8.49 (d, J=2.0 Hz, 1H), 6.59 (d, J=4.8 Hz, 1H), 5.20 (s, 1H), 4.33-4.36 (m, 1H), 3.03-3.24 (m, 2H), 2.79-2.92 (m, 1H), 2.63-2.74 (m, 1H), 2.04-2.28 (m, 4H), 1.51 (s, 6H). LC-MS: m/z 464.2 $[M+H]^+$.

The absolute stereochemistry for each separated isomer was not determined.

Method C4

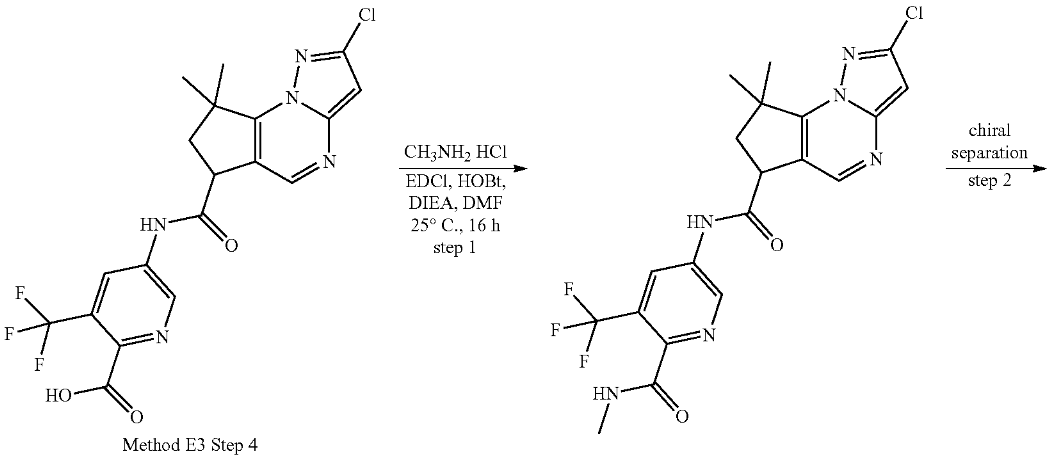

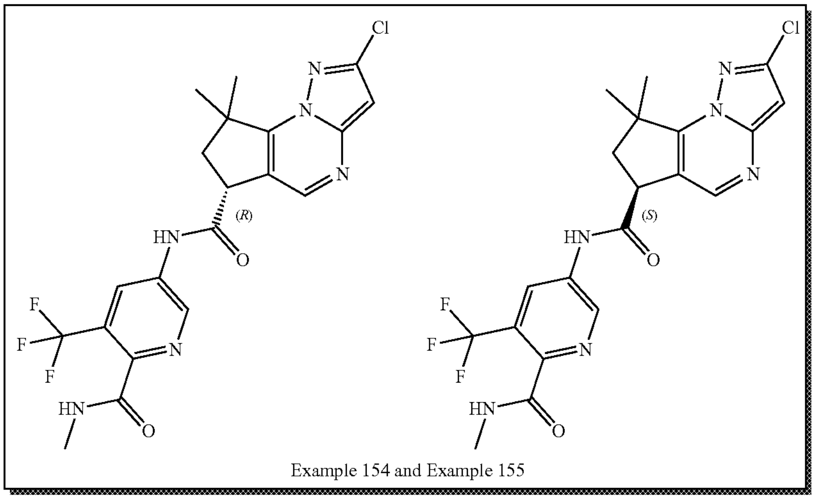

Example 154 and Example 155

Examples 154 and 155: Single Enantiomers Obtained from a Racemic Mixture Containing (R)-2-chloro-8,8-dimethyl-N-(6-(methylcarbamoyl)-5~(trifluoromethyl)pyridin-3-yl)-7,8-dihydro-6H-cyclopenta[e]pyrazolo[1,5-a]pyrimidine-6-carboxamide and (S)-2-chloro-8,8-dimethyl-N-(6-(methylcarbamoyl)-5~(trifluoromethyl)pyridin-3-yl)-7,8-dihydro-611-cyclopenta[e]pyrazolo[1,5-a]pyrimidine-6-carboxamide Step 1: 2-chloro-8,8-dimethyl-N-(6-(methylcarbamoyl)-5~(trifluoromethyl)pyridin-3-yl)-7,8-dihydro-6H-cyclopenta[e]pyrazolo[1,5-a]pyrimidine-6-carboxamide

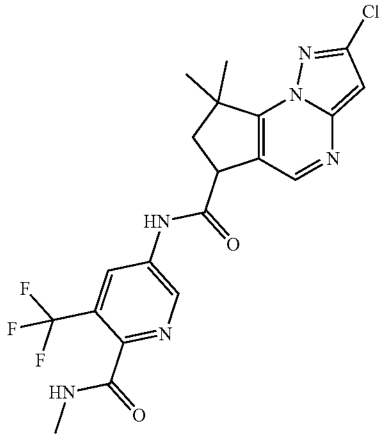 [SMILES: CNC(=O)c1ncc(NC(=O)C2CC(C)(C)c3c2cnc2cc(Cl)nn32)cc1C(F)(F)F]

To a solution of 5~(2-chloro-8,8-dimethyl-7,8-dihydro-6H-cyclopenta[e]pyrazolo[1,5-a]pyrimidine-6-carboxamido)-3-(trifluoromethyl)picolinic acid (Method E3 step 4; 160 mg, 352.6 μmol) in DMF (2 mL) were added methylamine hydrochloride salt (36 mg, 529 μmol), EDCI (101 mg, 529 μmol), HOBT (72 mg, 529 μmol) and DIEA (68 mg, 528.9 μmol). The resulting mixture was stirred at 25° C. for 16 h. The resulting mixture was concentrated under reduced pressure. The residue was submitted to Prep-HPLC purification and the collected fractions were lyophilized to give 2-chloro-8,8-dimethyl-N-(6-(methylcarbamoyl)-5-(trifluoromethyl)pyridin-3-yl)-7,8-dihydro-6H-cyclopenta[e]pyrazolo[1,5-a]pyrimidine-6-carboxamide (60 mg, 36% yield) as a white solid. LC-MS: m/z 467 $[M+H]^+$.

Step 2: Separation of Enantiomers to Obtain (R)-2-chloro-8,8-dimethyl-N-(6-(methylcarbamoyl)-5~(trifluoromethyl)pyridin-3-yl)-7,8-dihydro-6H-cyclopenta[e]pyrazolo[1,5-a]pyrimidine-6-carboxamide and (S)-2-chloro-8,8-dimethyl-N-(6-(methylcarbamoyl)-5-(trifluoromethyl)pyridin-3-yl)-7,8-dihydro-6H-cyclopenta[e]pyrazolo[1,5-a]pyrimidine-6-carboxamide

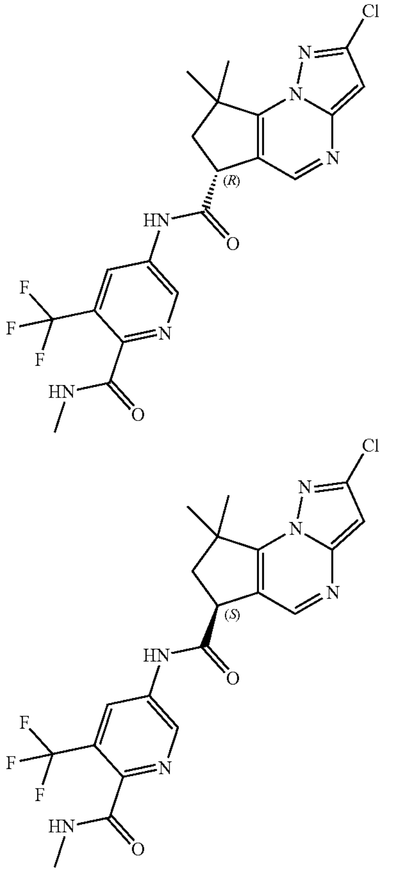

Example 154 and Example 155

60 mg of 2-chloro-8,8-dimethyl-N-(6-(methylcarbamoyl)-5~(trifluoromethyl)pyridin-3-yl)-7,8-dihydro-6H-cyclopenta[e]pyrazolo[1,5-a]pyrimidine-6-carboxamide were submitted to chiral HPLC purification (Column: CHIRAL ART Cellulose-SB, 2*25 cm, 5 μm; Mobile Phase A: Hex (0.5% 2M $NH_3$-MeOH)-HPLC, Mobile Phase B: EtOH-HPLC; Flow rate: 20 mL/min; isocratic 15% B in 22 min; Wave Length: 220/254 nm; RT1(min): 15.369; RT2(min): 19.039; Sample Solvent: EtOH-HPLC; Injection Volume: 0.8 mL; Number Of Runs: 6). The first eluting isomer was concentrated and lyophilized to afford Example 154 (19.2 mg, 32% yield) as a white solid. The second eluting isomer was concentrated and lyophilized to afford Example 155 (19.3 mg, 32% yield) as a white solid.

Example 154: $^1$H NMR (400 MHz, DMSO-$d_6$) δ: 11.02 (s, 1H), 9.00 (d, J=2.0 Hz, 1H), 8.65 (s, 1H), 8.57-8.61 (m, 2H), 6.95 (s, 1H), 4.42-4.46 (m, 1H), 2.78 (d, J=4.4 Hz, 3H), 2.53-2.58 (m, 1H), 2.30-2.38 (m, 1H), 1.63 (s, 3H), 1.56 (s, 3H). LC-MS: m/z 467.0 $[M+H]^+$.

Example 155: $^1$H NMR (400 MHz, DMSO-$d_6$) δ: 11.03 (s, 1H), 9.00 (d, J=2.0 Hz, 1H), 8.65 (s, 1H), 8.57-8.60 (m, 2H), 6.95 (s, 1H), 4.42-4.46 (m, 1H), 2.78 (d, J=4.8 Hz, 3H), 2.53-2.58 (m, 1H), 2.30-2.37 (m, 1H), 1.64 (s, 3H), 1.56 (s, 3H). LC-MS: m/z 467.0 $[M+H]^+$
The absolute stereochemistry for each separated isomer was not determined.
Method D4
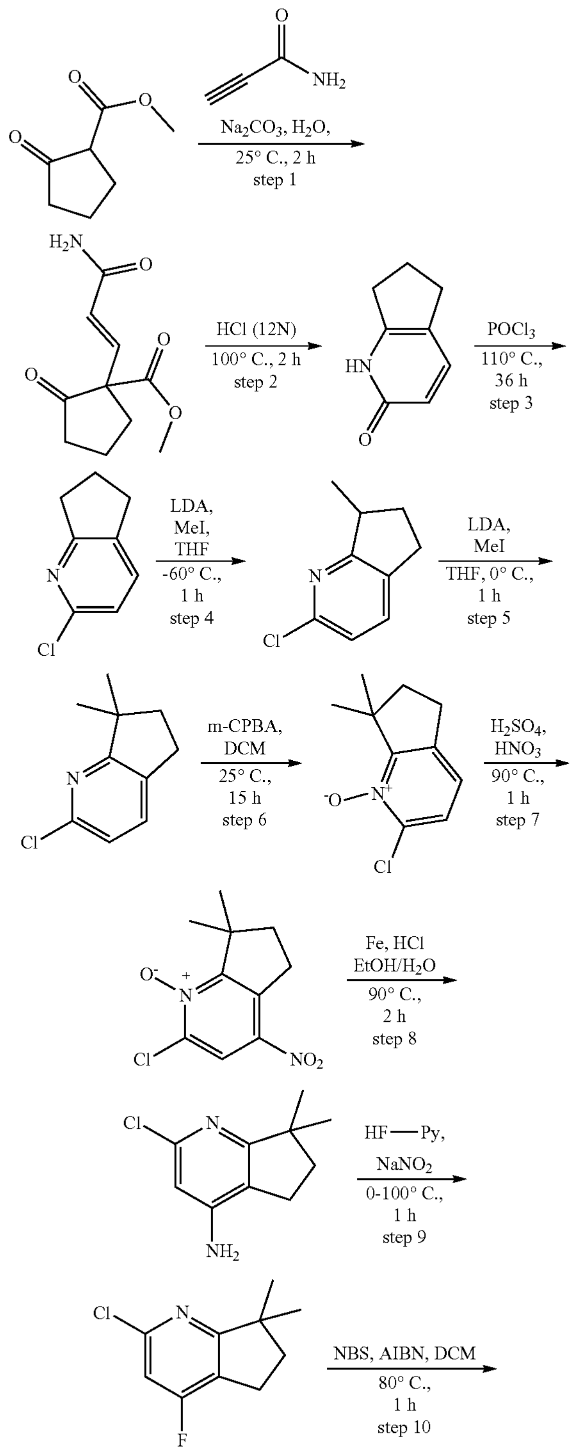
-continued
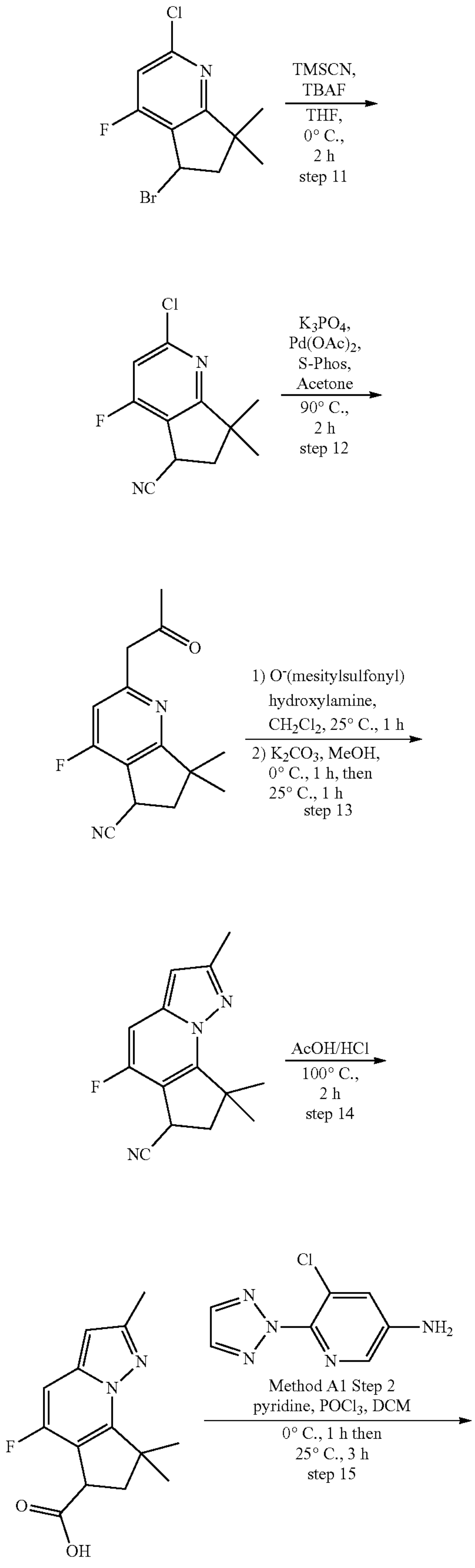

-continued

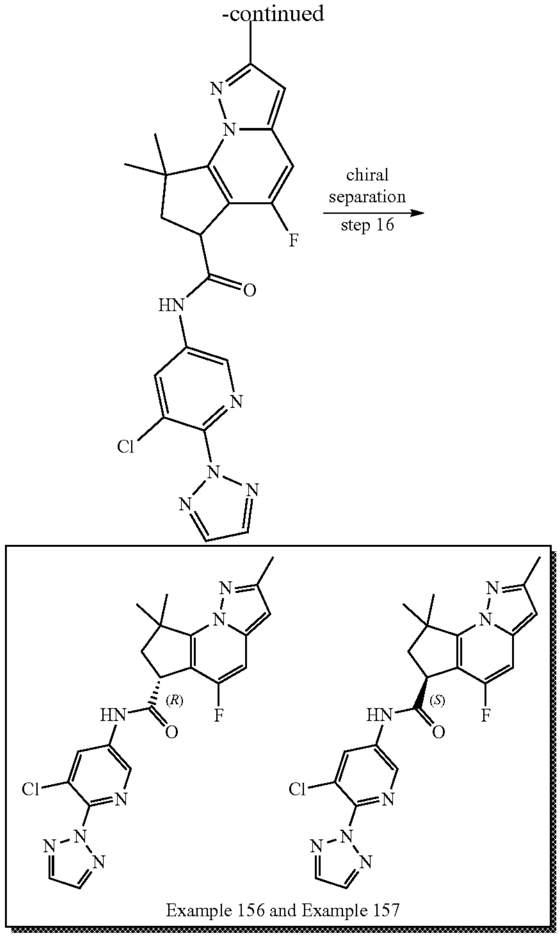

Example 156 and Example 157

Examples 156 and 157: Single Enantiomers Obtained from a Racemic Mixture Containing (R)—N-(5-chloro-6-(2H-1,2,3-triazol-2-yl)pyridin-3-yl)-5-fluoro-2,8,8-trimethyl-7,8-dihydro-6H-cyclopenta[e]pyrazolo[1,5-a]pyridine-6-carboxamide and (S)—N-(5-chloro-6-(2H-1,2,3-triazol-2-yl)pyridin-3-yl)-5-fluoro-2,8,8-trimethyl-7,8-dihydro-6H-cyclopenta[e]pyrazolo[1,5-a]pyridine-6-carboxamide Step 1: methyl (E)-1-(3-amino-3-oxoprop-1-en-1-yl)-2-oxocyclopentane-1-carboxylate

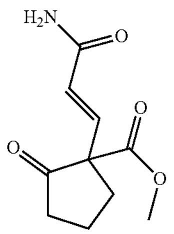

To a solution of prop-2-ynamide (206.5 g, 3.0 mol) and sodium carbonate (186.4 g, 1.7 mol) in water (3.0 L) was added methyl 2-oxocyclopentanecarboxylate (250 g, 1.7 mol) dropwise at 0° C. The reaction mixture was stirred at 25° C. for 2 h. The precipitated solid was collected by filtration to afford methyl (F)-1-(3-amino-3-oxoprop-1-en-1-yl)-2-oxocyclopentane-1-carboxylate (300 g, 80% yield) as an off-white solid. $^1$H NMR (300 MHz, DMSO-$d_6$) δ 6.72-6.73 (m, 1H), 5.71-5.75 (m, 1H), 3.42 (s, 3H), 2.39-2.46 (m, 1H), 2.10-2.16 (m, 1H), 1.93-2.00 (m, 1H), 1.74-1.81 (m, 1H), 1.55-1.65 (m, 2H). LC-MS: m/z 212 [M+H]$^+$.

Step 2:1,5,6,7-tetrahydro-2H-cyclopenta[b]pyridin-2-one

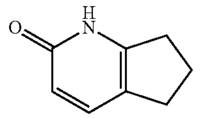

A solution of methyl (F)-1-(3-amino-3-oxoprop-1-en-1-yl)-2-oxocyclopentane-1-carboxylate (130 g, 615.5 mmol) in 12 M HCl (100 mL) was stirred at 100° C. for 2 h. The mixture was cooled to 25° C. and concentrated under reduced pressure. The residue was diluted with water (600 mL). The pH was adjusted to 7-8 with 1M sodium hydroxide solution. The precipitated solid was collected by filtration to afford 1,5,6,7-tetrahydro-2H-cyclopenta[b]pyridin-2-one (58 g, crude) as light yellow solid. $^1$H NMR (400 MHz, DMSO-$d_6$) δ 11.71 (br, 1H), 7.31-7.36 (m, 1H), 6.07-6.11 (m, 1H), 2.59-2.71 (m, 4H), 1.97-2.04 (m, 2H). LC-MS: m/z 136 [M+H]$^+$.

Step 3: 2-chloro-6,7-dihydro-5H-cyclopenta[b]pyridine

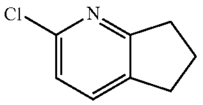

A mixture of 1,5,6,7-tetrahydro-2H-cyclopenta[b]pyridin-2-one (84 g, 621.5 mmol) in phosphoryl trichloride (400 mL) was stirred at 110° C. for 36 h. The reaction mixture was quenched with saturated aqueous sodium bicarbonate solution (1000 mL). The resulting solution was extracted with ethyl acetate (3×700 mL). The combined organic layers were dried over anhydrous sodium sulfate and concentrated under reduced pressure. The residue was applied onto a silica gel column and eluted with EtOAc/PE (1:1) to afford 2-chloro-6,7-dihydro-5H-cyclopenta[b]pyridine (67 g, 70% yield) as yellow solid. $^1$H NMR (400 MHz, Chloroform-d) δ 7.44 (d, J=8.0 Hz, 1H), 7.06 (d, J=8.0 Hz, 1H), 2.92-3.01 (m, 2H), 2.89-2.90 (m, 2H), 2.05-2.19 (m, 2H). LC-MS: m/z 154 [M+H]$^+$.

Step 4: 2-chloro-7-methyl-6,7-dihydro-5H-cyclopenta[b]pyridine

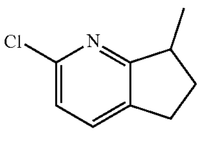

To a stirred mixture of 2-chloro-6,7-dihydro-5H-cyclopenta[b]pyridine (50 g, 325.5 mmol) in THF (1000 mL) was added LDA (410 mL, 820 mmol, 2 N) dropwise at −60° C. under nitrogen atmosphere. The mixture was stirred at −60° C. for 30 min. Then a solution of iodomethane (277.2 g, 1.95 mol) in THF (100 mL) was added dropwise at −60° C. The mixture was stirred at −60° C. for 1 h. The reaction mixture was quenched with ammonium chloride solution (1000 mL). The resulting solution was extracted with ethyl acetate (3×1000 mL). The combined organic layers were washed with brine (1000 mL), dried over anhydrous sodium sulfate and concentrated under reduced pressure. The residue was applied onto a silica gel column and eluted with EtOAc/PE (1:9) to afford 2-chloro-7-methyl-6,7-dihydro-5H-cyclopenta[b]pyridine (33 g, 60% yield) as yellow oil. LC-MS: m/z 168 $[M+H]^+$.

Step 5: 2-chloro-7,7-dimethyl-6,7-dihydro-5H-cyclopenta[b]pyridine

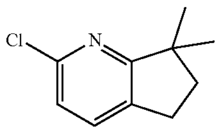

To a stirred mixture of 2-chloro-7-methyl-6,7-dihydro-5H-cyclopenta[b]pyridine (80 g, 477.2 mmol) in THF (4000 mL) was added LDA (715 mL, 1.43 mol, 2 N) dropwise at 0° C. under nitrogen atmosphere. The mixture was stirred at 0° C. for 30 min. Then a solution of iodomethane (203.2 g, 1.43 mol) in THF (100 mL) was added dropwise at 0° C. The mixture was stirred at 0° C. for 1 h. The reaction mixture was quenched with ammonium chloride solution (4000 mL). The resulting solution was extracted with ethyl acetate (3×3000 mL). The combined organic layers were washed with brine (3000 mL), dried over anhydrous sodium sulfate and concentrated under reduced pressure. The residue was applied onto a silica gel column and eluted with EtOAc/PE (1:8) to afford 2-chloro-7,7-dimethyl-6,7-dihydro-5H-cyclopenta[b]pyridine (33 g, 38% yield) as yellow oil. LC-MS: m/z 182 $[M+H]^+$.

Step 6: 2-chloro-7,7-dimethyl-6,7-dihydro-5H-cyclopenta[b]pyridine 1-oxide

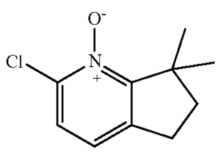

To a mixture of 2-chloro-7,7-dimethyl-5,6-dihydrocyclopenta[b]pyridine (38 g, 209.2 mmol) in DCM (800 mL) was added 3-chlorobenzoperoxoic acid (180.5 g, 1.1 mol) in portions at 0° C. The reaction mixture was stirred at 25° C. for 16 h. The reaction mixture was quenched with saturated aqueous sodium sulfite solution (500 mL). The resulting solution was extracted with DCM (2×500 mL). The combined organic layers were dried over anhydrous sodium sulfate and concentrated under reduced pressure. The residue was applied onto a silica gel column and eluted with EtOAc/PE (1:2) to give 2-chloro-7,7-dimethyl-6,7-dihydro-5H-cyclopenta[b]pyridine 1-oxide (32 g, 77% yield) as light yellow solid. $^1$H NMR (300 MHz, Chloroform-d) δ 7.29-7.38 (m, 1H), 7.00-7.04 (m, 1H), 2.87-2.92 (m, 2H), 2.02-2.07 (m, 2H), 1.54 (s, 6H). LC-MS: m/z 198 $[M+H]^+$.

Step 7: 2-chloro-7,7-dimethyl-4-nitro-6,7-dihydro-5H-cyclopenta[b]pyridine 1-oxide

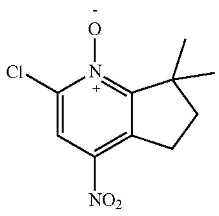

To a mixture of 2-chloro-7,7-dimethyl-6,7-dihydro-5H-cyclopenta[b]pyridine 1-oxide (32 g, 161.9 mmol) in sulfuric acid (64 mL) was added a mixture of nitric acid (64 mL) and sulfuric acid (64 mL) dropwise at 0° C. The resulting mixture was stirred at 90° C. for 1 h. The reaction mixture was cooled to 25° C. and diluted with ice water (600 mL). The pH was adjusted to 7-8 with 4N sodium hydroxide solution. The resulting solution was extracted with ethyl acetate (3×800 mL). The combined organic layers were dried over anhydrous sodium sulfate and concentrated under reduced pressure. The residue was applied onto a silica gel column and eluted with EtOAc/PE (1:3) to afford 2-chloro-7,7-dimethyl-4-nitro-6,7-dihydro-5H-cyclopenta[b]pyridine 1-oxide (12 g, 30% yield) as light yellow solid. $^1$H NMR (300 MHz, Chloroform-d) δ 8.22 (s, 1H), 3.39-3.45 (m, 2H), 2.11-2.17 (m, 2H), 1.55 (s, 6H). LC-MS: m/z 243 $[M+H]^+$.

Step 8: 2-chloro-7,7-dimethyl-6,7-dihydro-5H-cyclopenta[b]pyridin-4-amine

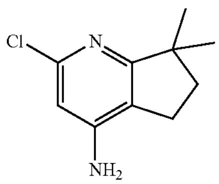

To a mixture of 2-chloro-7,7-dimethyl-4-nitro-6,7-dihydro-5H-cyclopenta[b]pyridine 1-oxide (4 g, 16.5 mmol) in EtOH (30 mL) and water (9 mL) was added Fe (4.6 g, 82.4 mmol) and ammonium chloride (4.4 g, 82.4 mmol). The reaction mixture was stirred at 90° C. for 2 h. After cooled to 25° C., the solid was filtered out. The filtrate was concentrated under reduced pressure.

The residue was diluted with water (100 mL), and the resulting solution was extracted with ethyl acetate (3×100 mL). The combined organic layers were dried over anhydrous sodium sulfate and concentrated under reduced pressure. The residue was applied onto a silica gel column and eluted with EtOAc/PE (1:1) to afford 2-chloro-7,7-dimethyl-6,7-dihydro-5H-cyclopenta[b]pyridin-4-amine (2.5 g, 71% yield) as white solid. $^1$H NMR (300 MHz, Chloroform-d) δ

6.39 (s, 1H), 4.11 (br, 2H), 2.58-2.63 (m, 2H), 1.97-2.07 (m, 2H), 1.27 (s, 6H). LC-MS: m/z 197 [M+H]$^+$.

Step 9: 2-chloro-4-fluoro-7,7-dimethyl-6,7-dihydro-5H-cyclopenta[b]pyridine

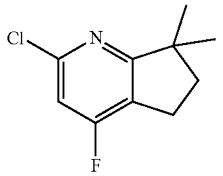

To a solution of Hydrogen fluoride in pyridine (200 mL, 70%) was added 2-chloro-7,7-dimethyl-6,7-dihydro-5H-cyclopenta[b]pyridin-4-amine (10.0 g, 50.8 mmol) at 0° C. in portions. The mixture was stirred at 0° C. for 15 min. Then Sodium nitrite (27.0 g, 391.4 mmol) was added in portions at 0° C. The mixture was stirred at 0° C. for 0.5 h, then stirred at 100° C. for additional 0.5 h. The reaction mixture was cooled to 25° C. and quenched with ice and 0.5 N sodium hydroxide solution (200 mL). The resulting mixture was extracted with ethyl acetate (3×300 mL). The combined organic layers were dried over anhydrous sodium sulfate and concentrated under reduced pressure. The residue was applied onto a silica gel column and eluted with EtOAc/PE (1:10) to afford 2-chloro-4-fluoro-7,7-dimethyl-6,7-dihydro-5H-cyclopenta[b]pyridine (6.2 g, 57% yield) as a yellow solid. LC-MS: m/z 200 [M+H]$^+$.

Step 10: 5-bromo-2-chloro-4-fluoro-7,7-dimethyl-6,7-dihydro-5H-cyclopenta[b]pyridine

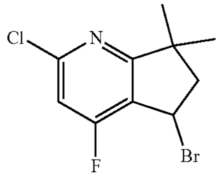

To a stirred solution of 2-chloro-4-fluoro-7,7-dimethyl-6,7-dihydro-5H-cyclopenta[b]pyridine (5.5 g, 27.5 mmol) in 1,2-dichloroethane (50 mL) were added NBS (5.4 g, 30.3 mmol) and AIBN (452 mg, 2.8 mmol). The mixture was stirred at 80° C. for 1 h under nitrogen atmosphere. The mixture was cooled to 25° C. and concentrated under reduced pressure. The residue was applied onto a silica gel column and eluted with EtOAc/PE (1:3) to afford 5-bromo-2-chloro-4-fluoro-7,7-dimethyl-6,7-dihydro-5H-cyclopenta [b]pyridine (6.4 g, 83% yield) as a yellow oil. LC-MS: m/z 278 [M+H]$^+$. 11: 2-chloro-4-fluoro-7,7-dimethyl-6,7-dihydro-5H-cyclopenta[b]pyridine-5-carbonitrile

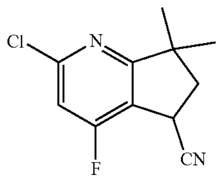

To a stirred solution of 5-bromo-2-chloro-4-fluoro-7,7-dimethyl-6,7-dihydro-5H-cyclopenta[b]pyridine (6.4 g, 23.0 mmol) in THF (40 mL) was added TMSCN (11.4 g, 114.9 mmol) and TBAF (68.9 mL, 1 M in THF). The mixture was stirred at 0° C. for 2 h. The reaction mixture was quenched with water (80 mL). The resulting solution was extracted with ethyl acetate (3×100 mL). The combined organic layers were washed with brine (100 mL), dried over anhydrous sodium sulfate and concentrated under reduced pressure. The residue was applied onto a silica gel column and eluted with EtOAc/PE (1:4) to afford 2-chloro-4-fluoro-7,7-dimethyl-6,7-dihydro-5H-cyclopenta[b]pyridine-5-carbonitrile (3.2 g, 62% yield) as a yellow oil. LC-MS:m/z 225 [M+H]$^+$.

Step 12: 4-fluoro-7,7-dimethyl-2-(2-oxopropyl)-6,7-dihydro-5H-cyclopenta[b]pyridine-5-carbonitrile

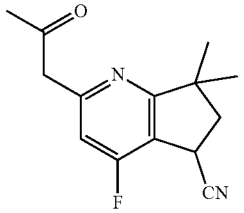 [SMILES: CC(=O)Cc1cc(F)c2c(n1)C(C)(C)CC2C#N]

To a solution of 2-chloro-4-fluoro-7,7-dimethyl-6,7-dihydro-5H-cyclopenta[b]pyridine-5-carbonitrile (2.0 g, 8.9 mmol) in acetone (50 mL) were added potassium phosphate (4.7 g, 22.2 mmol), $Pd(OAc)_2$ (1.4 g, 1.8 mmol) and S-Phos (1.5 g, 3.6 mmol). The mixture was stirred at 90° C. for 2 h under nitrogen atmosphere. After cooled to 25° C., the solid was filtered out. The filtrate was concentrated under reduced pressure. The residue was applied onto a silica gel column and eluted with EtOAc/PE (1:3) to afford 4-fluoro-7,7-dimethyl-2-(2-oxopropyl)-6,7-dihydro-5H-cyclopenta[b] pyridine-5-carbonitrile (1.2 g, 55% yield) as a yellow oil. LC-MS:m/z 247 [M+H]$^+$.

Step 13: 5-fluoro-2,8,8-trimethyl-7,8-dihydro-6H-cyclopenta[e]pyrazolo[1,5-a]pyridine-6-carbonitrile

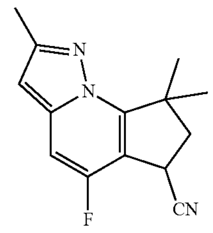

To a stirred solution of ethyl (E)-N-((mesitylsulfonyl)oxy)acetimidate (2.5 g, 8.8 mmol) in dioxane (5 mL) was added perchloric acid (1.7 g, 16.8 mmol, 70%) dropwise at 0° C. under nitrogen atmosphere. The resulting mixture was stirred at 0° C. for 30 min under nitrogen atmosphere. Then water (12 mL) was added dropwise at 0° C. The precipitated solid was collected and diluted with DCM (50 mL). The organic phase was dried over anhydrous sodium sulfate to give a mixture (M1). To a stirred solution of 4-fluoro-7,7-dimethyl-2-(2-oxopropyl)-6,7-dihydro-5H-cyclopenta[b]pyridine-5-carbonitrile (1.2 g, 4.9 mmol) in DCM (20 mL) was added the mixture (M1) dropwise at 0° C. under nitrogen atmosphere. The resulting mixture was stirred at 25° C. for 1 h under nitrogen atmosphere. The resulting mixture was concentrated under reduced pressure. The residue was diluted with MeOH (20 mL). Then $K_2CO_3$ (2.4 g, 17.6 mmol) was added in portions at 0° C. The resulting mixture was stirred at 25° C. for 2 h. The resulting mixture was diluted with water (150 mL). The resulting solution was extracted with ethyl acetate (3×250 mL). The combined organic layers were dried over anhydrous sodium sulfate and concentrated under reduced pressure. The residue was applied onto a silica gel column and eluted with EtOAc/PE (1:10) to afford 5-fluoro-2,8,8-trimethyl-7,8-dihydro-6H-cyclopenta[e]pyrazolo[1,5-a]pyridine-6-carbonitrile (170 mg, 12% yield) as a yellow oil. LC-MS: m/z 244 $[M+H]^+$.

Step 14: 5-fluoro-2,8,8-trimethyl-7,8-dihydro-6H-cyclopenta[e]pyrazolo[1,5-a]pyridine-6-carboxylic acid

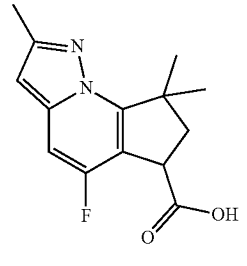 [SMILES: Cc1cc2cc(F)c3c(n2n1)C(C)(C)CC3C(=O)O]

To a stirred solution of 5-fluoro-2,8,8-trimethyl-7,8-dihydro-6H-cyclopenta[e]pyrazolo[1,5-a]pyridine-6-carbonitrile (170 mg, 698.9 μmol) in 12 M HCl (2 mL) and AcOH (2 mL) were stirred at 100° C. for 2 h. The mixture was allowed to cool down to 25° C.

The reaction mixture was diluted with water (20 mL). The resulting solution was extracted with ethyl acetate (3×30 mL). The combined organic layers were dried over anhydrous sodium sulfate and concentrated under reduced pressure to give 5-fluoro-2,8,8-trimethyl-7,8-dihydro-6H-cyclopenta[e]pyrazolo[1,5-a]pyridine-6-carboxylic acid (170 mg, 92% yield) as a purple solid. LC-MS: m/z 263 $[M+H]^+$.

Step 15: N-(5-chloro-6-(2H-1,2,3-triazol-2-yl)pyridin-3-yl)-5-fluoro-2,8,8-trimethyl-7,8-dihydro-6H-cyclopenta[e]pyrazolo[1,5-a]pyridine-6-carboxamide

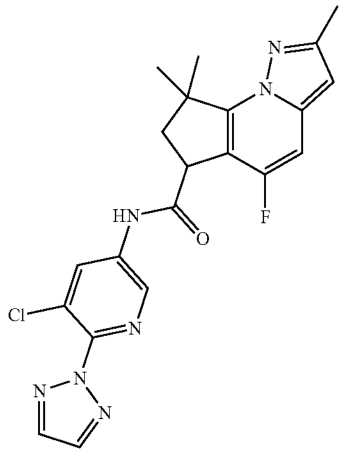

To a stirred solution of 5-fluoro-2,8,8-trimethyl-7,8-dihydro-6H-cyclopenta[e]pyrazolo[1,5-a]pyridine-6-carboxylic acid (170 mg, 648.2 μmol) in DCM (10 mL) was added pyridine (512.7 mg, 6.5 mmol) and phosphoryl trichloride (298 mg, 1.9 mmol) at 0° C. The resulting mixture was stirred at 0° C. for 1 h. 5-chloro-6-(2H-1,2,3-triazol-2-yl)pyridin-3-amine (Method A1 step 2; 316.9 mg, 1.6 mmol) was added, and the resulting mixture was stirred at 25° C. for 3 h. The mixture was concentrated under reduced pressure. The residue was submitted to Prep-HPLC purification and the collected fractions were lyophilized to give N-(5-chloro-6-(2H-1,2,3-triazol-2-yl)pyridin-3-yl)-5-fluoro-2,8,8-trimethyl-7,8-dihydro-6H-cyclopenta[e]pyrazolo[1,5-a]pyridine-6-carboxamide (50 mg, 17% yield) as a white solid. LC-MS: m/z 440 $[M+H]^+$.

Step 16: Separation of Enantiomers to Obtain (R)—N-(5-chloro-6-(2H-1,2,3-triazol-2-yl)pyridin-3-yl)-5-fluoro-2,8,8-trimethyl-7,8-dihydro-6H-cyclopenta[e]pyrazolo[1,5-a]pyridine-6-carboxamide and (S)—N-(5-chloro-6-(2H-1,2,3-triazol-2-yl)pyridin-3-yl)-5-fluoro-2,8,8-trimethyl-7,8-dihydro-6H-cyclopenta[e]pyrazolo[1,5-a]pyridine-6-carboxamide Example 156

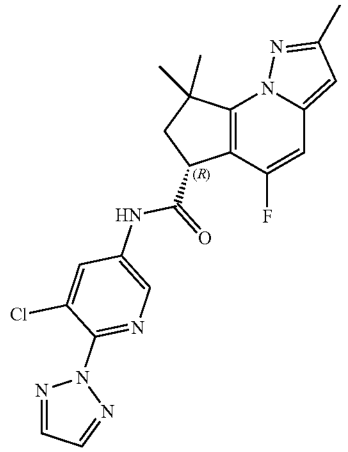

and

-continued

Example 157

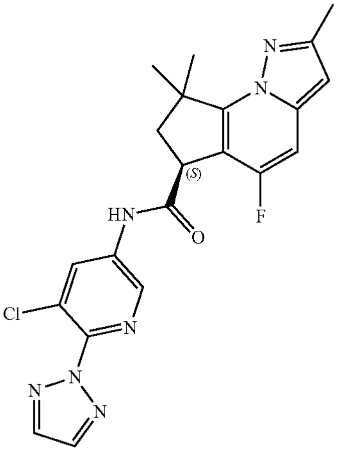

50 mg of N-(5-chloro-6-(2H-1,2,3-triazol-2-yl)pyridin-3-yl)-5-fluoro-2,8,8-trimethyl-7,8-dihydro-6H-cyclopenta[e]pyrazolo[1,5-a]pyridine-6-carboxamide were submitted to chiral HPLC purification (Column: Column: CHIRALPAK IA, 2*25 cm, 20 μm; Mobile Phase A: Hex(0.1% FA)-HPLC, Mobile Phase B: EtOH-HPLC; Flow rate: 20 mL/min; isocratic 50% B in 6.5 min; Wave Length: 220/254 nm; RT1(min): 4.17; RT2(min): 5.51; Sample Solvent: EtOH-HPLC; Injection Volume: 0.3 mL; Number Of Runs: 6). The first eluting isomer was concentrated and lyophilized to afford Example 156 (10.0 mg, 20% yield) as a white solid. The second eluting isomer was concentrated and lyophilized to afford Example 157 (11.5 mg, 23% yield) as a white solid.

Example 156: $^1H$ NMR (400 MHz, DMSO-$d_6$) δ 11.06 (s, 1H), 8.71 (d, J=2.0 Hz, 1H), 8.57 (d, J=2.4 Hz, 1H), 8.17 (s, 2H), 7.31 (d, J=9.6 Hz, 1H), 6.42 (s, 1H), 4.35-4.39 (m, 1H), 2.58-2.59 (m, 1H), 2.41 (s, 3H), 2.24-2.28 (m, 1H), 1.65 (s, 3H), 1.58 (s, 3H). LC-MS: m/z 440.0 $[M+H]^+$.

Example 157: $^1H$ NMR (400 MHz, DMSO-$d_6$) δ 11.06 (s, 1H), 8.71 (d, J=2.4 Hz, 1H), 8.57 (d, J=2.0 Hz, 1H), 8.16 (s, 2H), 7.31 (d, J=9.6 Hz, 1H), 6.42 (s, 1H), 4.35-4.39 (m, 1H), 2.58-2.60 (m, 1H), 2.41 (s, 3H), 2.24-2.28 (m, 1H), 1.65 (s, 3H), 1.57 (s, 3H). LC-MS: m/z 440.0 $[M+H]^+$.

The absolute stereochemistry for each separated isomer was not determined.

Method E4

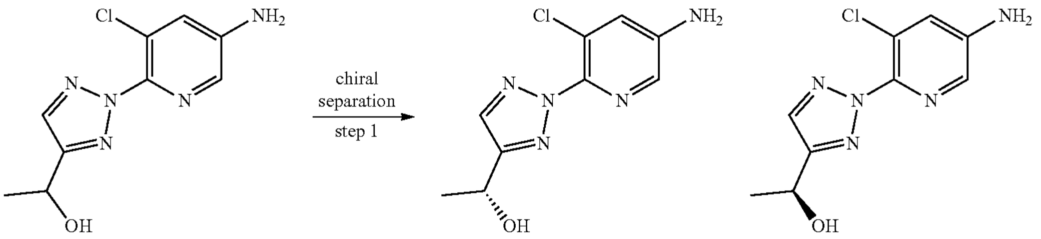

Method Y1 Step 8 — Method E4 Step 1-1 — Method E4 Step 1-2

-continued
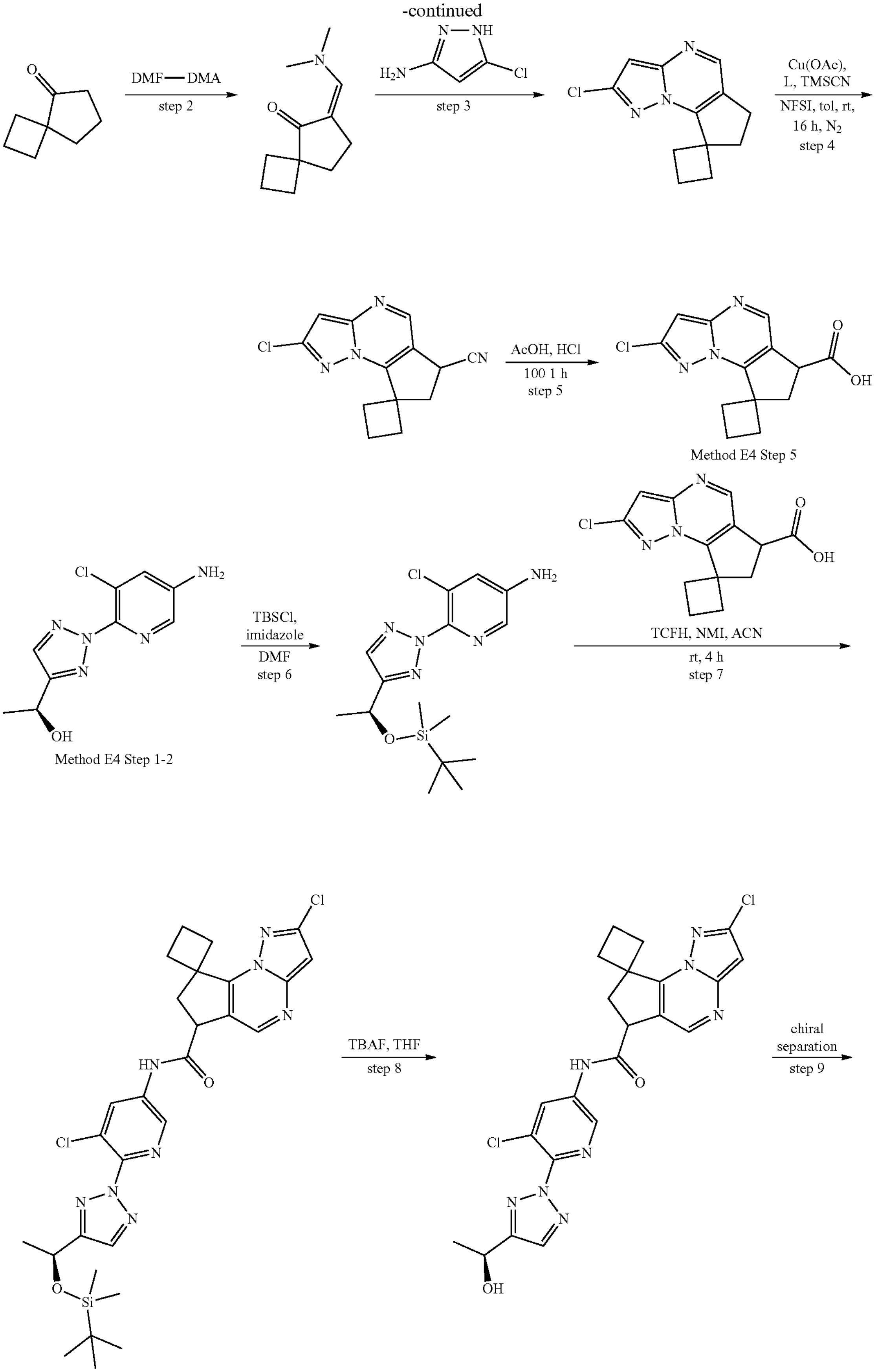

-continued

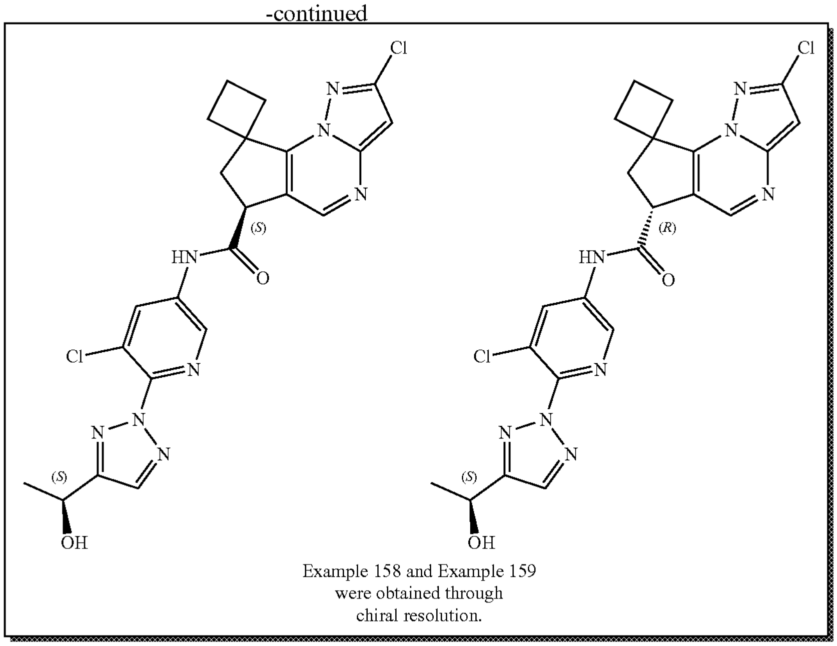

Example 158 and Example 159 were obtained through chiral resolution.

L

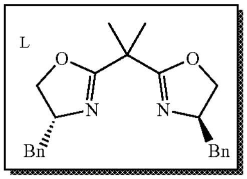

Examples 158 and 159: Single Enantiomers Obtained from a Racemic Mixture Containing (S)-2'-chloro-N-(5-chloro-6-(4-((S)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide and (R)-2'-chloro-N-(5-chloro-6-(4-((S)-1-hydroxyethyl)-2H-1,2,3-triazol-2-yl)pyridin-3-yl)-6',7'-dihydrospiro[cyclobutane-1,8'-cyclopenta[a]pyrazolo[1,5-a]pyrimidine]-6'-carboxamide

Step 1: (R)-1-(2-(5-amino-3-chloropyridin-2-yl)-2H-1,2,3-triazol-4-yl)ethan-1-ol and (5) 1-(2-(5-amino-3-chloropyridin-2-yl)-2H-1,2,3-triazol-4-yl)ethan-1-ol Method E4

Step 1-1

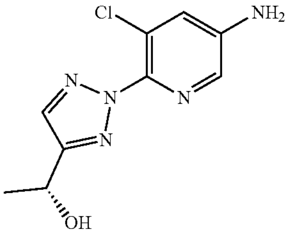

-continued

Method E4

Step 1-2

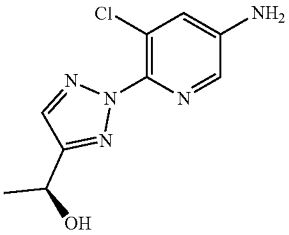

1.1 g of 1-(2-(5-amino-3-chloropyridin-2-yl)-2H-1,2,3-triazol-4-yl)ethan-1-ol (Method Y1 step 8) were submitted to chiral SFC purification (Column: OptiChiral-C9-5, 3*25 cm, 5 μm; Mobile Phase A: $CO_2$, Mobile Phase B: ACN: MEOH=2:1(0.1% 2M NH3·MEOH); Flow rate: 70 mL/min; Gradient: isocratic 50% B; Column Temperature(° C.): 35; Back Pressure(bar): 100; Wave Length: 220 nm; RT1(min): 5.31; RT2(min): 9.03; Sample Solvent: MeOH Preparative; Injection Volume: 4.8 mL; Number Of Runs: 13). The first eluting isomer was concentrated to afford (R)-1-(2-(5-amino-3-chloropyridin-2-yl)-2H-1,2,3-triazol-4-yl)ethan-1-ol (Method E4 step 1-1; 450 mg) as a light yellow oil. LC-MS: m/z 240 $[M+H]^+$. The second eluting isomer was concentrated to afford (5)-1-(2-(5-amino-3-chloropyridin-2-yl)-2H-1,2,3-triazol-4-yl)ethan-1-ol (Method E4 step 1-2; 400 mg) as a light yellow oil. LC-MS: m/z 240 $[M+H]^+$.

The absolute stereochemistry for each separated isomer was not determined.

Step 2: (Z)-6-((dimethylamino)methylene)spiro[3.4]octan-5-one

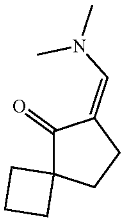

A mixture of spiro[3.4]octan-5-one (5 g, 40.2 mmol) in DMF-DMA (20 mL) was stirred at 100° C. for 16 h. The reaction mixture was concentrated under reduced pressure to afford (Z)-6-((dimethylamino)methylene)spiro[3.4]octan-5-one (7 g, crude) as a yellow solid. LC-MS: m/z 180 $[M+H]^+$.

Step 3: 2'-chloro-6',7'-dihydrospiro[cyclobutane-1,8'-cyclopenta[e]pyrazolo[1,5-a]pyrimidine]

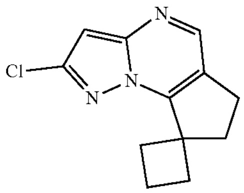 [SMILES: Clc1cc2ncc3c(n2n1)C1(CCC1)CC3]

To a stirred solution of (Z)-6-((dimethylamino)methylene)spiro[3.4]octan-5-one (1 g, 5.5 mmol) in AcOH (20 mL) was added 5-chloro-1H-pyrazol-3-amine (786 mg, 6.6 mmol) at 25° C. The resulting mixture was stirred at 100° C. for 1 h. The mixture was allowed to cool down to 25° C. The resulting mixture was concentrated under reduced pressure. The residue was applied on a silica gel column and eluted with EtOAc/PE (1:2) to give 2'-chloro-6',7'-dihydrospiro[cyclobutane-1,8'-cyclopenta[e]pyrazolo[1,5-a]pyrimidine] (600 mg, 44% yield) as a yellow solid. LC-MS: m/z 234 $[M+H]^+$.

Step 4: 2'-chloro-6',7'-dihydrospiro[cyclobutane-1,8'-cyclopenta[e]pyrazolo[1,5-a]pyrimidine]-6'-carbonitrile

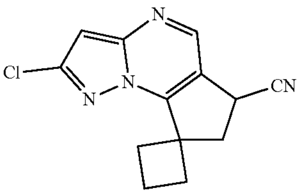 [SMILES: N#CC1CC2(CCC2)c2c1cnc1cc(Cl)nn21]

To a stirred solution of 2'-chloro-6',7'-dihydrospiro[cyclobutane-1,8'-cyclopenta[e]pyrazolo[1,5-a]pyrimidine] (1.0 g, 4.3 mmol) in toluene (200 mL) were added (4R)-4-benzyl-2-[1-[(4R)-4-benzyl-4,5-dihydrooxazol-2-yl]-1-methyl-ethyl]-4,5-dihydrooxazole (230 mg, 641 μmol), acetoxycopper (100 mg, 855 μmol), N-(benzenesulfonyl)-N-fluoro-benzenesulfonamide (2.2 g, 6.4 mmol) and TMSCN (2.1 g, 21.2 mmol). The reaction mixture was stirred at 25° C. for 16 h under nitrogen atmosphere. The resulting mixture was concentrated under reduced pressure. The residue was applied onto a silica gel column and eluted with EtOAc/PE (1:1) to give 2'-chloro-6',7'-dihydrospiro[cyclobutane-1,8'-cyclopenta[e]pyrazolo[1,5-a]pyrimidine]-6'-carbonitrile (320 mg, 30% yield) as a yellow solid. LC-MS (ES, m/z): 259 $[M+H]^+$.

Step 5: 2'-chloro-6',7'-dihydrospiro[cyclobutane-1,8'-cyclopenta[e]pyrazolo[1,5-a]pyrimidine]-6'-carboxylic acid

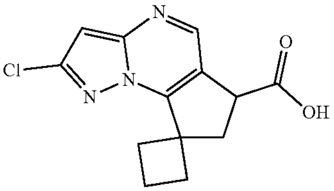 [SMILES: O=C(O)C1CC2(CCC2)c2c1cnc1cc(Cl)nn21]

To a stirred solution of 2'-chloro-6',7'-dihydrospiro[cyclobutane-1,8'-cyclopenta[e]pyrazolo[1,5-a]pyrimidine]-6'-carbonitrile (320 mg, 1.2 mmol) in AcOH (2 mL) was added 12 M HCl (2 mL). The resulting mixture was stirred at 100° C. for 1 h. The mixture was allowed to cool down to 25° C. The resulting mixture was concentrated under reduced pressure. The residue was diluted with water (30 mL). The resulting solution was extracted with ethyl acetate (3×30 mL). The combined organic layers were dried over anhydrous sodium sulfate and concentrated under reduced pressure. The residue was applied onto a silica gel column and eluted with MeOH/DCM (1:10) to give 2'-chloro-6',7'-dihydrospiro[cyclobutane-1,8'-cyclopenta[e]pyrazolo[1,5-a]pyrimidine]-6'-carboxylic acid (150 mg, 45% yield) as a yellow solid.

LC-MS (ES, m/z): 278 $[M+H]^+$.

Step 6: (5)-6-(4-(1-((tert-butyldimethylsilyl)oxy)ethyl)-2H-1,2,3-triazol-2-yl)-5-(trifluoromethyl)pyridin-3-amine

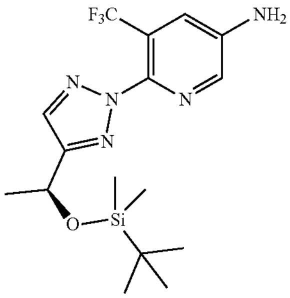 [SMILES: C[C@H](O[Si](C)(C)C(C)(C)C)c1cnn(-c2ncc(N)cc2C(F)(F)F)n1]

To a stirred solution of (S')-1-(2-(5-amino-3-(trifluoromethyl)pyridin-2-yl)-2H-1,2,3-triazol-4-yl)ethan-1-ol (Method E4 step 1-2; 240 mg, 0.6 mmol) in DMF (2 mL) were added TBSCl (108 mg, 0.7 mmol) and imidazole (204 mg, 3.0 mmol). The mixture was stirred at 25° C. for 16 h. The reaction mixture was quenched with water (10 mL). The resulting solution was extracted with ethyl acetate (3×10 mL). The combined organic layers were washed with water (3×10 mL), dried over anhydrous sodium sulfate and concentrated under reduced pressure. The residue was applied onto a silica gel column and eluted with EtOAc/PE (1:2) to give (S)-6-(4-(1-((tert-butyldimethylsilyl)oxy)ethyl)-2H-1,2,3-triazol-2-yl)-5-~(trifluoromethyl)pyridin-3-amine (90 mg, 38% yield) as a light yellow solid. LC-MS: m/z 388 $[M+H]^+$.

Step 7: N-(6-(4-((S)-1-((tert-butyldimethylsilyl)oxy)ethyl)-2H-1,2,3-triazol-2-yl)-5-chloropyridin-3-yl)-2'-chloro-6',7'-dihydrospiro[cyclobutane-1,8'-cyclopenta[e]pyrazolo[1,5-a]pyrimidine]-6'-carboxamide

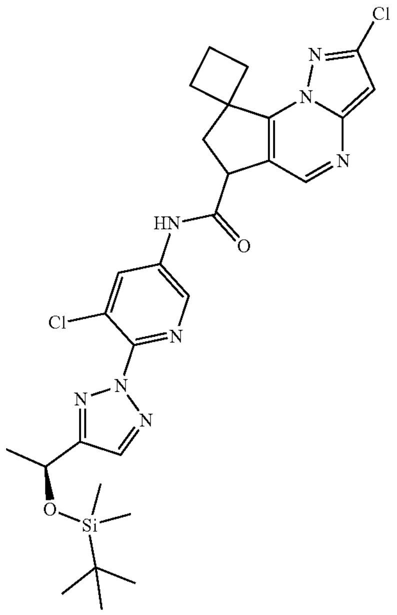 [SMILES: C[C@H](O[Si](C)(C)C(C)(C)C)c1cnn(-c2ncc(NC(=O)C3CC4(CCC4)c4c3cnc3cc(Cl)nn43)cc2Cl)n1]

To a stirred solution of (S)-6-(4-(1-((tert-butyldimethylsilyl)oxy)ethyl)-2H-1,2,3-triazol-2-yl)-5-~(trifluoromethyl)pyridin-3-amine (76 mg, 216.3 μmol) in ACN (10 mL) were added 2'-chloro-6',7'-dihydrospiro[cyclobutane-1,8'-cyclopenta[e]pyrazolo[1,5-a]pyrimidine]-6'-carboxylic acid (60 mg, 216.7 μmol), TCFH (242 mg, 0.8 mmol) and NMI (106 mg, 1.3 mmol). The mixture was stirred at 25° C. for 4 h. The resulting mixture was concentrated under reduced pressure. The residue was submitted to Prep-HPLC purification and the collected fractions were lyophilized to give N-(6-(4-((S)-1-((tert-butyldimethylsilyl)oxy)ethyl)-2H-1,2,3-triazol-2-yl)-5-chloropyridin-3-yl)-2'-chloro-6',7'-dihydrospiro[cyclobutane-1,8'-cyclopenta[e]pyrazolo[1,5-a]pyrimidine]-6'-carboxamide (100 mg, 62% yield) as a white solid. LC-MS: m/z 613 $[M+H]^+$.

Step 8: 2'-chloro-N-(5-chloro-6-(4-((S)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide

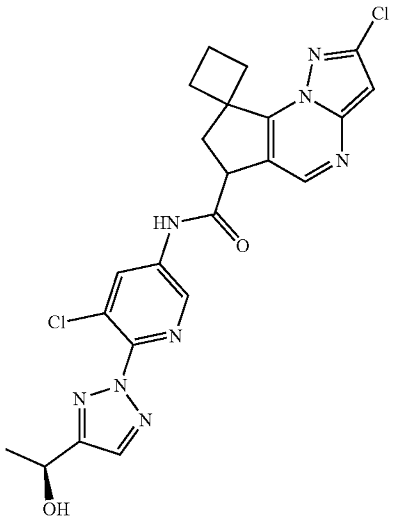 [SMILES: C[C@H](O)c1cnn(-c2ncc(NC(=O)C3CC4(CCC4)c4c3cnc3cc(Cl)nn43)cc2Cl)n1]

To a stirred solution of N-(6-(4-((S)-1-((tert-butyldimethylsilyl)oxy)ethyl)-2H-1,2,3-triazol-2-yl)-5-chloropyridin-3-yl)-2'-chloro-6',7'-dihydrospiro[cyclobutane-1,8'-cyclopenta[e]pyrazolo[1,5-a]pyrimidine]-6'-carboxamide (90 mg, 146.7 μmol) in THF (10 mL) were added TBAF (904 μL, 1M in THF). The mixture was stirred at 25° C. for 2 h. The reaction mixture was diluted with water (100 mL). The resulting solution was extracted with ethyl acetate (2×100 mL). The combined organic layers were dried over anhydrous sodium sulfate and concentrated under reduced pressure. The residue was submitted to Prep-HPLC purification and the collected fractions were lyophilized to give 2'-chloro-N-(5-chloro-6-(4-((S)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide (50 mg, 64% yield) as a white solid. LC-MS: m/z 499 $[M+H]^+$.

Step 9: Separation of Enantiomers to Obtain (S)-2'-chloro-N-(5-chloro-6-(4-((S)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide and (R)-2'-chloro-N-(5-chloro-6-(4-((S)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide Example 158

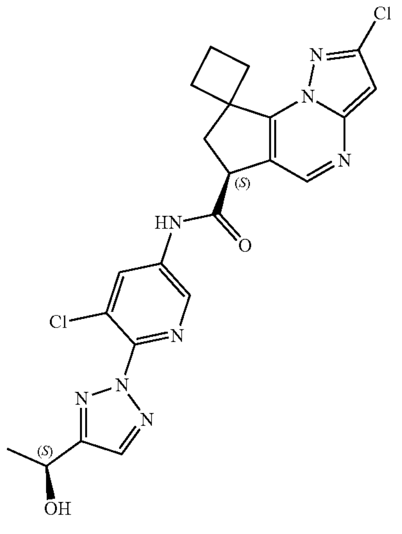

and

-continued

Example 159

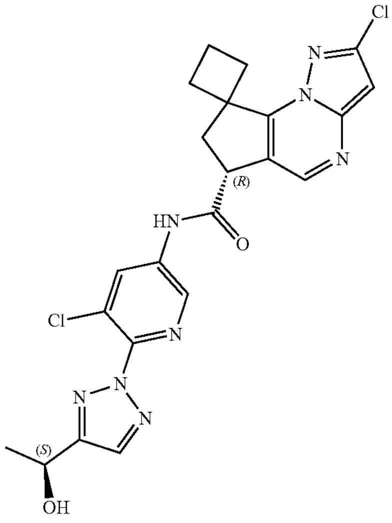

50 mg of 2'-chloro-N-(5-chloro-6-(4-((S)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide were submitted to chiral HPLC purification (Column: CHIRAL ART Cellulose-SC, 2*25 cm, 5 μm; Mobile Phase A: Hex:DCM=3:1(0.5% 2M $NH_3$-MeOH)-HPLC, Mobile Phase B: EtOH-HPLC; Flow rate: 20 mL/min; isocratic 30% B in 17 min; Wave Length: 220/254 nm; RT1(min): 12.07; RT2(min): 15.37; Sample Solvent: ETOH:DCM=1:1; Injection Volume: 1 mL; Number Of Runs: 3). The first eluting isomer was concentrated and lyophilized to afford Example 158 (7.6 mg, 15% yield) as a white solid. The second eluting isomer was concentrated and lyophilized to afford Example 159 (9.9 mg, 19% yield) as a white solid.

Example 158: $^1$H NMR (300 MHz, DMSO-$d_6$) δ: 11.03 (s, 1H), 8.70 (d, J=2.1 Hz, 1H), 8.64 (s, 1H), 8.54 (d, J=2.1 Hz, 1H), 8.02 (s, 1H), 6.97 (s, 1H), 5.52 (d, J=5.1 Hz, 1H), 4.92-4.96 (m, 1H), 4.39 (dd, J=5.1, 8.7 Hz, 1H), 3.12-3.29 (m, 2H), 2.90 (dd, J=8.4, 13.2 Hz, 1H), 2.70 (dd, J=5.4, 13.5 Hz, 1H), 2.00-2.30 (m, 4H), 1.45 (d, J=6.6 Hz, 3H). LC-MS: m/z 499.1 $[M+H]^+$.

Example 159: $^1$H NMR (300 MHz, DMSO-$d_6$) δ: 11.04 (s, 1H), 8.70 (d, J=2.4 Hz, 1H), 8.64 (s, 1H), 8.54 (d, J=2.4 Hz, 1H), 8.02 (s, 1H), 6.97 (s, 1H), 5.52 (d, J=5.1 Hz, 1H), 4.92-4.96 (m, 1H), 4.39 (dd, J=5.1, 8.7 Hz, 1H), 3.12-3.21 (m, 2H), 2.90 (dd, J=8.7, 13.5 Hz, 1H), 2.72 (dd, J=5.4, 13.5 Hz, 1H), 2.00-2.30 (m, 4H), 1.46 (d, J=6.6 Hz, 3H). LC-MS: m/z 499.1 $[M+H]^+$.

The absolute stereochemistry for each separated isomer was not determined.

Method F4
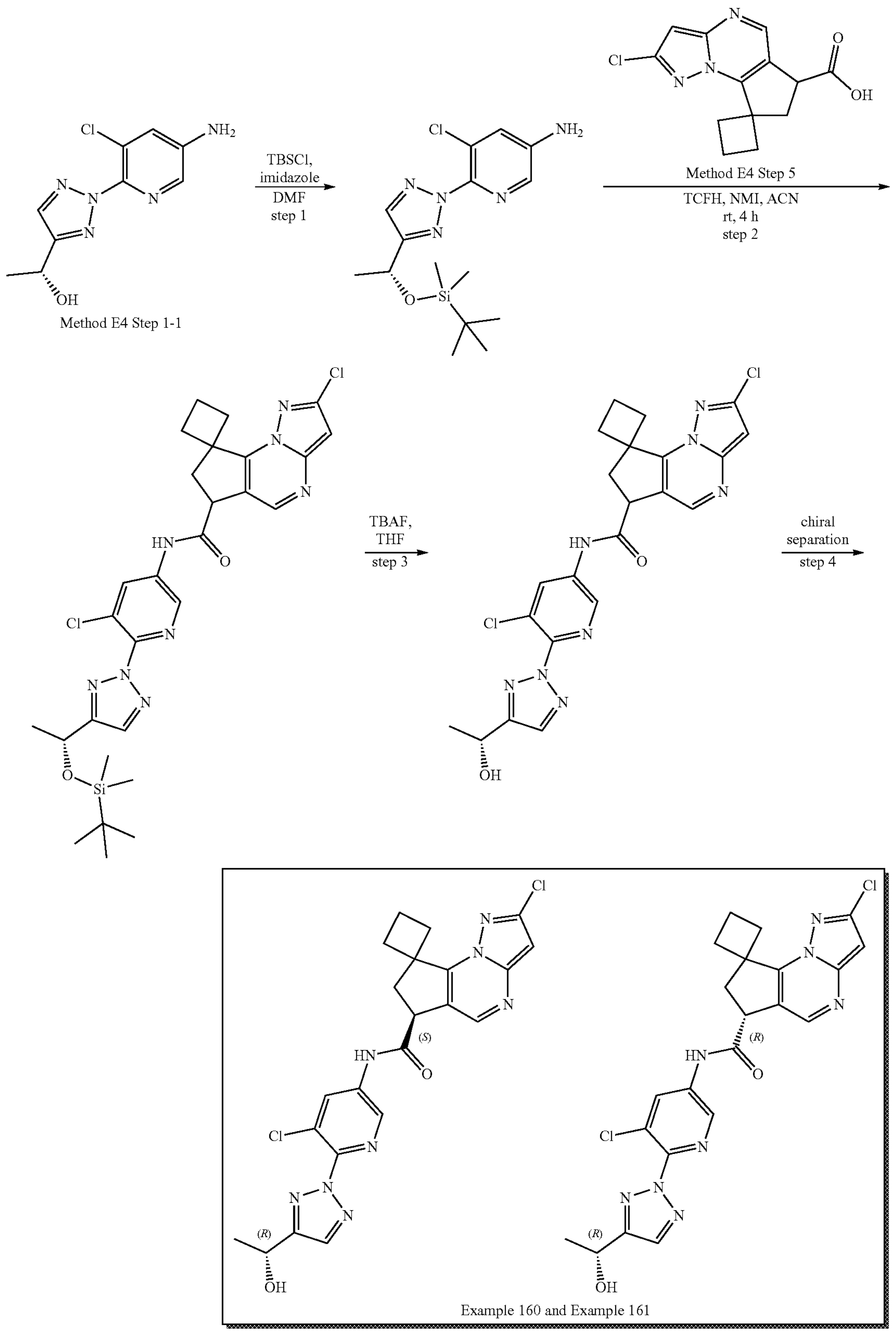
Example 160 and Example 161

Examples 160 and 161: Single Enantiomers Obtained from a Racemic Mixture Containing (S)-2'-chloro-N-(5-chloro-6-(4-((R)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide and (R)-2'-chloro-N-(5-chloro-6-(4-((R)-1-hydroxyethyl)-2H-1,2,3-triazol-2-yl)pyridin-3-yl)-6',7'-dihydrospiro[cyclobutane-1,8'-cyclopenta[e]pyrazolo[1,5-a]pyrimidine]-6'-carboxamide The title compounds were synthesized similarly to Example 158 and 159 using (R)-1-(2-(5-amino-3-(trifluoromethyl)pyridin-2-yl)-2H-1,2,3-triazol-4-yl)ethan-1-ol (Method E4 step 1-1). The final compounds were purified by chiral HPLC (Column: CHIRAL ART Cellulose-SC, 2*25 cm, 5 μm; Mobile Phase A: Hex(0.1% FA)-HPLC, Mobile Phase B: EtOH-HPLC; Flow rate: 20 mL/min; isocratic 50% B in 16.5 min; Wave Length: 254/220 nm; RT1(min): 11.46; RT2(min): 14.74; Sample Solvent: EtOH-HPLC; Injection Volume: 0.8 mL; Number Of Runs: 3). The first eluting isomer was concentrated and lyophilized to afford Example 160 (9.8 mg, 38.8% yield) as a white solid. The second eluting isomer was concentrated and lyophilized to afford Example 161 (6 mg, 23.8% yield) as a white solid.

Example 160: $^1$H NMR (400 MHz, DMSO-$d_6$) δ: 11.05 (s, 1H), 8.70 (d, J=2.4 Hz, 1H), 8.65 (s, 1H), 8.54 (d, J=2.4 Hz, 1H), 8.02 (s, 1H), 6.97 (s, 1H), 5.53 (br, 1H), 4.92-4.97 (m, 1H), 4.40 (dd, J=5.2, 8.8 Hz, 1H), 3.10-3.21 (m, 2H), 2.90 (dd, J=8.8, 13.2 Hz, 1H), 2.70 (dd, J=5.2, 13.2 Hz, 1H), 2.20-2.22 (m, 4H), 1.45 (d, J=6.8 Hz, 3H). LC-MS: m/z 499.1 $[M+H]^+$.

Example 161: $^1$H NMR (400 MHz, DMSO-$d_6$) δ: 11.05 (s, 1H), 8.70 (d, J=2.4 Hz, 1H), 8.65 (s, 1H), 8.54 (d, J=2.4 Hz, 1H), 8.03 (s, 1H), 6.97 (s, 1H), 5.53 (br, 1H), 4.92-4.98 (m, 1H), 4.40 (dd, J=5.2, 8.8 Hz, 1H), 3.10-3.21 (m, 2H), 2.90 (dd, J=8.8, 13.2 Hz, 1H), 2.70 (dd, J=5.2, 13.2 Hz, 1H), 2.20-2.22 (m, 4H), 1.45 (d, J=6.4 Hz, 3H). LC-MS: m/z 499.1 $[M+H]^+$.

The absolute stereochemistry for each separated isomer was not determined.

Method G4

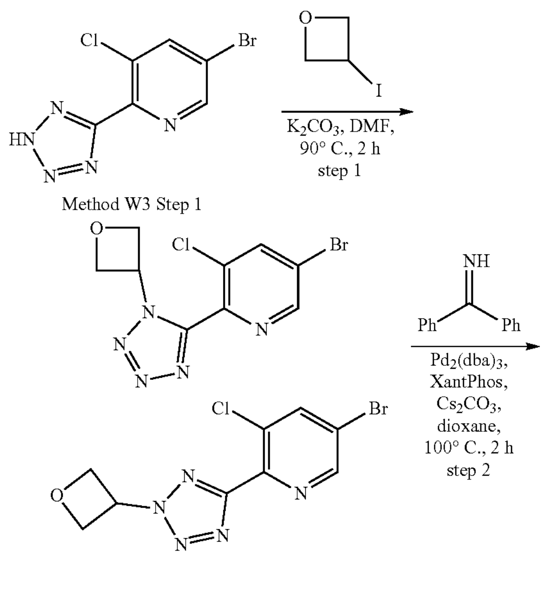

-continued

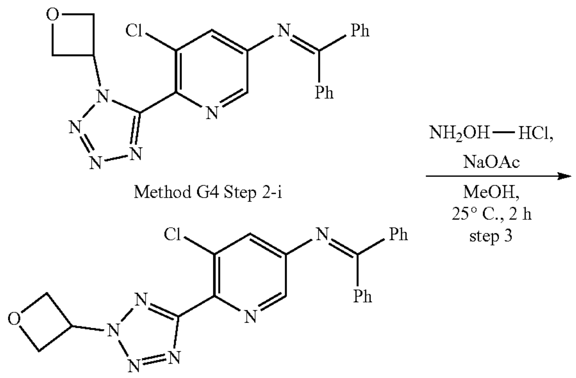

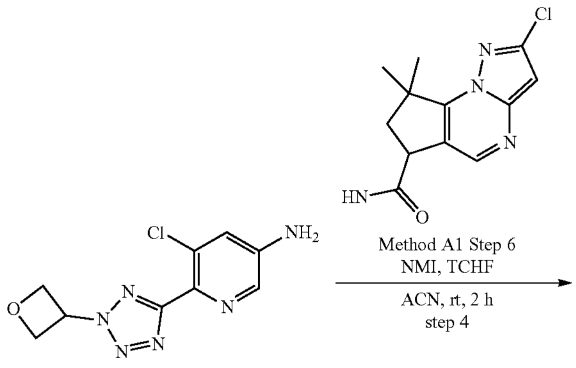

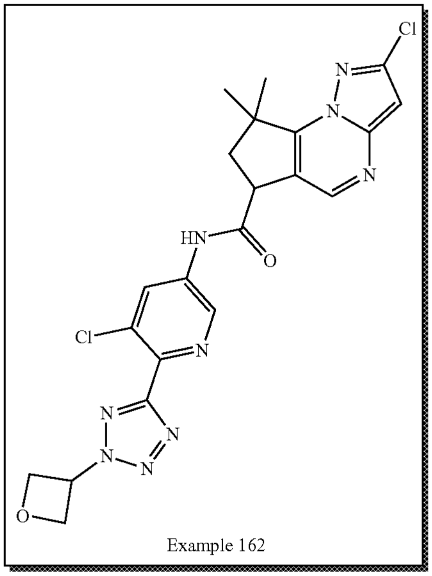

Example 162

Example 162: 2-chloro-N-(5-chloro-6-(2-(oxetan-3-yl)-2H-tetrazol-5-yl)pyridin-3-yl)-8,8-dimethyl-7,8-dihydro-6H-cyclopenta[e]pyrazolo[1,5-a]pyrimidine-6-carboxamide Step 1: mixture of 5-bromo-3-chloro-2-(2-(oxetan-3-yl)-2H-tetrazol-5-yl)pyridine and 5-bromo-3-chloro-2-(1-(oxetan-3-yl)-1H-tetrazol-5-yl)pyridine

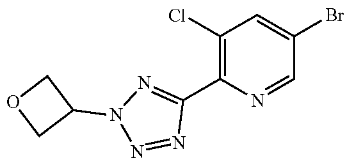

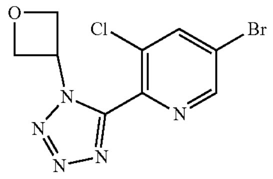

To a stirred solution of 5-bromo-3-chloro-2-(2H-tetrazol-5-yl)pyridine (Method W3 step 1; 1.0 g, 3.8 mmol) in DMF (10 mL) were added 3-iodooxetane (1.4 g, 7.6 mmol) and $K_2CO_3$ (1.1 g, 7.6 mmol). The mixture was stirred at 90° C. for 2 h. The mixture was cooled to 25° C. The reaction mixture was diluted with water (50 mL). The resulting solution was extracted with ethyl acetate (3×50 mL). The combined organic layers were washed with water (3×50 mL), dried over anhydrous sodium sulfate and concentrated under reduced pressure. The residue was applied on a silica gel column and eluted with EtOAc/PE (1:1) to give a mixture of 5-bromo-3-chloro-2-(2-(oxetan-3-yl)-2H-tetrazol-5-yl)pyridine and 5-bromo-3-chloro-2-(1-(oxetan-3-yl)-1H-tetrazol-5-yl)pyridine (600 mg, 50% yield) as a white solid. LC-MS: m/z 316 $[M+H]^+$.

Step 2: N-(5-chloro-6-(2-(oxetan-3-yl)-2H-tetrazol-5-yl)pyridin-3-yl)-1,1-diphenylmethanimine and N-(5-chloro-6-(1-(oxetan-3-yl)-1H-tetrazol-5-yl)pyridin-3-yl)-1,1-diphenylmethanimine

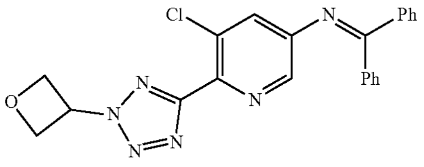

-continued

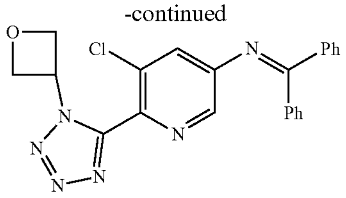

To a stirred solution of a mixture of 5-bromo-3-chloro-2-(2-(oxetan-3-yl)-2H-tetrazol-5-yl)pyridine and 5-bromo-3-chloro-2-(1-(oxetan-3-yl)-1H-tetrazol-5-yl)pyridine (600 mg, 1.9 mmol) in dioxane (20 mL) were added diphenylmethanimine (688 mg, 3.8 mmol), $Cs_2CO_3$ (1.2 g, 3.8 mmol), XantPhos (439 mg, 0.8 mmol) and $Pd_2(dba)_3$ (393 mg, 0.4 mmol). The mixture was stirred at 100° C. for 2 h under nitrogen atmosphere. The reaction mixture was cooled to 25° C. and quenched with water (50 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:2) to give N-(5-chloro-6-(2-(oxetan-3-yl)-2H-tetrazol-5-yl)pyridin-3-yl)-1,1-diphenylmethanimine (280 mg, 18% yield) as a yellow oil and N-(5-chloro-6-(1-(oxetan-3-yl)-1H-tetrazol-5-yl)pyridin-3-yl)-1,1-diphenylmethanimine (Method G4 step 2-i; 120 mg, 15% yield) as a yellow oil. LC-MS: m/z 417 $[M+H]^+$.

Step 3: 5-chloro-6-(2-(oxetan-3-yl)-2H-tetrazol-5-yl)pyridin-3-amine

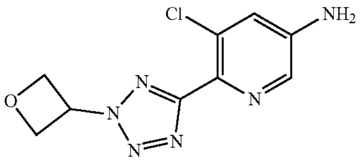 [SMILES: Nc1cnc(-c2nnn(C3COC3)n2)c(Cl)c1]

To a stirred solution of N-(5-chloro-6-(2-(oxetan-3-yl)-2H-tetrazol-5-yl)pyridin-3-yl)-1,1-diphenylmethanimine (280 mg, 671 μmol) in MeOH (10 mL) were added hydroxylamine hydrochloride (93 mg, 1.3 mmol) and sodium acetate (107 mg, 1.3 mmol). The mixture was stirred at 25° C. for 2 h. The reaction mixture was quenched with water (30 mL). The resulting solution was extracted with ethyl acetate (3×30 mL). The combined organic layers were dried over anhydrous sodium sulfate and concentrated under reduced pressure. The residue was applied onto a silica gel column and eluted with EtOAc/PE (1:1) to give 5-chloro-6-(2-(oxetan-3-yl)-2H-tetrazol-5-yl)pyridin-3-amine (100 mg, 59% yield) as a white solid. $^1H$ NMR (400 MHz, DMSO-$d_6$) δ 8.02 (d, J=2.4 Hz, 1H), 7.11 (d, J=2.4 Hz, 1H), 6.18-6.25 (m, 1H), 6.15 (s, 2H), 5.05-5.13 (m, 2H), 4.95-5.00 (m, 2H). LC-MS: m/z 253 $[M+H]^+$.

Step 4: 2-chloro-N-(5-chloro-6-(2-(oxetan-3-yl)-2H-tetrazol-5-yl)pyridin-3-yl)-8,8-dimethyl-7,8-dihydro-6H-cyclopenta[e]pyrazolo[1,5-a]pyrimidine-6-carboxamide Example 162

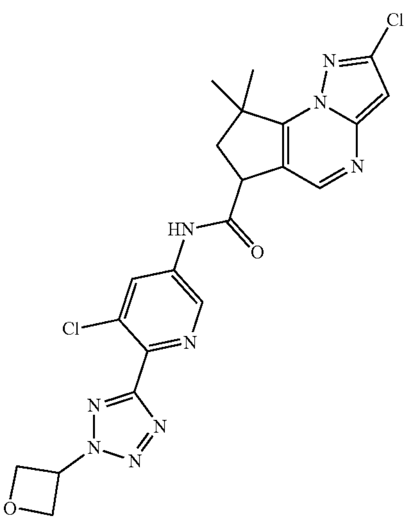

To a solution of 5-chloro-6-(2-(oxetan-3-yl)-2H-tetrazol-5-yl)pyridin-3-amine (100 mg, 395 μmol) in ACN (10 mL) were added 2-chloro-8,8-dimethyl-7,8-dihydro-6H-cyclopenta[e]pyrazolo[1,5-a]pyrimidine-6-carboxylic acid (Method A1 step 6; 104 mg, 395 μmol) TCFH (442 mg, 1.6 mmol) and NMI (131 mg, 1.6 mmol). The resulting mixture was stirred at 25° C. for 2 h. The reaction mixture was concentrated under reduced pressure. The residue was submitted to Prep-HPLC purification and the collected fractions were lyophilized to give Example 162 (2.4 mg, 1% yield) as a white solid.

Example 162: $^1$H NMR (400 MHz, DMSO-$d_6$) δ 11.04 (s, 1H), 8.88 (d, J=2.2 Hz, 1H), 8.65 (s, 1H), 8.53 (d, J=2.2 Hz, 1H), 6.95 (s, 1H), 6.26-6.53 (m, 1H), 5.13-5.14 (m, 2H), 4.99-5.01 (m, 2H), 4.44-4.47 (m, 1H), 2.58-2.67 (m, 1H), 2.31-2.34 (m, 1H), 1.64 (s, 3H), 1.56 (s, 3H). LC-MS: m/z 500.0 [M+H]$^+$.

Method 114

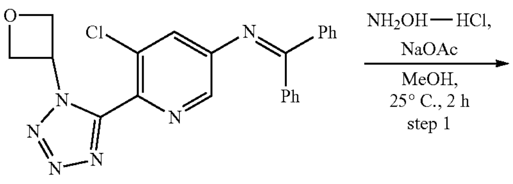

Method G4 Step 2-i

-continued

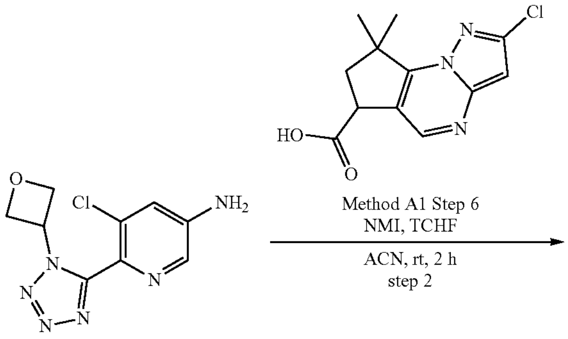

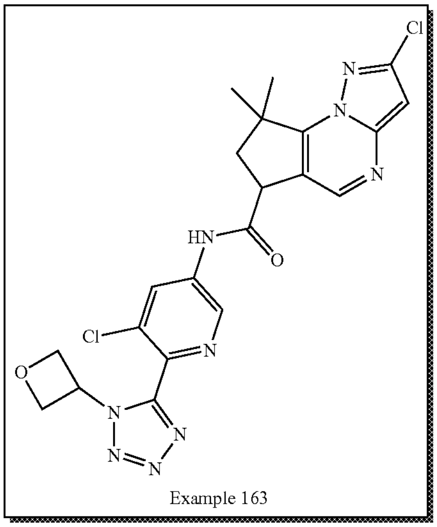

Example 163

Example 163: 2-chloro-N-(5-chloro-6-(1-(oxetan-3-yl)-1H-tetrazol-5-yl)pyridin-3-yl)-8,8-dimethyl-7,8-dihydro-6H-cyclopenta[e]pyrazolo[1,5-a]pyrimidine-6-carboxamide The title compound was synthesized similarly to Example 162 using N-(5-chloro-6-(1-(oxetan-3-yl)-1H-tetrazol-5-yl)pyridin-3-yl)-1,1-diphenylmethanimine (Method G4 step 2-i).

Example 163: $^1$H NMR (400 MHz, DMSO-$d_6$) δ 11.10 (s, 1H), 8.89 (d, J=2.0 Hz, 1H), 8.64 (s, 1H), 8.53 (d, J=2.0 Hz, 1H), 6.95 (s, 1H), 5.85-5.90 (m, 1H), 4.98-4.99 (m, 4H), 4.44-4.48 (m, 1H), 2.55-2.60 (m, 1H), 2.11-2.34 (m, 1H), 1.64 (s, 3H), 1.56 (s, 3H). LC-MS: m/z 500.0 [M+H]$^+$.

Method I4

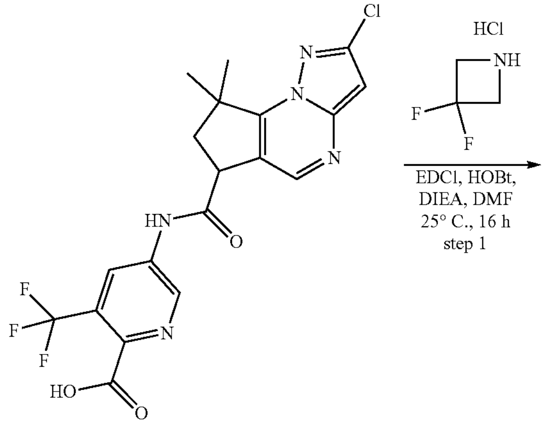

Method E3 Step 4

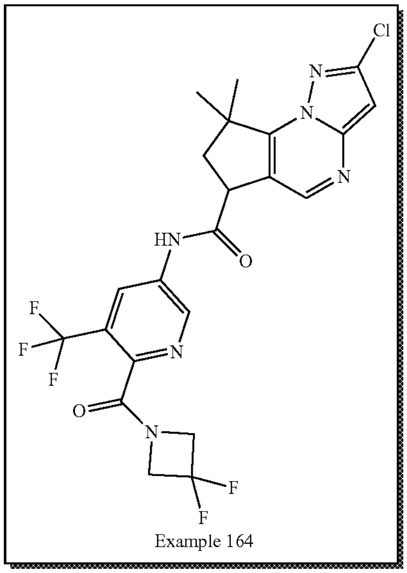

Example 164

Example 164: 2-chloro-N-(6-(3,3-difluoroazetidine-1-carbonyl)-5~(trifluoromethyl)pyridin-3-yl)-8,8-dimethyl-7,8-dihydro-6H-cyclopenta[e]pyrazolo[1,5-a]pyrimidine-6-carboxamide Step 1: 2-chloro-N-(6-(3,3-difluoroazetidine-1-carbonyl)-5~(trifluoromethyl)pyridin-3-yl)-8,8-dimethyl-7,8-dihydro-6H-cyclopenta[e]pyrazolo[1,5-a]pyrimidine-6-carboxamide Example 164

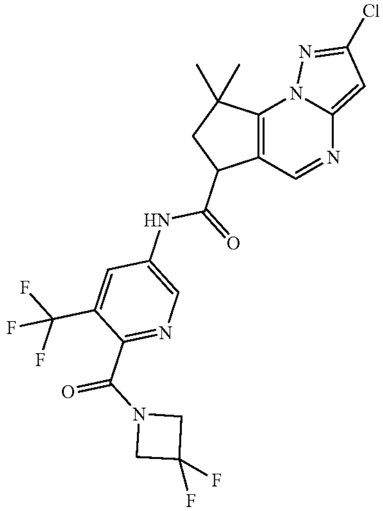

To a solution of 5~(2-chloro-8,8-dimethyl-7,8-dihydro-6H-cyclopenta[e]pyrazolo[1,5-a]pyrimidine-6-carboxamido)-3-(trifluoromethyl)picolinic acid (Method E3 step 4; 30 mg, 66.1 μmol) in DMF (0.5 mL) were added 3,3-difluoroazetidine hydrogen chloride salt (10 mg, 79.3 μmol) EDCI (19 mg, 99.2 μmol), HOBT (13 mg, 99.2 μmol) and DIEA (43 mg, 330.5 μmol). The resulting mixture was stirred at 25° C. for 16 h. The reaction mixture was concentrated under reduced pressure. The residue was submitted to Prep-HPLC purification and the collected fractions were lyophilized to give Example 164 (4.1 mg, 12% yield) as a yellow solid.

Example 164: $^1$H NMR (400 MHz, DMSO-$d_6$) δ: 11.12 (s, 1H), 9.01 (d, J=2.4 Hz, 1H), 8.65 (s, 1H), 8.63 (d, J=2.0 Hz, 1H), 6.95 (s, 1H), 4.53-4.63 (m, 4H), 4.45 (dd, J=6.0, 9.2 Hz, 1H), 2.52-2.59 (m, 1H), 2.32 (dd, J=6.4, 13.2 Hz, 1H), 1.63 (s, 3H), 1.56 (s, 3H). LC-MS: m/z 529.1 $[M+H]^+$.

Method J4

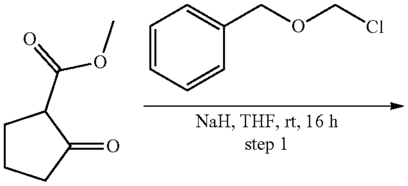

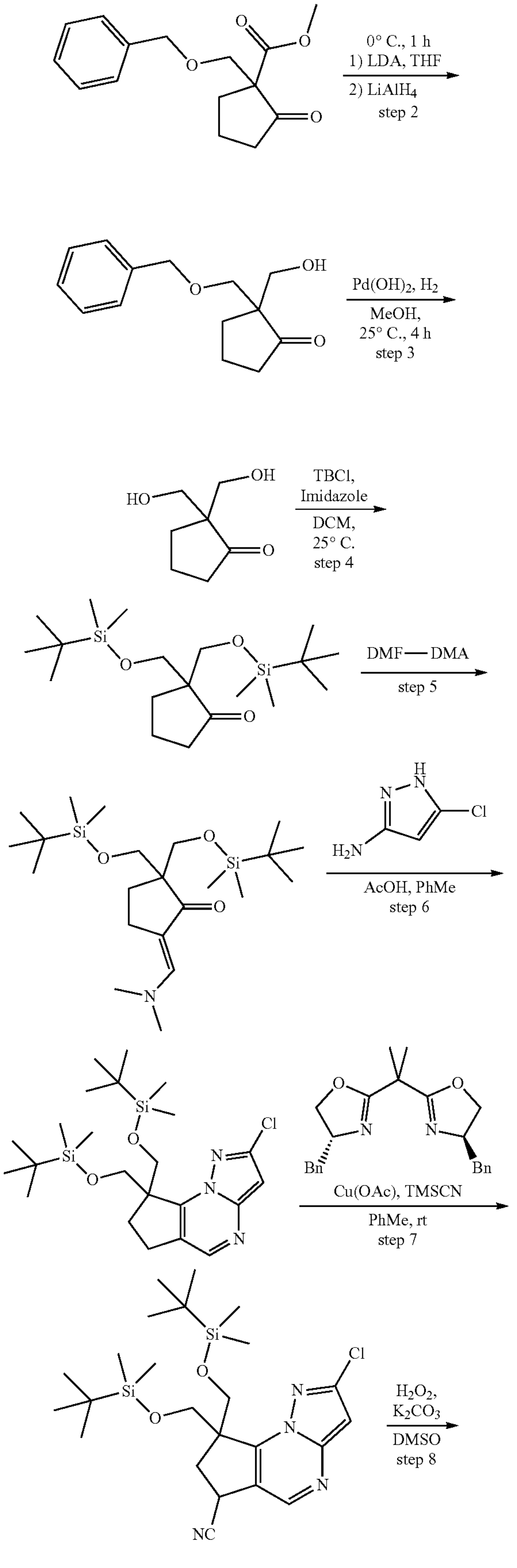
0° C., 1 h
1) LDA, THF
2) $LiAlH_4$
step 2
$Pd(OH)_2$, $H_2$
MeOH,
25° C., 4 h
step 3
TBCl,
Imidazole
DCM,
25° C.
step 4
DMF—DMA
step 5
AcOH, PhMe
step 6
Cu(OAc), TMSCN
PhMe, rt
step 7
$H_2O_2$,
$K_2CO_3$
DMSO
step 8
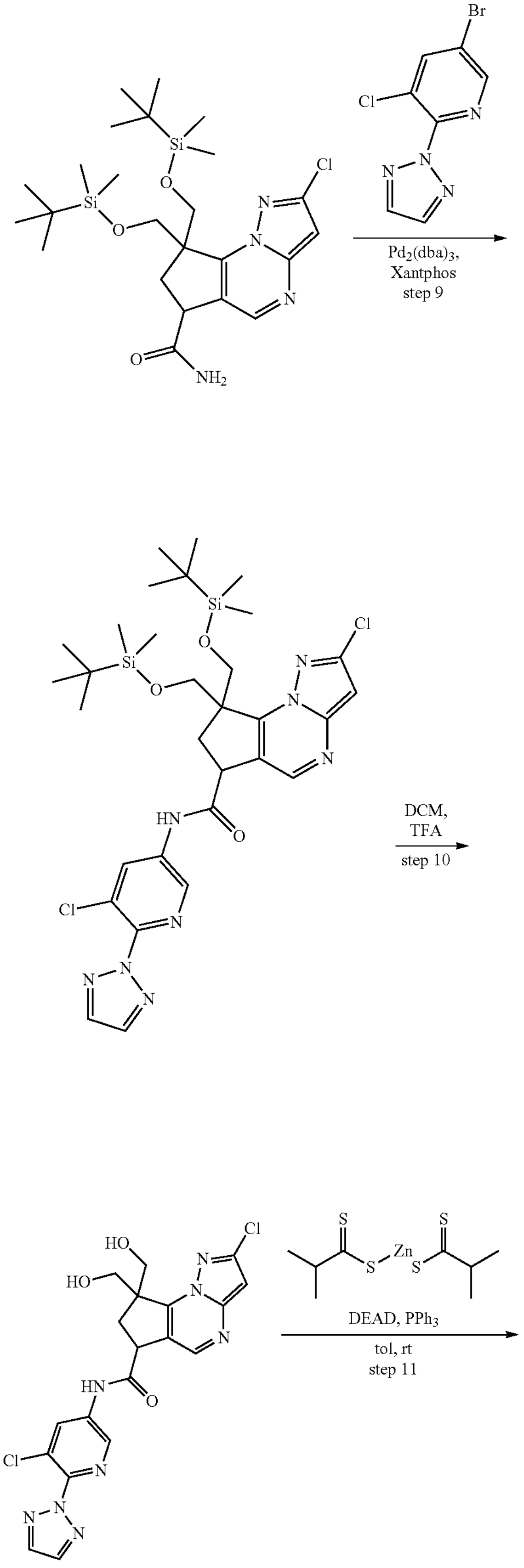
$Pd_2(dba)_3$,
Xantphos
step 9
DCM,
TFA
step 10
DEAD, $PPh_3$
tol, rt
step 11

-continued

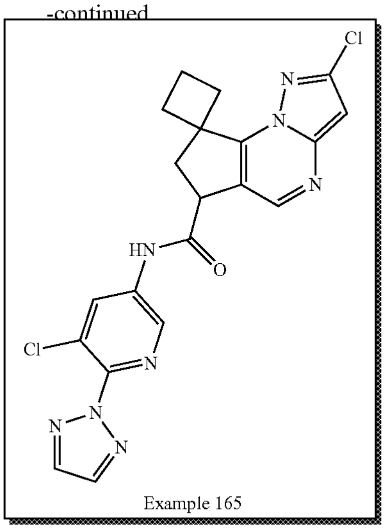

Example 165

Examples 165: 2-chloro-N-(5-chloro-6-(2H-1,2,3-triazol-2-yl)pyridin-3-yl)-6,7-dihydrospiro[cyclopenta[e]pyrazolo[1,5-a]pyrimidine-8,3'-oxetane]-6-carboxamide Step 1: methyl 1-((benzyloxy)methyl)-2-oxocyclopentane-1-carboxylate

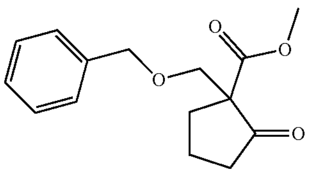 [SMILES: COC(=O)C1(COCc2ccccc2)CCCC1=O]

To a stirred solution of methyl 2-oxocyclopentane-1-carboxylate (20 g, 140.8 mmol) in THF (200 mL) was added NaH (6.8 g, 169.1 mmol, 60% in mineral oil) in portions at 0° C. The mixture was stirred at 25° C. for 1 h. ((Chloromethoxy)methyl)benzene (26.4 g, 169.1 mmol) was added dropwise at 0° C., and the resulting mixture was stirred at 25° C. for 16 h. The reaction mixture was quenched with water (500 mL) and extracted with ethyl acetate (3×500 mL). The combined organic layers were washed with brine (600 mL), dried over anhydrous sodium sulfate and concentrated under reduced pressure. The residue was applied onto a silica gel column and eluted with EtOAc/PE (1:3) to give methyl 1-((benzyloxy)methyl)-2-oxocyclopentane-1-carboxylate (15 g, 40% yield) as a yellow oil. LC-MS (ES, m/z): 263 $[M+H]^+$.

Step 2: 2-((benzyloxy)methyl)-2-(hydroxymethyl) cyclopentan-1-one

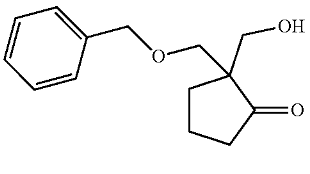 [SMILES: O=C1CCCC1(CO)COCc1ccccc1]

To a stirred mixture of methyl 1-((benzyloxy)methyl)-2-oxocyclopentane-1-carboxylate (20 g, 76.3 mmol) in THF (200 mL) was added LDA (45.8 mL, 91.6 mmol, 2 M in THF) dropwise at 0° C., and it was stirred at 0° C. for 1 h. Lithium Aluminum Hydride (4.4 g, 115.8 mmol) was added in portions, and the reaction mixture was stirred at 25° C. for 2 h. The reaction mixture was quenched with ice water (500 mL) and extracted with ethyl acetate (2×500 mL). The combined organic layers were dried over anhydrous sodium sulfate and concentrated under reduced pressure. The combined organic layers were washed with brine (700 mL), dried over anhydrous sodium sulfate and concentrated under reduced pressure. The residue was applied onto a silica gel column and eluted with EtOAc/PE (1:1) to give 2-((benzyloxy)methyl)-2-(hydroxymethyl)cyclopentan-1-one (12 g, 67% yield) as yellow oil. LC-MS: m/z 235 $[M+H]^+$.

Step 3: 2,2-bis(hydroxymethyl)cyclopentan-1-one

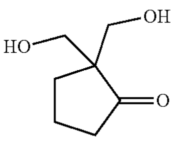

To a mixture of 2-((benzyloxy)methyl)-2-(hydroxymethyl)cyclopentan-1-one (12 g, 51.3 mmol) in MeOH (350 mL) was added $Pd(OH)_2$ on carbon (4 g, 10%). The resulting mixture was stirred at 25° C. for 4 h under hydrogen atmosphere. The solids were filtered out and the filtrate was concentrated under reduced pressure. The residue was applied onto a silica gel column and eluted with MeOH/DCM (1:10) to give 2,2-bis(hydroxymethyl)cyclopentan-1-one (4 g, 54% yield) as a yellow oil. LC-MS: m/z 145 $[M+H]^+$.

Step 4: 2,2-bis(((tert-butyl dimethyl silyl)oxy)methyl)cyclopentan-1-one

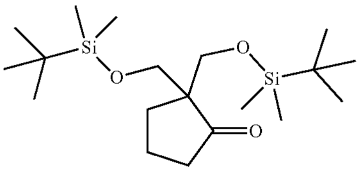 [SMILES: CC(C)(C)[Si](C)(C)OCC1(CO[Si](C)(C)C(C)(C)C)CCCC1=O]

To a stirred solution of 2,2-bis(hydroxymethyl)cyclopentan-1-one (4 g, 27.8 mmol) in DCM (100 mL) were added TBSCl (10.5 g, 69.5 mmol) and imidazole (5.7 g, 83.4 mmol). The mixture was stirred at 25° C. for 16 h. The reaction mixture was quenched with water (300 mL) and extracted with DCM (2×300 mL). The combined organic layers were dried over anhydrous sodium sulfate and concentrated under reduced pressure. The residue was applied onto a silica gel column and eluted with EtOAc/PE (1:10) to give 2,2-bis(((tert-butyldimethylsilyl)oxy)methyl)cyclopentan-1-one (7.5 g, 72% yield) as a light yellow oil. LC-MS: m/z 373 $[M+H]^+$.

Step 5: (E)-2,2-bis(((tert-butyldimethylsilyl)oxy) methyl)-5-((dimethylamino)methylene)cyclopentan-1-one

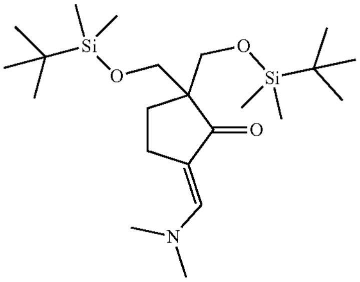 [SMILES: CN(C)/C=C1\CCC(CO[Si](C)(C)C(C)(C)C)(CO[Si](C)(C)C(C)(C)C)C1=O]

A solution of 2,2-bis(((tert-butyldimethylsilyl)oxy) methyl)cyclopentan-1-one (7.5 g, 20.1 mmol) in DMF-DMA (60 mL) was stirred at 100° C. for 16 h. The mixture was allowed to cool down to 25° C. and concentrated under reduced pressure. The residue was applied onto a silica gel column and eluted with EtOAc/PE (1:10) to give (E)-2,2-bis(((tert-butyldimethylsilyl)oxy)methyl)-5-((dimethylamino)methylene)cyclopentan-1-one (6 g, 70% yield) as a yellow oil. LC-MS: m/z 428 $[M+H]^+$.

Step 6: 8,8-bis(((tert-butyldimethylsilyl)oxy) methyl)-2-chloro-7,8-dihydro-6H-cyclopenta[e]pyrazolo[1,5-a]pyrimidine

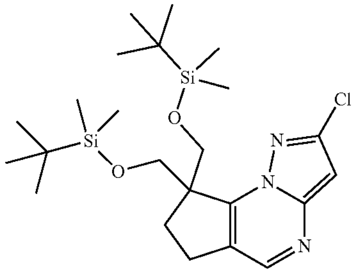 [SMILES: CC(C)(C)[Si](C)(C)OCC1(CO[Si](C)(C)C(C)(C)C)CCc2cnc3cc(Cl)nn3c21]

To a stirred solution of (E)-2,2-bis(((tert-butyldimethylsilyl)oxy)methyl)-5-((dimethylamino)methylene)cyclopentan-1-one (6 g, 14.1 mmol) in toluene (50 mL) was added 5-chloro-1H-pyrazol-3-amine (1.7 g, 14.1 mmol) and AcOH (5 mL) at 25° C. The resulting mixture was stirred at 95° C. for 16 h. The mixture was allowed to cool down to 25° C. The reaction mixture was concentrated under reduced pressure. The residue was applied on a silica gel column and eluted with EtOAc/PE (1:5) to give 8,8-bis(((tert-butyldimethylsilyl)oxy)methyl)-2-chloro-7,8-dihydro-6H-cyclopenta[e]pyrazolo[1,5-a]pyrimidine (5.3 g, 78% yield) as a yellow oil. $^1H$ NMR (300 MHz, DMSO-$d_6$) δ: 8.64 (s, 1H), 6.94 (s, 1H), 4.46 (d, J=9.6 Hz, 2H), 3.89 (d, J=9.6 Hz, 2H), 3.05-3.14 (m, 2H), 2.43-2.51 (m, 2H), 0.85 (s, 18H), 0.05 (s, 6H), 0.21 (s, 6H). LC-MS (ES, m/z):482 $[M+H]^+$.

Step 7: 8,8-bis(((tert-butyldimethylsilyl)oxy) methyl)-2-chloro-7,8-dihydro-6H-cyclopenta[e]pyrazolo[1,5-a]pyrimidine-6-carbonitrile

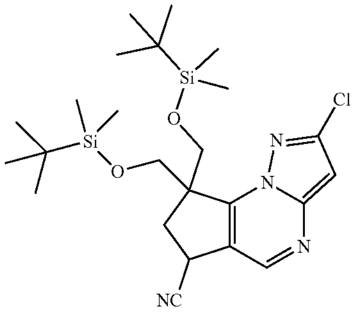 [SMILES: CC(C)(C)[Si](C)(C)OCC1(CO[Si](C)(C)C(C)(C)C)CC(C#N)c2cnc3cc(Cl)nn3c21]

To a stirred solution of 8,8-bis(((tert-butyldimethylsilyl) oxy)methyl)-2-chloro-7,8-dihydro-6H-cyclopenta[e]pyrazolo[1,5-a]pyrimidine (5.3 g, 11.1 mmol) in toluene (300 mL) were added (4R)-4-benzyl-2-[1-[(4R)-4-benzyl-4,5-dihydrooxazol-2-yl]-1-methyl-ethyl]-4,5-dihydrooxazole (L, 470 mg, 1.3 mmol), acetoxycopper (283 mg, 2.3 mmol), N-fluoro-N-(phenylsulfonyl)benzenesulfonamide (5.3 g, 16.7 mmol) and TMSCN (5.7 g, 55.6 mmol). The reaction mixture was stirred at 25° C. for 16 h under nitrogen atmosphere. The resulting mixture was concentrated under reduced pressure. The residue was applied onto a silica gel column and eluted with EtOAc/PE (1:5) to give 8,8-bis(((tert-butyldimethylsilyl)oxy)methyl)-2-chloro-7,8-dihydro-6H-cyclopenta[e]pyrazolo[1,5-a]pyrimidine-6-carbonitrile (2.9 g, 52% yield) as a light yellow solid. LC-MS: m/z 507 $[M+H]^+$.

Step 8: 8,8-bis(((tert-butyldimethyl silyl)oxy) methyl)-2-chloro-7,8-dihydro-6H-cyclopenta[e]pyrazolo[1,5-a]pyrimidine-6-carboxamide

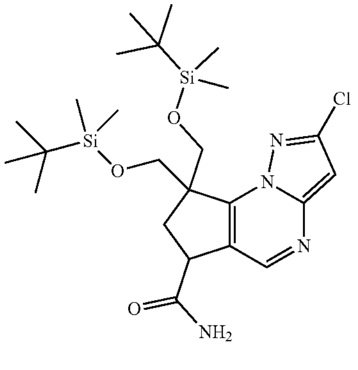 [SMILES: CC(C)(C)[Si](C)(C)OCC1(CO[Si](C)(C)C(C)(C)C)CC(C(N)=O)c2cnc3cc(Cl)nn3c21]

To a stirred solution of 8,8-bis(((tert-butyldimethylsilyl) oxy)methyl)-2-chloro-7,8-dihydro-6H-cyclopenta[e]pyrazolo[1,5-a]pyrimidine-6-carbonitrile (2 g, 3.9 mmol) in DMSO (15 mL) were added $K_2CO_3$ (1.2 g, 7.8 mmol) and $H_2O_2$ (0.9 g, 7.8 mmol, 30% in water). The reaction mixture was stirred at 60° C. for 2 h. The reaction mixture was quenched with water (100 mL). The resulting solution was extracted with ethyl acetate (3×100 mL). The combined organic layers were dried over anhydrous sodium sulfate and concentrated under reduced pressure. The residue was applied on a silica gel column and eluted with EtOAc/PE (1:1) to give 8,8-bis(((tert-butyldimethylsilyl)oxy)methyl)-2-chloro-7,8-dihydro-6H-cyclopenta[e]pyrazolo[1,5-a]pyrimidine-6-carboxamide (1.2 g, 58% yield) as a yellow solid. LC-MS: m/z 525 $[M+H]^+$.

Step 9: 8,8-bis(((tert-butyldimethylsilyl)oxy)methyl)-2-chloro-N-(5-chloro-6-(2H-1,2,3-triazol-2-yl)pyridin-3-yl)-7,8-dihydro-6H-cyclopenta[e]pyrazolo[1,5-a]pyrimidine-6-carboxamide

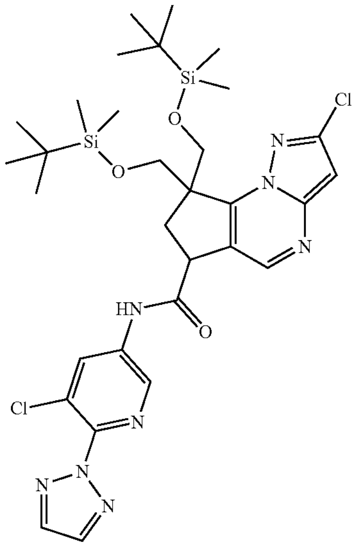 [SMILES: CC(C)(C)[Si](C)(C)OCC1(CO[Si](C)(C)C(C)(C)C)CC(C(=O)Nc2cnc(-n3nccn3)c(Cl)c2)c2cnc3cc(Cl)nn3c21]

To a stirred solution of 8,8-bis(((tert-butyldimethylsilyl)oxy)methyl)-2-chloro-7,8-dihydro-6H-cyclopenta[e]pyrazolo[1,5-a]pyrimidine-6-carboxamide (300 mg, 571.2 μmol) in toluene (15 mL) were added XantPhos (66 mg, 114.2 μmol), $Pd_2(dba)_3$ (104 mg, 114.2 μmol), $Cs_2CO_3$ (279 mg, 856.8 μmol), $Al(OTf)_3$ (27 mg, 57.1 μmol) and 5-bromo-3-chloro-2-(2H-1,2,3-triazol-2-yl)pyridine (178 mg, 685.4 μmol). The reaction mixture was stirred at 110° C. for 4 h under nitrogen atmosphere. The reaction mixture was quenched with water (150 mL) and extracted with ethyl acetate (3×150 mL). The combined organic layers were dried over anhydrous sodium sulfate and concentrated under reduced pressure. The residue was applied on a silica gel column and eluted with EtOAc/PE (2:1) to give 8,8-bis(((tert-butyldimethylsilyl)oxy)methyl)-2-chloro-N-(5-chloro-6-(2H-1,2,3-triazol-2-yl)pyridin-3-yl)-7,8-dihydro-6H-cyclopenta[e]pyrazolo[1,5-a]pyrimidine-6-carboxamide (150 mg, 22% yield) as a white solid. LC-MS: m/z 703 $[M+H]^+$.

Step 10: 2-chloro-N-(5-chloro-6-(2H-1,2,3-triazol-2-yl)pyridin-3-yl)-8,8-bis(hydroxymethyl)-7,8-dihydro-6H-cyclopenta[e]pyrazolo[1,5-a]pyrimidine-6-carboxamide

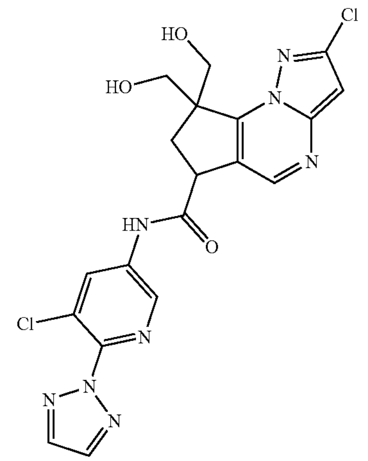 [SMILES: O=C(Nc1cnc(-n2nccn2)c(Cl)c1)C1CC(CO)(CO)c2c1cnc1cc(Cl)nn21]

To a stirred solution of 8,8-bis(((tert-butyldimethylsilyl)oxy)methyl)-2-chloro-N-(5-chloro-6-(2H-1,2,3-triazol-2-yl)pyridin-3-yl)-7,8-dihy dro-6H-cyclopenta[e]pyrazolo[1,5-a]pyrimidine-6-carboxamide (150 mg, 213.1 μmol) in DCM (10 mL) was added TFA (2 mL). The reaction mixture was stirred at 25° C. for 4 h under nitrogen atmosphere. The reaction mixture was quenched with water (50 mL) and extracted with DCM (3×50 mL). The combined organic layers were dried over anhydrous sodium sulfate and concentrated under reduced pressure. The residue was applied on a silica gel column and eluted with MeOH/DCM (1:10) to give 2-chloro-N-(5-chloro-6-(2H-1,2,3-triazol-2-yl)pyridin-3-yl)-8,8-bis(hydroxymethyl)-7,8-dihydro-6H-cyclopenta[e]pyrazolo[1,5-a]pyrimidine-6-carboxamide (70 mg, 48% yield) as an off-white solid. LC-MS: m/z 475 $[M+H]^+$.

Step 11: 2-chloro-N-(5-chloro-6-(2H-1,2,3-triazol-2-yl)pyridin-3-yl)-6,7-dihydrospiro[cyclopenta[e]pyrazolo[1,5-a]pyrimidine-8,3'-oxetane]-6-carboxamide

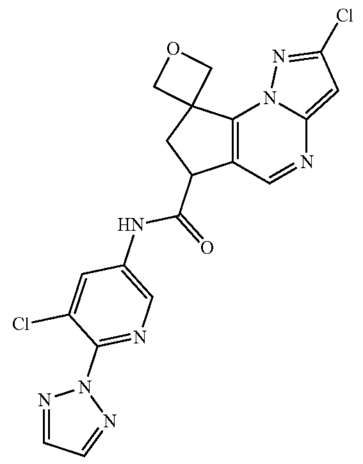 [SMILES: O=C(Nc1cnc(-n2nccn2)c(Cl)c1)C1CC2(COC2)c2c1cnc1cc(Cl)nn21]

To a stirred solution of 2-chloro-N-(5-chloro-6-(2H-1,2,3-triazol-2-yl)pyridin-3-yl)-8,8-bis(hydroxymethyl)-7,8-dihydro-6H-cyclopenta[e]pyrazolo[1,5-a]pyrimidine-6-carboxamide (100 mg, 215.8 μmol) in THE (10 mL) were added triphenylphosphane (113 mg, 431.6 μmol), bis((2-methylpropanethioyl)thio)zinc (L1, 99 mg, 323.7 μmol) and diethyl (E)-diazene-1,2-dicarboxylate (75 mg, 431.6 μmol). The reaction mixture was stirred at 25° C. for 16 h under nitrogen atmosphere. The reaction mixture was quenched with water (80 mL) and extracted with ethyl acetate (2×80 mL). The combined organic layers were dried over anhydrous sodium sulfate and concentrated under reduced pressure. The residue was applied on a silica gel column and eluted with EtOAc/PE (2:1) to give the crude product. The crude product was submitted to Prep-HPLC purification and the collected fractions were lyophilized to give Example 165 (10 mg, 10% yield) as a white solid.

Example 165: $^1H$ NMR (300 MHz, DMSO-$d_6$) δ: 11.11 (br, 1H), 8.70 (s, 1H), 8.69 (d, J=2.1 Hz, 1H), 8.54 (d, J=2.1 Hz, 1H), 8.16 (s, 2H), 7.03 (s, 1H), 5.54 (d, J=6.0 Hz, 1H), 5.39 (d, J=6.0 Hz, 1H), 4.68 (d, J=6.0 Hz, 1H), 4.60 (d, J=6.0 Hz, 1H), 4.39-4.43 (m, 1H), 2.92-3.06 (m, 2H). LC-MS: m/z 456.9 $[M+H]^+$.

Method K4

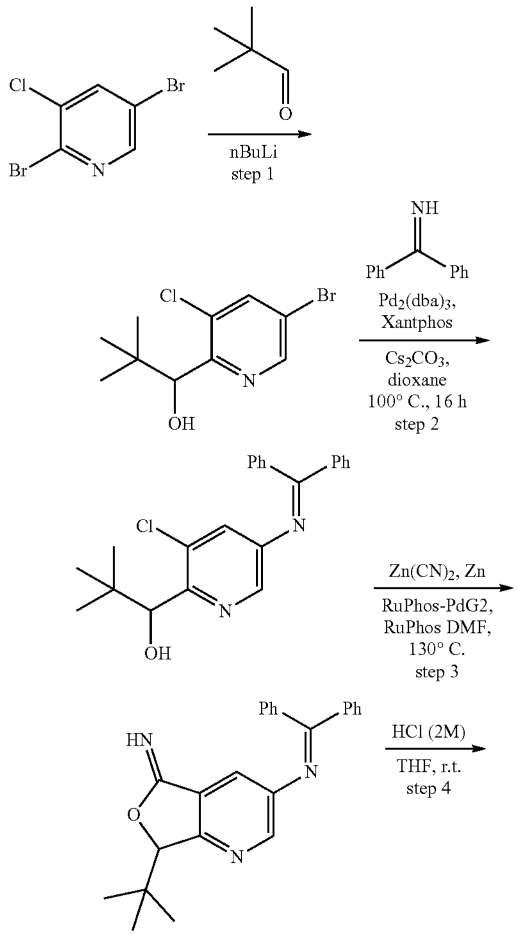

-continued

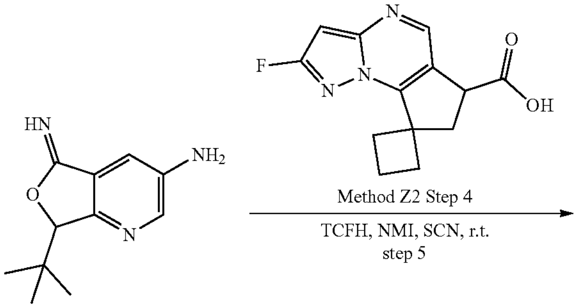

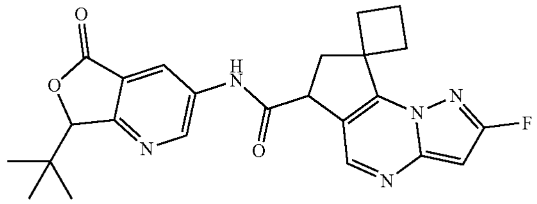
Example 166

Example 166: N-(7-(tert-butyl)-5-oxo-5,7-dihydrofuro[3,4-b]pyridin-3-yl)-2'-fluoro-6',7'-dihydrospiro[cyclobutane-1,8'-cyclopenta[a]pyrazolo[1,5-a]pyrimidine]-6'-carboxamide Step 1:1-(5-bromo-3-chloropyridin-2-yl)-2,2-dimethylpropan-1-ol

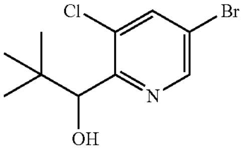

To a stirred solution of 2,5-dibromo-3-chloropyridine (5 g, 18.4 mmol) in Toluene (30 mL) was added n-BuLi (8.2 mL, 2.5 N) dropwise at −78° C. under nitrogen atmosphere. The reaction mixture was stirred at −78° C. for 0.5 h. Pivalaldehyde (1.9 g, 22.1 mmol) was added dropwise at 78° C. It was stirred at −78° C. for 1 h then warmed to 25° C. and stirred for 16 h. The reaction mixture was quenched with water (100 mL) and extracted with ethyl acetate (3×100 mL). The combined organic layers were dried over anhydrous sodium sulfate and concentrated under reduced pressure. The residue was applied onto a silica gel column and eluted with EtOAc/PE (1:2) to give 1-(5-bromo-3-chloropyridin-2-yl)-2,2-dimethylpropan-1-ol (5.13 g, 62% yield) as a colorless oil. LC-MS: m/z 278 $[M+H]^+$.

Step 2:1-(3-chloro-5-((diphenylmethylene)amino) pyridin-2-yl)-2,2-dimethylpropan-1-ol

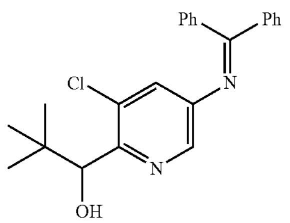 [SMILES: CC(C)(C)C(O)c1ncc(N=C(c2ccccc2)c2ccccc2)cc1Cl]

To a stirred mixture of 1-(5-bromo-3-chloropyridin-2-yl)-2,2-dimethylpropan-1-ol (2 g, 7.2 mmol) in dioxane (40 mL) were added diphenylmethanimine (1.3 g, 7.2 mmol), $Cs_2CO_3$ (4.7 g, 14.3 mmol), XantPhos (831 mg, 1.4 mmol) and $Pd_2(dba)_3$ (747 mg, 721.7 μmol). The mixture was stirred at 100° C. for 16 h under nitrogen atmosphere. The mixture was cooled to 25° C., diluted with water (100 mL) and extracted with ethyl acetate (3×100 mL). The combined organic layers were dried over anhydrous sodium sulfate and concentrated under reduced pressure. The residue was applied onto a silica gel column and eluted with EtOAc/PE (1:9) to give 1-(3-chloro-5-((diphenylmethylene)amino) pyridin-2-yl)-2,2-dimethylpropan-1-ol (1.9 g, 69% yield) as a yellow oil. LC-MS: m/z 379 $[M+H]^+$.

Step 3: 7-(tert-butyl)-3-((diphenylmethylene)amino) furo[3,4-b]pyridin-5(7H)-imine

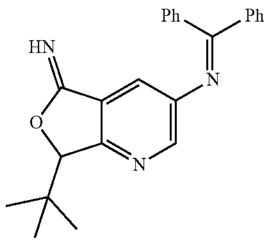 [SMILES: CC(C)(C)C1OC(=N)c2cc(N=C(c3ccccc3)c3ccccc3)cnc21]

To a stirred solution of 1-(3-chloro-5-((diphenylmethylene)amino)pyridin-2-yl)-2,2-dimethylpropan-1-ol (1.5 g, 4 mmol) in DMF (20 mL) were added $Zn(CN)_2$ (512 mg, 4.3 mmol), Zn (13 mg, 198.4 μmol), RuPhos-Pd G2 (332 mg, 396.8 μmol) and RuPhos (185 mg, 396.8 μmol).

The resulting mixture was stirred at 130° C. for 1.2 h under nitrogen. The mixture was cooled to 25° C., diluted with water (100 mL) and extracted with ethyl acetate (3×100 mL). The combined organic layers were dried over anhydrous sodium sulfate and concentrated under reduced pressure. The residue was applied onto a silica gel column and eluted with EtOAc/PE (1:3) to give 7-(tert-butyl)-3-((diphenylmethylene)amino)furo[3,4-b]pyridin-5(7H)-imine (380 mg, 26% yield) as a yellow solid. LC-MS: m/z 370 $[M+H]^+$.

Step 4: 7-(tert-butyl)-5-imino-5,7-dihydrofuro[3,4-b]pyridin-3-amine

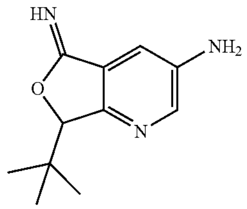

To a stirred solution of 7-(tert-butyl)-3-((diphenylmethylene)amino)furo[3,4-b]pyridin-5(7H)-imine (100 mg, 271 μmol) in THE (5 mL) was added 2 M HCl (300 μL). The mixture was stirred at 25° C. for 10 min. The reaction mixture was diluted with water (30 mL) and extracted with ethyl acetate (3×30 mL). The combined organic layers were dried over anhydrous sodium sulfate and concentrated under reduced pressure. The residue was applied onto a silica gel column and eluted with EtOAc/PE (1:1) to give 7-(tert-butyl)-5-imino-5,7-dihydrofuro[3,4-b]pyridin-3-amine (35 mg, 63% yield) as a yellow solid. LC-MS: m/z 206 $[M+H]^+$.

Step 5: N-(7-(tert-butyl)-5-oxo-5,7-dihydrofuro[3,4-b]pyridin-3-yl)-2'-fluoro-6',7'-dihydrospiro[cyclobutane-1,8'-cyclopenta[e]pyrazolo[1,5-a]pyrimidine]-6'-carboxamide Example 166

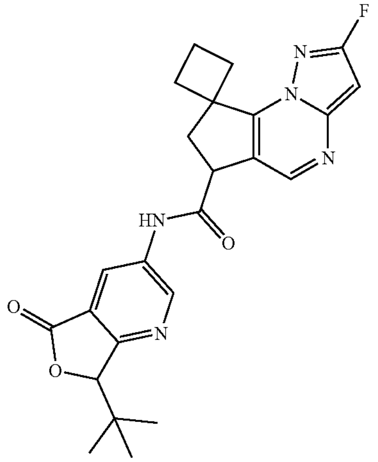

Analogously to Method Z2 Step 5, Example 166 (3 mg, 4% yield) was obtained as a white solid.

Example 166: $^1H$ NMR (400 MHz, DMSO-$d_6$) δ: 10.95 (s, 1H), 8.98 (t, J=2.4 Hz, 1H), 8.62 (d, J=2.4 Hz, 1H), 8.55 (t, J=2.4 Hz, 1H), 6.58 (d, J=4.8 Hz, 1H), 5.31 (s, 1H), 4.37 (dd, J=5.2, 8.8 Hz, 1H), 3.07-3.18 (m, 2H), 2.84-2.90 (m, 1H), 2.66-2.72 (m, 1H), 2.07-2.25 (m, 4H), 0.99 (s, 9H). LC-MS: m/z 450 $[M+H]^+$.

Method L4
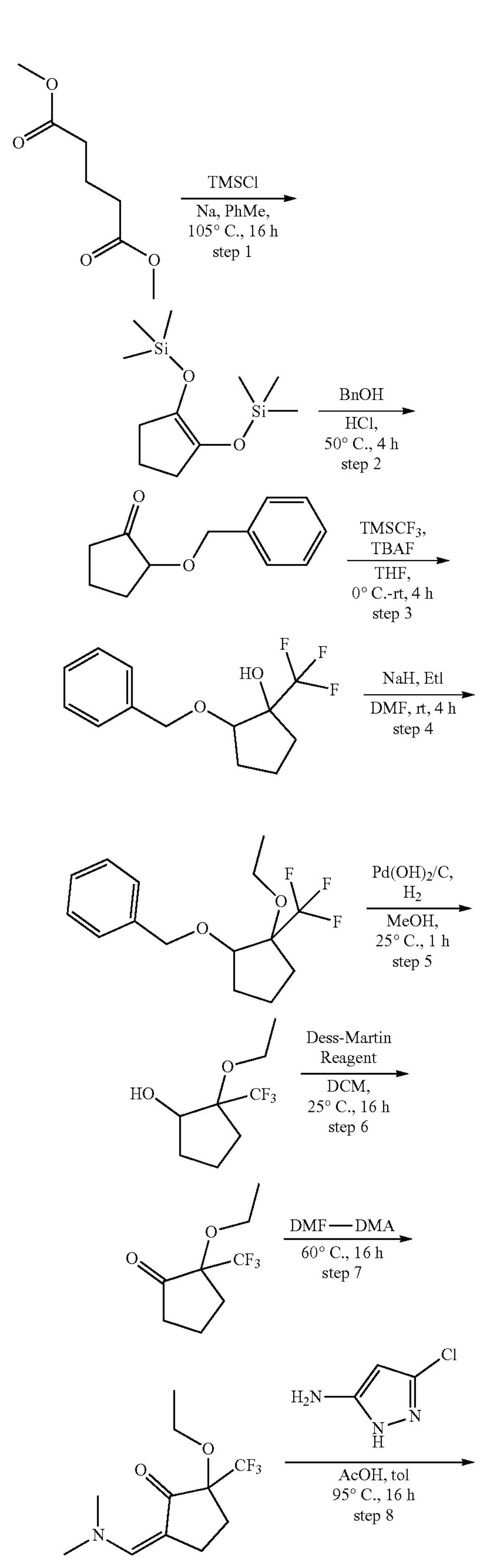
-continued
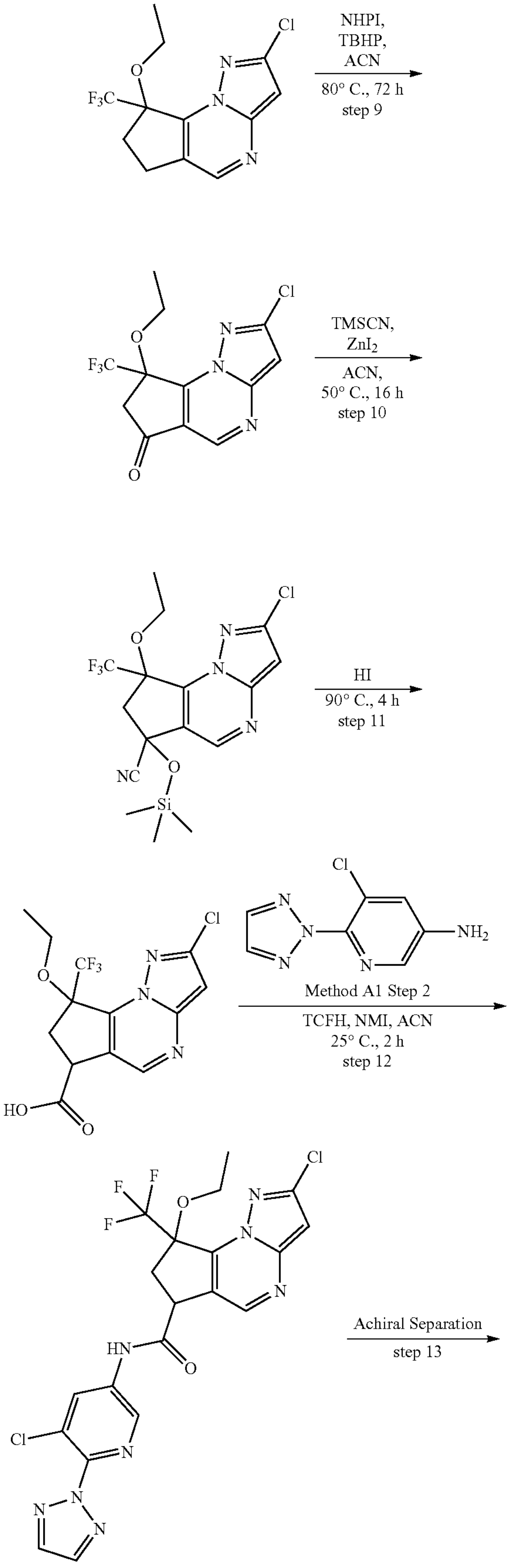

-continued

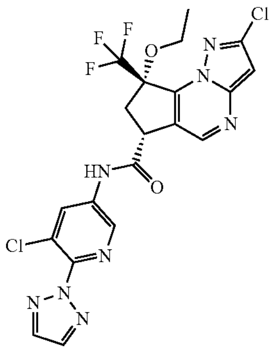

cis
racemate
Example 167

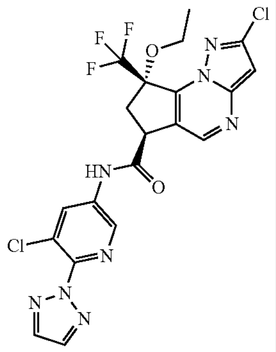

trans
racemate
Example 168

Examples 167 and 168: (cis)-2-chloro-N-(5-chloro-6-(2H-1,2,3-triazol-2-yl)pyridin-3-yl)-8-ethoxy-8-(trifluoromethyl)-7,8-dihydro-6H-cyclopenta[e]pyrazolo[1,5-a]pyrimidine-6-carboxamide and (trans)-2-chloro-N-(5-chloro-6-(2H-1,2,3-triazol-2-yl)pyridin-3-yl)-8-ethoxy-8-(trifluoromethyl)-7,8-dihydro-6H-cyclopenta[e]pyrazolo[1,5-a]pyrimidine-6-carboxamide Step 1: 1,2-bis((trimethylsilyl)oxy)cyclopent-1-ene

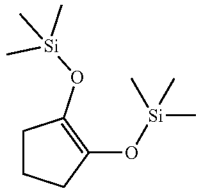

To a stirred solution of Sodium (107.6 g, 4.6 mol) in toluene (3000 mL) were added dimethyl glutarate (150 g, 936.5 mmol) and chlorotrimethylsilane (508.7 g, 4.6 mol) at 25° C. The resulting mixture was stirred at 105° C. for 16 h. The mixture was cooled to 25° C. The solid was filtered out. The filtrate was concentrated under reduced pressure to give 1,2-bis((trimethylsilyl)oxy)cyclopent-1-ene (180 g, crude) as an oil. LC-MS: m/z 245 $[M+H]^+$.

Step 2: 2-(benzyloxy)cyclopentan-1-one

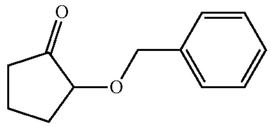 [SMILES: O=C1CCCC1OCc1ccccc1]

To a stirred solution of phenylmethanol (91.3 g, 845.0 mmol) in HCl (112 mL, 4.0 M in diethyl ether) was added 1,2-bis((trimethylsilyl)oxy)cyclopent-1-ene (180 g, 736.27 mmol) at 0° C. The reaction mixture was stirred at 50° C. for 4 h. The mixture was cooled to 25° C. The reaction mixture was concentrated under reduced pressure. The residue was applied onto a silica gel column and eluted with EtOAc/PE (1:4) to afford 2-(benzyloxy)cyclopentan-1-one (110 g, 78% yield) as a yellow oil. LC-MS: m/z 191 $[M+H]^+$.

Step 3: 2-(benzyloxy)-1-(trifluoromethyl)cyclopentan-1-ol

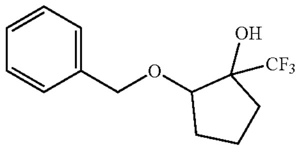 [SMILES: OC1(C(F)(F)F)CCCC1OCc1ccccc1]

To a stirred solution of 2-(benzyloxy)cyclopentan-1-one (110 g, 578.2 mmol) in THF (2000 mL) were added trimethyl(trifluoromethyl)silane (164.4 g, 1156.4 mmol) and TBAF (2.9 L, 1 M in THF) in portions at 0° C. The reaction mixture was stirred at 25° C. for 4 h. The reaction was quenched with water (2000 mL) and extracted with ethyl acetate (3×2000 mL). The combined organic layers were washed with brine (3×2000 mL), dried over anhydrous sodium sulfate and concentrated under reduced pressure. The residue was applied onto a silica gel column and eluted with EtOAc/PE (1:4) to afford 2-(benzyloxy)-1-(trifluoromethyl)cyclopentan-1-ol (30 g, 11% yield) as a yellow oil. LC-MS: m/z 261 $[M+H]^+$.

Step 4: (((2-ethoxy-2-(trifluoromethyl)cyclopentyl)oxy)methyl)benzene

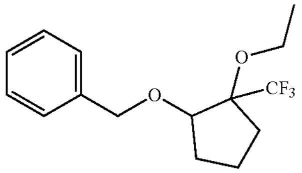 [SMILES: CCOC1(C(F)(F)F)CCCC1OCc1ccccc1]

To a stirred mixture of 2-(benzyloxy)-1-(trifluoromethyl)cyclopentan-1-ol (30 g, 115.2 mmol) in DMF (400 mL) was added NaH (9.2 g, 230 mmol, 60% in mineral oil) at 0° C. The resulting mixture was stirred at 0° C. for 30 min. Then iodoethane (53.9 g, 345.8 mmol) was added. The mixture was stirred at 25° C. for 4 h. The reaction mixture was quenched with water (600 mL) and was extracted with ethyl acetate (3×500 mL). The combined organic layers were dried over anhydrous sodium sulfate and concentrated under reduced pressure. The residue was applied onto a silica gel column and eluted with EtOAc/PE (1:5) to afford (((2-ethoxy-2-(trifluoromethyl)cyclopentyl)oxy)methyl)benzene (30 g, 51% yield) as a yellow oil. $^1H$ NMR (300 MHz, Chloroform-d) δ: 7.46-7.25 (m, 5H), 4.75 (d, J=12 Hz, 1H), 4.62 (d, J=12 Hz, 1H), 4.01 (t, J=7.5 Hz, 1H), 3.71-3.85 (m, 2H), 2.01-2.15 (m, 2H), 1.80-1.95 (m, 2H), 1.48-1.64 (m, 1H), 1.28 (t, J=7.0 Hz, 3H), 0.89-0.97 (m, 1H). LC-MS: m/z 289 $[M+H]^+$.

Step 5: 2-ethoxy-2-(trifluoromethyl)cyclopentan-1-ol

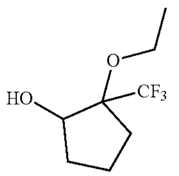

To a stirred solution of (((2-ethoxy-2-(trifluoromethyl) cyclopentyl)oxy)methyl)benzene (30 g, 104.0 mmol) in MeOH (500 mL) was added $Pd(OH)_2$ on carbon (3.0 g, 10%). The reaction mixture was stirred at 25° C. for 1 h under hydrogen atmosphere. The solid was filtered out. The filtrate was concentrated under reduced pressure to afford 2-ethoxy-2-(trifluoromethyl)cyclopentan-1-ol (16 g, 54% yield) as a yellow oil. $^1$H NMR (300 MHz, Chloroform-d) δ 4.12-4.32 (m, 1H), 3.78-3.86 (m, 2H), 2.69 (br, 1H), 2.04-2.17 (m, 1H), 1.80-2.08 (m, 2H), 1.55-1.71 (m, 2H), 1.25 (t, J=6.9, 3H), 0.81-0.90 (m, 1H). LC-MS: m/z 199 $[M+H]^+$.

Step 6: 2-ethoxy-2-(trifluoromethyl)cyclopentan-1-one

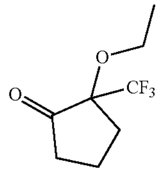

To a stirred solution of 2-ethoxy-2-(trifluoromethyl)cyclopentan-1-ol (16 g, 80.7 mmol) in DCM (300 mL) was added Dess-Martin periodinane (68.5 g, 161.4 mmol). The reaction mixture was stirred at 25° C. for 16 h. The solid was filtered out. The filtrate was diluted with DCM (300 mL). The resulting solution was washed with saturated aqueous sodium bisulfite solution (300 mL) and saturated aqueous sodium bicarbonate solution (300 mL), dried over anhydrous sodium sulfate and concentrated under reduced pressure. The residue was applied onto a silica gel column and eluted with EtOAc/PE (1:9) to give 2-ethoxy-2-(trifluoromethyl)cyclopentan-1-one (7.7 g, 35% yield) as a yellow oil. LC-MS: m/z 197 $[M+H]^+$.

Step 7: (Z)-5-((dimethylamino)methylene)-2-ethoxy-2-(trifluoromethyl)cyclopentan-1-one

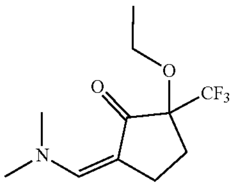 [SMILES: CCOC1(C(F)(F)F)CC/C(=C/N(C)C)C1=O]

A solution of 2-ethoxy-2-(trifluoromethyl)cyclopentan-1-one (7.7 g, 39.2 mmol) in DMF-DMA (80 mL) was stirred at 60° C. for 16 h. The mixture was allowed to cool down to 25° C. The resulting solution was concentrated under reduced pressure to give (Z)-5-((dimethylamino)methylene)-2-ethoxy-2-(trifluoromethyl)cyclopentan-1-one (10 g, crude) as a yellow oil. LC-MS: m/z 252 $[M+H]^+$.

Step 8: 2-chloro-8-ethoxy-8-(trifluoromethyl)-7,8-dihydro-6H-cyclopenta[e]pyrazolo[1,5-a]pyrimidine

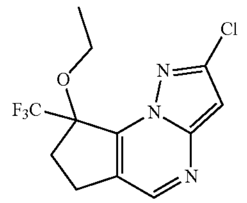 [SMILES: CCOC1(C(F)(F)F)CCc2cnc3cc(Cl)nn3c21]

To a solution of (Z)-5-((dimethylamino)methylene)-2-ethoxy-2-(trifluoromethyl)cyclopentan-1-one (10 g, 39.8 mmol) in toluene (200 mL) were added 3-chloro-1H-pyrazol-5-amine (4.6 g, 39.8 mmol) and AcOH (20 mL). The resulting mixture was stirred at 95° C. for 16 h. The mixture was concentrated under reduced pressure. The residue was applied onto a silica gel column and eluted with EtOAc/PE (1:2) to afford 2-chloro-8-ethoxy-8-(trifluoromethyl)-7,8-dihydro-6H-cyclopenta[e]pyrazolo[1,5-a]pyrimidine (5 g, 38% yield) as a yellow solid. 1H NMR (300 MHz, DMSO-$d_6$) δ 8.74 (s, 1H), 7.07 (s, 1H), 3.55-3.67 (m, 1H), 2.98-3.24 (m, 3H), 2.50-2.72 (m, 2H), 1.12 (t, J=6.9 Hz, 3H). LC-MS: m/z 306 $[M+H]^+$.

Step 9: 2-chloro-8-ethoxy-8-(trifluoromethyl)-7,8-dihydro-6H-cyclopenta[e]pyrazolo[1,5-a]pyrimidin-6-one

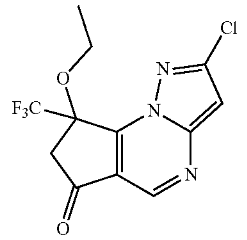 [SMILES: CCOC1(C(F)(F)F)CC(=O)c2cnc3cc(Cl)nn3c21]

To a solution of 2-chloro-8-ethoxy-8-(trifluoromethyl)-7,8-dihydro-6H-cyclopenta[e]pyrazolo[1,5-a]pyrimidine (5 g, 16.3 mmol) in ACN (200 mL) were added 2-hydroxyisoindoline-1,3-dione (13.3 g, 81.7 mmol) and tert-butyl hydroperoxide (31.5 g, 245.3 mmol). The resulting mixture was stirred at 80° C. for 72 h. The mixture was allowed to cool down to 25° C. and concentrated under reduced pressure. The residue was diluted with water (100 mL).

The resulting solution was extracted with ethyl acetate (3×200 mL). The combined organic layers were dried over anhydrous sodium sulfate and concentrated under reduced pressure. The residue was applied onto a silica gel column and eluted with EtOAc/PE (1:2) to afford 2-chloro-8-ethoxy- 8-(trifluoromethyl)-7,8-dihydro-6H-cyclopenta[e]pyrazolo[1,5-a]pyrimidin-6-one (1.4 g, 26% yield) as a yellow solid. LC-MS: m/z 320 [M+H]$^+$.

Step 10: 2-chloro-8-ethoxy-8-(trifluoromethyl)-6-((trimethyl silyl)oxy)-7,8-dihydro-6H-cyclopenta[e]pyrazolo[1,5-a]pyrimidine-6-carbonitrile

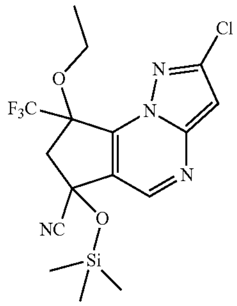 [SMILES: CCOC1(C(F)(F)F)CC(C#N)(O[Si](C)(C)C)c2cnc3cc(Cl)nn3c21]

To a solution of 2-chloro-8-ethoxy-8-(trifluoromethyl)-7,8-dihydro-6H-cyclopenta[e]pyrazolo[1,5-a]pyrimidin-6-one (500 mg, 1.6 mmol) in ACN (20 mL) were added zinc(II) iodide (2.5 g, 7.8 mmol) and TMSCN (4.7 g, 46.9 mmol) at 25° C. The resulting mixture was stirred at 50° C. for 16 h. The reaction mixture was cooled to 25° C., quenched with water (50 mL) and extracted with ethyl acetate (3×50 mL). The combined organic layers were washed with brine (50 mL), dried over anhydrous sodium sulfate and concentrated under reduced pressure to afford 2-chloro-8-ethoxy-8-(trifluoromethyl)-6-((trimethylsilyl)oxy)-7,8-dihydro-6H-cyclopenta[e]pyrazolo[1,5-a]pyrimidine-6-carbonitrile (500 mg, crude) as a brown solid. LC-MS: m/z 419 [M+H]$^+$.

Step 11: 2-chloro-8-ethoxy-8-(trifluoromethyl)-7,8-dihydro-6H-cyclopenta[e]pyrazolo[1,5-a]pyrimidine-6-carboxylic acid

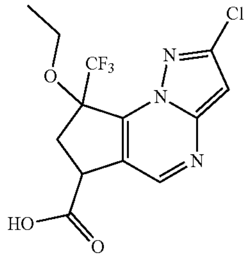 [SMILES: CCOC1(C(F)(F)F)CC(C(=O)O)c2cnc3cc(Cl)nn3c21]

A solution of 2-chloro-8-ethoxy-8-(trifluoromethyl)-6-((trimethylsilyl)oxy)-7,8-dihydro-6H-cyclopenta[e]pyrazolo[1,5-a]pyrimidine-6-carbonitrile (200 mg, 477 μmol) in hydroiodic acid (5 mL, 57% in water) was stirred at 90° C. for 4 h. The reaction mixture was cooled to 25° C., quenched with aqueous sodium thiosulfate solution (50 mL) and extracted with ethyl acetate (3×50 mL). The combined organic layers were dried over anhydrous sodium sulfate and concentrated under reduced pressure. The residue was applied onto a silica gel column and eluted with DCM/MeOH (5:1) to give 2-chloro-8-ethoxy-8-(trifluoromethyl)-7,8-dihydro-6H-cyclopenta[e]pyrazolo[1,5-a]pyrimidine-6-carboxylic acid (50 mg, 29% yield) as a brown solid. LC-MS: m/z 350 [M+H]$^+$.

Step 12: 2-chloro-N-(5-chloro-6-(2H-1,2,3-triazol-2-yl)pyridin-3-yl)-8-ethoxy-8-(trifluoromethyl)-7,8-dihydro-6H-cyclopenta[e]pyrazolo[1,5-a]pyrimidine-6-carboxamide

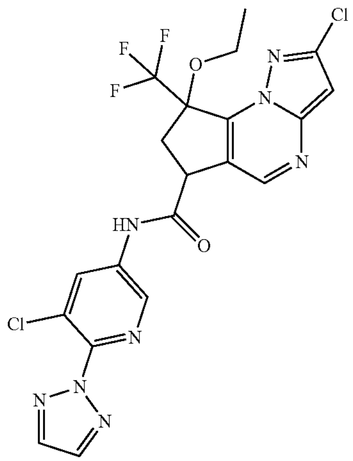 [SMILES: CCOC1(C(F)(F)F)CC(C(=O)Nc2cnc(-n3nccn3)c(Cl)c2)c2cnc3cc(Cl)nn3c21]

Analogously to Method Z2 Step 5, the title compound (5.1 mg, 3% yield) was obtained as an off-white solid. LC-MS: m/z 527 [M+H]$^+$.

Step 13: (cis)-2-chloro-N-(5-chloro-6-(2H-1,2,3-triazol-2-yl)pyridin-3-yl)-8-ethoxy-8-(trifluoromethyl)-7,8-dihydro-6H-cyclopenta[e]pyrazolo[1,5-a]pyrimidine-6-carboxamide and (trans)-2-chloro-N-(5-chloro-6-(2H-1,2,3-triazol-2-yl)pyridin-3-yl)-8-ethoxy-8-(trifluoromethyl)-7,8-dihydro-6H-cyclopenta[e]pyrazolo[1,5-a]pyrimidine-6-carboxamide Example 167

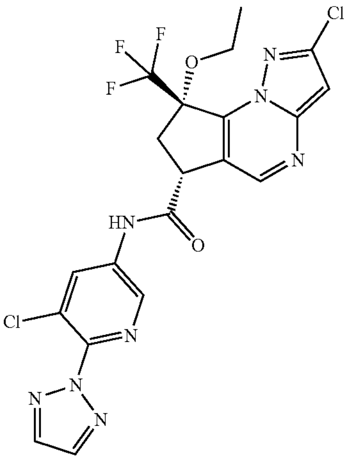

cis
racemate

-continued

Example 168

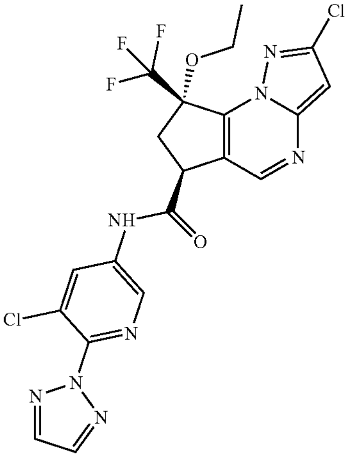

trans
racemate 4 mg of 2-chloro-N-(5-chloro-6-(2H-1,2,3-triazol-2-yl)pyridin-3-yl)-8-ethoxy-8-(trifluoromethyl)-7,8-dihydro-6H-cyclopenta[e]pyrazolo[1,5-a]pyrimidine-6-carboxamide were submitted to achiral-SFC purification (Column: DAICEL DCpak P4VP, 2*25 cm, 5 μm; Mobile Phase A: $CO_2$, Mobile Phase B: MeOH(0.1% 2M $NH_3$-MEOH); Flow rate: 50 mL/min; isocratic 37% B; Column Temperature(° C.): 35; Back Pressure(bar): 100; Wave Length: 254 nm; RT1 (min): 2.84; RT2(min): 4.58; Sample Solvent: MeOH-HPLC; Injection Volume: 1.5 mL; Number Of Runs: 2). The first eluting isomer was concentrated and lyophilized to afford Example 167 (2 mg, 49% yield) as a yellow solid. The second eluting isomer was concentrated and lyophilized to afford Example 168 (0.8 mg, 19% yield) as a yellow solid.

Example 167: $^1$H NMR (400 MHz, DMSO-$d_6$) δ 11.26 (s, 1H), 8.82 (s, 1H), 8.73 (d, J=2 Hz, 1H), 8.60 (d, J=2 Hz, 1H), 8.18 (s, 2H), 7.16 (s, 1H), 4.46 (t, J=7.6 Hz, 1H), 3.70-3.74 (m, 1H), 3.12-3.18 (m, 1H), 3.02-3.08 (m, 1H), 2.86-2.96 (m, 1H), 1.17 (t, J=6.8 Hz, 3H). LC-MS: m/z 527.0 $[M+H]^+$.

Example 168: $^1$H NMR (400 MHz, DMSO-$d_6$) δ 11.20 (s, 1H), 8.85 (s, 1H), 8.72 (d, J=2 Hz, 1H), 8.56 (d, J=2 Hz, 1H), 8.18 (s, 2H), 7.16 (s, 1H), 4.69 (t, J=7.6 Hz, 1H), 3.57-3.61 (m, 1H), 3.17-3.20 (m, 1H), 3.02-3.08 (m, 1H), 2.87-2.91 (m, 1H), 1.11 (t, J=6.8 Hz, 3H). LC-MS: m/z 527.0 $[M+H]^+$.

The stereochemistry for each separated isomer was not determined.

Method M4

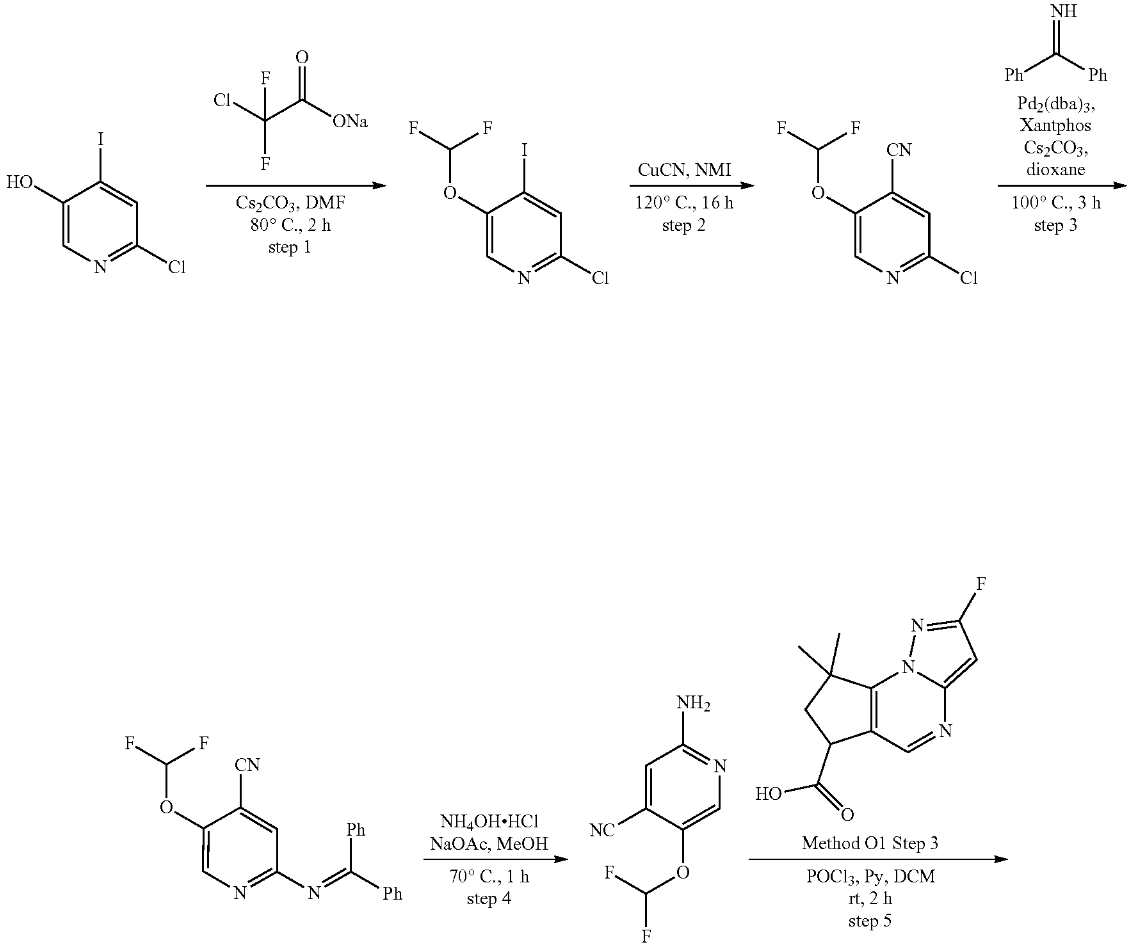

-continued

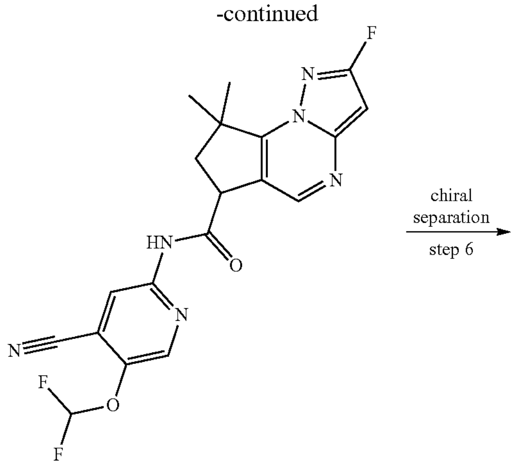

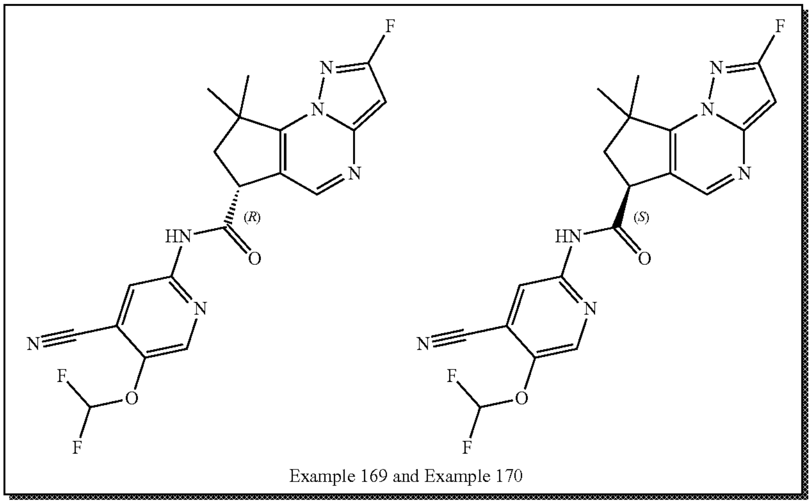

Example 169 and Example 170

Examples 169 and 170: Single Enantiomers Obtained from a Racemic Mixture Containing (R)—N-(4-cyano-5-(difluoromethoxy)pyridin-2-yl)-2-fluoro-8,8-dimethyl-7,8-dihydro-6H-cyclopenta[e]pyrazolo[1,5-a]pyrimidine-6-carboxamide and (S)—N-(4-cyano-5-(difluoromethoxy)pyridin-2-yl)-2-fluoro-8,8-dimethyl-7,8-dihydro-6H-cyclopenta[e]pyrazolo[1,5-a]pyrimidine-6-carboxamide Step 1: 2-chloro-5-(difluoromethoxy)-4-iodopyridine

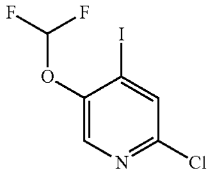 [SMILES: FC(F)Oc1cnc(Cl)cc1I]

To a stirred solution of 6-chloro-4-iodopyridin-3-ol (2 g, 7.8 mmol) in DMF (20 mL) were added sodium 2-chloro-2,2-difluoroacetate (2.4 g, 15.7 mmol) and $Cs_2CO_3$ (5.1 g, 15.7 mmol). The reaction mixture was stirred at 80° C. for 2 h. The reaction was quenched with water (100 mL) and extracted with ethyl acetate (3×100 mL). The combined organic layers were dried over anhydrous sodium sulfate and concentrated under reduced pressure. The residue was applied on a silica gel column and eluted with EtOAc/PE (1/9) to give 2-chloro-5-(difluoromethoxy)-4-iodopyridine (2 g, 83% yield) as a white solid. $^1$H NMR (400 MHz, DMSO-$d_6$) δ: 8.26 (s, 1H), 8.19 (s, 1H), 7.35 (t, J=72.5 Hz, 1H). LC-MS: m/z 306 [M+H]$^+$.

Step 2: 2-chloro-5-(difluoromethoxy)isonicotinonitrile

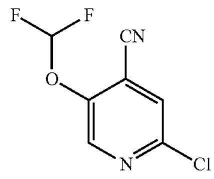 [SMILES: N#Cc1cc(Cl)ncc1OC(F)F]

To a stirred solution of 2-chloro-5-(difluoromethoxy)-4-iodopyridine (1.8 g, 5.9 mmol) in NMP (10 mL) was added CuCN (1.1 g, 11.8 mmol). The resulting mixture was stirred at 120° C. for 16 h. The reaction was quenched with water (100 mL) and extracted with ethyl acetate (3×100 mL). The combined organic layers were dried over anhydrous sodium sulfate and concentrated under reduced pressure. The residue was applied on a silica gel column and eluted with EtOAc/PE (1/4) to give 2-chloro-5-(difluoromethoxy)isonicotinonitrile (900 mg, 75% yield) as a colorless oil. $^1$H NMR (400 MHz, Chloroform-d) δ: 8.56 (s, 1H), 7.64 (s, 1H), 6.73 (t, J=70.8 Hz, 1H). LC-MS: m/z 205 $[M+H]^+$.

Step 3: 5-(difluoromethoxy)-2-((diphenylmethylene)amino)isonicotinonitrile

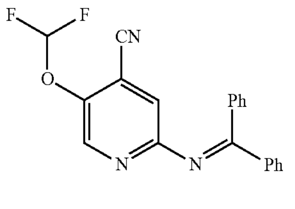 [SMILES: N#Cc1cc(N=C(c2ccccc2)c2ccccc2)ncc1OC(F)F]

To a stirred solution of 2-chloro-5-(difluoromethoxy)isonicotinonitrile (900 mg, 4.4 mmol) in dioxane (10 mL) were added diphenylmethanimine (797 mg, 4.4 mmol), $Cs_2CO_3$ (2.9 g, 8.8 mmol), Xantphos (509 mg, 879.9 μmol) and $Pd_2(dba)_3$ (911 mg, 880 μmol). The resulting mixture was stirred at 100° C. for 3 h under nitrogen. The reaction was quenched with water (50 mL) and extracted with ethyl acetate (3×50 mL). The combined organic layers were dried over anhydrous sodium sulfate and concentrated under reduced pressure. The residue was applied onto a silica gel column and eluted with EtOAc/PE (1:2) to give 5-(difluoromethoxy)-2-((diphenylmethylene)amino)isonicotinonitrile (800 mg, 52% yield) as a yellow oil. LC-MS: m/z 350 $[M+H]^+$.

Step 4: 2-amino-5-(difluoromethoxy)isonicotinonitrile

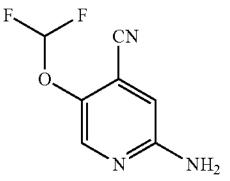 [SMILES: N#Cc1cc(N)ncc1OC(F)F]

To a solution of 5-(difluoromethoxy)-2-((diphenylmethylene)amino)isonicotinonitrile (400 mg, 1.2 mmol) in MeOH (8 mL) were added sodium acetate (234 mg, 2.9 mmol) and hydroxylamine hydrochloride (166 mg, 2.4 mmol). The resulting mixture was stirred at 70° C. for 1 h. The reaction was quenched with water (50 mL) and extracted with ethyl acetate (3×30 mL). The combined organic layers were dried over anhydrous sodium sulfate and concentrated under reduced pressure. The residue was applied onto a silica gel column and eluted with EtOAc/PE (1:1) to give 2-amino-5-(difluoromethoxy)isonicotinonitrile (80 mg, 37% yield) as a white solid. LC-MS: m/z 186 $[M+H]^+$.

Step 5: N-(4-cyano-5-(difluoromethoxy)pyridin-2-yl)-2-fluoro-8,8-dimethyl-7,8-dihydro-6H-cyclopenta[e]pyrazolo[1,5-a]pyrimidine-6-carboxamide

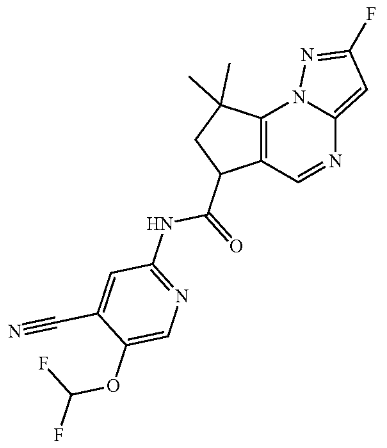 [SMILES: CC1(C)CC(C(=O)Nc2cc(C#N)c(OC(F)F)cn2)c2cnc3cc(F)nn3c21]

To a stirred solution of 2-fluoro-8,8-dimethyl-7,8-dihydro-6H-cyclopenta[e]pyrazolo[1,5-a]pyrimidine-6-carboxylic acid (Method 01 step 3; 39 mg, 156 μmol) in DCM (2 mL) were added pyridine (123 mg, 1.6 mmol) and phosphoryl trichloride (72 mg, 469.4 μmol) at 0° C. The resulting mixture was stirred at 0° C. for 1 h. 2-amino-5-(difluoromethoxy)isonicotinonitrile (35 mg, 188 μmol) was added, and the resulting mixture was stirred at 25° C. for 1 h. The mixture was concentrated under reduced pressure. The residue was submitted to Prep-HPLC purification and the collected fractions were lyophilized to give N-(4-cyano-5-(difluoromethoxy)pyridin-2-yl)-2-fluoro-8,8-dimethyl-7,8-dihydro-6H-cyclopenta[e]pyrazolo[1,5-a]pyrimidine-6-carboxamide (30 mg, 46% yield) as a white solid. LC-MS: m/z 417 $[M+H]^+$.

Step 6: Separation of Enantiomers to Obtain (R)—N-(4-cyano-5-(difluoromethoxy)pyridin-2-yl)-2-fluoro-8,8-dimethyl-7,8-dihydro-6H-cyclopenta[e]pyrazolo[1,5-a]pyrimidine-6-carboxamide and (S)—N-(4-cyano-5-(difluoromethoxy)pyridin-2-yl)-2-fluoro-8,8-dimethyl-7,8-dihydro-6H-cyclopenta[e]pyrazolo[1,5-a]pyrimidine-6-carboxamide

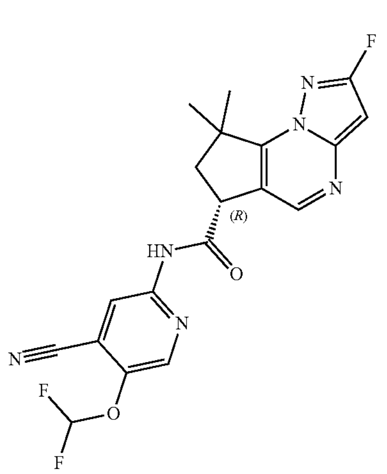

-continued

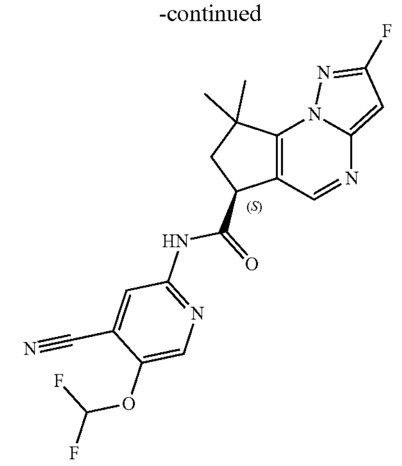

Example 169 and
Example 170

36 mg of N-(4-cyano-5-(difluoromethoxy)pyridin-2-yl)-2-fluoro-8,8-dimethyl-7,8-dihydro-6H-cyclopenta[e]pyrazolo[1,5-a]pyrimidine-6-carboxamide were submitted to chiral HPLC purification (Column: CHIRAL ART Cellulose-SA, 2*25 cm, 5 μm; Mobile Phase A: Hex(0.1% FA)-HPLC, Mobile Phase B: EtOH-HPLC; Flow rate: 20 mL/min; isocratic 40% B in 13 min; Wave Length: 220/254 nm; RT1(min): 4.66; RT2(min): 10.80; Sample Solvent: EtOH-HPLC; Injection Volume: 1.5 mL; Number Of Runs: 2). The first eluting isomer was concentrated and lyophilized to afford Example 169 (17.8 mg, 49% yield) as a white solid. The second eluting isomer was concentrated and lyophilized to afford Example 170 (11.0 mg, 30% yield) as a white solid.

Example 169: $^{1}H$ NMR (400 MHz, DMSO-$d_6$) δ: 11.50 (s, 1H), 8.63 (s, 1H), 8.57 (s, 1H), 8.46 (s, 1H), 7.44 (t, J=72.0 Hz, 1H), 6.55 (d, J=4.8 Hz, 1H), 4.51 (dd, J=9.2, 6.0 Hz, 1H), 2.51-2.56 (m, 1H), 2.26-2.31 (m, 1H), 1.61 (s, 3H), 1.53 (s, 3H). LC-MS: m/z 417 $[M+H]^+$.

Example 170: $^{1}H$ NMR (400 MHz, DMSO-$d_6$) δ: 11.50 (s, 1H), 8.63 (s, 1H), 8.57 (s, 1H), 8.46 (s, 1H), 7.43 (t, J=72.0 Hz, 1H), 6.55 (d, J=4.8 Hz, 1H), 4.51 (dd, J=9.2, 6.0 Hz, 1H), 2.50-2.56 (m, 1H), 2.26-2.31 (m, 1H), 1.61 (s, 3H), 1.53 (s, 3H). LC-MS: m/z 417 $[M+H]^+$.

The absolute stereochemistry for each separated isomer was not determined.

Method N4

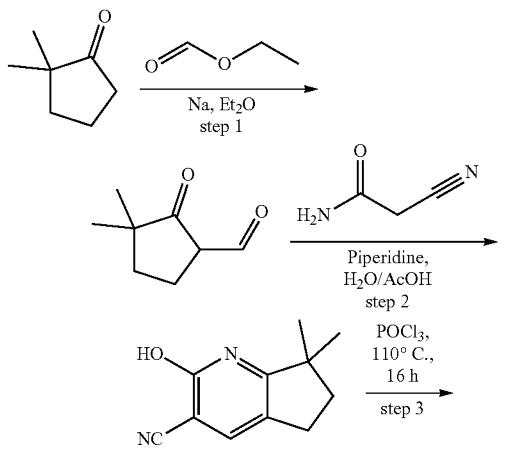

-continued

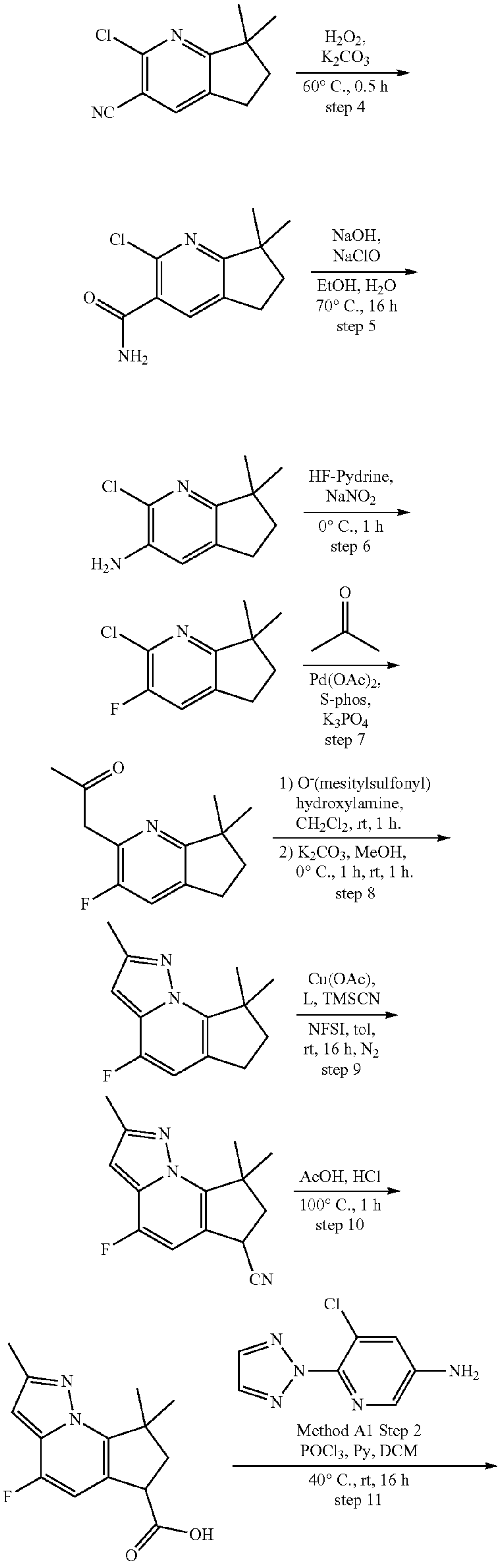

-continued

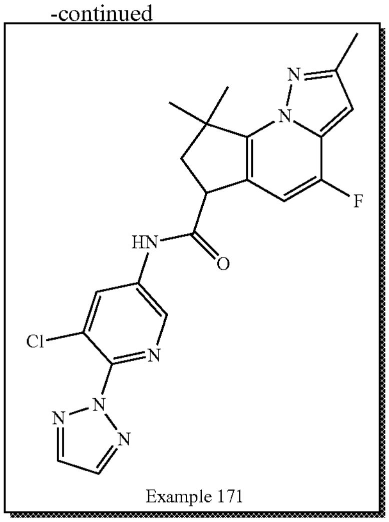

Example 171

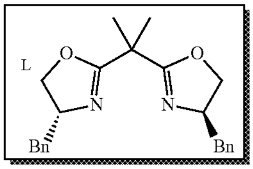

Example 171: N-(5-chloro-6-(2H-1,2,3-triazol-2-yl)pyridin-3-yl)-4-fluoro-2,8,8-trimethyl-7,8-dihydro-6H-cyclopenta[e]pyrazolo[1,5-a]pyridine-6-carboxamide Step 1: 3,3-dimethyl-2-oxocyclopentane-1-carbaldehyde

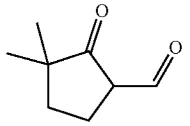

To a stirred mixture of Sodium (8 g, 348.0 mmol, 60%) in ethoxyethane (500 mL) was added 2,2-dimethylcyclopentan-1-one (52 g, 463.6 mmol) dropwise at 0° C. The reaction mixture was stirred at 25° C. for 1 h. Ethyl formate (40 g, 540.0 mmol) was added dropwise and it was stirred at 25° C. for 24 h. The reaction mixture was quenched with methanol (200 mL). The solids were filtered out and the filtrate was concentrated under reduced pressure to give 3,3-dimethyl-2-oxocyclopentane-1-carbaldehyde (60 g, crude) as yellow solid. LC-MS: m/z 141 $[M+H]^+$.

Step 2: 2-hydroxy-7,7-dimethyl-6,7-dihydro-5H-cyclopenta[b]pyridine-3-carbonitrile

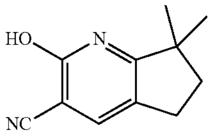

To a stirred mixture of 3,3-dimethyl-2-oxocyclopentane-1-carbaldehyde (62 g, 442.3 mmol) in water (150 mL) were added 2-cyanoacetamide (37.5 g, 446.0 mmol), piperidine (37.6 g, 442.3 mmol) and AcOH (15 mL). The reaction mixture was stirred at 100° C. for 16 h. The mixture was allowed to cool down to 25° C. The pH was adjusted to 8 with saturated aqueous sodium bicarbonate solution. The resulting mixture was extracted with ethyl acetate (3×100 mL). The combined organic layers were washed with brine, dried over anhydrous sodium sulfate and concentrated under reduced pressure. The residue was applied onto a silica gel column and eluted with EtOAc/PE (1:1) to give 2-hydroxy-7,7-dimethyl-6,7-dihydro-5H-cyclopenta[b]pyridine-3-carbonitrile (15 g, 18% yield) as yellow solid. LC-MS (ES, m/z): 189 $[M+H]^+$.

Step 3: 2-chloro-7,7-dimethyl-6,7-dihydro-5H-cyclopenta[b]pyridine-3-carbonitrile

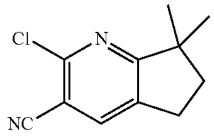

A mixture of 2-hydroxy-7,7-dimethyl-6,7-dihydro-5H-cyclopenta[b]pyridine-3-carbonitrile (1 g, 5.3 mmol) in phosphoryl trichloride (50 mL) was stirred at 110° C. for 2 h. The resulting mixture was concentrated under reduced pressure. The residue was dissolved in ethyl acetate (100 mL). The organic layer was washed with saturated aqueous sodium bicarbonate solution (100 mL) and brine (100 ml), dried over anhydrous sodium sulfate and concentrated under reduced pressure. The residue was applied onto a silica gel column and eluted with EtOAc/PE (1:10) to give 2-chloro-7,7-dimethyl-6,7-dihydro-5H-cyclopenta[b]pyridine-3-carbonitrile (3.5 g, 63% yield) as yellow solid. LC-MS (ES, m/z): 207 $[M+H]^+$.

Step 4: 2-chloro-7,7-dimethyl-6,7-dihydro-5H-cyclopenta[b]pyridine-3-carboxamide

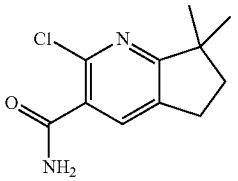

To a stirred solution of 2-chloro-7,7-dimethyl-6,7-dihydro-5H-cyclopenta[b]pyridine-3-carbonitrile (6.9 g, 33.4 mmol) in DMSO (78 mL) were added hydrogen peroxide (10.9 g, 320.5 mmol) and potassium carbonate (9.4 g, 68.0 mmol). The reaction mixture was stirred at 60° C. for 0.5 h. The reaction mixture was quenched with water (500 mL). The resulting solution was extracted with ethyl acetate (3×200 mL). The combined organic layers were washed with brine (500 mL), dried over anhydrous sodium sulfate and concentrated under reduced pressure to give 2-chloro-7,7-dimethyl-6,7-dihydro-5H-cyclopenta[b]pyridine-3-carboxamide (7 g, 93% yield) as yellow oil. LC-MS (ES, m/z): 225 $[M+H]^+$.

Step 5: 2-chloro-7,7-dimethyl-6,7-dihydro-5H-cyclopenta[b]pyridin-3-amine

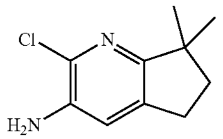

To a stirred mixture of 2-chloro-7,7-dimethyl-6,7-dihydro-5H-cyclopenta[b]pyridine-3-carboxamide (800 mg, 3.6 mmol) in ethoxyethane (20 mL) and water (10 mL) were added sodium hydroxide (570 mg, 14.2 mmol) and Sodium hypochlorite (1.1 g, 14.2 mmol). The reaction mixture was stirred at 70° C. for 16 h. The mixture was allowed to cool down to 25° C. and extracted with ethyl acetate (3×100 mL). The combined organic layers were washed with brine (200 mL), dried over anhydrous sodium sulfate and concentrated under reduced pressure. The residue was applied onto a silica gel column and eluted with EtOAc/PE (1:1) to give 2-chloro-7,7-dimethyl-6,7-dihydro-5H-cyclopenta[b]pyridin-3-amine (530 mg, 75% yield) as a white solid. LC-MS (ES, m/z): 197 [M+H]$^+$.

Step 6: 2-chloro-3-fluoro-7,7-dimethyl-6,7-dihydro-5H-cyclopenta[b]pyridine

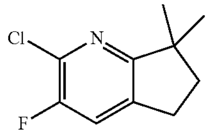

Analogously to Method D4 Step 9, 2-chloro-3-fluoro-7,7-dimethyl-6,7-dihydro-5H-cyclopenta[b]pyridine (2.5 g, 41% yield) was obtained as a yellow oil. LC-MS (ES, m/z): 200 [M+H]$^+$.

Step 7: 1-(3-fluoro-7,7-dimethyl-6,7-dihydro-5H-cyclopenta[b]pyridin-2-yl)propan-2-one

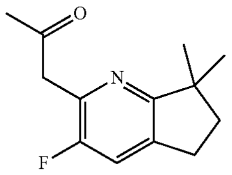 [SMILES: CC(=O)Cc1nc2c(cc1F)CCC2(C)C]

Analogously to Method D4 Step 12, 1-(3-fluoro-7,7-dimethyl-6,7-dihydro-5H-cyclopenta[b]pyridin-2-yl)propan-2-one (350 mg, 71% yield) was obtained as colorless oil. LC-MS (ES, m/z): 222 [M+H]$^+$.

Step 8: 4-fluoro-2,8,8-trimethyl-7,8-dihydro-6H-cyclopenta[e]pyrazolo[1,5-a]pyridine

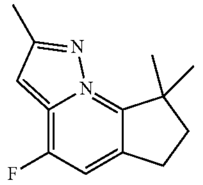

Analogously to Method D4 Step 13, 4-fluoro-2,8,8-trimethyl-7,8-dihydro-6H-cyclopenta[e]pyrazolo[1,5-a]pyridine (700 mg, 32% yield) was obtained as colorless oil. LC-MS (ES, m/z): 219 [M+H]$^+$.

Step 9: 4-fluoro-2,8,8-trimethyl-7,8-dihydro-6H-cyclopenta[e]pyrazolo[1,5-a]pyridine-6-carbonitrile

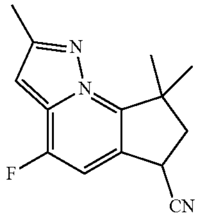

Analogously to Method A1 Step 5, 4-fluoro-2,8,8-trimethyl-7,8-dihydro-6H-cyclopenta[e]pyrazolo[1,5-a]pyridine-6-carbonitrile (80 mg, 4% yield) was obtained as a yellow oil. LC-MS (ES, m/z): 244 [M+H]$^+$.

Step 10: 4-fluoro-2,8,8-trimethyl-7,8-dihydro-6H-cyclopenta[e]pyrazolo[1,5-a]pyridine-6-carboxylic acid

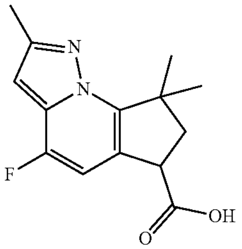 [SMILES: Cc1cc2c(F)cc3c(n2n1)C(C)(C)CC3C(=O)O]

Analogously to Method A1 Step 6, 4-fluoro-2,8,8-trimethyl-7,8-dihydro-6H-cyclopenta[e]pyrazolo[1,5-a]pyridine-6-carboxylic acid (15 mg, 17% yield) was obtained as a yellow solid. LC-MS (ES, m/z): 263 [M+H]$^+$.

Step 11: N-(5-chloro-6-(2H-1,2,3-triazol-2-yl)pyridin-3-yl)-4-fluoro-2,8,8-trimethyl-7,8-dihydro-6H-cyclopenta[e]pyrazolo[1,5-a]pyridine-6-carboxamide
Example 171
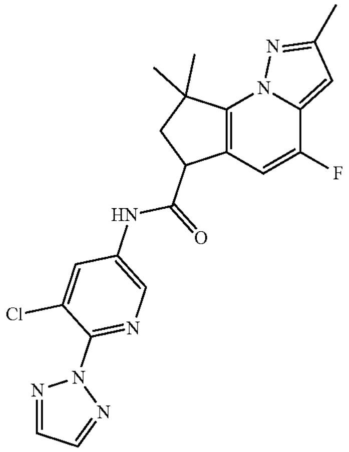
Analogously to Method M4 Step 5, Example 171 (6.6 mg, 31% yield) was obtained as a white solid.
Example 171: $^1$H NMR (300 MHz, DMSO-$d_6$) δ: 11.01 (s, 1H), 8.73 (d, J=2.4 Hz, 1H), 8.58 (d, J=2.4 Hz, 1H), 8.17 (s, 2H), 7.14 (d, J=10.2 Hz, 1H), 6.59 (s, 1H), 4.29 (dd, J=6.3, 9.0 Hz, 1H), 2.51-2.56 (m, 1H), 2.46 (s, 3H), 2.35 (dd, J=6.3, 13.2 Hz, 1H), 1.65 (s, 3H), 1.53 (s, 3H). LC-MS: m/z 440 [M+H]$^+$.
Method O4
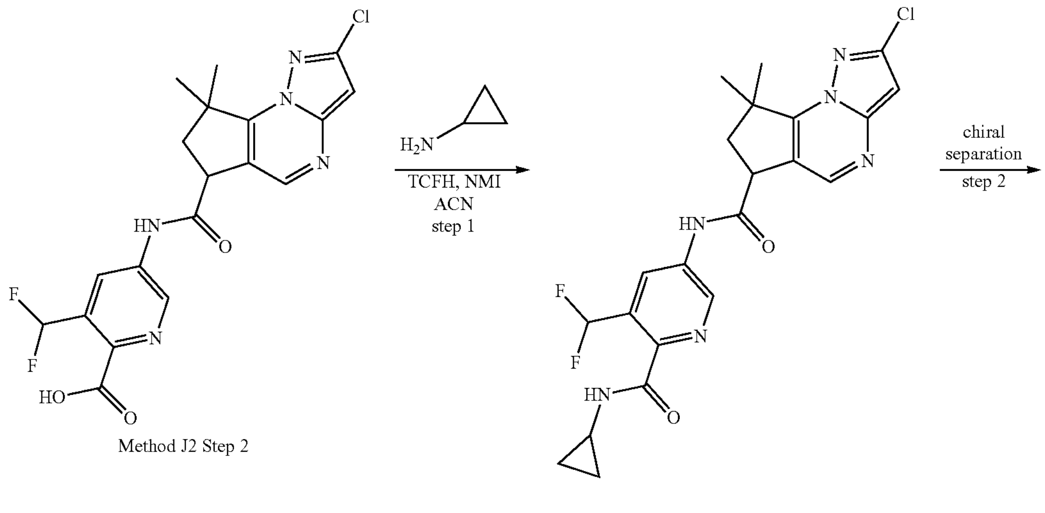
Method J2 Step 2

-continued

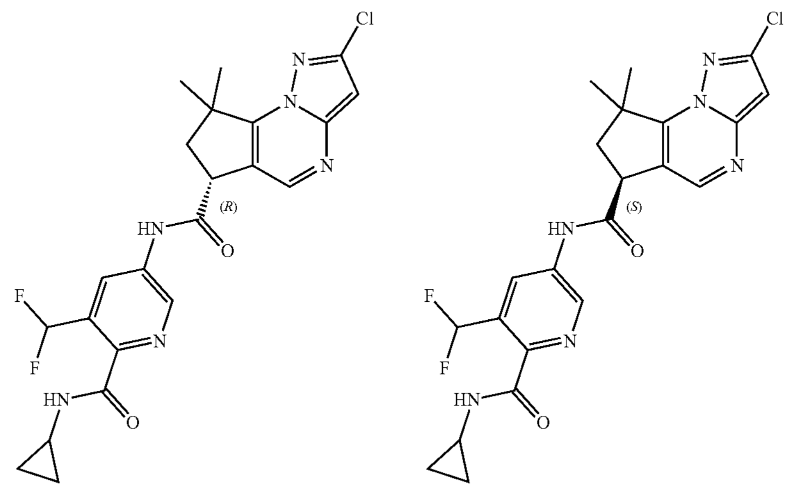

Example 172 and Example 173

Examples 172 and 173: Single Enantiomers Obtained from a Racemic Mixture Containing (R)-2-chloro-N-(6-(cyclopropylcarbamoyl)-5-(difluoromethyl)pyridin-3-yl)-8,8-dimethyl-7,8-dihydro-6H-cyclopenta[e]pyrazolo[1,5-a]pyrimidine-6-carboxamide and (S)-2-chloro-N-(6-(cyclopropylcarbamoyl)-5-(difluoromethyl)pyridin-3-yl)-8,8-dimethyl-7,8-dihydro-6H-cyclopenta[e]pyrazolo[1,5-a]pyrimidine-6-carboxamide Step 1: 2-chloro-N-(6-(cyclopropylcarbamoyl)-5-(difluoromethyl)pyridin-3-yl)-8,8-dimethyl-7,8-dihydro-6H-cyclopenta[e]pyrazolo[1,5-a]pyrimidine-6-carboxamide

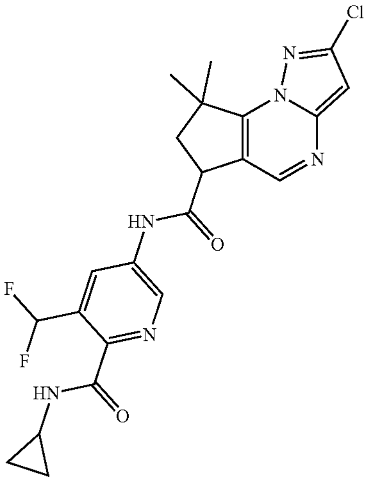 [SMILES: CC1(C)CC(C(=O)Nc2cnc(C(=O)NC3CC3)c(C(F)F)c2)c2cnc3cc(Cl)nn3c21]

To a stirred mixture of 5~(2-chloro-8,8-dimethyl-7,8-dihydro-6H-cyclopenta[e]pyrazolo[1,5-a]pyrimidine-6-carboxamido)-3-(difluoromethyl)picolinic acid (Method J2 step 2; 50 mg, 115 µcool) in ACN (1 mL) were added cyclopropanamine (10 mg, 172 µmol), NMI (28 mg, 344 µcool) and TCFH (97 mg, 344 µmol). The mixture was stirred at 25° C. for 16 h. The resulting mixture was concentrated under reduced pressure. The residue was submitted to Prep-HPLC purification and the collected fractions were lyophilized to give 2-chloro-N-(6-(cyclopropylcarbamoyl)-5-(difluoromethyl)pyridin-3-yl)-8,8-dimethyl-7,8-dihydro-6H-cyclopenta[e]pyrazolo[1,5-a]pyrimidine-6-carboxamide (6.8 mg, 12% yield) as a white solid. LC-MS: m/z 475 $[M+H]^+$.

Step 2: Separation of Enantiomers to Obtain (R)-2-chloro-N-(6-(cyclopropylcarbamoyl)-5-(difluoromethyl)pyridin-3-yl)-8,8-dimethyl-7,8-dihydro-6H-cyclopenta[e]pyrazolo[1,5-a]pyrimidine-6-carboxamide and (S)-2-chloro-N-(6-(cyclopropylcarbamoyl)-5-(difluoromethyl)pyridin-3-yl)-8,8-dimethyl-7,8-dihydro-6H-cyclopenta[e]pyrazolo[1,5-a]pyrimidine-6-carboxamide

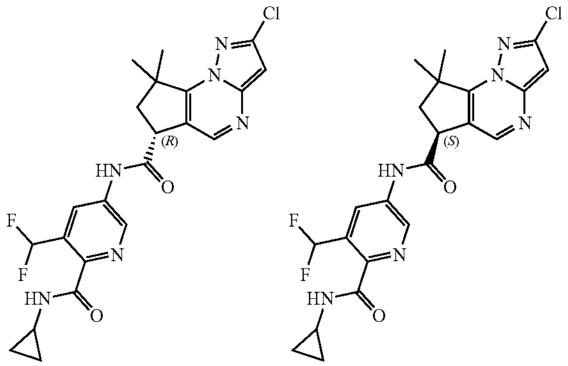

Example 172
and
Example 173

15 mg of 2-chloro-N-(6-(cyclopropylcarbamoyl)-5-(difluoromethyl)pyridin-3-yl)-8,8-dimethyl-7,8-dihydro-6H-cyclopenta[e]pyrazolo[1,5-a]pyrimidine-6-carboxamide were submitted to chiral HPLC purification (Column: CHIRALPAK IG, 2*25 cm, 5 µm; Mobile Phase A: Hex(0.1%

FA)-HPLC, Mobile Phase B: EtOH-HPLC; Flow rate: 20 mL/min; isocratic 40% B in 12 min; Wave Length: 220/254 nm; RT1(min): 8.973; RT2(min): 10.333; Sample Solvent: EtOH-HPLC; Injection Volume: 0.5 mL; Number Of Runs: 4). The first eluting isomer was concentrated and lyophilized to afford Example 172 (3.3 mg, 44% yield) as a white solid. The second eluting isomer was concentrated and lyophilized to afford Example 173 (2.5 mg, 33% yield) as a white solid.

Example 172: $^1$H NMR (400 MHz, DMSO-$d_6$) δ 11.01 (s, 1H), 8.96 (d, J=2.0 Hz, 1H), 8.86 (d, J=4.8 Hz, 1H), 8.65 (s, 1H), 8.55 (d, J=2.0 Hz, 1H), 7.89 (t, J=55.6 Hz, 1H), 6.95 (s, 1H), 4.44 (dd, J=6.4, 9.2 Hz, 1H), 2.86-2.94 (m, 1H), 2.56 (dd, J=9.2, 13.2 Hz, 1H), 2.32 (dd, J=6.4, 13.2 Hz, 1H), 1.63 (s, 3H), 1.56 (s, 3H), 0.65-0.73 (m, 4H). LC-MS: m/z 475 $[M+H]^+$.

Example 173: $^1$H NMR (400 MHz, DMSO-$d_6$) δ 11.02 (s, 1H), 8.96 (d, J=2.4 Hz, 1H), 8.86 (d, J=4.8 Hz, 1H), 8.65 (s, 1H), 8.55 (d, J=2.4 Hz, 1H), 7.89 (t, J=55.2 Hz, 1H), 6.95 (s, 1H), 4.44 (dd, J=6.4, 8.8 Hz, 1H), 2.86-2.94 (m, 1H), 2.56 (dd, J=9.2, 12.8 Hz, 1H), 2.33 (dd, J=6.4, 12.8 Hz, 1H), 1.63 (s, 3H), 1.56 (s, 3H), 0.65-0.73 (m, 4H). LC-MS: m/z 475 $[M+H]^+$.

The absolute stereochemistry for each separated isomer was not determined.

Method P4

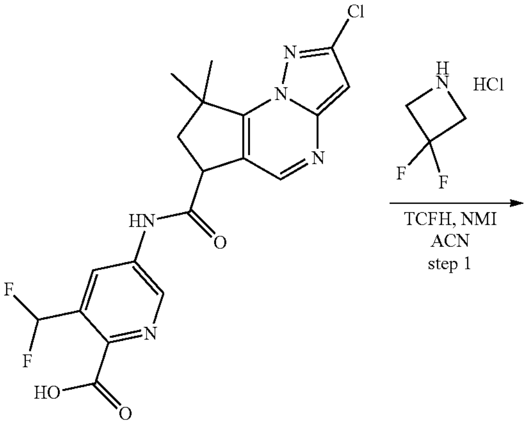

Method J2 Step 2

-continued

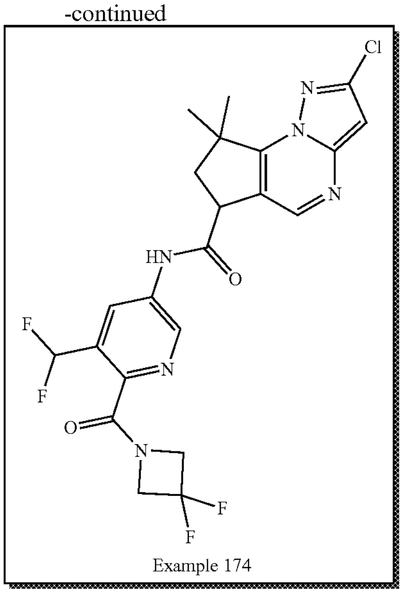

Example 174

Example 174: 2-chloro-N-(6-(3,3-difluoroazetidine-1-carbonyl)-5-(difluoromethyl)pyridin-3-yl)-8,8-dimethyl-7,8-dihydro-6H-cyclopenta[e]pyrazolo[1,5-a]pyrimidine-6-carboxamide Step 1: 2-chloro-N-(6-(3,3-difluoroazetidine-1-carbonyl)-5-(difluoromethyl)pyridin-3-yl)-8,8-dimethyl-7,8-dihydro-6H-cyclopenta[e]pyrazolo[1,5-a]pyrimidine-6-carboxamide Example 174

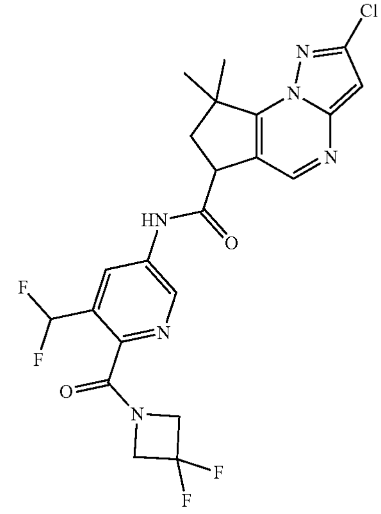

Analogously to Method 04 Step 1, Example 174 (18.4 mg, 31% yield) was obtained as a white solid.

Example 174: $^1$H NMR (400 MHz, DMSO-$d_6$) δ 11.01 (s, 1H), 8.94 (d, J=2.0 Hz, 1H), 8.65 (s, 1H), 8.56 (d, J=2.0 Hz, 1H), 7.57 (t, J=55.2 Hz, 1H), 6.95 (s, 1H), 4.85 (t, J=12.8 Hz, 2H), 4.36-4.57 (m, 3H), 2.57 (dd, J=9.2, 13.2 Hz, 1H), 2.33 (dd, J=6.4, 13.2 Hz, 1H), 1.64 (s, 3H), 1.56 (s, 3H). LC-MS: m/z 511 $[M+H]^+$.

Method Q4

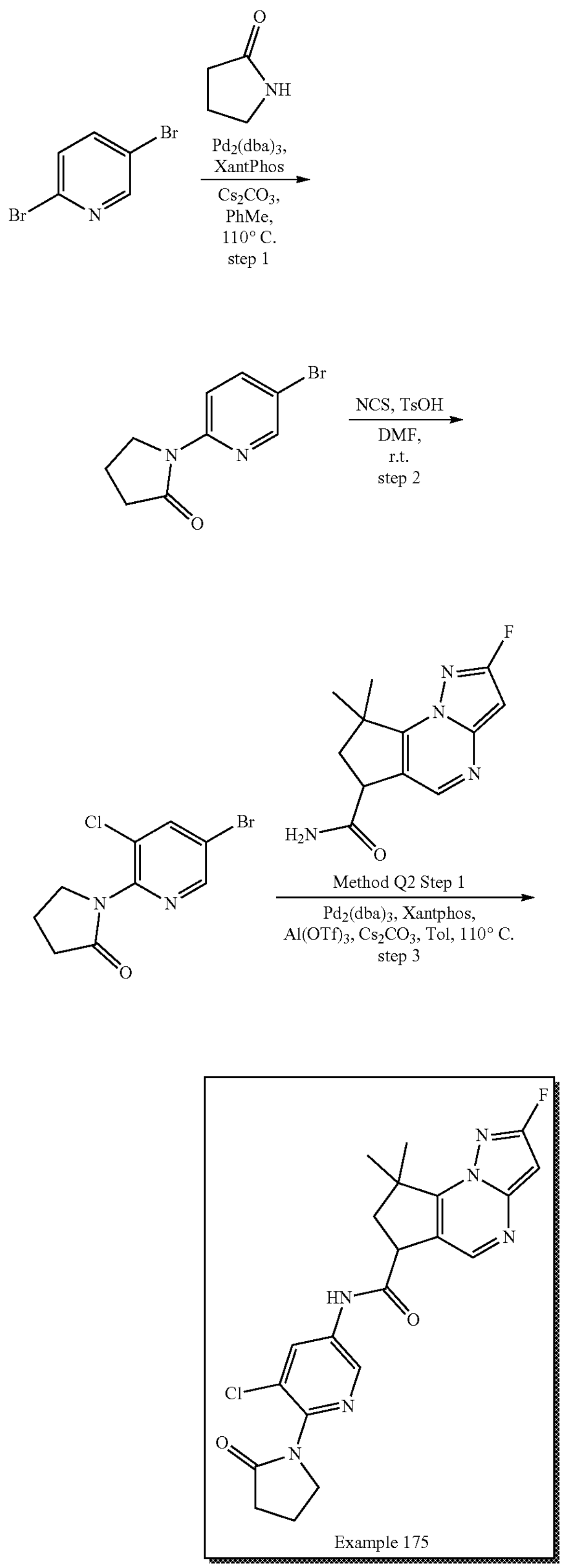

Example 175: N-(5-chloro-6-(2-oxopyrrolidin-1-yl)pyridin-3-yl)-2-fluoro-8,8-dimethyl-7,8-dihydro-6H-cyclopenta[e]pyrazolo[1,5-a]pyrimidine-6-carboxamide Step 1:1-(5-bromopyridin-2-yl)pyrrolidin-2-one

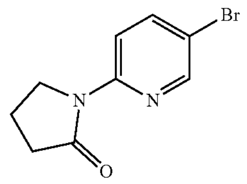 [SMILES: O=C1CCCN1c1ccc(Br)cn1]

To a stirred mixture of 2,5-dibromopyridine (1.0 g, 4.2 mmol) in toluene (20 mL) were added pyrrolidin-2-one (360 mg, 4.2 mmol), XantPhos (492 mg, 851 μmol), $Pd_2(dba)_3$ (440 mg, 425 μmol) and $Cs_2CO_3$ (2.8 g, 8.5 mmol) at 25° C. The resulting mixture was stirred at 110° C. for 12 h under nitrogen atmosphere. The mixture was allowed to cool down to 25° C., quenched with water (100 mL) and extracted with ethyl acetate (3×100 mL). The combined organic layers were dried over anhydrous sodium sulfate and concentrated under reduced pressure. The residue was applied onto a silica gel column and eluted with EtOAc/PE (1:9) to give 1-(5-bromopyridin-2-yl)pyrrolidin-2-one (0.7 g, 68% yield) as a white solid. LC-MS: m/z 241 $[M+H]^+$.

Step 2:1-(5-bromo-3-chloropyridin-2-yl)pyrrolidin-2-one

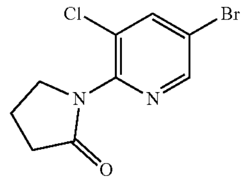 [SMILES: O=C1CCCN1c1ncc(Br)cc1Cl]

To a stirred mixture of 1-(5-bromopyridin-2-yl)pyrrolidin-2-one (650 mg, 2.7 mmol) in DMF (10 mL) were added NCS (1.1 g, 8.1 mmol) and TsOH (51.5 mg, 27 μmol). The mixture was stirred at 25° C. for 60 h under nitrogen atmosphere. The reaction mixture was diluted with water (50 mL) and extracted with ethyl acetate (3×50 mL). The combined organic layers were dried over anhydrous sodium sulfate and concentrated under reduced pressure. The residue was applied onto a silica gel column and eluted with EtOAc/PE (3:1) to give 1-(5-bromo-3-chloropyridin-2-yl)pyrrolidin-2-one (200 mg, 27% yield) as a yellow solid. LC-MS: m/z 275 $[M+H]^+$.

Step 3: N-(5-chloro-6-(2-oxopyrrolidin-1-yl)pyridin-3-yl)-2-fluoro-8,8-dimethyl-7,8-dihydro-6H-cyclopenta[e]pyrazolo[1,5-a]pyrimidine-6-carboxamide Example 175

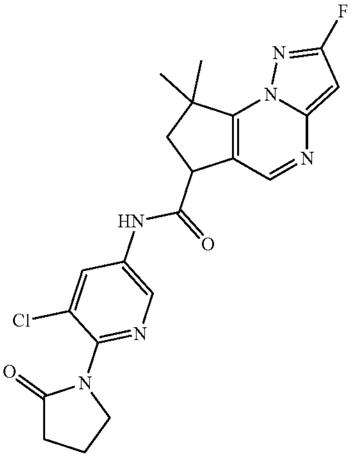

To a stirred mixture of 1-(5-bromo-3-chloropyridin-2-yl)pyrrolidin-2-one (55.5 mg, 201 μmol) and 2-fluoro-8,8-dimethyl-7,8-dihydro-6H-cyclopenta[e]pyrazolo[1,5-a]pyrimidine-6-carboxamide (Method Q2 step 1; 50 mg, 201 μmol) in toluene (5 mL) were added XantPhos (23 mg, 40 μmol), $Pd_2(dba)_3$ (37 mg, 40 μmol), $Cs_2CO_3$ (98 mg, 302 μmol) and $Al(OTf)_3$ (9 mg, 20 μmol) at 25° C. The resulting mixture was stirred at 110° C. for 2 h under nitrogen atmosphere.

The mixture was allowed to cool down to 25° C., diluted with water (30 mL) and extracted with DCM (3x30 mL). The combined organic layers were dried over anhydrous sodium sulfate and concentrated under reduced pressure. The residue was submitted to Prep-HPLC purification and the collected fractions were lyophilized to give Example 175 (17.9 mg, 20% yield) as a white solid.

Example 175: $^1H$ NMR (400 MHz, DMSO-$d_6$) δ: 10.81 (s, 1H), 8.60-8.63 (m, 2H), 8.34 (d, J=2.4 Hz, 1H), 6.55 (d, J=4.8 Hz, 1H), 4.39 (dd, J=6.4, 9.2 Hz, 1H), 3.79 (t, J=7.2 Hz, 2H), 2.52 (dd, J=9.2, 13.2 Hz, 1H), 2.45 (t, J=8.0 Hz, 2H), 2.30 (dd, J=6.4, 13.2 Hz, 1H), 2.11-2.18 (m, 2H), 1.61 (s, 3H), 1.58 (s, 3H). LC-MS: m/z 443 $[M+H]^+$.

Method R4

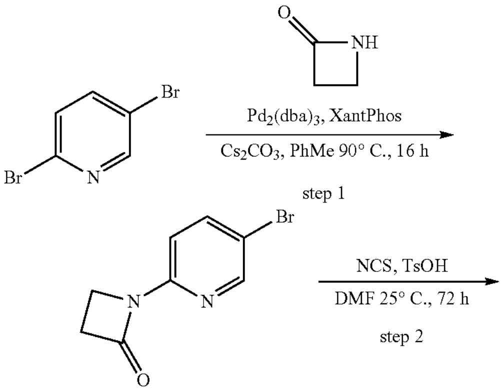

-continued

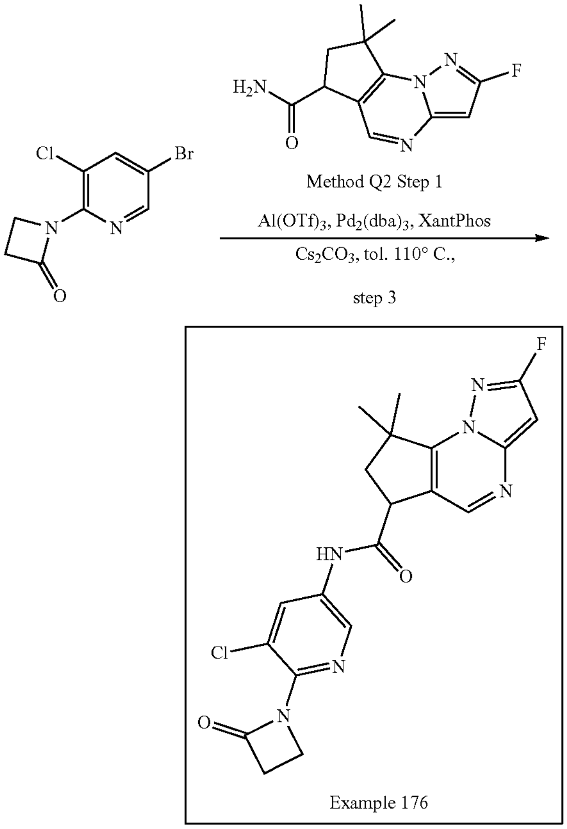

Example 176

Example 176: N-(5-chloro-6-(2-oxoazetidin-1-yl)pyridin-3-yl)-2-fluoro-8,8-dimethyl-7,8-dihydro-6H-cyclopenta[e]pyrazolo[1,5-a]pyrimidine-6-carboxamide Analogously to Example 175 using azetidin-2-one, Example 176 (20 mg, 18% yield) was obtained as a white solid.

Example 176: $^1H$ NMR (300 MHz, DMSO-$d_6$) δ: 10.73 (s, 1H), 8.59 (s, 1H), 8.52 (d, J=2.4 Hz, 1H), 8.31 (d, J=2.1 Hz, 1H), 6.55 (d, J=4.8 Hz, 1H), 4.38 (dd, J=6.3, 9.0 Hz, 1H), 3.80 (t, J=4.8 Hz, 2H), 3.09 (t, J=4.8 Hz, 2H), 2.51-2.54 (m, 1H), 2.30 (dd, J=6.3, 12.9 Hz, 1H), 1.61 (s, 3H), 1.53 (s, 3H). LC-MS: m/z 429 $[M+H]^+$.

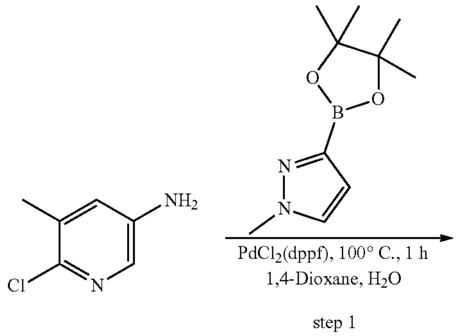

-continued

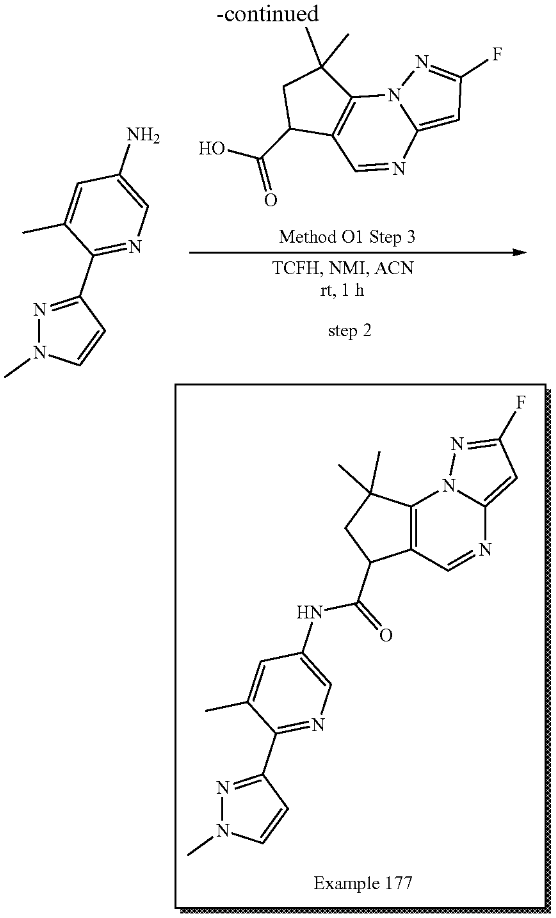

Method S4

Example 177: 2-fluoro-8,8-dimethyl-N-(5-methyl-6-(1-methyl-1H-pyrazol-3-yl)pyridin-3-yl)-7,8-dihydro-6H-cyclopenta[e]pyrazolo[1,5-a]pyrimidine-6-carboxamide

Step 1:5-Methyl-6-(1-methyl-1H-pyrazol-3-yl)pyridin-3-amine

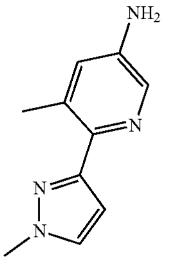

To a stirred solution of 6-chloro-5-methylpyridin-3-amine (400 mg, 2.8 mmol) and 1-methyl-3-(4,4,5,5-tetramethyl-1,3,2-dioxaborolan-2-yl)-1H-pyrazole (583 mg, 2.8 mmol) in 1,4-Dioxane (5 mL) and water (1 mL) were added 1,1'-Bis (diphenylphosphino)ferrocene-palladium(II)dichloride dichloromethane complex (229 mg, 280.5 μmol) and $K_2CO_3$ (1.2 g, 8.4 mmol). The mixture was stirred at 100° C. for 1 h under nitrogen atmosphere. The reaction mixture was quenched with water (20 mL) and extracted with ethyl acetate (3×20 mL). The combined organic layers were dried over anhydrous sodium sulfate and concentrated under reduced pressure. The residue was submitted to Prep-HPLC purification and the collected fractions were lyophilized to give 5-methyl-6-(1-methyl-1H-pyrazol-3-yl)pyridin-3-amine(450 mg, 78% yield) as a white solid. $^1$H NMR (300 MHz, DMSO-$d_6$) δ 7.80 (d, J=2.4 Hz, 1H), 7.62 (d, J=2.1 Hz, 1H), 6.76 (d, J=2.7 Hz, 1H), 6.56 (d, J=2.1 Hz, 1H), 5.25 (s, 2H), 3.85 (s, 3H), 2.44 (s, 3H). LC-MS: m/z 189 [M+H]$^+$.

Step 2: 2-Fluoro-8,8-dimethyl-N-(5-methyl-6-(1-methyl-1H-pyrazol-3-yl)pyridin-3-yl)-7,8-dihydro-6H-cyclopenta[e]pyrazolo[1,5-a]pyrimidine-6-carboxamide Example 177

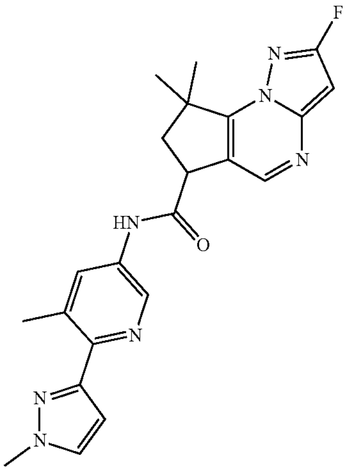

Analogously to Method G4 Step 4, Example 177 (33 mg, 49% yield) was obtained as a white solid.

Example 177: $^1$H NMR (400 MHz, DMSO-$d_6$) δ 10.54 (s, 1H), 8.64 (d, J=2.4 Hz, 1H), 8.60 (s, 1H), 7.98 (d, J=2.0 Hz, 1H), 7.73 (d, J=2.0 Hz, 1H), 6.73 (d, J=2.0 Hz, 1H), 6.56 (d, J=4.8 Hz, 1H), 4.39 (dd, J=6.4, 9.2 Hz, 1H), 3.91 (s, 3H), 2.58 (s, 3H), 2.52 (dd, J=9.2, 12.8 Hz, 1H), 2.30 (dd, J=6.4, 13.2 Hz, 1H), 1.63 (s, 3H), 1.54 (s, 3H). LC-MS: m/z 420 [M+H]$^+$.

Method T4

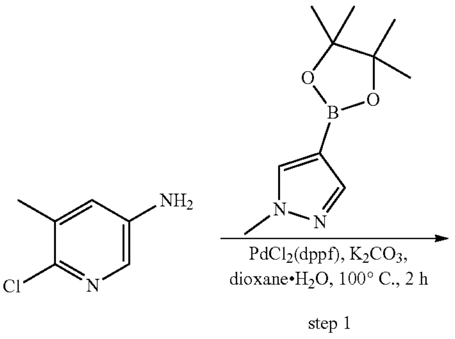

-continued

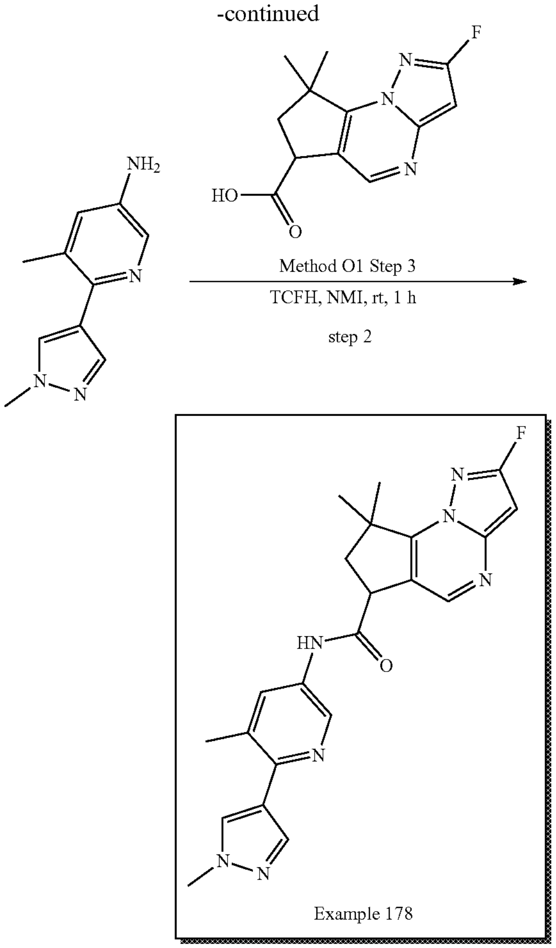

Example 178

Example 178: 2-fluoro-8,8-dimethyl-N-(5-methyl-6-(1-methyl-1H-pyrazol-4-yl)pyridin-3-yl)-7,8-dihydro-6H-cyclopenta[e]pyrazolo[1,5-a]pyrimidine-6-carboxamide Analogously to Example 177 using 1-methyl-4-(4,4,5,5-tetramethyl-1,3,2-dioxaborolan-2-yl)-1H-pyrazole, Example 178 (25.6 mg, 28% yield) was obtained as a white solid.

Example 178: $^1$H NMR (400 Hz, DMSO-$d_6$) δ: 10.50 (s, 1H), 8.61 (d, J=2.4 Hz, 1H), 8.60 (s, 1H), 8.14 (s, 1H), 7.95 (d, J=2.0 Hz, 1H), 7.89 (s, 1H), 6.56 (d, J=5.2 Hz, 1H), 4.39 (dd, J=6.4, 9.2 Hz, 1H), 3.90 (s, 3H), 2.51-2.55 (m, 1H), 2.42 (s, 3H), 2.30 (dd, J=6.4, 13.2 Hz, 1H), 1.63 (s, 3H), 1.54 (s, 3H). LC-MS: m/z 420 $[M+H]^+$.

Method U4

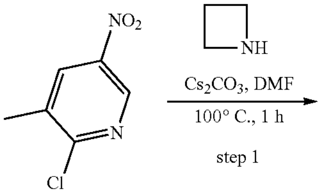

-continued

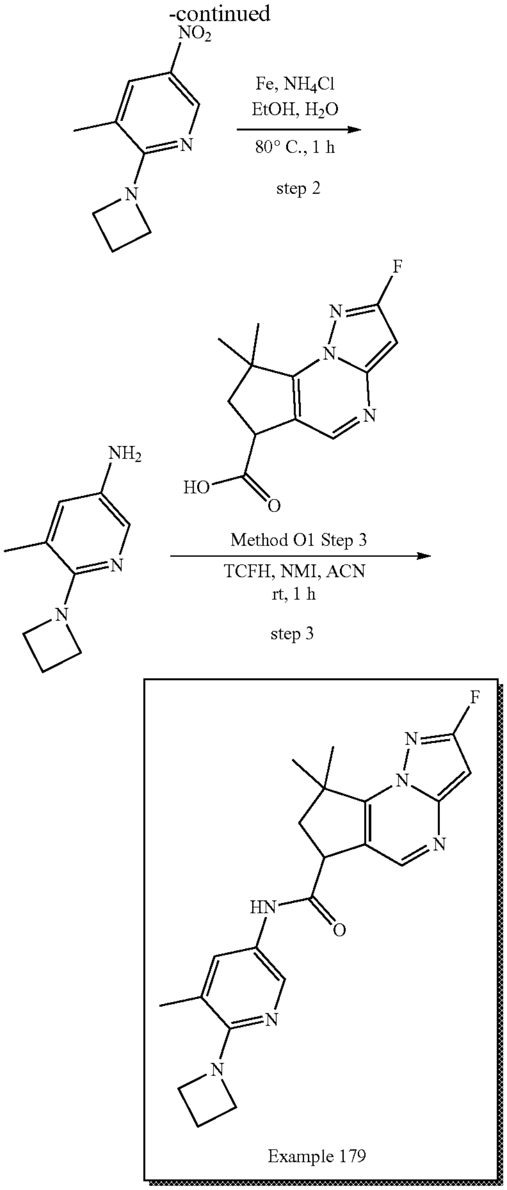

Example 179

Example 179: N-(6-(azetidin-1-yl)-5-methylpyridin-3-yl)-2-fluoro-8,8-dimethyl-7,8-dihydro-6H-cyclopenta[e]pyrazolo[1,5-a]pyrimidine-6-carboxamide Step 1: 2-(Azetidin-1-yl)-3-methyl-5-nitropyridine

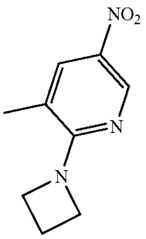

To a stirred solution of 2-chloro-3-methyl-5-nitropyridine (700 mg, 4 mmol) in DMF (10 mL) were added azetidine (347 mg, 6 mmol) and $Cs_2CO_3$ (3.9 g, 12.1 mmol). The mixture was stirred at 100° C. for 1 h. The reaction mixture was quenched with water (50 mL) and extracted with ethyl acetate (3×50 mL). The combined organic layers were dried over anhydrous sodium sulfate and concentrated under reduced pressure. The residue was applied onto a silica gel column and eluted with EtOAc/PE (1:3) to give 2-(azetidin-1-yl)-3-methyl-5-nitropyridine (650 mg, 82% yield) as a white solid. $^1$H NMR (300 MHz, DMSO-$d_6$) δ 8.79 (d, J=2.7 Hz, 1H), 7.96-7.98 (m, 1H), 4.37 (t, J=7.8 Hz, 4H), 2.25-2.38 (m, 5H). LC-MS: m/z 194 $[M+H]^+$.

Step 2: 6-(Azetidin-1-yl)-5-methylpyridin-3-amine

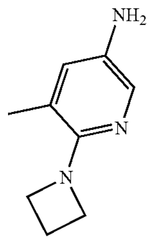

To a stirred solution of 2-(azetidin-1-yl)-3-methyl-5-nitropyridine (600 mg, 3.1 mmol) in EtOH (9 mL) and water (3 ml) were added iron powder (520 mg, 9.3 mmol) and $NH_4Cl$ (830 mg, 15.5 mmol). The mixture was stirred at 80° C. for 1 h. The reaction mixture was filtered, and the filtrate was concentrated under reduced pressure. The residue was diluted with water (50 mL) and extracted with ethyl acetate (3×50 mL). The combined organic layers were dried over anhydrous sodium sulfate and concentrated under reduced pressure. The residue was purified by prep-HPLC purification, and the collected fractions were concentrated under reduced pressure to give 6-(azetidin-1-yl)-5-methylpyridin-3-amine (200 mg, 38% yield) as a yellow oil. LC-MS: m/z 164 $[M+H]^+$.

Step 3: N-(6-(azetidin-1-yl)-5-methylpyridin-3-yl)-2-fluoro-8,8-dimethyl-7,8-dihydro-6H-cyclopenta[e]pyrazolo[1,5-a]pyrimidine-6-carboxamide Example 179

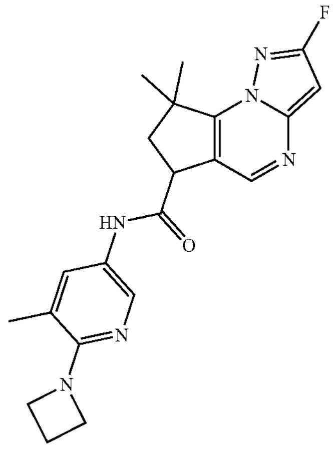

Analogously to Method G4 Step 4, Example 179 (62.8 mg, 65% yield) was obtained as a white solid.

Examples 179: $^1$H NMR (300 MHz, DMSO-$d_6$) δ 10.13 (s, 1H), 8.55 (s, 1H), 8.15 (d, J=2.1 Hz, 1H), 7.59 (d, J=2.1 Hz, 1H), 6.54 (d, J=4.8 Hz, 1H), 4.30 (dd, J=6.3, 9.0 Hz, 1H), 3.97 (t, J=7.5 Hz, 4H), 2.45-2.55 (m, 1H), 2.18-2.30 (m, 3H), 2.11 (s, 3H), 1.61 (s, 3H), 1.52 (s, 3H). LC-MS: m/z 395 $[M+H]^+$.

Method V4

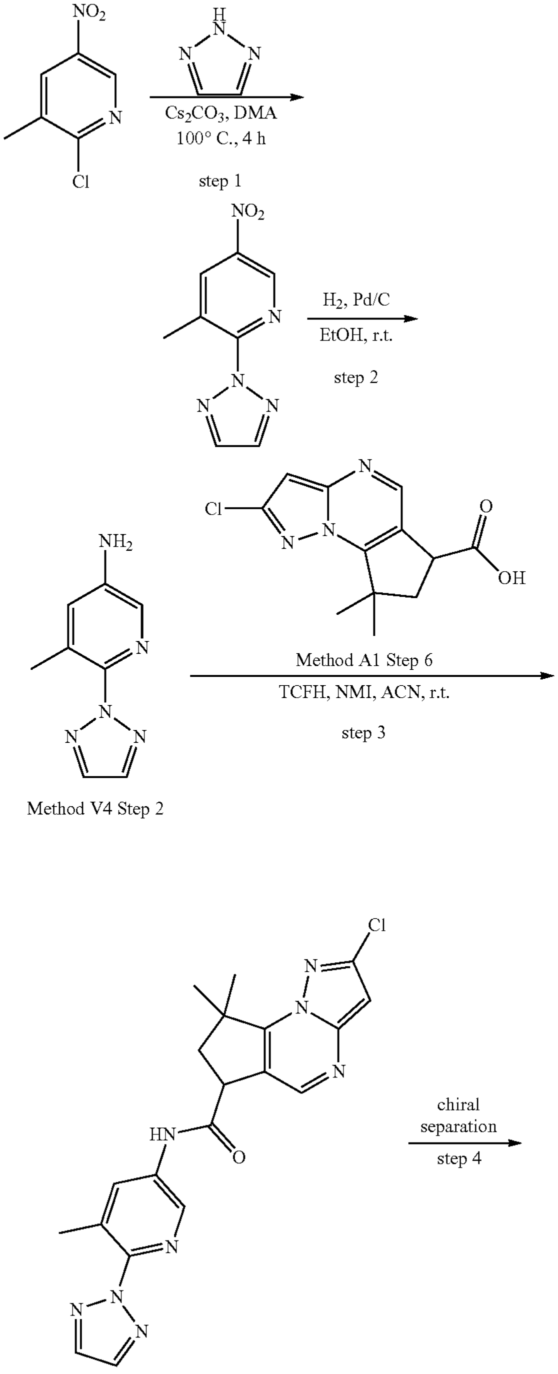

-continued

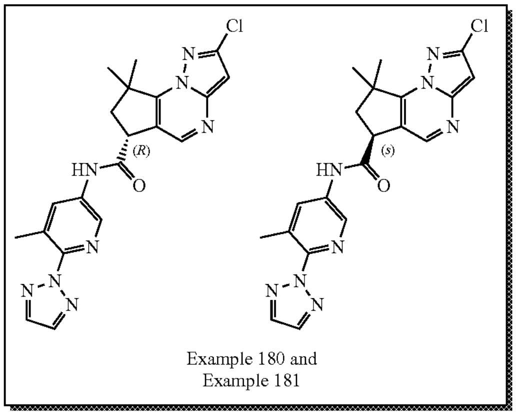

Example 180 and
Example 181

Examples 180 and 181: Single Enantiomers Obtained from a Racemic Mixture Containing (R)-2-chloro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide and (S)-2-chloro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide Step 1: 3-methyl-5-nitro-2-(2H-1,2,3-triazol-2-yl)pyridine

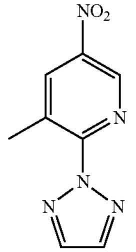

To a stirred solution of 2-chloro-3-methyl-5-nitropyridine (5 g, 28.9 mmol) and 2H-1,2,3-triazole (4 g, 57.9 mmol) in DMA (50 mL) was added $Cs_2CO_3$ (25.5 g, 78.5 mmol). The reaction mixture was stirred at 100° C. for 4 h. The reaction mixture was quenched with water (200 mL) and extracted with ethyl acetate (3×250 mL). The combined organic layers were washed with brine, dried over anhydrous sodium sulfate and concentrated under reduced pressure. The residue was applied on a silica gel column and eluted with EtOAc/PE (1:1) to give 3-methyl-5-nitro-2-(2H-1,2,3-triazol-2-yl)pyridine (1 g, 16% yield) as a yellow solid. LC-MS: m/z 206 $[M+H]^+$.

Step 2: 5-methyl-6-(2H-1,2,3-triazol-2-yl)pyridin-3-amine

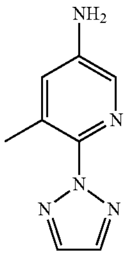

To a solution of 3-methyl-5-nitro-2-(2H-1,2,3-triazol-2-yl)pyridine (1 g, 4.9 mmol) in ethanol (20 mL) was added Pd/C (200 mg, 10%). The resulting mixture was stirred at 25° C. for 24 h under hydrogen atmosphere. The solids were filtered out. The filtrate was concentrated under reduced pressure to afford 5-methyl-6-(2H-1,2,3-triazol-2-yl)pyridin-3-amine (Method V4 step 2; 230 mg, 27% yield) as a yellow solid. LC-MS: m/z 176 $[M+H]^+$.

Step 3: 2-chloro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide

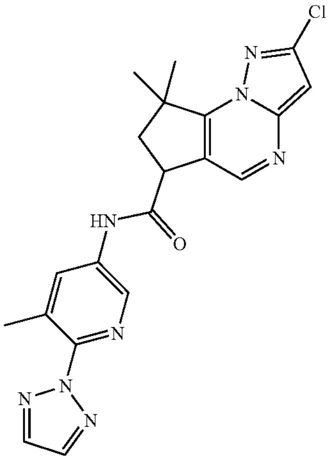 [SMILES: Cc1cc(NC(=O)C2CC(C)(C)c3c2cnc2cc(Cl)nn32)cnc1-n1nccn1]

Analogously to Method G4 Step 4, 2-chloro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide (64 mg, 20% yield) was obtained as a white solid. LC-MS: m/z 423 $[M+H]^+$.

Step 4: Separation of Enantiomers to Obtain (R)-2-chloro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide and (S)-2-chloro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide

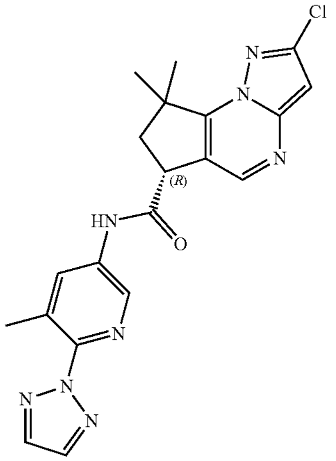

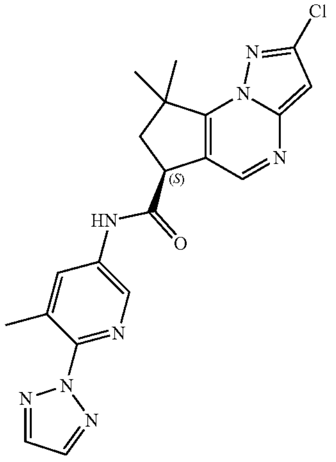

Example 180 and Example 181

60 mg of 2-chloro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide were submitted to chiral HPLC purification (Column: CHIRAL ART Amylose-SA, 2×25 cm, 5 μm; Mobile Phase A: Hex:DCM=3:1 (0.5% 2M $NH_3$-MeOH)-HPLC, Mobile Phase B: EtOH-HPLC; Flow rate: 20 mL/min; isocratic 50% B in 7.5 min; Wave Length: 220/254 nm; RT1(min): 4.164; RT2(min): 5.843; Sample Solvent: EtOH-HPLC; Injection Volume: 0.6 mL; Number Of Runs: 3). The first eluting isomer was concentrated and lyophilized to afford Example 180 (13.8 mg, 22%) as a white solid. The second eluting isomer was concentrated and lyophilized to afford Example 181 (16 mg, 26%) as a white solid.

Example 180: $^1H$ NMR (300 MHz, DMSO-$d_6$) δ 10.80 (s, 1H), 8.63-8.66 (m, 2H), 8.25 (d, J=1.8 Hz, 1H), 8.11 (s, 2H), 6.95 (s, 1H), 4.45 (dd, J=6.3, 9.0 Hz, 1H), 2.57 (dd, J=9.0, 13.2 Hz, 1H), 2.33 (dd, J=6.3, 13.2 Hz, 1H), 2.20 (s, 3H), 1.65 (s, 3H), 1.57 (s, 3H). LC-MS: m/z 423 $[M+H]^+$.

Example 181: $^1H$ NMR (300 MHz, DMSO-$d_6$) δ 10.80 (s, 1H), 8.63-8.66 (m, 2H), 8.25 (d, J=2.1 Hz, 1H), 8.11 (s, 2H), 6.95 (s, 1H), 4.45 (dd, J=6.3, 9.0 Hz, 1H), 2.57 (dd, J=9.0, 13.2 Hz, 1H), 2.33 (dd, J=6.3, 13.2 Hz, 1H), 2.20 (s, 3H), 1.65 (s, 3H), 1.57 (s, 3H). LC-MS: m/z 423 $[M+H]^+$.

The absolute stereochemistry for each separated isomer was not determined.

Method W4

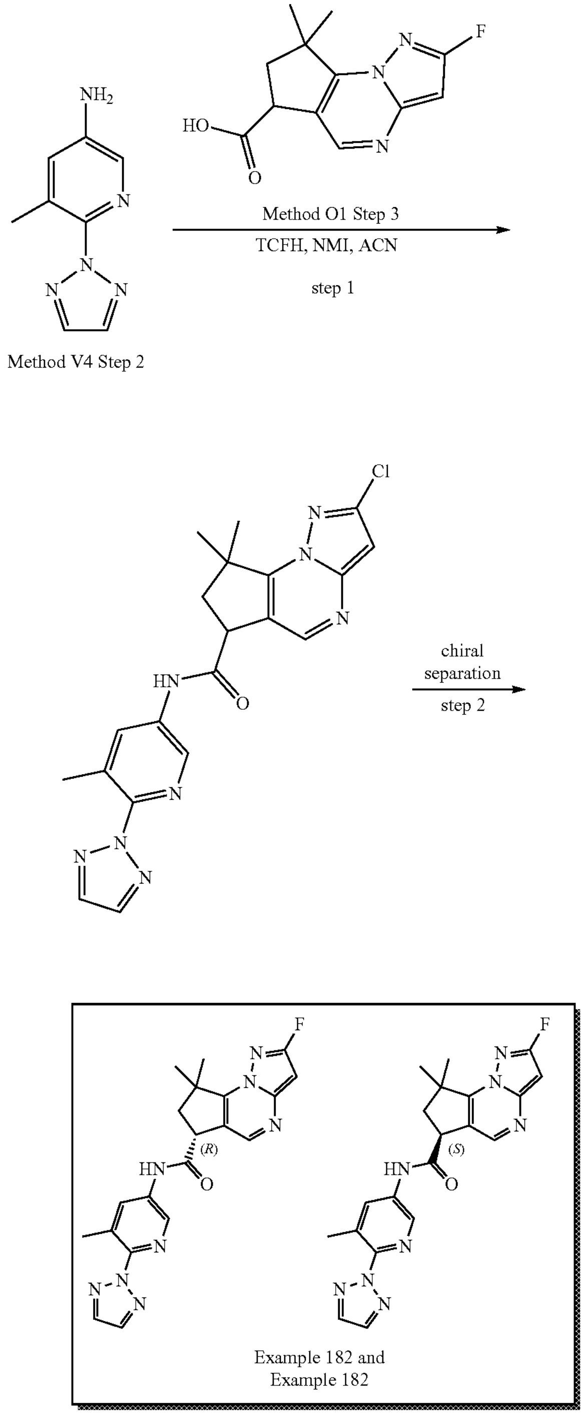

Example 182 and Example 182

Examples 182 and 183: Single Enantiomers Obtained from a Racemic Mixture Containing (R)-2-fluoro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide and (S)-2-fluoro-8,8-dimethyl-N-(5-methyl-6-(2H-1,2,3-triazol-2-yl)pyridin-3-yl)-7,8-dihydro-6H-cyclopenta[e]pyrazolo[1,5-a]pyrimidine-6-carboxamide The title compounds were prepared similarly to Example 180 and 181 using 2-fluoro-8,8-dimethyl-7,8-dihydro-6H-cyclopenta[e]pyrazolo[1,5-a]pyrimidine-6-carboxylic acid. The final compounds were purified by chiral HPLC purification (Column: CHIRAL ART Amylose-SA, 2×25 cm, 5 μm; Mobile Phase A: Hex:DCM=3:1(0.5% 2M $NH_3$-MeOH)-HPLC, Mobile Phase B: EtOH-HPLC; Flow rate: 20 mL/min; isocratic 50% B in 9 min; Wave Length: 220/254 nm; RT1(min): 4.213; RT2(min): 5.765; Sample Solvent: EtOH-HPLC; Injection Volume: 0.7 mL; Number of Runs: 5). The first eluting isomer was concentrated and lyophilized to afford Example 182 (5.7 mg, 51%) as a white solid. The second eluting isomer was concentrated and lyophilized to afford Example 183 (7.6 mg, 67%) as a white solid.

Example 182: $^1$H NMR (300 MHz, DMSO-$d_6$) δ 10.82 (s, 1H), 8.65 (d, J=2.4 Hz, 1H), 8.63 (s, 1H), 8.25 (d, J=2.1 Hz, 1H), 8.11 (s, 2H), 6.56 (d, J=4.8 Hz, 1H), 4.44 (dd, J=6.3, 9.0 Hz, 1H), 2.55 (dd, J=9.0, 13.2 Hz, 1H), 2.33 (dd, J=6.3, 13.2 Hz, 1H), 2.20 (s, 3H), 1.64 (s, 3H), 1.55 (s, 3H). LC-MS: m/z 407 $[M+H]^+$ Example 183: $^1$H NMR (300 MHz, DMSO-$d_6$) δ 10.81 (s, 1H), 8.65 (d, J=2.4 Hz, 1H), 8.63 (s, 1H), 8.25 (d, J=1.8 Hz, 1H), 8.09 (s, 2H), 6.56 (d, J=5.1 Hz, 1H), 4.44 (dd, J=6.3, 9.0 Hz, 1H), 2.56 (dd, J=9.0, 13.2 Hz, 1H), 2.33 (dd, J=6.3, 13.2 Hz, 1H), 2.20 (s, 3H), 1.64 (s, 3H), 1.55 (s, 3H). LC-MS: m/z 407 $[M+H]^+$.

The absolute stereochemistry for each separated isomer was not determined.

Method X4

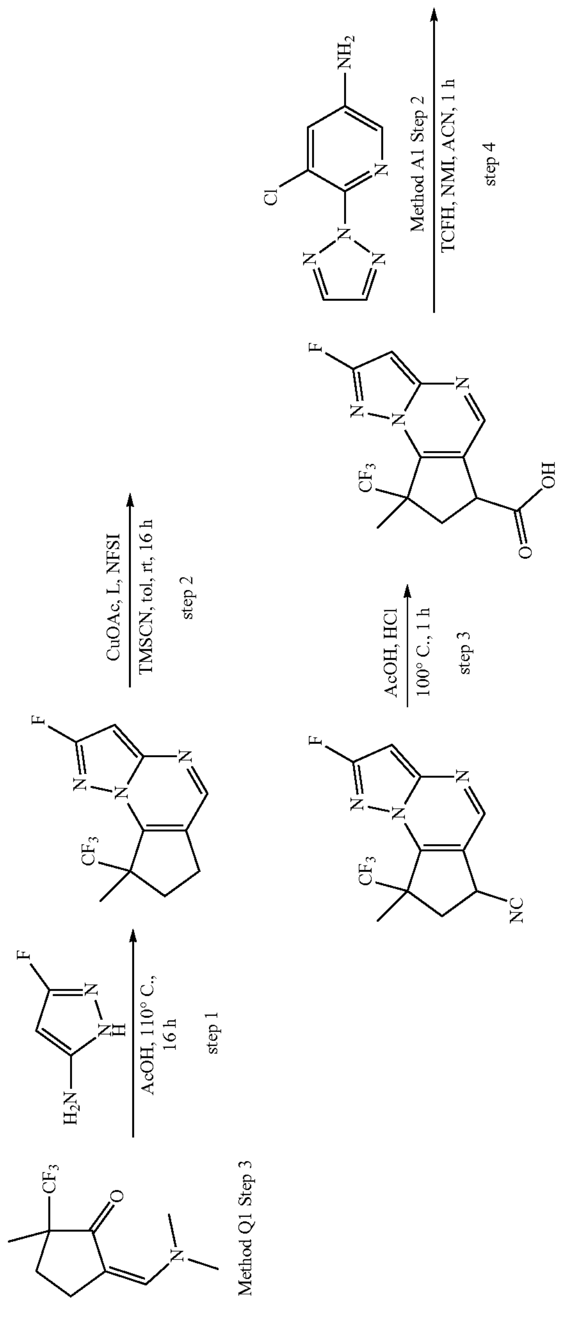
Method Q1 Step 3
AcOH, 110° C.,
16 h
step 1
CuOAc, L, NFSI
TMSCN, tol, rt, 16 h
step 2
AcOH, HCl
100° C., 1 h
step 3
Method A1 Step 2
TCFH, NMI, ACN, 1 h
step 4

-continued
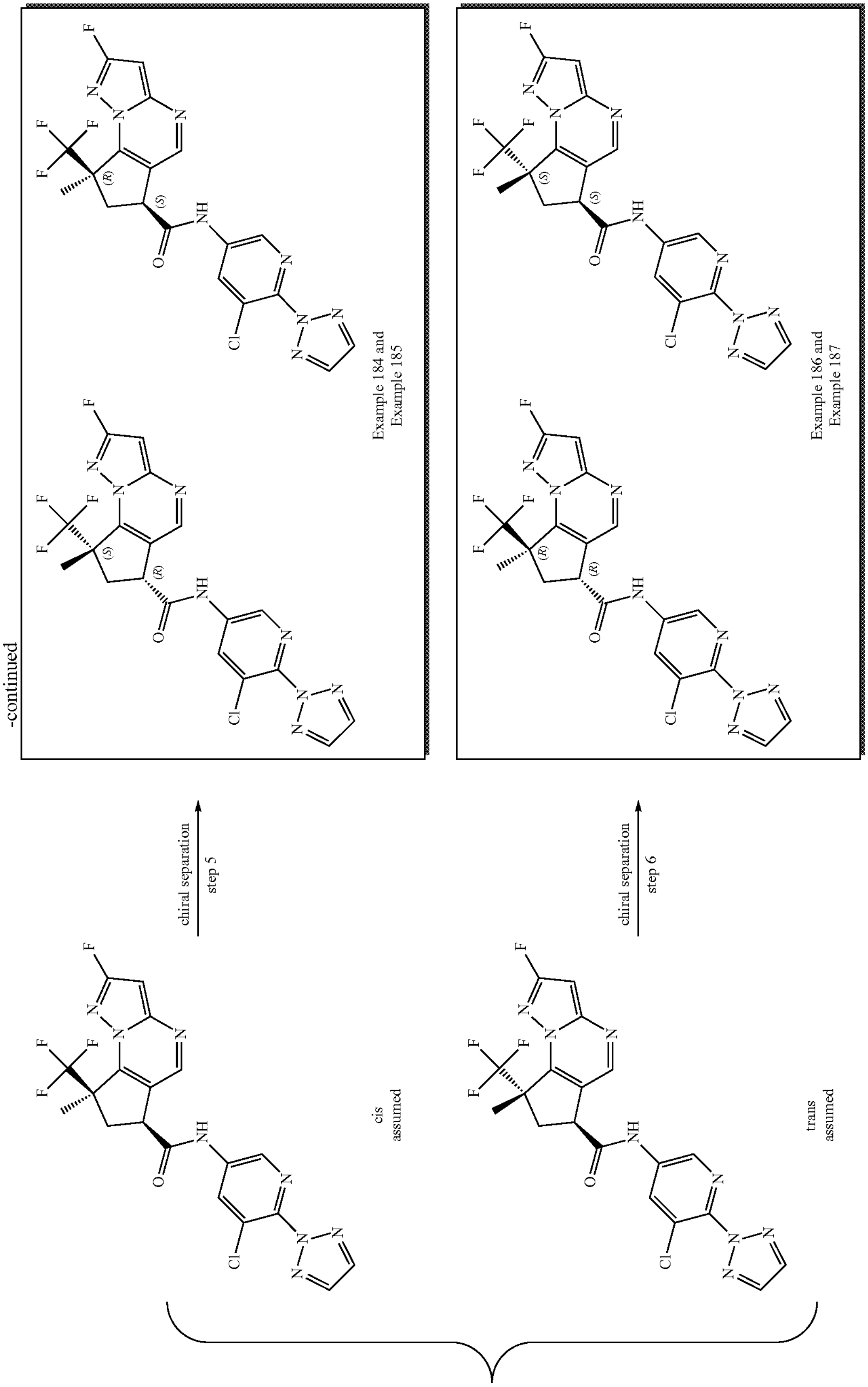

Examples 184 and 185: Single Enantiomers Obtained from a Racemic Mixture Containing (6R, 8S)—N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide and (6S,8R)—N-(5-chloro-6-(2H-1,2,3-triazol-2-yl)pyridine-3-yl)-2-fluoro-8-methyl-8-(trifluoromethyl)-7,8-dihydro-6H-cyclopenta[e]pyrazolo[1,5-a]pyrimidine-6-carboxamide Examples 186 and 187: Single enantiomers obtained from a racemic mixture containing (6R, 8R)—N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide and (6S,8S)—N-(5-chloro-6-(2H-1,2,3-triazol-2-yl)pyridine-3-yl)-2-fluoro-8-methyl-8-(trifluoromethyl)-7,8-dihydro-6H-cyclopenta[e]pyrazolo[1,5-a]pyrimidine-6-carboxamide Step 1: 2-fluoro-8-methyl-8-(trifluoromethyl)-7,8-dihydro-6H-cyclopenta[e]pyrazolo[1,5-a]pyrimidine

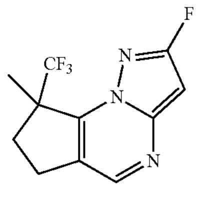 [SMILES: CC1(C(F)(F)F)CCc2cnc3cc(F)nn3c21]

Analogously to Method Q1 Step 4, 2-fluoro-8-methyl-8-(trifluoromethyl)-7,8-dihydro-6H-cyclopenta[e]pyrazolo[1,5-a]pyrimidine (2 g, 15% yield) was obtained as a yellow solid. LC-MS (ES, m/z): 260 $[M+H]^+$.

Step 2: 2-fluoro-8-methyl-8-(trifluoromethyl)-7,8-dihydro-6H-cyclopenta[e]pyrazolo[1,5-a]pyrimidine-6-carbonitrile

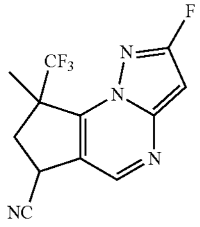 [SMILES: CC1(C(F)(F)F)CC(C#N)c2cnc3cc(F)nn3c21]

Analogously to Method Q1 Step 5, 2-fluoro-8-methyl-8-(trifluoromethyl)-7,8-dihydro-6H-cyclopenta[e]pyrazolo[1,5-a]pyrimidine-6-carbonitrile (220 mg, 10% yield) was obtained as an off-white solid. LC-MS: m/z 285 $[M+H]^+$.

Step 3: 2-fluoro-8-methyl-8-(trifluoromethyl)-7,8-dihydro-6H-cyclopenta[e]pyrazolo[1,5-a]pyrimidine-6-carboxylic acid

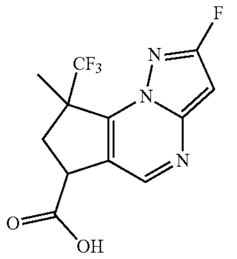 [SMILES: CC1(C(F)(F)F)CC(C(=O)O)c2cnc3cc(F)nn3c21]

Analogously to Method Q1 Step 6, 2-fluoro-8-methyl-8-(trifluoromethyl)-7,8-dihydro-6H-cyclopenta[e]pyrazolo[1,5-a]pyrimidine-6-carboxylic acid (62 mg, 27% yield) was obtained as a yellow oil. LC-MS: m/z 304 $[M+H]^+$.

Step 4: (cis)-N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide and (trans)-N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide

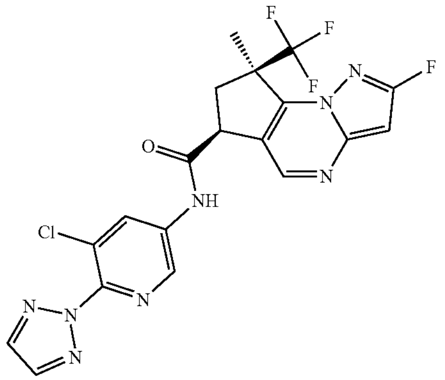

cis
assumed

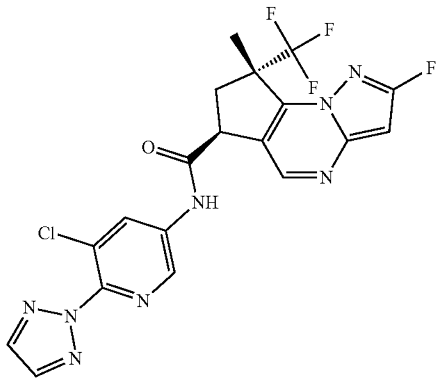

trans
assumed

Analogously to Method G4 Step 4, (cis)-N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide (20 mg, 19% yield) and (trans)-N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide (10 mg, 10% yield) were both obtained as white solids. LC-MS: m/z 481 $[M+H]^+$ and m/z 481 $[M+H]^+$. The relative stereochemistry for the separated, racemic diastereomers was not determined.

Step 5: Separation of Enantiomers to Obtain (6R, 8S)—N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide and (6S,8R)—N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide

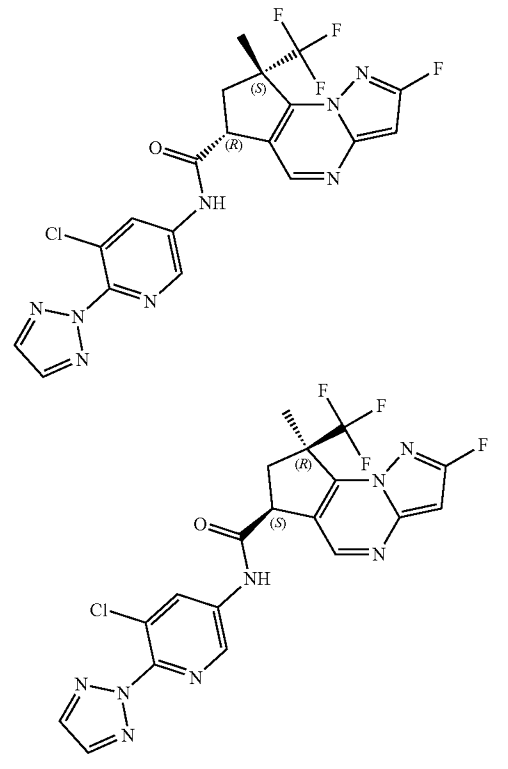

Example 184 and Example 185

20 mg of (cis)-N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide were submitted to chiral-HPLC purification (Column: CHIRAL ART Amylose-SA, 2×25 cm, 5 μm; Mobile Phase A: Hex:DCM=3:1(0.5% 2M $NH_3$-MeOH)-HPLC, Mobile Phase B: EtOH-HPLC; Flow rate: 20 mL/min; isocratic 20% B in 12 min; Wave Length: 220/254 nm; RT1(min): 6.921; RT2(min): 9.982; Sample Solvent: EtOH-HPLC; Injection Volume: 2.5 mL; Number Of Runs: 1). The first eluting isomer was concentrated and lyophilized to afford Example 184 (3.9 mg, 19% yield) as a white solid. The second eluting isomer was concentrated and lyophilized to afford Example 185 (3.7 mg, 18% yield) as a white solid.

Example 184: $^1H$ NMR (400 MHz, DMSO-$d_6$) δ 11.20 (s, 1H), 8.77 (s, 1H), 8.73 (d, J=2.0 Hz, 1H), 8.58 (d, J=2.0 Hz, 1H), 8.19 (s, 2H), 6.72 (d, J=5.2 Hz, 1H), 4.56 (t, J=8.4 Hz, 1H), 3.10 (dd, J=8.0, 14.0 Hz, 1H), 2.52-2.54 (m, 1H), 1.92 (s, 3H). LC-MS: m/z 481 $[M+H]^+$.

Example 185: $^1H$ NMR (400 MHz, DMSO-$d_6$) 11.19 (s, 1H), 8.77 (s, 1H), 8.74 (d, J=2.4 Hz, 1H), 8.59 (d, J=2.4 Hz, 1H), 8.19 (s, 2H), 6.72 (d, J=5.2 Hz, 1H), 4.56 (t, J=8.4 Hz, 1H), 3.10 (dd, J=8.4, 14.0 Hz, 1H), 2.52-2.54 (m, 1H), 1.92 (s, 3H). LC-MS: m/z 481 $[M+H]^+$.

Step 6: Separation of Enantiomers to Obtain (6R, 8R)—N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide and (6S,8S)—N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide

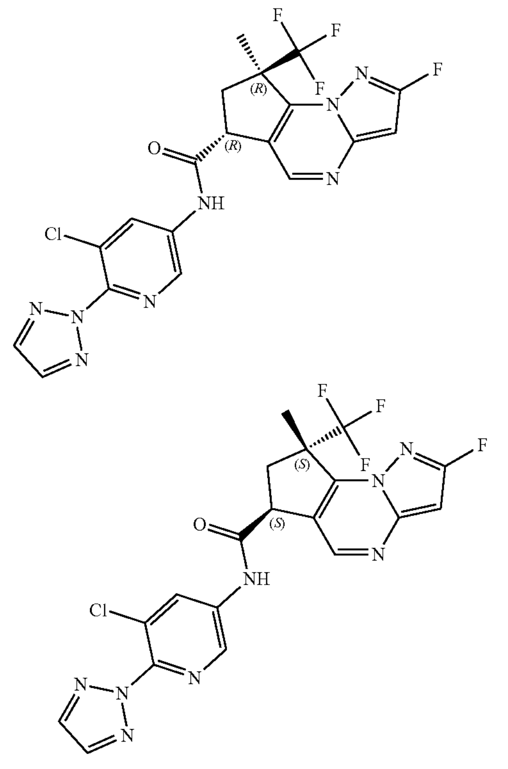

Example 186 and Example 187

10 mg of (trans)-N-(5-chloro-6-(2H-1,2,3-triazol-2-yl)pyridin-3-yl)-2-fluoro-8-methyl-8-(trifluoromethyl)-7,8-dihydro-6H-cyclopenta[e]pyrazolo[1,5-a]pyrimidine-6-carboxamide were submitted to chiral-HPLC purification (Column: CHIRAL ART Amylose-SA, 2*25 cm, 5 μm; Mobile Phase A: Hex:DCM=3:1(0.5% 2M $NH_3$-MeOH)-HPLC, Mobile Phase B: EtOH-HPLC; Flow rate: 20 mL/min; isocratic 10% B in 12 min; Wave Length: 220/254 nm; RT1(min): 7.28; RT2(min): 10.554; Sample Solvent:

EtOH-HPLC; Injection Volume: 3.8 mL; Number Of Runs: 1). The first eluting isomer was concentrated and lyophilized to afford Example 186 (1.8 mg, 17% yield) as a white solid. The second eluting isomer was concentrated and lyophilized to afford Example 187 (1.1 mg, 10% yield) as a white solid.

Example 186: $^1$H NMR (400 MHz, DMSO-$d_6$) δ 11.14 (s, 1H), 8.77 (s, 1H), 8.74 (d, J=2.4 Hz, 1H), 8.58 (d, J=2.0 Hz, 1H), 8.18 (s, 2H), 6.72 (d, J=5.2 Hz, 1H), 4.57 (dd, J=5.2, 10.0 Hz, 1H), 2.89 (dd, J=5.2, 14.0 Hz, 1H), 2.74 (dd, J=9.6, 14.0 Hz, 1H), 1.81 (s, 3H). LC-MS: m/z 481 $[M+H]^+$.

Example 187: $^1$H NMR (400 MHz, DMSO-$d_6$) δ 11.15 (s, 1H), 8.77 (s, 1H), 8.74 (d, J=2.0 Hz, 1H), 8.58 (d, J=1.6 Hz, 1H), 8.18 (s, 2H), 6.72 (d, J=5.2 Hz, 1H), 4.57 (dd, J=5.2, 9.6 Hz, 1H), 2.89 (dd, J=5.2, 14.4 Hz, 1H), 2.74 (dd, J=9.6, 14.4 Hz, 1H), 1.81 (s, 3H). LC-MS: m/z 481 $[M+H]^+$.

The absolute stereochemistry for each separated isomer was not determined.

Method Y4

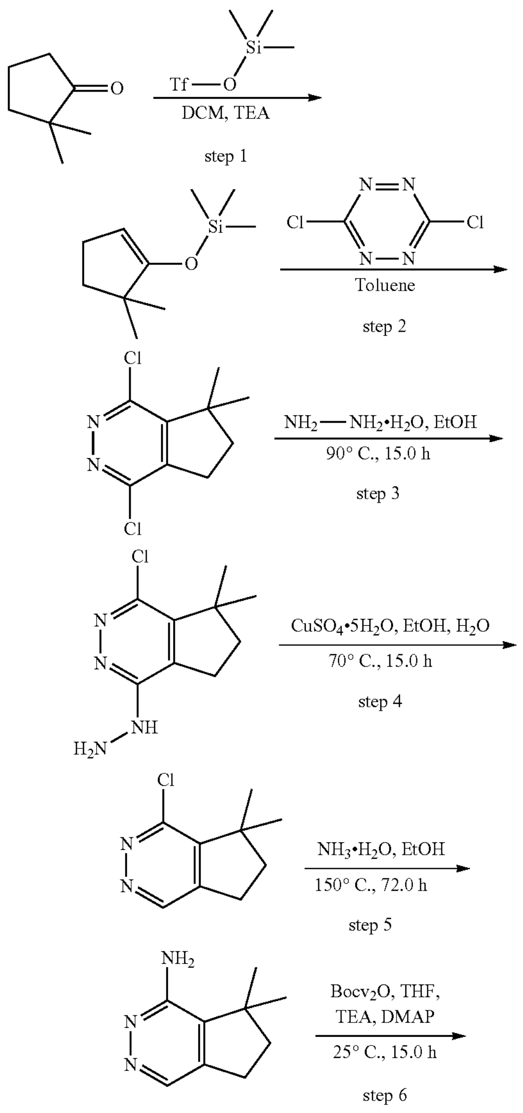

-continued

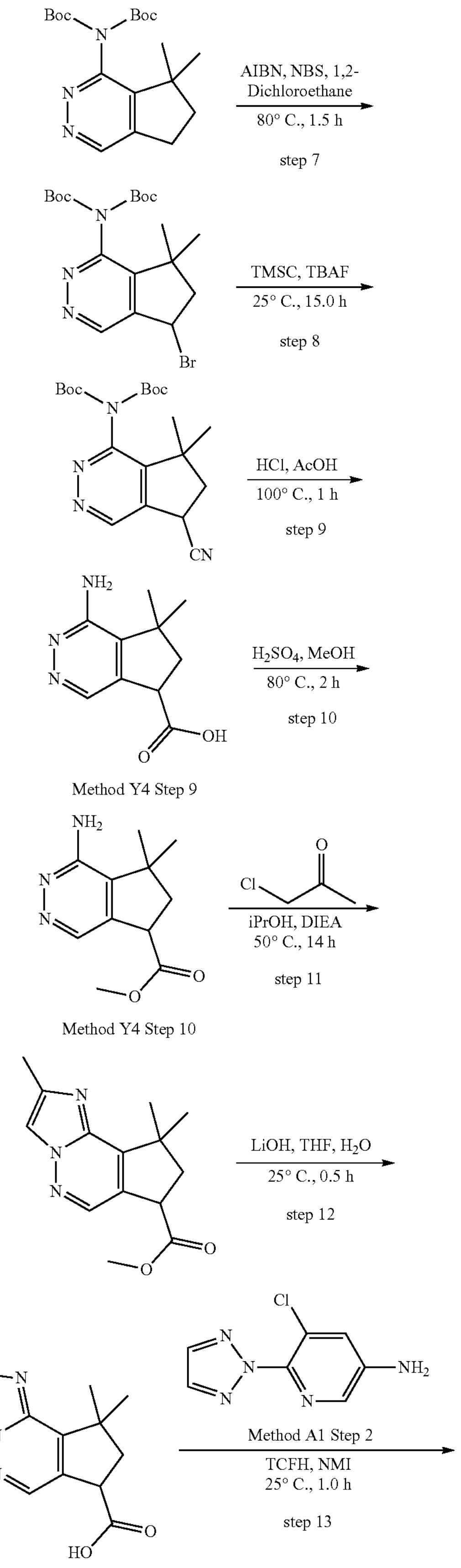

-continued

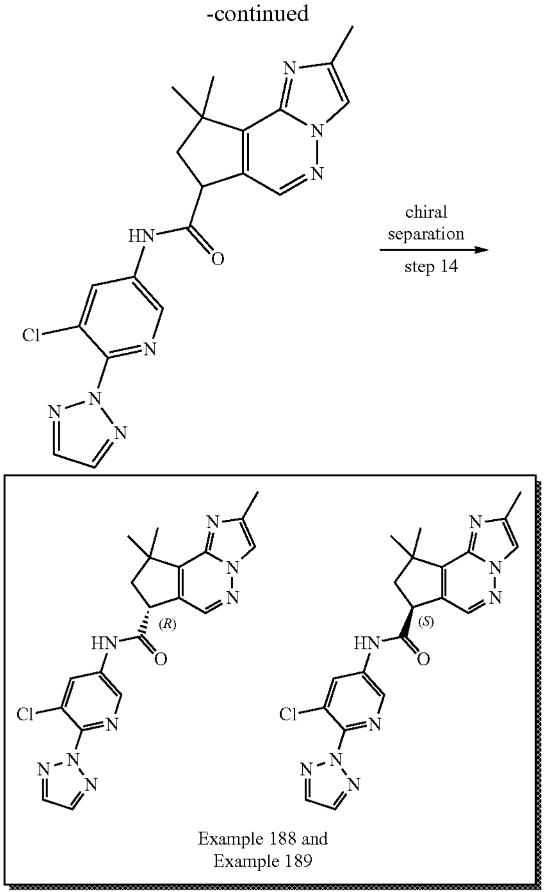

Example 188 and
Example 189

Examples 188 and 189: Single Enantiomers Obtained from a Racemic Mixture Containing (R)—N-(5-chloro-6-(2H-1,2,3-triazol-2-yl)pyridin-3-yl)-2,9,9-trimethyl-8,9-dihydro-7H-cyclopenta[d]imidazo[1,2-b]pyridazine-7-carboxamide and (S)—N-(5-chloro-6-(2H-1,2,3-triazol-2-yl)pyridin-3-yl)-2,9,9-trimethyl-8,9-dihydro-7H-cyclopenta[d]imidazo[1,2-b]pyridazine-7-carboxamide Step 1: ((5,5-Dimethylcyclopent-1-en-1-yl)oxy)trimethylsilane

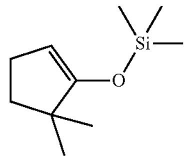

To a stirred solution of 2,2-dimethylcyclopentan-1-one (55 g, 490.3 mmol) in dichloromethane (600 mL) were added N,N-diethylethanamine (198 g, 1.9 mol) and trimethylsilyl trifluoromethanesulfonate (272 g, 1.2 mol) at 0° C. The resulting mixture was stirred at 0° C. for 3 h. The reaction was quenched by the addition of ice water (500 mL) at −10° C. and extracted with ethyl acetate (2×600 mL). The combined organic layers were washed with brine (3×600 mL), dried over anhydrous sodium sulfate and concentrated under reduced pressure to afford ((5,5-dimethylcyclopent-1-en-1-yl)oxy)trimethylsilane (59 g, crude) as a yellow oil.

Step 2:1,4-dichloro-5,5-dimethyl-6,7-dihydro-5H-cyclopenta[d]pyridazine

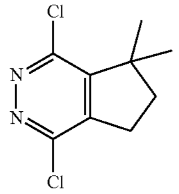

A mixture of 3,6-dichloro-1,2,4,5-tetrazine (3 g, 19.8 mmol) and ((5,5-dimethylcyclopent-1-en-1-yl)oxy)trimethylsilane (4 g, 23.8 mmol) in toluene (40 mL) was stirred at 120° C. for 1.5 h. The mixture was allowed to cool down to 25° C. and concentrated under reduced pressure. The residue was applied on a silica gel column and eluted with EtOAc/PE (1:9) to afford 1,4-dichloro-5,5-dimethyl-6,7-dihydro-5H-cyclopenta[d]pyridazine (2.7 g, 62% yield) as a yellow solid. LC-MS: m/z 217 $[M+H]^+$.

Step 3: 4-chloro-1-hydrazineyl-5,5-dimethyl-6,7-dihydro-5H-cyclopenta[d]pyridazine

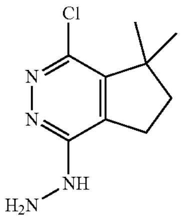

A mixture of 1,4-dichloro-5,5-dimethyl-6,7-dihydro-5H-cyclopenta[d]pyridazine (2.4 g, 11.0 mmol) in hydrazine hydrate (40 mL, 80%) and ethanol (20 mL) was stirred at 90° C. for 15 h. The mixture was allowed to cool down to 25° C. and concentrated under reduced pressure. The residue was applied on a silica gel column and eluted with MeOH/DCM (1:9) to afford 4-chloro-1-hydrazineyl-5,5-dimethyl-6,7-dihydro-5H-cyclopenta[d]pyridazine (1.7 g, 70% yield) as a yellow solid. LC-MS: m/z 213 $[M+H]^+$.

Step 4: 1-chloro-7,7-dimethyl-6,7-dihydro-5H-cyclopenta[d]pyridazine

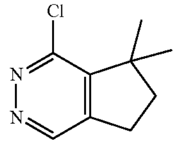

To a stirred mixture of 4-chloro-1-hydrazineyl-5,5-dimethyl-6,7-dihydro-5H-cyclopenta[d]pyridazine (1.7 g, 7.9 mmol) in ethanol (20 mL) and water (20 mL) was added copper sulfate (6 g, 40.0 mmol) at 0° C. The resulting mixture was stirred at 70° C. for 15 h. The mixture was allowed to cool down to 25° C. The reaction mixture was filtered, and the filtrate was concentrated under reduced pressure. The residue was applied on a silica gel column and eluted with EtOAC/PE (4:1) to afford 1-chloro-7,7-dimethyl-6,7-dihydro-5H-cyclopenta[d]pyridazine (800 mg, 59% yield) as a yellow solid. LC-MS: m/z 183 $[M+H]^+$.

Step 5: 7,7-dimethyl-6,7-dihydro-5H-cyclopenta[d]pyridazin-1-amine

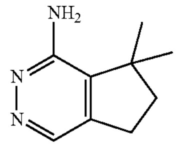

A mixture of 1-chloro-7,7-dimethyl-6,7-dihydro-5H-cyclopenta[d]pyridazine (3 g, 11.6 mmol) in ammonium hydroxide (150 mL) and ethanol (12 mL) was stirred at 150° C. for 72 h. The mixture was allowed to cool down to 25° C. and concentrated under reduced pressure. The residue was applied on a silica gel column and eluted with MeOH/DCM (1:9) to afford 7,7-dimethyl-6,7-dihydro-5H-cyclopenta[d]pyridazin-1-amine (1.0 g, 35% yield) as a yellow solid. LC-MS: m/z 164 $[M+H]^+$.

Step 6: Tert-butyl N-tert-butoxycarbonyl-N-(5,5-dimethyl-6,7-dihydrocyclopenta[d]pyridazin-4-yl)carbamate

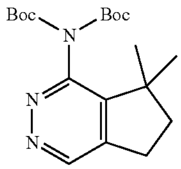 [SMILES: CC(C)(C)OC(=O)N(C(=O)OC(C)(C)C)c1nncc2c1C(C)(C)CC2]

To a stirred solution of 7,7-dimethyl-6,7-dihydro-5H-cyclopenta[d]pyridazin-1-amine (1.7 g, 10.4 mmol) in tetrahydrofuran (50 mL) were added di-tert-butyl dicarbonate (9 g, 41.6 mmol), N,N-diethylethanamine (6 g, 62.4 mmol) and N,N-dimethylpyridin-4-amine (127 mg, 1.0 mmol) at 0° C. The resulting mixture was stirred at 25° C. for 15 h. The reaction was quenched with water (80 mL) and extracted with ethyl acetate (3×100 mL). The combined organic layers were washed with brine (300 mL), dried over anhydrous sodium sulfate and concentrated under reduced pressure. The residue was applied on a silica gel column and eluted with EtOAc/PE (2:3) to afford tert-butyl N-tert-butoxycarbonyl-N-(5,5-dimethyl-6,7-dihydrocyclopenta[d]pyridazin-4-yl)carbamate (1.2 g, 32% yield) as a yellow solid. $^1$H NMR (400 MHz, DMSO-$d_6$) δ 9.18 (s, 1H), 2.99 (t, J=7.3 Hz, 2H), 1.93 (t, J=7.3 Hz, 2H), 1.37 (s, 18H), 1.24 (s, 6H). LC-MS: m/z 364 $[M+H]^+$.

Step 7: Tert-butyl N-(7-bromo-5,5-dimethyl-6,7-dihydrocyclopenta[d]pyridazin-4-yl)-N-tert-butoxy-carbonyl-carbamate

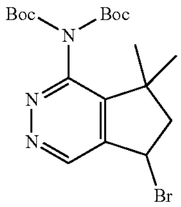 [SMILES: CC(C)(C)OC(=O)N(C(=O)OC(C)(C)C)c1nncc2c1C(C)(C)CC2Br]

To a stirred mixture of tert-butyl N-tert-butoxycarbonyl-N-(5,5-dimethyl-6,7-dihydrocyclopenta[d]pyridazin-4-yl)carbamate (1 g, 2.7 mmol) and benzoyl peroxide (999 mg, 4.1 mmol) in chloroform (15 mL) was added N-bromosuccinimide (489 mg, 2.7 mmol). The resulting mixture was stirred at 80° C. for 1.5 h. The mixture was allowed to cool down to 25° C., quenched with saturated aqueous sodium thiosulfate (5 mL), diluted with water (20 mL) and extracted with DCM (3×20 mL). The combined organic layers were dried over anhydrous sodium sulfate and concentrated under reduced pressure. The residue was applied on a silica gel column and eluted with EtOAC/PE (1:3) to afford tert-butyl N-(7-bromo-5,5-dimethyl-6,7-dihydrocyclopenta[d]pyridazin-4-yl)-N-tert-butoxycarbonyl-carbamate (640 mg, 49% yield) as a yellow solid. $^1$H NMR (400 MHz, DMSO-$d_6$) δ 9.37 (s, 1H), 5.84-5.87 (m, 1H), 2.71-2.66 (m, 1H), 2.32-2.37 (m, 1H), 1.43 (s, 3H), 1.35-1.38 (m, 18H), 1.27 (s, 3H). LC-MS: m/z 442 $[M+H]^+$.

Step 8: Tert-butyl N-tert-butoxycarbonyl-N-(7-cyano-5,5-dimethyl-6,7-dihydrocyclopenta[d]pyridazin-4-yl)carbamate

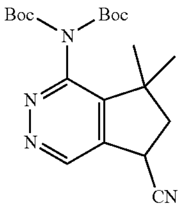 [SMILES: CC(C)(C)OC(=O)N(C(=O)OC(C)(C)C)c1nncc2c1C(C)(C)CC2C#N]

A solution of trimethylsilylformonitrile (403.7 mg, 4.07 mmol) in tetrabutylammonium fluoride (1.1 g, 4.1 mmol, 4.1 mL, 1M in THF) was stirred at 25° C. for 1 h. To the above mixture was added a solution of tert-butyl N-(7-bromo-5,5-dimethyl-6,7-dihydrocyclopenta[d]pyridazin-4-yl)-N-tert-butoxycarbonyl-carbamate (1.2 g, 2.7 mmol) in ACN (10 mL). The mixture was stirred at 25° C. for 15 h. The reaction mixture was concentrated under reduced pressure and purified by reversed phase column chromatography to afford tert-butyl N-tert-butoxycarbonyl-N-(7-cyano-5,5-dimethyl-6,7-dihydrocyclopenta[d]pyridazin-4-yl)carbamate (400 mg, 34.2% yield) as a yellow solid. $^1$H NMR (300 MHz, DMSO-$d_6$) δ: 9.45 (s, 1H), 4.85-4.91 (m, 1H), 2.43-2.48 (m, 1H), 2.22-2.29 (m, 1H), 1.37 (s, 21H), 1.22 (s, 3H). LC-MS: m/z 389 $[M+H]^+$.

Step 9: 1-amino-7,7-dimethyl-6,7-dihydro-5H-cyclopenta[d]pyridazine-5-carboxylic acid

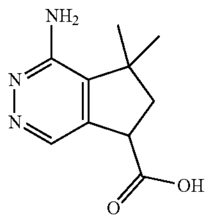

To a stirred solution of tert-butyl N-tert-butoxycarbonyl-N-(7-cyano-5,5-dimethyl-6,7-dihydrocyclopenta[d] pyridazin-4-yl)carbamate (250 mg, 643.6 μmol) in AcOH (1.5 mL) was added 12 M HCl (1 mL). The mixture was stirred at 100° C. for 1 h. The reaction mixture was concentrated under reduced pressure. The residue was purified by reversed phase column chromatography to afford 1-amino-7,7-dimethyl-6,7-dihydro-5H-cyclopenta[d] pyridazine-5-carboxylic acid (Method Y4 step 9; 120 mg, 80% yield) as a yellow oil. LC-MS: m/z 208 $[M+H]^+$.

Step 10: methyl 1-amino-7,7-dimethyl-6,7-dihydro-5H-cyclopenta[d]pyridazine-5-carboxylate

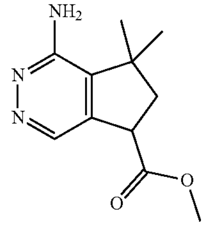 [SMILES: COC(=O)C1CC(C)(C)c2c1cnnc2N]

To a stirred solution of 1-amino-7,7-dimethyl-6,7-dihydro-5H-cyclopenta[d]pyridazine-5-carboxylic acid (400 mg, 1.9 mmol) in MeOH (6 mL) was added sulfuric acid (300 mg, 3.1 mmol). The mixture was stirred at 80° C. for 2 h. The reaction mixture was cooled down to 25° C. The pH was adjusted to 7 with saturated aqueous sodium bicarbonate solution. The mixture was purified by reversed phase column chromatography to afford methyl 1-amino-7,7-dimethyl-6,7-dihydro-5H-cyclopenta[d]pyridazine-5-carboxylate (Method Y4 step 10; 250 mg, 54% yield) as a yellow oil. LC-MS: m/z 222 $[M+H]^+$.

Step 11: methyl 2,9,9-trimethyl-8,9-dihydro-7H-cyclopenta[d]imidazo[1,2-b]pyridazine-7-carboxylate

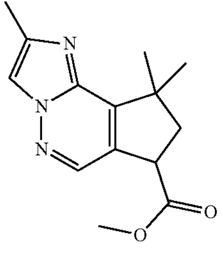 [SMILES: COC(=O)C1CC(C)(C)c2c1cnn1cc(C)nc21]

To a stirred solution of methyl 1-amino-7,7-dimethyl-6,7-dihydro-5H-cyclopenta[d]pyridazine-5-carboxylate (210 mg, 949.1 μmol) in iPrOH (100 mL) were added 1-chloropropan-2-one (351.3 mg, 3.8 mmol) and DIEA (428.5 mg, 3.3 mmol). The reaction mixture was stirred at 50° C. for 14 h. The reaction mixture was cooled to 25° C. and concentrated under reduced pressure. The residue was applied onto a silica gel column and eluted with EtOAc/PE (1:3) to give methyl 2,9,9-trimethyl-8,9-dihydro-7H-cyclopenta[d]imidazo[1,2-b]pyridazine-7-carboxylate (46 mg, 18% yield) as a yellow oil. $^1$H NMR (400 MHz, Chloroform-d) δ: 8.35 (s, 1H), 7.77 (s, 1H), 4.18-4.22 (m, 1H), 3.81 (s, 3H), 2.54 (s, 3H), 2.36-2.48 (m, 2H), 1.70 (s, 3H), 1.58 (s, 3H). LC-MS: m/z 260 $[M+H]^+$.

Step 12: 2,9,9-trimethyl-8,9-dihydro-7H-cyclopenta [d]imidazo[1,2-b]pyridazine-7-carboxylic acid

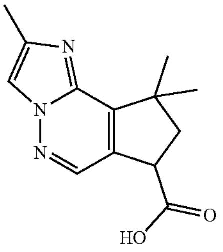 [SMILES: Cc1cn2ncc3c(c2n1)C(C)(C)CC3C(=O)O]

To a stirred solution of methyl 2,9,9-trimethyl-8,9-dihydro-7H-cyclopenta[d]imidazo[1,2-b]pyridazine-7-carboxylate (70 mg, 270 μmol) in THE (9 mL) and water (9 mL) was added lithium hydroxide (13 mg, 540 μmol). The reaction mixture was stirred at 25° C. for 0.5 h. The reaction mixture was concentrated under reduced pressure. The residue was diluted with water (5 mL). The pH was adjusted to 2-3 with 1 M HCl. The mixture was extracted with ethyl acetate (2×20 mL). The combined organic layers were concentrated under reduced pressure. The crude product was purified by reversed phase column and the collected fractions were concentrated under reduced pressure to afford 2,9,9-trimethyl-8,9-dihydro-7H-cyclopenta[d]imidazo[1,2-b]pyridazine-7-carboxylic acid (40 mg, 61% yield) as an off-white solid. LC-MS: m/z 246 $[M+H]^+$.

Step 13: N-(5-chloro-6-(2H-1,2,3-triazol-2-yl)pyridin-3-yl)-2,9,9-trimethyl-8,9-dihydro-7H-cyclopenta[d]imidazo[1,2-b]pyridazine-7-carboxamide

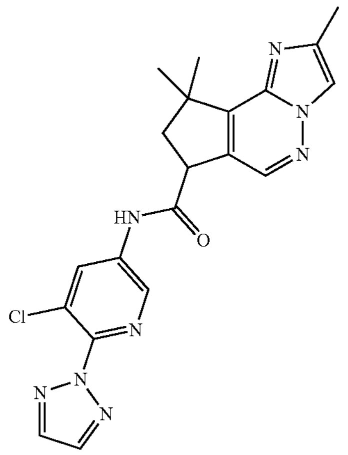 [SMILES: Cc1cn2ncc3c(c2n1)C(C)(C)CC3C(=O)Nc1cnc(-n2nccn2)c(Cl)c1]

Analogously to Method G4 Step 4, N-(5-chloro-6-(2H-1,2,3-triazol-2-yl)pyridin-3-yl)-2,9,9-trimethyl-8,9-dihydro-7H-cyclopenta[d]imidazo[1,2-b]pyridazine-7-carboxamide (80 mg, 51% yield) was obtained as a white solid. LC-MS: m/z 423 $[M+H]^+$.

Step 14: Separation of Enantiomers to Obtain (R)—N-(5-chloro-6-(2H-1,2,3-triazol-2-yl)pyridin-3-yl)-2,9,9-trimethyl-8,9-dihydro-7H-cyclopenta[d]imidazo[1,2-b]pyridazine-7-carboxamide and (S)—N-(5-chloro-6-(2H-1,2,3-triazol-2-yl)pyridin-3-yl)-2,9,9-trimethyl-8,9-dihydro-7H-cyclopenta[d]imidazo[1,2-b]pyridazine-7-carboxamide Example 188

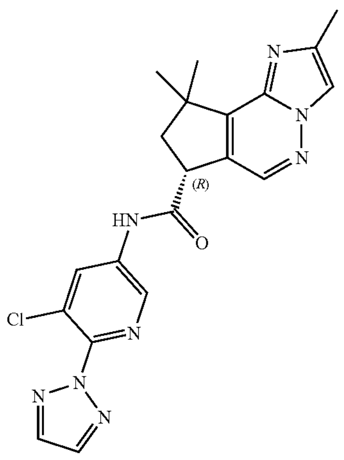

and

-continued

Example 189

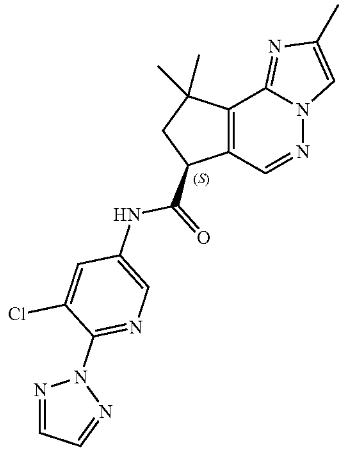

80 mg of N-(5-chloro-6-(2H-1,2,3-triazol-2-yl)pyridin-3-yl)-2,9,9-trimethyl-8,9-dihydro-7H-cyclopenta[d]imidazo[1,2-b]pyridazine-7-carboxamide were submitted to chiral HPLC purification (Column: CHIRAL ART Cellulose-SC, 2*25 cm, 5 μm; Mobile Phase A: Hex:DCM=3:1(0.5% 2M $NH_3$-MeOH)-HPLC, Mobile Phase B: EtOH-HPLC; Flow rate: 20 mL/min; isocratic 20% B in 11 min; Wave Length: 220/254 nm; RT1(min): 8.87; RT2(min): 10.21; Sample Solvent: EtOH-HPLC; Injection Volume: 0.4 mL; Number of Runs: 7). The first eluting isomer was concentrated and lyophilized to afford Example 188 (12.8 mg, 16% yield) as a white solid. The second eluting isomer was concentrated and lyophilized to afford Example 189 (15.1 mg, 19% yield) as a white solid.

Example 188: $^1H$ NMR (400 MHz, DMSO-$d_6$) δ: 11.08 (s, 1H), 8.73 (d, J=2.4 Hz, 1H), 8.59 (d, J=2.4 Hz, 1H), 8.56 (s, 1H), 8.17 (s, 2H), 8.14 (s, 1H), 4.45 (t, J=7.6 Hz, 1H), 2.61-2.62 (m, 1H), 2.44 (s, 3H), 2.29 (dd, J=7.2, 13.2 Hz, 1H), 1.62 (s, 3H), 1.50 (s, 3H). LC-MS: m/z 423 $[M+H]^+$.

Example 189: $^1H$ NMR (400 MHz, DMSO-$d_6$) δ: 11.07 (s, 1H), 8.73 (d, J=2.4 Hz, 1H), 8.59 (d, J=2.4 Hz, 1H), 8.50 (s, 1H), 8.17 (s, 2H), 8.09 (s, 1H), 4.44 (t, J=8.0 Hz, 1H), 2.57-2.58 (m, 1H), 2.42 (s, 3H), 2.29 (dd, J=7.2, 13.2 Hz, 1H), 1.62 (s, 3H), 1.49 (s, 3H). LC-MS: m/z 423 $[M+H]^+$.

The absolute stereochemistry for each separated isomer was not determined.

Method Z4

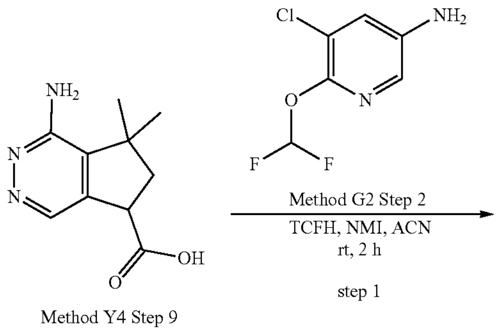

-continued

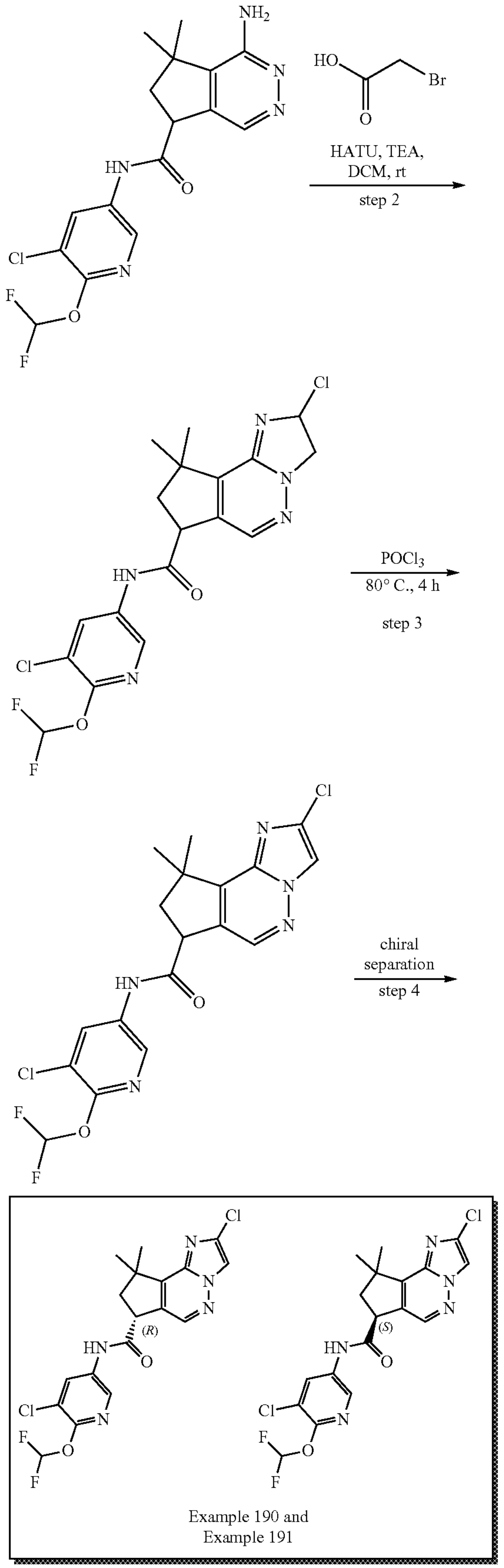

Examples 190 and 191: Single Enantiomers Obtained from a Racemic Mixture Containing (R)-2-chloro-N-(5-chloro-6-(difluoromethoxy)pyridin-3-yl)-9,9-dimethyl-8,9-dihydro-7H-cyclopenta[d]imidazo[1,2-b]pyridazine-7-carboxamide and (8)-2-chloro-N-(5-chloro-6-(difluoromethoxy)pyridin-3-yl)-9,9-dimethyl-8,9-dihydro-7H-cyclopenta[d]imidazo[1,2-b]pyridazine-7-carboxamide

Step 1:1-amino-N-(5-chloro-6-(difluoromethoxy)pyridin-3-yl)-7,7-dimethyl-6,7-dihydro-5H-cyclopenta[d]pyridazine-5-carboxamide

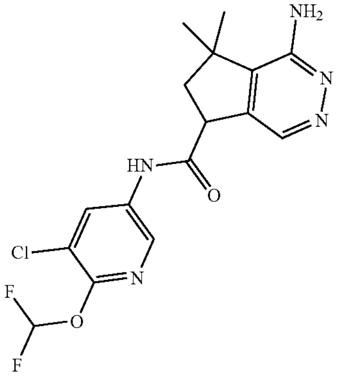 [SMILES: CC1(C)CC(C(=O)Nc2cnc(OC(F)F)c(Cl)c2)c2cnnc(N)c21]

Analogously to Method G4 Step 4, 1-amino-N-(5-chloro-6-(difluoromethoxy)pyridin-3-yl)-7,7-dimethyl-6,7-dihydro-5H-cyclopenta[d]pyridazine-5-carboxamide (50 mg, 45% yield) was obtained as a yellow oil. LC-MS: m/z 384 $[M+H]^+$.

Step 2: N-(5-chloro-6-(difluoromethoxy)pyridin-3-yl)-9,9-dimethyl-2-oxo-2,7,8,9-tetrahydro-3H-cyclopenta[d]imidazo[1,2-b]pyridazine-7-carboxamide

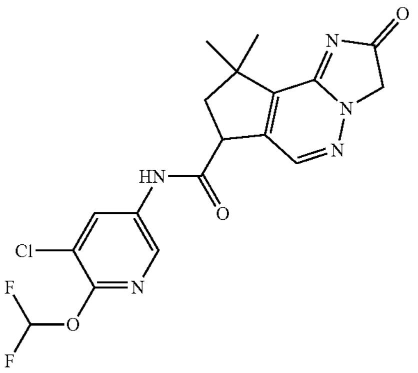 [SMILES: CC1(C)CC(C(=O)Nc2cnc(OC(F)F)c(Cl)c2)C2=C1C1=NC(=O)CN1N=C2]

To a stirred solution of 1-amino-N-(5-chloro-6-(difluoromethoxy)pyridin-3-yl)-7,7-dimethyl-6,7-dihydro-5H-cyclopenta[d]pyridazine-5-carboxamide (50 mg, 130 μmol) in DCM (3 mL) were added HATU (100 mg, 261 μmol), 2-bromoacetic acid (36 mg, 261 μmol) and N,N-diethylethanamine (40 mg, 391 μmol). The resulting mixture was stirred at 25° C. for 1 h. More N,N-diethylethanamine was added until the reaction was completed according to TLC. The reaction mixture was quenched with water (20 mL) and extracted with DCM (2×20 mL). The combined organic layers were dried over anhydrous sodium sulfate and concentrated under reduced pressure. The residue was applied onto a silica gel column and eluted with MeOH/DCM (1:20) to give N-(5-chloro-6-(difluoromethoxy)pyridin-3-yl)-9,9-dimethyl-2-oxo-2,7,8,9-tetrahydro-3H-cyclopenta[d]imidazo[1,2-b]pyridazine-7-carboxamide (20 mg, 30% yield) as a yellow oil. LC-MS: m/z 424 $[M+H]^+$.

Step 3: 2-Chloro-N-(5-chloro-6-(difluoromethoxy)pyridin-3-yl)-9,9-dimethyl-8,9-dihydro-7H-cyclopenta[d]imidazo[1,2-b]pyridazine-7-carboxamide

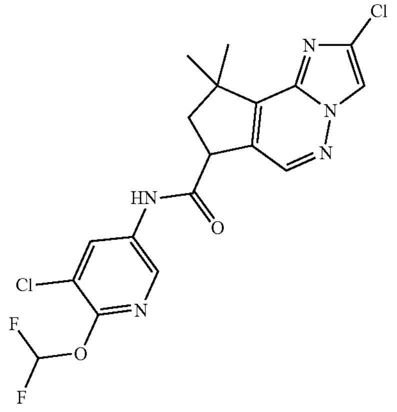 [SMILES: CC1(C)CC(C(=O)Nc2cnc(OC(F)F)c(Cl)c2)c2cnn3cc(Cl)nc3c21]

To a stirred solution of N-(5-chloro-6-(difluoromethoxy)pyridin-3-yl)-9,9-dimethyl-2-oxo-2,7,8,9-tetrahydro-3H-cyclopenta[d]imidazo[1,2-b]pyridazine-7-carboxamide (40 mg, 94 μmol) in ACN (2 mL) was added phosphoryl trichloride (289 mg, 1.9 mmol). The mixture was stirred at 80° C. for 4 h. The reaction mixture was concentrated under reduced pressure. The residue was applied onto a silica gel column and eluted with MeOH/DCM (1:20) to give 2-chloro-N-(5-chloro-6-(difluoromethoxy)pyridin-3-yl)-9,9-dimethyl-8,9-dihydro-7H-cyclopenta[d]imidazo[1,2-b]pyridazine-7-carboxamide (20 mg, 43% yield) as a yellow oil. LC-MS: m/z 442 $[M+H]^+$.

Step 4: Separation of Enantiomers to Obtain (R)-2-chloro-N-(5-chloro-6-(difluoromethoxy)pyridin-3-yl)-9,9-dimethyl-8,9-dihydro-7H-cyclopenta[d]imidazo[1,2-b]pyridazine-7-carboxamide and (S)-2-chloro-N-(5-chloro-6-(difluoromethoxy)pyridin-3-yl)-9,9-dimethyl-8,9-dihydro-7H-cyclopenta[d]imidazo[1,2-b]pyridazine-7-carboxamide Example 190

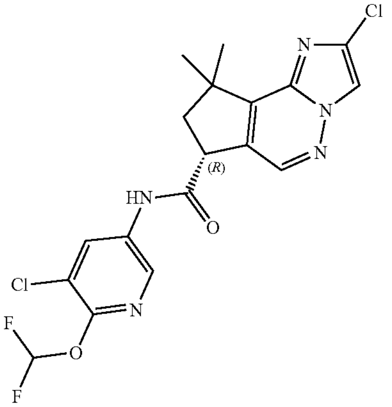

and

Example 191

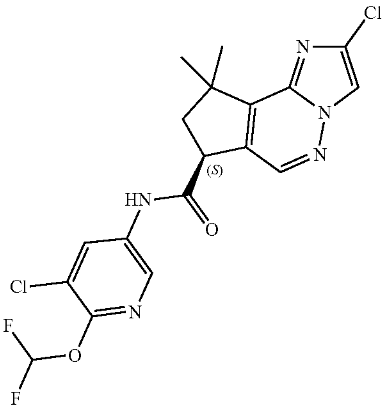

20 mg of 2-chloro-N-(5-chloro-6-(difluoromethoxy)pyridin-3-yl)-9,9-dimethyl-8,9-dihydro-7H-cyclopenta[d]imidazo[1,2-b]pyridazine-7-carboxamide were submitted to chiral HPLC purification (Column: CHIRAL ART Cellulose-SC, 2×25 cm, 5 μm; Mobile Phase A: Hex (0.1% FA)-HPLC, Mobile Phase B: EtOH-HPLC; Flow rate: 20 mL/min; isocratic 15% B in 7.5 min; Wave Length: 220/254 nm; RT1(min): 5.86; RT2(min): 6.82; Sample Solvent: EtOH-HPLC; Injection Volume: 0.5 mL; Number Of Runs: 7). The first eluting isomer was concentrated and lyophilized to afford Example 190 (3.1 mg, 10% yield) as a white solid. The second eluting isomer was concentrated and lyophilized to afford Example 191 (4.4 mg, 14% yield) as a white solid.

Example 190: $^1H$ NMR (300 MHz, Chloroform-d) δ: 8.37 (s, 1H), 8.31 (d, J=2.4 Hz, 1H), 8.14 (d, J=2.4 Hz, 1H), 7.93 (s, 1H), 7.44 (s, 1H), 7.40 (t, J=72.3 Hz, 1H), 4.24 (t, J=8.1 Hz, 1H), 2.56 (dd, J=8.7, 12.9 Hz, 1H), 2.36 (dd, J=8.1, 12.9 Hz, 1H), 1.75 (s, 3H), 1.55 (s, 3H). LC-MS: m/z 442 $[M+H]^+$.

Example 191: $^1H$ NMR (300 MHz, Chloroform-d) δ: 8.37 (s, 1H), 8.31 (d, J=2.4 Hz, 1H), 8.13 (d, J=2.4 Hz, 1H), 7.93 (s, 1H), 7.40 (t, J=72.3 Hz, 1H), 7.38 (s, 1H), 4.24 (t, J=8.1

Hz, 1H), 2.56 (dd, J=8.7, 12.9 Hz, 1H), 2.36 (dd, J=8.1, 12.9 Hz, 1H), 1.74 (s, 3H), 1.55 (s, 3H). LC-MS: m/z 442 $[M+H]^+$.
The absolute stereochemistry for each separated isomer was not determined.
Method A5
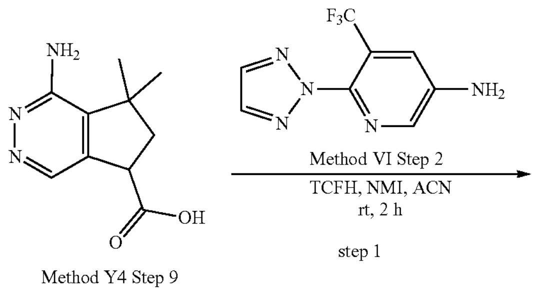
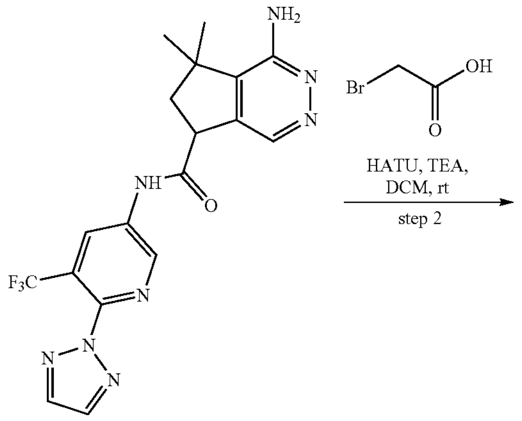
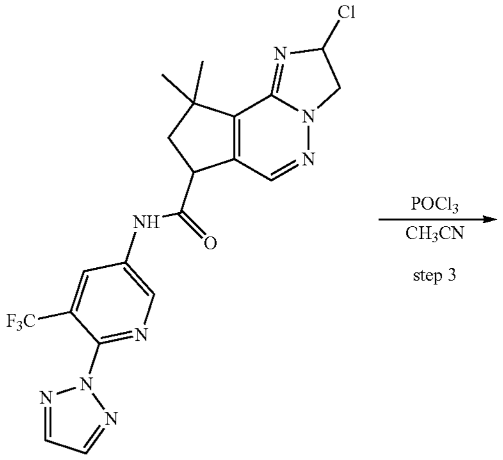
-continued
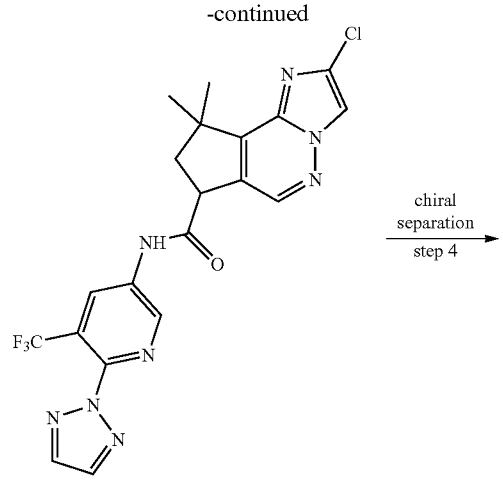
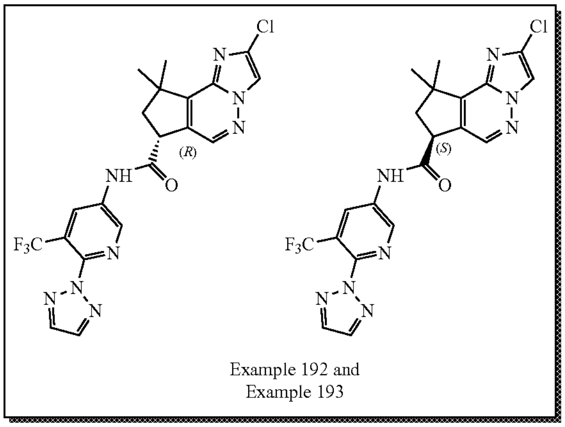
Example 192 and
Example 193

Examples 192 and 193: Single Enantiomers Obtained from a Racemic Mixture Containing (R)—N-(6-(2H-1,2,3-triazol-2-yl)-5~(trifluoromethyl)pyridin-3-yl)-2-chloro-9,9-dimethyl-8,9-dihydro-7H-cyclopenta[d]imidazo[1,2-b]pyridazine-7-carboxamide and (S)—N-(6-(2H-1,2,3-triazol-2-yl)-5~(trifluoromethyl)pyridin-3-yl)-2-chloro-9,9-dimethyl-8,9-dihydro-7H-cyclopenta[d]imidazo[1,2-b]pyridazine-7-carboxamide Step 1: N-(6-(2H-1,2,3-triazol-2-yl)-5~(trifluoromethyl)pyridin-3-yl)-1-amino-7,7-dimethyl-6,7-dihydro-5H-cyclopenta[d]pyridazine-5-carboxamide

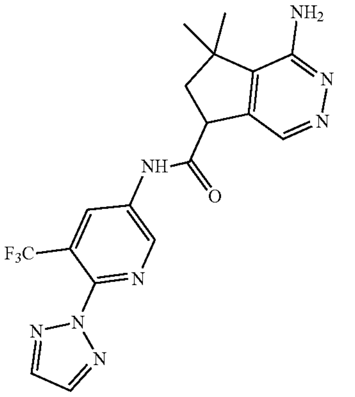 [SMILES: CC1(C)CC(C(=O)Nc2cnc(-n3nccn3)c(C(F)(F)F)c2)c2cnnc(N)c21]

Analogously to Method G4 Step 4, N-(6-(2H-1,2,3-triazol-2-yl)-5-(trifluoromethyl)pyridin-3-yl)-1-amino-7,7-dimethyl-6,7-dihydro-5H-cyclopenta[d]pyridazine-5-carboxamide (500 mg, 44% yield) was obtained as an off-white solid. $^1$H NMR (400 MHz, DMSO-$d_6$) δ 11.19 (s, 1H), 9.02 (d, J=2.4 Hz, 1H), 8.80 (d, J=2.4 Hz, 1H), 8.54 (s, 1H), 8.19 (s, 2H), 6.15 (s, 2H), 4.29-4.20 (m, 1H), 2.29 (m, 1H), 2.18 (m, 1H), 1.44 (s, 3H), 1.32 (s, 3H). LC-MS: m/z 419 [M+H]$^+$.

Step 2: N-(6-(2H-1,2,3-triazol-2-yl)-5~(trifluoromethyl)pyridin-3-yl)-9,9-dimethyl-2-oxo-2,7,8,9-tetrahydro-3H-cyclopenta[d]imidazo[1,2-b]pyridazine-7-carboxamide

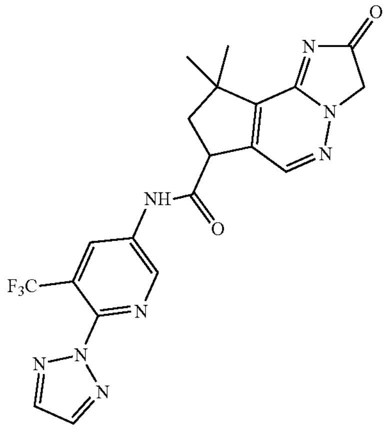 [SMILES: CC1(C)CC(C(=O)Nc2cnc(-n3nccn3)c(C(F)(F)F)c2)C2=C1C1=NC(=O)CN1N=C2]

Analogously to Method Z4 Step 2, N-(6-(2H-1,2,3-triazol-2-yl)-5-(trifluoromethyl)pyridin-3-yl)-9,9-dimethyl-2-oxo-2,7,8,9-tetrahydro-3H-cyclopenta[d]imidazo[1,2-b]pyridazine-7-carboxamide (80 mg, 12% yield) was obtained as a yellow oil. LC-MS: m/z 459 [M+H]$^+$.

Step 3: N-(6-(2H-1,2,3-triazol-2-yl)-5~(trifluoromethyl)pyridin-3-yl)-2-chloro-9,9-dimethyl-8,9-dihydro-7H-cyclopenta[d]imidazo[1,2-b]pyridazine-7-carboxamide

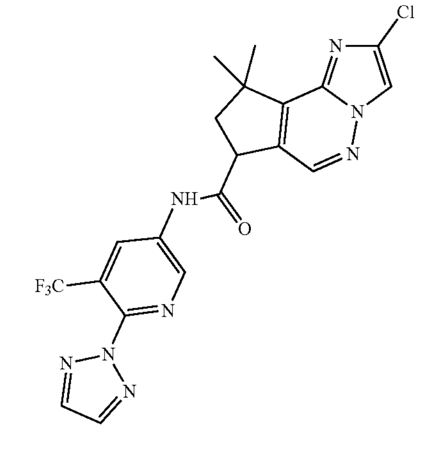 [SMILES: CC1(C)CC(C(=O)Nc2cnc(-n3nccn3)c(C(F)(F)F)c2)c2cnn3cc(Cl)nc3c21]

Analogously to Method Z4 Step 3, N-(6-(2H-1,2,3-triazol-2-yl)-5-(trifluoromethyl)pyridin-3-yl)-2-chloro-9,9-dimethyl-8,9-dihydro-7H-cyclopenta[d]imidazo[1,2-b]pyridazine-7-carboxamide (22 mg, 27% yield) was obtained as a white solid. LC-MS: m/z 477 [M+H]$^+$.

Step 4: Separation of Enantiomers to Obtain (R)—N-(6-(2H-1,2,3-triazol-2-yl)-5-(trifluoromethyl)pyridin-3-yl)-2-chloro-9,9-dimethyl-8,9-dihydro-7H-cyclopenta[d]imidazo[1,2-b]pyridazine-7-carboxamide and (S)—N-(6-(2H-1,2,3-triazol-2-yl)-5~(trifluoromethyl)pyridin-3-yl)-2-chloro-9,9-dimethyl-8,9-dihydro-7H-cyclopenta[d]imidazo[1,2-b]pyridazine-7-carboxamide Example 192

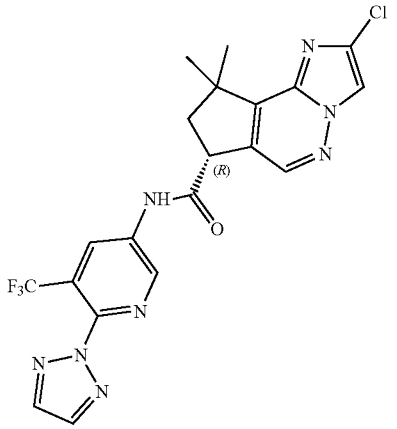

and

-continued

Example 193

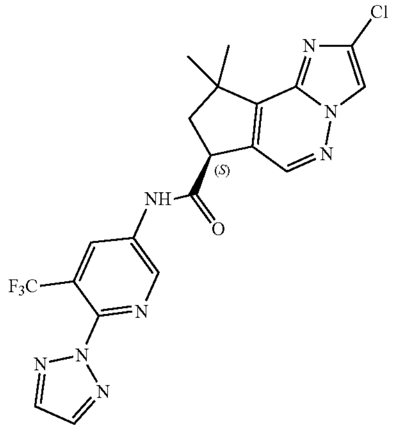

22 mg of N-(6-(2H-1,2,3-triazol-2-yl)-5-(trifluoromethyl)pyridin-3-yl)-2-chloro-9,9-dimethyl-8,9-dihydro-7H-cyclopenta[d]imidazo[1,2-b]pyridazine-7-carboxamide were submitted to chiral HPLC purification (Column: CHIRAL ART Cellulose-SC, 2×25 cm, 5 μm; Mobile Phase A: Hex(0.1% FA)-HPLC, Mobile Phase B: EtOH-HPLC; Flow rate: 20 mL/min; isocratic 30% B in 12.5 min; Wave Length: 254/220 nm; RT1(min): 8.4; RT2(min): 10.32; Sample Solvent: EtOH-HPLC; Injection Volume: 2 mL; Number Of Runs: 1). The first eluting isomer was concentrated and lyophilized to afford Example 192 (8.8 mg, 40% yield) as a white solid. The second eluting isomer was concentrated and lyophilized to afford Example 193 (8.4 mg, 38% yield) as a white solid.

Example 192: $^1$H NMR (300 MHz, Chloroform-d) δ: 8.85 (s, 2H), 8.43 (s, 1H), 8.08 (s, 1H), 7.95 (s, 1H), 7.94 (s, 2H), 4.33-4.40 (m, 1H), 2.60-2.66 (m, 1H), 2.31-2.42 (m, 1H), 1.78 (s, 3H), 1.58 (s, 3H). LC-MS: m/z 477 $[M+H]^+$.

Example 193: $^1$H NMR (300 MHz, Chloroform-d) δ: 8.85 (s, 2H), 8.44 (s, 1H), 8.08 (s, 1H), 7.96 (s, 1H), 7.94 (s, 2H), 4.35-4.41 (m, 1H), 2.57-2.70 (m, 1H), 2.39-2.47 (m, 1H), 1.78 (s, 3H), 1.59 (s, 3H). LC-MS: m/z 477 $[M+H]^+$.

The absolute stereochemistry for each separated isomer was not determined.

Method B5

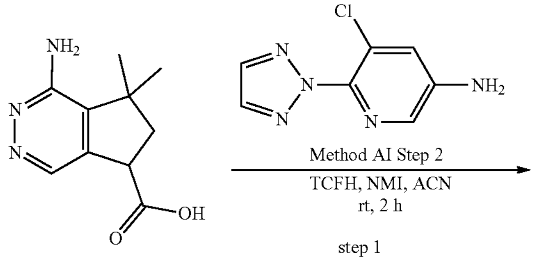

Method Y4 Step 9

-continued

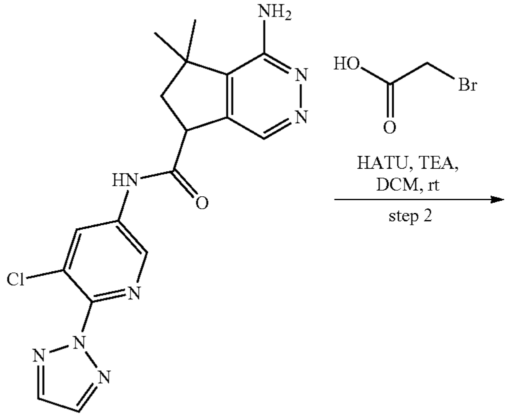

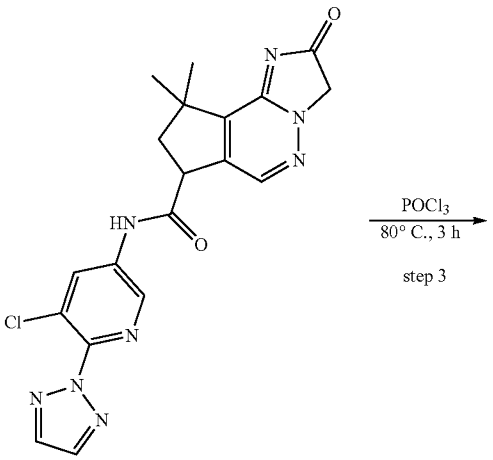

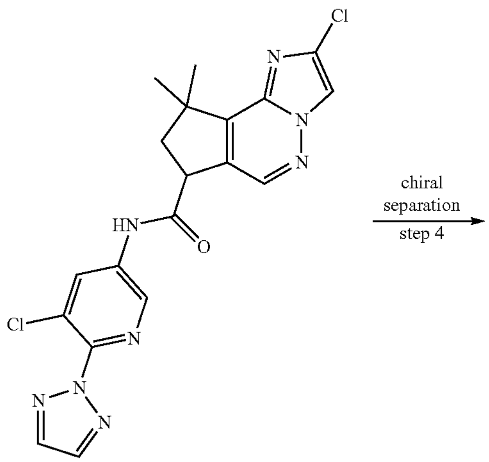

-continued

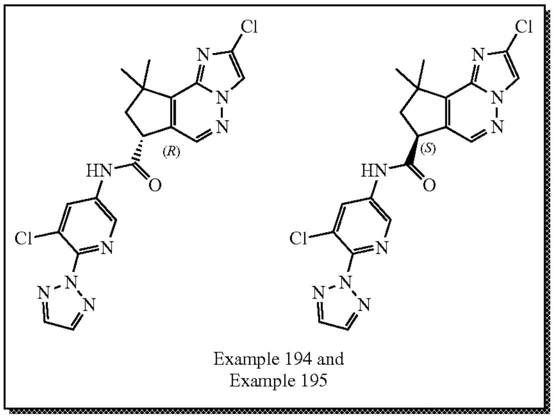

Example 194 and
Example 195

Examples 194 and 195: Single Enantiomers Obtained from a Racemic Mixture Containing (R)-2-chloro-N-(5-chloro-6-(2H-1,2,3-triazol-2-yl)pyridin-3-yl)-9,9-dimethyl-8,9-dihydro-7H-cyclopenta[d]imidazo[1,2-b]pyridazine-7-carboxamide and (8)-2-chloro-N-(5-chloro-6-(2H-1,2,3-triazol-2-yl)pyridin-3-yl)-9,9-dimethyl-8,9-dihydro-7H-cyclopenta[d]imidazo[1,2-b]pyridazine-7-carboxamide Step 1:1-amino-N-(5-chloro-6-(2H-1,2,3-triazol-2-yl)pyridin-3-yl)-7,7-dimethyl-6,7-dihydro-5H-cyclopenta[d]pyridazine-5-carboxamide

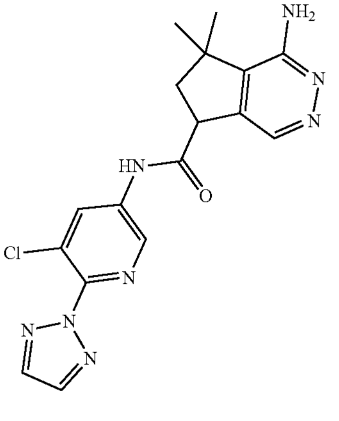 [SMILES: CC1(C)CC(C(=O)Nc2cnc(-n3nccn3)c(Cl)c2)c2cnnc(N)c21]

Analogously to Method G4 Step 4, 1-amino-N-(5-chloro-6-(2H-1,2,3-triazol-2-yl)pyridin-3-yl)-7,7-dimethyl-6,7-dihydro-5H-cyclopenta[d]pyridazine-5-carboxamide (300 mg, 53.9% yield) was obtained as a white solid. $^{1}H$ NMR (400 MHz, DMSO-$d_6$) δ: 11.07 (s, 1H), 8.72 (d, J=2.0 Hz, 1H), 8.58 (d, J=2.4 Hz, 1H), 8.52 (s, 1H), 8.18 (s, 2H), 6.17 (s, 2H), 4.21-4.25 (m, 1H), 2.25-2.31 (m, 1H), 2.13-2.18 (m, 1H), 1.47 (s, 3H), 1.32 (s, 3H). LC-MS: m/z 385 $[M+H]^+$.

Step 2: N-(5-chloro-6-(2H-1,2,3-triazol-2-yl)pyridin-3-yl)-9,9-dimethyl-2-oxo-2,7,8,9-tetrahydro-3H-cyclopenta[d]imidazo[1,2-b]pyridazine-7-carboxamide

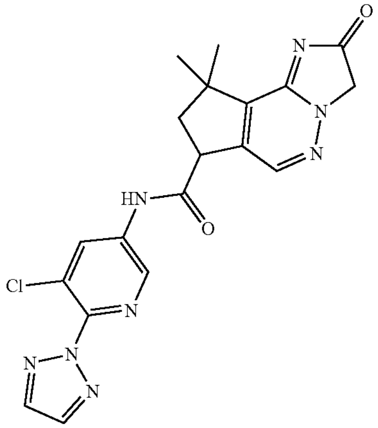 [SMILES: CC1(C)CC(C(=O)Nc2cnc(-n3nccn3)c(Cl)c2)C2=C1C1=NC(=O)CN1N=C2]

Analogously to Method Z4 Step 2, N-(5-chloro-6-(2H-1,2,3-triazol-2-yl)pyridin-3-yl)-9,9-dimethyl-2-oxo-2,7,8,9-tetrahydro-3H-cyclopenta[d]imidazo[1,2-b]pyridazine-7-carboxamide (60 mg, 15% yield) was obtained as a yellow oil. LC-MS: m/z 425 $[M+H]^+$.

Step 3: 2-Chloro-N-(5-chloro-6-(2H-1,2,3-triazol-2-yl)pyridin-3-yl)-9,9-dimethyl-8,9-dihydro-7H-cyclopenta[d]imidazo[1,2-b]pyridazine-7-carboxamide

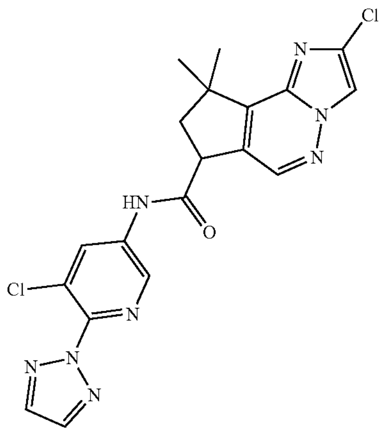 [SMILES: CC1(C)CC(C(=O)Nc2cnc(-n3nccn3)c(Cl)c2)c2cnn3cc(Cl)nc3c21]

Analogously to Method Z4 Step 3, 2-chloro-N-(5-chloro-6-(2H-1,2,3-triazol-2-yl)pyridin-3-yl)-9,9-dimethyl-8,9-dihydro-7H-cyclopenta[d]imidazo[1,2-b]pyridazine-7-carboxamide (30 mg, 44.57% yield) was obtained as an off-white solid. LC-MS: m/z 443 $[M+H]^+$.

Step 4: Separation of Enantiomers to Obtain (R)-2-chloro-N-(5-chloro-6-(2H-1,2,3-triazol-2-yl)pyridin-3-yl)-9,9-dimethyl-8,9-dihydro-7H-cyclopenta[d]imidazo[1,2-b]pyridazine-7-carboxamide and (S)-2-chloro-N-(5-chloro-6-(2H-1,2,3-triazol-2-yl)pyridin-3-yl)-9,9-dimethyl-8,9-dihydro-7H-cyclopenta[d]imidazo[1,2-b]pyridazine-7-carboxamide Example 194

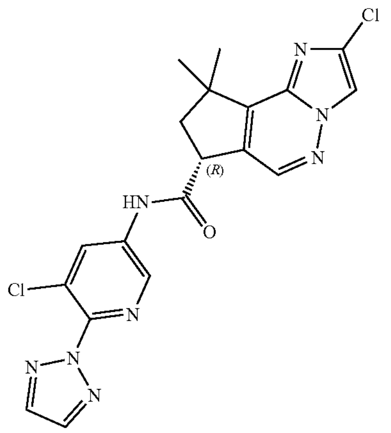

and

-continued

Example 195

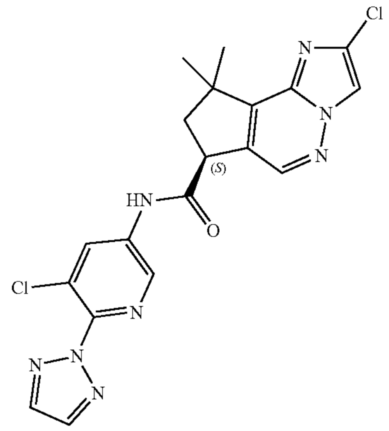

30 mg of 2-Chloro-N-(5-chloro-6-(2H-1,2,3-triazol-2-yl)pyridin-3-yl)-9,9-dimethyl-8,9-dihydro-7H-cyclopenta[d]imidazo[1,2-b]pyridazine-7-carboxamide were submitted to chiral HPLC purification (Column: CHIRAL ART Cellulose-SC, 2×25 cm, 5 μm; Mobile Phase A: Hex(0.1% FA)-HPLC, Mobile Phase B: EtOH-HPLC; Flow rate: 20 mL/min; isocratic 50% B in 12 min; Wave Length: 254/220 nm; RT1(min): 8.33; RT2(min): 10.53; Sample Solvent: EtOH-HPLC; Injection Volume: 1.5 mL; Number Of Runs: 3). The first eluting isomer was concentrated and lyophilized to afford Example 194 (13.1 mg, 43% yield) as a white solid. The second eluting isomer was concentrated and lyophilized to afford Example 195 (13.0 mg, 43.1% yield) as a white solid.

Example 194: $^1H$ NMR (300 MHz, Chloroform-d) δ: 8.67 (s, 1H), 8.50 (s, 1H), 8.42 (s, 1H), 7.99 (s, 1H), 7.95 (s, 1H), 7.94 (s, 2H), 4.30-4.35 (m, 1H), 2.56-2.63 (m, 1H), 2.36-2.42 (m, 1H), 1.76 (s, 3H), 1.57 (s, 3H). LC-MS: m/z 443 $[M+H]^+$.

Example 195: $^1H$ NMR (300 MHz, Chloroform-d) δ: 8.68 (s, 1H), 8.50 (s, 1H), 8.42 (s, 1H), 7.95 (s, 1H), 7.94 (s, 2H), 7.92 (s, 1H), 4.25-4.40 (m, 1H), 2.52-2.65 (m, 1H), 2.32-2.46 (m, 1H), 1.76 (s, 3H), 1.57 (s, 3H). LC-MS: m/z 443 $[M+H]^+$.

The absolute stereochemistry for each separated isomer was not determined.

Method C5
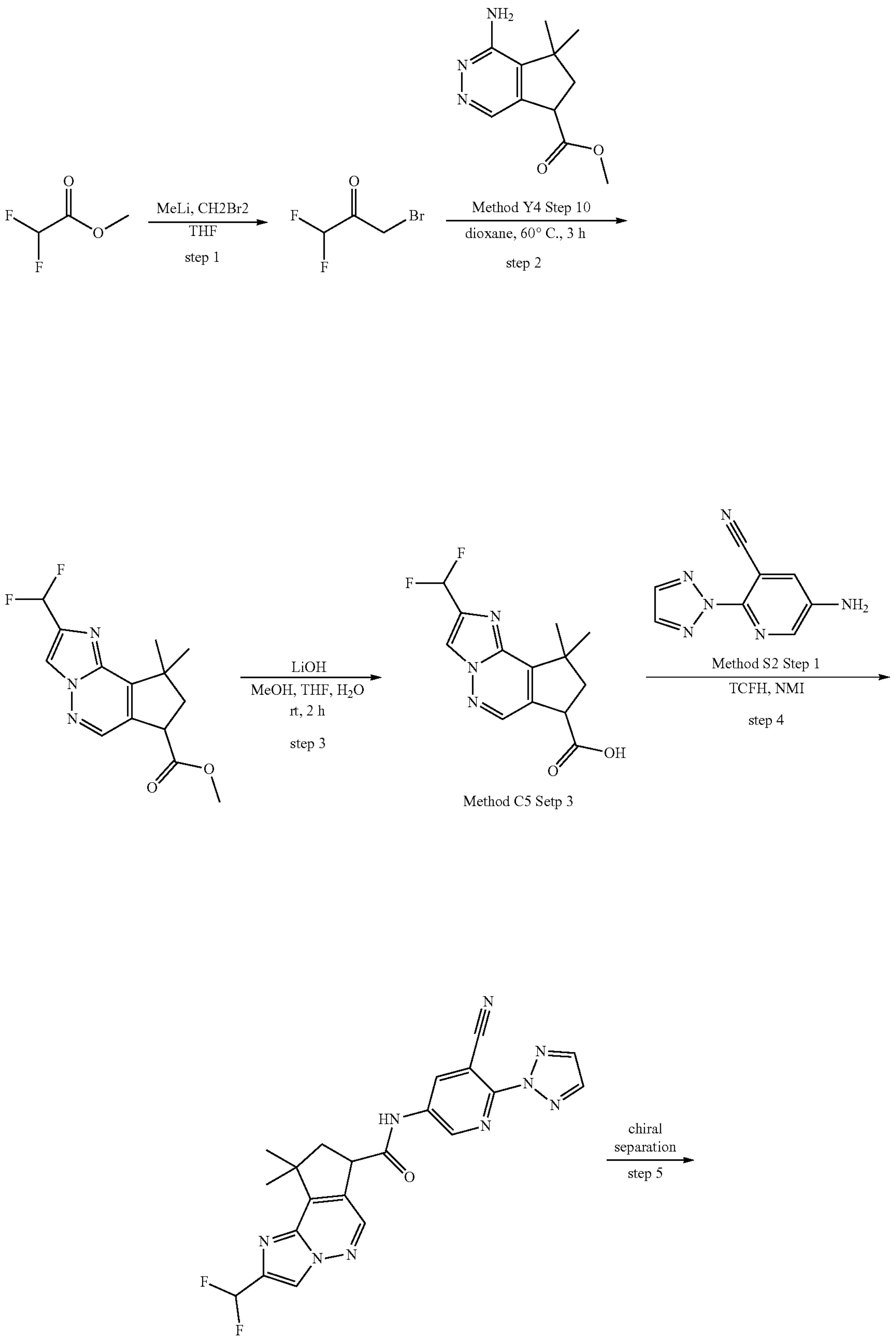

-continued

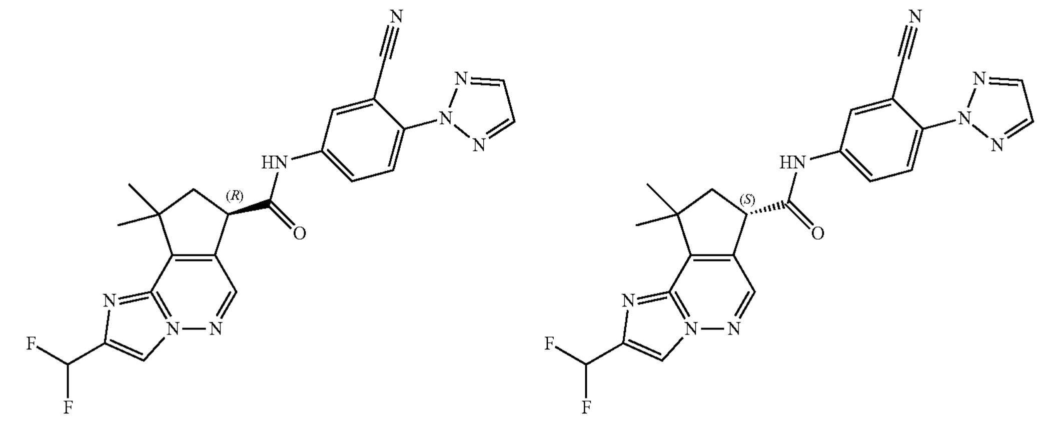

Example 196 and
Example 197

Examples 196 and 197: Single Enantiomers Obtained from a Racemic Mixture Containing (R)—N-(5-cyano-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide and (S)—N-(5-cyano-6-(2H-1,2,3-triazol-2-yl) pyridin-3-yl)-2-(difluoromethyl)-9,9-dimethyl-8,9-dihydro-7H-cyclopenta[d]imidazo[1,2-b]pyridazine-7-carboxamide Step 1: 3-bromo-1,1-difluoropropan-2-one

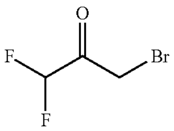

To a mixture of methyl 2,2-difluoroacetate (2.0 g, 16.0 mmol) and dibromomethane (5.6 g, 32.0 mmol) in THE (60 mL) was added methyllithium (1.6 M in diethyl ether, 20.0 mL) dropwise at −78° C. The resulting mixture was stirred at −78° C. for 1 h. The reaction was quenched with AcOH (3.5 mL), diluted with water (100 mL) and extracted with ethyl acetate (2×100 mL). The combined organic layers were dried over anhydrous sodium sulfate and concentrated under reduced pressure to afford 3-bromo-1,1-difluoropropan-2-one (1.5 g, 54% yield) as a yellow oil.

The crude product was used in the next step without further purification.

Step 2: methyl 2-(difluoromethyl)-9,9-dimethyl-8,9-dihydro-7H-cyclopenta[d]imidazo[1,2-b]pyridazine-7-carboxylate

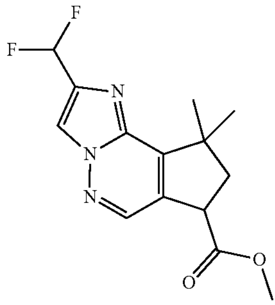 [SMILES: COC(=O)C1CC(C)(C)c2c1cnn1cc(C(F)F)nc21]

To a stirred solution of methyl 1-amino-7,7-dimethyl-6,7-dihydro-5H-cyclopenta[d]pyridazine-5-carboxylate (100 mg, 451.9 μmol) in dioxane (4 mL) were added 3-bromo-1,1-difluoropropan-2-one (155 mg, 896.2 μmol) and 4 Å molecular sieves. The mixture was stirred at 60° C. for 3 h. The reaction mixture was cooled down to 25° C., filtered, and the filtrate was concentrated under reduced pressure. The residue was applied onto a silica gel column and eluted with EtOAc/PE (1:2) to give methyl 2-(difluoromethyl)-9,9-dimethyl-8,9-dihydro-7H-cyclopenta[d]imidazo[1,2-b] pyridazine-7-carboxylate (60 mg, 38% yield) as a yellow oil. LC-MS: m/z 296 $[M+H]^+$.

Step 3: 2-(difluoromethyl)-9,9-dimethyl-8,9-dihydro-7H-cyclopenta[d]imidazo[1,2-b]pyridazine-7-carboxylic acid

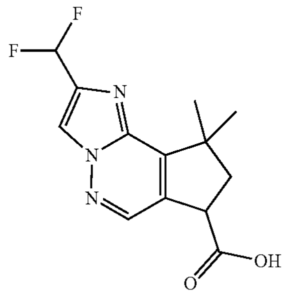 [SMILES: CC1(C)CC(C(=O)O)c2cnn3cc(C(F)F)nc3c21]

Analogously to Method Y4 Step 12, 2-(difluoromethyl)-9,9-dimethyl-8,9-dihydro-7H-cyclopenta[d]imidazo[1,2-b]pyridazine-7-carboxylic acid (Method C5 step 3; 30 mg, 48.3% yield) was obtained as a white solid. $^1$H NMR (300 MHz, DMSO-$d_6$) δ: 12.89 (s, 1H), 8.63 (s, 2H), 7.21 (t, J=54.7 Hz, 1H), 4.27-4.33 (m, 1H), 2.35-2.42 (m, 1H), 2.23-2.29 (m, 1H), 1.53 (s, 3H), 1.48 (s, 3H). LC-MS: m/z 282 $[M+H]^+$.

Step 4: N-(5-cyano-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide

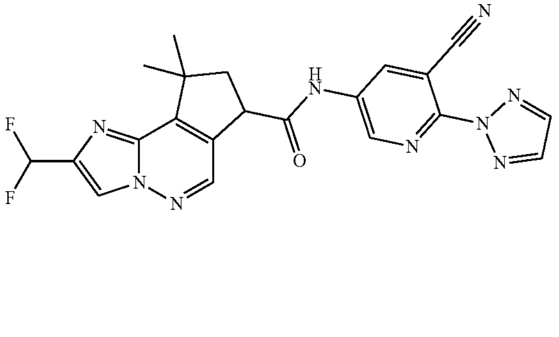 [SMILES: CC1(C)CC(C(=O)Nc2cnc(-n3nccn3)c(C#N)c2)c2cnn3cc(C(F)F)nc3c21]

Analogously to Method G4 Step 4, N-(5-cyano-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide (27 mg, 30% yield) was obtained as a white solid. LC-MS: m/z 450 $[M+H]^+$.

Step 5: Separation of Enantiomers to Obtain (R)—N-(5-cyano-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide and (S)—N-(5-cyano-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide Example 196

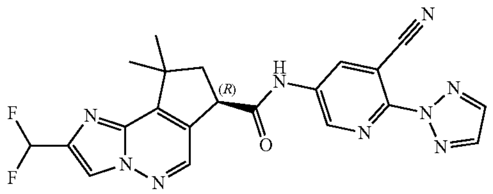

and

Example 197

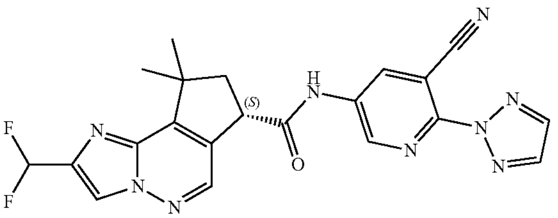

27 mg of N-(5-cyano-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide were submitted to chiral HPLC purification (Column: CHIRAL ART Cellulose-SC, 2*25 cm, 5 μm; Mobile Phase A: Hex:DCM=3:1(0.5% 2M $NH_3$-MeOH)-HPLC, Mobile Phase B: EtOH-HPLC; Flow rate: 20 mL/min; isocratic 10% B in 18 min; Wave Length: 220/254 nm; RT1(min): 11.82; RT2 (min): 16.93; Sample Solvent: ETOH:DCM=1:1; Injection Volume: 1 mL; Number Of Runs: 2). The first eluting isomer was concentrated and lyophilized to afford Example 196 (11.4 mg, 42% yield) as a white solid. The second eluting isomer was concentrated and lyophilized to afford Example 197 (11.1 mg, 40% yield) as a white solid.

Example 196: $^1$H NMR (300 MHz, DMSO-$d_6$) δ 11.12 (s, 1H), 8.98 (d, J=2.4 Hz, 1H), 8.78 (d, J=2.7 Hz, 1H), 8.65-8.67 (m, 2H), 8.30 (s, 2H), 7.22 (t, J=54.6 Hz, 1H), 4.49 (dd, J=7.2, 9.0 Hz, 1H), 2.55 (dd, J=9.0, 12.9 Hz, 1H), 2.29 (dd, J=7.2, 12.9 Hz, 1H), 1.63 (s, 3H), 1.51 (s, 3H). LC-MS: m/z 450 $[M+H]^+$.

Example 197: $^1$H NMR (300 MHz, DMSO-$d_6$) δ11.12 (s, 1H), 8.98 (d, J=2.4 Hz, 1H), 8.78 (d, J=2.7 Hz, 1H), 8.65-8.67 (m, 2H), 8.30 (s, 2H), 7.22 (t, J=54.9 Hz, 1H), 4.49 (dd, J=7.2, 9.0 Hz, 1H), 2.55 (dd, J=9.0, 12.9 Hz, 1H), 2.29 (dd, J=7.2, 12.9 Hz, 1H), 1.63 (s, 3H), 1.51 (s, 3H). LC-MS: m/z 450 $[M+H]^+$.

The absolute stereochemistry for each separated isomer was not determined.

Method D5
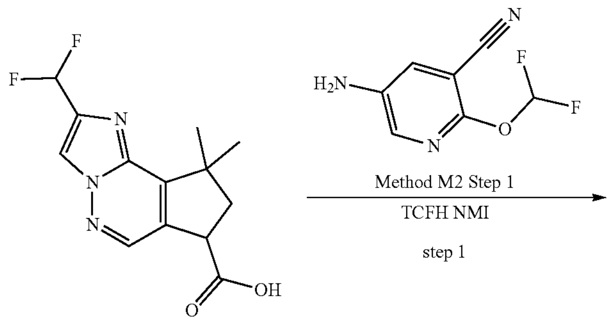
Method C5 Step 3
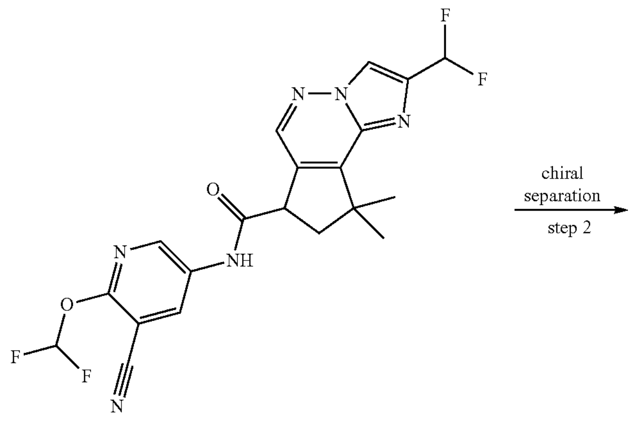
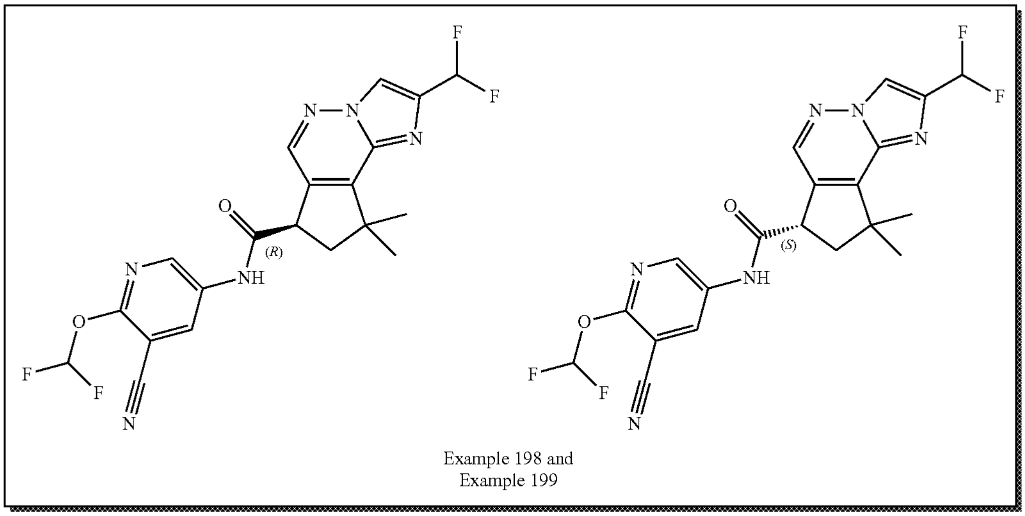
Example 198 and
Example 199

Examples 198 and 199: Single Enantiomers Obtained from a Racemic Mixture Containing (R)—N-(5-cyano-6-(difluoromethoxy)pyridin-3-yl)-2-(difluoromethyl)-9,9-dimethyl-8,9-dihydro-7H-cyclopenta[d]imidazo[1,2-b]pyridazine-7-carboxamide and (S)—N-(5-cyano-6-(difluoromethoxy)pyridin-3-yl)-2-(difluoromethyl)-9,9-dimethyl-8,9-dihydro-7H-cyclopenta[d]imidazo[1,2-b]pyridazine-7-carboxamide Step 1: N-(5-cyano-6-(difluoromethoxy)pyridin-3-yl)-2-(difluoromethyl)-9,9-dimethyl-8,9-dihydro-7H-cyclopenta[d]imidazo[1,2-b]pyridazine-7-carboxamide

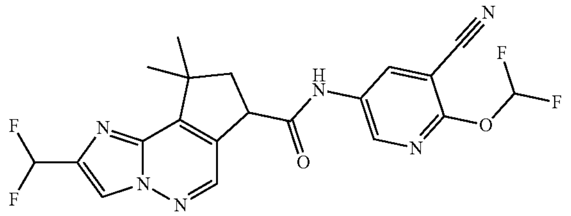 [SMILES: CC1(C)CC(C(=O)Nc2cnc(OC(F)F)c(C#N)c2)c2cnn3cc(C(F)F)nc3c21]

Analogously to Method G4 Step 4, N-(5-cyano-6-(difluoromethoxy)pyridin-3-yl)-2-(difluoromethyl)-9,9-dimethyl-8,9-dihydro-7H-cyclopenta[d]imidazo[1,2-b]pyridazine-7-carboxamide (50 mg, 48% yield) was obtained as an off-white solid. LC-MS: m/z 449 $[M+H]^+$.

Step 2: Separation of Enantiomers to Obtain (R)—N-(5-cyano-6-(difluoromethoxy)pyridin-3-yl)-2-(difluoromethyl)-9,9-dimethyl-8,9-dihydro-7H-cyclopenta[d]imidazo[1,2-b]pyridazine-7-carboxamide and (S)—N-(5-cyano-6-(difluoromethoxy)pyridin-3-yl)-2-(difluoromethyl)-9,9-dimethyl-8,9-dihydro-7H-cyclopenta[d]imidazo[1,2-b]pyridazine-7-carboxamide Example 198

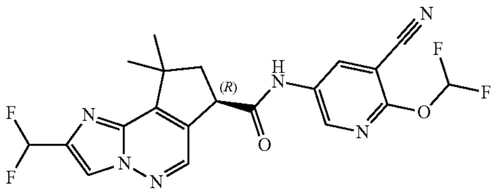

and

-continued

Example 199

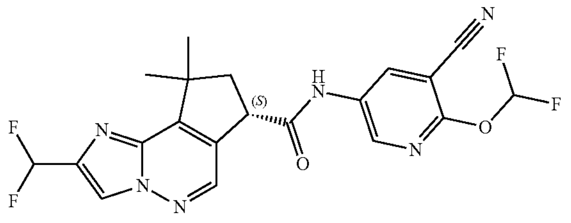

60 mg of N-(5-cyano-6-(difluoromethoxy)pyridin-3-yl)-2-(difluoromethyl)-9,9-dimethyl-8,9-dihydro-7H-cyclopenta[d]imidazo[1,2-b]pyridazine-7-carboxamide were submitted to chiral HPLC purification (Column: CHIRAL ART Cellulose-SC, 2*25 cm, 5 μm; Mobile Phase A: Hex (0.5% 2M $NH_3$-MeOH)-HPLC, Mobile Phase B: EtOH-HPLC; Flow rate: 20 mL/min; isocratic 15% B in 13 min; Wave Length: 254/220 nm; RT1(min): 8.66; RT2(min): 10.87; Sample Solvent: EtOH-HPLC; Injection Volume: 0.6 mL; Number of Runs: 4). The first eluting isomer was concentrated and lyophilized to afford Example 198 (21.8 mg, 35% yield) as a white solid. The second eluting isomer was concentrated and lyophilized to afford Example 199 (21.5 mg, 35% yield) as a white solid.

Example 198: $^1H$ NMR (300 MHz, Chloroform-d) δ 8.55 (d, J=2.7 Hz, 1H), 8.50 (d, J=2.4 Hz, 1H), 8.45 (s, 1H), 8.23 (s, 1H), 7.93 (s, 1H), 7.44 (t, J=71.4 Hz, 1H), 6.95 (t, J=54.9 Hz, 1H), 4.34 (t, J=8.1 Hz, 1H), 2.62 (dd, J=8.7, 12.9 Hz, 1H), 2.38 (dd, J=7.8, 12.9 Hz, 1H), 1.76 (s, 3H), 1.58 (s, 3H). LC-MS: m/z 449 $[M+H]^+$.

Example 199: $^1H$ NMR (300 MHz, Chloroform-d) δ 8.55 (d, J=2.4 Hz, 1H), 8.49 (d, J=2.4 Hz, 1H), 8.43 (s, 1H), 8.23 (s, 1H), 7.85 (s, 1H), 7.44 (t, J=71.4 Hz, 1H), 6.94 (t, J=55.2 Hz, 1H), 4.31 (t, J=8.4 Hz, 1H), 2.61 (dd, J=8.4, 12.9 Hz, 1H), 2.37 (dd, J=7.8, 12.9 Hz, 1H), 1.76 (s, 3H), 1.57 (s, 3H). LC-MS: m/z 449 $[M+H]^+$.

The absolute stereochemistry for each separated isomer was not determined.

Method E5

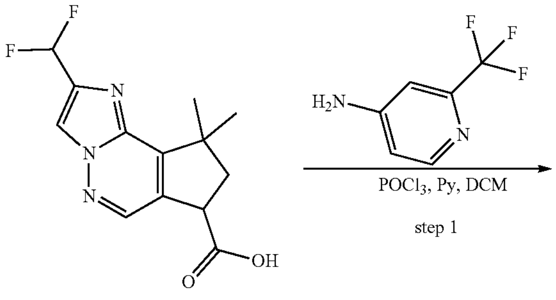

Method C5 Step 3

-continued

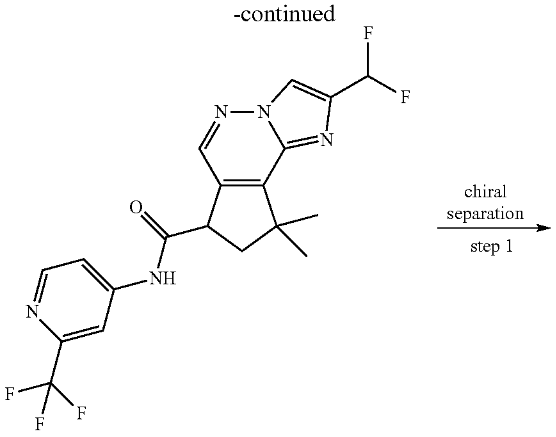

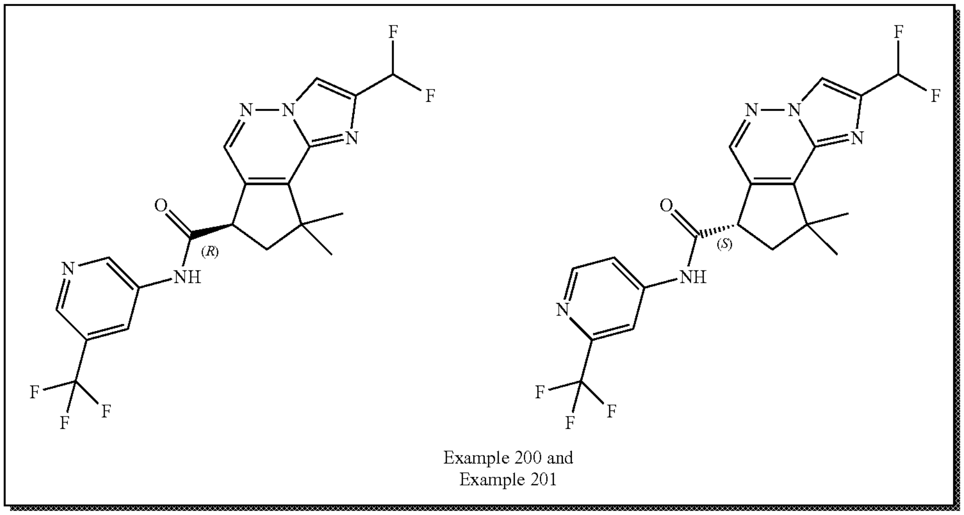

Example 200 and
Example 201

Examples 200 and 201: Single Enantiomers Obtained from a Racemic Mixture Containing (R)-2-(difluoromethyl)-9,9-dimethyl-N-(2-(trifluoromethyl)pyridin-4-yl)-8,9-dihydro-7H-cyclopenta[d]imidazo[1,2-b]pyridazine-7-carboxamide and (S)-2-(difluoromethyl)-9,9-dimethyl-N-(2-(trifluoromethyl)pyridin-4-yl)-8,9-dihydro-7H-cyclopenta[d]imidazo[1,2-b]pyridazine-7-carboxamide Step 1. 2-(difluoromethyl)-9,9-dimethyl-N-(2-(trifluoromethyl)pyridin-4-yl)-8,9-dihydro-7H-cyclopenta[d]imidazo[1,2-b]pyridazine-7-carboxamide

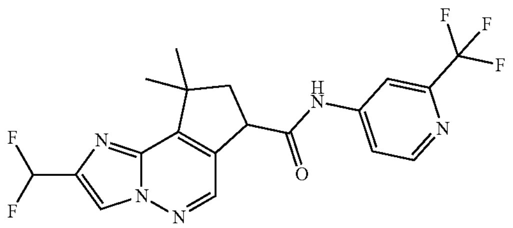 [SMILES: CC1(C)CC(C(=O)Nc2ccnc(C(F)(F)F)c2)c2cnn3cc(C(F)F)nc3c21]

To a stirred solution of 2-(difluoromethyl)-9,9-dimethyl-8,9-dihydro-7H-cyclopenta[d]imidazo[1,2-b]pyridazine-7-carboxylic acid (Method C5 step 3; 50 mg, 177.8 μmol) in DCM (4 mL) was added pyridine (141 mg, 1.8 mmol). A solution of phosphoryl trichloride (82 mg, 533 μmol) in DCM (0.2 mL) was added at 0° C., and the mixture was stirred at 0° C. for 1 h. A solution of 2-(trifluoromethyl)pyridin-4-amine (35 mg, 213 μmol) in DCM (0.3 mL) was added at 0° C., and it was stirred at 25° C. for 1 h. The reaction was quenched with water (20 mL) and extracted with DCM (2×20 mL). The combined organic layers were dried over anhydrous sodium sulfate and concentrated under reduced pressure. The residue was submitted to Prep-HPLC purification and the collected fractions were lyophilized to give 2-(difluoromethyl)-9,9-dimethyl-N-(2-(trifluoromethyl)pyridin-4-yl)-8,9-dihydro-7H-cyclopenta[d]imidazo[1,2-b]pyridazine-7-carboxamide (30 mg, 39% yield) as a white solid. LC-MS: m/z 426 $[M+H]^+$.

Step 2. Separation of enantiomers to obtain (R)-2-(difluoromethyl)-9,9-dimethyl-N-(2-(trifluoromethyl)pyridin-4-yl)-8,9-dihydro-7H-cyclopenta[d]imidazo[1,2-b]pyridazine-7-carboxamide and (S)-2-(difluoromethyl)-9,9-dimethyl-N-(2-(trifluoromethyl)pyridin-4-yl)-8,9-dihydro-7H-cyclopenta[d]imidazo[1,2-b]pyridazine-7-carboxamide Example 200

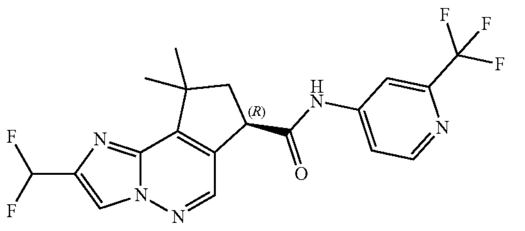

and

Example 201

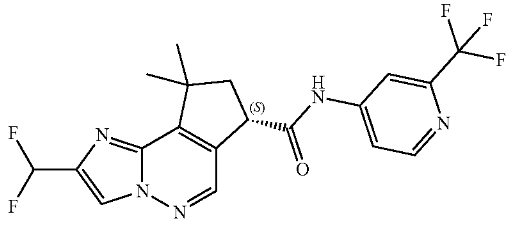

30 mg of 2-(difluoromethyl)-9,9-dimethyl-N-(2-(trifluoromethyl)pyridin-4-yl)-8,9-dihydro-7H-cyclopenta[d]imidazo[1,2-b]pyridazine-7-carboxamide were submitted to chiral HPLC purification (Column: CHIRAL ART Cellulose-SC, 2×25 cm, 5 μm; Mobile Phase A: Hex:DCM=3:1 (0.5% 2M $NH_3$-MeOH)-HPLC, Mobile Phase B: EtOH-HPLC; Flow rate: 20 mL/min; isocratic 5% B in 10 min; Wave Length: 220/254 nm; RT1(min): 6.91; RT2(min): 8.67; Sample Solvent: ETOH:DCM=1:1; Injection Volume: 0.5 mL; Number of Runs: 4). The first eluting isomer was concentrated and lyophilized to afford Example 200 (6.7 mg, 21% yield) as a white solid. The second eluting isomer was concentrated and lyophilized to afford Example 201 (6.8 mg, 22.6% yield) as a white solid.

Example 200: $^1$H NMR (300 MHz, DMSO-$d_6$) δ: 11.08 (s, 1H), 8.60-8.70 (m, 3H), 8.18 (d, J=2.1 Hz, 1H), 7.80-7.82 (m, 1H), 7.21 (t, J=54.9 Hz, 1H), 4.45 (dd, J=7.2, 8.7 Hz, 1H), 2.51-2.57 (m, 1H), 2.24 (dd, J=7.2, 13.2 Hz, 1H), 1.60 (s, 3H), 1.50 (s, 3H). LC-MS: m/z 426 $[M+H]^+$.

Example 201: $^1$H NMR (300 MHz, DMSO-$d_6$) δ: 11.08 (s, 1H), 8.64-8.65 (m, 3H), 8.18 (d, J=2.1 Hz, 1H), 7.80-7.86 (m, 1H), 7.22 (t, J=54.6 Hz, 1H), 4.45 (dd, J=7.2, 9.0 Hz, 1H), 2.57-2.66 (m, 1H), 2.24 (dd, J=7.2, 12.9 Hz, 1H), 1.60 (s, 3H), 1.50 (s, 3H). LC-MS: m/z 426 $[M+H]^+$.

The absolute stereochemistry for each separated isomer was not determined.

Method F5

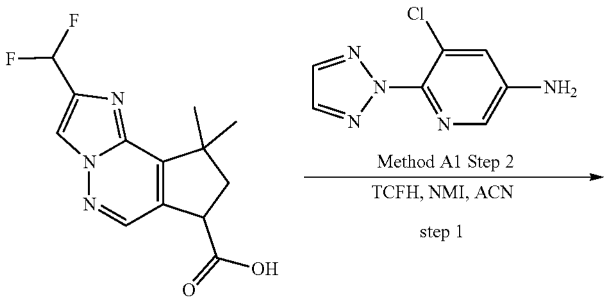

Method C5 Step 3

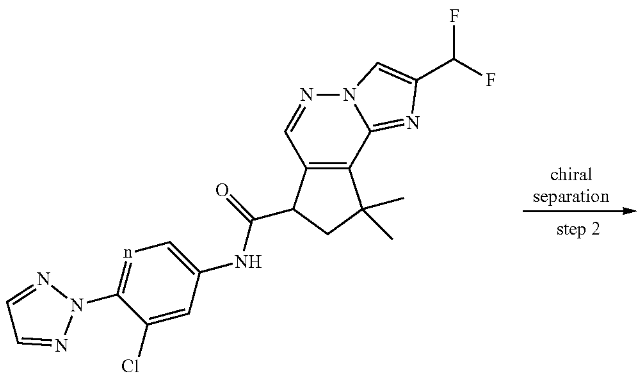

-continued

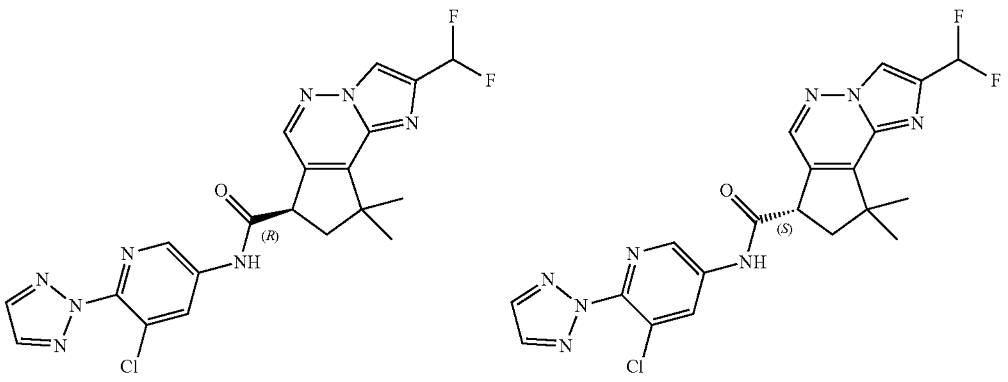

Example 202 and
Example 203

Examples 202 and 203: Single Enantiomers Obtained from a Racemic Mixture Containing (R)—N-(5-chloro-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide and (S)—N-(5-chloro-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide Step 1: N-(5-chloro-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide

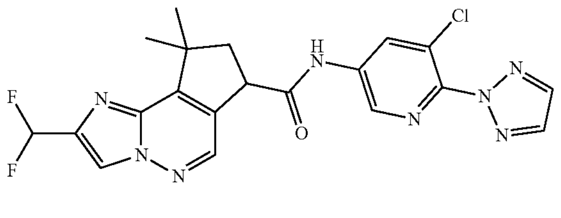 [SMILES: CC1(C)CC(C(=O)Nc2cnc(-n3nccn3)c(Cl)c2)c2cnn3cc(C(F)F)nc3c21]

Analogously to Method G4 Step 4, N-(5-chloro-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide (20 mg, 24% yield) was obtained as an off-white solid. LC-MS: m/z 459 [M+H]$^+$.

Step 2: Separation of Enantiomers to Obtain (R)—N-(5-chloro-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide and (S)—N-(5-chloro-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide Example 202

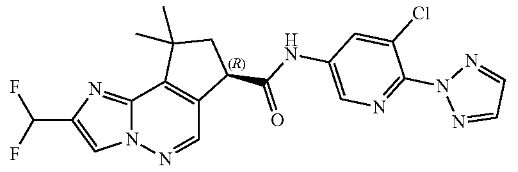

and

Example 203

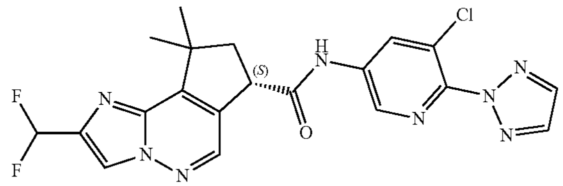

22 mg of N-(5-chloro-6-(2H-1,2,3-triazol-2-yl)pyridin-3-yl)-2-(difluoromethyl)-9,9-dimethyl-8,9-dihydro-7H-cyclopenta[d]imidazo[1,2-b]pyridazine-7-carboxamide were submitted to chiral HPLC purification (Column: CHIRAL ART Cellulose-SC, 2×25 cm, 5 μm; Mobile Phase A: Hex: DCM=3:1(0.5% 2M $NH_3$-MeOH)-HPLC, Mobile Phase B: EtOH-HPLC; Flow rate: 20 mL/min; isocratic 10% B in 16 min; Wave Length: 220/254 nm; RT1(min): 11.73; RT2 (min): 14.82; Sample Solvent: EtOH:DCM=1:1; Injection Volume: 1.1 mL; Number Of Runs: 3). The first eluting isomer was concentrated and lyophilized to afford Example 202 (8.2 mg, 36.7% yield) as a light-yellow solid. The second eluting isomer was concentrated and lyophilized to afford Example 203 (7.1 mg, 32.2% yield) as a white solid.

Example 202: $^1$H NMR (300 MHz, DMSO-$d_6$) δ: 11.09 (s, 1H), 8.73 (d, J=2.4 Hz, 1H), 8.66-8.67 (m, 2H), 8.59 (d, J=2.4 Hz, 1H), 8.18 (s, 2H), 7.22 (t, J=54.9 Hz, 1H), 4.48

(dd, J=7.5, 9.0 Hz, 1H), 2.54-2.58 (m, 1H), 2.28 (dd, J=7.2, 13.2 Hz, 1H), 1.63 (s, 3H), 1.51 (s, 3H). LC-MS: m/z 459 $[M+H]^+$.

Example 203: $^1$H NMR (300 MHz, DMSO-$d_6$) δ: 11.08 (s, 1H), 8.73 (d, J=2.4 Hz, 1H), 8.66-8.67 (m, 2H), 8.59 (d, J=2.4 Hz, 1H), 8.18 (s, 2H), 7.22 (t, J=54.9 Hz, 1H), 4.48 (dd, J=7.2, 9.0 Hz, 1H), 2.54-2.58 (m, 1H), 2.29 (dd, J=7.2, 13.2 Hz, 1H), 1.63 (s, 3H), 1.51 (s, 3H). LC-MS: m/z 459 $[M+H]^+$.

The absolute stereochemistry for each separated isomer was not determined.

Biological Assays

MALT1 Protease Assays

MALT1 protease activity was assessed in an in vitro assay using a tetrapeptide as substrate and full-length MALT1 protein His-MALT1(1-824) purified from baculovirus-infected insect cells. The tetrapeptide substrate is Ac-LRSR-AMC (SM Biochemicals) with $K_m$ measured at around 100 μM.

The final assay buffer includes 1 nM (Assay 2) or 2 nM (Assay 1) of MALT1 full-length protein, 50 μM Ac-LRSR-AMC substrate, 50 mM Tris pH 7.5, 600 mM Sodium Citrate, 1 mM DTT, 1 mM EDTA, and 0.05% BSA in 384-well plate format using black microtiter square well plates (Optiplate 384-F, Perkin Elmer).

Test compounds were dissolved in 100% DMSO at stock of 10 mM, with final DMSO concentration 0.1%. Test compounds were pre-incubated with MALT1 protein for 2 h at room temperature. Substrate was added after the pre-incubation and fluorescence signal was measured using Envision at excitation 355 nm and emission 460 nm after 8 hr incubation at RT. Increase in the assay signal was linear over this period and proportional with increase in the enzyme content.

The fluorescence units were transformed to percentage of remaining activity by using the high control (HC, median of fluorescence signal from wells containing MALT1 protein, substrate, and DMSO) and low control (LC, median of fluorescence signal from wells with substrate only) with the formula below:

$$\%\text{Remaining Activity} = 100\% \times \frac{\text{Signal}_{Sample} - \text{Signal}_{LC}}{\text{Signal}_{HC} - \text{Signal}_{LC}}$$

$IC_{50}$ and Hill coefficients were obtained using Graph Pad Prism (Graph Pad software, Inc, USA) with non-linear regression analysis. MALT1 inhibition $IC_{50}$ values of certain compounds described herein are provided in Tables A and B below.

Human IL10 Secretion Assays

IL10 is one of the cytokines that are regulated via activation of NF-kB signaling. For example, in ABC-DLBCL cell lines, the activated NF-kB signaling leads to increased IL10 secretion. Inhibition of NF-kB signaling has been shown leading to decreased IL10 secretion.

Assay 1: OCI-LY10 cells were seeded in IMEM supplemented with 20% fetal bovine serum at $3\times10^5$ cells per well in 96-well round bottom plates (Corning 3799, Corning), treated with 100 nL of 3-fold serial compound dilutions, starting at 10 mM. The final vehicle concentration was 0.1% DMSO in all wells. After 24 h incubation, the cells were transferred to 96-PCR plates (Axygen: PCR-96-FLT-C) and centrifuged, then 16 μL of cell culture media was transferred to HTRF plates and IL10 levels were measured using human IL-10 Assay Kits (Cisbio) using HTRF format. The signals were transformed to percentage of remaining activity by using the high control (HC, median of signal from wells containing cells treated with DMSO) and low control (LC, median of signal from wells with no cells). IC50 values (nM) were determined using 4-parametric curve-fitting and Hill coefficient obtained using Graph Pad Prism (Graph Pad software, Inc, USA) with non-linear regression analysis.

Assay 2: OCI-LY10 cells were seeded in IMEM supplemented with 20% fetal bovine serum at $4.8\times10^5$ cells per 160 μL per well in 96-well V-bottom cell culture plates (corning, 3894), treated with 120 nL of 3-fold serial compound dilutions, starting at 4 mM. The final vehicle concentration was 0.075% DMSO in all wells. After a 24 h incubation, human IL-10 precoated plates (Meso Scale Discovery) were washed 3 times with PBST, and 50 μL culture medium was aspirated into the MSD plate and incubated at 4° C. overnight. The supernatant was then discarded, and the wells were washed 3 times with PB ST. SULFO-TAG Anti-human IL-10 Antibody (50×) was diluted 50-fold according to the Meso Scale Protocol, then 25 μL of SULFO-TAG Anti-human IL-10 Antibody (1×) was added. After 2 h of incubation at RT, the supernatant was discarded, and the well was washed 3 times with PBST. 2×read buffer was added and the signal was read on an MSD Sector S600. The effect of a particular compound on IL10 secretion is shown relative to the effect of DMSO; set as 100%. $IC_{50}$ values (nM) were determined using 4-parametric curve-fitting.

The biological activity of certain compounds using the assays described above are shown in Tables A and B. The MALT1 $IC_{50}$ and IL10 secretion cell assay $IC_{50}$ ranges are as follows: A denotes $IC_{50}$<10 nM; B denotes 10 nM≤$IC_{50}$<100 nM; C denotes 100 nM≤$IC_{50}$<1000 nM; D denotes $IC_{50}$≥1000 nM. NA denotes value not determined with that assay for the specified compound.

TABLE A $IC_{50}$ Values for Selected Compounds of Formula (I) using Assay 1

| Example No. | MALT1 $IC_{50}$ [nM] Assay 1 | IL-10 Secretion $IC_{50}$ [nM] Assay 1 |
|---|---|---|
| 1 | C | NA |
| 2 | A | C |
| 3 | D | NA |
| 4 | B | C |
| 5 | D | NA |
| 6 | A | C |
| 7 | B | NA |
| 8 | D | NA |
| 9 | B | C |
| 10 | D | NA |
| 11 | B | C |
| 12 | D | NA |
| 13 | B | C |
| 14 | D | NA |
| 15 | C | NA |
| 16 | D | NA |
| 17 | B | NA |
| 18 | C | NA |
| 19 | C | NA |
| 20 | D | NA |
| 21 | B | D |
| 22 | C | NA |
| 23 | A | C |
| 24 | D | NA |
| 25 | B | C |
| 26 | D | NA |
| 27 | D | NA |
| 28 | C | NA |

TABLE A-continued

IC$_{50}$ Values for Selected Compounds of Formula (I) using Assay 1

| Example No. | MALT1 IC$_{50}$ [nM] Assay 1 | IL-10 Secretion IC$_{50}$ [nM] Assay 1 |
|---|---|---|
| 29 | B | C |
| 30 | D | NA |
| 31 | A | C |
| 32 | D | NA |
| 33 | A | B |
| 34 | D | NA |
| 35 | B | D |
| 36 | A | C |
| 37 | B | D |
| 38 | A | C |
| 39 | B | NA |
| 40 | B | NA |
| 41 | C | NA |
| 42 | D | NA |

TABLE B

IC$_{50}$ Values for Selected Compounds of Formula (I) using Assay 2

| Example No. | MALT1 IC$_{50}$ [nM] Assay 2 | IL-10 Secretion IC$^{50}$ [nM] Assay 2 |
|---|---|---|
| 43 | B | NA |
| 44 | A | C |
| 45 | D | NA |
| 46 | D | NA |
| 47 | A | C |
| 48 | B | NA |
| 49 | A | C |
| 50 | D | NA |
| 51 | A | C |
| 52 | C | NA |
| 53 | C | NA |
| 54 | A | C |
| 55 | B | NA |
| 56 | A | C |
| 57 | C | NA |
| 58 | B | NA |
| 59 | B | NA |
| 60 | C | NA |
| 61 | B | NA |
| 62 | B | NA |
| 63 | C | NA |
| 64 | B | C |
| 65 | C | NA |
| 66 | B | C |
| 67 | C | NA |
| 68 | A | C |
| 69 | D | NA |
| 70 | D | NA |
| 71 | C | NA |
| 72 | D | NA |
| 73 | A | B |
| 74 | D | NA |
| 75 | B | C |
| 76 | D | NA |
| 77 | A | B |
| 78 | C | NA |
| 79 | A | B |
| 80 | D | NA |
| 81 | B | C |
| 82 | B | NA |
| 83 | C | NA |
| 84 | A | B |
| 85 | C | NA |
| 86 | D | NA |
| 87 | D | NA |
| 88 | B | NA |
| 89 | A | C |

TABLE B-continued

IC$_{50}$ Values for Selected Compounds of Formula (I) using Assay 2

| Example No. | MALT1 IC$_{50}$ [nM] Assay 2 | IL-10 Secretion IC$^{50}$ [nM] Assay 2 |
|---|---|---|
| 90 | D | NA |
| 91 | B | C |
| 92 | C | NA |
| 93 | D | NA |
| 94 | B | NA |
| 95 | B | C |
| 96 | C | NA |
| 97 | B | C |
| 98 | D | NA |
| 99 | C | NA |
| 100 | C | NA |
| 101 | B | C |
| 102 | C | NA |
| 103 | A | C |
| 104 | D | NA |
| 105 | D | NA |
| 106 | B | NA |
| 107 | A | B |
| 108 | A | C |
| 109 | D | NA |
| 110 | B | NA |
| 111 | A | B |
| 112 | C | NA |
| 113 | D | NA |
| 114 | C | NA |
| 115 | B | NA |
| 116 | C | NA |
| 117 | B | NA |
| 118 | B | NA |
| 119 | C | NA |
| 120 | B | NA |
| 121 | C | NA |
| 122 | A | C |
| 123 | B | D |
| 124 | C | NA |
| 125 | D | NA |
| 126 | B | NA |
| 127 | D | NA |
| 128 | B | C |
| 129 | C | NA |
| 130 | B | NA |
| 131 | D | NA |
| 132 | B | NA |
| 133 | D | NA |
| 134 | D | NA |
| 135 | C | NA |
| 136 | C | NA |
| 137 | D | NA |
| 138 | D | NA |
| 139 | D | NA |
| 140 | C | NA |
| 141 | D | NA |
| 142 | D | NA |
| 143 | C | NA |
| 144 | B | NA |
| 145 | A | C |
| 146 | B | NA |
| 147 | D | NA |
| 148 | D | NA |
| 149 | B | C |
| 150 | B | NA |
| 151 | A | B |
| 152 | C | NA |
| 153 | D | NA |
| 154 | D | NA |
| 155 | B | NA |
| 156 | D | NA |
| 157 | B | D |
| 158 | B | C |
| 159 | D | NA |
| 160 | A | B |
| 161 | D | NA |
| 162 | B | NA |

TABLE B-continued

| IC50 Values for Selected Compounds of Formula (I) using Assay 2 | | |
|---|---|---|
| Example No. | MALT1 $IC_{50}$ [nM] Assay 2 | IL-10 Secretion $IC^{50}$ [nM] Assay 2 |
| 163 | C | NA |
| 164 | C | NA |
| 165 | D | NA |
| 166 | D | NA |
| 167 | C | NA |
| 168 | C | NA |
| 169 | D | NA |
| 170 | B | NA |
| 171 | B | NA |
| 172 | D | NA |
| 173 | B | NA |
| 174 | C | NA |
| 175 | D | NA |
| 176 | C | NA |
| 177 | C | NA |
| 178 | D | NA |
| 179 | D | NA |
| 180 | D | NA |
| 181 | B | NA |
| 182 | D | NA |
| 183 | B | NA |

TABLE B-continued

| IC50 Values for Selected Compounds of Formula (I) using Assay 2 | | |
|---|---|---|
| Example No. | MALT1 $IC_{50}$ [nM] Assay 2 | IL-10 Secretion $IC^{50}$ [nM] Assay 2 |
| 184 | C | NA |
| 185 | A | NA |
| 186 | C | NA |
| 187 | B | NA |
| 188 | C | NA |
| 189 | A | C |
| 190 | C | NA |
| 191 | A | C |
| 192 | C | NA |
| 193 | A | B |
| 194 | C | NA |
| 195 | A | B |
| 196 | C | NA |
| 197 | B | NA |
| 198 | D | NA |
| 199 | B | NA |
| 200 | C | NA |
| 201 | C | NA |
| 202 | C | NA |
| 203 | B | NA |

What is claimed is:

1. A compound of Formula (I):

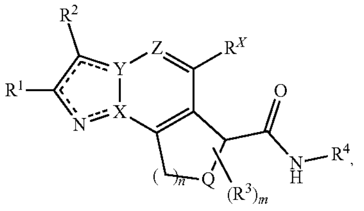

(I)

or a pharmaceutically acceptable salt thereof, wherein:

each ⎓ is a single or double bond;

Q is —$CH_2$—, O, or NH;

X is N or C;

Y is N or C;

Z is N or CRS;

wherein when one of X and Y is N, the other of X and Y is C;

$R^X$ is hydrogen or halogen;

n is 1, 2, or 3;

$R^1$ is hydrogen, halogen, cyano, hydroxyl, C1-C3 alkoxy, C1-C3 haloalkoxy, C1-C3 haloalkyl, —$NR^AR^B$, or C1-C3 alkyl optionally substituted with 1-3 substituents selected from hydroxyl and C1-C3 alkoxy;

$R^2$ is hydrogen, halogen, amino, or C1-C3 alkyl;

each $R^3$ is independently deuterium, halogen, hydroxyl, C3-C6 cycloalkyl, C1-C3 alkyl, C1-C3 alkoxy, C1-C3 haloalkoxy, or C1-C3 haloalkyl; or two $R^3$ together with the carbon atom to which they are attached come together to form an oxo group, a 4-8 membered heterocyclyl, or a C3-C8 cycloalkyl;

m is 0, 1, 2, or 3;

$R^4$ is phenyl or 5-9 membered heteroaryl; wherein each $R^4$ group is optionally substituted with 1-3 substituents independently selected from $R^6$;

$R^5$ is hydrogen, halogen, cyano, hydroxyl, C1-C3 alkoxy, C1-C3 haloalkoxy, C1-C3 haloalkyl, —$NR^CR^D$, or C1-C3 alkyl; and each $R^6$ is independently selected from halogen; cyano; amino; —N=(S═O)(C1-C3 alkyl)$_2$; —S(═O)$_p$(C1-C3 alkyl); —(C═O)$NR^ER^F$; C1-C3 alkoxy; C1-C3 haloalkyl optionally substituted with hydroxyl; C1-C3 haloalkoxy; 5-6 membered heteroaryl optionally substituted with halogen, cyano, hydroxyl, C1-C3 alkoxy, C1-C3 haloalkoxy, amino, C1-C3 haloalkyl, 4-6 membered heterocyclyl, or C1-C3 alkyl optionally substituted with hydroxyl or —$NR^ER^F$; C1-C4 alkyl optionally substituted with hydroxyl, —$NR^ER^F$, or C1-C3 alkoxy; 3-8 membered heterocyclyl; and C3-C6 cycloalkoxy;

p is 1 or 2; and $R^A$, $R^B$, $R^C$, $R^D$, $R^E$, and $R^F$, are independently hydrogen, C1-C3 alkyl, C3-C6 cycloalkyl, or $R^A$ and $R^B$, or $R^C$ and $R^D$, or $R^E$ and $R^F$, together with the nitrogen atom to which they are attached come together to form a 4-6 membered heterocyclyl optionally substituted with 1-2 halogens.

2. The compound of claim 1, wherein;

X is C and Y is C; or

X is N and Y is C; or

X is C and Y is N.

3. The compound of claim 1, wherein Z is N.

4. The compound of claim 1, wherein Z is $CR^5$.

5. The compound of claim 1, wherein Q is —$CH_2$—.

6. The compound of claim 1, wherein Q is O.

7. The compound of claim 1, wherein $R^1$ is hydrogen, halogen, cyano, hydroxyl, C1-C3 haloalkyl, or C1-C3 alkyl optionally substituted with 1-3 substituents selected from hydroxyl and C1-C3 alkoxy.

8. The compound of claim 1, wherein $R^1$ is hydrogen, halogen, or C1-C3 alkyl.

9. The compound of claim 1, wherein n is 1 or 2.

10. The compound of claim 1, wherein m is 2 or 3.

11. The compound of claim 1, wherein each $R^3$ is independently deuterium, halogen, hydroxyl, C3-C6 cycloalkyl, C1-C3 alkyl, C1-C3 haloalkyl, C1-C3 alkoxy, or C1-C3 haloalkoxy.

12. The compound of claim 1, wherein:

m is 2 and each $R^3$ is methyl; or m is 2 and one $R^3$ is methyl and the other $R^3$ is trifluoromethyl; or m is 2 and one $R^3$ is trifluoromethyl and the other $R^3$ is ethoxy; or m is 2 and the two $R^3$ together with the carbon atom to which they are attached come together to form a 4-8 membered heterocyclyl, optionally wherein the 4-8 membered heterocyclyl is oxetanyl or tetrahydropyranyl; or m is 2 and the two $R^3$ together with the carbon atom to which they are attached form a C3-C8 cycloalkyl, optionally wherein the C3-C8 cycloalkyl is cyclopropyl or cyclobutyl; or m is 3; two $R^3$ are methyl, and one $R^3$ is selected from the group consisting of methyl and hydroxyl.

13. The compound of claim 1, wherein $R^4$ is 5-9 membered heteroaryl optionally substituted with 1-3 independently selected $R^6$.

14. The compound of claim 1, wherein:

(i) at least one of $R^6$ is halogen; or (ii) at least one of $R^6$ is cyano; or (iii) at least one of $R^6$ is —(C═O)$NR^ER^F$, optionally wherein:

$R^E$ and $R^F$ are independently hydrogen, C1-C3 alkyl, or C3-C6 cycloalkyl; or one of $R^E$ and $R^F$ is hydrogen and the other of $R^E$ and $R^F$ is C1-C3 alkyl or C3-C6 cycloalkyl; or one of $R^E$ and $R^F$ is C1-C3 alkyl and the other of $R^E$ and $R^F$ is C3-C6 cycloalkyl; or $R^E$ and $R^F$ together with the nitrogen atom to which they are attached come together to form a 4-6 membered heterocyclyl optionally substituted with 1-2 halogens; or (iv) at least one of $R^6$ is —N=(S═O)(C1-C3 alkyl)$_2$; or (v) at least one of $R^6$ is C1-C3 alkoxy; or (vi) at least one of $R^6$ is C1-C3 haloalkyl optionally substituted with hydroxyl; or (vii) at least one of $R^6$ is C1-C3 haloalkoxy; or (viii) at least one of $R^6$ is 5-6 membered heteroaryl optionally substituted with halogen, cyano, hydroxyl, C1-C3 alkoxy, C1-C3 haloalkoxy, C1-C3 alkyl optionally substituted with hydroxyl or —$NR^ER^F$, amino, or C1-C3 haloalkyl; or (ix) at least one of $R^6$ is C1-C4 alkyl optionally substituted with hydroxyl, —$NR^ER^F$, or C1-C3 alkoxy; or (x) at least one of $R^6$ is 3-8 membered heterocyclyl; or (xi) at least one of $R^6$ is C3-C6 cycloalkoxy; or (xii) at least one of $R^6$ is cyclopropoxy.

15. The compound of claim 1, wherein $R^4$ is 3-pyridyl or 4-pyridyl substituted with 1-3 independently selected $R^6$.

16. The compound of claim 1, wherein $R^4$ is

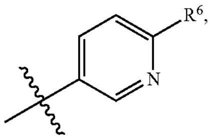

,

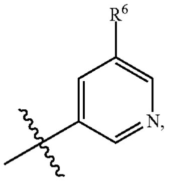

, or

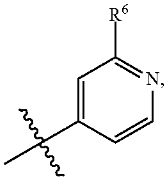

, wherein the wavy line crosses the bond that connects to the —C(═O)NH— moiety of Formula (I).

17. The compound of claim 16, wherein $R^6$ is selected from the group consisting of cyano, halogen, C1-C3 haloalkyl optionally substituted with hydroxyl, C1-C3 haloalkoxy, and C1-C3 alkoxy.

18. The compound of claim 1, wherein $R^4$ is

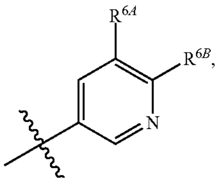

,

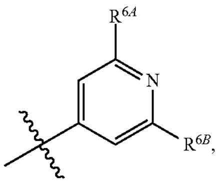

,

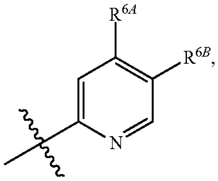

, or

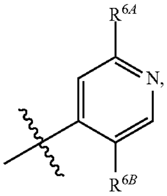

, wherein $R^{6A}$ and $R^{6B}$ are independently selected from $R^6$ and the wavy line crosses the bond that connects to the —C(═O)NH— moiety of Formula (I).

19. The compound of claim 18, wherein $R^{6A}$ is selected from the group consisting of: cyano, halogen, C1-C3 alkyl, C1-C3 alkoxy, and C1-C3 haloalkyl; and $R^{6B}$ is selected from the group consisting of: 5-6 membered heteroaryl optionally substituted with cyano, C1-C3 alkyl optionally substituted with hydroxyl, 4-6 membered heterocyclyl, or amino; —N=(S═O)(C1-C3 alkyl)$_2$; —(C═O)NR$^E$R$^F$; C1-C3 alkoxy; C1-C3 haloalkyl optionally substituted with hydroxyl; C1-C3 haloalkoxy; cyano; C3-C6 cycloalkoxy; and C1-C3 alkyl optionally substituted with hydroxyl.

20. The compound of claim 1, wherein $R^4$ is

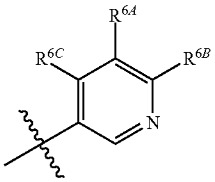

or

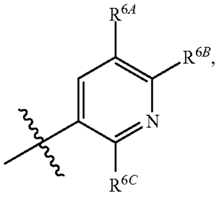

, wherein $R^{6A}$, $R^{6B}$, and $R^{6C}$ are independently selected from $R^6$ and the wavy line crosses the bond that connects to the —C(═O)NH— moiety of Formula (I).

21. The compound of claim 20, wherein $R^{6A}$ is selected from the group consisting of: cyano, halogen, C1-C3 alkyl, C1-C3 alkoxy, and C1-C3 haloalkyl;

$R^{6B}$ is selected from the group consisting of: 5-6 membered heteroaryl optionally substituted with cyano, C1-C3 alkyl, or amino; —(C═O)$NR^ER^F$; C1-C3 alkoxy; C1-C3 haloalkyl; C1-C3 haloalkoxy; cyano; and C1-C3 alkyl; and $R^{6C}$ is selected from the group consisting of: cyano, halogen, C1-C3 alkyl, C1-C3 alkoxy, and C1-C3 haloalkyl.

22. The compound of claim 1, wherein $R^5$ is hydrogen or halogen, optionally wherein the halogen is fluoro.

23. The compound of claim 1, wherein $R^X$ is halogen, optionally wherein the halogen is fluoro.

24. The compound of claim 1, wherein $R^X$ is hydrogen.

25. The compound of claim 1, wherein the compound is selected from the group consisting of:

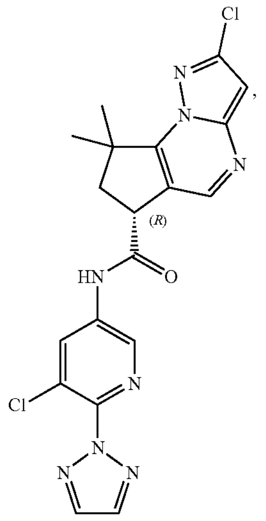

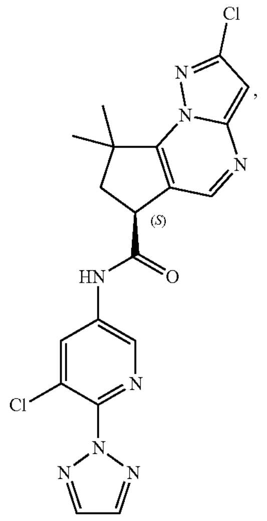

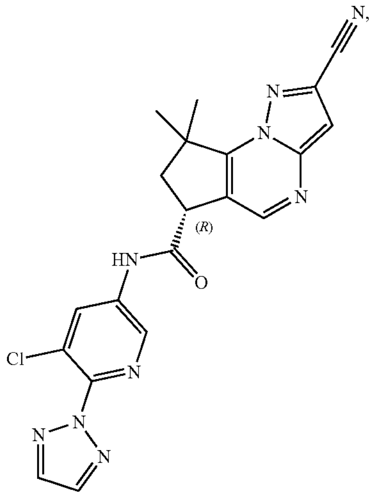

-continued

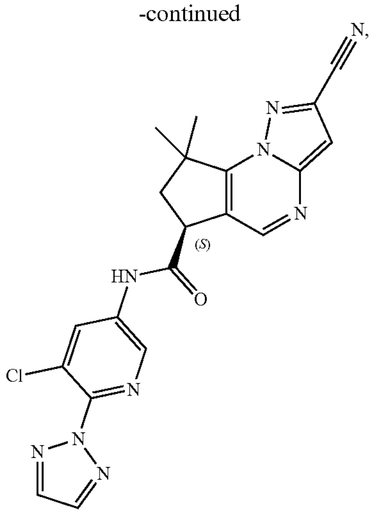

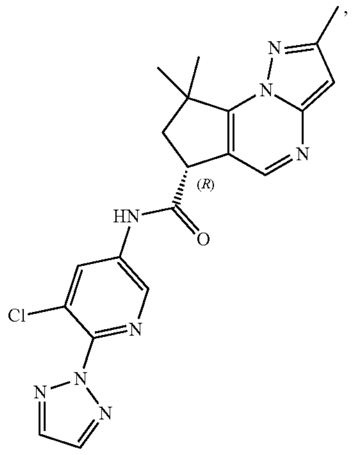

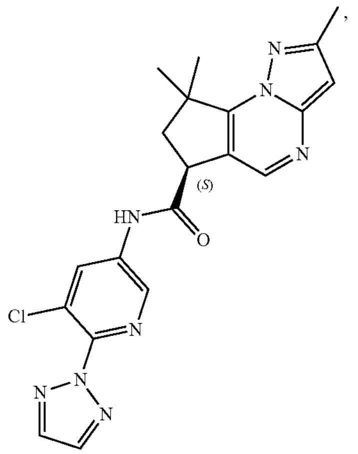

-continued
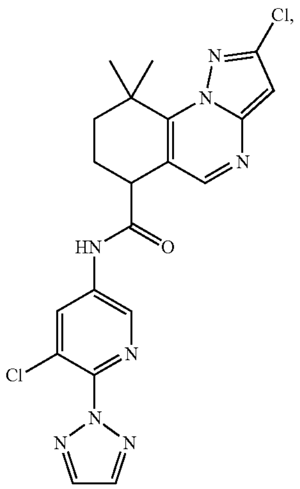
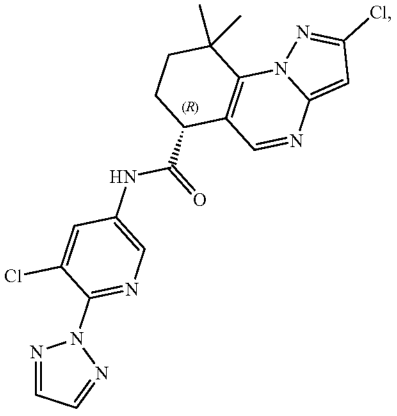
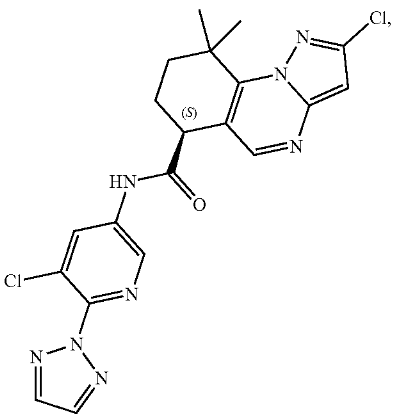
-continued
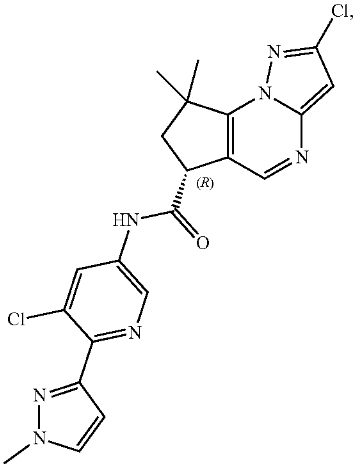
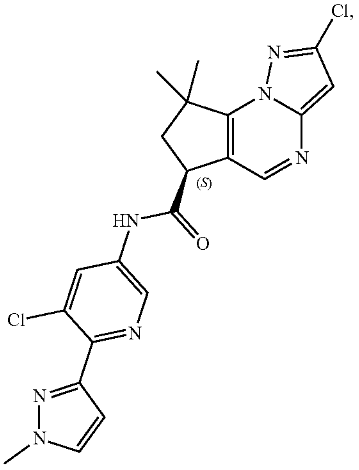
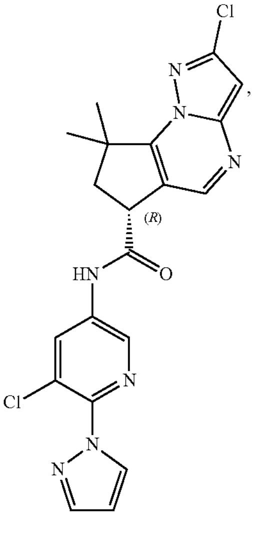
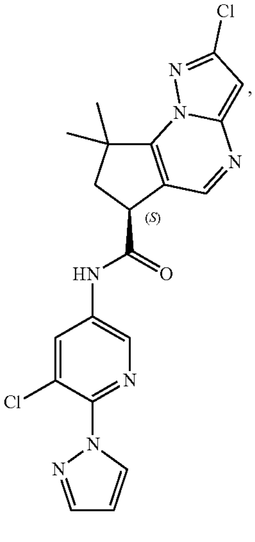

-continued
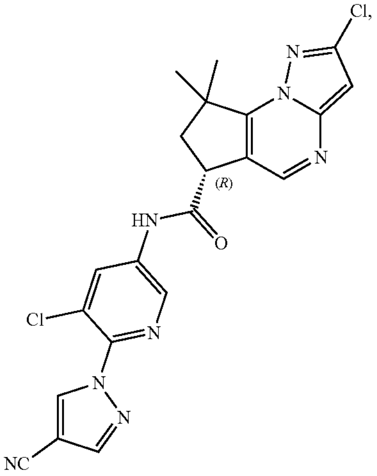
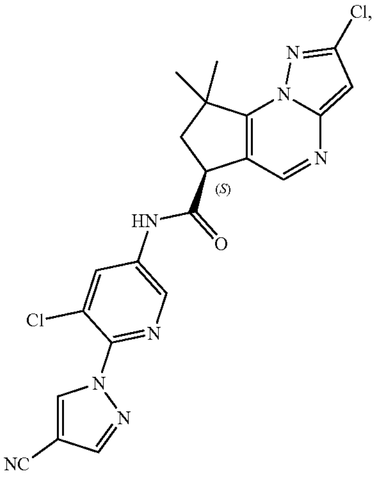
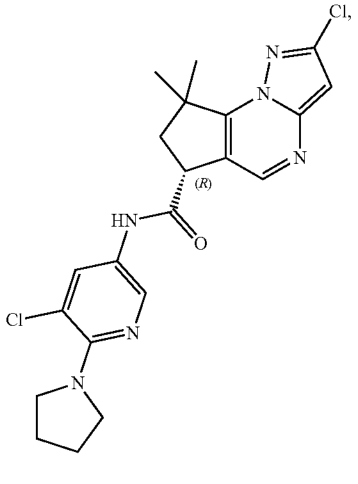
-continued
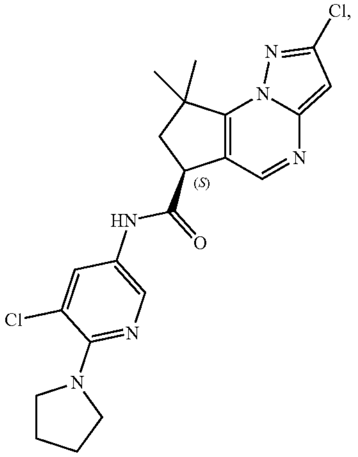
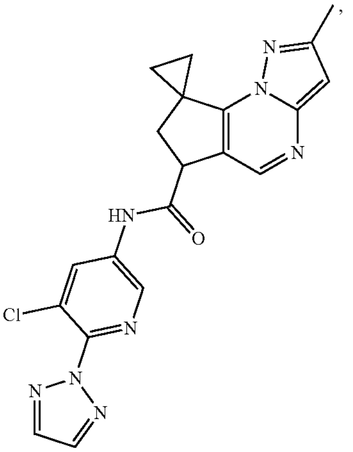
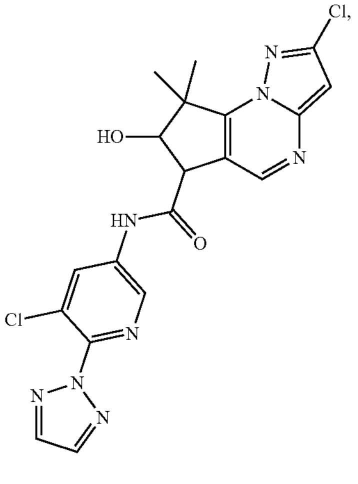

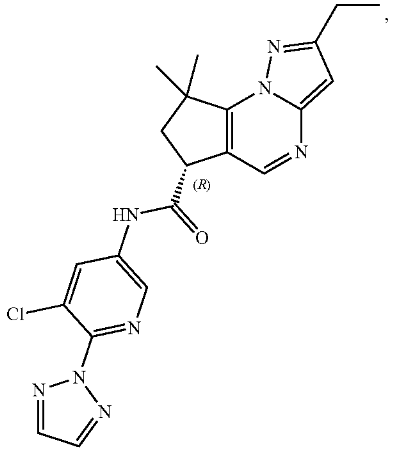
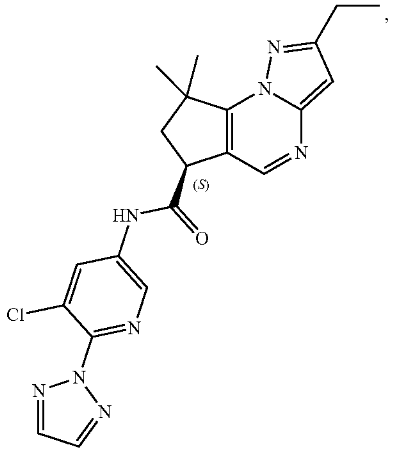
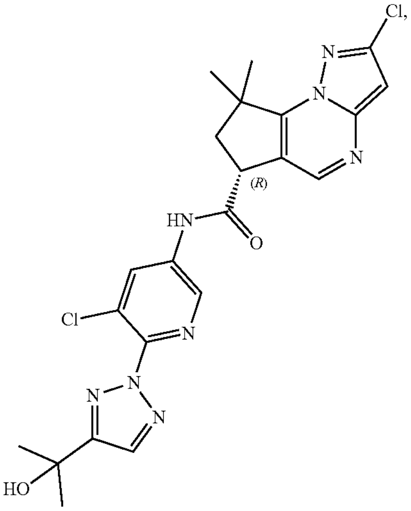
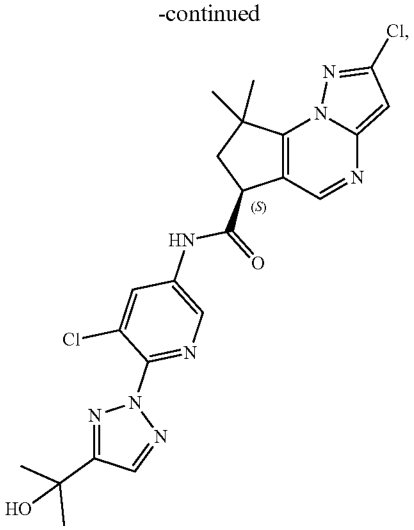
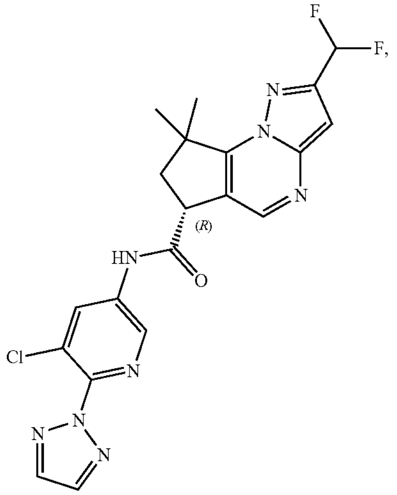
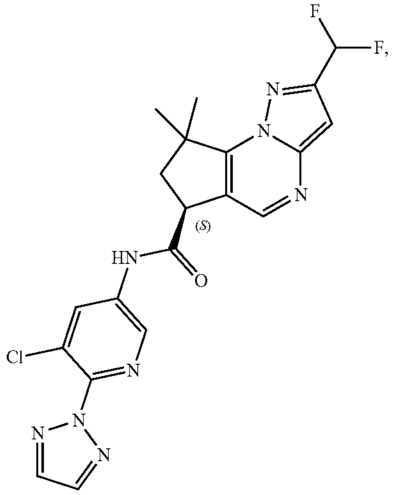

-continued
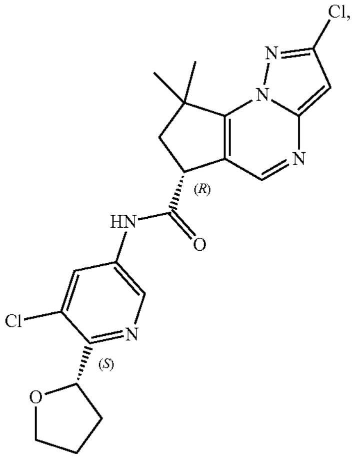
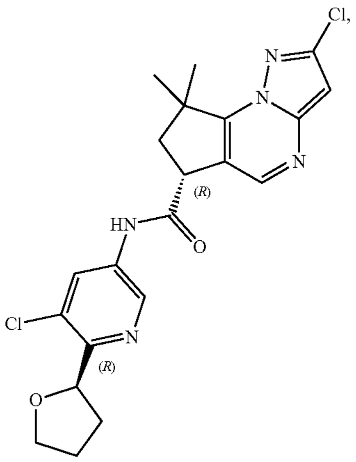
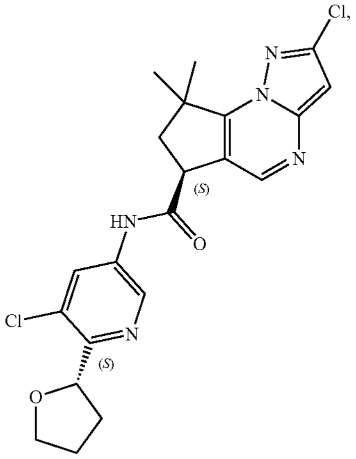
-continued
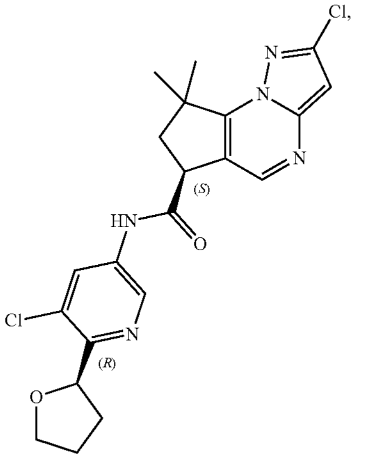
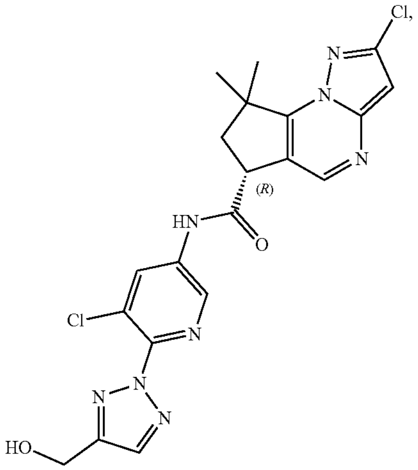
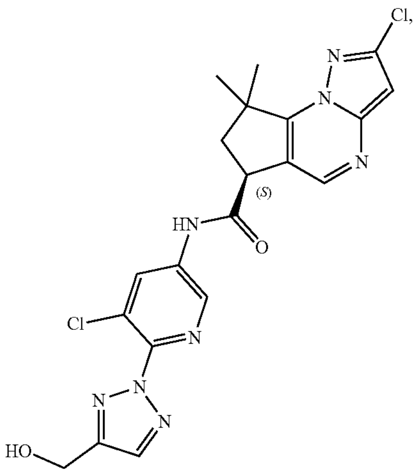

-continued
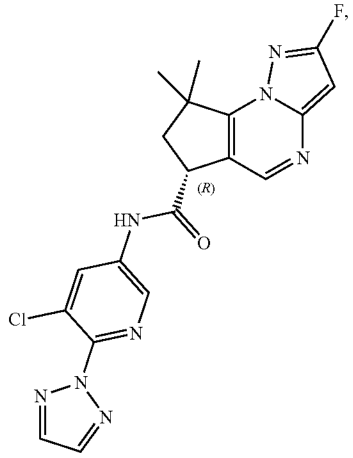
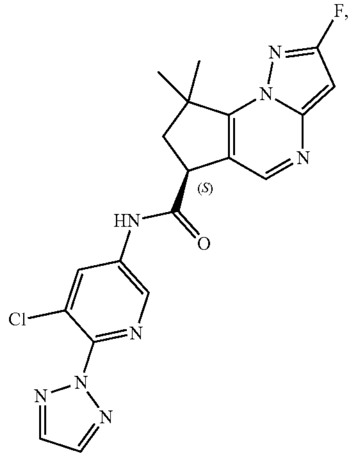
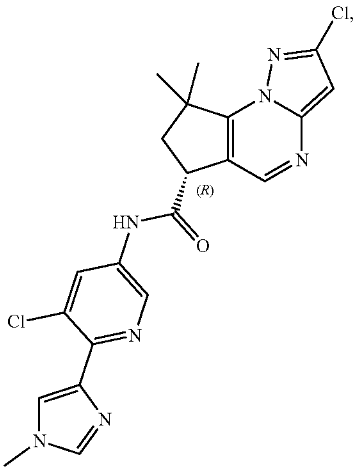
-continued
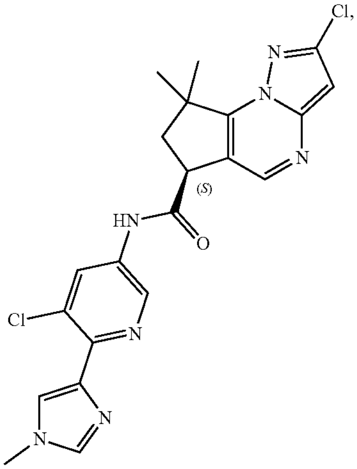
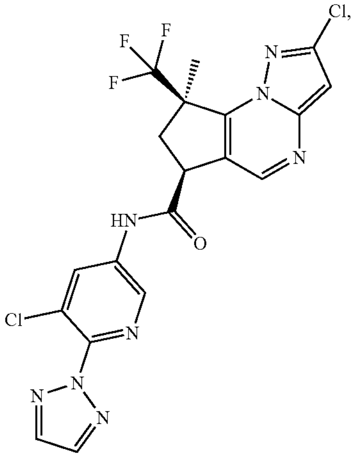
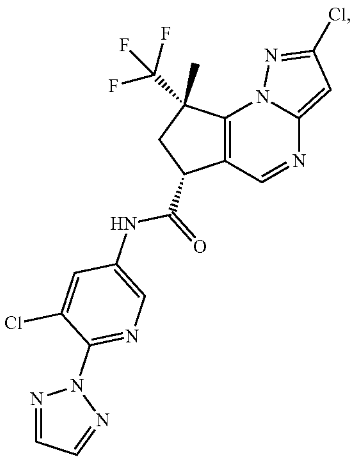

-continued
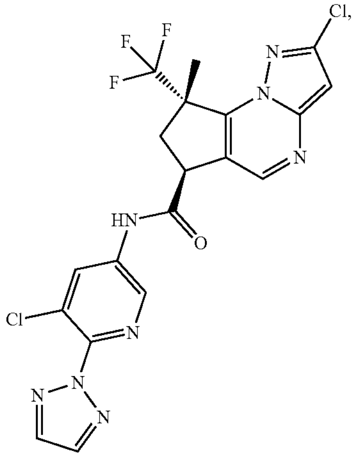
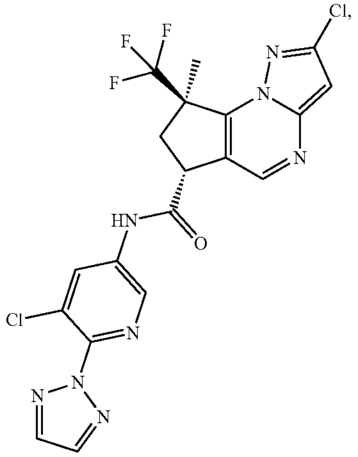
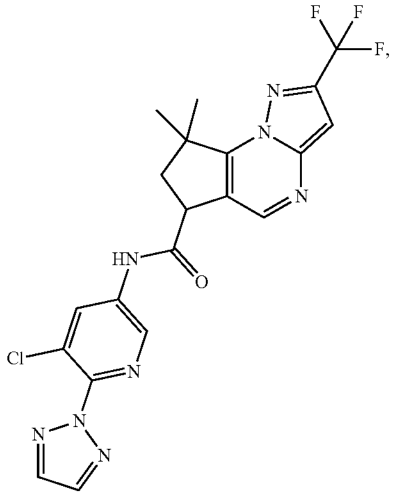
-continued
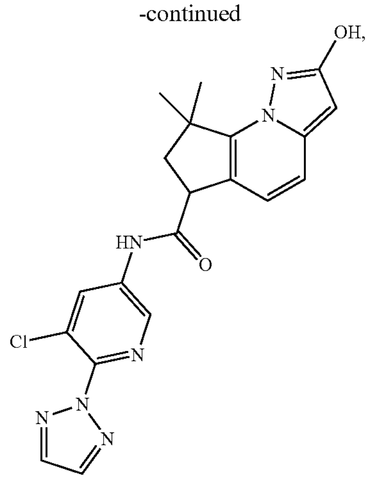
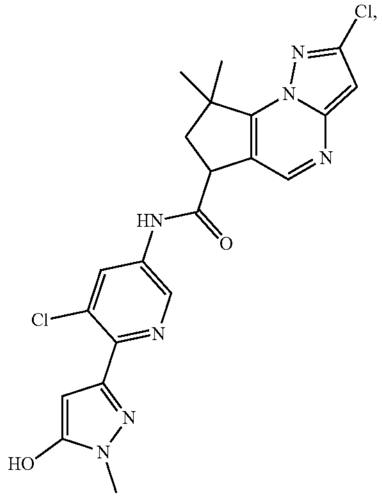
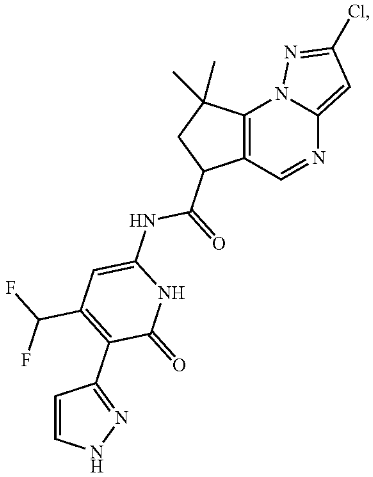

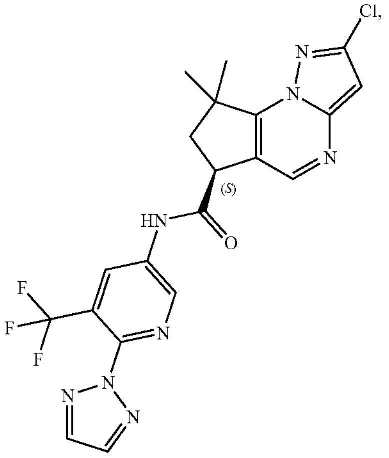
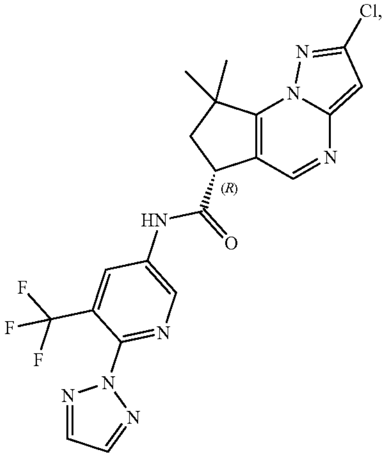
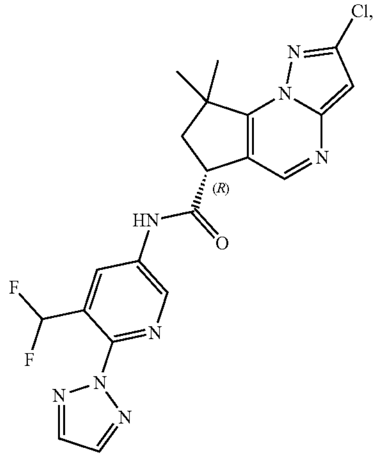
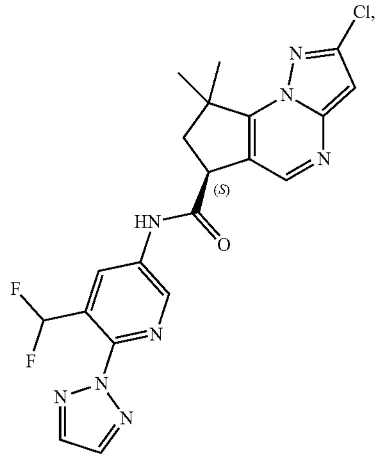
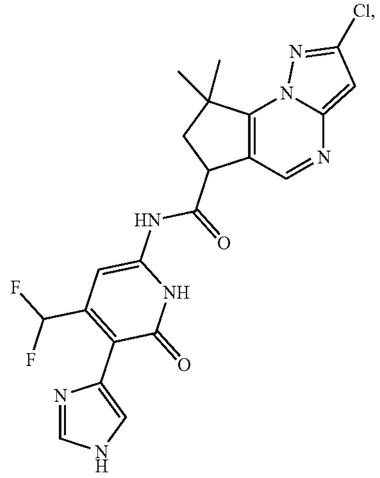
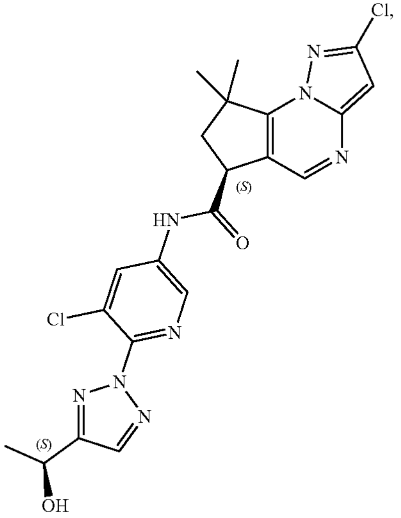

-continued
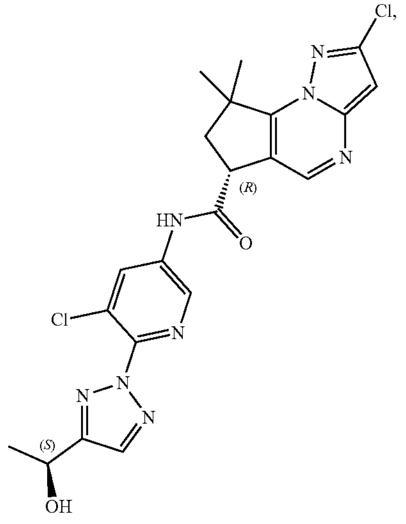
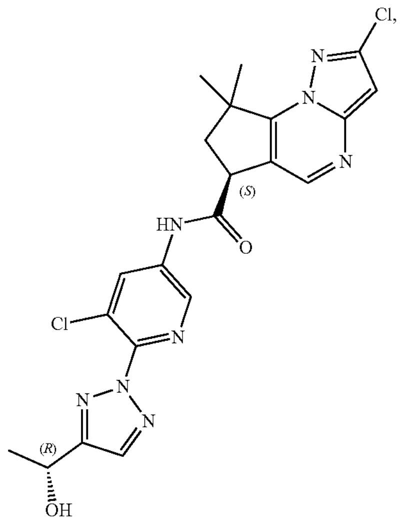
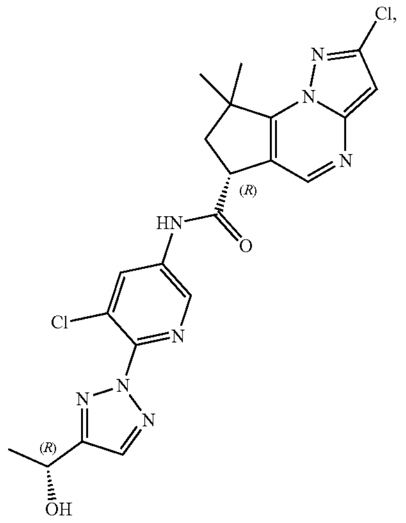
-continued
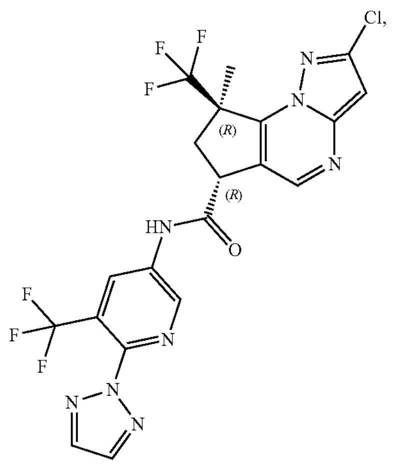
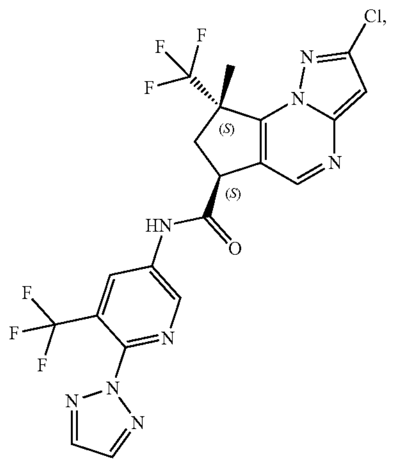
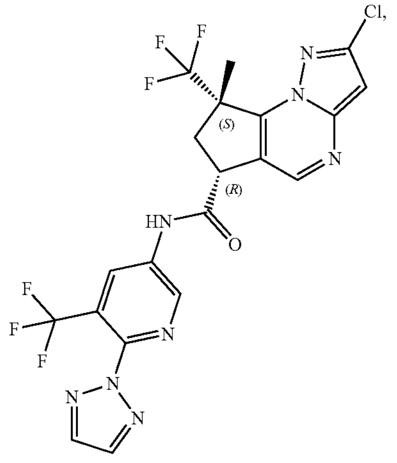

-continued
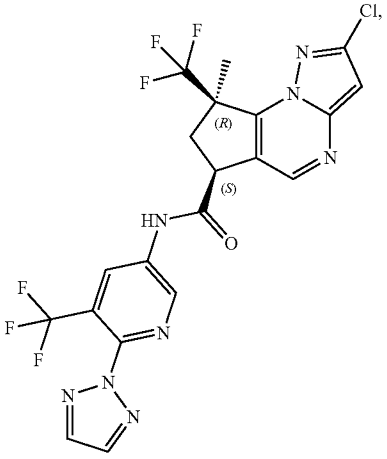
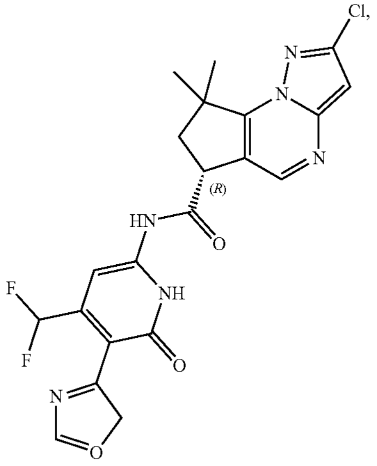
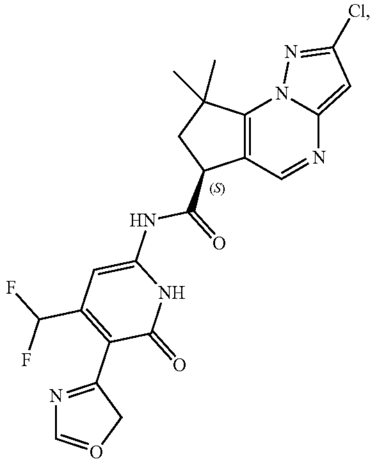
-continued
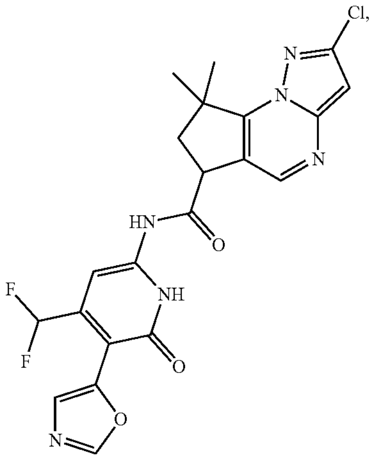
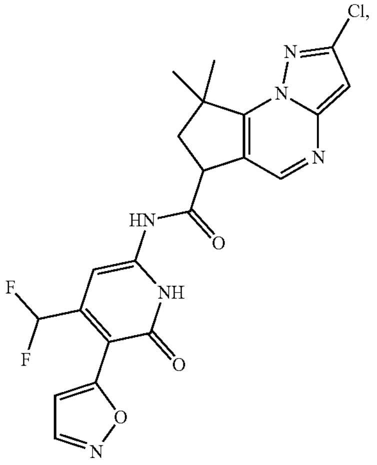
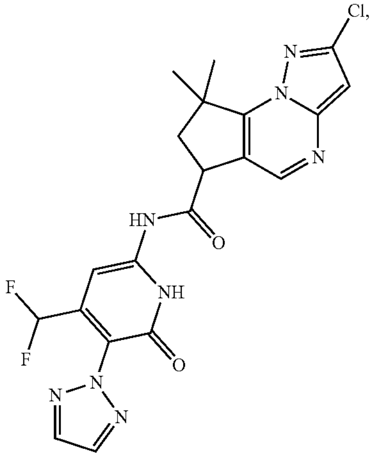

-continued
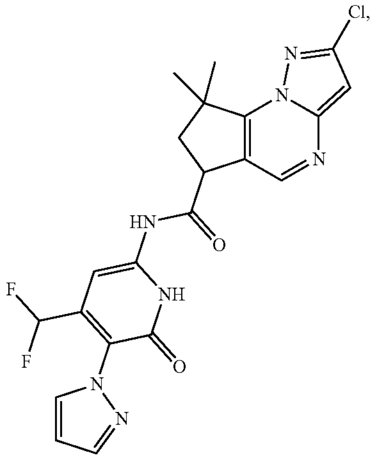
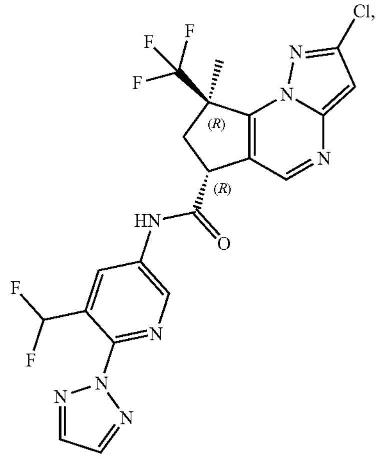
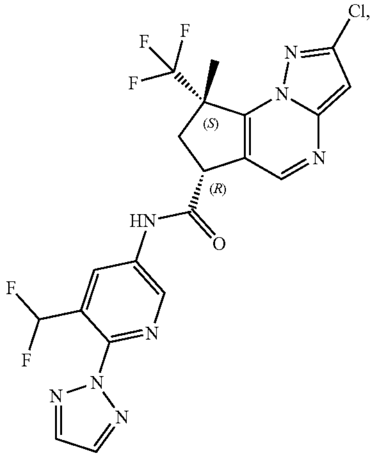
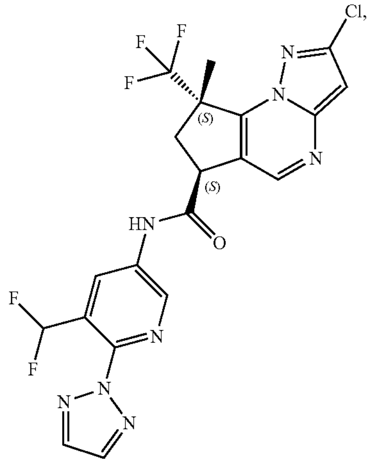
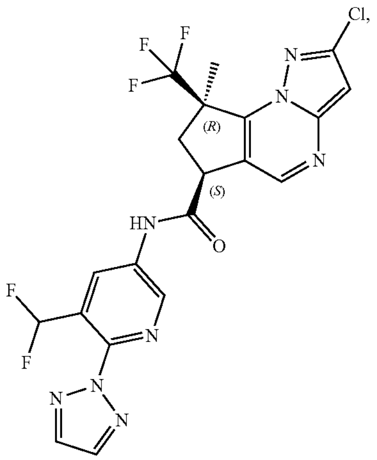
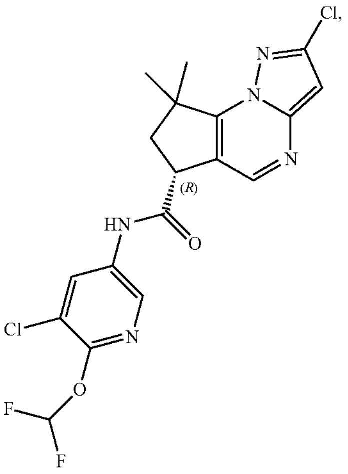

-continued
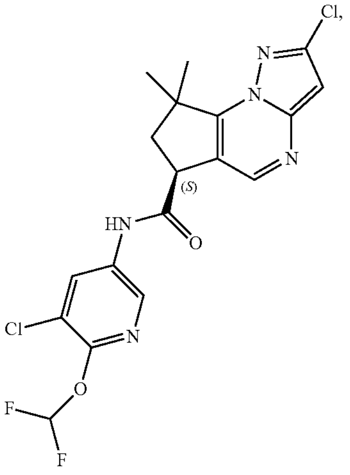
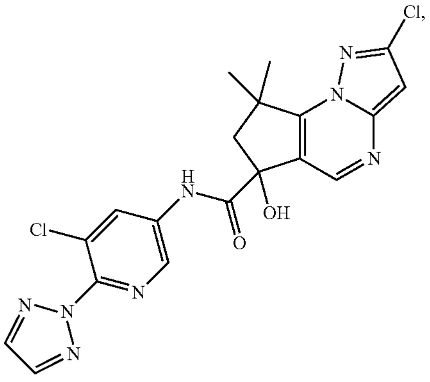
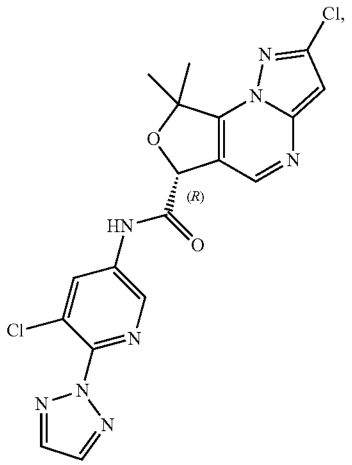
-continued
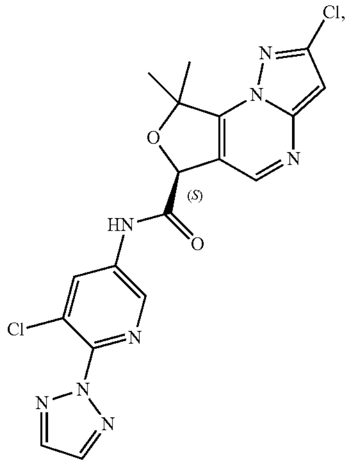
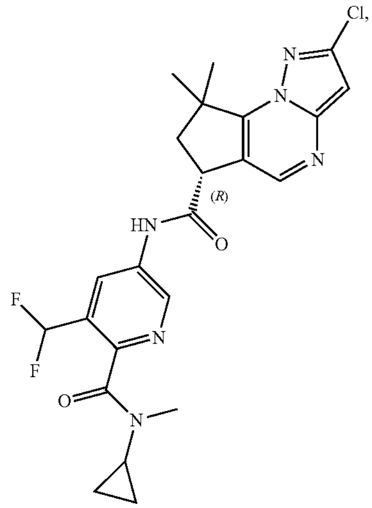
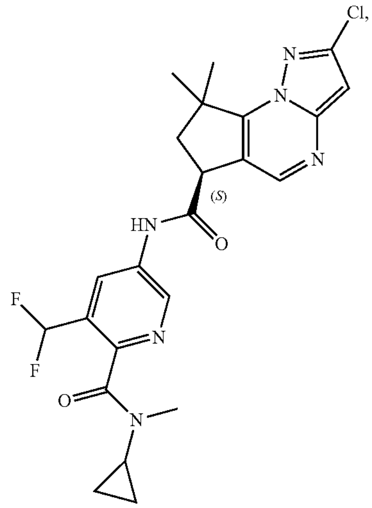

-continued
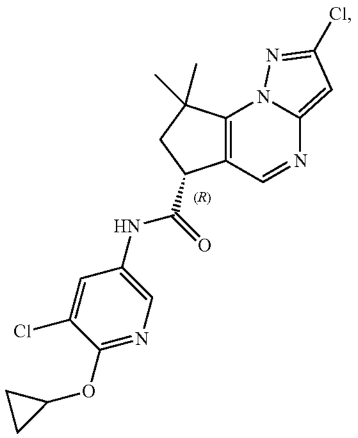
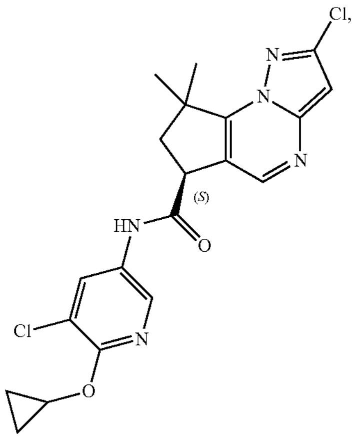
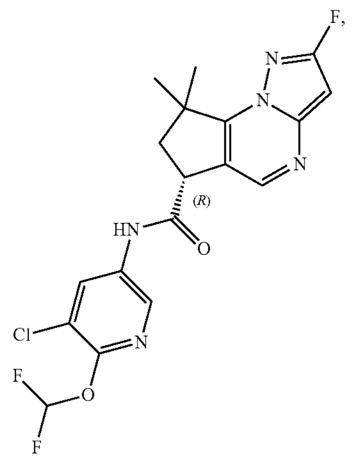
-continued
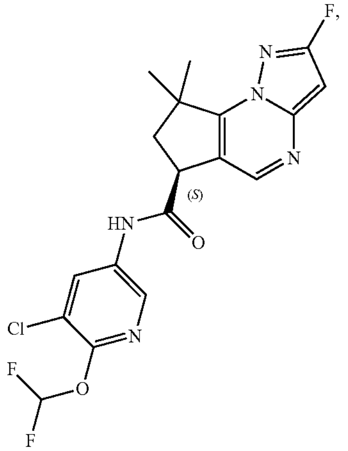
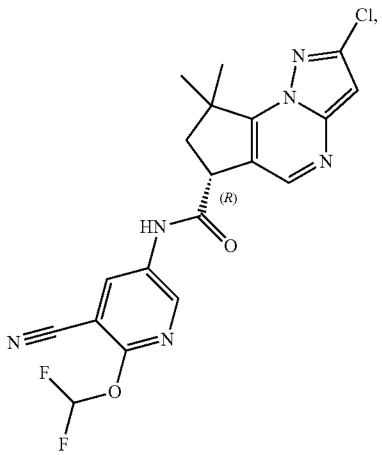
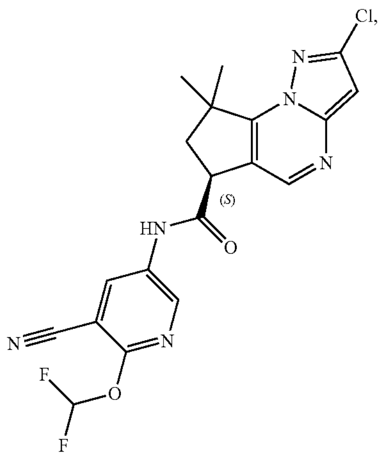

-continued
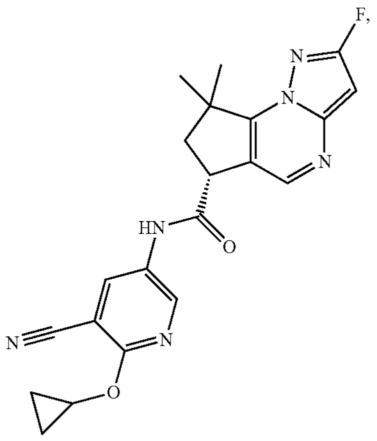
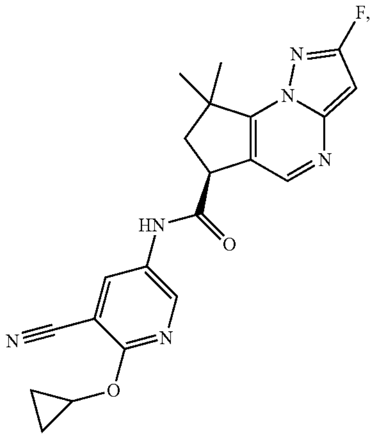
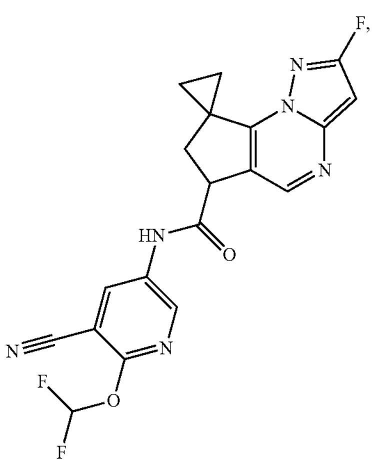
-continued
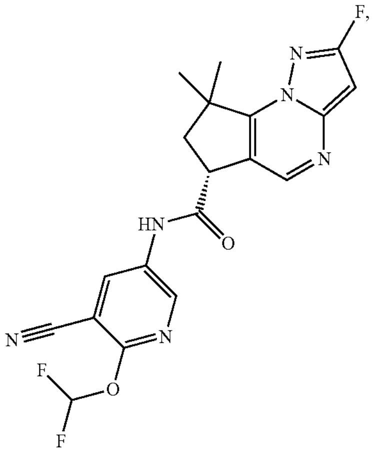
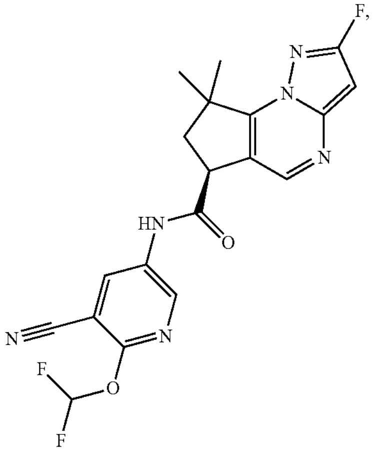
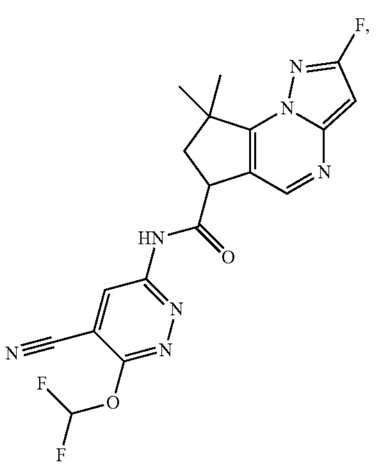

-continued
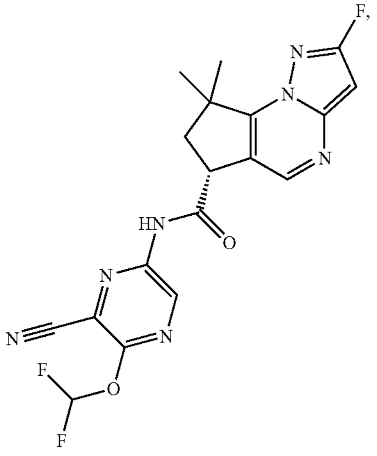
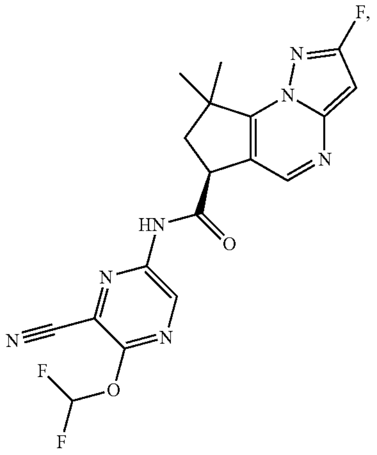
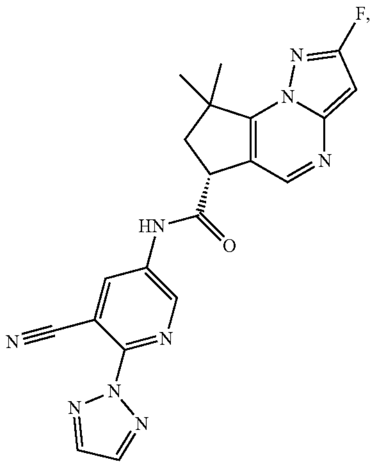
-continued
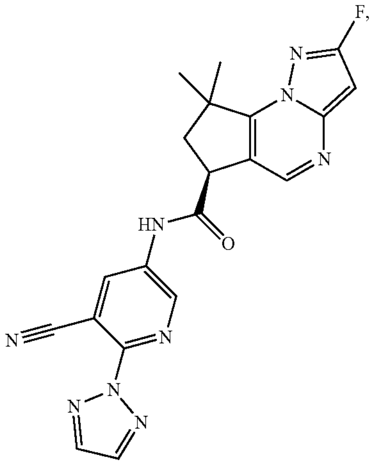
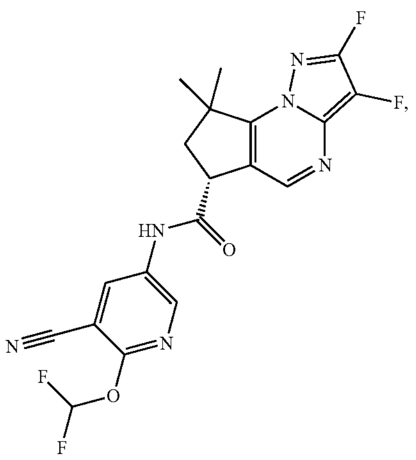
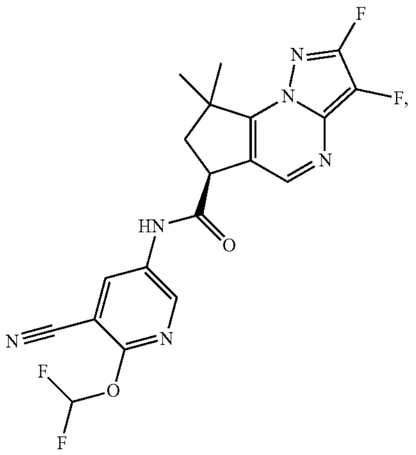

-continued
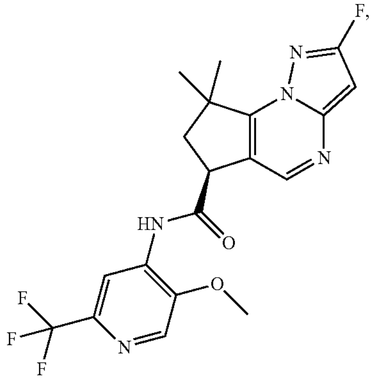
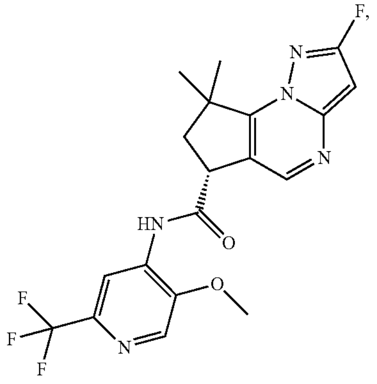
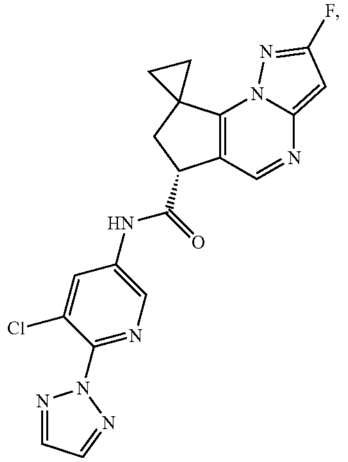
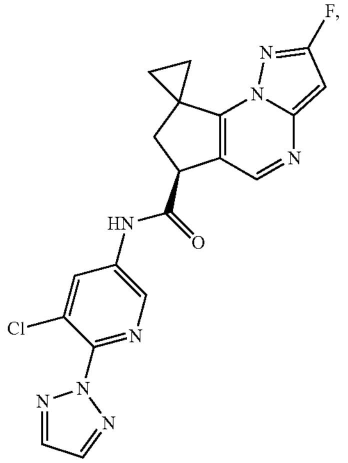
-continued
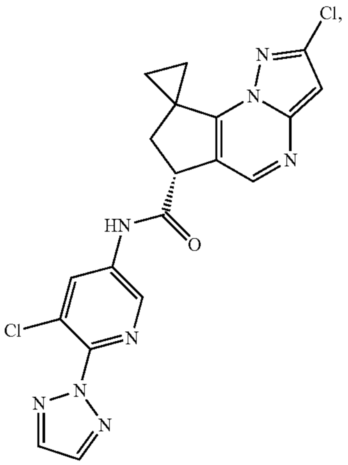
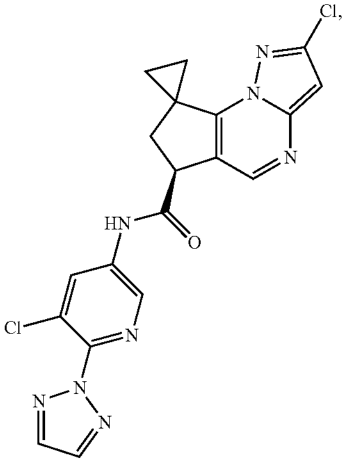
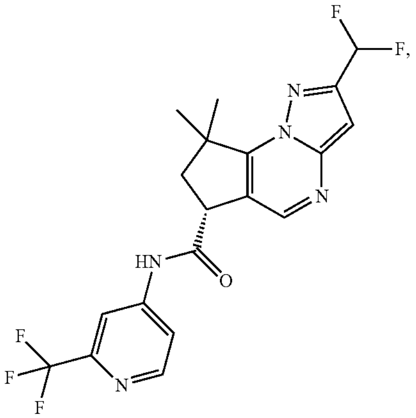

-continued
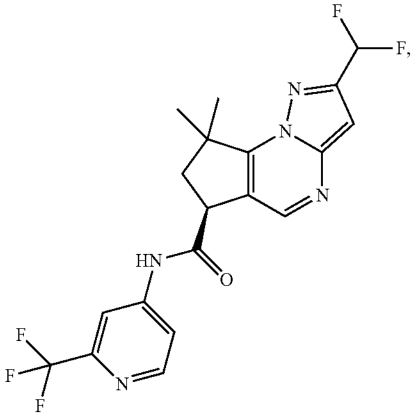
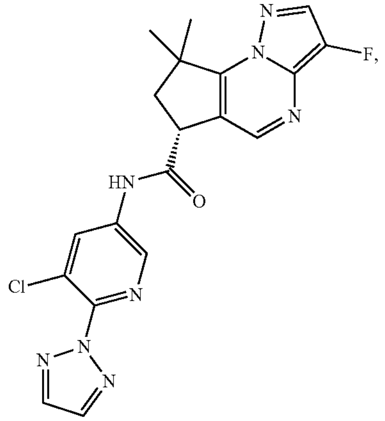
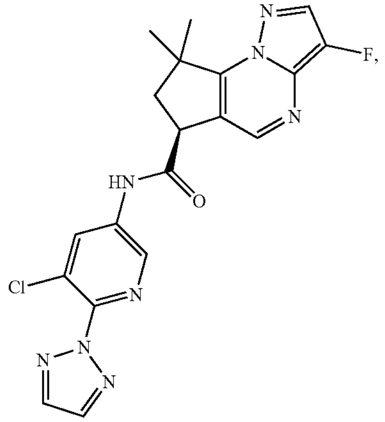
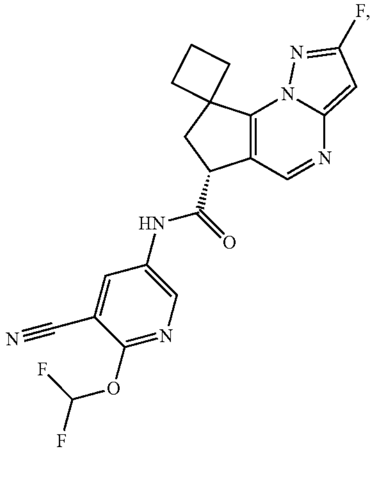
-continued
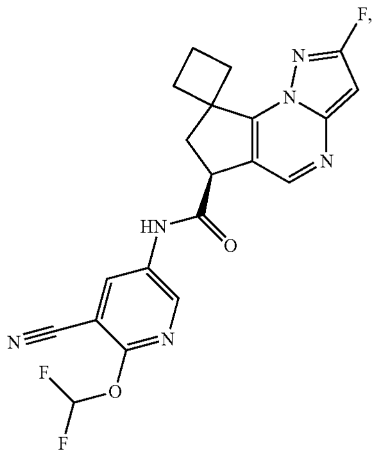
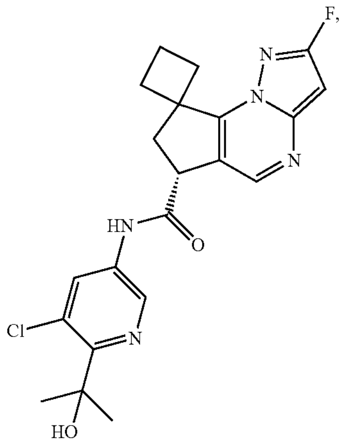
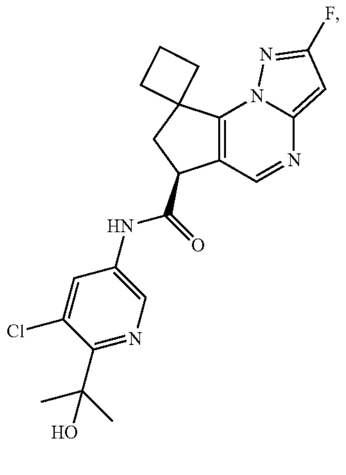

-continued
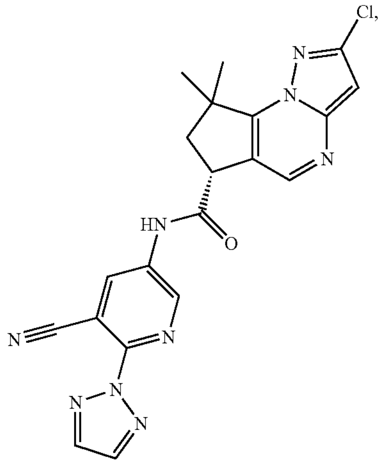
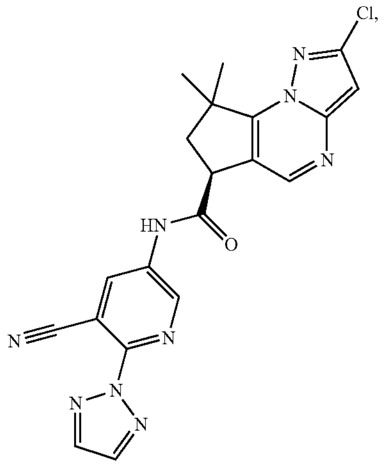
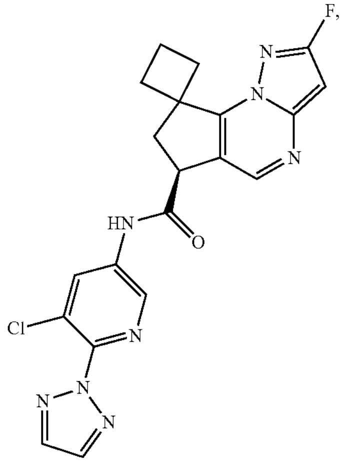
-continued
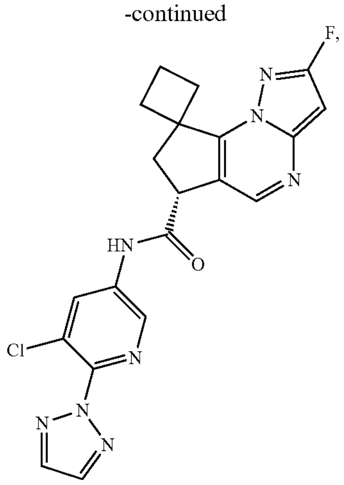
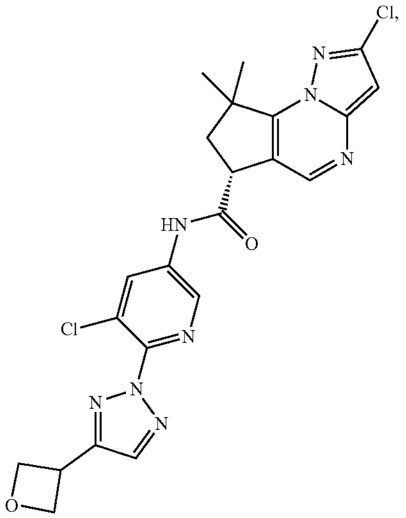
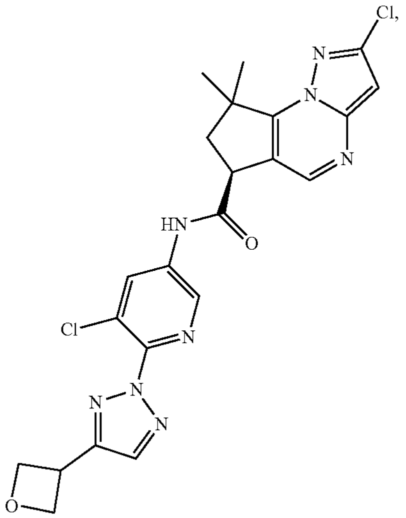

-continued
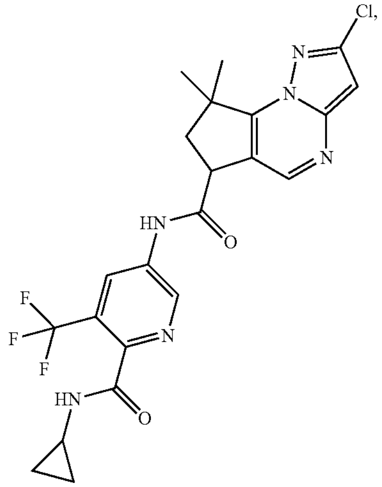
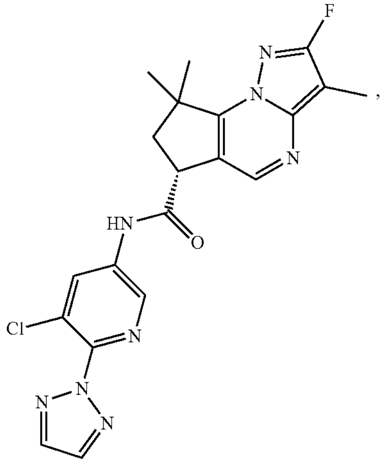
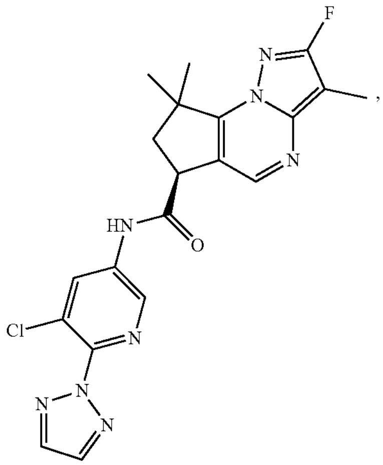
-continued
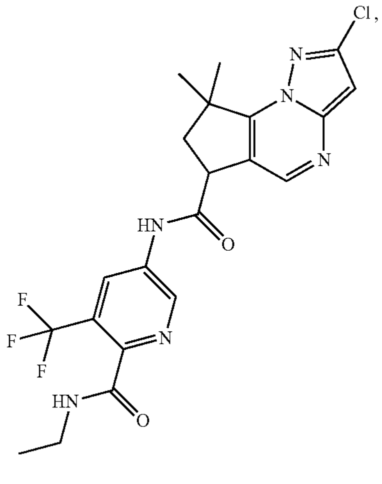
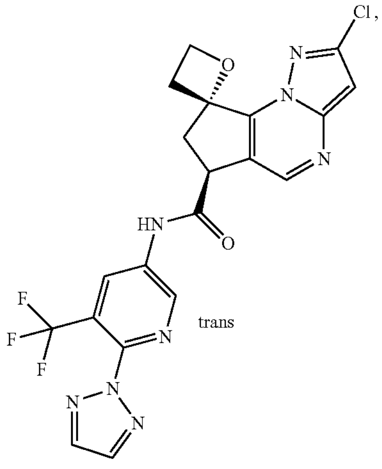
trans
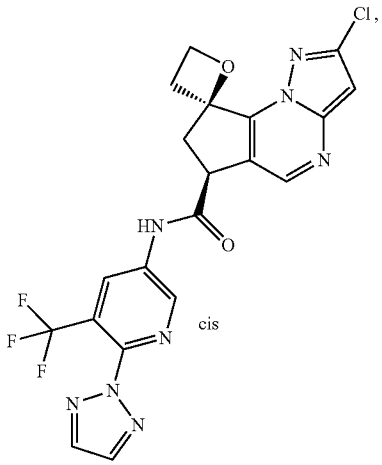
cis -continued
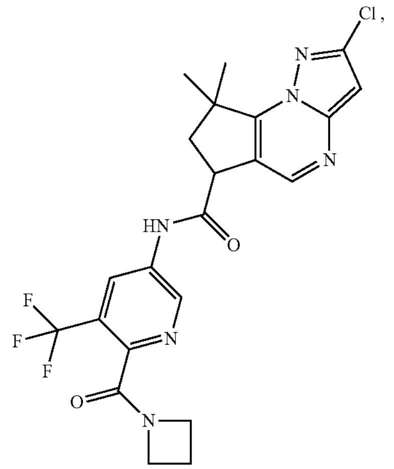
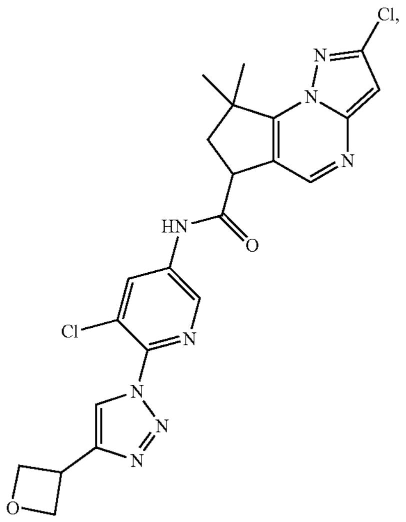
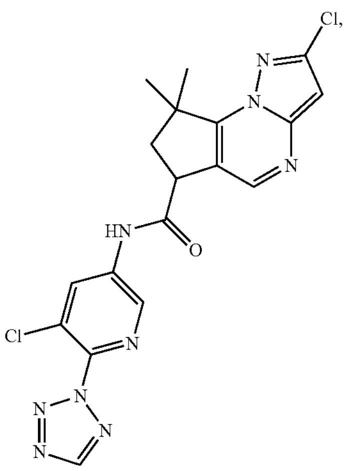
-continued
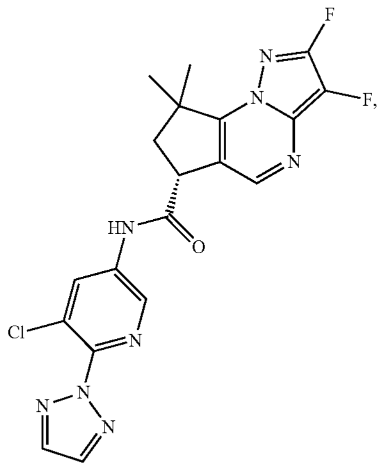
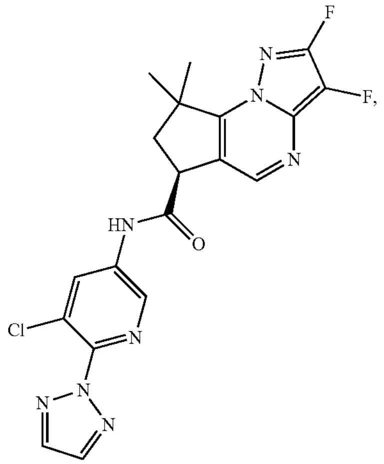
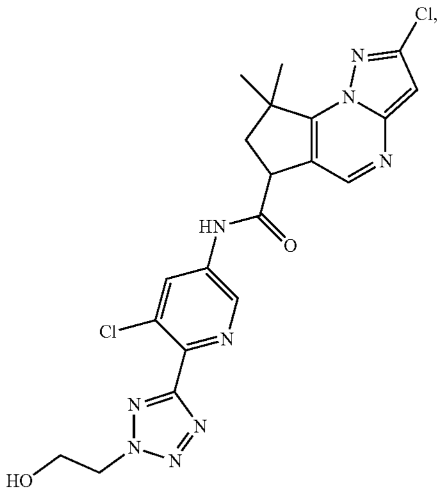

-continued
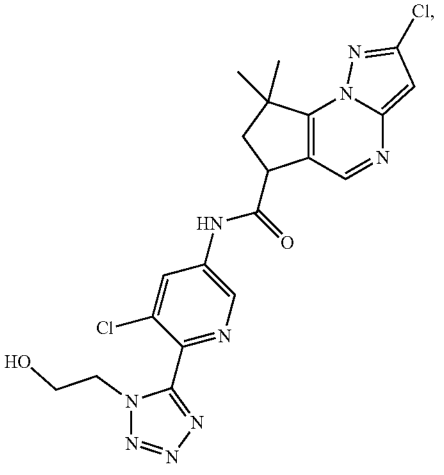
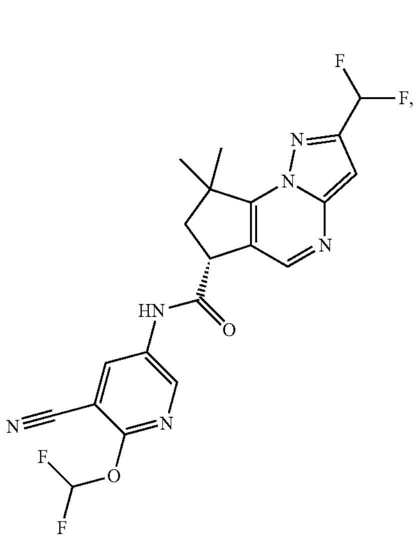
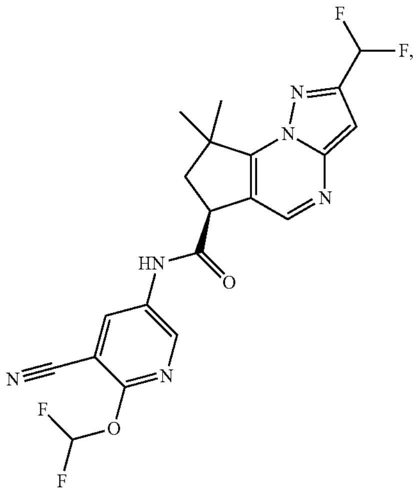
-continued
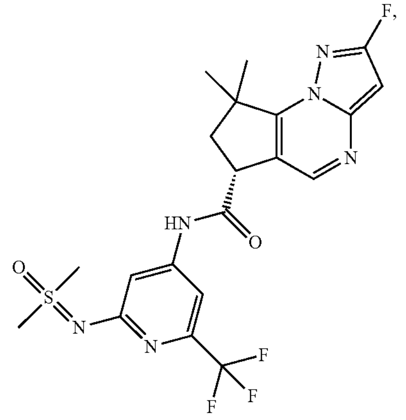
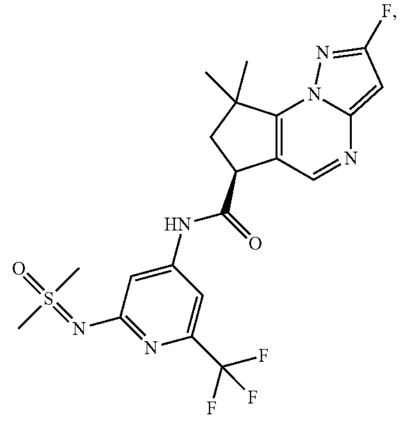
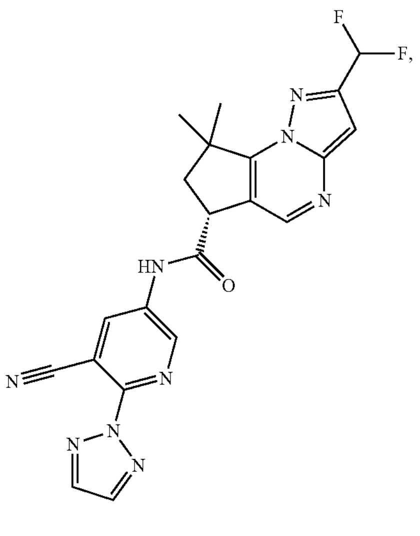

-continued
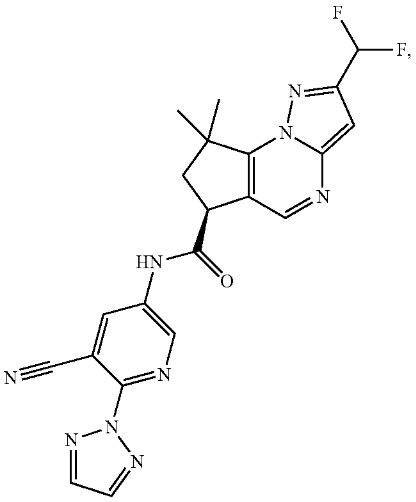
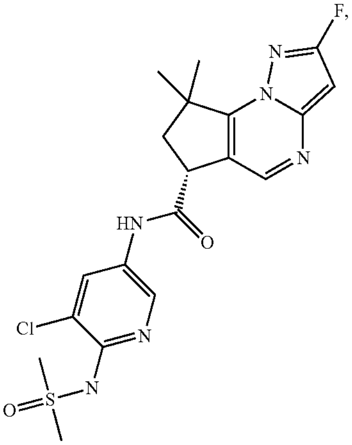
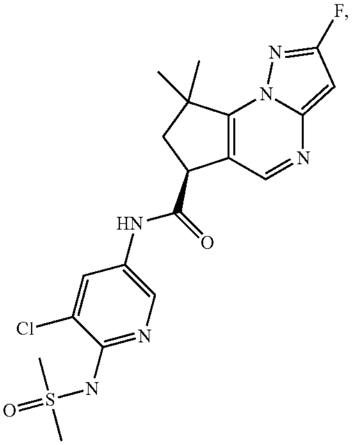
-continued
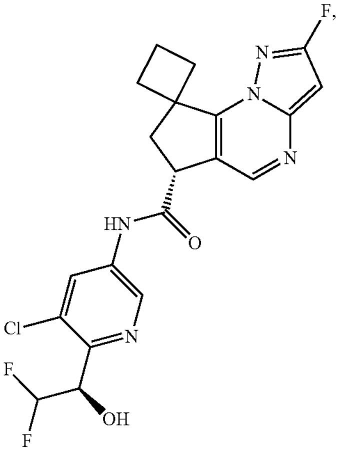
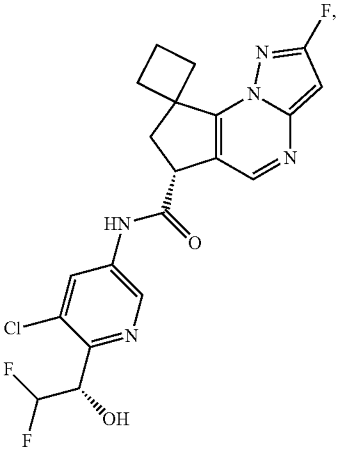
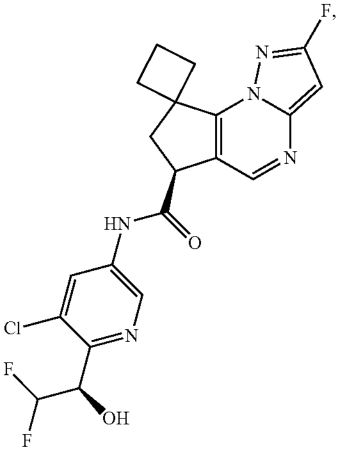

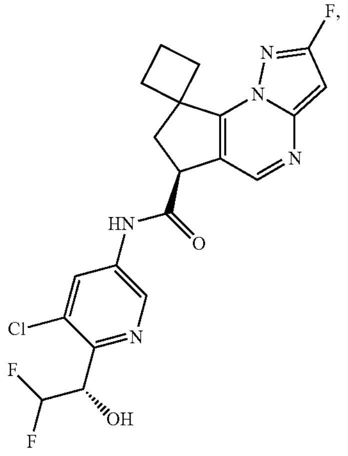
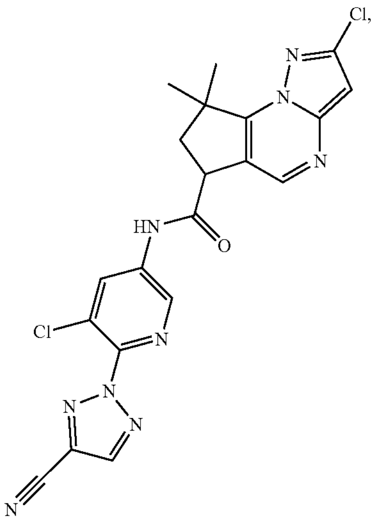
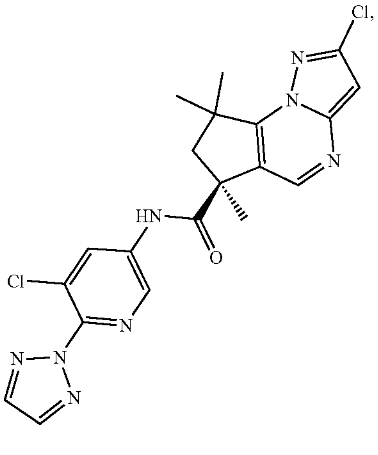
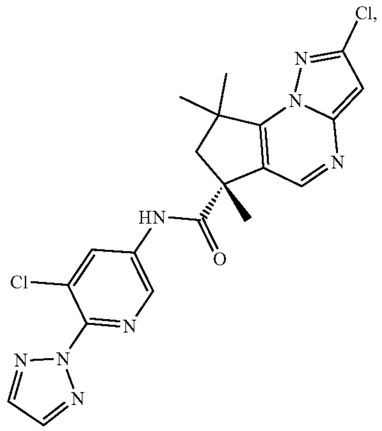
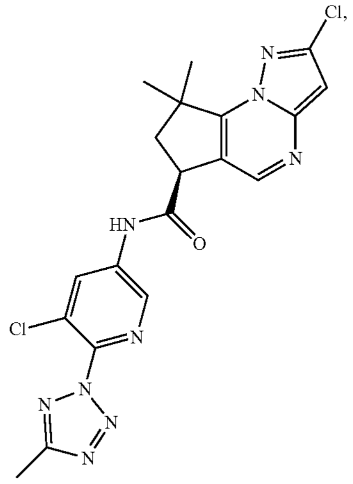
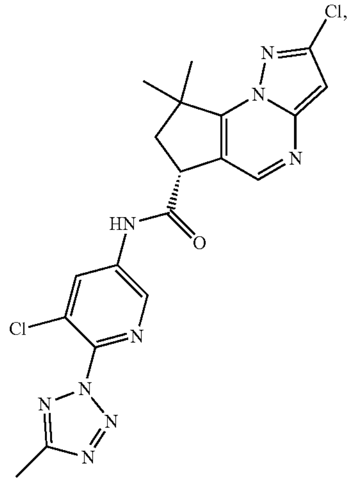

-continued
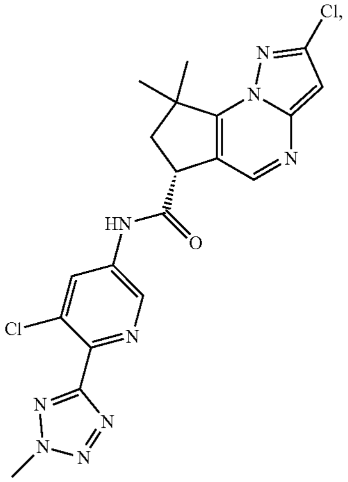
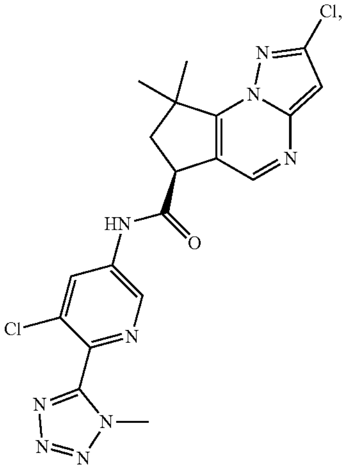
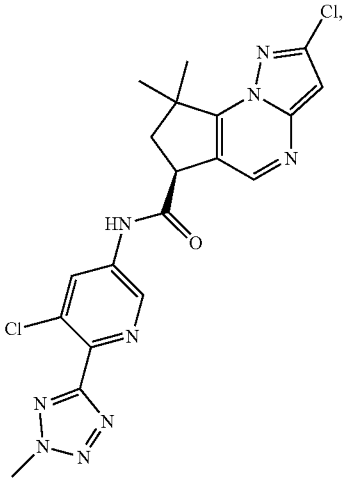
-continued
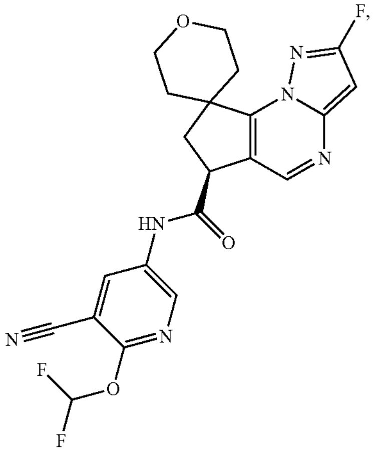
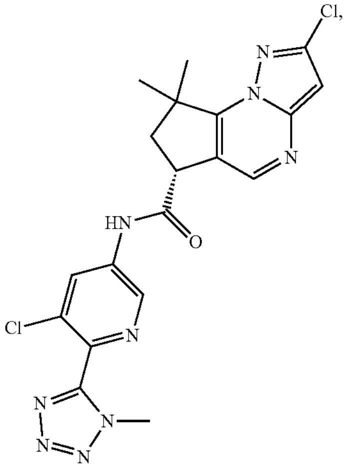
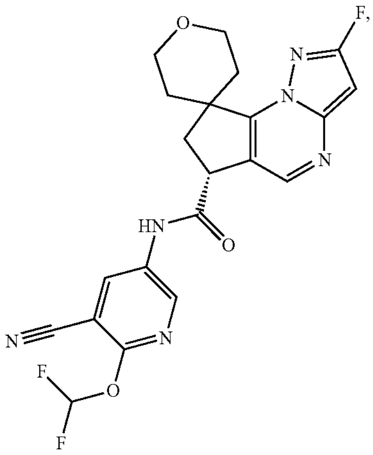

-continued
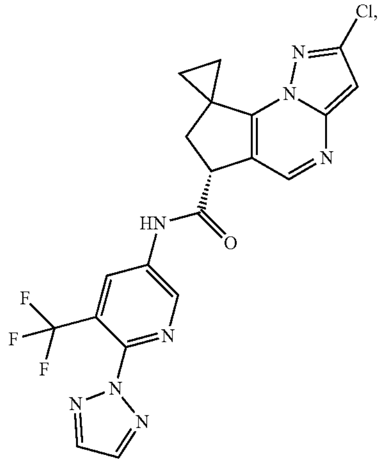
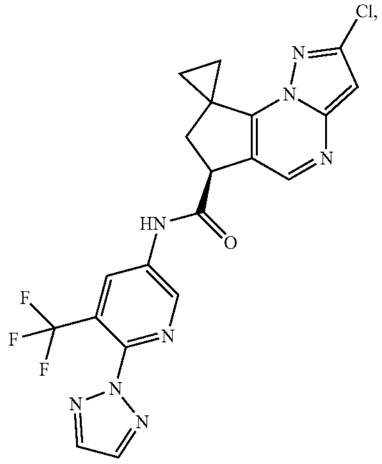
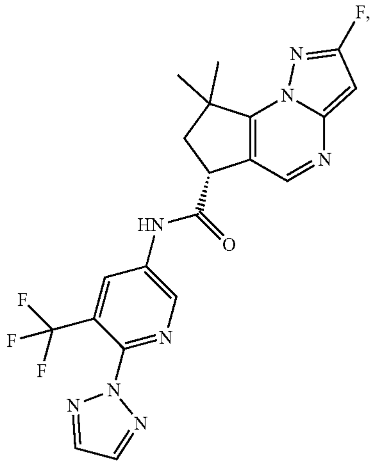
-continued
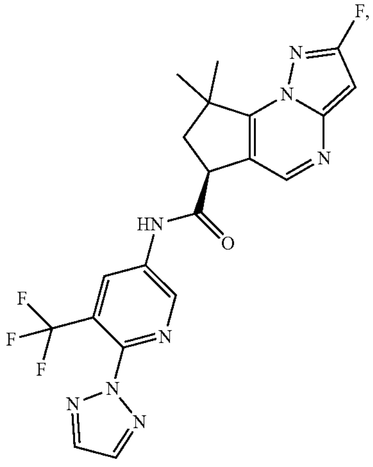
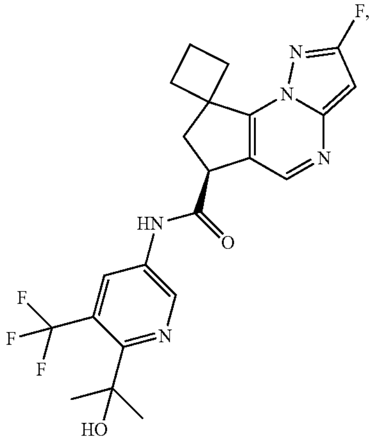
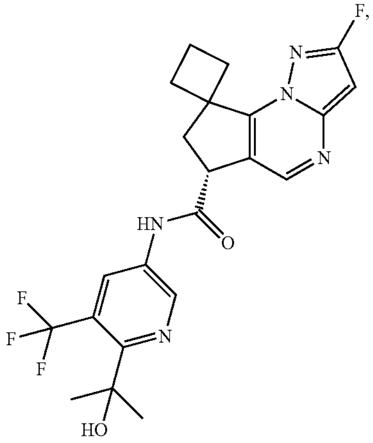

-continued
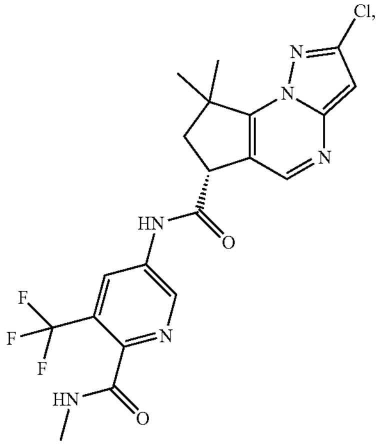
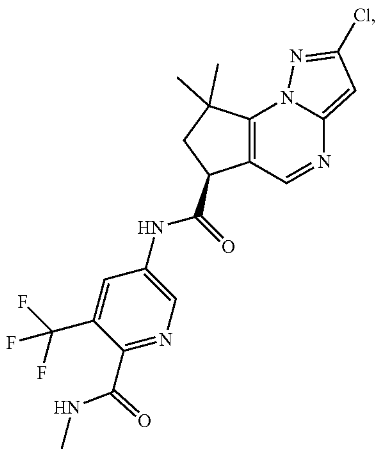
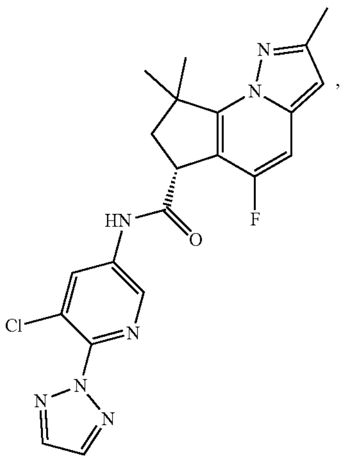
-continued
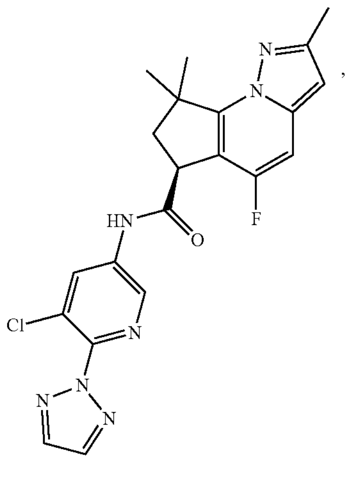
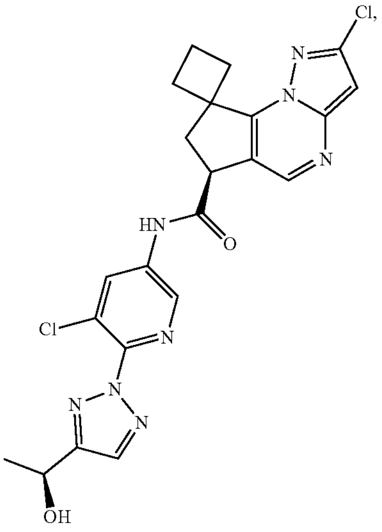
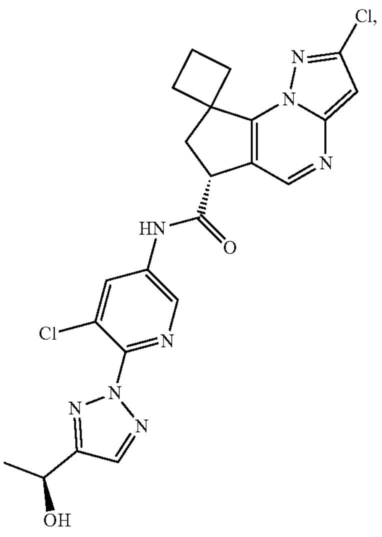

-continued
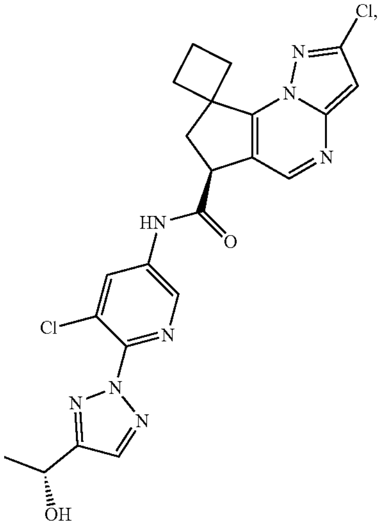
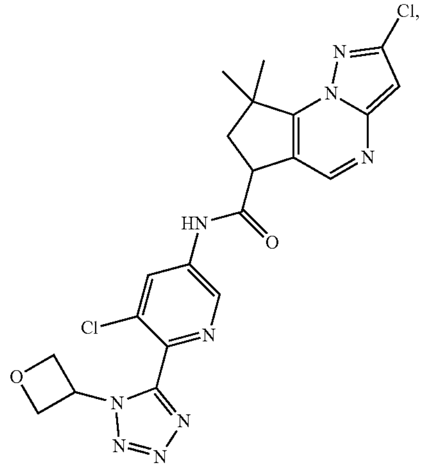
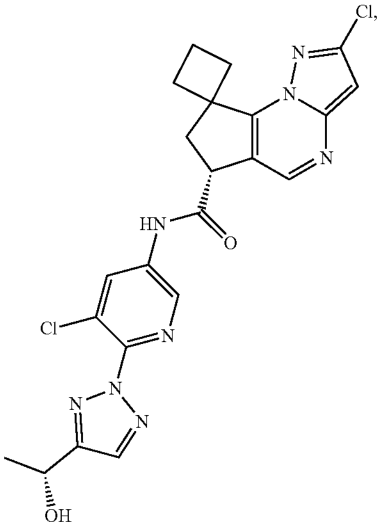
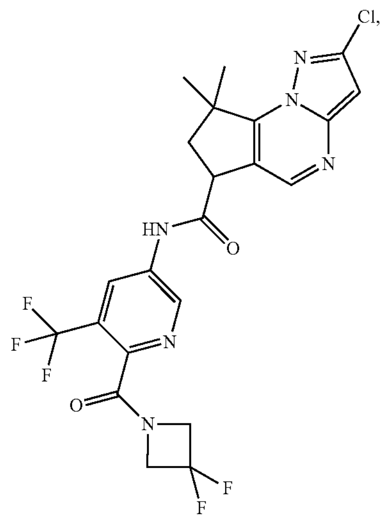
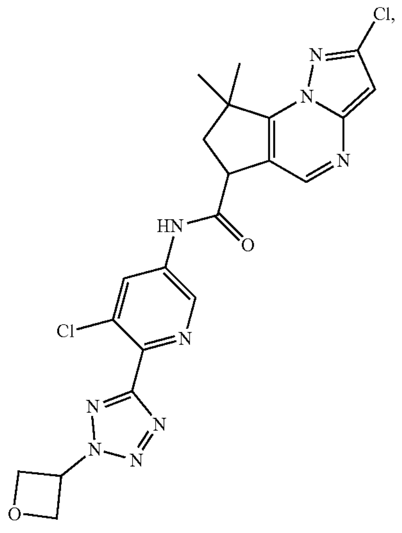
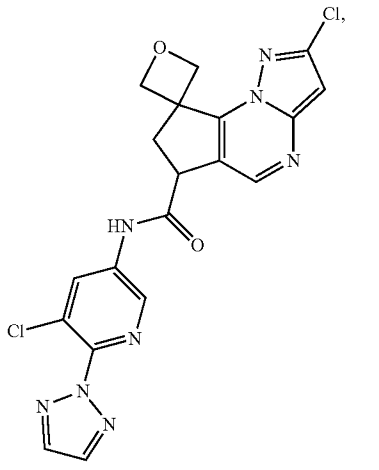
-continued -continued
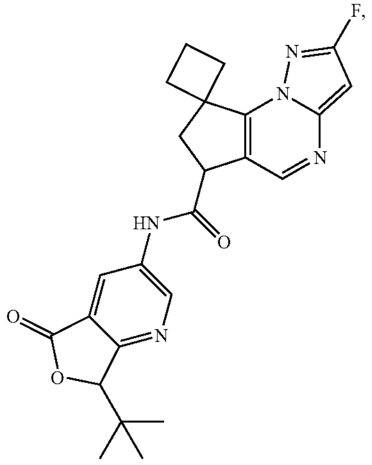
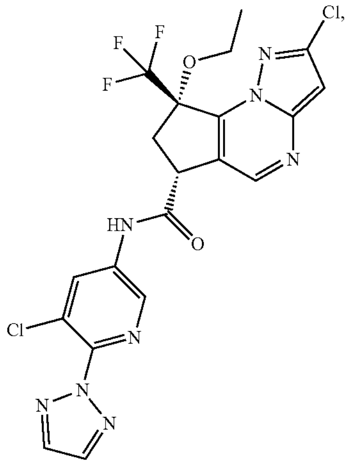
cis
racemic
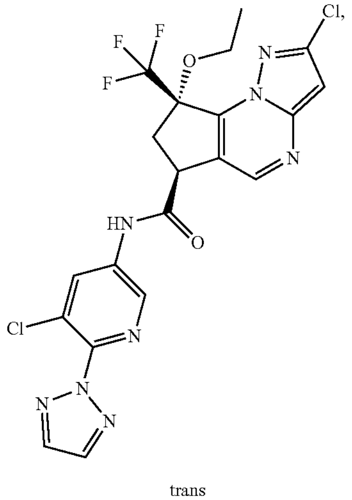
trans
racemic
-continued
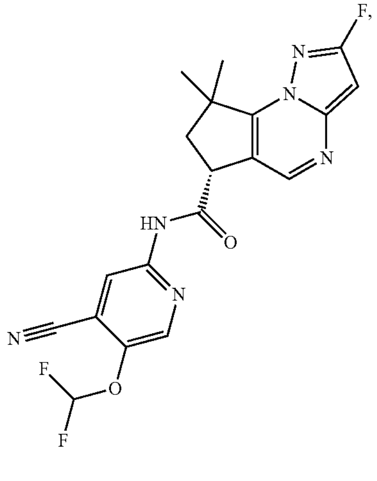
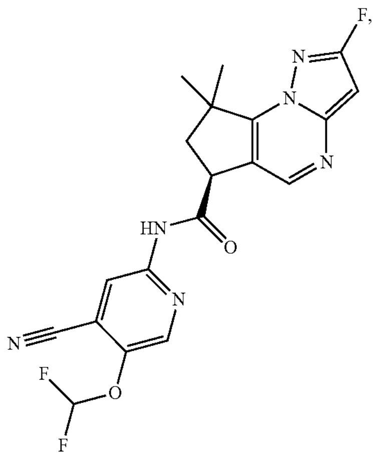
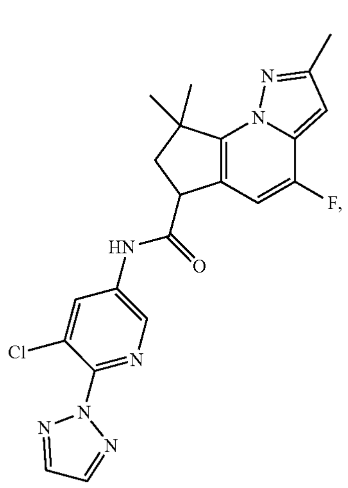

-continued
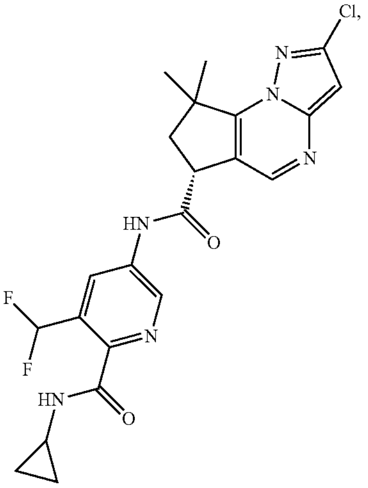
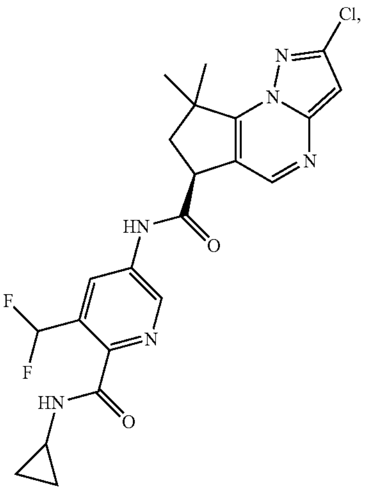
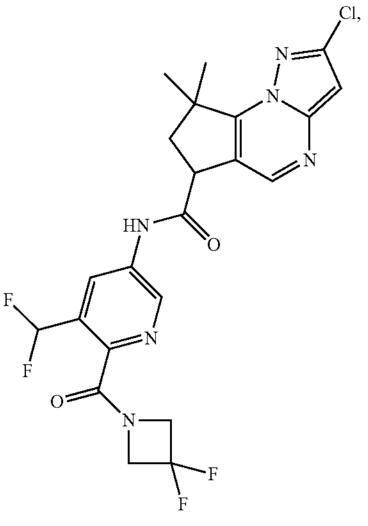
-continued
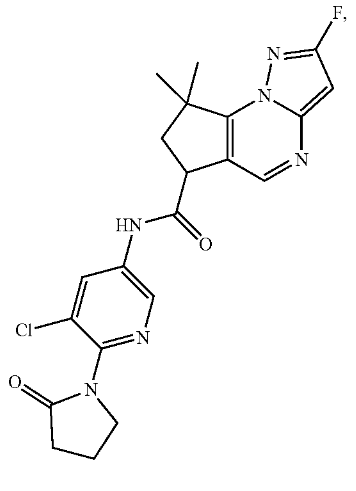
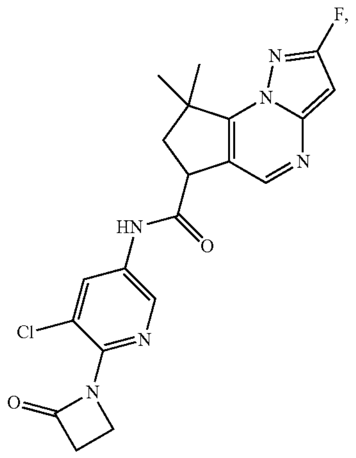
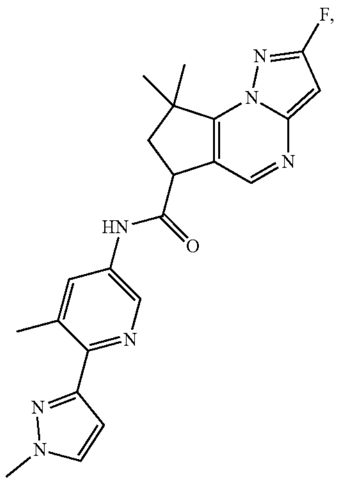

-continued
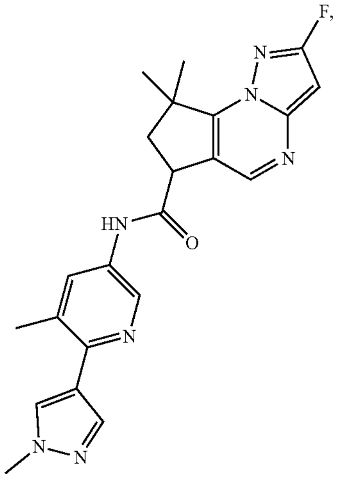
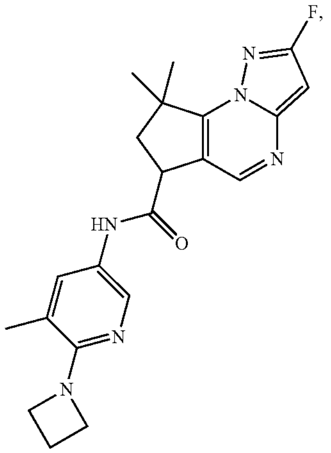
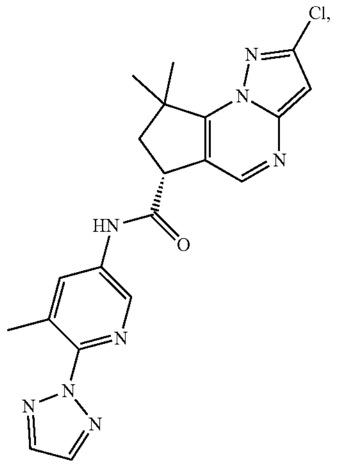
-continued
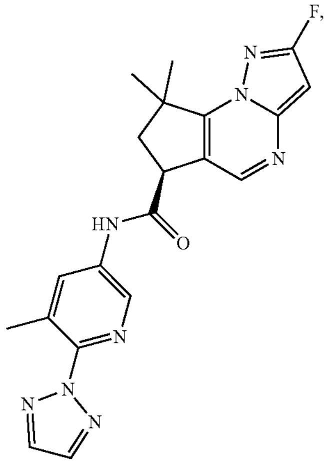
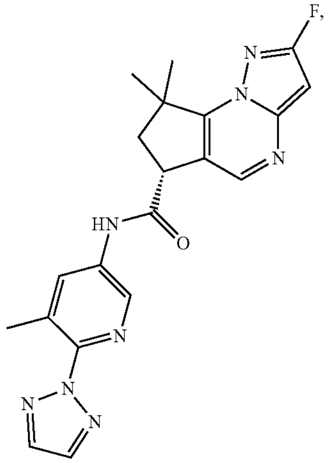
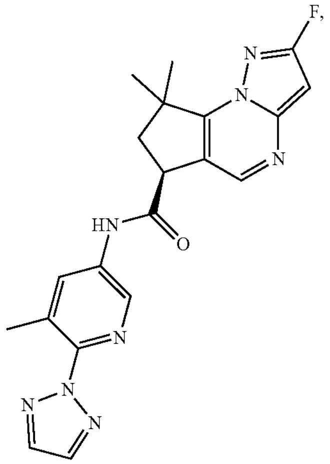

-continued
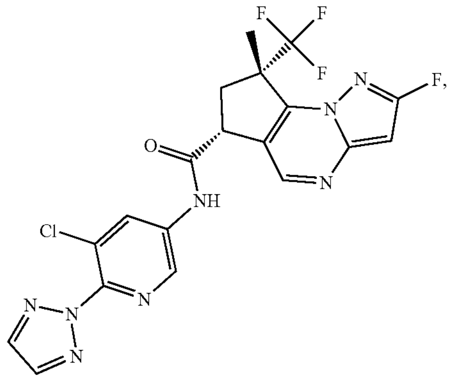
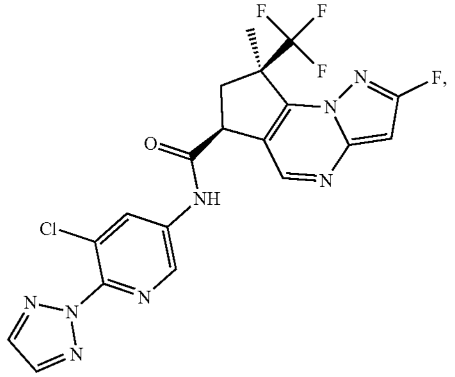
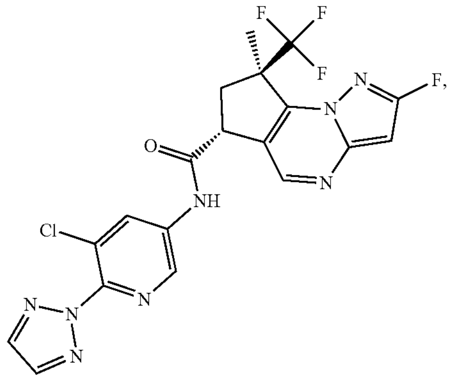
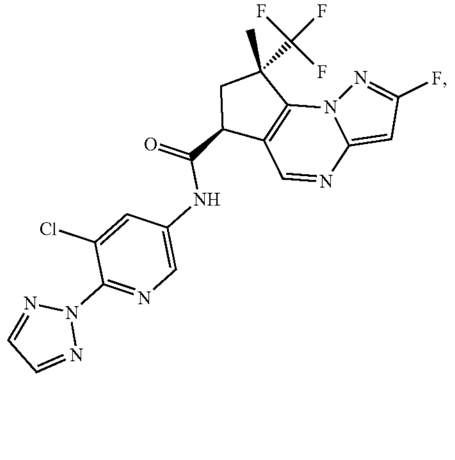
-continued
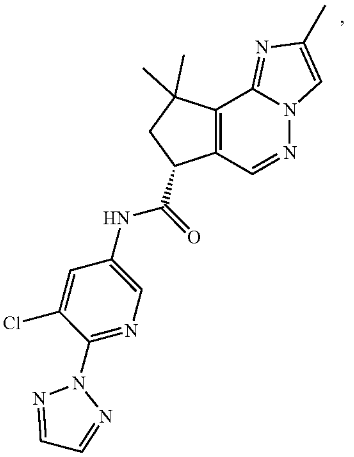
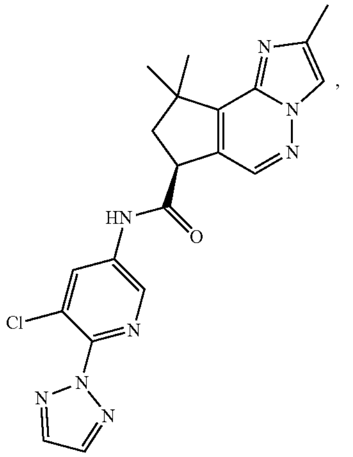
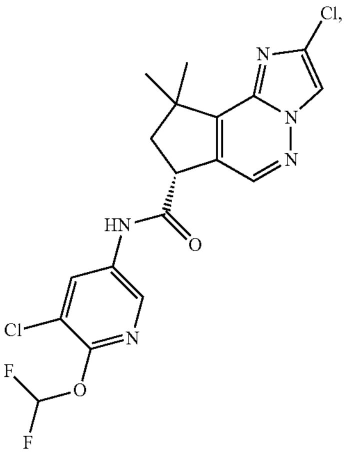

-continued
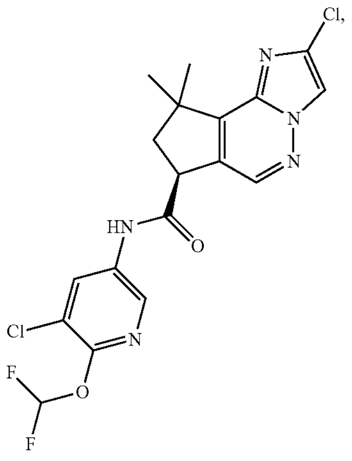
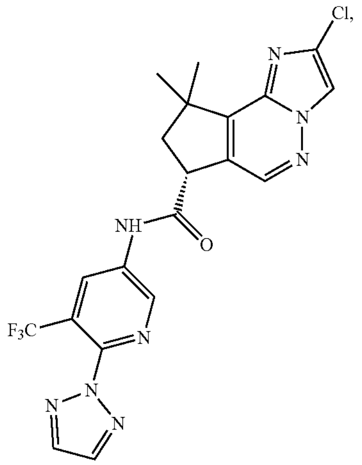
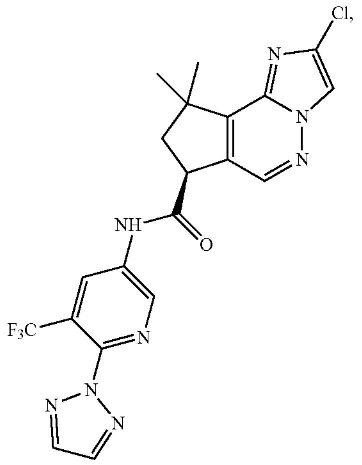
-continued
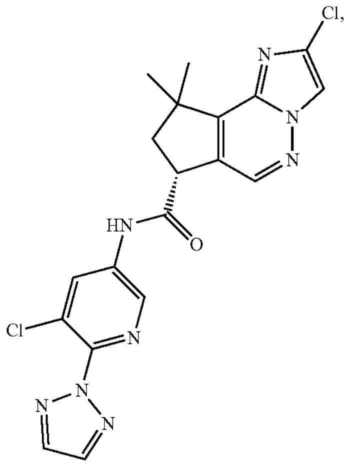
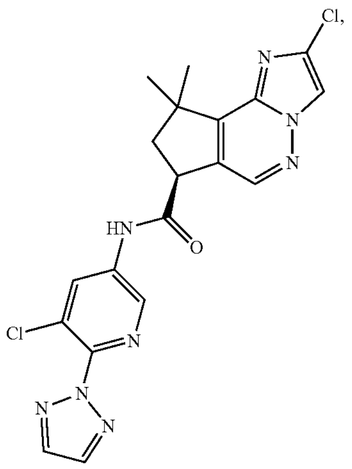
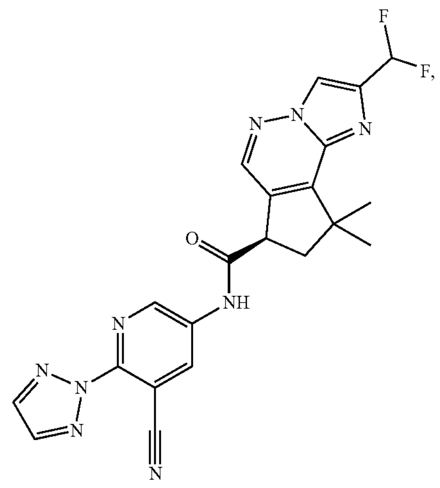

-continued
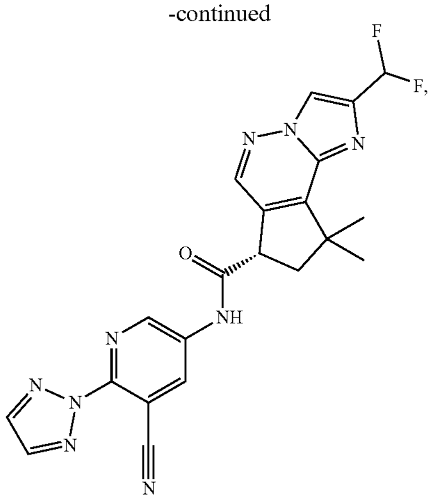
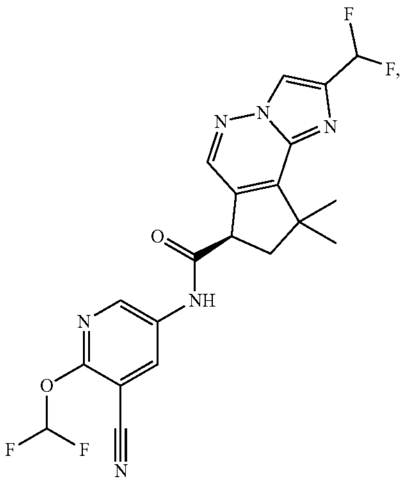
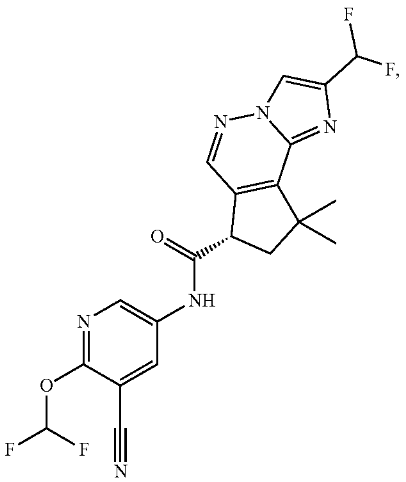
-continued
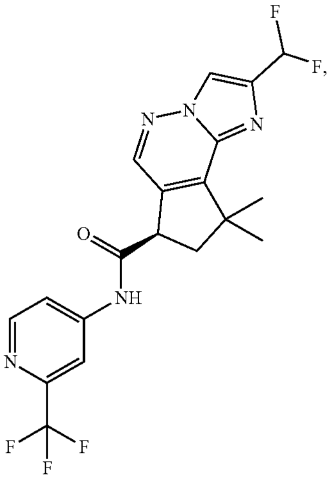
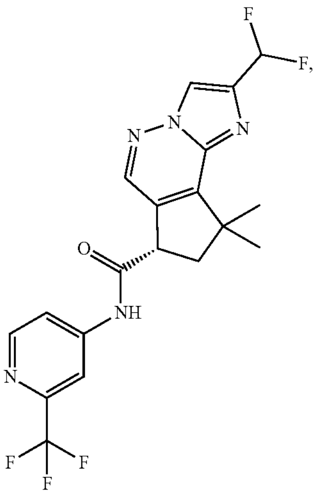
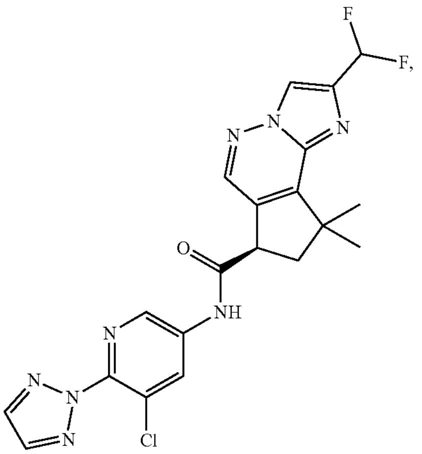
and -continued

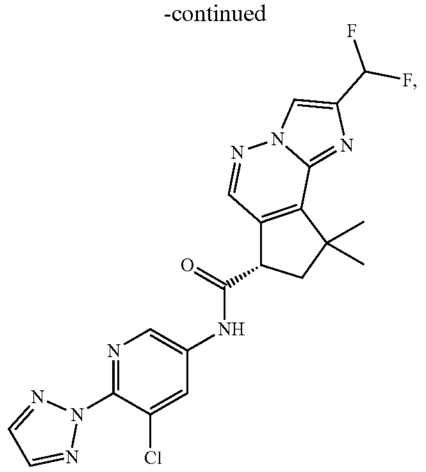

or a pharmaceutically acceptable salt thereof.

26. A pharmaceutical composition comprising a compound of claim 1, or a pharmaceutically acceptable salt thereof, and at least one pharmaceutically acceptable excipient.

27. A method for treating cancer in a subject in need thereof, comprising administering to the subject an effective amount of a compound of claim 1 or a pharmaceutically acceptable salt thereof.

28. A method of treating a MALT1-associated cancer in a subject, comprising administering to a subject identified or diagnosed as having a MALT1-associated cancer an effective amount of a compound of claim 1 or a pharmaceutically acceptable salt thereof.

29. The method of claim 27, further comprising administering an additional therapy or therapeutic agent to the subject.

30. A method for treating an autoimmune disorder in a subject in need thereof, comprising administering to the subject an effective amount of a compound of claim 1 or a pharmaceutically acceptable salt thereof.

31. A method of treating a MALT1-associated autoimmune disorder in a subject, comprising administering to a subject identified or diagnosed as having a MALT1-associated autoimmune disorder an effective amount of a compound of claim 1 or a pharmaceutically acceptable salt thereof.

32. A method for treating an inflammatory disorder in a subject in need thereof, comprising administering to the subject an effective amount of a compound of claim 1 or a pharmaceutically acceptable salt thereof.

33. A method of treating a MALT1-associated inflammatory disorder in a subject, comprising administering to a subject identified or diagnosed as having a MALT1-associated inflammatory disorder an effective amount of a compound of claim 1 or a pharmaceutically acceptable salt thereof.

* * * * *